US009078442B2

(12) United States Patent
Willms et al.

(10) Patent No.: US 9,078,442 B2
(45) Date of Patent: Jul. 14, 2015

(54) HERBICIDALLY AND FUNGICIDALLY ACTIVE 3-PHENYLISOXAZOLINE-5-CARBOXAMIDES AND 3-PHENYLISOXAZOLINE-5-THIOAMIDES

(75) Inventors: Lothar Willms, Hofheim (DE); Monika H Schmitt, Frankfurt (DE); Thomas Frenzel, Köln (DE); Klaus Bernhard Haaf, Kelkheim (DE); Isolde Häuser-Hahn, Leverkusen (DE); Ines Heinemann, Hofheim (DE); Elmar Gatzweiler, Bad Nauheim (DE); Christopher Hugh Rosinger, Hofheim (DE); Heinz Kehne, Hofheim (DE); Jan Dittgen, Frankfurt (DE); Dieter Feucht, Eschborn (DE); Martin Jeffrey Hills, Idstein (DE); Philippe Rinolfi, Châtillon d'Azergues (FR)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 30 days.

(21) Appl. No.: 14/006,280

(22) PCT Filed: Mar. 26, 2012

(86) PCT No.: PCT/EP2012/055323
§ 371 (c)(1), (2), (4) Date: Dec. 17, 2013

(87) PCT Pub. No.: WO2012/130798
PCT Pub. Date: Oct. 4, 2012

(65) Prior Publication Data

US 2014/0100108 A1 Apr. 10, 2014

(30) Foreign Application Priority Data

Mar. 31, 2011 (EP) .................................... 11160613

(51) Int. Cl.

| | |
|---|---|
| *A01N 25/32* | (2006.01) |
| *A01N 43/40* | (2006.01) |
| *A01N 43/36* | (2006.01) |
| *A01N 43/54* | (2006.01) |
| *A01N 43/82* | (2006.01) |
| *A01N 43/78* | (2006.01) |
| *A01N 43/80* | (2006.01) |
| *A61K 31/505* | (2006.01) |
| *A61K 31/44* | (2006.01) |
| *A61K 31/41* | (2006.01) |
| *A61K 31/425* | (2006.01) |
| *A61K 31/42* | (2006.01) |
| *C07D 239/24* | (2006.01) |
| *C07D 401/02* | (2006.01) |
| *C07D 261/02* | (2006.01) |
| *C07D 413/02* | (2006.01) |
| *C07D 285/08* | (2006.01) |
| *C07D 271/06* | (2006.01) |
| *C07D 413/04* | (2006.01) |

(Continued)

(52) U.S. Cl.
CPC ............... *A01N 43/80* (2013.01); *A01N 25/32* (2013.01); *A01N 43/40* (2013.01); *A01N 43/54* (2013.01); *A01N 43/56* (2013.01); *A01N 43/82* (2013.01); *A61K 31/505* (2013.01); *C07D 261/02* (2013.01); *C07D 261/04* (2013.01); *C07D 271/06* (2013.01); *C07D 413/04* (2013.01); *C07D 413/12* (2013.01); *C07D 417/12* (2013.01)

(58) Field of Classification Search
USPC ......... 504/105, 106, 112, 130, 136, 138, 139, 504/239, 252, 262, 265, 266, 271; 514/256, 514/274, 340, 361, 364, 365, 378; 544/316, 544/333; 546/272.1; 548/128, 131, 204, 548/240
See application file for complete search history.

(56) References Cited

FOREIGN PATENT DOCUMENTS

| | | |
|---|---|---|
| DE | 40 17 665 | 12/1991 |
| DE | 40 26 018 | 2/1992 |

(Continued)

OTHER PUBLICATIONS

International Search Report for PCT/EP2012/055323 Mailed May 24, 2012.
Extended European Search Report for EP 11 16 0613 (Aug. 19, 2011).
Gucma,et al., "Synthesis and biological activity of 3-substituted isoxazolecarboxamides", Monatsh Chem, vol. 141, (2010), pp. 461-469.

(Continued)

*Primary Examiner* — Samantha Shterengarts
(74) *Attorney, Agent, or Firm* — Miles & Stockbridge, P.C.

(57) ABSTRACT

3-Phenylisoxazoline-5-carboxamides and 3-phenylisoxazoline-5-thioamides of the formula (I) and their use as herbicides and fungicides are described.

(I)

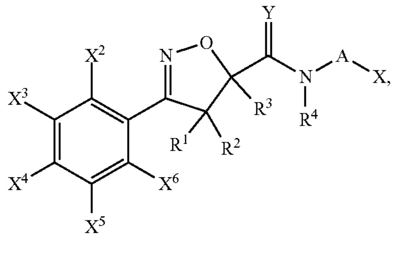

In this formula (I), X, $X^2$ to $X^6$, $R^1$ to $R^4$ are radicals such as hydrogen, halogen and organic radicals such as substituted alkyl. A is a bond or a divalent unit. Y is a chalcogen.

19 Claims, No Drawings

(51) Int. Cl.

| | |
|---|---|
| *A01N 43/56* | (2006.01) |
| *C07D 261/04* | (2006.01) |
| *C07D 413/12* | (2006.01) |
| *C07D 417/12* | (2006.01) |

(56) References Cited

FOREIGN PATENT DOCUMENTS

| | | |
|---|---|---|
| EP | 0 520 371 | 12/1992 |
| WO | 95/14680 | 6/1995 |
| WO | 95/14681 | 6/1995 |
| WO | 98/57937 | 12/1998 |
| WO | 99/05130 | 2/1999 |
| WO | 2005/021515 | 3/2005 |
| WO | 2005/021516 | 3/2005 |
| WO | 2005/051931 | 6/2005 |
| WO | 2008/035315 | 3/2008 |

OTHER PUBLICATIONS

Gucma, et al.,"Synthesis of 3-Substituted Isoxazolecarboxamides Potential Fungicides", Letters in Organic Chemistry, vol. 7, (2010), pp. 502-507.

3rd Party Observation for application No. EP20120713928, took place on Mar. 30, 2015, Publication No. EP2691379, Bayer IP GmbH, Date of Publication May 2, 2014.

HERBICIDALLY AND FUNGICIDALLY ACTIVE 3-PHENYLISOXAZOLINE-5-CARBOXAMIDES AND 3-PHENYLISOXAZOLINE-5-THIOAMIDES

CROSS REFERENCE TO RELATED APPLICATIONS

This application is a §371 National Stage Application of PCT/EP2012/055323, filed Mar. 26, 2012, which claims priority to European Application No. 11160613.3, filed Mar. 31, 2011.

BACKGROUND OF THE INVENTION

1. Field of the Invention

The invention relates to the technical field of herbicides and fungicides, especially that of herbicides for selective control of broad-leaved weeds and weed grasses in crops of useful plants.

2. Description of Related Art

Specifically, it relates to substituted 3-phenylisoxazoline-5-carboxamides and 3-phenylisoxazoline-5-thioamides, to processes for their preparation and to their use as herbicides and fungicides.

WO1995/014681 A1, WO1995/014680 A1, WO 2008/035315 A1, WO2005/051931 A1 and WO2005/021515 A1 each describe, inter alia, 3-phenylisoxazoline-5-carboxamides which are substituted at the phenyl ring in the 3- and 4-positions by alkoxy radicals. WO1998/057937 A1 describes, inter alia, compounds which are substituted at the phenyl ring in the 4-position by an alkoxy radical. WO2006/016237 A1 describes, inter alia, compounds which are substituted at the phenyl ring by an amido radical. The compounds described in the documents mentioned above are disclosed in these documents as being pharmacologically active. WO2005/021516 A1 discloses the compounds 3-({[3-(3-tert-butylphenyl)-5-ethyl-4,5-dihydro-1,2-oxazol-5-yl]carbonyl}amino)-5-fluoro-4-oxopentanoic acid and 3-({[3-(3-tert-butylphenyl)-5-isopropyl-4,5-dihydro-1,2-oxazol-5-yl]carbonyl}amino)-5-fluoro-4-oxopentanoic acid as being pharmacologically active.

DE 4026018 A1 and EP 520371 A2 and DE 4017665 disclose 3-phenylisoxazoline-5-carboxamides which carry a hydrogen atom in position 5 of the isoxazoline ring. In these documents, these compounds are described as agrochemically active safeners, that is to say as compounds which eliminate the unwanted herbicidal effect of herbicides on crop plants. A herbicidal action of these compounds is not disclosed.

Monatshefte Chemie (2010) 141, 461 and Letters in Organic Chemistry (2010), 7, 502 also disclose 3-phenylisoxazoline-5-carboxamides carrying a hydrogen atom in position 5 of the isoxazoline ring. Some of the compounds mentioned have fungicidal action. None of the publications mentioned above discloses a herbicidal action of such 3-phenylisoxazoline-5-carboxamides.

SUMMARY

It is an object of the present invention to provide herbicidally and fungicidally active compounds.

It has been found that substituted 3-phenylisoxazoline-5-carboxamides and 3-phenylisoxazoline-5-thioamides are particularly suitable for use as herbicides and fungicides. The present invention provides 3-phenylisoxazoline-5-carboxamides and 3-phenylisoxazoline-5-thioamides of the formula (I)

(I)

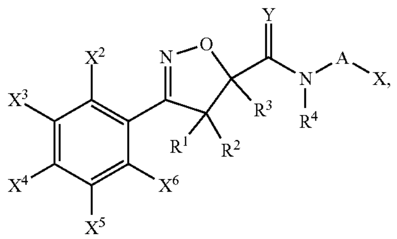

in which $R^1$ and $R^2$ independently of one another are each hydrogen, fluorine, chlorine, bromine, iodine, cyano, or $(C_1-C_4)$-alkyl or $(C_1-C_4)$-alkoxy substituted by in each case m radicals from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, $(C_1-C_3)$-alkylcarbonyloxy or $S(O)_nR^5$, or $(C_1-C_6)$-alkyl, $(C_3-C_6)$-cycloalkyl, $(C_2-C_6)$-alkenyl or $(C_2-C_6)$-alkynyl substituted by in each case m radicals from the group consisting of fluorine, chlorine, bromine, iodine, cyano, $(C_1-C_4)$-alkoxy and hydroxy, or $(C_1-C_6)$-alkylcarbonyl, $(C_2-C_6)$-alkenylcarbonyl or $(C_3-C_6)$-cycloalkylcarbonyl substituted by in each case m radicals from the group consisting of fluorine, chlorine, bromine, iodine, cyano and $(C_1-C_6)$-alkoxy;

$R^4$ is hydrogen, cyano, or $(C_1-C_8)$-alkyl or $(C_3-C_8)$-cycloalkyl substituted by in each case m radicals from the group consisting of fluorine, chlorine, bromine, iodine, cyano, hydroxy and $(C_1-C_6)$-alkoxy;

A is a bond or a divalent unit from the group consisting of

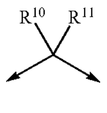

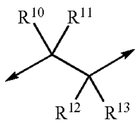

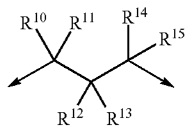

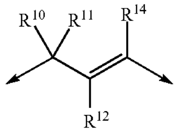

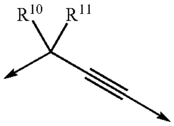

and

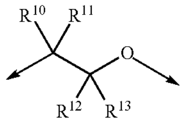

$R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or $(C_1-C_6)$-alkyl, $(C_3-C_5)$-cycloalkyl, $(C_2-C_6)$-alkenyl, $(C_2-C_6)$-alkynyl, each of which is substituted by m radicals from the group consisting of fluorine, chlorine, bromine, iodine, hydroxy and cyano or $(C_1-C_6)$-alkoxy, $(C_3-C_6)$-cycloalkoxy, $(C_2-C_6)$-alkenyloxy or $(C_2-C_6)$-alkynyloxy, each of which is substituted by m radicals from the group consisting of fluorine, chlorine, bromine, iodine, cyano and ($C_1$-$C_2$)-alkoxy;

Y is oxygen or sulfur;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl substituted by in each case m radicals from the group consisting of fluorine, chlorine, bromine, iodine, cyano, hydroxy, $OR^7$, $X^1$, $OX^1$, $NHX^1$, $S(O)_nR^5$, $SO_2NR^6R^7$, $SO_2NR^6R^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6){=}NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements from the group consisting of $NR^7$ and $NCOR^7$ as ring atoms, where a carbon atom carries p oxo groups;

$X^1$ is a 5- or 6-membered saturated, partially unsaturated, fully unsaturated or aromatic ring which is constructed of r carbon atoms, s nitrogen atoms, n sulphur atoms and n oxygen atoms and which is substituted by n radicals from the group consisting of $R^6$, $R^{6a}$, $R^8$ and $R^9$;

$X^2$, $X^4$ and $X^6$ independently of one another are each hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl, each of which is substituted by m radicals from the group consisting of fluorine, chlorine, bromine, iodine, cyano and ($C_1$-$C_4$)-alkoxy;

$X^3$ is fluorine, chlorine, bromine, iodine, hydroxy, cyano, nitro, $SF_5$, $CONR^8SO_2R^5$, $CONR^6R^8$, $COR^6$, $CO_2R^8$, $CONR^6R^8$, $C(R^6){=}NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals from the group consisting of fluorine, chlorine, bromine, iodine, hydroxy and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals from the group consisting of fluorine, chlorine, bromine, iodine, cyano and ($C_1$-$C_2$)-alkoxy, $X^5$ is hydrogen or $X^3$;

$R^5$ is ($C_1$-$C_6$)-alkyl or ($C_3$-$C_6$)-cycloalkyl, each of which is substituted by m radicals from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or ($C_1$-$C_6$)-alkoxy, ($C_3$-$C_6$)-alkenyloxy or ($C_3$-$C_6$)-alkynyloxy, each of which is substituted by m radicals from the group consisting of fluorine, chlorine, bromine, cyano and ($C_1$-$C_2$)-alkoxy;

$R^7$ is hydrogen or ($C_1$-$C_6$)-alkyl, ($C_3$-$C_6$)-cycloalkyl, ($C_2$-$C_4$)-alkenyl or ($C_2$-$C_4$)-alkynyl, each of which is substituted by m radicals from the group consisting of fluorine, chlorine, bromine, cyano and ($C_1$-$C_2$)-alkoxy;

$R^8$ is $R^7$;

$R^9$ is ($C_1$-$C_3$)-alkyl or ($C_1$-$C_3$)-alkoxy;

k is 3, 4, 5 or 6;

m is 0, 1, 2, 3, 4 or 5;

n is 0, 1 or 2;

p is 0 or 1;

q is 3, 4 or 5;

r is 1, 2, 3, 4 or 5;

s is 0, 1, 2, 3 or 4;

with the proviso that $X^3$ and $X^4$ are not both substituted or unsubstituted alkoxy.

DETAILED DESCRIPTION OF A PREFERRED EMBODIMENT

Alkyl means saturated straight-chain or branched hydrocarbon radicals having the number of carbon atoms stated in each case, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl means straight-chain or branched alkyl groups where some or all of the hydrogen atoms in these groups may be replaced by halogen atoms, for example $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkenyl means unsaturated straight-chain or branched hydrocarbon radicals having the number of carbon atoms stated in each case and one double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl means straight-chain or branched hydrocarbon radicals having the number of carbon atoms stated in each case and a triple bond in any position, for example $C_2$-$C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Alkoxy means saturated, straight-chain or branched alkoxy radicals having the number of carbon atoms stated in each case, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-di-methylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy means straight-chain or branched alkoxy radicals having the number of carbon atoms stated in each case, where in these groups some or all of the hydrogen atoms may be replaced by halogen atoms as mentioned above, for example $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2-difluoroethoxy, 2,2-dichloro-2-fluoroethoxy, 2,2,2-trichloroethoxy, pentafluoroethoxy and 1,1,1-trifluoroprop-2-oxy.

Depending on the nature and the attachment of the substituents, the compounds of the formula (I) may be present as stereoisomers. When, for example, one or more asymmetrically substituted carbon atoms and/or sulfoxides are present, enantiomers and diastereomers may occur. Stereoisomers can be obtained from the mixtures obtained in the preparation by customary separation methods, for example by chromatographic separation processes. It is equally possible to selectively prepare stereoisomers by using stereoselective reactions using optically active starting materials and/or auxiliaries. The invention also relates to all stereoisomers and mixtures thereof which are encompassed by the formula (I) but not defined specifically. For the sake of simplicity, however, compounds of the formula (I) are always referred to below, although both the pure compounds and also, if appropriate, mixtures having different proportions of isomeric compounds are meant.

Depending on the nature of the substituents defined above, the compounds of the formula (I) have acidic properties and can form salts, if appropriate also inner salts, or adducts with inorganic or organic bases or with metal ions.

If the compounds of the formula (I) carry hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

When a group is polysubstituted by radicals, this means that this group is substituted by one or more identical or different radicals from those mentioned.

In all the formulae specified hereinafter, the substituents and symbols have the same definition as in formula (I), unless defined differently. Arrows in a chemical formula indicate the points of attachment to the remainder of the molecule.

Preference is given to 3-phenylisoxazoline-5-carboxamides and 3-phenylisoxazoline-5-thioamides of the formula (I) in which $R^1$ and $R^2$ independently of one another are each hydrogen, fluorine, chlorine, bromine, iodine, cyano, or ($C_1$-$C_4$)-alkyl or ($C_1$-$C_4$)-alkoxy substituted by in each case m radicals from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, ($C_1$-$C_3$)-alkylcarbonyloxy or $S(O)_nR^5$, or ($C_1$-$C_6$)-alkyl, ($C_3$-$C_6$)-cycloalkyl, ($C_2$-$C_6$)-alkenyl or ($C_2$-$C_6$)-alkynyl substituted by in each case m radicals from the group consisting of fluorine, chlorine, bromine, iodine, cyano, ($C_1$-$C_4$)-alkoxy and hydroxy, or ($C_1$-$C_6$)-alkylcarbonyl, ($C_2$-$C_6$)-alkenylcarbonyl or ($C_3$-$C_6$)-cycloalkylcarbonyl substituted by in each case m radicals from the group consisting of fluorine, chlorine, bromine, iodine, cyano and ($C_1$-$C_6$)-alkoxy;

$R^4$ is hydrogen, cyano, or ($C_1$-$C_8$)-alkyl or ($C_3$-$C_8$)-cycloalkyl substituted by in each case m radicals from the group consisting of fluorine, chlorine, bromine, iodine, cyano, hydroxy and ($C_1$-$C_6$)-alkoxy;

A is a bond or a divalent unit from the group consisting of

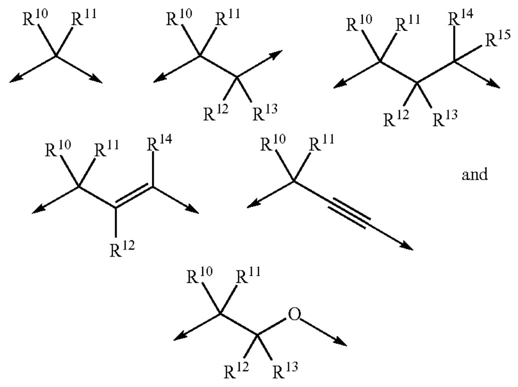

and $R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals from the group consisting of fluorine, chlorine, bromine, iodine, hydroxy and cyano;

or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals from the group consisting of fluorine, chlorine, bromine, iodine, cyano and ($C_1$-$C_2$)-alkoxy, Y is oxygen or sulfur;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl substituted by in each case m radicals from the group consisting of fluorine, chlorine, bromine, iodine, cyano, hydroxy, $OR^7$, $X^1$, $OX^1$, $NHX^1$, $S(O)_nR^5$, $SO_2NR^6R^7$, $SO_2NR^6R^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6){=}NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements from the group consisting of $NR^7$ and $NCOR^7$ as ring atoms, where a carbon atom carries p oxo groups;

$X^1$ is a ring, substituted by n radicals from the group consisting of $R^6$, $R^{6a}$, $R^8$ and $R^9$, from the group consisting of

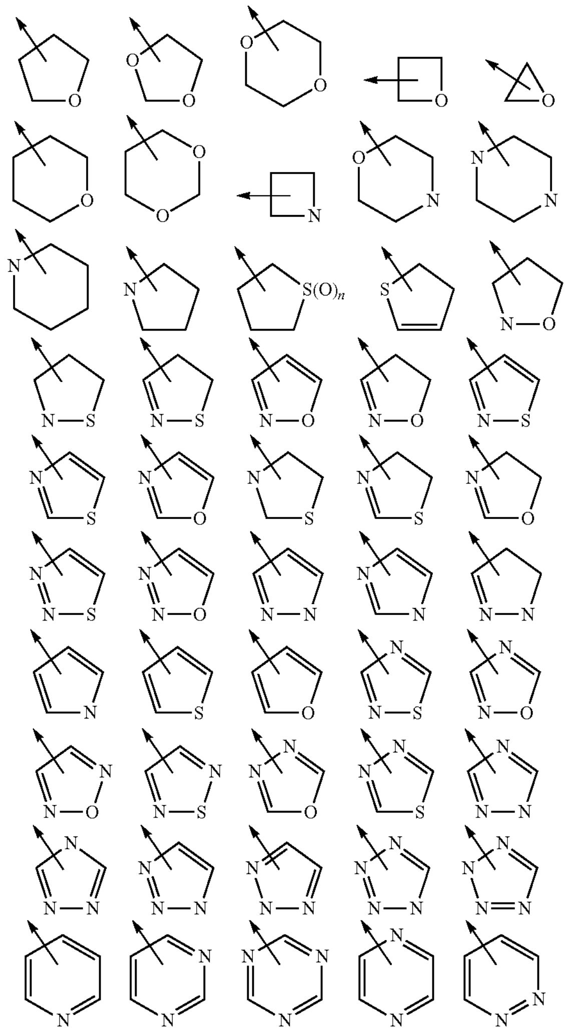

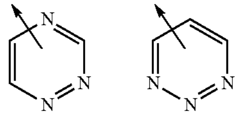

and

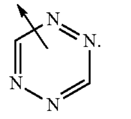

$X^2$, $X^4$ and $X^6$ independently of one another are each hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl, each of which is substituted by m radicals from the group consisting of fluorine, chlorine, bromine, iodine, cyano and $(C_1-C_4)$-alkoxy;

$X^3$ is fluorine, chlorine, bromine, iodine, hydroxy, cyano, nitro, $SF_5$, $CONR^8SO_2R^5$, $CONR^6R^8$, $COR^6$, $CO_2R^8$, $CONR^6R^8$, $C(R^6){=}NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl, each of which is substituted by m radicals from the group consisting of fluorine, chlorine, bromine, iodine, hydroxy and cyano, or $(C_1-C_6)$-alkoxy, $(C_3-C_6)$-cycloalkoxy, $(C_2-C_6)$-alkenyloxy or $(C_2-C_6)$-alkynyloxy, each of which is substituted by m radicals from the group consisting of fluorine, chlorine, bromine, iodine, cyano and $(C_1-C_2)$-alkoxy, $X^5$ is hydrogen or $X^3$;

$R^5$ is $(C_1-C_6)$-alkyl or $(C_3-C_6)$-cycloalkyl, each of which is substituted by m radicals from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or $(C_1-C_6)$-alkoxy, $(C_2-C_6)$-alkenyloxy or $(C_2-C_6)$-alkynyloxy, each of which is substituted by m radicals from the group consisting of fluorine, chlorine, bromine, cyano and $(C_1-C_2)$-alkoxy;

$R^7$ is hydrogen or $(C_1-C_6)$-alkyl, $(C_3-C_6)$-cycloalkyl, $(C_2-C_4)$-alkenyl or $(C_2-C_4)$-alkynyl, each of which is substituted by m radicals from the group consisting of fluorine, chlorine, bromine, cyano and $(C_1-C_2)$-alkoxy;

$R^8$ is $R^7$;

$R^9$ is $(C_1-C_3)$-alkyl or $(C_1-C_3)$-alkoxy;

k is 3, 4, 5 or 6;

m is 0, 1, 2, 3, 4 or 5;

n is 0, 1 or 2;

p is 0 or 1;

q is 3, 4 or 5;

with the proviso that $X^3$ and $X^4$ are not both substituted or unsubstituted alkoxy.

Particular preference is given to 3-phenylisoxazoline-5-carboxamides and 3-phenylisoxazoline-5-thioamides of the formula (I) in which $R^1$ and $R^2$ independently of one another are each hydrogen, fluorine, chlorine, bromine, iodine, cyano, or $(C_1-C_4)$-alkyl substituted by in each case m radicals from the group consisting of fluorine, chlorine, bromine, iodine and cyano, $R^3$ is fluorine, chlorine or cyano, or $(C_1-C_6)$-alkyl, $(C_3-C_6)$-cycloalkyl, $(C_2-C_6)$-alkenyl or $(C_2-C_6)$-alkynyl, each of which is substituted by m radicals from the group consisting of fluorine and chlorine, or $(C_1-C_6)$-alkylcarbonyl which is substituted by m radicals from the group consisting of fluorine and chlorine;

A is a bond or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, C(iPr)$CH_3$, $CH(CH_2$iPr)$CH_2$, $CH_2CH{=}CH$, $C(CH_3)_2C{\equiv}C$, $CH(CF_3)CH_2$, $CH(CH_3)CH_2O$, $CH_2CH_2O$, CH(cPr)$CH_2O$, $CH(CH_2OCH_3)$, $CH(CH_2CH_2SCH_3)$, CH(COOH), $CH(COOCH_3)$, CH(COOH)$CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

$R^4$ is hydrogen or $(C_1-C_8)$-alkyl;

Y is oxygen or sulfur;

X is hydrogen, cyano, hydroxy, $X^1$, or $(C_1-C_{12})$-alkyl, $(C_3-C_8)$-cycloalkyl, $(C_2-C_{12})$-alkenyl or $(C_2-C_{12})$-alkynyl, each of which is substituted by m radicals from the group consisting of fluorine, chlorine, cyano, hydroxy, $OR^7$, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring, substituted by n radicals from the group consisting of $R^6$, $R^{6a}$, $R^8$ and $R^9$, from the group consisting of

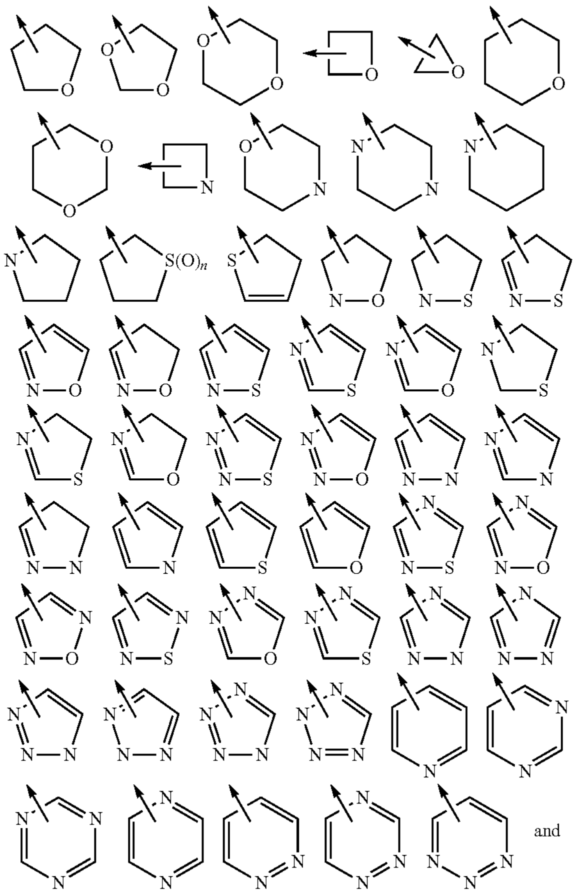

and

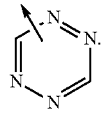

$X^2$, $X^4$ and $X^6$ independently of one another are each hydrogen, fluorine or chlorine, or $(C_1-C_4)$-alkyl or $(C_1-C_4)$-alkoxy, each of which is substituted by m radicals from the group consisting of fluorine, chlorine, cyano and $(C_1-C_4)$-alkoxy;

$X^3$ is fluorine, chlorine, bromine, cyano, or $(C_1-C_6)$-alkyl which is in each case substituted by m radicals from the group consisting of fluorine and chlorine;

or $(C_1-C_6)$-alkoxy which is substituted by m radicals from the group consisting of fluorine and chlorine;

$X^5$ is hydrogen or $X^3$;

$R^5$ is methyl or ethyl;

$R^6$ is hydrogen or $R^5$;

$R^{6a}$ is fluorine, chlorine, bromine, iodine, cyano, hydroxy, $S(O)_nR^5$ or $(C_1-C_6)$-alkoxy, $(C_2-C_6)$-alkenyloxy or $(C_2-C_6)$-alkynyloxy, each of which is substituted by m radicals from the group consisting of fluorine, chlorine, bromine, cyano and $(C_1-C_2)$-alkoxy;

$R^7$ is hydrogen or $(C_1-C_6)$-alkyl which is substituted by in each case m radicals from the group consisting of fluorine and chlorine;

$R^8$ is $R^7$;

$R^9$ is $(C_1-C_3)$-alkoxy;

m is 0, 1, 2 or 3;

n is 0, 1 or 2;

with the proviso that $X^3$ and $X^4$ are not both substituted or unsubstituted alkoxy.

The compounds described in the documents mentioned above not only have pharmacological action but also, surprisingly, herbicidal action in the case of the 3-phenylisoxazoline-5-carboxamides and 3-phenylisoxazoline-5-thioamides. Accordingly, the present invention furthermore provides the use of 3-phenylisoxazoline-5-carboxamides and 3-phenylisoxazoline-5-thioamides of the formula (Ia) as herbicides.

(Ia)

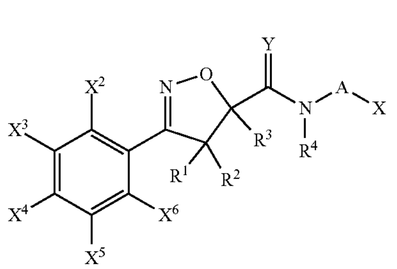

In formula (Ia), the radicals and indices have the following meanings:

$R^1$ and $R^2$ independently of one another are each hydrogen, fluorine, chlorine, bromine, iodine, cyano, or $(C_1-C_4)$-alkyl or $(C_1-C_4)$-alkoxy substituted by in each case m radicals from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, $(C_1-C_3)$-alkylcarbonyloxy or $S(O)_nR^5$, or $(C_1-C_6)$-alkyl, $(C_3-C_6)$-cycloalkyl, $(C_2-C_6)$-alkenyl or $(C_2-C_6)$-alkynyl substituted by in each case m radicals from the group consisting of fluorine, chlorine, bromine, iodine, cyano, $(C_1-C_4)$-alkoxy and hydroxy, or $(C_1-C_6)$-alkylcarbonyl, $(C_2-C_6)$-alkenylcarbonyl or $(C_3-C_6)$-cycloalkylcarbonyl substituted by in each case m radicals from the group consisting of fluorine, chlorine, bromine, iodine, cyano and $(C_1-C_6)$-alkoxy;

$R^4$ is hydrogen, cyano, hydroxy, or $(C_1-C_8)$-alkyl or $(C_3-C_8)$-cycloalkyl substituted by in each case m radicals from the group consisting of fluorine, chlorine, bromine, iodine, cyano, hydroxy and $(C_1-C_6)$-alkoxy;

A is a bond or a divalent unit from the group consisting of

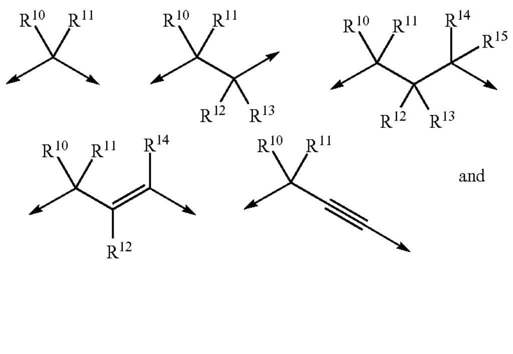

and

-continued

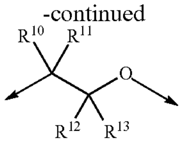

$R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals from the group consisting of fluorine, chlorine, bromine, iodine, hydroxy and cyano;

or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals from the group consisting of fluorine, chlorine, bromine, iodine, cyano and ($C_1$-$C_2$)-alkoxy, Y is oxygen or sulfur;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl substituted by in each case m radicals from the group consisting of fluorine, chlorine, bromine, iodine, cyano, hydroxy, $OR^7$, $X^1$, $OX^1$, $NHX^1$, $S(O)_nR^5$, $SO_2NR^6R^7$, $SO_2NR^6R^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6){=}NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements from the group consisting of $NR^7$ and $NCOR^7$ as ring atoms, where a carbon atom carries p oxo groups;

$X^1$ is a 5- or 6-membered saturated, partially unsaturated, fully unsaturated or aromatic ring which is constructed of r carbon atoms, s nitrogen atoms, n sulphur atoms and n oxygen atoms and which is substituted by n radicals from the group consisting of $R^6$, $R^{6a}$, $R^8$ and $R^9$;

or phenyl which is substituted by n radicals from the group consisting of $R^6$, $R^8$ and $R^9$;

$X^2$, $X^4$ and $X^6$ independently of one another are each hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl, each of which is substituted by m radicals from the group consisting of fluorine, chlorine, bromine, iodine, cyano and ($C_1$-$C_4$)-alkoxy;

$X^3$ is hydrogen, fluorine, chlorine, bromine, iodine, hydroxy, cyano, nitro, $SF_5$, $CONR^8SO_2R^5$, $CONR^6R^8$, $COR^6$, $CO_2R^8$, $CONR^6R^8$, $C(R^6){=}NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals from the group consisting of fluorine, chlorine, bromine, iodine, hydroxy and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals from the group consisting of fluorine, chlorine, bromine, iodine, cyano and ($C_1$-$C_2$)-alkoxy, $X^5$ is hydrogen or $X^3$;

$R^5$ is ($C_1$-$C_6$)-alkyl or ($C_3$-$C_6$)-cycloalkyl, each of which is substituted by m radicals from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or ($C_1$-$C_6$)-alkoxy, ($C_2$-$C_6$)-alkenyloxy or ($C_2$-$C_6$)-alkynyloxy, each of which is substituted by m radicals from the group consisting of fluorine, chlorine, bromine, cyano and ($C_1$-$C_2$)-alkoxy;

$R^7$ is hydrogen or ($C_1$-$C_6$)-alkyl, ($C_3$-$C_6$)-cycloalkyl, ($C_2$-$C_4$)-alkenyl or ($C_2$-$C_4$)-alkynyl, each of which is substituted by m radicals from the group consisting of fluorine, chlorine, bromine, cyano and ($C_1$-$C_2$)-alkoxy;

$R^8$ is $R^7$;

$R^9$ is ($C_1$-$C_3$)-alkyl or ($C_1$-$C_3$)-alkoxy;

k is 3, 4, 5 or 6;

m is 0, 1, 2, 3, 4 or 5;

n is 0, 1 or 2;

p is 0 or 1;

q is 3, 4 or 5;

r is 1, 2, 3, 4 or 5;

s is 0, 1, 2, 3 or 4.

Preferably suitable as herbicides are 3-phenylisoxazoline-5-carboxamides and 3-phenylisoxazoline-5-thioamides of the formula (Ia) in which $R^1$ and $R^2$ independently of one another are each hydrogen, fluorine, chlorine, bromine, iodine, cyano, or ($C_1$-$C_4$)-alkyl or ($C_1$-$C_4$)-alkoxy substituted by in each case m radicals from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, ($C_1$-$C_3$)-alkylcarbonyloxy or $S(O)_nR^5$, or ($C_1$-$C_6$)-alkyl, ($C_3$-$C_6$)-cycloalkyl, ($C_2$-$C_6$)-alkenyl or ($C_2$-$C_6$)-alkynyl substituted by in each case m radicals from the group consisting of fluorine, chlorine, bromine, iodine, cyano, ($C_1$-$C_4$)-alkoxy and hydroxy, or ($C_1$-$C_6$)-alkylcarbonyl, ($C_2$-$C_6$)-alkenylcarbonyl or ($C_3$-$C_6$)-cycloalkylcarbonyl substituted by in each case m radicals from the group consisting of fluorine, chlorine, bromine, iodine, cyano and ($C_1$-$C_6$)-alkoxy;

$R^4$ is hydrogen, cyano, hydroxy, or ($C_1$-$C_8$)-alkyl or ($C_3$-$C_8$)-cycloalkyl substituted by in each case m radicals from the group consisting of fluorine, chlorine, bromine, iodine, cyano, hydroxy and ($C_1$-$C_6$)-alkoxy;

A is a bond or a divalent unit from the group consisting of

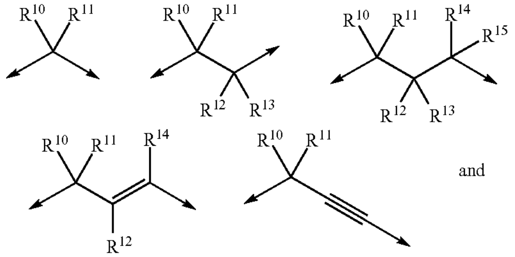

and

-continued

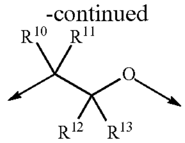

$R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or $(C_1-C_6)$-alkyl, $(C_3-C_5)$-cycloalkyl, $(C_2-C_6)$-alkenyl, $(C_2-C_6)$-alkynyl, each of which is substituted by m radicals from the group consisting of fluorine, chlorine, bromine, iodine, hydroxy and cyano;

or $(C_1-C_6)$-alkoxy, $(C_3-C_6)$-cycloalkoxy, $(C_2-C_6)$-alkenyloxy or $(C_2-C_6)$-alkynyloxy, each of which is substituted by m radicals from the group consisting of fluorine, chlorine, bromine, iodine, cyano and $(C_1-C_2)$-alkoxy, Y is oxygen or sulfur;

X is hydrogen, cyano, hydroxy, $X^1$, or $(C_1-C_{12})$-alkyl, $(C_3-C_8)$-cycloalkyl, $(C_2-C_{12})$-alkenyl or $(C_2-C_{12})$-alkynyl substituted by in each case m radicals from the group consisting of fluorine, chlorine, bromine, iodine, cyano, hydroxy, $X^1$, $OX^1$, $NHX^1$, $S(O)_nR^5$, $SO_2NR^6R^7$, $SO_2NR^6R^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)$=$NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements from the group consisting of $NR^7$ and $NCOR^7$ as ring atoms, where a carbon atom carries p oxo groups;

$X^1$ is a ring, substituted by n radicals from the group consisting of $R^6$, $R^{6a}$, $R^8$ and $R^9$, from the group consisting of

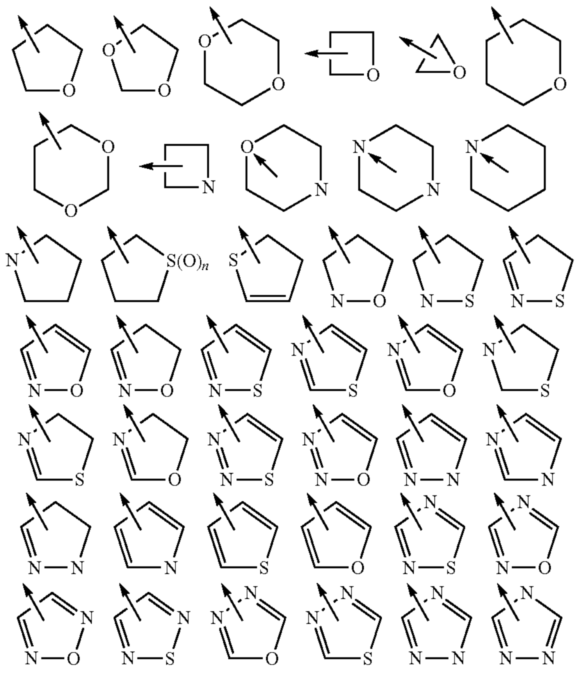

-continued

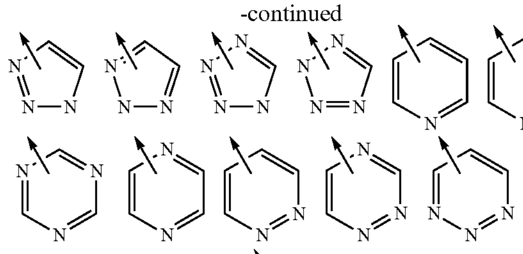

and

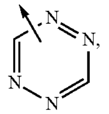

or phenyl which is substituted by n radicals from the group consisting of $R^6$, $R^8$ and $R^9$;

$X^2$, $X^4$ and $X^6$ independently of one another are each hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl, each of which is substituted by m radicals from the group consisting of fluorine, chlorine, bromine, iodine, cyano and $(C_1-C_4)$-alkoxy;

$X^3$ is hydrogen, fluorine, chlorine, bromine, iodine, hydroxy, cyano, nitro, $SF_5$, $CONR^8SO_2R^5$, $CONR^6R^8$, $COR^6$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl, each of which is substituted by m radicals from the group consisting of fluorine, chlorine, bromine, iodine, hydroxy and cyano, or $(C_1-C_6)$-alkoxy, $(C_3-C_6)$-cycloalkoxy, $(C_2-C_6)$-alkenyloxy or $(C_2-C_6)$-alkynyloxy, each of which is substituted by m radicals from the group consisting of fluorine, chlorine, bromine, iodine, cyano and $(C_1-C_2)$-alkoxy, $X^5$ is hydrogen or $X^3$;

$R^5$ is $(C_1-C_6)$-alkyl or $(C_3-C_6)$-cycloalkyl, each of which is substituted by m radicals from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or $(C_1-C_6)$-alkoxy, $(C_2-C_6)$-alkenyloxy or $(C_2-C_6)$-alkynyloxy, each of which is substituted by m radicals from the group consisting of fluorine, chlorine, bromine, cyano and $(C_1-C_2)$-alkoxy;

$R^7$ is hydrogen or $(C_1-C_6)$-alkyl, $(C_3-C_6)$-cycloalkyl, $(C_2-C_4)$-alkenyl or $(C_2-C_4)$-alkynyl, each of which is substituted by m radicals from the group consisting of fluorine, chlorine, bromine, cyano and $(C_1-C_2)$-alkoxy;

$R^8$ is $R^7$;

$R^9$ is $(C_1-C_3)$-alkyl or $(C_1-C_3)$-alkoxy;

k is 3, 4, 5 or 6;

m is 0, 1, 2, 3, 4 or 5;

n is 0, 1 or 2;

p is 0 or 1;

q is 3, 4 or 5.

Particularly preferably suitable as herbicides are 3-phenylisoxazoline-5-carboxamides and 3-phenylisoxazoline-5-thioamides of the formula (Ia) in which $R^1$ and $R^2$ independently of one another are each hydrogen, fluorine, chlorine, bromine, iodine, cyano, or $(C_1-C_4)$-alkyl substituted by in each case m radicals from the group consisting of fluorine, chlorine, bromine, iodine and cyano, $R^3$ is fluorine, chlorine or cyano, or $(C_1\text{-}C_6)$-alkyl, $(C_3\text{-}C_6)$-cycloalkyl, $(C_2\text{-}C_6)$-alkenyl or $(C_2\text{-}C_6)$-alkynyl, each of which is substituted by m radicals from the group consisting of fluorine and chlorine, or $(C_1\text{-}C_6)$-alkylcarbonyl which is substituted by m radicals from the group consisting of fluorine and chlorine;

$R^4$ is hydrogen, hydroxy or $(C_1\text{-}C_8)$-alkyl;

A is a bond or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH{=}CH$, $C(CH_3)_2C{\equiv}C$, $CH(CF_3)CH_2$, $CH(CH_3)CH_2O$, $CH_2CH_2O$, $CH(cPr)CH_2O$, $CH(CH_2OCH_3)$, $CH(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

Y is oxygen or sulfur;

X is hydrogen, cyano, hydroxy, $X^1$, or $(C_1\text{-}C_{12})$-alkyl, $(C_3\text{-}C_8)$-cycloalkyl, $(C_2\text{-}C_{12})$-alkenyl or $(C_2\text{-}C_{12})$-alkynyl, each of which is substituted by m radicals from the group consisting of fluorine, chlorine, cyano, hydroxy, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring, substituted by n radicals from the group consisting of $R^6$, $R^{6a}$, $R^8$ and $R^9$, from the group consisting of

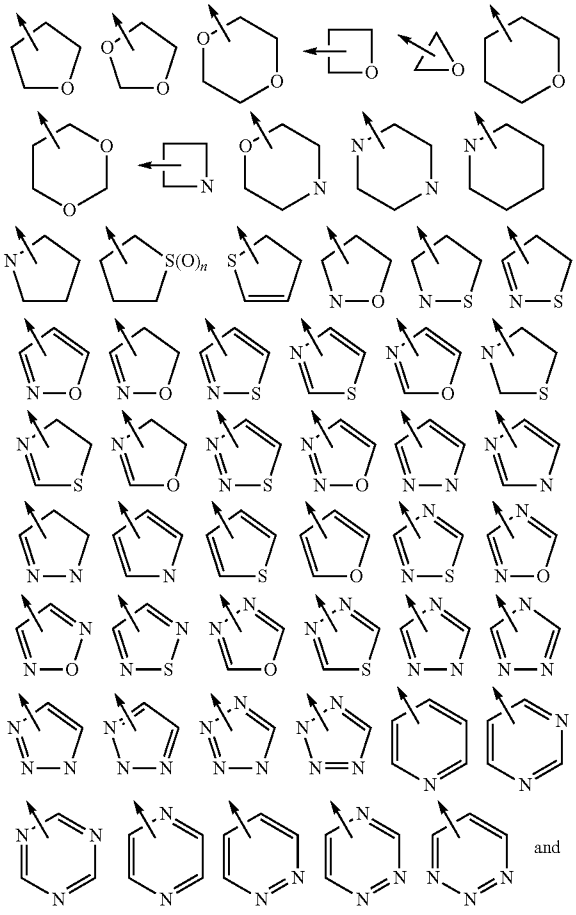

and

-continued

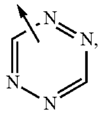

or phenyl which is substituted by n radicals from the group consisting of $R^6$, $R^8$ and $R^9$;

$X^2$, $X^4$ and $X^6$ independently of one another are each hydrogen, fluorine or chlorine, or $(C_1\text{-}C_4)$-alkyl or $(C_1\text{-}C_4)$-alkoxy, each of which is substituted by m radicals from the group consisting of fluorine, chlorine, cyano and $(C_1\text{-}C_4)$-alkoxy;

$X^3$ is hydrogen, fluorine, chlorine, bromine, cyano, or $(C_1\text{-}C_6)$-alkyl which is in each case substituted by m radicals from the group consisting of fluorine and chlorine;

or $(C_1\text{-}C_6)$-alkoxy which is substituted by m radicals from the group consisting of fluorine and chlorine;

$X^5$ is hydrogen or $X^3$;

$R^5$ is methyl or ethyl;

$R^6$ is hydrogen or $R^5$;

$R^{6a}$ is fluorine, chlorine, bromine, iodine, cyano, hydroxy, $S(O)_nR^5$ or $(C_1\text{-}C_6)$-alkoxy, $(C_2\text{-}C_6)$-alkenyloxy or $(C_2\text{-}C_6)$-alkynyloxy, each of which is substituted by m radicals from the group consisting of fluorine, chlorine, bromine, cyano and $(C_1\text{-}C_2)$-alkoxy;

$R^7$ is hydrogen or $(C_1\text{-}C_6)$-alkyl which is substituted by in each case m radicals from the group consisting of fluorine and chlorine;

$R^8$ is $R^7$;

$R^9$ is $(C_1\text{-}C_3)$-alkoxy;

m is 0, 1, 2 or 3;

n is 0, 1 or 2.

The compounds according to the invention can be prepared by reactions known per se to the person skilled in the art by the reaction sequence shown in scheme 1, for example.

Scheme 1:

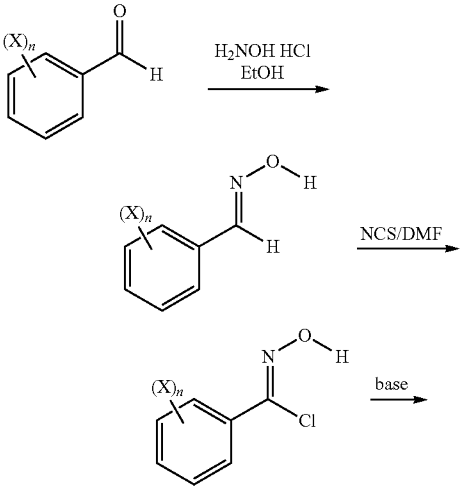

-continued

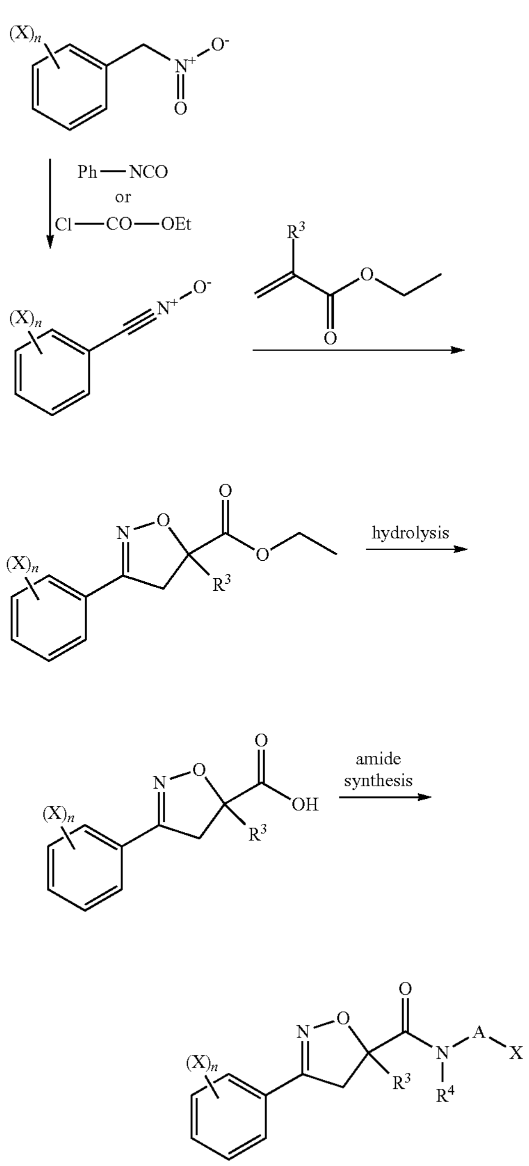

In scheme 1 and in the schemes below, $(X)_n$ denotes the substituents $X^2$, $X^3$, $X^4$, $X^5$ and $X^6$. Such 1,3-dipolar cycloadditions of nitrile oxides with suitable dipolarophiles are described, for example, in Reviews: 1,3 dipolar Cycloaddition Chemistry, Padwa, ed. Wiley, New York, 1984; Kanemasa and Tsuge, Heterocycles 1990, 30, 719.

Compounds according to the invention which are substituted in the 4- and 5-positions of the isoxazoline ring system can also be prepared by 1,3-dipolar cycloaddition by using suitable 1,2-disubstituted olefins as dipolarophiles. In most cases, this reaction affords diastereomer mixtures which can be separated by column chromatography. Optically active isoxazolines can be obtained by chiral HPLC of suitable precursors or end products and also by enantioselective reactions such as, for example, enzymatic ester or amide cleavage or by using chiral auxiliaries at the dipolarophile, as described by Olssen (J. Org. Chem. 1988, 53, 2468).

Compounds according to the invention can also be prepared by using suitably substituted alkenes which are commercially available as starting material. Thus, suitably substituted acrylic esters or acrylamides may be used.

Scheme 2:

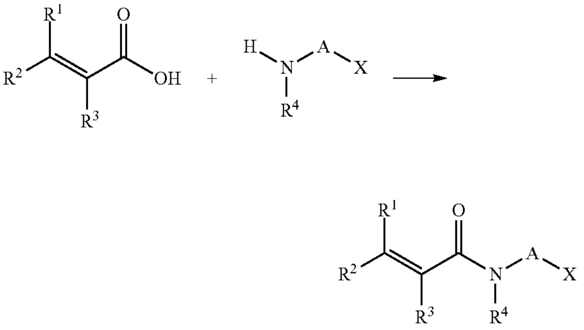

Carbodiimides such as EDCI, for example, are suitable for activating the acrylic acid (Chen, F. M. F.; Benoiton, N. L. Synthesis 1979, 709). For the preparation of acrylamides, see U.S. Pat. No. 2,521,902, JP60112746, J. of Polymer Science 1979, 17 (6), 1655. Suitably substituted acrylamides can be reacted in a 1,3-cycloaddition reaction with nitrile oxides to give the compounds according to the invention.

Scheme 3:

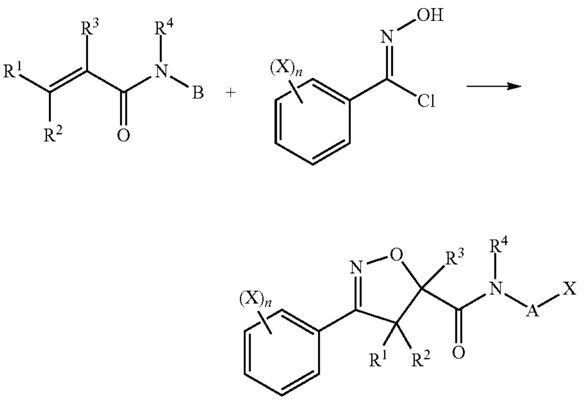

Transformations of the functional groups $R^3$ can be carried out both at the stage of the alkenes and at the stage of the isoxazolines. Scheme 4 describes the access to various $R^3$-substituted isoxazolines.

Scheme 4:

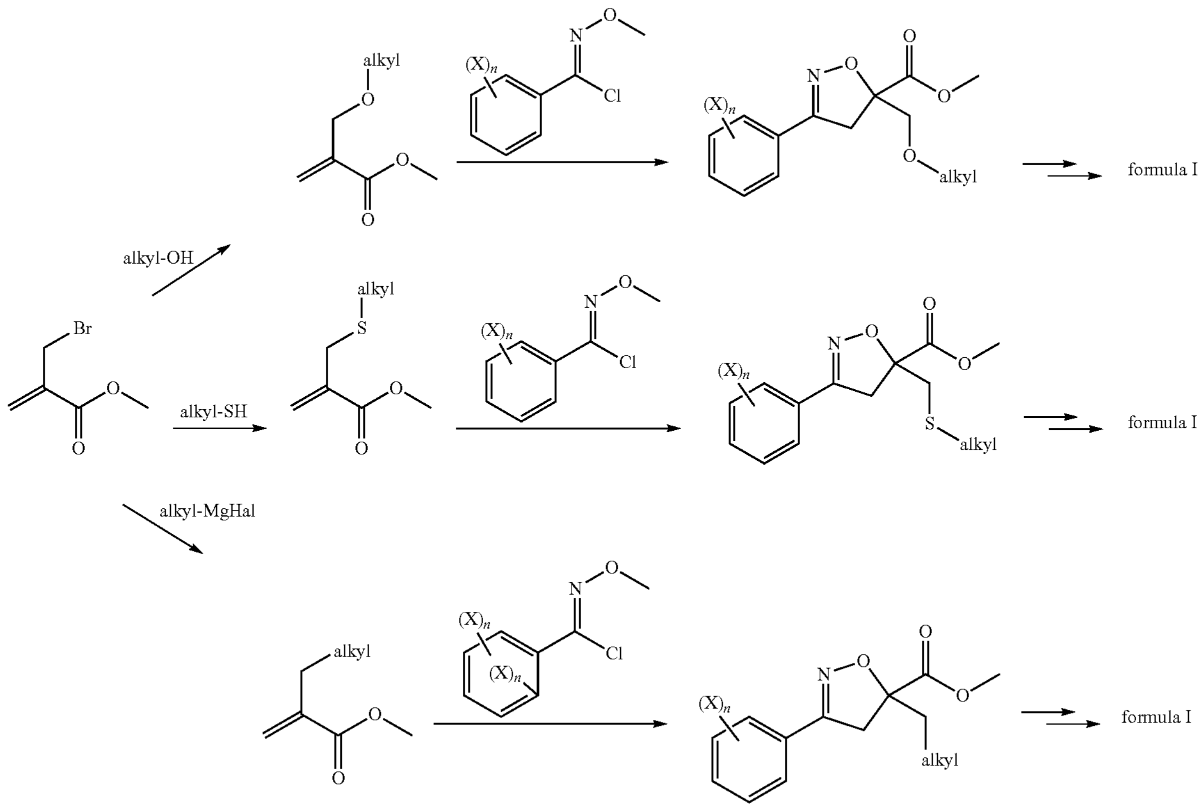

Under basic conditions, methyl 2-bromomethylacrylate which is commercially available can be reacted with alcohols to give methyl 2-alkoxymethylacrylates, which then react with chloroximes via the nitrile oxides to give 3-phenyl-5-methoxycarbonylisoxazolines. In an analogous manner, it is possible to obtain thioethers which can then be oxidized to give the corresponding sulfoxides or sulfones. Various 2-alkylacrylic esters can be prepared starting from methyl 2-bromomethylacrylates, for example by reaction with organometallic reagents. Such methods are described, for example, in Metzger, Albrecht; Piller, Fabian M.; Knochel, Paul; Chemical Communications, 2008, 44, pp. 5824-5826, and they are also known from WO2006/33551.

Compounds according to the invention having a cyano group as substituent $R^3$ can be constructed analogously using suitable cyanoacrylates such as, for example, ethyl 2-cyanoacrylate. Suitably substituted crotonic esters can be employed for preparing $R^2$- and $R^3$-disubstituted isoxazolines. Some crotonic esters are commercially available, and they can also be prepared from ethyl 3-bromoacrylate, for example, by nucleophilic substitution reactions. Such methods are described, for example, in Birkofer, L.; Hempel, K. Chem. Ber., 1963, 96, 1373; Tanoury, G. J.; Chen, M.; Dong, Y.; Forslund, R. E.; Magdziak, D.; Organic Letters, 2008, 10, 185.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the formula (I) and salts thereof can be prepared completely or partially by solid-phase supported methods. For this purpose, individual intermediates or all intermediates in the synthesis or a synthesis adapted for the corresponding procedure are bound to a synthesis resin. Solid-phase supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Either on a solid phase or in the liquid phase, the performance of single or multiple synthesis steps can be supported by the use of microwave technology. The technical literature describes a number of experimental protocols, for example Microwaves in Organic and Medicinal Chemistry (editors: C. O. Kappe and A. Stadler), Wiley, 2005.

The preparation by the process described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), collectively referred to hereinafter as "inventive compounds", have excellent herbicidal efficacy against a broad spectrum of economically important monocotyledonous and dicotyledonous annual harmful plants. The active ingredients also have good control over perennial weed plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active ingredients are applied post-emergence to the green parts of the plants, there is stoppage of growth after the treatment, and the harmful plants remain at the growth stage of the time of application, or they die completely after a certain time, such that competition by the weeds, which is harmful to the crop plants, is thus eliminated very early and in a lasting manner.

Although the inventive compounds have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, especially *Zea* and *Triticum*, are damaged only to an insignificant extent, if at all, depending on the structure of the respective inventive compound and the application rate thereof. For these reasons, the present compounds are very suitable for selective control of unwanted plant growth in plant crops such as agriculturally useful plants or ornamentals.

In addition, the inventive compounds (depending on their particular structure and the application rate deployed) have outstanding growth-regulating properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting vegetative growth plays a major role for many monocotyledonous and dicotyledonous crops, since, for example, this can reduce or completely prevent lodging.

Owing to their herbicidal and plant growth-regulating properties, the active compounds can also be used to control harmful plants in crops of known genetically modified plants or of those yet to be developed. In general, the transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other special properties relate, for example, to the harvested material with regard to quantity, quality, storability, composition and specific constituents. For instance, there are known transgenic plants with an elevated starch content or altered starch quality, or with a different fatty acid composition in the harvested material. Further special properties may be tolerance or resistance to abiotic stress factors, for example heat, cold, drought, salinity and ultraviolet radiation.

Preference is given to the use of the compounds of the formula (I) according to the invention or salts thereof in economically important transgenic crops of useful plants and ornamental plants, for example of cereals such as wheat, barley, rye, oats, sorghum and millet, rice, cassava and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to existing plants consist, for example, in traditional breeding methods and the generation of mutants. Alternatively, novel plants with altered properties can be generated with the aid of recombinant methods (see, for example, EP 0221044, EP 0131624). Described were, for example, several cases of genetic modifications of crop plants for the purpose of modifying the starch synthesized in the plants (for example WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soybean with the tradename or the designation Optimum™ GAT™ (glyphosate ALS tolerant).

- transgenic crop plants, for example cotton, which are capable of producing *Bacillus thuringiensis* toxins (Bt toxins), which make the plants resistant to certain pests (EP 0142924 A, EP 0193259 A),
- transgenic crop plants having a modified fatty acid composition (WO 91/013972 A),
- genetically modified crop plants with novel constituents or secondary metabolites, for example novel phytoalexins, which bring about an increased disease resistance (EP 0309862 A, EP 0464461 A),
- genetically modified plants with reduced photorespiration which feature higher yields and higher stress tolerance (EP 0305398 A),
- transgenic crop plants which produce pharmaceutically or diagnostically important proteins ("molecular pharming"),
- transgenic crop plants which are notable for higher yields or better quality,
- transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

To carry out such recombinant manipulations, nucleic acid molecules which allow mutagenesis or a sequence change by recombination of DNA sequences can be introduced into plasmids. With the aid of standard methods, it it possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone", VCH Weinheim 2nd edition 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The inventive compounds (I) can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients, or to any desired combinations of these active ingredients.

The inventive compounds can be used with particular preference in transgenic crop plants which are resistant to a combination of glyphosates and glufosinates, glyphosates and sulfonylureas or imidazolinones. Very particularly preferably, the compounds according to the invention can be used in transgenic crop plants such as e.g. corn or soybean with the tradename or the name Optimum™ GAT™ (glyphosate ALS tolerant).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) and the compounds of the formula (Ia) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant-growth-regulating compositions which comprise the compounds according to the invention.

The inventive compounds can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes. These individual types of formulation are known in principle and are described, for example, in: Winnacker-Kichler, "Chemische Technologie" [Chemical Technology], Volume 7, C. Hanser Verlag Munich, 4. ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th ed. 1986.

Based on these formulations, it is also possible to produce combinations with other active compounds, such as, for example, insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To produce the wettable powders, the herbicidal active compounds are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto granulated inert material capable of adsorption or by applying active compound concentrates to the surface of carrier substances, such as sand, kaolinites or granulated inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of inventive compounds. In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2009 and literature cited therein. Examples of known herbicides or plant growth regulators which can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. In this list, one or else, in some cases, more than one application form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bifenox, bicyclopyrone, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl] ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl(2,4-dichlorophenoxy) acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

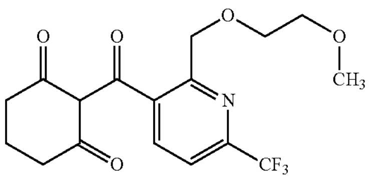

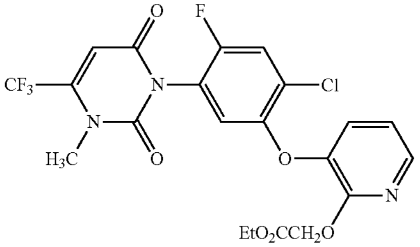

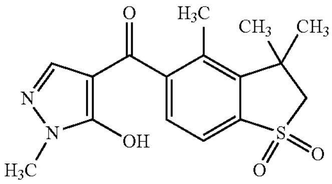

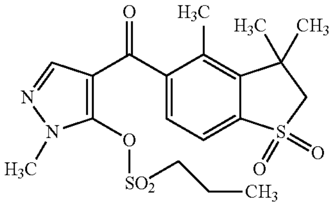

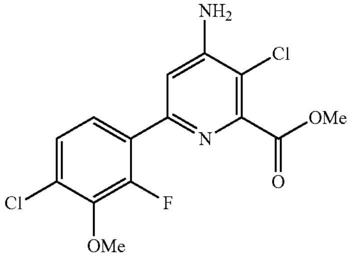

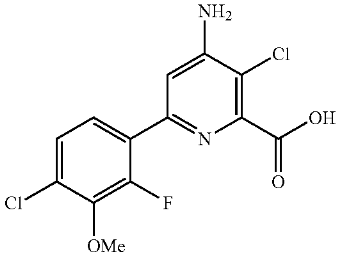

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more active substance, but it is preferably between 0.005 and 750 g/ha.

In addition to the herbicidal properties, the compounds according to the invention also have good fungicidal properties. The present invention therefore also relates to a composition for controlling unwanted microorganisms which comprises the active compounds according to the invention. These are preferably fungicidal compositions which comprise agriculturally suitable auxiliaries, solvents, carriers, surfactants or extenders.

Furthermore, the invention also relates to a method for controlling unwanted microorganisms, characterized in that the active compounds according to the invention are applied to the phytopathogenic fungi and/or their habitat. According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers may also be used. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks.

Suitable liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention. It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes. The compositions and formulations according to the invention generally comprise between 0.05 and 99% by weight, 0.01 and 98% by weight, preferably between 0.1 and 95% by weight, particularly preferably between 0.5 and 90% of active compound, very particularly preferably between 10 and 70% by weight. The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active ingredients with at least one customary extender, solvent or diluent, emulsifier, dispersant and/or binder or fixing agent, wetting agent, water repellent, if appropriate siccatives and UV stabilizers and if appropriate dyes and pigments, antifoams, preservatives, secondary thickeners, tackifiers, gibberellins and also other processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The invention furthermore includes a method for treating seed.

The invention furthermore relates to seed which has been treated in accordance with one of the methods described in the previous paragraph. The seeds according to the invention are employed in methods for the protection of seed from unwanted microorganisms. In these methods, seed treated with at least one active compound according to the invention is employed. The active compounds or compositions according to the invention are also suitable for treating seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection compositions being employed.

The present invention therefore also relates to a method for the protection of seed and germinating plants, from attack by phytopathogenic fungi, by treating the seed with a composition according to the invention. The invention also relates to the use of the compositions according to the invention for treatment of seed for protection of the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection agents. Owing to the concerns regarding a possible impact of the crop protection agents on the environment and the health of humans and animals, there are efforts to reduce the amount of active compounds applied.

One of the advantages of the present invention is that the particular systemic properties of the active compounds and compositions according to the invention mean that treatment of the seed with these active compounds and compositions not only protects the seed itself, but also the resulting plants after emergence, from phytopathogenic fungi. In this manner, the immediate treatment of the crop at the time of sowing or shortly thereafter can be dispensed with.

It is likewise considered to be advantageous that the active compounds or compositions according to the invention can be used especially also for transgenic seed, in which case the plant which grows from this seed is capable of expressing a protein which acts against pests. By virtue of the treatment of such seed with the active compounds or compositions according to the invention, merely the expression of the protein, for example an insecticidal protein, can control certain pests. Surprisingly, a further synergistic effect may be observed here, which additionally increases the effectiveness of the protection against attack by pests.

The compositions according to the invention are suitable for protecting seed of any plant variety which is employed in agriculture, in the greenhouse, in forests or in horticulture and viticulture. In particular, this takes the form of seed of cereals (such as wheat, barley, rye, triticale, sorghum/millet and oats), corn, cotton, soybeans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). The treatment of the seed of cereals (such as wheat, barley, rye, triticale and oats), corn and rice is of particular importance. As also described below, the treatment of transgenic seed with the active compounds or compositions according to the invention is of particular significance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European corn borer and/or the Western corn rootworm. Particularly preferably, the heterologous gene originates from *Bacillus thuringiensis*.

In the context of the present invention, the composition according to the invention is applied to the seed either alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430, U.S. Pat. No. 5,876,739, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples include the dyes known by the names Rhodamine B, C.I. Pigment Red 112 and C.I. Solvent Red 1. Suitable wetting agents which may be present in the seed-dressing formulations which can be used in accordance with the invention are all substances which promote wetting and which are conventionally used for the formulation of agrochemically active compounds. Usable with preference are alkylnaphthalenesulfonates, such as diisopropyl- or diisobutylnaphthalenesulfonates. Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulfated derivatives thereof. Suitable anionic dispersants are, in particular, lignosulfonates, polyacrylic acid salts and arylsulfonate/formaldehyde condensates.

Antifoams which may be present in the seed-dressing formulations which can be used in accordance with the invention are all foam-inhibiting substances conventionally used for the formulation of agrochemically active compounds. Silicone antifoams and magnesium stearate can preferably be used. Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed dressing formulations usable in accordance with the invention are all substances usable for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

The active compounds or compositions according to the invention have a potent microbicidal activity and can be employed for controlling undesirable microorganisms, such as fungi and bacteria, in crop protection and in the protection of materials.

Fungicides can be used in crop protection for control of *Plasmodiophoromycetes, Oomycetes, Chytridiomycetes, Zygomycetes, Ascomycetes, Basidiomycetes* and *Deuteromycetes.*

Bactericides can be used in crop protection for control of *Pseudomonadaceae, Rhizobiaceae, Enterobacteriaceae, Corynebacteriaceae* and *Streptomycetaceae.* The fungicidal compositions according to the invention can be used for the curative or protective control of phytopathogenic fungi. The invention therefore also relates to curative and protective methods for controlling phytopathogenic fungi by the use of the active compounds or compositions according to the invention, which are applied to the seed, the plant or plant parts, the fruit or the soil in which the plants grow. The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

The fact that the active compounds are well tolerated by plants at the concentrations required for controlling plant diseases allows the treatment of above-ground parts of plants, of propagation stock and seeds, and of the soil.

All plants and plant parts can be treated in accordance with the invention. Plants are understood here to mean all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

The active compounds according to the invention are suitable for the protection of plants and plant organs, for increasing the harvest yields, for improving the quality of the harvested crop, while being well tolerated by plants, having favorable toxicity to warm-blooded species and being environmentally friendly. They can preferably be used as crop protection compositions. They are active against normally sensitive and resistant species and against all or some stages of development. Plants which can be treated in accordance with the invention include the following main crop plants: corn, soybean, cotton, *Brassica* oil seeds such as *Brassica napus* (e.g. Canola), *Brassica rapa, B. juncea* (e.g. (field) mustard) and *Brassica carinata,* rice, wheat, sugar beet, sugar cane, oats, rye, barley, millet and sorghum, triticale, flax, grapes and various fruit and vegetables from various botanic taxa, for example Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana plants and banana plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, aubergines), Liliaceae sp., Compositae sp. (for example lettuce, artichokes and chicory—including root chicory, endive or common chicory), Umbelliferae sp. (for example carrots, parsley, celery and celeriac), Cucurbitaceae sp. (for example cucumbers—including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress and chinese cabbage), Leguminosae sp. (for example peanuts, peas, and beans—for example common beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and in each case genetically modified types of these plants.

As mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term “parts” or “parts of plants” or “plant parts” has been explained above. More preferably, plants of the plant cultivars which are commercially available or are in use are treated in accordance with the invention. Plant cultivars are understood to mean plants having new properties (“traits”) and which have been obtained by conventional breeding, by mutagenesis or by recombinant DNA techniques. They may be cultivars, varieties, bio- or genotypes.

The treatment method according to the invention can be used in the treatment of genetically modified organisms (GMOs), e.g. plants or seeds. Genetically modified plants (or transgenic plants) are plants in which a heterologous gene has been stably integrated into the genome. The expression “heterologous gene” essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive (“synergistic”) effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period within which protection is achieved generally extends for from to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Examples of nematode-resistant plants are described, for example, in the following U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166, 209, 11/762,886, 12/364,335, 11/763,947, 12/252,453, 12/209,354, 12/491,396 and 12/497,221.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance. Plants and plant cultivars which can likewise be treated in accordance with the invention are those plants which are characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (for example in corn) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate by various methods. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium 20 *Agrobacterium* sp. (Barry et al., 1992, Curr. Topics Plant Physiol. 7, 139-145), the genes encoding a petunia EPSPS (Shah et al., 1986, Science 233, 478-481), a tomato EPSPS (Gasser et al., 1988, J. Biol. Chem. 263, 4280-4289) or an Eleusine EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes. Plants which express EPSPS genes which impart glyphosate tolerance have been described. Plants which express other genes which impart glyphosate tolerance, for example decarboxylase genes, have been described.

Other herbicide-resistant plants are, for example, plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD-inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants are described in WO 99/34008 and WO 02/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio) benzoates, and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed Science 2002, 50, 700-712). The production of sulphonylurea-tolerant plants and imidazolinone-tolerant plants has been described. Further sulphonylurea- and imidazolinone-tolerant plants have also been described. Further plants tolerant to imidazolinone and/or sulphonylurea can be obtained by induced mutagenesis, by selection in cell cultures in the presence of the herbicide or by mutation breeding (cf., for example, for soybeans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al. (Microbiology and Molecular Biology Reviews 1998, 62, 807-813), updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, for example proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1999141 and WO 2007/107302), or those proteins encoded by synthetic genes as described in U.S. patent application Ser. No. 12/249,016; or 2) a crystal protein from *Bacillus thuringiensis* or *a* portion thereof which is insecticidal in the presence of a second crystal protein other than *Bacillus thuringiensis* or a portion thereof, such as the binary toxin made up of the Cy34 and Cy35 crystal protein (Nat. Biotechnol. 2001, 19, 668-72; Applied Environm. Microbiol. 2006, 71, 1765-1774) or the binary toxin which consists of Cry1A or Cry1F proteins, and the Cry2Aa or Cry2Ab or Cry2Ae proteins (U.S. patent application Ser. No. 12/214,022 and EP08010791.5); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bbl protein in corn events MON863 or MON88017, or the Cry3A protein in corn event MIR$^{604}$; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 5) to 7) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102; or 9) a secreted protein from *Bacillus thuringiensis* or *Bacillus cereus* which is insecticidal in the presence of a crystal protein from *Bacillus thuringiensis*, such as the binary toxin made up of the proteins VIP3 and Cry1A or Cry1F (U.S. patent applications 61/126083 and 61/195019), or the binary toxin made up of the VIP3 protein and the Cry2Aa or Cry2Ab or Cry2Ae proteins (U.S. patent application Ser. No. 12/214,022 and EP 08010791.5); or 10) a protein according to point 9) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein). Of course, insect-resistant transgenic plants, as used herein, also include any plant comprising a combination of genes encoding the proteins of any one of the abovementioned classes 1 to 10. In one embodiment, an insect-resistant plant contains more than one transgene encoding a protein of any one of the abovementioned classes 1 to 10, to expand the range of target insect species affected or to delay insect resistance development to the plants, by using different proteins insecticidal to the same target insect species but having a different mode of action, such as binding to different receptor binding sites in the insect.

In the present context, an "insect-resistant transgenic plant" additionally includes any plant containing at least one transgene comprising a sequence for production of double-stranded RNA which, after consumption of food by an insect pest, prevents the growth of this pest.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance.

Particularly useful stress-tolerant plants include the following:

a. plants which contain a transgene capable of reducing the expression and/or the activity of the poly(ADP-ribose)polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability in the harvested product and/or altered properties of specific compounds of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications.

2) Transgenic plants which synthesize non starch carbohydrate polymers or which synthesize non starch carbohydrate polymers with altered properties in comparison to wild type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

4) Transgenic plants or hybrid plants such as onions with particular properties, such as "high soluble solids content", "low pungency" (LP) and/or "long storage" (LS). Plants or plant varieties (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;

b) plants, such as cotton plants, which contain an altered form of rsw2 or rsw3 homologous nucleic acids, such as cotton plants with an increased expression of sucrose phosphate synthase;

c) plants, such as cotton plants, with an increased expression of sucrose synthase;

d) plants, such as cotton plants, wherein the timing of the plasmodesmatal gating at the basis of the fiber cell is altered, for example through downregulation of fiber-selective β-1,3-glucanase;

e) plants, such as cotton plants, which have fibers with altered reactivity, for example through expression of the N-acetylglucosaminetransferase gene, including nodC, and chitin synthase genes.

Plants or plant varieties (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics, and include:

a) plants, such as oilseed rape plants, which produce oil having a high oleic acid content;

b) plants, such as oilseed rape plants, which produce oil having a low linolenic acid content;

c) plants, such as oilseed rape plants, producing oil having a low level of saturated fatty acids.

Plants or plant cultivars (which can be obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering. Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/not_reg.html. At the filing date of this application, the petitions with the following information were either granted or pending at the APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which non-regulated status is being requested.

APHIS documents: Various documents which have been published by APHIS with regard to the petition or can be obtained from APHIS on request.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potatoes). Examples of herbicide-tolerant plants which may be mentioned are corn varieties, cotton varieties and soybean varieties which are available under the following trade names: Roundup Ready® (glyphosate tolerance, for example corn, cotton, soybean), Liberty Link® (phosphinotricin tolerance, for example oilseed rape), IMI® (imidazolinone tolerance) and SCS® (sulfonylurea tolerance), for example corn. Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://cera-gmc.org/index.php?evidcode=&hstIDXCode=&gType=&AbbrCode=&atCode=&stCode=&colDCode=&action=gm_crop_database&mode=Submit).

The active compounds or compositions according to the invention can also be used in the protection of materials, for protection of industrial materials against attack and destruction by unwanted microorganisms, for example fungi and insects. Furthermore, the compounds according to the invention can be used alone or in combinations with other active compounds as antifouling compositions. Industrial materials in the present context are understood as meaning non-living materials which have been prepared for use in industry. For example, industrial materials which are intended to be protected by active compounds according to the invention from microbial change or destruction can be adhesives, sizes, paper, wallpaper, and board, textiles, carpets, leather, wood, paints and plastic articles, cooling lubricants and other materials which can be infected with, or destroyed by, microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood. The inventive active ingredients or compositions may prevent adverse effects, such as rotting, decay, discoloration, decoloration or formation of mould. Moreover, the compounds according to the invention can be employed for protecting objects which come into contact with saltwater or brackish water, in particular hulls, screens, nets, buildings, moorings and signalling systems, against fouling.

The method according to the invention for controlling unwanted fungi can also be employed for protecting storage goods. Here, storage goods are to be understood as meaning natural substances of vegetable or animal origin or processing products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The active compounds according to the invention may prevent disadvantageous effects, such as rotting, decay, discoloration, decoloration or formation of mould.

Some pathogens of fungal diseases which can be treated according to the invention may be mentioned by way of example, but not by way of limitation: Diseases caused by powdery mildew pathogens, such as, for example, *Blumeria* species, such as, for example, *Blumeria graminis; Podosphaera* species, such as, for example, *Podosphaera leucotricha; Sphaerotheca* species, such as, for example, *Sphaerotheca fuliginea; Uncinula* species, such as, for example, *Uncinula necator*; diseases caused by rust disease pathogens, such as, for example, *Gymnosporangium* species, such as, for example, *Gymnosporangium sabinae; Hemileia* species, such as, for example, *Hemileia vastatrix; Phakopsora* species, such as, for example, *Phakopsora pachyrhizi* and *Phakopsora meibomiae; Puccinia* species, such as, for example, *Puccinia recondita* or *Puccinia triticina; Uromyces* species, such as, for example, *Uromyces appendiculatus*; diseases caused by pathogens from the group of the Oomycetes, such as, for example, *Bremia* species, such as, for example, *Bremia lactucae; Peronospora* species, such as, for example, *Peronospora pisi* or *P. brassicae; Phytophthora* species, such as, for example *Phytophthora infestans; Plasmopara* species, such as, for example, *Plasmopara viticola; Pseudoperonospora* species, such as, for example, *Pseudoperonospora humuli* or *Pseudoperonospora cubensis; Pythium* species, such as, for example, *Pythium ultimum*; leaf blotch diseases and leaf wilt diseases caused, for example, by *Alternaria* species, such as, for example, *Alternaria solani; Cercospora* species, such as, for example, *Cercospora beticola; Cladiosporium* species, such as, for example, *Cladiosporium cucumerinum; Cochliobolus* species, such as, for example, *Cochliobolus sativus* (conidia form: *Drechslera*, syn: *Helminthosporium*); *Colletotrichum* species, such as, for example, *Colletotrichum lindemuthanium; Cycloconium* species, such as, for example, *Cycloconium oleaginum; Diaporthe* species, such as, for example, *Diaporthe citri; Elsinoe* species, such as, for example, *Elsinoe fawcettii; Gloeosporium* species, such as, for example, *Gloeosporium laeticolor; Glomerella* species, such as, for example, *Glomerella cingulata; Guignardia* species, such as, for example, *Guignardia bidwelli; Leptosphaeria* species, such as, for example, *Leptosphaeria maculans; Magnaporthe* species, such as, for example, *Magnaporthe grisea; Microdochium* species, such as, for example, *Microdochium nivale; Mycosphaerella* species, such as, for example, *Mycosphaerella graminicola* and *M. fijiensis; Phaeosphaeria* species, such as, for example, *Phaeosphaeria nodorum; Pyrenophora* species, such as, for example, *Pyrenophora teres; Ramularia* species, such as, for example, *Ramularia collo-cygni; Rhynchosporium* species, such as, for example, *Rhynchosporium secalis; Septoria* species, such as, for example, *Septoria apii; Typhula* species, such as, for example, *Typhula incarnata; Venturia* species, such as, for example, *Venturia inaequalis*; root and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example *Rhizoctonia solani; Tapesia* species, such as, for example, *Tapesia acuformis; Thielaviopsis* species, such as, for example, *Thielaviopsis basicola*; ear and panicle diseases (including corn cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as for example, *Septoria nodorum*; diseases caused by smut fungi, such as, for example, *Sphacelotheca* species, such as, for example, *Sphacelotheca reiliana; Tilletia* species, such as, for example, *Tilletia caries; T. controversa; Urocystis* species, such as, for example, *Urocystis occulta; Ustilago* species, such as, for example, *Ustilago nuda; U. nuda tritici*; fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *P. purpurogenum; Sclerotinia* species, such as, for example, *Sclerotinia sclerotiorum; Verticilium* species, such as, for example, *Verticilium alboatrum*; seed- and soil-borne rot and wilt diseases, and also diseases of seedlings, caused, for example, by *Fusarium* species, such as, for example, *Fusarium culmorum; Phytophthora* species, such as, for example, *Phytophthora cactorum; Pythium* species, such as, for example, *Pythium ultimum; Rhizoctonia* species, such as, for example, *Rhizoctonia solani; Sclerotium* species, such as, for example, *Sclerotium rolfsii*; cancerous diseases, galls and witches' broom caused, for example, by *Nectria* species, such as, for example, *Nectria galligena*; wilt diseases caused, for example, by *Monilinia* species, such as, for example, *Monilinia laxa;* deformations of leaves, flowers and fruits caused, for example, by *Taphrina* species, such as, for example, *Taphrina deformans*; degenerative diseases of woody plants caused, for example, by *Esca* species, such as, for example, *Phaemoniella clamydospora* and *Phaeoacremonium aleophilum* and *Fomitiporia mediterranea*; diseases of flowers and seeds caused, for example, by *Botrytis* species, such as, for example, *Botrytis cinerea*; diseases of plant tubers caused, for example, by *Rhizoctonia* species, such as, for example, *Rhizoctonia solani; Helminthosporium* species, such as, for example, *Helminthosporium solani*; diseases caused by bacteriopathogens, such as, for example, *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora.*

Preference is given to controlling the following diseases of soybeans: Fungal diseases on leaves, stems, pods and seeds caused, for example, by *Alternaria* leaf spot (*Alternaria* spec. atrans *tenuissima*), Anthracnose (*Colletotrichum gloeosporoides* dematium var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), phyllostica leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), *rhizoctonia* aerial, foliage, and web blight (*Rhizoctonia solani*), rust (*Phakopsora pachyrhizi, Phakopsora meibomiae*), scab (*Sphaceloma glycines*), *stemphylium* leaf blight (*Stemphylium botryosum*), target spot (*Corynespora cassiicola*). Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), *sclerotinia* southern blight (*Sclerotinia rolfsii*), *thielaviopsis* root rot (*Thielaviopsis basicola*).

Microorganisms capable of degrading or altering the industrial materials include, for example, bacteria, fungi, yeasts, algae and slime organisms. The active compounds according to the invention preferably act against fungi, in particular moulds, wood-discoloring and wood-destroying fungi (*Basidiomycetes*), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Escherichia*, such as *Escherichia coli; Pseudomonas*, such as *Pseudomonas aeruginosa; Staphylococcus*, such as *Staphylococcus aureus.*

In addition, the active compounds according to the invention also have very good antimycotic activity. They have a very broad antimycotic activity spectrum, especially against dermatophytes and yeasts, molds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means constitutes a restriction of the mycotic spectrum covered, and is merely of illustrative character.

Accordingly, the active compounds according to the invention can be used both in medical and in non-medical applications.

When using the active compounds according to the invention as fungicides, the application rates can be varied within a relatively wide range, depending on the kind of application. The application rate of the active compounds according to the invention is

- in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);
- in the case of seed treatment: from 2 to 200 g per 100 kg of seed, preferably from to 150 g per 100 kg of seed, more preferably from 2.5 to 25 g per 100 kg of seed, even more preferably from 2.5 to 12.5 g per 100 kg of seed;
- in the case of soil treatment: from 0.1 to 10 000 g/ha, preferably from 1 to 5000 g/ha.

These application rates are mentioned only by way of example and are not limiting in the sense of the invention.

The active compounds or compositions according to the invention can thus be employed for protecting plants for a certain period of time after treatment against attack by the pathogens mentioned. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment. In addition, by the treatment according to the invention it is possible to reduce the mycotoxin content in the harvested material and the foodstuffs and feedstuffs prepared therefrom. Particular, but not exclusive, mention may be made here of the following mycotoxins: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active compounds.

The examples which follow illustrate the invention in more detail.

A. CHEMICAL EXAMPLES

1. Preparation of methyl N-{[3-(3,5-dichlorophenyl)-5-methyl-4,5-dihydro-1,2-oxazol-5-yl]carbonyl}glycinate (Example 6.454)

Intermediate 1: 3,5-Dichlorobenzaldehyde oxime 80 ml of ethanol were added to 23.82 g (342.8 mmol) of hydroxylamine hydrochloride. After addition of 28.12 g (342.8 mmol) of sodium acetate, a solution of 50.00 g (285.7 mmol) of 3,5-dichlorobenzaldehyde in 100 ml ethanol was added dropwise within a period of 30 min, the mixture was stirred for 2 h and then allowed to stand overnight. The reaction mixture was concentrated to dryness, 500 ml of $CH_2Cl_2$ were then added and the mixture was washed with 400 ml of water. The aqueous phase was washed once with 100 ml of $CH_2Cl_2$, the organic phase was dried over $Na_2SO_4$, filtered off and concentrated. The residue was used without further purification. Yield: 56.50 g (98%)

$^1$H NMR ($CDCl_3$): σ=7.36 (s, 1H, Ar—H), 7.47 (s, 2H, Ar—H), 7.63 (s br, 1H, OH), 8.02 (s, 1H, HC═NOH).

Intermediate 2: 3,5-Dichloro-N-hydroxybenzenecarboximidoyl chloride 30.00 g (157.9 mmol) of 3,5-dichlorobenzaldehyde oxime were initially charged in ml of 0.5M HCl in DMF, and 116.7 g (189.5 mmol) of Oxone (potassium peroxomonosulfate) were added a little at a time at room temperature (RT). So that the internal temperature of the reaction mixture did not exceed 50° C., the mixture was cooled with an ice bath. After 2 h, the reaction solution was poured into 1 l of ice water and extracted twice with 500 ml of ether each time. The combined organic phases were then washed with 400 ml of 0.5M aqueous HCl and with 200 ml of saturated NaCl solution, dried over Na2SO4, filtered off and concentrated. The residue was used without further purification. Yield: 28.40 g (80%)

$^1$H NMR ($CDCl_3$): σ=7.43 (s, 1H, Ar—H), 7.74 (s, 2H, Ar—H), 8.03 (s br, 1H, OH).

Intermediate 3: Ethyl 3-(3,5-dichlorophenyl)-5-methyl-4,5-dihydro-1,2-oxazole-5-carboxylate 5.00 g (22.3 mmol) were dissolved in 150 ml of 2-propanol, and 12.71 g (111.4 mmol) of ethyl methacrylate were added. At RT, 9.36 g (111.4 mmol) of $NaHCO_3$ were added to this solution, and the mixture was heated at 40° C. for 2 h. The solids were then filtered off, and the filtrate was concentrated on a rotary evaporator. The crude product was purified by chromatography (silica gel, ethyl acetate/n-heptane 1:1). Yield: 6.50 g (92%)

$^1$H NMR ($CDCl_3$): σ=1.34 (t, J=8 Hz, 3H, $CH_2CH_3$), 1.72 (s, 3H, C—$CH_3$), 3.14 (d $H_A$ of AB, J=19 Hz, 1H, N═C—$CH_AH_B$), 3.84 (d $H_B$ of AB, J=19 Hz, 1H, N═C—$CH_AH_B$), 4.26 (q, J=8 Hz, 2H, $CH_2CH_3$), 7.40 (s, 1H, Ar—H), 7.54 (s, 2H, Ar—H).

Intermediate 4: 3-(3,5-Dichlorophenyl)-5-methyl-4,5-dihydro-1,2-oxazole-5-carboxylic acid 5.00 g (16.55 mmol) of ethyl 3-(3,5-dichlorophenyl)-5-methyl-4,5-dihydro-1,2-oxazole-5-carboxylate were dissolved in 50 ml of ethanol, and 24.82 ml of 1N NaOH were then added. After 1 h of stirring at RT, the solvent was removed, 100 ml of water were added and the aqueous phase was adjusted to pH 2 by addition of 2N HCl. The product formed was obtained by extraction with 100 ml of ethyl acetate, drying the organic phase over Na2SO4, filtration and concentration.

Yield: 4.30 g (90%)

$^1$H NMR ($CDCl_3$): σ=1.78 (s, 3H, C—$CH_3$), 3.24 (d $H_A$ of AB, J=19 Hz, 1H, N═C—$CH_AH_B$), 3.83 (d $H_B$ of AB, J=19 Hz, 1H, N═C—$CH_AH_B$), 7.42 (s, 1H, Ar—H), 7.53 (s, 2H, Ar—H).

2. Preparation of methyl N-{[3-(3,5-dichlorophenyl)-5-methyl-4,5-dihydro-1,2-oxazol-5-yl]carbonyl}glycinate (Example 6.454)

100 ml of $CH_2Cl_2$ and 70 mg of dimethylformamide were added to 5.00 g (18.2 mmol) of 3-(3,5-dichlorophenyl)-5-methyl-4,5-dihydro-1,2-oxazole-5-carboxylic acid. At RT, 3.47 g (27.4 mmol) of oxalyl chloride were added slowly with stirring. After 30 min, the solution was concentrated and the residue (intermediate 5) was used without further purification (crude yield 5.50 g). 4.72 g (37.6 mmol) of glycine methyl ester hydrochloride in 100 ml of dichloromethane were initially charged together with 7.61 g (75.2 mmol) of triethylamine at RT. The crude product described above was taken up in a little $CH_2Cl_2$ and slowly added dropwise at RT, and the mixture was then stirred for 30 min. For work-up, the mixture was then extracted with 1N HCl and subsequently with saturated NaCl solution. The organic phase was dried over $Na_2SO_4$, filtered and concentrated. Chromatography on silica gel in ethyl acetate: n-heptane 1:1 gave the product. Yield: 5.80 g (85%)

$^1$H NMR ($CDCl_3$): σ=1.75 (s, 3H, C—$CH_3$), 3.20 (d $H_A$ of AB, J=19 Hz, 1H, N═C—$CH_AH_B$), 3.76 (s, 3H, O—$CH_3$), 3.78 (d $H_B$ of AB, J=19 Hz, 1H, N═C—$CH_AH_B$), 4.04 (d Ab spectrum, $J_{AB}$=15 Hz, 2H, $CH_2$═C═O), 7.26 (s br, 1H, NH), 7.41 (s, 1H, Ar—H), 7.53 (s, 2H, Ar—H).

3. Preparation of N-{[3-(3,5-dichlorophenyl)-5-methyl-4,5-dihydro-1,2-oxazol-5-yl]carbonyl}glycine (Example 6.420)

23.2 ml of 1N NaOH in water were added dropwise to a solution of 4.00 g (11.6 mmol) of methyl N-{[3-(3,5-dichlorophenyl)-5-methyl-4,5-dihydro-1,2-oxazol-5-yl]carbonyl}glycinate in 100 ml of methanol. After 30 min, the solvent was removed under reduced pressure, the residue was taken up in 50 ml of water and the mixture was acidified with 2N HCl. The product was isolated by repeated extraction with methylene chloride, concentrating the organic phase, drying over $Na_2SO_4$, filtration and re-concentration. Yield: 3.80 g (94%)

$^1H$ NMR ($CDCl_3$): σ=1.75 (s, 3H, C—$CH_3$), 3.21 (d $H_A$ of AB, J=19 Hz, 1H, N═C—$CH_AH_B$), 3.79 (d $H_B$ of AB, J=19 Hz, 1H, N═C—$CH_AH_B$), 4.08 (d Ab spectrum, $J_{AB}$=15 Hz, 2H, $CH_2$═C═O), 7.35 (t br, J=7 Hz, 1H, NH), 7.41 (s, 1H, Ar—H), 7.51 (s, 2H, Ar—H).

4. Preparation of 3-(3,5-dichlorophenyl)-5-methyl-N-{2-[(methylsulfonyl)amino]-2-oxoethyl}-4,5-dihydro-1,2-oxazole-5-carboxamide (Example 6.339)

50 ml of $CH_2Cl_2$ and 40 mg of dimethylformamide were added to 1.50 g (4.53 mmol) of N-{[3-(3,5-dichlorophenyl)-5-methyl-4,5-dihydro-1,2-oxazol-5-yl]carbonyl}glycine. At RT, 0.862 g (6.79 mmol) of oxalyl chloride were added slowly with stirring. After min, the solution was concentrated on a rotary evaporator and used without further purification (crude yield 1.60 g). 400 mg of this crude product (intermediate 6) were dissolved in 5 ml $CH_2Cl_2$ and added dropwise to a solution of 108 mg (1.14 mmol) of methanesulfonamide, 14 mg (0.11 mmol) of dimethylaminopyridine and mg (2.29 mmol) of triethylamine in 10 ml of $CH_2Cl_2$. After 2 h, the solvent was removed under reduced pressure and the crude product was chromatographed on silica gel using ethyl acetate/n-heptane (1:1). Yield: 160 mg (34%)

$^1H$ NMR (DMSO-$D_6$): σ=1.57 (s, 3H, C—$CH_3$), 3.18 (s, 3H, $O_2S$—$CH_3$), 3.42 (d $H_A$ of AB, J=19 Hz, 1H, N═C—$CH_AH_B$), 3.72 (d $H_B$ of AB, 1H, J=19 Hz, 1H, N═C—$CH_AH_B$), 3.78 (AB spectrum, $J_{AB}$=15 Hz, 2H, $CH_2$═C═O), 7.71 (s, 2H, Ar—H), 7.75 (s, H, Ar—H), 8.24 (t br, J=6 Hz, 1H, NH).

5. Preparation of N-tert-butyl-3-(3,5-dichlorophenyl)-5-methyl-4,5-dihydro-1,2-oxazole-5-carboxamide (Example 6.117)

100 ml of $CH_2Cl_2$ and 70 mg of dimethylformamide were added to 5.00 g (18.2 mmol) of 3-(3,5-dichlorophenyl)-5-methyl-4,5-dihydro-1,2-oxazole-5-carboxylic acid. At RT, 3.47 g (27.4 mmol) of oxalyl chloride were added slowly with stirring. After 30 min, the solution was concentrated and used without further purification (crude yield 5.50 g). 200 mg (0.68 mmol) of this crude product were taken up in 3 ml $CH_2Cl_2$ and added dropwise to a solution of 50 mg (0.68 mmol) of tert butylamine, 69 mg (0.68 mmol) of triethylamine and 10 mg of dimethylaminopyridine in 50 ml of $CH_2Cl_2$ at C. For work-up, the mixture was extracted with water, with saturated $NaHCO_3$ solution and once more with water. Drying of the organic phases, filtration and removal of the solvent under reduced pressure gave the product.

Yield: 100 mg (43%)

$^1H$ NMR ($CDCl_3$): σ=1.37 (s, 9H, C—$(CH_3)_3$), 1.68 (s, 3H, $CH_3$), 3.14 (d $H_A$ of AB, J=18 Hz, 1H, N═C—$CH_AH_B$), 3.76 (d $H_B$ of AB, 1H, J=18 Hz, N═C—$CH_AH_B$), 6.61 (s br, 1H, NH), 7.42 (s, 1H, Ar—H), 7.53 (s, 2H, Ar—H).

6. Preparation of N-cyclopropyl-3-(3,5-dichlorophenyl)-5-(hydroxymethyl)-4,5-dihydro-1,2-oxazole-5-carboxamide (Example 10.042)

Intermediate 7: Ethyl 3-(3,5-dichlorophenyl)-5-(hydroxymethyl)-4,5-dihydro-1,2-oxazole-5-carboxylate 3.00 g (15.8 mmol) of 3,5-dichlorobenzaldehyde oxime were stirred in 100 ml of DMF together with 2.21 g (16.6 mmol) of N-chlorosuccinimide at RT for 4 h. 3.08 g (23.7 mmol) of ethyl 2-(hydroxymethyl)acrylate and 2.40 g (23.7 mmol) of triethylamine were then added, and the mixture was stirred at RT for 18 h. The reaction solution was concentrated under reduced pressure, and $CH_2Cl_2$ and water were then added. The aqueous phase was re-extracted once with $CH_2Cl_2$, and the combined organic phases were washed twice with water, dried over $Na_2SO_4$, filtered and concentrated. After chromatography on silica gel using n-heptane:ethyl acetate (3:1), the product was obtained. Yield: 3.10 g (62%)

$^1H$ NMR ($CDCl_3$): σ=1.33 (t, J=8 Hz, 3H, $CH_2$═$CH_3$), 2.07 (m, 1H, OH), 3.62 (AB spectrum, $J_{AB}$=15 Hz, 2H, $CH_AH_B$—C═N), 4.28 (q, J=8 Hz, 2H, $CH_2$═$CH_3$), 7.42 (s, 1H, Ar—H), 7.56 (s, 2H, Ar—H).

Intermediate 8: 3-(3,5-Dichlorophenyl)-5-(hydroxymethyl)-4,5-dihydro-1,2-oxazole-5-carboxylic acid 2.80 g (8.80 mmol) of ethyl 3-(3,5-dichlorophenyl)-5-(hydroxymethyl)-4,5-dihydro-1,2-oxazole-5-carboxylate were dissolved in 100 ml of methanol, and a solution of mg (11.4 mmol) of NaOH in 20 ml of water was added. After 18 h of stirring at RT, the solvents were removed under reduced pressure, water and methylene chloride were added and the organic phase was separated off. On acidification of the aqueous phase, the product separated off as a white precipitate, which was filtered off and dried.

Yield: 2.22 g (87%)

$^1H$ NMR ($CDCl_3$): σ=3.65 (AB spectrum, $J_{AB}$=16 Hz, 2H, $CH_AH_B$—C═N), 4.02 (AB spectrum, $J_{AB}$=12 Hz, 2H, $CH_AH_B$—OH), 7.43 (s, 1H, Ar—H), 7.56 (s, 2H, Ar—H).

7. Preparation of N-cyclopropyl-3-(3,5-dichlorophenyl)-5-(hydroxymethyl)-4,5-dihydro-1,2-oxazole-5-carboxamide (Example 10.042)

400 mg (1.38 mmol) of 3-(3,5-dichlorophenyl)-5-(hydroxymethyl)-4,5-dihydro-1,2-oxazole-5-carboxylic acid were initially charged in 50 ml of methylene chloride, and mg (1.38 mmol) of N-[3-(dimethylamino)propyl]-N'-ethylcarbodiimide hydrochloride, 10 mg of DMAP as catalyst and 79 mg (1.38 mmol) of cyclopropylamine were added and the mixture was stirred at RT for 18 h. The reaction solution was washed in each case once with aqueous $NaHCO_3$, 2N HCl and water. The mixture was then dried over $MgSO_4$, filtered and concentrated under reduced pressure. The product was obtained after separation by RP-HPLC (acetonitrile:water).

Yield: 80 mg (18%)

$^1H$ NMR ($CDCl_3$/TMS): σ=0.55 (m, 2H, c-Pr—HH), 0.82 (m, 2H, c-Pr—HH), 2.78 (m, 1H, NH—CH), 3.58 (AB spectrum, $J_{AB}$=19 Hz, 2H, $CH_AH_B$—C═N), 3.91 $J_{AB}$=14 Hz, 2H, $CH_AH_B$—OH), 6.82 (s br, 1H, NH), 7.45 (s, 1H, Ar—H), 7.53 (s, 2H, Ar—H).

8. Preparation of 5-cyano-3-(3,5-difluorophenyl)-N-[(1-ethyl-3-methyl-1H-pyrazol-4-yl)methyl]-4,5-dihydro-1,2-oxazole-5-carboxamide (Ex.: 4.074)

Intermediate 9: Ethyl 5-cyano-3-(3,5-difluorophenyl)-4,5-dihydro-1,2-oxazole-5-carboxylate NCS (850 mg, 6.37 mmol) was added to a solution of 3,5-difluorobenzaldehyde oxime (1.00 g, 6.37 mmol) in DMF (60 ml), and the mixture was stirred at 40° C. for 1 h. Heating was then switched off, and ethyl 2-cyanoacrylate (1.20 g, 9.55 mmol) and $NaHCO_3$ (561 mg, 6.68 mmol) were added. The mixture was stirred at RT for 2 h, and water (400 ml) was then added. The mixture was extracted with MTBE (3×50 ml), and the combined organic phases were washed with dilute sulfuric acid (0.5 M, ml), dried over $Na_2SO_4$ and concentrated. Chromatography of the residue on silica gel using the mobile phase heptane/EtOAc gave 810 mg of slightly contaminated ethyl 5-cyano-3-(3,5-difluorophenyl)-4,5-dihydro-1,2-oxazole-5-carboxylate, which was used without further purification.

$^1$H NMR (DMSO $D_6$): σ=1.26 (t, 3H); 4.25-4.44 (m, 3H); 4.48 (d, 1H); 7.41-7.51 (m, 3H).

Intermediate 10: 5-Cyano-3-(3,5-difluorophenyl)-4,5-dihydro-1,2-oxazole-5-carboxylic acid In THF as reaction solvent, intermediate 9 was hydrolyzed analogously to the procedure of intermediate 4 to give the carboxylic acid intermediate 10. Yield: 25%

$^1$H NMR (DMSO d6/TMS): Q=4.23 (d, 1H, CHH); 4.41 (d, 1H, CHH); 7.40-7.53 (m, 3H, Ar—H).

9. Preparation of 5-cyano-3-(3,5-difluorophenyl)-N-[(1-ethyl-3-methyl-1H-pyrazol-4-yl)methyl]-4,5-dihydro-1,2-oxazole-5-carboxamide (Ex.: 4.074)

50 mg (0.19 mmol) of 5-cyano-3-(3,5-difluorophenyl)-4,5-dihydro-1,2-oxazole-5-carboxylic acid were initially charged in 4 ml of $CH_2Cl_2$, and 57 mg (0.30 mmol) of N-[3-(dimethylamino)propyl]-N'-ethylcarbodiimide hydrochloride, 27 mg (0.20 mmol) of 1-hydroxybenzotriazole and 30 mg (0.22 mmol) of (1-ethyl-3-methyl-1H-pyrazol-4-yl)methylamine were added and the mixture was stirred at RT for 18 h. The solution was washed in each case once with aqueous $NaHCO_3$, 2N HCl and water. The mixture was then dried over $Na_2SO_4$, filtered and concentrated under reduced pressure. Chromatography on silica gel in ethyl acetate/n-heptane gave the product.

Yield: 30 mg (23%)

$^1$H NMR ($CDCl_3$): σ=1.45 (t, 3H, $CH_2CH_3$); 2.21 (s, 3H, C—$CH_3$); 3.98 (d, 1H, isoxazoline-CHH); 4.07 (q, 2H, N—$CH_2CH_3$); 4.10 (d, 1H, isoxazoline-CHH); 4.23-4.41 (m, 2H, NH—$CH_2$), 6.76 (s br, 1H, NH); 6.94 (m, 1H, Ph-H); 7.17 (m, 2H, Ph-H); 7.30 (s, 1H, pyrazole-H).

10. Preparation of ethyl 3-(3-cyclopropyl-5-fluorophenyl)-5-methyl-4,5-dihydro-1,2-oxazole-5-carboxylate Intermediate 11

A mixture of ethyl 3-(3-bromo-5-fluorophenyl)-5-methyl-4,5-dihydro-1,2-oxazole-5-carboxylate (300 mg, 0.91 mmol), cyclopropylboronic acid (312 mg, 3.64 mmol), potassium carbonate (502 mg, 3.64 mmol), water (0.70 ml, 38.86 mmol) and toluene (6.3 ml) was degassed for 5 min by passing through nitrogen.

Tricyclohexylphosphane (38 mg, 0.14 mmol) and palladium(II) acetate (20 mg, 0.02 mmol) were then added, and the reaction mixture was heated in a microwave oven in a closed vessel at 130° C. for 30 min. After cooling, water (20 ml) was added, and the mixture was extracted with EtOAc (3×20 ml). The combined organic phases were dried over sodium sulfate and the solvent was removed under reduced pressure. Chromatography of the residue on silica gel using the mobile phase heptane/EtOAc gave 130 mg (49%) of ethyl 3-(3-cyclopropyl-5-fluorophenyl)-5-methyl-4,5-dihydro-1,2-oxazole-5-carboxylate.

$^1$H NMR ($CDCl_3$/TMS): σ=0.72 (m, 2H); 1.02 (m, 2H); 1.32 (t, 3H); 1.71 (s, 1H); 1.91 (m, 1H); 3.16 (d, 1H); 3.84 (d, 1H); 4.26 (m, 2H); 6.79 (m, 1H); 7.12 (m, 1H); 7.17 (m, 1H).

Intermediate 12: Ethyl 3-(3-ethyl-5-fluorophenyl)-5-methyl-4,5-dihydro-1,2-oxazole-5-carboxylate Ethyl 3-(3-bromo-5-fluorophenyl)-5-methyl-4,5-dihydro-1,2-oxazole-5-carboxylate (1000 mg, 3.03 mmol), potassium carbonate (1.67 g, 12.12 mmol) and tetrakis(triphenylphosphane)palladium (350 mg, 0.30 mmol) were suspended in DMF (10 ml). Triethylborane (1M in hexane, 4.24 ml, 4.24 mmol) was then added, and the reaction mixture was heated in a microwave oven at 150° C. for 30 min. After cooling, water (20 ml), sulfuric acid (1 M, 5 ml) and $CH_2Cl_2$ (20 ml) were added, and the mixture was shaken. The organic phase was then dried over $Na_2SO_4$, and the solvent was removed under reduced pressure. Chromatography of the residue on silica gel using the mobile phase heptane/EtOAc gave 701 mg (83%) of ethyl 3-(3-ethyl-5-fluorophenyl)-5-methyl-4,5-dihydro-1,2-oxazole-5-carboxylate.

$^1$H NMR ($CDCl_3$): σ=1.25 (t, 3H); 1.32 (t, 3H); 1.71 (s, 3H); 2.67 (m, 2H); 3.18 (d, 1H); 3.86 (d, 1H); 4.26 (m, 2H); 6.96 (m, 1H); 7.18 (m, 1H); 7.27 (m, 1H).

Intermediates 11 and 12 were hydrolyzed analogously to the procedure for intermediate 10 and converted analogously to the procedures for example 6.339 into the compounds according to the invention.

11. Preparation of 3-(3,5-difluorophenyl)-5-methyl-N-(1H-pyrazol-4-ylmethyl)-4,5-dihydro-1,2-oxazole-5-carboxamide (Ex.: 1.261)

1-(1H-Pyrazol-4-yl)methanamine hydrochloride (609 mg, 4.56 mmol), N,N-diisopropylethylamine (1.61 g, 12.44 mmol), HOBt (506 mg, 4.15 mmol) and EDCI (1.59 g, 8.29 mmol) were added to a solution of 3-(3,5-difluorophenyl)-5-methyl-4,5-dihydro-1,2-oxazole-5-carboxylic acid (1.00 g, 4.15 mmol) in dichloromethane (30 ml), and the mixture was stirred at RT for 16 h. $H_2SO_4$ (0.5M, 10 ml) was then added, and the mixture was diluted with $CH_2Cl_2$ (20 ml). The aqueous phase was extracted with $CH_2Cl_2$ (2×20 ml), the combined organic phases were washed with saturated $NaHCO_3$ solution (30 ml) and dried over $Na_2SO_4$, and the solvent was removed. This gave 1.2 g of 3-(3,5-difluorophenyl)-5-methyl-N-(1H-pyrazol-4-ylmethyl)-4,5-dihydro-1,2-oxazole-5-carboxamide which was used without further purification.

$^1$H NMR ($CDCl_3$): σ=1.72 (s, 3H); 3.17 (d, 1H); 3.77 (d, 1H); 4.28 (dd, 1H); 4.41 (dd, 1H); 6.87 (m, 1H); 7.01 (brt, 1H); 7.14 (m, 2H); 7.53 (brs, 2H).

12. Preparation of N-{[1-(cyanomethyl)-1H-pyrazol-4-yl]methyl}-3-(3,5-difluorophenyl)-5-methyl-4,5-dihydro-1,2-oxazole-5-carboxamide (Ex.: 1.103)

At 0° C., NaH (60% by weight suspension in mineral oil, 30 mg, 0.75 mmol) was added to a solution of 3-(3,5-difluorophenyl)-5-methyl-N-(1H-pyrazol-4-ylmethyl)-4,5-dihydro-1,2-oxazole-5-carboxamide (200 mg, 0.62 mmol) in DMF (10 ml), and the mixture was stirred for 15 min. The mixture was then warmed to RT, and bromoacetonitrile (225 mg, 1.87 mmol) was added. The mixture was stirred at RT for h and then at 60° C. for 4 h. After cooling to RT, sulfuric acid (0.5M, 10 ml) was added, and the mixture was extracted with EtOAc (3×20 ml). The combined organic phases were then dried over $Na_2SO_4$, and the solvent was removed under reduced pressure. The residue was chromatographed on silica gel using the mobile phase heptane/EtOAc, giving N-{[1-(cyanomethyl)-1H-pyrazol-4-yl]methyl}-3-(3,5-difluorophenyl)-5-methyl-4,5-dihydro-1,2-oxazole-5-carboxamide (144 mg, 64%).

$^1$H NMR ($CDCl_3$): σ=1.72 (s, 3H); 3.19 (d, 1H); 3.76 (d, 1H); 4.23 (dd, 1H); 4.38 (dd, 1H); 5.02 (s, 2H); 6.88 (m, 1H); 7.04 (brt, 1H); 7.16 (m, 2H); 7.49 (s, 1H); 7.50 (s, 1H).

12. Preparation of N-[(3-chloro-1-ethyl-1H-pyrazol-4-yl)methyl]-3-(3,5-dichlorophenyl)-5-methyl-4,5-dihydro-1,2-oxazole-5-carboxamide (Ex.: 1.344)

(3-Amino-1-ethyl-1H-pyrazole-4-carbonitrile hydrochloride) was prepared analogously to Schmidt et al. Helvetiva Chimica Acta 1959, 42, 763 and 770 and reacted further as follows:

Intermediate 15:
3-Chloro-1-ethyl-1H-pyrazole-4-carbonitrile 1.00 g (7.34 mmol) of 3-amino-1-ethyl-1H-pyrazole-4-carbonitrile hydrochloride was dissolved in semi-concentrated hydrochloric acid (50 ml), the mixture was cooled to 0° C. and sodium nitrite (532 mg, 7.71 mmol) was added. The mixture formed was stirred at 0° C. for 45 minutes and then added dropwise to a solution, pre-heated to 60° C., of copper (I) chloride (727 mg, 7.34 mmol) in semiconcentrated hydrochloric acid, with evolution of gas. The reaction mixture was stirred at 60° C. for 2 hours, cooled to RT and extracted with $CH_2Cl_2$ (3×50 ml). The combined organic phases were dried over $Na_2SO_4$, the solvent was removed and the residue was chromatographed on silica gel using the mobile phase dichloromethane/methanol. This gave 630 mg (55%) of 3-chloro-1-ethyl-1H-pyrazole-4-carbonitrile.

$^1$H NMR (DMSO-$D_6$/TMS): =1.37 (t, 3H); 4.17 (q, 2H); 8.68 (s, 1H).

Intermediate 16:
1-(3-Chloro-1-ethyl-1H-pyrazol-4-yl)methanamine

Concentrated ammonia solution (20 ml) and Raney nickel (1.2 g, 40% by weight suspension in water) were added to a solution of 3-chloro-1-ethyl-1H-pyrazole-4-carbonitrile (620 mg, 3.99 mmol) in methanol (40 ml), and the mixture was then hydrogenated with vigourous stirring under an atmosphere of hydrogen for 16 hours. For work-up, the reaction mixture was filtered through Celite and the filtrate was concentrated under reduced pressure. This gave 645 mg of 1-(3-chloro-1-ethyl-1H-pyrazol-4-yl)methanamine which was used without further purification.

$^1$H NMR (DMSO-$D_6$): σ=1.33 (t, 3H); 3.48 (s, 2H); 4.04 (q, 2H); 7.67 (s, 1H).

13. Preparation of N-[(3-chloro-1-ethyl-1H-pyrazol-4-yl)methyl]-3-(3,5-dichlorophenyl)-5-methyl-4,5-dihydro-1,2-oxazole-5-carboxamide (Ex.: 1.344)

Intermediate 5 was reacted analogously to the preparation of example 6.454 with intermediate 16 to give the compounds according to the invention such as, for example, 1.344.

14. Preparation of N-cyclopropyl-3-(3-fluoro-5-methylphenyl)-5-methyl-4,5-dihydro-1,2-oxazole-5-carbothioamide (Example 6.084)

N-Cyclopropyl-3-(3-fluoro-5-methylphenyl)-5-methyl-4,5-dihydro-1,2-oxazole-5-carboxamide (Example 6.083) (41 mg, 0.15 mmol) and 4-methoxyphenyldithiophosphonic anhydride (71 mg, 0.18 mmol) were dissolved in toluene (10 ml) and THF (5 ml), and the mixture was heated at 100° C. for 4 h. The mixture was then cooled to RT and concentrated under reduced pressure. Chromatography of the residue on silica gel using the mobile phase heptane/EtOAc gave 32 mg (74%) of N-cyclopropyl-3-(3-fluoro-5-methylphenyl)-5-methyl-4,5-dihydro-1,2-oxazole-5-carbothioamide.

$^1$H NMR ($CDCl_3$): σ=0.69 (m, 2H); 0.95 (m, 2H); 1.86 (s, 3H); 2.36 (s, 3H); 3.25 (m, 1H), 3.37 (d, 1H); 4.23 (d, 1H); 6.93 (m, 1H); 7.13-7.23 (m, 2H); 8.60 (brs, 1H).

The compounds mentioned in the tables below can be obtained analogously to the preparation of the compounds mentioned above and in accordance with the general statements on the preparation. The NMR data for examples disclosed in these tables are listed either in conventional form (δ values, number of hydrogen atoms, multiplet splitting) or as NMR peak lists. In the NMR peak list method, the NMR data of selected examples are stated in the form of NMR peak lists, where for each signal peak first the δ value in ppm and then the signal intensity are listed separated by a gap. The δ value—signal intensity number pairs for different signal peaks are listed with separation from one another by semicolons. Listed separated by a gap. The δ value—signal intensity number pairs for different signal peaks are listed with separation from one another by semicolons.

TABLE 1

Compounds of the general formula (I) according to the invention in which $R^2$ is hydrogen and $R^3$ is methyl and aryl is the radical

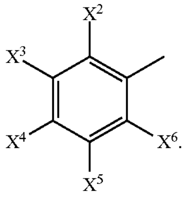

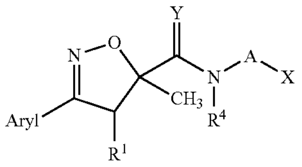

| No. | Aryl | $R^1$ | Y | $R^4$ | A | X | Physical data |
|---|---|---|---|---|---|---|---|
| 1.001 | 3,5-$Cl_2$—Ph | H | O | H | bond | 1,2-oxazol-3-yl | [$CDCl_3$] 9.26 0.97; 8.32 2.41; 8.32 2.58; 8.32 2.57; 8.32 2.45; 7.53 7.11; 7.52 7.88; 7.43 1.98; 7.43 3.40; 7.42 1.69; 7.26 11.99; 7.04 3.06; 7.04 3.02; 7.04 |

TABLE 1-continued

Compounds of the general formula (I) according to the invention in which $R^2$ is hydrogen and $R^3$ is methyl and aryl is the radical

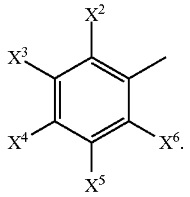

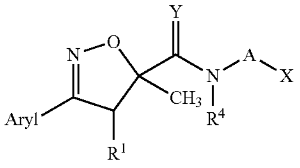

| No. | Aryl | $R^1$ | Y | $R^4$ | A | X | Physical data |
|---|---|---|---|---|---|---|---|
| | | | | | | | 3.03; 5.30 1.76; 3.88 2.84; 3.83 3.28; 3.31 3.02; 3.27 2.63; 1.82 16.00; 1.57 6.60; 0.00 6.62 |
| 1.002 | 3,5-$(CF_3)_2$—Ph | H | O | H | bond | 1,3-dimethyl-1H-pyrazol-5-yl | [$CDCl_3$] 1.88 (s, 3H); 2.22 (s, 3H); 3.37 (d, 1H); 3.68 (s, 3H); 3.99 (d, 1H); 6.14 (s, 1H); 7.95 (m, 1H); 8.10 (m, 2H); 8.48 (s, 1H). |
| 1.003 | 3,5-$Cl_2$—Ph | H | O | H | bond | 1,3-dimethyl-1H-pyrazol-5-yl | [$CDCl_3$] 1.83 (s, 3H); 2.22 (s, 3H); 3.28 (d, 1H); 3.66 (s, 3H); 3.87 (d, 1H); 6.12 (s, 1H); 7.44 (m. 1H); 7.52 (m, 2H); 8.39 (s, 1H). |
| 1.004 | 3,5-$Cl_2$—Ph | H | O | H | bond | 1,3-oxazol-2-yl | [$CDCl_3$] 7.52 8.67; 7.52 9.35; 7.48 0.32; 7.47 0.35; 7.47 0.51; 7.46 1.78; 7.44 0.33; 7.43 1.90; 7.42 3.02; 7.42 1.69; 7.42 0.66; 7.26 22.84; 7.26 0.36; 7.09 2.12; 3.95 0.83; 3.90 0.95; 3.31 1.44; 3.26 1.25; 1.83 16.00; 1.79 0.40; 1.75 1.36; 1.59 0.41; 1.26 0.73; 0.01 0.37; 0.00 13.67; −0.01 0.44; −0.01 0.35; −0.01 0.50 |
| 1.005 | 3,5-$Cl_2$—Ph | H | O | H | bond | 1,3-thiazol-2-yl | [$CDCl_3$] 10.13 0.65; 7.55 0.39; 7.55 0.43; 7.53 3.80; 7.52 7.14; 7.52 11.01; 7.43 1.92; 7.42 3.34; 7.42 1.64; 7.26 19.67; 7.03 3.48; 7.02 3.39; 5.30 1.70; 3.92 2.79; 3.88 3.21; 3.34 3.07; 3.30 2.64; 1.85 16.00; 1.70 0.99; 1.58 7.67; 1.28 0.47; 1.26 0.47; 1.25 0.61; 1.14 0.42; 0.00 10.22; −0.01 0.39 |
| 1.006 | 3,5-$Cl_2$—Ph | H | O | H | bond | 1,5-dimethyl-1H-pyrazol-4-yl | [$CDCl_3$] 1.81 (s, 3H); 2.17 (s, 3H); 3.25 (d, 1H); 3.77 (s, 3H); 3.87 (d, 1H); 7.43 (m, 1H); 7.53 (m, 2H); 7.60 (s, 1H); 8.04 (s, 1H). |
| 1.007 | 3,5-$F_2$—Ph | H | O | H | bond | 1,5-dimethyl-1H-pyrazol-4-yl | [$CDCl_3$] 8.06 0.80; 7.61 3.41; 7.26 17.20; 7.20 1.33; 7.19 1.67; 7.19 0.94; 7.18 0.92; 7.18 1.61; 7.17 1.37; 6.93 0.33; 6.92 0.61; 6.90 0.68; 6.90 1.22; 6.89 0.60; 6.88 0.35; 6.88 0.61; 5.30 1.25; 3.89 2.32; 3.85 2.65; 3.76 16.00; 3.28 2.45; 3.24 2.15; 2.17 13.71; 2.05 0.53; 1.82 13.38; 1.61 5.90; 0.00 7.22 |
| 1.008 | Ph | H | O | H | bond | 1,5-dimethyl-1H-pyrazol-4-yl | [$CDCl_3$] 1.81 (s, 3H); 2.17 (s, 3H); 3.32 (d, 1H); 3.76 (s, 3H); 3.92 (d, 1H); 7.43 (m, 3H); 7.61 (s, 1H); 7.66 (m, 2H); 8.12 (s, 1H). |
| 1.009 | 3-F—Ph | H | O | H | bond | 1,5-dimethyl-1H-pyrazol-4-yl | [$CDCl_3$] 1.71 (s, 3H); 2.17 (s, 3H); 3.30 (d, 1H); 3.75 (s, 3H); 3.89 (d, 1H); 7.15 (m, 1H); |

TABLE 1-continued

Compounds of the general formula (I) according to the invention in which $R^2$ is hydrogen and $R^3$ is methyl and aryl is the radical

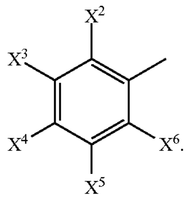

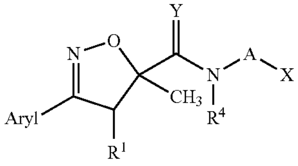

| No. | Aryl | $R^1$ | Y | $R^4$ | A | X | Physical data |
|---|---|---|---|---|---|---|---|
| | | | | | | | 7.39 (m, 3H); 7.61 (s, 1H); 8.10 (brs, 1H). |
| 1.010 | 3-Me—Ph | H | O | H | bond | 1,5-dimethyl-1H-pyrazol-4-yl | [$CDCl_3$] 8.13 1.07; 7.61 3.95; 7.49 2.09; 7.45 1.03; 7.43 1.33; 7.32 0.91; 7.31 2.17; 7.29 1.44; 7.26 12.80; 7.24 0.81; 5.30 0.76; 3.93 2.37; 3.89 2.70; 3.75 16.00; 3.32 2.60; 3.28 2.27; 2.38 11.07; 2.16 14.72; 1.81 13.99; 1.61 3.49 |
| 1.011 | 3,5-$F_2$—Ph | H | O | H | bond | 1-ethyl-3-(methoxy-carbonyl)-1H-pyrazol-4-yl | [$CDCl_3$] 10.23 1.04; 8.22 4.70; 7.26 14.83; 7.20 1.44; 7.19 1.72; 7.18 1.79; 7.17 1.35; 6.89 0.34; 6.89 0.60; 6.87 0.68; 6.87 1.18; 6.86 0.60; 6.85 0.35; 6.84 0.59; 4.25 1.07; 4.23 3.35; 4.21 3.40; 4.19 1.11; 4.00 16.00; 3.85 2.11; 3.80 2.43; 3.28 2.29; 3.24 1.99; 1.82 12.39; 1.57 1.72; 1.52 3.65; 1.50 7.73; 1.48 3.56; 0.00 1.95 |
| 1.012 | 3,5-$Cl_2$—Ph | H | O | H | bond | 1-ethyl-3-(methoxy-carbonyl)-1H-pyrazol-4-yl | [$CDCl_3$] 10.23 1.48; 8.22 5.01; 7.55 4.84; 7.55 5.49; 7.54 5.81; 7.54 6.30; 7.52 0.49; 7.40 1.46; 7.40 2.45; 7.40 2.67; 7.40 1.46; 7.39 1.49; 7.31 0.53; 7.26 60.88; 7.26 71.58; 7.21 0.36; 7.00 0.42; 4.24 1.17; 4.23 3.59; 4.21 3.70; 4.19 1.25; 4.00 14.96; 4.00 16.00; 3.85 2.25; 3.81 2.61; 3.49 0.33; 3.28 2.52; 3.24 2.21; 2.01 1.27; 2.00 1.46; 1.82 13.37; 1.54 25.51; 1.54 28.25; 1.52 4.02; 1.50 7.54; 1.50 8.14; 1.48 3.74; 1.29 0.34; 1.27 1.12; 0.90 0.52; 0.88 1.29; 0.86 0.60; 0.00 8.13; 0.00 9.59 |
| 1.013 | 3-F—Ph | H | O | H | bond | 1-ethyl-3-(methoxy-carbonyl)-1H-pyrazol-4-yl | [$CDCl_3$] 10.25 1.27; 8.23 4.99; 7.42 0.95; 7.42 1.22; 7.39 3.77; 7.38 1.07; 7.37 1.21; 7.36 1.06; 7.35 0.51; 7.34 0.39; 7.26 11.12; 7.14 0.39; 7.13 0.61; 7.13 0.39; 7.12 1.02; 7.11 0.77; 7.10 0.38; 7.09 0.53; 7.09 0.37; 4.24 1.19; 4.22 3.71; 4.21 3.77; 4.19 1.26; 4.00 16.00; 3.88 2.31; 3.83 2.68; 3.32 2.62; 3.27 2.26; 1.81 13.74; 1.58 2.48; 1.52 3.87; 1.50 7.97; 1.48 3.83; 0.00 1.37 |
| 1.014 | Ph | H | O | H | bond | 1-ethyl-3-(methoxy-carbonyl)-1H-pyrazol-4-yl | [$CDCl_3$] 10.26 0.69; 8.23 4.15; 7.67 1.55; 7.67 1.74; 7.67 0.76; 7.66 0.62; 7.66 0.62; 7.66 1.26; 7.65 1.97; 7.42 0.45; 7.42 0.56; 7.41 0.38; 7.41 1.35; 7.41 2.65; 7.40 2.67; 7.40 1.30; 7.40 |

TABLE 1-continued

Compounds of the general formula (I) according to the invention in which $R^2$ is hydrogen and $R^3$ is methyl and aryl is the radical

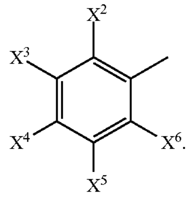

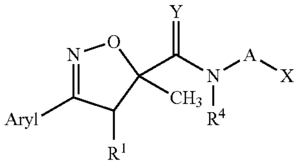

| No. | Aryl | $R^1$ | Y | $R^4$ | A | X | Physical data |
|---|---|---|---|---|---|---|---|
| | | | | | | | 1.30; 7.39 0.85; 7.39 1.44; 7.39 1.43; 7.38 0.32; 7.38 0.46; 7.26 13.20; 4.24 0.97; 4.22 3.11; 4.20 3.15; 4.19 1.01; 4.00 16.00; 3.90 2.08; 3.86 2.36; 3.34 2.19; 3.30 1.92; 1.81 11.37; 1.60 1.47; 1.52 3.51; 1.50 7.66; 1.48 3.43; 0.00 2.23 |
| 1.015 | 3,5-$F_2$—Ph | H | O | H | bond | 1-ethyl-3-methyl-1H-pyrazol-4-yl | [$CDCl_3$] 8.22 0.91; 7.90 4.07; 7.26 21.25; 7.19 1.55; 7.18 1.91; 7.18 1.08; 7.17 1.04; 7.17 1.86; 7.16 1.61; 6.92 0.39; 6.91 0.71; 6.91 0.36; 6.90 0.79; 6.89 1.42; 6.89 0.71; 6.88 0.40; 6.87 0.70; 6.86 0.34; 5.30 0.69; 4.09 1.20; 4.07 3.77; 4.06 3.81; 4.04 1.24; 3.87 2.66; 3.83 3.01; 3.29 2.78; 3.25 2.42; 2.24 16.00; 1.82 15.05; 1.60 6.98; 1.46 4.74; 1.44 10.13; 1.42 4.63; 0.00 9.11 |
| 1.016 | 3-F—Ph | H | O | H | bond | 1-ethyl-3-methyl-1H-pyrazol-4-yl | [$CDCl_3$] 8.26 0.86; 7.90 4.01; 7.41 0.61; 7.41 0.86; 7.40 1.67; 7.40 0.99; 7.39 2.59; 7.39 3.38; 7.38 2.42; 7.38 1.58; 7.26 22.10; 7.17 0.45; 7.16 0.51; 7.15 0.59; 7.14 0.70; 7.14 0.36; 7.14 0.79; 7.13 0.46; 7.12 0.40; 7.12 0.42; 7.11 0.36; 4.09 1.21; 4.07 3.81; 4.05 3.86; 4.04 1.26; 3.90 2.80; 3.86 3.20; 3.32 2.94; 3.28 2.59; 2.24 16.00; 1.81 15.45; 1.61 5.16; 1.45 4.91; 1.44 10.59; 1.42 4.82; 0.00 8.44 |
| 1.017 | 3,5-$Cl_2$—Ph | H | O | H | bond | 1-ethyl-3-methyl-1H-pyrazol-4-yl | [$CDCl_3$] 8.21 1.15; 7.90 4.32; 7.53 6.18; 7.53 6.82; 7.43 1.68; 7.42 2.98; 7.42 1.42; 7.27 21.50; 4.09 1.20; 4.07 3.76; 4.06 3.81; 4.04 1.25; 3.88 2.50; 3.84 2.84; 3.29 2.70; 3.24 2.36; 2.24 16.00; 1.81 14.15; 1.73 5.93; 1.46 4.39; 1.44 9.15; 1.42 4.26; 0.00 9.00 |
| 1.018 | Ph | H | O | H | bond | 1-ethyl-3-methyl-1H-pyrazol-4-yl | [$CDCl_3$] 8.30 0.93; 7.91 4.19; 7.66 1.94; 7.66 2.25; 7.65 1.04; 7.65 0.75; 7.64 1.99; 7.64 2.61; 7.45 0.59; 7.44 0.80; 7.43 1.37; 7.43 5.00; 7.42 2.08; 7.42 0.82; 7.41 1.09; 7.41 2.21; 7.41 0.40; 7.40 0.35; 7.40 0.39; 7.40 0.65; 7.39 0.32; 7.39 0.47; 7.26 17.77; 5.30 1.45; 4.09 1.19; 4.07 3.77; 4.05 3.84; 4.03 1.27; 3.93 2.70; 3.89 3.11; 3.35 2.90; 3.30 2.55; 2.23 16.00; 1.81 15.25; 1.62 6.56; 1.45 4.62; 1.43 9.84; 1.42 4.56; 0.00 7.35 |

TABLE 1-continued

Compounds of the general formula (I) according to the invention in which $R^2$ is hydrogen and $R^3$ is methyl and aryl is the radical

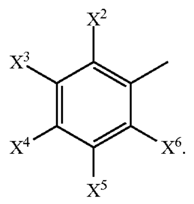

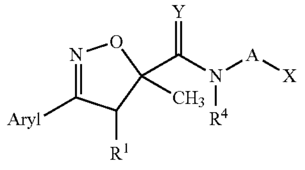

| No. | Aryl | $R^1$ | Y | $R^4$ | A | X | Physical data |
|---|---|---|---|---|---|---|---|
| 1.019 | 3,5-$Cl_2$—Ph | H | O | H | bond | 1-methyl-1H-1,2,4-triazol-3-yl | [$CDCl_3$] 8.10 0.43; 8.07 0.47; 7.88 0.41; 7.86 0.48; 7.81 2.88; 7.59 0.38; 7.54 0.81; 7.53 1.05; 7.53 5.66; 7.52 6.33; 7.46 0.39; 7.44 1.66; 7.44 2.81; 7.43 1.39; 7.40 0.38; 7.26 12.37; 6.37 1.49; 3.88 1.87; 3.84 2.15; 3.82 2.03; 3.76 16.00; 3.32 2.29; 3.27 2.01; 1.84 12.69; 1.72 1.69; 1.43 0.38; 1.25 1.44; 1.22 0.35; 0.00 1.71 |
| 1.020 | 3,5-$F_2$—Ph | H | O | H | bond | 1-methyl-1H-1,2,4-triazol-3-yl | [$CDCl_3$] 7.81 3.93; 7.26 13.19; 7.19 1.26; 7.18 1.55; 7.18 0.90; 7.17 0.91; 7.17 1.55; 7.16 1.31; 6.93 0.55; 6.92 0.63; 6.91 1.12; 6.90 0.55; 6.89 0.33; 6.89 0.56; 3.87 1.95; 3.83 2.24; 3.76 16.00; 3.32 2.20; 3.28 1.90; 1.85 12.25; 0.00 1.97 |
| 1.021 | 3,5-$Cl_2$—Ph | H | O | H | bond | 1-methyl-1H-imidazol-2-yl | [$CDCl_3$] 7.56 5.66; 7.56 5.85; 7.38 1.52; 7.37 2.65; 7.37 1.35; 7.26 9.62; 6.76 2.41; 6.75 2.56; 6.61 2.36; 6.60 2.19; 5.30 0.86; 4.02 2.15; 3.98 2.36; 3.53 16.00; 3.16 2.34; 3.12 2.15; 1.77 12.90; 0.00 5.12 |
| 1.022 | 3,5-$F_2$—Ph | H | O | H | bond | 1-methyl-1H-pyrazol-4-yl | [$CDCl_3$] 8.47 0.72; 7.89 3.14; 7.46 3.05; 7.26 15.96; 7.18 1.26; 7.17 1.56; 7.17 0.90; 7.16 0.86; 7.16 1.55; 7.15 1.29; 6.91 0.57; 6.89 0.64; 6.89 1.15; 6.88 0.57; 6.87 0.33; 6.87 0.57; 3.87 16.00; 3.83 2.49; 3.29 2.31; 3.24 2.02; 1.80 12.47; 1.60 5.44; 0.00 6.63 |
| 1.023 | 3,5-$Cl_2$—Ph | H | O | H | bond | 1-methyl-1H-pyrazol-4-yl | [$CDCl_3$] 1.80 (s, 3H); 3.25 (d, 1H); 3.84 (d, 1H); 3.87 (s, 3H); 7.41 (m, 1H); 7.46 (m, 1H); 7.52 (m, 2H); 7.89 (s, 1H); 8.45 (s, 1H). |
| 1.024 | 3-F—Ph | H | O | H | bond | 1-methyl-1H-pyrazol-4-yl | [$CDCl_3$] 1.80 (s, 3H); 3.29 (d, 1H); 3.84 (s, 3H); 3.88 (d, 1H); 7.14 (m, 1H); 7.38 (m, 3H); 7.46 (s, 1H); 7.89 (s, 1H); 8.52 (brs, 1H). |
| 1.025 | Ph | H | O | H | bond | 1-methyl-1H-pyrazol-4-yl | [$CDCl_3$] 1.70 (s, 3H); 3.32 (d, 1H); 3.88 (s, 3H); 3.90 (d, 1H); 7.42 (m, 4H); 7.64 (m, 2H); 7.89 (s, 1H); 8.54 (s, 1H). |
| 1.026 | 3,5-$Cl_2$—Ph | H | O | H | bond | 1-propyl-1H-1,2,4-triazol-3-yl | [$CDCl_3$] 9.21 1.38; 7.93 3.37; 7.52 6.67; 7.51 7.43; 7.42 1.82; 7.41 3.28; 7.41 1.65; 7.26 20.45; 4.10 2.58; 4.08 4.73; 4.07 2.73; 3.96 2.58; 3.92 2.90; 3.28 2.96; 3.23 2.65; 1.95 1.55; 1.93 3.05; 1.91 3.10; 1.89 1.65; 1.88 |

TABLE 1-continued

Compounds of the general formula (I) according to the invention in which $R^2$ is hydrogen and $R^3$ is methyl and aryl is the radical

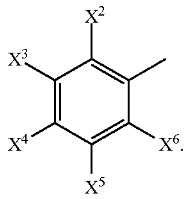

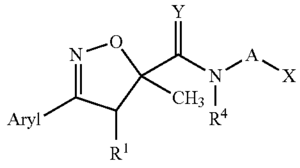

| No. | Aryl | $R^1$ | Y | $R^4$ | A | X | Physical data |
|---|---|---|---|---|---|---|---|
| | | | | | | | 0.38; 1.83 16.00; 0.95 4.66; 0.94 9.41; 0.92 4.39; 0.00 5.84 |
| 1.027 | 3,5-$F_2$—Ph | H | O | H | bond | 1-propyl-1H-1,2,4-triazol-3-yl | [$CDCl_3$] 9.06 1.53; 7.88 4.99; 7.52 0.73; 7.28 0.32; 7.28 0.41; 7.26 97.61; 7.26 128.81; 7.25 0.88; 7.18 0.36; 7.17 2.02; 7.17 2.32; 7.15 2.53; 7.15 1.93; 7.13 0.34; 7.00 0.72; 6.91 0.43; 6.90 0.75; 6.90 0.38; 6.89 0.86; 6.88 1.48; 6.87 0.70; 6.86 0.46; 6.86 0.72; 4.10 2.61; 4.08 4.85; 4.06 2.70; 3.95 2.67; 3.91 3.06; 3.28 2.88; 3.24 2.58; 2.17 2.32; 2.17 3.09; 2.00 0.42; 1.96 0.36; 1.95 1.50; 1.93 3.03; 1.91 3.18; 1.89 1.66; 1.87 0.40; 1.83 16.00; 1.54 40.63; 1.17 0.39; 0.95 4.54; 0.93 9.06; 0.92 4.17; 0.01 1.55; 0.00 27.43; 0.00 29.98; 0.00 36.77; −0.01 1.40; −0.01 1.35 |
| 1.028 | 3,5-$Cl_2$—Ph | H | O | H | bond | 2-(2-ethoxy-2-oxoethyl)phenyl | [$CDCl_3$] 9.58 0.97; 7.82 1.20; 7.81 1.28; 7.80 1.33; 7.79 1.36; 7.55 7.86; 7.55 8.63; 7.42 2.11; 7.42 3.70; 7.41 1.86; 7.33 0.60; 7.33 0.66; 7.32 0.99; 7.31 1.13; 7.30 0.68; 7.29 0.77; 7.26 22.38; 7.25 0.97; 7.24 0.98; 7.23 1.57; 7.22 1.33; 7.17 1.05; 7.16 1.10; 7.15 1.42; 7.14 1.44; 7.13 0.58; 7.13 0.57; 4.24 1.51; 4.23 4.85; 4.21 5.04; 4.19 1.65; 3.93 2.85; 3.89 3.18; 3.58 6.51; 3.27 2.91; 3.23 2.60; 1.86 16.00; 1.62 2.55; 1.32 5.80; 1.30 11.97; 1.28 5.50; 0.00 13.25; −0.01 0.38 |
| 1.029 | 3,5-$Cl_2$—Ph | H | O | H | bond | 2-(methoxy-carbonyl)phenyl | [$CDCl_3$] 1.84 (s, 3H); 3.28 (d, 1H); 3.90 (d, 1H); 3.98 (s, 3H); 7.13 (m, 1H); 7.39 (m, 1H); 7.52-7.57 (m, 3H); 8.07 (m, 1H); 8.71 (m, 1H). |
| 1.030 | 3,5-$Cl_2$—Ph | H | O | H | bond | 2-(methyl-carbamoyl)phenyl | [$CDCl_3$] 1.83 (s, 3H); 3.05 (d, 3H); 3.22 (d, 1H); 3.87 (d, 1H); 6.17 (s br, 1H); 7.12 (t, 1H); 7.40 (s, 1H); 7.47 (d, 1H); 7.50 (m, 1H); 7.58 (s, 2H); 8.62 (d, 1H). |
| 1.031 | 3,5-$Cl_2$—Ph | H | O | H | bond | 2,4-dichloro-6-(methyl-carbamoyl)phenyl | [$CDCl_3$] 1.80 (s, 3H), 2.86 (d, 3H); 3.24 (d, 1H); 3.84 (d, 1H); 6.10 (d br, 1H); 7.41 (m, 2H); 7.52 (d, 1H); 7.56 (d, 2H); 8.84 (s, 1H) |
| 1.032 | 3,5-$Cl_2$—Ph | H | O | H | bond | 2,4-difluorophenyl | [$CDCl_3$] 1.83 (s, 3H); 3.28 (d, 1H); 3.89 (d, 1H); 6.88 (m, 2H); 7.42 (m, 1H); 7.54 (m, |

TABLE 1-continued

Compounds of the general formula (I) according to the invention in which $R^2$ is hydrogen and $R^3$ is methyl and aryl is the radical

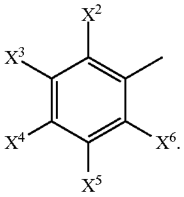

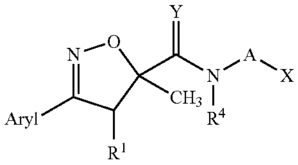

| No. | Aryl | $R^1$ | Y | $R^4$ | A | X | Physical data |
|---|---|---|---|---|---|---|---|
| | | | | | | | 2H); 8.22 (m, 1H); 8.71 (br, 1H). |
| 1.033 | 3,5-$Cl_2$—Ph | H | O | H | bond | 2-carboxyphenyl | [$CDCl_3$] 1.85 (s, 3H); 3.27 (d, 1H); 3.89 (d, 1H); 7.17 (m, 1H); 7.39 (m, 1H); 7.56 (m, 2H); 7.59 (m, 1H); 8.11 (m, 1H); 8.72 (m, 1H). |
| 1.034 | 3,5-$Cl_2$—Ph | H | O | H | bond | 2-chloropyridin-3-yl | [DMSO-$D_6$] 1.70 (s, 3H); 3.56 (d, 1H); 3.92 (d, 1H); 7.47 (m, 1H); 7.77 (m, 3H); 8.14 (m, 1H); 8.27 (m, 1H); 9.75 (s, 1H). |
| 1.035 | 3,5-$Cl_2$—Ph | H | O | H | bond | 3-(2-methoxy-2-oxoethyl)phenyl | [$CDCl_3$] 1.82 (s, 3H); 3.25 (d, 1H); 3.62 (s, 2H); 3.70 (s, 3H); 3.89 (d, 1H); 7.17 (d, 1H); 7.29 (t, 1H); 7.42 (m, 1H); 7.52 (m, 4H); 8.54 (s br, 1H) |
| 1.036 | 3,5-$Cl_2$—Ph | H | O | H | bond | 3-(carboxymethyl)-phenyl | [$CDCl_3$] 1.72 (s, 3H); 3.26 (d, 1H); 3.67 (s, 2H); 3.89 (d, 1H); 7.08 (d, 2H); 7.32 (t, 1H); 7.42 (m, 1H); 7.53 (m, 2H); 7.58 (t, 1H); 8.56 (s br, 1H) |
| 1.037 | 3,5-$Cl_2$—Ph | H | O | H | bond | 3-(ethoxy-carbonyl)-1H-1,2,4-triazol-5-yl | [$CDCl_3$] 9.83 0.37; 8.10 0.87; 8.08 0.93; 7.88 0.87; 7.86 0.96; 7.61 0.45; 7.60 0.45; 7.59 0.64; 7.59 0.77; 7.58 0.42; 7.57 0.52; 7.57 0.50; 7.53 0.59; 7.52 7.75; 7.51 8.30; 7.49 0.56; 7.48 0.54; 7.47 0.47; 7.47 0.77; 7.46 0.56; 7.45 0.49; 7.45 0.50; 7.44 2.26; 7.43 3.76; 7.43 1.92; 7.26 40.94; 6.75 0.35; 6.37 3.06; 4.49 1.61; 4.48 5.10; 4.46 5.16; 4.44 1.70; 3.88 2.56; 3.83 3.00; 3.38 3.02; 3.34 2.60; 2.04 0.39; 1.85 16.00; 1.83 0.62; 1.72 0.50; 1.69 0.50; 1.59 0.50; 1.57 0.61; 1.45 5.42; 1.43 11.15; 1.41 5.36; 1.40 0.33; 1.27 0.40; 1.26 1.56; 0.01 0.43; 0.00 16.68; −0.01 0.63 |
| 1.038 | 3,5-$F_2$—Ph | H | O | H | bond | 3-(ethoxy-carbonyl)-1H-1,2,4-triazol-5-yl | [$CDCl_3$] 1.44 (t, 3H); 1.84 (s, 3H); 3.34 (d, 1H); 3.84 (d, 1H); 4.47 (q, 2H); 6.89 (m, 1H); 7.17 (m, 2H); 9.80 (sbr, 1H); 11.65 (sbr, 1H). |
| 1.039 | 3,5-$Cl_2$—Ph | H | O | H | bond | 3-(methoxy-carbonyl)phenyl | [$CDCl_3$] 1.84 (s, 3H); 3.27 (d, 3H); 3.22 (d, 1H); 3.90 (d, 1H); 3.91 (s, 3H); 7.22 (m, 1H); 7.42 (m, 1H); 7.51 (m, 2H); 7.83 (d, 1H); 7.88 (d, 1H); 8.16 (s, 1H); 8.63 (s, 1H). |
| 1.040 | 3-F—Ph | H | O | H | bond | 3-(methoxy-carbonyl)phenyl | [$CDCl_3$] 1.83 (t, 3H); 3.32 (d, 1H); 3.92 (s, 3H); 3.93 (d, 1H); 7.15 (m. 1H); 7.40 (m, 4H); 7.83 (d, 1H); 7.88 (d, 1H); 8.17 (s, 1H); 8.72 (s br, 1H). |

TABLE 1-continued

Compounds of the general formula (I) according to the invention in which $R^2$ is hydrogen and $R^3$ is methyl and aryl is the radical

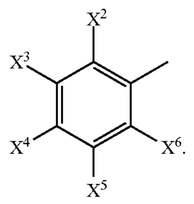

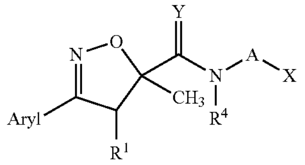

| No. | Aryl | $R^1$ | Y | $R^4$ | A | X | Physical data |
|---|---|---|---|---|---|---|---|
| 1.041 | 3-F—Ph | H | O | H | bond | 3-(methyl-carbamoyl)phenyl | [$CDCl_3$] 1.86 (s, 3H); 3.00 (d, 3H); 3.32 (d, 1H); 3.92 (d, 1H); 6.13 (bs, 1H); 7.14 (bs, 1H); 7.40 (m, 4H); 7.56 (d, 1H); 7.68 (d, 1H); 8.04 (s, 1H); 8.71 (m, 1H). |
| 1.042 | 3,5-$Cl_2$—Ph | H | O | H | bond | 3,5-dichlorophenyl | [$CDCl_3$] 1.82 (s, 3H); 3.28 (d, 1H); 3.87 (d, 1H); 7.13 (s, 1H); 7.43 (s, 1H); 7.52 (s, 2H); 7.55 (s, 2H); 8.57 (s, 1H). |
| 1.043 | 3,5-$Cl_2$—Ph | H | O | H | bond | 3,5-dimethoxyphenyl | [$CDCl_3$] 1.82 (s, 3H); 3.25 (d, 1H); 3.78 (s, 6H); 3.88 (d, 1H); 6.26 (t, 1H); 6.32 (d, 2H); 7.43 (m, 1H); 7.54 (m, 2H); 8.50 (s br, 1H). |
| 1.044 | Ph | H | O | H | bond | 3,5-dimethyl-1H-pyrazol-4-yl | [$CDCl_3$] 1.83 (s, 3H); 2.14 (s, 6H); 3.32 (d, 1H); 3.91 (d, 1H); 7.44 (m, 3H); 7.68 (m, 2H); 7.96 (s, 1H). |
| 1.045 | 3,5-$Cl_2$—Ph | H | O | H | bond | 3,5-dimethyl-1H-pyrazol-4-yl | [$CDCl_3$] 1.74 (s, 3H); 2.13 (s, 6H); 3.26 (d, 1H); 3.49 (s, 1H); 3.85 (d, 1H); 7.43 (m, 1H); 7.53 (m, 2H); 7.88 (s, 1H). |
| 1.046 | 3-F—Ph | H | O | H | bond | 3,5-dimethyl-1H-pyrazol-4-yl | [$CDCl_3$] 1.73 (s, 3H); 2.14 (s, 6H); 3.31 (d, 1H); 3.78 (s, 3H); 3.89 (d, 1H); 7.15 (m, 1H); 7.40 (m, 3H); 7.92 (brs, 1H). |
| 1.047 | 3,5-$Cl_2$—Ph | H | O | H | bond | 3-[2-(methylamino)-2-oxoethyl]phenyl | [$CDCl_3$] 1.72 (s, 3H); 2.77 (d, 3H); 3.28 (d, 1H); 3.57 (s, 2H); 3.88 (d, 1H); 5.36 (s br, 1H); 7.15 (d, 1H); 7.34 (m, 1H); 7.44 (m, 1H); 7.49 (dd, 1H); 7.52 (m, 1H); 8.58 (s, 1H) |
| 1.048 | 3,5-$Cl_2$—Ph | H | O | H | bond | 3-carboxyphenyl | [$CDCl_3$] 1.84 (t, 3H); 3.30 (d, 1H); 3.92 (d, 1H); 7.43 (m, 1H); 7.48 (d, 1H); 7.52 (d, 1H); 7.53 (m, 1H); 7.86 (d, 1H); 8.02 (d, 1H); 8.25 (m, 1H); 8.83 (s, 1H). |
| 1.049 | 3-F—Ph | H | O | H | bond | 3-carboxyphenyl | [$CDCl_3$] 1.85 (s, 3H); 3.36 (d, 1H); 3.95 (d, 1H); 7.15 (m, 1H); 7.40 (m, 4H); 7.86 (dd, 1H); 8.15 (dd, 1H); 8.36 (m, 1H); 9.11 (s, 1H). |
| 1.050 | 3,5-$Cl_2$—Ph | H | O | H | bond | 3-chloropyridin-2-yl | [$CDCl_3$] 1.88 (s, 3H); 3.29 (d, 1H); 3.96 (d, 1H); 7.02 (m, 1H); 7.42 (m, 1H); 7.55 (m, 2H); 7.91 (m, 1H); 8.46 (m, 1H); 9.38 (br, 1H). |
| 1.051 | 3,5-$Cl_2$—Ph | H | O | H | bond | 3-cyclopropyl-1,2,4-thiadiazol-5-yl | [$CDCl_3$] 1.04 (m, 4H); 1.84 (s, 3H); 2.22 (m, 1H); 3.35 (d, 1H); 3.86 (d, 1H); 7.43 (t, 1H); 7.52 (d, 2H) |
| 1.052 | 3,5-$Cl_2$—Ph | H | O | H | bond | 3-methyl-1,2-oxazol-5-yl | [$CDCl_3$] 9.28 1.09; 7.53 6.35; 7.52 6.97; 7.44 1.83; 7.43 3.07; 7.43 1.49; 7.26 11.05; 6.25 |

TABLE 1-continued

Compounds of the general formula (I) according to the invention in which $R^2$ is hydrogen and $R^3$ is methyl and aryl is the radical

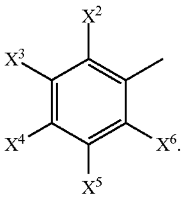

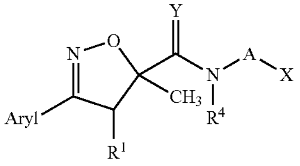

| No. | Aryl | $R^1$ | Y | $R^4$ | A | X | Physical data |
|---|---|---|---|---|---|---|---|
| | | | | | | | 4.72; 5.30 1.52; 3.87 2.47; 3.83 2.88; 3.33 2.69; 3.28 2.33; 2.27 16.00; 1.82 14.13; 1.58 7.64; 0.00 6.41 |
| 1.053 | 3,5-$Cl_2$—Ph | H | O | H | bond | 3-methyl-1-propyl-1H-pyrazol-4-yl | [$CDCl_3$] 8.19 1.25; 7.88 4.51; 7.53 6.29; 7.53 6.93; 7.52 1.04; 7.43 1.72; 7.42 3.18; 7.42 1.50; 7.31 0.69; 7.26 158.03; 7.21 0.67; 7.00 0.86; 3.98 2.29; 3.96 3.86; 3.94 2.36; 3.88 2.48; 3.84 2.80; 3.28 2.69; 3.24 2.30; 2.23 16.00; 2.04 0.34; 1.87 1.36; 1.85 2.45; 1.83 2.59; 1.81 15.35; 1.79 0.38; 1.59 0.37; 1.55 0.41; 1.55 0.48; 1.54 0.53; 1.54 0.66; 1.54 0.85; 1.54 1.20; 1.54 88.62; 1.53 0.97; 1.53 0.76; 1.53 0.65; 1.53 0.57; 1.53 0.56; 1.52 0.44; 1.52 0.37; 1.49 0.36; 1.26 0.38; 0.92 4.16; 0.90 8.51; 0.88 3.96; 0.15 0.41; 0.05 0.43; 0.01 2.52; 0.01 1.05; 0.01 1.17; 0.00 92.27; −0.01 2.32; −0.01 3.10; −0.05 0.36; −0.15 0.41 |
| 1.054 | 3,5-$F_2$—Ph | H | O | H | bond | 3-methyl-1-propyl-1H-pyrazol-4-yl | [$CDCl_3$] 8.20 1.24; 7.89 4.62; 7.52 0.39; 7.26 70.62; 7.19 1.48; 7.18 2.10; 7.17 2.06; 7.16 1.72; 7.15 0.38; 7.00 0.40; 6.92 0.36; 6.91 0.67; 6.90 0.36; 6.89 0.75; 6.89 1.34; 6.88 0.72; 6.87 0.39; 6.87 0.67; 6.86 0.36; 3.98 2.32; 3.96 4.25; 3.94 2.45; 3.87 2.47; 3.83 2.85; 3.28 2.74; 3.24 2.39; 2.23 16.00; 1.87 1.40; 1.85 2.73; 1.83 2.81; 1.81 15.25; 1.79 0.41; 1.79 0.33; 1.54 11.23; 1.26 0.38; 0.92 4.08; 0.90 8.22; 0.88 4.12; 0.01 1.18; 0.00 47.59; −0.01 1.98 |
| 1.055 | 3-F—Ph | H | O | H | bond | 3-methyl-1-propyl-1H-pyrazol-4-yl | [$CDCl_3$] 8.25 1.16; 7.89 4.56; 7.41 0.97; 7.40 1.68; 7.40 1.16; 7.39 3.93; 7.38 2.57; 7.38 1.50; 7.26 17.75; 7.16 0.41; 7.15 0.53; 7.15 0.57; 7.14 0.83; 7.13 0.76; 7.13 0.53; 7.12 0.59; 7.11 0.35; 3.98 2.33; 3.96 4.17; 3.94 2.43; 3.90 2.49; 3.86 2.85; 3.32 2.77; 3.27 2.42; 2.23 16.00; 1.86 1.39; 1.85 2.69; 1.83 2.75; 1.81 15.22; 1.79 0.38; 1.78 0.34; 1.58 3.63; 0.92 4.10; 0.90 8.22; 0.88 3.83; 0.00 9.09; −0.01 0.32 |
| 1.056 | Ph | H | O | H | bond | 3-methyl-1-propyl-1H-pyrazol-4-yl | [$CDCl_3$] 8.29 1.05; 7.89 4.33; 7.66 1.79; 7.66 2.23; 7.65 1.13; 7.64 2.14; 7.64 2.49; 7.52 0.46; 7.44 0.79; 7.43 4.89; 7.42 |

TABLE 1-continued

Compounds of the general formula (I) according to the invention in which $R^2$ is hydrogen and $R^3$ is methyl and aryl is the radical

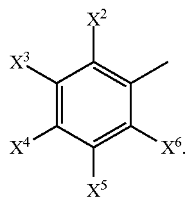

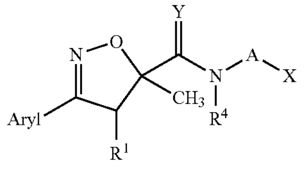

| No. | Aryl | $R^1$ | Y | $R^4$ | A | X | Physical data |
|---|---|---|---|---|---|---|---|
| | | | | | | | 2.14; 7.41 2.48; 7.39 0.62; 7.39 0.45; 7.26 80.36; 7.00 0.44; 3.98 2.21; 3.96 3.93; 3.94 2.31; 3.93 2.54; 3.89 2.86; 3.34 2.75; 3.30 2.38; 2.23 15.40; 2.04 0.59; 1.86 1.31; 1.85 2.54; 1.83 2.61; 1.81 16.00; 1.79 0.38; 1.78 0.35; 1.54 9.85; 1.26 0.42; 0.92 4.03; 0.90 8.15; 0.88 3.80; 0.01 1.47; 0.00 55.99; −0.01 1.90; −0.01 1.93 |
| 1.057 | 3,5-$Cl_2$—Ph | H | O | H | bond | 4-(2-ethoxy-2-oxoethyl)phenyl | [$CDCl_3$] 1.23 (t, 3H); 1.81 (s, 3H); 3.26 (d, 1H); 3.56 (s, 2H); 3.90 (d, 1H); 4.12 (q, 2H); 7.26 (m, 2H); 7.41 (m, 1H); 7.53 (m, 4H), 8.53 (s br, 1H) |
| 1.058 | 3,5-$Cl_2$—Ph | H | O | H | bond | 4-(carboxymethyl)-phenyl | [$CDCl_3$] 1.70 (s, 3H); 3.27 (d, 1H); 3.64 (s, 2H); 3.88 (d, 1H); 7.28 (m, 2H); 7.43 (t, 1H), 7.54 (m, 4H); 8.55 (s, 1H) |
| 1.059 | 3,5-$F_2$—Ph | H | O | H | bond | 4-(methoxy-carbonyl)-3-thienyl | [$CDCl_3$] 11.22 0.73; 8.06 1.57; 8.06 3.85; 8.04 3.37; 8.04 1.35; 7.26 12.82; 7.21 1.26; 7.20 1.51; 7.20 0.92; 7.19 0.88; 7.19 1.55; 7.18 1.25; 6.88 0.55; 6.87 0.62; 6.86 1.10; 6.86 0.55; 6.85 0.32; 6.84 0.55; 3.95 16.00; 3.89 2.07; 3.85 2.36; 3.29 2.17; 3.25 1.91; 1.84 11.83; 1.58 4.96; 0.00 5.75 |
| 1.060 | 3,5-$Cl_2$—Ph | H | O | H | bond | 4-(methoxy-carbonyl)phenyl | [$CDCl_3$] 1.83 (s, 3H); 3.29 (d, 1H); 3.90 (d, 1H); 3.90 (s, 3H); 7.42 (m, 1H); 7.53 (m, 2H); 7.66 (d, 2H); 8.03 (d, 2H); 8.71 (br, 1H). |
| 1.061 | 3,5-$Cl_2$—Ph | H | O | H | bond | 4,5-dimethyl-4H-1,2,4-triazol-3-yl | [$CDCl_3$] 7.55 6.58; 7.55 6.74; 7.38 2.32; 7.38 4.04; 7.37 2.04; 7.26 28.18; 6.37 0.36; 4.00 2.31; 3.96 2.54; 3.82 0.38; 3.76 0.35; 3.75 0.34; 3.49 0.49; 3.48 13.57; 3.18 0.77; 3.18 2.92; 3.16 0.52; 3.15 0.48; 3.13 2.75; 2.41 14.12; 1.77 16.00; 1.72 0.39; 1.64 0.91; 1.62 1.78; 1.60 3.89; 1.59 3.10; 1.50 3.19; 1.48 3.16; 1.25 1.28; 0.00 5.06 |
| 1.062 | 3,5-$F_2$—Ph | H | O | H | bond | 4,5-dimethyl-4H-1,2,4-triazol-3-yl | [$CDCl_3$] 1.78 (s, 3H); 2.39 (s, 3H); 3.17 (d, 1H); 3.45 (s, 3H); 3.96 (d, 1H); 6.87 (brt, 1H); 7.21 (d, 2H). |
| 1.063 | 3,5-$Cl_2$—Ph | H | O | H | bond | 4,6-dimethoxy-pyrimidin-2-yl | [$CDCl_3$] 1.83 (s, 3H); 3.26 (d, 1H); 3.95 (s, 6H); 3.96 (d, 1H); 5.80 (s, 1H); 7.43 (s, 1H); 7.53 (s, 2H), |
| 1.064 | 3,5-$Cl_2$—Ph | H | O | H | bond | 4-carboxyphenyl | [$CDCl_3$] 1.84 (t, 3H); 3.30 (d, 1H); 3.90 (d, 1H); 7.43 (m, 1H); 7.48 (d, 1H); 7.52 (d, 1H); |

TABLE 1-continued

Compounds of the general formula (I) according to the invention in which $R^2$ is hydrogen and $R^3$ is methyl and aryl is the radical

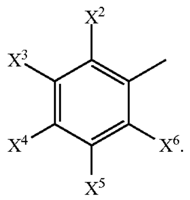

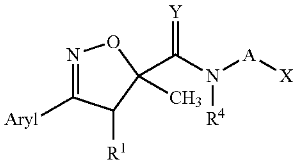

| No. | Aryl | $R^1$ | Y | $R^4$ | A | X | Physical data |
|---|---|---|---|---|---|---|---|
| | | | | | | | 7.53 (m, 1H); 7.71 (d, 2H); 8.08 (d, 2H); 8.73 (s, 1H). |
| 1.065 | 3,5-$Cl_2$—Ph | H | O | H | bond | 4-chloro-2-(methoxy-carbonyl)-6-methylphenyl | [$CDCl_3$] 1.84 (s, 3H), 2.20 (s, 3H); 3.24 (d, 1H); 3.85 (d, 1H); 3.85 (s, 3H); 7.42 (m, 2H); 7.56 (d, 2H); 7.78 (d, 1H); 9.57 (s, 1H) |
| 1.066 | 3,5-$Cl_2$—Ph | H | O | H | bond | 4-chloro-2-methyl-6-(methyl-carbamoyl)phenyl | [$CDCl_3$] 1.72 (s, 3H), 2.19 (s, 3H); 2.85 (d, 3H); 3.22 (d, 1H); 3.83 (d, 1H); 5.97 (m br, 1H); 7.28 (m, 2H); 7.42 (t, 1H); 7.57 (d, 2H); 9.18 (s, 1H) |
| 1.067 | 3,5-$Cl_2$—Ph | H | O | H | bond | 4-chlorophenyl | [$CDCl_3$] 1.82 (s, 3H); 3.28 (d, 1H); 3.89 (d, 1H); 7.30 (m, 2H); 7.43 (m, 1H); 7.54 (m, 4H); 8.55 (br, 1H). |
| 1.068 | 3,5-$Cl_2$—Ph | H | O | H | bond | 4-chloropyridin-2-yl | [$CDCl_3$] 1.81 (s, 3H); 3.28 (d, 1H); 3.87 (d, 1H); 7.09 (m, 1H); 7.42 (m, 1H); 7.53 (m, 2H); 8.21 (d, 1H); 8.28 (d, 1H); 9.17 (br, 1H). |
| 1.069 | 3,5-$F_2$—Ph | H | O | H | bond | 4-cyano-1-ethyl-1H-pyrazol-3-yl | [$CDCl_3$] 8.85 1.26; 7.76 5.35; 7.26 18.75; 7.19 1.72; 7.18 2.11; 7.18 1.30; 7.17 1.32; 7.17 2.19; 7.16 1.72; 7.15 0.33; 6.92 0.43; 6.92 0.75; 6.91 0.39; 6.90 0.85; 6.89 1.49; 6.89 0.75; 6.88 0.45; 6.87 0.75; 6.87 0.37; 4.15 1.35; 4.13 4.20; 4.11 4.28; 4.10 1.43; 3.94 2.78; 3.89 3.17; 3.31 2.99; 3.27 2.62; 2.05 0.42; 1.85 16.00; 1.58 4.82; 1.51 4.92; 1.49 10.24; 1.47 4.81; 0.00 4.71 |
| 1.070 | 3,5-$Cl_2$—Ph | H | O | H | bond | 4-cyano-1H-pyrazol-3-yl | [$CDCl_3$] 1.85 (s, 3H); 3.34 (d, 1H); 3.88 (d, 1H); 7.45 (m, 1H); 7.54 (m, 2H); 7.78 (s, 1H); 9.29 (s, 1H). |
| 1.071 | Ph | H | O | H | bond | 4-cyano-1H-pyrazol-3-yl | [$CDCl_3$] 1.85 (s, 3H); 3.40 (d, 1H); 3.93 (d, 1H); 7.44 (m, 3H); 7.67 (m, 2H); 7.76 (s, 1H); 9.43 (brs, 1H). |
| 1.072 | 3-F—Ph | H | O | H | bond | 4-cyano-1H-pyrazol-3-yl | [$CDCl_3$] 1.86 (s, 3H); 3.39 (d, 1H); 3.95 (d, 1H); 7.17 (m, 1H); 7.40 (m, 3H); 7.82 (m, 1H; 9.64 (brs, 1H). |
| 1.073 | 3,5-$Cl_2$—Ph | H | O | H | bond | 4-ethylpyridin-2-yl | [$CDCl_3$] 1.25 (t, 3H); 1.81 (s, 3H); 2.66 (q, 2H); 3.26 (d, 1H); 3.88 (d, 1H); 6.92 (d, 1H); 7.40 (m, 1H); 7.52 (m, 2H); 8.05 (s, 1H); 8.19 (d, 1H); 9.09 (bs, 1H). |
| 1.074 | 3,5-$F_2$—Ph | H | O | H | bond | 4-formyl-3-(1-methylcyclo-propyl)-1,2-oxazol-5-yl | [$CDCl_3$] 0.88 (t, 2H); 1.11 (t, 2H); 1.51 (s, 3H); 1.84 (s, 3H); 3.31 (d, 1H); 3.88 (d, 1H); 6.90 (t, 1H); 7.18 (q, 2H); 9.91 (s, 1H); 11.32 (s, 1H). |

TABLE 1-continued

Compounds of the general formula (I) according to the invention in which $R^2$ is hydrogen and $R^3$ is methyl and aryl is the radical

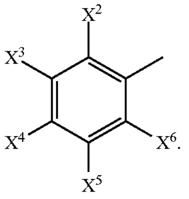

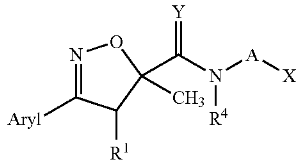

| No. | Aryl | $R^1$ | Y | $R^4$ | A | X | Physical data |
|---|---|---|---|---|---|---|---|
| 1.075 | 3,5-$Cl_2$—Ph | H | O | H | bond | 4-methoxypyridin-2-yl | [CD3OD] 1.79 (s, 3H); 3.48 (d, 1H); 3.90 (s, 3H); 3.93 (d, 1H); 6.78 (m, 1H); 7.56 (m, 1H); 7.69 (m, 2H); 7.78 (m, 1H); 8.13 (d, 1H). |
| 1.076 | 3,5-$Cl_2$—Ph | H | O | H | bond | 4-methyl-1,2,5-oxadiazol-3-yl | [$CDCl_3$] 8.82 0.79; 7.54 5.03; 7.53 5.61; 7.45 1.46; 7.45 2.41; 7.45 1.17; 7.26 9.40; 3.88 1.96; 3.84 2.28; 3.35 2.09; 3.30 1.80; 2.40 16.00; 1.85 11.21; 1.57 6.00; 0.00 5.05 |
| 1.077 | 3,5-$F_2$—Ph | H | O | H | bond | 4-methyl-1,3-thiazol-2-yl | [$CDCl_3$] 9.85 0.50; 7.26 10.92; 7.17 1.63; 7.17 2.05; 7.16 1.26; 7.15 2.08; 7.15 1.64; 6.91 0.39; 6.91 0.71; 6.90 0.37; 6.89 0.80; 6.89 1.43; 6.88 0.71; 6.87 0.41; 6.87 0.71; 6.86 0.35; 6.57 2.96; 6.57 2.81; 3.88 2.72; 3.84 3.15; 3.32 2.99; 3.28 2.58; 2.35 11.96; 2.35 10.98; 1.83 16.00; 1.62 1.46; 0.00 5.18 |
| 1.078 | 3,5-$Cl_2$—Ph | H | O | H | bond | 4-methyl-1,3-thiazol-2-yl | [$CDCl_3$] 9.83 0.74; 8.03 0.38; 7.69 0.34; 7.67 0.39; 7.57 0.42; 7.55 0.33; 7.52 7.46; 7.52 7.78; 7.42 3.33; 7.42 3.30; 7.31 0.51; 7.26 151.54; 7.26 143.68; 6.99 0.80; 6.57 4.28; 6.23 1.57; 3.88 2.58; 3.84 2.97; 3.32 2.87; 3.28 2.60; 2.35 16.00; 1.83 15.60; 1.55 28.18; 1.51 0.42; 1.30 0.33; 1.26 0.82; 0.90 0.43; 0.88 0.74; 0.86 0.46; 0.15 0.33; 0.00 50.62; 0.00 47.33 |
| 1.079 | Ph | H | O | H | bond | 4-methylpyridin-2-yl | [$CDCl_3$] 1.71 (s, 3H); 2.35 (s, 3H); 3.32 (d, 1H); 3.92 (d, 1H); 6.89 (d, 1H); 7.38-7.43 (m, 3H); 7.65 (m, 2H); 8.04 (s, 1H); 8.16 (d, 1H); 9.18 (br, 1H). |
| 1.080 | 2,4-$Cl_2$—Ph | H | O | H | bond | 4-methylpyridin-2-yl | [D4-MeOD] 1.65 (s, 3H); 2.35 (s, 3H); 3.36 (d, 1H); 3.89 (d, 1H); 6.68 (br, 2H); 7.41 (dd, 1H); 7.58 (d, 1H); 7.62 (d, 1H); 7.72 (d, 1H). |
| 1.081 | 3,5-$Cl_2$—Ph | H | O | H | bond | 4-methylpyridin-2-yl | [$CDCl_3$] 1.81 (s, 3H); 2.36 (s, 3H); 3.27 (d, 1H); 3.88 (d, 1H); 6.90 (d, 1H); 7.40 (m, 1H); 7.53 (m, 2H); 8.01 (s, 1H); 8.17 (d, 1H); 9.08 (s, 1H). |
| 1.082 | 3,5-$Cl_2$—Ph | H | O | H | bond | 4-pentylpyridin-2-yl | [$CDCl_3$] 9.36 0.32; 8.18 1.84; 8.18 2.22; 8.17 1.90; 8.17 2.27; 8.07 2.37; 8.07 2.48; 8.07 2.12; 7.54 8.47; 7.53 9.66; 7.52 1.72; 7.41 2.20; 7.41 4.20; 7.40 1.89; 7.36 0.39; 7.31 1.15; 7.31 0.64; 7.31 0.49; 7.31 0.45; 7.30 |

TABLE 1-continued

Compounds of the general formula (I) according to the invention in which $R^2$ is hydrogen and $R^3$ is methyl and aryl is the radical

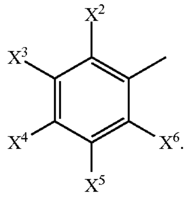

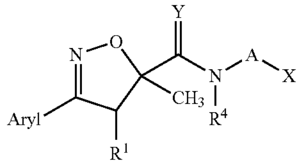

| No. | Aryl | $R^1$ | Y | $R^4$ | A | X | Physical data |
|---|---|---|---|---|---|---|---|
| | | | | | | | 0.38; 7.29 0.33; 7.29 0.32; 7.29<br>0.32; 7.29 0.35; 7.28 0.33; 7.28<br>0.37; 7.28 0.38; 7.28 0.42; 7.28<br>0.41; 7.28 0.52; 7.28 0.50; 7.28<br>0.50; 7.27 0.48; 7.27 0.56; 7.27<br>0.59; 7.27 0.62; 7.27 0.58; 7.27<br>0.68; 7.27 0.68; 7.27 0.85; 7.27<br>0.99; 7.27 1.15; 7.27 1.26; 7.27<br>1.44; 7.26 1.85; 7.26 2.37; 7.26<br>3.26; 7.26 4.79; 7.26 9.08; 7.26<br>326.48; 7.25 3.71; 7.25<br>2.57; 7.25 1.96; 7.25 1.40; 7.25<br>1.01; 7.25 0.69; 7.25 0.73; 7.25<br>0.48; 7.25 0.50; 7.25 0.43; 7.00<br>1.74; 6.94 1.41; 6.94 1.44; 6.93<br>1.36; 6.92 1.40; 3.91 2.92; 3.87<br>3.28; 3.29 3.00; 3.24 2.62; 2.64<br>1.69; 2.62 2.03; 2.60 1.81; 1.83<br>16.00; 1.71 7.73; 1.68 0.67; 1.66<br>1.02; 1.64 1.20; 1.62 0.65; 1.62<br>0.92; 1.60 0.41; 1.36 0.35; 1.34<br>1.14; 1.34 1.84; 1.33 3.23; 1.32<br>2.98; 1.31 2.13; 1.30 0.72; 1.29<br>0.39; 1.28 0.36; 1.26 1.46; 1.00<br>0.66; 0.90 2.08; 0.89 7.05; 0.87<br>2.04; 0.15 0.46; 0.05 0.45; 0.03<br>0.40; 0.01 0.35; 0.01 4.35; 0.01<br>1.67; 0.01 0.87; 0.00 0.87; 0.00<br>1.08; 0.00 2.04; 0.00 3.81; 0.00<br>160.54; 0.00 67.27; 0.00<br>5.98; 0.00 3.73; −0.01 2.44; −0.01<br>1.84; −0.01 1.46; −0.01 4.79;<br>−0.01 2.37; −0.01 1.79; −0.01<br>0.85; −0.01 0.74; −0.01 0.61;<br>−0.01 0.52; −0.01 0.46; −0.02<br>0.42; −0.02 0.41; −0.02 0.36;<br>−0.15 0.46 |
| 1.083 | 2,4-$Cl_2$—Ph | H | O | H | bond | 4-pentylpyridin-2-yl | [$CDCl_3$] 9.11 1.10; 8.20<br>2.11; 8.18 2.15; 8.05 2.58; 8.05<br>2.52; 7.62 3.11; 7.59 3.52; 7.52<br>0.48; 7.45 2.94; 7.44 3.16; 7.29<br>2.13; 7.29 1.99; 7.27 2.11; 7.27<br>2.69; 7.26 81.13; 7.00 0.47; 6.92<br>1.43; 6.91 1.40; 6.91 1.42; 6.90<br>1.37; 4.05 2.97; 4.01 3.45; 3.52<br>3.29; 3.47 2.82; 2.63 1.84; 2.61<br>2.24; 2.59 1.96; 1.82 16.00; 1.68<br>0.37; 1.66 0.97; 1.64 1.24; 1.62<br>0.67; 1.62 0.96; 1.60 0.39; 1.55<br>35.26; 1.36 0.33; 1.34 2.16; 1.33<br>2.55; 1.32 3.37; 1.31 1.85; 1.30<br>0.84; 1.26 0.37; 0.91 2.14; 0.89<br>6.37; 0.88 0.87; 0.87 2.01; 0.01<br>1.01; 0.00 33.60; −0.01 0.97 |

TABLE 1-continued

Compounds of the general formula (I) according to the invention in which $R^2$ is hydrogen and $R^3$ is methyl and aryl is the radical

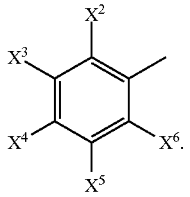

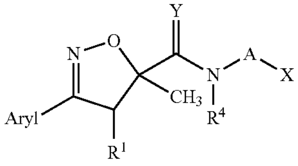

| No. | Aryl | $R^1$ | Y | $R^4$ | A | X | Physical data |
|---|---|---|---|---|---|---|---|
| 1.084 | 3,5-$Cl_2$—Ph | H | O | H | bond | 5-(methoxy-carbonyl)-1,3-thiazol-4-yl | [$CDCl_3$] 1.87 (s, 3H); 3.29 (d, 1H); 3.95 (d, 1H); 3.97 (s, 3H); 7.41 (m, 1H); 7.55 (m, 2H); 8.86 (s, 1H); 11.15 (s, 1H). |
| 1.085 | 3,5-$F_2$—Ph | H | O | H | bond | 5-(methoxy-carbonyl)-1,3-thiazol-4-yl | [$CDCl_3$] 1.88 (s, 3H); 3.28 (d, 1H); 3.95 (d, 1H); 3.97 (s, 3H); 6.88 (m, 1H); 7.20 (m, 2H); 8.87 (s, 1H); 11.16 (s, 1H). |
| 1.086 | 3,5-$Cl_2$—Ph | H | O | H | bond | 5-chloro-4-methylpyridin-2-yl | [$CDCl_3$] 1.81 (s, 3H); 2.39 (s, 3H); 3.28 (d, 1H); 3.87 (d, 1H); 7.41 (m, 1H); 7.52 (m, 2H); 8.12 (s, 1H); 8.20 (s, 1H); 9.08 (br, 1H). |
| 1.087 | 3,5-$Cl_2$—Ph | H | O | H | bond | 5-Fluor-4-methylpyridin-2-yl | [$CDCl_3$] 1.81 (s, 3H); 2.32 (s, 3H); 3.28 (d, 1H); 3.87 (d, 1H); 7.41 (m, 1H); 7.52 (m, 2H); 8.05 (s, 1H); 8.09 (d, 1H); 9.07 (br, 1H). |
| 1.088 | 3,5-$Cl_2$—Ph | H | O | H | bond | 5-methoxy-1-methyl-1H-1,2,4-triazol-3-yl | [$CDCl_3$] 1.80 (s, 3H); 3.24 (d, 1H); 3.58 (s, 3H); 3.91 (d, 1H); 4.08 (s, 3H); 7.41 (m, 1H); 7.50 (m, 2H); 8.81 (sbr, 1H). |
| 1.089 | 3,5-$F_2$—Ph | H | O | H | bond | 5-methoxy-1-methyl-1H-1,2,4-triazol-3-yl | [$CDCl_3$] 8.84 1.11; 7.52 0.34; 7.52 0.43; 7.26 59.24; 7.26 74.44; 7.16 1.61; 7.16 1.79; 7.16 1.82; 7.15 1.64; 7.14 1.94; 7.14 1.59; 7.14 1.25; 7.00 0.35; 7.00 0.40; 6.91 0.35; 6.90 0.55; 6.89 0.67; 6.88 0.94; 6.88 1.13; 6.88 0.55; 6.87 0.57; 6.86 0.35; 6.86 0.55; 4.07 12.92; 4.06 16.00; 3.96 0.37; 3.93 1.65; 3.93 2.01; 3.89 1.91; 3.89 2.26; 3.58 12.37; 3.58 15.11; 3.26 2.12; 3.22 1.84; 2.05 0.45; 2.04 0.55; 1.82 9.97; 1.81 11.73; 1.54 11.47; 1.54 13.70; 1.26 0.35; 0.01 0.43; 0.01 0.62; 0.00 16.33; 0.00 20.92; −0.01 0.88; −0.01 0.70 |
| 1.090 | Ph | H | O | H | bond | 5-methylpyridin-2-yl | [$CDCl_3$] 1.82 (s, 3H), 2.30 (s, 3H); 3.22 (d, 1H); 3.93 (d, 1H); 7.41 (m, 3H); 7.50 (m, 1H); 7.65 (m, 1H); 8.08 (d, 1H); 8.13 (d, 1H); 9.16 (s, 1H) |
| 1.091 | 3,5-$Cl_2$—Ph | H | O | H | bond | 6-chloropyridin-2-yl | [$CDCl_3$] 9.15 1.14; 8.14 2.35; 8.14 2.19; 8.12 2.60; 7.69 1.44; 7.67 2.72; 7.65 1.40; 7.53 7.23; 7.53 7.63; 7.42 2.01; 7.42 3.41; 7.41 1.68; 7.26 12.99; 7.12 2.56; 7.12 2.42; 7.10 2.43; 7.10 2.21; 5.30 0.50; 3.89 2.80; 3.85 3.20; 3.29 2.99; 3.25 2.62; 1.81 16.00; 1.56 8.95; 0.00 6.84 |
| 1.092 | 3,5-$Cl_2$—Ph | H | O | H | bond | 6-chloropyridin-3-yl | [$CDCl_3$] 1.82 (s, 3H); 3.30 (d, 1H); 3.89 (d, 1H); 7.30 (m, |

TABLE 1-continued

Compounds of the general formula (I) according to the invention in which $R^2$ is hydrogen and $R^3$ is methyl and aryl is the radical

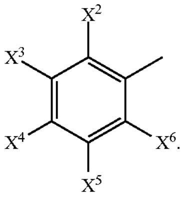

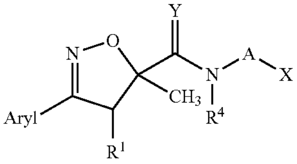

| No. | Aryl | $R^1$ | Y | $R^4$ | A | X | Physical data |
|---|---|---|---|---|---|---|---|
| | | | | | | | 1H); 7.43 (m, 1H); 7.54 (m, 2H); 8.12 (m, 1H); 8.50 (m, 1H); 8.62 (br, 1H). |
| 1.093 | 3,5-$Cl_2$—Ph | H | O | H | bond | pyridin-2-yl | [$CDCl_3$] 1.81 (s, 3H); 3.26 (d, 1H); 3.89 (d, 1H); 7.08 (m, 1H); 7.40 (m, 1H); 7.52 (m, 2H); 7.71 (m, 1H); 8.19 (d, 1H); 8.31 (d, 1H); 9.12 (bs, 1H). |
| 1.094 | 3,5-$Cl_2$—Ph | H | O | H | bond | pyridin-4-yl | [$CDCl_3$] 1.82 (s, 3H); 3.30 (d, 1H); 3.90 (d, 1H); 7.42 (s, 1H); 7.51 (m, 2H); 7. 52 (s, 2H); 8.54 (m, 2H); 8.67 (s, 1H). |
| 1.095 | 3,5-$F_2$—Ph | H | O | H | $CH_2$ | 1-(2,2,2-trifluoroethyl)-1H-pyrazol-4-yl | [$CDCl_3$] 7.51 3.82; 7.45 3.45; 7.26 19.66; 7.16 1.66; 7.16 2.08; 7.14 2.17; 7.14 1.67; 7.04 0.63; 6.91 0.39; 6.91 0.71; 6.90 0.36; 6.89 0.78; 6.88 1.40; 6.88 0.71; 6.87 0.41; 6.86 0.71; 6.86 0.35; 4.68 1.28; 4.66 3.97; 4.64 4.04; 4.62 1.38; 4.41 0.83; 4.39 0.82; 4.37 1.49; 4.36 1.48; 4.28 1.51; 4.27 1.51; 4.25 0.85; 4.23 0.85; 3.80 2.66; 3.75 3.08; 3.22 2.91; 3.17 2.54; 1.73 16.00; 1.57 10.03; 1.26 0.40; 0.00 8.60 |
| 1.096 | 3,5-$F_2$—Ph | H | O | H | $CH_2$ | 1-(2-chloroethyl)-1H-pyrazol-4-yl | [$CDCl_3$] 7.47 3.82; 7.43 3.83; 7.26 16.45; 7.17 0.40; 7.17 0.38; 7.16 1.80; 7.15 2.23; 7.14 2.26; 7.13 1.76; 7.13 0.35; 7.12 0.35; 7.01 0.68; 7.00 0.52; 6.91 0.46; 6.90 0.78; 6.90 0.43; 6.89 0.91; 6.88 1.53; 6.87 0.80; 6.86 0.49; 6.86 0.77; 6.85 0.39; 4.39 2.86; 4.37 5.54; 4.36 3.27; 4.34 1.52; 4.27 1.50; 4.26 1.51; 4.24 0.81; 4.22 0.80; 3.86 3.10; 3.85 5.56; 3.83 2.86; 3.80 2.68; 3.76 3.06; 3.21 2.89; 3.17 2.51; 2.00 0.34; 1.78 0.63; 1.73 16.00; 0.00 7.97; −0.01 0.36 |
| 1.097 | 3,5-$Cl_2$—Ph | H | O | H | $CH_2$ | 1-(2-methoxy-2-oxoethyl)-1H-pyrazol-4-yl | [$CDCl_3$] 1.72 (s, 3H); 3.18 (d, 1H); 3.75 (s, 3H); 3.78 (d, 1H); 4.23 (dd, 1H); 4.39 (dd, 1H); 4.88 (s, 2H); 6.99 (brt, 1H); 7.40 (m, 2H); 7.48 (s, 1H); 7.52 (m, 2H). |
| 1.098 | 3,5-$F_2$—Ph | H | O | H | $CH_2$ | 1-(2-methoxy-2-oxoethyl)-1H-pyrazol-4-yl | [$CDCl_3$] 1.72 (s, 3H); 3.18 (d, 1H); 3.77 (s, 3H); 3.79 (d, 1H); 4.26 (dd, 1H); 4.38 (dd, 1H); 4.87 (s, 2H); 6.87 (m, 1H); 7.01 (brt, 1H); 7.15 (m, 2H); 7.41 (s, 1H); 7.47 (s, 1H). |
| 1.099 | 3-F—Ph | H | O | H | $CH_2$ | 1-(2-methoxy-2-oxoethyl)-1H-pyrazol-4-yl | [$CDCl_3$] 1.72 (s, 3H); 3.22 (d, 1H); 3.76 (s, 3H); 3.80 (d, 1H); 4.25 (dd, 1H); 4.38 (dd, 1H); |

TABLE 1-continued
Compounds of the general formula (I) according to the invention in which $R^2$ is hydrogen and $R^3$ is methyl and aryl is the radical
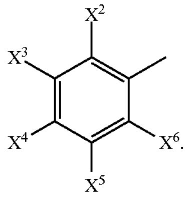
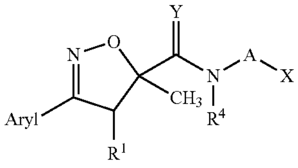
| No. | Aryl | $R^1$ | Y | $R^4$ | A | X | Physical data |
|---|---|---|---|---|---|---|---|
| | | | | | | | 4.86 (s, 2H); 7.05 (brt, 1H); 7.14 (m, 1H); 7.36 (m, 3H); 7.41 (s, 1H); 7.47 (s, 1H). |
| 1.100 | 3,5-$F_2$—Ph | H | O | H | $CH_2$ | 1-(3-carboxypropyl)-1H-pyrazol-4-yl | [$CDCl_3$] 7.52 0.80; 7.43 3.52; 7.35 3.53; 7.31 0.48; 7.30 0.41; 7.26 132.99; 7.18 0.37; 7.16 1.66; 7.16 2.27; 7.15 1.54; 7.14 2.20; 7.14 1.91; 7.13 0.40; 7.03 0.71; 7.00 0.81; 6.91 0.40; 6.91 0.67; 6.90 0.41; 6.89 0.89; 6.88 1.41; 6.88 0.81; 6.87 0.46; 6.86 0.73; 6.86 0.37; 4.36 0.61; 4.34 0.60; 4.32 1.51; 4.31 1.44; 4.28 1.45; 4.27 1.43; 4.24 0.65; 4.23 0.66; 4.21 2.07; 4.20 3.63; 4.18 2.12; 3.86 1.28; 3.82 2.41; 3.78 2.71; 3.49 0.46; 3.21 2.69; 3.17 2.34; 2.36 1.08; 2.35 1.11; 2.34 2.44; 2.34 2.30; 2.32 2.13; 2.19 0.76; 2.17 2.05; 2.16 2.61; 2.14 1.72; 2.12 0.64; 2.06 0.44; 2.00 0.94; 1.97 0.71; 1.95 0.74; 1.94 0.82; 1.89 1.11; 1.87 1.10; 1.84 1.17; 1.82 1.18; 1.81 1.16; 1.79 1.13; 1.78 1.14; 1.76 1.05; 1.73 16.00; 1.65 0.60; 1.62 0.51; 1.58 0.42; 1.56 0.44; 1.25 0.45; 0.01 2.40; 0.00 10.31; 0.00 64.67; −0.01 3.17 |
| 1.101 | 3,5-$F_2$—Ph | H | O | H | $CH_2$ | 1-(3-methoxy-3-oxopropyl)-1H-pyrazol-4-yl | [$CDCl_3$] 7.42 2.92; 7.39 2.88; 7.26 26.97; 7.17 1.60; 7.16 1.90; 7.16 1.14; 7.15 1.20; 7.15 1.91; 7.14 1.52; 6.96 0.56; 6.91 0.43; 6.90 0.71; 6.90 0.38; 6.89 0.83; 6.88 1.37; 6.87 0.69; 6.86 0.47; 6.86 0.70; 6.85 0.33; 4.39 2.18; 4.37 5.06; 4.35 2.58; 4.33 1.20; 4.32 1.19; 4.25 1.16; 4.23 1.22; 4.21 0.68; 4.20 0.73; 3.80 2.32; 3.76 2.66; 3.68 16.00; 3.67 1.65; 3.66 0.93; 3.65 0.82; 3.21 2.46; 3.17 2.15; 2.90 2.10; 2.88 4.20; 2.87 2.02; 1.88 0.33; 1.86 0.32; 1.85 0.35; 1.83 0.35; 1.82 0.35; 1.72 13.55; 0.01 0.44; 0.00 13.40; −0.01 0.51 |
| 1.102 | 3,5-$F_2$—Ph | H | O | H | $CH_2$ | 1-(4-methoxy-4-oxobutyl)-1H-pyrazol-4-yl | [DMSO-$D_6$] 8.45 0.48; 8.44 0.99; 8.42 0.50; 7.51 3.44; 7.40 2.14; 7.39 1.49; 7.38 2.21; 7.37 1.72; 7.36 0.78; 7.36 0.54; 7.28 3.79; 5.75 0.44; 4.12 2.40; 4.10 2.36; 4.05 1.74; 4.04 3.73; 4.02 1.80; 3.77 1.78; 3.72 2.18; 3.56 16.00; 3.39 2.12; 3.34 1.75; 3.31 18.05; 2.52 0.39; 2.51 7.75; 2.51 17.47; 2.50 25.14; 2.50 |

TABLE 1-continued

Compounds of the general formula (I) according to the invention in which $R^2$ is hydrogen and $R^3$ is methyl and aryl is the radical

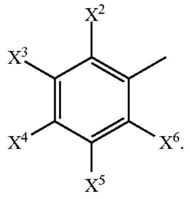

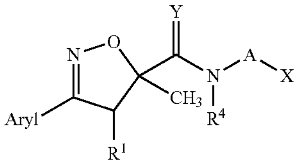

| No. | Aryl | $R^1$ | Y | $R^4$ | A | X | Physical data |
|---|---|---|---|---|---|---|---|
| | | | | | | | 18.54; 2.49 8.83; 2.24 1.53; 2.22 3.43; 2.21 2.02; 1.98 0.47; 1.96 1.62; 1.94 2.23; 1.92 1.38; 1.91 0.36; 1.55 10.93; 0.00 3.78 |
| 1.103 | 3,5-$F_2$—Ph | H | O | H | $CH_2$ | 1-(cyanomethyl)-1H-pyrazol-4-yl | [$CDCl_3$] 7.51 4.12; 7.50 4.02; 7.26 29.40; 7.18 0.33; 7.16 1.71; 7.16 2.21; 7.15 1.51; 7.15 2.17; 7.14 1.76; 7.13 0.41; 7.13 0.37; 7.07 0.71; 6.91 0.43; 6.91 0.72; 6.90 0.41; 6.89 0.85; 6.89 1.43; 6.88 0.76; 6.87 0.47; 6.86 0.72; 6.86 0.38; 5.04 0.40; 5.03 10.88; 5.01 0.34; 4.40 0.76; 4.39 0.77; 4.36 1.40; 4.35 1.38; 4.28 1.43; 4.26 1.44; 4.24 0.80; 4.23 0.79; 3.80 2.43; 3.75 2.82; 3.49 0.46; 3.22 2.68; 3.18 2.34; 1.79 0.38; 1.78 0.42; 1.73 16.00; 1.66 1.05; 0.00 13.18; −0.01 0.71 |
| 1.104 | 3,5-$Cl_2$—Ph | H | O | H | $CH_2$ | 1-(cyanomethyl)-1H-pyrazol-4-yl | [$CDCl_3$] 1.72 (s, 3H); 3.20 (d, 1H); 3.78 (d, 1H); 4.23 (dd, 1H); 4.38 (dd, 1H); 5.02 (s, 2H); 7.05 (brt, 1H); 7.41 (m, 1H); 7.50 (m, 4H). |
| 1.105 | 3-F—Ph | H | O | H | $CH_2$ | 1-(cyanomethyl)-1H-pyrazol-4-yl | [$CDCl_3$] 1.72 (s, 3H); 3.22 (d, 1H); 3.80 (d, 1H); 4.25 (dd, 1H); 4.38 (dd, 1H); 5.01 (s, 2H); 7.12 (m, 2H); 7.38 (m, 3H); 7.51 (d, 2H). |
| 1.106 | 3,5-$F_2$—Ph | H | O | H | $CH_2$ | 1,3,5-trimethyl-1H-pyrazol-4-yl | [$CDCl_3$] 7.41 0.51; 7.27 0.41; 7.26 42.48; 7.21 0.53; 7.16 1.64; 7.15 1.94; 7.15 1.08; 7.14 1.03; 7.14 1.86; 7.13 1.50; 6.91 0.42; 6.90 0.73; 6.90 0.35; 6.89 0.77; 6.88 1.32; 6.87 0.61; 6.86 0.39; 6.86 0.60; 6.85 0.36; 6.69 0.54; 4.29 0.89; 4.28 0.91; 4.25 1.55; 4.24 1.49; 4.15 1.58; 4.14 1.58; 4.12 0.95; 4.10 0.83; 3.81 2.51; 3.76 2.84; 3.70 15.05; 3.20 2.65; 3.16 2.29; 2.20 0.33; 2.17 16.00; 2.15 14.66; 2.04 0.80; 1.72 14.64; 1.57 0.32; 1.55 14.14; 1.26 0.35; 0.15 0.39; 0.01 1.48; 0.00 28.60; −0.05 0.36 |
| 1.107 | Ph | H | O | H | $CH_2$ | 1,3,5-trimethyl-1H-pyrazol-4-yl | [$CDCl_3$] 7.63 2.05; 7.63 2.61; 7.61 2.35; 7.61 2.81; 7.52 0.65; 7.43 0.99; 7.42 5.31; 7.40 2.50; 7.39 0.70; 7.38 0.47; 7.31 0.44; 7.26 118.69; 7.21 0.37; 7.00 0.65; 6.78 0.82; 4.28 0.91; 4.27 0.94; 4.24 1.64; 4.23 1.62; 4.16 1.57; 4.14 1.66; 4.12 0.95; 4.11 0.96; 3.86 2.68; 3.82 3.01; 3.69 15.37; 3.26 2.80; 3.22 2.44; 2.16 16.00; 2.15 |

TABLE 1-continued

Compounds of the general formula (I) according to the invention in which $R^2$ is hydrogen and $R^3$ is methyl and aryl is the radical

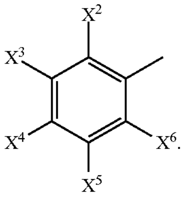

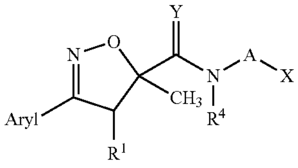

| No. | Aryl | $R^1$ | Y | $R^4$ | A | X | Physical data |
|---|---|---|---|---|---|---|---|
| | | | | | | | 15.52; 2.04 0.44; 2.00 0.38; 1.72 15.33; 1.60 0.41; 1.55 105.29; 1.50 0.37; 1.26 0.39; 0.01 1.93; 0.00 61.75; 0.00 23.97; −0.01 3.13 |
| 1.108 | 3,5-$Cl_2$—Ph | H | O | H | $CH_2$ | 1,3,5-trimethyl-1H-pyrazol-4-yl | [$CDCl_3$] 1.71 (s, 3H); 2.15 (s, 3H); 2.16 (s, 3H); 3.18 (d, 1H); 3.69 (s, 3H); 3.79 (d, 1H); 4.12 (dd, 1H); 4.26 (dd, 1H); 6.69 (br, 1H); 7.41 (m, 1H); 7.50 (M, 2H). |
| 1.109 | 3,5-$Cl_2$—Ph | H | O | H | $CH_2$ | 1,3-diisopropyl-1H-pyrazol-4-yl | [$CDCl_3$] 7.51 5.98; 7.50 6.72; 7.42 1.67; 7.41 2.93; 7.41 1.46; 7.26 17.63; 7.23 4.35; 6.80 0.67; 6.37 0.80; 4.44 0.42; 4.43 1.08; 4.41 1.47; 4.39 1.11; 4.38 0.49; 4.35 0.67; 4.33 0.71; 4.31 1.58; 4.30 1.56; 4.26 1.59; 4.25 1.60; 4.22 0.68; 4.21 0.66; 3.82 2.50; 3.78 2.85; 3.21 2.70; 3.17 2.39; 2.96 0.40; 2.95 1.06; 2.93 1.47; 2.91 1.11; 2.89 0.45; 1.73 14.51; 1.72 0.47; 1.60 3.57; 1.45 10.05; 1.43 9.95; 1.26 0.33; 1.24 8.19; 1.22 16.00; 1.21 8.05; 0.00 7.91 |
| 1.110 | 3,5-$F_2$—Ph | H | O | H | $CH_2$ | 1,3-diisopropyl-1H-pyrazol-4-yl | [$CDCl_3$] 7.26 23.51; 7.24 4.35; 7.17 0.36; 7.16 1.75; 7.15 2.03; 7.15 1.18; 7.14 1.18; 7.14 2.07; 7.13 1.67; 6.91 0.43; 6.90 0.76; 6.90 0.42; 6.89 0.89; 6.88 1.53; 6.87 0.81; 6.86 0.50; 6.86 0.80; 6.85 0.43; 6.81 0.58; 4.44 0.43; 4.43 1.12; 4.41 1.52; 4.39 1.14; 4.38 0.47; 4.35 0.64; 4.33 0.65; 4.31 1.57; 4.30 1.55; 4.27 1.58; 4.25 1.60; 4.23 0.63; 4.22 0.64; 3.82 2.75; 3.77 3.14; 3.21 2.87; 3.17 2.53; 2.96 0.42; 2.95 1.11; 2.93 1.53; 2.91 1.15; 2.89 0.46; 1.74 16.00; 1.71 0.89; 1.60 5.24; 1.45 12.82; 1.43 12.69; 1.26 0.49; 1.24 8.74; 1.22 10.66; 1.22 10.11; 1.20 8.60; 0.00 10.24; −0.01 0.34 |
| 1.111 | 3,5-$F_2$—Ph | H | O | H | $CH_2$ | 1,3-dimethyl-1H-pyrazol-4-yl | [$CDCl_3$] 1.74 (s, 3H); 2.18 (s, 3H); 3.18 (d, 1H); 3.77 (d, 1H); 3.78 (s, 3H); 4.18 (dd, 1H), 4.30 (dd, 1H); 6.86 (m, 2H); 7.15 (m, 2H) |
| 1.112 | 3-F—Ph | H | O | H | $CH_2$ | 1,3-dimethyl-1H-pyrazol-4-yl | [$CDCl_3$] 1.73 (s, 3H); 2.18 (s, 3H); 3.22 (d, 1H); 3.78 (s, 3H); 3.81 (d, 1H); 4.18 (dd, 1H); 4.30 (dd, 1H); 6.89 (brt, 1H); 7.13 (m, 1H); 7.21 (s, 1H); 7.37 (m, 1H). |

TABLE 1-continued

Compounds of the general formula (I) according to the invention in which $R^2$ is hydrogen and $R^3$ is methyl and aryl is the radical

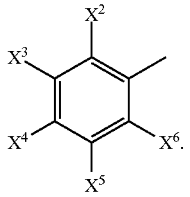

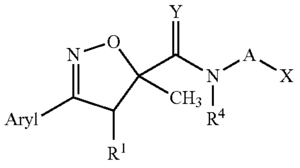

| No. | Aryl | $R^1$ | Y | $R^4$ | A | X | Physical data |
|---|---|---|---|---|---|---|---|
| 1.113 | 3-Me—Ph | H | O | H | $CH_2$ | 1,3-dimethyl-1H-pyrazol-4-yl | [$CDCl_3$] 7.46 2.36; 7.42 1.14; 7.40 1.52; 7.31 1.04; 7.29 2.37; 7.27 1.61; 7.26 11.68; 7.25 1.80; 7.23 0.82; 7.19 3.90; 6.93 0.71; 4.31 0.81; 4.30 0.80; 4.27 1.65; 4.26 1.62; 4.21 1.66; 4.19 1.66; 4.17 0.82; 4.16 0.79; 3.85 2.66; 3.81 3.06; 3.77 16.00; 3.26 2.91; 3.21 2.52; 2.37 12.07; 2.18 15.47; 1.72 15.63; 1.64 3.94 |
| 1.114 | Ph | H | O | H | $CH_2$ | 1,3-dimethyl-1H-pyrazol-4-yl | [$CDCl_3$] 1.72 (s, 3H); 2.18 (s, 3H); 3.24 (d, 1H); 3.78 (s, 3H); 3.83 (d, 1H); 4.19 (dd, 1H); 4.29 (dd, 1H); 6.93 (brt, 1H); 7.20 (s, 1H); 7.41 (m, 3H); 7.62 (m, 2H). |
| 1.115 | 3-Cl—Ph | H | O | H | $CH_2$ | 1,3-dimethyl-1H-pyrazol-4-yl | [$CDCl_3$] 1.72 (s, 3H); 2.18 (s, 3H); 3.21 (d, 1H); 3.78 (s, 1H); 3.81 (d, 1H); 4.18 (dd, 1H); 4.30 (dd, 1H), 6.88 (t br, 1H); 7.21 (s, 1H); 7.38 (m, 2H); 7.48 (d, 1H); 7.64 (s, 1H) |
| 1.116 | 3,5-$Cl_2$—Ph | H | O | H | $CH_2$ | 1,3-dimethyl-1H-pyrazol-4-yl | [$CDCl_3$] 1.71 (s, 3H); 2.19 (s, 3H); 3.18 (d, 1H); 3.78 (d, 1H); 3.78 (s, 3H); 4.18 (dd, 1H); 4.29 (dd, 1H); 6.82 (br, 1H); 7.20 (s, 1H); 7.41 (m, 1H); 7.50 (m, 2H). |
| 1.117 | 3,5-$(CF_3)_2$—Ph | H | O | H | $CH_2$ | 1,3-dimethyl-1H-pyrazol-4-yl | [$CDCl_3$] 1.75 (s, 3H); 2.19 (s, 3H); 3.28 (d, 1H); 3.79 (s, 3H); 3.91 (d, 1H); 4.17 (dd, 1H); 4.31 (dd, 1H); 6.80 (m, 1H); 7.21 (s, 1H); 7.91 (m, 1H); 8.07 (m, 2H). |
| 1.118 | 2,5-$F_2$—Ph | H | O | H | $CH_2$ | 1,3-dimethyl-1H-pyrazol-4-yl | [$CDCl_3$] 7.50 0.40; 7.50 0.41; 7.50 0.46; 7.50 0.43; 7.49 0.51; 7.48 0.85; 7.48 0.73; 7.47 0.42; 7.47 0.44; 7.47 0.43; 7.46 0.44; 7.46 0.41; 7.27 0.35; 7.27 0.44; 7.26 0.60; 7.26 0.92; 7.26 35.52; 7.26 1.96; 7.26 1.23; 7.26 0.87; 7.26 0.66; 7.25 0.52; 7.25 0.43; 7.25 0.35; 7.22 3.34; 7.12 0.76; 7.11 0.90; 7.11 1.61; 7.10 0.74; 7.10 1.61; 7.09 1.93; 7.09 1.00; 7.09 0.99; 7.08 1.01; 7.08 0.83; 6.84 0.47; 5.30 1.32; 4.32 0.72; 4.31 0.71; 4.28 1.52; 4.27 1.50; 4.22 1.54; 4.21 1.56; 4.18 0.74; 4.17 0.72; 3.91 1.28; 3.91 1.33; 3.87 1.55; 3.86 1.54; 3.79 15.36; 3.34 1.42; 3.34 1.47; 3.30 1.27; 3.29 1.27; 2.19 14.93; 2.09 1.82; 2.04 0.45; 1.73 0.45; 1.72 16.00; 1.57 0.97; 1.26 0.39; 0.01 0.44; 0.00 0.45; 0.00 0.78; 0.00 |

TABLE 1-continued

Compounds of the general formula (I) according to the invention in which $R^2$ is hydrogen and $R^3$ is methyl and aryl is the radical

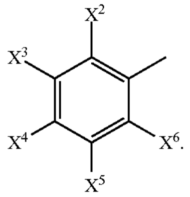

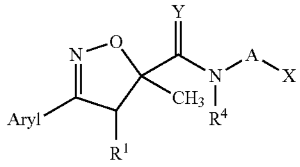

| No. | Aryl | $R^1$ | Y | $R^4$ | A | X | Physical data |
|---|---|---|---|---|---|---|---|
| | | | | | | | 17.06; 0.00 1.37; 0.00 0.89; 0.00 0.59; −0.01 0.43; −0.01 0.34; −0.01 0.63; −0.01 0.60 |
| 1.119 | 2,3,4-$F_3$—Ph | H | O | H | $CH_2$ | 1,3-dimethyl-1H-pyrazol-4-yl | [$CDCl_3$] 7.52 0.34; 7.52 0.35; 7.51 0.35; 7.51 0.41; 7.50 0.46; 7.50 0.48; 7.50 0.45; 7.49 0.41; 7.49 0.37; 7.49 0.46; 7.49 0.47; 7.48 0.46; 7.48 0.45; 7.48 0.38; 7.47 0.33; 7.46 0.35; 7.27 0.44; 7.26 0.70; 7.26 31.31; 7.26 0.36; 7.22 2.93; 7.05 0.37; 7.05 0.38; 7.04 0.38; 7.03 1.05; 7.03 0.73; 7.01 0.69; 7.01 0.99; 7.00 0.36; 6.99 0.34; 6.99 0.34; 6.84 0.43; 5.30 2.43; 4.32 0.65; 4.31 0.66; 4.28 1.41; 4.27 1.39; 4.22 1.42; 4.21 1.44; 4.19 0.67; 4.17 0.66; 3.91 1.16; 3.90 1.19; 3.86 1.39; 3.86 1.37; 3.79 14.69; 3.33 1.21; 3.32 1.26; 3.28 1.09; 3.28 1.09; 2.18 13.90; 2.09 2.12; 1.74 0.37; 1.72 16.00; 1.58 0.84; 1.56 0.51; 1.26 0.65; 0.01 0.35; 0.00 0.32; 0.00 13.80; −0.01 0.45 |
| 1.120 | 3,5-$F_2$—Ph | H | O | H | $CH_2$ | 1,3-dimethyl-1H-pyrazol-5-yl | [$CDCl_3$] 7.26 12.97; 7.17 1.40; 7.16 1.75; 7.16 1.04; 7.15 0.99; 7.15 1.76; 7.14 1.46; 7.01 0.50; 7.00 0.36; 6.92 0.35; 6.91 0.64; 6.91 0.32; 6.90 0.71; 6.89 1.27; 6.89 0.63; 6.88 0.37; 6.87 0.64; 5.93 3.42; 4.53 0.81; 4.51 0.80; 4.49 1.33; 4.47 1.31; 4.38 1.35; 4.36 1.36; 4.34 0.83; 4.32 0.82; 3.80 2.43; 3.76 2.80; 3.72 16.00; 3.23 2.62; 3.19 2.28; 2.21 13.32; 1.74 14.28; 1.61 4.05; 0.00 7.05 |
| 1.121 | Ph | H | O | H | $CH_2$ | 1,3-dimethyl-1H-pyrazol-5-yl | [$CDCl_3$] 7.64 1.84; 7.64 2.07; 7.63 0.79; 7.63 0.71; 7.63 0.67; 7.62 1.77; 7.62 2.32; 7.45 0.64; 7.44 0.81; 7.44 0.50; 7.43 1.33; 7.43 3.92; 7.42 1.85; 7.42 0.68; 7.41 0.92; 7.41 1.88; 7.41 0.36; 7.40 0.33; 7.39 0.60; 7.39 0.47; 7.26 11.88; 7.10 0.41; 5.92 2.99; 4.52 0.70; 4.50 0.69; 4.48 1.20; 4.46 1.18; 4.38 1.22; 4.36 1.21; 4.34 0.72; 4.32 0.70; 3.86 2.66; 3.82 3.05; 3.71 16.00; 3.29 2.77; 3.25 2.41; 2.20 12.17; 1.74 14.80; 1.66 1.50; 0.00 5.30 |
| 1.122 | 3,5-$Cl_2$—Ph | H | O | H | $CH_2$ | 1,3-dimethyl-1H-pyrazol-5-yl | [$CDCl_3$] 1.74 (s, 3H); 2.21 (s, 3H); 3.21 (d, 1H); 3.72 (s, 3H); 3.79 (d, 1H); 4.33 (dd, 1H); |

TABLE 1-continued

Compounds of the general formula (I) according to the invention in which $R^2$ is hydrogen and $R^3$ is methyl and aryl is the radical

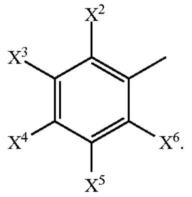

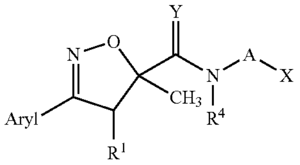

| No. | Aryl | $R^1$ | Y | $R^4$ | A | X | Physical data |
|---|---|---|---|---|---|---|---|
| | | | | | | | 4.51 (dd, 1H); 5.30 (s, 1H); 5.92 (s, 1H); 6.98 (br, 1H); 7.42 (m, 1H); 7.51 (m, 2H). |
| 1.123 | 3,5-$(CF_3)_2$—Ph | H | O | H | $CH_2$ | 1,3-dimethyl-1H-pyrazol-5-yl | [$CDCl_3$] 1.62 (s, 3H); 2.06 (s, 3H); 3.15 (d, 1H); 3.58 (s, 3H); 3.76 (d, 1H); 4.19 (dd, 1H); 4.38 (dd, 1H); 5.79 (s, 1H); 6.83 (br, 1H); 7.79 (m, 1H); 7.92 (m, 2H). |
| 1.124 | 3,5-$F_2$—Ph | H | O | H | $CH_2$ | 1,3-oxazol-4-yl | [$CDCl_3$] 1.73 (s, 3H); 3.18 (d, 1H); 3.78 (d, 1H); 4.31 (dd, 1H); 4.52 (dd, 1H); 6.88 (m, 1H); 7.15 (m, 2H); 7.21 (brt, 1H); 7.58 (s, 1H); 7.83 (s, 1H). |
| 1.125 | 3,5-$Cl_2$—Ph | H | O | H | $CH_2$ | 1,3-oxazol-4-yl | [$CDCl_3$] 1.71 (s, 3H); 3.19 (d, 1H); 3.79 (d, 1H); 4.32 (dd, 1H), 4.45 (dd, 1H); 7.23 (brt, 1H); 7.40 (m, 1H); 7.50 (m, 2H); 7.58 (s, 1H); 7.85 (s, 1H). |
| 1.126 | 3-F—Ph | H | O | H | $CH_2$ | 1,3-oxazol-4-yl | [$CDCl_3$] 1.72 (s, 3H); 3.22 (d, 1H); 3.81 (d, 1H); 4.32 (dd, 1H), 4.45 (dd, 1H); 7.13 (m, 1H); 7.27 (m, 1H); 7.38 (m, 3H); 7.56 (s, 1H); 7.83 (s, 1H). |
| 1.127 | Ph | H | O | H | $CH_2$ | 1,3-oxazol-4-yl | [$CDCl_3$] 1.73 (s, 3H); 3.25 (d, 1H); 3.84 (d, 1H); 4.33 (dd, 1H), 4.45 (dd, 1H); 7.30 (brt, 1H); 7.41 (m, 3H); 7.56 (s, 1H); 7.63 (m, 2H); 7.83 (s, 1H). |
| 1.128 | 3,5-$Cl_2$—Ph | H | O | H | $CH_2$ | 1,3-th iazol-2-yl | [$CDCl_3$] 7.72 2.36; 7.72 2.45; 7.57 0.39; 7.57 0.39; 7.56 0.56; 7.55 0.36; 7.52 7.76; 7.52 8.32; 7.42 2.09; 7.42 3.54; 7.41 1.74; 7.28 3.60; 7.27 3.54; 7.26 35.63; 7.25 0.33; 4.86 0.94; 4.84 0.94; 4.82 2.12; 4.80 2.07; 4.76 2.10; 4.74 2.15; 4.72 0.97; 4.70 0.95; 3.84 2.81; 3.80 3.22; 3.25 2.92; 3.20 2.57; 2.05 1.46; 1.77 16.00; 1.58 4.21; 1.28 0.56; 1.26 1.21; 1.24 0.47; 0.88 0.84; 0.86 0.32; 0.00 8.71; −0.01 0.33 |
| 1.129 | 3,5-$F_2$—Ph | H | O | H | $CH_2$ | 1,3-thiazol-2-yl | [$CDCl_3$] 7.73 2.20; 7.72 2.27; 7.56 0.53; 7.52 1.40; 7.29 0.40; 7.28 3.24; 7.28 0.78; 7.28 0.69; 7.28 0.69; 7.28 0.96; 7.28 1.22; 7.27 3.74; 7.27 1.55; 7.27 1.58; 7.27 1.86; 7.27 2.27; 7.27 2.95; 7.26 238.72; 7.26 5.48; 7.26 4.30; 7.26 3.42; 7.26 2.79; 7.25 2.46; 7.25 2.02; 7.25 1.92; 7.25 1.65; 7.25 1.47; 7.25 1.33; 7.25 1.14; 7.25 1.00; 7.25 0.86; 7.25 0.83; 7.25 0.79; 7.25 0.69; 7.24 0.64; 7.24 0.61; 7.24 0.53; 7.24 0.49; 7.24 0.49; 7.24 |

TABLE 1-continued

Compounds of the general formula (I) according to the invention in which $R^2$ is hydrogen and $R^3$ is methyl and aryl is the radical

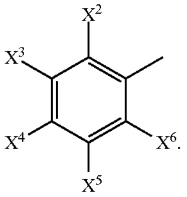

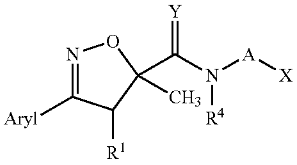

| No. | Aryl | $R^1$ | Y | $R^4$ | A | X | Physical data |
|---|---|---|---|---|---|---|---|
| | | | | | | | 0.42; 7.24 0.39; 7.24 0.36; 7.24 0.35; 7.21 0.80; 7.19 0.32; 7.18 1.77; 7.17 1.92; 7.17 1.09; 7.16 1.21; 7.16 2.07; 7.15 1.61; 7.00 1.36; 6.92 0.40; 6.91 0.74; 6.90 0.35; 6.89 0.86; 6.89 1.43; 6.88 0.73; 6.87 0.45; 6.87 0.72; 6.86 0.34; 4.86 0.87; 4.85 0.85; 4.82 1.87; 4.81 1.85; 4.76 1.90; 4.74 1.88; 4.72 0.87; 4.70 0.84; 3.84 2.66; 3.79 3.07; 3.25 2.79; 3.21 2.43; 2.05 0.45; 2.01 1.06; 1.77 16.00; 1.56 0.35; 1.55 54.40; 1.54 1.23; 1.54 0.97; 1.54 0.79; 1.54 0.69; 1.54 0.57; 1.54 0.52; 1.54 0.46; 1.54 0.41; 1.54 0.33; 1.26 0.34; 0.01 0.39; 0.01 1.84; 0.00 55.92; 0.00 2.28; 0.00 1.58; 0.00 1.09; −0.01 0.94; −0.01 0.91; −0.01 0.95; −0.01 1.77; −0.01 0.39; −0.01 0.33 |
| 1.130 | 3,5-$Cl_2$—Ph | H | O | H | $CH_2$ | 1,4-dimethyl-5-oxo-4,5-dihydro-1H-1,2,4-triazol-3-yl | [$CDCl_3$] 1.73 (s, 3H); 3.20 (s, 3H); 3.21 (d, 1H); 3.41 (s, 3H); 3.77 (d, 1H); 4.30 (dd, 1H), 4.42 (dd, 1H); 7.23 (t, 1H); 7.42 (m, 1H); 7.51 (m, 2H). |
| 1.131 | 3,5-$F_2$—Ph | H | O | H | $CH_2$ | 1,4-dimethyl-5-oxo-4,5-dihydro-1H-1,2,4-triazol-3-yl | [$CDCl_3$] 1.75 (s, 3H); 3.20 (s, 3H); 3.22 (d, 1H); 3.41 (s, 3H); 3.78 (d, 1H); 4.30 (dd, 1H), 4.43 (dd, 1H); 6.91 (m, 1H); 7.16 (m, 2H); 7.26 (brt, 1H). |
| 1.132 | 3-F—Ph | H | O | H | $CH_2$ | 1,4-dimethyl-5-oxo-4,5-dihydro-1H-1,2,4-triazol-3-yl | [$CDCl_3$] 1.75 (s, 3H); 3.20 (s, 3H); 3.25 (d, 1H); 3.40 (s, 3H); 3.80 (d, 1H); 4.31 (dd, 1H), 4.43 (dd, 1H); 7.14 (m, 1H); 7.28 (brt, 1H); 7.37 (m, 3H). |
| 1.133 | 3,5-$F_2$—Ph | H | O | H | $CH_2$ | 1,5-dimethyl-1H-pyrazol-3-yl | [$CDCl_3$] 7.52 0.55; 7.31 0.61; 7.26 97.79; 7.21 0.72; 7.18 0.33; 7.16 1.70; 7.16 2.37; 7.14 2.23; 7.14 1.82; 7.13 0.40; 7.00 0.55; 6.90 0.34; 6.89 0.63; 6.89 0.32; 6.88 0.70; 6.87 1.24; 6.86 0.63; 6.85 0.35; 6.85 0.62; 6.84 0.32; 5.89 2.98; 4.44 0.74; 4.42 0.74; 4.40 1.52; 4.39 1.50; 4.33 1.52; 4.32 1.52; 4.30 0.74; 4.28 0.73; 3.82 2.38; 3.77 2.79; 3.72 16.00; 3.20 2.62; 3.16 2.29; 2.22 12.31; 2.04 0.67; 1.74 14.41; 1.54 31.53; 1.26 0.45; 0.05 0.38; 0.01 1.90; 0.00 68.11; −0.01 2.23; −0.05 0.51 |
| 1.134 | 3,5-$Cl_2$—Ph | H | O | H | $CH_2$ | 1,5-dimethyl-1H-pyrazol-3-yl | [$CDCl_3$] 7.51 5.35; 7.51 6.08; 7.41 1.47; 7.40 2.66; 7.40 1.37; 7.26 13.60; 7.26 12.28; 7.16 0.41; 7.15 0.65; 5.88 |

TABLE 1-continued

Compounds of the general formula (I) according to the invention in which $R^2$ is hydrogen and $R^3$ is methyl and aryl is the radical

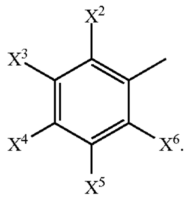

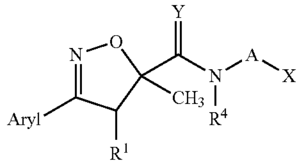

| No. | Aryl | $R^1$ | Y | $R^4$ | A | X | Physical data |
|---|---|---|---|---|---|---|---|
| | | | | | | | 3.33; 4.43 0.73; 4.42 0.73; 4.39 1.63; 4.38 1.62; 4.33 1.64; 4.32 1.65; 4.30 0.74; 4.28 0.73; 3.82 2.38; 3.78 2.70; 3.72 16.00; 3.20 2.62; 3.16 2.30; 2.22 14.04; 1.74 14.00; 1.65 0.65; 0.00 4.79; 0.00 4.36 |
| 1.135 | Ph | H | O | H | $CH_2$ | 1,5-dimethyl-1H-pyrazol-3-yl | [$CDCl_3$] 7.64 1.72; 7.64 2.06; 7.64 1.00; 7.63 1.79; 7.62 2.37; 7.52 0.37; 7.43 0.49; 7.42 0.72; 7.41 3.83; 7.41 3.64; 7.40 2.07; 7.39 0.43; 7.38 0.54; 7.26 64.62; 7.23 0.33; 7.21 0.68; 7.00 0.36; 5.89 3.05; 4.44 0.73; 4.43 0.73; 4.40 1.51; 4.39 1.50; 4.33 1.52; 4.32 1.52; 4.30 0.74; 4.28 0.73; 3.87 2.50; 3.83 2.85; 3.71 16.00; 3.27 2.72; 3.22 2.37; 2.21 12.20; 2.04 0.49; 1.73 14.63; 1.54 14.77; 1.26 0.32; 0.01 1.23; 0.00 45.83; −0.01 1.49 |
| 1.136 | 3,5-$F_2$—Ph | H | O | H | $CH_2$ | 1,5-dimethyl-1H-pyrazol-4-yl | [$CDCl_3$] 1.72 (s, 3H); 2.20 (s, 3H); 3.17 (d, 1H); 3.74 (s, 3H); 3.78 (d, 1H); 4.18 (dd, 1H); 4.30 (dd, 1H); 6.83 (m, 1H); 6.88 (m, 1H); 7.14 (m, 2H); 7.33 (s, 1H). |
| 1.137 | 3-F—Ph | H | O | H | $CH_2$ | 1,5-dimethyl-1H-pyrazol-4-yl | [$CDCl_3$] 1.71 (s, 3H); 2.19 (s, 3H); 3.21 (d, 1H); 3.75 (s, 3H); 3.81 (d, 1H); 4.16 (dd, 1H); 4.30 (dd, 1H); 6.88 (brt, 1H); 7.12 (m, 1H); 7.38 (m, 4H). |
| 1.138 | 3,5-$Cl_2$—Ph | H | O | H | $CH_2$ | 1,5-dimethyl-1H-pyrazol-4-yl | [$CDCl_3$] 1.71 (s, 3H); 2.20 (s, 3H); 3.18 (d, 1H); 3.76 (s, 3H); 3.79 (d, 1H); 4.16 (dd, 1H); 4.30 (dd, 1H); 6.81 (br, 1H); 7.32 (s, 1H); 7.41 (m, 1H); 7.50 (m, 2H). |
| 1.139 | Ph | H | O | H | $CH_2$ | 1,5-dimethyl-1H-pyrazol-4-yl | [$CDCl_3$] 1.71 (s, 3H); 2.17 (s, 3H); 3.25 (d, 1H); 3.75 (s, 3H); 3.84 (d, 1H); 4.16 (dd, 1H), 4.30 (dd, 1H); 6.91 (brt, 1H); 7.32 (s, 1H); 7.41 (m, 3H); 7.62 (m, 2H). |
| 1.140 | 3,5-$F_2$—Ph | H | O | H | $CH_2$ | 1-acetyl-1H-pyrazol-4-yl | [$CDCl_3$] 8.15 3.53; 7.63 3.64; 7.26 11.37; 7.26 12.92; 7.16 1.72; 7.16 2.10; 7.16 2.05; 7.14 2.18; 7.14 1.73; 7.13 0.38; 7.10 0.71; 6.91 0.36; 6.91 0.62; 6.90 0.33; 6.89 0.72; 6.89 1.23; 6.88 0.63; 6.87 0.39; 6.86 0.62; 4.43 0.77; 4.41 0.77; 4.39 1.44; 4.38 1.43; 4.31 1.44; 4.29 1.46; 4.27 0.78; 4.26 0.77; 3.80 2.29; 3.76 2.65; 3.23 2.56; 3.18 |

TABLE 1-continued
Compounds of the general formula (I) according to the invention in which $R^2$ is hydrogen and $R^3$ is methyl and aryl is the radical
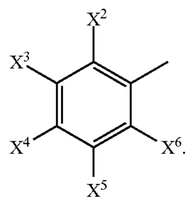
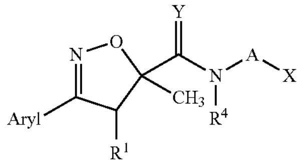
| No. | Aryl | $R^1$ | Y | $R^4$ | A | X | Physical data |
|---|---|---|---|---|---|---|---|
| | | | | | | | 2.21; 2.67 14.56; 2.67 16.00; 1.74 13.89; 1.57 0.69; 1.26 0.36; 0.00 4.39; 0.00 4.95 |
| 1.141 | 3-F—Ph | H | O | H | $CH_2$ | 1-acetyl-1H-pyrazol-4-yl | [$CDCl_3$] 1.72 (s, 3H); 2.67 (s, 3H); 3.24 (d, 1H); 3.81 (d, 1H); 4.28 (dd, 1H); 4.40 (dd, 1H); 7.15 (m, 2H); 7.38 (m, 2H); 7.62 (s, 1H); 8.15 (s, 1H). |
| 1.142 | 3,5-$F_2$—Ph | H | O | H | $CH_2$ | 1-butyl-3-methyl-1H-pyrazol-4-yl | [$CDCl_3$] 7.52 0.50; 7.37 0.56; 7.26 84.96; 7.26 81.87; 7.23 4.43; 7.16 2.41; 7.14 2.40; 7.14 2.03; 7.12 0.34; 7.00 0.53; 6.91 0.45; 6.90 0.73; 6.90 0.43; 6.89 0.83; 6.88 1.50; 6.88 0.90; 6.87 0.75; 6.86 1.19; 6.85 0.96; 4.33 0.93; 4.32 0.91; 4.30 1.64; 4.28 1.63; 4.21 1.60; 4.19 1.63; 4.17 0.93; 4.16 0.89; 4.03 0.33; 4.02 2.72; 4.00 4.33; 3.98 2.43; 3.81 2.59; 3.76 2.99; 3.21 2.75; 3.17 2.41; 2.20 2.31; 2.19 16.00; 1.95 0.44; 1.89 2.17; 1.82 0.83; 1.80 1.82; 1.79 2.66; 1.77 1.98; 1.75 0.98; 1.73 15.02; 1.36 0.44; 1.34 1.33; 1.32 2.17; 1.30 2.11; 1.28 1.28; 1.26 0.52; 1.26 0.46; 0.96 0.59; 0.94 4.33; 0.92 8.07; 0.91 3.52; 0.01 1.05; 0.00 38.37; 0.00 36.55; −0.01 1.50 |
| 1.143 | 3,5-$F_2$—Ph | H | O | butyl | $CH_2$ | 1-butyl-3-methyl-1H-pyrazol-4-yl | [$CDCl_3$] 7.52 0.65; 7.36 3.55; 7.31 0.46; 7.31 0.35; 7.26 125.02; 7.26 112.36; 7.21 4.00; 7.20 4.14; 7.19 4.02; 7.00 0.72; 6.89 0.93; 6.88 1.03; 6.87 1.61; 6.86 1.86; 6.84 0.94; 6.84 0.94; 4.97 1.37; 4.93 1.49; 4.68 1.90; 4.64 2.15; 4.46 1.76; 4.41 1.89; 4.36 2.45; 4.32 2.71; 4.31 1.85; 4.27 1.61; 4.10 2.50; 4.07 2.22; 4.04 1.72; 4.02 3.32; 4.01 3.16; 3.99 4.58; 3.97 2.42; 3.73 0.50; 3.72 0.56; 3.70 0.60; 3.69 0.81; 3.68 0.67; 3.67 0.63; 3.66 0.53; 3.40 0.37; 3.38 0.53; 3.36 0.62; 3.35 0.82; 3.33 0.44; 3.24 0.58; 3.23 0.69; 3.21 0.68; 3.21 1.00; 3.20 0.66; 3.18 0.60; 3.17 0.58; 3.13 2.54; 3.12 3.26; 3.09 0.88; 3.08 2.73; 3.08 3.64; 3.06 0.55; 3.04 0.40; 2.25 11.35; 2.23 16.00; 1.84 1.22; 1.82 3.12; 1.80 6.53; 1.78 6.96; 1.76 13.70; 1.70 0.88; 1.68 15.29; 1.65 0.63; 1.65 0.64; 1.64 0.74; 1.63 0.77; 1.62 0.83; 1.61 0.77; 1.59 0.64; 1.52 |

TABLE 1-continued
Compounds of the general formula (I) according to the invention in which $R^2$ is hydrogen and $R^3$ is methyl and aryl is the radical
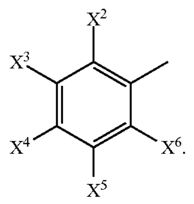
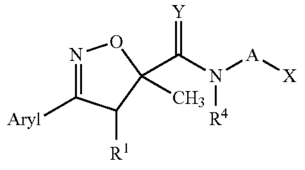
| No. | Aryl | $R^1$ | Y | $R^4$ | A | X | Physical data |
|---|---|---|---|---|---|---|---|
| | | | | | | | 0.51; 1.50 0.95; 1.48 1.33; 1.46 1.13; 1.44 0.65; 1.42 0.53; 1.41 0.88; 1.39 1.38; 1.37 1.73; 1.34 1.66; 1.32 2.40; 1.32 2.60; 1.30 3.94; 1.28 4.41; 1.26 3.55; 1.24 1.38; 1.22 0.38; 0.99 4.25; 0.97 7.99; 0.95 4.70; 0.93 9.51; 0.91 13.00; 0.89 9.35; 0.87 2.88; 0.01 2.81; 0.00 56.27; 0.00 51.17; −0.01 2.20; −0.15 0.33 |
| 1.144 | 3,5-$F_2$—Ph | H | O | H | $CH_2$ | 1-butyl-5-methyl-1H-pyrazol-4-yl | [$CDCl_3$] 7.52 0.41; 7.35 3.69; 7.31 0.35; 7.26 75.57; 7.22 0.61; 7.16 1.73; 7.15 2.11; 7.14 2.10; 7.00 0.40; 6.91 0.38; 6.90 0.66; 6.89 0.38; 6.88 0.76; 6.88 1.36; 6.87 0.70; 6.86 0.47; 6.86 0.76; 6.85 0.47; 6.82 0.68; 4.33 0.89; 4.32 0.89; 4.30 1.55; 4.28 1.54; 4.20 1.43; 4.19 1.42; 4.16 0.81; 4.15 0.81; 4.02 2.08; 4.01 3.67; 3.99 2.69; 3.97 0.36; 3.81 2.39; 3.76 2.73; 3.20 2.52; 3.16 2.19; 2.20 14.31; 2.19 2.67; 1.81 0.80; 1.79 1.69; 1.77 2.48; 1.75 2.07; 1.72 16.00; 1.36 1.05; 1.34 1.78; 1.32 1.90; 1.30 1.24; 1.28 0.44; 1.26 0.40; 0.96 3.79; 0.94 7.40; 0.93 1.43; 0.92 3.19; 0.91 0.57; 0.01 0.90; 0.00 34.47; −0.01 1.27 |
| 1.145 | 3,5-$F_2$—Ph | H | O | H | $CH_2$ | 1-cyclopropyl-1H-pyrazol-4-yl | [$CDCl_3$] 7.52 1.43; 7.38 8.41; 7.31 1.48; 7.26 254.37; 7.22 0.42; 7.21 0.91; 7.18 0.35; 7.16 1.60; 7.16 2.20; 7.14 2.03; 7.14 1.79; 7.13 0.35; 7.00 1.45; 6.93 0.65; 6.91 0.57; 6.90 0.81; 6.90 0.44; 6.89 0.83; 6.88 1.43; 6.88 0.78; 6.87 0.43; 6.86 0.69; 6.85 0.38; 4.36 0.79; 4.34 0.79; 4.32 1.54; 4.31 1.55; 4.24 1.57; 4.23 1.54; 4.20 0.83; 4.19 0.80; 3.80 2.64; 3.76 3.07; 3.56 0.67; 3.55 0.82; 3.54 1.29; 3.53 0.95; 3.52 0.72; 3.51 0.35; 3.21 2.91; 3.17 2.53; 1.73 16.00; 1.53 54.52; 1.10 0.47; 1.09 1.04; 1.08 2.11; 1.08 2.00; 1.07 2.00; 1.07 2.04; 1.06 0.86; 1.05 0.35; 1.03 0.57; 1.01 0.92; 1.00 1.60; 1.00 1.69; 0.98 1.89; 0.97 0.98; 0.96 0.47; 0.15 0.49; 0.05 0.67; 0.01 2.96 |
| 1.146 | Ph | H | O | H | $CH_2$ | 1-cyclopropyl-1H-pyrazol-4-yl | [$CDCl_3$] 7.64 2.22; 7.64 2.35; 7.63 1.09; 7.63 0.90; 7.63 1.05; 7.62 2.05; 7.62 2.11; 7.62 2.63; 7.44 0.69; 7.43 0.88; 7.43 |

TABLE 1-continued
Compounds of the general formula (I) according to the invention in which $R^2$ is hydrogen and $R^3$ is methyl and aryl is the radical
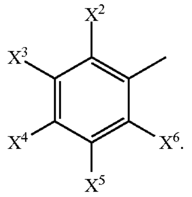
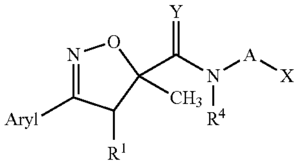
| No. | Aryl | $R^1$ | Y | $R^4$ | A | X | Physical data |
|---|---|---|---|---|---|---|---|
| | | | | | | | 2.10; 7.42 4.85; 7.42 1.88; 7.41 0.98; 7.41 1.41; 7.40 2.10; 7.40 0.38; 7.40 0.40; 7.39 0.47; 7.39 0.70; 7.38 0.49; 7.38 3.28; 7.37 2.84; 7.27 1.48; 7.26 13.00; 7.03 0.53; 4.35 0.66; 4.33 0.65; 4.31 1.36; 4.30 1.34; 4.25 1.38; 4.23 1.38; 4.21 0.68; 4.19 0.66; 3.86 2.75; 3.82 3.17; 3.55 0.33; 3.54 0.67; 3.53 0.80; 3.52 1.28; 3.51 0.95; 3.51 0.69; 3.50 0.35; 3.27 2.99; 3.23 2.61; 1.73 16.00; 1.63 1.72; 1.09 0.34; 1.09 0.37; 1.08 1.12; 1.08 1.05; 1.07 1.39; 1.07 1.86; 1.07 1.91; 1.06 1.41; 1.06 1.67; 1.06 1.54; 1.05 0.74; 1.05 0.61; 1.03 0.32; 1.02 0.35; 1.00 0.72; 0.99 0.68; 0.99 1.13; 0.98 1.48; 0.98 1.31; 0.98 1.53; 0.97 0.84; 0.97 1.19; 0.96 1.70; 0.96 1.47; 0.96 0.95; 0.96 0.78; 0.95 0.40; 0.95 0.35; 0.00 0.54 |
| 1.147 | 3-F—Ph | H | O | H | $CH_2$ | 1-cyclopropyl-1H-pyrazol-4-yl | [$CDCl_3$] 7.39 1.28; 7.39 0.93; 7.38 0.84; 7.38 0.84; 7.38 2.50; 7.38 4.86; 7.37 4.17; 7.37 4.61; 7.37 2.25; 7.36 3.18; 7.36 1.32; 7.36 0.95; 7.36 0.70; 7.35 0.49; 7.35 0.38; 7.35 0.34; 7.26 22.71; 7.16 0.46; 7.15 0.49; 7.15 0.54; 7.15 0.47; 7.14 0.49; 7.14 0.53; 7.13 0.46; 7.13 0.51; 7.13 0.57; 7.13 0.76; 7.12 0.65; 7.11 0.67; 7.11 0.38; 7.00 0.38; 6.98 0.40; 4.35 0.64; 4.34 0.65; 4.32 1.25; 4.30 1.23; 4.24 1.27; 4.23 1.29; 4.21 0.66; 4.19 0.65; 3.83 2.86; 3.79 3.26; 3.55 0.58; 3.54 0.66; 3.53 1.11; 3.52 0.84; 3.51 0.61; 3.24 2.92; 3.20 2.56; 1.73 16.00; 1.60 3.01; 1.10 0.40; 1.09 0.43; 1.09 1.03; 1.08 0.86; 1.08 1.08; 1.08 1.24; 1.08 1.68; 1.07 1.79; 1.07 1.16; 1.07 1.27; 1.07 1.42; 1.06 1.68; 1.06 0.77; 1.05 0.69; 1.04 0.39; 1.03 0.40; 1.02 0.37; 1.02 0.33; 1.01 0.72; 1.00 0.76; 1.00 0.99; 0.99 1.18; 0.99 1.24; 0.99 1.19; 0.99 1.38; 0.99 1.07; 0.98 0.81; 0.98 1.00; 0.97 1.24; 0.97 1.52; 0.97 1.44; 0.97 0.94; 0.97 0.84; 0.96 0.39; 0.95 0.39; 0.00 7.69 |
| 1.148 | 3,5-$Cl_2$—Ph | H | O | H | $CH_2$ | 1-cyclopropyl-1H-pyrazol-4-yl | [$CDCl_3$] 7.51 7.47; 7.51 7.24; 7.42 2.23; 7.41 3.29; 7.41 1.50; 7.38 7.46; 7.26 22.13; 6.93 0.79; 4.36 0.82; 4.34 0.81; 4.32 |

TABLE 1-continued
Compounds of the general formula (I) according to the invention in which $R^2$ is hydrogen and $R^3$ is methyl and aryl is the radical
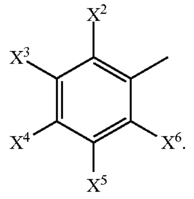
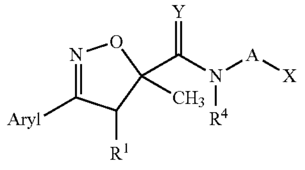
| No. | Aryl | $R^1$ | Y | $R^4$ | A | X | Physical data |
|---|---|---|---|---|---|---|---|
| | | | | | | | 1.53; 4.30 1.51; 4.24 1.56; 4.23 1.55; 4.20 0.84; 4.19 0.81; 3.81 2.72; 3.77 3.14; 3.57 0.34; 3.56 0.68; 3.55 0.91; 3.54 1.31; 3.53 1.00; 3.52 0.72; 3.51 0.36; 3.21 2.94; 3.16 2.59; 1.72 16.00; 1.58 5.42; 1.10 0.44; 1.10 0.39; 1.09 1.18; 1.09 1.39; 1.09 2.03; 1.08 2.23; 1.08 2.44; 1.08 2.20; 1.08 2.01; 1.07 2.17; 1.07 2.19; 1.07 1.67; 1.06 0.98; 1.06 0.70; 1.05 0.43; 1.03 0.69; 1.02 0.33; 1.01 0.95; 1.01 0.74; 1.00 1.51; 1.00 1.90; 1.00 1.87; 1.00 1.79; 1.00 1.83; 0.99 0.90; 0.99 1.65; 0.98 2.13; 0.98 2.11; 0.98 1.70; 0.98 1.16; 0.97 0.79; 0.96 0.53; 0.96 0.38; 0.01 0.37 |
| 1.149 | 3,5-$Cl_2$—Ph | H | O | H | $CH_2$ | 1-ethyl-1H-pyrazol-4-yl | [$CDCl_3$] 1.46 (t, 3H); 1.71 (s, 3H); 3.18 (d, 1H); 3.78 (d, 1H); 4.12 (q, 2H); 4.22 (dd, 1H); 4.36 (dd, 1H) 6.95 (brt, 1H); 7.32 (s, 1H); 7.41 (m, 2H); 7.5 (m, 2H). |
| 1.150 | 3-F—Ph | H | O | H | $CH_2$ | 1-ethyl-1H-pyrazol-4-yl | [$CDCl_3$] 7.41 3.98; 7.39 1.74; 7.38 2.21; 7.37 3.16; 7.36 3.71; 7.32 4.18; 7.26 31.06; 7.26 29.78; 7.21 0.70; 7.15 0.47; 7.15 0.80; 7.14 0.52; 7.13 0.70; 7.13 0.83; 7.13 1.02; 7.12 0.68; 7.11 0.65; 7.10 0.40; 6.99 0.80; 4.38 0.86; 4.37 0.89; 4.34 1.64; 4.33 1.65; 4.26 1.66; 4.25 1.69; 4.22 0.89; 4.21 0.92; 4.15 1.38; 4.13 4.23; 4.11 4.29; 4.09 1.44; 3.84 2.63; 3.79 3.02; 3.24 2.94; 3.20 2.55; 1.73 16.00; 1.68 0.36; 1.55 10.77; 1.47 4.45; 1.45 8.92; 1.45 8.59; 1.44 4.35; 0.00 19.85; 0.00 19.57; −0.01 1.17; −0.05 0.45 |
| 1.151 | 3,5-$F_2$—Ph | H | O | H | $CH_2$ | 1-ethyl-1H-pyrazol-4-yl | [$CDCl_3$] 7.52 0.44; 7.41 3.00; 7.33 3.13; 7.26 75.96; 7.16 1.60; 7.16 1.89; 7.15 1.12; 7.15 1.06; 7.14 1.96; 7.14 1.59; 7.00 0.46; 6.95 0.50; 6.91 0.43; 6.90 0.73; 6.90 0.38; 6.89 0.81; 6.88 1.42; 6.87 0.68; 6.86 0.42; 6.86 0.70; 6.85 0.35; 4.39 0.77; 4.37 0.76; 4.35 1.39; 4.33 1.35; 4.26 1.39; 4.25 1.42; 4.22 0.80; 4.21 0.77; 4.15 1.40; 4.14 4.33; 4.12 4.39; 4.10 1.45; 3.81 2.72; 3.76 3.13; 3.21 2.87; 3.17 2.51; 2.04 0.40; 1.73 16.00; 1.54 |

TABLE 1-continued
Compounds of the general formula (I) according to the invention in which $R^2$ is hydrogen and $R^3$ is methyl and aryl is the radical
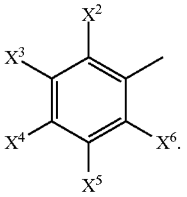
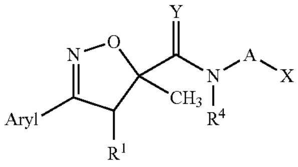
| No. | Aryl | $R^1$ | Y | $R^4$ | A | X | Physical data |
|---|---|---|---|---|---|---|---|
| | | | | | | | 35.26; 1.48 4.92; 1.46 10.11; 1.44 4.79; 0.01 1.52; 0.00 53.05; −0.01 1.65 |
| 1.152 | 3-Br-5-$CF_3$—Ph | H | O | H | $CH_2$ | 1-ethyl-1H-pyrazol-4-yl | [$CDCl_3$] 7.96 2.96; 7.81 4.99; 7.41 4.48; 7.33 4.60; 7.26 23.80; 7.26 19.92; 6.94 0.92; 4.39 0.96; 4.37 0.97; 4.35 1.70; 4.34 1.70; 4.26 1.71; 4.24 1.73; 4.22 1.04; 4.21 0.98; 4.15 1.47; 4.14 4.49; 4.12 4.61; 4.10 1.58; 3.86 2.65; 3.82 3.04; 3.25 2.94; 3.20 2.59; 1.74 16.00; 1.59 7.83; 1.48 4.91; 1.48 4.29; 1.46 9.87; 1.46 8.46; 1.44 4.88; 1.44 4.18; 1.26 0.51 |
| 1.153 | 3-Me—Ph | H | O | H | $CH_2$ | 1-ethyl-1H-pyrazol-4-yl | [$CDCl_3$] 7.46 2.06; 7.42 1.00; 7.40 4.65; 7.31 3.56; 7.29 2.25; 7.27 1.47; 7.26 14.31; 7.25 1.57; 7.23 0.73; 7.03 0.58; 4.37 0.74; 4.36 0.73; 4.33 1.46; 4.32 1.45; 4.26 1.48; 4.25 1.49; 4.22 0.76; 4.21 0.74; 4.14 1.41; 4.12 4.38; 4.10 4.45; 4.08 1.49; 3.85 2.72; 3.81 3.12; 3.26 2.94; 3.21 2.57; 2.37 11.06; 1.72 16.00; 1.62 4.92; 1.46 4.86; 1.45 9.89; 1.43 4.77 |
| 1.154 | 3-F-5-MeO—Ph | H | O | H | $CH_2$ | 1-ethyl-1H-pyrazol-4-yl | [$CDCl_3$] 7.41 3.38; 7.33 3.49; 7.26 12.23; 7.26 11.60; 7.00 0.49; 6.99 0.75; 6.96 1.37; 6.95 2.13; 6.95 1.91; 6.94 0.97; 6.94 0.97; 6.93 1.24; 6.93 0.90; 6.92 0.84; 6.91 1.15; 6.91 0.91; 6.70 0.69; 6.69 1.30; 6.69 0.77; 6.67 0.73; 6.67 1.32; 6.66 0.76; 4.38 0.74; 4.36 0.74; 4.34 1.40; 4.33 1.42; 4.26 1.42; 4.25 1.45; 4.22 0.77; 4.21 0.78; 4.15 1.36; 4.14 0.39; 4.13 4.15; 4.11 4.20; 4.09 1.44; 3.83 0.86; 3.82 16.00; 3.81 3.38; 3.77 2.70; 3.22 2.57; 3.18 2.25; 2.04 1.38; 1.72 13.66; 1.62 1.78; 1.48 0.46; 1.48 0.46; 1.47 3.95; 1.47 3.93; 1.46 0.60; 1.46 8.11; 1.45 7.88; 1.44 4.06; 1.44 3.93; 1.28 0.44; 1.27 0.44; 1.26 0.94; 1.26 0.97; 1.24 0.42; 1.24 0.40 |
| 1.155 | 3-Cl-5-Et—Ph | H | O | H | $CH_2$ | 1-ethyl-1H-pyrazol-4-yl | [$CDCl_3$] 7.44 1.48; 7.44 2.47; 7.43 1.59; 7.41 3.20; 7.34 1.52; 7.34 2.55; 7.33 1.57; 7.32 3.37; 7.26 42.16; 7.25 1.57; 7.24 2.21; 7.24 1.32; 7.00 0.66; 6.99 0.64; 4.38 0.75; 4.36 0.76; 4.34 1.41; 4.33 1.39; 4.26 1.43; 4.25 1.44; 4.22 0.78; 4.21 0.77; 4.15 |

TABLE 1-continued

Compounds of the general formula (I) according to the invention in which $R^2$ is hydrogen and $R^3$ is methyl and aryl is the radical

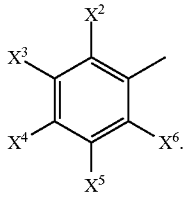

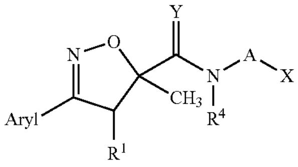

| No. | Aryl | $R^1$ | Y | $R^4$ | A | X | Physical data |
|---|---|---|---|---|---|---|---|
| | | | | | | | 1.48; 4.13 4.56; 4.11 4.63; 4.09 1.53; 3.83 2.77; 3.79 3.16; 3.23 2.93; 3.19 2.58; 2.68 0.89; 2.66 2.73; 2.64 2.80; 2.62 0.96; 1.72 16.00; 1.57 12.03; 1.47 5.15; 1.45 10.52; 1.44 5.05; 1.26 5.05; 1.24 10.40; 1.22 4.79; 0.01 0.54 |
| 1.156 | 3,5-$(MeO)_2$—Ph | H | O | H | $CH_2$ | 1-ethyl-1H-pyrazol-4-yl | [$CDCl_3$] 7.41 1.72; 7.32 1.79; 7.26 7.13; 7.01 0.36; 6.77 2.71; 6.77 2.80; 6.52 0.72; 6.52 1.31; 6.51 0.66; 4.38 0.37; 4.36 0.37; 4.34 0.72; 4.33 0.71; 4.26 0.71; 4.25 0.71; 4.23 0.37; 4.21 0.36; 4.14 0.64; 4.12 1.93; 4.11 1.95; 4.09 0.66; 3.82 1.18; 3.80 16.00; 3.78 1.36; 3.24 1.27; 3.20 1.10; 1.72 6.71; 1.60 1.88; 1.47 2.07; 1.45 4.16; 1.43 2.01 |
| 1.157 | 3-Me-5-$CF_3O$—Ph | H | O | H | $CH_2$ | 1-ethyl-1H-pyrazol-4-yl | [$CDCl_3$] 7.41 3.96; 7.35 2.68; 7.33 3.29; 7.31 2.03; 7.26 30.75; 7.26 27.68; 7.09 1.95; 7.00 0.62; 6.99 0.77; 4.38 0.87; 4.37 0.87; 4.34 1.58; 4.33 1.57; 4.26 1.61; 4.25 1.63; 4.22 0.89; 4.21 0.89; 4.15 1.54; 4.13 4.46; 4.11 4.49; 4.09 1.51; 3.84 2.69; 3.79 3.08; 3.24 2.99; 3.19 2.60; 2.41 0.52; 2.40 12.94; 1.73 16.00; 1.58 13.55; 1.49 0.37; 1.47 4.73; 1.45 9.64; 1.43 4.81 |
| 1.158 | 3,5-$Cl_2$-4-MeO—Ph | H | O | H | $CH_2$ | 1-ethyl-1H-pyrazol-4-yl | [$CDCl_3$] 7.57 10.49; 7.41 3.29; 7.33 3.15; 7.26 19.79; 6.96 0.75; 4.37 0.65; 4.36 0.65; 4.34 1.26; 4.32 1.24; 4.26 1.24; 4.24 1.23; 4.22 0.67; 4.21 0.65; 4.15 1.16; 4.13 3.43; 4.12 3.45; 4.10 1.15; 3.93 16.00; 3.80 2.06; 3.75 2.36; 3.19 2.23; 3.15 1.96; 1.72 12.07; 1.58 8.40; 1.48 3.83; 1.46 7.67; 1.44 3.67 |
| 1.159 | Ph | H | O | H | $CH_2$ | 1-ethyl-1H-pyrazol-4-yl | [$CDCl_3$] 1.43 (t, 3H); 1.73 (s, 3H); 3.24 (d, 1H); 3.82 (d, 1H); 4.11 (q, 2H); 4.23 (dd, 1H); 4.35 (dd, 1H) 7.03 (brt, 1H); 7.31 (s, 1H); 7.42 (m, 4H); 7.63 (m, 2H). |
| 1.160 | 3-F-5-MeS—Ph | H | O | H | $CH_2$ | 1-ethyl-1H-pyrazol-4-yl | [$CDCl_3$] 7.41 2.98; 7.33 3.06; 7.26 25.80; 7.24 1.41; 7.24 2.52; 7.23 1.53; 7.10 0.68; 7.10 0.93; 7.09 0.76; 7.08 0.69; 7.08 0.82; 7.07 0.91; 7.07 0.73; 7.00 0.76; 7.00 1.18; 6.99 0.76; 6.98 1.07; 6.97 1.39; 6.97 1.17; 4.38 0.68; 4.37 0.68; 4.34 1.26; 4.33 |

TABLE 1-continued

Compounds of the general formula (I) according to the invention in which $R^2$ is hydrogen and $R^3$ is methyl and aryl is the radical

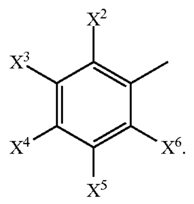

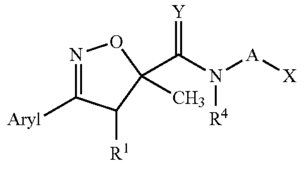

| No. | Aryl | $R^1$ | Y | $R^4$ | A | X | Physical data |
|---|---|---|---|---|---|---|---|
| | | | | | | | 1.23; 4.26 1.27; 4.25 1.29; 4.22 0.70; 4.21 0.69; 4.15 1.18; 4.13 3.59; 4.11 3.63; 4.10 1.21; 3.82 2.18; 3.77 2.50; 3.22 2.37; 3.18 2.07; 2.49 16.00; 1.72 12.84; 1.58 2.39; 1.48 3.97; 1.46 8.02; 1.44 3.89; 0.01 0.33; 0.00 11.07 |
| 1.161 | 3,5-(tert•Bu)$_2$—Ph | H | O | H | $CH_2$ | 1-ethyl-1H-pyrazol-4-yl | [$CDCl_3$] 1.32 (s, 18H); 1.45 (t, 3H); 1.73 (s, 3H); 3.28 (d, 1H); 3.88 (d, 1H); 4.11 (q, 2H); 4.23 (dd, 1H); 4.36 (dd, 1H); 7.06 (brt, 1H); 7.32 (s, 1H); 7.41 (s, 1H); 7.48 (m, 2H); 7.50 (m, 1H). |
| 1.162 | 3-$CF_3$—Ph | H | O | H | $CH_2$ | 1-ethyl-1H-pyrazol-4-yl | [$CDCl_3$] 7.90 1.92; 7.81 1.04; 7.79 1.22; 7.70 0.90; 7.68 1.18; 7.57 1.00; 7.55 1.59; 7.53 0.67; 7.41 3.09; 7.33 3.32; 7.26 16.84; 7.00 0.49; 6.99 0.58; 4.39 0.78; 4.37 0.79; 4.35 1.42; 4.34 1.41; 4.26 1.44; 4.25 1.45; 4.23 0.81; 4.21 0.80; 4.15 1.45; 4.13 4.46; 4.11 4.51; 4.09 1.51; 3.89 2.74; 3.85 3.14; 3.28 2.90; 3.24 2.55; 2.04 1.42; 1.74 16.00; 1.60 3.56; 1.47 4.99; 1.45 10.29; 1.43 4.97; 1.28 0.43; 1.26 0.93; 1.24 0.41 |
| 1.163 | 4-MeO—Ph | H | O | H | $CH_2$ | 1-ethyl-1H-pyrazol-4-yl | [$CDCl_3$] 7.58 0.38; 7.58 3.60; 7.57 1.14; 7.56 1.18; 7.56 3.76; 7.55 0.44; 7.40 3.21; 7.31 3.19; 7.26 20.25; 7.05 0.59; 6.93 0.42; 6.93 3.81; 6.92 1.16; 6.91 1.11; 6.90 3.47; 6.90 0.39; 4.37 0.69; 4.36 0.69; 4.34 1.31; 4.32 1.29; 4.26 1.32; 4.24 1.32; 4.22 0.72; 4.21 0.69; 4.14 1.22; 4.12 3.74; 4.10 3.78; 4.08 1.27; 3.84 16.00; 3.83 2.56; 3.79 2.56; 3.24 2.50; 3.20 2.18; 1.71 13.29; 1.58 3.61; 1.47 3.99; 1.45 8.03; 1.43 3.90; 0.01 0.34 |
| 1.164 | 3,5-$Et_2$—Ph | H | O | H | $CH_2$ | 1-ethyl-1H-pyrazol-4-yl | [$CDCl_3$] 7.41 3.68; 7.32 3.71; 7.29 5.25; 7.26 11.13; 7.26 9.36; 7.10 2.29; 7.10 2.30; 7.07 0.46; 7.06 0.77; 7.05 0.49; 4.37 0.76; 4.36 0.75; 4.34 1.44; 4.32 1.42; 4.25 1.43; 4.24 1.45; 4.22 0.78; 4.20 0.78; 4.14 1.23; 4.12 3.79; 4.10 3.85; 4.08 1.30; 3.87 2.25; 3.82 2.57; 3.27 2.45; 3.23 2.14; 2.76 6.78; 2.76 5.45; 2.67 1.86; 2.65 5.85; 2.63 6.04; 2.61 2.10; 1.72 13.36; 1.66 3.22; 1.46 4.17; 1.46 3.72; 1.45 8.42; 1.44 |

TABLE 1-continued

Compounds of the general formula (I) according to the invention in which $R^2$ is hydrogen and $R^3$ is methyl and aryl is the radical

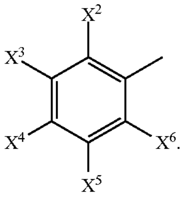

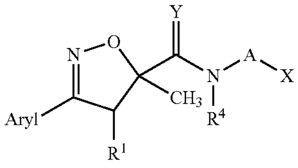

| No. | Aryl | $R^1$ | Y | $R^4$ | A | X | Physical data |
|---|---|---|---|---|---|---|---|
| | | | | | | | 7.41; 1.43 4.11; 1.43 3.64; 1.25 7.91; 1.24 16.00; 1.23 14.46; 1.22 7.56; 1.22 6.91; 0.00 1.40 |
| 1.165 | 4-EtO—Ph | H | O | H | $CH_2$ | 1-ethyl-1H-pyrazol-4-yl | [$CDCl_3$] 7.56 4.61; 7.54 4.80; 7.40 4.63; 7.31 4.42; 7.26 18.39; 7.26 19.23; 7.05 1.14; 6.91 4.83; 6.89 4.43; 4.37 0.94; 4.36 0.96; 4.34 1.83; 4.32 1.81; 4.26 1.84; 4.24 1.84; 4.22 0.98; 4.21 0.95; 4.14 1.41; 4.14 1.43; 4.12 4.33; 4.12 4.35; 4.10 4.42; 4.10 4.45; 4.09 1.52; 4.08 1.72; 4.08 1.82; 4.07 4.22; 4.07 4.12; 4.06 4.27; 4.05 4.15; 4.04 1.40; 4.04 1.35; 3.83 2.66; 3.83 2.62; 3.79 3.02; 3.78 2.99; 3.24 2.97; 3.24 2.93; 3.19 2.56; 3.19 2.51; 1.71 16.00; 1.71 15.77; 1.59 3.90; 1.47 4.61; 1.46 4.74; 1.45 11.30; 1.45 13.67; 1.43 12.69; 1.43 12.59; 1.41 4.24; 1.41 4.09; 0.00 8.84 |
| 1.166 | 3-Et—Ph | H | O | H | $CH_2$ | 1-ethyl-1H-pyrazol-4-yl | [$CDCl_3$] 7.49 1.93; 7.49 2.03; 7.44 0.60; 7.43 1.04; 7.43 0.67; 7.42 0.91; 7.42 1.53; 7.41 3.28; 7.34 0.96; 7.32 5.07; 7.31 0.39; 7.30 1.37; 7.28 0.90; 7.28 1.55; 7.27 1.08; 7.26 18.40; 7.05 0.56; 4.38 0.73; 4.36 0.73; 4.34 1.37; 4.32 1.35; 4.26 1.39; 4.25 1.40; 4.22 0.75; 4.21 0.73; 4.14 1.42; 4.12 4.44; 4.10 4.50; 4.08 1.49; 3.86 2.82; 3.82 3.23; 3.27 2.97; 3.23 2.62; 2.70 0.86; 2.68 2.66; 2.66 2.73; 2.64 0.93; 1.73 16.00; 1.64 8.89; 1.47 5.17; 1.45 10.70; 1.43 5.09; 1.26 5.07; 1.24 10.79; 1.22 4.89 |
| 1.167 | 3-iPr—Ph | H | O | H | $CH_2$ | 1-ethyl-1H-pyrazol-4-yl | [$CDCl_3$] 1.25 (d, 6H); 1.45 (t, 3H); 1.72 (s, 3H); 2.94 (m, 1H); 3.26 (d, 1H); 3.85 (d, 1H); 4.11 (q, 2H); 4.23 (dd, 1H); 4.36 (dd, 1H); 7.06 (brt, 1H); 7.31 (m, 3H); 7.41 (d, 2H); 7.52 (s, 1H). |
| 1.168 | 3,5-$F_2$—Ph | H | O | H | $CH_2$ | 1-ethyl-1H-pyrazol-5-yl | [$CDCl_3$] 7.43 2.59; 7.43 2.70; 7.26 13.57; 7.26 10.23; 7.16 1.57; 7.16 1.51; 7.16 2.21; 7.15 1.30; 7.14 2.04; 7.14 2.06; 7.14 1.79; 7.13 0.32; 7.05 0.66; 6.92 0.40; 6.91 0.73; 6.91 0.38; 6.90 0.80; 6.89 1.45; 6.89 0.75; 6.88 0.43; 6.87 0.73; 6.86 0.36; 6.14 2.60; 6.14 2.71; 4.59 |

TABLE 1-continued

Compounds of the general formula (I) according to the invention in which $R^2$ is hydrogen and $R^3$ is methyl and aryl is the radical

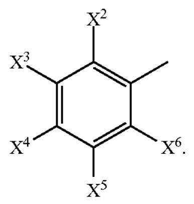

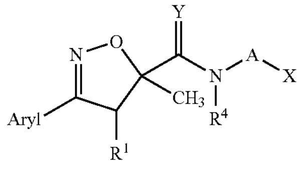

| No. | Aryl | $R^1$ | Y | $R^4$ | A | X | Physical data |
|---|---|---|---|---|---|---|---|
| | | | | | | | 0.87; 4.57 0.86; 4.55 1.59; 4.53 1.57; 4.46 1.60; 4.45 1.61; 4.42 0.87; 4.41 0.86; 4.13 1.27; 4.11 3.97; 4.09 4.10; 4.07 1.39; 3.81 2.67; 3.77 3.07; 3.24 2.91; 3.20 2.52; 1.75 16.00; 1.60 4.48; 1.40 4.50; 1.38 9.42; 1.36 4.45; 0.00 7.29; 0.00 5.48; −0.01 0.32 |
| 1.169 | 3,5-$Cl_2$—Ph | H | O | H | $CH_2$ | 1-ethyl-1H-pyrazol-5-yl | [$CDCl_3$] 1.38 (t, 3H); 2.24 (s, 3H); 3.21 (d, 1H); 3.80 (d, 1H); 4.10 (q, 2H); 4.42 (dd, 1H); 4.56 (dd, 1H); 6.15 (s, 1H); 7.02 (br, 1H); 7.42 (m, 1H); 7.51 (m, 2H). |
| 1.170 | Ph | H | O | H | $CH_2$ | 1-ethyl-1H-pyrazol-5-yl | [$CDCl_3$] 7.64 1.87; 7.63 2.28; 7.62 0.78; 7.62 2.41; 7.61 2.61; 7.44 0.90; 7.43 1.47; 7.43 4.31; 7.42 3.49; 7.42 3.30; 7.41 2.70; 7.40 0.39; 7.39 0.66; 7.39 0.50; 7.26 10.77; 7.13 0.60; 6.14 2.50; 6.14 2.58; 4.58 0.83; 4.56 0.82; 4.54 1.59; 4.52 1.57; 4.46 1.60; 4.44 1.60; 4.42 0.84; 4.41 0.83; 4.12 1.32; 4.10 4.16; 4.08 4.26; 4.06 1.42; 3.86 2.71; 3.82 3.14; 3.30 3.00; 3.26 2.61; 1.74 16.00; 1.64 3.15; 1.38 4.40; 1.37 9.17; 1.35 4.36; 0.00 4.61 |
| 1.171 | 3,5-$F_2$—Ph | H | O | H | $CH_2$ | 1-ethyl-3-methyl-1H-pyrazol-4-yl | [$CDCl_3$] 1.43 (t, 3H); 1.73 (s, 3H); 2.19 (s, 3H); 3.19 (d, 1H); 3.79 (d, 1H); 4.04 (q, 2H); 4.18 (dd, 1H); 4.32 (dd, 1H); 6.83 (brt, 1H); 6.88 (m, 1H); 7.13 (m, 2H); 7.24 (s, 1H). |
| 1.172 | 3-Me—Ph | H | O | H | $CH_2$ | 1-ethyl-3-methyl-1H-pyrazol-4-yl | [$CDCl_3$] 7.46 2.74; 7.42 1.28; 7.40 1.73; 7.31 1.10; 7.29 2.58; 7.27 1.73; 7.26 14.40; 7.26 13.53; 7.25 2.01; 7.25 2.24; 7.23 5.08; 6.92 0.83; 4.32 0.85; 4.30 0.86; 4.28 1.74; 4.27 1.74; 4.21 1.74; 4.20 1.83; 4.18 0.87; 4.16 0.89; 4.06 1.38; 4.04 3.99; 4.03 4.00; 4.01 1.34; 3.85 2.49; 3.85 2.38; 3.81 2.84; 3.81 2.72; 3.26 2.77; 3.21 2.41; 2.37 13.96; 2.19 1.22; 2.18 16.00; 1.72 14.87; 1.62 3.17; 1.44 4.25; 1.44 4.00; 1.42 8.66; 1.42 8.08; 1.40 4.28; 1.40 3.97; 1.39 0.61; 1.39 0.56; 0.00 5.51; 0.00 5.27 |
| 1.173 | 3-Br-5-F—Ph | H | O | H | $CH_2$ | 1-ethyl-3-methyl-1H-pyrazol-4-yl | [$CDCl_3$] 1.44 (t, 3H); 1.72 (s, 3H); 2.19 (s, 3H); 3.19 (d, 1H); 3.79 (d, 1H); 4.05 (q, 2H); 4.18 (dd, 1H); 4.31 (dd, 1H); 6.82 (br, 1H); 7.24 (s, 1H); 7.31 (m, 1H); 7.55 (s, 1H). |

TABLE 1-continued

Compounds of the general formula (I) according to the invention in which $R^2$ is hydrogen and $R^3$ is methyl and aryl is the radical

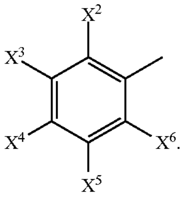

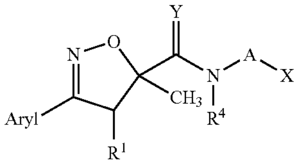

| No. | Aryl | $R^1$ | Y | $R^4$ | A | X | Physical data |
|---|---|---|---|---|---|---|---|
| 1.174 | 3,4,5-$F_3$—Ph | H | O | H | $CH_2$ | 1-ethyl-3-methyl-1H-pyrazol-4-yl | [$CDCl_3$] 1.45 (t, 3H); 1.72 (s, 3H); 2.18 (s, 3H); 3.18 (d, 1H); 3.78 (d, 1H); 4.05 (q, 2H); 4.18 (dd, 1H), 4.32 (dd, 1H); 6.81 (t br, 1H); 7.25 (m, 2H) |
| 1.175 | 3,4-$F_2$—Ph | H | O | H | $CH_2$ | 1-ethyl-3-methyl-1H-pyrazol-4-yl | [$CDCl_3$] 1.44 (t, 3H); 1.72 (s, 3H); 2.19 (s, 3H); 3.19 (d, 1H); 3.80 (d, 1H); 4.05 (q, 2H); 4.18 (dd, 1H); 4.31 (dd, 1H); 6.85 (m, 1H); 7.20 (m, 1H); 7.24 (s, 1H); 7.31 (m, 1H); 7.51 (m, 1H). |
| 1.176 | 3,5-$F_2$—Ph | H | S | H | $CH_2$ | 1-ethyl-3-methyl-1H-pyrazol-4-yl | [DMSO-$D_6$] 1.24 (t, 3H); 1.72 (s, 3H); 2.09 (s, 3H); 3.58 (d, 1H); 3.94 (q, 2H); 4.12 (d, 1H); 4.52 (dd, 1H); 4.58 (dd, 1H); 7.33-7.42 (m, 3H); 7.51 (s, 1H). |
| 1.177 | 3-F-5-Me—Ph | H | O | H | $CH_2$ | 1-ethyl-3-methyl-1H-pyrazol-4-yl | [$CDCl_3$] 7.26 13.44; 7.26 0.47; 7.26 0.34; 7.23 3.51; 7.19 1.83; 7.19 1.99; 7.17 0.59; 7.17 0.78; 7.15 0.56; 7.14 0.77; 6.96 0.75; 6.94 0.76; 6.88 0.51; 4.33 0.74; 4.31 0.74; 4.29 1.41; 4.27 1.40; 4.21 1.44; 4.20 1.45; 4.17 0.77; 4.16 0.76; 4.07 1.23; 4.05 3.85; 4.03 3.92; 4.02 1.29; 3.82 2.61; 3.78 3.00; 3.23 2.77; 3.18 2.43; 2.37 10.07; 2.18 16.00; 1.72 15.24; 1.62 4.86; 1.45 4.78; 1.43 9.87; 1.41 4.69; 0.00 7.74 |
| 1.178 | 3-Cl-5-CN—Ph | H | O | H | $CH_2$ | 1-ethyl-3-methyl-1H-pyrazol-4-yl | [$CDCl_3$] 1.44 (t, 3H); 1.73 (s, 3H); 2.23 (s, 3H); 3.20 (d, 1H); 3.80 (d, 1H); 4.10-4.20 (m, 3H); 4.32 (dd, 1H); 6.89 (brt, 1H); 7.2 (s, 1H); 7.67 (m, 1H); 7.79 (m, 1H); 7.82 (m, 1H). |
| 1.179 | 3-F—Ph | H | O | H | $CH_2$ | 1-ethyl-3-methyl-1H-pyrazol-4-yl | [$CDCl_3$] 1.42 (t, 3H); 1.72 (s, 3H); 2.14 (s, 3H); 3.21 (d, 1H); 3.81 (d, 1H); 4.03 (q, 2H); 4.18 (dd, 1H); 4.31 (dd, 1H); 6.86 (brt, 1H); 7.12 (m, 1H); 7.24 (s, 1H); 7.39 (m, 3H). |
| 1.180 | 3-cPr-5-F—Ph | H | O | H | $CH_2$ | 1-ethyl-3-methyl-1H-pyrazol-4-yl | [$CDCl_3$] 7.26 28.93; 7.26 29.09; 7.23 4.18; 7.12 1.21; 7.12 1.19; 7.11 3.17; 7.11 2.51; 7.10 1.31; 6.87 0.77; 6.82 0.86; 6.82 1.19; 6.80 0.86; 6.79 1.19; 4.33 0.84; 4.31 0.84; 4.29 1.60; 4.28 1.57; 4.21 1.59; 4.20 1.71; 4.18 0.85; 4.16 0.90; 4.07 1.55; 4.05 4.18; 4.04 4.06; 4.02 1.33; 3.82 2.38; 3.78 2.73; 3.23 2.68; 3.18 2.34; 2.20 1.30; 2.19 16.00; 1.92 0.58; 1.91 0.63; 1.90 1.19; 1.89 |

TABLE 1-continued

Compounds of the general formula (I) according to the invention in which $R^2$ is hydrogen and $R^3$ is methyl and aryl is the radical

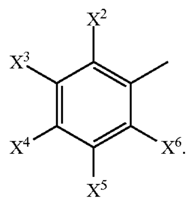

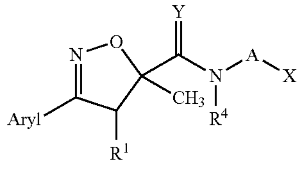

| No. | Aryl | $R^1$ | Y | $R^4$ | A | X | Physical data |
|---|---|---|---|---|---|---|---|
| | | | | | | | 0.69; 1.88 0.66; 1.87 0.32; 1.72 14.19; 1.58 4.59; 1.45 4.14; 1.45 4.16; 1.43 8.44; 1.43 8.51; 1.41 4.37; 1.41 4.21; 1.39 0.65; 1.04 0.70; 1.03 2.07; 1.03 2.16; 1.02 1.12; 1.01 2.17; 1.01 2.01; 1.00 0.84; 1.00 0.84; 0.73 0.84; 0.72 2.65; 0.71 2.23; 0.71 2.09; 0.70 2.77; 0.69 0.73; 0.01 0.43; 0.00 11.95 |
| 1.181 | 3-Cl-5-Me—Ph | H | O | H | $CH_2$ | 1-ethyl-3-methyl-1H-pyrazol-4-yl | [$CDCl_3$] 1.42 (t, 3H); 1.72 (s, 3H); 2.18 (s, 3H); 2.36 (s, 3H); 3.20 (d, 1H); 3.80 (d, 1H); 4.03 (q, 2H); 4.18 (dd, 1H); 4.30 (dd, 1H); 6.87 (t, 1H); 7.23 (m, 2H); 7.30 (m, 1H); 7.42 (m, 1H). |
| 1.182 | 3-F-5-MeO—Ph | H | O | H | $CH_2$ | 1-ethyl-3-methyl-1H-pyrazol-4-yl | [$CDCl_3$] 7.28 2.92; 7.26 15.44; 6.95 1.82; 6.95 1.53; 6.94 1.20; 6.93 1.19; 6.93 1.40; 6.93 1.19; 6.92 1.15; 6.91 1.15; 6.91 1.15; 6.91 0.88; 6.70 0.69; 6.70 1.21; 6.69 0.63; 6.68 0.71; 6.67 1.21; 6.67 0.62; 5.30 0.71; 4.33 0.59; 4.31 0.58; 4.29 1.18; 4.28 1.15; 4.22 1.18; 4.21 1.20; 4.18 0.61; 4.17 0.60; 4.13 0.97; 4.11 3.00; 4.11 0.36; 4.10 3.04; 4.08 1.01; 3.82 16.00; 3.81 2.32; 3.76 2.46; 3.23 2.24; 3.18 1.96; 2.22 12.43; 1.72 12.06; 1.46 3.75; 1.44 7.89; 1.42 3.75; 1.40 0.52; 0.00 4.80 |
| 1.183 | 2,5-$Me_2$—Ph | H | O | H | $CH_2$ | 1-ethyl-3-methyl-1H-pyrazol-4-yl | [$CDCl_3$] 7.36 0.34; 7.26 11.54; 7.24 4.07; 7.16 0.83; 7.14 3.07; 7.12 3.74; 7.10 0.91; 6.97 0.70; 5.30 0.94; 4.31 0.51; 4.30 0.50; 4.27 1.99; 4.26 1.98; 4.25 1.97; 4.24 2.00; 4.21 0.51; 4.20 0.52; 4.07 1.43; 4.05 4.03; 4.03 3.99; 4.01 1.33; 3.89 2.56; 3.85 2.95; 3.31 2.85; 3.27 2.51; 2.44 11.73; 2.32 11.71; 2.20 1.49; 2.19 16.00; 1.73 15.02; 1.65 1.71; 1.44 4.46; 1.43 9.13; 1.41 4.49; 1.39 0.79; 1.37 0.36; 0.00 2.54; 0.00 1.90 |
| 1.184 | 3-$CF_3O$—Ph | H | O | H | $CH_2$ | 1-ethyl-3-methyl-1H-pyrazol-4-yl | [$CDCl_3$] 1.43 (t, 3H); 1.74 (s, 3H); 2.18 (s, 3H); 3.22 (d, 1H); 3.82 (d, 1H); 4.04 (q, 2H); 4.18 (dd, 1H); 4.31 (dd, 1H); 6.88 (brt, 1H); 7.23 (s, 1H); 7.28 (m, 1H); 7.43 (m, 1H); 7.51 (m, 2H). |

TABLE 1-continued

Compounds of the general formula (I) according to the invention in which $R^2$ is hydrogen and $R^3$ is methyl and aryl is the radical

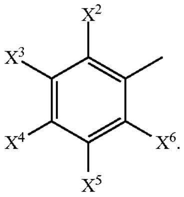

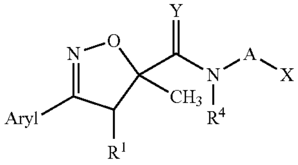

| No. | Aryl | $R^1$ | Y | $R^4$ | A | X | Physical data |
|---|---|---|---|---|---|---|---|
| 1.185 | 3-Cl-5-Et—Ph | H | O | H | $CH_2$ | 1-ethyl-3-methyl-1H-pyrazol-4-yl | [$CDCl_3$] 7.43 2.61; 7.43 1.84; 7.35 0.33; 7.33 2.81; 7.26 21.08; 7.25 2.71; 7.24 4.30; 6.88 0.82; 6.87 0.54; 4.33 0.84; 4.32 0.84; 4.29 1.54; 4.28 1.53; 4.21 1.56; 4.20 1.62; 4.17 0.86; 4.16 0.88; 4.07 1.54; 4.06 4.15; 4.04 4.03; 4.02 1.34; 3.84 2.45; 3.79 2.81; 3.24 2.70; 3.19 2.37; 2.68 1.04; 2.66 3.19; 2.64 3.28; 2.62 1.14; 2.20 1.24; 2.19 16.00; 2.05 1.34; 1.73 14.43; 1.60 6.76; 1.45 4.33; 1.43 8.75; 1.41 4.51; 1.39 0.72; 1.38 0.35; 1.28 0.38; 1.26 4.89; 1.24 9.36; 1.22 4.44; 0.00 8.30 |
| 1.186 | 2,3,5-$F_3$—Ph | H | O | H | $CH_2$ | 1-ethyl-3-methyl-1H-pyrazol-4-yl | [$CDCl_3$] 1.44 (t, 3H); 1.72 (s, 3H); 2.19 (s, 3H); 3.32 (dd, 1H); 3.90 (dd, 1H); 4.05 (q, 2H); 4.20 (dd, 1H); 4.31 (dd, 1H); 6.80 (brt, 1H); 7.00 (m, 1H); 7.28 (m, 2H). |
| 1.187 | 3-Et-5-F—Ph | H | O | H | $CH_2$ | 1-ethyl-3-methyl-1H-pyrazol-4-yl | [$CDCl_3$] 1.25 (t, 3H); 1.43 (t, 3H); 1.72 (s, 3H); 2.19 (s, 3H); 2.66 (q, 2H); 3.21 (dd, 1H); 3.82 (dd, 1H); 4.04 (m, 2H); 4.18 (dd, 1H); 4.31 (dd, 1H); 6.89 (brt, 1H); 6.98 (d, 1H); 7.17 (d, 1H); 7.22 (d, 2H). |
| 1.188 | 3-F-5-$CF_3$—Ph | H | O | H | $CH_2$ | 1-ethyl-3-methyl-1H-pyrazol-4-yl | [$CDCl_3$] 1.44 (t, 3H); 1.74 (s, 3H); 2.20 (s, 3H); 3.23 (d, 1H); 3.85 (d, 1H); 4.06 (q, 2H); 4.18 (dd, 1H), 4.32 (dd, 1H); 6.83 (t br, 1H); 7.24 (s, 1H); 7.38 (d, 1H); 7.54 (d, 1H); 7.65 (s, 1H) |
| 1.189 | 3-Br-5-$CF_3$—Ph | H | O | H | $CH_2$ | 1-ethyl-3-methyl-1H-pyrazol-4-yl | [$CDCl_3$] 1.44 (t, 3H); 1.73 (s, 3H); 2.19 (s, 3H); 3.22 (d, 1H); 3.85 (d, 1H); 4.06 (q, 2H); 4.18 (dd, 1H); 4.32 (dd, 1H); 6.82 (t br, 1H); 7.26 (s, 1H); 7.82 (m, 2H); 7.95 (s, 1H). |
| 1.190 | 3-Cl-5-MeO—Ph | H | O | H | $CH_2$ | 1-ethyl-3-methyl-1H-pyrazol-4-yl | [$CDCl_3$] 1.44 (t, 3H); 1.73 (s, 3H); 2.22 (s, 3H); 3.20 (d, 1H); 3.78 (d, 1H); 3.82 (s, 3H); 4.09 (q, 2H); 4.19 (dd, 1H), 4.30 (dd, 1H); 6.89 (t br, 1H); 6.96 (t, 1H); 7.06 (t, 1H); 7.18 (t, 1H) |
| 1.191 | 3-Cl-4-F—Ph | H | O | H | $CH_2$ | 1-ethyl-3-methyl-1H-pyrazol-4-yl | [$CDCl_3$] 1.43 (t, 3H); 1.72 (s, 3H); 2.19 (s, 3H); 3.19 (d, 1H); 3.80 (d, 1H); 4.06 (q, 2H); 4.19 (dd, 1H); 4.30 (dd, 1H); 6.84 (s br, 1H); 7.18 (t, 1H); 7.24 (s, 1H); 7.50 (m, 1H); 7.71 (m, 1H). |

TABLE 1-continued

Compounds of the general formula (I) according to the invention in which $R^2$ is hydrogen and $R^3$ is methyl and aryl is the radical

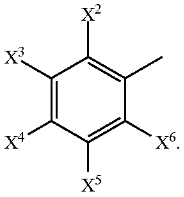

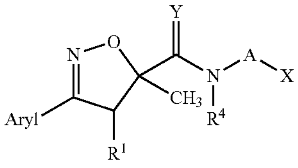

| No. | Aryl | $R^1$ | Y | $R^4$ | A | X | Physical data |
|---|---|---|---|---|---|---|---|
| 1.192 | 2,3-$F_2$—Ph | H | O | H | $CH_2$ | 1-ethyl-3-methyl-1H-pyrazol-4-yl | [$CDCl_3$] 7.52 0.53; 7.52 0.75; 7.51 0.43; 7.50 1.09; 7.50 1.07; 7.49 0.49; 7.48 0.51; 7.48 0.82; 7.48 0.42; 7.27 0.48; 7.26 20.96; 7.25 4.64; 7.23 0.61; 7.23 0.99; 7.21 0.46; 7.20 0.41; 7.15 0.55; 7.14 0.48; 7.13 0.58; 7.13 0.58; 7.12 0.84; 7.12 0.77; 7.11 0.81; 7.11 0.76; 7.10 0.41; 7.10 0.34; 7.09 0.33; 6.85 0.64; 4.33 0.70; 4.31 0.70; 4.29 1.61; 4.28 1.60; 4.24 1.64; 4.22 1.65; 4.20 0.72; 4.19 0.70; 4.08 1.23; 4.07 3.81; 4.05 3.86; 4.03 1.28; 3.93 1.27; 3.93 1.26; 3.89 1.52; 3.88 1.45; 3.36 1.45; 3.36 1.43; 3.32 1.28; 3.31 1.21; 2.19 15.59; 2.00 0.86; 1.78 0.45; 1.73 16.00; 1.46 4.54; 1.44 9.35; 1.42 4.45; 1.26 0.59; 0.01 0.36; 0.00 10.73; −0.01 0.40 |
| 1.193 | 3-Cl-5-$CF_3$—Ph | H | O | H | $CH_2$ | 1-ethyl-3-methyl-1H-pyrazol-4-yl | [$CDCl_3$] 1.43 (t, 3H); 1.74 (s, 3H); 2.20 (s, 3H); 3.23 (d, 1H); 3.85 (d, 1H); 4.06 (q, 2H); 4.18 (dd, 1H), 4.32 (dd, 1H); 6.83 (t br, 1H); 7.24 (s, 1H); 7.66 (s, 1H), 7.76 (s, 1H); 7.80 (s, 1H) |
| 1.194 | 3,5-$Me_2$—Ph | H | O | H | $CH_2$ | 1-ethyl-3-methyl-1H-pyrazol-4-yl | [$CDCl_3$] 1.42 (t, 3H); 1.71 (s, 3H); 2.20 (s, 3H); 2.32 (s, 6H); 3.22 (d, 1H); 3.82 (d, 1H); 4.05 (q, 2H); 4.19 (dd, 1H); 4.30 (dd, 1H); 6.93 (t br, 1H); 7.07 (s, 1H); 7.24 (m, 3H). |
| 1.195 | 3-Cl—Ph | H | O | H | $CH_2$ | 1-ethyl-3-methyl-1H-pyrazol-4-yl | [$CDCl_3$] 1.43 (t, 3H); 1.72 (s, 3H); 2.18 (s, 3H); 3.22 (d, 1H); 3.82 (d, 1H); 4.04 (q, 2H); 4.19 (dd, 1H); 4.30 (dd, 1H); 6.88 (s br, 1H); 7.26 (s, 1H); 7.34 (m, 1H); 7.41 (m, 1H); 7.50 (m, 1H); 7.64 (m, 1H). |
| 1.196 | 3-MeO—Ph | H | O | H | $CH_2$ | 1-ethyl-3-methyl-1H-pyrazol-4-yl | [$CDCl_3$] 1.42 (t, 3H); 1.72 (s, 3H); 2.21 (s, 3H); 3.24 (d, 1H); 3.82 (d, 1H); 3.82 (s, 3H); 4.07 (q, 2H); 4.19 (dd, 1H); 4.29 (dd, 1H); 6.92 (br, 1H); 6.97 (m, 1H); 7.15-7.33 (m, 3H). |
| 1.197 | 3-Cl-5-F—Ph | H | O | H | $CH_2$ | 1-ethyl-3-methyl-1H-pyrazol-4-yl | [$CDCl_3$] 1.44 (t, 3H); 1.72 (s, 3H); 2.19 (s, 3H); 3.18 (d, 1H); 3.80 (d, 1H); 4.07 (q, 2H); 4.18 (dd, 1H); 4.31 (dd, 1H); 6.83 (t br, 1H); 7.16 (d, 1H); 7.27 (m, 1H); 7.38 (s, 1H). |
| 1.198 | 3-CN-5-F—Ph | H | O | H | $CH_2$ | 1-ethyl-3-methyl-1H-pyrazol-4-yl | [$CDCl_3$] 7.69 3.12; 7.61 0.76; 7.61 1.17; 7.60 0.98; 7.59 0.77; 7.58 1.17; 7.58 0.95; 7.43 1.02; 7.43 1.08; 7.42 0.95; 7.41 |

TABLE 1-continued

Compounds of the general formula (I) according to the invention in which $R^2$ is hydrogen and $R^3$ is methyl and aryl is the radical

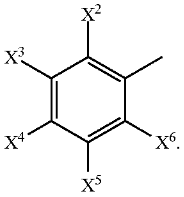

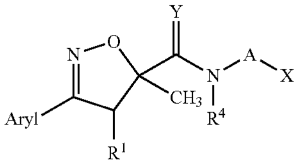

| No. | Aryl | $R^1$ | Y | $R^4$ | A | X | Physical data |
|---|---|---|---|---|---|---|---|
| | | | | | | | 1.05; 7.41 1.08; 7.40 0.94; 7.26 19.34; 7.25 4.61; 6.79 0.79; 5.30 1.55; 4.35 0.92; 4.33 0.92; 4.31 1.78; 4.30 1.74; 4.20 1.54; 4.19 1.56; 4.17 0.94; 4.15 0.93; 4.09 1.28; 4.07 3.96; 4.05 4.03; 4.03 1.35; 3.85 2.46; 3.81 2.80; 3.22 2.70; 3.18 2.38; 2.24 0.84; 2.19 16.00; 1.96 0.48; 1.75 0.41; 1.74 14.63; 1.59 2.10; 1.46 4.23; 1.45 0.65; 1.44 8.54; 1.42 4.20; 1.26 0.83; 0.00 9.21; −0.01 0.45 |
| 1.199 | 3-CN—Ph | H | O | H | $CH_2$ | 1-ethyl-3-methyl-1H-pyrazol-4-yl | [$CDCl_3$] 1.43 (t, 3H); 1.74 (s, 3H); 2.18 (s, 3H); 3.22 (d, 1H); 3.85 (d, 1H); 4.05 (q, 2H); 4.18 (dd, 1H); 4.32 (dd, 1H); 6.84 (s br, 1H); 7.55 (t, 1H); 7.72 (d, 2H); 7.84 (d, 1H); 7.92 (s, 1H). |
| 1.200 | 3-Br-5-Cl—Ph | H | O | H | $CH_2$ | 1-ethyl-3-methyl-1H-pyrazol-4-yl | [$CDCl_3$] 1.44 (t, 3H); 1.72 (s, 3H); 2.20 (s, 3H); 3.18 (d, 1H); 3.79 (d, 1H); 4.07 (q, 2H); 4.18 (dd, 1H); 4.31 (dd, 1H); 6.83 (br, 1H); 7.56 (m, 2H); 7.66 (m, 1H). |
| 1.201 | 2,3,4-$F_3$—Ph | H | O | H | $CH_2$ | 1-ethyl-3-methyl-1H-pyrazol-4-yl | [$CDCl_3$] 7.52 0.33; 7.52 0.33; 7.51 0.36; 7.50 0.52; 7.50 0.54; 7.49 0.44; 7.49 0.39; 7.49 0.55; 7.48 0.53; 7.48 0.38; 7.47 0.33; 7.46 0.34; 7.26 12.90; 7.25 3.75; 7.05 0.35; 7.05 0.36; 7.04 0.38; 7.03 1.00; 7.03 0.71; 7.01 0.67; 7.01 0.96; 7.00 0.36; 6.83 0.54; 5.30 0.34; 4.33 0.73; 4.32 0.71; 4.29 1.51; 4.28 1.49; 4.23 1.54; 4.21 1.54; 4.19 0.74; 4.18 0.73; 4.08 1.25; 4.06 3.86; 4.05 3.92; 4.03 1.29; 3.91 1.17; 3.91 1.19; 3.87 1.40; 3.86 1.36; 3.33 1.28; 3.32 1.31; 3.28 1.15; 3.28 1.14; 2.19 16.00; 1.72 15.18; 1.61 2.68; 1.46 4.51; 1.44 9.34; 1.42 4.50; 1.26 0.69; 0.00 6.71; 0.00 6.48 |
| 1.202 | 3,5-$Cl_2$-4-MeO—Ph | H | O | H | $CH_2$ | 1-ethyl-3-methyl-1H-pyrazol-4-yl | [$CDCl_3$] 7.57 10.18; 7.26 15.38; 7.24 3.41; 6.84 0.68; 6.82 0.44; 4.33 0.71; 4.31 0.72; 4.29 1.31; 4.28 0.34; 4.28 1.32; 4.21 1.26; 4.19 1.31; 4.17 0.71; 4.16 0.71; 4.08 1.14; 4.06 3.31; 4.04 3.30; 4.02 1.12; 3.93 16.00; 3.80 2.08; 3.76 2.36; 3.19 2.22; 3.15 1.95; 2.22 0.32; 2.21 0.51; 2.20 0.59; 2.19 13.08; 2.09 0.32; 1.72 11.88; 1.69 0.46; 1.61 1.37; 1.45 3.77; 1.45 0.72; 1.44 7.57; 1.42 3.72; 0.00 6.17 |

TABLE 1-continued

Compounds of the general formula (I) according to the invention in which $R^2$ is hydrogen and $R^3$ is methyl and aryl is the radical

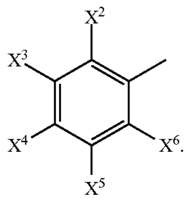

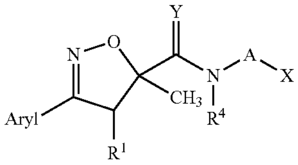

| No. | Aryl | $R^1$ | Y | $R^4$ | A | X | Physical data |
|---|---|---|---|---|---|---|---|
| 1.203 | Ph | H | O | H | $CH_2$ | 1-ethyl-3-methyl-1H-pyrazol-4-yl | [$CDCl_3$] 1.43 (t, 3H); 1.73 (s, 3H); 2.18 (s, 3H); 3.23 (d, 1H); 3.83 (d, 1H); 4.03 (q, 2H); 4.18 (dd, 1H); 4.30 (dd, 1H); 6.92 (s br, 1H); 7.22 (s, 1H); 7.40 (m, 3H); 7.65 (d, 2H). |
| 1.204 | 2,5-$F_2$—Ph | H | O | H | $CH_2$ | 1-ethyl-3-methyl-1H-pyrazol-4-yl | [$CDCl_3$] 1.43 (t, 3H); 1.72 (s, 3H); 2.19 (s, 3H); 3.32 (dd, 1H); 3.90 (dd, 1H); 4.05 (q, 2H); 4.20 (dd, 1H); 4.30 (dd, 1H); 6.82 (brt, 1H); 7.10 (m, 2H); 7.27 (m, 1H); 7.48 (m, 1H). |
| 1.205 | 3,5-$Br_2$—Ph | H | O | H | $CH_2$ | 1-ethyl-3-methyl-1H-pyrazol-4-yl | [$CDCl_3$] 1.43 (t, 3H); 1.71 (s, 3H); 2.20 (s, 3H); 3.17 (d, 1H); 3.78 (d, 1H); 4.05 (q, 2H); 4.17 (dd, 1H); 4.41 (dd, 1H); 6.80 (m, 1H); 7.22 (s, 1H); 7.70 (m, 3H). |
| 1.206 | 2-F—Ph | H | O | H | $CH_2$ | 1-ethyl-3-methyl-1H-pyrazol-4-yl | [$CDCl_3$] 1.44 (t, 3H); 1.72 (s, 3H); 1.98 (s, 3H), 3.35 (dd, 1H); 3.91 (dd, 1H); 4.05 (q, 2H); 4.21 (dd, 1H); 4.30 (dd, 1H); 6.89 (t br, 1H); 7.16 (m, 2H); 7.26 (s, 1H); 7.42 (q, 1H); 7.75 (t, 1H) |
| 1.207 | 2,5-$Cl_2$—Ph | H | O | H | $CH_2$ | 1-ethyl-3-methyl-1H-pyrazol-4-yl | [$CDCl_3$] 1.44 (t, 3H); 1.73 (s, 3H); 2.21 (s, 3H); 3.38 (d, 1H); 3.94 (d, 3H); 4.07 (q, 2H); 4.26, 4.27 (dq, 2H), 6.88 (br, 1H); 7.34 (m, 2H); 7.57 (m, 1H). |
| 1.208 | 3,5-$Et_2$—Ph | H | O | H | $CH_2$ | 1-ethyl-3-methyl-1H-pyrazol-4-yl | [$CDCl_3$] 7.29 4.67; 7.27 0.33; 7.26 19.58; 7.26 22.91; 7.23 3.38; 7.10 2.07; 7.10 2.11; 6.93 0.67; 6.92 0.44; 4.32 0.70; 4.31 0.71; 4.29 1.35; 4.27 1.34; 4.21 1.34; 4.20 1.38; 4.17 0.72; 4.16 0.71; 4.06 1.03; 4.05 3.13; 4.03 3.18; 4.01 1.08; 3.87 2.00; 3.83 2.27; 3.27 2.18; 3.22 1.92; 2.98 0.53; 2.77 0.62; 2.77 0.72; 2.71 0.43; 2.67 1.80; 2.65 5.65; 2.63 6.00; 2.61 2.27; 2.19 0.73; 2.19 12.98; 1.72 11.68; 1.69 0.36; 1.58 2.01; 1.44 3.25; 1.44 3.63; 1.42 6.59; 1.42 7.52; 1.41 0.40; 1.40 3.23; 1.40 3.61; 1.39 0.42; 1.39 0.38; 1.26 6.95; 1.25 7.51; 1.24 14.13; 1.24 16.00; 1.22 0.79; 1.22 7.96; 1.21 0.52; 1.20 0.55; 1.20 0.55; 0.00 7.61 |
| 1.209 | 3-$CF_3$S—Ph | H | O | H | $CH_2$ | 1-ethyl-3-methyl-1H-pyrazol-4-yl | [$CDCl_3$] 7.92 2.55; 7.75 1.44; 7.73 1.72; 7.73 1.52; 7.73 1.29; 7.71 1.45; 7.50 1.64; 7.48 |

TABLE 1-continued

Compounds of the general formula (I) according to the invention in which $R^2$ is hydrogen and $R^3$ is methyl and aryl is the radical

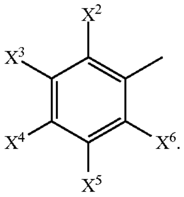

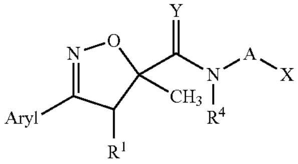

| No. | Aryl | $R^1$ | Y | $R^4$ | A | X | Physical data |
|---|---|---|---|---|---|---|---|
| | | | | | | | 2.75; 7.46 1.20; 7.35 0.39; 7.26 11.57; 7.24 4.12; 6.87 0.76; 6.86 0.52; 5.30 0.84; 4.34 0.93; 4.33 0.93; 4.30 1.65; 4.29 1.63; 4.21 1.54; 4.20 1.59; 4.18 0.88; 4.16 0.89; 4.07 1.37; 4.06 3.98; 4.04 3.99; 4.02 1.33; 3.88 2.47; 3.83 2.83; 3.27 2.72; 3.22 2.38; 2.22 0.42; 2.20 1.59; 2.19 16.00; 1.74 14.53; 1.64 1.52; 1.45 4.48; 1.43 9.00; 1.41 4.69; 1.39 0.83; 1.37 0.39; 1.25 0.85 |
| 1.210 | 3-EtO—Ph | H | O | H | $CH_2$ | 1-ethyl-3-methyl-1H-pyrazol-4-yl | [$CDCl_3$] 1.41 (t, 3H); 1.42 (t, 3H); 1.72 (s, 3H); 2.17 (s, 3H); 3.23 (d, 1H); 3.80 (d, 1H); 4.00-4.07 (m, 4H); 4.18 (dd, 1H); 4.29 (dd, 1H); 6.90 (t, 1H); 6.95 (m, 1H); 7.13 (m, 1H); 7.19 (m, 1H); 7.23 (s, 1H); 7.30 (m, 1H). |
| 1.211 | 3,5-$Cl_2$—Ph | $CH_3$ | O | H | $CH_2$ | 1-ethyl-3-methyl-1H-pyrazol-4-yl | [$CDCl_3$] 1.18 (d, 3H); 1.44 (t, 3H); 1.61 (s, 3H); 2.22 (s, 3H); 3.45 (q, 1H); 4.06 (q, 2H); 4.29 dq, 2H); 6.75 (br, 1H); 7.30 (s, 1H); 7.42 (m, 1H); 7.52 (m, 2H). |
| 1.212 | 2-F-3-Me—Ph | H | O | H | $CH_2$ | 1-ethyl-3-methyl-1H-pyrazol-4-yl | [$CDCl_3$] 7.57 0.54; 7.56 0.58; 7.56 0.58; 7.55 1.14; 7.53 0.61; 7.53 0.61; 7.52 0.62; 7.28 0.56; 7.27 0.61; 7.27 0.61; 7.27 0.50; 7.27 0.48; 7.26 13.83; 7.26 1.36; 7.26 1.35; 7.24 3.98; 7.24 0.85; 7.08 1.35; 7.06 2.25; 7.04 1.05; 6.90 0.63; 4.32 0.62; 4.30 0.62; 4.28 1.67; 4.26 1.65; 4.24 1.67; 4.22 1.69; 4.20 0.64; 4.19 0.62; 4.07 1.40; 4.06 4.08; 4.04 4.07; 4.02 1.34; 3.93 1.25; 3.92 1.35; 3.88 1.53; 3.88 1.56; 3.37 1.40; 3.36 1.50; 3.32 1.25; 3.32 1.28; 2.30 6.24; 2.29 6.46; 2.20 1.14; 2.19 16.00; 1.72 15.70; 1.72 1.94; 1.65 2.07; 1.45 4.98; 1.43 10.36; 1.41 5.12; 1.40 0.69; 0.00 2.51 |
| 1.213 | 2-Cl-5-F—Ph | H | O | H | $CH_2$ | 1-ethyl-3-methyl-1H-pyrazol-4-yl | [$CDCl_3$] 1.44 (t, 3H); 1.72 (s, 3H); 2.21 (s, 3H); 3.40 (d, 1H); 3.96 (d, 1H); 4.05 (q, 2H); 4.26 (m, 2H); 6.88 (br, 1H); 7.08 (m, 1H); 7.31 (dd, 1H); 7.39 (dd, 1H). |
| 1.214 | 3,5-$F_2$—Ph | H | O | $CH_3$ | $CH_2$ | 1-ethyl-3-methyl-1H-pyrazol-4-yl | [$CDCl_3$] 7.52 0.37; 7.39 1.72; 7.31 0.51; 7.31 0.43; 7.28 0.32; 7.28 0.41; 7.28 0.37; 7.28 0.41; 7.28 0.49; 7.28 0.52; 7.26 67.92; 7.26 48.29; 7.25 |

TABLE 1-continued

Compounds of the general formula (I) according to the invention in which $R^2$ is hydrogen and $R^3$ is methyl and aryl is the radical

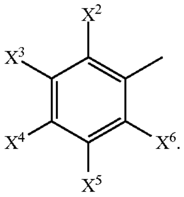

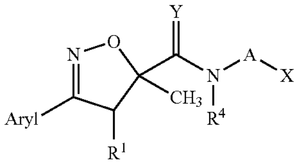

| No. | Aryl | $R^1$ | Y | $R^4$ | A | X | Physical data |
|---|---|---|---|---|---|---|---|
| | | | | | | | 0.98; 7.24 0.64; 7.21 2.04; 7.21 2.22; 7.20 4.44; 7.18 3.36; 7.00 0.39; 6.89 1.22; 6.87 2.38; 6.85 1.03; 6.84 1.21; 5.30 2.12; 5.30 1.59; 5.01 0.79; 4.97 0.87; 4.51 1.94; 4.47 2.91; 4.46 1.21; 4.42 1.02; 4.39 2.59; 4.35 2.68; 4.32 6.18; 4.28 5.18; 4.11 0.53; 4.09 1.61; 4.08 2.07; 4.07 2.09; 4.06 4.55; 4.04 4.31; 4.02 1.47; 3.19 15.82; 3.14 1.08; 3.11 2.82; 3.10 1.02; 3.07 2.62; 2.85 5.61; 2.26 5.54; 2.22 16.00; 1.78 5.43; 1.73 0.42; 1.70 15.75; 1.63 0.37; 1.58 40.69; 1.47 1.63; 1.45 7.42; 1.44 10.40; 1.42 4.51; 1.29 0.32; 1.26 0.55; 1.26 0.65; 0.92 0.35; 0.01 0.94; 0.01 1.03; 0.01 0.97; 0.00 35.05; 0.00 26.19; −0.01 1.95; −0.01 1.47; −0.02 0.38 |
| 1.215 | 3,4-$Cl_2$—Ph | H | O | H | $CH_2$ | 1-ethyl-3-methyl-1H-pyrazol-4-yl | [$CDCl_3$] 1.45 (t, 3H); 1.74 (s, 3H); 2.21 (s, 3H); 3.20 (d, 1H); 3.80 (d, 1H); 4.08 (q, 1H), 4.18 (dd, 1H); 4.31 (dd, 1H); 6.86 (t br, 1H); 7.47 (m, 2H); 7.72 (d, 1H) |
| 1.216 | 3-$NO_2$—Ph | H | O | H | $CH_2$ | 1-ethyl-3-methyl-1H-pyrazol-4-yl | [$CDCl_3$] 8.47 1.32; 8.46 2.11; 8.46 1.45; 8.30 0.83; 8.30 0.91; 8.29 0.83; 8.29 0.83; 8.28 0.90; 8.28 0.95; 8.27 0.90; 8.27 0.86; 7.99 0.83; 7.98 1.17; 7.98 0.86; 7.97 0.95; 7.96 1.31; 7.96 0.93; 7.63 1.48; 7.61 2.38; 7.59 1.28; 7.27 0.53; 7.27 9.53; 7.26 0.64; 7.26 0.59; 7.26 3.61; 6.85 0.53; 5.30 0.86; 4.35 0.81; 4.34 0.81; 4.31 1.37; 4.30 1.35; 4.21 1.43; 4.20 1.42; 4.18 0.85; 4.16 0.83; 4.08 1.26; 4.06 3.90; 4.04 3.95; 4.03 1.31; 3.93 2.63; 3.89 3.00; 3.30 2.78; 3.26 2.46; 2.19 16.00; 1.76 14.95; 1.64 4.40; 1.45 4.74; 1.44 9.80; 1.42 4.67; 0.00 6.03 |
| 1.217 | 3-Cl-4-Me—Ph | H | O | H | $CH_2$ | 1-ethyl-3-methyl-1H-pyrazol-4-yl | [$CDCl_3$] 1.42 (t, 3H); 1.73 (s, 3H); 2.18 (s, 3H); 2.40 (s, 3H); 3.22 (d, 1H), 3.80 (d, 1H); 4.05 (q, 2H); 4.18 (dd, 1H); 4.30 (dd, 1H); 6.89 (t br, 1H); 7.24 (m, 1H); 7.40 (m, 1H); 7.62 (d, 2H) |
| 1.218 | 2-Cl-3-F-5-MeO—Ph | H | O | H | $CH_2$ | 1-ethyl-3-methyl-1H-pyrazol-4-yl | [$CDCl_3$] 7.31 3.16; 7.26 12.88; 6.96 0.63; 6.90 1.32; 6.90 1.44; 6.89 1.53; 6.89 1.38; 6.81 1.30; 6.81 1.10; 6.79 1.27; 6.78 1.13; 4.28 3.64; 4.27 3.58; 4.16 |

TABLE 1-continued

Compounds of the general formula (I) according to the invention in which $R^2$ is hydrogen and $R^3$ is methyl and aryl is the radical

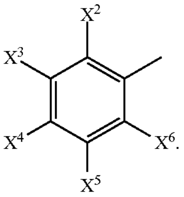

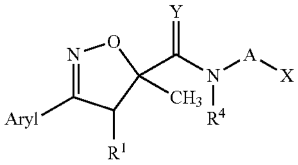

| No. | Aryl | $R^1$ | Y | $R^4$ | A | X | Physical data |
|---|---|---|---|---|---|---|---|
| | | | | | | | 1.00; 4.14 3.12; 4.12 3.17; 4.10 1.07; 3.97 2.16; 3.92 2.50; 3.82 0.79; 3.81 16.00; 3.41 2.51; 3.36 2.17; 2.25 13.42; 2.23 0.68; 1.74 12.30; 1.72 0.71; 1.47 3.60; 1.46 0.35; 1.45 7.37; 1.44 0.50; 1.43 3.54; 1.43 0.43; 1.41 0.61; 0.00 1.62 |
| 1.219 | 3-F-5-MeS—Ph | H | O | H | $CH_2$ | 1-ethyl-3-methyl-1H-pyrazol-4-yl | [$CDCl_3$] 7.26 15.45; 7.26 15.07; 7.24 6.50; 7.10 1.07; 7.10 1.31; 7.09 1.15; 7.08 1.08; 7.07 1.31; 7.07 1.13; 7.00 1.34; 6.98 1.25; 6.86 0.85; 4.33 0.83; 4.32 0.82; 4.30 1.55; 4.28 1.55; 4.21 1.52; 4.20 1.55; 4.18 0.83; 4.16 0.83; 4.08 1.25; 4.06 3.63; 4.04 3.64; 4.02 1.23; 3.82 3.35; 3.78 2.56; 3.78 2.40; 3.22 2.48; 3.18 2.16; 2.50 16.00; 2.49 14.74; 2.49 0.51; 2.30 0.68; 2.30 0.63; 2.23 0.33; 2.20 0.50; 2.19 14.54; 1.73 13.42; 1.61 3.69; 1.45 3.89; 1.45 3.70; 1.43 7.82; 1.43 7.38; 1.42 3.88; 1.41 3.61; 0.00 6.05 |
| 1.220 | 4-Cl-3,5-$F_2$—Ph | H | O | H | $CH_2$ | 1-ethyl-3-methyl-1H-pyrazol-4-yl | [$CDCl_3$] 1.44 (t, 3H); 1.72 (s, 3H); 2.20 (s, 3H); 3.18 (d, 1H); 3.79 (d, 1H); 4.09 (q, 2H); 4.18 (dd, 1H); 4.32 (dd, 1H); 6.82 (brt, 1H); 7.24 (m, 1H); 7.28 (m, 1H) |
| 1.221 | 3-tert•BuOCONH—Ph | H | O | H | $CH_2$ | 1-ethyl-3-methyl-1H-pyrazol-4-yl | [$CDCl_3$] 1.43 (t, 3H); 1.51 (s, 9H); 1.72 (s, 3H); 2.17 (s, 3H); 3.23 (d, 1H); 3.81 (d, 1H); 4.03 (q, 2H); 4.18 (dd, 1H); 4.30 (dd, 1H); 6.51 (brs, 1H); 6.91 (t, 1H); 7.23 (s, 1H); 7.26-7.32 (m, 2H); 7.38 (m, 1H); 7.69 (brs, 1H). |
| 1.222 | 3,5-$Cl_2$—Ph | H | O | H | $CH_2$ | 1-ethyl-3-methyl-1H-pyrazol-4-yl | [$CDCl_3$] 1.45 (t, 3H); 1.73 (s, 3H); 2.19 (s, 3H); 3.18 (d, 1H); 3.80 (d, 1H); 4.06 (q, 2H); 4.19 (dd, 1H); 4.30 (dd, 1H); 6.82 (t br, 1H); 7.25 (s, 1H); 7.42 (m, 1H); 7.51 (m, 2H) |
| 1.223 | R001 | H | O | H | $CH_2$ | 1-ethyl-3-methyl-1H-pyrazol-4-yl | [$CDCl_3$] 1.43 (t, 3H); 1.72 (s, 3H); 2.18 (s, 3H); 3.20 (d, 1H); 3.79 (d, 1H); 3.80 (s, 3H); 4.04 (q, 2H); 4.18 (dd, 1H); 4.32 (dd, 1H); 5.94 (s, 1H); 6.81 (t, 1H); 7.16 (m, 1H); 7.25 (s, 1H); 7.30 (m, 1H); 7.41 (m, 1H). |
| 1.224 | 3,5-$(CF_3)_2$—Ph | H | O | H | $CH_2$ | 1-ethyl-3-methyl-1H-pyrazol-4-yl | [$CDCl_3$] 1.43 (t, 3H), 1.78 (s, 3H); 2.20 (s, 3H); 3.16 (d, 1H); 3.82 (d, 1H); 4.05 (q, 2H); 4.18 (dd, 1H), 4.36 (dd, 1H); 6.82 (t |

TABLE 1-continued

Compounds of the general formula (I) according to the invention in which $R^2$ is hydrogen and $R^3$ is methyl and aryl is the radical

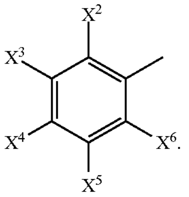

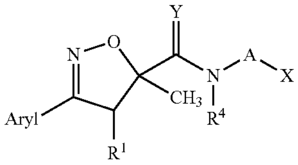

| No. | Aryl | $R^1$ | Y | $R^4$ | A | X | Physical data |
|---|---|---|---|---|---|---|---|
| | | | | | | | br, 1H); 7.92 (s, 1H); 8.07 (s, 2H) |
| 1.225 | 3-Cl-5-$HOCH_2$—Ph | H | O | H | $CH_2$ | 1-ethyl-3-methyl-1H-pyrazol-4-yl | [DMSO-$D_6$] 8.32 0.51; 8.30 1.09; 8.29 0.52; 7.59 2.23; 7.55 1.31; 7.55 2.15; 7.54 1.31; 7.46 1.37; 7.46 1.85; 7.45 1.20; 7.39 3.87; 5.76 3.16; 5.44 1.32; 5.42 3.09; 5.41 1.41; 4.54 2.80; 4.52 2.88; 4.07 1.48; 4.06 1.59; 4.06 1.63; 4.05 1.51; 3.97 1.15; 3.95 3.69; 3.93 3.74; 3.91 1.19; 3.75 1.86; 3.70 2.30; 3.39 2.24; 3.35 1.88; 3.33 47.45; 3.31 0.51; 2.52 0.43; 2.52 0.56; 2.51 10.63; 2.51 24.37; 2.50 34.53; 2.50 24.50; 2.49 10.94; 2.05 16.00; 1.55 11.33; 1.28 4.83; 1.26 10.59; 1.24 4.69; 0.00 3.79 |
| 1.226 | 3-OH—Ph | H | O | H | $CH_2$ | 1-ethyl-3-methyl-1H-pyrazol-4-yl | [$CDCl_3$] 1.40 (t, 3H); 1.71 (s, 3H); 2.14 (s, 3H); 3.21 (d, 1H); 3.79 (d, 1H); 4.02 (q, 2H); 4.24 (m, 2H); 6.91 (m, 1H); 7.00 (t, 1H); 7.13 (m, 2H); 7.23-7.27 (m, 2H); 7.30-7.80 (brs, 1H). |
| 1.227 | 3-F-5-$MeSO_2$—Ph | H | O | H | $CH_2$ | 1-ethyl-3-methyl-1H-pyrazol-4-yl | [$CDCl_3$] 7.94 3.41; 7.94 3.33; 7.72 1.41; 7.71 1.33; 7.70 1.38; 7.70 1.27; 7.66 1.36; 7.66 1.40; 7.64 1.35; 7.64 1.38; 7.52 0.40; 7.26 67.63; 7.26 59.37; 7.00 0.35; 6.81 1.08; 4.35 0.88; 4.33 0.89; 4.31 1.50; 4.30 1.48; 4.21 1.51; 4.19 1.51; 4.17 0.92; 4.16 0.91; 4.09 1.18; 4.07 3.63; 4.05 3.66; 4.03 1.26; 3.90 2.29; 3.85 2.57; 3.26 2.54; 3.22 2.21; 3.13 0.57; 3.09 16.00; 2.77 7.93; 2.77 6.89; 2.22 0.59; 2.19 14.67; 1.75 13.64; 1.55 9.70; 1.46 3.89; 1.44 7.86; 1.44 7.12; 1.42 3.83; 1.40 0.33; 1.25 1.80; 0.01 0.74 |
| 1.228 | 3,5-$Cl_2$—Ph | H | O | cyclopropyl | $CH_2$ | 1-ethyl-3-methyl-1H-pyrazol-4-yl | |
| 1.229 | 2,4-$Cl_2$—Ph | H | O | H | $CH_2$ | 1-ethyl-3-methyl-1H-pyrazol-4-yl | [$CDCl_3$] 1.45 (t, 3H); 1.74 (s, 3H); 2.20 (s, 3H); 3.38 (d, 1H); 3.94 (d, 1H); 4.06 (q, 2H); 4.28 (m, 2H), 6.87 (t br, 1H); 7.28 (m, 2H); 7.45 (d, 1H), 7.50 (d, 1H) |
| 1.230 | 3,5-(tert•Bu)$_2$—Ph | H | O | H | $CH_2$ | 1-ethyl-3-methyl-1H-pyrazol-4-yl | [$CDCl_3$] 7.51 0.43; 7.50 0.40; 7.47 0.93; 7.47 0.93; 7.47 0.98; 7.26 3.07; 7.26 2.42; 7.23 0.65; 4.05 0.58; 4.03 0.58; 3.90 0.33; 3.86 0.37; 3.30 0.37; 3.26 0.33; 2.19 2.32; 1.73 1.97; 1.44 |

TABLE 1-continued

Compounds of the general formula (I) according to the invention in which $R^2$ is hydrogen and $R^3$ is methyl and aryl is the radical

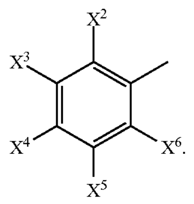

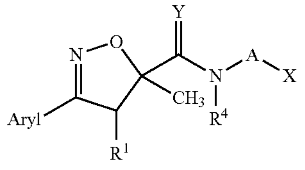

| No. | Aryl | $R^1$ | Y | $R^4$ | A | X | Physical data |
|---|---|---|---|---|---|---|---|
| | | | | | | | 0.62; 1.42 1.25; 1.42 1.12; 1.40 0.63; 1.33 16.00; 0.00 0.96; 0.00 0.78 |
| 1.231 | 3-$NH_2CO$—Ph | H | O | H | $CH_2$ | 1-ethyl-3-methyl-1H-pyrazol-4-yl | [$CDCl_3$] 8.07 1.65; 8.07 2.84; 8.06 1.93; 7.90 0.92; 7.90 1.34; 7.90 1.36; 7.89 1.13; 7.88 1.06; 7.88 1.47; 7.88 1.52; 7.87 1.24; 7.79 0.92; 7.79 1.36; 7.79 1.13; 7.77 1.12; 7.77 1.60; 7.77 1.27; 7.53 1.44; 7.51 2.53; 7.49 1.15; 7.26 17.85; 7.25 4.25; 6.91 0.53; 6.90 0.90; 6.89 0.55; 5.30 5.02; 4.32 0.75; 4.31 0.74; 4.29 1.58; 4.27 1.56; 4.22 1.60; 4.21 1.61; 4.19 0.77; 4.17 0.76; 4.07 1.27; 4.05 3.94; 4.03 4.00; 4.01 1.32; 3.91 2.48; 3.87 2.82; 3.29 2.67; 3.25 2.36; 2.19 16.00; 1.85 1.45; 1.74 14.62; 1.44 4.75; 1.42 9.88; 1.40 4.68; 0.00 7.83; 0.00 3.62; −0.01 0.37 |
| 1.232 | 3-$NH_2$—Ph | H | O | H | $CH_2$ | 1-ethyl-3-methyl-1H-pyrazol-4-yl | [$CDCl_3$] 1.42 (t, 3H); 1.70 (s, 3H); 2.17 (s, 3H); 3.20 (d, 1H); 3.79 (d, 1H); 4.03 (q, 2H); 4.18 (dd, 1H); 4.29 (dd, 1H); 6.91 (t, 1H); 6.93-7.00 (m, 2H); 7.18 (m, 1H); 7.22 (s, 1H). |
| 1.233 | 2-$CF_3$—Ph | H | O | H | $CH_2$ | 1-ethyl-3-methyl-1H-pyrazol-4-yl | [$CDCl_3$] 1.45 (t, 3H), 1.73 (s, 3H); 2.22 (s, 3H); 3.25 (d, 1H); 3.75 (d, 1H); 4.04 (q, 2H); 4.28 (d, 2H); 6.91 (t br, 1H); 7.28 (s, 1H); 7.44 (d, 1H); 7.58 (m, 2H); 7.75 (d, 1H) |
| 1.234 | 2-EtO-3,4,5,6-$F_4$—Ph | H | O | H | $CH_2$ | 1-ethyl-3-methyl-1H-pyrazol-4-yl | [$CDCl_3$] 1.33 (t, 3H); 1.45 (t, 3H); 1.72 (s, 3H); 2.22 (s, 3H); 3.25 (d, 1H); 3.73 (d, 1H); 4.09 (q, 2H); 4.16 (m, 2H); 4.26 (m, 2H); 6.90 (brt, 1H); 7.27 (s, 1H). |
| 1.235 | $F_5$—Ph | H | O | H | $CH_2$ | 1-ethyl-3-methyl-1H-pyrazol-4-yl | [$CDCl_3$] 1.44 (t, 3H); 1.73 (s, 3H); 2.20 (s, 3H); 3.31 (d, 1H); 3.83 (d, 1H); 4.06 (q, 1H); 4.22 (dd, 1H); 4.30 (dd, 1H); 6.81 (brt, 1H); 7.26 (s, 1H). |
| 1.236 | 3-(2-MeOEtO)—Ph | H | O | H | $CH_2$ | 1-ethyl-3-methyl-1H-pyrazol-4-yl | [$CDCl_3$] 1.41 (t, 3H); 1.71 (s, 3H); 2.14 (s, 3H); 3.20 (d, 1H); 3.43 (s, 3H); 3.73 (m, 2H); 3.80 (d, 1H); 4.03 (q, 2H); 4.12 (m, 2H); 4.17 (dd, 1H); 4.29 (dd, 1H); 6.89 (t, 1H); 7.00 (m, 1H); 7.15 (m, 1H); 7.22 (m, 2H); 7.29 (m, 1H). |
| 1.237 | 2,3,5,6-$F_4$-4-MeO—Ph | H | O | H | $CH_2$ | 1-ethyl-3-methyl-1H-pyrazol-4-yl | [$CDCl_3$] 1.45 (t, 3H); 1.72 (s, 3H); 2.20 (s, 3H); 3.31 (d, 1H); 3.82 (d, 1H); 4.06 (q, 2H); 4.15 (m, 3H); 4.23 (dd, 1H); 4.29 |

TABLE 1-continued

Compounds of the general formula (I) according to the invention in which $R^2$ is hydrogen and $R^3$ is methyl and aryl is the radical

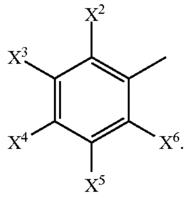

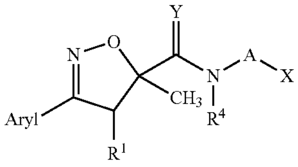

| No. | Aryl | $R^1$ | Y | $R^4$ | A | X | Physical data |
|---|---|---|---|---|---|---|---|
| | | | | | | | (dd, 1H); 6.86 (brt, 1H); 7.26 (s, 1H). |
| 1.238 | 3-Ac—Ph | H | O | H | $CH_2$ | 1-ethyl-3-methyl-1H-pyrazol-4-yl | [$CDCl_3$] 8.18 2.59; 8.03 1.36; 8.01 1.46; 7.85 1.30; 7.83 1.47; 7.55 1.36; 7.53 2.45; 7.51 1.13; 7.27 15.04; 7.26 14.58; 7.25 3.70; 6.89 0.80; 6.88 0.53; 4.34 0.81; 4.33 0.79; 4.30 1.46; 4.29 1.42; 4.22 1.38; 4.20 1.45; 4.18 0.78; 4.17 0.81; 4.08 1.24; 4.06 3.53; 4.04 3.51; 4.02 1.17; 3.92 2.13; 3.88 2.45; 3.31 2.39; 3.27 2.09; 2.63 16.00; 2.24 0.51; 2.20 1.15; 2.19 13.85; 1.75 12.57; 1.63 1.55; 1.45 3.78; 1.43 7.51; 1.41 3.81; 1.39 0.62; 0.00 5.81; 0.00 5.58 |
| 1.239 | 2,3,5-$F_3$-4,6-$(MeO)_2$—Ph | H | O | H | $CH_2$ | 1-ethyl-3-methyl-1H-pyrazol-4-yl | [$CDCl_3$] 1.45 (t, 3H); 1.72 (s, 3H); 2.20 (s, 3H); 3.28 (d, 1H); 3.73 (d, 1H); 3.86 (m, 3H); 4.06 (q, 1H); 4.09 (m, 3H); 4.27 (m, 2H); 6.91 (brt, 1H); 7.27 (s, 1H). |
| 1.240 | 2,3,6-$Cl_3$—Ph | H | O | H | $CH_2$ | 1-ethyl-3-methyl-1H-pyrazol-4-yl | [$CDCl_3$] 1.46 (t, 3H), 1.77 (d, 3H); 2.26 (s, 3H); 3.22 (d, 1H); 3.65 (m, 1H); 4.10 (q, 1H); 4.28 (m, 2H); 7.00 (t br, 1H); 7.42 (m, 2H); 7.88 (d, 1H) |
| 1.241 | 3-iPrO—Ph | H | O | H | $CH_2$ | 1-ethyl-3-methyl-1H-pyrazol-4-yl | [$CDCl_3$] 1.32 (d, 6H); 1.42 (t, 3H); 1.72 (s, 3H); 2.19 (s, 3H); 3.21 (d, 1H); 3.80 (d, 1H); 4.03 (q, 2H); 4.18 (dd, 1H); 4.29 (dd, 1H); 4.55 (sept, 1H); 6.90 (t, 1H); 6.93 (m, 1H); 7.12 (m, 1H); 7.17 (m, 1H); 7.22 (s, 1H); 7.28 (m, 1H). |
| 1.242 | 3-$CF_3$—Ph | H | O | H | $CH_2$ | 1-ethyl-3-methyl-1H-pyrazol-4-yl | [$CDCl_3$] 7.90 1.79; 7.81 0.97; 7.79 1.11; 7.70 0.84; 7.68 1.09; 7.57 0.94; 7.55 1.49; 7.53 0.61; 7.26 28.75; 7.24 3.57; 6.87 0.54; 4.34 0.77; 4.33 0.76; 4.30 1.36; 4.29 1.34; 4.21 1.40; 4.20 1.40; 4.18 0.80; 4.16 0.78; 4.07 1.30; 4.05 4.00; 4.04 4.06; 4.02 1.34; 3.90 2.78; 3.85 3.13; 3.28 2.88; 3.24 2.53; 2.19 16.00; 1.75 15.80; 1.58 3.30; 1.45 5.21; 1.43 10.81; 1.41 5.08; 0.01 0.41; 0.00 12.87 |
| 1.243 | 3-Me-5-$CF_3O$—Ph | H | O | H | $CH_2$ | 1-ethyl-3-methyl-1H-pyrazol-4-yl | [$CDCl_3$] 7.35 3.02; 7.31 2.35; 7.27 1.92; 7.27 11.98; 7.26 13.45; 7.24 4.48; 7.10 2.25; 6.88 1.00; 4.34 0.91; 4.32 0.90; 4.30 1.64; 4.28 1.62; 4.21 1.67; 4.20 1.65; 4.17 0.93; 4.16 0.91; 4.07 1.49; 4.06 4.00; 4.04 4.00; 4.02 |

TABLE 1-continued
Compounds of the general formula (I) according to the invention in which $R^2$ is hydrogen and $R^3$ is methyl and aryl is the radical
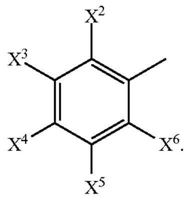
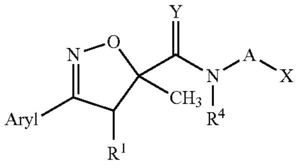
| No. | Aryl | $R^1$ | Y | $R^4$ | A | X | Physical data |
|---|---|---|---|---|---|---|---|
| | | | | | | | 1.35; 3.84 2.39; 3.80 2.75; 3.24 2.69; 3.20 2.34; 2.54 0.65; 2.41 0.85; 2.40 13.31; 2.27 0.87; 2.19 16.00; 1.73 14.42; 1.63 6.06; 1.46 0.49; 1.45 4.36; 1.43 8.47; 1.41 4.10; 1.26 0.35; 0.01 0.42; 0.00 2.65; 0.00 2.93 |
| 1.244 | 3,5-(MeO)$_2$—Ph | H | O | H | $CH_2$ | 1-ethyl-3-methyl-1H-pyrazol-4-yl | [$CDCl_3$] 7.26 11.93; 7.23 1.66; 6.89 0.33; 6.77 2.76; 6.77 2.75; 6.52 0.74; 6.52 1.27; 6.51 0.62; 4.32 0.33; 4.31 0.33; 4.29 0.67; 4.27 0.66; 4.22 0.67; 4.21 0.70; 4.18 0.34; 4.17 0.34; 4.07 0.58; 4.05 1.70; 4.03 1.69; 4.01 0.56; 3.83 1.10; 3.80 16.00; 3.78 1.28; 3.24 1.16; 3.20 1.01; 2.20 0.34; 2.19 6.77; 1.72 6.15; 1.59 1.02; 1.45 2.00; 1.43 4.07; 1.41 1.94 |
| 1.245 | 4-EtO—Ph | H | O | H | $CH_2$ | 1-ethyl-3-methyl-1H-pyrazol-4-yl | [$CDCl_3$] 7.57 0.40; 7.56 3.92; 7.54 1.25; 7.54 4.52; 7.26 22.59; 7.22 4.21; 7.21 0.32; 6.94 0.96; 6.92 0.62; 6.92 0.72; 6.91 4.33; 6.89 1.24; 6.89 4.22; 4.32 0.81; 4.30 0.81; 4.28 1.61; 4.27 1.59; 4.21 1.60; 4.20 1.69; 4.17 0.82; 4.16 0.82; 4.09 1.28; 4.07 4.13; 4.06 1.62; 4.05 4.32; 4.04 4.22; 4.04 1.76; 4.03 4.11; 4.01 1.38; 3.83 2.52; 3.79 2.88; 3.23 2.78; 3.19 2.44; 2.19 0.69; 2.18 16.00; 1.71 14.80; 1.59 4.87; 1.44 4.35; 1.44 5.17; 1.43 8.95; 1.42 10.08; 1.41 4.49; 1.40 4.85; 1.39 0.37 |
| 1.246 | 4-MeO—Ph | H | O | H | $CH_2$ | 1-ethyl-3-methyl-1H-pyrazol-4-yl | [$CDCl_3$] 7.58 3.33; 7.57 3.81; 7.57 1.07; 7.55 4.02; 7.55 3.40; 7.55 3.42; 7.55 0.59; 7.54 0.39; 7.26 18.89; 7.26 18.13; 7.22 4.10; 6.93 1.25; 6.92 4.18; 6.92 4.58; 6.90 3.84; 4.32 0.74; 4.32 0.72; 4.30 0.74; 4.30 0.72; 4.28 1.47; 4.28 1.46; 4.27 1.47; 4.27 1.43; 4.21 1.46; 4.21 1.46; 4.20 1.52; 4.20 1.48; 4.17 0.74; 4.17 0.74; 4.16 0.75; 4.16 0.74; 4.06 1.15; 4.06 1.15; 4.05 3.44; 4.04 3.35; 4.03 3.47; 4.02 3.36; 4.01 1.17; 4.01 1.12; 3.84 15.85; 3.84 16.00; 3.83 2.75; 3.79 2.58; 3.79 2.60; 3.24 2.42; 3.24 2.40; 3.20 2.12; 3.19 2.10; 2.18 13.77; 2.18 13.46; 1.72 13.19; 1.71 |

TABLE 1-continued

Compounds of the general formula (I) according to the invention in which $R^2$ is hydrogen and $R^3$ is methyl and aryl is the radical

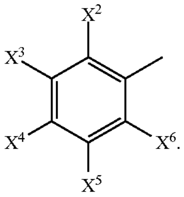

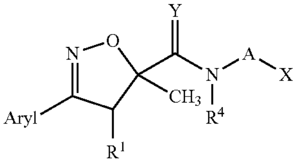

| No. | Aryl | $R^1$ | Y | $R^4$ | A | X | Physical data |
|---|---|---|---|---|---|---|---|
| | | | | | | | 12.83; 1.62 1.49; 1.44 3.86; 1.44 3.76; 1.42 7.89; 1.42 7.70; 1.40 3.88; 1.40 3.68; 0.00 8.71 |
| 1.247 | 3-Et—Ph | H | O | H | $CH_2$ | 1-ethyl-3-methyl-1H-pyrazol-4-yl | [$CDCl_3$] 7.49 2.29; 7.43 1.08; 7.41 1.56; 7.34 1.03; 7.32 2.38; 7.31 0.38; 7.30 1.45; 7.28 1.68; 7.26 13.92; 7.23 3.96; 6.93 0.68; 4.32 0.82; 4.31 0.79; 4.29 1.53; 4.27 1.52; 4.21 1.55; 4.20 1.57; 4.17 0.82; 4.16 0.82; 4.06 1.24; 4.05 3.88; 4.03 3.96; 4.01 1.33; 3.87 2.54; 3.83 2.91; 3.27 2.76; 3.23 2.44; 2.70 0.93; 2.68 2.91; 2.66 3.01; 2.64 1.04; 2.19 16.00; 1.73 14.80; 1.65 2.54; 1.44 4.50; 1.42 9.29; 1.40 4.48; 1.26 4.44; 1.24 9.15; 1.22 4.33 |
| 1.248 | 3-iPr—Ph | H | O | H | $CH_2$ | 1-ethyl-3-methyl-1H-pyrazol-4-yl | [$CDCl_3$] 1.26 (d, 6H); 1.42 (t, 3H); 1.73 (s, 3H); 2.19 (s, 3H); 2.93 (m, 1H); 3.27 (d, 1H); 3.86 (d, 1H); 4.03 (q, 2H); 4.19 (dd, 1H); 4.30 (dd, 1H); 6.95 (brt, 1H); 7.23 (s, 1H); 7.32 (m, 2H); 7.42 (d, 1H); 7.52 (s, 1H). |
| 1.249 | 4-F-3,5-$Me_2$—Ph | H | O | H | $CH_2$ | 1-ethyl-3-methyl-1H-pyrazol-4-yl | [$CDCl_3$] 7.29 2.77; 7.28 0.35; 7.28 2.36; 7.28 2.83; 7.27 0.49; 7.27 0.51; 7.26 21.60; 7.23 3.33; 6.90 0.57; 5.30 0.46; 4.32 0.68; 4.32 0.68; 4.30 0.69; 4.30 0.67; 4.28 1.35; 4.28 1.34; 4.27 1.34; 4.21 1.38; 4.20 1.40; 4.17 0.71; 4.17 0.71; 4.16 0.70; 4.16 0.69; 4.06 1.26; 4.05 3.92; 4.03 3.99; 4.01 1.33; 3.82 2.61; 3.78 2.98; 3.22 2.60; 3.17 2.29; 2.27 12.57; 2.26 12.27; 2.18 15.23; 1.71 16.00; 1.61 5.16; 1.44 5.58; 1.42 11.75; 1.40 5.45 |
| 1.250 | 3-Cl-5-$CF_3O$—Ph | H | O | H | $CH_2$ | 1-ethyl-3-methyl-1H-pyrazol-4-yl | [$CDCl_3$] 1.43 (t, 3H); 1.73 (s, 3H); 2.19 (s, 3H); 3.20 (d, 1H); 3.81 (d, 1H); 4.05 (q, 2H); 4.18 (dd, 1H); 4.33 (dd, 1H) 6.81 (brt, 1H); 7.23 (s, 1H); 7.29 (s, 1H); 7.40 (brs, 1H); 7.53 (brs, 1H). |
| 1.251 | 3,5-$F_2$—Ph | H | O | H | $CH_2$ | 1-ethyl-3-methyl-1H-pyrazol-5-yl | [$CDCl_3$] 7.26 16.00; 7.16 1.62; 7.16 1.94; 7.15 1.18; 7.15 1.10; 7.14 2.04; 7.14 1.65; 7.01 0.57; 7.00 0.45; 6.92 0.40; 6.91 0.73; 6.91 0.37; 6.90 0.82; 6.89 1.45; 6.88 0.72; 6.87 0.43; 6.87 0.73; 6.86 0.35; 5.91 3.72; 4.52 0.83; 4.50 0.82; 4.48 1.55; 4.46 1.54; 4.40 1.56; 4.38 1.58; 4.36 |

TABLE 1-continued
Compounds of the general formula (I) according to the invention in which $R^2$ is hydrogen and $R^3$ is methyl and aryl is the radical
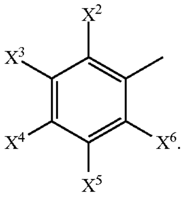
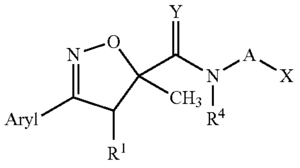
| No. | Aryl | $R^1$ | Y | $R^4$ | A | X | Physical data |
|---|---|---|---|---|---|---|---|
| | | | | | | | 0.84; 4.34 0.83; 4.04 1.18; 4.03 3.73; 4.01 3.85; 3.99 1.29; 3.80 2.74; 3.76 3.16; 3.23 2.90; 3.19 2.54; 2.96 0.61; 2.88 0.53; 2.22 15.50; 1.74 16.00; 1.63 2.44; 1.36 4.49; 1.34 9.57; 1.33 4.41 |
| 1.252 | 3,5-$Cl_2$—Ph | H | O | H | $CH_2$ | 1-ethyl-3-methyl-1H-pyrazol-5-yl | [$CDCl_3$] 7.51 5.99; 7.51 6.01; 7.50 6.51; 7.43 1.75; 7.43 1.78; 7.42 2.85; 7.42 1.38; 7.26 13.91; 7.26 13.04; 7.01 0.47; 7.00 0.82; 6.99 0.47; 5.91 4.13; 4.51 0.90; 4.50 0.89; 4.48 1.63; 4.46 1.60; 4.39 1.64; 4.37 1.64; 4.35 0.91; 4.34 0.89; 4.04 1.21; 4.03 3.77; 4.01 3.86; 3.99 1.29; 3.81 2.53; 3.76 2.91; 3.23 2.82; 3.19 2.45; 2.22 16.00; 1.74 15.05; 1.63 1.69; 1.36 4.14; 1.35 8.56; 1.33 4.09 |
| 1.253 | 3-F—Ph | H | O | H | $CH_2$ | 1-ethyl-3-methyl-1H-pyrazol-5-yl | [$CDCl_3$] 7.42 0.35; 7.40 0.34; 7.40 1.17; 7.38 2.41; 7.38 3.50; 7.37 2.89; 7.37 2.98; 7.36 1.24; 7.36 1.75; 7.36 1.73; 7.26 10.58; 7.26 11.11; 7.16 0.52; 7.16 0.77; 7.14 0.86; 7.14 0.85; 7.14 1.12; 7.13 0.52; 7.12 0.62; 7.11 0.34; 7.06 0.80; 5.91 4.45; 4.51 0.89; 4.50 0.88; 4.47 1.74; 4.46 1.72; 4.40 1.74; 4.38 1.74; 4.36 0.89; 4.34 0.87; 4.04 1.25; 4.02 3.80; 4.00 3.86; 3.99 1.29; 3.83 2.44; 3.83 2.47; 3.79 2.85; 3.27 2.79; 3.22 2.41; 2.21 16.00; 1.74 15.05; 1.63 3.50; 1.36 4.02; 1.34 8.03; 1.34 8.23; 1.32 3.87; 1.32 3.91; 0.00 1.32 |
| 1.254 | Ph | H | O | H | $CH_2$ | 1-ethyl-3-methyl-1H-pyrazol-5-yl | [$CDCl_3$] 7.64 1.92; 7.64 3.57; 7.63 3.05; 7.63 1.46; 7.62 3.63; 7.61 2.86; 7.46 0.37; 7.44 1.39; 7.44 1.10; 7.43 2.05; 7.43 5.96; 7.41 1.76; 7.41 3.22; 7.40 0.77; 7.39 0.91; 7.39 0.93; 7.39 0.68; 7.38 0.52; 7.27 10.81; 7.26 12.17; 7.10 1.03; 5.91 4.67; 4.51 0.89; 4.49 0.85; 4.49 0.89; 4.47 1.78; 4.45 1.76; 4.39 1.79; 4.38 1.71; 4.38 1.78; 4.36 0.87; 4.36 0.91; 4.34 0.88; 4.04 1.23; 4.03 1.34; 4.02 3.76; 4.02 4.02; 4.00 3.86; 4.00 4.09; 3.98 1.35; 3.98 1.39; 3.86 2.44; 3.86 2.66; 3.82 2.84; 3.82 3.08; 3.30 2.73; 3.29 2.95; 3.25 2.36; 3.25 2.55; 2.21 14.91; 2.21 15.78; 1.74 |

TABLE 1-continued
Compounds of the general formula (I) according to the invention in which $R^2$ is hydrogen and $R^3$ is methyl and aryl is the radical
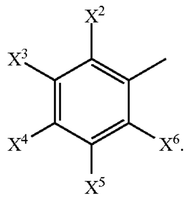
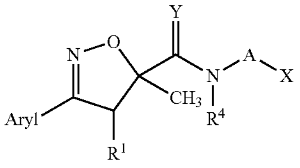
| No. | Aryl | $R^1$ | Y | $R^4$ | A | X | Physical data |
|---|---|---|---|---|---|---|---|
| | | | | | | | 14.84; 1.74 16.00; 1.64 3.96; 1.35 3.97; 1.35 4.37; 1.34 8.13; 1.33 8.95; 1.32 4.03; 1.32 4.27; 0.00 1.85; 0.00 2.03 |
| 1.255 | 3,5-$F_2$—Ph | H | O | H | $CH_2$ | 1H-1,2,3-triazol-5-yl | [$CDCl_3$] 7.62 4.10; 7.52 0.73; 7.33 0.57; 7.26 128.08; 7.16 1.50; 7.16 1.90; 7.16 1.19; 7.15 1.13; 7.14 1.92; 7.14 1.60; 7.00 0.70; 6.91 0.36; 6.90 0.69; 6.90 0.37; 6.89 0.77; 6.88 1.38; 6.88 0.68; 6.87 0.39; 6.86 0.68; 6.85 0.34; 4.65 0.76; 4.63 0.78; 4.61 1.72; 4.59 1.71; 4.55 1.75; 4.53 1.76; 4.51 0.80; 4.50 0.77; 3.81 2.62; 3.77 3.00; 3.49 0.54; 3.23 2.85; 3.19 2.48; 2.04 0.55; 2.00 0.69; 1.94 0.34; 1.90 0.42; 1.88 0.37; 1.84 0.38; 1.83 0.39; 1.81 0.37; 1.78 0.37; 1.76 0.39; 1.74 16.00; 1.70 0.35; 1.69 0.34; 0.01 0.88 |
| 1.256 | 3,5-$F_2$—Ph | H | O | H | $CH_2$ | 1H-pyrazol-3-yl | [$CDCl_3$] 7.52 2.79; 7.51 2.87; 7.41 0.77; 7.26 19.61; 7.17 0.33; 7.17 0.33; 7.16 1.75; 7.16 2.32; 7.14 2.30; 7.14 1.86; 7.12 0.37; 6.90 0.41; 6.90 0.73; 6.89 0.41; 6.88 0.85; 6.88 1.46; 6.87 0.78; 6.86 0.46; 6.85 0.75; 6.85 0.39; 6.22 2.58; 6.22 2.62; 4.57 0.81; 4.55 0.81; 4.53 1.67; 4.51 1.66; 4.46 1.67; 4.45 1.69; 4.42 0.83; 4.41 0.82; 3.82 2.61; 3.78 2.99; 3.23 2.93; 3.19 2.56; 1.74 16.00; 0.00 7.33 |
| 1.257 | 3,5-$Cl_2$—Ph | H | O | H | $CH_2$ | 1H-pyrazol-3-yl | [$CDCl_3$] 7.52 2.81; 7.51 2.91; 7.50 6.72; 7.50 7.13; 7.42 0.80; 7.41 2.37; 7.40 3.58; 7.40 1.75; 7.26 21.65; 6.22 2.31; 6.22 2.27; 4.56 0.83; 4.55 0.84; 4.53 1.78; 4.51 1.75; 4.46 1.76; 4.45 1.80; 4.42 0.86; 4.41 0.84; 3.83 2.90; 3.79 3.31; 3.23 3.09; 3.18 2.70; 1.74 16.00 |
| 1.258 | 3-F—Ph | H | O | H | $CH_2$ | 1H-pyrazol-3-yl | [$CDCl_3$] 7.51 3.12; 7.51 2.98; 7.47 0.84; 7.41 0.37; 7.39 2.31; 7.38 1.29; 7.38 1.40; 7.37 2.32; 7.37 4.14; 7.36 4.38; 7.35 0.55; 7.27 15.61; 7.26 15.63; 7.15 0.54; 7.14 0.84; 7.14 0.50; 7.13 0.87; 7.13 0.84; 7.12 1.10; 7.12 0.66; 7.11 0.63; 7.10 0.39; 6.22 2.95; 6.22 2.76; 4.57 0.86; 4.56 0.87; 4.53 1.72; 4.52 1.71; 4.46 1.73; 4.45 1.75; 4.42 0.89; 4.41 0.87; 3.85 2.61; 3.85 2.52; 3.81 2.99; 3.81 2.90; 3.27 |

TABLE 1-continued

Compounds of the general formula (I) according to the invention in which $R^2$ is hydrogen and $R^3$ is methyl and aryl is the radical

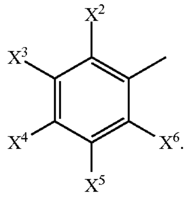

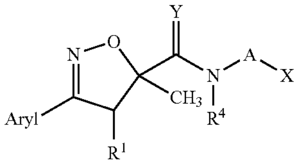

| No. | Aryl | $R^1$ | Y | $R^4$ | A | X | Physical data |
|---|---|---|---|---|---|---|---|
| | | | | | | | 2.94; 3.22 2.57; 1.74 15.89; 1.74 16.00; 0.00 5.60; 0.00 5.93 |
| 1.259 | Ph | H | O | H | $CH_2$ | 1H-pyrazol-3-yl | [$CDCl_3$] 7.64 1.98; 7.63 2.33; 7.63 1.20; 7.63 1.06; 7.62 0.86; 7.62 2.24; 7.61 2.79; 7.52 0.36; 7.50 3.22; 7.50 3.22; 7.43 0.66; 7.43 0.93; 7.42 1.56; 7.41 5.24; 7.41 2.47; 7.41 0.94; 7.40 1.22; 7.40 2.47; 7.39 0.45; 7.39 0.46; 7.38 0.67; 7.38 0.38; 7.37 0.50; 7.26 19.17; 6.21 2.44; 6.21 2.50; 4.57 0.79; 4.55 0.80; 4.53 1.50; 4.52 1.48; 4.45 1.50; 4.44 1.52; 4.41 0.81; 4.40 0.79; 3.88 2.83; 3.83 3.22; 3.29 3.06; 3.25 2.65; 1.74 16.00 |
| 1.260 | 3,5-$Cl_2$—Ph | H | O | H | $CH_2$ | 1H-pyrazol-4-yl | [$CDCl_3$] 1.72 (s, 3H); 3.19 (d, 1H); 3.79 (d, 1H); 4.29 (dd, 1H); 4.41 (dd, 1H); 6.99 (brt, 1H); 7.41 (m, 1H); 7.52 (m, 4H). |
| 1.261 | 3,5-$F_2$—Ph | H | O | H | $CH_2$ | 1H-pyrazol-4-yl | [$CDCl_3$] 7.54 7.25; 7.52 1.62; 7.32 0.39; 7.31 0.47; 7.28 0.35; 7.28 0.41; 7.28 0.44; 7.28 0.40; 7.28 0.42; 7.28 0.45; 7.28 0.52; 7.28 0.54; 7.28 0.64; 7.27 0.66; 7.27 0.70; 7.27 0.74; 7.27 0.75; 7.27 0.87; 7.27 0.88; 7.27 0.99; 7.27 1.06; 7.27 1.21; 7.27 1.39; 7.27 1.72; 7.27 2.21; 7.26 2.80; 7.26 288.21; 7.25 0.92; 7.24 0.42; 7.21 0.38; 7.16 1.58; 7.16 1.88; 7.15 1.01; 7.15 0.94; 7.14 1.92; 7.14 1.62; 7.01 0.42; 7.00 1.81; 6.91 0.39; 6.90 0.70; 6.90 0.34; 6.89 0.82; 6.88 1.46; 6.88 0.74; 6.87 0.43; 6.86 0.67; 6.85 0.37; 4.44 0.72; 4.43 0.73; 4.41 1.35; 4.39 1.31; 4.32 1.35; 4.31 1.32; 4.29 0.73; 4.27 0.69; 3.81 2.72; 3.76 3.07; 3.49 0.52; 3.22 2.73; 3.17 2.35; 2.04 0.44; 2.00 0.41; 1.73 16.00; 1.55 3.56; 1.43 0.37; 1.26 0.42; 0.15 0.39; 0.01 3.11; 0.00 114.06; −0.01 1.78; −0.01 3.68; −0.01 0.57; −0.01 0.48; −0.15 0.34 |
| 1.262 | 3-F—Ph | H | O | H | $CH_2$ | 1H-pyrazol-4-yl | [$CDCl_3$] 1.72 (s, 3H); 3.21 (d, 1H); 3.80 (d, 1H); 4.29 (dd, 1H); 4.41 (dd, 1H); 7.05 (t, 1H); 7.12 (m, 1H); 7.36 (m, 3H); 7.52 (s, 2H). |
| 1.263 | 3,5-$F_2$—Ph | H | O | H | $CH_2$ | 1-isobutyl-1H-pyrazol-4-yl | [$CDCl_3$] 7.52 0.50; 7.41 3.70; 7.29 3.76; 7.26 93.83; 7.16 1.58; 7.16 2.07; 7.14 1.19; 7.14 1.99; 7.14 1.70; 7.12 0.32; 7.00 |

TABLE 1-continued
Compounds of the general formula (I) according to the invention in which $R^2$ is hydrogen and $R^3$ is methyl and aryl is the radical
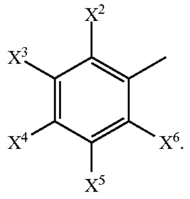
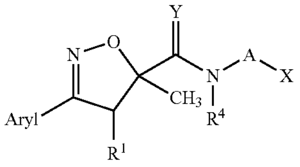
| No. | Aryl | $R^1$ | Y | $R^4$ | A | X | Physical data |
|---|---|---|---|---|---|---|---|
| | | | | | | | 0.58; 6.97 0.63; 6.91 0.42; 6.90 0.74; 6.90 0.42; 6.89 0.83; 6.88 1.45; 6.88 0.73; 6.87 0.44; 6.86 0.73; 6.85 0.36; 4.38 0.77; 4.37 0.80; 4.35 1.45; 4.33 1.47; 4.26 1.46; 4.25 1.48; 4.23 0.81; 4.21 0.79; 3.86 5.64; 3.84 5.78; 3.81 2.71; 3.76 3.09; 3.21 2.90; 3.17 2.56; 2.19 0.42; 2.17 0.87; 2.15 1.08; 2.14 0.86; 2.12 0.45; 1.73 16.00; 1.55 45.98; 0.89 12.96; 0.87 12.68; 0.01 1.63; 0.00 61.95; −0.01 2.08 |
| 1.264 | 3,5-$Cl_2$—Ph | H | O | H | $CH_2$ | 1-isobutyl-1H-pyrazol-4-yl | [$CDCl_3$] 7.54 0.71; 7.53 0.79; 7.51 6.40; 7.50 7.26; 7.42 1.88; 7.41 3.32; 7.40 4.59; 7.28 4.24; 7.26 23.44; 6.95 0.74; 4.38 0.84; 4.36 0.83; 4.34 1.59; 4.32 1.56; 4.26 1.66; 4.25 2.13; 4.23 0.32; 4.23 0.85; 4.21 0.84; 3.86 5.59; 3.84 5.70; 3.82 0.38; 3.81 2.63; 3.77 3.00; 3.20 2.87; 3.17 0.40; 3.16 2.54; 2.19 0.46; 2.17 0.95; 2.15 1.19; 2.14 0.95; 2.12 0.50; 1.72 15.72; 1.57 4.51; 0.89 16.00; 0.87 15.61; 0.01 0.34; 0.00 13.39; −0.01 0.50 |
| 1.265 | 3-F—Ph | H | O | H | $CH_2$ | 1-isobutyl-1H-pyrazol-4-yl | [$CDCl_3$] 7.41 0.46; 7.40 3.94; 7.39 1.38; 7.38 1.11; 7.38 1.10; 7.38 2.12; 7.37 2.33; 7.37 2.38; 7.37 2.60; 7.36 3.43; 7.36 1.37; 7.28 4.08; 7.26 27.54; 7.26 19.79; 7.15 0.43; 7.15 0.73; 7.14 0.49; 7.13 0.65; 7.13 0.63; 7.13 0.70; 7.13 0.97; 7.12 0.65; 7.11 0.65; 7.10 0.37; 7.00 0.63; 7.00 0.59; 4.38 0.80; 4.36 0.80; 4.34 1.55; 4.33 1.54; 4.27 1.57; 4.25 1.57; 4.23 0.82; 4.22 0.80; 3.85 5.50; 3.83 6.54; 3.79 3.06; 3.24 2.93; 3.20 2.58; 2.18 0.45; 2.16 0.91; 2.15 1.14; 2.13 0.92; 2.11 0.48; 1.73 16.00; 1.56 5.65; 0.88 15.05; 0.86 14.70; 0.01 0.38; 0.00 15.01; 0.00 10.96; −0.01 0.54; −0.01 0.37 |
| 1.266 | Ph | H | O | H | $CH_2$ | 1-isobutyl-1H-pyrazol-4-yl | [$CDCl_3$] 7.65 0.39; 7.64 1.99; 7.64 2.39; 7.63 1.25; 7.62 2.24; 7.62 2.65; 7.43 0.71; 7.43 0.87; 7.42 5.57; 7.41 2.55; 7.40 6.49; 7.39 0.72; 7.38 0.46; 7.27 3.96; 7.26 15.25; 7.05 0.61; 4.38 0.76; 4.36 0.76; 4.34 1.52; 4.32 1.50; 4.27 1.53; 4.26 0.33; 4.25 1.55; 4.24 0.41; 4.23 0.86; 4.22 0.78; 3.86 2.71; 3.84 5.54; 3.82 |

TABLE 1-continued

Compounds of the general formula (I) according to the invention in which $R^2$ is hydrogen and $R^3$ is methyl and aryl is the radical

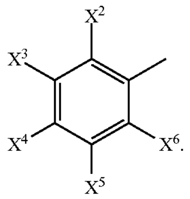

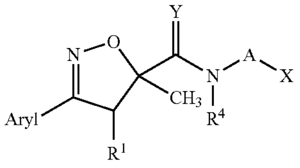

| No. | Aryl | $R^1$ | Y | $R^4$ | A | X | Physical data |
|---|---|---|---|---|---|---|---|
| | | | | | | | 5.75; 3.82 3.44; 3.27 2.96; 3.23 2.60; 2.18 0.44; 2.16 0.88; 2.14 1.12; 2.12 0.91; 2.11 0.47; 1.73 16.00; 1.72 1.66; 1.59 1.54; 0.87 15.62; 0.86 15.25; 0.00 9.32; −0.01 0.35 |
| 1.267 | 3,5-$F_2$—Ph | H | O | H | $CH_2$ | 1-isopropyl-1H-pyrazol-4-yl | [$CDCl_3$] 1.47 (d, 6H); 1.72 (s, 3H); 3.18 (d, 1H); 3.79 (d, 1H); 4.23 (dd, 1H); 4.35 (dd, 1H); 4.45 (m, 1H); 6.88 (m, 1H); 6.94 (brt, 1H); 7.15 (m, 2H); 7.33 (s, 1H); 7.40 (s, 1H). |
| 1.268 | 3-F—Ph | H | O | H | $CH_2$ | 1-isopropyl-1H-pyrazol-4-yl | [$CDCl_3$] 1.46 (d, 6H); 1.72 (s, 3H); 3.21 (d, 1H); 3.80 (d, 1H); 4.21 (dd, 1H); 4.34 (dd, 1H); 4.45 (sept, 1H); 6.97 (t, 1H); 7.13 (m, 1H); 7.33-7.42 (m, 5H). |
| 1.269 | 3,5-$Cl_2$—Ph | H | O | H | $CH_2$ | 1-isopropyl-1H-pyrazol-4-yl | [$CDCl_3$] 1.46 (d, 6H); 1.72 (s, 3H); 3.18 (d, 1H); 3.77 (d, 1H); 4.20 (dd, 1H); 4.33 (dd, 1H); 4.45 (sept, 1H); 6.94 (t, 1H); 7.33 (s, 1H); 7.41 (m, 2H); 7.50 (m, 2H). |
| 1.270 | Ph | H | O | H | $CH_2$ | 1-isopropyl-1H-pyrazol-4-yl | [$CDCl_3$] 1.45 (d, 6H); 1.71 (s, 3H); 3.23 (d, 1H); 3.82 (d, 1H); 4.22 (dd, 1H); 4.35 (dd, 1H); 4.44 (sept, 1H); 7.02 (t, 1H); 7.33 (s, 1H); 7.37-7.45 (m, 5H); 7.62 (m, 2H). |
| 1.271 | 2,3,4-$F_3$—Ph | H | O | H | $CH_2$ | 1-isopropyl-1H-pyrazol-4-yl | [$CDCl_3$] 7.52 0.37; 7.51 0.36; 7.51 0.58; 7.51 0.61; 7.51 0.62; 7.50 0.45; 7.49 0.64; 7.49 0.61; 7.49 0.61; 7.48 0.39; 7.47 0.34; 7.47 0.33; 7.41 3.59; 7.36 3.81; 7.26 1.53; 7.26 11.24; 7.26 10.58; 7.05 0.34; 7.05 0.36; 7.04 0.39; 7.03 0.97; 7.03 0.69; 7.01 0.67; 7.01 0.94; 7.00 0.38; 6.99 0.33; 6.99 0.33; 6.94 0.60; 5.30 2.25; 5.30 2.14; 4.48 0.43; 4.47 1.10; 4.45 1.50; 4.43 1.14; 4.42 0.46; 4.38 0.74; 4.37 0.74; 4.34 1.49; 4.33 1.49; 4.28 1.52; 4.26 1.53; 4.24 0.76; 4.23 0.75; 3.91 1.16; 3.91 1.19; 3.87 1.38; 3.86 1.37; 3.33 1.33; 3.32 1.36; 3.28 1.17; 3.28 1.17; 1.72 14.50; 1.60 7.48; 1.49 16.00; 1.47 15.87; 1.26 0.41; 0.00 0.82; 0.00 5.61; 0.00 5.58; 0.00 5.49 |
| 1.272 | 2,5-$F_2$—Ph | H | O | H | $CH_2$ | 1-isopropyl-1H-pyrazol-4-yl | [$CDCl_3$] 1.48 (d, 6H); 1.71 (s, 3H); 3.32 (dd, 1H); 3.89 (dd, 1H); 4.25 (dd, 1H); 4.35 (dd, |

TABLE 1-continued

Compounds of the general formula (I) according to the invention in which $R^2$ is hydrogen and $R^3$ is methyl and aryl is the radical

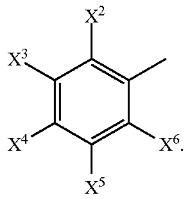

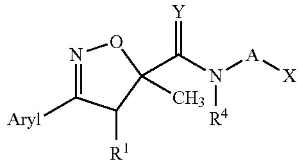

| No. | Aryl | $R^1$ | Y | $R^4$ | A | X | Physical data |
|---|---|---|---|---|---|---|---|
| | | | | | | | 1H); 4.45 (m, 1H); 6.95 (brt, 1H); 7.10 (m, 2H); 7.35 (s, 1H); 7.41 (s, 1H); 7.49 (m, 1H). |
| 1.273 | 3,5-$Cl_2$—Ph | H | O | H | $CH_2$ | 1-methyl-1H-imidazol-4-yl | [$CDCl_3$] 1.72 (s, 3H); 3.17 (d, 1H); 3.64 (s, 3H); 3.79 (d, 1H); 4.30 (dd, 1H), 4.39 (dd, 1H); 6.79 (brs, 1H); 7.21 (brs, 1H); 7.37 (brs, 1H); 7.40 (m, 1H); 7.50 (m, 2H). |
| 1.274 | 3,5-$F_2$—Ph | H | O | H | $CH_2$ | 1-methyl-1H-imidazol-4-yl | [$CDCl_3$] 1.72 (s, 3H); 3.17 (d, 1H); 3.63 (s, 3H); 3.78 (d, 1H); 4.30 (dd, 1H); 4.40 (dd, 1H); 6.76 (s, 1H); 6.85 (m, 1H); 7.15 (m, 2H); 7.21 (brt, 1H); 7.35 (s, 1H). |
| 1.275 | Ph | H | O | H | $CH_2$ | 1-methyl-1H-imidazol-4-yl | [$CDCl_3$] 1.73 (s, 3H); 3.23 (d, 1H); 3.61 (s, 3H); 3.84 (d, 1H); 4.31 (dd, 1H), 4.40 (dd, 1H); 6.76 (s, 1H); 7.27 (brt, 1H); 7.33 (s, 1H); 7.40 (m, 3H); 7.62 (m, 2H). |
| 1.276 | 3-F—Ph | H | O | H | $CH_2$ | 1-methyl-1H-imidazol-4-yl | [$CDCl_3$] 1.72 (s, 3H); 3.21 (d, 1H); 3.63 (s, 3H); 3.81 (d, 1H); 4.31 (dd, 1H), 4.40 (dd, 1H); 6.77 (s, 1H); 7.12 (m, 1H); 7.35 (m, 4H). |
| 1.277 | 3,5-$Cl_2$—Ph | H | O | H | $CH_2$ | 1-methyl-1H-imidazol-5-yl | [$CDCl_3$] 1.73 (s, 3H); 3.20 (d, 1H); 3.55 (s, 3H); 3.79 (d, 1H); 4.38 (dd, 1H), 4.52 (dd, 1H); 6.93 (brt, 1H); 6.98 (s, 1H); 7.41 (m, 2H); 7.50 (m, 2H). |
| 1.278 | 3,5-$F_2$—Ph | H | O | H | $CH_2$ | 1-methyl-1H-imidazol-5-yl | [$CDCl_3$] 1.73 (s, 3H); 3.20 (d, 1H); 3.55 (s, 3H); 3.78 (d, 1H); 4.38 (dd, 1H); 4.54 (dd, 1H); 6.89 (m, 1H); 6.95 (brt, 1H); 7.15 (m, 2H); 7.42 (s, 1H). |
| 1.279 | 3-F—Ph | H | O | H | $CH_2$ | 1-methyl-1H-imidazol-5-yl | [$CDCl_3$] 1.72 (s, 3H); 3.22 (d, 1H); 3.53 (s, 3H); 3.81 (d, 1H); 4.38 (dd, 1H), 4.52 (dd, 1H); 6.96 (s, 1H); 7.00 (brt, 1H); 7.15 (m, 1H); 7.39 (m, 4H). |
| 1.280 | 3,5-$F_2$—Ph | H | O | H | $CH_2$ | 1-methyl-1H-pyrazol-4-yl | [$CDCl_3$] 7.52 0.65; 7.40 2.58; 7.30 2.63; 7.26 114.23; 7.25 1.76; 7.25 0.54; 7.25 0.42; 7.24 0.38; 7.24 0.34; 7.16 1.48; 7.16 1.70; 7.15 1.02; 7.15 0.97; 7.14 1.84; 7.14 1.46; 7.00 0.65; 6.95 0.46; 6.91 0.37; 6.90 0.66; 6.90 0.32; 6.89 0.75; 6.88 1.29; 6.87 0.64; 6.86 0.38; 6.86 0.64; 4.38 0.66; 4.36 0.68; 4.34 1.23; 4.32 1.20; 4.25 1.25; 4.24 1.24; 4.22 0.69; 4.20 0.67; 3.86 16.00; 3.80 2.45; 3.76 2.82; 3.21 2.52; 3.16 2.22; 1.72 14.47; 1.54 49.34; 0.01 |

TABLE 1-continued

Compounds of the general formula (I) according to the invention in which $R^2$ is hydrogen and $R^3$ is methyl and aryl is the radical

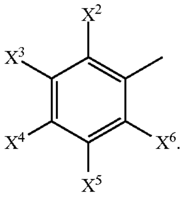

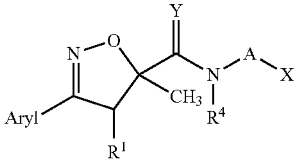

| No. | Aryl | $R^1$ | Y | $R^4$ | A | X | Physical data |
|---|---|---|---|---|---|---|---|
| | | | | | | | 0.46; 0.01 2.22; 0.00 77.89; −0.01 1.83; −0.01 1.64; −0.01 1.81; −0.01 2.77; −0.01 0.54; −0.01 0.48; −0.01 0.39; −0.01 0.36 |
| 1.281 | 3-F-5-MeO—Ph | H | O | H | $CH_2$ | 1-methyl-1H-pyrazol-4-yl | [$CDCl_3$] 7.41 0.36; 7.39 3.32; 7.30 3.43; 7.26 12.04; 7.00 0.66; 6.99 0.74; 6.95 2.21; 6.95 1.81; 6.94 1.01; 6.93 1.22; 6.93 0.88; 6.92 0.89; 6.91 1.14; 6.91 0.86; 6.70 0.78; 6.69 1.32; 6.69 0.71; 6.67 0.80; 6.67 1.31; 6.66 0.68; 4.37 0.75; 4.36 0.74; 4.33 1.42; 4.32 1.40; 4.26 1.44; 4.24 1.43; 4.22 0.78; 4.20 0.74; 3.88 1.01; 3.85 15.83; 3.83 1.44; 3.82 16.00; 3.80 2.52; 3.76 2.65; 3.22 2.56; 3.18 2.22; 2.09 0.36; 2.04 0.75; 1.72 13.70; 1.61 0.91; 1.28 0.33; 1.26 0.89; 0.00 5.76 |
| 1.282 | 3-F—Ph | H | O | H | $CH_2$ | 1-methyl-1H-pyrazol-4-yl | [$CDCl_3$] 7.52 0.39; 7.41 0.37; 7.39 4.05; 7.38 2.12; 7.37 2.49; 7.37 2.53; 7.37 2.92; 7.36 3.00; 7.30 3.45; 7.26 66.10; 7.16 0.47; 7.15 0.66; 7.13 0.84; 7.12 0.58; 7.11 0.59; 7.11 0.34; 7.00 0.94; 4.37 0.75; 4.36 0.78; 4.34 1.38; 4.32 1.36; 4.26 1.40; 4.24 1.43; 4.22 0.77; 4.20 0.78; 3.85 16.00; 3.83 2.40; 3.79 2.73; 3.24 2.64; 3.20 2.30; 1.72 14.27; 1.55 63.99; 0.00 33.19; −0.01 1.52 |
| 1.283 | Ph | H | O | H | $CH_2$ | 1-methyl-1H-pyrazol-4-yl | [$CDCl_3$] 7.64 0.36; 7.62 0.37; 7.62 0.41; 7.42 0.79; 7.40 0.39; 7.39 0.61; 7.29 0.60; 7.26 16.06; 3.86 0.41; 3.85 2.56; 3.81 0.44; 3.27 0.42; 3.23 0.37; 1.72 2.31; 1.62 16.00; 0.00 8.07; −0.01 0.42 |
| 1.284 | 3,5-$(CF_3)_2$—Ph | H | O | H | $CH_2$ | 1-methyl-1H-pyrazol-4-yl | [$CDCl_3$] 1.76 (s, 3H); 3.28 (d, 1H); 3.85 (s, 3H); 3.90 (d, 1H); 4.23 (dd, 1H); 4.36 (dd, 1H); 6.93 (br, 1H); 7.30 (s, 1H); 7.40 (s, 1H); 7.92 (s, 1H); 8.06 (s, 2H). |
| 1.285 | 3,5-$Cl_2$—Ph | H | O | H | $CH_2$ | 1-methyl-1H-pyrazol-4-yl | [$CDCl_3$] 1.72 (s, 3H); 3.18 (d, 1H); 3.79 (d, 1H); 3.86 (s, 3H); 4.22 (dd, 1H); 4.34 (dd, 1H); 6.93 (br, 1H); 7.29 (s, 1H); 7.39 (s, 1H); 7.41 (m, 1H); 7.50 (m, 2H). |
| 1.286 | 3-Me-5-$CF_3O$—Ph | H | O | H | $CH_2$ | 1-methyl-1H-pyrazol-4-yl | [$CDCl_3$] 7.40 2.99; 7.34 1.93; 7.31 1.48; 7.30 3.11; 7.27 10.68; 7.09 1.39; 7.02 0.34; 7.01 0.57; 6.99 0.35; 5.30 0.90; 4.38 0.66; 4.36 0.67; 4.34 1.21; 4.32 1.20; 4.25 1.22; 4.24 1.24; 4.21 |

TABLE 1-continued

Compounds of the general formula (I) according to the invention in which $R^2$ is hydrogen and $R^3$ is methyl and aryl is the radical

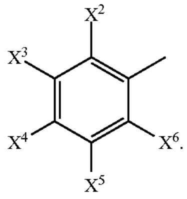

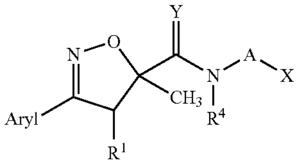

| No. | Aryl | $R^1$ | Y | $R^4$ | A | X | Physical data |
|---|---|---|---|---|---|---|---|
| | | | | | | | 0.69; 4.20 0.68; 3.89 0.38; 3.86 16.00; 3.83 2.27; 3.79 2.54; 3.24 2.39; 3.20 2.11; 2.40 9.36; 1.72 12.84; 1.66 2.71; 1.26 0.42 |
| 1.287 | 3-$CF_3$—Ph | H | O | H | $CH_2$ | 1-methyl-1H-pyrazol-4-yl | [$CDCl_3$] 7.89 1.74; 7.81 0.94; 7.79 1.09; 7.69 0.81; 7.68 1.08; 7.57 0.89; 7.55 1.42; 7.53 0.60; 7.40 2.97; 7.30 3.03; 7.26 12.31; 7.00 0.55; 4.38 0.69; 4.36 0.68; 4.34 1.25; 4.33 1.23; 4.26 1.26; 4.24 1.27; 4.22 0.70; 4.21 0.70; 4.13 0.74; 4.11 0.75; 3.89 2.37; 3.85 16.00; 3.84 2.86; 3.28 2.52; 3.24 2.21; 2.04 3.30; 1.74 13.61; 1.62 3.32; 1.28 0.93; 1.26 1.95; 1.24 0.90 |
| 1.288 | 3-Me—Ph | H | O | H | $CH_2$ | 1-methyl-1H-pyrazol-4-yl | [$CDCl_3$] 7.46 1.48; 7.42 0.72; 7.40 1.00; 7.39 2.45; 7.31 0.74; 7.29 1.78; 7.28 2.57; 7.27 1.17; 7.26 9.48; 7.25 1.12; 7.23 0.52; 7.04 0.40; 4.36 0.57; 4.35 0.57; 4.32 1.13; 4.31 1.12; 4.25 1.14; 4.24 1.15; 4.22 0.58; 4.20 0.57; 3.84 16.00; 3.80 2.47; 3.26 2.30; 3.21 2.01; 2.37 8.27; 1.72 12.47; 1.63 2.43; 0.00 3.98 |
| 1.289 | 3,5-$F_2$—Ph | H | O | H | $CH_2$ | 1-methyl-1H-pyrazol-5-yl | [$CDCl_3$] 1.74 (s, 3H); 3.21 (d, 1H); 3.78 (d, 1H); 3.81 (s, 3H); 4.40 (dd, 1H); 4.56 (dd, 1H); 6.15 (d, 1H); 6.89 (m, 1H); 7.04 (brt, 1H); 7.15 (m, 2H); 7.39 (d, 1H). |
| 1.290 | 3-F—Ph | H | O | H | $CH_2$ | 1-methyl-1H-pyrazol-5-yl | [$CDCl_3$] 1.74 (s, 3H); 3.24 (d, 1H); 3.79 (s, 3H); 3.81 (d, 1H); 4.41 (dd, 1H); 4.55 (dd, 1H); 6.15 (s, 1H); 7.10 (brt, 1H); 7.14 (m, 1H); 7.38 (m, 4H). |
| 1.291 | 3,5-$Cl_2$—Ph | H | O | H | $CH_2$ | 1-methyl-1H-pyrazol-5-yl | [$CDCl_3$] 1.75 (s, 3H); 3.22 (d, 1H); 3.79 (d, 1H); 3.81 (s, 3H); 4.40 (dd, 1H); 4.58 (dd, 1H); 6.15 (s, 1H); 7.02 (br, 1H); 7.39 (s, 1H); 7.43 (m, 1H); 7.51 (m, 1H). |
| 1.292 | Ph | H | O | H | $CH_2$ | 1-methyl-1H-pyrazol-5-yl | [$CDCl_3$] 1.74 (s, 3H); 3.28 (d, 1H); 3.79 (s, 3H); 3.82 (d, 1H); 4.41 (dd, 1H), 4.56 (dd, 1H); 6.13 (m, 1H); 7.12 (brt, 1H); 7.41 (m, 4H); 7.63 (m, 2H). |
| 1.293 | 3,5-$Cl_2$—Ph | H | O | H | $CH_2$ | 1-methyl-1H-pyrrol-2-yl | [$CDCl_3$] 1.72 (s, 3H); 3.19 (d, 1H); 3.51 (s, 3H); 3.80 (d, 1H); 4.31 (dd, 1H); 4.51 (dd, 1H); 6.07 (m, 2H); 6.60 (m, 1H); 6.88 (br, 1H); 7.41 (m, 1H); 7.51 (m, 2H). |
| 1.294 | 3-F—Ph | H | O | H | $CH_2$ | 1-methyl-1H-tetrazol-5-yl | [$CDCl_3$] 1.74 (s, 3H); 3.23 (d, 1H); 3.83 (d, 1H); 4.30 (s, 3H); |

TABLE 1-continued

Compounds of the general formula (I) according to the invention in which $R^2$ is hydrogen and $R^3$ is methyl and aryl is the radical

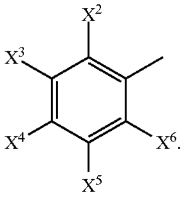

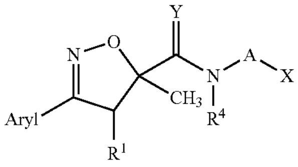

| No. | Aryl | $R^1$ | Y | $R^4$ | A | X | Physical data |
|---|---|---|---|---|---|---|---|
| | | | | | | | 4.64 (dd, 1H); 4.78 (dd, 1H); 7.12 (m, 1H); 7.35-7.40 (m, 3H); 7.43 (brt, 1H). |
| 1.295 | 3,5-$Cl_2$—Ph | H | O | H | $CH_2$ | 1-methyl-3-(trifluoromethyl)-1H-pyrazol-4-yl | D2 [$CDCl_3$] 7.51 5.96; 7.50 6.75; 7.42 1.67; 7.41 2.95; 7.41 1.46; 7.39 3.08; 7.26 29.10; 7.26 27.48; 7.08 0.45; 7.07 0.76; 7.05 0.46; 4.43 0.59; 4.42 0.58; 4.40 1.32; 4.38 1.31; 4.34 1.31; 4.32 1.30; 4.30 0.58; 4.29 0.57; 3.89 13.73; 3.77 2.68; 3.73 3.09; 3.20 2.99; 3.16 2.60; 1.70 16.00; 1.55 12.91; 0.01 0.46; 0.00 15.78; 0.00 15.27; −0.01 0.54; −0.01 0.55 |
| 1.296 | 3,5-$Cl_2$—Ph | H | O | H | $CH_2$ | 1-methyl-3-(trifluoromethyl)-1H-pyrazol-4-yl | D1 [$CDCl_3$] 1.70 (s, 3H); 3.18 (d, 1H); 3.73 (d, 1H); 3.89 (s, 3H); 4.31 (dd, 1H); 4.41 (dd, 1H); 7.07 (brt, 1H); 7.40 (m, 2H); 7.50 (m, 2H). |
| 1.297 | 3,5-$F_2$—Ph | H | O | H | $CH_2$ | 1-methyl-3-(trifluoromethyl)-1H-pyrazol-4-yl | [$CDCl_3$] 7.40 2.73; 7.26 16.49; 7.16 1.57; 7.15 2.06; 7.14 1.16; 7.14 2.02; 7.13 1.72; 7.12 0.36; 7.10 0.37; 7.09 0.62; 6.91 0.39; 6.90 0.71; 6.90 0.36; 6.89 0.79; 6.88 1.42; 6.88 0.72; 6.87 0.41; 6.86 0.72; 6.86 0.35; 4.44 0.53; 4.42 0.52; 4.40 1.17; 4.39 1.16; 4.34 1.15; 4.33 1.15; 4.30 0.52; 4.29 0.51; 3.90 12.20; 3.77 2.65; 3.73 3.06; 3.21 2.89; 3.16 2.50; 1.71 16.00; 1.68 2.71; 0.00 8.44 |
| 1.298 | 3-F—Ph | H | O | H | $CH_2$ | 1-methyl-3-(trifluoromethyl)-1H-pyrazol-4-yl | [$CDCl_3$] 1.70 (s, 3H); 3.21 (d, 1H); 3.78 (d, 1H); 3.88 (s, 3H); 4.31 (dd, 1H); 4.41 (dd, 1H); 7.13 (m, 1H); 7.37 (m, 4H). |
| 1.299 | Ph | H | O | H | $CH_2$ | 1-methyl-3-(trifluoromethyl)-1H-pyrazol-4-yl | [$CDCl_3$] 1.71 (s, 3H); 3.25 (d, 1H); 3.81 (d, 1H); 3.88 (s, 3H); 4.31 (dd, 1H); 4.40 (dd, 1H); 7.18 (brt, 1H); 7.36 (s, 1H); 7.41 (m, 3H); 7.62 (m, 2H). |
| 1.300 | 3,5-$F_2$—Ph | H | O | H | $CH_2$ | 1-methyl-5-(trifluoromethyl)-1H-pyrazol-4-yl | [$CDCl_3$] 7.41 3.44; 7.26 17.64; 7.26 18.22; 7.17 0.39; 7.17 0.34; 7.16 1.88; 7.15 2.27; 7.14 2.34; 7.14 1.64; 7.13 1.72; 7.03 0.68; 6.91 0.39; 6.90 0.71; 6.90 0.39; 6.89 0.79; 6.88 1.41; 6.88 0.76; 6.87 0.44; 6.86 0.73; 6.85 0.39; 4.48 0.40; 4.46 0.40; 4.44 1.01; 4.42 1.02; 4.39 1.03; 4.38 1.05; 4.35 0.41; 4.34 0.44; 4.02 0.48; 4.01 0.39; 4.01 0.34; 3.97 10.65; 3.80 2.66; 3.75 3.05; 3.21 2.95; 3.17 2.58; 1.72 16.00; 1.71 0.48; 1.69 0.41; 1.56 |

TABLE 1-continued
Compounds of the general formula (I) according to the invention in which $R^2$ is hydrogen and $R^3$ is methyl and aryl is the radical
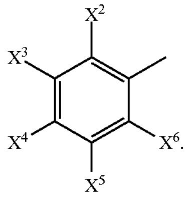
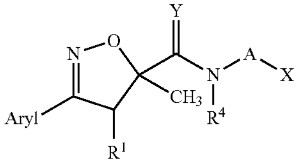
| No. | Aryl | $R^1$ | Y | $R^4$ | A | X | Physical data |
|---|---|---|---|---|---|---|---|
| | | | | | | | 5.92; 1.26 0.39; 0.00 10.17; 0.00 10.06; −0.01 0.38; −0.01 0.36 |
| 1.301 | 3,5-$F_2$—Ph | H | O | H | $CH_2$ | 1-propyl-1H-pyrazol-3-yl | [$CDCl_3$] 7.29 2.59; 7.29 2.74; 7.26 34.70; 7.20 0.67; 7.18 0.55; 7.18 0.54; 7.17 0.39; 7.17 1.63; 7.16 2.25; 7.16 1.65; 7.15 1.21; 7.15 2.10; 7.14 1.87; 6.90 0.38; 6.89 0.71; 6.89 0.39; 6.88 0.78; 6.87 1.44; 6.86 0.76; 6.85 0.41; 6.85 0.73; 6.84 0.37; 6.11 2.54; 6.10 2.66; 4.52 0.78; 4.50 0.77; 4.48 1.68; 4.46 1.65; 4.42 1.67; 4.40 1.69; 4.38 0.79; 4.36 0.79; 4.03 2.62; 4.02 4.25; 4.00 2.70; 3.83 2.70; 3.78 3.07; 3.21 2.89; 3.17 2.54; 1.90 0.37; 1.88 1.53; 1.86 2.84; 1.85 2.76; 1.83 1.55; 1.81 0.37; 1.74 16.00; 1.56 23.90; 0.92 4.55; 0.90 9.19; 0.88 4.26; 0.01 0.56; 0.01 0.34; 0.00 20.71; −0.01 0.88 |
| 1.302 | 3,5-$Cl_2$—Ph | H | O | H | $CH_2$ | 1-propyl-1H-pyrazol-3-yl | [$CDCl_3$] 7.52 0.60; 7.51 6.30; 7.51 7.45; 7.51 3.58; 7.41 1.80; 7.40 3.34; 7.40 2.10; 7.29 2.85; 7.29 3.03; 7.26 71.25; 7.26 34.89; 7.20 0.61; 7.19 0.87; 7.00 0.45; 6.10 2.78; 6.10 2.97; 4.51 0.79; 4.50 0.82; 4.47 1.81; 4.46 1.81; 4.41 1.79; 4.40 1.84; 4.38 0.78; 4.36 0.79; 4.03 2.80; 4.01 4.71; 4.00 2.88; 3.83 2.67; 3.79 3.10; 3.21 2.93; 3.16 2.58; 1.90 0.41; 1.88 1.60; 1.86 3.05; 1.85 3.05; 1.83 1.65; 1.81 0.42; 1.74 16.00; 1.55 53.38; 1.25 0.34; 0.92 4.68; 0.90 9.24; 0.89 4.34; 0.01 1.21; 0.00 42.28; 0.00 21.65 |
| 1.303 | 3-F—Ph | H | O | H | $CH_2$ | 1-propyl-1H-pyrazol-3-yl | [$CDCl_3$] 7.40 0.90; 7.39 1.20; 7.39 1.31; 7.39 1.82; 7.37 4.73; 7.36 3.03; 7.29 2.87; 7.28 2.76; 7.26 4.51; 7.26 19.30; 7.23 0.71; 7.15 0.50; 7.14 0.82; 7.13 0.55; 7.13 0.61; 7.12 0.75; 7.12 0.86; 7.12 0.79; 7.11 0.74; 7.11 0.45; 7.10 0.67; 7.10 0.34; 7.10 0.38; 6.11 2.86; 6.10 2.69; 4.52 0.77; 4.51 0.76; 4.48 1.59; 4.47 1.58; 4.41 1.60; 4.40 1.60; 4.38 0.78; 4.36 0.76; 4.03 2.60; 4.01 4.03; 3.99 2.67; 3.86 2.75; 3.81 3.12; 3.25 2.93; 3.20 2.58; 1.90 0.35; 1.88 1.48; 1.86 2.66; 1.84 2.65; 1.83 1.53; 1.81 0.37; 1.74 16.00; 1.59 13.86; 0.92 4.60; 0.90 2.62; 0.90 9.37; 0.88 |

TABLE 1-continued
Compounds of the general formula (I) according to the invention in which $R^2$ is hydrogen and $R^3$ is methyl and aryl is the radical
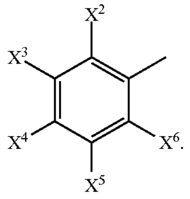
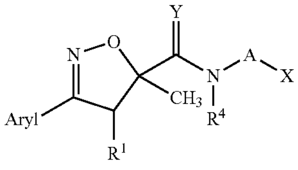
| No. | Aryl | $R^1$ | Y | $R^4$ | A | X | Physical data |
|---|---|---|---|---|---|---|---|
| | | | | | | | 4.30; 0.01 0.46; 0.00 2.76; 0.00 11.58; −0.01 0.53 |
| 1.304 | Ph | H | O | H | $CH_2$ | 1-propyl-1H-pyrazol-3-yl | [$CDCl_3$] 7.64 1.97; 7.64 2.38; 7.64 1.23; 7.63 2.06; 7.62 2.76; 7.43 0.58; 7.42 0.84; 7.41 4.28; 7.41 1.98; 7.39 2.36; 7.39 0.54; 7.38 0.62; 7.37 0.39; 7.28 2.76; 7.28 3.01; 7.26 32.01; 6.11 2.63; 6.10 2.74; 4.52 0.83; 4.51 0.82; 4.48 1.65; 4.47 1.63; 4.41 1.65; 4.40 1.65; 4.37 0.84; 4.36 0.83; 4.03 2.63; 4.01 4.28; 3.99 2.73; 3.88 2.71; 3.84 3.10; 3.27 2.98; 3.23 2.62; 1.90 0.35; 1.88 1.49; 1.86 2.77; 1.84 2.80; 1.82 1.55; 1.81 0.37; 1.74 16.00; 1.57 23.73; 0.92 4.52; 0.90 9.11; 0.88 4.24; 0.01 0.51; 0.00 18.77 |
| 1.305 | 3,5-$F_2$—Ph | H | O | H | $CH_2$ | 1-propyl-1H-pyrazol-4-yl | [$CDCl_3$] 7.52 0.75; 7.41 3.56; 7.31 3.69; 7.26 142.19; 7.16 1.57; 7.16 2.05; 7.15 1.14; 7.14 1.98; 7.14 1.68; 7.00 0.84; 6.96 0.60; 6.91 0.43; 6.90 0.74; 6.90 0.35; 6.89 0.80; 6.88 1.45; 6.88 0.73; 6.87 0.42; 6.86 0.71; 6.85 0.33; 4.38 0.81; 4.37 0.80; 4.35 1.44; 4.33 1.41; 4.26 1.47; 4.25 1.46; 4.22 0.80; 4.21 0.82; 4.04 2.72; 4.02 4.30; 4.01 2.79; 3.81 2.72; 3.76 3.13; 3.21 2.90; 3.17 2.52; 1.88 1.51; 1.86 2.75; 1.84 2.71; 1.83 1.53; 1.81 0.36; 1.73 16.00; 1.56 0.42; 1.55 79.71; 1.54 0.44; 1.26 0.33; 0.91 4.61; 0.89 9.32; 0.87 4.33; 0.15 0.41; 0.01 2.54; 0.00 94.39; −0.01 2.96; −0.15 0.38 |
| 1.306 | 3,5-$Cl_2$—Ph | H | O | H | $CH_2$ | 1-propyl-1H-pyrazol-4-yl | [$CDCl_3$] 7.51 6.39; 7.50 7.37; 7.42 1.90; 7.41 1.61; 7.41 3.44; 7.41 2.96; 7.40 5.57; 7.31 4.47; 7.26 13.23; 7.26 9.24; 6.95 0.78; 4.38 0.88; 4.36 0.87; 4.34 1.64; 4.33 1.62; 4.26 1.65; 4.25 1.66; 4.22 0.89; 4.21 0.88; 4.04 2.77; 4.02 4.97; 4.00 2.88; 3.81 2.69; 3.77 3.07; 3.20 2.94; 3.16 2.58; 1.90 0.33; 1.88 1.63; 1.86 3.14; 1.84 3.09; 1.82 1.63; 1.81 0.37; 1.72 16.00; 1.61 0.72; 0.91 4.62; 0.89 9.23; 0.87 4.32; 0.00 7.35; 0.00 5.30 |
| 1.307 | 3-F—Ph | H | O | H | $CH_2$ | 1-propyl-1H-pyrazol-4-yl | [$CDCl_3$] 7.40 4.44; 7.39 1.61; 7.38 2.11; 7.37 3.04; 7.36 3.72; 7.30 4.45; 7.26 10.82; 7.15 0.43; 7.15 0.76; 7.14 0.50; 7.13 0.68; 7.12 1.00; 7.12 0.69; 7.11 |

TABLE 1-continued
Compounds of the general formula (I) according to the invention in which $R^2$ is hydrogen and $R^3$ is methyl and aryl is the radical
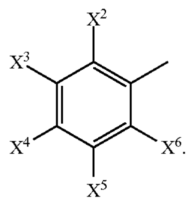
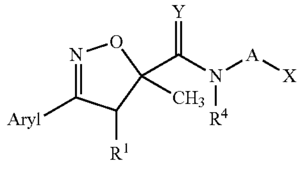
| No. | Aryl | $R^1$ | Y | $R^4$ | A | X | Physical data |
|---|---|---|---|---|---|---|---|
| | | | | | | | 0.65; 7.10 0.38; 7.00 0.72; 4.38 0.87; 4.36 0.87; 4.34 1.67; 4.33 1.65; 4.26 1.69; 4.25 1.68; 4.23 0.89; 4.21 0.88; 4.03 2.73; 4.01 4.99; 4.00 2.82; 3.84 2.65; 3.79 3.02; 3.24 2.98; 3.20 2.58; 1.89 0.36; 1.87 1.59; 1.85 3.10; 1.84 3.11; 1.82 1.63; 1.80 0.37; 1.73 16.00; 1.61 1.47; 0.91 4.45; 0.89 8.75; 0.87 4.17; 0.00 6.26; 0.00 5.65 |
| 1.308 | Ph | H | O | H | $CH_2$ | 1-propyl-1H-pyrazol-4-yl | [$CDCl_3$] 7.64 1.93; 7.64 1.82; 7.64 2.30; 7.64 2.29; 7.63 1.20; 7.63 0.87; 7.62 2.37; 7.62 2.73; 7.44 0.61; 7.43 0.88; 7.42 1.61; 7.42 5.36; 7.40 6.43; 7.39 0.58; 7.39 0.69; 7.38 0.46; 7.30 4.05; 7.26 14.51; 7.26 11.85; 7.04 0.59; 4.37 0.80; 4.36 0.80; 4.34 1.56; 4.32 1.55; 4.26 1.58; 4.25 1.60; 4.23 0.83; 4.21 0.82; 4.02 2.69; 4.01 4.60; 3.99 2.80; 3.86 2.68; 3.82 3.04; 3.27 2.95; 3.23 2.58; 1.88 0.37; 1.87 1.53; 1.85 2.91; 1.83 2.93; 1.81 1.57; 1.79 0.38; 1.73 16.00; 1.61 1.03; 1.25 0.35; 0.90 4.48; 0.88 8.95; 0.86 4.22; 0.00 8.32; 0.00 7.50; −0.01 0.33 |
| 1.309 | 3,5-$F_2$—Ph | H | O | propyl | $CH_2$ | 1-propyl-1H-pyrazol-4-yl | [$CDCl_3$] 7.52 0.38; 7.47 3.26; 7.45 3.21; 7.42 4.15; 7.35 4.12; 7.26 64.00; 7.21 1.88; 7.20 3.86; 7.18 2.36; 7.18 1.87; 7.17 0.33; 7.00 0.36; 6.89 0.61; 6.89 0.64; 6.88 0.81; 6.88 0.96; 6.87 1.25; 6.87 1.29; 6.86 1.55; 6.86 1.02; 6.85 0.66; 6.85 0.65; 6.84 0.77; 6.83 0.36; 5.01 1.23; 4.97 1.37; 4.67 1.59; 4.63 1.80; 4.44 1.99; 4.40 2.12; 4.36 4.30; 4.32 1.80; 4.31 3.05; 4.09 2.39; 4.08 1.94; 4.06 4.03; 4.04 3.44; 4.02 4.57; 4.01 2.60; 3.74 0.35; 3.73 0.39; 3.72 0.49; 3.70 0.59; 3.69 0.46; 3.68 0.47; 3.67 0.42; 3.38 0.36; 3.37 0.35; 3.36 0.45; 3.35 0.50; 3.32 0.39; 3.23 0.49; 3.22 0.62; 3.20 0.58; 3.19 0.77; 3.18 0.54; 3.17 0.54; 3.16 0.51; 3.15 0.50; 3.14 2.28; 3.12 2.92; 3.11 0.64; 3.11 0.67; 3.10 0.49; 3.09 2.40; 3.08 2.90; 1.91 1.10; 1.90 0.42; 1.89 2.20; 1.88 1.62; 1.87 2.33; 1.86 2.93; 1.85 1.43; 1.84 2.90; 1.84 0.58; 1.83 1.62; 1.81 0.61; 1.80 0.52; 1.79 0.37; 1.79 |

TABLE 1-continued
Compounds of the general formula (I) according to the invention in which $R^2$ is hydrogen and $R^3$ is methyl and aryl is the radical
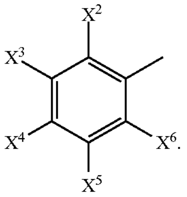
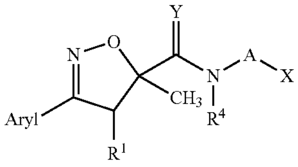
| No. | Aryl | $R^1$ | Y | $R^4$ | A | X | Physical data |
|---|---|---|---|---|---|---|---|
| | | | | | | | 0.53; 1.78 0.55; 1.77 12.56; 1.76 0.97; 1.74 0.45; 1.74 0.44; 1.72 0.53; 1.72 0.46; 1.71 0.57; 1.70 0.49; 1.69 0.59; 1.69 0.50; 1.67 16.00; 1.58 6.96; 1.55 0.93; 1.55 0.87; 1.53 0.97; 1.51 0.81; 1.49 0.48; 1.25 1.69; 1.25 0.38; 0.98 3.49; 0.96 7.33; 0.94 3.44; 0.93 3.41; 0.92 0.59; 0.91 6.74; 0.90 4.70; 0.89 3.61; 0.88 9.19; 0.88 3.93; 0.86 4.67; 0.86 6.42; 0.84 2.76; 0.01 0.96; 0.00 38.78; −0.01 1.37 |
| 1.310 | 3,5-$F_2$—Ph | H | O | H | $CH_2$ | 1-tert-butyl-1H-pyrazol-4-yl | [$CDCl_3$] 7.44 3.39; 7.43 3.66; 7.43 3.39; 7.26 21.91; 7.26 9.39; 7.19 0.39; 7.18 0.36; 7.18 0.47; 7.17 0.63; 7.16 1.82; 7.16 2.08; 7.16 1.14; 7.15 1.10; 7.14 1.85; 7.14 1.66; 6.93 0.48; 6.91 0.50; 6.90 0.79; 6.90 0.45; 6.89 0.90; 6.88 1.49; 6.87 0.83; 6.87 0.34; 6.86 0.52; 6.86 0.76; 6.85 0.41; 4.39 0.76; 4.38 0.78; 4.35 1.35; 4.34 1.36; 4.27 1.62; 4.26 1.43; 4.25 0.90; 4.24 0.44; 4.23 0.80; 4.22 0.76; 3.86 0.47; 3.82 0.59; 3.82 2.81; 3.77 3.16; 3.21 3.01; 3.17 2.69; 3.13 0.44; 1.76 1.22; 1.73 16.00; 1.72 2.93; 1.59 6.95; 1.58 1.78; 1.56 64.21; 1.45 1.08; 1.26 0.41; 0.00 13.46; 0.00 6.09; −0.01 0.40 |
| 1.311 | 3,5-$Cl_2$—Ph | H | O | H | $CH_2$ | 1-tert-butyl-1H-pyrazol-4-yl | [$CDCl_3$] 1.42 (t, 3H); 1.70 (s, 3H); 2.67 (t, 2H); 3.20 (d, 1H); 3.44 (m, 2H); 3.79 (d, 1H); 4.08 (q, 2H); 6.92 (brt, 1H); 7.12 (m, 1H); 7.32 (s, 1H); 7.38 (m, 3H). |
| 1.312 | Ph | H | O | H | $CH_2$ | 1-tert-butyl-1H-pyrazol-4-yl | [$CDCl_3$] 7.67 0.40; 7.67 0.49; 7.66 0.39; 7.65 0.54; 7.65 0.57; 7.65 0.88; 7.64 2.19; 7.64 2.36; 7.64 1.19; 7.63 0.95; 7.63 1.06; 7.62 1.97; 7.62 2.64; 7.43 3.88; 7.42 8.85; 7.41 2.89; 7.40 1.81; 7.40 2.60; 7.39 0.51; 7.39 0.51; 7.39 0.67; 7.38 0.33; 7.38 0.47; 7.26 15.04; 7.01 0.50; 7.00 0.36; 4.38 0.70; 4.37 0.70; 4.34 1.37; 4.33 1.36; 4.27 1.41; 4.26 1.84; 4.24 1.00; 4.24 0.75; 4.23 0.56; 4.22 0.73; 3.91 0.51; 3.87 2.89; 3.83 3.19; 3.27 3.20; 3.23 2.89; 3.19 0.51; 1.75 1.37; 1.73 16.00; 1.72 0.74; 1.72 3.21; 1.60 6.03; 1.55 0.59; 1.54 57.62; 1.26 0.42; 0.00 9.08 |

TABLE 1-continued

Compounds of the general formula (I) according to the invention in which $R^2$ is hydrogen and $R^3$ is methyl and aryl is the radical

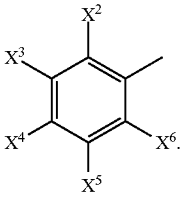

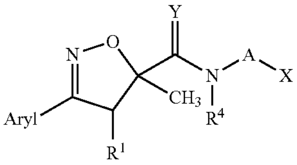

| No. | Aryl | $R^1$ | Y | $R^4$ | A | X | Physical data |
|---|---|---|---|---|---|---|---|
| 1.313 | 3,5-$Cl_2$—Ph | H | O | H | $CH_2$ | 2-(methoxy-carbonyl)phenyl | [$CDCl_3$] 1.68 (s, 3H), 3.14 (d, 1H); 3.74 (d, 1H); 3.92 (s, 3H); 4.65 (m, 2H); 7.22 (m, 1H); 7.36 (m, 2H); 7.46 (d, 1H); 7.49 (m, 2H); 7.80 (t br, 1H); 7.98 (d, 1H) |
| 1.314 | 3,5-$Cl_2$—Ph | H | O | H | $CH_2$ | 2,4-dichlorophenyl | [$CDCl_3$] 1.74 (s, 3H); 3.19 (d, 1H); 3.78 (d, 1H); 4.43 (dd, 1H); 4.54 (dd, 1H); 7.20 (m, 4H); 7.41 (d, 1H); 7.51 (s, 2H). |
| 1.315 | 3,5-$Cl_2$—Ph | H | O | H | $CH_2$ | 2-carboxyphenyl | [$CDCl_3$] 1.68 (s, 3H); 3.15 (d, 1H); 3.72 (d, 1H); 4.68 (m, 2H); 7.38-7.41 (m, 2H); 7.45-7.55 (m, 4H); 7.79 (br, 1H); 8.04 (d, 1H). |
| 1.316 | 3,5-$Cl_2$—Ph | H | O | H | $CH_2$ | 2-chlorophenyl | [$CDCl_3$] 1.74 (s, 3H); 3.19 (d, 1H); 3.80 (d, 1H); 4.48 (dd, 1H); 4.59 (dd, 1H); 7.17 (t br, 1H); 7.22 (m, 2H); 7.30 (m, 1H); 7.38 (m, 1H); 7.42 (m, 1H); 7.52 (m, 2H). |
| 1.317 | 3,5-$F_2$—Ph | H | O | H | $CH_2$ | 2-chloropyridin-4-yl | [$CDCl_3$] 8.32 2.44; 8.31 2.46; 7.31 0.95; 7.26 8.86; 7.26 15.05; 7.20 0.36; 7.18 2.54; 7.18 2.76; 7.16 5.81; 7.15 0.38; 7.08 2.04; 7.06 2.00; 6.93 0.59; 6.92 0.74; 6.92 0.40; 6.91 1.18; 6.90 1.46; 6.90 0.73; 6.89 0.60; 6.88 0.74; 6.88 0.35; 4.53 0.77; 4.51 0.76; 4.49 1.64; 4.47 1.61; 4.42 1.64; 4.41 1.63; 4.38 0.78; 4.37 0.76; 3.83 2.61; 3.78 3.03; 3.26 2.92; 3.22 2.52; 1.78 16.00; 1.57 4.41; 0.00 3.44 |
| 1.318 | 3-F—Ph | H | O | H | $CH_2$ | 2-chloropyridin-4-yl | [$CDCl_3$] 8.31 2.15; 8.30 2.22; 7.41 1.66; 7.40 1.06; 7.40 0.99; 7.40 1.70; 7.39 3.07; 7.39 2.26; 7.38 3.46; 7.37 0.64; 7.37 0.48; 7.35 0.59; 7.34 0.37; 7.26 20.32; 7.18 0.50; 7.17 0.83; 7.17 2.41; 7.16 2.69; 7.16 2.67; 7.15 0.78; 7.15 0.86; 7.14 0.60; 7.14 0.61; 7.13 0.40; 7.07 1.35; 7.07 1.29; 7.07 1.23; 7.06 1.36; 7.06 1.27; 7.06 1.22; 4.52 0.57; 4.51 0.57; 4.48 1.31; 4.47 1.29; 4.42 1.32; 4.41 1.32; 4.38 0.59; 4.37 0.58; 3.85 2.70; 3.81 3.13; 3.29 2.97; 3.25 2.56; 1.78 16.00; 1.57 3.74 |
| 1.319 | 3-F—Ph | H | O | H | $CH_2$ | 2H-tetrazol-5-yl | [DMSO-$D_6$] 1.57 (s, 3H); 3.42 (d, 1H); 3.74 (d, 1H); 4.57 (d, 2H); 7.32 (m, 1H); 7.50 (m, 3H); 8.85 (t, 1H). |
| 1.320 | 3,5-$F_2$—Ph | H | O | H | $CH_2$ | 2-methyl-1,3-thiazol-4-yl | [$CDCl_3$] 1.73 (s, 3H); 2.68 (s, 3H); 3.20 (d, 1H); 3.79 (d, 1H); |

TABLE 1-continued

Compounds of the general formula (I) according to the invention in which $R^2$ is hydrogen and $R^3$ is methyl and aryl is the radical

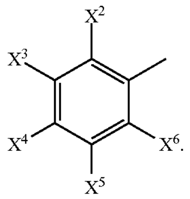

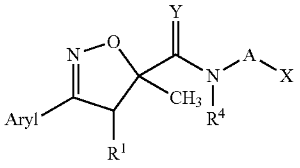

| No. | Aryl | $R^1$ | Y | $R^4$ | A | X | Physical data |
|---|---|---|---|---|---|---|---|
| | | | | | | | 4.45 (dd, 1H); 4.55 (dd, 1H); 6.86 (m, 1H); 6.92 (s, 1H); 7.15 (m, 2H); 7.32 (brt, 1H). |
| 1.321 | 3,5-$Cl_2$—Ph | H | O | H | $CH_2$ | 2-methyl-1,3-thiazol-4-yl | [$CDCl_3$] 1.73 (s, 3H); 2.68 (s, 3H); 3.19 (d, 1H); 3.80 (d, 1H); 4.45 (dd, 1H); 4.54 (dd, 1H); 6.91 (s, 1H); 7.31 (brt, 1H); 7.41 (m, 1H); 7.51 (m, 2H). |
| 1.322 | 3-F—Ph | H | O | H | $CH_2$ | 2-methyl-1,3-thiazol-4-yl | [$CDCl_3$] 1.75 (s, 3H); 2.69 (s, 3H); 3.21 (d, 1H); 3.82 (d, 1H); 4.47 (dd, 1H); 4.55 (dd, 1H); 6.92 (s, 1H); 7.14 (m, 1H); 7.38 (m, 4H). |
| 1.323 | Ph | H | O | H | $CH_2$ | 2-methyl-1,3-thiazol-4-yl | [$CDCl_3$] 1.74 (s, 3H); 2.68 (s, 3H); 3.26 (d, 1H); 3.85 (d, 1H); 4.46 (dd, 1H); 4.55 (dd, 1H); 6.91 (s, 1H); 7.40 (m, 4H); 7.53 (m, 2H). |
| 1.324 | 3-F—Ph | H | O | H | $CH_2$ | 2-methyl-2H-tetrazol-5-yl | [$CDCl_3$] 1.72 (s, 3H); 3.23 (d, 1H); 3.74 (d, 1H); 4.10 (s, 3H); 4.64 (dd, 1H); 4.78 (dd, 1H); 7.12 (m, 1H); 7.32-7.40 (m, 3H); 7.65 (brt, 1H). |
| 1.325 | 3,5-$Cl_2$—Ph | H | O | H | $CH_2$ | 3-(cyclopropyl-carbamoyl)-1,2-oxazol-5-yl | [$CDCl_3$] 7.52 0.73; 7.51 7.08; 7.51 7.91; 7.43 1.99; 7.42 3.46; 7.42 1.65; 7.31 0.75; 7.29 0.44; 7.28 0.86; 7.28 0.86; 7.27 0.64; 7.27 0.64; 7.26 99.79; 7.21 0.50; 7.00 0.53; 6.82 0.63; 6.61 4.31; 4.70 0.70; 4.68 0.69; 4.66 1.24; 4.64 1.22; 4.56 1.25; 4.54 1.28; 4.52 0.71; 4.50 0.69; 3.80 2.77; 3.76 3.20; 3.24 3.00; 3.20 2.60; 2.89 0.49; 2.88 0.86; 2.87 1.21; 2.86 1.17; 2.85 0.91; 2.84 0.50; 1.74 16.00; 1.56 39.76; 0.89 0.63; 0.88 1.60; 0.87 2.47; 0.86 2.33; 0.86 1.84; 0.85 1.01; 0.84 0.82; 0.66 0.80; 0.65 1.63; 0.64 1.81; 0.64 1.78; 0.63 1.80; 0.63 1.61; 0.62 0.58; 0.05 0.34; 0.01 1.36; 0.00 51.65; −0.01 1.60 |
| 1.326 | 3,5-$F_2$—Ph | H | O | H | $CH_2$ | 3-(difluoromethyl)-1-methyl-1H-pyrazol-4-yl | [$CDCl_3$] 7.36 3.84; 7.26 15.31; 7.26 15.25; 7.17 0.35; 7.16 1.68; 7.15 2.33; 7.15 1.59; 7.14 1.58; 7.14 2.51; 7.13 2.33; 7.13 0.95; 7.12 1.05; 6.90 0.39; 6.90 0.74; 6.89 0.43; 6.88 0.80; 6.88 1.47; 6.87 0.84; 6.86 0.44; 6.85 0.75; 6.85 0.44; 6.80 1.34; 6.66 2.75; 6.53 1.37; 4.46 0.55; 4.44 0.54; 4.42 1.58; 4.41 1.56; 4.38 1.56; 4.37 1.59; 4.35 0.55; 4.33 0.54; 3.86 10.66; 3.77 2.68; 3.73 3.10; 3.20 2.98; 3.15 |

TABLE 1-continued

Compounds of the general formula (I) according to the invention in which $R^2$ is hydrogen and $R^3$ is methyl and aryl is the radical

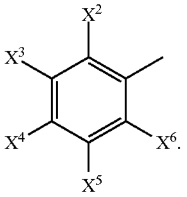

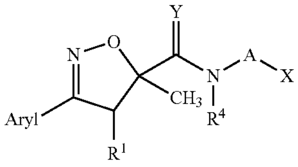

| No. | Aryl | $R^1$ | Y | $R^4$ | A | X | Physical data |
|---|---|---|---|---|---|---|---|
| | | | | | | | 2.60; 1.70 16.00; 1.59 3.73; 0.00 6.68 |
| 1.327 | 3,5-$Cl_2$—Ph | H | O | H | $CH_2$ | 3-(ethoxy-carbonyl)-1,2-oxazol-5-yl | [$CDCl_3$] 7.51 7.01; 7.51 6.83; 7.43 2.21; 7.42 3.23; 7.32 0.59; 7.31 1.13; 7.29 0.66; 7.26 18.18; 6.57 4.79; 4.71 0.90; 4.69 0.90; 4.67 1.75; 4.65 1.72; 4.59 1.74; 4.57 1.75; 4.55 0.91; 4.53 0.91; 4.45 1.46; 4.44 4.46; 4.42 4.51; 4.40 1.50; 4.13 0.84; 4.11 0.85; 3.80 2.61; 3.76 3.03; 3.24 2.96; 3.20 2.56; 2.04 3.60; 1.74 16.00; 1.56 11.58; 1.42 4.65; 1.40 9.39; 1.38 4.52; 1.31 0.50; 1.29 0.71; 1.28 2.03; 1.27 2.48; 1.26 3.02; 1.24 1.19; 0.90 1.09; 0.88 2.65; 0.87 1.20; 0.00 12.27 |
| 1.328 | 3,5-$F_2$—Ph | H | O | H | $CH_2$ | 3-(methoxy-carbonyl)phenyl | [$CDCl_3$] 7.96 0.43; 7.96 0.81; 7.96 0.48; 7.94 0.46; 7.94 0.90; 7.94 0.53; 7.91 1.28; 7.91 1.25; 7.91 0.75; 7.45 0.44; 7.45 0.36; 7.43 0.66; 7.43 1.15; 7.43 0.68; 7.42 1.06; 7.42 1.12; 7.40 1.30; 7.38 0.44; 7.26 13.69; 7.19 0.39; 7.19 0.59; 7.18 0.42; 7.17 1.43; 7.17 1.59; 7.17 0.87; 7.16 0.79; 7.15 1.43; 7.15 1.25; 6.91 0.52; 6.89 0.58; 6.89 1.04; 6.88 0.52; 6.86 0.52; 6.37 0.49; 4.59 0.46; 4.58 0.43; 4.56 0.74; 4.54 0.70; 4.44 0.73; 4.43 0.73; 4.41 0.45; 4.39 0.46; 4.37 0.38; 4.35 0.38; 3.89 16.00; 3.89 0.35; 3.84 2.00; 3.80 2.27; 3.24 2.18; 3.20 1.92; 2.07 0.45; 2.05 0.50; 1.80 0.39; 1.77 11.63; 1.57 5.45; 1.39 0.41; 1.37 0.80; 1.36 0.39; 0.00 8.16 |
| 1.329 | 3,5-$Cl_2$—Ph | H | O | H | $CH_2$ | 3-(methyl-carbamoyl)-1,2-oxazol-5-yl | [$CDCl_3$] 7.52 6.90; 7.51 7.47; 7.43 2.03; 7.42 3.31; 7.42 1.64; 7.31 0.57; 7.29 0.93; 7.28 0.67; 7.26 50.29; 6.75 0.53; 6.61 4.44; 4.71 0.85; 4.69 0.83; 4.67 1.45; 4.65 1.43; 4.56 1.45; 4.55 1.45; 4.52 0.84; 4.51 0.82; 3.81 2.75; 3.76 3.14; 3.24 3.02; 3.20 2.62; 3.00 9.53; 2.98 9.59; 2.01 0.33; 1.75 16.00; 1.57 16.45; 1.25 0.40; 0.00 23.50; −0.01 1.11 |
| 1.330 | 3,5-$Cl_2$—Ph | H | O | H | $CH_2$ | 3,4-dichlorophenyl | [$CDCl_3$] 1.75 (s, 3H); 3.21 (d, 1H); 3.90 (d, 1H); 4.32 (dd, 1H); 4.45 (dd, 1H); 7.09 (m, |

TABLE 1-continued

Compounds of the general formula (I) according to the invention in which $R^2$ is hydrogen and $R^3$ is methyl and aryl is the radical

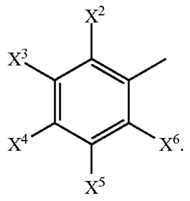

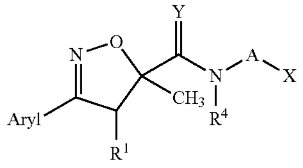

| No. | Aryl | $R^1$ | Y | $R^4$ | A | X | Physical data |
|---|---|---|---|---|---|---|---|
| | | | | | | | 1H); 7.18 (s br, 1H); 7.31 (m, 1H); 7.36 (d, 1H); 7.42 (m, 1H); 7.51 (s, 2H). |
| 1.331 | 3,5-$F_2$—Ph | H | O | H | $CH_2$ | 3,5-dichloro-1-methyl-1H-pyrazol-4-yl | [$CDCl_3$] 1.73 (s, 3H); 3.19 (d, 1H); 3.78 (d, 1H); 3.79 (s, 3H); 4.25 (dd, 1H); 4.33 (dd, 1H); 6.89 (m, 1H); 6.96 (tbr, 1H); 7.15 (m, 2H). |
| 1.332 | 3,5-$F_2$—Ph | H | O | H | $CH_2$ | 3,5-difluoropyridin-2-yl | [$CDCl_3$] 8.29 2.21; 8.29 2.25; 7.87 0.54; 7.26 23.18; 7.23 0.73; 7.23 0.72; 7.21 0.87; 7.21 0.87; 7.21 0.87; 7.20 0.81; 7.19 0.36; 7.19 0.85; 7.18 1.69; 7.18 1.35; 7.18 1.92; 7.17 1.12; 7.17 1.14; 7.16 1.98; 7.16 1.58; 6.90 0.39; 6.90 0.72; 6.89 0.35; 6.88 0.79; 6.88 1.42; 6.87 0.70; 6.86 0.42; 6.86 0.72; 6.85 0.34; 4.69 0.37; 4.68 0.37; 4.65 0.56; 4.65 0.87; 4.64 0.57; 4.64 0.59; 4.63 0.87; 4.63 0.54; 4.59 0.54; 4.59 0.87; 4.58 0.59; 4.58 0.60; 4.57 0.87; 4.57 0.55; 4.54 0.38; 4.53 0.38; 3.84 2.75; 3.80 3.18; 3.24 2.95; 3.19 2.59; 1.77 16.00; 1.58 17.14; 1.26 0.32; 0.88 0.44; 0.01 0.34; 0.00 10.62; 0.00 11.54; 0.00 0.64; −0.01 0.35; −0.01 0.37 |
| 1.333 | 3,5-$Cl_2$—Ph | H | O | H | $CH_2$ | 3,5-difluoropyridin-2-yl | [$CDCl_3$] 8.30 2.13; 8.29 2.19; 7.86 0.50; 7.53 7.57; 7.52 8.20; 7.41 1.99; 7.41 3.60; 7.40 1.73; 7.27 0.45; 7.27 0.80; 7.26 56.66; 7.23 0.78; 7.23 0.75; 7.21 0.82; 7.21 0.83; 7.21 0.82; 7.20 0.78; 7.19 0.77; 7.18 0.74; 4.68 0.32; 4.64 0.50; 4.64 0.79; 4.63 0.53; 4.63 0.53; 4.63 0.77; 4.62 0.50; 4.59 0.48; 4.58 0.79; 4.58 0.54; 4.57 0.54; 4.57 0.79; 4.57 0.52; 4.54 0.33; 4.53 0.33; 3.84 2.87; 3.80 3.27; 3.23 2.94; 3.19 2.60; 2.05 0.45; 1.77 16.00; 1.56 37.88; 1.26 0.38; 0.01 0.72; 0.00 0.63; 0.00 1.09; 0.00 25.92; 0.00 1.17; 0.00 0.48; −0.01 0.37; −0.01 0.81 |
| 1.334 | Ph | H | O | H | $CH_2$ | 3,5-difluoropyridin-2-yl | [$CDCl_3$] 8.28 1.95; 8.27 2.01; 7.90 0.43; 7.66 2.05; 7.65 2.14; 7.65 0.91; 7.65 0.76; 7.65 0.75; 7.64 1.60; 7.63 2.60; 7.63 0.45; 7.43 0.56; 7.43 0.70; 7.43 0.43; 7.42 1.72; 7.42 3.18; 7.42 3.28; 7.42 1.64; 7.41 1.62; 7.41 1.07; 7.40 1.29; 7.40 1.86; 7.40 1.92; 7.39 0.42; 7.39 0.60; 7.38 |

TABLE 1-continued
Compounds of the general formula (I) according to the invention in which $R^2$ is hydrogen and $R^3$ is methyl and aryl is the radical
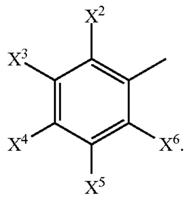
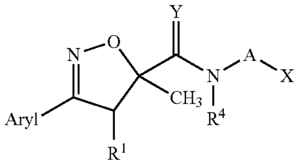
| No. | Aryl | $R^1$ | Y | $R^4$ | A | X | Physical data |
|---|---|---|---|---|---|---|---|
| | | | | | | | 0.37; 7.27 0.38; 7.27 0.54; 7.26 47.88; 7.26 0.80; 7.26 0.56; 7.26 0.42; 7.26 0.33; 7.22 0.72; 7.21 0.69; 7.20 0.73; 7.19 0.81; 7.19 0.77; 7.19 0.77; 7.17 0.70; 7.17 0.69; 4.65 0.46; 4.65 0.72; 4.64 0.50; 4.64 0.48; 4.63 0.71; 4.63 0.47; 4.59 0.44; 4.58 0.72; 4.58 0.51; 4.57 0.48; 4.57 0.73; 4.57 0.49; 4.54 0.32; 4.53 0.33; 3.90 2.91; 3.85 3.27; 3.30 2.95; 3.25 2.58; 1.76 16.00; 1.57 9.44; 0.01 0.55; 0.00 0.32; 0.00 0.63; 0.00 1.13; 0.00 24.20; −0.01 0.34; −0.01 0.64 |
| 1.335 | 3,5-$Cl_2$—Ph | H | O | H | $CH_2$ | 3-carboxy-1,2-oxazol-5-yl | [$CDCl_3$] 7.52 3.59; 7.51 3.77; 7.43 1.96; 7.39 0.41; 7.38 0.61; 7.31 0.77; 7.26 111.63; 7.21 0.60; 7.00 0.58; 6.61 2.05; 5.30 16.00; 4.72 0.35; 4.71 0.42; 4.68 0.69; 4.67 0.67; 4.61 0.66; 4.59 0.68; 4.57 0.38; 4.55 0.37; 3.82 1.00; 3.77 1.16; 3.50 0.70; 3.26 1.11; 3.21 1.08; 2.15 0.63; 2.03 0.57; 2.01 1.16; 1.87 2.84; 1.85 2.59; 1.75 7.19; 1.70 0.64; 1.69 0.68; 1.64 0.34; 1.30 0.36; 1.29 0.51; 1.28 0.53; 1.25 1.32; 1.23 0.44; 1.06 0.35; 1.05 0.51; 0.90 0.33; 0.89 0.54; 0.88 0.61; 0.87 0.57; 0.86 0.37; 0.05 0.33; 0.01 1.30; 0.00 49.81; −0.01 2.80; −0.05 0.36 |
| 1.336 | 3,5-$F_2$—Ph | H | O | H | $CH_2$ | 3-chloro-1-ethyl-1H-pyrazol-4-yl | [$CDCl_3$] 7.52 0.38; 7.45 0.49; 7.33 3.98; 7.26 0.37; 7.26 0.54; 7.26 0.93; 7.26 74.06; 7.16 1.57; 7.16 2.06; 7.15 1.10; 7.15 1.08; 7.14 1.86; 7.14 1.70; 7.02 0.46; 7.00 0.49; 6.91 0.47; 6.90 0.80; 6.90 0.40; 6.89 0.90; 6.88 1.63; 6.88 0.78; 6.87 0.47; 6.86 0.81; 6.85 0.39; 4.34 0.86; 4.33 0.78; 4.31 1.67; 4.29 1.44; 4.23 1.56; 4.22 1.52; 4.19 0.84; 4.18 0.79; 4.17 0.57; 4.15 0.53; 4.09 1.32; 4.07 4.17; 4.05 4.23; 4.03 1.38; 3.79 2.72; 3.77 0.35; 3.75 3.15; 3.21 0.38; 3.21 2.83; 3.17 2.48; 1.73 1.90; 1.72 16.00; 1.55 28.44; 1.46 5.15; 1.45 11.08; 1.43 0.74; 1.43 5.19; 1.42 1.24; 1.40 0.59; 0.01 0.93; 0.00 0.35; 0.00 0.57; 0.00 1.08; 0.00 1.72; 0.00 38.90; −0.01 0.40; −0.01 0.33; −0.01 1.13 |

TABLE 1-continued

Compounds of the general formula (I) according to the invention in which $R^2$ is hydrogen and $R^3$ is methyl and aryl is the radical

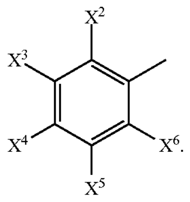

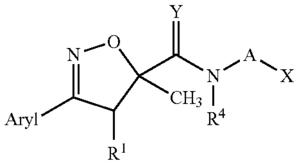

| No. | Aryl | $R^1$ | Y | $R^4$ | A | X | Physical data |
|---|---|---|---|---|---|---|---|
| 1.337 | 3-F—Ph | H | O | H | $CH_2$ | 3-chloro-1-ethyl-1H-pyrazol-4-yl | [$CDCl_3$] 7.45 0.36; 7.39 0.97; 7.39 0.66; 7.39 0.96; 7.38 2.00; 7.38 2.21; 7.38 1.95; 7.37 2.54; 7.37 1.01; 7.37 1.82; 7.36 3.05; 7.36 1.10; 7.36 1.16; 7.36 1.18; 7.32 3.99; 7.26 30.75; 7.26 0.42; 7.25 0.35; 7.16 0.47; 7.15 0.71; 7.15 0.46; 7.14 0.47; 7.14 0.54; 7.13 0.63; 7.13 0.57; 7.13 0.73; 7.12 0.52; 7.11 0.57; 7.11 0.40; 7.06 0.47; 4.34 0.79; 4.33 0.72; 4.30 1.57; 4.29 1.44; 4.23 1.56; 4.22 1.48; 4.20 0.79; 4.18 0.77; 4.16 0.39; 4.14 0.40; 4.08 1.33; 4.06 4.20; 4.04 4.28; 4.02 1.41; 3.82 2.78; 3.78 3.19; 3.25 0.33; 3.24 2.98; 3.20 2.60; 1.73 1.47; 1.72 16.00; 1.56 11.67; 1.46 4.94; 1.44 10.15; 1.43 0.51; 1.42 4.82; 1.41 0.87; 1.39 0.41; 0.01 0.45; 0.00 16.94; −0.01 0.51 |
| 1.338 | Ph | H | O | H | $CH_2$ | 3-chloro-1-ethyl-1H-pyrazol-4-yl | [$CDCl_3$] 1.42 (t, 3H); 1.72 (s, 3H); 3.25 (d, 1H); 3.82 (d, 1H); 4.02 (q, 2H); 4.21 (dd, 1H); 4.31 (dd, 1H) 7.10 (brt, 1H); 7.31 (s, 1H); 7.41 (m, 3H); 7.62 (m, 2H). |
| 1.339 | 3,5-$Cl_2$—Ph | H | O | H | $CH_2$ | 3-chloro-1-ethyl-1H-pyrazol-4-yl | [$CDCl_3$] 1.44 (t, 3H); 1.72 (s, 3H); 3.19 (d, 1H); 3.78 (d, 1H); 4.05 (q, 2H); 4.21 (dd, 1H); 4.31 (dd, 1H); 7.01 (brt, 1H); 7.32 (s, 1H); 7.41 (m, 1H); 7.52 (m, 2H). |
| 1.340 | 3,5-$F_2$—Ph | H | O | H | $CH_2$ | 3-chloro-1-isopropyl-1H-pyrazol-4-yl | [$CDCl_3$] 7.34 4.71; 7.26 25.61; 7.26 27.54; 7.17 1.81; 7.16 2.11; 7.15 2.26; 7.14 1.68; 7.13 0.33; 7.01 0.75; 7.00 0.63; 6.91 0.39; 6.91 0.67; 6.90 0.37; 6.89 0.78; 6.88 1.33; 6.88 0.70; 6.87 0.43; 6.86 0.68; 6.86 0.36; 4.40 0.45; 4.38 1.12; 4.36 1.53; 4.35 1.01; 4.34 1.24; 4.34 0.94; 4.33 0.53; 4.31 1.74; 4.30 1.66; 4.23 1.68; 4.22 1.68; 4.20 0.90; 4.18 0.88; 3.80 2.42; 3.76 2.80; 3.21 2.73; 3.17 2.37; 1.73 14.58; 1.57 6.09; 1.47 16.00; 1.45 15.86; 1.26 0.44; 0.01 0.50; 0.00 11.25; 0.00 10.96 |
| 1.341 | 3-F—Ph | H | O | H | $CH_2$ | 3-chloro-1-isopropyl-1H-pyrazol-4-yl | [$CDCl_3$] 1.47 (d, 6H); 1.72 (s, 3H); 3.21 (d, 1H); 3.80 (d, 1H); 4.21 (dd, 1H); 4.31 (dd, 1H); 4.35 (m, 1H); 7.06 (brt, 1H); |

TABLE 1-continued

Compounds of the general formula (I) according to the invention in which $R^2$ is hydrogen and $R^3$ is methyl and aryl is the radical

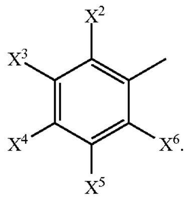

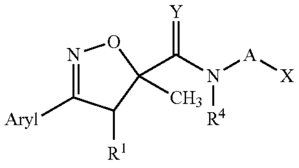

| No. | Aryl | $R^1$ | Y | $R^4$ | A | X | Physical data |
|---|---|---|---|---|---|---|---|
| | | | | | | | 7.12 (m, 1H); 7.32 (s, 1H); 7.38 (m, 3H). |
| 1.342 | 3,5-$F_2$—Ph | H | S | H | $CH_2$ | 3-chloro-1-isopropyl-1H-pyrazol-4-yl | [$CDCl_3$] 1.48 (d, 6H); 1.88 (s, 3H); 3.38 (d, 1H); 4.22 (d, 1H); 4.38 (m, 1H); 4.55 (dd, 1H); 4.69 (dd, 1H); 6.88 (m, 1H); 7.15 (m, 2H); 7.47 (s, 1H); 8.77 (brs, 1H). |
| 1.343 | 3,5-$Cl_2$—Ph | H | O | H | $CH_2$ | 3-chloro-1-isopropyl-1H-pyrazol-4-yl | [$CDCl_3$] 1.46 (d, 6H); 1.72 (s, 3H); 3.18 (d, 1H); 3.78 (d, 1H); 4.21 (dd, 1H); 4.31 (dd, 1H); 4.35 (m, 1H); 7.00 (brt, 1H); 7.32 (s, 1H); 7.41 (m, 1H); 7.50 (m, 2H). |
| 1.344 | 3,5-$Cl_2$—Ph | H | O | H | $CH_2$ | 3-chloro-1-methyl-1H-pyrazol-4-yl | [$CDCl_3$] 8.67 0.51; 7.52 4.66; 7.27 0.39; 7.26 51.54; 7.26 56.03; 7.21 0.38; 7.16 1.63; 7.16 2.08; 7.15 1.76; 7.14 2.10; 7.14 1.68; 7.14 1.47; 6.91 0.35; 6.90 0.63; 6.90 0.33; 6.89 0.71; 6.88 1.25; 6.87 0.64; 6.86 0.39; 6.86 0.63; 4.71 0.83; 4.70 0.81; 4.67 1.60; 4.66 1.56; 4.59 1.56; 4.58 1.57; 4.55 0.83; 4.54 0.83; 4.26 2.36; 4.22 2.60; 3.85 0.61; 3.85 14.49; 3.85 16.00; 3.83 0.47; 3.40 2.48; 3.35 2.27; 1.89 13.85; 1.87 0.48; 1.72 1.09; 0.01 0.71; 0.01 0.82; 0.00 24.85; 0.00 26.54 |
| 1.345 | 3,5-$F_2$—Ph | H | O | H | $CH_2$ | 3-chloro-1-methyl-1H-pyrazol-4-yl | [$CDCl_3$] 7.52 0.44; 7.31 4.17; 7.26 77.29; 7.16 1.36; 7.16 1.88; 7.14 1.92; 7.14 1.48; 7.04 0.60; 7.00 0.44; 6.91 0.35; 6.90 0.62; 6.90 0.32; 6.89 0.69; 6.88 1.21; 6.88 0.62; 6.86 0.38; 6.86 0.63; 4.33 0.77; 4.32 0.79; 4.30 1.56; 4.28 1.52; 4.23 1.57; 4.21 1.57; 4.19 0.79; 4.17 0.75; 3.81 16.00; 3.78 2.37; 3.74 2.73; 3.21 2.58; 3.16 2.27; 1.72 14.31; 1.64 2.38; 0.01 1.08; 0.00 39.43; 0.00 34.74; −0.01 1.33 |
| 1.346 | 3,5-$F_2$—Ph | H | O | H | $CH_2$ | 3-chloro-1-methyl-5-(trifluoromethyl)-1H-pyrazol-4-yl | [$CDCl_3$] 7.52 0.60; 7.26 105.68; 7.15 1.59; 7.15 2.16; 7.13 2.11; 7.13 1.69; 7.00 0.61; 6.95 0.74; 6.91 0.44; 6.90 0.75; 6.90 0.40; 6.89 0.80; 6.88 1.39; 6.87 0.70; 6.86 0.42; 6.86 0.70; 6.85 0.37; 4.47 0.45; 4.45 0.43; 4.43 1.26; 4.41 1.24; 4.39 1.25; 4.38 1.26; 4.35 0.45; 4.34 0.43; 3.94 9.74; 3.79 2.65; 3.74 3.02; 3.20 2.92; 3.16 2.55; 2.04 0.63; 1.71 16.00; 1.53 |

TABLE 1-continued

Compounds of the general formula (I) according to the invention in which $R^2$ is hydrogen and $R^3$ is methyl and aryl is the radical

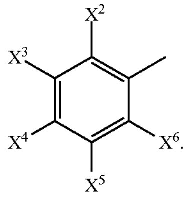

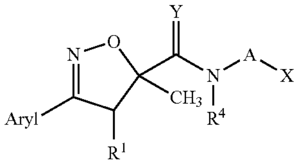

| No. | Aryl | $R^1$ | Y | $R^4$ | A | X | Physical data |
|---|---|---|---|---|---|---|---|
| | | | | | | | 59.62; 1.26 0.49; 0.01 1.75; 0.00 62.15; −0.01 1.98; −0.01 2.16 |
| 1.347 | 3,5-$Cl_2$—Ph | H | O | H | $CH_2$ | 3-chloro-5-(trifluoromethyl)-pyridin-2-yl | [$CDCl_3$] 1.79 (s, 3H); 3.22 (d, 1H); 3.82 (d, 1H); 4.71 (dq, 2H); 7.41 (m, 1H); 7.52 (m, 2H); 7.92 (s, 1H); 8.16 (br, 1H); 8.73 (s, 1H). |
| 1.348 | 3,5-$Cl_2$—Ph | H | O | H | $CH_2$ | 3-chlorophenyl | [$CDCl_3$] 1.76 (s, 3H); 3.20 (d, 1H); 3.82 (d, 1H); 4.35 (dd, 1H); 4.48 (dd, 1H); 7.13 (m, 2H); 7.22 (s, 1H); 7.23 (s, 2H); 7.43 (m, 1H); 7.52 (s, 2H). |
| 1.349 | 3,5-$F_2$—Ph | H | O | H | $CH_2$ | 3-chloropyridin-4-yl | [$CDCl_3$] 8.56 3.38; 8.43 1.91; 8.42 1.96; 7.30 0.88; 7.29 0.55; 7.26 17.59; 7.26 17.74; 7.19 0.34; 7.17 4.78; 7.16 4.55; 7.15 2.57; 7.14 0.36; 6.93 0.40; 6.93 0.41; 6.92 0.75; 6.92 0.43; 6.91 0.82; 6.90 0.83; 6.90 1.49; 6.89 0.84; 6.88 0.45; 6.88 0.45; 6.88 0.76; 6.87 0.42; 4.62 0.75; 4.60 0.74; 4.58 1.91; 4.56 1.88; 4.53 1.90; 4.51 1.91; 4.49 0.76; 4.47 0.74; 3.82 2.64; 3.77 3.05; 3.25 2.96; 3.20 2.57; 1.77 16.00; 1.75 0.36; 1.61 1.56 |
| 1.350 | 3-F—Ph | H | O | H | $CH_2$ | 3-chloropyridin-4-yl | [$CDCl_3$] 8.55 4.27; 8.42 2.40; 8.40 2.44; 7.43 0.35; 7.41 1.77; 7.40 2.00; 7.39 3.11; 7.38 3.24; 7.38 4.09; 7.35 0.82; 7.33 0.51; 7.26 12.59; 7.17 2.91; 7.16 3.02; 7.15 1.16; 7.14 0.66; 7.13 0.64; 7.13 0.37; 5.30 1.27; 4.61 0.63; 4.60 0.63; 4.57 1.90; 4.56 1.87; 4.53 1.90; 4.52 1.90; 4.49 0.63; 4.48 0.62; 3.85 2.63; 3.81 3.05; 3.28 2.97; 3.24 2.57; 1.77 16.00; 1.60 2.12 |
| 1.351 | 3,5-$F_2$—Ph | H | O | H | $CH_2$ | 3-cyclopropyl-1,2,4-oxadiazol-5-yl | [$CDCl_3$] 0.96 (m, 2H); 1.01 (m, 2H); 2.05 (m, 1H); 3.22 (d, 1H); 3.79 (d, 1H); 4.57 (dd, 1H); 4.67 (dd, 1H); 6.89 (m, 1H); 7.17 (m, 2H); 7.40 (brt, 1H). |
| 1.352 | 3,5-$Cl_2$—Ph | H | O | H | $CH_2$ | 3-cyclopropyl-1,2,4-oxadiazol-5-yl | [$CDCl_3$] 0.96 (m, 2H); 1.02 (m, 2H); 1.77 (s, 3H); 2.05 (m, 1H); 3.21 (d, 1H); 3.79 (d, 1H); 4.57 (dd, 1H); 4.66 (dd, 1H); 7.38 (brt, 1H); 7.42 (m, 1H); 7.52 (m, 2H). |
| 1.353 | 3-F—Ph | H | O | H | $CH_2$ | 3-cyclopropyl-1,2,4-oxadiazol-5-yl | [$CDCl_3$] 0.95 (m, 2H); 1.00 (m, 2H); 1.77 (s, 3H); 2.05 (m, 1H); 3.26 (d, 1H); 3.81 (d, 1H); 4.55 (dd, 1H); 4.68 (dd, 1H); 7.15 (m, 1H); 7.39 (m, 3H); 7.43 (brt, 1H). |

TABLE 1-continued
Compounds of the general formula (I) according to the invention in which $R^2$ is hydrogen and $R^3$ is methyl and aryl is the radical
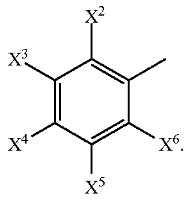
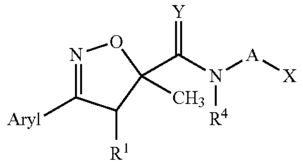
| No. | Aryl | $R^1$ | Y | $R^4$ | A | X | Physical data |
|---|---|---|---|---|---|---|---|
| 1.354 | Ph | H | O | H | $CH_2$ | 3-cyclopropyl-1,2,4-oxadiazol-5-yl | [$CDCl_3$] 0.99 (m, 4H); 1.75 (s, 3H); 2.04 (m, 1H); 3.29 (d, 1H); 3.83 (d, 1H); 4.55 (dd, 1H); 4.68 (dd, 1H); 7.45 (m, 4H); 7.64 (m, 2H). |
| 1.355 | 3,5-$F_2$—Ph | H | O | H | $CH_2$ | 3-furyl | [$CDCl_3$] 7.52 0.87; 7.38 1.02; 7.37 2.30; 7.37 1.70; 7.36 0.69; 7.36 1.83; 7.36 2.06; 7.36 1.67; 7.36 1.24; 7.35 0.52; 7.31 0.66; 7.27 0.33; 7.27 0.34; 7.27 0.39; 7.27 0.52; 7.26 0.75; 7.26 157.65; 7.26 1.82; 7.25 1.18; 7.25 0.90; 7.25 0.69; 7.25 0.52; 7.25 0.41; 7.25 0.35; 7.21 0.51; 7.17 1.57; 7.16 0.95; 7.16 1.85; 7.16 0.91; 7.16 0.87; 7.15 0.77; 7.15 0.91; 7.15 1.70; 7.14 1.55; 7.00 1.01; 6.97 0.35; 6.91 0.40; 6.90 0.71; 6.90 0.34; 6.89 0.80; 6.88 1.39; 6.88 0.69; 6.87 0.40; 6.86 0.72; 6.86 0.34; 6.33 1.43; 6.33 1.38; 6.32 1.60; 6.32 1.46; 6.32 1.62; 6.32 1.44; 6.32 1.52; 4.38 0.52; 4.38 0.52; 4.37 0.52; 4.37 0.52; 4.34 0.90; 4.34 0.92; 4.33 0.87; 4.33 0.88; 4.25 0.98; 4.23 0.95; 4.23 0.96; 4.21 0.56; 4.21 0.56; 4.20 0.54; 4.20 0.54; 3.82 2.69; 3.77 3.05; 3.22 2.72; 3.17 2.38; 1.74 16.00; 1.59 0.32; 1.55 0.37; 1.55 0.40; 1.55 0.47; 1.54 0.57; 1.54 0.73; 1.54 0.93; 1.54 1.30; 1.54 2.09; 1.54 74.37; 1.54 2.25; 1.53 1.41; 1.53 0.97; 1.53 0.75; 1.53 0.61; 1.53 0.51; 1.53 0.41; 1.53 0.34; 0.01 1.76; 0.00 0.38; 0.00 0.53; 0.00 0.99; 0.00 68.17; 0.00 2.09; 0.00 1.24; −0.01 0.80; −0.01 0.62; −0.01 0.56; −0.01 1.89; −0.01 0.96 |
| 1.356 | 3-F—Ph | H | O | H | $CH_2$ | 3-furyl | [$CDCl_3$] 7.52 0.39; 7.39 1.44; 7.39 0.99; 7.39 0.80; 7.38 0.80; 7.38 1.38; 7.38 1.77; 7.37 3.20; 7.37 3.76; 7.37 3.89; 7.36 2.12; 7.36 2.29; 7.36 2.29; 7.35 1.79; 7.27 0.37; 7.27 0.47; 7.26 0.63; 7.26 70.77; 7.26 73.42; 7.16 0.41; 7.15 0.61; 7.15 0.40; 7.14 0.40; 7.14 0.50; 7.13 0.55; 7.13 0.75; 7.12 0.58; 7.12 0.57; 7.11 0.36; 7.02 0.38; 7.00 0.53; 6.33 1.56; 6.32 1.62; 6.32 1.67; 6.32 1.63; 6.32 1.62; 6.32 1.56; 4.38 0.56; 4.38 0.56; 4.37 0.56; 4.36 0.56; 4.34 0.96; 4.34 0.98; 4.33 0.98; 4.25 1.03; 4.25 |

TABLE 1-continued

Compounds of the general formula (I) according to the invention in which $R^2$ is hydrogen and $R^3$ is methyl and aryl is the radical

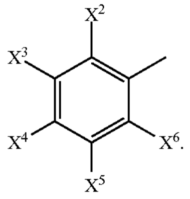

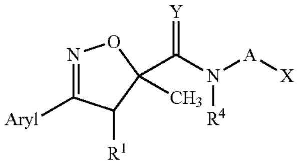

| No. | Aryl | $R^1$ | Y | $R^4$ | A | X | Physical data |
|---|---|---|---|---|---|---|---|
| | | | | | | | 1.04; 4.23 1.05; 4.23 1.02; 4.21 0.59; 4.21 0.60; 4.20 0.58; 3.85 2.74; 3.80 3.14; 3.25 2.95; 3.21 2.58; 1.74 16.00; 1.55 0.39; 1.55 0.51; 1.55 0.75; 1.55 1.22; 1.54 32.18; 1.54 1.07; 1.54 0.79; 1.54 0.61; 1.54 0.48; 1.54 0.38; 0.01 0.82; 0.01 0.88; 0.00 0.36; 0.00 29.48; 0.00 30.65; 0.00 2.21; 0.00 1.50; 0.00 0.95; 0.00 0.63; −0.01 0.49; −0.01 0.42; −0.01 0.95; −0.01 0.94 |
| 1.357 | 3,5-$Cl_2$—Ph | H | O | H | $CH_2$ | 3-furyl | [$CDCl_3$] 1.73 (S, 3H); 3.20 (d, 1H); 3.80 (d, 1H); 4.23 (dd, 1H); 4.36 (dd, 1H); 6.33 (m, 1H); 6.94 (s br, 1H); 7.37 (m, 2H); 7.42 (m, 1H); 7.52 (s, 2H). |
| 1.358 | Ph | H | O | H | $CH_2$ | 3-furyl | [$CDCl_3$] 7.65 1.86; 7.64 2.18; 7.64 1.00; 7.63 0.78; 7.63 2.01; 7.62 2.55; 7.52 1.10; 7.44 0.62; 7.44 0.80; 7.43 1.49; 7.42 4.80; 7.42 1.89; 7.41 2.28; 7.40 0.38; 7.39 0.61; 7.38 0.40; 7.37 1.03; 7.36 2.66; 7.36 2.32; 7.35 2.26; 7.35 2.26; 7.31 0.32; 7.26 173.76; 7.26 189.74; 7.24 0.41; 7.06 0.46; 7.00 1.07; 6.32 1.96; 6.32 1.86; 6.32 1.86; 6.32 1.75; 4.38 0.66; 4.36 0.66; 4.34 1.12; 4.33 1.10; 4.25 1.18; 4.23 1.16; 4.21 0.66; 4.20 0.65; 3.87 2.69; 3.83 3.15; 3.28 2.99; 3.24 2.60; 2.04 0.59; 1.74 16.00; 1.54 81.11; 1.54 83.13; 1.26 0.57; 0.15 0.37; 0.01 2.37; 0.01 0.81; 0.00 76.16; 0.00 84.48; −0.01 2.53; −0.01 2.63; −0.15 0.36 |
| 1.359 | 3,5-$Cl_2$—Ph | H | O | H | $CH_2$ | 3-isopropyl-1-methyl-1H-pyrazol-4-yl | [$CDCl_3$] 1.21 (t, 6H); 1.71 (s, 3H); 2.92 (m, 1H); 3.19 (d, 1H); 3.78 (d, 1H); 3.80 (s, 3H); 4.21 (dd, 1H); 4.31 (dd, 1H); 6.81 (brt, 1H); 7.19 (s, 1H); 7.40 (m, 1H); 7.49 (d, 2H). |
| 1.360 | 3,5-$F_2$—Ph | H | O | H | $CH_2$ | 3-isopropyl-1-methyl-1H-pyrazol-4-yl | [$CDCl_3$] 1.21 (t, 6H); 1.72 (s, 3H); 2.92 (m, 1H); 3.19 (d, 1H); 3.76 (d, 1H); 3.81 (s, 3H); 4.22 (dd, 1H); 4.31 (dd, 1H); 6.81 (brt, 1H); 6.88 (m, 1H); 7.14 (m, 2H); 7.19 (s, 1H). |
| 1.361 | 3-F—Ph | H | O | H | $CH_2$ | 3-isopropyl-1-methyl-1H-pyrazol-4-yl | [$CDCl_3$] 1.20 (t, 6H); 1.73 (s, 3H); 2.92 (m, 1H); 3.22 (d, 1H); 3.79 (s, 3H); 3.81 (d, 1H); 4.22 (dd, 1H); 4.30 (dd, 1H); 6.88 (brt, 1H); 7.12 (m, 1H); 7.19 (s, 1H); 7.36 (m, 3H). |

TABLE 1-continued

Compounds of the general formula (I) according to the invention in which $R^2$ is hydrogen and $R^3$ is methyl and aryl is the radical

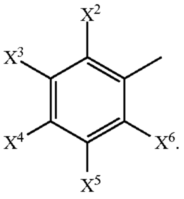

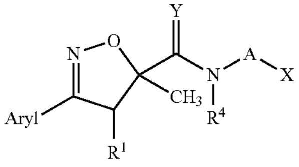

| No. | Aryl | $R^1$ | Y | $R^4$ | A | X | Physical data |
|---|---|---|---|---|---|---|---|
| 1.362 | Ph | H | O | H | $CH_2$ | 3-isopropyl-1-methyl-1H-pyrazol-4-yl | [$CDCl_3$] 1.21 (t, 6H); 1.72 (s, 3H); 2.91 (m, 1H); 3.25 (d, 1H); 3.77 (s, 3H); 3.84 (d, 1H); 4.23 (dd, 1H); 4.31 (dd, 1H); 6.91 (brt, 1H); 7.18 (s, 1H); 7.40 (m, 3H); 7.62 (m, 2H). |
| 1.363 | 3,5-$F_2$—Ph | H | O | H | $CH_2$ | 3-methyl-1H-pyrazol-4-yl | [$CDCl_3$] 7.44 3.16; 7.26 17.77; 7.17 0.32; 7.16 1.64; 7.16 1.94; 7.15 1.11; 7.14 1.08; 7.14 1.97; 7.14 1.59; 6.91 0.81; 6.90 1.25; 6.90 0.78; 6.89 1.12; 6.88 1.60; 6.88 0.79; 6.87 0.45; 6.86 0.75; 6.85 0.36; 4.38 0.83; 4.36 0.82; 4.34 1.49; 4.33 1.46; 4.25 1.51; 4.24 1.51; 4.22 0.84; 4.20 0.82; 3.82 2.73; 3.77 3.12; 3.21 2.89; 3.17 2.53; 2.25 15.43; 2.04 0.33; 1.73 16.00; 0.00 10.27 |
| 1.364 | 3-F—Ph | H | O | H | $CH_2$ | 3-methyl-1-propyl-1H-pyrazol-4-yl | [$CDCl_3$] 0.89 (t, 3H); 1.72 (s, 3H); 1.82 (m, 2H); 2.18 (s, 3H); 3.23 (d, 1H); 3.82 (d, 1H); 3.93 (t, 2H); 4.19 (dd, 1H); 4.31 (dd, 1H) 6.88 (brt, 1H); 7.13 (m, 1H); 7.22 (s, 1H); 7.38 (m, 1H). |
| 1.365 | 3,5-$F_2$—Ph | H | O | H | $CH_2$ | 3-methyl-1-propyl-1H-pyrazol-4-yl | [$CDCl_3$] 7.52 1.85; 7.31 0.80; 7.27 0.39; 7.27 0.46; 7.27 0.40; 7.27 0.50; 7.27 0.46; 7.27 0.62; 7.27 0.77; 7.27 0.90; 7.27 1.03; 7.26 1.53; 7.26 2.05; 7.26 3.14; 7.26 332.85; 7.26 6.86; 7.26 4.46; 7.25 3.12; 7.25 2.45; 7.25 1.90; 7.25 1.51; 7.25 1.27; 7.25 1.15; 7.25 0.94; 7.25 0.84; 7.25 0.70; 7.25 0.67; 7.25 0.62; 7.25 0.64; 7.25 0.56; 7.24 0.57; 7.24 0.57; 7.24 0.46; 7.24 0.43; 7.24 0.40; 7.24 0.37; 7.24 0.40; 7.24 0.37; 7.24 0.35; 7.24 0.38; 7.24 0.46; 7.23 0.60; 7.23 3.48; 7.23 0.43; 7.23 0.34; 7.21 0.94; 7.17 0.33; 7.16 1.74; 7.16 1.85; 7.15 0.99; 7.14 0.99; 7.14 1.84; 7.14 1.64; 7.00 1.96; 6.91 0.45; 6.90 0.71; 6.90 0.41; 6.89 0.87; 6.88 1.53; 6.88 0.73; 6.87 0.57; 6.86 0.99; 6.86 0.64; 6.85 0.49; 4.33 0.72; 4.32 0.69; 4.30 1.29; 4.28 1.22; 4.21 1.29; 4.20 1.32; 4.17 0.72; 4.16 0.74; 3.97 2.23; 3.96 3.10; 3.94 2.29; 3.81 2.77; 3.77 3.13; 3.75 0.33; 3.49 0.40; 3.43 0.33; 3.21 2.80; 3.17 2.45; 2.19 15.22; 2.01 0.37; 1.87 0.34; 1.86 1.35; 1.84 2.28; 1.82 2.30; 1.80 1.37; 1.78 0.36; 1.73 16.00; 1.63 0.43; 1.62 0.50; 1.58 |

TABLE 1-continued

Compounds of the general formula (I) according to the invention in which $R^2$ is hydrogen and $R^3$ is methyl and aryl is the radical

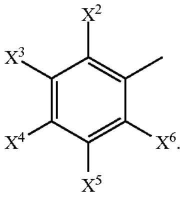

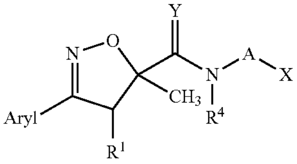

| No. | Aryl | $R^1$ | Y | $R^4$ | A | X | Physical data |
|---|---|---|---|---|---|---|---|
| | | | | | | | 42.77; 0.91 4.52; 0.89 9.54; 0.88 4.24; 0.15 0.54; 0.05 0.52; 0.05 0.52; 0.01 0.40; 0.01 0.51; 0.01 0.47; 0.01 0.66; 0.01 1.06; 0.01 4.56; 0.01 0.99; 0.01 1.25; 0.00 1.59; 0.00 2.50; 0.00 5.15; 0.00 193.65; 0.00 1.83; −0.01 1.38; −0.01 1.16; −0.01 5.12; −0.01 0.53; −0.01 0.39; −0.05 0.47; −0.15 0.57 |
| 1.366 | 3-Cl-5-F—Ph | H | O | H | $CH_2$ | 3-methyl-1-propyl-1H-pyrazol-4-yl | [$CDCl_3$] 0.88 (t, 3H); 1.73 (s, 3H); 1.82 (m, 2H); 2.18 (s, 3H); 3.18 (d, 1H); 3.78 (d, 1H); 3.95 (t, 2H); 4.18 (dd, 1H), 4.30 (dd, 1H); 6.83 (t br, 1H); 7.16 (m, 1H); 7.21 (m, 1H); 7.25 (m, 1H); 7.39 (s, 1H) |
| 1.367 | 3-Cl-5-$CF_3O$—Ph | H | O | H | $CH_2$ | 3-methyl-1-propyl-1H-pyrazol-4-yl | [$CDCl_3$] 7.54 1.80; 7.54 2.98; 7.53 1.95; 7.40 2.12; 7.29 1.95; 7.26 17.41; 7.23 4.10; 6.82 0.82; 4.34 0.87; 4.33 0.87; 4.30 1.48; 4.29 1.49; 4.21 1.51; 4.19 1.52; 4.17 0.88; 4.16 0.88; 3.96 2.45; 3.95 4.03; 3.93 2.55; 3.83 2.50; 3.79 2.86; 3.22 2.72; 3.18 2.39; 2.49 0.48; 2.19 16.00; 1.87 0.36; 1.86 1.44; 1.84 2.66; 1.82 2.71; 1.80 1.49; 1.78 0.44; 1.73 14.75; 1.58 10.80; 0.91 4.39; 0.89 8.64; 0.88 4.02; 0.01 0.36; 0.00 11.05; −0.01 0.60 |
| 1.368 | 3-F-5-Me—Ph | H | O | H | $CH_2$ | 3-methyl-1-propyl-1H-pyrazol-4-yl | [$CDCl_3$] 7.26 27.17; 7.22 3.48; 7.19 1.95; 7.19 2.00; 7.19 1.56; 7.19 1.10; 7.17 0.59; 7.17 0.75; 7.16 0.53; 7.15 0.56; 7.15 0.75; 6.97 0.58; 6.96 0.66; 6.96 0.75; 6.96 0.64; 6.96 0.56; 6.94 0.60; 6.94 0.68; 6.94 0.76; 6.94 0.65; 6.94 0.57; 6.89 0.52; 4.33 0.71; 4.31 0.72; 4.29 1.34; 4.27 1.32; 4.21 1.37; 4.20 1.39; 4.17 0.73; 4.16 0.72; 3.96 2.36; 3.94 3.25; 3.92 2.43; 3.83 2.77; 3.78 3.16; 3.23 2.86; 3.19 2.51; 2.37 9.59; 2.18 16.00; 1.85 1.35; 1.83 2.34; 1.81 2.30; 1.79 1.38; 1.77 0.33; 1.72 15.66; 1.61 8.31; 0.91 4.59; 0.89 9.55; 0.87 4.24; 0.00 11.60; −0.01 0.34 |
| 1.369 | 3-Me—Ph | H | O | H | $CH_2$ | 3-methyl-1-propyl-1H-pyrazol-4-yl | [$CDCl_3$] 7.46 2.90; 7.46 2.86; 7.42 1.35; 7.40 1.81; 7.31 1.10; 7.29 2.49; 7.27 1.69; 7.26 12.96; 7.26 16.61; 7.25 2.27; 7.23 1.01; 7.21 4.61; 6.93 0.93; 4.32 0.84; 4.31 0.84; 4.28 1.69; 4.27 1.68; 4.21 1.70; 4.20 |

TABLE 1-continued
Compounds of the general formula (I) according to the invention in which $R^2$ is hydrogen and $R^3$ is methyl and aryl is the radical
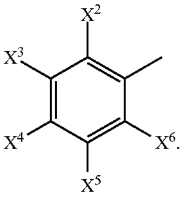
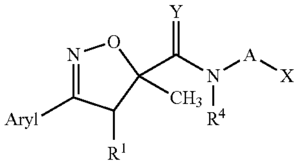
| No. | Aryl | $R^1$ | Y | $R^4$ | A | X | Physical data |
|---|---|---|---|---|---|---|---|
| | | | | | | | 1.71; 4.18 0.85; 4.16 0.83; 3.95 2.51; 3.93 4.74; 3.91 2.59; 3.86 2.14; 3.85 2.56; 3.81 2.45; 3.81 2.93; 3.26 2.81; 3.21 2.45; 2.37 13.79; 2.18 16.00; 1.84 1.43; 1.82 2.90; 1.81 3.00; 1.79 1.56; 1.77 0.37; 1.72 15.27; 1.61 4.62; 0.90 4.27; 0.89 7.05; 0.89 8.50; 0.87 3.38; 0.87 3.94; 0.00 5.36; 0.00 6.77 |
| 1.370 | 3-Cl-5-Me—Ph | H | O | H | $CH_2$ | 3-methyl-1-propyl-1H-pyrazol-4-yl | [$CDCl_3$] 7.42 2.49; 7.31 2.67; 7.31 2.70; 7.26 18.06; 7.23 2.39; 7.21 4.21; 6.87 0.83; 4.32 0.82; 4.31 0.82; 4.28 1.58; 4.27 1.58; 4.21 1.60; 4.20 1.62; 4.17 0.83; 4.16 0.82; 3.95 2.51; 3.94 4.19; 3.92 2.58; 3.82 2.52; 3.78 2.89; 3.22 2.76; 3.18 2.42; 2.49 0.42; 2.35 12.21; 2.18 16.00; 1.87 0.35; 1.85 1.46; 1.83 2.74; 1.81 2.79; 1.79 1.52; 1.77 0.36; 1.72 15.00; 1.58 9.03; 0.91 4.38; 0.89 8.57; 0.87 4.02; 0.00 11.36; −0.01 0.66 |
| 1.371 | 3-Cl-4-F—Ph | H | O | H | $CH_2$ | 3-methyl-1-propyl-1H-pyrazol-4-yl | [$CDCl_3$] 7.72 1.34; 7.71 1.46; 7.70 1.42; 7.70 1.41; 7.52 2.40; 7.52 2.42; 7.51 0.81; 7.51 0.71; 7.50 0.77; 7.49 0.74; 7.49 0.92; 7.48 0.86; 7.48 0.85; 7.47 0.87; 7.32 0.40; 7.32 0.48; 7.31 0.72; 7.28 0.38; 7.28 0.39; 7.28 0.36; 7.28 0.66; 7.27 0.68; 7.27 0.68; 7.27 0.73; 7.26 418.07; 7.26 405.44; 7.22 3.71; 7.21 0.50; 7.21 2.06; 7.20 1.67; 7.18 2.75; 7.16 1.64; 6.99 2.30; 6.86 0.67; 5.30 0.33; 4.33 0.80; 4.32 0.75; 4.29 1.42; 4.28 1.37; 4.21 1.46; 4.19 1.47; 4.17 0.95; 4.16 0.81; 3.96 2.34; 3.94 3.53; 3.92 2.38; 3.83 2.47; 3.78 2.78; 3.22 2.58; 3.17 2.27; 2.82 0.44; 2.81 0.47; 2.81 0.46; 2.18 16.00; 2.01 0.33; 1.85 1.38; 1.83 2.40; 1.82 2.38; 1.80 1.37; 1.78 0.42; 1.72 14.57; 1.59 0.43; 1.54 200.23; 1.49 1.12; 1.43 0.64; 1.29 0.36; 1.25 0.71; 1.23 0.34; 1.14 0.38; 1.13 0.54; 0.91 4.17; 0.89 8.38; 0.87 3.90; 0.82 0.32; 0.15 0.88; 0.01 4.91; 0.01 5.09; 0.00 189.69; 0.00 185.15; −0.01 6.80; −0.01 6.55; −0.05 0.95; −0.15 0.86 |

TABLE 1-continued

Compounds of the general formula (I) according to the invention in which $R^2$ is hydrogen and $R^3$ is methyl and aryl is the radical

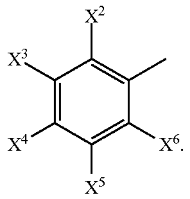

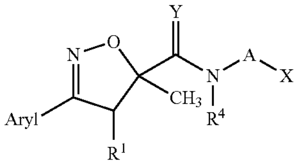

| No. | Aryl | $R^1$ | Y | $R^4$ | A | X | Physical data |
|---|---|---|---|---|---|---|---|
| 1.372 | 3-$CF_3O$—Ph | H | O | H | $CH_2$ | 3-methyl-1-propyl-1H-pyrazol-4-yl | [$CDCl_3$] 7.54 0.32; 7.53 1.34; 7.53 1.73; 7.53 1.15; 7.52 1.25; 7.52 1.53; 7.52 1.30; 7.52 1.15; 7.52 1.83; 7.51 1.89; 7.51 0.70; 7.47 2.05; 7.45 3.60; 7.43 1.62; 7.30 0.49; 7.30 0.82; 7.30 0.88; 7.29 0.79; 7.29 0.54; 7.28 0.43; 7.28 0.43; 7.28 0.66; 7.28 0.72; 7.28 0.49; 7.27 0.71; 7.27 0.44; 7.27 0.50; 7.27 0.38; 7.27 0.33; 7.27 0.39; 7.27 0.51; 7.26 39.15; 7.26 0.54; 7.26 0.41; 7.22 3.37; 6.88 0.51; 4.34 0.72; 4.34 0.72; 4.33 0.72; 4.32 0.70; 4.30 1.22; 4.29 1.24; 4.21 1.28; 4.21 1.28; 4.20 1.31; 4.17 0.74; 4.17 0.74; 4.16 0.75; 3.96 2.36; 3.94 3.13; 3.92 2.43; 3.86 2.92; 3.82 3.30; 3.26 2.94; 3.21 2.60; 2.19 15.74; 1.87 0.32; 1.85 1.38; 1.83 2.32; 1.81 2.27; 1.80 1.41; 1.78 0.35; 1.74 16.00; 1.60 9.25; 0.91 4.81; 0.89 10.42; 0.87 4.43; 0.01 0.48; 0.00 0.63; 0.00 16.73; 0.00 1.11; 0.00 0.76; 0.00 0.49; −0.01 0.53 |
| 1.373 | 4-Cl-3,5-$F_2$—Ph | H | O | H | $CH_2$ | 3-methyl-1-propyl-1H-pyrazol-4-yl | [$CDCl_3$] 7.52 1.69; 7.31 1.02; 7.26 305.96; 7.24 5.09; 7.23 1.40; 7.23 4.24; 7.21 1.17; 7.20 0.40; 7.00 1.75; 6.81 0.74; 4.34 0.93; 4.32 0.82; 4.30 1.47; 4.29 1.46; 4.20 1.46; 4.19 1.48; 4.17 0.86; 4.16 0.82; 3.97 2.46; 3.95 3.88; 3.93 2.52; 3.80 2.63; 3.76 2.92; 3.49 0.50; 3.19 2.80; 3.15 2.44; 2.81 1.15; 2.26 0.39; 2.18 16.00; 2.00 1.23; 1.88 0.35; 1.86 1.51; 1.84 2.62; 1.82 2.63; 1.80 1.52; 1.78 0.37; 1.73 15.60; 1.61 0.94; 1.56 192.72; 1.52 0.75; 1.51 0.93; 1.48 0.41; 1.43 2.24; 1.42 0.43; 1.25 0.52; 1.24 0.55; 1.22 1.30; 1.13 0.49; 0.92 4.51; 0.90 9.03; 0.88 4.28; 0.15 0.59; 0.05 0.51; 0.01 4.71; 0.00 145.67; −0.01 6.74; −0.05 0.55; −0.15 0.61 |
| 1.374 | 3,5-$Cl_2$—Ph | H | O | H | $CH_2$ | 3-methyl-1-propyl-1H-pyrazol-4-yl | [$CDCl_3$] 0.90 (t, 3H); 1.72 (s, 3H); 1.82 (m, 2H); 2.19 (s, 3H); 3.19 (d, 1H); 3.80 (d, 1H); 3.95 (t, 2H); 4.18 (dd, 1H); 4.30 (dd, 1H); 6.82 (t br, 1H); 7.22 (s, 1H); 7.41 (m, 1H), 7.51 (m, 2H) |

TABLE 1-continued

Compounds of the general formula (I) according to the invention in which $R^2$ is hydrogen and $R^3$ is methyl and aryl is the radical

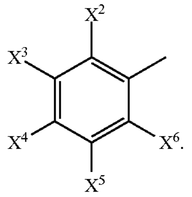

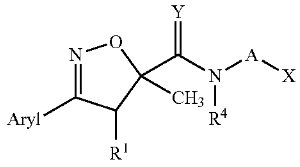

| No. | Aryl | $R^1$ | Y | $R^4$ | A | X | Physical data |
|---|---|---|---|---|---|---|---|
| 1.375 | Ph | H | O | H | $CH_2$ | 3-methyl-1-propyl-1H-pyrazol-4-yl | [$CDCl_3$] 0.88 (t, 3H); 1.72 (s, 3H); 1.81 (m, 2H); 2.19 (s, 3H); 3.25 (d, 1H); 3.84 (d, 1H); 3.92 (t, 2H); 4.19 (dd, 1H); 4.30 (dd, 1H); 6.92 (brt, 1H); 7.21 (s, 1H); 7.41 (m, 3H); 7.63 (m, 2H). |
| 1.376 | 3,5-$Cl_2$—Ph | H | O | H | $CH_2$ | 4-(methoxy-carbonyl)phenyl | [$CDCl_3$] 1.76 (s, 3H); 3.21 (d, 1H); 3.81 (d, 1H); 3.91 (s, 3H); 4.41 (dd, 1H); 4.57 (dd, 1H); 7.22 (br, 1H); 7.29 (d, 2H); 7.42 (m, 1H); 7.52 (m, 2H); 7.99 (d, 2H). |
| 1.377 | 3,5-$F_2$—Ph | H | O | H | $CH_2$ | 4-(trifluoromethyl)-1,3-thiazol-2-yl | [$CDCl_3$] 1.78 (s, 3H); 3.22 (d, 1H); 3.80 (d, 1H); 4.73 (dd, 1H); 4.83 (dd, 1H); 6.90 (m, 1H); 7.16 (m, 2H); 7.58 (brt, 1H); 7.70 (s, 1H). |
| 1.378 | 3-F—Ph | H | O | H | $CH_2$ | 4-(trifluoromethyl)-1,3-thiazol-2-yl | [$CDCl_3$] 1.77 (s, 3H); 3.28 (d, 1H); 3.83 (d, 1H); 4.74 (dd, 1H); 4.84 (dd, 1H); 7.15 (m, 1H); 7.38 (m, 3H); 7.62 (brt, 1H); 7.69 (s, 1H). |
| 1.379 | 3,5-$Cl_2$—Ph | H | O | H | $CH_2$ | 4-(trifluoromethyl)-1,3-thiazol-2-yl | [$CDCl_3$] 1.78 (s, 3H); 3.24 (d, 1H); 3.81 (d, 1H); 4.73 (dd, 1H); 4.82 (dd, 1H); 7.42 (m, 1H); 7.51 (m, 2H); 7.57 (brt, 1H); 7.70 (s, 1H). |
| 1.380 | Ph | H | O | H | $CH_2$ | 4-(trifluoromethyl)-1,3-thiazol-2-yl | [$CDCl_3$] 1.78 (s, 3H); 3.30 (d, 1H); 3.85 (d, 1H); 4.72 (dd, 1H); 4.82 (dd, 1H); 7.42 (m, 3H); 7.64 (m, 4H). |
| 1.381 | 3,5-$Cl_2$—Ph | H | O | H | $CH_2$ | 4-(trifluoromethyl)-phenyl | [$CDCl_3$] 1.76 (s, 3H); 3.23 (d, 1H); 3.82 (d, 1H); 4.41 (dd, 1H); 4.58 (dd, 1H); 7.20 (s br, 1H); 7.37 (d, 2H); 7.43 (s, 1H); 7.51 (s, 2H); 7.58 (d, 2H). |
| 1.382 | 3,5-$Cl_2$—Ph | H | O | H | $CH_2$ | 4-carboxyphenyl | [$CDCl_3$] 1.77 (s, 3H); 3.22 (d, 1H); 3.82 (d, 1H); 4.42 (dd, 1H); 4.58 (dd, 1H); 7.22 (br, 1H); 7.31 (d, 2H); 7.42 (t, 1H); 7.51 (d, 2H); 8.02 (d, 2H). |
| 1.383 | 3,5-$F_2$—Ph | H | O | H | $CH_2$ | 4-chloro-1-ethyl-1H-pyrazol-3-yl | [$CDCl_3$] 7.35 5.28; 7.26 15.30; 7.26 15.86; 7.21 0.43; 7.19 0.72; 7.19 0.65; 7.18 0.75; 7.17 0.57; 7.17 1.89; 7.16 2.25; 7.16 1.38; 7.15 1.46; 7.15 2.25; 7.14 1.69; 7.14 0.32; 7.13 0.34; 6.90 0.41; 6.90 0.71; 6.89 0.37; 6.88 0.84; 6.87 1.43; 6.87 0.71; 6.86 0.44; 6.85 0.72; 6.85 0.36; 4.52 0.75; 4.50 0.74; 4.48 2.11; 4.47 2.08; 4.44 2.09; 4.43 2.12; 4.40 0.76; 4.39 0.77; 4.10 1.41; 4.09 4.37; 4.07 4.44; 4.05 1.49; 3.84 2.69; 3.80 3.08; 3.22 |

TABLE 1-continued

Compounds of the general formula (I) according to the invention in which $R^2$ is hydrogen and $R^3$ is methyl and aryl is the radical

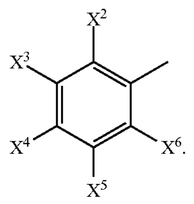

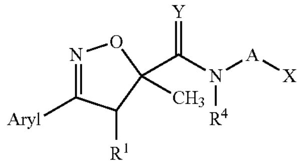

| No. | Aryl | $R^1$ | Y | $R^4$ | A | X | Physical data |
|---|---|---|---|---|---|---|---|
| | | | | | | | 2.96; 3.18 2.60; 1.76 16.00; 1.61 8.50; 1.46 4.63; 1.44 9.29; 1.43 4.53; 0.00 5.91 |
| 1.384 | 3,5-$Cl_2$—Ph | H | O | H | $CH_2$ | 4-chloro-1-ethyl-1H-pyrazol-3-yl | [$CDCl_3$] 7.51 6.81; 7.51 7.29; 7.41 1.86; 7.41 3.20; 7.40 1.53; 7.35 5.32; 7.26 19.03; 7.21 0.34; 7.20 0.44; 7.19 0.71; 7.18 0.43; 4.51 0.68; 4.50 0.70; 4.47 2.13; 4.46 2.11; 4.44 2.11; 4.42 2.11; 4.40 0.71; 4.39 0.70; 4.10 1.46; 4.08 4.51; 4.06 4.56; 4.05 1.51; 3.84 2.78; 3.80 3.16; 3.22 2.99; 3.17 2.62; 1.75 16.00; 1.61 8.99; 1.46 5.13; 1.44 10.41; 1.43 5.00; 0.00 7.24 |
| 1.385 | 3-F—Ph | H | O | H | $CH_2$ | 4-chloro-1-ethyl-1H-pyrazol-3-yl | [$CDCl_3$] 7.41 0.40; 7.40 0.92; 7.39 1.23; 7.39 1.16; 7.39 1.53; 7.37 3.63; 7.37 3.95; 7.37 3.81; 7.36 2.59; 7.34 5.10; 7.26 15.01; 7.22 0.75; 7.21 0.47; 7.21 0.49; 7.15 0.53; 7.14 0.79; 7.14 0.52; 7.13 0.58; 7.12 0.79; 7.12 0.86; 7.11 0.58; 7.11 0.51; 7.10 0.37; 4.52 0.78; 4.51 0.77; 4.48 2.00; 4.47 1.96; 4.44 1.98; 4.42 1.98; 4.40 0.78; 4.38 0.75; 4.10 1.39; 4.08 4.25; 4.06 4.31; 4.04 1.44; 3.87 2.72; 3.83 3.09; 3.25 2.96; 3.21 2.59; 1.75 16.00; 1.62 6.44; 1.46 4.78; 1.44 9.73; 1.42 4.66; 0.00 0.75; 0.00 5.99 |
| 1.386 | Ph | H | O | H | $CH_2$ | 4-chloro-1-ethyl-1H-pyrazol-3-yl | [$CDCl_3$] 7.64 1.94; 7.64 2.77; 7.64 1.77; 7.63 1.20; 7.63 2.11; 7.62 3.13; 7.43 0.56; 7.43 0.93; 7.42 0.76; 7.42 1.88; 7.41 4.62; 7.41 3.43; 7.41 2.75; 7.40 1.41; 7.40 2.59; 7.39 0.60; 7.38 0.79; 7.38 0.49; 7.37 0.49; 7.33 4.82; 7.26 16.29; 7.26 5.72; 4.52 0.81; 4.51 0.82; 4.49 1.84; 4.47 1.85; 4.43 1.84; 4.42 1.88; 4.39 0.83; 4.38 0.82; 4.09 1.34; 4.07 4.18; 4.06 4.27; 4.04 1.44; 3.89 2.81; 3.89 1.14; 3.85 3.19; 3.85 1.32; 3.28 2.96; 3.24 2.61; 1.75 16.00; 1.63 6.06; 1.45 4.98; 1.45 1.90; 1.44 10.31; 1.43 3.77; 1.42 4.97; 1.41 1.88; 0.00 6.64 |
| 1.387 | 3,5-$F_2$—Ph | H | O | H | $CH_2$ | 4-chloro-1-methyl-1H-pyrazol-3-yl | [$CDCl_3$] 7.52 1.03; 7.52 1.35; 7.31 4.61; 7.27 0.40; 7.27 0.47; 7.27 0.72; 7.27 0.76; 7.27 0.78; 7.27 0.96; 7.27 1.41; 7.27 2.07; 7.26 177.85; 7.26 239.59; 7.24 0.61; 7.18 1.16; 7.17 2.60; 7.16 2.83; 7.16 3.01; 7.15 1.43; 7.15 2.29; 7.15 |

TABLE 1-continued
Compounds of the general formula (I) according to the invention in which $R^2$ is hydrogen and $R^3$ is methyl and aryl is the radical
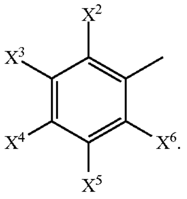
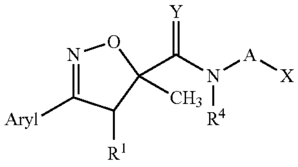
| No. | Aryl | $R^1$ | Y | $R^4$ | A | X | Physical data |
|---|---|---|---|---|---|---|---|
| | | | | | | | 2.58; 7.14 2.42; 7.14 1.82; 7.00 0.99; 7.00 1.34; 6.89 0.75; 6.87 1.12; 6.87 1.41; 6.86 0.81; 6.85 0.71; 4.51 0.70; 4.49 0.64; 4.47 1.79; 4.46 1.83; 4.43 1.86; 4.42 1.80; 4.39 0.66; 4.38 0.61; 3.84 1.91; 3.83 2.51; 3.82 11.98; 3.82 16.00; 3.79 2.23; 3.79 2.81; 3.21 2.73; 3.17 2.34; 2.04 0.54; 2.00 0.56; 1.75 11.53; 1.75 15.16; 1.53 98.94; 1.53 135.51; 1.26 0.67; 0.15 0.66; 0.01 2.78; 0.01 2.15; 0.01 4.38; 0.00 111.84; 0.00 149.03; −0.01 7.27; −0.02 0.75; −0.15 0.58 |
| 1.388 | 3,5-$Cl_2$—Ph | H | O | H | $CH_2$ | 4-chloro-1-methyl-1H-pyrazol-3-yl | [$CDCl_3$] 7.52 1.07; 7.51 5.70; 7.51 6.33; 7.41 1.54; 7.40 2.81; 7.40 1.41; 7.31 4.71; 7.27 0.43; 7.26 165.43; 7.25 0.53; 7.25 0.56; 7.21 1.08; 7.18 0.37; 7.17 0.55; 7.16 0.48; 6.99 0.89; 4.50 0.57; 4.49 0.58; 4.46 1.74; 4.45 1.72; 4.43 1.72; 4.41 1.74; 4.39 0.61; 4.38 0.58; 3.83 2.44; 3.82 16.00; 3.79 2.79; 3.21 2.62; 3.17 2.29; 1.75 14.00; 1.58 0.45; 1.53 78.32; 1.48 0.57; 0.15 0.46; 0.05 0.51; 0.01 2.75; 0.00 0.54; 0.00 107.18; −0.01 3.69; −0.01 0.85; −0.01 0.70; −0.01 0.47; −0.02 0.36; −0.05 0.72; −0.15 0.44 |
| 1.389 | 3-F—Ph | H | O | H | $CH_2$ | 4-chloro-1-methyl-1H-pyrazol-3-yl | [$CDCl_3$] 7.52 0.32; 7.40 0.65; 7.39 0.90; 7.39 0.95; 7.39 0.96; 7.38 1.20; 7.37 2.99; 7.37 3.28; 7.37 3.15; 7.36 2.43; 7.36 2.18; 7.30 4.29; 7.27 0.38; 7.26 57.27; 7.25 0.37; 7.22 0.39; 7.21 0.52; 7.21 0.59; 7.21 0.57; 7.20 0.41; 7.15 0.41; 7.14 0.69; 7.13 0.45; 7.13 0.43; 7.12 0.58; 7.12 0.67; 7.12 0.63; 7.11 0.64; 7.10 0.42; 7.09 0.33; 7.00 0.33; 4.51 0.66; 4.50 0.66; 4.47 1.69; 4.46 1.68; 4.43 1.69; 4.41 1.73; 4.39 0.67; 4.38 0.63; 3.86 2.54; 3.82 3.02; 3.81 16.00; 3.25 2.76; 3.20 2.40; 1.75 14.84; 1.55 0.33; 1.54 34.64; 0.01 0.99; 0.01 0.49; 0.00 34.63; −0.01 1.34 |
| 1.390 | Ph | H | O | H | $CH_2$ | 4-chloro-1-methyl-1H-pyrazol-3-yl | [$CDCl_3$] 7.64 1.78; 7.64 2.14; 7.63 0.98; 7.63 0.81; 7.63 0.80; 7.63 1.72; 7.62 2.37; 7.43 0.49; 7.42 0.70; 7.42 0.47; 7.41 3.48; 7.41 3.63; 7.40 1.58; 7.40 1.14; 7.39 2.09; 7.39 0.40; 7.38 |

TABLE 1-continued

Compounds of the general formula (I) according to the invention in which $R^2$ is hydrogen and $R^3$ is methyl and aryl is the radical

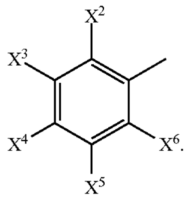

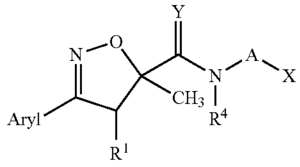

| No. | Aryl | $R^1$ | Y | $R^4$ | A | X | Physical data |
|---|---|---|---|---|---|---|---|
| | | | | | | | 0.57; 7.37 0.33; 7.30 4.31; 7.26 13.90; 7.24 0.51; 4.51 0.72; 4.50 0.72; 4.48 1.68; 4.46 1.66; 4.42 1.67; 4.41 1.68; 4.38 0.72; 4.37 0.71; 3.89 2.63; 3.85 3.00; 3.80 16.00; 3.27 2.79; 3.23 2.46; 1.75 14.92; 1.61 2.36; 0.00 6.64 |
| 1.391 | 3,5-$F_2$—Ph | H | O | H | $CH_2$ | 4-chloro-1-methyl-1H-pyrazol-5-yl | [$CDCl_3$] 7.52 0.36; 7.37 4.22; 7.26 63.40; 7.26 56.54; 7.16 2.10; 7.14 1.99; 7.14 1.80; 7.12 0.56; 7.12 0.57; 7.10 0.71; 7.00 0.37; 6.92 0.34; 6.91 0.63; 6.91 0.38; 6.90 0.66; 6.89 1.23; 6.89 0.69; 6.87 0.37; 6.87 0.62; 6.86 0.35; 4.59 0.84; 4.58 0.85; 4.55 1.52; 4.54 1.51; 4.46 1.50; 4.45 1.52; 4.42 0.87; 4.41 0.83; 3.84 16.00; 3.84 14.95; 3.78 2.20; 3.74 2.54; 3.23 2.48; 3.19 2.14; 1.73 13.36; 1.56 41.05; 1.26 0.46; 0.01 1.08; 0.00 37.67; 0.00 34.28 |
| 1.392 | 3-F—Ph | H | O | H | $CH_2$ | 4-chloro-1-methyl-1H-pyrazol-5-yl | [$CDCl_3$] 7.52 0.96; 7.42 0.39; 7.40 1.06; 7.37 7.51; 7.35 1.87; 7.31 0.39; 7.26 162.54; 7.26 163.50; 7.16 0.89; 7.14 1.24; 7.14 1.60; 7.12 1.03; 6.99 0.99; 4.59 0.91; 4.58 0.93; 4.55 1.63; 4.54 1.57; 4.46 1.65; 4.45 1.63; 4.42 0.87; 4.41 1.01; 3.83 15.72; 3.83 16.00; 3.81 2.28; 3.77 2.60; 3.26 2.58; 3.22 2.16; 2.04 0.43; 1.72 13.89; 1.58 0.35; 1.54 95.44; 1.26 0.68; 0.15 0.55; 0.01 2.98; 0.00 98.68; 0.00 98.58; −0.01 5.71; −0.150.57 |
| 1.393 | 3,5-$Cl_2$—Ph | H | O | H | $CH_2$ | 4-chloro-1-methyl-1H-pyrazol-5-yl | [$CDCl_3$] 7.52 0.48; 7.52 0.61; 7.51 7.06; 7.51 6.43; 7.50 5.85; 7.43 2.70; 7.42 3.03; 7.38 4.19; 7.26 67.35; 7.26 75.87; 7.09 0.97; 7.00 0.39; 7.00 0.45; 4.59 0.85; 4.58 0.82; 4.55 1.47; 4.54 1.46; 4.46 1.55; 4.44 1.47; 4.42 0.86; 4.41 0.85; 3.85 14.70; 3.84 16.00; 3.79 2.05; 3.79 2.14; 3.75 2.43; 3.74 2.52; 3.23 2.42; 3.18 2.11; 1.72 12.69; 1.72 13.17; 1.54 52.34; 1.54 56.59; 1.26 0.32; 0.00 41.10; 0.00 46.73 |
| 1.394 | Ph | H | O | H | $CH_2$ | 4-chloro-1-methyl-1H-pyrazol-5-yl | [$CDCl_3$] 7.64 1.70; 7.63 2.25; 7.62 2.29; 7.61 2.57; 7.52 0.76; 7.44 1.01; 7.43 1.36; 7.43 3.99; 7.41 2.45; 7.39 0.62; 7.37 4.05; 7.31 0.43; 7.30 0.42; 7.26 |

TABLE 1-continued

Compounds of the general formula (I) according to the invention in which $R^2$ is hydrogen and $R^3$ is methyl and aryl is the radical

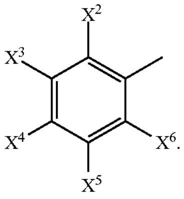

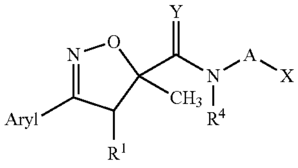

| No. | Aryl | $R^1$ | Y | $R^4$ | A | X | Physical data |
|---|---|---|---|---|---|---|---|
| | | | | | | | 144.79; 7.26 132.96; 7.16 0.69; 6.99 0.81; 4.59 0.79; 4.58 0.82; 4.55 1.54; 4.54 1.54; 4.46 1.47; 4.45 1.42; 4.42 0.82; 4.41 0.90; 3.84 2.31; 3.82 16.00; 3.80 2.71; 3.29 2.51; 3.25 2.20; 2.04 0.98; 1.72 13.36; 1.58 0.32; 1.54 120.21; 1.53 107.70; 1.28 0.33; 1.26 0.78; 0.15 0.46; 0.01 2.19; 0.00 88.13; 0.00 80.75; −0.15 0.44 |
| 1.395 | 3,5-$Cl_2$—Ph | H | O | H | $CH_2$ | 4-chlorophenyl | [$CDCl_3$] 1.74 (s, 3H); 3.19 (d, 1H); 3.79 (d, 1H); 4.32 (dd, 1H); 4.49 (dd, 1H); 7.13 (s br, 1H); 7.18 (d, 2H); 7.29 (d, 2H); 7.42 (s, 1H); 7.50 (s, 2H). |
| 1.396 | 3,5-$Cl_2$—Ph | H | O | H | $CH_2$ | 4-methoxyphenyl | [$CDCl_3$] 1.74 (s, 3H); 3.20 (d, 1H); 3.79 (s, 3H); 3.82 (d, 1H); 4.28 (dd, 1H); 4.45 (dd, 1H); 6.86 (d, 2H); 7.02 (t br, 1H); 7.18 (d, 2H); 7.41 (s, 1H); 7.52 (s, 2H). |
| 1.397 | 3,5-$Cl_2$—Ph | H | O | H | $CH_2$ | 4-methyl-4H-1,2,4-triazol-3-yl | [$CDCl_3$] 8.08 3.72; 7.58 0.37; 7.57 0.61; 7.51 6.53; 7.50 6.50; 7.42 1.94; 7.41 2.95; 7.41 1.35; 7.27 16.74; 4.73 0.87; 4.71 0.87; 4.69 1.59; 4.67 1.55; 4.60 1.52; 4.59 1.54; 4.56 0.85; 4.55 0.83; 3.79 2.29; 3.74 2.63; 3.68 16.00; 3.23 2.52; 3.19 2.19; 1.73 13.33; 1.69 1.09; 0.01 0.32 |
| 1.398 | 3-F—Ph | H | O | H | $CH_2$ | 4-methyl-4H-1,2,4-triazol-3-yl | [$CDCl_3$] 8.07 4.30; 7.56 0.79; 7.39 1.03; 7.38 2.94; 7.38 3.81; 7.37 3.34; 7.35 1.11; 7.35 1.10; 7.27 14.48; 7.27 14.37; 7.16 0.41; 7.15 0.69; 7.15 0.48; 7.14 0.51; 7.14 0.85; 7.13 0.71; 7.13 0.75; 7.12 0.58; 7.12 0.43; 7.11 0.35; 4.74 0.88; 4.72 0.88; 4.70 1.65; 4.68 1.64; 4.62 1.64; 4.60 1.67; 4.58 0.90; 4.56 0.88; 3.81 2.35; 3.77 2.76; 3.67 16.00; 3.27 2.69; 3.22 2.32; 1.73 14.28; 1.69 1.42; 0.00 5.33 |
| 1.399 | Ph | H | O | H | $CH_2$ | 4-methyl-4H-1,2,4-triazol-3-yl | [$CDCl_3$] 8.06 3.60; 7.64 1.70; 7.63 1.95; 7.63 0.85; 7.62 0.70; 7.62 1.96; 7.61 2.30; 7.55 0.48; 7.44 0.61; 7.44 0.78; 7.43 0.52; 7.43 1.34; 7.42 3.92; 7.42 1.89; 7.41 0.69; 7.41 0.98; 7.40 2.06; 7.40 0.34; 7.39 0.34; 7.39 0.56; 7.38 0.44; 7.27 17.00; 7.26 13.73; 4.74 0.85; 4.72 0.84; 4.70 1.64; 4.68 1.61; 4.62 1.57; 4.61 1.59; 4.58 0.83; 4.57 0.81; 3.84 2.31; 3.79 2.70; 3.66 16.00; 3.29 |

TABLE 1-continued
Compounds of the general formula (I) according to the invention in which $R^2$ is hydrogen and $R^3$ is methyl and aryl is the radical
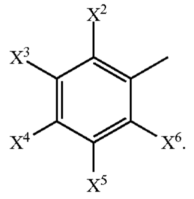
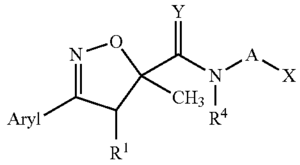
| No. | Aryl | $R^1$ | Y | $R^4$ | A | X | Physical data |
|---|---|---|---|---|---|---|---|
| | | | | | | | 2.62; 3.25 2.27; 1.73 13.77; 1.69 0.91; 0.00 6.24 |
| 1.400 | 3,5-$F_2$—Ph | H | O | H | $CH_2$ | 4-methyl-4H-1,2,4-triazol-3-yl | [$CDCl_3$] 8.08 4.34; 7.56 0.70; 7.27 11.51; 7.27 13.27; 7.16 1.55; 7.16 2.06; 7.14 2.08; 7.14 1.64; 6.91 0.35; 6.91 0.64; 6.90 0.34; 6.89 0.73; 6.88 1.29; 6.88 0.67; 6.87 0.40; 6.86 0.67; 6.86 0.35; 4.73 0.91; 4.72 0.90; 4.69 1.68; 4.68 1.67; 4.61 1.63; 4.59 1.65; 4.57 0.91; 4.55 0.89; 3.78 2.32; 3.74 2.79; 3.73 0.44; 3.68 16.00; 3.23 2.69; 3.19 2.33; 1.73 14.36; 1.68 1.83; 0.00 5.36 |
| 1.401 | 3,5-$F_2$—Ph | H | O | H | $CH_2$ | 5-(difluoromethoxy)-1-methyl-1H-pyrazol-3-yl | [$CDCl_3$] 7.82 0.44; 7.27 11.11; 7.23 0.57; 7.22 0.39; 7.17 1.51; 7.16 1.81; 7.16 1.10; 7.15 1.89; 7.14 1.46; 6.91 0.39; 6.90 0.65; 6.89 0.33; 6.88 0.73; 6.88 1.27; 6.87 0.64; 6.86 0.38; 6.86 0.64; 6.65 1.39; 6.47 2.85; 6.29 1.44; 5.76 2.76; 4.43 0.73; 4.42 0.73; 4.39 1.53; 4.38 1.52; 4.33 1.53; 4.31 1.55; 4.29 0.75; 4.28 0.73; 4.23 0.47; 4.22 0.49; 3.82 2.41; 3.78 2.76; 3.68 16.00; 3.22 2.61; 3.18 2.28; 1.75 14.15; 1.64 3.80; 1.54 0.52; 1.53 1.03; 1.51 0.51 |
| 1.402 | 3,5-$F_2$—Ph | H | O | H | $CH_2$ | 5-(methoxy-carbonyl)-2-furyl | [$CDCl_3$] 7.27 42.59; 7.26 46.94; 7.24 1.86; 7.21 1.12; 7.19 0.88; 7.18 0.73; 7.17 1.49; 7.17 3.19; 7.16 2.73; 7.16 1.83; 7.15 2.80; 7.15 3.39; 7.14 1.83; 7.14 0.75; 7.13 0.59; 7.11 2.15; 7.10 2.27; 7.10 2.49; 7.09 2.36; 6.91 0.82; 6.90 0.84; 6.90 0.39; 6.89 0.70; 6.89 1.69; 6.88 1.68; 6.88 0.76; 6.87 0.51; 6.87 0.93; 6.86 0.91; 6.34 2.00; 6.33 2.04; 6.33 2.25; 6.33 2.27; 6.33 2.23; 6.32 2.17; 6.32 2.07; 4.59 0.68; 4.57 0.71; 4.55 1.42; 4.54 1.43; 4.53 1.50; 4.53 1.47; 4.47 1.41; 4.46 1.49; 4.46 1.50; 4.44 0.75; 4.42 0.75; 4.14 0.45; 4.13 0.48; 4.12 0.49; 4.11 0.51; 3.88 14.89; 3.88 16.00; 3.80 2.10; 3.80 2.21; 3.76 2.42; 3.76 2.56; 3.23 2.30; 3.22 2.41; 3.19 2.01; 3.18 2.10; 2.05 1.90; 2.04 2.06; 1.74 13.03; 1.74 13.41; 1.55 22.13; 1.55 23.62; 1.52 1.08; 1.31 0.32; 1.28 1.01; 1.28 1.33; 1.26 2.33; 1.26 1.90; 1.25 0.85; 1.24 0.80; 0.90 |

TABLE 1-continued
Compounds of the general formula (I) according to the invention in which $R^2$ is hydrogen and $R^3$ is methyl and aryl is the radical
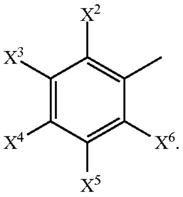
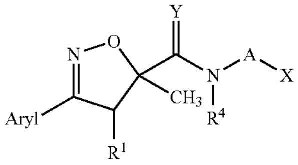
| No. | Aryl | $R^1$ | Y | $R^4$ | A | X | Physical data |
|---|---|---|---|---|---|---|---|
| | | | | | | | 0.58; 0.89 1.22; 0.88 1.29; 0.87 0.66; 0.01 0.41; 0.01 17.29; 0.00 19.28 |
| 1.403 | 3,5-$Cl_2$—Ph | H | O | H | $CH_2$ | 5-(methoxy-carbonyl)-2-furyl | [$CDCl_3$] 7.52 5.18; 7.51 5.71; 7.51 5.67; 7.51 5.86; 7.42 1.76; 7.42 2.49; 7.42 2.60; 7.41 1.39; 7.41 1.39; 7.27 5.00; 7.26 42.29; 7.26 48.17; 7.21 0.57; 7.19 0.85; 7.10 2.46; 7.09 2.39; 6.33 2.10; 6.33 2.26; 6.32 2.05; 6.32 2.06; 4.58 0.65; 4.56 0.64; 4.54 1.36; 4.52 1.33; 4.47 1.34; 4.46 1.35; 4.43 0.64; 4.42 0.63; 4.15 0.44; 4.13 1.33; 4.11 1.34; 4.10 0.46; 3.89 1.74; 3.88 14.79; 3.88 16.00; 3.81 2.15; 3.76 2.46; 3.22 2.42; 3.18 2.09; 2.05 0.68; 2.04 5.55; 2.04 5.72; 1.73 12.92; 1.55 2.86; 1.55 21.14; 1.55 22.06; 1.31 0.71; 1.28 3.23; 1.27 3.55; 1.26 4.76; 1.26 4.77; 1.24 1.73; 1.24 1.79; 0.90 1.49; 0.89 1.09; 0.88 3.73; 0.87 1.63; 0.01 2.48; 0.00 17.38 |
| 1.404 | 3-F—Ph | H | O | H | $CH_2$ | 5-(methoxy-carbonyl)-2-furyl | [$CDCl_3$] 7.39 1.67; 7.39 1.23; 7.39 1.14; 7.39 1.34; 7.38 3.13; 7.37 2.85; 7.37 3.49; 7.37 3.23; 7.31 0.48; 7.26 26.32; 7.26 31.32; 7.26 3.24; 7.21 0.51; 7.21 0.44; 7.16 0.41; 7.15 0.69; 7.15 0.46; 7.14 0.69; 7.14 0.75; 7.13 0.76; 7.13 0.89; 7.12 0.59; 7.12 0.53; 7.11 0.37; 7.11 0.40; 7.10 2.15; 7.09 2.28; 6.33 1.99; 6.33 1.97; 6.32 2.10; 6.32 2.00; 4.59 0.72; 4.57 0.71; 4.55 1.42; 4.53 1.42; 4.47 1.40; 4.46 1.42; 4.43 0.72; 4.42 0.73; 4.15 0.38; 4.15 0.43; 4.13 1.17; 4.13 1.31; 4.12 1.22; 4.11 1.31; 4.10 0.42; 4.10 0.44; 3.88 13.73; 3.87 16.00; 3.83 1.95; 3.83 2.18; 3.83 0.57; 3.79 2.23; 3.79 2.48; 3.26 2.16; 3.26 2.34; 3.22 1.89; 3.21 2.05; 2.05 5.13; 2.04 5.82; 1.74 11.75; 1.74 12.88; 1.55 11.22; 1.31 0.35; 1.28 1.91; 1.28 2.38; 1.27 1.96; 1.26 4.05; 1.26 4.17; 1.24 1.60; 1.24 1.73; 0.90 0.82; 0.88 1.84; 0.88 2.05; 0.87 0.91; 0.01 0.36; 0.00 10.83; 0.00 12.97 |
| 1.405 | Ph | H | O | H | $CH_2$ | 5-(methoxy-carbonyl)-2-furyl | [$CDCl_3$] 7.65 2.73; 7.64 2.62; 7.63 2.91; 7.62 2.30; 7.44 1.44; 7.42 5.43; 7.41 2.25; 7.41 |

TABLE 1-continued
Compounds of the general formula (I) according to the invention in which $R^2$ is hydrogen and $R^3$ is methyl and aryl is the radical
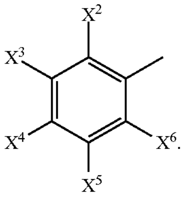
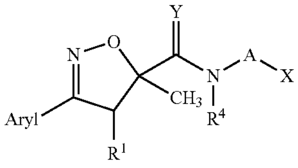
| No. | Aryl | $R^1$ | Y | $R^4$ | A | X | Physical data |
|---|---|---|---|---|---|---|---|
| | | | | | | | 2.40; 7.39 0.64; 7.39 0.71; 7.38 0.40; 7.31 0.68; 7.26 47.54; 7.09 2.68; 7.09 2.26; 6.32 2.47; 6.31 1.95; 4.59 0.73; 4.57 0.71; 4.55 1.36; 4.53 1.30; 4.46 1.40; 4.45 1.33; 4.42 0.73; 4.41 0.67; 4.13 0.52; 4.11 0.52; 3.87 16.00; 3.86 2.41; 3.81 2.61; 3.28 2.52; 3.24 2.20; 2.04 2.18; 1.73 13.64; 1.55 24.65; 1.28 1.07; 1.26 1.55; 1.24 0.67; 0.90 0.38; 0.88 0.78; 0.86 0.34; 0.00 19.24 |
| 1.406 | 3,5-$F_2$—Ph | H | O | H | $CH_2$ | 5-chloro-1-methyl-1H-pyrazol-4-yl | [$CDCl_3$] 7.44 4.20; 7.26 24.36; 7.26 18.27; 7.17 0.35; 7.15 2.60; 7.15 2.46; 7.14 2.57; 7.13 2.59; 7.12 0.55; 6.95 0.95; 6.91 0.49; 6.90 0.80; 6.90 0.69; 6.89 0.84; 6.88 1.47; 6.88 1.25; 6.86 0.53; 6.86 0.80; 6.85 0.66; 4.35 0.80; 4.34 0.84; 4.31 1.65; 4.30 1.68; 4.24 1.63; 4.23 1.70; 4.21 0.86; 4.19 0.85; 3.82 16.00; 3.81 12.72; 3.81 3.51; 3.76 2.68; 3.76 2.14; 3.21 2.54; 3.17 2.22; 1.73 13.99; 1.72 11.36; 1.57 3.22 |
| 1.407 | 3-F—Ph | H | O | H | $CH_2$ | 5-chloro-1-methyl-1H-pyrazol-4-yl | [$CDCl_3$] 7.44 3.37; 7.39 0.81; 7.39 0.54; 7.38 0.76; 7.38 1.56; 7.37 1.44; 7.37 1.88; 7.36 2.15; 7.36 2.12; 7.36 0.96; 7.35 0.51; 7.35 0.32; 7.26 17.24; 7.16 0.36; 7.15 0.43; 7.15 0.40; 7.15 0.34; 7.14 0.39; 7.13 0.44; 7.13 0.40; 7.13 0.65; 7.12 0.33; 7.12 0.32; 7.11 0.52; 7.00 0.36; 6.99 0.37; 4.35 0.67; 4.33 0.66; 4.31 1.33; 4.30 1.31; 4.24 1.33; 4.23 1.35; 4.21 0.68; 4.19 0.66; 3.83 2.15; 3.81 16.00; 3.79 2.47; 3.24 2.29; 3.20 1.99; 1.73 12.38; 1.58 3.25 |
| 1.408 | 3,5-$F_2$—Ph | H | S | H | $CH_2$ | 5-chloro-1-methyl-1H-pyrazol-4-yl | [$CDCl_3$] 8.67 0.41; 7.52 3.81; 7.26 176.76; 7.17 1.31; 7.16 1.80; 7.15 0.99; 7.15 1.67; 7.14 1.56; 7.00 1.03; 6.90 0.62; 6.90 0.33; 6.89 0.67; 6.88 1.21; 6.88 0.63; 6.87 0.34; 6.86 0.59; 6.86 0.33; 4.71 0.71; 4.70 0.71; 4.67 1.30; 4.66 1.30; 4.59 1.33; 4.58 1.36; 4.55 0.71; 4.54 0.73; 4.26 2.17; 4.22 2.35; 3.90 0.40; 3.88 0.75; 3.85 16.00; 3.83 0.48; 3.40 2.20; 3.36 1.98; 1.89 12.31; 1.87 0.48; 1.55 69.67; 0.01 1.86; 0.00 67.37 |

TABLE 1-continued

Compounds of the general formula (I) according to the invention in which $R^2$ is hydrogen and $R^3$ is methyl and aryl is the radical

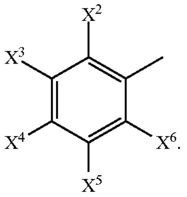

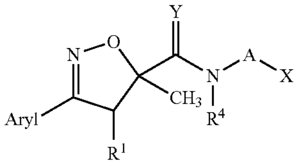

| No. | Aryl | $R^1$ | Y | $R^4$ | A | X | Physical data |
|---|---|---|---|---|---|---|---|
| 1.409 | 3,5-$Cl_2$—Ph | H | O | H | $CH_2$ | 5-chloro-1-methyl-1H-pyrazol-4-yl | [$CDCl_3$] 7.51 5.21; 7.50 5.80; 7.44 3.50; 7.42 1.47; 7.41 2.48; 7.41 1.24; 7.26 15.36; 6.94 0.50; 4.35 0.69; 4.33 0.70; 4.31 1.38; 4.30 1.36; 4.24 1.37; 4.23 1.40; 4.20 0.71; 4.19 0.70; 3.82 16.00; 3.81 2.43; 3.77 2.46; 3.21 2.30; 3.16 2.02; 1.72 12.34; 1.58 5.23; 0.00 5.81 |
| 1.410 | Ph | H | O | H | $CH_2$ | 5-chloro-1-methyl-1H-pyrazol-4-yl | [$CDCl_3$] 7.64 1.81; 7.64 3.28; 7.63 2.82; 7.63 1.80; 7.62 2.72; 7.62 3.66; 7.61 2.40; 7.45 0.35; 7.43 4.91; 7.43 2.39; 7.42 5.50; 7.42 5.90; 7.41 1.84; 7.40 3.09; 7.40 0.74; 7.39 0.77; 7.39 0.71; 7.38 0.55; 7.38 0.36; 7.27 1.36; 7.27 9.74; 7.26 10.07; 7.03 0.94; 4.35 0.75; 4.35 0.79; 4.34 0.74; 4.33 0.77; 4.31 1.52; 4.31 1.61; 4.30 1.51; 4.29 1.55; 4.24 1.52; 4.24 1.64; 4.23 1.54; 4.23 1.57; 4.21 0.75; 4.20 0.81; 4.19 0.74; 4.19 0.76; 3.86 2.23; 3.86 2.30; 3.82 3.37; 3.82 4.82; 3.81 15.62; 3.81 16.00; 3.28 2.46; 3.27 2.57; 3.23 2.16; 3.23 2.23; 1.73 13.49; 1.72 13.88; 1.62 1.55; 1.62 1.55; 0.01 0.48; 0.01 0.49; 0.00 3.16 |
| 1.411 | 3,5-$Cl_2$—Ph | H | O | H | $CH_2$ | 5-chloro-1-methyl-3-(trifluoromethyl)-1H-pyrazol-4-yl | [$CDCl_3$] 7.52 0.41; 7.50 7.28; 7.49 8.02; 7.42 2.12; 7.41 3.64; 7.41 1.71; 7.26 65.74; 7.00 0.39; 6.98 0.36; 6.96 0.62; 6.95 0.37; 6.23 0.82; 4.44 0.48; 4.43 0.48; 4.40 1.26; 4.39 1.24; 4.36 1.25; 4.34 1.24; 4.32 0.48; 4.31 0.48; 3.90 1.49; 3.88 11.93; 3.78 2.81; 3.74 3.20; 3.19 2.99; 3.15 2.62; 1.72 0.41; 1.70 16.00; 1.54 17.56; 0.01 0.81 |
| 1.412 | 3,5-$F_2$—Ph | H | O | H | $CH_2$ | 5-chloro-1-methyl-3-(trifluoromethyl)-1H-pyrazol-4-yl | [$CDCl_3$] 7.52 0.49; 7.31 0.42; 7.26 85.11; 7.16 0.40; 7.15 1.61; 7.14 2.18; 7.13 2.16; 7.12 1.71; 7.11 0.33; 7.00 0.64; 6.97 0.74; 6.91 0.41; 6.90 0.72; 6.89 0.38; 6.88 0.78; 6.88 1.41; 6.87 0.73; 6.86 0.42; 6.86 0.73; 6.85 0.38; 4.44 0.54; 4.42 0.54; 4.40 1.61; 4.39 1.62; 4.36 1.60; 4.35 1.61; 4.33 0.54; 4.31 0.52; 3.88 14.11; 3.78 2.65; 3.73 3.03; 3.49 0.42; 3.20 2.97; 3.15 2.56; 2.04 0.98; 2.00 0.98; 1.71 16.00; 1.53 33.64; 1.26 0.63; 0.01 0.39; 0.00 10.90; −0.01 0.44 |

TABLE 1-continued

Compounds of the general formula (I) according to the invention in which $R^2$ is hydrogen and $R^3$ is methyl and aryl is the radical

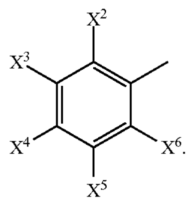

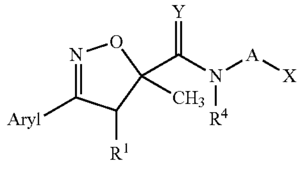

| No. | Aryl | $R^1$ | Y | $R^4$ | A | X | Physical data |
|---|---|---|---|---|---|---|---|
| 1.413 | 3,5-$F_2$—Ph | H | O | H | $CH_2$ | 5-methoxy-1,3-dimethyl-1H-pyrazol-4-yl | [$CDCl_3$] 7.26 11.82; 7.16 1.26; 7.15 1.53; 7.15 0.92; 7.14 1.00; 7.14 1.54; 7.13 1.22; 6.90 0.54; 6.89 0.63; 6.88 1.05; 6.87 0.54; 6.86 0.35; 6.86 0.55; 6.80 0.48; 4.33 0.74; 4.31 0.75; 4.29 1.36; 4.27 1.34; 4.21 1.36; 4.19 1.37; 4.17 0.76; 4.16 0.74; 3.88 16.00; 3.81 1.95; 3.76 2.23; 3.60 11.76; 3.21 2.07; 3.16 1.82; 2.13 11.80; 1.73 11.51; 0.00 3.94 |
| 1.414 | 3,5-$Cl_2$—Ph | H | O | H | $CH_2$ | 5-methoxy-1,3-dimethyl-1H-pyrazol-4-yl | [$CDCl_3$] 7.50 4.80; 7.50 5.32; 7.42 1.38; 7.41 2.29; 7.41 1.11; 7.26 20.41; 6.79 0.60; 4.33 0.77; 4.31 0.76; 4.29 1.37; 4.27 1.35; 4.20 1.36; 4.19 1.38; 4.16 0.79; 4.15 0.77; 3.98 0.33; 3.88 16.00; 3.82 0.33; 3.81 1.99; 3.77 2.30; 3.62 0.33; 3.60 12.40; 3.20 2.13; 3.16 1.88; 2.13 12.41; 1.72 11.62; 1.26 0.60; 0.00 4.49 |
| 1.415 | 3-F—Ph | H | O | H | $CH_2$ | 5-methoxy-1,3-dimethyl-1H-pyrazol-4-yl | [$CDCl_3$] 7.39 0.62; 7.38 0.42; 7.38 1.21; 7.37 1.95; 7.37 1.47; 7.36 1.21; 7.36 1.37; 7.36 0.70; 7.35 0.60; 7.35 0.70; 7.26 12.60; 7.15 0.32; 7.15 0.34; 7.13 0.40; 7.13 0.37; 7.13 0.46; 7.11 0.42; 4.32 0.66; 4.31 0.66; 4.28 1.23; 4.27 1.21; 4.21 1.22; 4.19 1.25; 4.17 0.67; 4.16 0.65; 3.87 16.00; 3.84 1.81; 3.79 2.05; 3.59 10.13; 3.24 1.87; 3.20 1.64; 2.12 10.19; 1.73 10.16; 1.61 0.36; 0.00 5.11 |
| 1.416 | Ph | H | O | H | $CH_2$ | 5-methoxy-1,3-dimethyl-1H-pyrazol-4-yl | [$CDCl_3$] 7.63 1.54; 7.63 1.90; 7.62 0.94; 7.62 0.71; 7.61 1.88; 7.61 2.10; 7.43 0.68; 7.42 1.22; 7.42 4.21; 7.41 1.83; 7.41 0.71; 7.40 2.10; 7.39 0.34; 7.39 0.54; 7.38 0.36; 7.26 13.06; 6.88 0.52; 4.32 0.77; 4.30 0.77; 4.28 1.51; 4.26 1.51; 4.21 1.51; 4.19 1.53; 4.17 0.78; 4.16 0.76; 3.87 16.00; 3.86 2.38; 3.82 2.48; 3.59 13.48; 3.27 2.39; 3.22 2.09; 2.12 13.52; 1.73 12.73; 1.62 0.58; 0.00 3.28; 0.00 3.72 |
| 1.417 | 3,5-$Cl_2$—Ph | H | O | H | $CH_2$ | 5-methyl-1,2,4-oxadiazol-3-yl | [$CDCl_3$] 7.52 5.67; 7.52 6.11; 7.42 1.50; 7.42 2.66; 7.41 1.29; 7.31 0.62; 7.26 91.38; 7.25 0.51; 7.21 0.67; 7.00 0.51; 4.64 0.69; 4.62 0.70; 4.60 1.59; 4.58 1.55; 4.54 1.55; 4.52 1.58; 4.50 0.69; 4.48 0.67; 3.83 2.17; 3.79 2.48; 3.23 2.23; 3.19 1.97; 2.56 |

TABLE 1-continued

Compounds of the general formula (I) according to the invention in which $R^2$ is hydrogen and $R^3$ is methyl and aryl is the radical

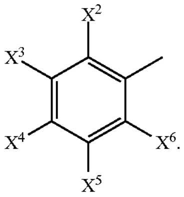

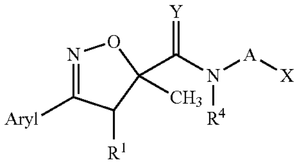

| No. | Aryl | $R^1$ | Y | $R^4$ | A | X | Physical data |
|---|---|---|---|---|---|---|---|
| | | | | | | | 16.00; 1.76 12.48; 1.55 14.58; 0.01 0.90 |
| 1.418 | 3,5-$F_2$—Ph | H | O | H | $CH_2$ | 5-methyl-1,2,4-oxadiazol-3-yl | [$CDCl_3$] 7.52 0.35; 7.32 0.42; 7.31 0.33; 7.26 62.01; 7.17 1.30; 7.17 1.60; 7.17 0.93; 7.16 0.91; 7.15 1.58; 7.15 1.33; 7.00 0.35; 6.90 0.60; 6.89 0.66; 6.88 1.17; 6.88 0.58; 6.87 0.34; 6.86 0.58; 4.64 0.78; 4.63 0.78; 4.60 1.67; 4.59 1.64; 4.54 1.65; 4.52 1.67; 4.49 0.77; 4.48 0.76; 3.83 2.28; 3.78 2.61; 3.23 2.44; 3.19 2.13; 2.56 16.00; 1.76 13.57; 1.55 25.12; 0.01 0.51 |
| 1.419 | 3-F—Ph | H | O | H | $CH_2$ | 5-methyl-1,2,4-oxadiazol-3-yl | [$CDCl_3$] 7.52 0.38; 7.40 0.51; 7.40 0.71; 7.39 1.32; 7.38 3.31; 7.38 1.98; 7.37 1.25; 7.37 2.42; 7.36 0.55; 7.36 0.55; 7.26 67.60; 7.25 0.72; 7.25 0.60; 7.25 0.54; 7.25 0.44; 7.25 0.36; 7.25 0.34; 7.16 0.36; 7.15 0.62; 7.14 0.34; 7.14 0.34; 7.14 0.44; 7.13 0.53; 7.13 0.50; 7.12 0.36; 7.12 0.44; 7.00 0.37; 4.65 0.78; 4.63 0.77; 4.61 1.54; 4.59 1.51; 4.53 1.52; 4.52 1.53; 4.49 0.78; 4.47 0.76; 3.86 2.26; 3.81 2.58; 3.27 2.37; 3.22 2.07; 2.55 16.00; 1.76 13.06; 1.55 18.31; 0.01 0.51; 0.00 18.00 |
| 1.420 | Ph | H | O | H | $CH_2$ | 5-methyl-1,2,4-oxadiazol-3-yl | [$CDCl_3$] 7.65 1.65; 7.65 1.84; 7.64 0.83; 7.64 0.64; 7.64 0.66; 7.63 1.44; 7.63 1.48; 7.63 2.06; 7.44 0.51; 7.43 0.67; 7.43 1.33; 7.42 3.54; 7.42 1.53; 7.41 1.28; 7.41 1.15; 7.40 1.92; 7.40 0.59; 7.40 0.63; 7.39 0.68; 7.39 0.81; 7.39 0.48; 7.38 0.57; 7.26 24.74; 4.65 0.84; 4.64 0.83; 4.61 1.55; 4.60 1.53; 4.52 1.53; 4.51 1.55; 4.48 0.84; 4.47 0.82; 3.88 2.34; 3.84 2.70; 3.29 2.50; 3.25 2.19; 2.54 16.00; 1.76 13.44; 1.62 3.77 |
| 1.421 | 3,5-$Cl_2$—Ph | H | O | H | $CH_2$ | 5-methyl-1,2-oxazol-3-yl | [$CDCl_3$] 1.73 (s, 3H); 2.39 (s, 3H); 3.20 (d, 1H); 3.79 (d, 1H); 4.40 (dd, 1H); 4.52 (dd, 1H); 5.90 (s, 1H); 7.41 (m, 1H); 7.51 (m, 2H). |
| 1.422 | 3-Cl-5-$CF_3$—Ph | H | O | H | $CH_2$ | 5-methyl-1,2-oxazol-3-yl | [$CDCl_3$] 1.75 (s, 3H); 2.39 (s, 3H); 3.25 (d, 1H); 3.84 (d, 1H); 4.40 (dd, 1H); 4.54 (dd, 1H); 5.90 (s, 1H); 7.66 (s, 1H); 7.77 (s, 1H); 7.81 (s, 1H). |
| 1.423 | 3,5-$F_2$—Ph | H | O | H | $CH_2$ | 5-methyl-1,2-oxazol-3-yl | [$CDCl_3$] 1.73 (s, 3H); 2.38 (s, 3H); 3.20 (d, 1H); 3.79 (d, 1H); |

TABLE 1-continued

Compounds of the general formula (I) according to the invention in which $R^2$ is hydrogen and $R^3$ is methyl and aryl is the radical

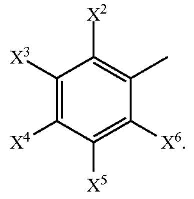

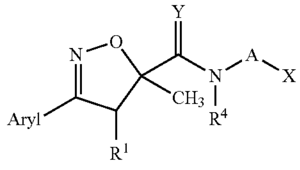

| No. | Aryl | $R^1$ | Y | $R^4$ | A | X | Physical data |
|---|---|---|---|---|---|---|---|
| | | | | | | | 4.41 (dd, 1H); 4.53 (dd, 1H); 5.90 (s, 1H); 6.88 (m, 1H); 7.17 (m, 2H); 7.24 (m, 1H). |
| 1.424 | 3-F—Ph | H | O | H | $CH_2$ | 5-methyl-1,2-oxazol-3-yl | [$CDCl_3$] 1.74 (s, 3H); 2.38 (s, 3H); 3.24 (d, 1H); 3.81 (d, 1H); 4.40 (dd, 1H); 4.52 (dd, 1H); 5.90 (s, 1H); 7.13 (m, 1H); 7.28 (m, 1H); 7.38 (m, 3H). |
| 1.425 | Ph | H | O | H | $CH_2$ | 5-methyl-1,2-oxazol-3-yl | [$CDCl_3$] 1.74 (s, 3H); 2.38 (s, 3H); 3.27 (d, 1H); 3.84 (d, 1H); 4.40 (dd, 1H); 4.52 (dd, 1H); 7.31 (brt, 1H); 7.41 (m, 3H); 7.63 (m, 2H). |
| 1.426 | 3,5-$Cl_2$—Ph | H | O | H | $CH_2$ | 5-methyl-1H-1,2,4-triazol-3-yl | [$CDCl_3$] 7.68 0.44; 7.49 7.78; 7.49 8.37; 7.40 2.20; 7.39 3.75; 7.39 1.79; 7.26 33.19; 4.59 0.72; 4.58 0.73; 4.55 2.04; 4.54 1.99; 4.52 1.97; 4.50 2.02; 4.48 0.72; 4.47 0.70; 3.83 2.50; 3.78 2.83; 3.22 2.93; 3.18 2.58; 2.44 16.00; 1.73 15.92; 1.25 0.47; 0.01 0.37 |
| 1.427 | 3-F—Ph | H | O | H | $CH_2$ | 5-methyl-1H-1,2,4-triazol-3-yl | [$CDCl_3$] 7.73 0.51; 7.38 1.66; 7.36 2.89; 7.36 3.84; 7.35 4.09; 7.34 2.12; 7.27 19.87; 7.26 20.72; 7.14 0.47; 7.14 0.84; 7.13 0.57; 7.12 0.89; 7.11 1.02; 7.11 0.74; 7.10 0.68; 7.09 0.42; 4.60 0.79; 4.59 0.79; 4.56 1.93; 4.55 1.91; 4.52 1.88; 4.50 1.92; 4.48 0.78; 4.46 0.77; 3.85 2.38; 3.80 2.73; 3.26 2.95; 3.22 2.57; 2.43 15.07; 1.73 16.00; 1.25 0.48; 1.25 0.48; 0.00 7.32 |
| 1.428 | Ph | H | O | H | $CH_2$ | 5-methyl-1H-1,2,4-triazol-3-yl | [$CDCl_3$] 7.72 0.43; 7.63 2.23; 7.62 2.61; 7.61 0.94; 7.61 2.57; 7.60 2.89; 7.42 0.83; 7.42 0.99; 7.41 1.73; 7.41 5.05; 7.40 2.41; 7.39 0.89; 7.39 2.70; 7.38 0.44; 7.37 0.73; 7.36 0.53; 7.26 25.59; 4.60 0.87; 4.58 0.87; 4.56 2.00; 4.54 1.95; 4.50 1.95; 4.49 1.99; 4.47 0.87; 4.45 0.84; 3.87 2.24; 3.82 2.57; 3.28 3.02; 3.24 2.65; 2.42 14.43; 1.73 16.00; 1.25 0.55 |
| 1.429 | 3,5-$F_2$—Ph | H | O | H | $CH_2$ | 5-methyl-1H-1,2,4-triazol-3-yl | [$CDCl_3$] 7.64 0.55; 7.26 33.51; 7.16 1.62; 7.15 2.01; 7.14 2.03; 7.13 1.60; 6.90 0.39; 6.89 0.69; 6.89 0.36; 6.87 0.80; 6.87 1.38; 6.86 0.69; 6.85 0.42; 6.85 0.70; 6.84 0.34; 4.60 0.74; 4.58 0.75; 4.56 1.91; 4.54 1.86; 4.51 1.87; 4.50 1.91; 4.47 0.76; 4.46 0.73; 3.82 2.44; 3.78 2.78; 3.23 2.70; 3.18 2.37; 2.44 16.00; 2.05 |

TABLE 1-continued

Compounds of the general formula (I) according to the invention in which $R^2$ is hydrogen and $R^3$ is methyl and aryl is the radical

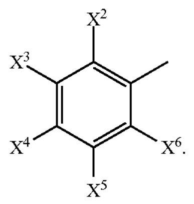

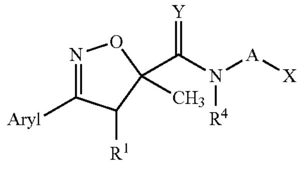

| No. | Aryl | $R^1$ | Y | $R^4$ | A | X | Physical data |
|---|---|---|---|---|---|---|---|
| | | | | | | | 0.40; 1.74 14.32; 1.25 0.58; 0.01 0.41 |
| 1.430 | 3-F—Ph | H | O | H | $CH_2$ | 5-methyl-1-propyl-1H-pyrazol-4-yl | [$CDCl_3$] 7.39 1.08; 7.38 2.31; 7.37 3.27; 7.37 2.70; 7.36 2.63; 7.36 3.08; 7.35 5.40; 7.26 11.73; 7.15 0.49; 7.15 0.69; 7.14 0.47; 7.13 0.74; 7.13 0.78; 7.12 0.89; 7.12 0.63; 7.11 0.66; 7.10 0.36; 6.87 0.69; 4.33 0.88; 4.32 0.86; 4.30 1.55; 4.28 1.54; 4.21 1.57; 4.19 1.57; 4.17 0.88; 4.16 0.88; 3.98 2.57; 3.96 3.58; 3.94 2.65; 3.84 2.64; 3.79 3.01; 3.24 2.87; 3.20 2.52; 2.19 16.00; 1.84 1.34; 1.82 2.45; 1.80 2.47; 1.79 1.42; 1.77 0.35; 1.72 15.60; 1.62 2.17; 0.93 4.28; 0.91 8.64; 0.89 3.95; 0.00 6.58 |
| 1.431 | 3,5-$F_2$—Ph | H | O | H | $CH_2$ | 5-methyl-1-propyl-1H-pyrazol-4-yl | [$CDCl_3$] 7.35 4.05; 7.26 10.55; 7.16 1.72; 7.15 2.03; 7.15 1.23; 7.14 2.14; 7.13 1.56; 6.91 0.41; 6.90 0.71; 6.89 0.38; 6.88 0.83; 6.88 1.43; 6.87 0.73; 6.86 0.48; 6.86 0.79; 6.85 0.50; 6.83 0.65; 4.34 0.88; 4.32 0.87; 4.30 1.54; 4.28 1.52; 4.21 1.55; 4.19 1.56; 4.17 0.90; 4.16 0.90; 3.99 2.54; 3.97 3.39; 3.95 2.63; 3.81 2.60; 3.77 2.98; 3.21 2.79; 3.16 2.44; 2.19 16.00; 1.85 1.31; 1.83 2.39; 1.81 2.42; 1.79 1.37; 1.77 0.35; 1.72 15.34; 1.64 1.22; 0.93 4.26; 0.91 8.69; 0.89 3.92; 0.00 5.41 |
| 1.432 | 3,5-$Cl_2$—Ph | H | O | H | $CH_2$ | 5-methyl-1-propyl-1H-pyrazol-4-yl | [$CDCl_3$] 7.50 7.38; 7.50 7.70; 7.42 2.17; 7.41 3.51; 7.41 1.67; 7.35 4.09; 7.26 19.28; 6.81 0.75; 4.33 0.89; 4.32 0.88; 4.30 1.50; 4.28 1.49; 4.20 1.53; 4.19 1.54; 4.16 0.90; 4.15 0.91; 3.99 2.63; 3.97 3.60; 3.95 2.71; 3.81 2.67; 3.77 3.04; 3.20 2.84; 3.16 2.50; 2.19 16.00; 1.85 1.36; 1.83 2.48; 1.81 2.52; 1.79 1.43; 1.77 0.36; 1.72 15.52; 1.59 6.83; 0.93 4.42; 0.91 9.05; 0.89 4.10; 0.00 10.07; −0.01 0.41 |
| 1.433 | Ph | H | O | H | $CH_2$ | 5-methyl-1-propyl-1H-pyrazol-4-yl | [$CDCl_3$] 7.64 2.08; 7.63 2.55; 7.62 2.53; 7.61 2.83; 7.43 0.99; 7.42 5.46; 7.40 2.68; 7.39 0.53; 7.38 0.66; 7.38 0.44; 7.35 4.30; 7.26 10.37; 6.90 0.78; 4.33 0.89; 4.31 0.87; 4.29 1.60; 4.28 1.58; 4.21 1.62; 4.19 1.62; 4.17 0.89; 4.16 0.88; 3.98 2.55; 3.96 3.87; 3.94 2.66; 3.86 2.58; 3.82 |

TABLE 1-continued
Compounds of the general formula (I) according to the invention in which $R^2$ is hydrogen and $R^3$ is methyl and aryl is the radical
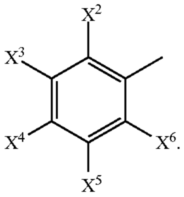
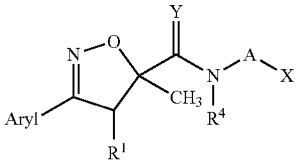
| No. | Aryl | $R^1$ | Y | $R^4$ | A | X | Physical data |
|---|---|---|---|---|---|---|---|
| | | | | | | | 2.95; 3.27 2.85; 3.22 2.49; 2.18 16.00; 1.84 1.37; 1.82 2.62; 1.80 2.64; 1.78 1.46; 1.76 0.36; 1.72 15.47; 1.62 2.24; 0.92 4.21; 0.91 8.36; 0.89 3.91; 0.00 5.76 |
| 1.434 | 3,5-$F_2$—Ph | H | O | H | $CH_2$ | 5-methylfuran-2-yl | [$CDCl_3$] 7.52 0.36; 7.31 0.49; 7.27 54.95; 7.26 60.44; 7.19 0.39; 7.18 1.59; 7.17 3.06; 7.17 3.63; 7.16 2.93; 7.16 2.69; 7.15 3.67; 7.15 3.16; 7.14 1.69; 7.04 1.21; 7.00 0.42; 7.00 0.40; 6.91 0.37; 6.91 0.89; 6.91 0.79; 6.90 0.91; 6.89 0.87; 6.89 1.78; 6.88 1.54; 6.88 1.60; 6.88 1.72; 6.87 0.85; 6.87 0.91; 6.86 0.85; 6.85 0.33; 6.09 1.83; 6.09 3.72; 6.08 2.20; 5.88 3.15; 4.47 0.73; 4.46 0.83; 4.46 0.73; 4.45 0.83; 4.43 1.34; 4.43 1.54; 4.42 1.35; 4.41 1.46; 4.34 1.33; 4.33 1.56; 4.33 1.43; 4.32 1.51; 4.30 0.74; 4.30 0.87; 4.29 0.75; 4.28 0.79; 3.82 2.48; 3.81 2.68; 3.78 2.83; 3.77 3.04; 3.22 2.71; 3.21 2.88; 3.18 2.38; 3.17 2.52; 2.25 11.76; 2.25 13.32; 1.75 14.97; 1.74 16.00; 1.55 30.42; 1.54 31.95; 0.02 0.75; 0.01 23.06 |
| 1.435 | 3,5-$Cl_2$—Ph | H | O | H | $CH_2$ | 5-methylfuran-2-yl | [$CDCl_3$] 7.52 0.70; 7.51 6.46; 7.51 11.81; 7.50 7.02; 7.42 1.68; 7.41 4.28; 7.41 4.14; 7.40 1.75; 7.31 0.34; 7.26 81.02; 7.25 75.72; 7.25 9.23; 7.21 0.38; 7.02 1.29; 7.00 0.73; 6.99 0.59; 6.08 3.01; 5.88 2.62; 5.88 2.85; 5.87 2.80; 4.45 0.84; 4.44 0.90; 4.42 1.57; 4.40 1.58; 4.33 1.57; 4.31 1.67; 4.29 0.87; 4.28 0.92; 3.82 2.69; 3.81 2.62; 3.77 3.05; 3.77 3.03; 3.21 2.86; 3.21 2.88; 3.17 2.51; 3.16 2.50; 2.25 14.09; 1.73 15.83; 1.73 16.00; 1.54 39.43; 1.53 37.82; 1.30 0.42; 1.26 2.03; 0.89 0.80; 0.88 1.76; 0.88 1.73; 0.86 0.84; 0.01 0.84 |
| 1.436 | 3-F—Ph | H | O | H | $CH_2$ | 5-methylfuran-2-yl | [$CDCl_3$] 7.40 0.72; 7.39 1.99; 7.38 2.17; 7.37 4.43; 7.36 4.68; 7.26 30.33; 7.26 27.21; 7.15 0.43; 7.15 0.76; 7.14 0.52; 7.14 0.48; 7.13 0.75; 7.13 0.78; 7.12 0.97; 7.12 0.61; 7.12 0.44; 7.11 0.63; 7.10 0.50; 7.08 0.62; 6.08 1.83; 6.07 2.09; 5.88 1.56; 5.87 1.50; 5.87 1.56; 4.46 |

TABLE 1-continued

Compounds of the general formula (I) according to the invention in which $R^2$ is hydrogen and $R^3$ is methyl and aryl is the radical

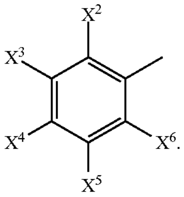

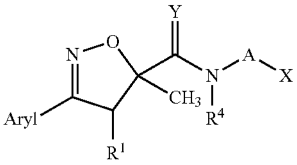

| No. | Aryl | $R^1$ | Y | $R^4$ | A | X | Physical data |
|---|---|---|---|---|---|---|---|
| | | | | | | | 0.76; 4.45 0.75; 4.43 1.35; 4.41 1.34; 4.33 1.37; 4.32 1.38; 4.29 0.77; 4.28 0.76; 3.84 2.66; 3.80 3.05; 3.25 2.95; 3.20 2.57; 2.24 11.28; 1.74 16.00; 1.55 13.28; 0.01 0.36; 0.01 0.35; 0.00 12.58 |
| 1.437 | Ph | H | O | H | $CH_2$ | 5-methylfuran-2-yl | [$CDCl_3$] 7.65 1.88; 7.64 1.90; 7.64 2.32; 7.64 1.09; 7.64 1.16; 7.63 2.30; 7.62 2.62; 7.52 0.36; 7.52 0.34; 7.43 0.63; 7.43 0.84; 7.42 1.86; 7.42 5.05; 7.41 1.95; 7.40 2.32; 7.40 2.48; 7.39 0.47; 7.39 0.59; 7.38 0.37; 7.27 0.36; 7.27 0.40; 7.27 0.45; 7.27 0.54; 7.27 0.68; 7.27 0.84; 7.26 68.32; 7.26 63.06; 7.11 0.57; 7.00 0.38; 6.99 0.33; 6.08 1.93; 6.07 2.02; 5.87 1.58; 5.86 1.46; 4.46 0.77; 4.45 0.76; 4.43 1.33; 4.41 1.30; 4.32 1.33; 4.31 1.35; 4.29 0.80; 4.27 0.75; 3.87 2.71; 3.87 2.52; 3.83 3.07; 3.82 2.90; 3.27 2.94; 3.23 2.54; 2.24 11.33; 1.73 16.00; 1.55 47.19; 1.54 42.26; 0.01 0.68; 0.01 0.76; 0.00 22.88 |
| 1.438 | 3,5-$F_2$—Ph | H | O | H | $CH_2$ | 6-chloropyridin-3-yl | [$CDCl_3$] 8.30 2.48; 8.30 2.57; 7.57 1.25; 7.57 1.26; 7.56 1.36; 7.55 1.46; 7.55 1.47; 7.54 1.55; 7.52 0.37; 7.52 0.33; 7.30 2.80; 7.27 2.57; 7.27 0.54; 7.26 63.77; 7.26 55.95; 7.22 0.99; 7.18 0.40; 7.17 0.40; 7.16 2.55; 7.16 2.85; 7.15 2.70; 7.14 2.68; 7.14 2.68; 7.14 2.65; 7.13 0.40; 7.00 0.34; 6.92 0.78; 6.91 0.68; 6.90 0.83; 6.89 1.54; 6.89 1.37; 6.88 0.46; 6.87 0.79; 6.87 0.69; 4.53 0.93; 4.52 0.93; 4.50 1.52; 4.48 1.55; 4.39 1.56; 4.37 1.53; 4.35 0.95; 4.33 0.94; 3.80 2.62; 3.80 2.28; 3.76 3.03; 3.76 2.67; 3.24 2.89; 3.23 2.55; 3.19 2.51; 3.19 2.18; 1.74 16.00; 1.74 14.09; 1.54 28.84; 1.54 26.68; 1.26 0.50; 0.88 0.41; 0.01 0.70 |
| 1.439 | Ph | H | O | H | $CH_2$ | 6-chloropyridin-3-yl | [$CDCl_3$] 1.73 (s, 3H); 3.28 (d, 1H); 3.82 (d, 1H); 4.35 (dd, 1H); 4.50 (dd, 1H); 7.26 (d, 1H); 7.31 (s br, 1H); 7.42 (m, 3H); 7.56 (d, 1H); 7.63 (d, 2H); 8.30 (s, 1H). |
| 1.440 | 3-Cl-5-$CF_3$—Ph | H | O | H | $CH_2$ | 6-chloropyridin-3-yl | [$CDCl_3$] 1.76 (s, 3H); 3.26 (d, 1H); 3.85 (d, 1H); 4.36 (dd, |

TABLE 1-continued

Compounds of the general formula (I) according to the invention in which $R^2$ is hydrogen and $R^3$ is methyl and aryl is the radical

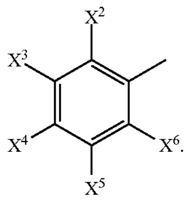

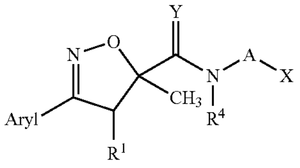

| No. | Aryl | $R^1$ | Y | $R^4$ | A | X | Physical data |
|---|---|---|---|---|---|---|---|
| | | | | | | | 1H), 4.52 (dd, 1H); 7.20 (t br, 1H); 7.28 (d, 1H); 7.56 (dd, 1H); 7.68 (s, 1H); 7.75 (s, 1H); 7.80 (s, 1H); 8.30 (d, 1H) |
| 1.441 | 3-F—Ph | H | O | H | $CH_2$ | 6-chloropyridin-3-yl | [$CDCl_3$] 8.30 2.63; 7.57 1.51; 7.56 1.20; 7.55 1.73; 7.54 1.34; 7.52 0.32; 7.42 0.39; 7.40 1.26; 7.39 2.76; 7.38 2.86; 7.38 2.49; 7.38 3.19; 7.37 4.36; 7.36 1.88; 7.36 1.87; 7.29 3.03; 7.26 57.38; 7.17 0.79; 7.17 0.87; 7.16 0.77; 7.16 0.51; 7.15 1.17; 7.14 1.34; 7.14 0.57; 7.13 0.57; 7.13 0.69; 7.12 0.36; 4.53 0.86; 4.52 0.84; 4.50 1.45; 4.48 1.41; 4.39 1.46; 4.38 1.47; 4.35 0.88; 4.34 0.83; 3.83 2.65; 3.79 3.07; 3.27 2.90; 3.23 2.50; 1.74 16.00; 1.54 25.87 |
| 1.442 | 3,5-$Cl_2$—Ph | H | O | H | $CH_2$ | 6-chloropyridin-3-yl | [$CDCl_3$] 8.30 1.91; 8.30 1.97; 7.57 1.21; 7.56 1.20; 7.55 1.43; 7.54 1.36; 7.51 7.13; 7.50 7.84; 7.43 2.12; 7.43 3.48; 7.42 1.67; 7.30 2.54; 7.28 2.23; 7.26 36.30; 7.23 0.44; 7.21 0.71; 7.21 0.70; 4.53 0.79; 4.52 0.78; 4.49 1.31; 4.48 1.29; 4.39 1.32; 4.37 1.33; 4.35 0.81; 4.33 0.79; 3.81 2.73; 3.76 3.14; 3.23 2.93; 3.19 2.54; 2.04 0.36; 1.74 16.00; 1.55 5.92; 1.55 15.26; 0.01 0.51; 0.00 5.95 |
| 1.443 | 3,5-$F_2$—Ph | H | O | H | $CH_2$ | furan-2-yl | [$CDCl_3$] 7.52 0.75; 7.35 1.73; 7.35 1.86; 7.35 1.83; 7.35 1.89; 7.27 0.35; 7.26 134.54; 7.17 1.52; 7.16 1.81; 7.16 0.91; 7.15 0.93; 7.15 1.69; 7.14 1.56; 7.08 0.37; 7.00 0.75; 6.91 0.39; 6.90 0.68; 6.90 0.34; 6.89 0.76; 6.88 1.39; 6.87 0.67; 6.86 0.39; 6.86 0.70; 6.85 0.33; 6.32 1.15; 6.31 1.20; 6.31 1.46; 6.31 1.37; 6.22 1.46; 6.22 1.56; 6.21 0.51; 6.21 1.24; 6.21 1.33; 4.53 0.59; 4.52 0.58; 4.49 1.10; 4.48 1.07; 4.40 1.09; 4.39 1.11; 4.36 0.62; 4.35 0.60; 3.81 2.73; 3.77 3.12; 3.22 2.78; 3.17 2.44; 1.74 16.00; 1.54 0.40; 1.54 0.57; 1.54 0.84; 1.54 1.26; 1.54 64.62; 1.53 0.34; 0.01 1.49; 0.00 58.14; −0.01 1.64 |
| 1.444 | 3,5-$Cl_2$—Ph | H | O | H | $CH_2$ | furan-2-yl | [$CDCl_3$] 1.73 (s, 3H); 3.19 (d, 1H); 3.81 (d, 1H); 4.38 (dd, 1H); 4.51 (dd, 1H); 6.22 (m, 1H); 6.31 (m, 1H); 7.08 (t br, |

TABLE 1-continued
Compounds of the general formula (I) according to the invention in which $R^2$ is hydrogen and $R^3$ is methyl and aryl is the radical
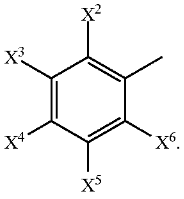
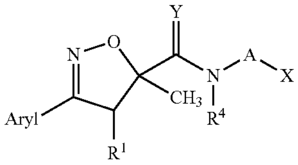
| No. | Aryl | $R^1$ | Y | $R^4$ | A | X | Physical data |
|---|---|---|---|---|---|---|---|
| | | | | | | | 1H); 7.36 (m 1H); 7.41 (m, 1H); 7.50 (s, 1H). |
| 1.445 | 3-F—Ph | H | O | H | $CH_2$ | furan-2-yl | [$CDCl_3$] 7.52 0.57; 7.39 2.00; 7.39 0.81; 7.38 0.76; 7.38 1.36; 7.38 1.25; 7.37 2.94; 7.37 1.20; 7.36 3.92; 7.36 0.34; 7.35 0.32; 7.35 1.73; 7.35 1.71; 7.34 1.75; 7.34 1.68; 7.27 0.39; 7.27 0.51; 7.27 0.67; 7.26 0.92; 7.26 1.40; 7.26 101.89; 7.26 106.83; 7.25 0.33; 7.25 0.32; 7.16 0.49; 7.15 0.72; 7.14 0.47; 7.14 0.64; 7.13 0.80; 7.13 0.87; 7.13 1.12; 7.12 0.76; 7.11 0.81; 7.11 0.50; 7.00 0.57; 6.31 1.20; 6.31 1.22; 6.31 1.40; 6.30 1.40; 6.21 1.44; 6.21 1.45; 6.21 1.27; 6.21 1.23; 4.53 0.66; 4.52 0.65; 4.50 1.15; 4.48 1.12; 4.40 1.17; 4.38 1.17; 4.36 0.67; 4.34 0.66; 3.84 2.75; 3.80 3.14; 3.25 2.98; 3.21 2.60; 1.74 16.00; 1.55 0.34; 1.54 52.19; 1.54 54.57; 1.54 1.14; 1.53 0.87; 1.53 0.68; 1.53 0.55; 1.53 0.47; 1.53 0.37; 0.01 1.11; 0.00 0.39; 0.00 42.69; 0.00 45.16; −0.01 1.34; −0.01 1.35 |
| 1.446 | Ph | H | O | H | $CH_2$ | furan-2-yl | [$CDCl_3$] 7.65 1.92; 7.64 2.03; 7.64 0.97; 7.64 0.86; 7.63 0.73; 7.63 1.36; 7.63 1.81; 7.62 2.40; 7.52 0.74; 7.44 0.57; 7.43 0.72; 7.43 1.48; 7.42 4.17; 7.42 1.69; 7.41 1.57; 7.41 1.09; 7.41 1.00; 7.40 1.32; 7.40 1.89; 7.40 2.10; 7.39 0.37; 7.39 0.56; 7.38 0.38; 7.34 1.61; 7.34 2.16; 7.34 1.99; 7.34 2.20; 7.27 0.36; 7.27 0.33; 7.27 0.36; 7.27 0.40; 7.27 0.54; 7.27 0.74; 7.26 0.88; 7.26 1.13; 7.26 1.56; 7.26 133.91; 7.26 56.66; 7.25 0.96; 7.25 0.73; 7.25 0.58; 7.25 0.49; 7.25 0.36; 7.16 0.43; 7.16 0.40; 7.00 0.75; 6.31 1.12; 6.30 1.19; 6.30 1.46; 6.29 1.38; 6.21 1.52; 6.21 1.86; 6.21 1.04; 6.20 0.63; 6.20 1.34; 6.20 1.59; 6.20 0.88; 4.53 0.67; 4.52 0.66; 4.50 1.16; 4.48 1.13; 4.39 1.17; 4.38 1.16; 4.35 0.70; 4.34 0.67; 3.87 2.82; 3.83 3.21; 3.28 2.85; 3.24 2.49; 2.04 0.38; 1.74 16.00; 1.54 0.37; 1.54 0.47; 1.54 0.60; 1.54 0.82; 1.54 51.53; 1.53 0.59; 1.53 0.46; 1.53 0.36; 1.53 0.32; 1.26 |

TABLE 1-continued

Compounds of the general formula (I) according to the invention in which $R^2$ is hydrogen and $R^3$ is methyl and aryl is the radical

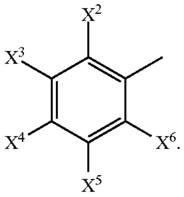

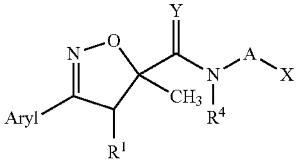

| No. | Aryl | $R^1$ | Y | $R^4$ | A | X | Physical data |
|---|---|---|---|---|---|---|---|
| | | | | | | | 0.38; 1.25 0.33; 0.01 1.63; 0.01 0.82; 0.00 0.48; 0.00 66.29; 0.00 25.10; −0.01 1.71 |
| 1.447 | 3,5-$Cl_2$—Ph | H | O | H | $CH_2$ | phenyl | [$CDCl_3$] 1.75 (s, 3H); 3.21 (d, 1H); 3.81 (d, 1H); 4.36 (dd, 1H); 4.53 (dd, 1H); 7.10 (t br, 1H); 7.27 (m, 2H); /.32 (m, 3H); 7.41 (m, 1H); 7.52 (d, 1H); 7.52 (s, 2H). |
| 1.448 | 3,5-$Cl_2$—Ph | H | O | $CO_2C_2H_5CH_3$ | $CH_2$ | phenyl | Rotamere [DMSO-$D_6$] 1.14 (t, 3H); 1.19 (t, 3H); 1.63 (s, 3H); 1.68 (s, 3H); 3.43 (d, 1H); 3.50 (d, 1H); 3.70 (d, 1H); 3.95 (d, 1H); 4.0-4.13 (m, 6H); 4.17 (d, 1H); 4.33 (d, 1H); 4.42 (d, 1H); 4.55 (d, 1H); 4.82 (d, 1H); 5.15 (d, 1H); 7.20-7.40 (m, 10H); 7.70 (d, 4H); 7.76 (s, 2H). |
| 1.449 | 3,5-$Cl_2$—Ph | H | O | H | $CH_2$ | pyridin-2-yl | |
| 1.450 | 3,5-$F_2$—Ph | H | O | H | $CH_2$ | pyridin-2-yl | [$CDCl_3$] 8.57 1.62; 8.57 1.61; 8.56 1.62; 7.89 0.94; 7.67 0.99; 7.66 0.71; 7.65 2.03; 7.64 1.41; 7.63 1.16; 7.62 0.79; 7.27 5.76; 7.26 12.20; 7.22 2.55; 7.20 3.55; 7.18 3.84; 7.18 3.12; 7.17 1.74; 7.16 2.41; 7.16 2.95; 7.16 1.66; 7.15 0.41; 7.14 0.35; 6.90 0.71; 6.89 0.85; 6.89 0.44; 6.88 1.41; 6.87 1.65; 6.86 0.73; 6.85 0.72; 6.85 0.82; 6.84 0.34; 5.30 0.50; 4.65 0.75; 4.63 0.72; 4.61 1.67; 4.59 1.63; 4.54 1.68; 4.53 1.64; 4.50 0.76; 4.49 0.72; 3.85 2.64; 3.80 3.04; 3.23 2.90; 3.19 2.54; 1.77 16.00; 1.63 1.24; 0.01 2.44; 0.00 5.22 |
| 1.451 | 3-F—Ph | H | O | H | $CH_2$ | pyridin-2-yl | [$CDCl_3$] 8.56 1.24; 8.56 1.13; 8.55 1.25; 8.55 1.11; 7.89 0.60; 7.66 0.71; 7.65 0.75; 7.64 1.43; 7.63 1.51; 7.62 0.86; 7.61 0.89; 7.41 1.05; 7.40 0.99; 7.40 0.95; 7.39 2.28; 7.38 3.57; 7.38 3.26; 7.38 3.95; 7.36 1.33; 7.26 15.90; 7.22 1.68; 7.21 1.69; 7.20 1.02; 7.20 1.00; 7.19 2.01; 7.19 1.03; 7.18 0.98; 7.17 0.84; 7.17 0.84; 7.15 0.45; 7.14 0.46; 7.13 0.64; 7.13 0.62; 7.13 0.76; 7.12 0.70; 7.12 0.81; 7.12 0.78; 7.11 0.47; 7.11 0.46; 7.10 0.66; 7.10 0.36; 5.30 0.56; 4.65 0.67; 4.63 0.67; 4.61 1.48; 4.59 1.47; 4.54 1.47; 4.53 1.49; 4.50 0.68; 4.49 0.67; 3.88 2.73; 3.83 3.08; 3.27 2.92; 3.22 2.58; 1.77 16.00; 1.65 0.86 |

TABLE 1-continued

Compounds of the general formula (I) according to the invention in which $R^2$ is hydrogen and $R^3$ is methyl and aryl is the radical

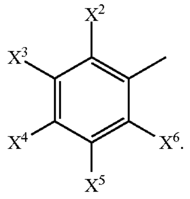

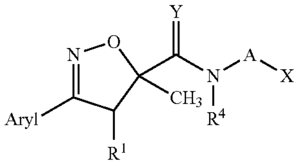

| No. | Aryl | $R^1$ | Y | $R^4$ | A | X | Physical data |
|---|---|---|---|---|---|---|---|
| 1.452 | 4-Cl—Ph | H | O | H | $CH_2$ | pyridin-2-yl | |
| 1.453 | 3,5-$F_2$—Ph | H | O | H | $CH_2$ | pyridin-3-yl | [$CDCl_3$] 8.53 3.35; 7.59 1.31; 7.57 1.50; 7.52 0.42; 7.52 0.40; 7.27 1.41; 7.26 75.63; 7.26 68.90; 7.24 1.35; 7.21 0.34; 7.18 1.03; 7.18 1.08; 7.16 2.85; 7.16 3.07; 7.16 2.81; 7.15 2.67; 7.15 2.83; 7.14 2.37; 7.13 0.38; 7.00 0.41; 6.99 0.38; 6.91 0.49; 6.91 0.71; 6.91 0.73; 6.91 0.41; 6.90 0.39; 6.89 0.98; 6.89 1.44; 6.89 1.45; 6.88 0.79; 6.88 0.70; 6.87 0.49; 6.87 0.73; 6.87 0.73; 6.86 0.39; 4.57 0.98; 4.56 0.95; 4.54 1.57; 4.52 1.54; 4.41 1.59; 4.40 1.58; 4.37 1.01; 4.36 0.99; 3.82 2.61; 3.82 2.62; 3.78 3.03; 3.78 3.00; 3.24 2.89; 3.24 2.92; 3.20 2.50; 3.19 2.54; 1.75 15.95; 1.75 16.00; 1.55 11.83; 0.00 30.35 |
| 1.454 | 3-F—Ph | H | O | H | $CH_2$ | pyridin-3-yl | [$CDCl_3$] 8.54 3.24; 8.53 3.41; 7.59 1.33; 7.57 1.47; 7.52 0.45; 7.42 0.34; 7.40 1.36; 7.39 2.93; 7.38 3.46; 7.38 3.24; 7.37 4.08; 7.36 1.93; 7.27 11.58; 7.26 71.53; 7.26 74.33; 7.26 9.85; 7.23 1.87; 7.21 0.72; 7.17 0.56; 7.16 0.96; 7.15 0.91; 7.14 1.17; 7.13 0.78; 7.12 0.70; 7.11 0.39; 7.00 0.40; 4.57 0.90; 4.56 0.89; 4.54 1.47; 4.52 1.45; 4.41 1.48; 4.40 1.47; 4.38 0.93; 4.36 0.92; 3.85 2.62; 3.81 3.01; 3.27 2.96; 3.23 2.56; 1.76 16.00; 1.56 11.26; 0.01 4.85; 0.00 29.18; 0.00 30.29 |
| 1.455 | 3,5-$Cl_2$—Ph | H | O | H | $CH_2$ | pyridin-3-yl | [$CDCl_3$] 1.74 (s, 3H); 3.21 (d, 1H); 3.80 (d, 1H); 4.37 (dd, 1H); 4.55 (dd, 1H); 7.18 (br, 1H); 7.24-7.27 (m, 1H); 7.41 (m, 1H); 7.51 (m, 2H); 7.58 (m, 1H); 8.53 (br, 2H). |
| 1.456 | 3,5-$F_2$—Ph | H | O | H | $CH_2$ | pyridin-4-yl | [$CDCl_3$] 8.56 2.98; 8.54 3.16; 7.52 0.85; 7.51 0.56; 7.43 0.33; 7.40 0.75; 7.39 0.85; 7.38 0.54; 7.37 0.62; 7.37 0.64; 7.35 0.53; 7.30 4.38; 7.28 0.87; 7.26 149.32; 7.26 118.15; 7.23 1.26; 7.21 3.03; 7.20 5.76; 7.18 3.32; 7.16 3.57; 7.16 4.19; 7.15 4.14; 7.14 4.25; 7.11 1.19; 7.10 0.49; 7.09 0.51; 7.07 0.48; 7.00 1.07; 6.92 0.76; 6.90 1.31; 6.90 1.31; 6.88 0.85; 6.87 0.45; 4.57 0.95; 4.55 1.00; 4.53 1.61; 4.51 1.50; 4.42 1.52; 4.40 1.60; 4.38 |

TABLE 1-continued

Compounds of the general formula (I) according to the invention in which $R^2$ is hydrogen and $R^3$ is methyl and aryl is the radical

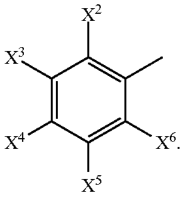

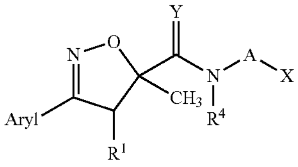

| No. | Aryl | $R^1$ | Y | $R^4$ | A | X | Physical data |
|---|---|---|---|---|---|---|---|
| | | | | | | | 0.93; 4.36 1.00; 3.83 2.68; 3.79 2.95; 3.25 2.95; 3.21 2.46; 1.83 0.45; 1.78 16.00; 1.73 0.55; 1.68 0.41; 1.59 1.12; 1.54 30.97; 1.49 1.26; 1.26 0.36; 0.14 0.49; 0.13 0.43; 0.05 1.81; 0.02 0.43; 0.00 61.59 |
| 1.457 | 3-F—Ph | H | O | H | $CH_2$ | pyridin-4-yl | [$CDCl_3$] 8.55 2.90; 8.54 3.42; 8.53 3.89; 7.52 0.45; 7.41 1.65; 7.41 1.92; 7.40 1.47; 7.40 2.02; 7.39 2.85; 7.39 3.79; 7.39 3.67; 7.38 4.50; 7.31 0.81; 7.31 0.77; 7.29 0.85; 7.28 0.56; 7.26 78.33; 7.26 54.01; 7.18 0.47; 7.17 0.74; 7.17 0.78; 7.16 0.51; 7.15 4.10; 7.15 4.16; 7.14 4.20; 7.13 4.34; 7.00 0.45; 4.56 0.75; 4.54 0.80; 4.52 1.39; 4.50 1.40; 4.42 1.38; 4.41 1.44; 4.38 0.79; 4.37 0.80; 3.86 2.66; 3.86 1.94; 3.82 3.05; 3.82 2.23; 3.29 2.93; 3.28 2.14; 3.24 2.54; 3.24 1.86; 1.78 16.00; 1.78 11.87; 1.55 9.99; 0.01 0.89; 0.00 31.86 |
| 1.458 | 3,5-$Cl_2$—Ph | H | O | H | $CH_2$ | pyridin-4-yl | [$CDCl_3$] 1.79 (s, 3H); 3.23 (d, 1H); 3.83 (d, 1H); 4.38 (dd, 1H); 4.54 (dd, 1H); 7.13 (d, 2H); 7.25 (s, 1H); 7.43 (m, 1H); 7.52 (s, 2H); 8.56 (d, 2H). |
| 1.459 | 3,5-$Cl_2$—Ph | H | O | H | $CH_2$ | pyrimidin-2-yl | [$CDCl_3$] 1.80 (s, 3H); 3.22 (d, 1H); 3.84 (d, 1H); 4.70 (q, 2H); 7.23 (t, 1H); 7.40 (t, 1H); 7.50 (d, 2H); 8.00 (t br, 1H); 8.71 (d, 2H) |
| 1.460 | 3-$CF_3O$—Ph | H | O | H | $CH_2$ | pyrimidin-2-yl | [$CDCl_3$] 1.80 (s, 3H); 3.27 (d, 1H); 3.88 (d, 1H); 4.64 (dd, 1H); 4.73 (dd, 1H); 7.19 (m, 1H); 7.27 (m, 1H); 7.43 (m, 1H); 7.54 (m, 2H); 8.02 (brt, 1H); 8.69 (d, 2H). |
| 1.461 | 3-EtO—Ph | H | O | H | $CH_2$ | pyrimidin-2-yl | [$CDCl_3$] 1.41 (t, 3H); 1.77 (s, 3H); 3.25 (d, 1H); 3.87 (d, 1H); 4.04 (q, 2H); 4.65 (dd, 1H); 4.73 (dd, 1H); 6.95 (m, 1H); 7.13-7.23 (m, 3H); 7.29 (m, 1H); 8.04 (brt, 1H); 8.69 (d, 2H). |
| 1.462 | 3,5-$F_2$—Ph | H | O | H | $CH_2CH_2$ | 1-(2,2,2-trifluoroethyl)-1H-pyrazol-4-yl | |
| 1.463 | 3,5-$F_2$—Ph | H | O | H | $CH_2CH_2$ | 1-(2-chloroethyl)-1H-pyrazol-4-yl | |
| 1.464 | 3,5-$Cl_2$—Ph | H | O | H | $CH_2CH_2$ | 1-(2-methoxy-2-oxoethyl)-1H-pyrazol-4-yl | |

TABLE 1-continued

Compounds of the general formula (I) according to the invention in which $R^2$ is hydrogen and $R^3$ is methyl and aryl is the radical

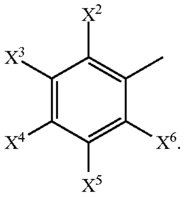

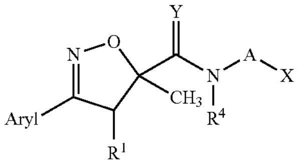

| No. | Aryl | $R^1$ | Y | $R^4$ | A | X | Physical data |
|---|---|---|---|---|---|---|---|
| 1.465 | 3,5-$F_2$—Ph | H | O | H | $CH_2CH_2$ | 1-(3-carboxypropyl)-1H-pyrazol-4-yl | |
| 1.466 | 3,5-$F_2$—Ph | H | O | H | $CH_2CH_2$ | 1-(3-methoxy-3-oxopropyl)-1H-pyrazol-4-yl | |
| 1.467 | 3,5-$F_2$—Ph | H | O | H | $CH_2CH_2$ | 1-(4-methoxy-4-oxobutyl)-1H-pyrazol-4-yl | |
| 1.468 | 3,5-$Cl_2$—Ph | H | O | H | $CH_2CH_2$ | 1-(cyanomethyl)-1H-pyrazol-4-yl | |
| 1.469 | 3,5-$F_2$—Ph | H | O | H | $CH_2CH_2$ | 1-(cyanomethyl)-1H-pyrazol-4-yl | |
| 1.470 | 3-F—Ph | H | O | H | $CH_2CH_2$ | 1-(cyanomethyl)-1H-pyrazol-4-yl | |
| 1.471 | 3,5-$(CF_3)_2$—Ph | H | O | H | $CH_2CH_2$ | 1,3-dimethyl-1H-pyrazol-4-yl | |
| 1.472 | 3,5-$Cl_2$—Ph | H | O | H | $CH_2CH_2$ | 1,3-dimethyl-1H-pyrazol-4-yl | |
| 1.473 | 3,5-$F_2$—Ph | H | O | H | $CH_2CH_2$ | 1,3-dimethyl-1H-pyrazol-4-yl | |
| 1.474 | 3-Cl—Ph | H | O | H | $CH_2CH_2$ | 1,3-dimethyl-1H-pyrazol-4-yl | |
| 1.475 | 3-F—Ph | H | O | H | $CH_2CH_2$ | 1,3-dimethyl-1H-pyrazol-4-yl | |
| 1.476 | 3-Me—Ph | H | O | H | $CH_2CH_2$ | 1,3-dimethyl-1H-pyrazol-4-yl | |
| 1.477 | Ph | H | O | H | $CH_2CH_2$ | 1,3-dimethyl-1H-pyrazol-4-yl | |
| 1.478 | 3,5-$(CF_3)_2$—Ph | H | O | H | $CH_2CH_2$ | 1,3-dimethyl-1H-pyrazol-5-yl | |
| 1.479 | 3,5-$Cl_2$—Ph | H | O | H | $CH_2CH_2$ | 1,3-dimethyl-1H-pyrazol-5-yl | |
| 1.480 | 3,5-$F_2$—Ph | H | O | H | $CH_2CH_2$ | 1,3-dimethyl-1H-pyrazol-5-yl | |
| 1.481 | Ph | H | O | H | $CH_2CH_2$ | 1,3-dimethyl-1H-pyrazol-5-yl | |
| 1.482 | 3,5-$Cl_2$—Ph | H | O | H | $CH_2CH_2$ | 1,3-oxazol-4-yl | |
| 1.483 | 3,5-$F_2$—Ph | H | O | H | $CH_2CH_2$ | 1,3-oxazol-4-yl | |
| 1.484 | 3-F—Ph | H | O | H | $CH_2CH_2$ | 1,3-oxazol-4-yl | |
| 1.485 | 3,5-$Cl_2$—Ph | H | O | H | $CH_2CH_2$ | 1,3-thiazol-2-yl | |
| 1.486 | 3,5-$F_2$—Ph | H | O | H | $CH_2CH_2$ | 1,3-thiazol-2-yl | |
| 1.487 | 3,5-$Cl_2$—Ph | H | O | H | $CH_2CH_2$ | 1,4-dimethyl-5-oxo-4,5-dihydro-1H-1,2,4-triazol-3-yl | |
| 1.488 | 3,5-$F_2$—Ph | H | O | H | $CH_2CH_2$ | 1,5-dimethyl-1H-pyrazol-3-yl | |
| 1.489 | 3,5-$Cl_2$—Ph | H | O | H | $CH_2CH_2$ | 1,5-dimethyl-1H-pyrazol-4-yl | |
| 1.490 | 3,5-$F_2$—Ph | H | O | H | $CH_2CH_2$ | 1,5-dimethyl-1H-pyrazol-4-yl | |
| 1.491 | 3-F—Ph | H | O | H | $CH_2CH_2$ | 1,5-dimethyl-1H-pyrazol-4-yl | |
| 1.492 | Ph | H | O | H | $CH_2CH_2$ | 1,5-dimethyl-1H-pyrazol-4-yl | |

TABLE 1-continued

Compounds of the general formula (I) according to the invention in which $R^2$ is hydrogen and $R^3$ is methyl and aryl is the radical

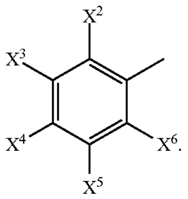

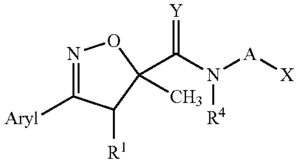

| No. | Aryl | $R^1$ | Y | $R^4$ | A | X | Physical data |
|---|---|---|---|---|---|---|---|
| 1.493 | 3,5-$F_2$—Ph | H | O | H | $CH_2CH_2$ | 1-acetyl-1H-pyrazol-4-yl | |
| 1.494 | 3,5-$F_2$—Ph | H | O | H | $CH_2CH_2$ | 1-butyl-3-methyl-1H-pyrazol-4-yl | |
| 1.495 | 3,5-$F_2$—Ph | H | O | H | $CH_2CH_2$ | 1-butyl-5-methyl-1H-pyrazol-4-yl | |
| 1.496 | 3,5-$Cl_2$—Ph | H | O | H | $CH_2CH_2$ | 1-cyclopropyl-1H-pyrazol-4-yl | |
| 1.497 | 3,5-$F_2$—Ph | H | O | H | $CH_2CH_2$ | 1-cyclopropyl-1H-pyrazol-4-yl | |
| 1.498 | 3-F—Ph | H | O | H | $CH_2CH_2$ | 1-cyclopropyl-1H-pyrazol-4-yl | |
| 1.499 | Ph | H | O | H | $CH_2CH_2$ | 1-cyclopropyl-1H-pyrazol-4-yl | |
| 1.500 | 3,5-$Cl_2$-4-MeO—Ph | H | O | H | $CH_2CH_2$ | 1-ethyl-1H-pyrazol-4-yl | |
| 1.501 | 3,5-$Cl_2$—Ph | H | O | H | $CH_2CH_2$ | 1-ethyl-1H-pyrazol-4-yl | [$CDCl_3$] 1.43 (t, 3H); 1.70 (s, 3H); 2.66 (t, 2H); 3.15 (d, 1H); 3.42 (m, 2H); 3.77 (d, 1H); 4.09 (q, 1H); 6.87 (brt, 1H); 7.19 (s, 1H); 7.31 (s, 1H); 7.41 (m, 1H); 7.50 (m, 2H). |
| 1.502 | 3,5-$F_2$—Ph | H | O | H | $CH_2CH_2$ | 1-ethyl-1H-pyrazol-4-yl | [$CDCl_3$] 1.44 (t, 3H); 1.70 (s, 3H); 2.67 (t, 2H); 3.16 (d, 1H); 3.43 (m, 2H); 3.75 (d, 1H); 4.09 (q, 1H); 6.87 (m, 2H); 7.15 (m, 2H); 7.19 (s, 1H); 7.31 (s, 1H). |
| 1.503 | 3,5-$(MeO)_2$—Ph | H | O | H | $CH_2CH_2$ | 1-ethyl-1H-pyrazol-4-yl | |
| 1.504 | 3-Br-5-$CF_3$—Ph | H | O | H | $CH_2CH_2$ | 1-ethyl-1H-pyrazol-4-yl | |
| 1.505 | 3-Cl-5-Et—Ph | H | O | H | $CH_2CH_2$ | 1-ethyl-1H-pyrazol-4-yl | |
| 1.506 | 3-F-5-MeO—Ph | H | O | H | $CH_2CH_2$ | 1-ethyl-1H-pyrazol-4-yl | |
| 1.507 | 3-F—Ph | H | O | H | $CH_2CH_2$ | 1-ethyl-1H-pyrazol-4-yl | [$CDCl_3$] 1.56 (d, 9H); 1.72 (s, 3H); 3.19 (d, 1H); 3.79 (d, 1H); 4.24 (dd, 1H); 4.35 (dd, 1H); 6.91 (brt, 1H); 7.42 (m, 3H); 7.51 (d, 2H). |
| 1.508 | 3-Me-5-$CF_3O$—Ph | H | O | H | $CH_2CH_2$ | 1-ethyl-1H-pyrazol-4-yl | |
| 1.509 | 3-Me—Ph | H | O | H | $CH_2CH_2$ | 1-ethyl-1H-pyrazol-4-yl | |
| 1.510 | Ph | H | O | H | $CH_2CH_2$ | 1-ethyl-1H-pyrazol-4-yl | [$CDCl_3$] 1.41 (t, 3H); 1.70 (s, 3H); 2.66 (t, 2H); 3.22 (d, 1H); 3.41 (q, 2H); 3.81 (d, 1H); 4.05 (m, 1H); 6.96 (brt, 1H); 7.17 (s, 1H); 7.31 (s, 1H); 7.41 (m, 3H); 7.63 (m, 2H). |
| 1.511 | 3,5-$Cl_2$—Ph | H | O | H | $CH_2CH_2$ | 1-ethyl-1H-pyrazol-5-yl | |
| 1.512 | 3,5-$F_2$—Ph | H | O | H | $CH_2CH_2$ | 1-ethyl-1H-pyrazol-5-yl | |

TABLE 1-continued

Compounds of the general formula (I) according to the invention in which $R^2$ is hydrogen and $R^3$ is methyl and aryl is the radical

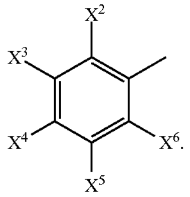

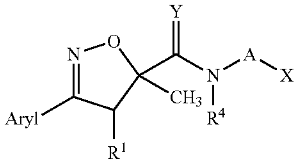

| No. | Aryl | $R^1$ | Y | $R^4$ | A | X | Physical data |
|---|---|---|---|---|---|---|---|
| 1.513 | Ph | H | O | H | $CH_2CH_2$ | 1-ethyl-1H-pyrazol-5-yl | |
| 1.514 | 2,3,4-$F_3$—Ph | H | O | H | $CH_2CH_2$ | 1-ethyl-3-methyl-1H-pyrazol-4-yl | |
| 1.515 | 2,3,5-$F_3$—Ph | H | O | H | $CH_2CH_2$ | 1-ethyl-3-methyl-1H-pyrazol-4-yl | |
| 1.516 | 2,3-$F_2$—Ph | H | O | H | $CH_2CH_2$ | 1-ethyl-3-methyl-1H-pyrazol-4-yl | |
| 1.517 | 2,5-$Cl_2$—Ph | H | O | H | $CH_2CH_2$ | 1-ethyl-3-methyl-1H-pyrazol-4-yl | |
| 1.518 | 2,5-$F_2$—Ph | H | O | H | $CH_2CH_2$ | 1-ethyl-3-methyl-1H-pyrazol-4-yl | |
| 1.519 | 2,5-$Me_2$—Ph | H | O | H | $CH_2CH_2$ | 1-ethyl-3-methyl-1H-pyrazol-4-yl | |
| 1.520 | 2-F-3-Me—Ph | H | O | H | $CH_2CH_2$ | 1-ethyl-3-methyl-1H-pyrazol-4-yl | |
| 1.521 | 2-F—Ph | H | O | H | $CH_2CH_2$ | 1-ethyl-3-methyl-1H-pyrazol-4-yl | |
| 1.522 | 3-$CF_3O$—Ph | H | O | H | $CH_2CH_2$ | 1-ethyl-3-methyl-1H-pyrazol-4-yl | |
| 1.523 | 3,4,5-$F_3$—Ph | H | O | H | $CH_2CH_2$ | 1-ethyl-3-methyl-1H-pyrazol-4-yl | |
| 1.524 | 3,4-$F_2$—Ph | H | O | H | $CH_2CH_2$ | 1-ethyl-3-methyl-1H-pyrazol-4-yl | |
| 1.525 | 3,5-$Br_2$—Ph | H | O | H | $CH_2CH_2$ | 1-ethyl-3-methyl-1H-pyrazol-4-yl | |
| 1.526 | 3,5-$Cl_2$-4-MeO—Ph | H | O | H | $CH_2CH_2$ | 1-ethyl-3-methyl-1H-pyrazol-4-yl | |
| 1.527 | 3,5-$Cl_2$—Ph | $CH_3$ | O | H | $CH_2CH_2$ | 1-ethyl-3-methyl-1H-pyrazol-4-yl | |
| 1.528 | 3,5-$Cl_2$—Ph | H | O | H | $CH_2CH_2$ | 1-ethyl-3-methyl-1H-pyrazol-4-yl | |
| 1.529 | 3,5-$Et_2$—Ph | H | O | H | $CH_2CH_2$ | 1-ethyl-3-methyl-1H-pyrazol-4-yl | |
| 1.530 | 3,5-$F_2$—Ph | H | O | H | $CH_2CH_2$ | 1-ethyl-3-methyl-1H-pyrazol-4-yl | [$CDCl_3$] 7.27 0.40; 7.26 0.59; 7.26 1.06; 7.26 30.79; 7.26 0.63; 7.26 0.46; 7.26 0.35; 7.18 0.34; 7.17 1.64; 7.16 1.95; 7.16 1.06; 7.15 1.03; 7.15 1.90; 7.14 1.67; 7.10 3.34; 6.91 0.44; 6.91 0.78; 6.90 0.42; 6.89 0.96; 6.88 1.74; 6.88 1.01; 6.87 0.89; 6.86 1.14; 6.86 0.64; 4.05 1.17; 4.03 3.67; 4.01 3.80; 3.99 1.28; 3.77 2.77; 3.73 3.16; 3.43 0.71; 3.42 1.00; 3.41 1.36; 3.40 1.99; 3.38 1.31; 3.37 0.69; 3.19 2.85; 3.14 2.51; 2.61 1.71; 2.59 3.38; 2.57 1.52; 2.19 15.86; 1.73 0.34; 1.70 16.00; 1.59 0.49; 1.57 0.45; 1.43 5.12; 1.41 10.77; 1.40 5.03; 0.01 0.39; 0.00 0.39; 0.00 0.64; 0.00 16.83; 0.00 0.35; −0.01 0.55 |
| 1.531 | 3,5-$F_2$—Ph | H | S | H | $CH_2CH_2$ | 1-ethyl-3-methyl-1H-pyrazol-4-yl | |

TABLE 1-continued

Compounds of the general formula (I) according to the invention in which $R^2$ is hydrogen and $R^3$ is methyl and aryl is the radical

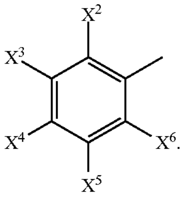

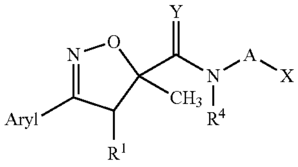

| No. | Aryl | $R^1$ | Y | $R^4$ | A | X | Physical data |
|---|---|---|---|---|---|---|---|
| 1.532 | 3,5-$Me_2$—Ph | H | O | H | $CH_2CH_2$ | 1-ethyl-3-methyl-1H-pyrazol-4-yl | |
| 1.533 | 3-$CF_3S$—Ph | H | O | H | $CH_2CH_2$ | 1-ethyl-3-methyl-1H-pyrazol-4-yl | |
| 1.534 | 3-Br-5-$CF_3$—Ph | H | O | H | $CH_2CH_2$ | 1-ethyl-3-methyl-1H-pyrazol-4-yl | |
| 1.535 | 3-Br-5-Cl—Ph | H | O | H | $CH_2CH_2$ | 1-ethyl-3-methyl-1H-pyrazol-4-yl | |
| 1.536 | 3-Br-5-F—Ph | H | O | H | $CH_2CH_2$ | 1-ethyl-3-methyl-1H-pyrazol-4-yl | |
| 1.537 | 3-Cl-4-F—Ph | H | O | H | $CH_2CH_2$ | 1-ethyl-3-methyl-1H-pyrazol-4-yl | |
| 1.538 | 3-Cl-5-$CF_3$—Ph | H | O | H | $CH_2CH_2$ | 1-ethyl-3-methyl-1H-pyrazol-4-yl | |
| 1.539 | 3-Cl-5-CN—Ph | H | O | H | $CH_2CH_2$ | 1-ethyl-3-methyl-1H-pyrazol-4-yl | |
| 1.540 | 3-Cl-5-Et—Ph | H | O | H | $CH_2CH_2$ | 1-ethyl-3-methyl-1H-pyrazol-4-yl | |
| 1.541 | 3-Cl-5-F—Ph | H | O | H | $CH_2CH_2$ | 1-ethyl-3-methyl-1H-pyrazol-4-yl | |
| 1.542 | 3-Cl-5-MeO—Ph | H | O | H | $CH_2CH_2$ | 1-ethyl-3-methyl-1H-pyrazol-4-yl | |
| 1.543 | 3-Cl-5-Me—Ph | H | O | H | $CH_2CH_2$ | 1-ethyl-3-methyl-1H-pyrazol-4-yl | |
| 1.544 | 3-Cl-5-$CF_3O$—Ph | H | O | H | $CH_2CH_2$ | 1-ethyl-3-methyl-1H-pyrazol-4-yl | |
| 1.545 | 3-Cl—Ph | H | O | H | $CH_2CH_2$ | 1-ethyl-3-methyl-1H-pyrazol-4-yl | |
| 1.546 | 3-CN-5-F—Ph | H | O | H | $CH_2CH_2$ | 1-ethyl-3-methyl-1H-pyrazol-4-yl | |
| 1.547 | 3-CN—Ph | H | O | H | $CH_2CH_2$ | 1-ethyl-3-methyl-1H-pyrazol-4-yl | |
| 1.548 | 3-cPr-5-F—Ph | H | O | H | $CH_2CH_2$ | 1-ethyl-3-methyl-1H-pyrazol-4-yl | |
| 1.549 | 3-EtO—Ph | H | O | H | $CH_2CH_2$ | 1-ethyl-3-methyl-1H-pyrazol-4-yl | |
| 1.550 | 3-Et-5-F—Ph | H | O | H | $CH_2CH_2$ | 1-ethyl-3-methyl-1H-pyrazol-4-yl | |
| 1.551 | 3-F-5-$CF_3$—Ph | H | O | H | $CH_2CH_2$ | 1-ethyl-3-methyl-1H-pyrazol-4-yl | |
| 1.552 | 3-F-5-MeO—Ph | H | O | H | $CH_2CH_2$ | 1-ethyl-3-methyl-1H-pyrazol-4-yl | |
| 1.553 | 3-F-5-Me—Ph | H | O | H | $CH_2CH_2$ | 1-ethyl-3-methyl-1H-pyrazol-4-yl | |
| 1.554 | 3-F—Ph | H | O | H | $CH_2CH_2$ | 1-ethyl-3-methyl-1H-pyrazol-4-yl | |
| 1.555 | 3-MeO—Ph | H | O | H | $CH_2CH_2$ | 1-ethyl-3-methyl-1H-pyrazol-4-yl | |
| 1.556 | 3-Me—Ph | H | O | H | $CH_2CH_2$ | 1-ethyl-3-methyl-1H-pyrazol-4-yl | |
| 1.557 | Ph | H | O | H | $CH_2CH_2$ | 1-ethyl-3-methyl-1H-pyrazol-4-yl | |
| 1.558 | 3,5-$Cl_2$—Ph | H | O | H | $CH_2CH_2$ | 1-ethyl-3-methyl-1H-pyrazol-5-yl | |
| 1.559 | 3,5-$F_2$—Ph | H | O | H | $CH_2CH_2$ | 1-ethyl-3-methyl-1H-pyrazol-5-yl | |

TABLE 1-continued

Compounds of the general formula (I) according to the invention in which $R^2$ is hydrogen and $R^3$ is methyl and aryl is the radical

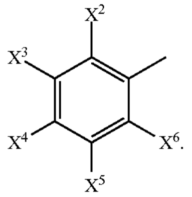

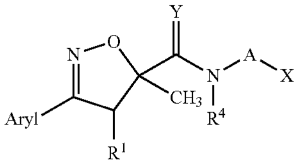

| No. | Aryl | $R^1$ | Y | $R^4$ | A | X | Physical data |
| --- | --- | --- | --- | --- | --- | --- | --- |
| 1.560 | 3-F—Ph | H | O | H | $CH_2CH_2$ | 1-ethyl-3-methyl-1H-pyrazol-5-yl | |
| 1.561 | 3,5-$F_2$—Ph | H | O | H | $CH_2CH_2$ | 1H-1,2,3-triazol-5-yl | |
| 1.562 | 3,5-$Cl_2$—Ph | H | O | H | $CH_2CH_2$ | 1H-pyrazol-1-yl | [$CDCl_3$] 7.52 0.63; 7.52 0.75; 7.50 8.66; 7.50 8.73; 7.50 9.45; 7.42 1.88; 7.42 3.15; 7.41 1.49; 7.41 1.54; 7.29 2.91; 7.28 3.05; 7.26 100.59; 7.26 113.65; 7.16 0.50; 7.14 0.76; 7.00 0.61; 7.00 0.63; 6.20 1.68; 6.19 2.97; 6.19 1.62; 4.28 2.40; 4.26 4.16; 4.25 2.75; 3.75 2.68; 3.73 0.89; 3.72 1.86; 3.71 2.28; 3.70 4.21; 3.70 2.04; 3.69 0.76; 3.68 0.70; 3.17 3.00; 3.13 2.58; 1.69 16.00; 1.54 66.42; 0.01 1.37; 0.00 35.70; 0.00 40.12; −0.01 1.69 |
| 1.563 | 3,5-$F_2$—Ph | H | O | H | $CH_2CH_2$ | 1H-pyrazol-1-yl | [$CDCl_3$] 7.52 0.70; 7.50 2.15; 7.49 2.17; 7.31 0.58; 7.29 2.30; 7.28 2.33; 7.27 0.32; 7.27 0.38; 7.27 0.40; 7.26 125.75; 7.25 0.59; 7.24 0.35; 7.17 0.46; 7.16 2.10; 7.15 2.57; 7.14 1.82; 7.14 2.56; 7.13 2.07; 7.12 0.44; 7.00 0.69; 6.91 0.40; 6.90 0.70; 6.90 0.37; 6.89 0.82; 6.88 1.40; 6.88 0.73; 6.87 0.41; 6.86 0.72; 6.85 0.35; 6.19 1.68; 6.18 2.72; 6.18 1.65; 4.28 2.27; 4.26 3.90; 4.25 2.55; 3.74 2.70; 3.73 0.78; 3.73 0.76; 3.72 1.53; 3.71 2.03; 3.70 4.11; 3.69 0.72; 3.68 0.67; 3.17 2.88; 3.13 2.50; 1.69 16.00; 1.59 0.34; 1.54 71.20; 0.01 1.45; 0.00 46.73; −0.01 1.60 |
| 1.564 | 3,5-$Cl_2$—Ph | H | O | H | $CH_2CH_2$ | 1H-pyrazol-4-yl | [$CDCl_3$] 1.72 (s, 3H); 3.04 (t, 2H); 3.17 (d, 1H); 3.54 (q, 2H); 3.73 (d, 1H); 6.78 (m, 1H); 6.88 (m, 1H), 6.93 (t br, 1H); 7.12 (m, 1H); 7.42 (m, 1H); 7.50 (m, 2H). |
| 1.565 | 3,5-$F_2$—Ph | H | O | H | $CH_2CH_2$ | 1H-pyrazol-4-yl | |
| 1.566 | 3-F—Ph | H | O | H | $CH_2CH_2$ | 1H-pyrazol-4-yl | |
| 1.567 | 3,5-$Cl_2$—Ph | H | O | H | $CH_2CH_2$ | 1-isobutyl-1H-pyrazol-4-yl | |
| 1.568 | 3,5-$F_2$—Ph | H | O | H | $CH_2CH_2$ | 1-isobutyl-1H-pyrazol-4-yl | |
| 1.569 | 3-F—Ph | H | O | H | $CH_2CH_2$ | 1-isobutyl-1H-pyrazol-4-yl | |
| 1.570 | Ph | H | O | H | $CH_2CH_2$ | 1-isobutyl-1H-pyrazol-4-yl | |
| 1.571 | 3,5-$Cl_2$—Ph | H | O | H | $CH_2CH_2$ | 1-isopropyl-1H-pyrazol-4-yl | |

TABLE 1-continued

Compounds of the general formula (I) according to the invention in which $R^2$ is hydrogen and $R^3$ is methyl and aryl is the radical

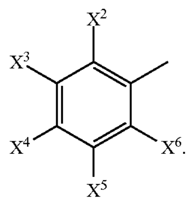

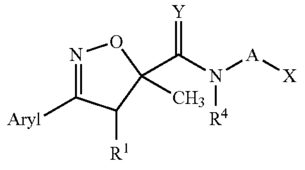

| No. | Aryl | $R^1$ | Y | $R^4$ | A | X | Physical data |
|---|---|---|---|---|---|---|---|
| 1.572 | 3,5-$F_2$—Ph | H | O | H | $CH_2CH_2$ | 1-isopropyl-1H-pyrazol-4-yl | |
| 1.573 | 3-F—Ph | H | O | H | $CH_2CH_2$ | 1-isopropyl-1H-pyrazol-4-yl | |
| 1.574 | Ph | H | O | H | $CH_2CH_2$ | 1-isopropyl-1H-pyrazol-4-yl | |
| 1.575 | 3,5-$(CF_3)_2$—Ph | H | O | H | $CH_2CH_2$ | 1-methyl-1H-pyrazol-4-yl | |
| 1.576 | 3,5-$Cl_2$—Ph | H | O | H | $CH_2CH_2$ | 1-methyl-1H-pyrazol-4-yl | |
| 1.577 | 3,5-$F_2$—Ph | H | O | H | $CH_2CH_2$ | 1-methyl-1H-pyrazol-4-yl | |
| 1.578 | 3-F-5-MeO—Ph | H | O | H | $CH_2CH_2$ | 1-methyl-1H-pyrazol-4-yl | |
| 1.579 | 3-F—Ph | H | O | H | $CH_2CH_2$ | 1-methyl-1H-pyrazol-4-yl | |
| 1.580 | 3-Me—Ph | H | O | H | $CH_2CH_2$ | 1-methyl-1H-pyrazol-4-yl | |
| 1.581 | Ph | H | O | H | $CH_2CH_2$ | 1-methyl-1H-pyrazol-4-yl | |
| 1.582 | 3,5-$Cl_2$—Ph | H | O | H | $CH_2CH_2$ | 1-methyl-1H-pyrazol-5-yl | |
| 1.583 | 3,5-$F_2$—Ph | H | O | H | $CH_2CH_2$ | 1-methyl-1H-pyrazol-5-yl | |
| 1.584 | 3-F—Ph | H | O | H | $CH_2CH_2$ | 1-methyl-1H-pyrazol-5-yl | |
| 1.585 | Ph | H | O | H | $CH_2CH_2$ | 1-methyl-1H-pyrazol-5-yl | |
| 1.586 | 3,5-$Cl_2$—Ph | H | O | H | $CH_2CH_2$ | 1-methyl-3-(trifluoromethyl)-1H-pyrazol-4-yl | D1 |
| 1.587 | 3,5-$Cl_2$—Ph | H | O | H | $CH_2CH_2$ | 1-methyl-3-(trifluoromethyl)-1H-pyrazol-4-yl | D2 |
| 1.588 | 3,5-$F_2$—Ph | H | O | H | $CH_2CH_2$ | 1-methyl-5-(trifluoromethyl)-1H-pyrazol-4-yl | |
| 1.589 | 3,5-$Cl_2$—Ph | H | O | H | $CH_2CH_2$ | 1-propyl-1H-pyrazol-3-yl | |
| 1.590 | 3,5-$F_2$—Ph | H | O | H | $CH_2CH_2$ | 1-propyl-1H-pyrazol-3-yl | |
| 1.591 | 3,5-$Cl_2$—Ph | H | O | H | $CH_2CH_2$ | 1-propyl-1H-pyrazol-4-yl | |
| 1.592 | 3,5-$F_2$—Ph | H | O | H | $CH_2CH_2$ | 1-propyl-1H-pyrazol-4-yl | |
| 1.593 | 3-F—Ph | H | O | H | $CH_2CH_2$ | 1-propyl-1H-pyrazol-4-yl | |
| 1.594 | Ph | H | O | H | $CH_2CH_2$ | 1-propyl-1H-pyrazol-4-yl | |
| 1.595 | 3,5-$Cl_2$—Ph | H | O | H | $CH_2CH_2$ | 1-tert-butyl-1H-pyrazol-4-yl | |
| 1.596 | 3,5-$F_2$—Ph | H | O | H | $CH_2CH_2$ | 1-tert-butyl-1H-pyrazol-4-yl | |
| 1.597 | Ph | H | O | H | $CH_2CH_2$ | 1-tert-butyl-1H-pyrazol-4-yl | |

TABLE 1-continued

Compounds of the general formula (I) according to the invention in which $R^2$ is hydrogen and $R^3$ is methyl and aryl is the radical

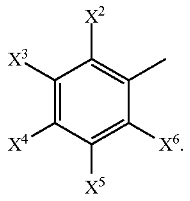

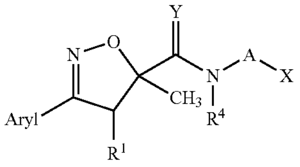

| No. | Aryl | $R^1$ | Y | $R^4$ | A | X | Physical data |
|---|---|---|---|---|---|---|---|
| 1.598 | 3,5-$Cl_2$—Ph | H | O | H | $CH_2CH_2$ | 2,4-dichlorophenyl | |
| 1.599 | 3,5-$F_2$—Ph | H | O | H | $CH_2CH_2$ | 2-chloropyridin-4-yl | |
| 1.600 | 3-F—Ph | H | O | H | $CH_2CH_2$ | 2-chloropyridin-4-yl | |
| 1.601 | 3,5-$Cl_2$—Ph | H | O | H | $CH_2CH_2$ | 2-methoxyphenyl | |
| 1.602 | 3,5-$Cl_2$—Ph | H | O | H | $CH_2CH_2$ | 2-methyl-1,3-thiazol-4-yl | |
| 1.603 | 3,5-$F_2$—Ph | H | O | H | $CH_2CH_2$ | 2-methyl-1,3-thiazol-4-yl | |
| 1.604 | 3,5-$Cl_2$—Ph | H | O | H | $CH_2CH_2$ | 2-Thienyl | |
| 1.605 | 3,5-$Cl_2$—Ph | H | O | H | $CH_2CH_2$ | 3-(cyclopropyl-carbamoyl)-1,2-oxazol-5-yl | |
| 1.606 | 3,5-$Cl_2$—Ph | H | O | H | $CH_2CH_2$ | 3-(ethoxy-carbonyl)-1,2-oxazol-5-yl | |
| 1.607 | 3,5-$F_2$—Ph | H | O | H | $CH_2CH_2$ | 3-(methoxy-carbonyl)phenyl | |
| 1.608 | 3,5-$Cl_2$—Ph | H | O | H | $CH_2CH_2$ | 3,4-dimethoxyphenyl | [$CDCl_3$] 1.68 (s, 3H); 2.75 (t, 2H); 3.15 (d, 1H); 3.50 (q, 2H); 3.72 (d, 1H); 3.83 (s, 3H); 3.86 (s, 3H); 6.64-6.75 (m, 3H); 6.84 (t br, 1H); 7.42 (s, 1H); 7.50 (s, 2H). |
| 1.609 | 3,5-$F_2$—Ph | H | O | H | $CH_2CH_2$ | 3,5-difluoropyridin-2-yl | |
| 1.610 | 3,5-$Cl_2$—Ph | H | O | H | $CH_2CH_2$ | 3,5-dimethyl-1H-pyrazol-1-yl | [$CDCl_3$] 7.50 8.32; 7.49 8.31; 7.41 2.52; 7.41 3.73; 7.40 1.71; 7.28 0.46; 7.28 0.46; 7.28 0.45; 7.28 0.45; 7.28 0.49; 7.28 0.50; 7.27 3.74; 7.26 24.82; 7.26 0.71; 7.26 0.62; 7.25 0.57; 7.25 0.53; 7.25 0.44; 7.25 0.42; 7.25 0.40; 5.74 3.18; 4.09 1.48; 4.07 3.44; 4.06 2.01; 3.74 2.80; 3.71 0.60; 3.70 3.27; 3.69 0.53; 3.69 0.58; 3.67 1.38; 3.66 0.82; 3.66 1.33; 3.65 1.32; 3.64 0.62; 3.63 1.18; 3.62 0.54; 3.61 0.38; 3.60 0.32; 3.17 2.96; 3.13 2.58; 2.19 15.10; 2.14 13.05; 2.14 12.06; 1.69 16.00; 1.63 1.73; 0.01 0.42; 0.00 8.94 |
| 1.611 | 3,5-$F_2$—Ph | H | O | H | $CH_2CH_2$ | 3,5-dimethyl-1H-pyrazol-1-yl | [$CDCl_3$] 7.26 38.77; 7.15 0.45; 7.15 0.61; 7.13 0.57; 7.13 0.48; 6.88 0.39; 5.74 0.96; 4.09 0.36; 4.07 0.88; 4.06 0.53; 3.74 0.73; 3.70 0.86; 3.67 0.41; 3.66 0.41; 3.65 0.38; 3.63 0.34; 3.17 0.81; 3.13 0.70; 2.19 4.40; 2.14 4.15; 1.69 4.42; 1.54 16.00; 0.01 0.43; 0.00 14.06 |

TABLE 1-continued

Compounds of the general formula (I) according to the invention in which $R^2$ is hydrogen and $R^3$ is methyl and aryl is the radical

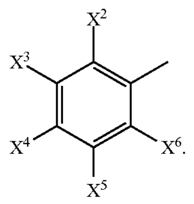

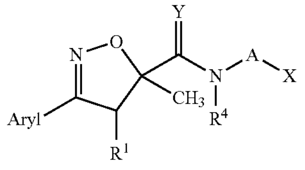

| No. | Aryl | $R^1$ | Y | $R^4$ | A | X | Physical data |
|---|---|---|---|---|---|---|---|
| 1.612 | 3,5-$Cl_2$—Ph | H | O | H | $CH_2CH_2$ | 3-carboxy-1,2-oxazol-5-yl | |
| 1.613 | 3,5-$Cl_2$—Ph | H | O | H | $CH_2CH_2$ | 3-chloro-1-ethyl-1H-pyrazol-4-yl | |
| 1.614 | 3,5-$F_2$—Ph | H | O | H | $CH_2CH_2$ | 3-chloro-1-ethyl-1H-pyrazol-4-yl | |
| 1.615 | 3-F—Ph | H | O | H | $CH_2CH_2$ | 3-chloro-1-ethyl-1H-pyrazol-4-yl | |
| 1.616 | Ph | H | O | H | $CH_2CH_2$ | 3-chloro-1-ethyl-1H-pyrazol-4-yl | |
| 1.617 | 3,5-$Cl_2$—Ph | H | O | H | $CH_2CH_2$ | 3-chloro-1-isopropyl-1H-pyrazol-4-yl | |
| 1.618 | 3,5-$F_2$—Ph | H | O | H | $CH_2CH_2$ | 3-chloro-1-isopropyl-1H-pyrazol-4-yl | |
| 1.619 | 3,5-$F_2$—Ph | H | S | H | $CH_2CH_2$ | 3-chloro-1-isopropyl-1H-pyrazol-4-yl | |
| 1.620 | 3-F—Ph | H | O | H | $CH_2CH_2$ | 3-chloro-1-isopropyl-1H-pyrazol-4-yl | |
| 1.621 | 3,5-$Cl_2$—Ph | H | O | H | $CH_2CH_2$ | 3-chloro-1-methyl-1H-pyrazol-4-yl | |
| 1.622 | 3,5-$F_2$—Ph | H | O | H | $CH_2CH_2$ | 3-chloro-1-methyl-1H-pyrazol-4-yl | |
| 1.623 | 3,5-$F_2$—Ph | H | O | H | $CH_2CH_2$ | 3-chloropyridin-4-yl | |
| 1.624 | 3-F—Ph | H | O | H | $CH_2CH_2$ | 3-chloropyridin-4-yl | |
| 1.625 | 3,5-$Cl_2$—Ph | H | O | H | $CH_2CH_2$ | 3-cyclopropyl-1,2,4-oxadiazol-5-yl | |
| 1.626 | 3,5-$F_2$—Ph | H | O | H | $CH_2CH_2$ | 3-cyclopropyl-1,2,4-oxadiazol-5-yl | |
| 1.627 | 3,5-$F_2$—Ph | H | O | H | $CH_2CH_2$ | 3-furyl | |
| 1.628 | 3,5-$Cl_2$—Ph | H | O | H | $CH_2CH_2$ | 3-methyl-1H-pyrazol-1-yl | [$CDCl_3$] 1.69 (s, 3H); 2.26 (s, 3H); 3.15 (d, 1H); 3.65 (m, 2H); 3.72 (d, 1H); 4.16 (t, 2H); 5.95 (s, 1H); 7.13 (m, 1H); 7.17 (brt, 1H); 7.41 (s, 1H); 7.50 (s, 2H). |
| 1.629 | 3,5-$F_2$—Ph | H | O | H | $CH_2CH_2$ | 3-methyl-1H-pyrazol-1-yl | [$CDCl_3$] 1.69 (s, 3H); 2.25 (s, 3H); 3.15 (d, 1H); 3.65 (m, 2H); 3.72 (d, 1H); 4.16 (t, 2H); 5.94 (m, 1H); 6.88 (m, 1H); 7.14 (m, 3H); 7.17 (brt, 1H). |
| 1.630 | 3,5-$F_2$—Ph | H | O | H | $CH_2CH_2$ | 3-methyl-1H-pyrazol-4-yl | |
| 1.631 | 3-$CF_3$O—Ph | H | O | H | $CH_2CH_2$ | 3-methyl-1-propyl-1H-pyrazol-4-yl | |

TABLE 1-continued

Compounds of the general formula (I) according to the invention in which $R^2$ is hydrogen and $R^3$ is methyl and aryl is the radical

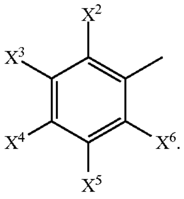

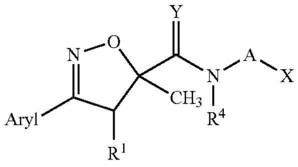

| No. | Aryl | $R^1$ | Y | $R^4$ | A | X | Physical data |
|---|---|---|---|---|---|---|---|
| 1.632 | 3,5-$Cl_2$—Ph | H | O | H | $CH_2CH_2$ | 3-methyl-1-propyl-1H-pyrazol-4-yl | |
| 1.633 | 3,5-$F_2$—Ph | H | O | H | $CH_2CH_2$ | 3-methyl-1-propyl-1H-pyrazol-4-yl | |
| 1.634 | 3-Cl-4-F—Ph | H | O | H | $CH_2CH_2$ | 3-methyl-1-propyl-1H-pyrazol-4-yl | |
| 1.635 | 3-Cl-5-$CF_3O$—Ph | H | O | H | $CH_2CH_2$ | 3-methyl-1-propyl-1H-pyrazol-4-yl | |
| 1.636 | 3-Cl-5-F—Ph | H | O | H | $CH_2CH_2$ | 3-methyl-1-propyl-1H-pyrazol-4-yl | |
| 1.637 | 3-Cl-5-Me—Ph | H | O | H | $CH_2CH_2$ | 3-methyl-1-propyl-1H-pyrazol-4-yl | |
| 1.638 | 3-F-5-Me—Ph | H | O | H | $CH_2CH_2$ | 3-methyl-1-propyl-1H-pyrazol-4-yl | |
| 1.639 | 3-F—Ph | H | O | H | $CH_2CH_2$ | 3-methyl-1-propyl-1H-pyrazol-4-yl | |
| 1.640 | 3-Me—Ph | H | O | H | $CH_2CH_2$ | 3-methyl-1-propyl-1H-pyrazol-4-yl | |
| 1.641 | 4-Cl-3,5-$F_2$—Ph | H | O | H | $CH_2CH_2$ | 3-methyl-1-propyl-1H-pyrazol-4-yl | |
| 1.642 | Ph | H | O | H | $CH_2CH_2$ | 3-methyl-1-propyl-1H-pyrazol-4-yl | |
| 1.643 | 3,5-$Cl_2$—Ph | H | O | H | $CH_2CH_2$ | 4-(methoxy-carbonyl)phenyl | |
| 1.644 | 3,5-$Cl_2$—Ph | H | O | H | $CH_2CH_2$ | 4-(trifluoromethyl)-1,3-thiazol-2-yl | [$CDCl_3$] 7.62 3.25; 7.52 0.34; 7.49 6.14; 7.49 7.28; 7.42 1.78; 7.41 3.12; 7.41 1.63; 7.26 55.91; 7.26 55.47; 7.25 0.84; 7.23 0.75; 7.22 0.38; 7.22 0.37; 7.21 0.59; 3.78 0.56; 3.77 2.84; 3.75 1.49; 3.73 1.56; 3.72 3.45; 3.71 0.66; 3.71 1.44; 3.69 1.50; 3.67 0.72; 3.66 0.57; 3.28 2.64; 3.26 5.25; 3.24 2.30; 3.19 3.05; 3.14 2.63; 2.05 0.88; 1.70 16.00; 1.56 11.27; 1.26 0.53; 0.01 0.36; 0.00 12.33; 0.00 12.25; −0.01 0.55 |
| 1.645 | 3,5-$F_2$—Ph | H | O | H | $CH_2CH_2$ | 4-(trifluoromethyl)-1,3-thiazol-2-yl | [$CDCl_3$] 7.61 3.08; 7.61 2.67; 7.52 0.49; 7.26 84.49; 7.25 0.75; 7.23 0.39; 7.16 0.36; 7.16 0.37; 7.15 1.87; 7.15 2.06; 7.14 1.21; 7.14 1.36; 7.13 2.16; 7.13 1.62; 7.00 0.47; 6.91 0.46; 6.90 0.74; 6.90 0.39; 6.89 0.90; 6.88 |

TABLE 1-continued

Compounds of the general formula (I) according to the invention in which $R^2$ is hydrogen and $R^3$ is methyl and aryl is the radical

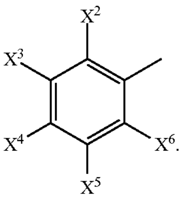

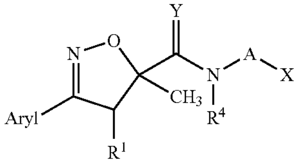

| No. | Aryl | $R^1$ | Y | $R^4$ | A | X | Physical data |
|---|---|---|---|---|---|---|---|
| | | | | | | | 1.48; 6.88 0.73; 6.87 0.46; 6.86 0.73; 6.86 0.34; 3.78 0.56; 3.76 3.05; 3.75 1.38; 3.73 1.44; 3.72 3.38; 3.71 1.37; 3.69 1.47; 3.68 0.65; 3.67 0.57; 3.66 0.54; 3.28 2.55; 3.26 5.07; 3.25 2.15; 3.19 2.94; 3.15 2.55; 2.01 0.39; 1.70 16.00; 1.55 20.74; 1.26 0.32; 0.01 0.98; 0.00 20.24; −0.01 0.65 |
| 1.646 | 3-F—Ph | H | O | H | $CH_2CH_2$ | 4-(trifluoromethyl)-1,3-thiazol-2-yl | |
| 1.647 | 3,5-$Cl_2$—Ph | H | O | H | $CH_2CH_2$ | 4-chloro-1H-pyrazol-1-yl | [$CDCl_3$] 7.51 6.63; 7.51 7.39; 7.42 1.86; 7.42 3.31; 7.41 1.64; 7.39 4.76; 7.27 5.38; 7.26 34.46; 7.11 0.67; 7.09 0.41; 4.22 2.29; 4.20 3.22; 4.19 2.62; 3.75 2.71; 3.70 4.10; 3.69 2.38; 3.68 2.06; 3.66 1.01; 3.18 2.98; 3.14 2.58; 1.69 16.00; 1.56 11.81 |
| 1.648 | 3,5-$F_2$—Ph | H | O | H | $CH_2CH_2$ | 4-chloro-1H-pyrazol-1-yl | [$CDCl_3$] 7.39 4.29; 7.27 5.04; 7.26 17.44; 7.18 0.37; 7.17 0.35; 7.17 1.81; 7.16 2.23; 7.15 2.44; 7.14 1.99; 7.14 0.76; 7.13 0.83; 7.12 0.83; 6.91 0.41; 6.91 0.72; 6.90 0.39; 6.89 0.83; 6.89 1.43; 6.88 0.74; 6.87 0.45; 6.86 0.72; 6.86 0.37; 4.22 2.41; 4.21 3.14; 4.19 2.71; 3.75 2.75; 3.71 1.49; 3.70 3.59; 3.69 2.97; 3.68 2.54; 3.67 1.21; 3.19 3.01; 3.14 2.60; 2.04 0.60; 1.69 16.00; 1.61 1.54; 1.26 0.45 |
| 1.649 | 3,5-$Cl_2$—Ph | H | O | H | $CH_2CH_2$ | 4-chloro-1-methyl-1H-pyrazol-3-yl | |
| 1.650 | 3,5-$F_2$—Ph | H | O | H | $CH_2CH_2$ | 4-chloro-1-methyl-1H-pyrazol-3-yl | |
| 1.651 | 3-F—Ph | H | O | H | $CH_2CH_2$ | 4-chloro-1-methyl-1H-pyrazol-3-yl | |
| 1.652 | 3,5-$F_2$—Ph | H | O | H | $CH_2CH_2$ | 4-chloro-1-methyl-1H-pyrazol-5-yl | |
| 1.653 | 3,5-$Cl_2$—Ph | H | O | H | $CH_2CH_2$ | 4-methoxyphenyl | |
| 1.654 | 3,5-$Cl_2$—Ph | H | O | H | $CH_2CH_2$ | 4-methyl-1H-pyrazol-1-yl | [$CDCl_3$] 1.69 (s, 3H); 2.00 (s, 3H); 3.15 (d, 1H); 3.66 (q, 2H); 3.73 (d, 1H); 4.18 (t, 2H); 7.04 (s, 1H); 7.14 (brt, 1H); 7.28 (s, 1H); 7.41 (s, 1H); 7.50 (s, 2H). |
| 1.655 | 3,5-$F_2$—Ph | H | O | H | $CH_2CH_2$ | 4-methyl-1H-pyrazol-1-yl | [$CDCl_3$] 7.28 3.07; 7.26 16.50; 7.17 0.60; 7.17 0.61; 7.16 2.19; 7.15 2.56; 7.15 1.63; 7.14 1.61; 7.14 2.45; 7.13 1.88; 7.13 |

TABLE 1-continued

Compounds of the general formula (I) according to the invention in which $R^2$ is hydrogen and $R^3$ is methyl and aryl is the radical

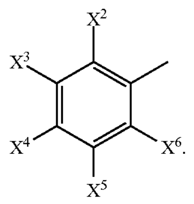

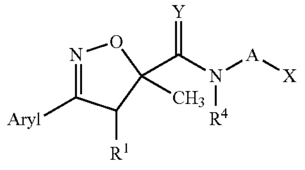

| No. | Aryl | $R^1$ | Y | $R^4$ | A | X | Physical data |
|---|---|---|---|---|---|---|---|
| | | | | | | | 0.40; 7.12 0.40; 7.05 2.82; 6.91 0.41; 6.90 0.73; 6.90 0.37; 6.89 0.84; 6.88 1.45; 6.87 0.73; 6.86 0.44; 6.86 0.74; 6.85 0.36; 4.19 1.83; 4.18 3.30; 4.17 0.48; 4.16 2.34; 3.75 2.77; 3.71 3.19; 3.70 0.68; 3.69 0.70; 3.68 1.56; 3.67 1.83; 3.67 1.74; 3.66 1.59; 3.65 0.64; 3.65 0.61; 3.18 2.89; 3.13 2.53; 2.00 10.31; 2.00 12.04; 1.69 16.00; 1.63 0.89; 0.00 6.50 |
| 1.656 | 3,5-$Cl_2$—Ph | H | O | H | $CH_2CH_2$ | 5-chloro-1-methyl-1H-pyrazol-4-yl | |
| 1.657 | 3,5-$F_2$—Ph | H | O | H | $CH_2CH_2$ | 5-chloro-1-methyl-1H-pyrazol-4-yl | |
| 1.658 | 3,5-$F_2$—Ph | H | S | H | $CH_2CH_2$ | 5-chloro-1-methyl-1H-pyrazol-4-yl | |
| 1.659 | 3-F—Ph | H | O | H | $CH_2CH_2$ | 5-chloro-1-methyl-1H-pyrazol-4-yl | |
| 1.660 | Ph | H | O | H | $CH_2CH_2$ | 5-chloro-1-methyl-1H-pyrazol-4-yl | |
| 1.661 | 3,5-$Cl_2$—Ph | H | O | H | $CH_2CH_2$ | 5-methoxy-1,3-dimethyl-1H-pyrazol-4-yl | |
| 1.662 | 3,5-$F_2$—Ph | H | O | H | $CH_2CH_2$ | 5-methoxy-1,3-dimethyl-1H-pyrazol-4-yl | |
| 1.663 | 3-F—Ph | H | O | H | $CH_2CH_2$ | 5-methoxy-1,3-dimethyl-1H-pyrazol-4-yl | |
| 1.664 | 3,5-$Cl_2$—Ph | H | O | H | $CH_2CH_2$ | 5-methyl-1,2,4-oxadiazol-3-yl | |
| 1.665 | 3,5-$F_2$—Ph | H | O | H | $CH_2CH_2$ | 5-methyl-1,2,4-oxadiazol-3-yl | |
| 1.666 | 3,5-$Cl_2$—Ph | H | O | H | $CH_2CH_2$ | 5-methyl-1,2-oxazol-3-yl | |
| 1.667 | 3,5-$Cl_2$—Ph | H | O | H | $CH_2CH_2$ | 5-methyl-1H-pyrazol-1-yl | [$CDCl_3$] 7.50 6.36; 7.49 7.27; 7.42 1.80; 7.41 3.13; 7.41 1.58; 7.37 2.36; 7.36 2.49; 7.26 20.60; 7.25 0.52; 7.25 0.52; 7.25 0.53; 7.23 0.69; 7.22 0.44; 5.96 2.22; 5.96 2.26; 4.16 2.07; 4.15 3.00; 4.14 2.65; 3.74 2.85; 3.72 1.21; 3.71 2.60; 3.70 3.63; 3.69 2.16; 3.69 2.13; 3.68 0.88; 3.17 3.02; 3.12 2.63; 2.21 13.79; 2.19 0.48; 1.68 16.00; 1.64 1.93; 0.00 5.63 |
| 1.668 | 3,5-$F_2$—Ph | H | O | H | $CH_2CH_2$ | 5-methyl-1H-pyrazol-1-yl | [$CDCl_3$] 7.52 0.58; 7.36 2.39; 7.36 2.17; 7.31 0.55; 7.26 |

TABLE 1-continued

Compounds of the general formula (I) according to the invention in which $R^2$ is hydrogen and $R^3$ is methyl and aryl is the radical

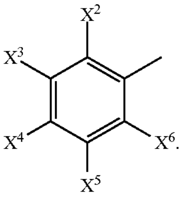

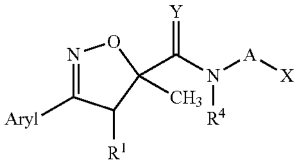

| No. | Aryl | $R^1$ | Y | $R^4$ | A | X | Physical data |
|---|---|---|---|---|---|---|---|
| | | | | | | | 24.83; 7.26 100.68; 7.25 0.77; 7.25 0.63; 7.25 0.60; 7.25 0.59; 7.24 0.57; 7.24 0.53; 7.23 0.64; 7.17 0.32; 7.15 1.79; 7.15 2.18; 7.14 1.43; 7.13 2.12; 7.13 1.68; 7.00 0.56; 6.91 0.42; 6.90 0.72; 6.89 0.39; 6.88 0.85; 6.88 1.44; 6.87 0.71; 6.86 0.43; 6.86 0.71; 6.85 0.35; 5.96 2.24; 5.96 2.16; 4.17 1.88; 4.15 2.93; 4.14 2.49; 3.74 2.75; 3.72 1.20; 3.71 2.41; 3.70 4.77; 3.68 0.86; 3.17 2.90; 3.13 2.48; 2.21 12.75; 2.04 0.88; 1.68 16.00; 1.55 36.39; 1.26 0.57; 0.01 1.19; 0.00 9.13; 0.00 37.39; −0.01 1.13 |
| 1.669 | 3,5-$Cl_2$—Ph | H | O | H | $CH_2CH_2$ | 5-methyl-1-propyl-1H-pyrazol-4-yl | |
| 1.670 | 3,5-$F_2$—Ph | H | O | H | $CH_2CH_2$ | 5-methyl-1-propyl-1H-pyrazol-4-yl | |
| 1.671 | 3-F—Ph | H | O | H | $CH_2CH_2$ | 5-methyl-1-propyl-1H-pyrazol-4-yl | |
| 1.672 | Ph | H | O | H | $CH_2CH_2$ | 5-methyl-1-propyl-1H-pyrazol-4-yl | |
| 1.673 | 3,5-$F_2$—Ph | H | O | H | $CH_2CH_2$ | 6-chloropyridin-3-yl | |
| 1.674 | 3,5-$F_2$—Ph | H | O | H | $CH_2CH_2$ | furan-2-yl | |
| 1.675 | 3,5-$Cl_2$—Ph | H | O | H | $CH_2CH_2$ | phenyl | |
| 1.676 | 3,5-$Cl_2$—Ph | H | O | H | $CH_2CH_2$ | pyridin-2-yl | |
| 1.677 | 3,5-$F_2$—Ph | H | O | H | $CH_2CH_2$ | pyridin-2-yl | [CDCl3] 1.68 (s, 3H); 2.84 (m, 2H); 3.16 (d, 1H); 3.51 (m, 1H); 3.58 (m, 1H); 3.72 (d, 1H); 6.90 (m, 2H); 7.15 (m, 3H); 7.48 (m, 1H); 8.45 (m, 2H). |
| 1.678 | 3,5-$Cl_2$—Ph | H | O | H | $CH_2CH_2$ | pyridin-3-yl | [$CDCl_3$] 1.68 (s, 3H); 2.83 (t, 2H); 3.14 (d, 1H); 3.45-3.62 (m, 2H); 3.71 (d, 1H); 6.87 (br, 1H); 7.18 (m, 1H); 7.42 (m, 1H); 7.49 (m, 3H); 8.45 (m, 2H). |
| 1.679 | 3,5-$F_2$—Ph | H | O | H | $CH_2CH_2$ | pyridin-3-yl | [CDCl3] 1.68 (s, 3H); 2.83 (m, 2H); 3.16 (d, 1H); 3.51 (m, 1H); 3.57 (m, 1H); 3.72 (d, 1H); 6.90 (m, 2H); 7.15 (m, 3H); 7.48 (m, 1H); 8.45 (m, 2H). |
| 1.680 | 3-Cl-5-$CF_3$—Ph | H | O | H | $CH_2CH_2$ | pyridin-3-yl | [$CDCl_3$] 1.69 (s, 3H); 2.83 (t, 2H); 3.19 (d, 1H); 3.45-3.62 (m, 2H); 3.76 (d, 1H); 6.86 (br, |

TABLE 1-continued

Compounds of the general formula (I) according to the invention in which $R^2$ is hydrogen and $R^3$ is methyl and aryl is the radical

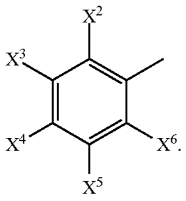

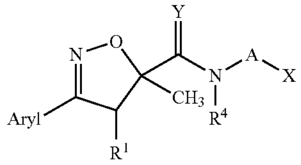

| No. | Aryl | $R^1$ | Y | $R^4$ | A | X | Physical data |
|---|---|---|---|---|---|---|---|
| | | | | | | | 1H); 7.18 (m, 1H); 7.49 (m, 1H); 7.67 (s, 1H); 7.74 (s, 1H); 7.79 (s, 1H); 8.44 (m, 1H). |
| 1.681 | 3-F—Ph | H | O | H | $CH_2CH_2$ | pyridin-3-yl | |
| 1.682 | 3,5-$Cl_2$—Ph | H | O | H | $CH_2CH_2$ | pyridin-4-yl | [$CDCl_3$] 1.68 (s, 3H); 2.81 (t, 2H); 3.15 (d, 1H); 3.55 (m, 2H); 3.70 (d, 1H); 6.85 (br, 1H); 7.09 (d, 2H); 7.42 (m, 1H); 7.49 (m, 2H); 8.48 (d, 2H). |
| 1.683 | 3,5-$F_2$—Ph | H | O | H | $CH_2CH_2$ | pyridin-4-yl | [CDCl3] 1.68 (s, 3H); 2.83 (m, 2H); 3.16 (d, 1H); 3.56 (m, 2H); 3.69 (d, 1H); 6.90 (m, 2H); 7.09 (m, 2H); 7.17 (m, 2H); 8.46 (s, 2H). |
| 1.684 | 3-Cl-5-$CF_3$—Ph | H | O | H | $CH_2CH_2$ | pyridin-4-yl | [$CDCl_3$] 1.69 (s, 3H); 2.82 (t, 2H); 3.19 (d, 1H); 3.47-3.63 (m, 2H); 3.77 (d, 1H); 6.85 (br, 1H); 7.09 (m, 2H); 7.68 (s, 1H); 7.75 (s, 1H); 7.79 (s, 1H); 8.48 (m, 2H). |
| 1.685 | 3-F—Ph | H | O | H | $CH_2CH_2$ | pyridin-4-yl | |
| 1.686 | 3,5-$Cl_2$—Ph | H | O | H | $CH_2CH_2$ | pyrimidin-2-yl | |
| 1.687 | 3,5-$F_2$—Ph | H | O | H | $CHCH_3$ | 1-(2,2,2-trifluoroethyl)-1H-pyrazol-4-yl | |
| 1.688 | 3,5-$F_2$—Ph | H | O | H | $CHCH_3$ | 1-(2-chloroethyl)-1H-pyrazol-4-yl | |
| 1.689 | 3,5-$Cl_2$—Ph | H | O | H | $CHCH_3$ | 1-(2-methoxy-2-oxoethyl)-1H-pyrazol-4-yl | |
| 1.690 | 3,5-$F_2$—Ph | H | O | H | $CHCH_3$ | 1-(3-carboxypropyl)-1H-pyrazol-4-yl | |
| 1.691 | 3,5-$F_2$—Ph | H | O | H | $CHCH_3$ | 1-(3-methoxy-3-oxopropyl)-1H-pyrazol-4-yl | |
| 1.692 | 3,5-$F_2$—Ph | H | O | H | $CHCH_3$ | 1-(4-methoxy-4-oxobutyl)-1H-pyrazol-4-yl | |
| 1.693 | 3,5-$Cl_2$—Ph | H | O | H | $CHCH_3$ | 1-(cyanomethyl)-1H-pyrazol-4-yl | |
| 1.694 | 3,5-$F_2$—Ph | H | O | H | $CHCH_3$ | 1-(cyanomethyl)-1H-pyrazol-4-yl | |
| 1.695 | 3-F—Ph | H | O | H | $CHCH_3$ | 1-(cyanomethyl)-1H-pyrazol-4-yl | |
| 1.696 | 3,5-$(CF_3)_2$—Ph | H | O | H | $CHCH_3$ | 1,3-dimethyl-1H-pyrazol-4-yl | |
| 1.697 | 3,5-$Cl_2$—Ph | H | O | H | $CHCH_3$ | 1,3-dimethyl-1H-pyrazol-4-yl | |
| 1.698 | 3,5-$F_2$—Ph | H | O | H | $CHCH_3$ | 1,3-dimethyl-1H-pyrazol-4-yl | |
| 1.699 | 3-Cl—Ph | H | O | H | $CHCH_3$ | 1,3-dimethyl-1H-pyrazol-4-yl | |
| 1.700 | 3-F—Ph | H | O | H | $CHCH_3$ | 1,3-dimethyl-1H-pyrazol-4-yl | |

TABLE 1-continued

Compounds of the general formula (I) according to the invention in which $R^2$ is hydrogen and $R^3$ is methyl and aryl is the radical

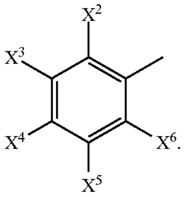

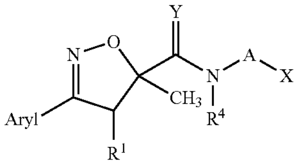

| No. | Aryl | $R^1$ | Y | $R^4$ | A | X | Physical data |
|---|---|---|---|---|---|---|---|
| 1.701 | 3-Me—Ph | H | O | H | $CHCH_3$ | 1,3-dimethyl-1H-pyrazol-4-yl | |
| 1.702 | Ph | H | O | H | $CHCH_3$ | 1,3-dimethyl-1H-pyrazol-4-yl | |
| 1.703 | 3,5-$(CF_3)_2$—Ph | H | O | H | $CHCH_3$ | 1,3-dimethyl-1H-pyrazol-5-yl | |
| 1.704 | 3,5-$Cl_2$—Ph | H | O | H | $CHCH_3$ | 1,3-dimethyl-1H-pyrazol-5-yl | |
| 1.705 | 3,5-$F_2$—Ph | H | O | H | $CHCH_3$ | 1,3-dimethyl-1H-pyrazol-5-yl | |
| 1.706 | Ph | H | O | H | $CHCH_3$ | 1,3-dimethyl-1H-pyrazol-5-yl | |
| 1.707 | 3,5-$Cl_2$—Ph | H | O | H | $CHCH_3$ | 1,3-oxazol-4-yl | |
| 1.708 | 3,5-$F_2$—Ph | H | O | H | $CHCH_3$ | 1,3-oxazol-4-yl | |
| 1.709 | 3-F—Ph | H | O | H | $CHCH_3$ | 1,3-oxazol-4-yl | |
| 1.710 | 3,5-$Cl_2$—Ph | H | O | H | $CHCH_3$ | 1,3-thiazol-2-yl | [$CDCl_3$] 7.74 2.63; 7.73 2.86; 7.68 2.66; 7.67 2.91; 7.54 6.31; 7.54 8.10; 7.52 6.48; 7.51 8.25; 7.48 0.92; 7.46 1.03; 7.44 1.07; 7.43 2.38; 7.42 4.37; 7.42 3.14; 7.42 3.67; 7.41 3.90; 7.41 2.53; 7.28 3.25; 7.28 3.37; 7.27 0.50; 7.27 0.53; 7.26 48.23; 7.21 3.19; 7.20 3.25; 5.41 0.62; 5.39 2.17; 5.38 3.38; 5.36 2.44; 5.34 0.66; 3.86 2.64; 3.81 3.01; 3.80 2.71; 3.76 3.05; 3.23 3.04; 3.22 3.20; 3.19 2.63; 3.18 2.81; 1.77 15.88; 1.75 16.00; 1.68 8.14; 1.66 8.20; 1.63 8.12; 1.61 8.13; 1.57 10.13; 1.26 0.42; 0.00 10.96; −0.01 0.87 |
| 1.711 | 3,5-$F_2$—Ph | H | O | H | $CHCH_3$ | 1,3-thiazol-2-yl | [$CDCl_3$] 7.74 2.35; 7.74 2.43; 7.68 2.50; 7.67 2.59; 7.49 0.80; 7.47 0.91; 7.45 0.90; 7.43 0.83; 7.29 2.79; 7.28 2.77; 7.28 2.79; 7.28 2.75; 7.26 34.71; 7.26 34.31; 7.20 3.13; 7.20 3.19; 7.19 4.75; 7.19 5.00; 7.17 3.83; 7.15 2.58; 7.15 1.98; 6.92 0.42; 6.91 0.71; 6.91 0.75; 6.90 0.94; 6.90 1.18; 6.89 1.43; 6.89 1.43; 6.89 1.47; 6.88 1.48; 6.88 1.48; 6.88 1.51; 6.87 1.12; 6.86 0.74; 6.86 0.71; 6.85 0.35; 5.42 0.61; 5.40 2.20; 5.38 3.14; 5.36 2.19; 5.35 0.60; 3.85 2.49; 3.81 2.86; 3.80 2.63; 3.76 3.00; 3.24 3.06; 3.23 2.91; 3.19 2.62; 3.18 2.52; 1.77 16.00; 1.75 15.23; 1.68 8.12; 1.66 8.07; 1.64 7.72; 1.62 7.68; 1.58 7.44; 1.26 0.40; 0.00 7.82; 0.00 7.86 |

TABLE 1-continued

Compounds of the general formula (I) according to the invention in which $R^2$ is hydrogen and $R^3$ is methyl and aryl is the radical

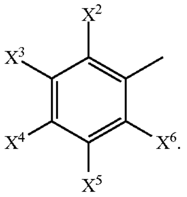

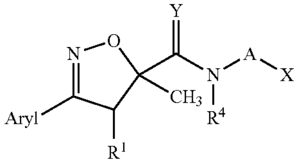

| No. | Aryl | $R^1$ | Y | $R^4$ | A | X | Physical data |
|---|---|---|---|---|---|---|---|
| 1.712 | 3,5-$Cl_2$—Ph | H | O | H | $CHCH_3$ | 1,4-dimethyl-5-oxo-4,5-dihydro-1H-1,2,4-triazol-3-yl | |
| 1.713 | 3,5-$F_2$—Ph | H | O | H | $CHCH_3$ | 1,5-dimethyl-1H-pyrazol-3-yl | |
| 1.714 | 3,5-$Cl_2$—Ph | H | O | H | $CHCH_3$ | 1,5-dimethyl-1H-pyrazol-4-yl | |
| 1.715 | 3,5-$F_2$—Ph | H | O | H | $CHCH_3$ | 1,5-dimethyl-1H-pyrazol-4-yl | |
| 1.716 | 3-F—Ph | H | O | H | $CHCH_3$ | 1,5-dimethyl-1H-pyrazol-4-yl | |
| 1.717 | Ph | H | O | H | $CHCH_3$ | 1,5-dimethyl-1H-pyrazol-4-yl | |
| 1.718 | 3,5-$F_2$—Ph | H | O | H | $CHCH_3$ | 1-acetyl-1H-pyrazol-4-yl | |
| 1.719 | 3,5-$F_2$—Ph | H | O | H | $CHCH_3$ | 1-butyl-3-methyl-1H-pyrazol-4-yl | |
| 1.720 | 3,5-$F_2$—Ph | H | O | H | $CHCH_3$ | 1-butyl-5-methyl-1H-pyrazol-4-yl | |
| 1.721 | 3,5-$Cl_2$—Ph | H | O | H | $CHCH_3$ | 1-cyclopropyl-1H-pyrazol-4-yl | |
| 1.722 | 3,5-$F_2$—Ph | H | O | H | $CHCH_3$ | 1-cyclopropyl-1H-pyrazol-4-yl | |
| 1.723 | 3-F—Ph | H | O | H | $CHCH_3$ | 1-cyclopropyl-1H-pyrazol-4-yl | |
| 1.724 | Ph | H | O | H | $CHCH_3$ | 1-cyclopropyl-1H-pyrazol-4-yl | |
| 1.725 | 3,5-$Cl_2$-4-MeO—Ph | H | O | H | $CHCH_3$ | 1-ethyl-1H-pyrazol-4-yl | |
| 1.726 | 3,5-$Cl_2$—Ph | H | O | H | $CHCH_3$ | 1-ethyl-1H-pyrazol-4-yl | |
| 1.727 | 3,5-$F_2$—Ph | H | O | H | $CHCH_3$ | 1-ethyl-1H-pyrazol-4-yl | |
| 1.728 | 3,5-$(MeO)_2$—Ph | H | O | H | $CHCH_3$ | 1-ethyl-1H-pyrazol-4-yl | |
| 1.729 | 3-Br-5-$CF_3$—Ph | H | O | H | $CHCH_3$ | 1-ethyl-1H-pyrazol-4-yl | |
| 1.730 | 3-Cl-5-Et—Ph | H | O | H | $CHCH_3$ | 1-ethyl-1H-pyrazol-4-yl | |
| 1.731 | 3-F-5-MeO—Ph | H | O | H | $CHCH_3$ | 1-ethyl-1H-pyrazol-4-yl | |
| 1.732 | 3-F—Ph | H | O | H | $CHCH_3$ | 1-ethyl-1H-pyrazol-4-yl | |
| 1.733 | 3-Me-5-$CF_3O$—Ph | H | O | H | $CHCH_3$ | 1-ethyl-1H-pyrazol-4-yl | |
| 1.734 | 3-Me—Ph | H | O | H | $CHCH_3$ | 1-ethyl-1H-pyrazol-4-yl | |
| 1.735 | Ph | H | O | H | $CHCH_3$ | 1-ethyl-1H-pyrazol-4-yl | |
| 1.736 | 3,5-$Cl_2$—Ph | H | O | H | $CHCH_3$ | 1-ethyl-1H-pyrazol-5-yl | |
| 1.737 | 3,5-$F_2$—Ph | H | O | H | $CHCH_3$ | 1-ethyl-1H-pyrazol-5-yl | |
| 1.738 | Ph | H | O | H | $CHCH_3$ | 1-ethyl-1H-pyrazol-5-yl | |

TABLE 1-continued

Compounds of the general formula (I) according to the invention in which $R^2$ is hydrogen and $R^3$ is methyl and aryl is the radical

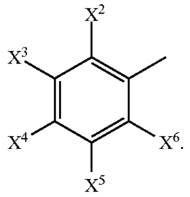

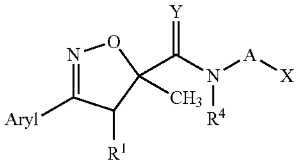

| No. | Aryl | $R^1$ | Y | $R^4$ | A | X | Physical data |
|---|---|---|---|---|---|---|---|
| 1.739 | 2,3,4-$F_3$—Ph | H | O | H | $CHCH_3$ | 1-ethyl-3-methyl-1H-pyrazol-4-yl | |
| 1.740 | 2,3,5-$F_3$—Ph | H | O | H | $CHCH_3$ | 1-ethyl-3-methyl-1H-pyrazol-4-yl | |
| 1.741 | 2,3-$F_2$—Ph | H | O | H | $CHCH_3$ | 1-ethyl-3-methyl-1H-pyrazol-4-yl | |
| 1.742 | 2,5-$Cl_2$—Ph | H | O | H | $CHCH_3$ | 1-ethyl-3-methyl-1H-pyrazol-4-yl | |
| 1.743 | 2,5-$F_2$—Ph | H | O | H | $CHCH_3$ | 1-ethyl-3-methyl-1H-pyrazol-4-yl | |
| 1.744 | 2,5-$Me_2$—Ph | H | O | H | $CHCH_3$ | 1-ethyl-3-methyl-1H-pyrazol-4-yl | |
| 1.745 | 2-F-3-Me—Ph | H | O | H | $CHCH_3$ | 1-ethyl-3-methyl-1H-pyrazol-4-yl | |
| 1.746 | 2-F—Ph | H | O | H | $CHCH_3$ | 1-ethyl-3-methyl-1H-pyrazol-4-yl | |
| 1.747 | 3-$CF_3O$—Ph | H | O | H | $CHCH_3$ | 1-ethyl-3-methyl-1H-pyrazol-4-yl | |
| 1.748 | 3,4,5-$F_3$—Ph | H | O | H | $CHCH_3$ | 1-ethyl-3-methyl-1H-pyrazol-4-yl | |
| 1.749 | 3,4-$F_2$—Ph | H | O | H | $CHCH_3$ | 1-ethyl-3-methyl-1H-pyrazol-4-yl | |
| 1.750 | 3,5-$Br_2$—Ph | H | O | H | $CHCH_3$ | 1-ethyl-3-methyl-1H-pyrazol-4-yl | |
| 1.751 | 3,5-$Cl_2$-4-MeO—Ph | H | O | H | $CHCH_3$ | 1-ethyl-3-methyl-1H-pyrazol-4-yl | |
| 1.752 | 3,5-$Cl_2$—Ph | $CH_3$ | O | H | $CHCH_3$ | 1-ethyl-3-methyl-1H-pyrazol-4-yl | |
| 1.753 | 3,5-$Cl_2$—Ph | H | O | H | $CHCH_3$ | 1-ethyl-3-methyl-1H-pyrazol-4-yl | |
| 1.754 | 3,5-$Cl_2$—Ph | H | O | H | $CHCH_3$ | 1-ethyl-3-methyl-1H-pyrazol-4-yl | [$CDCl_3$] 7.53 6.75; 7.52 7.49; 7.42 1.82; 7.42 3.25; 7.41 1.60; 7.26 17.29; 7.24 3.91; 6.77 0.63; 6.75 0.65; 5.03 0.72; 5.02 0.82; 5.01 0.82; 5.00 0.73; 4.11 1.19; 4.09 3.75; 4.07 3.83; 4.05 1.27; 3.83 2.53; 3.79 2.86; 3.20 2.67; 3.15 2.37; 2.22 16.00; 1.70 14.45; 1.61 6.29; 1.49 4.66; 1.47 9.86; 1.45 4.60; 1.43 6.60; 1.41 6.58; 0.00 9.19 |
| 1.755 | 3,5-$Et_2$—Ph | H | O | H | $CHCH_3$ | 1-ethyl-3-methyl-1H-pyrazol-4-yl | |
| 1.756 | 3,5-$F_2$—Ph | H | O | H | $CHCH_3$ | 1-ethyl-3-methyl-1H-pyrazol-4-yl | |
| 1.757 | 3,5-$F_2$—Ph | H | O | H | $CHCH_3$ | 1-ethyl-3-methyl-1H-pyrazol-4-yl | [$CDCl_3$] 7.26 18.73; 7.26 9.73; 7.24 4.53; 7.19 0.48; 7.18 1.71; 7.17 2.44; 7.17 1.96; 7.16 2.42; 7.15 2.07; 7.14 0.43; 6.91 0.41; 6.91 0.74; 6.90 0.43; 6.89 0.88; 6.89 1.47; 6.88 0.84; 6.87 0.53; 6.86 0.75; 6.86 0.42; 6.78 0.84; 6.76 0.85; 5.04 0.89; 5.02 1.20; 5.00 0.94; 4.11 1.29; 4.09 3.89; 4.07 3.97; 4.05 1.40; 3.83 2.54; 3.78 2.97; 3.20 2.88; 3.16 |

TABLE 1-continued

Compounds of the general formula (I) according to the invention in which $R^2$ is hydrogen and $R^3$ is methyl and aryl is the radical

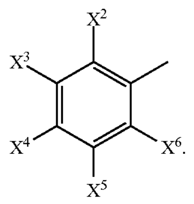

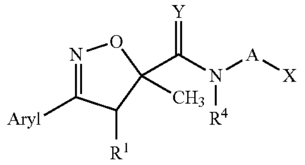

| No. | Aryl | $R^1$ | Y | $R^4$ | A | X | Physical data |
|---|---|---|---|---|---|---|---|
| | | | | | | | 2.55; 2.23 16.00; 2.06 0.90; 1.74 0.82; 1.71 15.13; 1.59 12.31; 1.48 4.64; 1.47 9.47; 1.45 4.58; 1.43 7.35; 1.42 7.46; 1.40 0.35; 0.01 0.39; 0.00 9.71; 0.00 4.83; −0.01 0.47 |
| 1.758 | 3,5-$F_2$—Ph | H | S | H | $CHCH_3$ | 1-ethyl-3-methyl-1H-pyrazol-4-yl | |
| 1.759 | 3,5-$Me_2$—Ph | H | O | H | $CHCH_3$ | 1-ethyl-3-methyl-1H-pyrazol-4-yl | |
| 1.760 | 3-$CF_3$S—Ph | H | O | H | $CHCH_3$ | 1-ethyl-3-methyl-1H-pyrazol-4-yl | |
| 1.761 | 3-Br-5-$CF_3$—Ph | H | O | H | $CHCH_3$ | 1-ethyl-3-methyl-1H-pyrazol-4-yl | |
| 1.762 | 3-Br-5-Cl—Ph | H | O | H | $CHCH_3$ | 1-ethyl-3-methyl-1H-pyrazol-4-yl | |
| 1.763 | 3-Br-5-F—Ph | H | O | H | $CHCH_3$ | 1-ethyl-3-methyl-1H-pyrazol-4-yl | |
| 1.764 | 3-Cl-4-F—Ph | H | O | H | $CHCH_3$ | 1-ethyl-3-methyl-1H-pyrazol-4-yl | |
| 1.765 | 3-Cl-5-$CF_3$—Ph | H | O | H | $CHCH_3$ | 1-ethyl-3-methyl-1H-pyrazol-4-yl | |
| 1.766 | 3-Cl-5-CN—Ph | H | O | H | $CHCH_3$ | 1-ethyl-3-methyl-1H-pyrazol-4-yl | |
| 1.767 | 3-Cl-5-Et—Ph | H | O | H | $CHCH_3$ | 1-ethyl-3-methyl-1H-pyrazol-4-yl | |
| 1.768 | 3-Cl-5-F—Ph | H | O | H | $CHCH_3$ | 1-ethyl-3-methyl-1H-pyrazol-4-yl | |
| 1.769 | 3-Cl-5-MeO—Ph | H | O | H | $CHCH_3$ | 1-ethyl-3-methyl-1H-pyrazol-4-yl | |
| 1.770 | 3-Cl-5-Me—Ph | H | O | H | $CHCH_3$ | 1-ethyl-3-methyl-1H-pyrazol-4-yl | |
| 1.771 | 3-Cl-5-$CF_3$O—Ph | H | O | H | $CHCH_3$ | 1-ethyl-3-methyl-1H-pyrazol-4-yl | |
| 1.772 | 3-Cl—Ph | H | O | H | $CHCH_3$ | 1-ethyl-3-methyl-1H-pyrazol-4-yl | |
| 1.773 | 3-CN-5-F—Ph | H | O | H | $CHCH_3$ | 1-ethyl-3-methyl-1H-pyrazol-4-yl | |
| 1.774 | 3-CN—Ph | H | O | H | $CHCH_3$ | 1-ethyl-3-methyl-1H-pyrazol-4-yl | |
| 1.775 | 3-cPr-5-F—Ph | H | O | H | $CHCH_3$ | 1-ethyl-3-methyl-1H-pyrazol-4-yl | |
| 1.776 | 3-EtO—Ph | H | O | H | $CHCH_3$ | 1-ethyl-3-methyl-1H-pyrazol-4-yl | |
| 1.777 | 3-Et-5-F—Ph | H | O | H | $CHCH_3$ | 1-ethyl-3-methyl-1H-pyrazol-4-yl | |
| 1.778 | 3-F-5-$CF_3$—Ph | H | O | H | $CHCH_3$ | 1-ethyl-3-methyl-1H-pyrazol-4-yl | |
| 1.779 | 3-F-5-MeO—Ph | H | O | H | $CHCH_3$ | 1-ethyl-3-methyl-1H-pyrazol-4-yl | |
| 1.780 | 3-F-5-Me—Ph | H | O | H | $CHCH_3$ | 1-ethyl-3-methyl-1H-pyrazol-4-yl | |
| 1.781 | 3-F—Ph | H | O | H | $CHCH_3$ | 1-ethyl-3-methyl-1H-pyrazol-4-yl | |
| 1.782 | 3-F—Ph | H | O | H | $CHCH_3$ | 1-ethyl-3-methyl-1H-pyrazol-4-yl | [$CDCl_3$] 7.41 0.64; 7.40 1.03; 7.40 1.60; 7.39 0.35; 7.39 |

TABLE 1-continued

Compounds of the general formula (I) according to the invention in which $R^2$ is hydrogen and $R^3$ is methyl and aryl is the radical

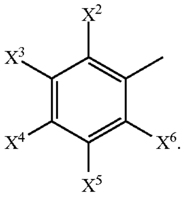

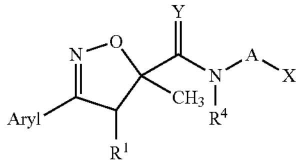

| No. | Aryl | $R^1$ | Y | $R^4$ | A | X | Physical data |
|---|---|---|---|---|---|---|---|
| | | | | | | | 2.16; 7.38 4.31; 7.38 1.43; 7.38 4.53; 7.37 0.44; 7.37 0.34; 7.26 17.26; 7.24 3.62; 7.18 0.32; 7.16 0.45; 7.16 0.64; 7.15 0.48; 7.14 0.44; 7.14 0.56; 7.14 0.60; 7.13 0.88; 7.13 0.58; 7.12 0.36; 7.12 0.53; 7.11 0.39; 6.83 0.50; 6.80 0.51; 5.04 0.67; 5.02 0.74; 5.02 0.75; 5.00 0.68; 4.10 1.18; 4.09 3.76; 4.07 3.86; 4.05 1.27; 4.02 0.34; 4.00 0.34; 3.86 2.76; 3.81 3.14; 3.81 0.42; 3.23 3.11; 3.19 2.73; 2.23 16.00; 2.06 1.38; 1.74 1.36; 1.71 15.54; 1.62 5.19; 1.49 0.72; 1.48 5.07; 1.47 0.77; 1.47 10.86; 1.45 4.98; 1.43 6.78; 1.42 0.75; 1.41 6.76; 1.40 1.05; 1.38 0.46; 0.00 9.79 |
| 1.783 | 3-MeO—Ph | H | O | H | $CHCH_3$ | 1-ethyl-3-methyl-1H-pyrazol-4-yl | |
| 1.784 | 3-Me—Ph | H | O | H | $CHCH_3$ | 1-ethyl-3-methyl-1H-pyrazol-4-yl | |
| 1.785 | Ph | H | O | H | $CHCH_3$ | 1-ethyl-3-methyl-1H-pyrazol-4-yl | [$CDCl_3$] 1.38 (t, 3H); 1.46 (d, 3H); 1.73 (s, 3H); 2.04 (s, 3H); 3.23 (d, 1H); 3.80 (d, 1H); 3.97 (q, 2H); 4.98 (m, 1H); 6.90 (brd, 1H); 7.16 (s, 1H); 7.40 (m, 3H); 7.60 (m, 2H). |
| 1.786 | Ph | H | O | H | $CHCH_3$ | 1-ethyl-3-methyl-1H-pyrazol-4-yl | [$CDCl_3$] 1.40 (d, 3H); 1.44 (t, 3H); 1.71 (s, 3H); 2.22 (s, 3H); 3.23 (d, 1H); 3.85 (d, 1H); 4.07 (q, 2H); 5.00 (m, 1H); 6.85 (brd, 1H); 7.23 (s, 1H); 7.43 (m, 3H); 7.63 (m, 2H). |
| 1.787 | 3,5-$Cl_2$—Ph | H | O | H | $CHCH_3$ | 1-ethyl-3-methyl-1H-pyrazol-5-yl | |
| 1.788 | 3,5-$F_2$—Ph | H | O | H | $CHCH_3$ | 1-ethyl-3-methyl-1H-pyrazol-5-yl | |
| 1.789 | 3-F—Ph | H | O | H | $CHCH_3$ | 1-ethyl-3-methyl-1H-pyrazol-5-yl | |
| 1.790 | 3,5-$F_2$—Ph | H | O | H | $CHCH_3$ | 1H-1,2,3-triazol-5-yl | |
| 1.791 | 3,5-$Cl_2$—Ph | H | O | H | $CHCH_3$ | 1H-pyrazol-4-yl | |
| 1.792 | 3,5-$F_2$—Ph | H | O | H | $CHCH_3$ | 1H-pyrazol-4-yl | |
| 1.793 | 3-F—Ph | H | O | H | $CHCH_3$ | 1H-pyrazol-4-yl | |
| 1.794 | 3,5-$Cl_2$—Ph | H | O | H | $CHCH_3$ | 1-isobutyl-1H-pyrazol-4-yl | |
| 1.795 | 3,5-$F_2$—Ph | H | O | H | $CHCH_3$ | 1-isobutyl-1H-pyrazol-4-yl | |
| 1.796 | 3-F—Ph | H | O | H | $CHCH_3$ | 1-isobutyl-1H-pyrazol-4-yl | |
| 1.797 | Ph | H | O | H | $CHCH_3$ | 1-isobutyl-1H-pyrazol-4-yl | |
| 1.798 | 3,5-$Cl_2$—Ph | H | O | H | $CHCH_3$ | 1-isopropyl-1H-pyrazol-4-yl | |

TABLE 1-continued

Compounds of the general formula (I) according to the invention in which $R^2$ is hydrogen and $R^3$ is methyl and aryl is the radical

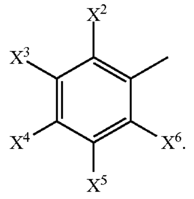

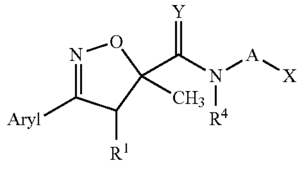

| No. | Aryl | $R^1$ | Y | $R^4$ | A | X | Physical data |
|---|---|---|---|---|---|---|---|
| 1.799 | 3,5-$F_2$—Ph | H | O | H | $CHCH_3$ | 1-isopropyl-1H-pyrazol-4-yl | [$CDCl_3$] 7.52 0.41; 7.43 2.11; 7.34 4.86; 7.26 74.34; 7.24 3.11; 7.21 0.57; 7.18 0.96; 7.18 1.30; 7.17 0.82; 7.17 0.85; 7.16 1.43; 7.16 2.00; 7.16 1.96; 7.15 1.83; 7.15 1.19; 7.14 1.05; 7.14 1.73; 7.13 1.39; 7.00 0.43; 6.91 0.51; 6.91 1.16; 6.90 1.19; 6.89 1.24; 6.89 2.04; 6.88 1.94; 6.87 1.11; 6.86 0.93; 6.86 0.85; 6.85 0.39; 5.09 0.48; 5.08 0.67; 5.07 0.66; 5.06 0.78; 5.05 0.55; 5.04 0.63; 4.48 0.71; 4.47 0.97; 4.45 0.73; 4.43 0.39; 4.41 0.96; 4.39 1.29; 4.37 0.99; 4.36 0.40; 3.82 1.64; 3.79 2.23; 3.78 1.89; 3.75 2.59; 3.21 1.83; 3.20 2.48; 3.17 1.61; 3.16 2.18; 1.74 13.10; 1.71 9.72; 1.56 18.56; 1.51 14.63; 1.49 14.54; 1.46 4.56; 1.44 4.70; 1.44 16.00; 1.42 15.68; 0.01 1.21; 0.00 43.28; −0.01 1.79 |
| 1.800 | 3-F—Ph | H | O | H | $CHCH_3$ | 1-isopropyl-1H-pyrazol-4-yl | |
| 1.801 | Ph | H | O | H | $CHCH_3$ | 1-isopropyl-1H-pyrazol-4-yl | |
| 1.802 | 3,5-$(CF_3)_2$—Ph | H | O | H | $CHCH_3$ | 1-methyl-1H-pyrazol-4-yl | |
| 1.803 | 3,5-$Cl_2$—Ph | H | O | H | $CHCH_3$ | 1-methyl-1H-pyrazol-4-yl | [$CDCl_3$] 7.50 5.86; 7.50 6.01; 7.50 6.52; 7.49 5.46; 7.42 1.73; 7.41 1.98; 7.41 2.82; 7.41 2.55; 7.40 1.13; 7.34 4.08; 7.27 2.17; 7.26 13.77; 7.26 12.56; 7.20 4.08; 6.89 0.83; 6.87 0.84; 5.06 0.91; 5.04 1.26; 5.02 0.90; 3.82 16.00; 3.82 14.54; 3.78 2.30; 3.78 2.08; 3.77 0.33; 3.74 2.68; 3.74 2.45; 3.19 2.56; 3.19 2.36; 3.15 2.23; 3.15 2.04; 1.73 13.73; 1.73 12.71; 1.62 3.14; 1.51 6.78; 1.49 6.77 |
| 1.804 | 3,5-$Cl_2$—Ph | H | O | H | $CHCH_3$ | 1-methyl-1H-pyrazol-4-yl | [$CDCl_3$] 7.53 5.68; 7.53 6.21; 7.53 7.07; 7.52 6.46; 7.43 1.78; 7.42 6.62; 7.30 4.17; 7.27 16.45; 7.26 16.08; 6.89 0.89; 6.87 0.93; 5.07 0.92; 5.05 1.29; 5.03 0.96; 3.89 16.00; 3.88 15.89; 3.83 2.33; 3.82 2.36; 3.78 2.66; 3.78 2.67; 3.21 2.54; 3.20 2.56; 3.16 2.25; 3.16 2.24; 1.70 13.66; 1.70 13.77; 1.62 3.73; 1.46 6.70; 1.46 6.76; 1.44 6.80; 1.44 6.84; 0.00 6.90; 0.00 6.98 |

TABLE 1-continued

Compounds of the general formula (I) according to the invention in which $R^2$ is hydrogen and $R^3$ is methyl and aryl is the radical

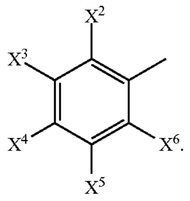

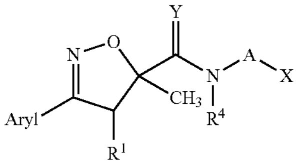

| No. | Aryl | $R^1$ | Y | $R^4$ | A | X | Physical data |
|---|---|---|---|---|---|---|---|
| 1.805 | 3,5-$F_2$—Ph | H | O | H | $CHCH_3$ | 1-methyl-1H-pyrazol-4-yl | [$CDCl_3$] 7.34 3.14; 7.27 6.92; 7.26 15.76; 7.21 3.20; 7.16 1.67; 7.15 1.60; 7.15 1.84; 7.15 1.07; 7.14 1.36; 7.14 2.02; 7.13 1.29; 7.13 1.43; 6.91 0.61; 6.90 1.11; 6.90 0.82; 6.89 1.13; 6.88 1.83; 6.88 1.05; 6.87 0.53; 6.86 0.73; 6.85 0.35; 5.06 0.72; 5.05 0.92; 5.03 0.69; 3.82 16.00; 3.78 2.34; 3.74 2.67; 3.20 2.47; 3.16 2.16; 1.74 13.54; 1.62 2.86; 1.51 6.42; 1.49 6.36; 0.00 2.87; 0.00 6.89 |
| 1.806 | 3,5-$F_2$—Ph | H | O | H | $CHCH_3$ | 1-methyl-1H-pyrazol-4-yl | [$CDCl_3$] 7.42 3.67; 7.30 3.64; 7.27 12.80; 7.26 13.85; 7.19 0.33; 7.18 1.66; 7.18 2.06; 7.17 1.34; 7.16 2.16; 7.16 1.65; 7.15 0.37; 7.14 0.34; 6.92 0.47; 6.91 0.80; 6.90 0.66; 6.89 1.40; 6.89 1.70; 6.88 1.12; 6.87 1.06; 6.87 0.98; 6.86 0.52; 5.07 0.83; 5.06 1.06; 5.04 0.84; 3.88 16.00; 3.82 2.43; 3.78 2.71; 3.21 2.62; 3.17 2.30; 1.70 13.98; 1.61 3.88; 1.46 6.84; 1.44 6.82; 1.26 0.46; 0.00 5.59 |
| 1.807 | 3-F-5-MeO—Ph | H | O | H | $CHCH_3$ | 1-methyl-1H-pyrazol-4-yl | |
| 1.808 | 3-F—Ph | H | O | H | $CHCH_3$ | 1-methyl-1H-pyrazol-4-yl | [$CDCl_3$] 7.39 0.90; 7.38 0.71; 7.38 1.66; 7.37 2.08; 7.37 1.47; 7.37 2.15; 7.36 1.95; 7.36 2.29; 7.36 0.92; 7.35 1.02; 7.33 2.72; 7.26 14.38; 7.26 0.38; 7.19 2.81; 7.16 0.43; 7.15 0.48; 7.15 0.48; 7.15 0.33; 7.14 0.49; 7.14 0.60; 7.13 0.79; 7.12 0.38; 7.12 0.36; 7.11 0.55; 6.94 0.44; 6.93 0.44; 5.07 0.62; 5.05 0.73; 5.03 0.61; 3.88 0.38; 3.81 2.61; 3.80 16.00; 3.77 2.64; 3.24 2.46; 3.19 2.14; 1.74 13.01; 1.62 1.78; 1.51 6.16; 1.49 6.11; 0.00 6.19 |
| 1.809 | 3-F—Ph | H | O | H | $CHCH_3$ | 1-methyl-1H-pyrazol-4-yl | [$CDCl_3$] 7.42 3.97; 7.42 3.93; 7.41 0.94; 7.41 2.18; 7.41 2.45; 7.40 1.07; 7.40 2.30; 7.39 5.40; 7.39 4.69; 7.38 5.10; 7.38 4.07; 7.37 0.60; 7.30 3.83; 7.27 16.70; 7.27 8.64; 7.26 16.31; 7.17 0.42; 7.16 0.85; 7.16 1.06; 7.15 0.79; 7.14 0.96; 7.14 1.01; 7.14 1.22; 7.13 1.08; 7.13 0.77; 7.13 0.70; 7.12 0.45; 7.11 0.40; 6.94 0.98; 6.92 0.99; 5.08 0.96; 5.06 1.46; 5.04 0.98; 3.89 16.00; 3.88 15.81; 3.85 2.41; 3.85 2.39; 3.81 2.93; 3.81 |

TABLE 1-continued

Compounds of the general formula (I) according to the invention in which $R^2$ is hydrogen and $R^3$ is methyl and aryl is the radical

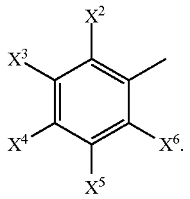

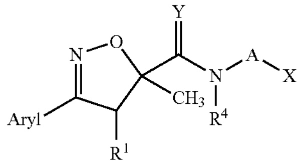

| No. | Aryl | $R^1$ | Y | $R^4$ | A | X | Physical data |
|---|---|---|---|---|---|---|---|
| | | | | | | | 3.91; 3.80 1.29; 3.25 2.59; 3.24 2.62; 3.20 2.28; 3.20 2.26; 1.74 1.04; 1.74 1.04; 1.71 14.27; 1.70 14.05; 1.62 3.69; 1.62 3.98; 1.51 0.44; 1.51 0.44; 1.49 0.45; 1.49 0.44; 1.46 6.81; 1.46 6.81; 1.44 6.81; 1.44 6.69; 0.01 7.41; 0.00 4.05; 0.00 7.68 |
| 1.810 | 3-Me—Ph | H | O | H | $CHCH_3$ | 1-methyl-1H-pyrazol-4-yl | |
| 1.811 | Ph | H | O | H | $CHCH_3$ | 1-methyl-1H-pyrazol-4-yl | [$CDCl_3$] 7.64 2.08; 7.63 2.18; 7.63 1.05; 7.63 0.84; 7.62 0.91; 7.62 1.71; 7.62 1.83; 7.61 2.35; 7.44 0.68; 7.44 0.79; 7.43 1.12; 7.43 1.85; 7.42 4.43; 7.42 1.89; 7.41 0.94; 7.41 1.26; 7.41 1.65; 7.40 1.95; 7.40 1.85; 7.40 0.37; 7.40 0.35; 7.39 0.41; 7.39 0.62; 7.38 0.43; 7.33 2.78; 7.26 16.64; 7.18 2.84; 6.99 0.46; 6.97 0.47; 5.07 0.65; 5.05 0.77; 5.05 0.76; 5.03 0.63; 3.88 0.39; 3.83 2.52; 3.79 2.97; 3.78 16.00; 3.26 2.64; 3.22 2.30; 1.74 14.04; 1.70 0.37; 1.63 3.50; 1.50 6.48; 1.49 6.44 |
| 1.812 | Ph | H | O | H | $CHCH_3$ | 1-methyl-1H-pyrazol-4-yl | [$CDCl_3$] 7.67 1.63; 7.66 3.31; 7.66 2.84; 7.65 1.87; 7.65 2.62; 7.64 3.71; 7.64 2.76; 7.62 0.37; 7.62 0.44; 7.61 0.34; 7.45 0.45; 7.45 1.02; 7.43 5.75; 7.43 5.92; 7.43 5.08; 7.42 6.12; 7.42 6.13; 7.40 1.18; 7.40 0.90; 7.40 0.67; 7.39 0.51; 7.30 3.91; 7.27 10.71; 7.26 11.57; 7.22 0.34; 6.98 0.98; 6.96 1.00; 5.07 0.95; 5.06 1.46; 5.04 0.99; 3.94 0.42; 3.88 14.61; 3.88 16.00; 3.87 3.31; 3.83 3.13; 3.83 3.14; 3.78 1.23; 3.78 1.26; 3.27 2.43; 3.27 2.66; 3.23 2.15; 3.23 2.40; 1.76 0.38; 1.74 1.00; 1.74 1.07; 1.71 13.35; 1.70 14.05; 1.66 0.46; 1.65 0.42; 1.64 3.83; 1.64 3.56; 1.51 0.66; 1.50 0.67; 1.49 0.62; 1.49 0.62; 1.46 6.37; 1.45 6.69; 1.44 6.51; 1.43 6.68; 0.01 4.67; 0.00 5.29 |
| 1.813 | 3,5-$Cl_2$—Ph | H | O | H | $CHCH_3$ | 1-methyl-1H-pyrazol-5-yl | |
| 1.814 | 3,5-$F_2$—Ph | H | O | H | $CHCH_3$ | 1-methyl-1H-pyrazol-5-yl | |
| 1.815 | 3-F—Ph | H | O | H | $CHCH_3$ | 1-methyl-1H-pyrazol-5-yl | |
| 1.816 | Ph | H | O | H | $CHCH_3$ | 1-methyl-1H-pyrazol-5-yl | |

TABLE 1-continued

Compounds of the general formula (I) according to the invention in which $R^2$ is hydrogen and $R^3$ is methyl and aryl is the radical

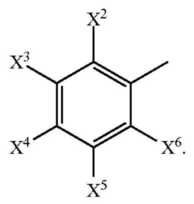

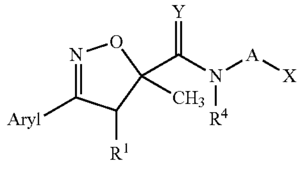

| No. | Aryl | $R^1$ | Y | $R^4$ | A | X | Physical data |
|---|---|---|---|---|---|---|---|
| 1.817 | 3,5-$Cl_2$—Ph | H | O | H | $CHCH_3$ | 1-methyl-3-(trifluoromethyl)-1H-pyrazol-4-yl | D1 |
| 1.818 | 3,5-$Cl_2$—Ph | H | O | H | $CHCH_3$ | 1-methyl-3-(trifluoromethyl)-1H-pyrazol-4-yl | D2 |
| 1.819 | 3,5-$F_2$—Ph | H | O | H | $CHCH_3$ | 1-methyl-5-(trifluoromethyl)-1H-pyrazol-4-yl | |
| 1.820 | 3,5-$Cl_2$—Ph | H | O | H | $CHCH_3$ | 1-propyl-1H-pyrazol-3-yl | |
| 1.821 | 3,5-$F_2$—Ph | H | O | H | $CHCH_3$ | 1-propyl-1H-pyrazol-3-yl | |
| 1.822 | 3,5-$Cl_2$—Ph | H | O | H | $CHCH_3$ | 1-propyl-1H-pyrazol-4-yl | |
| 1.823 | 3,5-$F_2$—Ph | H | O | H | $CHCH_3$ | 1-propyl-1H-pyrazol-4-yl | |
| 1.824 | 3-F—Ph | H | O | H | $CHCH_3$ | 1-propyl-1H-pyrazol-4-yl | |
| 1.825 | Ph | H | O | H | $CHCH_3$ | 1-propyl-1H-pyrazol-4-yl | |
| 1.826 | 3,5-$Cl_2$—Ph | H | O | H | $CHCH_3$ | 1-tert-butyl-1H-pyrazol-4-yl | |
| 1.827 | 3,5-$F_2$—Ph | H | O | H | $CHCH_3$ | 1-tert-butyl-1H-pyrazol-4-yl | |
| 1.828 | Ph | H | O | H | $CHCH_3$ | 1-tert-butyl-1H-pyrazol-4-yl | |
| 1.829 | 3,5-$F_2$—Ph | H | O | H | $CHCH_3$ | 2-chloropyridin-4-yl | |
| 1.830 | 3-F—Ph | H | O | H | $CHCH_3$ | 2-chloropyridin-4-yl | |
| 1.831 | 3,5-$Cl_2$—Ph | H | O | H | $CHCH_3$ | 2-methyl-1,3-thiazol-4-yl | |
| 1.832 | 3,5-$F_2$—Ph | H | O | H | $CHCH_3$ | 2-methyl-1,3-thiazol-4-yl | |
| 1.833 | 3,5-$Cl_2$—Ph | H | O | H | $CHCH_3$ | 3-(cyclopropyl-carbamoyl)-1,2-oxazol-5-yl | |
| 1.834 | 3,5-$Cl_2$—Ph | H | O | H | $CHCH_3$ | 3-(ethoxy-carbonyl)-1,2-oxazol-5-yl | |
| 1.835 | 3,5-$F_2$—Ph | H | O | H | $CHCH_3$ | 3-(methoxy-carbonyl)phenyl | |
| 1.836 | 3,5-$F_2$—Ph | H | O | H | $CHCH_3$ | 3,5-difluoropyridin-2-yl | |
| 1.837 | 3,5-$Cl_2$—Ph | H | O | H | $CHCH_3$ | 3-carboxy-1,2-oxazol-5-yl | |
| 1.838 | 3,5-$Cl_2$—Ph | H | O | H | $CHCH_3$ | 3-chloro-1-ethyl-1H-pyrazol-4-yl | |
| 1.839 | 3,5-$F_2$—Ph | H | O | H | $CHCH_3$ | 3-chloro-1-ethyl-1H-pyrazol-4-yl | |
| 1.840 | 3-F—Ph | H | O | H | $CHCH_3$ | 3-chloro-1-ethyl-1H-pyrazol-4-yl | |
| 1.841 | Ph | H | O | H | $CHCH_3$ | 3-chloro-1-ethyl-1H-pyrazol-4-yl | |

TABLE 1-continued

Compounds of the general formula (I) according to the invention in which $R^2$ is hydrogen and $R^3$ is methyl and aryl is the radical

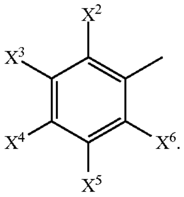

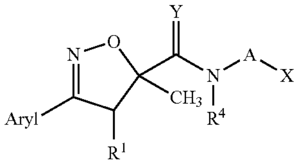

| No. | Aryl | $R^1$ | Y | $R^4$ | A | X | Physical data |
|---|---|---|---|---|---|---|---|
| 1.842 | 3,5-$Cl_2$—Ph | H | O | H | $CHCH_3$ | 3-chloro-1-isopropyl-1H-pyrazol-4-yl | |
| 1.843 | 3,5-$F_2$—Ph | H | O | H | $CHCH_3$ | 3-chloro-1-isopropyl-1H-pyrazol-4-yl | |
| 1.844 | 3,5-$F_2$—Ph | H | S | H | $CHCH_3$ | 3-chloro-1-isopropyl-1H-pyrazol-4-yl | |
| 1.845 | 3-F—Ph | H | O | H | $CHCH_3$ | 3-chloro-1-isopropyl-1H-pyrazol-4-yl | |
| 1.846 | 3,5-$Cl_2$—Ph | H | O | H | $CHCH_3$ | 3-chloro-1-methyl-1H-pyrazol-4-yl | |
| 1.847 | 3,5-$F_2$—Ph | H | O | H | $CHCH_3$ | 3-chloro-1-methyl-1H-pyrazol-4-yl | |
| 1.848 | 3,5-$F_2$—Ph | H | O | H | $CHCH_3$ | 3-chloropyridin-4-yl | |
| 1.849 | 3-F—Ph | H | O | H | $CHCH_3$ | 3-chloropyridin-4-yl | |
| 1.850 | 3,5-$Cl_2$—Ph | H | O | H | $CHCH_3$ | 3-cyclopropyl-1,2,4-oxadiazol-5-yl | |
| 1.851 | 3,5-$F_2$—Ph | H | O | H | $CHCH_3$ | 3-cyclopropyl-1,2,4-oxadiazol-5-yl | |
| 1.852 | 3,5-$F_2$—Ph | H | O | H | $CHCH_3$ | 3-furyl | |
| 1.853 | 3,5-$F_2$—Ph | H | O | H | $CHCH_3$ | 3-methyl-1H-pyrazol-4-yl | |
| 1.854 | 3-$CF_3O$—Ph | H | O | H | $CHCH_3$ | 3-methyl-1-propyl-1H-pyrazol-4-yl | |
| 1.855 | 3,5-$Cl_2$—Ph | H | O | H | $CHCH_3$ | 3-methyl-1-propyl-1H-pyrazol-4-yl | |
| 1.856 | 3,5-$F_2$—Ph | H | O | H | $CHCH_3$ | 3-methyl-1-propyl-1H-pyrazol-4-yl | |
| 1.857 | 3-Cl-4-F—Ph | H | O | H | $CHCH_3$ | 3-methyl-1-propyl-1H-pyrazol-4-yl | |
| 1.858 | 3-Cl-5-$CF_3O$—Ph | H | O | H | $CHCH_3$ | 3-methyl-1-propyl-1H-pyrazol-4-yl | |
| 1.859 | 3-Cl-5-F—Ph | H | O | H | $CHCH_3$ | 3-methyl-1-propyl-1H-pyrazol-4-yl | |
| 1.860 | 3-Cl-5-Me—Ph | H | O | H | $CHCH_3$ | 3-methyl-1-propyl-1H-pyrazol-4-yl | |
| 1.861 | 3-F-5-Me—Ph | H | O | H | $CHCH_3$ | 3-methyl-1-propyl-1H-pyrazol-4-yl | |

TABLE 1-continued

Compounds of the general formula (I) according to the invention in which $R^2$ is hydrogen and $R^3$ is methyl and aryl is the radical

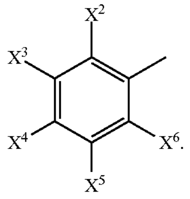

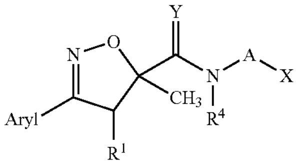

| No. | Aryl | $R^1$ | Y | $R^4$ | A | X | Physical data |
|---|---|---|---|---|---|---|---|
| 1.862 | 3-F—Ph | H | O | H | $CHCH_3$ | 3-methyl-1-propyl-1H-pyrazol-4-yl | |
| 1.863 | 3-Me—Ph | H | O | H | $CHCH_3$ | 3-methyl-1-propyl-1H-pyrazol-4-yl | |
| 1.864 | 4-Cl-3,5-$F_2$—Ph | H | O | H | $CHCH_3$ | 3-methyl-1-propyl-1H-pyrazol-4-yl | |
| 1.865 | Ph | H | O | H | $CHCH_3$ | 3-methyl-1-propyl-1H-pyrazol-4-yl | |
| 1.866 | 3,5-$Cl_2$—Ph | H | O | H | $CHCH_3$ | 4-(methoxy-carbonyl)phenyl | |
| 1.867 | 3,5-$Cl_2$—Ph | H | O | H | $CHCH_3$ | 4-(trifluoromethyl)-1,3-thiazol-2-yl | |
| 1.868 | 3,5-$F_2$—Ph | H | O | H | $CHCH_3$ | 4-(trifluoromethyl)-1,3-thiazol-2-yl | |
| 1.869 | 3-F—Ph | H | O | H | $CHCH_3$ | 4-(trifluoromethyl)-1,3-thiazol-2-yl | |
| 1.870 | 3,5-$Cl_2$—Ph | H | O | H | $CHCH_3$ | 4,5-dimethyl-1,3-thiazol-2-yl | [$CDCl_3$] 7.54 4.14; 7.53 4.10; 7.52 3.16; 7.52 2.93; 7.42 1.34; 7.42 2.61; 7.41 2.13; 7.41 0.76; 7.38 0.77; 7.37 0.69; 7.36 0.69; 7.26 24.06; 5.23 0.93; 5.21 1.37; 5.20 0.97; 3.84 1.59; 3.80 1.84; 3.79 1.19; 3.75 1.36; 3.22 1.32; 3.21 1.77; 3.17 1.15; 3.16 1.56; 2.32 7.49; 2.30 7.92; 2.23 16.00; 1.75 7.06; 1.74 9.55; 1.61 3.91; 1.60 2.63; 1.59 3.99; 1.56 4.81; 1.54 4.77; 0.00 4.89 |
| 1.871 | 3,5-$F_2$—Ph | H | O | H | $CHCH_3$ | 4,5-dimethyl-1,3-thiazol-2-yl | [$CDCl_3$] 7.38 0.96; 7.36 0.83; 7.26 15.75; 7.26 26.00; 7.19 1.82; 7.18 1.84; 7.18 2.00; 7.17 2.24; 7.17 2.87; 7.17 3.32; 7.16 1.80; 7.16 1.42; 7.15 1.65; 7.15 1.35; 7.15 1.14; 6.91 0.38; 6.90 0.83; 6.90 0.74; 6.89 0.59; 6.89 0.79; 6.88 1.64; 6.88 1.41; 6.87 0.62; 6.87 0.46; 6.86 0.84; 6.86 0.70; 5.25 0.38; 5.24 1.41; 5.22 1.98; 5.20 1.32; 5.18 0.37; 3.84 2.11; 3.80 2.49; 3.79 1.68; 3.75 1.85; 3.22 1.86; 3.21 2.32; 3.18 1.61; 3.17 2.04; 2.32 9.49; 2.30 10.22; 2.23 16.00; 1.75 9.87; 1.74 12.63; 1.61 5.02; 1.59 5.46; 1.59 5.55; 1.56 6.27; 1.55 6.17; 0.00 3.99; 0.00 6.40 |

TABLE 1-continued

Compounds of the general formula (I) according to the invention in which $R^2$ is hydrogen and $R^3$ is methyl and aryl is the radical

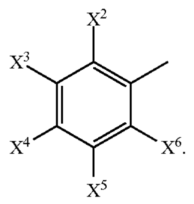

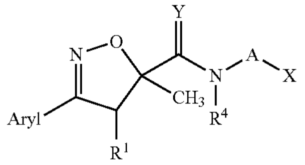

| No. | Aryl | $R^1$ | Y | $R^4$ | A | X | Physical data |
|---|---|---|---|---|---|---|---|
| 1.872 | 3,5-$Cl_2$—Ph | H | O | H | $CHCH_3$ | 4-chloro-1-methyl-1H-pyrazol-3-yl | |
| 1.873 | 3,5-$F_2$—Ph | H | O | H | $CHCH_3$ | 4-chloro-1-methyl-1H-pyrazol-3-yl | |
| 1.874 | 3-F—Ph | H | O | H | $CHCH_3$ | 4-chloro-1-methyl-1H-pyrazol-3-yl | |
| 1.875 | 3,5-$F_2$—Ph | H | O | H | $CHCH_3$ | 4-chloro-1-methyl-1H-pyrazol-5-yl | |
| 1.876 | 3,5-$Cl_2$—Ph | H | O | H | $CHCH_3$ | 5-chloro-1-methyl-1H-pyrazol-4-yl | |
| 1.877 | 3,5-$F_2$—Ph | H | O | H | $CHCH_3$ | 5-chloro-1-methyl-1H-pyrazol-4-yl | |
| 1.878 | 3,5-$F_2$—Ph | H | S | H | $CHCH_3$ | 5-chloro-1-methyl-1H-pyrazol-4-yl | |
| 1.879 | 3-F—Ph | H | O | H | $CHCH_3$ | 5-chloro-1-methyl-1H-pyrazol-4-yl | |
| 1.880 | Ph | H | O | H | $CHCH_3$ | 5-chloro-1-methyl-1H-pyrazol-4-yl | |
| 1.881 | 3,5-$Cl_2$—Ph | H | O | H | $CHCH_3$ | 5-methoxy-1,3-dimethyl-1H-pyrazol-4-yl | |
| 1.882 | 3,5-$F_2$—Ph | H | O | H | $CHCH_3$ | 5-methoxy-1,3-dimethyl-1H-pyrazol-4-yl | |
| 1.883 | 3-F—Ph | H | O | H | $CHCH_3$ | 5-methoxy-1,3-dimethyl-1H-pyrazol-4-yl | |
| 1.884 | 3,5-$Cl_2$—Ph | H | O | H | $CHCH_3$ | 5-methyl-1,2,4-oxadiazol-3-yl | |
| 1.885 | 3,5-$F_2$—Ph | H | O | H | $CHCH_3$ | 5-methyl-1,2,4-oxadiazol-3-yl | |
| 1.886 | 3,5-$Cl_2$—Ph | H | O | H | $CHCH_3$ | 5-methyl-1,2-oxazol-3-yl | |
| 1.887 | 3,5-$Cl_2$—Ph | H | O | H | $CHCH_3$ | 5-methyl-1,3-thiazol-2-yl | [$CDCl_3$] 7.54 6.64; 7.53 8.05; 7.53 4.80; 7.52 6.80; 7.52 4.83; 7.52 7.50; 7.51 4.48; 7.43 2.35; 7.42 3.96; 7.42 4.08; 7.42 3.82; 7.41 4.72; 7.41 3.30; 7.40 1.17; 7.38 1.02; 7.36 2.73; 7.35 3.46; 7.31 0.53; 7.29 2.37; 7.29 3.09; 7.29 2.05; 7.27 0.37; 7.27 0.62; 7.27 0.72; 7.27 0.79; 7.27 0.82; 7.27 0.84; 7.26 137.73; 7.26 86.19; 7.21 0.94; 7.21 0.42; 7.00 0.80; 7.00 0.50; 5.31 0.49; 5.30 1.04; 5.30 0.65; 5.29 1.79; 5.27 2.64; 5.25 |

TABLE 1-continued

Compounds of the general formula (I) according to the invention in which $R^2$ is hydrogen and $R^3$ is methyl and aryl is the radical

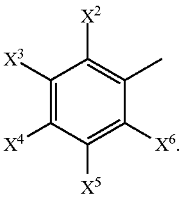

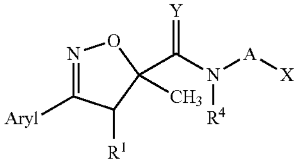

| No. | Aryl | $R^1$ | Y | $R^4$ | A | X | Physical data |
|---|---|---|---|---|---|---|---|
| | | | | | | | 1.93; 5.23 0.54; 3.85 2.68; 3.81 3.06; 3.79 2.54; 3.75 2.83; 3.23 2.75; 3.22 2.97; 3.19 2.39; 3.17 2.63; 2.45 9.25; 2.45 13.48; 2.37 8.38; 2.36 12.33; 2.01 0.63; 2.01 0.40; 1.76 14.48; 1.74 16.00; 1.63 7.29; 1.62 7.35; 1.59 7.90; 1.57 7.99; 1.56 36.32; 1.56 26.58; 1.26 0.37; 0.01 0.97; 0.01 0.69; 0.00 34.80; 0.00 20.73; −0.01 1.68 |
| 1.888 | 3,5-$F_2$—Ph | H | O | H | $CHCH_3$ | 5-methyl-1,3-thiazol-2-yl | [$CDCl_3$] 7.52 0.57; 7.44 0.38; 7.42 0.47; 7.41 0.67; 7.39 0.62; 7.36 2.34; 7.35 2.36; 7.31 0.35; 7.29 1.57; 7.29 1.63; 7.26 97.78; 7.19 1.65; 7.19 2.08; 7.18 1.21; 7.17 2.15; 7.17 2.72; 7.17 2.51; 7.17 2.34; 7.16 0.91; 7.15 1.49; 7.15 1.19; 7.00 0.56; 6.92 0.42; 6.91 0.81; 6.90 0.68; 6.90 0.86; 6.89 1.64; 6.88 1.29; 6.88 0.56; 6.87 0.50; 6.87 0.83; 6.86 0.64; 5.29 1.08; 5.27 1.54; 5.26 1.11; 3.84 2.75; 3.80 3.15; 3.79 1.83; 3.75 2.06; 3.23 2.02; 3.22 2.95; 3.19 1.76; 3.18 2.61; 2.45 8.88; 2.45 9.00; 2.36 5.78; 2.36 5.87; 2.05 0.59; 2.01 0.44; 1.76 10.58; 1.75 16.00; 1.63 5.15; 1.62 5.14; 1.59 7.73; 1.57 7.77; 1.56 19.07; 1.26 0.39; 0.01 0.76; 0.00 26.17; −0.01 0.88 |
| 1.889 | 3,5-$Cl_2$—Ph | H | O | H | $CHCH_3$ | 5-methyl-1-propyl-1H-pyrazol-4-yl | |
| 1.890 | 3,5-$F_2$—Ph | H | O | H | $CHCH_3$ | 5-methyl-1-propyl-1H-pyrazol-4-yl | |
| 1.891 | 3-F—Ph | H | O | H | $CHCH_3$ | 5-methyl-1-propyl-1H-pyrazol-4-yl | |
| 1.892 | Ph | H | O | H | $CHCH_3$ | 5-methyl-1-propyl-1H-pyrazol-4-yl | |
| 1.893 | 3,5-$F_2$—Ph | H | O | H | $CHCH_3$ | 6-chloropyridin-3-yl | |
| 1.894 | 3,5-$F_2$—Ph | H | O | H | $CHCH_3$ | furan-2-yl | |
| 1.895 | 3,5-$Cl_2$—Ph | H | O | H | $CHCH_3$ | pyridin-2-yl | |
| 1.896 | 3,5-$F_2$—Ph | H | O | H | $CHCH_3$ | pyridin-2-yl | |
| 1.897 | 3,5-$F_2$—Ph | H | O | H | $CHCH_3$ | pyridin-3-yl | |
| 1.898 | 3-F—Ph | H | O | H | $CHCH_3$ | pyridin-3-yl | |
| 1.899 | 3,5-$F_2$—Ph | H | O | H | $CHCH_3$ | pyridin-4-yl | |
| 1.900 | 3-F—Ph | H | O | H | $CHCH_3$ | pyridin-4-yl | |
| 1.901 | 3,5-$Cl_2$—Ph | H | O | H | $CHCH_3$ | pyrimidin-2-yl | |
| 1.902 | 3,5-$F_2$—Ph | H | O | H | $(CH_2)_3$ | 1-ethyl-3-methyl-1H-pyrazol-4-yl | [$CDCl_3$] 7.26 32.54; 7.18 0.33; 7.17 1.62; 7.16 1.21; 7.16 |

TABLE 1-continued
Compounds of the general formula (I) according to the invention in which $R^2$ is hydrogen and $R^3$ is methyl and aryl is the radical
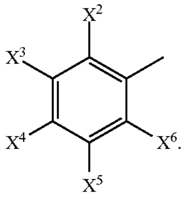
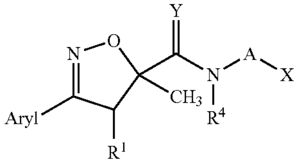
| No. | Aryl | $R^1$ | Y | $R^4$ | A | X | Physical data |
|---|---|---|---|---|---|---|---|
| | | | | | | | 1.90; 7.16 1.11; 7.15 1.07; 7.15 1.91; 7.14 1.62; 7.11 3.28; 6.91 0.43; 6.90 0.75; 6.89 0.39; 6.88 0.85; 6.88 1.49; 6.87 0.74; 6.86 0.48; 6.86 0.80; 6.85 0.50; 6.83 0.48; 4.07 1.28; 4.05 3.93; 4.03 3.97; 4.01 1.32; 3.80 2.73; 3.75 3.11; 3.36 0.42; 3.34 0.78; 3.32 1.00; 3.31 0.81; 3.29 0.37; 3.28 0.36; 3.26 0.44; 3.26 0.81; 3.25 0.92; 3.23 0.69; 3.21 0.44; 3.20 2.88; 3.16 2.52; 2.41 1.47; 2.39 2.44; 2.37 1.72; 2.15 15.84; 1.77 0.57; 1.75 1.65; 1.74 2.22; 1.73 16.00; 1.72 1.86; 1.70 0.48; 1.58 1.07; 1.44 4.93; 1.43 10.31; 1.41 4.87; 1.26 0.52; 0.01 0.40; 0.01 0.44; 0.00 16.62; 0.00 18.05; 0.00 1.48; 0.00 1.02; 0.00 0.67; 0.00 0.47; −0.01 0.37; −0.01 0.61; −0.01 0.59 |
| 1.903 | 3,5-$Cl_2$—Ph | H | O | H | $(CH_2)_3$ | 1H-pyrazol-1-yl | [$CDCl_3$] 7.53 2.61; 7.52 2.66; 7.51 7.25; 7.51 7.34; 7.41 2.16; 7.41 3.44; 7.40 1.66; 7.39 2.59; 7.38 2.58; 7.26 97.71; 7.07 0.76; 7.00 0.53; 6.24 1.96; 6.24 3.01; 6.23 1.71; 4.19 1.47; 4.18 1.39; 4.17 2.82; 4.17 2.59; 4.15 1.49; 4.15 1.44; 3.77 2.74; 3.72 3.09; 3.35 0.68; 3.33 0.96; 3.32 1.35; 3.30 1.21; 3.28 0.46; 3.26 0.46; 3.24 1.12; 3.23 1.22; 3.21 0.81; 3.19 0.62; 3.18 3.16; 3.13 2.56; 2.11 0.57; 2.09 1.98; 2.08 2.81; 2.06 1.82; 2.04 0.56; 1.70 16.00; 1.55 62.16; 0.01 1.70; 0.00 52.95; −0.01 2.15 |
| 1.904 | 3,5-$F_2$—Ph | H | O | H | $(CH_2)_3$ | 1H-pyrazol-1-yl | [$CDCl_3$] 7.53 2.65; 7.52 2.73; 7.39 2.68; 7.38 2.63; 7.26 41.82; 7.18 0.35; 7.17 1.80; 7.16 2.48; 7.15 2.44; 7.14 2.02; 7.13 0.38; 7.07 0.77; 6.90 0.42; 6.90 0.74; 6.89 0.43; 6.88 0.88; 6.88 1.49; 6.87 0.81; 6.86 0.48; 6.85 0.74; 6.85 0.41; 6.24 1.78; 6.24 2.99; 6.23 1.76; 4.19 1.53; 4.18 1.54; 4.17 2.80; 4.17 2.85; 4.15 1.51; 4.15 1.63; 3.76 2.67; 3.72 3.06; 3.35 0.65; 3.33 0.96; 3.32 1.36; 3.30 1.26; 3.29 0.48; 3.26 0.43; 3.25 1.18; 3.23 1.24; 3.21 0.87; 3.20 0.62; 3.18 3.09; 3.14 2.55; 2.11 0.58; 2.10 1.96; 2.08 2.83; 2.06 1.88; 2.04 1.13; 1.70 16.00; 1.56 36.92; 1.26 0.58; 0.00 22.43; −0.01 1.16 |

TABLE 1-continued

Compounds of the general formula (I) according to the invention in which $R^2$ is hydrogen and $R^3$ is methyl and aryl is the radical

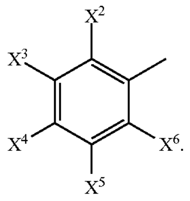

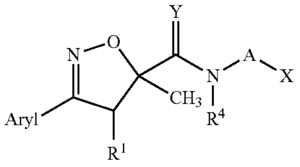

| No. | Aryl | $R^1$ | Y | $R^4$ | A | X | Physical data |
|---|---|---|---|---|---|---|---|
| 1.905 | 3-F—Ph | H | O | H | $(CH_2)_3$ | 1H-pyrazol-1-yl | [$CDCl_3$] 1.70 (s, 3H); 2.08 (m, 2H); 3.20 (d, 1H); 3.22 (m, 1H); 3.31 (m, 1H); 3.78 (d, 1H); 4.17 (m, 2H); 6.23 (t, 1H); 7.12 (m, 2H); 7.38 (m, 4H); 7.51 (s, 1H). |
| 1.906 | Ph | H | O | H | $(CH_2)_3$ | 1H-pyrazol-1-yl | [$CDCl_3$] 1.70 (s, 3H); 2.07 (m, 2H); 3.22 (m, 2H); 3.30 (m, 1H); 3.80 (d, 1H); 4.17 (m, 2H); 6.22 (t, 1H); 7.11 (brt, 1H); 7.42 (m, 4H); 7.51 (s, 1H); 7.63 (d, 2H). |
| 1.907 | 3-Me—Ph | H | O | H | $(CH_2)_3$ | 1H-pyrazol-1-yl | [$CDCl_3$] 7.52 2.15; 7.51 2.41; 7.51 2.38; 7.47 2.18; 7.47 2.06; 7.42 1.07; 7.41 1.39; 7.38 2.21; 7.38 2.47; 7.31 0.98; 7.29 2.23; 7.27 1.47; 7.27 11.66; 7.25 1.58; 7.23 0.75; 7.11 0.65; 6.23 1.81; 6.23 3.02; 6.22 2.16; 4.17 1.41; 4.17 1.54; 4.15 2.76; 4.15 3.09; 4.14 1.43; 4.13 1.61; 3.81 2.81; 3.77 3.21; 3.33 0.53; 3.31 0.81; 3.29 1.25; 3.28 1.17; 3.26 0.47; 3.25 0.52; 3.24 3.91; 3.22 1.17; 3.21 0.69; 3.20 0.75; 3.20 2.67; 3.19 0.67; 2.37 10.83; 2.11 0.60; 2.09 2.22; 2.07 3.20; 2.06 2.07; 2.04 0.49; 1.76 2.60; 1.70 16.00 |
| 1.908 | 3,5-$Cl_2$—Ph | H | O | H | $(CH_2)_3$ | Imidazol-2-yl | [$CDCl_3$] 1.74 (s, 3H); 2.01 (m, 2H); 3.18 (d, 1H); 3.24 (m, 1H); 3.32 (m, 1H); 3.76 (d, 1H); 3.94 (t, 2H); 6.88 (t br, 1H); 7.07 (s, 1H); 7.43 (m, 1H); 7.48 (s, 1H); 7.52 (m, 1H). |
| 1.909 | 3,5-$Cl_2$—Ph | H | O | H | $(CH_2)_3$ | phenyl | [$CDCl_3$] 1.51 (s, 3H); (1.99 m, 2H); 2.62 (t, 2H); 2.93 (m, 2H); 2.97 (d, 1H); 3.68 (d, 1H); 7.08-7.27 (m, 6H), 7.33 (m, 1H); 7.42 (m, 2H). |
| 1.910 | 3,5-$F_2$—Ph | H | O | H | $CH(CH_2CH_3)$ | 1-methyl-1H-pyrazol-4-yl | [$CDCl_3$] 0.95 (t, 3H); 1.74 (s, 3H); 1.83 (m, 2H); 3.18 (d, 1H); 3.75 (d, 1H); 3.81 (s, 3H); 4.84 (q, 1H); 6.87 (m, 2H); 7.12 (m, 2H); 7.18 (s, 1H); 7.31 (s, 1H). |
| 1.911 | 3,5-$F_2$—Ph | H | O | H | $CH(CH_2CH_3)$ | 1-methyl-1H-pyrazol-4-yl | [$CDCl_3$] 0.85 (t, 3H); 1.69 (s, 3H); 1.75 (m, 1H); 1.80 (m, 1H); 3.19 (d, 1H); 3.80 (d, 1H); 3.88 (s, 3H); 4.83 (q, 1H); 6.88 (m, 2H); 7.16 (m, 2H); 7.29 (s, 1H); 7.40 (s, 1H). |
| 1.912 | 3,5-$Cl_2$—Ph | H | O | H | $CH(CH_2CH_3)$ | 1-methyl-1H-pyrazol-4-yl | [$CDCl_3$] 0.96 (t, 3H); 1.75 (s, 3H); 1.82 (m, 2H); 3.17 (d, 1H); 3.75 (d, 1H); 3.81 (s, 3H); 4.85 (q, 1H); 6.86 (d, 1H); 7.18 |

TABLE 1-continued

Compounds of the general formula (I) according to the invention in which $R^2$ is hydrogen and $R^3$ is methyl and aryl is the radical

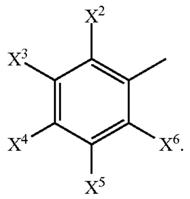

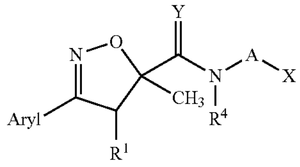

| No. | Aryl | $R^1$ | Y | $R^4$ | A | X | Physical data |
|---|---|---|---|---|---|---|---|
| | | | | | | | (d, 1H); 7.17 (s, 1H); 7.31 (s, 1H); 7.40 (t, 1H); 7.49 (m, 2H). |
| 1.913 | 3,5-$Cl_2$—Ph | H | O | H | $CH(CH_2CH_3)$ | 1-methyl-1H-pyrazol-4-yl | [$CDCl_3$] 0.86 (t, 3H); 1.68 (s, 3H); 1.75 (m, 1H); 1.81 (m, 1H); 3.19 (d, 1H); 3.80 (d, 1H); 3.88 (s, 3H); 4.83 (q, 1H); 6.87 (d, 1H); 7.29 (s, 1H); 7.41 (m, 2H); 7.52 (m, 2H). |
| 1.914 | 3-F—Ph | H | O | H | $CH(CH_2CH_3)$ | 1-methyl-1H-pyrazol-4-yl | [$CDCl_3$] 0.96 (t, 3H); 1.75 (s, 3H); 1.82 (m, 2H); 3.21 (d, 1H); 3.78 (d, 1H); 3.79 (s, 3H); 4.84 (q, 1H); 6.92 (d, 1H); 7.12 (m, 1H); 7.17 (s, 1H); 7.31 (s, 1H); 7.37 (m, 4H). |
| 1.915 | 3-F—Ph | H | O | H | $CH(CH_2CH_3)$ | 1-methyl-1H-pyrazol-4-yl | [$CDCl_3$] 0.85 (t, 3H); 1.69 (s, 3H); 1.73 (m, 1H); 1.80 (m, 1H); 3.22 (d, 1H); 3.82 (d, 1H); 3.88 (s, 3H); 4.82 (q, 1H); 6.91 (d, 1H); 7.13 (m, 1H); 7.28 (s, 1H); 7.39 (m, 4H). |
| 1.916 | Ph | H | O | H | $CH(CH_2CH_3)$ | 1-methyl-1H-pyrazol-4-yl | diastereomer D1: [$CDCl_3$] 0.95 (t, 3H); 1.75 (s, 3H); 1.82 (m, 2H); 3.22 (d, 1H); 3.76 (s, 3H); 3.80 (d, 1H); 4.85 (q, 1H); 6.96 (d, 1H); 7.16 (s, 1H); 7.31 (s, 1H); 7.41 (m, 3H); 7.62 (d, 2H). diastereomer D2: [$CDCl_3$] 0.84 (t, 3H); 1.70 (s, 3H); 1.72 (m, 1H); 1.79 (m, 1H); 3.26 (d, 1H); 3.85 (d, 1H); 3.88 (s, 3H); 4.85 (q, 1H); 6.95 (d, 1H); 7.29 (s, 1H); 7.42 (m, 4H); 7.64 (d, 2H). |
| 1.917 | 3,5-$Cl_2$—Ph | H | O | H | $C(CH_3)_2C{\equiv}C$ | 4-chlorophenyl | [$CDCl_3$] 1.70 (s, 6H), 3.18 (d, 1H); 3.80 (d, 1H); 6.93 (s, 1H); 7.22 (m, 1H); 7.24 (m, 1H); 7.32 (m, 2H); 7.41 (m, 1H); 7.52 (d, 2H) |
| 1.918 | 3,5-$Cl_2$—Ph | H | O | H | $CH(CH_3)CH_2O$ | 3,5-dichlorophenyl | [$CDCl_3$] 1.29 (d, 3H); 1.71 (s, 3H); 3.18 (d, 1H); 3.82 (d, 1H); 3.95 (m, 2H); 4.32 (m, 2H); 6.83 (s, 2H); 6.91 (d, 1H); 6.98 (s, 1H); 7.43 (s, 1H); 7.53 (s, 2H). |
| 1.919 | Ph | H | O | H | $CH(CH_3)CH_2O$ | 3,5-dichlorophenyl | [$CDCl_3$] 1.28 (dd, 3H), 1.72 (d, 3H); 3.24 (d, 1H); 3.78 (m, 1H); 3.88 (m, 1H); 3.93 (m, 1H); 4.30 (m, 1H); 6.72 (s, 1H); 6.84 (dd, 1H); 6.98 (m, 1H); 7.42 (m, 4H); 7.58 (d, 1H); 7.63 (m, 1H) |
| 1.920 | 3,5-$Cl_2$—Ph | H | O | H | $CH(CH_3)CH_2O$ | phenyl | [$CDCl_3$] 1.29 (ds, 3H); 1.69 (s, 3H); 3.17 (d, 1H); 3.80 (d, 1H); 3.97 (m, 2H); 4.31 (m, 1H); 6.90-7.00 (m, 4H); 7.25-7.30 |

TABLE 1-continued

Compounds of the general formula (I) according to the invention in which $R^2$ is hydrogen and $R^3$ is methyl and aryl is the radical

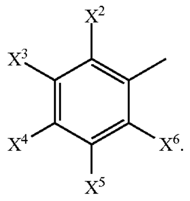

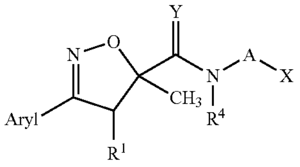

| No. | Aryl | $R^1$ | Y | $R^4$ | A | X | Physical data |
|---|---|---|---|---|---|---|---|
| | | | | | | | (m, 2H); 7.41 (m, 1H); 7.52 (m, 2H). |
| 1.921 | 3,5-$Cl_2$—Ph | H | O | H | $CH(CONHCH_3)$ | 4-chlorophenyl | diastereomer D1: [$CDCl_3$] 1.63 (s, 3H); 2.79 (d, 3H): 3.13 (d, 1H); 3.62 (d, 1H); 5.22 (d, 1H); 5.43 (s br, 1H); 7.25 (m, 4H); 7.33 (m, 2H), 7.40 (m, 1H); 7.98 (d, 1H). diastereomer D2: [$CDCl_3$] 1.75 (s, 3H); 2.82 (d, 3H): 3.17 (d, 1H); 3.75 (d, 1H); 5.24 (d, 1H); 5.43 (s br, 1H); 7.25 (m, 4H); 7.47 (m, 1H), 7.53 (m, 2H); 8.03 (d, 1H). |
| 1.922 | 3,5-$Cl_2$—Ph | H | O | H | $CH(CONHCH_3)CH_2$ | 4-chlorophenyl | diastereomer D1: [$CDCl_3$] 1.57 (s, 3H); 2.72 (d, 3H); 3.10 (m, 2H); 3.16 (d, 1H); 3.70 (d, 1H); 4.45 (m, 1H); 5.52 (s br, 1H); 7.03 (m, 4H); 7.28 (br, 1H); 7.42 (m, 1H); 7.50 (m, 2H). diastereomer D2: [$CDCl_3$] 1.69 (s, 3H); 2.82 (d, 3H); 2.88 (m, 2H); 3.07 (d, 1H); 3.34 (d, 1H); 4.55 (m, 1H); 5.73 (s br, 1H); 7.18 (m, 2H); 7.23 (m, 2H); 7.28 (br, 1H); 7.51 (m, 1H); 7.53 (m, 2H). |
| 1.923 | 3,5-$Cl_2$—Ph | H | O | H | $CH(CONHCH_3)CH_2$ | phenyl | diastereomer D1: [$CDCl_3$] 1.52 (s, 3H); 2.70 (d, 3H): 2.94 (m, 1H); 3.10 (m, 1H); 3.13 (d, 1H); 3.72 (d, 1H); 4.50 (m, 1H); 5.49 (s br, 1H); 7.08 (m, 2H); 7.10 (s br, 1H); 7.26 (m, 3H), 7.42 (m, 1H); 7.48 (m, 2H). diastereomer D2: [$CDCl_3$] 1.68 (s, 3H); 2.77 (d, 3H): 3.10 (m, 2H); 3.33 (d, 1H); 4.55 (m, 1H); 5.70 (s br, 1H); 7.08 (m, 2H); 7.20 (s br, 1H); 7.26 (m, 3H), 7.44 (m, 3H). |
| 1.924 | 3,5-$Cl_2$—Ph | H | O | H | $CH(COOCH_3)$ | 4-chlorophenyl | |
| 1.925 | 3,5-$Cl_2$—Ph | H | O | H | $CH(COOCH_3)$ | phenyl | [$CDCl_3$] 1.67, 1.79 (2 × s, ratio 1:1, 3H); 3.16, 3.20 (2 × d, ratio 1:1, 1H); 3.70, 3.75 (2 × s, ratio 1:1, 3H); 3.72, 3.79 (2 × d, ratio 1:1, 1H); 5.46 (m, 1H); 7.30-7.70 (m, 8H). |
| 1.926 | 3,5-$Cl_2$—Ph | H | O | H | $CH(COOCH_3)CH_2$ | 4-chlorophenyl | diastereomer D1 plus D2: [$CDCl_3$] 1.62 (s, 3H); 1.68 (s, 3H); 2.87 (m, 1H); 3.04 (m, 1H); 3.07 (d, 1H); 3.14 (d, 1H); 3.16 (m, 2H); 3.40 (d, 1H); 3.69 (s, 3H); 3.72 (d, 1H); 3.77 (s, 3H); 4.78 (m, 1H); 4.86 (m, 1H); 6.93 (d, 2H); 6.99 (d, 2H); |

TABLE 1-continued

Compounds of the general formula (I) according to the invention in which $R^2$ is hydrogen and $R^3$ is methyl and aryl is the radical

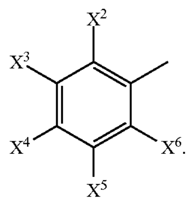

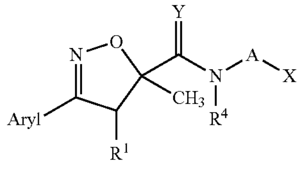

| No. | Aryl | $R^1$ | Y | $R^4$ | A | X | Physical data |
|---|---|---|---|---|---|---|---|
| | | | | | | | 7.08 (d, 2H), 7.18 (d, 2H); 7.40 (s, 1H); 7.47 (s, 1H), 7.50 (s, 2H); 7.50 (s, 2H). |
| 1.927 | 3,5-$Cl_2$—Ph | H | O | H | $CH(COOCH_3)CH_2$ | phenyl | diastereomer D1: [$CDCl_3$] 1.58 (s, 3H); 3.08 (m, 1H); 3.13 (d, 1H); 3.20 (m, 1H); 3.70 (s, 3H); 3.72 (d, 1H); 4.80 (m, 1H); 7.00 (m, 1H); 7.08 (m, 3H); 7.14 (m, 1H), 7.18 (s, br, 1H); 7.40 (s, 1H); 7.49 (s, 2H). diastereomer D2: [$CDCl_3$] 1.68 (s, 3H); 2.94 (m, 1H); 3.08 (d, 1H); 3.20 (m, 1H); 3.80 (s, 3H); 4.88 (m, 1H); 7.00 (m, 1H); 7.08 (m, 3H); 7.14 (m, 1H), 7.25 (s, br, 1H); 7.40 (s, 1H); 7.49 (s, 2H). |
| 1.928 | 3,5-$Cl_2$—Ph | H | O | H | CH(COOH) | 4-chlorophenyl | diastereomer D1: [$CDCl_3$] 1.68 (s, 3H); 3.17 (d, 1H); 3.70 (d, 1H); 5.49 (d, 1H); 7.24 (m, 2H); 7.30 (m, 2H), 7.36 (m, 1H); 7.49 (m, 2H); 7.68 (d, 1H). diastereomer D2: [$CDCl_3$] 1.78 (s, 3H); 3.20 (d, 1H); 3.78 (d, 1H); 5.49 (d, 1H); 7.24 (m, 2H); 7.30 (m, 2H), 7.40 (m, 1H); 7.53 (m, 2H); 7.72 (d, 1H). |
| 1.929 | 3,5-$Cl_2$—Ph | H | O | H | CH(CO2OH) | phenyl | diastereomer D1: [$CDCl_3$] 1.68 (s, 3H); 3.18 (d, 1H); 3.72 (d, 1H); 5.50 (d, 1H); 7.34 (m, 2H); 7.41 (m, 3H), 7.43 (m, 1H); 7.54 (m, 2H); 7.63 (d, 1H). diastereomer D2: [$CDCl_3$] 1.78 (s, 3H); 3.23 (d, 1H); 3.79 (d, 1H); 5.51 (d, 1H); 7.34 (m, 2H); 7.40 (m, 3H); 7.41 (m, 3H), 7.43 (m, 1H); 7.48 (m, 2H); 7.65 (d, 1H). |
| 1.930 | 3,5-$Cl_2$—Ph | H | O | H | $CH(COOH)CH_2$ | 4-chlorophenyl | diastereomer D1: [$CDCl_3$] 1.57 (s, 3H); 2.93 (m, 2H); 3.10 (d, 1H); 3.42 (d, 1H); 4.88 (m, 1H); 7.00 (m, 4H); 7.02 (s br, 1H); 7.42 (m, 1H); 7.46 (m, 2H). diastereomer D2: [$CDCl_3$] 1.68 (s, 3H); 3.09 (m, 1H); 3.17 (d, 1H); 3.29 (m, 1H); 3.73 (d, 1H); 4.80 (m, 1H); 7.12 (m, 2H); 7.18 (m, 2H); 7.30 (s br, 1H); 7.47 (m, 1H); 7.51 (m, 2H). |
| 1.931 | 3,5-$Cl_2$—Ph | H | O | H | $CH(CO_2H)CH_2$ | phenyl | diastereomer D1: [$CDCl_3$] 1.56 (s, 3H); 3.12 (m, 1H); 3.10 (d, 1H); 3.29 (m, 1H); 3.94 (d, 1H); 4.88 (m, 1H); 7.06 (m, 2H); 7.12-7.32 (m, 4H); 7.42 |

TABLE 1-continued

Compounds of the general formula (I) according to the invention in which $R^2$ is hydrogen and $R^3$ is methyl and aryl is the radical

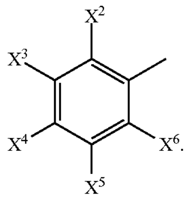

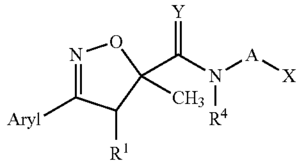

| No. | Aryl | $R^1$ | Y | $R^4$ | A | X | Physical data |
|---|---|---|---|---|---|---|---|
| | | | | | | | (m, 1H); 7.46 (m, 2H). diastereomer D2: [$CDCl_3$] 1.68 (s, 3H); 3.09 (m, 1H); 3.17 (d, 1H); 3.29 (m, 1H); 3.73 (d, 1H); 4.80 (m, 1H); 7.06 (m, 2H); 7.12-7.32 (m, 4H); 7.47 (m, 1H); 7.51 (m, 2H). |
| 1.932 | 3,5-$Cl_2$—Ph | H | O | H | CH(c-Pr)$CH_2$O | phenyl | [$CDCl_3$] 0.25-0.38 (m, 2H); 0.44-0.59 (m, 2H); 1.18 (m, 1H); 1.68 (s, 3H); 3.18 (d, 1H); 3.50 (m, 1H); 3.79 (d, 1H); 4.11 (m, 2H); 6.91-6.99 (m, 3H); 7.14 (br, 1H); 7.26-7.30 (m, 2H); 7.42 (m, 1H); 7.53 (m, 2H). |
| 1.933 | 3,5-$F_2$—Ph | H | O | H | $CH_2CH$═CH | 1-ethyl-3-methyl-1H-pyrazol-4-yl | [$CDCl_3$] 7.34 3.56; 7.27 0.34; 7.26 0.47; 7.26 0.71; 7.26 1.30; 7.26 38.58; 7.26 1.18; 7.26 0.76; 7.26 0.55; 7.26 0.42; 7.25 0.33; 7.19 0.33; 7.18 1.66; 7.17 1.13; 7.17 1.95; 7.17 1.20; 7.16 1.10; 7.16 2.00; 7.15 1.78; 7.14 0.37; 7.14 0.36; 6.91 0.73; 6.90 1.24; 6.90 0.79; 6.89 1.18; 6.88 1.75; 6.88 0.88; 6.87 0.52; 6.86 0.82; 6.85 0.41; 6.34 0.54; 6.34 1.08; 6.34 0.56; 6.30 0.63; 6.30 1.25; 6.30 0.65; 5.80 0.66; 5.79 1.47; 5.77 0.68; 5.76 0.57; 5.75 1.26; 5.73 0.60; 4.08 1.27; 4.08 0.36; 4.06 3.91; 4.05 4.16; 4.03 0.44; 4.03 1.40; 4.01 0.55; 4.01 0.54; 4.00 0.84; 3.99 0.88; 3.98 0.51; 3.98 0.51; 3.97 0.52; 3.97 0.52; 3.96 0.61; 3.95 0.78; 3.95 0.62; 3.94 0.51; 3.94 0.49; 3.82 2.77; 3.78 3.16; 3.22 2.95; 3.17 2.59; 2.24 16.00; 2.23 1.18; 2.16 0.41; 1.75 15.92; 1.74 1.30; 1.73 0.51; 1.57 17.92; 1.47 0.40; 1.46 5.11; 1.45 0.84; 1.44 10.90; 1.43 0.48; 1.43 0.52; 1.42 5.08; 0.01 0.55; 0.00 0.47; 0.00 0.79; 0.00 20.15; 0.00 0.92; 0.00 0.34; −0.01 0.57 |
| 1.934 | 3,5-$F_2$—Ph | H | O | H | $CH_2CH_2CONHCH_2$ | 1-ethyl-3-methyl-1H-pyrazol-4-yl | [DMSO-$D_6$] 1.39 (t, 3H); 1.52 (s, 3H); 2.04 (s, 3H); 2.25 (t, 2H); 3.29 (m, 2H); 3.32 (d, 1H); 3.70 (d, 1H); 3.98 (m, 4H); 7.39 (m, 3H); 7.45 (s, 1H); 8.05 (m, 2H). |
| 1.935 | 3,5-$Cl_2$—Ph | H | O | H | $CH_2CH_2O$ | 4-chlorophenyl | [$CDCl_3$] 1.72 (s, 3H); 3.18 (d, 1H); 3.57-3.72 (m, 2H); 3.75 (d, 1H); 4.00 (t, 2H); 6.79 (d, 2H); 7.20 (d, 2H); 7.20 (br, 1H); 7.40 (s, 1H); 7.49 (s, 2H). |

TABLE 1-continued
Compounds of the general formula (I) according to the invention in which $R^2$ is hydrogen and $R^3$ is methyl and aryl is the radical
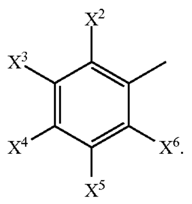
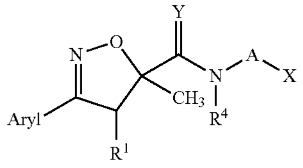
| No. | Aryl | $R^1$ | Y | $R^4$ | A | X | Physical data |
|---|---|---|---|---|---|---|---|
| 1.936 | 3,5-$Cl_2$—Ph | H | O | H | $CH_2CH_2O$ | phenyl | [$CDCl_3$] 1.72 (S, 3H); 3.18 (d, 1H); 3.58-3.77 (m, 2H); 3.77 (d, 1H); 4.05 (m, 2H); 6.88 (m, 2H); 6.92-6.99 (m, 1H); 7.20-7.28 (M, 2H); 7.40 (M, 1H); 7.49 (m, 2H). |
| 1.937 | Ph | H | O | H | $CH_2COH(CF_3)$ | 1-methyl-1H-1,2,4-triazol-5-yl | [$CDCl_3$] 7.83 6.36; 7.78 4.24; 7.63 2.23; 7.63 2.69; 7.63 2.84; 7.61 1.03; 7.61 3.18; 7.61 3.29; 7.56 1.32; 7.55 0.92; 7.54 1.84; 7.54 2.06; 7.54 2.14; 7.53 0.72; 7.52 2.34; 7.52 2.37; 7.52 2.64; 7.47 0.35; 7.47 0.44; 7.45 1.35; 7.45 1.70; 7.44 1.97; 7.43 5.27; 7.43 4.08; 7.42 3.92; 7.42 2.45; 7.41 3.42; 7.40 2.58; 7.40 1.26; 7.39 0.94; 7.39 0.65; 7.38 0.49; 7.31 0.53; 7.27 0.46; 7.27 0.57; 7.27 0.74; 7.26 100.80; 7.26 86.73; 7.21 0.39; 7.00 0.54; 6.25 5.69; 6.14 3.84; 4.29 0.65; 4.27 0.65; 4.25 1.21; 4.25 0.90; 4.24 1.24; 4.21 1.84; 4.20 1.86; 4.17 2.34; 4.15 2.38; 4.13 1.31; 4.12 1.09; 4.11 0.96; 4.09 16.00; 3.88 11.05; 3.74 2.90; 3.70 3.51; 3.65 1.97; 3.60 2.43; 3.28 3.37; 3.24 2.41; 3.24 2.93; 3.20 1.91; 2.04 3.35; 1.70 12.10; 1.60 17.88; 1.56 31.66; 1.56 24.86; 1.30 0.61; 1.28 1.91; 1.27 1.99; 1.26 3.02; 1.26 3.48; 1.26 2.90; 1.24 1.20; 1.24 1.03; 0.90 1.48; 0.88 4.11; 0.86 1.82; 0.01 1.02; 0.01 0.98; 0.01 0.57 |
| 1.938 | 3,5-$Cl_2$—Ph | H | O | H | $CH_2COH(CF_3)$ | 1-methyl-1H-1,2,4-triazol-5-yl | [$CDCl_3$] 7.85 5.98; 7.84 5.07; 7.80 4.22; 7.80 3.63; 7.52 1.71; 7.51 1.65; 7.50 8.10; 7.50 10.88; 7.49 7.80; 7.48 2.10; 7.43 4.95; 7.43 5.79; 7.43 4.72; 7.42 3.15; 7.42 6.85; 7.41 7.59; 7.31 0.35; 7.30 0.35; 7.29 0.56; 7.28 0.49; 7.28 0.81; 7.27 1.14; 7.27 1.43; 7.26 268.60; 7.26 202.07; 7.26 237.79; 7.25 2.02; 7.25 1.70; 7.24 0.98; 7.24 0.93; 7.24 0.60; 7.00 1.41; 6.99 1.31; 6.11 5.32; 6.04 3.83; 4.28 0.63; 4.27 0.74; 4.25 0.97; 4.25 1.36; 4.24 1.00; 4.23 1.38; 4.22 1.86; 4.20 1.84; 4.17 2.11; 4.16 1.87; 4.14 0.93; 4.12 0.86; 4.09 16.00; 3.95 11.40; 3.70 2.70; 3.65 3.21; 3.60 1.82; 3.56 2.26; 3.22 3.07; 3.19 2.34; 3.18 |

TABLE 1-continued
Compounds of the general formula (I) according to the invention in which $R^2$ is hydrogen and $R^3$ is methyl and aryl is the radical
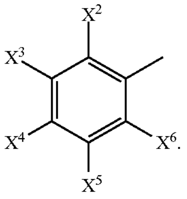
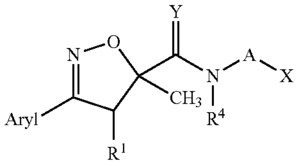
| No. | Aryl | $R^1$ | Y | $R^4$ | A | X | Physical data |
|---|---|---|---|---|---|---|---|
| | | | | | | | 2.57; 3.15 1.81; 3.14 1.70; 2.04 0.38; 1.70 11.69; 1.59 16.64; 1.59 14.58; 1.54 80.62; 1.54 60.66; 1.54 73.88; 1.32 0.91; 1.30 1.85; 1.26 8.92; 0.90 3.83; 0.88 8.90; 0.88 7.80; 0.86 4.15; 0.15 0.51; 0.00 110.55 |
| 1.939 | 3-F—Ph | H | O | H | $CH_2COH(CF_3)$ | 1-methyl-1H-1,2,4-triazol-5-yl | [$CDCl_3$] 7.84 5.85; 7.79 3.87; 7.53 1.51; 7.52 1.50; 7.42 0.52; 7.41 0.65; 7.41 1.33; 7.39 1.92; 7.38 1.39; 7.38 1.69; 7.37 4.65; 7.37 4.67; 7.37 4.62; 7.35 2.44; 7.35 1.75; 7.30 1.75; 7.29 0.97; 7.28 2.21; 7.28 2.27; 7.26 71.54; 7.26 97.60; 7.26 107.94; 7.17 1.34; 7.15 2.32; 7.14 0.56; 7.13 1.08; 7.13 0.77; 7.00 0.56; 6.19 1.76; 6.11 0.94; 4.29 0.62; 4.27 0.65; 4.25 1.32; 4.24 1.29; 4.22 1.89; 4.21 1.87; 4.18 2.47; 4.16 2.41; 4.15 0.45; 4.14 1.23; 4.13 1.14; 4.13 1.15; 4.11 0.98; 4.09 16.00; 3.91 11.02; 3.72 2.73; 3.68 3.23; 3.62 1.83; 3.58 2.24; 3.26 3.21; 3.22 2.38; 3.21 2.75; 3.18 1.80; 2.04 3.80; 1.70 11.53; 1.60 17.05; 1.56 9.39; 1.32 0.53; 1.31 1.18; 1.28 3.46; 1.27 5.69; 1.26 5.12; 1.26 4.71; 1.24 1.30; 1.24 1.45; 0.90 2.65; 0.88 6.57; 0.87 2.94; 0.01 1.95; 0.00 29.04; 0.00 38.75; 0.00 43.56 |
| 1.940 | 3,5-$F_2$—Ph | H | O | H | $CH_2COH(CF_3)$ | 1-methyl-1H-1,2,4-triazol-5-yl | [$CDCl_3$] 7.85 5.29; 7.84 6.53; 7.80 3.77; 7.79 4.63; 7.53 0.88; 7.52 1.11; 7.52 1.24; 7.51 1.50; 7.50 0.88; 7.26 50.09; 7.26 60.85; 7.25 0.81; 7.25 0.69; 7.25 0.62; 7.25 0.57; 7.25 0.43; 7.25 0.37; 7.25 0.33; 7.17 0.37; 7.16 0.34; 7.16 2.17; 7.15 2.58; 7.15 2.50; 7.14 2.20; 7.14 2.75; 7.13 2.10; 7.13 1.88; 7.13 0.35; 7.12 0.37; 7.08 1.56; 7.07 1.85; 7.07 1.81; 7.06 1.57; 7.06 2.03; 7.05 1.52; 7.05 1.37; 7.00 0.33; 6.93 0.52; 6.92 1.05; 6.92 1.00; 6.91 1.09; 6.90 2.09; 6.90 1.96; 6.89 0.75; 6.89 0.72; 6.89 0.52; 6.88 0.60; 6.88 1.08; 6.87 0.99; 6.14 5.74; 6.08 4.14; 4.29 0.62; 4.27 0.68; 4.26 0.87; 4.25 1.51; 4.23 1.38; 4.23 1.92; 4.21 1.82; 4.18 1.22; 4.18 1.70; 4.17 1.25; 4.16 1.67; 4.15 0.74; 4.14 0.81; 4.13 |

TABLE 1-continued
Compounds of the general formula (I) according to the invention in which $R^2$ is hydrogen and $R^3$ is methyl and aryl is the radical
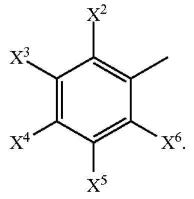
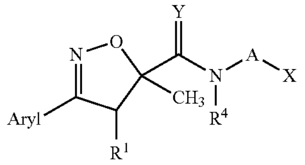
| No. | Aryl | $R^1$ | Y | $R^4$ | A | X | Physical data |
|---|---|---|---|---|---|---|---|
| | | | | | | | 1.13; 4.13 0.76; 4.11 0.60; 4.09 16.00; 3.94 11.63; 3.70 2.43; 3.70 2.88; 3.65 3.47; 3.60 2.11; 3.55 2.14; 3.55 2.56; 3.22 3.27; 3.19 2.50; 3.18 2.82; 3.15 2.01; 2.05 1.91; 2.04 2.40; 1.70 12.92; 1.60 18.11; 1.59 15.62; 1.59 18.53; 1.28 0.82; 1.28 1.02; 1.27 0.99; 1.26 1.63; 1.26 1.76; 1.24 0.63; 1.24 0.74; 0.90 0.47; 0.88 1.27; 0.86 0.54; 0.01 0.55; 0.01 0.75; 0.00 19.66 |
| 1.941 | 3,5-$Cl_2$—Ph | H | O | H | $CH_2COH(CF_3)$ | 1-methyl-1H-imidazol-2-yl | [$CDCl_3$] 7.52 0.84; 7.48 0.67; 7.42 1.65; 7.42 2.94; 7.41 2.93; 7.40 9.63; 7.39 5.68; 7.26 40.71; 7.26 137.28; 7.25 0.49; 7.25 0.41; 7.24 0.39; 7.00 0.77; 6.97 4.33; 6.97 3.41; 6.77 4.02; 6.77 3.09; 5.61 2.02; 4.26 0.67; 4.25 0.67; 4.23 1.17; 4.21 1.13; 4.14 1.33; 4.12 1.33; 4.10 0.79; 4.09 0.76; 3.67 12.05; 3.59 2.75; 3.55 3.33; 3.15 3.06; 3.11 2.55; 1.63 16.00; 1.55 19.52; 0.01 1.81; 0.00 15.46; 0.00 52.37 |
| 1.942 | 3,5-$Cl_2$—Ph | H | O | H | $CH_2COH(CF_3)$ | 1-methyl-1H-imidazol-2-yl | [$CDCl_3$] 7.52 1.07; 7.52 1.10; 7.49 6.97; 7.49 10.74; 7.48 7.92; 7.46 0.79; 7.43 2.21; 7.43 3.90; 7.43 3.70; 7.42 1.75; 7.40 0.73; 7.31 0.33; 7.27 18.45; 7.26 142.97; 7.26 124.58; 7.26 152.43; 7.00 0.87; 6.91 4.70; 6.84 5.35; 6.77 0.35; 5.74 1.63; 4.27 0.96; 4.25 1.00; 4.24 1.55; 4.22 1.50; 4.11 1.73; 4.10 1.68; 4.08 1.12; 4.06 1.07; 3.84 16.00; 3.68 0.94; 3.59 2.65; 3.55 3.22; 3.55 3.14; 3.17 3.17; 3.13 2.51; 3.13 2.54; 1.63 1.29; 1.60 16.38; 1.60 16.84; 1.55 36.29; 1.31 0.42; 1.27 1.87; 0.90 0.81; 0.88 1.56; 0.87 0.81; 0.01 7.97; 0.00 57.84; 0.00 49.73; 0.00 61.88 |
| 1.943 | 3,5-$F_2$—Ph | H | O | H | $CH_2COH(CF_3)$ | 1-methyl-imidazol-2-yl | [$CDCl_3$] 7.52 0.66; 7.48 1.07; 7.26 101.66; 7.16 0.39; 7.14 1.60; 7.14 2.30; 7.14 1.65; 7.13 1.29; 7.12 2.20; 7.12 2.02; 7.11 0.40; 7.07 1.38; 7.06 1.98; 7.05 1.12; 7.05 1.89; 7.04 1.78; 7.03 0.34; 7.00 0.56; 6.96 2.72; 6.96 3.40; 6.92 0.43; 6.91 0.83; 6.91 0.83; 6.90 3.49; 6.90 4.69; 6.89 1.94; 6.89 1.62; 6.88 |

TABLE 1-continued
Compounds of the general formula (I) according to the invention in which $R^2$ is hydrogen and $R^3$ is methyl and aryl is the radical
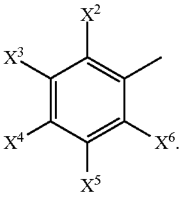
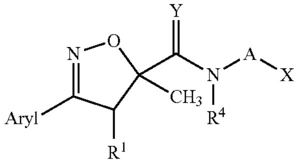
| No. | Aryl | $R^1$ | Y | $R^4$ | A | X | Physical data |
|---|---|---|---|---|---|---|---|
| | | | | | | | 1.61; 6.88 1.23; 6.87 0.94; 6.87 0.80; 6.86 0.81; 6.85 0.47; 6.84 3.17; 6.84 3.61; 6.76 2.68; 6.75 3.17; 5.75 2.34; 5.68 1.98; 4.27 0.64; 4.27 0.80; 4.26 0.73; 4.25 0.82; 4.24 1.12; 4.23 1.33; 4.22 1.17; 4.21 1.29; 4.13 1.31; 4.12 1.47; 4.11 1.37; 4.11 1.52; 4.09 0.86; 4.09 0.95; 4.08 0.81; 4.07 0.89; 3.83 11.86; 3.69 10.48; 3.60 2.34; 3.59 2.61; 3.55 2.80; 3.55 3.19; 3.18 2.90; 3.15 2.58; 3.13 2.41; 3.11 2.15; 2.04 0.63; 1.63 13.63; 1.60 16.00; 1.57 9.67; 1.28 0.38; 1.26 1.21; 1.26 1.07; 0.90 0.54; 0.88 1.63; 0.86 0.72; 0.01 1.14; 0.00 40.54 |
| 1.944 | 3-F—Ph | H | O | H | $CH_2COH(CF_3)$ | 1-methyl-imidazol-2-yl | [$CDCl_3$] 7.53 1.47; 7.52 1.42; 7.51 1.31; 7.42 0.48; 7.40 1.86; 7.38 1.90; 7.38 2.49; 7.36 5.93; 7.35 1.18; 7.34 2.11; 7.34 1.56; 7.33 1.40; 7.29 2.86; 7.28 1.30; 7.28 1.15; 7.26 49.56; 7.17 0.80; 7.16 0.89; 7.16 1.02; 7.16 1.15; 7.15 0.78; 7.15 1.47; 7.14 1.80; 7.13 1.88; 7.13 1.40; 7.13 1.27; 7.12 0.83; 7.11 0.87; 7.11 0.55; 7.11 0.48; 6.95 3.88; 6.95 2.61; 6.89 5.05; 6.89 3.56; 6.83 5.16; 6.72 3.80; 5.83 2.61; 5.76 1.95; 4.27 0.87; 4.26 1.02; 4.25 0.88; 4.25 1.02; 4.23 1.56; 4.23 1.78; 4.22 1.51; 4.21 1.68; 4.14 1.32; 4.13 2.62; 4.11 2.13; 4.11 0.85; 4.09 1.42; 4.08 1.03; 3.83 16.00; 3.67 12.09; 3.63 4.75; 3.59 5.89; 3.21 3.45; 3.18 2.61; 3.17 2.85; 3.14 2.15; 2.04 2.00; 1.63 14.89; 1.60 18.67; 1.28 0.58; 1.26 1.13; 1.26 1.23; 1.24 1.22; 1.24 0.57; 1.23 0.48; 0.00 16.48 |
| 1.945 | Ph | H | O | H | $CH_2COH(CF_3)$ | 1-methyl-imidazol-2-yl | [$CDCl_3$] 16.47 0.41; 7.66 0.33; 7.64 0.36; 7.62 3.46; 7.62 3.17; 7.60 3.26; 7.60 3.29; 7.58 0.51; 7.56 3.40; 7.55 3.45; 7.54 4.64; 7.53 4.05; 7.52 4.10; 7.50 1.04; 7.45 1.69; 7.44 1.51; 7.43 6.97; 7.42 3.97; 7.41 7.09; 7.39 3.56; 7.39 3.83; 7.37 1.13; 7.33 0.57; 7.32 0.55; 7.31 0.97; 7.26 340.78; 7.26 542.48; 7.23 0.52; 7.21 0.35; 7.00 1.92; 7.00 2.92; 6.94 4.50; 6.89 4.80; 6.82 4.97; 6.69 4.64; 5.84 3.07; 5.79 |

TABLE 1-continued
Compounds of the general formula (I) according to the invention in which $R^2$ is hydrogen and $R^3$ is methyl and aryl is the radical
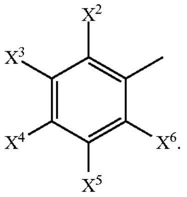
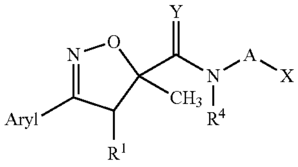
| No. | Aryl | $R^1$ | Y | $R^4$ | A | X | Physical data |
|---|---|---|---|---|---|---|---|
| | | | | | | | 2.59; 4.27 0.91; 4.26 1.05; 4.25 0.99; 4.24 1.05; 4.23 1.46; 4.22 1.83; 4.21 1.52; 4.14 1.53; 4.13 2.23; 4.12 1.94; 4.11 0.99; 4.10 1.28; 4.09 1.11; 4.08 1.08; 3.83 15.10; 3.66 16.00; 3.62 3.80; 3.62 3.57; 3.24 3.41; 3.21 3.05; 3.20 2.78; 3.17 2.57; 2.04 1.30; 2.00 0.62; 1.63 15.94; 1.60 18.20; 1.54 145.34; 1.37 0.34; 1.31 0.44; 1.26 1.76; 0.90 0.66; 0.88 1.50; 0.87 0.78; 0.15 0.80; 0.01 9.16; 0.00 135.48 |
| 1.946 | 3,5-$F_2$—Ph | H | O | H | $CH_2COH(CF_3)$ | 4-methyl-1,3-thiazol-2-yl | [$CDCl_3$] 7.27 4.31; 7.26 29.62; 7.26 29.02; 7.23 0.52; 7.12 1.05; 7.12 1.34; 7.10 1.32; 7.10 1.07; 7.08 0.38; 7.07 1.15; 7.07 1.48; 7.05 1.44; 7.05 1.17; 6.93 0.48; 6.92 0.51; 6.92 0.63; 6.91 1.09; 6.91 2.53; 6.90 2.50; 6.90 2.40; 6.90 1.14; 6.89 0.78; 6.89 0.58; 6.88 0.50; 6.87 0.45; 6.68 2.09; 6.24 2.96; 6.02 2.72; 4.07 3.77; 4.06 3.50; 3.64 1.33; 3.60 1.59; 3.58 1.50; 3.53 1.79; 3.17 1.56; 3.15 1.76; 3.12 1.31; 3.10 1.44; 2.47 0.33; 2.40 16.00; 1.63 9.26; 1.61 8.29; 1.56 6.75; 1.26 0.61; 0.01 1.73; 0.00 12.35 |
| 1.947 | Ph | H | O | H | $CH_2COH(CF_3)$ | 4-methyl-1,3-thiazol-2-yl | [$CDCl_3$] 7.60 2.32; 7.59 2.75; 7.59 1.22; 7.58 0.97; 7.58 2.84; 7.57 3.15; 7.55 1.75; 7.55 2.28; 7.54 1.13; 7.54 0.78; 7.53 2.99; 7.53 2.68; 7.52 1.00; 7.48 0.39; 7.47 0.37; 7.47 0.42; 7.46 1.54; 7.45 0.68; 7.45 1.29; 7.45 2.01; 7.44 2.16; 7.43 2.17; 7.43 4.73; 7.43 5.20; 7.42 1.87; 7.42 1.56; 7.41 2.03; 7.41 3.84; 7.41 3.29; 7.40 0.67; 7.39 1.19; 7.39 1.09; 7.39 1.14; 7.38 0.76; 7.33 0.56; 7.32 0.46; 7.32 0.46; 7.31 0.52; 7.31 0.64; 7.30 0.55; 7.30 0.56; 7.29 0.76; 7.29 0.75; 7.29 0.77; 7.29 0.78; 7.29 0.68; 7.29 0.67; 7.29 0.65; 7.29 0.64; 7.29 0.60; 7.28 0.60; 7.28 0.57; 7.28 0.57; 7.28 0.60; 7.28 0.61; 7.28 0.59; 7.28 0.61; 7.28 0.66; 7.28 0.65; 7.28 0.66; 7.28 0.67; 7.27 0.71; 7.27 0.73; 7.27 0.74; 7.27 0.79; 7.27 0.84; 7.27 0.90; 7.27 0.95; 7.27 1.10; 7.27 1.22; 7.27 1.38; 7.27 1.51; 7.26 166.07; 7.25 2.86; 7.25 |

TABLE 1-continued
Compounds of the general formula (I) according to the invention in which $R^2$ is hydrogen and $R^3$ is methyl and aryl is the radical
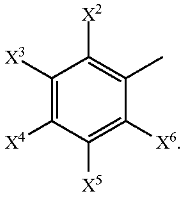
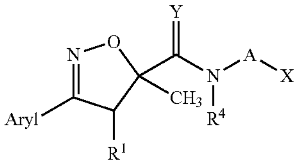
| No. | Aryl | $R^1$ | Y | $R^4$ | A | X | Physical data |
|---|---|---|---|---|---|---|---|
| | | | | | | | 1.62; 7.25 1.39; 7.25 1.23; 7.25 1.10; 7.25 0.94; 7.25 0.87; 7.25 0.78; 7.25 0.72; 7.24 0.65; 7.24 0.60; 7.24 0.58; 7.24 0.50; 7.24 0.44; 7.24 0.42; 7.24 0.39; 7.24 0.35; 7.00 0.94; 6.88 1.34; 6.88 3.49; 6.88 3.42; 6.87 1.26; 6.51 2.82; 6.51 2.79; 6.46 4.96; 6.14 7.40; 4.13 0.52; 4.11 0.81; 4.10 0.39; 4.08 1.77; 4.07 3.98; 4.06 1.76; 4.06 4.76; 4.04 1.29; 4.02 0.37; 4.00 0.36; 3.70 3.25; 3.65 3.85; 3.62 2.72; 3.58 3.26; 3.22 3.52; 3.19 2.97; 3.18 3.03; 3.15 2.45; 2.37 13.90; 2.37 13.45; 2.35 1 1.77; 2.35 11.40; 2.04 2.39; 1.72 0.33; 1.64 16.00; 1.60 18.82; 1.54 57.52; 1.53 0.32; 1.31 0.49; 1.29 0.65; 1.28 1.60; 1.27 2.36; 1.26 2.57; 1.24 0.87; 0.90 1.26; 0.88 4.36; 0.86 1.67; 0.01 1.85 |
| 1.948 | 3,5-$Cl_2$—Ph | H | O | H | $CH_2COH(CF_3)$ | 4-methyl-1,3-thiazol-2-yl | [$CDCl_3$] 7.52 2.26; 7.46 7.93; 7.46 9.60; 7.45 3.09; 7.44 4.22; 7.44 3.78; 7.43 4.15; 7.43 4.00; 7.43 2.18; 7.40 9.54; 7.40 7.86; 7.38 0.38; 7.36 0.33; 7.31 0.84; 7.30 0.43; 7.26 80.58; 7.26 377.95; 7.25 57.90; 7.24 1.87; 7.24 1.43; 7.24 1.24; 7.24 1.16; 7.23 0.84; 7.22 0.89; 7.22 0.94; 7.21 1.72; 7.20 1.45; 7.18 0.61; 7.18 0.41; 7.00 2.16; 6.90 4.01; 6.90 4.05; 6.67 3.89; 6.67 3.96; 6.26 5.54; 5.99 6.83; 4.13 0.35; 4.11 0.90; 4.08 2.89; 4.07 4.32; 4.06 4.63; 4.05 3.13; 4.05 2.44; 4.02 0.64; 4.02 0.58; 3.64 2.65; 3.60 3.16; 3.57 2.56; 3.52 3.03; 3.16 2.96; 3.14 3.10; 3.11 2.53; 3.10 2.44; 2.47 0.35; 2.41 13.68; 2.40 14.65; 2.39 14.86; 2.39 14.68; 2.04 1.63; 1.64 15.86; 1.60 16.00; 1.56 0.33; 1.54 28.37; 1.53 123.16; 1.53 20.61; 1.49 0.37; 1.48 0.32; 1.30 1.60; 1.26 7.45; 1.24 1.37; 0.90 2.99; 0.88 8.24; 0.86 3.51; 0.15 0.50; 0.05 0.37; 0.02 0.42; 0.01 29.86; 0.00 29.59; 0.00 134.62 |
| 1.949 | 3-F—Ph | H | O | H | $CH_2COH(CF_3)$ | 4-methyl-1,3-thiazol-2-yl | [$CDCl_3$] 7.52 1.27; 7.42 0.65; 7.42 0.69; 7.40 1.23; 7.40 1.60; 7.38 1.77; 7.38 1.91; 7.38 1.47; 7.38 1.30; 7.36 1.41; 7.36 1.10; 7.34 1.07; 7.34 1.48; 7.34 |

TABLE 1-continued

Compounds of the general formula (I) according to the invention in which $R^2$ is hydrogen and $R^3$ is methyl and aryl is the radical

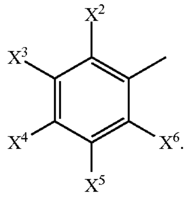

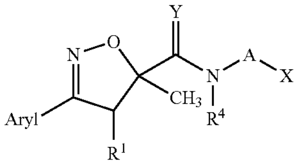

| No. | Aryl | $R^1$ | Y | $R^4$ | A | X | Physical data |
|---|---|---|---|---|---|---|---|
| | | | | | | | 2.76; 7.33 2.73; 7.33 1.48; 7.33 0.73; 7.32 1.61; 7.32 2.45; 7.32 2.47; 7.31 2.60; 7.31 1.32; 7.31 1.15; 7.30 1.41; 7.30 1.49; 7.30 1.70; 7.30 1.68; 7.30 1.66; 7.29 1.58; 7.29 1.10; 7.29 1.06; 7.29 1.03; 7.29 1.02; 7.29 1.22; 7.29 1.35; 7.28 4.07; 7.28 3.23; 7.28 3.80; 7.27 3.70; 7.27 4.08; 7.26 35.97; 7.26 237.65; 7.23 0.48; 7.18 0.56; 7.18 0.69; 7.18 0.66; 7.17 0.67; 7.17 0.84; 7.17 0.93; 7.16 1.48; 7.16 0.96; 7.15 1.12; 7.15 1.24; 7.15 1.20; 7.14 1.25; 7.14 1.23; 7.14 0.59; 7.13 0.59; 7.13 0.72; 7.13 0.59; 7.12 0.51; 7.12 0.47; 7.00 1.25; 6.89 3.51; 6.89 3.21; 6.59 2.90; 6.59 2.61; 6.35 4.34; 6.08 6.54; 4.11 0.45; 4.10 0.36; 4.07 3.50; 4.06 3.42; 4.06 3.74; 4.05 1.43; 3.67 2.71; 3.63 3.24; 3.60 2.28; 3.55 2.70; 3.20 2.93; 3.17 2.43; 3.15 2.48; 3.13 1.97; 2.38 14.29; 2.38 13.68; 2.38 1 1.77; 2.37 10.23; 2.04 1.02; 1.64 13.44; 1.60 16.00; 1.54 80.24; 1.31 0.48; 1.28 1.28; 1.27 2.14; 1.26 1.69; 1.24 0.49; 0.90 1.08; 0.88 3.17; 0.86 1.24; 0.15 0.33; 0.02 0.34; 0.02 0.34; 0.02 0.38; 0.02 0.48; 0.02 0.54; 0.02 0.61; 0.02 0.70; 0.01 0.81; 0.01 0.96; 0.01 1.15; 0.01 1.44; 0.01 1.71; 0.01 2.18; 0.01 5.52; 0.01 5.03; 0.00 13.55; 0.00 13.50 |
| 1.950 | 3,5-$F_2$—Ph | H | O | H | bond | 1-(2-chloropyrimidin-4-yl)-2-ethoxy-2-oxoethyl | [$CDCl_3$] D1 1.19 (t, 3H); 1.73 (s, 3H); 3.20 (d, 1H); 3.72 (d, 1H); 4.21 (q, 2H); 5.58 (d, 1H); 6.88 (m, 1H); 7.17 (m, 2H); 7.40 (d, 1H); 8.13 (d br, 1H); 8.60 (d, 1H). D2 1.26 (t, 3H); 1.79 (s, 3H); 3.22 (d, 1H); 3.78 (d, 1H); 4.24 (q, 2H); 5.60 (d, 1H); 6.88 (m, 1H); 7.17 (m, 2H); 7.44 (d, 1H); 8.14 (d br, 1H); 8.64 (d, 1H). |
| 1.951 | 3-F—Ph | H | O | H | bond | 1-(2-chloropyrimidin-4-yl)-2-ethoxy-2-oxoethyl | |
| 1.952 | 3,5-$F_2$—Ph | H | O | H | bond | 1-(6-chloropyrimidin-4-yl)-2-ethoxy-2-oxoethyl | [$CDCl_3$] D1 1.18 (t, 3H); 1.71 (s, 3H); 3.18 (d, 1H); 3.78 (d, 1H); 4.18 (q, 2H); 5.54 (s, 1H); 6.97 (m, 1H); 7.16 |

TABLE 1-continued

Compounds of the general formula (I) according to the invention in which $R^2$ is hydrogen and $R^3$ is methyl and aryl is the radical

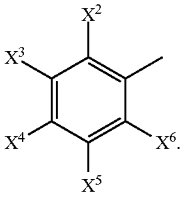

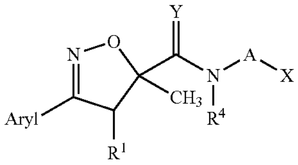

| No. | Aryl | $R^1$ | Y | $R^4$ | A | X | Physical data |
|---|---|---|---|---|---|---|---|
| | | | | | | | (m, 2H), 7.52 (s, 1H); 8.23 (d br, 1H); 8.93 (s, 1H). D2 1.26 (t, 3H); 1.80 (s, 3H); 3.23 (d, 1H); 3.74 (d, 1H); 4.26 (q, 2H); 5.57 (s, 1H); 6.97 (m, 1H); 7.18 (m, 2H), 7.57 (s, 1H); 8.25 (d br, 1H); 8.99 (s, 1H). |
| 1.953 | 3-F—Ph | H | O | H | bond | 1-(6-chloropyrimidin-4-yl)-2-ethoxy-2-oxoethyl | |
| 1.954 | 3,5-$F_2$—Ph | H | O | H | bond | 2,6-dimethylpyridin-4-yl | [$CDCl_3$] 1.82 (s, 3H); 2.50 (s, 6H); 3.28 (d, 1H); 3.87 (d, 1H); 6.90 (m, 1H); 7.17 (m, 2H); 7.22 (s, 2H); 8.55 (s br, 1H). |
| 1.955 | 3-F—Ph | H | O | H | bond | 2,6-dimethylpyridin-4-yl | |
| 1.956 | 3,5-$F_2$—Ph | H | O | H | bond | 2-chloropyridin-4-yl | |
| 1.957 | 3-F—Ph | H | O | H | bond | 3,5-dimethyl-1,2-oxazol-4-yl | [$CDCl_3$] 1.83 (s, 3H); 2.15 (s, 3H); 2.30 (s, 3H); 3.31 (d, 1H); 3.87 (d, 1H); 7.17 (m, 2H); 7.41 (m, 3H); 7.89 (s br, 1H). |
| 1.958 | 3,5-$F_2$—Ph | H | O | H | bond | 3-chloropyridin-2-yl | |
| 1.959 | 3,5-$F_2$—Ph | H | O | H | bond | pyridin-3-yl | |
| 1.960 | 3,5-$F_2$—Ph | H | O | H | bond | pyridin-4-yl | |
| 1.961 | 3,5-$F_2$—Ph | H | O | H | $CH_2$ | 1,2-oxazol-4-yl | |
| 1.962 | 3,5-$Cl_2$—Ph | H | O | H | $CH_2$ | 1,2-oxazol-4-yl | |
| 1.963 | 3-F—Ph | H | O | H | $CH_2$ | 1,2-oxazol-4-yl | |
| 1.964 | 3,5-$I_2$—Ph | H | O | H | $CH_2$ | 1-ethyl-1H-pyrazol-4-yl | [$CDCl_3$] 1.47 (t, 3H); 1.72 (s, 3H); 3.16 (d, 1H); 3.77 (d, 1H); 4.12 (q, 2H); 4.22 (dd, 1H); 4.35 (dd, 1H); 6.94 (t br, 1H); 7.33 (s, 1H); 7.42 (s, 1H); 7.92 (s, 2H); 8.09 (s, 1H). |
| 1.965 | 3-Br-5-Me—Ph | H | O | H | $CH_2$ | 1-ethyl-1H-pyrazol-4-yl | |
| 1.966 | 3-$SF_5$—Ph | H | O | H | $CH_2$ | 1-ethyl-1H-pyrazol-4-yl | |
| 1.967 | 3-(MeOCO)Ph | H | O | H | $CH_2$ | 1-ethyl-1H-pyrazol-4-yl | |
| 1.968 | 3-COOH—Ph | H | O | H | $CH_2$ | 1-ethyl-1H-pyrazol-4-yl | |
| 1.969 | 3-I—Ph | H | O | H | $CH_2$ | 1-ethyl-1H-pyrazol-4-yl | |
| 1.970 | 3-CN-5-$CF_3$—Ph | H | O | H | $CH_2$ | 1-ethyl-1H-pyrazol-4-yl | [$CDCl_3$] 1.47 (t, 3H); 1.76 (s, 3H); 3.26 (d, 1H); 3.89 (d, 1H); 4.14 (q, 2H); 4.22 (dd, 1H); 4.38 (dd, 1H); 6.92 (t, 1H); 7.35 (s, 1H); |

TABLE 1-continued

Compounds of the general formula (I) according to the invention in which $R^2$ is hydrogen and $R^3$ is methyl and aryl is the radical

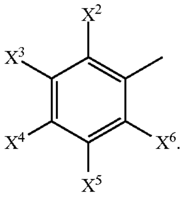

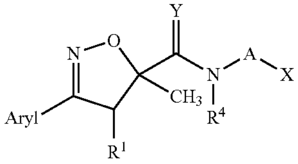

| No. | Aryl | $R^1$ | Y | $R^4$ | A | X | Physical data |
|---|---|---|---|---|---|---|---|
| | | | | | | | 7.44 (s, 1H); 7.96 (s, 1H); 8.09 (s, 1H). |
| 1.971 | 3,5-$CN_2$Ph | H | O | H | $CH_2$ | 1-ethyl-1H-pyrazol-4-yl | |
| 1.972 | 3,5-$I_2$—Ph | H | O | H | $CH_2$ | 1-ethyl-3-methyl-1H-pyrazol-4-yl | |
| 1.973 | 5-Br-2-F—Ph | H | O | H | $CH_2$ | 1-ethyl-3-methyl-1H-pyrazol-4-yl | |
| 1.974 | 2-F-5-MeO—Ph | H | O | H | $CH_2$ | 1-ethyl-3-methyl-1H-pyrazol-4-yl | |
| 1.975 | 3-$SF_5$—Ph | H | O | H | $CH_2$ | 1-ethyl-3-methyl-1H-pyrazol-4-yl | [$CDCl_3$] 1.43 (t, 3H); 1.75 (s, 3H); 2.19 (s, 3H); 3.25 (d, 1H); 3.87 (d, 1H); 4.05 (q, 2H); 4.18 (dd, 1H); 4.32 (dd, 1H); 6.85 (s br, 1H); 7.24 (s, 1H); 7.52 (t, 1H); 7.75 (d, 1H); 7.82 (d, 1H); 8.04 (s, 1H). |
| 1.976 | 3-($MeCOOCH_2$)-5-Cl—Ph | H | O | H | $CH_2$ | 1-ethyl-3-methyl-1H-pyrazol-4-yl | |
| 1.977 | 3-Cl-2-F-5-$CF_3$—Ph | H | O | H | $CH_2$ | 1-ethyl-3-methyl-1H-pyrazol-4-yl | [$CDCl_3$] 1.44 (t, 3H); 1.74 (s, 3H); 2.20 (s, 3H); 3.33 (d, 1H); 3.92 (d, 1H); 4.10 (q, 2H); 4.20 (dd, 1H); 4.31 (dd, 1H); 6.81 (t, 1H); 7.75 (m, 1H); 8.00 (m, 1H). |
| 1.978 | 3-Br-5-Me—Ph | H | O | H | $CH_2$ | 1-ethyl-3-methyl-1H-pyrazol-4-yl | [$CDCl_3$] 1.43 (t, 3H); 1.73 (s, 3H); 2.19 (s, 3H); 2.19 (s, 3H); 3.20 (d, 1H); 3.80 (d, 1H); 4.06 (q, 2H); 4.19 (dd, 1H); 4.31 (dd, 1H); 6.89 (t, 1H); 7.36 (s, 1H); 7.39 (s, 1H); 7.58 (s, 1H). |
| 1.979 | 3-($F_2$—MeO)Ph | H | O | H | $CH_2$ | 1-ethyl-3-methyl-1H-pyrazol-4-yl | [$CDCl_3$] 1.43 (t, 3H); 1.62 (s, 3H); 1.74 (s, 3H); 2.19 (s, 3H); 3.24 (d, 1H); 3.83 (d, 1H); 4.04 (q, 2H); 4.19 (dd, 1H); 4.32 (dd, 1H); 6.54 (t, 1H); 6.89 (t, 1H); 7.21 (m, 1H); 7.25 (s, 1H); 7.43 (m, 2H); 7.45 (s, 1H). |
| 1.980 | 3-(MeOCO)Ph | H | O | H | $CH_2$ | 1-ethyl-3-methyl-1H-pyrazol-4-yl | |
| 1.981 | 3-COOH—Ph | H | O | H | $CH_2$ | 1-ethyl-3-methyl-1H-pyrazol-4-yl | |
| 1.982 | 3-I—Ph | H | O | H | $CH_2$ | 1-ethyl-3-methyl-1H-pyrazol-4-yl | [$CDCl_3$] 1.43 (t, 3H); 1.72 (s, 3H); 2.18 (s, 3H); 3.20 (d, 1H); 3.80 (d, 2H); 4.05 (q, 2H); 4.23 (dq, 2H); 6.87 (br, t, 1H); 7.14 (t, 1H); 7.23 (s, 1H); 7.56 (m, 1H); 7.75 (m, 1H); 8.00 (m, 1H). |
| 1.983 | 3-CN-5-$CF_3$—Ph | H | O | H | $CH_2$ | 1-ethyl-3-methyl-1H-pyrazol-4-yl | [$CDCl_3$] 1.45 (t, 3H); 1.76 (s, 1H); 2.20 (s, 3H); 3.26 (d, 1H); 3.89 (d, 1H); 4.06 |

TABLE 1-continued

Compounds of the general formula (I) according to the invention in which $R^2$ is hydrogen and $R^3$ is methyl and aryl is the radical

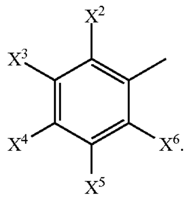

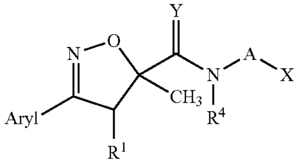

| No. | Aryl | $R^1$ | Y | $R^4$ | A | X | Physical data |
|---|---|---|---|---|---|---|---|
| | | | | | | | (q, 2H); 4.17 (dd, 1H); 4.33 (dd, 1H); 6.80 (br,t, 1H); 7.96 (s, 1H); 8.09 (s, 2H) |
| 1.984 | 3,5-$CN_2$Ph | H | O | H | $CH_2$ | 1-ethyl-3-methyl-1H-pyrazol-4-yl | |
| 1.985 | 3-Et-5-Me—Ph | H | O | H | $CH_2$ | 1-ethyl-3-methyl-1H-pyrazol-4-yl | [$CDCl_3$] 1.26 (t, 3H); 1.78 (s, 3H); 2.66 (q, 2H); 3.26 (d, 1H); 3.82 (d, 1H); 4.44 (dq, 2H); 7.06 (d, 1H); 7.16 (s, 1H), 7.32 (br,t, 1H); 7.35 (s, 1H); 7.45 (s, 1H); 8.31 (d, 1H) |
| 1.986 | 3-CN-5-Me—Ph | H | O | H | $CH_2$ | 1-ethyl-3-methyl-1H-pyrazol-4-yl | |
| 1.987 | 3-F-5-vinylPh | H | O | H | $CH_2$ | 1-ethyl-3-methyl-1H-pyrazol-4-yl | |
| 1.988 | 3-Br-5-CN—Ph | H | O | H | $CH_2$ | 1-ethyl-3-methyl-1H-pyrazol-4-yl | |
| 1.989 | 3-ethynyl-Ph | H | O | H | $CH_2$ | 1-ethyl-3-methyl-1H-pyrazol-4-yl | |
| 1.990 | 3,5-$F_2$—Ph | $CH_2CH_3$ | O | H | $CH_2$ | 1-ethyl-3-methyl-1H-pyrazol-4-yl | |
| 1.991 | 3-$CF_3$—Ph | H | O | H | $CH_2$ | 1-propyl-1H-pyrazol-4-yl | [$CDCl_3$] 0.88 (t, 3H); 1.75 (s, 3H); 1.84 (m, 2H); 3.26 (d, 1H); 3.87 (d, 1H); 4.02 (t, 2H); 4.30 (dq, 2H); 7.00 (br, t, 1H); 7.41 (s, 1H); 7.55 (t, 1H); 7.69 (d, 1H); 7.80 (d, 1H); 7.89 (s, 1H). |
| 1.992 | 3-Et-5-F—Ph | H | O | H | $CH_2$ | 1-propyl-1H-pyrazol-4-yl | |
| 1.993 | 3-($F_2$—MeO)Ph | H | O | H | $CH_2$ | 1-propyl-1H-pyrazol-4-yl | |
| 1.994 | 3,5-$F_2$—Ph | H | O | H | $CH_2$ | 2-(1H-Imidazol-1-yl)ethyl | |
| 1.995 | 3,5-$F_2$—Ph | H | O | H | $CH_2$ | 2-(2,2,2-trifluoroethoxy)-pyridin-4-yl | [$CDCl_3$] 1.79 (s, 3H); 3.23 (d, 1H); 3.81 (d, 1H); 4.44 (AB d, 2H); 4.73 (q, 2H); 6.69 (s, 1H); 6.83 (d, 1H); 6.90 (m, 1H); 7.17 (m, 2H); 7.27 (s br, 1H); 8.06 (d, 1H). |
| 1.996 | 3,5-$F_2$—Ph | H | O | H | $CH_2$ | 2-(difluoromethoxy)-pyridin-4-yl | [$CDCl_3$] 1.79 (s, 3H); 3.24 (d, 1H); 3.81 (d, 1H); 4.40 (dd, 1H); 4.54 (dd, 1H); 6.72 (s, 1H); 6.90 (m, 1H); 6.95 (d, 1H); 7.18 (m, 1H); 7.30 (t br, 1H); 7.43 (t, 1H); 8.12 (d, 1H). |
| 1.997 | 3,5-$F_2$—Ph | H | O | H | $CH_2$ | 2-(methylsulfanyl)-pyridin-4-yl | [$CDCl_3$] 1.78 (s, 3H); 2.52 (s, 3H); 3.23 (d, 1H); 3.81 (d, 1H); 4.35 (dd, 1H); 4.43 (dd, 1H); 6.81 (d, 1H); 6.88 (m, 1H); 6.92 (s, 1H); 7.17 (m, 2H); 7.25 (t br, 1H); 8.35 (d, 1H). |

TABLE 1-continued

Compounds of the general formula (I) according to the invention in which $R^2$ is hydrogen and $R^3$ is methyl and aryl is the radical

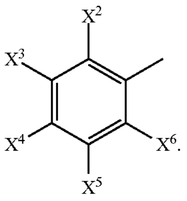

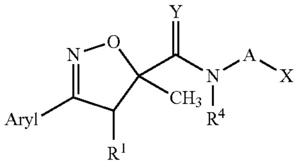

| No. | Aryl | $R^1$ | Y | $R^4$ | A | X | Physical data |
|---|---|---|---|---|---|---|---|
| 1.998 | 3,5-$F_2$—Ph | H | O | H | $CH_2$ | 2,5-dimethyl-1,3-oxazol-4-yl | |
| 1.999 | 3,5-$F_2$—Ph | H | O | H | $CH_2$ | 2,6-dichloropyridin-4-yl | [$CDCl_3$] 1.79 (s, 3H); 3.24 (d, 1H); 3.79 (d, 1H); 4.43 (AB, 2H); 6.90 (m, 1H); 7.10 (s, 2H); 7.19 (m, 2H); 7.34 (t br, 1H). |
| 1.1000 | 3,5-$F_2$—Ph | H | O | H | $CH_2$ | 2,6-dimethylpyridin-4-yl | |
| 1.1001 | 3,5-$Cl_2$—Ph | H | O | H | $CH_2$ | 2,6-dimethylpyridin-4-yl | |
| 1.1002 | 3-F—Ph | H | O | H | $CH_2$ | 2,6-dimethylpyridin-4-yl | |
| 1.1003 | 3,5-$F_2$—Ph | H | O | H | $CH_2$ | 2-bromopyridin-4-yl | |
| 1.1004 | 3-F—Ph | H | O | H | $CH_2$ | 2-bromopyridin-4-yl | [$CDCl_3$] 1.79 (s, 3H); 3.27 (d, 1H); 3.84 (d, 1H); 4.43 (AB d, 2H); 7.10 (d, 1H); 7.16 (m, 1H); 7.32 (s, 1H); 7.35 (t br, 1H); 7.38 (m, 2H); 7.41 (s, 1H); 8.28 (d, 1H) |
| 1.1005 | 3-Cl-5-F—Ph | H | O | H | $CH_2$ | 2-bromopyridin-4-yl | [$CDCl_3$] 1.78 (s, 3H); 3.24 (d, 1H); 3.81 (d, 1H); 4.43 (AB d, 2H); 7.10 (d, 1H); 7.18 (m, 1H); 7.28 (m, 3H); 7.42 (s, 1H); 8.30 (d, 1H). |
| 1.1006 | 3,5-$Cl_2$—Ph | H | O | H | $CH_2$ | 2-chloro-1,3-thiazol-5-yl | [$CDCl_3$] 1.73 (s, 3H); 3.21 (d, 1H); 3.75 (d, 1H); 4.45 (dd, 1H); 4.58 (dd, 1H); 7.27 (s br, 1H); 7.40 (s, 1H); 7.42 (s, 1H); 7.50 (s, 2H). |
| 1.1007 | 3,5-$F_2$—Ph | H | O | H | $CH_2$ | 2-chloro-1,3-thiazol-5-yl | [$CDCl_3$] 1.73 (s, 3H); 3.21 (d, 1H); 3.75 (d, 1H); 4.47 (dd, 1H); 4.58 (dd, 1H); 6.89 (m, 1H); 7.14 (m, 2H); 7.40 (s, 1H). |
| 1.1008 | 3-F—Ph | H | O | H | $CH_2$ | 2-chloro-1,3-thiazol-5-yl | [$CDCl_3$] 1.71 (s, 3H); 3.25 (d, 1H); 3.79 (d, 1H); 4.47 (dd, 1H); 4.60 (dd, 1H); 7.16 (m, 1H); 7.31 (s br, 1H); 7.38 (m, 4H). |
| 1.1009 | 3-$SF_5$—Ph | H | O | H | $CH_2$ | 2-chloropyridin-4-yl | |
| 1.1010 | 3-Br-5-Me—Ph | H | O | H | $CH_2$ | 2-chloropyridin-4-yl | |
| 1.1011 | 3-Cl-5-Et—Ph | H | O | H | $CH_2$ | 2-chloropyridin-4-yl | |
| 1.1012 | 3-$CF_3$—Ph | H | O | H | $CH_2$ | 2-chloropyridin-4-yl | [$CDCl_3$] 1.80 (s, 3H); 3.31 (d, 1H); 3.89 (dd, 2H); 4.43 (dq, 2H); 7.34 (br, t, 1H); 7.55 (t, 1H); 7.70 (d, 1H); 7.82 (d, 1H); 7.92 (s, 1H); 8.32 (d, 1H). |

TABLE 1-continued

Compounds of the general formula (I) according to the invention in which $R^2$ is hydrogen and $R^3$ is methyl and aryl is the radical

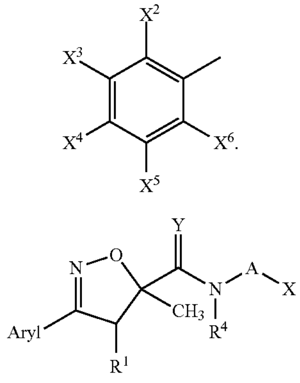

| No. | Aryl | $R^1$ | Y | $R^4$ | A | X | Physical data |
|---|---|---|---|---|---|---|---|
| 1.1013 | 3-I—Ph | H | O | H | $CH_2$ | 2-chloropyridin-4-yl | |
| 1.1014 | 3-CN-5-$CF_3$—Ph | H | O | H | $CH_2$ | 2-chloropyridin-4-yl | |
| 1.1015 | 3,5-$CN_2$Ph | H | O | H | $CH_2$ | 2-chloropyridin-4-yl | |
| 1.1016 | 3-Et-5-F—Ph | H | O | H | $CH_2$ | 2-chloropyridin-4-yl | |
| 1.1017 | 3-Br-5-CN—Ph | H | O | H | $CH_2$ | 2-chloropyridin-4-yl | |
| 1.1018 | 3-ethynyl-Ph | H | O | H | $CH_2$ | 2-chloropyridin-4-yl | |
| 1.1019 | 3-Me-5-$CF_3$O—Ph | H | O | H | $CH_2$ | 2-chloropyridin-4-yl | [$CDCl_3$] 1.78 (s, 3H); 2.40 (s, 3H); 3.27 (d, 1H); 3.83 (d, 1H); 4.45 (Abd, 2H); 7.07 (d, 1H); 7.12 (s, 1H); 7.16 (s, 1H); 7.33 (s, 1H); 7.34 (s, br, 1H); 7.36 (s, 1H); 8.31 (d, 1H). |
| 1.1020 | 3-Cl-5-F—Ph | H | O | H | $CH_2$ | 2-chloropyridin-4-yl | [$CDCl_3$] 1.78 (s, 3H); 3.24 (d, 1H); 3.81 (d, 1H); 4.40 (dd, 1H); 4.50 (dd, 1H); 7.06 (d, 1H); 7.16 (s, 1H); 7.18 (m, 1H); 7.28 (m, 2H); 7.42 (s, 1H); 8.31 (d, 1H). |
| 1.1021 | 3,5-$F_2$—Ph | $CH_2CH_3$ | O | H | $CH_2$ | 2-chloropyridin-4-yl | |
| 1.1022 | 3-F—Ph | H | O | H | $CH_2$ | 2-chloropyrimidin-4-yl | |
| 1.1023 | 3,5-$F_2$—Ph | H | O | H | $CH_2$ | 2-chloropyrimidin-4-yl | [$CDCl_3$] 1.79 (s, 3H); 3.24 (d, 1H); 3.81 (d, 1H); 4.50 (dd, 1H); 4.59 (dd, 1H); 6.90 (m, 1H); 7.16 (d, 1H); 7.19 (m, 2H); 7.60 (t br, 1H); 8.55 (d, 1H). |
| 1.1024 | 3,5-$F_2$—Ph | H | O | H | $CH_2$ | 2-cyanpyridin-4-yl | [$CDCl_3$] 1.79 (s, 3H); 3.25 (d, 1H); 3.80 (d, 1H); 4.43 (dd, 1H); 4.57 (dd, 1H); 6.92 (m, 1H); 7.18 (m, 2H); 7.36 (d, 1H); 7.37 (s br, 1H); 7.55 (s, 1H); 8.65 (d, 1H). |
| 1.1025 | 3,5-$F_2$—Ph | H | O | H | $CH_2$ | 2-cyclopropyl-pyridin-4-yl | [$CDCl_3$] 0.58 (m, 2H); 0.67 (m, 2H); 1.79 (s, 3H); 1.94 (m, 1H); 3.23 (d, 1H); 3.83 (d, 1H); 4.48 (dd, 1H); 4.47 (dd, 1H); 6.89 (m, 2H); 6.95 (s br, 1H); 7.17 (m, 3H); 8.37 (d, 1H). |
| 1.1026 | 3,5-$Cl_2$—Ph | H | O | H | $CH_2$ | 2-cyclopropyl-pyridin-4-yl | [$CDCl_3$] 0.97 (m, 4H); 1.78 (s, 3H); 1.94 (m, 1H); 3.23 (d, 1H); 3.82 (d, 1H); 4.36 (dd, 1H); 4.44 (dd, 1H); 6.87 |

TABLE 1-continued

Compounds of the general formula (I) according to the invention in which $R^2$ is hydrogen and $R^3$ is methyl and aryl is the radical

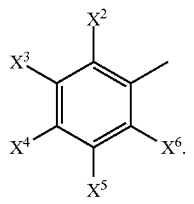

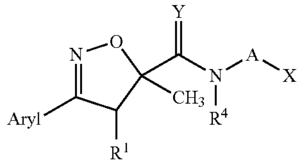

| No. | Aryl | $R^1$ | Y | $R^4$ | A | X | Physical data |
|---|---|---|---|---|---|---|---|
| | | | | | | | (d, 1H); 6.94 (s, 1H); 7.20 (t br, 1H); 7.43 (s, 1H); 7.52 (s, 2H); 8.35 (d, 1H). |
| 1.1027 | 3-F—Ph | H | O | H | $CH_2$ | 2-cyclopropyl-pyridin-4-yl | [$CDCl_3$] 0.95 (m, 4H); 1.78 (s, 3H); 1.91 (m, 1H); 3.26 (d, 1H); 3.86 (d, 1H); 4.37 (dd, 1H); 4.46 (dd, 1H); 6.87 (d, 1H); 6.94 (s, 1H); 7.15 (m, 1H); 7.27 (s br, 1H); 7.40 (m, 2H); 8.34 (d, 1H). |
| 1.1028 | 3,5-$F_2$—Ph | H | O | H | $CH_2$ | 2-ethynylpyridin-4-yl | [$CDCl_3$] 1.79 (s, 3H); 3.12 (s, 1H); 3.24 (d, 1H); 3.81 (d, 1H); 4.45 (cd, 2H); 6.90 (m, 1H); 7.12 (d, 1H); 7.15 (m, 2H); 7.28 (s br, 1H); 7.31 (s, 1H); 8.51 (d, 1H). |
| 1.1029 | 3,5-$F_2$—Ph | H | O | H | $CH_2$ | 2-ethoxypyridin-4-yl | [$CDCl_3$] 1.36 (t, 3H); 1.78 (s, 3H); 3.23 (d, 1H); 3.81 (d, 1H); 4.33 (q, 2H); 4.34 (dd, 1H); 4.47 (dd, 1H); 6.54 (s, 1H); 6.70 (d, 1H); 6.89 (m, 1H); 7.18 (m, 2H); 7.20 (s br, 1H); 8.06 (d, 1H); |
| 1.1030 | 3,5-$F_2$—Ph | H | O | H | $CH_2$ | 2-ethoxypyrimidin-4-yl | [$CDCl_3$] 1.42 (t, 3H); 1.78 (s, 3H); 3.22 (d, 1H); 3.81 (d, 1H); 4.42 (q, 2H); 4.43 (dd, 1H); 4.50 (dd, 1H); 6.81 (d, 1H); 6.89 (m, 1H); 7.16 (m, 2H); 7.71 (t br, 1H); 8.43 (d, 1H). |
| 1.1031 | 3-F—Ph | H | O | H | $CH_2$ | 2-ethoxypyrimidin-4-yl | |
| 1.1032 | 3,5-$F_2$—Ph | H | O | H | $CH_2$ | 2-ethylpyridin-4-yl | [$CDCl_3$] 1.25 (t, 3H); 1.79 (s, 3H); 2.77 (q, 2H); 3.23 (d, 1H); 3.82 d, 1H); 4.39 (dd, 1H); 4.49 (dd, 1H); 6.90 (m, 1H); 6.96 (d, 1H); 6.99 (s, 1H); 7.18 (m, 2H); 7.27 (s br, 1H); 8.45 (d, 1H). |
| 1.1033 | 3-F—Ph | H | O | H | $CH_2$ | 2-ethylpyridin-4-yl | [$CDCl_3$] 1.23 (t, 3H); 1.79 (s, 3H); 2.75 (q, 2H); 3.27 (d, 1H); 3.85 (d, 1H); 4.42 (AB d, 2H); 6.96 (d, 1H); 7.14 (m, 1H); 7.30 (t br, 1H); 7.38 (m, 2H); 7.41 (s, 1H); 8.44 (d, 1H); |
| 1.1034 | 3,5-$Cl_2$—Ph | H | O | H | $CH_2$ | 2-ethylpyridin-4-yl | [$CDCl_3$] 1.25 t, 3H); 1.78 (s, 3H); 2.77 (q, 2H); 3.22 (d, 1H); 3.82 (d, 1H); 4.43 (AB d, 2H); 6.95 (d, 1H); 6.98 (s, 1H); 7.22 (t br, 1H); 7.43 (s, 1H); 7.53 (s, 2H); 8.45 (d, 1H). |
| 1.1035 | 3,5-$Cl_2$—Ph | H | O | H | $CH_2$ | 2-fluoropyridin-4-yl | [$CDCl_3$] 1.78 (s, 3H); 3.24 (d, 1H); 3.81 (d, 1H); 4.42 |

TABLE 1-continued

Compounds of the general formula (I) according to the invention in which $R^2$ is hydrogen and $R^3$ is methyl and aryl is the radical

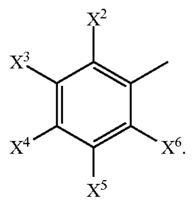

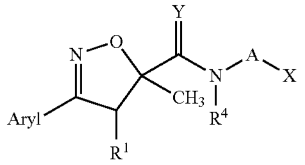

| No. | Aryl | $R^1$ | Y | $R^4$ | A | X | Physical data |
|---|---|---|---|---|---|---|---|
| | | | | | | | (dd, 1H); 4.57 (dd, 1H); 6.78 (s, 1H); 7.03 (m, 1H); 7.31 (t br, 1H); 7.43 (s, 1H); 7.51 (s, 2H); 8.17 (d, 1H). |
| 1.1036 | 3,5-$F_2$—Ph | H | O | H | $CH_2$ | 2-fluoropyridin-4-yl | [$CDCl_3$] 1.79 (s, 3H); 3.25 (d, 1H); 3.83 (d, 1H); 4.42 (dd, 1H); 4.57 (dd, 1H); 6.77 (s, 1H); 6.90 (m, 1H); 7.04 (m, 1H); 7.17 (m, 2H); 7.32 (t br, 1H); 8.15 (d, 1H). |
| 1.1037 | 3-F—Ph | H | O | H | $CH_2$ | 2-fluoropyridin-4-yl | [$CDCl_3$] 1.79 (s, 3H); 3.27 (d, 1H); 3.83 (d, 1H); 4.43 (dd, 1H); 4.56 (dd, 1H); 6.78 (s, 1H); 7.03 (m, 1H); 7.15 (m, 1H); 7.35 (s br, 1H); 7.40 (m, 3H); 8.13 (d, 1H). |
| 1.1038 | 3-Me-5-$CF_3O$—Ph | H | O | H | $CH_2$ | 2-fluoropyridin-4-yl | [$CDCl_3$] 1.78 (s, 3H); 2.40 (s, 3H); 3.27 (d, 1H); 3.84 (d, 1H); 4.43 (dd, 1H); 4.56 (dd, 1H); 6.78 (s, 1H); 7.03 (m, 1H); 7.12 (s, 1H); 7.33 (s, 1H); 7.37 (s, 1H); 8.14 (d, 1H). |
| 1.1039 | 3-Cl-5-F—Ph | H | O | H | $CH_2$ | 2-fluoropyridin-4-yl | [$CDCl_3$] 1.78 (s, 3H); 3.24 (d, 1H); 3.81 (d, 1H); 4.42 (dd, 1H); 4.56 (dd, 1H); 6.77 (s, 1H); 7.03 (d, 1H); 7.18 (m, 1H); 7.28 (m, 1H); 7.31 (t br, 1H); 7.42 (s, 1H); 8.16 (d, 1H); |
| 1.1040 | 3,5-$F_2$—Ph | H | O | H | $CH_2$ | 2-hydroxypyridin-4-yl | |
| 1.1041 | 3,5-$Cl_2$—Ph | H | O | H | $CH_2$ | 2-hydroxypyridin-4-yl | |
| 1.1042 | 3-F—Ph | H | O | H | $CH_2$ | 2-hydroxypyridin-4-yl | |
| 1.1043 | 3,5-$F_2$—Ph | H | O | H | $CH_2$ | 2-isopropoxy-pyridin-4-yl | [$CDCl_3$] 1.31 (d; 6H); 1.78 (s, 3H); 3.23 (d, 1H); 4.32 (dd, 1H); 4.47 (dd, 1H); 5.27 (sept, 1H); 6.50 (s, 1H); 6.67 (d, 1H); 6.90 (m, 1H); 7.20 (m, 3H); 8.06 (d, 1H). |
| 1.1044 | 3,5-$F_2$—Ph | H | O | H | $CH_2$ | 2-methoxypyridin-4-yl | [$CDCl_3$] 1.78 (s, 3H); 3.22 (d, 3H); 3.80 (d, 1H); 3.91 (s, 3H); 4.40 (dq, 2H); 6.56 (s, 1H); 6.72 (d, 1H); 6.89 (m, 1H); 7.18 (m, 2H); 7.19 (m, 1H); 8.09 (d, 1H). |
| 1.1045 | 3,5-$Cl_2$—Ph | H | O | H | $CH_2$ | 2-methoxypyridin-4-yl | |
| 1.1046 | 3-F—Ph | H | O | H | $CH_2$ | 2-methoxypyridin-4-yl | [$CDCl_3$] 1.78 (s, 3H); 3.26 (d, 1H); 3.83 (d, 1H); 3.90 (s, 3H); 4.40 (dq, 2H); 6.57 |

TABLE 1-continued

Compounds of the general formula (I) according to the invention in which $R^2$ is hydrogen and $R^3$ is methyl and aryl is the radical

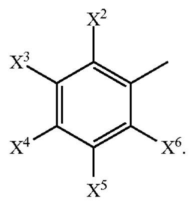

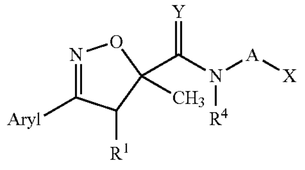

| No. | Aryl | $R^1$ | Y | $R^4$ | A | X | Physical data |
|---|---|---|---|---|---|---|---|
| | | | | | | | (m, 1H); 6.72 (d, 1H); 7.16 (m, 1H); 7.25 (m, 1H), 7.39 (m, 3H); 8.07 (d, 1H) |
| 1.1047 | 3-Cl-5-F—Ph | H | O | H | $CH_2$ | 2-methoxypyridin-4-yl | [$CDCl_3$] 1.78 (s, 3H); 3.23 (d, 1H); 3.81 (d, 1H); 3.91 (s, 3H); 4.34 (dd, 1H); 4.47 (dd, 1H); 6.57 (s, 1H); 6.72 (d, 1H); 7.18 (m, 1H), 7.19 (t br, 1H); 7.29 (d, 1H); 7.41 (s, 1H); 8.09 (d, 1H). |
| 1.1048 | 3,5-$F_2$—Ph | H | O | H | $CH_2$ | 2-methylpyridin-4-yl | [$CDCl_3$] 1.79 (s, 3H); 2.50 (s, 3H); 3.23 (d, 3H); 3.81 (d, 1H); 4.41 (dq, 2H); 6.91 (t, 1H); 6.95 (d, 1H); 6.99 (s, 1H); 7.18 (d, 2H); 7.24 (t, 2H); 8.42 (d, 1H). |
| 1.1049 | 3,5-$Cl_2$—Ph | H | O | H | $CH_2$ | 2-methylpyridin-4-yl | [$CDCl_3$] 1.78 (s, 3H); 2.51 (s, 3H); 3.22 (d, 3H); 3.81 (d, 1H); 4.41 (dq, 2H); 6.94 (d, 1H); 6.99 (s, 1H); 7.22 (br, t, 1H); 7.44 (s, 1H); 7.53 (s, 2H); 8.43 (d, 1H). |
| 1.1050 | 3-F—Ph | H | O | H | $CH_2$ | 2-methylpyridin-4-yl | |
| 1.1051 | 3,5-$F_2$—Ph | H | O | H | $CH_2$ | 2-propylpyridin-4-yl | [$CDCl_3$] 0.92 (t, 3H); 1.69 (m, 2H); 1.78 (s, 3H); 2.70 (dd, 2H); 3.22 (d, 1H); 3.82 (d, 1H); 4.39 (dd, 1H); 4.48 (dd, 1H); 6.91 (m, 1H); 7.16 (m, 2H); 7.24 (t br, 1H); 8.45 (d, 1H). |
| 1.1052 | 3-F—Ph | H | O | H | $CH_2$ | 2-propylpyridin-4-yl | |
| 1.1053 | 3,5-$Cl_2$—Ph | H | O | H | $CH_2$ | 2-propylpyridin-4-yl | |
| 1.1054 | 3,5-$F_2$—Ph | H | O | H | $CH_2$ | 2-tert-butylpyridin-4-yl | [$CDCl_3$] 1.30 (s, 9H); 1.80 (s, 3H); 3.25 (d, 1H); 3.42 (m, 1H); 3.83 (d, 1H); 4.50 (m, 1H); 6.92 (m, 2H); 7.16 (m, 3H); 8.48 (m, 1H). |
| 1.1055 | 3,5-$Cl_2$—Ph | H | O | H | $CH_2$ | 2-tert-butylpyridin-4-yl | |
| 1.1056 | 3-F—Ph | H | O | H | $CH_2$ | 2-tert-butylpyridin-4-yl | [$CDCl_3$] 1.29 (s, 9H); 1.80 (s, 3H); 3.28 (d, 1H); 3.87 (d, 1H); 4.46 (dq, 2H); 6.94 (m, 1H); 7.15 (m, 2H); 7.30 (br, s, 1H); 7.41 (m, 3H); 8.48 (m, 1H) |
| 1.1057 | 3-Me-5-$CF_3O$—Ph | H | O | H | $CH_2$ | 2-tert-butylpyridin-4-yl | [$CDCl_3$] 1.20 (s, 9H); 1.79 (s, 3H); 2.41 (s, 3H); 3.26 (d, 1H); 3.87 (d, 1H); 4.45 (AB d, 2H); 6.93 (d, 1H); 7.12 (s, 1H); 7.14 (s, 1H); 7.28 (s br, 1H); 7.34 (s, 1H); 7.36 (s, 1H); 8.48 (d, 1H). |

TABLE 1-continued

Compounds of the general formula (I) according to the invention in which $R^2$ is hydrogen and $R^3$ is methyl and aryl is the radical

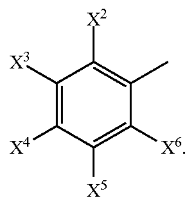

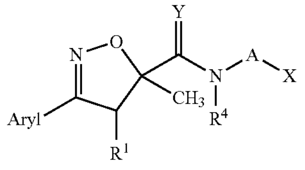

| No. | Aryl | $R^1$ | Y | $R^4$ | A | X | Physical data |
|---|---|---|---|---|---|---|---|
| 1.1058 | 3-Cl-5-F—Ph | H | O | H | $CH_2$ | 2-tert-butylpyridin-4-yl | [$CDCl_3$] 1.31 (s, 9H); 1.79 (s, 3H); 3.23 (d, 1H); 3.84 (d, 1H); 4.46 (AB d, 2H); 6.94 (d, 1H); 7.15 (s, 1H); 7.18 (m, 1H); 7.28 (m, 1H); 7.42 (s, 1H); 8.50 (d, 1H). |
| 1.1059 | 3-F—Ph | H | O | H | $CH_2$ | 3-(difluoromethyl)-1-methyl-1H-pyrazol-4-yl | |
| 1.1060 | 3,5-$F_2$—Ph | H | O | H | $CH_2$ | 3,5-diethyl-1,2-oxazol-4-yl | [$CDCl_3$] 1.24 (t, 3H); 1.26 (t, 3H); 1.72 (s, 1H); 2.60 (q, 2H); 2.74 (q, 2H); 3.19 (d, 1H); 3.76 (d, 1H); 4.15 (dd, 1H); 4.24 (dd, 1H); 6.82 (t br, 1H); 6.89 (m, 1H); 7.14 (m, 2H). |
| 1.1061 | 3-F—Ph | H | O | H | $CH_2$ | 3,5-diethyl-1,2-oxazol-4-yl | |
| 1.1062 | 3,5-$Cl_2$—Ph | H | O | H | $CH_2$ | 3,5-diethyl-1,2-oxazol-4-yl | |
| 1.1063 | 3-Cl-5-F—Ph | H | O | H | $CH_2$ | 3,5-diethyl-1,2-oxazol-4-yl | [$CDCl_3$] 1.23 (t, 3H); 1.25 (t, 3H); 1.72 (s, 3H); 2.60 (q, 2H); 2.74 (q, 2H); 3.20 (d, 1H); 3.77 (d, 1H); 4.14 (dd, 1H); 4.24 (dd, 1H); 6.82 (s br, 1H); 7.17 (m, 1H); 7.25 (m, 1H); 7.39 (s, 1H). |
| 1.1064 | 3,5-$F_2$—Ph | H | O | H | $CH_2$ | 3,5-dimethyl-1,2-oxazol-4-yl | [$CDCl_3$] 1.72 (s, 3H); 2.20 (s, 3H); 2.37 (d, 3H); 3.20 (d, 1H); 3.76 (d, 1H); 4.20 (dq, 2H); 6.88 (m, 1H); 7.15 (m, 1H). |
| 1.1065 | 3,5-$Cl_2$—Ph | H | O | H | $CH_2$ | 3,5-dimethyl-1,2-oxazol-4-yl | |
| 1.1066 | 3-F—Ph | H | O | H | $CH_2$ | 3,5-dimethyl-1,2-oxazol-4-yl | |
| 1.1067 | 3-F—Ph | H | O | H | $CH_2$ | 3,5-dimethyl-1,2-oxazol-4-yl | |
| 1.1068 | 3-Cl-5-F—Ph | H | O | H | $CH_2$ | 3,5-dimethyl-1,2-oxazol-4-yl | [$CDCl_3$] 1.72 (s, 3H); 2.20 (s, 3H); 2.37 (s, 3H); 3.20 (d, 1H); 3.77 (d, 1H); 4.12 (dd, 1H); 4.25 (dd, 1H); 6.88 (s br, 1H); 7.17 (m, 1H); 7.24 (m, 1H); 7.39 (s, 1H). |
| 1.1069 | 3,5-$F_2$—Ph | H | O | H | $CH_2$ | 3-Amino-1-ethyl-1H-pyrazol-4-yl | |
| 1.1070 | 3,5-$F_2$—Ph | H | O | H | $CH_2$ | 3-ethyl-5-methyl-1,2-oxazol-4-yl | [$CDCl_3$] 1.23 (t, 3H); 1.72 (s, 3H); 2.37 (s, 3H); 2.59 (q, 2H); 3.19 (d, 1H); 3.76 (d, 1H); 4.14 (dd, 1H); 4.24 (dd, 1H); 6.88 (m, 2H); 7.14 (m, 2H). |
| 1.1071 | 3-F—Ph | H | O | H | $CH_2$ | 3-ethyl-5-methyl-1,2-oxazol-4-yl | |

TABLE 1-continued

Compounds of the general formula (I) according to the invention in which $R^2$ is hydrogen and $R^3$ is methyl and aryl is the radical

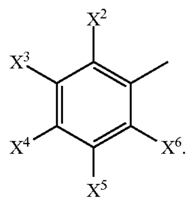

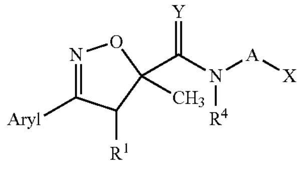

| No. | Aryl | $R^1$ | Y | $R^4$ | A | X | Physical data |
|---|---|---|---|---|---|---|---|
| 1.1072 | 3,5-$Cl_2$—Ph | H | O | H | $CH_2$ | 3-ethyl-5-methyl-1,2-oxazol-4-yl | [$CDCl_3$] 1.23 (t, 3H); 1.72 (s, 3H); 2.37 (s, 3H); 2.59 (q, 2H); 3.19 (d, 1H); 3.77 (d, 1H); 4.13 (dd, 1H); 4.24 (dd, 1H); 6.84 (t br, 1H); 7.42 (s, 1H); 7.49 (s, 2H). |
| 1.1073 | 3,5-$F_2$—Ph | H | O | H | $CH_2$ | 3-methyl-1,2,4-oxadiazol-5-yl | |
| 1.1074 | 3,5-$Cl_2$—Ph | H | O | H | $CH_2$ | 3-methyl-1,2,4-oxadiazol-5-yl | [$CDCl_3$] 1.77 (s, 3H); 2.36 (s, 3H); 3.23 (d, 1H); 3.80 (d, 1H); 4.65 (dq, 2H); 7.42 (s, 1H); 7.42 (br, t, 1H); 7.52 (s, 2H). |
| 1.1075 | 3-F—Ph | H | O | H | $CH_2$ | 3-methyl-1,2,4-oxadiazol-5-yl | |
| 1.1076 | 3-Br-5-Me—Ph | H | O | H | $CH_2$ | 3-methyl-1-propyl-1H-pyrazol-4-yl | |
| 1.1077 | 3-Et—Ph | H | O | H | $CH_2$ | 3-methyl-1-propyl-1H-pyrazol-4-yl | |
| 1.1078 | 3-$CF_3$—Ph | H | O | H | $CH_2$ | 3-methyl-1-propyl-1H-pyrazol-4-yl | [$CDCl_3$] 0.89 (t, 3H); 1.72 (s, 3H); 1.81 (m, 2H); 2.18 (s, 3H); 3.26 (d, 1H); 3.88 (d, 1H); 3.94 (dd, 2H); 4.25 (dq, 2H); 6.87 (br, t, 1H); 7.22 (s, 1H); 7.55 (t, 1H); 7.69 (d, 1H); 7.89 (s, 1H); 7.80 (d, 1H). |
| 1.1079 | 3-Cl-5-Et—Ph | H | O | H | $CH_2$ | 3-methyl-1-propyl-1H-pyrazol-4-yl | |
| 1.1080 | 3-Et-5-F—Ph | H | O | H | $CH_2$ | 3-methyl-1-propyl-1H-pyrazol-4-yl | |
| 1.1081 | 3-($F_2$—MeO)Ph | H | O | H | $CH_2$ | 3-methyl-1-propyl-1H-pyrazol-4-yl | |
| 1.1082 | 3-vinylPh | H | O | H | $CH_2$ | 3-methyl-1-propyl-1H-pyrazol-4-yl | |
| 1.1083 | 3-F—Ph | H | O | H | $CH_2$ | 4,5-dimethyl-4H-1,2,4-triazol-3-yl | |
| 1.1084 | 3,5-$F_2$—Ph | H | O | H | $CH_2$ | 4,5-dimethyl-4H-1,2,4-triazol-3-yl | [$CDCl_3$] 1.73 (s, 3H); 2.22 (s, 3H); 3.20 (d, 1H); 3.52 (s, 3H); 3.76 (d, 1H); 4.53 (dd, 1H); 4.68 (dd, 1H); 6.88 (m, 1H); 7.15 (m, 2H); 7.44 (t br, 1H). |
| 1.1085 | 3-F—Ph | H | O | H | $CH_2$ | 4,6-dimethoxy-pyrimidin-2-yl | [$CDCl_3$] 1.79 (s, 3H); 3.24 (d, 1H); 3.86 (d, 1H); 3.92 (s, 6H); 4.49 (m, 2H); 5.90 (s, 1H); 7.13 (m, 1H); 7.36 (m, 3H); 7.96 (s br, 1H). |
| 1.1086 | 3,5-$Cl_2$—Ph | H | O | H | $CH_2$ | 4,6-dimethoxy-pyrimidin-2-yl | |

TABLE 1-continued

Compounds of the general formula (I) according to the invention in which $R^2$ is hydrogen and $R^3$ is methyl and aryl is the radical

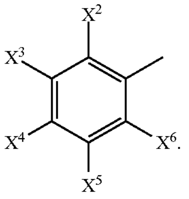

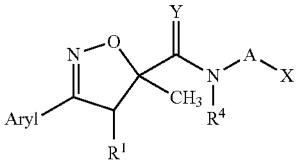

| No. | Aryl | $R^1$ | Y | $R^4$ | A | X | Physical data |
|---|---|---|---|---|---|---|---|
| 1.1087 | 3,5-$F_2$—Ph | H | O | H | $CH_2$ | 4,6-dimethoxy-pyrimidin-2-yl | |
| 1.1088 | 3,5-$F_2$—Ph | H | O | H | $CH_2$ | 5-ethyl-1,2,4-oxadiazol-3-yl | [$CDCl_3$] 1.35 (t, 3H); 1.76 (s, 3H); 2.88 (q, 2H); 3.21 (d, 1H); 3.81 (d, 1H); 4.54 (dq, 2H); 6.88 (m, 1H); 7.16 (m, 2H); 7.32 (br, t, 1H). |
| 1.1089 | 3,5-$Cl_2$—Ph | H | O | H | $CH_2$ | 5-ethyl-1,2,4-oxadiazol-3-yl | |
| 1.1090 | 3-F—Ph | H | O | H | $CH_2$ | 5-ethyl-1,2,4-oxadiazol-3-yl | |
| 1.1091 | 3,5-$F_2$—Ph | H | O | H | $CH_2$ | 5-methyl-1,2-oxazol-4-yl | [$CDCl_3$] 1.72 (s, 3H); 2.42 (s, 3H); 3.20 (d, 1H); 3.78 (d, 1H); 4.16 (dd, 1H); 4.29 (dd, 1H); 6.89 (m, 1H); 7.04 (t br, 1H); 7.15 (d, 2H); 8.13 (s, 1H). |
| 1.1092 | 3,5-$F_2$—Ph | H | O | H | $CH_2$ | 6-(trifluoromethyl)-pyridin-3-yl | [$CDCl_3$] D1 1.14 (d, 3H); 1.23 (t, 3H); 1.32 (d, 3H); 1.73 (s, 3H); 3.18 (d, 1H); 3.77 (d, 1h); 4.12 (m, 1H); 4.60 (m, 1H); 6.88 (m, 1H); 7.16 (m, 2H); 7.25 (s br, 1H). D2 1.17 (d, 3H); 1.26 (t, 3H); 1.36 (d, 3H); 1.74 (s, 3H); 3.19 (d, 1H); 3.79 (d, 1h); 4.33 (m, 1H); 4.60 (m, 1H); 6.88 (m, 1H); 7.16 (m, 2H); 7.25 (s br, 1H). |
| 1.1093 | 3,5-$Cl_2$—Ph | H | O | H | $CH_2$ | 6-(trifluoromethyl)-pyridin-3-yl | [$CDCl_3$] 1.75 (s, 3H); 3.23 (d, 1H); 3.80 (d, 1H); 4.46 (dd, 1H); 4.61 (dd, 1H); 7.29 (t br, 1H); 7.44 s, 1H); 7.51 (s, 1H); 7.65 (d, 1H); 7.76 (d, 1H); 8.63 (s, 1H). |
| 1.1094 | 3-F—Ph | H | O | H | $CH_2$ | 6-(trifluoromethyl)-pyridin-3-yl | |
| 1.1095 | 3-Me-5-$CF_3O$—Ph | H | O | H | $CH_2$ | 6-chloropyridin-3-yl | [$CDCl_3$] 1.74 (s, 3H); 2.40 (s, 3H); 3.24 (d, 1H); 3.81 (d, 1H); 4.36 (dd, 1H); 4.51 (dd, 1H); 7.10 (s, 1H); 7.28 (s, 1H); 7.31 (s, 1H); 7.34 (s, 1H); 7.55 (d, 1H); 8.30 (s, 1H). |
| 1.1096 | 3-F—Ph | H | O | H | $CH_2$ | 6-chloropyrimidin-4-yl | [$CDCl_3$] 1.79 (s, 3H); 3.27 (d, 1H); 3.84 (d, 1H); 4.54 (m, 2H); 7.15 (m, 1H); 7.24 (s, 1H); 7.40 (m, 3H); 7.21 (t br, 1H); 8.91 (s, 1H). |
| 1.1097 | 3,5-$F_2$—Ph | H | O | H | $CH_2$ | 6-chloropyrimidin-4-yl | [$CDCl_3$] 1.79 (s, 3H); 3.23 (d, 1H); 3.80 (d, 1H); 4.54 (m, 2H); 6.89 (m, 1H); 7.17 (m, 2H); 7.20 (t br, 1H); 8.92 (s, 1H). |

TABLE 1-continued

Compounds of the general formula (I) according to the invention in which $R^2$ is hydrogen and $R^3$ is methyl and aryl is the radical

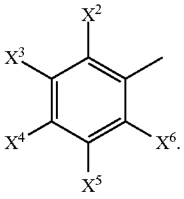

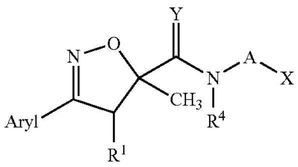

| No. | Aryl | $R^1$ | Y | $R^4$ | A | X | Physical data |
|---|---|---|---|---|---|---|---|
| 1.1098 | 3,5-$F_2$—Ph | H | O | H | $CH_2$ | 6-ethoxypyrimidin-4-yl | [$CDCl_3$] 1.37 (t, 3H); 1.76 (s, 3H); 3.22 (d, 1H); 3.81 (d, 1H); 4.43 (d, 2H); 4.42 (dd, 1H); 4.50 (dd, 1H); 6.55 (s, 1H); 6.89 (m, 1H); 7.18 (m, 2H); 7.67 (t br, 1H); 8,69 (s, 1H). |
| 1.1099 | 3-F—Ph | H | O | H | $CH_2$ | 6-ethoxypyrimidin-4-yl | [$CDCl_3$] 1.36 (t, 3H); 1.78 (s, 3H); 3.24 (d, 1H); 3.84 (d, 1H); 4.39 (d, 2H); 4.42 (dd, 1H); 4,47 (dd, 1H); 7.14 (m, 1H); 7.38 (m, 3H); 7.69 (t br, 1H); 8.67 (s, 1H). |
| 1.1100 | 3,5-$F_2$—Ph | H | O | $CH_3$ | $CH_2$ | furan-2-yl | |
| 1.1101 | 3,5-$F_2$—Ph | H | O | H | $CH_2$ | pyrimidin-2-yl | [$CDCl_3$] 1.80 (s, 1H); 3.22 (d, 1H); 3.85 (d, 1H); 4.70 (q d, 2H); 6.87 (m, 1H); 7.18 (m, 3H); 8.00 (s br, 1H); 8.70 d, 2H). |
| 1.1102 | 3,5-$F_2$—Ph | H | O | H | $CH(CH_3)$ | 2-Thienyl | [DMSO-$D_6$] 1.52 (d, 3H); 1.59 (s, 3H); 3.38 (d, 1H); 3.75 (d, 1H); 5.21 (m, 1H); 6.90 (m, 2H); 7.40 (m, 3H); 8.56 (d, 1H). |
| 1.1103 | 3,5-$F_2$—Ph | H | O | H | $CH_2CH_2$ | 2,4-dioxo-1,2,3,4-tetrahydropyrimidin-5-yl | [DMSO-$D_6$] 2.32 (m, 2H); 3.14 (m, 1H); 3.26 (m, 1H); 3.33 (d, 1H); 3.70 (d, 1H); 7.10 (d, 1H); 7.39 (m, 3H); 8.10 (t br, 1H); 10.59 (d, 1H); 10.96 (s, 1H). |
| 1.1104 | 3,5-$Cl_2$—Ph | H | O | H | $CH_2CH_2$ | 2,4-dioxo-1,2,3,4-tetrahydro-pyrimidin-5-yl | |

TABLE 2

Compounds of the general formula (I) according to the invention in which $R^2$ is hydrogen and $R^3$ is ethyl and aryl is the radical

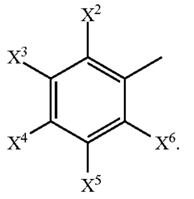

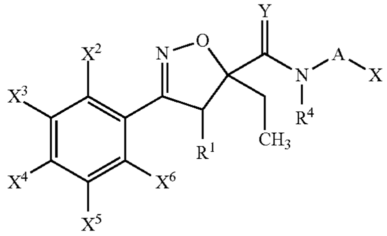

| No. | Aryl | $R^1$ | Y | $R^4$ | A | X | Physical data |
|---|---|---|---|---|---|---|---|
| 2.001 | 3,5-$Cl_2$—Ph | H | O | H | bond | 1,2-oxazol-3-yl | |
| 2.002 | 3,5-$(CF_3)_2$—Ph | H | O | H | bond | 1,3-dimethyl-1H-pyrazol-5-yl | |
| 2.003 | 3,5-$Cl_2$—Ph | H | O | H | bond | 1,3-dimethyl-1H-pyrazol-5-yl | [$CDCl_3$] 1.09 (t, 3H); 2.06 (m, 1H); 2.25 (s, 3H); 2.25 (m, 1H); 3.33 (d, 1H); 3.71 (s, 3H); 3.78 (d, 1H); 6.18 (s, 1H); 7.44 (m, 1H); 7.55 (m, 2H); 8.45 (s, 1H). |
| 2.004 | 3,5-$Cl_2$—Ph | H | O | H | bond | 1,3-oxazol-2-yl | |
| 2.005 | 3,5-$Cl_2$—Ph | H | O | H | bond | 1,3-thiazol-2-yl | |
| 2.006 | 3,5-$Cl_2$—Ph | H | O | H | bond | 1,5-dimethyl-1H-pyrazol-4-yl | |
| 2.007 | 3,5-$F_2$—Ph | H | O | H | bond | 1,5-dimethyl-1H-pyrazol-4-yl | |
| 2.008 | 3-F—Ph | H | O | H | bond | 1,5-dimethyl-1H-pyrazol-4-yl | |
| 2.009 | 3-Me—Ph | H | O | H | bond | 1,5-dimethyl-1H-pyrazol-4-yl | |
| 2.010 | Ph | H | O | H | bond | 1,5-dimethyl-1H-pyrazol-4-yl | |
| 2.011 | 3,5-$Cl_2$—Ph | H | O | H | bond | 1-ethyl-3-(methoxy-carbonyl)-1H-pyrazol-4-yl | |
| 2.012 | 3,5-$F_2$—Ph | H | O | H | bond | 1-ethyl-3-(methoxy-carbonyl)-1H-pyrazol-4-yl | |
| 2.013 | 3-F—Ph | H | O | H | bond | 1-ethyl-3-(methoxy-carbonyl)-1H-pyrazol-4-yl | |
| 2.014 | Ph | H | O | H | bond | 1-ethyl-3-(methoxy-carbonyl)-1H-pyrazol-4-yl | |
| 2.015 | 3,5-$Cl_2$—Ph | H | O | H | bond | 1-ethyl-3-methyl-1H-pyrazol-4-yl | |
| 2.016 | 3,5-$F_2$—Ph | H | O | H | bond | 1-ethyl-3-methyl-1H-pyrazol-4-yl | |
| 2.017 | 3-F—Ph | H | O | H | bond | 1-ethyl-3-methyl-1H-pyrazol-4-yl | |
| 2.018 | Ph | H | O | H | bond | 1-ethyl-3-methyl-1H-pyrazol-4-yl | |
| 2.019 | 3,5-$Cl_2$—Ph | H | O | H | bond | 1-methyl-1H-1,2,4-triazol-3-yl | |
| 2.020 | 3,5-$F_2$—Ph | H | O | H | bond | 1-methyl-1H-1,2,4-triazol-3-yl | |
| 2.021 | 3,5-$Cl_2$—Ph | H | O | H | bond | 1-methyl-1H-imidazol-2-yl | |
| 2.022 | 3,5-$Cl_2$—Ph | H | O | H | bond | 1-methyl-1H-pyrazol-4-yl | |
| 2.023 | 3,5-$F_2$—Ph | H | O | H | bond | 1-methyl-1H-pyrazol-4-yl | |
| 2.024 | 3-F—Ph | H | O | H | bond | 1-methyl-1H-pyrazol-4-yl | |

TABLE 2-continued

Compounds of the general formula (I) according to the invention in which $R^2$ is hydrogen and $R^3$ is ethyl and aryl is the radical

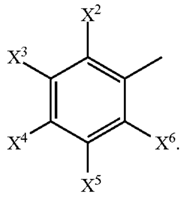

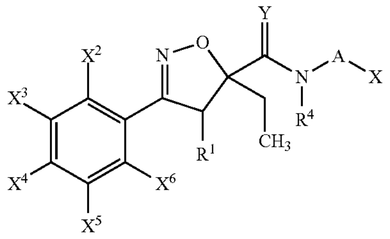

| No. | Aryl | $R^1$ | Y | $R^4$ | A | X | Physical data |
|---|---|---|---|---|---|---|---|
| 2.025 | Ph | H | O | H | bond | 1-methyl-1H-pyrazol-4-yl | |
| 2.026 | 3,5-$Cl_2$—Ph | H | O | H | bond | 1-propyl-1H-1,2,4-triazol-3-yl | |
| 2.027 | 3,5-$F_2$—Ph | H | O | H | bond | 1-propyl-1H-1,2,4-triazol-3-yl | |
| 2.028 | 3,5-$Cl_2$—Ph | H | O | H | bond | 2-(2-ethoxy-2-oxoethyl)phenyl | |
| 2.029 | 3,5-$Cl_2$—Ph | H | O | H | bond | 2-(methoxy-carbonyl)phenyl | |
| 2.030 | 3,5-$Cl_2$—Ph | H | O | H | bond | 2-(methylcarbamoyl)-phenyl | |
| 2.031 | 3,5-$Cl_2$—Ph | H | O | H | bond | 2,4-dichloro-6-(methylcarbamoyl)-phenyl | [$CDCl_3$] 1.09 (t, 3H), 2.05 (m, 1H); 2.26 (m, 1H); 3.31 (d, 1H); 3.78 (d, 1H); 7.42 (t, 1H); 7.55 (m, 2H); 7.64 (d, 1H); 8.18 (d, 1H); 9.03 (s br, 1H) |
| 2.032 | 3,5-$Cl_2$—Ph | H | O | H | bond | 2,4-difluorophenyl | |
| 2.033 | 3,5-$Cl_2$—Ph | H | O | H | bond | 2-carboxyphenyl | |
| 2.034 | 3,5-$Cl_2$—Ph | H | O | H | bond | 2-chloropyridin-3-yl | |
| 2.035 | 3,5-$Cl_2$—Ph | H | O | H | bond | 3-(2-methoxy-2-oxoethyl)phenyl | |
| 2.036 | 3,5-$Cl_2$—Ph | H | O | H | bond | 3-(carboxymethyl)-phenyl | |
| 2.037 | 3,5-$Cl_2$—Ph | H | O | H | bond | 3-(ethoxycarbonyl)-1H-1,2,4-triazol-5-yl | |
| 2.038 | 3,5-$Cl_2$—Ph | H | O | H | bond | 3-(ethoxycarbonyl)-1H-1,2,4-triazol-5-yl | |
| 2.039 | 3,5-$F_2$—Ph | H | O | H | bond | 3-(methoxy-carbonyl)phenyl | |
| 2.040 | 3,5-$Cl_2$—Ph | H | O | H | bond | 3-(methoxy-carbonyl)phenyl | |
| 2.041 | 3-F—Ph | H | O | H | bond | 3-(methylcarbamoyl)-phenyl | |
| 2.042 | 3-F—Ph | H | O | H | bond | 3,5-dichlorophenyl | |
| 2.043 | 3,5-$Cl_2$—Ph | H | O | H | bond | 3,5-dimethoxyphenyl | |
| 2.044 | 3,5-$Cl_2$—Ph | H | O | H | bond | 3,5-dimethyl-1H-pyrazol-4-yl | |
| 2.045 | 3,5-$Cl_2$—Ph | H | O | H | bond | 3,5-dimethyl-1H-pyrazol-4-yl | |
| 2.046 | 3-F—Ph | H | O | H | bond | 3,5-dimethyl-1H-pyrazol-4-yl | |
| 2.047 | Ph | H | O | H | bond | 3-[2-(methylamino)-2-oxoethyl]phenyl | |
| 2.048 | 3,5-$Cl_2$—Ph | H | O | H | bond | 3-carboxyphenyl | |
| 2.049 | 3,5-$Cl_2$—Ph | H | O | H | bond | 3-carboxyphenyl | |
| 2.050 | 3-F—Ph | H | O | H | bond | 3-chloropyridin-2-yl | |
| 2.051 | 3,5-$Cl_2$—Ph | H | O | H | bond | 3-cyclopropyl-1,2,4-thiadiazol-5-yl | |

TABLE 2-continued

Compounds of the general formula (I) according to the invention in which $R^2$ is hydrogen and $R^3$ is ethyl and aryl is the radical

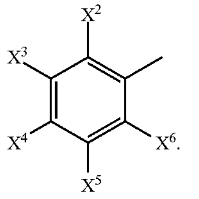

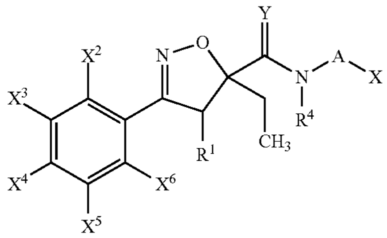

| No. | Aryl | $R^1$ | Y | $R^4$ | A | X | Physical data |
|---|---|---|---|---|---|---|---|
| 2.052 | 3,5-$Cl_2$—Ph | H | O | H | bond | 3-methyl-1,2-oxazol-5-yl | |
| 2.053 | 3,5-$Cl_2$—Ph | H | O | H | bond | 3-methyl-1-propyl-1H-pyrazol-4-yl | |
| 2.054 | 3,5-$Cl_2$—Ph | H | O | H | bond | 3-methyl-1-propyl-1H-pyrazol-4-yl | |
| 2.055 | 3,5-$F_2$—Ph | H | O | H | bond | 3-methyl-1-propyl-1H-pyrazol-4-yl | |
| 2.056 | 3-F—Ph | H | O | H | bond | 3-methyl-1-propyl-1H-pyrazol-4-yl | |
| 2.057 | Ph | H | O | H | bond | 4-(2-ethoxy-2-oxoethyl)phenyl | |
| 2.058 | 3,5-$Cl_2$—Ph | H | O | H | bond | 4-(carboxymethyl)-phenyl | |
| 2.059 | 3,5-$Cl_2$—Ph | H | O | H | bond | 4-(methoxy-carbonyl)-3-thienyl | |
| 2.060 | 3,5-$F_2$—Ph | H | O | H | bond | 4-(methoxy-carbonyl)phenyl | |
| 2.061 | 3,5-$Cl_2$—Ph | H | O | H | bond | 4,5-dimethyl-4H-1,2,4-triazol-3-yl | |
| 2.062 | 3,5-$Cl_2$—Ph | H | O | H | bond | 4,5-dimethyl-4H-1,2,4-triazol-3-yl | |
| 2.063 | 3,5-$F_2$—Ph | H | O | H | bond | 4,6-dimethoxypyrimidin-2-yl | |
| 2.064 | 3,5-$Cl_2$—Ph | H | O | H | bond | 4-carboxyphenyl | |
| 2.065 | 3,5-$Cl_2$—Ph | H | O | H | bond | 4-chloro-2-(methoxycarbonyl)-6-methylphenyl | |
| 2.066 | 3,5-$Cl_2$—Ph | H | O | H | bond | 4-chloro-2-methyl-6-(methylcarbamoyl)-phenyl | |
| 2.067 | 3,5-$Cl_2$—Ph | H | O | H | bond | 4-chlorophenyl | |
| 2.068 | 3,5-$Cl_2$—Ph | H | O | H | bond | 4-chloropyridin-2-yl | |
| 2.069 | 3,5-$Cl_2$—Ph | H | O | H | bond | 4-cyano-1-ethyl-1H-pyrazol-3-yl | |
| 2.070 | 3,5-$F_2$—Ph | H | O | H | bond | 4-cyano-1H-pyrazol-3-yl | |
| 2.071 | 3,5-$Cl_2$—Ph | H | O | H | bond | 4-cyano-1H-pyrazol-3-yl | |
| 2.072 | 3-F—Ph | H | O | H | bond | 4-cyano-1H-pyrazol-3-yl | |
| 2.073 | Ph | H | O | H | bond | 4-ethylpyridin-2-yl | |
| 2.074 | 3,5-$Cl_2$—Ph | H | O | H | bond | 4-formyl-3-(1-methylcyclopropyl)-1,2-oxazol-5-yl | |
| 2.075 | 3,5-$F_2$—Ph | H | O | H | bond | 4-methoxypyridin-2-yl | |
| 2.076 | 3,5-$Cl_2$—Ph | H | O | H | bond | 4-methyl-1,2,5-oxadiazol-3-yl | |
| 2.077 | 3,5-$Cl_2$—Ph | H | O | H | bond | 4-methyl-1,3-thiazol-2-yl | |

TABLE 2-continued

Compounds of the general formula (I) according to the invention in which $R^2$ is hydrogen and $R^3$ is ethyl and aryl is the radical

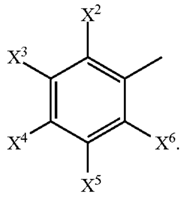

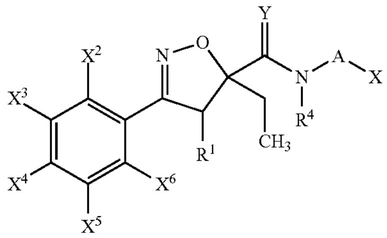

| No. | Aryl | $R^1$ | Y | $R^4$ | A | X | Physical data |
|---|---|---|---|---|---|---|---|
| 2.078 | 3,5-$Cl_2$—Ph | H | O | H | bond | 4-methyl-1,3-thiazol-2-yl | |
| 2.079 | 3,5-$F_2$—Ph | H | O | H | bond | 4-methylpyridin-2-yl | |
| 2.080 | 2,4-$Cl_2$—Ph | H | O | H | bond | 4-methylpyridin-2-yl | |
| 2.081 | 3,5-$Cl_2$—Ph | H | O | H | bond | 4-methylpyridin-2-yl | |
| 2.082 | Ph | H | O | H | bond | 4-pentylpyridin-2-yl | |
| 2.083 | 2,4-$Cl_2$—Ph | H | O | H | bond | 4-pentylpyridin-2-yl | |
| 2.084 | 3,5-$Cl_2$—Ph | H | O | H | bond | 5-(methoxy-carbonyl)-1,3-thiazol-4-yl | |
| 2.085 | 3,5-$F_2$—Ph | H | O | H | bond | 5-(methoxy-carbonyl)-1,3-thiazol-4-yl | [$CDCl_3$] 12.07 0.33; 9.10 2.14; 8.19 4.59; 8.17 4.58; 8.05 5.85; 7.52 3.19; 7.37 0.38; 7.36 0.32; 7.36 0.73; 7.31 0.95; 7.31 0.90; 7.31 1.11; 7.26 548.67; 7.24 1.58; 7.24 0.98; 7.23 0.78; 7.23 0.73; 7.23 0.65; 7.22 0.62; 7.21 1.91; 7.21 1.09; 7.21 1.36; 7.20 1.05; 7.19 3.92; 7.19 4.53; 7.18 2.84; 7.17 3.42; 7.17 4.97; 7.17 3.74; 7.16 1.03; 7.15 0.81; 7.00 3.05; 6.91 3.32; 6.91 3.01; 6.90 4.21; 6.90 3.61; 6.88 1.90; 6.87 3.10; 6.87 1.69; 6.86 0.98; 6.85 1.56; 3.81 4.95; 3.76 5.93; 3.56 0.48; 3.49 1.12; 3.32 5.31; 3.28 4.47; 2.63 3.62; 2.61 4.88; 2.59 4.00; 2.29 0.44; 2.27 1.41; 2.26 1.87; 2.24 2.47; 2.22 2.17; 2.20 0.72; 2.09 0.64; 2.07 2.02; 2.06 2.39; 2.04 2.06; 2.02 1.58; 2.01 1.87; 1.67 0.86; 1.65 2.18; 1.63 3.04; 1.62 2.35; 1.60 1.71; 1.59 0.44; 1.54 410.81; 1.51 1.09; 1.50 1.75; 1.45 0.40; 1.44 0.42; 1.36 0.93; 1.34 4.63; 1.33 6.03; 1.32 7.24; 1.31 4.50; 1.30 2.21; 1.28 0.80; 1.26 2.31; 1.23 0.37; 1.22 0.52; 1.21 0.33; 1.18 0.44; 1.10 |

TABLE 2-continued

Compounds of the general formula (I) according to the invention in which $R^2$ is hydrogen and $R^3$ is ethyl and aryl is the radical

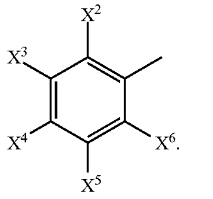

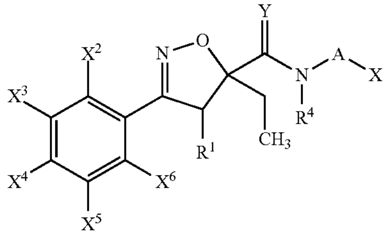

| No. | Aryl | $R^1$ | Y | $R^4$ | A | X | Physical data |
|---|---|---|---|---|---|---|---|
| | | | | | | | 7.40; 1.08 16.00; 1.06<br>6.92; 1.03 0.33; 0.93<br>0.40; 0.90 4.64; 0.89<br>13.24; 0.87 4.36; 0.84<br>0.58; 0.83 0.58; 0.81<br>0.50; 0.15 1.05; 0.10<br>0.41; 0.06 0.71; 0.05<br>0.62; 0.05 0.64; 0.02<br>0.41; 0.02 0.41; 0.02<br>0.49; 0.02 0.41; 0.02<br>0.54; 0.02 0.55; 0.02<br>0.72; 0.01 0.98; 0.01<br>1.15; 0.01 1.46; 0.01<br>11.29; 0.00 298.63; −0.01<br>12.22; −0.01 1.79; −0.01<br>1.67; −0.02 1.42; −0.02<br>1.23; −0.02 0.96; −0.02<br>0.92; −0.02 0.64; −0.03<br>0.50; −0.03 0.43; −0.05<br>0.90; −0.05 0.92; −0.15 1.07 |
| 2.086 | 3,5-$Cl_2$—Ph | H | O | H | bond | 5-chloro-4-methylpyridin-2-yl | |
| 2.087 | 3,5-$F_2$—Ph | H | O | H | bond | 5-Fluor-4-methylpyridin-2-yl | |
| 2.088 | 3,5-$Cl_2$—Ph | H | O | H | bond | 5-methoxy-1-methyl-1H-1,2,4-triazol-3-yl | |
| 2.089 | 3,5-$Cl_2$—Ph | H | O | H | bond | 5-methoxy-1-methyl-1H-1,2,4-triazol-3-yl | |
| 2.090 | 3,5-$Cl_2$—Ph | H | O | H | bond | 5-methylpyridin-2-yl | |
| 2.091 | 3,5-$F_2$—Ph | H | O | H | bond | 6-chloropyridin-2-yl | |
| 2.092 | Ph | H | O | H | bond | 6-chloropyridin-3-yl | |
| 2.093 | 3,5-$Cl_2$—Ph | H | O | H | bond | pyridin-2-yl | |
| 2.094 | 3,5-$Cl_2$—Ph | H | O | H | bond | pyridin-4-yl | |
| 2.095 | 3,5-$Cl_2$—Ph | H | O | H | bond | 1-(2,2,2-trifluoroethyl)-1H-pyrazol-4-yl | |
| 2.096 | 3,5-$Cl_2$—Ph | H | O | H | bond | 1-(2-chloroethyl)-1H-pyrazol-4-yl | |
| 2.097 | 3,5-$F_2$—Ph | H | O | H | $CH_2$ | 1-(2-methoxy-2-oxoethyl)-1H-pyrazol-4-yl | |
| 2.098 | 3,5-$F_2$—Ph | H | O | H | $CH_2$ | 1-(3-carboxypropyl)-1H-pyrazol-4-yl | |
| 2.099 | 3,5-$Cl_2$—Ph | H | O | H | $CH_2$ | 1-(3-methoxy-3-oxopropyl)-1H-pyrazol-4-yl | |
| 2.100 | 3,5-$F_2$—Ph | H | O | H | $CH_2$ | 1-(4-methoxy-4-oxobutyl)-1H-pyrazol-4-yl | |

TABLE 2-continued

Compounds of the general formula (I) according to the invention in which $R^2$ is hydrogen and $R^3$ is ethyl and aryl is the radical

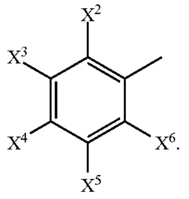

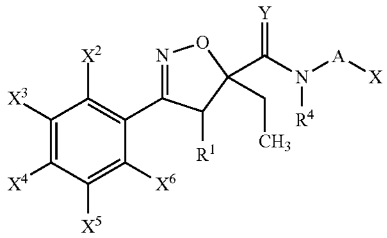

| No. | Aryl | $R^1$ | Y | $R^4$ | A | X | Physical data |
|---|---|---|---|---|---|---|---|
| 2.101 | 3,5-$F_2$—Ph | H | O | H | $CH_2$ | 1-(cyanomethyl)-1H-pyrazol-4-yl | |
| 2.102 | 3,5-$F_2$—Ph | H | O | H | $CH_2$ | 1-(cyanomethyl)-1H-pyrazol-4-yl | |
| 2.103 | 3,5-$Cl_2$—Ph | H | O | H | $CH_2$ | 1-(cyanomethyl)-1H-pyrazol-4-yl | |
| 2.104 | 3,5-$F_2$—Ph | H | O | H | $CH_2$ | 1,3-dimethyl-1H-pyrazol-4-yl | |
| 2.105 | 3-F—Ph | H | O | H | $CH_2$ | 1,3-dimethyl-1H-pyrazol-4-yl | |
| 2.106 | 3,5-$(CF_3)_2$—Ph | H | O | H | $CH_2$ | 1,3-dimethyl-1H-pyrazol-4-yl | |
| 2.107 | 3,5-$Cl_2$—Ph | H | O | H | $CH_2$ | 1,3-dimethyl-1H-pyrazol-4-yl | |
| 2.108 | 3,5-$F_2$—Ph | H | O | H | $CH_2$ | 1,3-dimethyl-1H-pyrazol-4-yl | |
| 2.109 | 3-Cl—Ph | H | O | H | $CH_2$ | 1,3-dimethyl-1H-pyrazol-4-yl | |
| 2.110 | 3-F—Ph | H | O | H | $CH_2$ | 1,3-dimethyl-1H-pyrazol-4-yl | |
| 2.111 | 3-Me—Ph | H | O | H | $CH_2$ | 1,3-dimethyl-1H-pyrazol-5-yl | |
| 2.112 | Ph | H | O | H | $CH_2$ | 1,3-dimethyl-1H-pyrazol-5-yl | |
| 2.113 | 3,5-$(CF_3)_2$—Ph | H | O | H | $CH_2$ | 1,3-dimethyl-1H-pyrazol-5-yl | |
| 2.114 | 3,5-$Cl_2$—Ph | H | O | H | $CH_2$ | 1,3-dimethyl-1H-pyrazol-5-yl | |
| 2.115 | 3,5-$F_2$—Ph | H | O | H | $CH_2$ | 1,3-oxazol-4-yl | |
| 2.116 | Ph | H | O | H | $CH_2$ | 1,3-oxazol-4-yl | |
| 2.117 | 3,5-$Cl_2$—Ph | H | O | H | $CH_2$ | 1,3-oxazol-4-yl | |
| 2.118 | 3,5-$F_2$—Ph | H | O | H | $CH_2$ | 1,3-thiazol-2-yl | |
| 2.119 | 3-F—Ph | H | O | H | $CH_2$ | 1,3-thiazol-2-yl | |
| 2.120 | 3,5-$Cl_2$—Ph | H | O | H | $CH_2$ | 1,4-dimethyl-5-oxo-4,5-dihydro-1H-1,2,4-triazol-3-yl | |
| 2.121 | 3,5-$F_2$—Ph | H | O | H | $CH_2$ | 1,5-dimethyl-1H-pyrazol-3-yl | |
| 2.122 | 3,5-$Cl_2$—Ph | H | O | H | $CH_2$ | 1,5-dimethyl-1H-pyrazol-4-yl | |
| 2.123 | 3,5-$F_2$—Ph | H | O | H | $CH_2$ | 1,5-dimethyl-1H-pyrazol-4-yl | |
| 2.124 | 3,5-$Cl_2$—Ph | H | O | H | $CH_2$ | 1,5-dimethyl-1H-pyrazol-4-yl | |
| 2.125 | 3,5-$F_2$—Ph | H | O | H | $CH_2$ | 1,5-dimethyl-1H-pyrazol-4-yl | |
| 2.126 | 3-F—Ph | H | O | H | $CH_2$ | 1-acetyl-1H-pyrazol-4-yl | |
| 2.127 | Ph | H | O | H | $CH_2$ | 1-butyl-3-methyl-1H-pyrazol-4-yl | |
| 2.128 | 3,5-$F_2$—Ph | H | O | H | $CH_2$ | 1-butyl-5-methyl-1H-pyrazol-4-yl | |

TABLE 2-continued

Compounds of the general formula (I) according to the invention in which $R^2$ is hydrogen and $R^3$ is ethyl and aryl is the radical

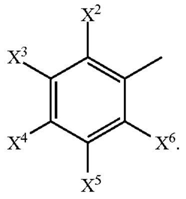

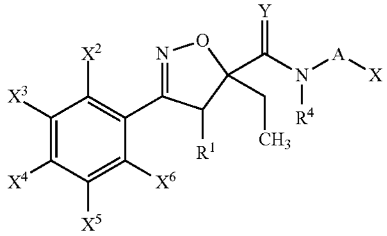

| No. | Aryl | $R^1$ | Y | $R^4$ | A | X | Physical data |
|---|---|---|---|---|---|---|---|
| 2.129 | 3,5-$F_2$—Ph | H | O | H | $CH_2$ | 1-cyclopropyl-1H-pyrazol-4-yl | |
| 2.130 | 3,5-$F_2$—Ph | H | O | H | $CH_2$ | 1-cyclopropyl-1H-pyrazol-4-yl | |
| 2.131 | 3,5-$Cl_2$—Ph | H | O | H | $CH_2$ | 1-cyclopropyl-1H-pyrazol-4-yl | |
| 2.132 | 3,5-$F_2$—Ph | H | O | H | $CH_2$ | 1-cyclopropyl-1H-pyrazol-4-yl | |
| 2.133 | 3-F—Ph | H | O | H | $CH_2$ | 1-ethyl-1H-pyrazol-4-yl | |
| 2.134 | Ph | H | O | H | $CH_2$ | 1-ethyl-1H-pyrazol-4-yl | |
| 2.135 | 3,5-$Cl_2$-4-MeO—Ph | H | O | H | $CH_2$ | 1-ethyl-1H-pyrazol-4-yl | |
| 2.136 | 3,5-$Cl_2$—Ph | H | O | H | $CH_2$ | 1-ethyl-1H-pyrazol-4-yl | [$CDCl_3$] 0.98 (t, 3H); 1.46 (t, 3H), 1.95 (m, 1H); 2.15 (m, 1H); 3.21 (d, 1H); 3.70 (d, 1H); 4.12 (q, 2H); 4.21 (dd, 1H), 4.38 (dd, 1H); 6.98 (t br, 1H); 7.33 (s, 1H); 7.40 (m, 2H), 7.50 (d, 2H) |
| 2.137 | 3,5-$F_2$—Ph | H | O | H | $CH_2$ | 1-ethyl-1H-pyrazol-4-yl | [CDCl3] 0.99 (t, 3H); 1.46 (t, 3H); 1.97 (m, 1H); 2.16 (m, 1H); 3.22 (d, 1H); 3.69 (d, 1H); 4.13 (q, 2H); 4.22 (dd, 1H); 4.41 (dd, 1H); 6.88 (t, 1H); 6.99 (s, 1H); 7.15 (d, 2H); 7.34 (s, 1H); 7.42 (s, 1H). |
| 2.138 | 3,5-$(MeO)_2$—Ph | H | O | H | $CH_2$ | 1-ethyl-1H-pyrazol-4-yl | |
| 2.139 | 3-Br-5-$CF_3$—Ph | H | O | H | $CH_2$ | 1-ethyl-1H-pyrazol-4-yl | |
| 2.140 | 3-Cl-5-Et—Ph | H | O | H | $CH_2$ | 1-ethyl-1H-pyrazol-4-yl | |
| 2.141 | 3-F-5-MeO—Ph | H | O | H | $CH_2$ | 1-ethyl-1H-pyrazol-4-yl | |
| 2.142 | 3-F—Ph | H | O | H | $CH_2$ | 1-ethyl-1H-pyrazol-4-yl | [CDCl3] 0.99 (t, 3H); 1.45 (t, 3H); 1.95 (m, 1H); 2.17 (m, 1H); 3.25 (d, 1H); 3.73 (d, 1H); 4.12 (q, 2H); 4.22 (dd, 1H); 4.39 (dd, 1H); 7.03 (s br, 1H); 7.13 (m, 1H); 7.38 (m, 3H). |
| 2.143 | 3-Me-5-$CF_3O$—Ph | H | O | H | $CH_2$ | 1-ethyl-1H-pyrazol-4-yl | |
| 2.144 | 3-Me—Ph | H | O | H | $CH_2$ | 1-ethyl-1H-pyrazol-5-yl | |
| 2.145 | Ph | H | O | H | $CH_2$ | 1-ethyl-1H-pyrazol-5-yl | |
| 2.146 | 3,5-$Cl_2$—Ph | H | O | H | $CH_2$ | 1-ethyl-1H-pyrazol-5-yl | |

TABLE 2-continued

Compounds of the general formula (I) according to the invention in which $R^2$ is hydrogen and $R^3$ is ethyl and aryl is the radical

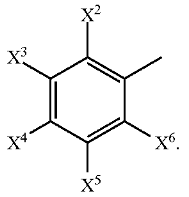

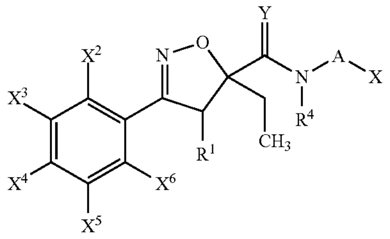

| No. | Aryl | $R^1$ | Y | $R^4$ | A | X | Physical data |
|---|---|---|---|---|---|---|---|
| 2.147 | 3,5-$F_2$—Ph | H | O | H | $CH_2$ | 1-ethyl-3-methyl-1H-pyrazol-4-yl | |
| 2.148 | Ph | H | O | H | $CH_2$ | 1-ethyl-3-methyl-1H-pyrazol-4-yl | |
| 2.149 | 2,3,4-$F_3$—Ph | H | O | H | $CH_2$ | 1-ethyl-3-methyl-1H-pyrazol-4-yl | |
| 2.150 | 2,3,5-$F_3$—Ph | H | O | H | $CH_2$ | 1-ethyl-3-methyl-1H-pyrazol-4-yl | |
| 2.151 | 2,3-$F_2$—Ph | H | O | H | $CH_2$ | 1-ethyl-3-methyl-1H-pyrazol-4-yl | |
| 2.152 | 2,5-$Cl_2$—Ph | H | O | H | $CH_2$ | 1-ethyl-3-methyl-1H-pyrazol-4-yl | |
| 2.153 | 2,5-$F_2$—Ph | H | O | H | $CH_2$ | 1-ethyl-3-methyl-1H-pyrazol-4-yl | |
| 2.154 | 2,5-$Me_2$—Ph | H | O | H | $CH_2$ | 1-ethyl-3-methyl-1H-pyrazol-4-yl | |
| 2.155 | 2-F-3-Me—Ph | H | O | H | $CH_2$ | 1-ethyl-3-methyl-1H-pyrazol-4-yl | |
| 2.156 | 2-F—Ph | H | O | H | $CH_2$ | 1-ethyl-3-methyl-1H-pyrazol-4-yl | |
| 2.157 | 3-$CF_3O$—Ph | H | O | H | $CH_2$ | 1-ethyl-3-methyl-1H-pyrazol-4-yl | |
| 2.158 | 3,4,5-$F_3$—Ph | H | O | H | $CH_2$ | 1-ethyl-3-methyl-1H-pyrazol-4-yl | |
| 2.159 | 3,4-$F_2$—Ph | H | O | H | $CH_2$ | 1-ethyl-3-methyl-1H-pyrazol-4-yl | [$CDCl_3$] 0.99 (t, 3H); 1.44 (t, 1H); 1.96 (m, 1H); 2.15 (m, 1H); 2.19 (s, 3H); 3.21 (d, 1H); 3.70 (d, 1H); 4.05 (q, 2H); 4.18 (dd, 1H); 4.33 (dd, 1H); 6.88 (brt, 1H); 7.27 (m, 3H); 7.51 (m, 1H) |
| 2.160 | 3,5-$Br_2$—Ph | H | O | H | $CH_2$ | 1-ethyl-3-methyl-1H-pyrazol-4-yl | [$CDCl_3$] 0.96 (t, 3H); 1.44 (t, 3H); 1.95 (m, 1H); 2.14 (m, 1H); 2.20 (s, 3H); 3.19 (d, 1H); 3.7 (d, 1H); 4.05 (q, 2H); 4.17 (dd, 1H); 4.32 (dd, 1H); 6.82 (m, 1H); 7.22 (s, 1H); 7.70 (m, 3H). |
| 2.161 | 3,5-$Cl_2$-4-MeO—Ph | H | O | H | $CH_2$ | 1-ethyl-3-methyl-1H-pyrazol-4-yl | |
| 2.162 | 3,5-$Cl_2$—Ph | $CH_3$ | O | H | $CH_2$ | 1-ethyl-3-methyl-1H-pyrazol-4-yl | |
| 2.163 | 3,5-$Cl_2$—Ph | H | O | H | $CH_2$ | 1-ethyl-3-methyl-1H-pyrazol-4-yl | [$CDCl_3$] 1.00 (t, 3H); 1.44 (t, 3H), 1.95 (m, 1H); 2.14 (m, 1H); 2.20 (s, 3H); 3.21 (d, 1H); 3.70 (d, 1H); 4.05 (q, 2H); 4.18 (dd, 1H), 4.32 (dd, 1H); 6.84 (t br, 1H); 7.40 (t, 1H), 7.50 (d, 2H) |
| 2.164 | 3,5-$Et_2$—Ph | H | O | H | $CH_2$ | 1-ethyl-3-methyl-1H-pyrazol-4-yl | |

TABLE 2-continued

Compounds of the general formula (I) according to the invention in which $R^2$ is hydrogen and $R^3$ is ethyl and aryl is the radical

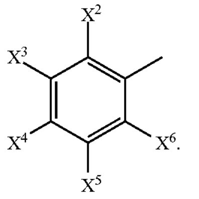

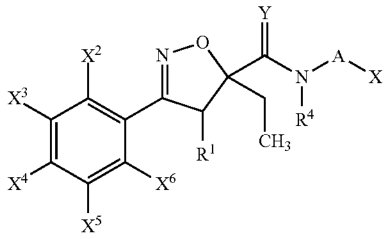

| No. | Aryl | $R^1$ | Y | $R^4$ | A | X | Physical data |
|---|---|---|---|---|---|---|---|
| 2.165 | 3,5-$F_2$—Ph | H | O | H | $CH_2$ | 1-ethyl-3-methyl-1H-pyrazol-4-yl | [$CDCl_3$] 7.52 0.89; 7.35 0.37; 7.31 0.43; 7.26 160.13; 7.25 4.77; 7.18 0.34; 7.17 1.62; 7.16 2.10; 7.15 2.04; 7.14 1.71; 7.00 0.86; 6.91 0.39; 6.90 0.72; 6.90 0.39; 6.88 0.85; 6.88 1.46; 6.87 0.81; 6.86 0.73; 6.86 1.08; 6.85 0.82; 5.30 0.47; 4.36 0.91; 4.34 0.85; 4.32 1.43; 4.31 1.41; 4.20 1.45; 4.19 1.46; 4.17 0.92; 4.15 0.90; 4.08 1.25; 4.08 0.48; 4.06 3.96; 4.04 3.96; 4.02 1.30; 3.72 2.57; 3.68 3.09; 3.24 2.60; 3.20 2.24; 2.81 0.72; 2.21 1.43; 2.19 16.00; 2.17 1.00; 2.15 1.19; 2.13 1.04; 2.12 0.33; 1.98 0.98; 1.96 1.23; 1.94 0.96; 1.93 0.76; 1.54 61.65; 1.45 4.71; 1.43 10.25; 1.42 4.74; 1.39 0.78; 1.38 0.35; 1.22 0.47; 1.13 0.44; 1.01 3.65; 0.99 7.73; 0.97 3.39; 0.15 0.46; 0.01 3.07; 0.00 104.92; −0.01 3.60; −0.15 0.44 |
| 2.166 | 3,5-$F_2$—Ph | H | S | H | $CH_2$ | 1-ethyl-3-methyl-1H-pyrazol-4-yl | |
| 2.167 | 3,5-$Me_2$—Ph | H | O | H | $CH_2$ | 1-ethyl-3-methyl-1H-pyrazol-4-yl | |
| 2.168 | 3-$CF_3$S—Ph | H | O | H | $CH_2$ | 1-ethyl-3-methyl-1H-pyrazol-4-yl | |
| 2.169 | 3-Br-5-$CF_3$—Ph | H | O | H | $CH_2$ | 1-ethyl-3-methyl-1H-pyrazol-4-yl | |
| 2.170 | 3-Br-5-Cl—Ph | H | O | H | $CH_2$ | 1-ethyl-3-methyl-1H-pyrazol-4-yl | |
| 2.171 | 3-Br-5-F—Ph | H | O | H | $CH_2$ | 1-ethyl-3-methyl-1H-pyrazol-4-yl | |
| 2.172 | 3-Cl-4-F—Ph | H | O | H | $CH_2$ | 1-ethyl-3-methyl-1H-pyrazol-4-yl | |
| 2.173 | 3-Cl-5-$CF_3$—Ph | H | O | H | $CH_2$ | 1-ethyl-3-methyl-1H-pyrazol-4-yl | |
| 2.174 | 3-Cl-5-CN—Ph | H | O | H | $CH_2$ | 1-ethyl-3-methyl-1H-pyrazol-4-yl | |
| 2.175 | 3-Cl-5-Et—Ph | H | O | H | $CH_2$ | 1-ethyl-3-methyl-1H-pyrazol-4-yl | |

TABLE 2-continued

Compounds of the general formula (I) according to the invention in which $R^2$ is hydrogen and $R^3$ is ethyl and aryl is the radical

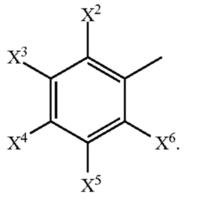

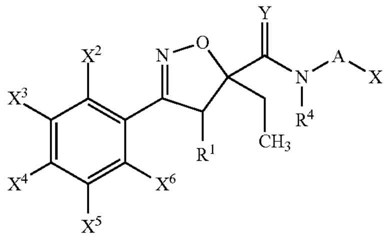

| No. | Aryl | $R^1$ | Y | $R^4$ | A | X | Physical data |
|---|---|---|---|---|---|---|---|
| 2.176 | 3-Cl-5-F—Ph | H | O | H | $CH_2$ | 1-ethyl-3-methyl-1H-pyrazol-4-yl | [$CDCl_3$] 7.52 1.17; 7.40 2.23; 7.39 1.50; 7.31 0.77; 7.31 0.48; 7.28 1.13; 7.27 1.34; 7.27 1.58; 7.27 1.78; 7.27 1.32; 7.27 1.34; 7.26 205.45; 7.25 3.10; 7.25 4.59; 7.21 0.88; 7.17 0.86; 7.17 1.14; 7.16 0.88; 7.15 0.93; 7.15 1.17; 7.14 0.81; 7.00 1.12; 6.84 0.60; 5.30 0.73; 4.36 0.86; 4.34 0.82; 4.32 1.33; 4.30 1.31; 4.20 1.31; 4.19 1.34; 4.17 0.84; 4.15 0.88; 4.08 1.28; 4.08 0.43; 4.06 4.02; 4.04 4.04; 4.03 1.32; 3.72 2.58; 3.68 3.07; 3.24 2.54; 3.20 2.20; 2.23 0.38; 2.21 1.16; 2.19 16.00; 2.19 1.11; 2.17 0.91; 2.15 1.15; 2.13 1.05; 2.10 0.43; 1.98 0.99; 1.96 1.16; 1.94 0.94; 1.92 0.72; 1.54 25.04; 1.45 5.19; 1.43 11.03; 1.42 5.16; 1.40 0.75; 1.38 0.36; 1.01 3.57; 0.99 7.85; 0.97 3.34; 0.15 0.47; 0.05 0.48; 0.01 3.79; 0.00 135.38; −0.01 4.15; −0.01 0.48; −0.05 0.54; −0.15 0.44 |
| 2.177 | 3-Cl-5-MeO—Ph | H | O | H | $CH_2$ | 1-ethyl-3-methyl-1H-pyrazol-4-yl | |
| 2.178 | 3-Cl-5-Me—Ph | H | O | H | $CH_2$ | 1-ethyl-3-methyl-1H-pyrazol-4-yl | |
| 2.179 | 3-Cl-5-$CF_3O$—Ph | H | O | H | $CH_2$ | 1-ethyl-3-methyl-1H-pyrazol-4-yl | |
| 2.180 | 3-Cl—Ph | H | O | H | $CH_2$ | 1-ethyl-3-methyl-1H-pyrazol-4-yl | |
| 2.181 | 3-CN-5-F—Ph | H | O | H | $CH_2$ | 1-ethyl-3-methyl-1H-pyrazol-4-yl | |
| 2.182 | 3-CN—Ph | H | O | H | $CH_2$ | 1-ethyl-3-methyl-1H-pyrazol-4-yl | |
| 2.183 | 3-cPr-5-F—Ph | H | O | H | $CH_2$ | 1-ethyl-3-methyl-1H-pyrazol-4-yl | |
| 2.184 | 3-EtO—Ph | H | O | H | $CH_2$ | 1-ethyl-3-methyl-1H-pyrazol-4-yl | |
| 2.185 | 3-Et-5-F—Ph | H | O | H | $CH_2$ | 1-ethyl-3-methyl-1H-pyrazol-4-yl | |

TABLE 2-continued

Compounds of the general formula (I) according to the invention in which $R^2$ is hydrogen and $R^3$ is ethyl and aryl is the radical

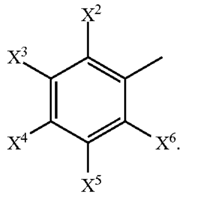

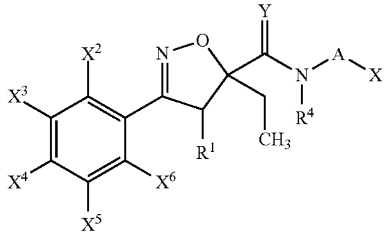

| No. | Aryl | $R^1$ | Y | $R^4$ | A | X | Physical data |
|---|---|---|---|---|---|---|---|
| 2.186 | 3-F-5-$CF_3$—Ph | H | O | H | $CH_2$ | 1-ethyl-3-methyl-1H-pyrazol-4-yl | |
| 2.187 | 3-F-5-MeO—Ph | H | O | H | $CH_2$ | 1-ethyl-3-methyl-1H-pyrazol-4-yl | |
| 2.188 | 3-F-5-Me—Ph | H | O | H | $CH_2$ | 1-ethyl-3-methyl-1H-pyrazol-4-yl | |
| 2.189 | 3-F—Ph | H | O | H | $CH_2$ | 1-ethyl-3-methyl-1H-pyrazol-4-yl | |
| 2.190 | 3-MeO—Ph | H | O | H | $CH_2$ | 1-ethyl-3-methyl-1H-pyrazol-4-yl | |
| 2.191 | 3-Me—Ph | H | O | H | $CH_2$ | 1-ethyl-3-methyl-1H-pyrazol-5-yl | |
| 2.192 | Ph | H | O | H | $CH_2$ | 1-ethyl-3-methyl-1H-pyrazol-5-yl | |
| 2.193 | 3,5-$Cl_2$—Ph | H | O | H | $CH_2$ | 1-ethyl-3-methyl-1H-pyrazol-5-yl | |
| 2.194 | 3,5-$F_2$—Ph | H | O | H | $CH_2$ | 1H-1,2,3-triazol-5-yl | |
| 2.195 | 3-F—Ph | H | O | H | $CH_2$ | 1H-pyrazol-4-yl | |
| 2.196 | 3,5-$F_2$—Ph | H | O | H | $CH_2$ | 1H-pyrazol-4-yl | |
| 2.197 | 3,5-$Cl_2$—Ph | H | O | H | $CH_2$ | 1H-pyrazol-4-yl | |
| 2.198 | 3,5-$F_2$—Ph | H | O | H | $CH_2$ | 1-isobutyl-1H-pyrazol-4-yl | |
| 2.199 | 3-F—Ph | H | O | H | $CH_2$ | 1-isobutyl-1H-pyrazol-4-yl | |
| 2.200 | 3,5-$Cl_2$—Ph | H | O | H | $CH_2$ | 1-isobutyl-1H-pyrazol-4-yl | |
| 2.201 | 3,5-$F_2$—Ph | H | O | H | $CH_2$ | 1-isobutyl-1H-pyrazol-4-yl | |
| 2.202 | 3-F—Ph | H | O | H | $CH_2$ | 1-isopropyl-1H-pyrazol-4-yl | |
| 2.203 | Ph | H | O | H | $CH_2$ | 1-isopropyl-1H-pyrazol-4-yl | |
| 2.204 | 3,5-$Cl_2$—Ph | H | O | H | $CH_2$ | 1-isopropyl-1H-pyrazol-4-yl | |
| 2.205 | 3,5-$F_2$—Ph | H | O | H | $CH_2$ | 1-isopropyl-1H-pyrazol-4-yl | |
| 2.206 | 3-F—Ph | H | O | H | $CH_2$ | 1-methyl-1H-pyrazol-4-yl | |
| 2.207 | Ph | H | O | H | $CH_2$ | 1-methyl-1H-pyrazol-4-yl | |
| 2.208 | 3,5-$(CF_3)_2$—Ph | H | O | H | $CH_2$ | 1-methyl-1H-pyrazol-4-yl | |
| 2.209 | 3,5-$Cl_2$—Ph | H | O | H | $CH_2$ | 1-methyl-1H-pyrazol-4-yl | |
| 2.210 | 3,5-$F_2$—Ph | H | O | H | $CH_2$ | 1-methyl-1H-pyrazol-4-yl | |
| 2.211 | 3-F-5-MeO—Ph | H | O | H | $CH_2$ | 1-methyl-1H-pyrazol-4-yl | |
| 2.212 | 3-F—Ph | H | O | H | $CH_2$ | 1-methyl-1H-pyrazol-4-yl | |
| 2.213 | 3-Me—Ph | H | O | H | $CH_2$ | 1-methyl-1H-pyrazol-5-yl | |

TABLE 2-continued

Compounds of the general formula (I) according to the invention in which $R^2$ is hydrogen and $R^3$ is ethyl and aryl is the radical

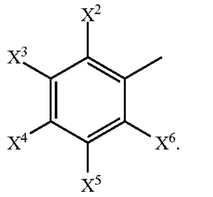

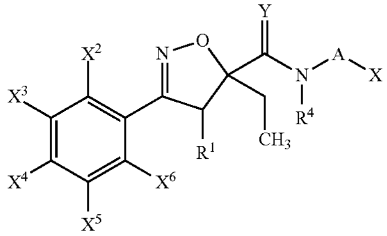

| No. | Aryl | $R^1$ | Y | $R^4$ | A | X | Physical data |
|---|---|---|---|---|---|---|---|
| 2.214 | Ph | H | O | H | $CH_2$ | 1-methyl-1H-pyrazol-5-yl | |
| 2.215 | 3,5-$Cl_2$—Ph | H | O | H | $CH_2$ | 1-methyl-1H-pyrazol-5-yl | |
| 2.216 | 3,5-$F_2$—Ph | H | O | H | $CH_2$ | 1-methyl-1H-pyrazol-5-yl | |
| 2.217 | 3-F—Ph | H | O | H | $CH_2$ | 1-methyl-3-(trifluoromethyl)-1H-pyrazol-4-yl | |
| 2.218 | Ph | H | O | H | $CH_2$ | 1-methyl-3-(trifluoromethyl)-1H-pyrazol-4-yl | |
| 2.219 | 3,5-$Cl_2$—Ph | H | O | H | $CH_2$ | 1-methyl-5-(trifluoromethyl)-1H-pyrazol-4-yl | D1 |
| 2.220 | 3,5-$Cl_2$—Ph | H | O | H | $CH_2$ | 1-propyl-1H-pyrazol-3-yl | D2 |
| 2.221 | 3,5-$F_2$—Ph | H | O | H | $CH_2$ | 1-propyl-1H-pyrazol-3-yl | |
| 2.222 | 3,5-$Cl_2$—Ph | H | O | H | $CH_2$ | 1-propyl-1H-pyrazol-4-yl | |
| 2.223 | 3,5-$F_2$—Ph | H | O | H | $CH_2$ | 1-propyl-1H-pyrazol-4-yl | |
| 2.224 | 3,5-$Cl_2$—Ph | H | O | H | $CH_2$ | 1-propyl-1H-pyrazol-4-yl | |
| 2.225 | 3,5-$F_2$—Ph | H | O | H | $CH_2$ | 1-propyl-1H-pyrazol-4-yl | |
| 2.226 | 3-F—Ph | H | O | H | $CH_2$ | 1-tert-butyl-1H-pyrazol-4-yl | |
| 2.227 | Ph | H | O | H | $CH_2$ | 1-tert-butyl-1H-pyrazol-4-yl | |
| 2.228 | 3,5-$Cl_2$—Ph | H | O | H | $CH_2$ | 1-tert-butyl-1H-pyrazol-4-yl | |
| 2.229 | 3,5-$F_2$—Ph | H | O | H | $CH_2$ | 2-chloropyridin-4-yl | |
| 2.230 | Ph | H | O | H | $CH_2$ | 2-chloropyridin-4-yl | |
| 2.231 | 3,5-$F_2$—Ph | H | O | H | $CH_2$ | 2-methyl-1,3-thiazol-4-yl | [$CDCl_3$] 1.04 (t, 3H); 2.03 (m, 1H); 2.20 (m, 1H); 3.28 (d, 1H); 3.70 (d, 1H); 4.38 (dd, 1H); 4.54 (dd, 1H); 6.91 (m, 1H); 7.09 (d, 1H); 7.16 (s, 1H); 7.18 (s, 2H); 7.34 (t br, 1H); 8.33 (d, 1H). |
| 2.232 | 3-F—Ph | H | O | H | $CH_2$ | 2-methyl-1,3-thiazol-4-yl | [$CDCl_3$] 1.04 (t, 3H); 2.01 (m, 1H); 2.20 (m, 1H); 3.30 (d, 1H); 3.74 (d, 1H); 4.38 (dd, 1H); 4.53 (dd, 1H); 7.05 (m, 1H); 7.14 (m, 2H); 7.35 (s br, 1H); 7.39 (m, 3H); 8.32 (d, 1H). |
| 2.233 | 3,5-$Cl_2$—Ph | H | O | H | $CH_2$ | 3-(cyclopropyl-carbamoyl)-1,2-oxazol-5-yl | |

TABLE 2-continued

Compounds of the general formula (I) according to the invention in which $R^2$ is hydrogen and $R^3$ is ethyl and aryl is the radical

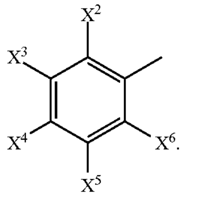

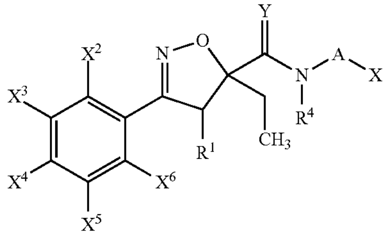

| No. | Aryl | $R^1$ | Y | $R^4$ | A | X | Physical data |
|---|---|---|---|---|---|---|---|
| 2.234 | 3,5-$F_2$—Ph | H | O | H | $CH_2$ | 3-(ethoxycarbonyl)-1,2-oxazol-5-yl | |
| 2.235 | 3,5-$Cl_2$—Ph | H | O | H | $CH_2$ | 3-(methoxy-carbonyl)phenyl | |
| 2.236 | 3,5-$Cl_2$—Ph | H | O | H | $CH_2$ | 3,5-difluoropyridin-2-yl | |
| 2.237 | 3,5-$F_2$—Ph | H | O | H | $CH_2$ | 3-carboxy-1,2-oxazol-5-yl | |
| 2.238 | 3,5-$F_2$—Ph | H | O | H | $CH_2$ | 3-chloro-1-ethyl-1H-pyrazol-4-yl | |
| 2.239 | 3,5-$Cl_2$—Ph | H | O | H | $CH_2$ | 3-chloro-1-ethyl-1H-pyrazol-4-yl | |
| 2.240 | 3,5-$Cl_2$—Ph | H | O | H | $CH_2$ | 3-chloro-1-ethyl-1H-pyrazol-4-yl | |
| 2.241 | 3,5-$F_2$—Ph | H | O | H | $CH_2$ | 3-chloro-1-ethyl-1H-pyrazol-4-yl | |
| 2.242 | 3-F—Ph | H | O | H | $CH_2$ | 3-chloro-1-isopropyl-1H-pyrazol-4-yl | |
| 2.243 | Ph | H | O | H | $CH_2$ | 3-chloro-1-isopropyl-1H-pyrazol-4-yl | |
| 2.244 | 3,5-$Cl_2$—Ph | H | O | H | $CH_2$ | 3-chloro-1-isopropyl-1H-pyrazol-4-yl | |
| 2.245 | 3,5-$F_2$—Ph | H | O | H | $CH_2$ | 3-chloro-1-isopropyl-1H-pyrazol-4-yl | |
| 2.246 | 3,5-$F_2$—Ph | H | S | H | $CH_2$ | 3-chloro-1-methyl-1H-pyrazol-4-yl | |
| 2.247 | 3-F—Ph | H | O | H | $CH_2$ | 3-chloro-1-methyl-1H-pyrazol-4-yl | |
| 2.248 | 3,5-$Cl_2$—Ph | H | O | H | $CH_2$ | 3-chloropyridin-4-yl | |
| 2.249 | 3,5-$F_2$—Ph | H | O | H | $CH_2$ | 3-chloropyridin-4-yl | |
| 2.250 | 3,5-$F_2$—Ph | H | O | H | $CH_2$ | 3-cyclopropyl-1,2,4-oxadiazol-5-yl | |
| 2.251 | 3-F—Ph | H | O | H | $CH_2$ | 3-cyclopropyl-1,2,4-oxadiazol-5-yl | |
| 2.252 | 3,5-$Cl_2$—Ph | H | O | H | $CH_2$ | 3-furyl | |
| 2.253 | 3,5-$F_2$—Ph | H | O | H | $CH_2$ | 3-methyl-1H-pyrazol-4-yl | |
| 2.254 | 3,5-$F_2$—Ph | H | O | H | $CH_2$ | 3-methyl-1-propyl-1H-pyrazol-4-yl | |
| 2.255 | 3,5-$F_2$—Ph | H | O | H | $CH_2$ | 3-methyl-1-propyl-1H-pyrazol-4-yl | |
| 2.256 | 3-$CF_3O$—Ph | H | O | H | $CH_2$ | 3-methyl-1-propyl-1H-pyrazol-4-yl | |
| 2.257 | 3,5-$Cl_2$—Ph | H | O | H | $CH_2$ | 3-methyl-1-propyl-1H-pyrazol-4-yl | [$CDCl_3$] 0.89 (t, 3H); 0.97 (t, 3H); 1.83 (m, 2H); 1.95 (m, 1H); 2.15 (m, 1H); 2.20 (s, 3H); 3.21 (d, 1H), 3.69 (d, 1H); 3.96 (t, 2H); 4.17 (dd, 1H); 4.32 (dd, |

TABLE 2-continued

Compounds of the general formula (I) according to the invention in which $R^2$ is hydrogen and $R^3$ is ethyl and aryl is the radical

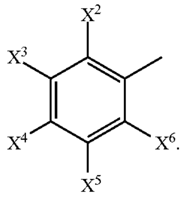

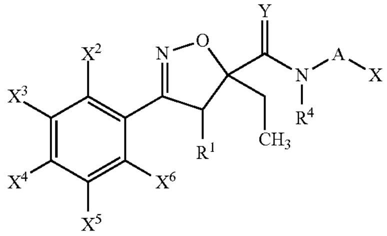

| No. | Aryl | $R^1$ | Y | $R^4$ | A | X | Physical data |
|---|---|---|---|---|---|---|---|
| | | | | | | | 1H); 6.87 (t br, 1H); 7.24 (s, 1H); 7.42 (t, 1H); 7.50 (d, 2H) |
| 2.258 | 3,5-$F_2$—Ph | H | O | H | $CH_2$ | 3-methyl-1-propyl-1H-pyrazol-4-yl | |
| 2.259 | 3-Cl-4-F—Ph | H | O | H | $CH_2$ | 3-methyl-1-propyl-1H-pyrazol-4-yl | |
| 2.260 | 3-Cl-5-$CF_3O$—Ph | H | O | H | $CH_2$ | 3-methyl-1-propyl-1H-pyrazol-4-yl | |
| 2.261 | 3-Cl-5-F—Ph | H | O | H | $CH_2$ | 3-methyl-1-propyl-1H-pyrazol-4-yl | |
| 2.262 | 3-Cl-5-Me—Ph | H | O | H | $CH_2$ | 3-methyl-1-propyl-1H-pyrazol-4-yl | |
| 2.263 | 3-F-5-Me—Ph | H | O | H | $CH_2$ | 3-methyl-1-propyl-1H-pyrazol-4-yl | |
| 2.264 | 3-F—Ph | H | O | H | $CH_2$ | 3-methyl-1-propyl-1H-pyrazol-4-yl | |
| 2.265 | 3-Me—Ph | H | O | H | $CH_2$ | 3-methyl-1-propyl-1H-pyrazol-4-yl | |
| 2.266 | 4-Cl-3,5-$F_2$—Ph | H | O | H | $CH_2$ | 4-(methoxy-carbonyl)phenyl | |
| 2.267 | Ph | H | O | H | $CH_2$ | 4-(trifluoromethyl)-1,3-thiazol-2-yl | |
| 2.268 | 3,5-$Cl_2$—Ph | H | O | H | $CH_2$ | 4-(trifluoromethyl)-1,3-thiazol-2-yl | |
| 2.269 | 3,5-$Cl_2$—Ph | H | O | H | $CH_2$ | 4-(trifluoromethyl)-1,3-thiazol-2-yl | |
| 2.270 | 3,5-$F_2$—Ph | H | O | H | $CH_2$ | 4-chloro-1-methyl-1H-pyrazol-3-yl | |
| 2.271 | 3-F—Ph | H | O | H | $CH_2$ | 4-chloro-1-methyl-1H-pyrazol-3-yl | |
| 2.272 | 3,5-$Cl_2$—Ph | H | O | H | $CH_2$ | 4-chloro-1-methyl-1H-pyrazol-3-yl | |
| 2.273 | 3,5-$F_2$—Ph | H | O | H | $CH_2$ | 4-chloro-1-methyl-1H-pyrazol-5-yl | |
| 2.274 | 3-F—Ph | H | O | H | $CH_2$ | 5-chloro-1-methyl-1H-pyrazol-4-yl | |
| 2.275 | 3,5-$F_2$—Ph | H | O | H | $CH_2$ | 5-chloro-1-methyl-1H-pyrazol-4-yl | |
| 2.276 | 3,5-$Cl_2$—Ph | H | O | H | $CH_2$ | 5-chloro-1-methyl-1H-pyrazol-4-yl | |
| 2.277 | 3,5-$F_2$—Ph | H | O | H | $CH_2$ | 5-chloro-1-methyl-1H-pyrazol-4-yl | |
| 2.278 | 3,5-$F_2$—Ph | H | S | H | $CH_2$ | 5-chloro-1-methyl-1H-pyrazol-4-yl | |
| 2.279 | 3-F—Ph | H | O | H | $CH_2$ | 5-methoxy-1,3-dimethyl-1H-pyrazol-4-yl | |
| 2.280 | Ph | H | O | H | $CH_2$ | 5-methoxy-1,3-dimethyl-1H-pyrazol-4-yl | |

TABLE 2-continued

Compounds of the general formula (I) according to the invention in which $R^2$ is hydrogen and $R^3$ is ethyl and aryl is the radical

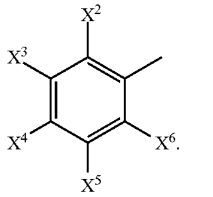

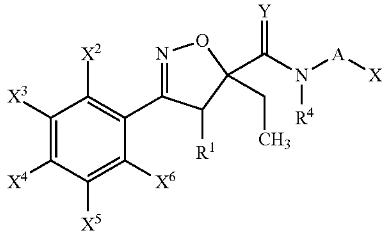

| No. | Aryl | $R^1$ | Y | $R^4$ | A | X | Physical data |
|---|---|---|---|---|---|---|---|
| 2.281 | 3,5-$Cl_2$—Ph | H | O | H | $CH_2$ | 5-methoxy-1,3-dimethyl-1H-pyrazol-4-yl | |
| 2.282 | 3,5-$F_2$—Ph | H | O | H | $CH_2$ | 5-methyl-1,2,4-oxadiazol-3-yl | |
| 2.283 | 3-F—Ph | H | O | H | $CH_2$ | 5-methyl-1,2,4-oxadiazol-3-yl | |
| 2.284 | 3,5-$Cl_2$—Ph | H | O | H | $CH_2$ | 5-methyl-1,2-oxazol-3-yl | |
| 2.285 | 3,5-$F_2$—Ph | H | O | H | $CH_2$ | 5-methyl-1-propyl-1H-pyrazol-4-yl | |
| 2.286 | 3,5-$Cl_2$—Ph | H | O | H | $CH_2$ | 5-methyl-1-propyl-1H-pyrazol-4-yl | |
| 2.287 | 3,5-$Cl_2$—Ph | H | O | H | $CH_2$ | 5-methyl-1-propyl-1H-pyrazol-4-yl | |
| 2.288 | 3,5-$F_2$—Ph | H | O | H | $CH_2$ | 5-methyl-1-propyl-1H-pyrazol-4-yl | |
| 2.289 | 3-F—Ph | H | O | H | $CH_2$ | 6-chloropyridin-3-yl | |
| 2.290 | Ph | H | O | H | $CH_2$ | furan-2-yl | |
| 2.291 | 3,5-$F_2$—Ph | H | O | H | $CH_2$ | pyridin-2-yl | |
| 2.292 | 3,5-$F_2$—Ph | H | O | H | $CH_2$ | pyridin-2-yl | |
| 2.293 | 3,5-$Cl_2$—Ph | H | O | H | $CH_2$ | pyridin-3-yl | |
| 2.294 | 3,5-$F_2$—Ph | H | O | H | $CH_2$ | pyridin-3-yl | |
| 2.295 | 3,5-$F_2$—Ph | H | O | H | $CH_2$ | pyridin-4-yl | |
| 2.296 | 3-F—Ph | H | O | H | $CH_2$ | pyridin-4-yl | |
| 2.297 | 3,5-$F_2$—Ph | H | O | H | $CH_2$ | pyrimidin-2-yl | |
| 2.298 | 3-F—Ph | H | O | H | $CH_2$ | 1-(2,2,2-trifluoroethyl)-1H-pyrazol-4-yl | |
| 2.299 | 3,5-$Cl_2$—Ph | H | O | H | $CH_2$ | 1-(2-chloroethyl)-1H-pyrazol-4-yl | |
| 2.300 | 3,5-$F_2$—Ph | H | O | H | $CH_2CH_2$ | 1-(2-methoxy-2-oxoethyl)-1H-pyrazol-4-yl | |
| 2.301 | 3,5-$F_2$—Ph | H | O | H | $CH_2CH_2$ | 1-(3-carboxypropyl)-1H-pyrazol-4-yl | |
| 2.302 | 3,5-$Cl_2$—Ph | H | O | H | $CH_2CH_2$ | 1-(3-methoxy-3-oxopropyl)-1H-pyrazol-4-yl | |
| 2.303 | 3,5-$F_2$—Ph | H | O | H | $CH_2CH_2$ | 1-(4-methoxy-4-oxobutyl)-1H-pyrazol-4-yl | |
| 2.304 | 3,5-$F_2$—Ph | H | O | H | $CH_2CH_2$ | 1-(cyanomethyl)-1H-pyrazol-4-yl | |
| 2.305 | 3,5-$F_2$—Ph | H | O | H | $CH_2CH_2$ | 1-(cyanomethyl)-1H-pyrazol-4-yl | |
| 2.306 | 3,5-$F_2$—Ph | H | O | H | $CH_2CH_2$ | 1-(cyanomethyl)-1H-pyrazol-4-yl | |
| 2.307 | 3,5-$Cl_2$—Ph | H | O | H | $CH_2CH_2$ | 1,3-dimethyl-1H-pyrazol-4-yl | |
| 2.308 | 3-F—Ph | H | O | H | $CH_2CH_2$ | 1,3-dimethyl-1H-pyrazol-4-yl | |

TABLE 2-continued

Compounds of the general formula (I) according to the invention in which $R^2$ is hydrogen and $R^3$ is ethyl and aryl is the radical

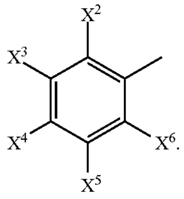

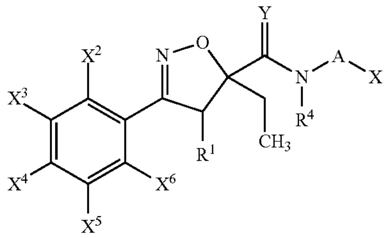

| No. | Aryl | $R^1$ | Y | $R^4$ | A | X | Physical data |
|---|---|---|---|---|---|---|---|
| 2.309 | 3,5-$F_2$—Ph | H | O | H | $CH_2CH_2$ | 1,3-dimethyl-1H-pyrazol-4-yl | |
| 2.310 | 3-F—Ph | H | O | H | $CH_2CH_2$ | 1,3-dimethyl-1H-pyrazol-4-yl | |
| 2.311 | 3-Me—Ph | H | O | H | $CH_2CH_2$ | 1,3-dimethyl-1H-pyrazol-4-yl | |
| 2.312 | Ph | H | O | H | $CH_2CH_2$ | 1,3-dimethyl-1H-pyrazol-4-yl | |
| 2.313 | 3-Cl—Ph | H | O | H | $CH_2CH_2$ | 1,3-dimethyl-1H-pyrazol-4-yl | |
| 2.314 | 3,5-$Cl_2$—Ph | H | O | H | $CH_2CH_2$ | 1,3-dimethyl-1H-pyrazol-5-yl | |
| 2.315 | 3,5-$(CF_3)_2$—Ph | H | O | H | $CH_2CH_2$ | 1,3-dimethyl-1H-pyrazol-5-yl | |
| 2.316 | 3,5-$F_2$—Ph | H | O | H | $CH_2CH_2$ | 1 ,3-dimethyl-1H-pyrazol-5-yl | |
| 2.317 | Ph | H | O | H | $CH_2CH_2$ | 1,3-dimethyl-1H-pyrazol-5-yl | |
| 2.318 | 3,5-$Cl_2$—Ph | H | O | H | $CH_2CH_2$ | 1,3-oxazol-4-yl | |
| 2.319 | 3,5-$(CF_3)_2$—Ph | H | O | H | $CH_2CH_2$ | 1,3-oxazol-4-yl | |
| 2.320 | 3,5-$F_2$—Ph | H | O | H | $CH_2CH_2$ | 1,3-oxazol-4-yl | |
| 2.321 | 3,5-$Cl_2$—Ph | H | O | H | $CH_2CH_2$ | 1,3-thiazol-2-yl | |
| 2.322 | 3-F—Ph | H | O | H | $CH_2CH_2$ | 1,3-thiazol-2-yl | |
| 2.323 | 3,5-$Cl_2$—Ph | H | O | H | $CH_2CH_2$ | 1,4-dimethyl-5-oxo-4,5-dihydro-1H-1,2,4-triazol-3-yl | |
| 2.324 | 3,5-$F_2$—Ph | H | O | H | $CH_2CH_2$ | 1,5-dimethyl-1H-pyrazol-3-yl | |
| 2.325 | 3,5-$Cl_2$—Ph | H | O | H | $CH_2CH_2$ | 1,5-dimethyl-1H-pyrazol-4-yl | |
| 2.326 | 3,5-$F_2$—Ph | H | O | H | $CH_2CH_2$ | 1,5-dimethyl-1H-pyrazol-4-yl | |
| 2.327 | 3,5-$F_2$—Ph | H | O | H | $CH_2CH_2$ | 1,5-dimethyl-1H-pyrazol-4-yl | |
| 2.328 | 3-F—Ph | H | O | H | $CH_2CH_2$ | 1,5-dimethyl-1H-pyrazol-4-yl | |
| 2.329 | 3,5-$Cl_2$—Ph | H | O | H | $CH_2CH_2$ | 1-acetyl-1H-pyrazol-4-yl | |
| 2.330 | Ph | H | O | H | $CH_2CH_2$ | 1-butyl-3-methyl-1H-pyrazol-4-yl | |
| 2.331 | 3,5-$F_2$—Ph | H | O | H | $CH_2CH_2$ | 1-butyl-5-methyl-1H-pyrazol-4-yl | |
| 2.332 | 3,5-$F_2$—Ph | H | O | H | $CH_2CH_2$ | 1-cyclopropyl-1H-pyrazol-4-yl | |
| 2.333 | 3,5-$F_2$—Ph | H | O | H | $CH_2CH_2$ | 1-cyclopropyl-1H-pyrazol-4-yl | |
| 2.334 | 3,5-$F_2$—Ph | H | O | H | $CH_2CH_2$ | 1-cyclopropyl-1H-pyrazol-4-yl | |
| 2.335 | Ph | H | O | H | $CH_2CH_2$ | 1-cyclopropyl-1H-pyrazol-4-yl | |
| 2.336 | 3-F—Ph | H | O | H | $CH_2CH_2$ | 1-ethyl-1H-pyrazol-4-yl | |

TABLE 2-continued

Compounds of the general formula (I) according to the invention in which $R^2$ is hydrogen and $R^3$ is ethyl and aryl is the radical

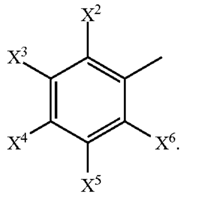

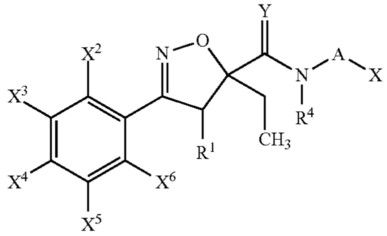

| No. | Aryl | $R^1$ | Y | $R^4$ | A | X | Physical data |
|---|---|---|---|---|---|---|---|
| 2.337 | 3,5-$Cl_2$—Ph | H | O | H | $CH_2CH_2$ | 1-ethyl-1H-pyrazol-4-yl | |
| 2.338 | 3,5-$Cl_2$—Ph | H | O | H | $CH_2CH_2$ | 1-ethyl-1H-pyrazol-4-yl | |
| 2.339 | 3-F—Ph | H | O | H | $CH_2CH_2$ | 1-ethyl-1H-pyrazol-4-yl | |
| 2.340 | 3,5-$F_2$—Ph | H | O | H | $CH_2CH_2$ | 1-ethyl-1H-pyrazol-4-yl | |
| 2.341 | 3-Br-5-$CF_3$—Ph | H | O | H | $CH_2CH_2$ | 1-ethyl-1H-pyrazol-4-yl | |
| 2.342 | 3-Me—Ph | H | O | H | $CH_2CH_2$ | 1-ethyl-1H-pyrazol-4-yl | |
| 2.343 | 3-F-5-MeO—Ph | H | O | H | $CH_2CH_2$ | 1-ethyl-1H-pyrazol-4-yl | |
| 2.344 | 3-Cl-5-Et—Ph | H | O | H | $CH_2CH_2$ | 1-ethyl-1H-pyrazol-4-yl | |
| 2.345 | 3,5-$(MeO)_2$—Ph | H | O | H | $CH_2CH_2$ | 1-ethyl-1H-pyrazol-4-yl | |
| 2.346 | 3-Me-5-$CF_3O$—Ph | H | O | H | $CH_2CH_2$ | 1-ethyl-1H-pyrazol-4-yl | |
| 2.347 | 3,5-$Cl_2$-4-MeO—Ph | H | O | H | $CH_2CH_2$ | 1-ethyl-1H-pyrazol-5-yl | |
| 2.348 | Ph | H | O | H | $CH_2CH_2$ | 1-ethyl-1H-pyrazol-5-yl | |
| 2.349 | 3,5-$F_2$—Ph | H | O | H | $CH_2CH_2$ | 1-ethyl-1H-pyrazol-5-yl | |
| 2.350 | 3,5-$Cl_2$—Ph | H | O | H | $CH_2CH_2$ | 1-ethyl-3-methyl-1H-pyrazol-4-yl | |
| 2.351 | Ph | H | O | H | $CH_2CH_2$ | 1-ethyl-3-methyl-1H-pyrazol-4-yl | |
| 2.352 | 3,5-$F_2$—Ph | H | O | H | $CH_2CH_2$ | 1-ethyl-3-methyl-1H-pyrazol-4-yl | |
| 2.353 | 3-Me—Ph | H | O | H | $CH_2CH_2$ | 1-ethyl-3-methyl-1H-pyrazol-4-yl | |
| 2.354 | 3-Br-5-F—Ph | H | O | H | $CH_2CH_2$ | 1-ethyl-3-methyl-1H-pyrazol-4-yl | |
| 2.355 | 3,4,5-$F_3$—Ph | H | O | H | $CH_2CH_2$ | 1-ethyl-3-methyl-1H-pyrazol-4-yl | |
| 2.356 | 3,4-$F_2$—Ph | H | O | H | $CH_2CH_2$ | 1-ethyl-3-methyl-1H-pyrazol-4-yl | |
| 2.357 | 3,5-$F_2$—Ph | H | S | H | $CH_2CH_2$ | 1-ethyl-3-methyl-1H-pyrazol-4-yl | |
| 2.358 | 3-F-5-Me—Ph | H | O | H | $CH_2CH_2$ | 1-ethyl-3-methyl-1H-pyrazol-4-yl | |
| 2.359 | 3-Cl-5-CN—Ph | H | O | H | $CH_2CH_2$ | 1-ethyl-3-methyl-1H-pyrazol-4-yl | |
| 2.360 | 3-F—Ph | H | O | H | $CH_2CH_2$ | 1-ethyl-3-methyl-1H-pyrazol-4-yl | |
| 2.361 | 3-cPr-5-F—Ph | H | O | H | $CH_2CH_2$ | 1-ethyl-3-methyl-1H-pyrazol-4-yl | |
| 2.362 | 3-Cl-5-Me—Ph | H | O | H | $CH_2CH_2$ | 1-ethyl-3-methyl-1H-pyrazol-4-yl | |

TABLE 2-continued

Compounds of the general formula (I) according to the invention in which $R^2$ is hydrogen and $R^3$ is ethyl and aryl is the radical

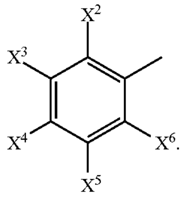

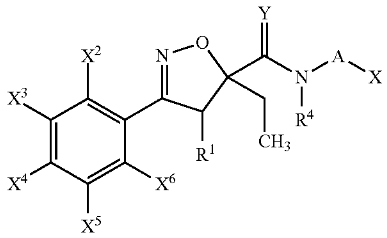

| No. | Aryl | $R^1$ | Y | $R^4$ | A | X | Physical data |
|---|---|---|---|---|---|---|---|
| 2.363 | 3-F-5-MeO—Ph | H | O | H | $CH_2CH_2$ | 1-ethyl-3-methyl-1H-pyrazol-4-yl | |
| 2.364 | 2,5-$Me_2$—Ph | H | O | H | $CH_2CH_2$ | 1-ethyl-3-methyl-1H-pyrazol-4-yl | |
| 2.365 | 3-$CF_3O$—Ph | H | O | H | $CH_2CH_2$ | 1-ethyl-3-methyl-1H-pyrazol-4-yl | |
| 2.366 | 3-Cl-5-Et—Ph | H | O | H | $CH_2CH_2$ | 1-ethyl-3-methyl-1H-pyrazol-4-yl | |
| 2.367 | 2,3,5-$F_3$—Ph | H | O | H | $CH_2CH_2$ | 1-ethyl-3-methyl-1H-pyrazol-4-yl | |
| 2.368 | 3-Et-5-F—Ph | H | O | H | $CH_2CH_2$ | 1-ethyl-3-methyl-1H-pyrazol-4-yl | |
| 2.369 | 3-F-5-$CF_3$—Ph | H | O | H | $CH_2CH_2$ | 1-ethyl-3-methyl-1H-pyrazol-4-yl | |
| 2.370 | 3-Br-5-$CF_3$—Ph | H | O | H | $CH_2CH_2$ | 1-ethyl-3-methyl-1H-pyrazol-4-yl | |
| 2.371 | 3-Cl-5-MeO—Ph | H | O | H | $CH_2CH_2$ | 1-ethyl-3-methyl-1H-pyrazol-4-yl | |
| 2.372 | 3-Cl-4-F—Ph | H | O | H | $CH_2CH_2$ | 1-ethyl-3-methyl-1H-pyrazol-4-yl | |
| 2.373 | 2,3-$F_2$—Ph | H | O | H | $CH_2CH_2$ | 1-ethyl-3-methyl-1H-pyrazol-4-yl | |
| 2.374 | 3-Cl-5-$CF_3$—Ph | H | O | H | $CH_2CH_2$ | 1-ethyl-3-methyl-1H-pyrazol-4-yl | |
| 2.375 | 3,5-$Me_2$—Ph | H | O | H | $CH_2CH_2$ | 1-ethyl-3-methyl-1H-pyrazol-4-yl | |
| 2.376 | 3-Cl—Ph | H | O | H | $CH_2CH_2$ | 1-ethyl-3-methyl-1H-pyrazol-4-yl | |
| 2.377 | 3-MeO—Ph | H | O | H | $CH_2CH_2$ | 1-ethyl-3-methyl-1H-pyrazol-4-yl | |
| 2.378 | 3-Cl-5-F—Ph | H | O | H | $CH_2CH_2$ | 1-ethyl-3-methyl-1H-pyrazol-4-yl | |
| 2.379 | 3-CN-5-F—Ph | H | O | H | $CH_2CH_2$ | 1-ethyl-3-methyl-1H-pyrazol-4-yl | |
| 2.380 | 3-CN—Ph | H | O | H | $CH_2CH_2$ | 1-ethyl-3-methyl-1H-pyrazol-4-yl | |
| 2.381 | 3-Br-5-Cl—Ph | H | O | H | $CH_2CH_2$ | 1-ethyl-3-methyl-1H-pyrazol-4-yl | |
| 2.382 | 2,3,4-$F_3$—Ph | H | O | H | $CH_2CH_2$ | 1-ethyl-3-methyl-1H-pyrazol-4-yl | |
| 2.383 | 3,5-$Cl_2$-4-MeO—Ph | H | O | H | $CH_2CH_2$ | 1-ethyl-3-methyl-1H-pyrazol-4-yl | |
| 2.384 | Ph | H | O | H | $CH_2CH_2$ | 1-ethyl-3-methyl-1H-pyrazol-4-yl | |
| 2.385 | 2,5-$F_2$—Ph | H | O | H | $CH_2CH_2$ | 1-ethyl-3-methyl-1H-pyrazol-4-yl | |
| 2.386 | 3,5-$Br_2$—Ph | H | O | H | $CH_2CH_2$ | 1-ethyl-3-methyl-1H-pyrazol-4-yl | |
| 2.387 | 2-F—Ph | H | O | H | $CH_2CH_2$ | 1-ethyl-3-methyl-1H-pyrazol-4-yl | |
| 2.388 | 2,5-$Cl_2$—Ph | H | O | H | $CH_2CH_2$ | 1-ethyl-3-methyl-1H-pyrazol-4-yl | |

TABLE 2-continued

Compounds of the general formula (I) according to the invention in which $R^2$ is hydrogen and $R^3$ is ethyl and aryl is the radical

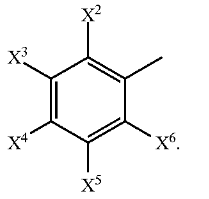

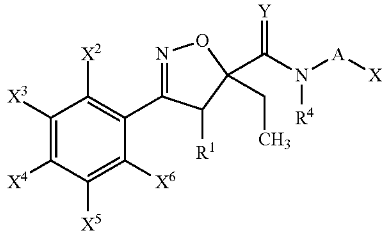

| No. | Aryl | $R^1$ | Y | $R^4$ | A | X | Physical data |
|---|---|---|---|---|---|---|---|
| 2.389 | 3,5-$Et_2$—Ph | H | O | H | $CH_2CH_2$ | 1-ethyl-3-methyl-1H-pyrazol-4-yl | |
| 2.390 | 3-$CF_3S$—Ph | H | O | H | $CH_2CH_2$ | 1-ethyl-3-methyl-1H-pyrazol-4-yl | |
| 2.391 | 3-EtO—Ph | H | O | H | $CH_2CH_2$ | 1-ethyl-3-methyl-1H-pyrazol-4-yl | |
| 2.392 | 3,5-$Cl_2$—Ph | $CH_3$ | O | H | $CH_2CH_2$ | 1-ethyl-3-methyl-1H-pyrazol-4-yl | |
| 2.393 | 2-F-3-Me—Ph | H | O | H | $CH_2CH_2$ | 1-ethyl-3-methyl-1H-pyrazol-5-yl | |
| 2.394 | 3-Cl-5-$CF_3O$—Ph | H | O | H | $CH_2CH_2$ | 1-ethyl-3-methyl-1H-pyrazol-5-yl | |
| 2.395 | 3,5-$F_2$—Ph | H | O | H | $CH_2CH_2$ | 1-ethyl-3-methyl-1H-pyrazol-5-yl | |
| 2.396 | 3,5-$Cl_2$—Ph | H | O | H | $CH_2CH_2$ | 1H-1,2,3-triazol-5-yl | |
| 2.397 | 3-F—Ph | H | O | H | $CH_2CH_2$ | 1H-pyrazol-4-yl | |
| 2.398 | 3,5-$F_2$—Ph | H | O | H | $CH_2CH_2$ | 1H-pyrazol-4-yl | |
| 2.399 | 3,5-$Cl_2$—Ph | H | O | H | $CH_2CH_2$ | 1H-pyrazol-4-yl | |
| 2.400 | 3,5-$F_2$—Ph | H | O | H | $CH_2CH_2$ | 1-isobutyl-1H-pyrazol-4-yl | |
| 2.401 | 3-F—Ph | H | O | H | $CH_2CH_2$ | 1-isobutyl-1H-pyrazol-4-yl | |
| 2.402 | 3,5-$F_2$—Ph | H | O | H | $CH_2CH_2$ | 1-isobutyl-1H-pyrazol-4-yl | |
| 2.403 | 3,5-$Cl_2$—Ph | H | O | H | $CH_2CH_2$ | 1-isobutyl-1H-pyrazol-4-yl | |
| 2.404 | 3-F—Ph | H | O | H | $CH_2CH_2$ | 1-isopropyl-1H-pyrazol-4-yl | |
| 2.405 | Ph | H | O | H | $CH_2CH_2$ | 1-isopropyl-1H-pyrazol-4-yl | |
| 2.406 | 3,5-$F_2$—Ph | H | O | H | $CH_2CH_2$ | 1-isopropyl-1H-pyrazol-4-yl | |
| 2.407 | 3-F—Ph | H | O | H | $CH_2CH_2$ | 1-isopropyl-1H-pyrazol-4-yl | |
| 2.408 | 3,5-$Cl_2$—Ph | H | O | H | $CH_2CH_2$ | 1-methyl-1H-pyrazol-4-yl | |
| 2.409 | Ph | H | O | H | $CH_2CH_2$ | 1-methyl-1H-pyrazol-4-yl | |
| 2.410 | 3,5-$F_2$—Ph | H | O | H | $CH_2CH_2$ | 1-methyl-1H-pyrazol-4-yl | |
| 2.411 | 3-F-5-MeO—Ph | H | O | H | $CH_2CH_2$ | 1-methyl-1H-pyrazol-4-yl | |
| 2.412 | 3-F—Ph | H | O | H | $CH_2CH_2$ | 1-methyl-1H-pyrazol-4-yl | |
| 2.413 | Ph | H | O | H | $CH_2CH_2$ | 1-methyl-1H-pyrazol-4-yl | |
| 2.414 | 3,5-$(CF_3)_2$—Ph | H | O | H | $CH_2CH_2$ | 1-methyl-1H-pyrazol-4-yl | |
| 2.415 | 3,5-$Cl_2$—Ph | H | O | H | $CH_2CH_2$ | 1-methyl-1H-pyrazol-5-yl | |
| 2.416 | 3-Me—Ph | H | O | H | $CH_2CH_2$ | 1-methyl-1H-pyrazol-5-yl | |

TABLE 2-continued

Compounds of the general formula (I) according to the invention in which $R^2$ is hydrogen and $R^3$ is ethyl and aryl is the radical

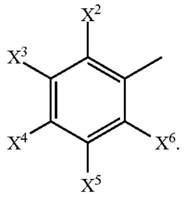

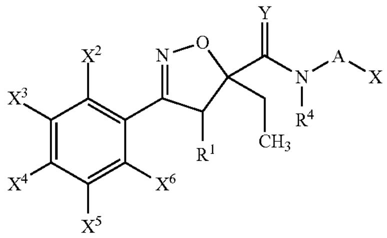

| No. | Aryl | $R^1$ | Y | $R^4$ | A | X | Physical data |
|---|---|---|---|---|---|---|---|
| 2.417 | 3,5-$F_2$—Ph | H | O | H | $CH_2CH_2$ | 1-methyl-1H-pyrazol-5-yl | |
| 2.418 | 3-F—Ph | H | O | H | $CH_2CH_2$ | 1-methyl-1H-pyrazol-5-yl | |
| 2.419 | 3,5-$Cl_2$—Ph | H | O | H | $CH_2CH_2$ | 1-methyl-3-(trifluoromethyl)-1H-pyrazol-4-yl | |
| 2.420 | Ph | H | O | H | $CH_2CH_2$ | 1-methyl-3-(trifluoromethyl)-1H-pyrazol-4-yl | |
| 2.421 | 3,5-$Cl_2$—Ph | H | O | H | $CH_2CH_2$ | 1-methyl-5-(trifluoromethyl)-1H-pyrazol-4-yl | D1 |
| 2.422 | 3,5-$Cl_2$—Ph | H | O | H | $CH_2CH_2$ | 1-propyl-1H-pyrazol-3-yl | D2 |
| 2.423 | 3,5-$F_2$—Ph | H | O | H | $CH_2CH_2$ | 1-propyl-1H-pyrazol-3-yl | |
| 2.424 | 3,5-$F_2$—Ph | H | O | H | $CH_2CH_2$ | 1-propyl-1H-pyrazol-4-yl | |
| 2.425 | 3,5-$Cl_2$—Ph | H | O | H | $CH_2CH_2$ | 1-propyl-1H-pyrazol-4-yl | |
| 2.426 | 3,5-$F_2$—Ph | H | O | H | $CH_2CH_2$ | 1-propyl-1H-pyrazol-4-yl | |
| 2.427 | 3,5-$Cl_2$—Ph | H | O | H | $CH_2CH_2$ | 1-propyl-1H-pyrazol-4-yl | |
| 2.428 | 3-F—Ph | H | O | H | $CH_2CH_2$ | 1-tert-butyl-1H-pyrazol-4-yl | |
| 2.429 | Ph | H | O | H | $CH_2CH_2$ | 1-tert-butyl-1H-pyrazol-4-yl | |
| 2.430 | 3,5-$F_2$—Ph | H | O | H | $CH_2CH_2$ | 1-tert-butyl-1H-pyrazol-4-yl | |
| 2.431 | 3,5-$Cl_2$—Ph | H | O | H | $CH_2CH_2$ | 2-chloropyridin-4-yl | |
| 2.432 | Ph | H | O | H | $CH_2CH_2$ | 2-chloropyridin-4-yl | |
| 2.433 | 3,5-$F_2$—Ph | H | O | H | $CH_2CH_2$ | 2-methyl-1,3-thiazol-4-yl | |
| 2.434 | 3-F—Ph | H | O | H | $CH_2CH_2$ | 2-methyl-1,3-thiazol-4-yl | |
| 2.435 | 3,5-$F_2$—Ph | H | O | H | $CH_2CH_2$ | 3-(cyclopropyl-carbamoyl)-1,2-oxazol-5-yl | |
| 2.436 | 3,5-$Cl_2$—Ph | H | O | H | $CH_2CH_2$ | 3-(ethoxycarbonyl)-1,2-oxazol-5-yl | |
| 2.437 | 3,5-$Cl_2$—Ph | H | O | H | $CH_2CH_2$ | 3-(methoxy-carbonyl)phenyl | |
| 2.438 | 3,5-$Cl_2$—Ph | H | O | H | $CH_2CH_2$ | 3,5-difluoropyridin-2-yl | |
| 2.439 | 3,5-$F_2$—Ph | H | O | H | $CH_2CH_2$ | 3-carboxy-1,2-oxazol-5-yl | |
| 2.440 | 3,5-$F_2$—Ph | H | O | H | $CH_2CH_2$ | 3-chloro-1-ethyl-1H-pyrazol-4-yl | |
| 2.441 | 3,5-$Cl_2$—Ph | H | O | H | $CH_2CH_2$ | 3-chloro-1-ethyl-1H-pyrazol-4-yl | |

TABLE 2-continued

Compounds of the general formula (I) according to the invention in which $R^2$ is hydrogen and $R^3$ is ethyl and aryl is the radical

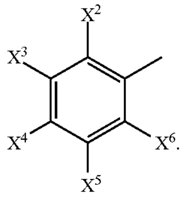

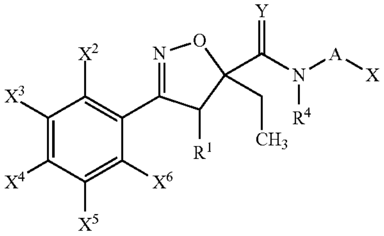

| No. | Aryl | $R^1$ | Y | $R^4$ | A | X | Physical data |
|---|---|---|---|---|---|---|---|
| 2.442 | 3,5-$F_2$—Ph | H | O | H | $CH_2CH_2$ | 3-chloro-1-ethyl-1H-pyrazol-4-yl | |
| 2.443 | 3-F—Ph | H | O | H | $CH_2CH_2$ | 3-chloro-1-ethyl-1H-pyrazol-4-yl | |
| 2.444 | Ph | H | O | H | $CH_2CH_2$ | 3-chloro-1-isopropyl-1H-pyrazol-4-yl | |
| 2.445 | 3,5-$Cl_2$—Ph | H | O | H | $CH_2CH_2$ | 3-chloro-1-isopropyl-1H-pyrazol-4-yl | |
| 2.446 | 3,5-$F_2$—Ph | H | O | H | $CH_2CH_2$ | 3-chloro-1-isopropyl-1H-pyrazol-4-yl | |
| 2.447 | 3-F—Ph | H | O | H | $CH_2CH_2$ | 3-chloro-1-isopropyl-1H-pyrazol-4-yl | |
| 2.448 | 3,5-$F_2$—Ph | H | S | H | $CH_2CH_2$ | 3-chloro-1-methyl-1H-pyrazol-4-yl | |
| 2.449 | 3,5-$Cl_2$—Ph | H | O | H | $CH_2CH_2$ | 3-chloro-1-methyl-1H-pyrazol-4-yl | |
| 2.450 | 3,5-$Cl_2$—Ph | H | O | H | $CH_2CH_2$ | 3-chloropyridin-4-yl | |
| 2.451 | 3,5-$F_2$—Ph | H | O | H | $CH_2CH_2$ | 3-chloropyridin-4-yl | |
| 2.452 | 3,5-$F_2$—Ph | H | O | H | $CH_2CH_2$ | 3-cyclopropyl-1,2,4-oxadiazol-5-yl | |
| 2.453 | 3-F—Ph | H | O | H | $CH_2CH_2$ | 3-cyclopropyl-1,2,4-oxadiazol-5-yl | |
| 2.454 | 3,5-$F_2$—Ph | H | O | H | $CH_2CH_2$ | 3-furyl | |
| 2.455 | 3,5-$Cl_2$—Ph | H | O | H | $CH_2CH_2$ | 3-methyl-1H-pyrazol-4-yl | |
| 2.456 | 3,5-$F_2$—Ph | H | O | H | $CH_2CH_2$ | 3-methyl-1-propyl-1H-pyrazol-4-yl | |
| 2.457 | 3,5-$F_2$—Ph | H | O | H | $CH_2CH_2$ | 3-methyl-1-propyl-1H-pyrazol-4-yl | |
| 2.458 | 3-F—Ph | H | O | H | $CH_2CH_2$ | 3-methyl-1-propyl-1H-pyrazol-4-yl | |
| 2.459 | 3,5-$F_2$—Ph | H | O | H | $CH_2CH_2$ | 3-methyl-1-propyl-1H-pyrazol-4-yl | |
| 2.460 | 3-Cl-5-F—Ph | H | O | H | $CH_2CH_2$ | 3-methyl-1-propyl-1H-pyrazol-4-yl | |
| 2.461 | 3-Cl-5-$CF_3O$—Ph | H | O | H | $CH_2CH_2$ | 3-methyl-1-propyl-1H-pyrazol-4-yl | |
| 2.462 | 3-F-5-Me—Ph | H | O | H | $CH_2CH_2$ | 3-methyl-1-propyl-1H-pyrazol-4-yl | |
| 2.463 | 3-Me—Ph | H | O | H | $CH_2CH_2$ | 3-methyl-1-propyl-1H-pyrazol-4-yl | |
| 2.464 | 3-Cl-5-Me—Ph | H | O | H | $CH_2CH_2$ | 3-methyl-1-propyl-1H-pyrazol-4-yl | |
| 2.465 | 3-Cl-4-F—Ph | H | O | H | $CH_2CH_2$ | 3-methyl-1-propyl-1H-pyrazol-4-yl | |
| 2.466 | 3-$CF_3O$—Ph | H | O | H | $CH_2CH_2$ | 3-methyl-1-propyl-1H-pyrazol-4-yl | |
| 2.467 | 4-Cl-3,5-$F_2$—Ph | H | O | H | $CH_2CH_2$ | 3-methyl-1-propyl-1H-pyrazol-4-yl | |

TABLE 2-continued

Compounds of the general formula (I) according to the invention in which $R^2$ is hydrogen and $R^3$ is ethyl and aryl is the radical

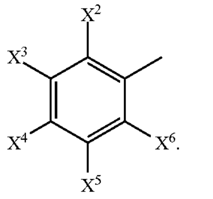

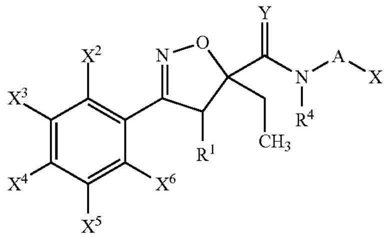

| No. | Aryl | $R^1$ | Y | $R^4$ | A | X | Physical data |
|---|---|---|---|---|---|---|---|
| 2.468 | 3,5-$Cl_2$—Ph | H | O | H | $CH_2CH_2$ | 4-(methoxy-carbonyl)phenyl | |
| 2.469 | Ph | H | O | H | $CH_2CH_2$ | 4-(trifluoromethyl)-1,3-thiazol-2-yl | |
| 2.470 | 3,5-$Cl_2$—Ph | H | O | H | $CH_2CH_2$ | 4-(trifluoromethyl)-1,3-thiazol-2-yl | |
| 2.471 | 3,5-$F_2$—Ph | H | O | H | $CH_2CH_2$ | 4-(trifluoromethyl)-1,3-thiazol-2-yl | |
| 2.472 | 3-F—Ph | H | O | H | $CH_2CH_2$ | 4-chloro-1-methyl-1H-pyrazol-3-yl | |
| 2.473 | 3,5-$Cl_2$—Ph | H | O | H | $CH_2CH_2$ | 4-chloro-1-methyl-1H-pyrazol-3-yl | |
| 2.474 | 3,5-$F_2$—Ph | H | O | H | $CH_2CH_2$ | 4-chloro-1-methyl-1H-pyrazol-3-yl | |
| 2.475 | 3,5-$Cl_2$—Ph | H | O | H | $CH_2CH_2$ | 4-chloro-1-methyl-1H-pyrazol-5-yl | |
| 2.476 | 3-F—Ph | H | O | H | $CH_2CH_2$ | 5-chloro-1-methyl-1H-pyrazol-4-yl | |
| 2.477 | 3,5-$F_2$—Ph | H | O | H | $CH_2CH_2$ | 5-chloro-1-methyl-1H-pyrazol-4-yl | |
| 2.478 | 3,5-$F_2$—Ph | H | O | H | $CH_2CH_2$ | 5-chloro-1-methyl-1H-pyrazol-4-yl | |
| 2.479 | 3-F—Ph | H | O | H | $CH_2CH_2$ | 5-chloro-1-methyl-1H-pyrazol-4-yl | |
| 2.480 | 3,5-$F_2$—Ph | H | S | H | $CH_2CH_2$ | 5-chloro-1-methyl-1H-pyrazol-4-yl | |
| 2.481 | 3,5-$Cl_2$—Ph | H | O | H | $CH_2CH_2$ | 5-methoxy-1,3-dimethyl-1H-pyrazol-4-yl | |
| 2.482 | Ph | H | O | H | $CH_2CH_2$ | 5-methoxy-1,3-dimethyl-1H-pyrazol-4-yl | |
| 2.483 | 3,5-$F_2$—Ph | H | O | H | $CH_2CH_2$ | 5-methoxy-1,3-dimethyl-1H-pyrazol-4-yl | |
| 2.484 | 3,5-$Cl_2$—Ph | H | O | H | $CH_2CH_2$ | 5-methyl-1,2,4-oxadiazol-3-yl | |
| 2.485 | 3-F—Ph | H | O | H | $CH_2CH_2$ | 5-methyl-1,2,4-oxadiazol-3-yl | |
| 2.486 | 3,5-$Cl_2$—Ph | H | O | H | $CH_2CH_2$ | 5-methyl-1,2-oxazol-3-yl | |
| 2.487 | 3,5-$F_2$—Ph | H | O | H | $CH_2CH_2$ | 5-methyl-1-propyl-1H-pyrazol-4-yl | |
| 2.488 | 3,5-$Cl_2$—Ph | H | O | H | $CH_2CH_2$ | 5-methyl-1-propyl-1H-pyrazol-4-yl | |
| 2.489 | 3-F—Ph | H | O | H | $CH_2CH_2$ | 5-methyl-1-propyl-1H-pyrazol-4-yl | |
| 2.490 | 3,5-$F_2$—Ph | H | O | H | $CH_2CH_2$ | 5-methyl-1-propyl-1H-pyrazol-4-yl | |
| 2.491 | 3,5-$Cl_2$—Ph | H | O | H | $CH_2CH_2$ | 6-chloropyridin-3-yl | |
| 2.492 | Ph | H | O | H | $CH_2CH_2$ | furan-2-yl | |
| 2.493 | 3,5-$F_2$—Ph | H | O | H | $CH_2CH_2$ | pyridin-2-yl | |
| 2.494 | 3,5-$F_2$—Ph | H | O | H | $CH_2CH_2$ | pyridin-2-yl | |

TABLE 2-continued

Compounds of the general formula (I) according to the invention in which $R^2$ is hydrogen and $R^3$ is ethyl and aryl is the radical

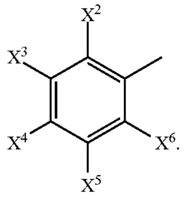

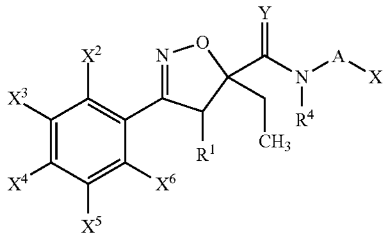

| No. | Aryl | $R^1$ | Y | $R^4$ | A | X | Physical data |
|---|---|---|---|---|---|---|---|
| 2.495 | 3,5-$Cl_2$—Ph | H | O | H | $CH_2CH_2$ | pyridin-3-yl | |
| 2.496 | 3,5-$F_2$—Ph | H | O | H | $CH_2CH_2$ | pyridin-3-yl | |
| 2.497 | 3,5-$F_2$—Ph | H | O | H | $CH_2CH_2$ | pyridin-4-yl | |
| 2.498 | 3-F—Ph | H | O | H | $CH_2CH_2$ | pyridin-4-yl | |
| 2.499 | 3,5-$F_2$—Ph | H | O | H | $CH_2CH_2$ | pyrimidin-2-yl | |
| 2.500 | 3-F—Ph | H | O | H | $CH_2CH_2$ | 1-(2,2,2-trifluoroethyl)-1H-pyrazol-4-yl | |
| 2.501 | 3,5-$Cl_2$—Ph | H | O | H | $CH_2CH_2$ | 1-(2-chloroethyl)-1H-pyrazol-4-yl | |
| 2.502 | 3,5-$F_2$—Ph | H | O | H | $CHCH_3$ | 1-(2-methoxy-2-oxoethyl)-1H-pyrazol-4-yl | |
| 2.503 | 3,5-$F_2$—Ph | H | O | H | $CHCH_3$ | 1-(3-carboxypropyl)-1H-pyrazol-4-yl | |
| 2.504 | 3,5-$Cl_2$—Ph | H | O | H | $CHCH_3$ | 1-(3-methoxy-3-oxopropyl)-1H-pyrazol-4-yl | |
| 2.505 | 3,5-$F_2$—Ph | H | O | H | $CHCH_3$ | 1-(4-methoxy-4-oxobutyl)-1H-pyrazol-4-yl | |
| 2.506 | 3,5-$F_2$—Ph | H | O | H | $CHCH_3$ | 1-(cyanomethyl)-1H-pyrazol-4-yl | |
| 2.507 | 3,5-$F_2$—Ph | H | O | H | $CHCH_3$ | 1-(cyanomethyl)-1H-pyrazol-4-yl | |
| 2.508 | 3,5-$F_2$—Ph | H | O | H | $CHCH_3$ | 1-(cyanomethyl)-1H-pyrazol-4-yl | |
| 2.509 | 3,5-$Cl_2$—Ph | H | O | H | $CHCH_3$ | 1,3-dimethyl-1H-pyrazol-4-yl | |
| 2.510 | 3-F—Ph | H | O | H | $CHCH_3$ | 1,3-dimethyl-1H-pyrazol-4-yl | |
| 2.511 | 3,5-$F_2$—Ph | H | O | H | $CHCH_3$ | 1,3-dimethyl-1H-pyrazol-4-yl | |
| 2.512 | 3-F—Ph | H | O | H | $CHCH_3$ | 1,3-dimethyl-1H-pyrazol-4-yl | |
| 2.513 | 3-Me—Ph | H | O | H | $CHCH_3$ | 1,3-dimethyl-1H-pyrazol-4-yl | |
| 2.514 | Ph | H | O | H | $CHCH_3$ | 1,3-dimethyl-1H-pyrazol-4-yl | |
| 2.515 | 3-Cl—Ph | H | O | H | $CHCH_3$ | 1,3-dimethyl-1H-pyrazol-4-yl | |
| 2.516 | 3,5-$Cl_2$—Ph | H | O | H | $CHCH_3$ | 1,3-dimethyl-1H-pyrazol-5-yl | |
| 2.517 | 3,5-$(CF_3)_2$—Ph | H | O | H | $CHCH_3$ | 1,3-dimethyl-1H-pyrazol-5-yl | |
| 2.518 | 3,5-$F_2$—Ph | H | O | H | $CHCH_3$ | 1,3-dimethyl-1H-pyrazol-5-yl | |
| 2.519 | Ph | H | O | H | $CHCH_3$ | 1,3-dimethyl-1H-pyrazol-5-yl | |
| 2.520 | 3,5-$Cl_2$—Ph | H | O | H | $CHCH_3$ | 1,3-oxazol-4-yl | |
| 2.521 | 3,5-$(CF_3)_2$—Ph | H | O | H | $CHCH_3$ | 1,3-oxazol-4-yl | |
| 2.522 | 3,5-$F_2$—Ph | H | O | H | $CHCH_3$ | 1,3-oxazol-4-yl | |

TABLE 2-continued

Compounds of the general formula (I) according to the invention in which $R^2$ is hydrogen and $R^3$ is ethyl and aryl is the radical

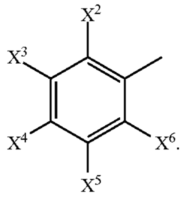

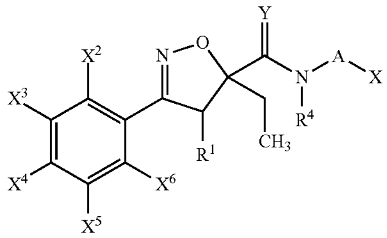

| No. | Aryl | $R^1$ | Y | $R^4$ | A | X | Physical data |
|---|---|---|---|---|---|---|---|
| 2.523 | 3,5-$Cl_2$—Ph | H | O | H | $CHCH_3$ | 1,3-thiazol-2-yl | |
| 2.524 | 3-F—Ph | H | O | H | $CHCH_3$ | 1,3-thiazol-2-yl | |
| 2.525 | 3,5-$Cl_2$—Ph | H | O | H | $CHCH_3$ | 1,4-dimethyl-5-oxo-4,5-dihydro-1H-1,2,4-triazol-3-yl | |
| 2.526 | 3,5-$F_2$—Ph | H | O | H | $CHCH_3$ | 1,5-dimethyl-1H-pyrazol-3-yl | |
| 2.527 | 3,5-$Cl_2$—Ph | H | O | H | $CHCH_3$ | 1,5-dimethyl-1H-pyrazol-4-yl | |
| 2.528 | 3,5-$F_2$—Ph | H | O | H | $CHCH_3$ | 1,5-dimethyl-1H-pyrazol-4-yl | |
| 2.529 | 3,5-$F_2$—Ph | H | O | H | $CHCH_3$ | 1,5-dimethyl-1H-pyrazol-4-yl | |
| 2.530 | 3-F—Ph | H | O | H | $CHCH_3$ | 1,5-dimethyl-1H-pyrazol-4-yl | |
| 2.531 | 3,5-$Cl_2$—Ph | H | O | H | $CHCH_3$ | 1-acetyl-1H-pyrazol-4-yl | |
| 2.532 | Ph | H | O | H | $CHCH_3$ | 1-butyl-3-methyl-1H-pyrazol-4-yl | |
| 2.533 | 3,5-$F_2$—Ph | H | O | H | $CHCH_3$ | 1-butyl-5-methyl-1H-pyrazol-4-yl | |
| 2.534 | 3,5-$F_2$—Ph | H | O | H | $CHCH_3$ | 1-cyclopropyl-1H-pyrazol-4-yl | |
| 2.535 | 3,5-$F_2$—Ph | H | O | H | $CHCH_3$ | 1-cyclopropyl-1H-pyrazol-4-yl | |
| 2.536 | 3,5-$F_2$—Ph | H | O | H | $CHCH_3$ | 1-cyclopropyl-1H-pyrazol-4-yl | |
| 2.537 | Ph | H | O | H | $CHCH_3$ | 1-cyclopropyl-1H-pyrazol-4-yl | |
| 2.538 | 3-F—Ph | H | O | H | $CHCH_3$ | 1-ethyl-1H-pyrazol-4-yl | |
| 2.539 | 3,5-$Cl_2$—Ph | H | O | H | $CHCH_3$ | 1-ethyl-1H-pyrazol-4-yl | |
| 2.540 | 3,5-$Cl_2$—Ph | H | O | H | $CHCH_3$ | 1-ethyl-1H-pyrazol-4-yl | |
| 2.541 | 3-F—Ph | H | O | H | $CHCH_3$ | 1-ethyl-1H-pyrazol-4-yl | |
| 2.542 | 3,5-$F_2$—Ph | H | O | H | $CHCH_3$ | 1-ethyl-1H-pyrazol-4-yl | |
| 2.543 | 3-Br-5-$CF_3$—Ph | H | O | H | $CHCH_3$ | 1-ethyl-1H-pyrazol-4-yl | |
| 2.544 | 3-Me—Ph | H | O | H | $CHCH_3$ | 1-ethyl-1H-pyrazol-4-yl | |
| 2.545 | 3-F-5-MeO—Ph | H | O | H | $CHCH_3$ | 1-ethyl-1H-pyrazol-4-yl | |
| 2.546 | 3-Cl-5-Et—Ph | H | O | H | $CHCH_3$ | 1-ethyl-1H-pyrazol-4-yl | |
| 2.547 | 3,5-$(MeO)_2$—Ph | H | O | H | $CHCH_3$ | 1-ethyl-1H-pyrazol-4-yl | |
| 2.548 | 3-Me-5-$CF_3O$—Ph | H | O | H | $CHCH_3$ | 1-ethyl-1H-pyrazol-4-yl | |
| 2.549 | 3,5-$Cl_2$-4-MeO—Ph | H | O | H | $CHCH_3$ | 1-ethyl-1H-pyrazol-5-yl | |

TABLE 2-continued

Compounds of the general formula (I) according to the invention in which $R^2$ is hydrogen and $R^3$ is ethyl and aryl is the radical

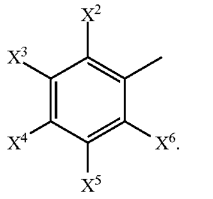

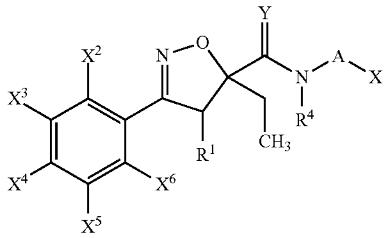

| No. | Aryl | $R^1$ | Y | $R^4$ | A | X | Physical data |
|---|---|---|---|---|---|---|---|
| 2.550 | Ph | H | O | H | $CHCH_3$ | 1-ethyl-1H-pyrazol-5-yl | |
| 2.551 | 3,5-$F_2$—Ph | H | O | H | $CHCH_3$ | 1-ethyl-1H-pyrazol-5-yl | |
| 2.552 | 3,5-$Cl_2$—Ph | H | O | H | $CHCH_3$ | 1-ethyl-3-methyl-1H-pyrazol-4-yl | |
| 2.553 | Ph | H | O | H | $CHCH_3$ | 1-ethyl-3-methyl-1H-pyrazol-4-yl | |
| 2.554 | 3,5-$F_2$—Ph | H | O | H | $CHCH_3$ | 1-ethyl-3-methyl-1H-pyrazol-4-yl | |
| 2.555 | 3-Me—Ph | H | O | H | $CHCH_3$ | 1-ethyl-3-methyl-1H-pyrazol-4-yl | |
| 2.556 | 3-Br-5-F—Ph | H | O | H | $CHCH_3$ | 1-ethyl-3-methyl-1H-pyrazol-4-yl | |
| 2.557 | 3,4,5-$F_3$—Ph | H | O | H | $CHCH_3$ | 1-ethyl-3-methyl-1H-pyrazol-4-yl | |
| 2.558 | 3,4-$F_2$—Ph | H | O | H | $CHCH_3$ | 1-ethyl-3-methyl-1H-pyrazol-4-yl | |
| 2.559 | 3,5-$F_2$—Ph | H | S | H | $CHCH_3$ | 1-ethyl-3-methyl-1H-pyrazol-4-yl | |
| 2.560 | 3-F-5-Me—Ph | H | O | H | $CHCH_3$ | 1-ethyl-3-methyl-1H-pyrazol-4-yl | |
| 2.561 | 3-Cl-5-CN—Ph | H | O | H | $CHCH_3$ | 1-ethyl-3-methyl-1H-pyrazol-4-yl | |
| 2.562 | 3-F—Ph | H | O | H | $CHCH_3$ | 1-ethyl-3-methyl-1H-pyrazol-4-yl | |
| 2.563 | 3-cPr-5-F—Ph | H | O | H | $CHCH_3$ | 1-ethyl-3-methyl-1H-pyrazol-4-yl | |
| 2.564 | 3-Cl-5-Me—Ph | H | O | H | $CHCH_3$ | 1-ethyl-3-methyl-1H-pyrazol-4-yl | |
| 2.565 | 3-F-5-MeO—Ph | H | O | H | $CHCH_3$ | 1-ethyl-3-methyl-1H-pyrazol-4-yl | |
| 2.566 | 2,5-$Me_2$—Ph | H | O | H | $CHCH_3$ | 1-ethyl-3-methyl-1H-pyrazol-4-yl | |
| 2.567 | 3-$CF_3O$—Ph | H | O | H | $CHCH_3$ | 1-ethyl-3-methyl-1H-pyrazol-4-yl | |
| 2.568 | 3-Cl-5-Et—Ph | H | O | H | $CHCH_3$ | 1-ethyl-3-methyl-1H-pyrazol-4-yl | |
| 2.569 | 2,3,5-$F_3$—Ph | H | O | H | $CHCH_3$ | 1-ethyl-3-methyl-1H-pyrazol-4-yl | |
| 2.570 | 3-Et-5-F—Ph | H | O | H | $CHCH_3$ | 1-ethyl-3-methyl-1H-pyrazol-4-yl | |
| 2.571 | 3-F-5-$CF_3$—Ph | H | O | H | $CHCH_3$ | 1-ethyl-3-methyl-1H-pyrazol-4-yl | |
| 2.572 | 3-Br-5-$CF_3$—Ph | H | O | H | $CHCH_3$ | 1-ethyl-3-methyl-1H-pyrazol-4-yl | |
| 2.573 | 3-Cl-5-MeO—Ph | H | O | H | $CHCH_3$ | 1-ethyl-3-methyl-1H-pyrazol-4-yl | |
| 2.574 | 3-Cl-4-F—Ph | H | O | H | $CHCH_3$ | 1-ethyl-3-methyl-1H-pyrazol-4-yl | |
| 2.575 | 2,3-$F_2$—Ph | H | O | H | $CHCH_3$ | 1-ethyl-3-methyl-1H-pyrazol-4-yl | |

TABLE 2-continued

Compounds of the general formula (I) according to the invention in which $R^2$ is hydrogen and $R^3$ is ethyl and aryl is the radical

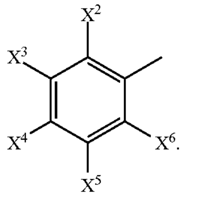

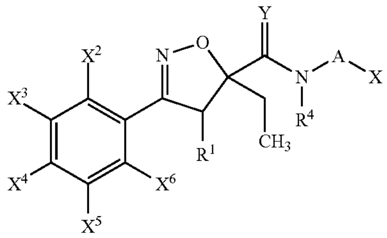

| No. | Aryl | $R^1$ | Y | $R^4$ | A | X | Physical data |
|---|---|---|---|---|---|---|---|
| 2.576 | 3-Cl-5-$CF_3$—Ph | H | O | H | $CHCH_3$ | 1-ethyl-3-methyl-1H-pyrazol-4-yl | |
| 2.577 | 3,5-$Me_2$—Ph | H | O | H | $CHCH_3$ | 1-ethyl-3-methyl-1H-pyrazol-4-yl | |
| 2.578 | 3-Cl—Ph | H | O | H | $CHCH_3$ | 1-ethyl-3-methyl-1H-pyrazol-4-yl | |
| 2.579 | 3-MeO—Ph | H | O | H | $CHCH_3$ | 1-ethyl-3-methyl-1H-pyrazol-4-yl | |
| 2.580 | 3-Cl-5-F—Ph | H | O | H | $CHCH_3$ | 1-ethyl-3-methyl-1H-pyrazol-4-yl | |
| 2.581 | 3-CN-5-F—Ph | H | O | H | $CHCH_3$ | 1-ethyl-3-methyl-1H-pyrazol-4-yl | |
| 2.582 | 3-CN—Ph | H | O | H | $CHCH_3$ | 1-ethyl-3-methyl-1H-pyrazol-4-yl | |
| 2.583 | 3-Br-5-Cl—Ph | H | O | H | $CHCH_3$ | 1-ethyl-3-methyl-1H-pyrazol-4-yl | |
| 2.584 | 2,3,4-$F_3$—Ph | H | O | H | $CHCH_3$ | 1-ethyl-3-methyl-1H-pyrazol-4-yl | |
| 2.585 | 3,5-$Cl_2$-4-MeO—Ph | H | O | H | $CHCH_3$ | 1-ethyl-3-methyl-1H-pyrazol-4-yl | |
| 2.586 | Ph | H | O | H | $CHCH_3$ | 1-ethyl-3-methyl-1H-pyrazol-4-yl | |
| 2.587 | 2,5-$F_2$—Ph | H | O | H | $CHCH_3$ | 1-ethyl-3-methyl-1H-pyrazol-4-yl | |
| 2.588 | 3,5-$Br_2$—Ph | H | O | H | $CHCH_3$ | 1-ethyl-3-methyl-1H-pyrazol-4-yl | |
| 2.589 | 2-F—Ph | H | O | H | $CHCH_3$ | 1-ethyl-3-methyl-1H-pyrazol-4-yl | |
| 2.590 | 2,5-$Cl_2$—Ph | H | O | H | $CHCH_3$ | 1-ethyl-3-methyl-1H-pyrazol-4-yl | |
| 2.591 | 3,5-$Et_2$—Ph | H | O | H | $CHCH_3$ | 1-ethyl-3-methyl-1H-pyrazol-4-yl | |
| 2.592 | 3-$CF_3$S—Ph | H | O | H | $CHCH_3$ | 1-ethyl-3-methyl-1H-pyrazol-4-yl | |
| 2.593 | 3-EtO—Ph | H | O | H | $CHCH_3$ | 1-ethyl-3-methyl-1H-pyrazol-4-yl | |
| 2.594 | 3,5-$Cl_2$—Ph | $CH_3$ | O | H | $CHCH_3$ | 1-ethyl-3-methyl-1H-pyrazol-4-yl | |
| 2.595 | 2-F-3-Me—Ph | H | O | H | $CHCH_3$ | 1-ethyl-3-methyl-1H-pyrazol-5-yl | |
| 2.596 | 3-Cl-5-$CF_3$O—Ph | H | O | H | $CHCH_3$ | 1-ethyl-3-methyl-1H-pyrazol-5-yl | |
| 2.597 | 3,5-$F_2$—Ph | H | O | H | $CHCH_3$ | 1-ethyl-3-methyl-1H-pyrazol-5-yl | |
| 2.598 | 3,5-$Cl_2$—Ph | H | O | H | $CHCH_3$ | 1H-1,2,3-triazol-5-yl | |
| 2.599 | 3-F—Ph | H | O | H | $CHCH_3$ | 1H-pyrazol-4-yl | |
| 2.600 | 3,5-$F_2$—Ph | H | O | H | $CHCH_3$ | 1H-pyrazol-4-yl | |
| 2.601 | 3,5-$Cl_2$—Ph | H | O | H | $CHCH_3$ | 1H-pyrazol-4-yl | |
| 2.602 | 3,5-$F_2$—Ph | H | O | H | $CHCH_3$ | 1-isobutyl-1H-pyrazol-4-yl | |
| 2.603 | 3-F—Ph | H | O | H | $CHCH_3$ | 1-isobutyl-1H-pyrazol-4-yl | |

TABLE 2-continued

Compounds of the general formula (I) according to the invention in which $R^2$ is hydrogen and $R^3$ is ethyl and aryl is the radical

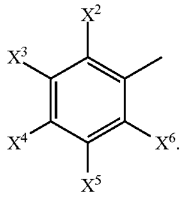

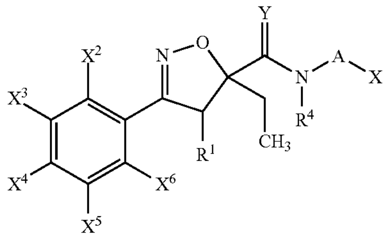

| No. | Aryl | $R^1$ | Y | $R^4$ | A | X | Physical data |
|---|---|---|---|---|---|---|---|
| 2.604 | 3,5-$F_2$—Ph | H | O | H | $CHCH_3$ | 1-isobutyl-1H-pyrazol-4-yl | |
| 2.605 | 3,5-$Cl_2$—Ph | H | O | H | $CHCH_3$ | 1-isobutyl-1H-pyrazol-4-yl | |
| 2.606 | 3-F—Ph | H | O | H | $CHCH_3$ | 1-isopropyl-1H-pyrazol-4-yl | |
| 2.607 | Ph | H | O | H | $CHCH_3$ | 1-isopropyl-1H-pyrazol-4-yl | |
| 2.608 | 3,5-$F_2$—Ph | H | O | H | $CHCH_3$ | 1-isopropyl-1H-pyrazol-4-yl | |
| 2.609 | 3-F—Ph | H | O | H | $CHCH_3$ | 1-isopropyl-1H-pyrazol-4-yl | |
| 2.610 | 3,5-$Cl_2$—Ph | H | O | H | $CHCH_3$ | 1-methyl-1H-pyrazol-4-yl | |
| 2.611 | Ph | H | O | H | $CHCH_3$ | 1-methyl-1H-pyrazol-4-yl | |
| 2.612 | 3,5-$F_2$—Ph | H | O | H | $CHCH_3$ | 1-methyl-1H-pyrazol-4-yl | |
| 2.613 | 3-F-5-MeO—Ph | H | O | H | $CHCH_3$ | 1-methyl-1H-pyrazol-4-yl | |
| 2.614 | 3-F—Ph | H | O | H | $CHCH_3$ | 1-methyl-1H-pyrazol-4-yl | |
| 2.615 | Ph | H | O | H | $CHCH_3$ | 1-methyl-1H-pyrazol-4-yl | |
| 2.616 | 3,5-$(CF_3)_2$—Ph | H | O | H | $CHCH_3$ | 1-methyl-1H-pyrazol-4-yl | |
| 2.617 | 3,5-$Cl_2$—Ph | H | O | H | $CHCH_3$ | 1-methyl-1H-pyrazol-5-yl | |
| 2.618 | 3-Me—Ph | H | O | H | $CHCH_3$ | 1-methyl-1H-pyrazol-5-yl | |
| 2.619 | 3,5-$F_2$—Ph | H | O | H | $CHCH_3$ | 1-methyl-1H-pyrazol-5-yl | |
| 2.620 | 3-F—Ph | H | O | H | $CHCH_3$ | 1-methyl-1H-pyrazol-5-yl | |
| 2.621 | 3,5-$Cl_2$—Ph | H | O | H | $CHCH_3$ | 1-methyl-3-(trifluoromethyl)-1H-pyrazol-4-yl | |
| 2.622 | Ph | H | O | H | $CHCH_3$ | 1-methyl-3-(trifluoromethyl)-1H-pyrazol-4-yl | |
| 2.623 | 3,5-$Cl_2$—Ph | H | O | H | $CHCH_3$ | 1-methyl-5-(trifluoromethyl)-1H-pyrazol-4-yl | D1 |
| 2.624 | 3,5-$Cl_2$—Ph | H | O | H | $CHCH_3$ | 1-propyl-1H-pyrazol-3-yl | D2 |
| 2.625 | 3,5-$F_2$—Ph | H | O | H | $CHCH_3$ | 1-propyl-1H-pyrazol-3-yl | |
| 2.626 | 3,5-$F_2$—Ph | H | O | H | $CHCH_3$ | 1-propyl-1H-pyrazol-4-yl | |
| 2.627 | 3,5-$Cl_2$—Ph | H | O | H | $CHCH_3$ | 1-propyl-1H-pyrazol-4-yl | |
| 2.628 | 3,5-$F_2$—Ph | H | O | H | $CHCH_3$ | 1-propyl-1H-pyrazol-4-yl | |

TABLE 2-continued

Compounds of the general formula (I) according to the invention in which $R^2$ is hydrogen and $R^3$ is ethyl and aryl is the radical

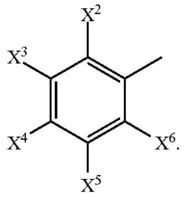

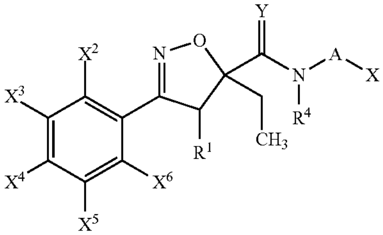

| No. | Aryl | $R^1$ | Y | $R^4$ | A | X | Physical data |
|---|---|---|---|---|---|---|---|
| 2.629 | 3,5-$Cl_2$—Ph | H | O | H | $CHCH_3$ | 1-propyl-1H-pyrazol-4-yl | |
| 2.630 | 3-F—Ph | H | O | H | $CHCH_3$ | 1-tert-butyl-1H-pyrazol-4-yl | |
| 2.631 | Ph | H | O | H | $CHCH_3$ | 1-tert-butyl-1H-pyrazol-4-yl | |
| 2.632 | 3,5-$F_2$—Ph | H | O | H | $CHCH_3$ | 1-tert-butyl-1H-pyrazol-4-yl | |
| 2.633 | 3,5-$Cl_2$—Ph | H | O | H | $CHCH_3$ | 2-chloropyridin-4-yl | |
| 2.634 | Ph | H | O | H | $CHCH_3$ | 2-chloropyridin-4-yl | |
| 2.635 | 3,5-$F_2$—Ph | H | O | H | $CHCH_3$ | 2-methyl-1,3-thiazol-4-yl | |
| 2.636 | 3-F—Ph | H | O | H | $CHCH_3$ | 2-methyl-1,3-thiazol-4-yl | |
| 2.637 | 3,5-$F_2$—Ph | H | O | H | $CHCH_3$ | 3-(cyclopropyl-carbamoyl)-1,2-oxazol-5-yl | |
| 2.638 | 3,5-$Cl_2$—Ph | H | O | H | $CHCH_3$ | 3-(ethoxycarbonyl)-1,2-oxazol-5-yl | |
| 2.639 | 3,5-$Cl_2$—Ph | H | O | H | $CHCH_3$ | 3-(methoxy-carbonyl)phenyl | |
| 2.640 | 3,5-$Cl_2$—Ph | H | O | H | $CHCH_3$ | 3,5-difluoropyridin-2-yl | |
| 2.641 | 3,5-$F_2$—Ph | H | O | H | $CHCH_3$ | 3-carboxy-1,2-oxazol-5-yl | |
| 2.642 | 3,5-$F_2$—Ph | H | O | H | $CHCH_3$ | 3-chloro-1-ethyl-1H-pyrazol-4-yl | |
| 2.643 | 3,5-$Cl_2$—Ph | H | O | H | $CHCH_3$ | 3-chloro-1-ethyl-1H-pyrazol-4-yl | |
| 2.644 | 3,5-$F_2$—Ph | H | O | H | $CHCH_3$ | 3-chloro-1-ethyl-1H-pyrazol-4-yl | |
| 2.645 | 3-F—Ph | H | O | H | $CHCH_3$ | 3-chloro-1-ethyl-1H-pyrazol-4-yl | |
| 2.646 | Ph | H | O | H | $CHCH_3$ | 3-chloro-1-isopropyl-1H-pyrazol-4-yl | |
| 2.647 | 3,5-$Cl_2$—Ph | H | O | H | $CHCH_3$ | 3-chloro-1-isopropyl-1H-pyrazol-4-yl | |
| 2.648 | 3,5-$F_2$—Ph | H | O | H | $CHCH_3$ | 3-chloro-1-isopropyl-1H-pyrazol-4-yl | |
| 2.649 | 3-F—Ph | H | O | H | $CHCH_3$ | 3-chloro-1-isopropyl-1H-pyrazol-4-yl | |
| 2.650 | 3,5-$F_2$—Ph | H | S | H | $CHCH_3$ | 3-chloro-1-methyl-1H-pyrazol-4-yl | |
| 2.651 | 3,5-$Cl_2$—Ph | H | O | H | $CHCH_3$ | 3-chloro-1-methyl-1H-pyrazol-4-yl | |
| 2.652 | 3,5-$Cl_2$—Ph | H | O | H | $CHCH_3$ | 3-chloropyridin-4-yl | |
| 2.653 | 3,5-$F_2$—Ph | H | O | H | $CHCH_3$ | 3-chloropyridin-4-yl | |
| 2.654 | 3,5-$F_2$—Ph | H | O | H | $CHCH_3$ | 3-cyclopropyl-1,2,4-oxadiazol-5-yl | |

TABLE 2-continued

Compounds of the general formula (I) according to the invention in which $R^2$ is hydrogen and $R^3$ is ethyl and aryl is the radical

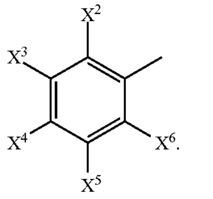

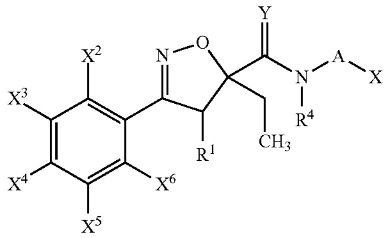

| No. | Aryl | $R^1$ | Y | $R^4$ | A | X | Physical data |
|---|---|---|---|---|---|---|---|
| 2.655 | 3-F—Ph | H | O | H | $CHCH_3$ | 3-cyclopropyl-1,2,4-oxadiazol-5-yl | |
| 2.656 | 3,5-$F_2$—Ph | H | O | H | $CHCH_3$ | 3-furyl | |
| 2.657 | 3,5-$Cl_2$—Ph | H | O | H | $CHCH_3$ | 3-methyl-1H-pyrazol-4-yl | |
| 2.658 | 3,5-$F_2$—Ph | H | O | H | $CHCH_3$ | 3-methyl-1-propyl-1H-pyrazol-4-yl | |
| 2.659 | 3,5-$F_2$—Ph | H | O | H | $CHCH_3$ | 3-methyl-1-propyl-1H-pyrazol-4-yl | |
| 2.660 | 3-F—Ph | H | O | H | $CHCH_3$ | 3-methyl-1-propyl-1H-pyrazol-4-yl | |
| 2.661 | 3,5-$F_2$—Ph | H | O | H | $CHCH_3$ | 3-methyl-1-propyl-1H-pyrazol-4-yl | |
| 2.662 | 3-Cl-5-F—Ph | H | O | H | $CHCH_3$ | 3-methyl-1-propyl-1H-pyrazol-4-yl | |
| 2.663 | 3-Cl-5-$CF_3O$—Ph | H | O | H | $CHCH_3$ | 3-methyl-1-propyl-1H-pyrazol-4-yl | |
| 2.664 | 3-F-5-Me—Ph | H | O | H | $CHCH_3$ | 3-methyl-1-propyl-1H-pyrazol-4-yl | |
| 2.665 | 3-Me—Ph | H | O | H | $CHCH_3$ | 3-methyl-1-propyl-1H-pyrazol-4-yl | |
| 2.666 | 3-Cl-5-Me—Ph | H | O | H | $CHCH_3$ | 3-methyl-1-propyl-1H-pyrazol-4-yl | |
| 2.667 | 3-Cl-4-F—Ph | H | O | H | $CHCH_3$ | 3-methyl-1-propyl-1H-pyrazol-4-yl | |
| 2.668 | 3-$CF_3O$—Ph | H | O | H | $CHCH_3$ | 3-methyl-1-propyl-1H-pyrazol-4-yl | |
| 2.669 | 4-Cl-3,5-$F_2$—Ph | H | O | H | $CHCH_3$ | 3-methyl-1-propyl-1H-pyrazol-4-yl | |
| 2.670 | 3,5-$Cl_2$—Ph | H | O | H | $CHCH_3$ | 4-(methoxy-carbonyl)phenyl | |
| 2.671 | Ph | H | O | H | $CHCH_3$ | 4-(trifluoromethyl)-1,3-thiazol-2-yl | |
| 2.672 | 3,5-$Cl_2$—Ph | H | O | H | $CHCH_3$ | 4-(trifluoromethyl)-1,3-thiazol-2-yl | |
| 2.673 | 3,5-$F_2$—Ph | H | O | H | $CHCH_3$ | 4-(trifluoromethyl)-1,3-thiazol-2-yl | |
| 2.674 | 3-F—Ph | H | O | H | $CHCH_3$ | 4-chloro-1-methyl-1H-pyrazol-3-yl | |
| 2.675 | 3,5-$Cl_2$—Ph | H | O | H | $CHCH_3$ | 4-chloro-1-methyl-1H-pyrazol-3-yl | |
| 2.676 | 3,5-$F_2$—Ph | H | O | H | $CHCH_3$ | 4-chloro-1-methyl-1H-pyrazol-3-yl | |
| 2.677 | 3,5-$Cl_2$—Ph | H | O | H | $CHCH_3$ | 4-chloro-1-methyl-1H-pyrazol-5-yl | |
| 2.678 | 3-F—Ph | H | O | H | $CHCH_3$ | 5-chloro-1-methyl-1H-pyrazol-4-yl | |
| 2.679 | 3,5-$F_2$—Ph | H | O | H | $CHCH_3$ | 5-chloro-1-methyl-1H-pyrazol-4-yl | |
| 2.680 | 3,5-$F_2$—Ph | H | O | H | $CHCH_3$ | 5-chloro-1-methyl-1H-pyrazol-4-yl | |
| 2.681 | 3-F—Ph | H | O | H | $CHCH_3$ | 5-chloro-1-methyl-1H-pyrazol-4-yl | |

TABLE 2-continued

Compounds of the general formula (I) according to the invention in which $R^2$ is hydrogen and $R^3$ is ethyl and aryl is the radical

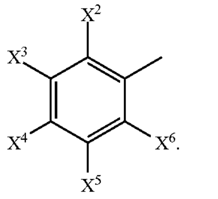

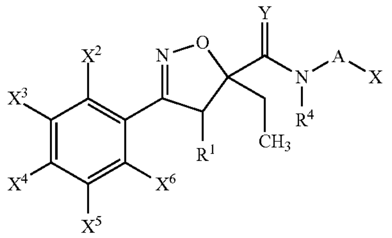

| No. | Aryl | $R^1$ | Y | $R^4$ | A | X | Physical data |
|---|---|---|---|---|---|---|---|
| 2.682 | 3,5-$F_2$—Ph | H | S | H | $CHCH_3$ | 5-chloro-1-methyl-1H-pyrazol-4-yl | |
| 2.683 | 3,5-$Cl_2$—Ph | H | O | H | $CHCH_3$ | 5-methoxy-1,3-dimethyl-1H-pyrazol-4-yl | |
| 2.684 | Ph | H | O | H | $CHCH_3$ | 5-methoxy-1,3-dimethyl-1H-pyrazol-4-yl | |
| 2.685 | 3,5-$F_2$—Ph | H | O | H | $CHCH_3$ | 5-methoxy-1,3-dimethyl-1H-pyrazol-4-yl | |
| 2.686 | 3,5-$Cl_2$—Ph | H | O | H | $CHCH_3$ | 5-methyl-1,2,4-oxadiazol-3-yl | |
| 2.687 | 3-F—Ph | H | O | H | $CHCH_3$ | 5-methyl-1,2,4-oxadiazol-3-yl | |
| 2.688 | 3,5-$Cl_2$—Ph | H | O | H | $CHCH_3$ | 5-methyl-1,2-oxazol-3-yl | |
| 2.689 | 3,5-$F_2$—Ph | H | O | H | $CHCH_3$ | 5-methyl-1-propyl-1H-pyrazol-4-yl | |
| 2.690 | 3,5-$Cl_2$—Ph | H | O | H | $CHCH_3$ | 5-methyl-1-propyl-1H-pyrazol-4-yl | |
| 2.691 | 3-F—Ph | H | O | H | $CHCH_3$ | 5-methyl-1-propyl-1H-pyrazol-4-yl | |
| 2.692 | 3,5-$F_2$—Ph | H | O | H | $CHCH_3$ | 5-methyl-1-propyl-1H-pyrazol-4-yl | |
| 2.693 | 3,5-$Cl_2$—Ph | H | O | H | $CHCH_3$ | 6-chloropyridin-3-yl | |
| 2.694 | Ph | H | O | H | $CHCH_3$ | furan-2-yl | |
| 2.695 | 3,5-$F_2$—Ph | H | O | H | $CHCH_3$ | pyridin-2-yl | |
| 2.696 | 3,5-$F_2$—Ph | H | O | H | $CHCH_3$ | pyridin-2-yl | |
| 2.697 | 3,5-$Cl_2$—Ph | H | O | H | $CHCH_3$ | pyridin-3-yl | |
| 2.698 | 3,5-$F_2$—Ph | H | O | H | $CHCH_3$ | pyridin-3-yl | |
| 2.699 | 3,5-$F_2$—Ph | H | O | H | $CHCH_3$ | pyridin-4-yl | |
| 2.700 | 3-F—Ph | H | O | H | $CHCH_3$ | pyridin-4-yl | |
| 2.701 | 3,5-$F_2$—Ph | H | O | H | $CHCH_3$ | pyrimidin-2-yl | |
| 2.702 | 3-F—Ph | H | O | H | $CHCH_3$ | pyridin-4-yl | |
| 2.703 | 3,5-$Cl_2$—Ph | H | O | H | $CHCH_3$ | pyrimidin-2-yl | |
| 2.704 | 3-F—Ph | H | O | H | bond | 3,5-dimethyl-1,2-oxazol-4-yl | |
| 2.705 | 3-F—Ph | H | O | H | $CH_2$ | 1,2-oxazol-4-yl | |
| 2.706 | 3,5-$F_2$—Ph | H | O | H | $CH_2$ | 2,5-dimethyl-1,3-oxazol-4-yl | |
| 2.707 | 3,5-$F_2$—Ph | H | O | H | $CH_2$ | 2-fluoropyridin-4-yl | [$CDCl_3$] 1.04 (t, 3H); 2.01 (m, 1H); 2.20 (m, 1H); 3.27 (d, 1H); 3.71 (d, 1H); 4.41 (dd, 1H); 4.59 (dd, 1H); 6.80 (s, 1H); 6.90 (m, 1H); 7.04 (d, 1H); 7.16 (m, 2H); 7.32 (t br, 1H); 8.15 (d, 1H). |
| 2.708 | 3-F—Ph | H | O | H | $CH_2$ | 2-fluoropyridin-4-yl | [$CDCl_3$] 1.04 (t, 3H); 2.03 (m, 1H); 2.20 (m, 1H); 3.30 (d, 1H); 3.74 (d, 1H); 4.41 (dd, 1H); 4.60 (dd, 1H); 6.78 (s, 1H); 7.05 (m, 1H); |

TABLE 2-continued

Compounds of the general formula (I) according to the invention in which $R^2$ is hydrogen and $R^3$ is ethyl and aryl is the radical

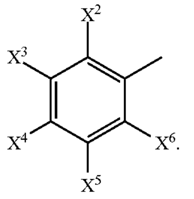

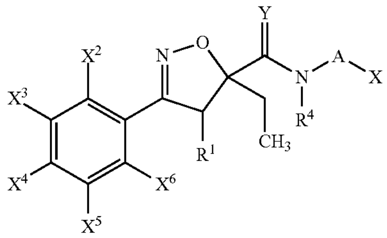

| No. | Aryl | $R^1$ | Y | $R^4$ | A | X | Physical data |
|---|---|---|---|---|---|---|---|
| | | | | | | | 7.14 (m, 1H); 7.33 (s br, 1H); 7.51 (m, 3H); 8.16 (d, 1H). |
| 2.709 | 3-F—Ph | H | O | H | $CH_2$ | 2-methoxypyridin-4-yl | [$CDCl_3$] 1.04 (t, 3H); 2.00 (m, 1H); 2.20 (m, 1H); 3.29 (d, 1H); 3.74 (d, 1H); 3.90 (s, 1H); 4.32 (dd, 1H); 4.51 (dd, 1H); 6.59 (s, 1H); 6.73 (d, 1H); 7.15 (m, 1H); 3.38 (m, 3H); 8.09 (d, 1H); |
| 2.710 | 3,5-$F_2$—Ph | H | O | H | $CH_2$ | 2-methoxypyridin-4-yl | [$CDCl_3$] 1.03 (t, 3H); 2.01 (m, 1H); 2.19 (m, 1H); 3.26 (d, 1H); 3.71 (d, 1H); 3.90 (s, 3H); 4.41 (AB d, 2H); 6.58 (s, 1H); 6.73 (d, 1H); 6.89 (m, 2H); 7.17 (m, 2H); 7.18 (s br, 1H); 8.08 (d, 1H). |
| 2.711 | 3,5-$F_2$—Ph | H | O | H | $CH_2$ | 3,5-diethyl-1,2-oxazol-4-yl | |
| 2.712 | 3-F—Ph | H | O | H | $CH_2$ | 3,5-dimethyl-1,2-oxazol-4-yl | |
| 2.713 | 3,5-$F_2$—Ph | H | O | H | $CH_2$ | 3,5-dimethyl-1,2-oxazol-4-yl | [$CDCl_3$] 0.98 (t, 3H); 1.95 (m, 1H); 2.13 (m, 1H); 2.21 (s, 3H); 2.38 (s, 3H); 3.23 (d, 1H); 6.68 (d, 1H); 4.11 (dd, 1H); 4.26 (dd, 1H); 6.88 (m, 2H); 7.15 (m, 2H). |
| 2.714 | 3,5-$Cl_2$—Ph | H | O | H | $CH_2$ | 3,5-dimethyl-1,2-oxazol-4-yl | [$CDCl_3$] 0.97 (t, 3H); 1.95 (m, 1H); 2.12 (m, 1H); 2.21 (s, 3H); 2.38 (s, 3H); 3.23 (d, 1H); 3.68 (d, 1H); 4.11 (dd, 1H); 4.27 (dd, 1H); 6.90 (t br, 1H); 7.42 (s, 1H); 7.51 (s, 2H). |
| 2.715 | 3,5-$F_2$—Ph | H | O | H | $CH_2$ | 3-chloro-5-(trifluoromethyl)-pyridin-2-yl | |
| 2.716 | 3,5-$F_2$—Ph | H | O | H | $CH_2$ | 3-ethyl-5-methyl-1,2-oxazol-4-yl | |
| 2.717 | 3-F—Ph | H | O | H | $CH_2$ | 3-ethyl-5-methyl-1,2-oxazol-4-yl | |
| 2.718 | 3-F—Ph | H | O | H | $CH_2$ | 6-(trifluoromethyl)-pyridin-3-yl | [$CDCl_3$] 1.01 (t, 3H); 1.99 (m, 1H); 2.17 (m, 1H); 3.29 (d, 1H); 3.73 (d, 1H); 4.45 (dd, 1H); 4.65 (dd, 1H); 7.15 (m, 1H); 7.38 (m, 3H); 7.63 (d, 1H); 7.77 (d, 1H); 8.65 (s, 1H). |
| 2.719 | 3,5-$F_2$—Ph | H | O | H | $CH_2CH_2$ | 3-chloro-5-(trifluoromethyl)-pyridin-2-yl | |

TABLE 3

Compounds of the general formula (I) according to the invention in which $R^2$ is hydrogen and $R^3$ is trifluoroomethyl and aryl is the radical

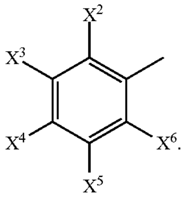

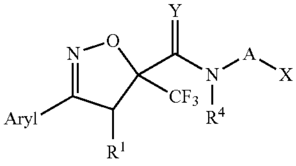

| No. | Aryl | $R^1$ | Y | $R^4$ | A | X | Physical data |
|---|---|---|---|---|---|---|---|
| 3.001 | 3,5-$Cl_2$—Ph | H | O | H | bond | 1,2-oxazol-3-yl | |
| 3.002 | 3,5-$(CF_3)_2$—Ph | H | O | H | bond | 1,3-dimethyl-1H-pyrazol-5-yl | |
| 3.003 | 3,5-$Cl_2$—Ph | H | O | H | bond | 1,3-dimethyl-1H-pyrazol-5-yl | |
| 3.004 | 3,5-$Cl_2$—Ph | H | O | H | bond | 1,3-oxazol-2-yl | |
| 3.005 | 3,5-$Cl_2$—Ph | H | O | H | bond | 1,3-thiazol-2-yl | |
| 3.006 | 3,5-$Cl_2$—Ph | H | O | H | bond | 1,5-dimethyl-1H-pyrazol-4-yl | |
| 3.007 | 3,5-$F_2$—Ph | H | O | H | bond | 1,5-dimethyl-1H-pyrazol-4-yl | |
| 3.008 | Ph | H | O | H | bond | 1,5-dimethyl-1H-pyrazol-4-yl | |
| 3.009 | 3-F—Ph | H | O | H | bond | 1,5-dimethyl-1H-pyrazol-4-yl | |
| 3.010 | 3-Me—Ph | H | O | H | bond | 1,5-dimethyl-1H-pyrazol-4-yl | |
| 3.011 | 3,5-$F_2$—Ph | H | O | H | bond | 1-ethyl-3-(methoxy-carbonyl)-1H-pyrazol-4-yl | |
| 3.012 | 3,5-$Cl_2$—Ph | H | O | H | bond | 1-ethyl-3-(methoxy-carbonyl)-1H-pyrazol-4-yl | |
| 3.013 | 3-F—Ph | H | O | H | bond | 1-ethyl-3-(methoxy-carbonyl)-1H-pyrazol-4-yl | |
| 3.014 | Ph | H | O | H | bond | 1-ethyl-3-(methoxy-carbonyl)-1H-pyrazol-4-yl | |
| 3.015 | 3,5-$F_2$—Ph | H | O | H | bond | 1-ethyl-3-methyl-1H-pyrazol-4-yl | |
| 3.016 | 3-F—Ph | H | O | H | bond | 1-ethyl-3-methyl-1H-pyrazol-4-yl | |
| 3.017 | 3,5-$Cl_2$—Ph | H | O | H | bond | 1-ethyl-3-methyl-1H-pyrazol-4-yl | |
| 3.018 | Ph | H | O | H | bond | 1-ethyl-3-methyl-1H-pyrazol-4-yl | |
| 3.019 | 3,5-$Cl_2$—Ph | H | O | H | bond | 1-methyl-1H-1,2,4-triazol-3-yl | |
| 3.020 | 3,5-$F_2$—Ph | H | O | H | bond | 1-methyl-1H-1,2,4-triazol-3-yl | |
| 3.021 | 3,5-$Cl_2$—Ph | H | O | H | bond | 1-methyl-1H-imidazol-2-yl | |
| 3.022 | 3,5-$F_2$—Ph | H | O | H | bond | 1-methyl-1H-pyrazol-4-yl | |
| 3.023 | 3,5-$Cl_2$—Ph | H | O | H | bond | 1-methyl-1H-pyrazol-4-yl | |
| 3.024 | 3-F—Ph | H | O | H | bond | 1-methyl-1H-pyrazol-4-yl | |
| 3.025 | Ph | H | O | H | bond | 1-methyl-1H-pyrazol-4-yl | |
| 3.026 | 3,5-$Cl_2$—Ph | H | O | H | bond | 1-propyl-1H-1,2,4-triazol-3-yl | |
| 3.027 | 3,5-$F_2$—Ph | H | O | H | bond | 1-propyl-1H-1,2,4-triazol-3-yl | |

TABLE 3-continued

Compounds of the general formula (I) according to the invention in which $R^2$ is hydrogen and $R^3$ is trifluoroomethyl and aryl is the radical

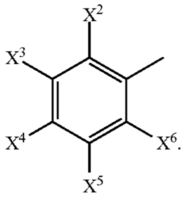

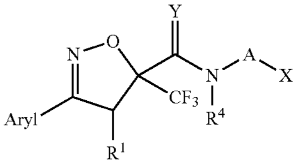

| No. | Aryl | $R^1$ | Y | $R^4$ | A | X | Physical data |
|---|---|---|---|---|---|---|---|
| 3.028 | 3,5-$Cl_2$—Ph | H | O | H | bond | 2-(2-ethoxy-2-oxoethyl)phenyl | |
| 3.029 | 3,5-$Cl_2$—Ph | H | O | H | bond | 2-(methoxy-carbonyl)phenyl | |
| 3.030 | 3,5-$Cl_2$—Ph | H | O | H | bond | 2-(methylcarbamoyl)-phenyl | |
| 3.031 | 3,5-$Cl_2$—Ph | H | O | H | bond | 2,4-dichloro-6-(methylcarbamoyl)-phenyl | |
| 3.032 | 3,5-$Cl_2$—Ph | H | O | H | bond | 2,4-difluorophenyl | |
| 3.033 | 3,5-$Cl_2$—Ph | H | O | H | bond | 2-carboxyphenyl | |
| 3.034 | 3,5-$Cl_2$—Ph | H | O | H | bond | 2-chloropyridin-3-yl | |
| 3.035 | 3,5-$Cl_2$—Ph | H | O | H | bond | 3-(2-methoxy-2-oxoethyl)phenyl | |
| 3.036 | 3,5-$Cl_2$—Ph | H | O | H | bond | 3-(carboxymethyl)-phenyl | |
| 3.037 | 3,5-$Cl_2$—Ph | H | O | H | bond | 3-(ethoxycarbonyl)-1H-1,2,4-triazol-5-yl | |
| 3.038 | 3,5-$F_2$—Ph | H | O | H | bond | 3-(ethoxycarbonyl)-1H-1,2,4-triazol-5-yl | |
| 3.039 | 3,5-$Cl_2$—Ph | H | O | H | bond | 3-(methoxy-carbonyl)phenyl | |
| 3.040 | 3-F—Ph | H | O | H | bond | 3-(methoxy-carbonyl)phenyl | |
| 3.041 | 3-F—Ph | H | O | H | bond | 3-(methylcarbamoyl)-phenyl | |
| 3.042 | 3,5-$Cl_2$—Ph | H | O | H | bond | 3,5-dichlorophenyl | |
| 3.043 | 3,5-$Cl_2$—Ph | H | O | H | bond | 3,5-dimethoxyphenyl | |
| 3.044 | Ph | H | O | H | bond | 3,5-dimethyl-1H-pyrazol-4-yl | |
| 3.045 | 3,5-$Cl_2$—Ph | H | O | H | bond | 3,5-dimethyl-1H-pyrazol-4-yl | |
| 3.046 | 3-F—Ph | H | O | H | bond | 3,5-dimethyl-1H-pyrazol-4-yl | |
| 3.047 | 3,5-$Cl_2$—Ph | H | O | H | bond | 3-[2-(methylamino)-2-oxoethyl] phenyl | |
| 3.048 | 3,5-$Cl_2$—Ph | H | O | H | bond | 3-carboxyphenyl | |
| 3.049 | 3-F—Ph | H | O | H | bond | 3-carboxyphenyl | |
| 3.050 | 3,5-$Cl_2$—Ph | H | O | H | bond | 3-chloropyridin-2-yl | |
| 3.051 | 3,5-$Cl_2$—Ph | H | O | H | bond | 3-cyclopropyl-1,2,4-thiadiazol-5-yl | |
| 3.052 | 3,5-$Cl_2$—Ph | H | O | H | bond | 3-methyl-1,2-oxazol-5-yl | |
| 3.053 | 3,5-$Cl_2$—Ph | H | O | H | bond | 3-methyl-1-propyl-1H-pyrazol-4-yl | |
| 3.054 | 3,5-$F_2$—Ph | H | O | H | bond | 3-methyl-1-propyl-1H-pyrazol-4-yl | |
| 3.055 | 3-F—Ph | H | O | H | bond | 3-methyl-1-propyl-1H-pyrazol-4-yl | |
| 3.056 | Ph | H | O | H | bond | 3-methyl-1-propyl-1H-pyrazol-4-yl | |
| 3.057 | 3,5-$Cl_2$—Ph | H | O | H | bond | 4-(2-ethoxy-2-oxoethyl)phenyl | |
| 3.058 | 3,5-$Cl_2$—Ph | H | O | H | bond | 4-(carboxymethyl)-phenyl | |

TABLE 3-continued

Compounds of the general formula (I) according to the invention in which $R^2$ is hydrogen and $R^3$ is trifluoroomethyl and aryl is the radical

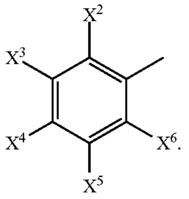

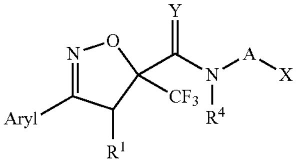

| No. | Aryl | $R^1$ | Y | $R^4$ | A | X | Physical data |
|---|---|---|---|---|---|---|---|
| 3.059 | 3,5-$F_2$—Ph | H | O | H | bond | 4-(methoxycarbonyl)-3-thienyl | |
| 3.060 | 3,5-$Cl_2$—Ph | H | O | H | bond | 4-(methoxy-carbonyl)phenyl | |
| 3.061 | 3,5-$Cl_2$—Ph | H | O | H | bond | 4,5-dimethyl-4H-1,2,4-triazol-3-yl | |
| 3.062 | 3,5-$F_2$—Ph | H | O | H | bond | 4,5-dimethyl-4H-1,2,4-triazol-3-yl | |
| 3.063 | 3,5-$Cl_2$—Ph | H | O | H | bond | 4,6-dimethoxypyrimidin-2-yl | |
| 3.064 | 3,5-$Cl_2$—Ph | H | O | H | bond | 4-carboxyphenyl | |
| 3.065 | 3,5-$Cl_2$—Ph | H | O | H | bond | 4-chloro-2-(methoxy-carbonyl)-6-methylphenyl | |
| 3.066 | 3,5-$Cl_2$—Ph | H | O | H | bond | 4-chloro-2-methyl-6-(methylcarbamoyl)-phenyl | |
| 3.067 | 3,5-$Cl_2$—Ph | H | O | H | bond | 4-chlorophenyl | |
| 3.068 | 3,5-$Cl_2$—Ph | H | O | H | bond | 4-chloropyridin-2-yl | |
| 3.069 | 3,5-$F_2$—Ph | H | O | H | bond | 4-cyano-1-ethyl-1H-pyrazol-3-yl | |
| 3.070 | 3,5-$Cl_2$—Ph | H | O | H | bond | 4-cyano-1H-pyrazol-3-yl | |
| 3.071 | Ph | H | O | H | bond | 4-cyano-1H-pyrazol-3-yl | |
| 3.072 | 3-F—Ph | H | O | H | bond | 4-cyano-1H-pyrazol-3-yl | |
| 3.073 | 3,5-$Cl_2$—Ph | H | O | H | bond | 4-ethylpyridin-2-yl | |
| 3.074 | 3,5-$F_2$—Ph | H | O | H | bond | 4-formyl-3-(1-methylcyclopropyl)-1,2-oxazol-5-yl | |
| 3.075 | 3,5-$Cl_2$—Ph | H | O | H | bond | 4-methoxypyridin-2-yl | |
| 3.076 | 3,5-$Cl_2$—Ph | H | O | H | bond | 4-methyl-1,2,5-oxadiazol-3-yl | |
| 3.077 | 3,5-$F_2$—Ph | H | O | H | bond | 4-methyl-1,3-thiazol-2-yl | |
| 3.078 | 3,5-$Cl_2$—Ph | H | O | H | bond | 4-methyl-1,3-thiazol-2-yl | |
| 3.079 | Ph | H | O | H | bond | 4-methylpyridin-2-yl | |
| 3.080 | 2,4-$Cl_2$—Ph | H | O | H | bond | 4-methylpyridin-2-yl | |
| 3.081 | 3,5-$Cl_2$—Ph | H | O | H | bond | 4-methylpyridin-2-yl | |
| 3.082 | 3,5-$Cl_2$—Ph | H | O | H | bond | 4-pentylpyridin-2-yl | |
| 3.083 | 2,4-$Cl_2$—Ph | H | O | H | bond | 4-pentylpyridin-2-yl | |
| 3.084 | 3,5-$Cl_2$—Ph | H | O | H | bond | 5-(methoxycarbonyl)-1,3-thiazol-4-yl | |
| 3.085 | 3,5-$F_2$—Ph | H | O | H | bond | 5-(methoxycarbonyl)-1,3-thiazol-4-yl | |
| 3.086 | 3,5-$Cl_2$—Ph | H | O | H | bond | 5-chloro-4-methylpyridin-2-yl | |
| 3.087 | 3,5-$Cl_2$—Ph | H | O | H | bond | 5-Fluor-4-methylpyridin-2-yl | |
| 3.088 | 3,5-$Cl_2$—Ph | H | O | H | bond | 5-methoxy-1-methyl-1H-1,2,4-triazol-3-yl | |
| 3.089 | 3,5-$F_2$—Ph | H | O | H | bond | 5-methoxy-1-methyl-1H-1,2,4-triazol-3-yl | |

TABLE 3-continued

Compounds of the general formula (I) according to the invention in which $R^2$ is hydrogen and $R^3$ is trifluoroomethyl and aryl is the radical

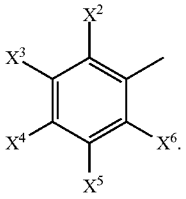

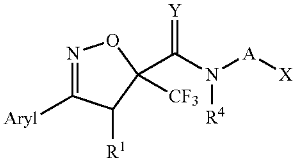

| No. | Aryl | $R^1$ | Y | $R^4$ | A | X | Physical data |
|---|---|---|---|---|---|---|---|
| 3.090 | Ph | H | O | H | bond | 5-methylpyridin-2-yl | |
| 3.091 | 3,5-$Cl_2$—Ph | H | O | H | bond | 6-chloropyridin-2-yl | |
| 3.092 | 3,5-$Cl_2$—Ph | H | O | H | bond | 6-chloropyridin-3-yl | |
| 3.093 | 3,5-$Cl_2$—Ph | H | O | H | bond | pyridin-2-yl | |
| 3.094 | 3,5-$Cl_2$—Ph | H | O | H | bond | pyridin-4-yl | |
| 3.095 | 3,5-$F_2$—Ph | H | O | H | $CH_2$ | 1-(2,2,2-trifluoroethyl)-1H-pyrazol-4-yl | |
| 3.096 | 3,5-$F_2$—Ph | H | O | H | $CH_2$ | 1-(2-chloroethyl)-1H-pyrazol-4-yl | |
| 3.097 | 3,5-$Cl_2$—Ph | H | O | H | $CH_2$ | 1-(2-methoxy-2-oxoethyl)-1H-pyrazol-4-yl | |
| 3.098 | 3,5-$F_2$—Ph | H | O | H | $CH_2$ | 1-(3-carboxypropyl)-1H-pyrazol-4-yl | |
| 3.099 | 3,5-$F_2$—Ph | H | O | H | $CH_2$ | 1-(3-methoxy-3-oxopropyl)-1H-pyrazol-4-yl | |
| 3.100 | 3,5-$F_2$—Ph | H | O | H | $CH_2$ | 1-(4-methoxy-4-oxobutyl)-1H-pyrazol-4-yl | |
| 3.101 | 3,5-$Cl_2$—Ph | H | O | H | $CH_2$ | 1-(cyanomethyl)-1H-pyrazol-4-yl | |
| 3.102 | 3,5-$F_2$—Ph | H | O | H | $CH_2$ | 1-(cyanomethyl)-1H-pyrazol-4-yl | |
| 3.103 | 3-F—Ph | H | O | H | $CH_2$ | 1-(cyanomethyl)-1H-pyrazol-4-yl | |
| 3.104 | 3,5-$(CF_3)_2$—Ph | H | O | H | $CH_2$ | 1,3-dimethyl-1H-pyrazol-4-yl | |
| 3.105 | 3,5-$Cl_2$—Ph | H | O | H | $CH_2$ | 1,3-dimethyl-1H-pyrazol-4-yl | |
| 3.106 | 3,5-$F_2$—Ph | H | O | H | $CH_2$ | 1,3-dimethyl-1H-pyrazol-4-yl | |
| 3.107 | 3-Cl—Ph | H | O | H | $CH_2$ | 1,3-dimethyl-1H-pyrazol-4-yl | |
| 3.108 | 3-F—Ph | H | O | H | $CH_2$ | 1,3-dimethyl-1H-pyrazol-4-yl | |
| 3.109 | 3-Me—Ph | H | O | H | $CH_2$ | 1,3-dimethyl-1H-pyrazol-4-yl | |
| 3.110 | Ph | H | O | H | $CH_2$ | 1,3-dimethyl-1H-pyrazol-4-yl | |
| 3.111 | 3,5-$(CF_3)_2$—Ph | H | O | H | $CH_2$ | 1,3-dimethyl-1H-pyrazol-5-yl | |
| 3.112 | 3,5-$Cl_2$—Ph | H | O | H | $CH_2$ | 1,3-dimethyl-1H-pyrazol-5-yl | |
| 3.113 | 3,5-$F_2$—Ph | H | O | H | $CH_2$ | 1,3-dimethyl-1H-pyrazol-5-yl | |
| 3.114 | Ph | H | O | H | $CH_2$ | 1,3-dimethyl-1H-pyrazol-5-yl | |
| 3.115 | 3,5-$Cl_2$—Ph | H | O | H | $CH_2$ | 1,3-oxazol-4-yl | |
| 3.116 | 3,5-$F_2$—Ph | H | O | H | $CH_2$ | 1,3-oxazol-4-yl | |
| 3.117 | 3-F—Ph | H | O | H | $CH_2$ | 1,3-oxazol-4-yl | |
| 3.118 | 3,5-$Cl_2$—Ph | H | O | H | $CH_2$ | 1,3-thiazol-2-yl | |
| 3.119 | 3,5-$F_2$—Ph | H | O | H | $CH_2$ | 1,3-thiazol-2-yl | |

TABLE 3-continued

Compounds of the general formula (I) according to the invention in which $R^2$ is hydrogen and $R^3$ is trifluoroomethyl and aryl is the radical

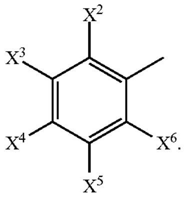

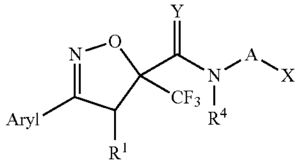

| No. | Aryl | $R^1$ | Y | $R^4$ | A | X | Physical data |
|---|---|---|---|---|---|---|---|
| 3.120 | 3,5-$Cl_2$—Ph | H | O | H | $CH_2$ | 1,4-dimethyl-5-oxo-4,5-dihydro-1H-1,2,4-triazol-3-yl | |
| 3.121 | 3,5-$F_2$—Ph | H | O | H | $CH_2$ | 1,5-dimethyl-1H-pyrazol-3-yl | |
| 3.122 | 3,5-$Cl_2$—Ph | H | O | H | $CH_2$ | 1,5-dimethyl-1H-pyrazol-4-yl | |
| 3.123 | 3,5-$F_2$—Ph | H | O | H | $CH_2$ | 1,5-dimethyl-1H-pyrazol-4-yl | |
| 3.124 | 3-F—Ph | H | O | H | $CH_2$ | 1,5-dimethyl-1H-pyrazol-4-yl | |
| 3.125 | Ph | H | O | H | $CH_2$ | 1,5-dimethyl-1H-pyrazol-4-yl | |
| 3.126 | 3,5-$F_2$—Ph | H | O | H | $CH_2$ | 1-acetyl-1H-pyrazol-4-yl | |
| 3.127 | 3,5-$F_2$—Ph | H | O | H | $CH_2$ | 1-butyl-3-methyl-1H-pyrazol-4-yl | |
| 3.128 | 3,5-$F_2$—Ph | H | O | H | $CH_2$ | 1-butyl-5-methyl-1H-pyrazol-4-yl | |
| 3.129 | 3,5-$Cl_2$—Ph | H | O | H | $CH_2$ | 1-cyclopropyl-1H-pyrazol-4-yl | |
| 3.130 | 3,5-$F_2$—Ph | H | O | H | $CH_2$ | 1-cyclopropyl-1H-pyrazol-4-yl | |
| 3.131 | 3-F—Ph | H | O | H | $CH_2$ | 1-cyclopropyl-1H-pyrazol-4-yl | |
| 3.132 | Ph | H | O | H | $CH_2$ | 1-cyclopropyl-1H-pyrazol-4-yl | |
| 3.133 | 3,5-$Cl_2$-4-MeO—Ph | H | O | H | $CH_2$ | 1-ethyl-1H-pyrazol-4-yl | |
| 3.134 | 3,5-$Cl_2$—Ph | H | O | H | $CH_2$ | 1-ethyl-1H-pyrazol-4-yl | |
| 3.135 | 3,5-$F_2$—Ph | H | O | H | $CH_2$ | 1-ethyl-1H-pyrazol-4-yl | |
| 3.136 | 3,5-$(MeO)_2$—Ph | H | O | H | $CH_2$ | 1-ethyl-1H-pyrazol-4-yl | |
| 3.137 | 3-Br-5-$CF_3$—Ph | H | O | H | $CH_2$ | 1-ethyl-1H-pyrazol-4-yl | |
| 3.138 | 3-Cl-5-Et—Ph | H | O | H | $CH_2$ | 1-ethyl-1H-pyrazol-4-yl | |
| 3.139 | 3-F-5-MeO—Ph | H | O | H | $CH_2$ | 1-ethyl-1H-pyrazol-4-yl | |
| 3.140 | 3-F—Ph | H | O | H | $CH_2$ | 1-ethyl-1H-pyrazol-4-yl | |
| 3.141 | 3-Me-5-$CF_3O$—Ph | H | O | H | $CH_2$ | 1-ethyl-1H-pyrazol-4-yl | |
| 3.142 | 3-Me—Ph | H | O | H | $CH_2$ | 1-ethyl-1H-pyrazol-4-yl | |
| 3.143 | Ph | H | O | H | $CH_2$ | 1-ethyl-1H-pyrazol-4-yl | |
| 3.144 | 3,5-$Cl_2$—Ph | H | O | H | $CH_2$ | 1-ethyl-1H-pyrazol-5-yl | |
| 3.145 | 3,5-$F_2$—Ph | H | O | H | $CH_2$ | 1-ethyl-1H-pyrazol-5-yl | |
| 3.146 | Ph | H | O | H | $CH_2$ | 1-ethyl-1H-pyrazol-5-yl | |

TABLE 3-continued

Compounds of the general formula (I) according to the invention in which $R^2$ is hydrogen and $R^3$ is trifluoroomethyl and aryl is the radical

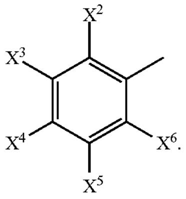

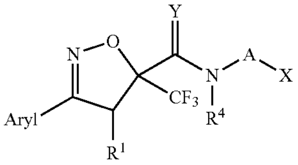

| No. | Aryl | $R^1$ | Y | $R^4$ | A | X | Physical data |
|---|---|---|---|---|---|---|---|
| 3.147 | 2,3,4-$F_3$—Ph | H | O | H | $CH_2$ | 1-ethyl-3-methyl-1H-pyrazol-4-yl | |
| 3.148 | 2,3,5-$F_3$—Ph | H | O | H | $CH_2$ | 1-ethyl-3-methyl-1H-pyrazol-4-yl | |
| 3.149 | 2,3-$F_2$—Ph | H | O | H | $CH_2$ | 1-ethyl-3-methyl-1H-pyrazol-4-yl | |
| 3.150 | 2,5-$Cl_2$—Ph | H | O | H | $CH_2$ | 1-ethyl-3-methyl-1H-pyrazol-4-yl | |
| 3.151 | 2,5-$F_2$—Ph | H | O | H | $CH_2$ | 1-ethyl-3-methyl-1H-pyrazol-4-yl | |
| 3.152 | 2,5-$Me_2$—Ph | H | O | H | $CH_2$ | 1-ethyl-3-methyl-1H-pyrazol-4-yl | |
| 3.153 | 2-F-3-Me—Ph | H | O | H | $CH_2$ | 1-ethyl-3-methyl-1H-pyrazol-4-yl | |
| 3.154 | 2-F—Ph | H | O | H | $CH_2$ | 1-ethyl-3-methyl-1H-pyrazol-4-yl | |
| 3.155 | 3-$CF_3O$—Ph | H | O | H | $CH_2$ | 1-ethyl-3-methyl-1H-pyrazol-4-yl | |
| 3.156 | 3,4,5-$F_3$—Ph | H | O | H | $CH_2$ | 1-ethyl-3-methyl-1H-pyrazol-4-yl | |
| 3.157 | 3,4-$F_2$—Ph | H | O | H | $CH_2$ | 1-ethyl-3-methyl-1H-pyrazol-4-yl | |
| 3.158 | 3,5-$Br_2$—Ph | H | O | H | $CH_2$ | 1-ethyl-3-methyl-1H-pyrazol-4-yl | |
| 3.159 | 3,5-$Cl_2$-4-MeO—Ph | H | O | H | $CH_2$ | 1-ethyl-3-methyl-1H-pyrazol-4-yl | |
| 3.160 | 3,5-$Cl_2$—Ph | $CH_3$ | O | H | $CH_2$ | 1-ethyl-3-methyl-1H-pyrazol-4-yl | |
| 3.161 | 3,5-$Cl_2$—Ph | H | O | H | $CH_2$ | 1-ethyl-3-methyl-1H-pyrazol-4-yl | [$CDCl_3$] 1.42 (t, 3H); 2.20 (s, 3H); 3.74 (d, 1H); 3.98 (d, 1H); 4.07 (q, 2H); 4.22 (dd, 1H); 4.49 (dd, 1H); 6.81 (m, 1H); 7.28 (s, 1H); 7.47 (m, 1H); 7.54 (m, 2H). |
| 3.162 | 3,5-$Et_2$—Ph | H | O | H | $CH_2$ | 1-ethyl-3-methyl-1H-pyrazol-4-yl | |
| 3.163 | 3,5-$F_2$—Ph | H | O | H | $CH_2$ | 1-ethyl-3-methyl-1H-pyrazol-4-yl | |
| 3.164 | 3,5-$F_2$—Ph | H | S | H | $CH_2$ | 1-ethyl-3-methyl-1H-pyrazol-4-yl | |
| 3.165 | 3,5-$Me_2$—Ph | H | O | H | $CH_2$ | 1-ethyl-3-methyl-1H-pyrazol-4-yl | |
| 3.166 | 3-$CF_3S$—Ph | H | O | H | $CH_2$ | 1-ethyl-3-methyl-1H-pyrazol-4-yl | |
| 3.167 | 3-Br-5-$CF_3$—Ph | H | O | H | $CH_2$ | 1-ethyl-3-methyl-1H-pyrazol-4-yl | |
| 3.168 | 3-Br-5-Cl—Ph | H | O | H | $CH_2$ | 1-ethyl-3-methyl-1H-pyrazol-4-yl | |
| 3.169 | 3-Br-5-F—Ph | H | O | H | $CH_2$ | 1-ethyl-3-methyl-1H-pyrazol-4-yl | |
| 3.170 | 3-Cl-4-F—Ph | H | O | H | $CH_2$ | 1-ethyl-3-methyl-1H-pyrazol-4-yl | [$CDCl_3$] 1.44 (t, 3H); 1.70 (s, 3H); 3.77 (d, 1H); 4.00 (d, 1H); 4.06 (q, 2H); 4.23 (dd, |

TABLE 3-continued

Compounds of the general formula (I) according to the invention in which $R^2$ is hydrogen and $R^3$ is trifluoroomethyl and aryl is the radical

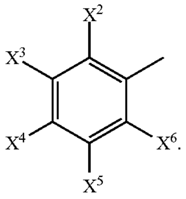

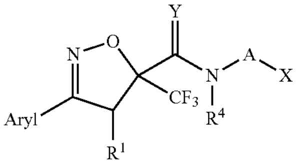

| No. | Aryl | $R^1$ | Y | $R^4$ | A | X | Physical data |
|---|---|---|---|---|---|---|---|
| | | | | | | | 1H), 4.40 (dd, 1H); 6.86 (t br, 1H); 7.23 (m, 1H); 7.52 (m, 1H); 7.74 (m, 1H). |
| 3.171 | 3-Cl-5-$CF_3$—Ph | H | O | H | $CH_2$ | 1-ethyl-3-methyl-1H-pyrazol-4-yl | |
| 3.172 | 3-Cl-5-CN—Ph | H | O | H | $CH_2$ | 1-ethyl-3-methyl-1H-pyrazol-4-yl | |
| 3.173 | 3-Cl-5-Et—Ph | H | O | H | $CH_2$ | 1-ethyl-3-methyl-1H-pyrazol-4-yl | |
| 3.174 | 3-Cl-5-F—Ph | H | O | H | $CH_2$ | 1-ethyl-3-methyl-1H-pyrazol-4-yl | |
| 3.175 | 3-Cl-5-MeO—Ph | H | O | H | $CH_2$ | 1-ethyl-3-methyl-1H-pyrazol-4-yl | |
| 3.176 | 3-Cl-5-Me—Ph | H | O | H | $CH_2$ | 1-ethyl-3-methyl-1H-pyrazol-4-yl | |
| 3.177 | 3-Cl-5-$CF_3O$—Ph | H | O | H | $CH_2$ | 1-ethyl-3-methyl-1H-pyrazol-4-yl | |
| 3.178 | 3-Cl—Ph | H | O | H | $CH_2$ | 1-ethyl-3-methyl-1H-pyrazol-4-yl | |
| 3.179 | 3-CN-5-F—Ph | H | O | H | $CH_2$ | 1-ethyl-3-methyl-1H-pyrazol-4-yl | |
| 3.180 | 3-CN—Ph | H | O | H | $CH_2$ | 1-ethyl-3-methyl-1H-pyrazol-4-yl | |
| 3.181 | 3-cPr-5-F—Ph | H | O | H | $CH_2$ | 1-ethyl-3-methyl-1H-pyrazol-4-yl | |
| 3.182 | 3-EtO—Ph | H | O | H | $CH_2$ | 1-ethyl-3-methyl-1H-pyrazol-4-yl | |
| 3.183 | 3-Et-5-F—Ph | H | O | H | $CH_2$ | 1-ethyl-3-methyl-1H-pyrazol-4-yl | |
| 3.184 | 3-F-5-$CF_3$—Ph | H | O | H | $CH_2$ | 1-ethyl-3-methyl-1H-pyrazol-4-yl | |
| 3.185 | 3-F-5-MeO—Ph | H | O | H | $CH_2$ | 1-ethyl-3-methyl-1H-pyrazol-4-yl | |
| 3.186 | 3-F-5-Me—Ph | H | O | H | $CH_2$ | 1-ethyl-3-methyl-1H-pyrazol-4-yl | |
| 3.187 | 3-F—Ph | H | O | H | $CH_2$ | 1-ethyl-3-methyl-1H-pyrazol-4-yl | |
| 3.188 | 3-MeO—Ph | H | O | H | $CH_2$ | 1-ethyl-3-methyl-1H-pyrazol-4-yl | |
| 3.189 | 3-Me—Ph | H | O | H | $CH_2$ | 1-ethyl-3-methyl-1H-pyrazol-4-yl | |
| 3.190 | Ph | H | O | H | $CH_2$ | 1-ethyl-3-methyl-1H-pyrazol-4-yl | |
| 3.191 | 3,5-$Cl_2$—Ph | H | O | H | $CH_2$ | 1-ethyl-3-methyl-1H-pyrazol-5-yl | |
| 3.192 | 3,5-$F_2$—Ph | H | O | H | $CH_2$ | 1-ethyl-3-methyl-1H-pyrazol-5-yl | |
| 3.193 | 3-F—Ph | H | O | H | $CH_2$ | 1-ethyl-3-methyl-1H-pyrazol-5-yl | |
| 3.194 | 3,5-$F_2$—Ph | H | O | H | $CH_2$ | 1H-1,2,3-triazol-5-yl | |
| 3.195 | 3,5-$Cl_2$—Ph | H | O | H | $CH_2$ | 1H-pyrazol-4-yl | |
| 3.196 | 3,5-$F_2$—Ph | H | O | H | $CH_2$ | 1H-pyrazol-4-yl | |
| 3.197 | 3-F—Ph | H | O | H | $CH_2$ | 1H-pyrazol-4-yl | |
| 3.198 | 3,5-$Cl_2$—Ph | H | O | H | $CH_2$ | 1-isobutyl-1H-pyrazol-4-yl | |

TABLE 3-continued

Compounds of the general formula (I) according to the invention in which $R^2$ is hydrogen and $R^3$ is trifluoroomethyl and aryl is the radical

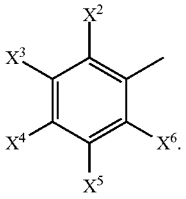

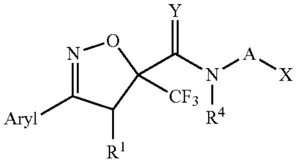

| No. | Aryl | $R^1$ | Y | $R^4$ | A | X | Physical data |
|---|---|---|---|---|---|---|---|
| 3.199 | 3,5-$F_2$—Ph | H | O | H | $CH_2$ | 1-isobutyl-1H-pyrazol-4-yl | |
| 3.200 | 3-F—Ph | H | O | H | $CH_2$ | 1-isobutyl-1H-pyrazol-4-yl | |
| 3.201 | Ph | H | O | H | $CH_2$ | 1-isobutyl-1H-pyrazol-4-yl | |
| 3.202 | 3,5-$Cl_2$—Ph | H | O | H | $CH_2$ | 1-isopropyl-1H-pyrazol-4-yl | |
| 3.203 | 3,5-$F_2$—Ph | H | O | H | $CH_2$ | 1-isopropyl-1H-pyrazol-4-yl | |
| 3.204 | 3-F—Ph | H | O | H | $CH_2$ | 1-isopropyl-1H-pyrazol-4-yl | |
| 3.205 | Ph | H | O | H | $CH_2$ | 1-isopropyl-1H-pyrazol-4-yl | |
| 3.206 | 3,5-$(CF_3)_2$—Ph | O | H | H | $CH_2$ | 1-methyl-1H-pyrazol-4-yl | |
| 3.207 | 3,5-$Cl_2$—Ph | H | O | H | $CH_2$ | 1-methyl-1H-pyrazol-4-yl | |
| 3.208 | 3,5-$F_2$—Ph | H | O | H | $CH_2$ | 1-methyl-1H-pyrazol-4-yl | |
| 3.209 | 3-F-5-MeO—Ph | H | O | H | $CH_2$ | 1-methyl-1H-pyrazol-4-yl | |
| 3.210 | 3-F—Ph | H | O | H | $CH_2$ | 1-methyl-1H-pyrazol-4-yl | |
| 3.211 | 3-Me—Ph | H | O | H | $CH_2$ | 1-methyl-1H-pyrazol-4-yl | |
| 3.212 | Ph | H | O | H | $CH_2$ | 1-methyl-1H-pyrazol-4-yl | |
| 3.213 | 3,5-$Cl_2$—Ph | H | O | H | $CH_2$ | 1-methyl-1H-pyrazol-5-yl | |
| 3.214 | 3,5-$F_2$—Ph | H | O | H | $CH_2$ | 1-methyl-1H-pyrazol-5-yl | |
| 3.215 | 3-F—Ph | H | O | H | $CH_2$ | 1-methyl-1H-pyrazol-5-yl | |
| 3.216 | Ph | H | O | H | $CH_2$ | 1-methyl-1H-pyrazol-5-yl | |
| 3.217 | 3,5-$Cl_2$—Ph | H | O | H | $CH_2$ | 1-methyl-3-(trifluoromethyl)-1H-pyrazol-4-yl | D1 |
| 3.218 | 3,5-$Cl_2$—Ph | H | O | H | $CH_2$ | 1-methyl-3-(trifluoromethyl)-1H-pyrazol-4-yl | D2 |
| 3.219 | 3,5-$F_2$—Ph | H | O | H | $CH_2$ | 1-methyl-5-(trifluoromethyl)-1H-pyrazol-4-yl | |
| 3.220 | 3,5-$Cl_2$—Ph | H | O | H | $CH_2$ | 1-propyl-1H-pyrazol-3-yl | |
| 3.221 | 3,5-$F_2$—Ph | H | O | H | $CH_2$ | 1-propyl-1H-pyrazol-3-yl | |
| 3.222 | 3,5-$Cl_2$—Ph | H | O | H | $CH_2$ | 1-propyl-1H-pyrazol-4-yl | |
| 3.223 | 3,5-$F_2$—Ph | H | O | H | $CH_2$ | 1-propyl-1H-pyrazol-4-yl | |
| 3.224 | 3-F—Ph | H | O | H | $CH_2$ | 1-propyl-1H-pyrazol-4-yl | |

TABLE 3-continued

Compounds of the general formula (I) according to the invention in which $R^2$ is hydrogen and $R^3$ is trifluoroomethyl and aryl is the radical

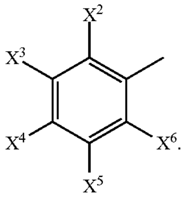

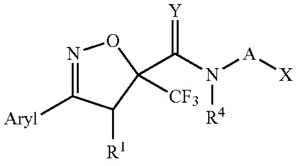

| No. | Aryl | $R^1$ | Y | $R^4$ | A | X | Physical data |
|---|---|---|---|---|---|---|---|
| 3.225 | Ph | H | O | H | $CH_2$ | 1-propyl-1H-pyrazol-4-yl | |
| 3.226 | 3,5-$Cl_2$—Ph | H | O | H | $CH_2$ | 1-tert-butyl-1H-pyrazol-4-yl | |
| 3.227 | 3,5-$F_2$—Ph | H | O | H | $CH_2$ | 1-tert-butyl-1H-pyrazol-4-yl | |
| 3.228 | Ph | H | O | H | $CH_2$ | 1-tert-butyl-1H-pyrazol-4-yl | |
| 3.229 | 3,5-$F_2$—Ph | H | O | H | $CH_2$ | 2-chloropyridin-4-yl | |
| 3.230 | 3-F—Ph | H | O | H | $CH_2$ | 2-chloropyridin-4-yl | |
| 3.231 | 3,5-$Cl_2$—Ph | H | O | H | $CH_2$ | 2-methyl-1,3-thiazol-4-yl | |
| 3.232 | 3,5-$F_2$—Ph | H | O | H | $CH_2$ | 2-methyl-1,3-thiazol-4-yl | |
| 3.233 | 3,5-$Cl_2$—Ph | H | O | H | $CH_2$ | 3-(cyclopropyl-carbamoyl)-1,2-oxazol-5-yl | |
| 3.234 | 3,5-$Cl_2$—Ph | H | O | H | $CH_2$ | 3-(ethoxycarbonyl)-1,2-oxazol-5-yl | |
| 3.235 | 3,5-$F_2$—Ph | H | O | H | $CH_2$ | 3-(methoxy-carbonyl)phenyl | |
| 3.236 | 3,5-$F_2$—Ph | H | O | H | $CH_2$ | 3,5-difluoropyridin-2-yl | |
| 3.237 | 3,5-$Cl_2$—Ph | H | O | H | $CH_2$ | 3-carboxy-1,2-oxazol-5-yl | |
| 3.238 | 3,5-$Cl_2$—Ph | H | O | H | $CH_2$ | 3-chloro-1-ethyl-1H-pyrazol-4-yl | |
| 3.239 | 3,5-$F_2$—Ph | H | O | H | $CH_2$ | 3-chloro-1-ethyl-1H-pyrazol-4-yl | |
| 3.240 | 3-F—Ph | H | O | H | $CH_2$ | 3-chloro-1-ethyl-1H-pyrazol-4-yl | |
| 3.241 | Ph | H | O | H | $CH_2$ | 3-chloro-1-ethyl-1H-pyrazol-4-yl | |
| 3.242 | 3,5-$Cl_2$—Ph | H | O | H | $CH_2$ | 3-chloro-1-isopropyl-1H-pyrazol-4-yl | |
| 3.243 | 3,5-$F_2$—Ph | H | O | H | $CH_2$ | 3-chloro-1-isopropyl-1H-pyrazol-4-yl | |
| 3.244 | 3,5-$F_2$—Ph | H | S | H | $CH_2$ | 3-chloro-1-isopropyl-1H-pyrazol-4-yl | |
| 3.245 | 3-F—Ph | H | O | H | $CH_2$ | 3-chloro-1-isopropyl-1H-pyrazol-4-yl | |
| 3.246 | 3,5-$Cl_2$—Ph | H | O | H | $CH_2$ | 3-chloro-1-methyl-1H-pyrazol-4-yl | |
| 3.247 | 3,5-$F_2$—Ph | H | O | H | $CH_2$ | 3-chloro-1-methyl-1H-pyrazol-4-yl | |
| 3.248 | 3,5-$F_2$—Ph | H | O | H | $CH_2$ | 3-chloropyridin-4-yl | |
| 3.249 | 3-F—Ph | H | O | H | $CH_2$ | 3-chloropyridin-4-yl | |
| 3.250 | 3,5-$Cl_2$—Ph | H | O | H | $CH_2$ | 3-cyclopropyl-1,2,4-oxadiazol-5-yl | |
| 3.251 | 3,5-$F_2$—Ph | H | O | H | $CH_2$ | 3-cyclopropyl-1,2,4-oxadiazol-5-yl | |
| 3.252 | 3,5-$F_2$—Ph | H | O | H | $CH_2$ | 3-furyl | |
| 3.253 | 3,5-$F_2$—Ph | H | O | H | $CH_2$ | 3-methyl-1H-pyrazol-4-yl | |
| 3.254 | 3-$CF_3O$—Ph | H | O | H | $CH_2$ | 3-methyl-1-propyl-1H-pyrazol-4-yl | |

TABLE 3-continued

Compounds of the general formula (I) according to the invention in which $R^2$ is hydrogen and $R^3$ is trifluoroomethyl and aryl is the radical

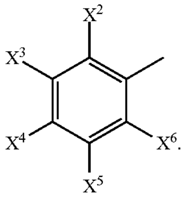

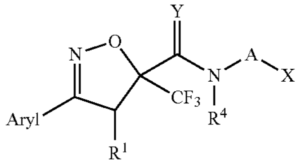

| No. | Aryl | $R^1$ | Y | $R^4$ | A | X | Physical data |
|---|---|---|---|---|---|---|---|
| 3.255 | 3,5-$Cl_2$—Ph | H | O | H | $CH_2$ | 3-methyl-1-propyl-1H-pyrazol-4-yl | |
| 3.256 | 3,5-$F_2$—Ph | H | O | H | $CH_2$ | 3-methyl-1-propyl-1H-pyrazol-4-yl | |
| 3.257 | 3-Cl-4-F—Ph | H | O | H | $CH_2$ | 3-methyl-1-propyl-1H-pyrazol-4-yl | [$CDCl_3$] 0.89 (t, 3H); 1.83 (q, 2H); 2.19 (s, 3H); 3.77 (d, 1H); 3.96 (m, 3H); 3.97 (d, 1H); 4.23 (dd, 1H), 4.40 (dd, 1H); 6.88 (m br, 1H); 7.21 (m, 1H); 7.52 (m, 1H); 7.73 (m, 1H) |
| 3.258 | 3-Cl-5-$CF_3O$—Ph | H | O | H | $CH_2$ | 3-methyl-1-propyl-1H-pyrazol-4-yl | |
| 3.259 | 3-Cl-5-F—Ph | H | O | H | $CH_2$ | 3-methyl-1-propyl-1H-pyrazol-4-yl | |
| 3.260 | 3-Cl-5-Me—Ph | H | O | H | $CH_2$ | 3-methyl-1-propyl-1H-pyrazol-4-yl | |
| 3.261 | 3-F-5-Me—Ph | H | O | H | $CH_2$ | 3-methyl-1-propyl-1H-pyrazol-4-yl | |
| 3.262 | 3-F—Ph | H | O | H | $CH_2$ | 3-methyl-1-propyl-1H-pyrazol-4-yl | |
| 3.263 | 3-Me—Ph | H | O | H | $CH_2$ | 3-methyl-1-propyl-1H-pyrazol-4-yl | |
| 3.264 | 4-Cl-3,5-$F_2$—Ph | H | O | H | $CH_2$ | 3-methyl-1-propyl-1H-pyrazol-4-yl | |
| 3.265 | Ph | H | O | H | $CH_2$ | 3-methyl-1-propyl-1H-pyrazol-4-yl | |
| 3.266 | 3,5-$Cl_2$—Ph | H | O | H | $CH_2$ | 4-(methoxy-carbonyl)phenyl | |
| 3.267 | 3,5-$Cl_2$—Ph | H | O | H | $CH_2$ | 4-(trifluoromethyl)-1,3-thiazol-2-yl | |
| 3.268 | 3,5-$F_2$—Ph | H | O | H | $CH_2$ | 4-(trifluoromethyl)-1,3-thiazol-2-yl | |
| 3.269 | 3-F—Ph | H | O | H | $CH_2$ | 4-(trifluoromethyl)-1,3-thiazol-2-yl | |
| 3.270 | 3,5-$Cl_2$—Ph | H | O | H | $CH_2$ | 4-chloro-1-methyl-1H-pyrazol-3-yl | |
| 3.271 | 3,5-$F_2$—Ph | H | O | H | $CH_2$ | 4-chloro-1-methyl-1H-pyrazol-3-yl | |
| 3.272 | 3-F—Ph | H | O | H | $CH_2$ | 4-chloro-1-methyl-1H-pyrazol-3-yl | |
| 3.273 | 3,5-$F_2$—Ph | H | O | H | $CH_2$ | 4-chloro-1-methyl-1H-pyrazol-5-yl | |
| 3.274 | 3,5-$Cl_2$—Ph | H | O | H | $CH_2$ | 5-chloro-1-methyl-1H-pyrazol-4-yl | |
| 3.275 | 3,5-$F_2$—Ph | H | O | H | $CH_2$ | 5-chloro-1-methyl-1H-pyrazol-4-yl | |
| 3.276 | 3,5-$F_2$—Ph | H | S | H | $CH_2$ | 5-chloro-1-methyl-1H-pyrazol-4-yl | |
| 3.277 | 3-F—Ph | H | O | H | $CH_2$ | 5-chloro-1-methyl-1H-pyrazol-4-yl | |
| 3.278 | Ph | H | O | H | $CH_2$ | 5-chloro-1-methyl-1H-pyrazol-4-yl | |

TABLE 3-continued

Compounds of the general formula (I) according to the invention in which $R^2$ is hydrogen and $R^3$ is trifluoroomethyl and aryl is the radical

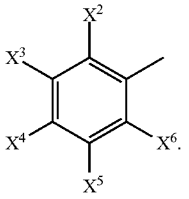

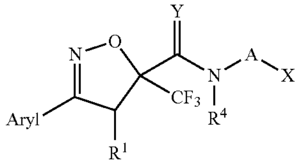

| No. | Aryl | $R^1$ | Y | $R^4$ | A | X | Physical data |
|---|---|---|---|---|---|---|---|
| 3.279 | 3,5-$Cl_2$—Ph | H | O | H | $CH_2$ | 5-methoxy-1,3-dimethyl-1H-pyrazol-4-yl | |
| 3.280 | 3,5-$F_2$—Ph | H | O | H | $CH_2$ | 5-methoxy-1,3-dimethyl-1H-pyrazol-4-yl | |
| 3.281 | 3-F—Ph | H | O | H | $CH_2$ | 5-methoxy-1,3-dimethyl-1H-pyrazol-4-yl | |
| 3.282 | 3,5-$Cl_2$—Ph | H | O | H | $CH_2$ | 5-methyl-1,2,4-oxadiazol-3-yl | |
| 3.283 | 3,5-$F_2$—Ph | H | O | H | $CH_2$ | 5-methyl-1,2,4-oxadiazol-3-yl | |
| 3.284 | 3,5-$Cl_2$—Ph | H | O | H | $CH_2$ | 5-methyl-1,2-oxazol-3-yl | |
| 3.285 | 3,5-$Cl_2$—Ph | H | O | H | $CH_2$ | 5-methyl-1-propyl-1H-pyrazol-4-yl | |
| 3.286 | 3,5-$F_2$—Ph | H | O | H | $CH_2$ | 5-methyl-1-propyl-1H-pyrazol-4-yl | |
| 3.287 | 3-F—Ph | H | O | H | $CH_2$ | 5-methyl-1-propyl-1H-pyrazol-4-yl | |
| 3.288 | Ph | H | O | H | $CH_2$ | 5-methyl-1-propyl-1H-pyrazol-4-yl | |
| 3.289 | 3,5-$F_2$—Ph | H | O | H | $CH_2$ | 6-chloropyridin-3-yl | |
| 3.290 | 3,5-$F_2$—Ph | H | O | H | $CH_2$ | furan-2-yl | |
| 3.291 | 3,5-$Cl_2$—Ph | H | O | H | $CH_2$ | pyridin-2-yl | |
| 3.292 | 3,5-$F_2$—Ph | H | O | H | $CH_2$ | pyridin-2-yl | |
| 3.293 | 3,5-$F_2$—Ph | H | O | H | $CH_2$ | pyridin-3-yl | |
| 3.294 | 3-F—Ph | H | O | H | $CH_2$ | pyridin-3-yl | |
| 3.295 | 3,5-$F_2$—Ph | H | O | H | $CH_2$ | pyridin-4-yl | |
| 3.296 | 3-F—Ph | H | O | H | $CH_2$ | pyridin-4-yl | |
| 3.297 | 3,5-$Cl_2$—Ph | H | O | H | $CH_2$ | pyrimidin-2-yl | |
| 3.298 | 3,5-$F_2$—Ph | H | O | H | $CH_2CH_2$ | 1-(2,2,2-trifluoroethyl)-1H-pyrazol-4-yl | |
| 3.299 | 3,5-$F_2$—Ph | H | O | H | $CH_2CH_2$ | 1-(2-chloroethyl)-1H-pyrazol-4-yl | |
| 3.300 | 3,5-$Cl_2$—Ph | H | O | H | $CH_2CH_2$ | 1-(2-methoxy-2-oxoethyl)-1H-pyrazol-4-yl | |
| 3.301 | 3,5-$F_2$—Ph | H | O | H | $CH_2CH_2$ | 1-(3-carboxypropyl)-1H-pyrazol-4-yl | |
| 3.302 | 3,5-$F_2$—Ph | H | O | H | $CH_2CH_2$ | 1-(3-methoxy-3-oxopropyl)-1H-pyrazol-4-yl | |
| 3.303 | 3,5-$F_2$—Ph | H | O | H | $CH_2CH_2$ | 1-(4-methoxy-4-oxobutyl)-1H-pyrazol-4-yl | |
| 3.304 | 3,5-$F_2$—Ph | H | O | H | $CH_2CH_2$ | 1-(cyanomethyl)-1H-pyrazol-4-yl | |
| 3.305 | 3,5-$Cl_2$—Ph | H | O | H | $CH_2CH_2$ | 1-(cyanomethyl)-1H-pyrazol-4-yl | |
| 3.306 | 3-F—Ph | H | O | H | $CH_2CH_2$ | 1-(cyanomethyl)-1H-pyrazol-4-yl | |
| 3.307 | 3,5-$F_2$—Ph | H | O | H | $CH_2CH_2$ | 1,3-dimethyl-1H-pyrazol-4-yl | |

TABLE 3-continued

Compounds of the general formula (I) according to the invention in which $R^2$ is hydrogen and $R^3$ is trifluoroomethyl and aryl is the radical

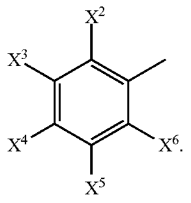

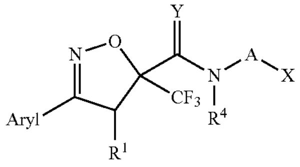

| No. | Aryl | $R^1$ | Y | $R^4$ | A | X | Physical data |
|---|---|---|---|---|---|---|---|
| 3.308 | 3-F—Ph | H | O | H | $CH_2CH_2$ | 1,3-dimethyl-1H-pyrazol-4-yl | |
| 3.309 | 3-Me—Ph | H | O | H | $CH_2CH_2$ | 1,3-dimethyl-1H-pyrazol-4-yl | |
| 3.310 | Ph | H | O | H | $CH_2CH_2$ | 1,3-dimethyl-1H-pyrazol-4-yl | |
| 3.311 | 3-Cl—Ph | H | O | H | $CH_2CH_2$ | 1,3-dimethyl-1H-pyrazol-4-yl | |
| 3.312 | 3,5-$Cl_2$—Ph | H | O | H | $CH_2CH_2$ | 1,3-dimethyl-1H-pyrazol-4-yl | |
| 3.313 | 3,5-$(CF_3)_2$—Ph | H | O | H | $CH_2CH_2$ | 1,3-dimethyl-1H-pyrazol-4-yl | |
| 3.314 | 3,5-$F_2$—Ph | H | O | H | $CH_2CH_2$ | 1,3-dimethyl-1H-pyrazol-5-yl | |
| 3.315 | Ph | H | O | H | $CH_2CH_2$ | 1,3-dimethyl-1H-pyrazol-5-yl | |
| 3.316 | 3,5-$Cl_2$—Ph | H | O | H | $CH_2CH_2$ | 1,3-dimethyl-1H-pyrazol-5-yl | |
| 3.317 | 3,5-$(CF_3)_2$—Ph | H | O | H | $CH_2CH_2$ | 1,3-dimethyl-1H-pyrazol-5-yl | |
| 3.318 | 3,5-$F_2$—Ph | H | O | H | $CH_2CH_2$ | 1,3-oxazol-4-yl | |
| 3.319 | 3,5-$Cl_2$—Ph | H | O | H | $CH_2CH_2$ | 1,3-oxazol-4-yl | |
| 3.320 | 3-F—Ph | H | O | H | $CH_2CH_2$ | 1,3-oxazol-4-yl | |
| 3.321 | 3,5-$Cl_2$—Ph | H | O | H | $CH_2CH_2$ | 1,3-thiazol-2-yl | |
| 3.322 | 3,5-$F_2$—Ph | H | O | H | $CH_2CH_2$ | 1,3-thiazol-2-yl | |
| 3.323 | 3,5-$Cl_2$—Ph | H | O | H | $CH_2CH_2$ | 1,4-dimethyl-5-oxo-4,5-dihydro-1H-1,2,4-triazol-3-yl | |
| 3.324 | 3,5-$F_2$—Ph | H | O | H | $CH_2CH_2$ | 1,5-dimethyl-1H-pyrazol-3-yl | |
| 3.325 | 3,5-$F_2$—Ph | H | O | H | $CH_2CH_2$ | 1,5-dimethyl-1H-pyrazol-4-yl | |
| 3.326 | 3-F—Ph | H | O | H | $CH_2CH_2$ | 1,5-dimethyl-1H-pyrazol-4-yl | |
| 3.327 | 3,5-$Cl_2$—Ph | H | O | H | $CH_2CH_2$ | 1,5-dimethyl-1H-pyrazol-4-yl | |
| 3.328 | Ph | H | O | H | $CH_2CH_2$ | 1,5-dimethyl-1H-pyrazol-4-yl | |
| 3.329 | 3,5-$F_2$—Ph | H | O | H | $CH_2CH_2$ | 1-acetyl-1H-pyrazol-4-yl | |
| 3.330 | 3,5-$F_2$—Ph | H | O | H | $CH_2CH_2$ | 1-butyl-3-methyl-1H-pyrazol-4-yl | |
| 3.331 | 3,5-$F_2$—Ph | H | O | H | $CH_2CH_2$ | 1-butyl-5-methyl-1H-pyrazol-4-yl | |
| 3.332 | 3,5-$F_2$—Ph | H | O | H | $CH_2CH_2$ | 1-cyclopropyl-1H-pyrazol-4-yl | |
| 3.333 | Ph | H | O | H | $CH_2CH_2$ | 1-cyclopropyl-1H-pyrazol-4-yl | |
| 3.334 | 3-F—Ph | H | O | H | $CH_2CH_2$ | 1-cyclopropyl-1H-pyrazol-4-yl | |
| 3.335 | 3,5-$Cl_2$—Ph | H | O | H | $CH_2CH_2$ | 1-cyclopropyl-1H-pyrazol-4-yl | |
| 3.336 | 3,5-$Cl_2$—Ph | H | O | H | $CH_2CH_2$ | 1-ethyl-1H-pyrazol-4-yl | |
| 3.337 | 3-F—Ph | H | O | H | $CH_2CH_2$ | 1-ethyl-1H-pyrazol-4-yl | |

TABLE 3-continued

Compounds of the general formula (I) according to the invention in which $R^2$ is hydrogen and $R^3$ is trifluoroomethyl and aryl is the radical

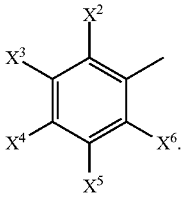

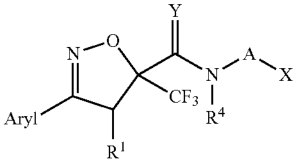

| No. | Aryl | $R^1$ | Y | $R^4$ | A | X | Physical data |
|---|---|---|---|---|---|---|---|
| 3.338 | 3,5-$F_2$—Ph | H | O | H | $CH_2CH_2$ | 1-ethyl-1H-pyrazol-4-yl | |
| 3.339 | 3-Br-5-$CF_3$—Ph | H | O | H | $CH_2CH_2$ | 1-ethyl-1H-pyrazol-4-yl | |
| 3.340 | 3-Me—Ph | H | O | H | $CH_2CH_2$ | 1-ethyl-1H-pyrazol-4-yl | |
| 3.341 | 3-F-5-MeO—Ph | H | O | H | $CH_2CH_2$ | 1-ethyl-1H-pyrazol-4-yl | |
| 3.342 | 3-Cl-5-Et—Ph | H | O | H | $CH_2CH_2$ | 1-ethyl-1H-pyrazol-4-yl | |
| 3.343 | 3,5-$(MeO)_2$—Ph | H | O | H | $CH_2CH_2$ | 1-ethyl-1H-pyrazol-4-yl | |
| 3.344 | 3-Me-5-$CF_3O$—Ph | H | O | H | $CH_2CH_2$ | 1-ethyl-1H-pyrazol-4-yl | |
| 3.345 | 3,5-$Cl_2$-4-MeO—Ph | H | O | H | $CH_2CH_2$ | 1-ethyl-1H-pyrazol-4-yl | |
| 3.346 | Ph | H | O | H | $CH_2CH_2$ | 1-ethyl-1H-pyrazol-4-yl | |
| 3.347 | 3,5-$F_2$—Ph | H | O | H | $CH_2CH_2$ | 1-ethyl-1H-pyrazol-5-yl | |
| 3.348 | 3,5-$Cl_2$—Ph | H | O | H | $CH_2CH_2$ | 1-ethyl-1H-pyrazol-5-yl | |
| 3.349 | Ph | H | O | H | $CH_2CH_2$ | 1-ethyl-1H-pyrazol-5-yl | |
| 3.350 | 3,5-$F_2$—Ph | H | O | H | $CH_2CH_2$ | 1-ethyl-3-methyl-1H-pyrazol-4-yl | |
| 3.351 | 3-Me—Ph | H | O | H | $CH_2CH_2$ | 1-ethyl-3-methyl-1H-pyrazol-4-yl | |
| 3.352 | 3-Br-5-F—Ph | H | O | H | $CH_2CH_2$ | 1-ethyl-3-methyl-1H-pyrazol-4-yl | |
| 3.353 | 3,4,5-$F_3$—Ph | H | O | H | $CH_2CH_2$ | 1-ethyl-3-methyl-1H-pyrazol-4-yl | |
| 3.354 | 3,4-$F_2$—Ph | H | O | H | $CH_2CH_2$ | 1-ethyl-3-methyl-1H-pyrazol-4-yl | |
| 3.355 | 3,5-$F_2$—Ph | H | S | H | $CH_2CH_2$ | 1-ethyl-3-methyl-1H-pyrazol-4-yl | |
| 3.356 | 3-F-5-Me—Ph | H | O | H | $CH_2CH_2$ | 1-ethyl-3-methyl-1H-pyrazol-4-yl | |
| 3.357 | 3-Cl-5-CN—Ph | H | O | H | $CH_2CH_2$ | 1-ethyl-3-methyl-1H-pyrazol-4-yl | |
| 3.358 | 3-F—Ph | H | O | H | $CH_2CH_2$ | 1-ethyl-3-methyl-1H-pyrazol-4-yl | |
| 3.359 | 3-cPr-5-F—Ph | H | O | H | $CH_2CH_2$ | 1-ethyl-3-methyl-1H-pyrazol-4-yl | |
| 3.360 | 3-Cl-5-Me—Ph | H | O | H | $CH_2CH_2$ | 1-ethyl-3-methyl-1H-pyrazol-4-yl | |
| 3.361 | 3-F-5-MeO—Ph | H | O | H | $CH_2CH_2$ | 1-ethyl-3-methyl-1H-pyrazol-4-yl | |
| 3.362 | 2,5-$Me_2$—Ph | H | O | H | $CH_2CH_2$ | 1-ethyl-3-methyl-1H-pyrazol-4-yl | |
| 3.363 | 3-$CF_3O$—Ph | H | O | H | $CH_2CH_2$ | 1-ethyl-3-methyl-1H-pyrazol-4-yl | |
| 3.364 | 3-Cl-5-Et—Ph | H | O | H | $CH_2CH_2$ | 1-ethyl-3-methyl-1H-pyrazol-4-yl | |
| 3.365 | 2,3,5-$F_3$—Ph | H | O | H | $CH_2CH_2$ | 1-ethyl-3-methyl-1H-pyrazol-4-yl | |

TABLE 3-continued

Compounds of the general formula (I) according to the invention in which $R^2$ is hydrogen and $R^3$ is trifluoroomethyl and aryl is the radical

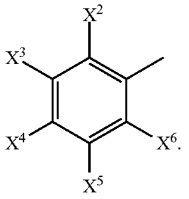

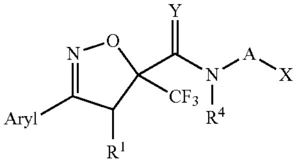

| No. | Aryl | $R^1$ | Y | $R^4$ | A | X | Physical data |
|---|---|---|---|---|---|---|---|
| 3.366 | 3-Et-5-F—Ph | H | O | H | $CH_2CH_2$ | 1-ethyl-3-methyl-1H-pyrazol-4-yl | |
| 3.367 | 3-F-5-$CF_3$—Ph | H | O | H | $CH_2CH_2$ | 1-ethyl-3-methyl-1H-pyrazol-4-yl | |
| 3.368 | 3-Br-5-$CF_3$—Ph | H | O | H | $CH_2CH_2$ | 1-ethyl-3-methyl-1H-pyrazol-4-yl | |
| 3.369 | 3-Cl-5-MeO—Ph | H | O | H | $CH_2CH_2$ | 1-ethyl-3-methyl-1H-pyrazol-4-yl | |
| 3.370 | 3-Cl-4-F—Ph | H | O | H | $CH_2CH_2$ | 1-ethyl-3-methyl-1H-pyrazol-4-yl | |
| 3.371 | 2,3-$F_2$—Ph | H | O | H | $CH_2CH_2$ | 1-ethyl-3-methyl-1H-pyrazol-4-yl | |
| 3.372 | 3-Cl-5-$CF_3$—Ph | H | O | H | $CH_2CH_2$ | 1-ethyl-3-methyl-1H-pyrazol-4-yl | |
| 3.373 | 3,5-$Me_2$—Ph | H | O | H | $CH_2CH_2$ | 1-ethyl-3-methyl-1H-pyrazol-4-yl | |
| 3.374 | 3-Cl—Ph | H | O | H | $CH_2CH_2$ | 1-ethyl-3-methyl-1H-pyrazol-4-yl | |
| 3.375 | 3-MeO—Ph | H | O | H | $CH_2CH_2$ | 1-ethyl-3-methyl-1H-pyrazol-4-yl | |
| 3.376 | 3-Cl-5-F—Ph | H | O | H | $CH_2CH_2$ | 1-ethyl-3-methyl-1H-pyrazol-4-yl | |
| 3.377 | 3-CN-5-F—Ph | H | O | H | $CH_2CH_2$ | 1-ethyl-3-methyl-1H-pyrazol-4-yl | |
| 3.378 | 3-CN—Ph | H | O | H | $CH_2CH_2$ | 1-ethyl-3-methyl-1H-pyrazol-4-yl | |
| 3.379 | 3-Br-5-Cl—Ph | H | O | H | $CH_2CH_2$ | 1-ethyl-3-methyl-1H-pyrazol-4-yl | |
| 3.380 | 2,3,4-$F_3$—Ph | H | O | H | $CH_2CH_2$ | 1-ethyl-3-methyl-1H-pyrazol-4-yl | |
| 3.381 | 3,5-$Cl_2$-4-MeO—Ph | H | O | H | $CH_2CH_2$ | 1-ethyl-3-methyl-1H-pyrazol-4-yl | |
| 3.382 | Ph | H | O | H | $CH_2CH_2$ | 1-ethyl-3-methyl-1H-pyrazol-4-yl | |
| 3.383 | 2,5-$F_2$—Ph | H | O | H | $CH_2CH_2$ | 1-ethyl-3-methyl-1H-pyrazol-4-yl | |
| 3.384 | 3,5-$Br_2$—Ph | H | O | H | $CH_2CH_2$ | 1-ethyl-3-methyl-1H-pyrazol-4-yl | |
| 3.385 | 2-F—Ph | H | O | H | $CH_2CH_2$ | 1-ethyl-3-methyl-1H-pyrazol-4-yl | |
| 3.386 | 2,5-$Cl_2$—Ph | H | O | H | $CH_2CH_2$ | 1-ethyl-3-methyl-1H-pyrazol-4-yl | |
| 3.387 | 3,5-$Et_2$—Ph | H | O | H | $CH_2CH_2$ | 1-ethyl-3-methyl-1H-pyrazol-4-yl | |
| 3.388 | 3-$CF_3$S—Ph | H | O | H | $CH_2CH_2$ | 1-ethyl-3-methyl-1H-pyrazol-4-yl | |
| 3.389 | 3-EtO—Ph | H | O | H | $CH_2CH_2$ | 1-ethyl-3-methyl-1H-pyrazol-4-yl | |
| 3.390 | 3,5-$Cl_2$—Ph | $CH_3$ | O | H | $CH_2CH_2$ | 1-ethyl-3-methyl-1H-pyrazol-4-yl | |
| 3.391 | 2-F-3-Me—Ph | H | O | H | $CH_2CH_2$ | 1-ethyl-3-methyl-1H-pyrazol-4-yl | |
| 3.392 | 3-Cl-5-$CF_3$O—Ph | H | O | H | $CH_2CH_2$ | 1-ethyl-3-methyl-1H-pyrazol-4-yl | |
| 3.393 | 3,5-$F_2$—Ph | H | O | H | $CH_2CH_2$ | 1-ethyl-3-methyl-1H-pyrazol-5-yl | |

TABLE 3-continued

Compounds of the general formula (I) according to the invention in which $R^2$ is hydrogen and $R^3$ is trifluoroomethyl and aryl is the radical

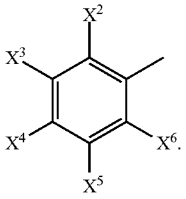

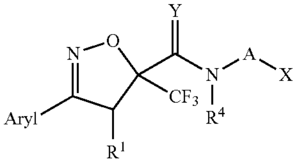

| No. | Aryl | $R^1$ | Y | $R^4$ | A | X | Physical data |
|---|---|---|---|---|---|---|---|
| 3.394 | 3,5-$Cl_2$—Ph | H | O | H | $CH_2CH_2$ | 1-ethyl-3-methyl-1H-pyrazol-5-yl | |
| 3.395 | 3-F—Ph | H | O | H | $CH_2CH_2$ | 1-ethyl-3-methyl-1H-pyrazol-5-yl | |
| 3.396 | 3,5-$F_2$—Ph | H | O | H | $CH_2CH_2$ | 1H-1,2,3-triazol-5-yl | |
| 3.397 | 3,5-$Cl_2$—Ph | H | O | H | $CH_2CH_2$ | 1H-pyrazol-4-yl | |
| 3.398 | 3,5-$F_2$—Ph | H | O | H | $CH_2CH_2$ | 1H-pyrazol-4-yl | |
| 3.399 | 3-F—Ph | H | O | H | $CH_2CH_2$ | 1H-pyrazol-4-yl | |
| 3.400 | 3,5-$F_2$—Ph | H | O | H | $CH_2CH_2$ | 1-isobutyl-1H-pyrazol-4-yl | |
| 3.401 | 3,5-$Cl_2$—Ph | H | O | H | $CH_2CH_2$ | 1-isobutyl-1H-pyrazol-4-yl | |
| 3.402 | 3-F—Ph | H | O | H | $CH_2CH_2$ | 1-isobutyl-1H-pyrazol-4-yl | |
| 3.403 | Ph | H | O | H | $CH_2CH_2$ | 1-isobutyl-1H-pyrazol-4-yl | |
| 3.404 | 3,5-$F_2$—Ph | H | O | H | $CH_2CH_2$ | 1-isopropyl-1H-pyrazol-4-yl | |
| 3.405 | 3-F—Ph | H | O | H | $CH_2CH_2$ | 1-isopropyl-1H-pyrazol-4-yl | |
| 3.406 | 3,5-$Cl_2$—Ph | H | O | H | $CH_2CH_2$ | 1-isopropyl-1H-pyrazol-4-yl | |
| 3.407 | Ph | H | O | H | $CH_2CH_2$ | 1-isopropyl-1H-pyrazol-4-yl | |
| 3.408 | 3,5-$F_2$—Ph | H | O | H | $CH_2CH_2$ | 1-methyl-1H-pyrazol-4-yl | |
| 3.409 | 3-F-5-MeO—Ph | H | O | H | $CH_2CH_2$ | 1-methyl-1H-pyrazol-4-yl | |
| 3.410 | 3-F—Ph | H | O | H | $CH_2CH_2$ | 1-methyl-1H-pyrazol-4-yl | |
| 3.411 | Ph | H | O | H | $CH_2CH_2$ | 1-methyl-1H-pyrazol-4-yl | |
| 3.412 | 3,5-$(CF_3)_2$—Ph | H | O | H | $CH_2CH_2$ | 1-methyl-1H-pyrazol-4-yl | |
| 3.413 | 3,5-$Cl_2$—Ph | H | O | H | $CH_2CH_2$ | 1-methyl-1H-pyrazol-4-yl | |
| 3.414 | 3-Me—Ph | H | O | H | $CH_2CH_2$ | 1-methyl-1H-pyrazol-4-yl | |
| 3.415 | 3,5-$F_2$—Ph | H | O | H | $CH_2CH_2$ | 1-methyl-1H-pyrazol-5-yl | |
| 3.416 | 3-F—Ph | H | O | H | $CH_2CH_2$ | 1-methyl-1H-pyrazol-5-yl | |
| 3.417 | 3,5-$Cl_2$—Ph | H | O | H | $CH_2CH_2$ | 1-methyl-1H-pyrazol-5-yl | |
| 3.418 | Ph | H | O | H | $CH_2CH_2$ | 1-methyl-1H-pyrazol-5-yl | |
| 3.419 | 3,5-$Cl_2$—Ph | H | O | H | $CH_2CH_2$ | 1-methyl-3-(trifluoromethyl)-1H-pyrazol-4-yl | D1 |
| 3.420 | 3,5-$Cl_2$—Ph | H | O | H | $CH_2CH_2$ | 1-methyl-3-(trifluoromethyl)-1H-pyrazol-4-yl | D2 |
| 3.421 | 3,5-$F_2$—Ph | H | O | H | $CH_2CH_2$ | 1-methyl-5-(trifluoromethyl)-1H-pyrazol-4-yl | |

TABLE 3-continued

Compounds of the general formula (I) according to the invention in which $R^2$ is hydrogen and $R^3$ is trifluoroomethyl and aryl is the radical

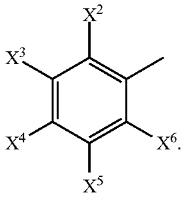

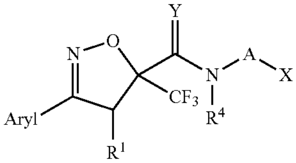

| No. | Aryl | $R^1$ | Y | $R^4$ | A | X | Physical data |
|---|---|---|---|---|---|---|---|
| 3.422 | 3,5-$F_2$—Ph | H | O | H | $CH_2CH_2$ | 1-propyl-1H-pyrazol-3-yl | |
| 3.423 | 3,5-$Cl_2$—Ph | H | O | H | $CH_2CH_2$ | 1-propyl-1H-pyrazol-3-yl | |
| 3.424 | 3,5-$F_2$—Ph | H | O | H | $CH_2CH_2$ | 1-propyl-1H-pyrazol-4-yl | |
| 3.425 | 3,5-$Cl_2$—Ph | H | O | H | $CH_2CH_2$ | 1-propyl-1H-pyrazol-4-yl | |
| 3.426 | 3-F—Ph | H | O | H | $CH_2CH_2$ | 1-propyl-1H-pyrazol-4-yl | |
| 3.427 | Ph | H | O | H | $CH_2CH_2$ | 1-propyl-1H-pyrazol-4-yl | |
| 3.428 | 3,5-$F_2$—Ph | H | O | H | $CH_2CH_2$ | 1-tert-butyl-1H-pyrazol-4-yl | |
| 3.429 | 3,5-$Cl_2$—Ph | H | O | H | $CH_2CH_2$ | 1-tert-butyl-1H-pyrazol-4-yl | |
| 3.430 | Ph | H | O | H | $CH_2CH_2$ | 1-tert-butyl-1H-pyrazol-4-yl | |
| 3.431 | 3,5-$F_2$—Ph | H | O | H | $CH_2CH_2$ | 2-chloropyridin-4-yl | |
| 3.432 | 3-F—Ph | H | O | H | $CH_2CH_2$ | 2-chloropyridin-4-yl | |
| 3.433 | 3,5-$F_2$—Ph | H | O | H | $CH_2CH_2$ | 2-methyl-1,3-thiazol-4-yl | |
| 3.434 | 3,5-$Cl_2$—Ph | H | O | H | $CH_2CH_2$ | 2-methyl-1,3-thiazol-4-yl | |
| 3.435 | 3,5-$Cl_2$—Ph | H | O | H | $CH_2CH_2$ | 3-(cyclopropyl-carbamoyl)-1,2-oxazol-5-yl | |
| 3.436 | 3,5-$Cl_2$—Ph | H | O | H | $CH_2CH_2$ | 3-(ethoxycarbonyl)-1,2-oxazol-5-yl | |
| 3.437 | 3,5-$F_2$—Ph | H | O | H | $CH_2CH_2$ | 3-(methoxy-carbonyl)phenyl | |
| 3.438 | 3,5-$F_2$—Ph | H | O | H | $CH_2CH_2$ | 3,5-difluoropyridin-2-yl | |
| 3.439 | 3,5-$Cl_2$—Ph | H | O | H | $CH_2CH_2$ | 3-carboxy-1,2-oxazol-5-yl | |
| 3.440 | 3,5-$F_2$—Ph | H | O | H | $CH_2CH_2$ | 3-chloro-1-ethyl-1H-pyrazol-4-yl | |
| 3.441 | 3-F—Ph | H | O | H | $CH_2CH_2$ | 3-chloro-1-ethyl-1H-pyrazol-4-yl | |
| 3.442 | Ph | H | O | H | $CH_2CH_2$ | 3-chloro-1-ethyl-1H-pyrazol-4-yl | |
| 3.443 | 3,5-$Cl_2$—Ph | H | O | H | $CH_2CH_2$ | 3-chloro-1-ethyl-1H-pyrazol-4-yl | |
| 3.444 | 3,5-$F_2$—Ph | H | O | H | $CH_2CH_2$ | 3-chloro-1-isopropyl-1H-pyrazol-4-yl | |
| 3.445 | 3-F—Ph | H | O | H | $CH_2CH_2$ | 3-chloro-1-isopropyl-1H-pyrazol-4-yl | |
| 3.446 | 3,5-$F_2$—Ph | H | S | H | $CH_2CH_2$ | 3-chloro-1-isopropyl-1H-pyrazol-4-yl | |
| 3.447 | 3,5-$Cl_2$—Ph | H | O | H | $CH_2CH_2$ | 3-chloro-1-isopropyl-1H-pyrazol-4-yl | |
| 3.448 | 3,5-$Cl_2$—Ph | H | O | H | $CH_2CH_2$ | 3-chloro-1-methyl-1H-pyrazol-4-yl | |
| 3.449 | 3,5-$F_2$—Ph | H | O | H | $CH_2CH_2$ | 3-chloro-1-methyl-1H-pyrazol-4-yl | |
| 3.450 | 3,5-$F_2$—Ph | H | O | H | $CH_2CH_2$ | 3-chloropyridin-4-yl | |

TABLE 3-continued

Compounds of the general formula (I) according to the invention in which $R^2$ is hydrogen and $R^3$ is trifluoroomethyl and aryl is the radical

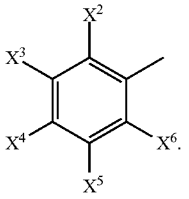

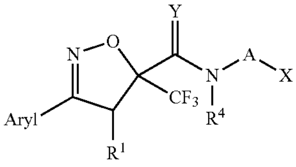

| No. | Aryl | $R^1$ | Y | $R^4$ | A | X | Physical data |
|---|---|---|---|---|---|---|---|
| 3.451 | 3-F—Ph | H | O | H | $CH_2CH_2$ | 3-chloropyridin-4-yl | |
| 3.452 | 3,5-$F_2$—Ph | H | O | H | $CH_2CH_2$ | 3-cyclopropyl-1,2,4-oxadiazol-5-yl | |
| 3.453 | 3,5-$Cl_2$—Ph | H | O | H | $CH_2CH_2$ | 3-cyclopropyl-1,2,4-oxadiazol-5-yl | |
| 3.454 | 3,5-$F_2$—Ph | H | O | H | $CH_2CH_2$ | 3-furyl | |
| 3.455 | 3,5-$F_2$—Ph | H | O | H | $CH_2CH_2$ | 3-methyl-1H-pyrazol-4-yl | |
| 3.456 | 3-F—Ph | H | O | H | $CH_2CH_2$ | 3-methyl-1-propyl-1H-pyrazol-4-yl | |
| 3.457 | 3,5-$F_2$—Ph | H | O | H | $CH_2CH_2$ | 3-methyl-1-propyl-1H-pyrazol-4-yl | |
| 3.458 | 3-Cl-5-F—Ph | H | O | H | $CH_2CH_2$ | 3-methyl-1-propyl-1H-pyrazol-4-yl | |
| 3.459 | 3-Cl-5-$CF_3O$—Ph | H | O | H | $CH_2CH_2$ | 3-methyl-1-propyl-1H-pyrazol-4-yl | |
| 3.460 | 3-F-5-Me—Ph | H | O | H | $CH_2CH_2$ | 3-methyl-1-propyl-1H-pyrazol-4-yl | |
| 3.461 | 3-Me—Ph | H | O | H | $CH_2CH_2$ | 3-methyl-1-propyl-1H-pyrazol-4-yl | |
| 3.462 | 3-Cl-5-Me—Ph | H | O | H | $CH_2CH_2$ | 3-methyl-1-propyl-1H-pyrazol-4-yl | |
| 3.463 | 3-Cl-4-F—Ph | H | O | H | $CH_2CH_2$ | 3-methyl-1-propyl-1H-pyrazol-4-yl | |
| 3.464 | 3-$CF_3O$—Ph | H | O | H | $CH_2CH_2$ | 3-methyl-1-propyl-1H-pyrazol-4-yl | |
| 3.465 | 4-Cl-3,5-$F_2$—Ph | H | O | H | $CH_2CH_2$ | 3-methyl-1-propyl-1H-pyrazol-4-yl | |
| 3.466 | 3,5-$Cl_2$—Ph | H | O | H | $CH_2CH_2$ | 3-methyl-1-propyl-1H-pyrazol-4-yl | |
| 3.467 | Ph | H | O | H | $CH_2CH_2$ | 3-methyl-1-propyl-1H-pyrazol-4-yl | |
| 3.468 | 3,5-$Cl_2$—Ph | H | O | H | $CH_2CH_2$ | 4-(methoxy-carbonyl)phenyl | |
| 3.469 | 3,5-$F_2$—Ph | H | O | H | $CH_2CH_2$ | 4-(trifluoromethyl)-1,3-thiazol-2-yl | |
| 3.470 | 3-F—Ph | H | O | H | $CH_2CH_2$ | 4-(trifluoromethyl)-1,3-thiazol-2-yl | |
| 3.471 | 3,5-$Cl_2$—Ph | H | O | H | $CH_2CH_2$ | 4-(trifluoromethyl)-1,3-thiazol-2-yl | |
| 3.472 | 3,5-$F_2$—Ph | H | O | H | $CH_2CH_2$ | 4-chloro-1-methyl-1H-pyrazol-3-yl | |
| 3.473 | 3,5-$Cl_2$—Ph | H | O | H | $CH_2CH_2$ | 4-chloro-1-methyl-1H-pyrazol-3-yl | |
| 3.474 | 3-F—Ph | H | O | H | $CH_2CH_2$ | 4-chloro-1-methyl-1H-pyrazol-3-yl | |
| 3.475 | 3,5-$F_2$—Ph | H | O | H | $CH_2CH_2$ | 4-chloro-1-methyl-1H-pyrazol-5-yl | |
| 3.476 | 3,5-$F_2$—Ph | H | O | H | $CH_2CH_2$ | 5-chloro-1-methyl-1H-pyrazol-4-yl | |
| 3.477 | 3-F—Ph | H | O | H | $CH_2CH_2$ | 5-chloro-1-methyl-1H-pyrazol-4-yl | |
| 3.478 | 3,5-$F_2$—Ph | H | S | H | $CH_2CH_2$ | 5-chloro-1-methyl-1H-pyrazol-4-yl | |
| 3.479 | 3,5-$Cl_2$—Ph | H | O | H | $CH_2CH_2$ | 5-chloro-1-methyl-1H-pyrazol-4-yl | |

TABLE 3-continued

Compounds of the general formula (I) according to the invention in which $R^2$ is hydrogen and $R^3$ is trifluoroomethyl and aryl is the radical

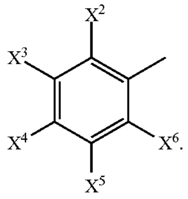

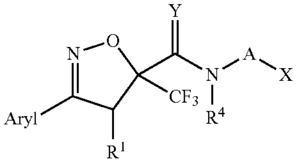

| No. | Aryl | $R^1$ | Y | $R^4$ | A | X | Physical data |
|---|---|---|---|---|---|---|---|
| 3.480 | Ph | H | O | H | $CH_2CH_2$ | 5-chloro-1-methyl-1H-pyrazol-4-yl | |
| 3.481 | 3,5-$F_2$—Ph | H | O | H | $CH_2CH_2$ | 5-methoxy-1,3-dimethyl-1H-pyrazol-4-yl | |
| 3.482 | 3,5-$Cl_2$—Ph | H | O | H | $CH_2CH_2$ | 5-methoxy-1,3-dimethyl-1H-pyrazol-4-yl | |
| 3.483 | 3-F—Ph | H | O | H | $CH_2CH_2$ | 5-methoxy-1,3-dimethyl-1H-pyrazol-4-yl | |
| 3.484 | 3,5-$Cl_2$—Ph | H | O | H | $CH_2CH_2$ | 5-methyl-1,2,4-oxadiazol-3-yl | |
| 3.485 | 3,5-$F_2$—Ph | H | O | H | $CH_2CH_2$ | 5-methyl-1,2,4-oxadiazol-3-yl | |
| 3.486 | 3,5-$Cl_2$—Ph | H | O | H | $CH_2CH_2$ | 5-methyl-1,2-oxazol-3-yl | |
| 3.487 | 3-F—Ph | H | O | H | $CH_2CH_2$ | 5-methyl-1-propyl-1H-pyrazol-4-yl | |
| 3.488 | 3,5-$F_2$—Ph | H | O | H | $CH_2CH_2$ | 5-methyl-1-propyl-1H-pyrazol-4-yl | |
| 3.489 | 3,5-$Cl_2$—Ph | H | O | H | $CH_2CH_2$ | 5-methyl-1-propyl-1H-pyrazol-4-yl | |
| 3.490 | Ph | H | O | H | $CH_2CH_2$ | 5-methyl-1-propyl-1H-pyrazol-4-yl | |
| 3.491 | 3,5-$F_2$—Ph | H | O | H | $CH_2CH_2$ | 6-chloropyridin-3-yl | |
| 3.492 | 3,5-$F_2$—Ph | H | O | H | $CH_2CH_2$ | furan-2-yl | |
| 3.493 | 3,5-$Cl_2$—Ph | H | O | H | $CH_2CH_2$ | pyridin-2-yl | |
| 3.494 | 3,5-$F_2$—Ph | H | O | H | $CH_2CH_2$ | pyridin-2-yl | |
| 3.495 | 3,5-$F_2$—Ph | H | O | H | $CH_2CH_2$ | pyridin-3-yl | |
| 3.496 | 3-F—Ph | H | O | H | $CH_2CH_2$ | pyridin-3-yl | |
| 3.497 | 3,5-$F_2$—Ph | H | O | H | $CH_2CH_2$ | pyridin-4-yl | |
| 3.498 | 3-F—Ph | H | O | H | $CH_2CH_2$ | pyridin-4-yl | |
| 3.499 | 3,5-$Cl_2$—Ph | H | O | H | $CH_2CH_2$ | pyrimidin-2-yl | |
| 3.500 | 3,5-$F_2$—Ph | H | O | H | $CHCH_3$ | 1-(2,2,2-trifluoroethyl)-1H-pyrazol-4-yl | |
| 3.501 | 3,5-$F_2$—Ph | H | O | H | $CHCH_3$ | 1-(2-chloroethyl)-1H-pyrazol-4-yl | |
| 3.502 | 3,5-$Cl_2$—Ph | H | O | H | $CHCH_3$ | 1-(2-methoxy-2-oxoethyl)-1H-pyrazol-4-yl | |
| 3.503 | 3,5-$F_2$—Ph | H | O | H | $CHCH_3$ | 1-(3-carboxypropyl)-1H-pyrazol-4-yl | |
| 3.504 | 3,5-$F_2$—Ph | H | O | H | $CHCH_3$ | 1-(3-methoxy-3-oxopropyl)-1H-pyrazol-4-yl | |
| 3.505 | 3,5-$F_2$—Ph | H | O | H | $CHCH_3$ | 1-(4-methoxy-4-oxobutyl)-1H-pyrazol-4-yl | |
| 3.506 | 3,5-$F_2$—Ph | H | O | H | $CHCH_3$ | 1-(cyanomethyl)-1H-pyrazol-4-yl | |
| 3.507 | 3,5-$Cl_2$—Ph | H | O | H | $CHCH_3$ | 1-(cyanomethyl)-1H-pyrazol-4-yl | |
| 3.508 | 3-F—Ph | H | O | H | $CHCH_3$ | 1-(cyanomethyl)-1H-pyrazol-4-yl | |

TABLE 3-continued

Compounds of the general formula (I) according to the invention in which $R^2$ is hydrogen and $R^3$ is trifluoroomethyl and aryl is the radical

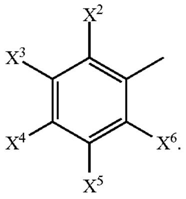

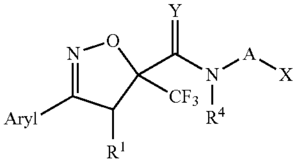

| No. | Aryl | $R^1$ | Y | $R^4$ | A | X | Physical data |
|---|---|---|---|---|---|---|---|
| 3.509 | 3,5-$F_2$—Ph | H | O | H | $CHCH_3$ | 1,3-dimethyl-1H-pyrazol-4-yl | |
| 3.510 | 3-F—Ph | H | O | H | $CHCH_3$ | 1,3-dimethyl-1H-pyrazol-4-yl | |
| 3.511 | 3-Me—Ph | H | O | H | $CHCH_3$ | 1,3-dimethyl-1H-pyrazol-4-yl | |
| 3.512 | Ph | H | O | H | $CHCH_3$ | 1,3-dimethyl-1H-pyrazol-4-yl | |
| 3.513 | 3-Cl—Ph | H | O | H | $CHCH_3$ | 1,3-dimethyl-1H-pyrazol-4-yl | |
| 3.514 | 3,5-$Cl_2$—Ph | H | O | H | $CHCH_3$ | 1,3-dimethyl-1H-pyrazol-4-yl | |
| 3.515 | 3,5-$(CF_3)_2$—Ph | H | O | H | $CHCH_3$ | 1,3-dimethyl-1H-pyrazol-4-yl | |
| 3.516 | 3,5-$F_2$—Ph | H | O | H | $CHCH_3$ | 1,3-dimethyl-1H-pyrazol-5-yl | |
| 3.517 | Ph | H | O | H | $CHCH_3$ | 1,3-dimethyl-1H-pyrazol-5-yl | |
| 3.518 | 3,5-$Cl_2$—Ph | H | O | H | $CHCH_3$ | 1,3-dimethyl-1H-pyrazol-5-yl | |
| 3.519 | 3,5-$(CF_3)_2$—Ph | H | O | H | $CHCH_3$ | 1,3-dimethyl-1H-pyrazol-5-yl | |
| 3.520 | 3,5-$F_2$—Ph | H | O | H | $CHCH_3$ | 1,3-oxazol-4-yl | |
| 3.521 | 3,5-$Cl_2$—Ph | H | O | H | $CHCH_3$ | 1,3-oxazol-4-yl | |
| 3.522 | 3-F—Ph | H | O | H | $CHCH_3$ | 1,3-oxazol-4-yl | |
| 3.523 | 3,5-$Cl_2$—Ph | H | O | H | $CHCH_3$ | 1,3-thiazol-2-yl | |
| 3.524 | 3,5-$F_2$—Ph | H | O | H | $CHCH_3$ | 1,3-thiazol-2-yl | |
| 3.525 | 3,5-$Cl_2$—Ph | H | O | H | $CHCH_3$ | 1,4-dimethyl-5-oxo-4,5-dihydro-1H-1,2,4-triazol-3-yl | |
| 3.526 | 3,5-$F_2$—Ph | H | O | H | $CHCH_3$ | 1,5-dimethyl-1H-pyrazol-3-yl | |
| 3.527 | 3,5-$F_2$—Ph | H | O | H | $CHCH_3$ | 1,5-dimethyl-1H-pyrazol-4-yl | |
| 3.528 | 3-F—Ph | H | O | H | $CHCH_3$ | 1,5-dimethyl-1H-pyrazol-4-yl | |
| 3.529 | 3,5-$Cl_2$—Ph | H | O | H | $CHCH_3$ | 1,5-dimethyl-1H-pyrazol-4-yl | |
| 3.530 | Ph | H | O | H | $CHCH_3$ | 1,5-dimethyl-1H-pyrazol-4-yl | |
| 3.531 | 3,5-$F_2$—Ph | H | O | H | $CHCH_3$ | 1-acetyl-1H-pyrazol-4-yl | |
| 3.532 | 3,5-$F_2$—Ph | H | O | H | $CHCH_3$ | 1-butyl-3-methyl-1H-pyrazol-4-yl | |
| 3.533 | 3,5-$F_2$—Ph | H | O | H | $CHCH_3$ | 1-butyl-5-methyl-1H-pyrazol-4-yl | |
| 3.534 | 3,5-$F_2$—Ph | H | O | H | $CHCH_3$ | 1-cyclopropyl-1H-pyrazol-4-yl | |
| 3.535 | Ph | H | O | H | $CHCH_3$ | 1-cyclopropyl-1H-pyrazol-4-yl | |
| 3.536 | 3-F—Ph | H | O | H | $CHCH_3$ | 1-cyclopropyl-1H-pyrazol-4-yl | |
| 3.537 | 3,5-$Cl_2$—Ph | H | O | H | $CHCH_3$ | 1-cyclopropyl-1H-pyrazol-4-yl | |
| 3.538 | 3,5-$Cl_2$—Ph | H | O | H | $CHCH_3$ | 1-ethyl-1H-pyrazol-4-yl | |

TABLE 3-continued

Compounds of the general formula (I) according to the invention in which $R^2$ is hydrogen and $R^3$ is trifluoroomethyl and aryl is the radical

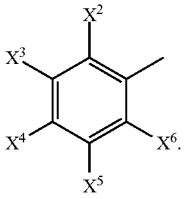

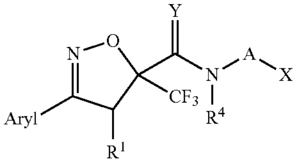

| No. | Aryl | $R^1$ | Y | $R^4$ | A | X | Physical data |
|---|---|---|---|---|---|---|---|
| 3.539 | 3-F—Ph | H | O | H | $CHCH_3$ | 1-ethyl-1H-pyrazol-4-yl | |
| 3.540 | 3,5-$F_2$—Ph | H | O | H | $CHCH_3$ | 1-ethyl-1H-pyrazol-4-yl | |
| 3.541 | 3-Br-5-$CF_3$—Ph | H | O | H | $CHCH_3$ | 1-ethyl-1H-pyrazol-4-yl | |
| 3.542 | 3-Me—Ph | H | O | H | $CHCH_3$ | 1-ethyl-1H-pyrazol-4-yl | |
| 3.543 | 3-F-5-MeO—Ph | H | O | H | $CHCH_3$ | 1-ethyl-1H-pyrazol-4-yl | |
| 3.544 | 3-Cl-5-Et—Ph | H | O | H | $CHCH_3$ | 1-ethyl-1H-pyrazol-4-yl | |
| 3.545 | 3,5-$(MeO)_2$—Ph | H | O | H | $CHCH_3$ | 1-ethyl-1H-pyrazol-4-yl | |
| 3.546 | 3-Me-5-$CF_3O$—Ph | H | O | H | $CHCH_3$ | 1-ethyl-1H-pyrazol-4-yl | |
| 3.547 | 3,5-$Cl_2$-4-MeO—Ph | H | O | H | $CHCH_3$ | 1-ethyl-1H-pyrazol-4-yl | |
| 3.548 | Ph | H | O | H | $CHCH_3$ | 1-ethyl-1H-pyrazol-4-yl | |
| 3.549 | 3,5-$F_2$—Ph | H | O | H | $CHCH_3$ | 1-ethyl-1H-pyrazol-5-yl | |
| 3.550 | 3,5-$Cl_2$—Ph | H | O | H | $CHCH_3$ | 1-ethyl-1H-pyrazol-5-yl | |
| 3.551 | Ph | H | O | H | $CHCH_3$ | 1-ethyl-1H-pyrazol-5-yl | |
| 3.552 | 3,5-$F_2$—Ph | H | O | H | $CHCH_3$ | 1-ethyl-3-methyl-1H-pyrazol-4-yl | |
| 3.553 | 3-Me—Ph | H | O | H | $CHCH_3$ | 1-ethyl-3-methyl-1H-pyrazol-4-yl | |
| 3.554 | 3-Br-5-F—Ph | H | O | H | $CHCH_3$ | 1-ethyl-3-methyl-1H-pyrazol-4-yl | |
| 3.555 | 3,4,5-$F_3$—Ph | H | O | H | $CHCH_3$ | 1-ethyl-3-methyl-1H-pyrazol-4-yl | |
| 3.556 | 3,4-$F_2$—Ph | H | O | H | $CHCH_3$ | 1-ethyl-3-methyl-1H-pyrazol-4-yl | |
| 3.557 | 3,5-$F_2$—Ph | H | S | H | $CHCH_3$ | 1-ethyl-3-methyl-1H-pyrazol-4-yl | |
| 3.558 | 3-F-5-Me—Ph | H | O | H | $CHCH_3$ | 1-ethyl-3-methyl-1H-pyrazol-4-yl | |
| 3.559 | 3-Cl-5-CN—Ph | H | O | H | $CHCH_3$ | 1-ethyl-3-methyl-1H-pyrazol-4-yl | |
| 3.560 | 3-F—Ph | H | O | H | $CHCH_3$ | 1-ethyl-3-methyl-1H-pyrazol-4-yl | |
| 3.561 | 3-cPr-5-F—Ph | H | O | H | $CHCH_3$ | 1-ethyl-3-methyl-1H-pyrazol-4-yl | |
| 3.562 | 3-Cl-5-Me—Ph | H | O | H | $CHCH_3$ | 1-ethyl-3-methyl-1H-pyrazol-4-yl | |
| 3.563 | 3-F-5-MeO—Ph | H | O | H | $CHCH_3$ | 1-ethyl-3-methyl-1H-pyrazol-4-yl | |
| 3.564 | 2,5-$Me_2$—Ph | H | O | H | $CHCH_3$ | 1-ethyl-3-methyl-1H-pyrazol-4-yl | |
| 3.565 | 3-$CF_3O$—Ph | H | O | H | $CHCH_3$ | 1-ethyl-3-methyl-1H-pyrazol-4-yl | |
| 3.566 | 3-Cl-5-Et—Ph | H | O | H | $CHCH_3$ | 1-ethyl-3-methyl-1H-pyrazol-4-yl | |

TABLE 3-continued

Compounds of the general formula (I) according to the invention in which $R^2$ is hydrogen and $R^3$ is trifluoroomethyl and aryl is the radical

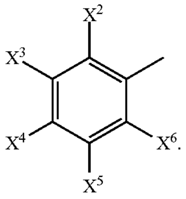

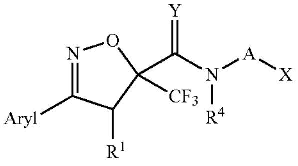

| No. | Aryl | $R^1$ | Y | $R^4$ | A | X | Physical data |
|---|---|---|---|---|---|---|---|
| 3.567 | 2,3,5-$F_3$—Ph | H | O | H | $CHCH_3$ | 1-ethyl-3-methyl-1H-pyrazol-4-yl | |
| 3.568 | 3-Et-5-F—Ph | H | O | H | $CHCH_3$ | 1-ethyl-3-methyl-1H-pyrazol-4-yl | |
| 3.569 | 3-F-5-$CF_3$—Ph | H | O | H | $CHCH_3$ | 1-ethyl-3-methyl-1H-pyrazol-4-yl | |
| 3.570 | 3-Br-5-$CF_3$—Ph | H | O | H | $CHCH_3$ | 1-ethyl-3-methyl-1H-pyrazol-4-yl | |
| 3.571 | 3-Cl-5-MeO—Ph | H | O | H | $CHCH_3$ | 1-ethyl-3-methyl-1H-pyrazol-4-yl | |
| 3.572 | 3-Cl-4-F—Ph | H | O | H | $CHCH_3$ | 1-ethyl-3-methyl-1H-pyrazol-4-yl | |
| 3.573 | 2,3-$F_2$—Ph | H | O | H | $CHCH_3$ | 1-ethyl-3-methyl-1H-pyrazol-4-yl | |
| 3.574 | 3-Cl-5-$CF_3$—Ph | H | O | H | $CHCH_3$ | 1-ethyl-3-methyl-1H-pyrazol-4-yl | |
| 3.575 | 3,5-$Me_2$—Ph | H | O | H | $CHCH_3$ | 1-ethyl-3-methyl-1H-pyrazol-4-yl | |
| 3.576 | 3-Cl—Ph | H | O | H | $CHCH_3$ | 1-ethyl-3-methyl-1H-pyrazol-4-yl | |
| 3.577 | 3-MeO—Ph | H | O | H | $CHCH_3$ | 1-ethyl-3-methyl-1H-pyrazol-4-yl | |
| 3.578 | 3-Cl-5-F—Ph | H | O | H | $CHCH_3$ | 1-ethyl-3-methyl-1H-pyrazol-4-yl | |
| 3.579 | 3-CN-5-F—Ph | H | O | H | $CHCH_3$ | 1-ethyl-3-methyl-1H-pyrazol-4-yl | |
| 3.580 | 3-CN—Ph | H | O | H | $CHCH_3$ | 1-ethyl-3-methyl-1H-pyrazol-4-yl | |
| 3.581 | 3-Br-5-Cl—Ph | H | O | H | $CHCH_3$ | 1-ethyl-3-methyl-1H-pyrazol-4-yl | |
| 3.582 | 2,3,4-$F_3$—Ph | H | O | H | $CHCH_3$ | 1-ethyl-3-methyl-1H-pyrazol-4-yl | |
| 3.583 | 3,5-$Cl_2$-4-MeO—Ph | H | O | H | $CHCH_3$ | 1-ethyl-3-methyl-1H-pyrazol-4-yl | |
| 3.584 | Ph | H | O | H | $CHCH_3$ | 1-ethyl-3-methyl-1H-pyrazol-4-yl | |
| 3.585 | 2,5-$F_2$—Ph | H | O | H | $CHCH_3$ | 1-ethyl-3-methyl-1H-pyrazol-4-yl | |
| 3.586 | 3,5-$Br_2$—Ph | H | O | H | $CHCH_3$ | 1-ethyl-3-methyl-1H-pyrazol-4-yl | |
| 3.587 | 2-F—Ph | H | O | H | $CHCH_3$ | 1-ethyl-3-methyl-1H-pyrazol-4-yl | |
| 3.588 | 2,5-$Cl_2$—Ph | H | O | H | $CHCH_3$ | 1-ethyl-3-methyl-1H-pyrazol-4-yl | |
| 3.589 | 3,5-$Et_2$—Ph | H | O | H | $CHCH_3$ | 1-ethyl-3-methyl-1H-pyrazol-4-yl | |
| 3.590 | 3-$CF_3$S—Ph | H | O | H | $CHCH_3$ | 1-ethyl-3-methyl-1H-pyrazol-4-yl | |
| 3.591 | 3-EtO—Ph | H | O | H | $CHCH_3$ | 1-ethyl-3-methyl-1H-pyrazol-4-yl | |
| 3.592 | 3,5-$Cl_2$—Ph | $CH_3$ | O | H | $CHCH_3$ | 1-ethyl-3-methyl-1H-pyrazol-4-yl | |
| 3.593 | 2-F-3-Me—Ph | H | O | H | $CHCH_3$ | 1-ethyl-3-methyl-1H-pyrazol-4-yl | |
| 3.594 | 3-Cl-5-$CF_3$O—Ph | H | O | H | $CHCH_3$ | 1-ethyl-3-methyl-1H-pyrazol-4-yl | |

TABLE 3-continued

Compounds of the general formula (I) according to the invention in which $R^2$ is hydrogen and $R^3$ is trifluoroomethyl and aryl is the radical

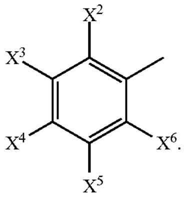

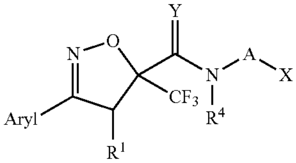

| No. | Aryl | $R^1$ | Y | $R^4$ | A | X | Physical data |
|---|---|---|---|---|---|---|---|
| 3.595 | 3,5-$F_2$—Ph | H | O | H | $CHCH_3$ | 1-ethyl-3-methyl-1H-pyrazol-5-yl | |
| 3.596 | 3,5-$Cl_2$—Ph | H | O | H | $CHCH_3$ | 1-ethyl-3-methyl-1H-pyrazol-5-yl | |
| 3.597 | 3-F—Ph | H | O | H | $CHCH_3$ | 1-ethyl-3-methyl-1H-pyrazol-5-yl | |
| 3.598 | 3,5-$F_2$—Ph | H | O | H | $CHCH_3$ | 1H-1,2,3-triazol-5-yl | |
| 3.599 | 3,5-$Cl_2$—Ph | H | O | H | $CHCH_3$ | 1H-pyrazol-4-yl | |
| 3.600 | 3,5-$F_2$—Ph | H | O | H | $CHCH_3$ | 1H-pyrazol-4-yl | |
| 3.601 | 3-F—Ph | H | O | H | $CHCH_3$ | 1H-pyrazol-4-yl | |
| 3.602 | 3,5-$F_2$—Ph | H | O | H | $CHCH_3$ | 1-isobutyl-1H-pyrazol-4-yl | |
| 3.603 | 3,5-$Cl_2$—Ph | H | O | H | $CHCH_3$ | 1-isobutyl-1H-pyrazol-4-yl | |
| 3.604 | 3-F—Ph | H | O | H | $CHCH_3$ | 1-isobutyl-1H-pyrazol-4-yl | |
| 3.605 | Ph | H | O | H | $CHCH_3$ | 1-isobutyl-1H-pyrazol-4-yl | |
| 3.606 | 3,5-$F_2$—Ph | H | O | H | $CHCH_3$ | 1-isopropyl-1H-pyrazol-4-yl | |
| 3.607 | 3-F—Ph | H | O | H | $CHCH_3$ | 1-isopropyl-1H-pyrazol-4-yl | |
| 3.608 | 3,5-$Cl_2$—Ph | H | O | H | $CHCH_3$ | 1-isopropyl-1H-pyrazol-4-yl | |
| 3.609 | Ph | H | O | H | $CHCH_3$ | 1-isopropyl-1H-pyrazol-4-yl | |
| 3.610 | 3,5-$F_2$—Ph | H | O | H | $CHCH_3$ | 1-methyl-1H-pyrazol-4-yl | |
| 3.611 | 3-F-5-MeO—Ph | H | O | H | $CHCH_3$ | 1-methyl-1H-pyrazol-4-yl | |
| 3.612 | 3-F—Ph | H | O | H | $CHCH_3$ | 1-methyl-1H-pyrazol-4-yl | |
| 3.613 | Ph | H | O | H | $CHCH_3$ | 1-methyl-1H-pyrazol-4-yl | |
| 3.614 | 3,5-$(CF_3)_2$—Ph | H | O | H | $CHCH_3$ | 1-methyl-1H-pyrazol-4-yl | |
| 3.615 | 3,5-$Cl_2$—Ph | H | O | H | $CHCH_3$ | 1-methyl-1H-pyrazol-4-yl | |
| 3.616 | 3-Me—Ph | H | O | H | $CHCH_3$ | 1-methyl-1H-pyrazol-4-yl | |
| 3.617 | 3,5-$F_2$—Ph | H | O | H | $CHCH_3$ | 1-methyl-1H-pyrazol-5-yl | |
| 3.618 | 3-F—Ph | H | O | H | $CHCH_3$ | 1-methyl-1H-pyrazol-5-yl | |
| 3.619 | 3,5-$Cl_2$—Ph | H | O | H | $CHCH_3$ | 1-methyl-1H-pyrazol-5-yl | |
| 3.620 | Ph | H | O | H | $CHCH_3$ | 1-methyl-1H-pyrazol-5-yl | |
| 3.621 | 3,5-$Cl_2$—Ph | H | O | H | $CHCH_3$ | 1-methyl-3-(trifluoromethyl)-1H-pyrazol-4-yl | D1 |
| 3.622 | 3,5-$Cl_2$—Ph | H | O | H | $CHCH_3$ | 1-methyl-3-(trifluoromethyl)-1H-pyrazol-4-yl | D2 |

TABLE 3-continued

Compounds of the general formula (I) according to the invention in which $R^2$ is hydrogen and $R^3$ is trifluoroomethyl and aryl is the radical

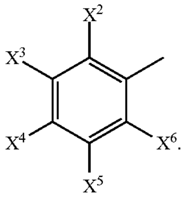

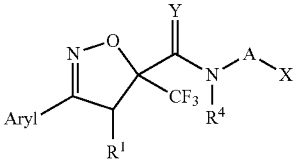

| No. | Aryl | $R^1$ | Y | $R^4$ | A | X | Physical data |
|---|---|---|---|---|---|---|---|
| 3.623 | 3,5-$F_2$—Ph | H | O | H | $CHCH_3$ | 1-methyl-5-(trifluoromethyl)-1H-pyrazol-4-yl | |
| 3.624 | 3,5-$F_2$—Ph | H | O | H | $CHCH_3$ | 1-propyl-1H-pyrazol-3-yl | |
| 3.625 | 3,5-$Cl_2$—Ph | H | O | H | $CHCH_3$ | 1-propyl-1H-pyrazol-3-yl | |
| 3.626 | 3,5-$F_2$—Ph | H | O | H | $CHCH_3$ | 1-propyl-1H-pyrazol-4-yl | |
| 3.627 | 3,5-$Cl_2$—Ph | H | O | H | $CHCH_3$ | 1-propyl-1H-pyrazol-4-yl | |
| 3.628 | 3-F—Ph | H | O | H | $CHCH_3$ | 1-propyl-1H-pyrazol-4-yl | |
| 3.629 | Ph | H | O | H | $CHCH_3$ | 1-propyl-1H-pyrazol-4-yl | |
| 3.630 | 3,5-$F_2$—Ph | H | O | H | $CHCH_3$ | 1-tert-butyl-1H-pyrazol-4-yl | |
| 3.631 | 3,5-$Cl_2$—Ph | H | O | H | $CHCH_3$ | 1-tert-butyl-1H-pyrazol-4-yl | |
| 3.632 | Ph | H | O | H | $CHCH_3$ | 1-tert-butyl-1H-pyrazol-4-yl | |
| 3.633 | 3,5-$F_2$—Ph | H | O | H | $CHCH_3$ | 2-chloropyridin-4-yl | |
| 3.634 | 3-F—Ph | H | O | H | $CHCH_3$ | 2-chloropyridin-4-yl | |
| 3.635 | 3,5-$F_2$—Ph | H | O | H | $CHCH_3$ | 2-methyl-1,3-thiazol-4-yl | |
| 3.636 | 3,5-$Cl_2$—Ph | H | O | H | $CHCH_3$ | 2-methyl-1,3-thiazol-4-yl | |
| 3.637 | 3,5-$Cl_2$—Ph | H | O | H | $CHCH_3$ | 3-(cyclopropyl-carbamoyl)-1,2-oxazol-5-yl | |
| 3.638 | 3,5-$Cl_2$—Ph | H | O | H | $CHCH_3$ | 3-(ethoxycarbonyl)-1,2-oxazol-5-yl | |
| 3.639 | 3,5-$F_2$—Ph | H | O | H | $CHCH_3$ | 3-(methoxy-carbonyl)phenyl | |
| 3.640 | 3,5-$F_2$—Ph | H | O | H | $CHCH_3$ | 3,5-difluoropyridin-2-yl | |
| 3.641 | 3,5-$Cl_2$—Ph | H | O | H | $CHCH_3$ | 3-carboxy-1,2-oxazol-5-yl | |
| 3.642 | 3,5-$F_2$—Ph | H | O | H | $CHCH_3$ | 3-chloro-1-ethyl-1H-pyrazol-4-yl | |
| 3.643 | 3-F—Ph | H | O | H | $CHCH_3$ | 3-chloro-1-ethyl-1H-pyrazol-4-yl | |
| 3.644 | Ph | H | O | H | $CHCH_3$ | 3-chloro-1-ethyl-1H-pyrazol-4-yl | |
| 3.645 | 3,5-$Cl_2$—Ph | H | O | H | $CHCH_3$ | 3-chloro-1-ethyl-1H-pyrazol-4-yl | |
| 3.646 | 3,5-$F_2$—Ph | H | O | H | $CHCH_3$ | 3-chloro-1-isopropyl-1H-pyrazol-4-yl | |
| 3.647 | 3-F—Ph | H | O | H | $CHCH_3$ | 3-chloro-1-isopropyl-1H-pyrazol-4-yl | |
| 3.648 | 3,5-$F_2$—Ph | H | S | H | $CHCH_3$ | 3-chloro-1-isopropyl-1H-pyrazol-4-yl | |
| 3.649 | 3,5-$Cl_2$—Ph | H | O | H | $CHCH_3$ | 3-chloro-1-isopropyl-1H-pyrazol-4-yl | |
| 3.650 | 3,5-$Cl_2$—Ph | H | O | H | $CHCH_3$ | 3-chloro-1-methyl-1H-pyrazol-4-yl | |

TABLE 3-continued

Compounds of the general formula (I) according to the invention in which $R^2$ is hydrogen and $R^3$ is trifluoroomethyl and aryl is the radical

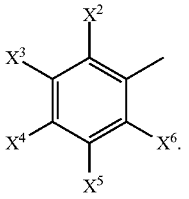

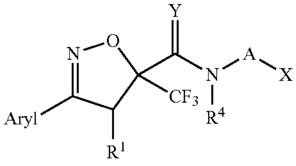

| No. | Aryl | $R^1$ | Y | $R^4$ | A | X | Physical data |
|---|---|---|---|---|---|---|---|
| 3.651 | 3,5-$F_2$—Ph | H | O | H | $CHCH_3$ | 3-chloro-1-methyl-1H-pyrazol-4-yl | |
| 3.652 | 3,5-$F_2$—Ph | H | O | H | $CHCH_3$ | 3-chloropyridin-4-yl | |
| 3.653 | 3-F—Ph | H | O | H | $CHCH_3$ | 3-chloropyridin-4-yl | |
| 3.654 | 3,5-$F_2$—Ph | H | O | H | $CHCH_3$ | 3-c-Pr-1,2,4-oxadiazol-5-yl | |
| 3.655 | 3,5-$Cl_2$—Ph | H | O | H | $CHCH_3$ | 3-c-Pr-1,2,4-oxadiazol-5-yl | |
| 3.656 | 3,5-$F_2$—Ph | H | O | H | $CHCH_3$ | 3-furyl | |
| 3.657 | 3,5-$F_2$—Ph | H | O | H | $CHCH_3$ | 3-methyl-1H-pyrazol-4-yl | |
| 3.658 | 3-F—Ph | H | O | H | $CHCH_3$ | 3-methyl-1-propyl-1H-pyrazol-4-yl | |
| 3.659 | 3,5-$F_2$—Ph | H | O | H | $CHCH_3$ | 3-methyl-1-propyl-1H-pyrazol-4-yl | |
| 3.660 | 3-Cl-5-F—Ph | H | O | H | $CHCH_3$ | 3-methyl-1-propyl-1H-pyrazol-4-yl | |
| 3.661 | 3-Cl-5-$CF_3$O—Ph | H | O | H | $CHCH_3$ | 3-methyl-1-propyl-1H-pyrazol-4-yl | |
| 3.662 | 3-F-5-Me—Ph | H | O | H | $CHCH_3$ | 3-methyl-1-propyl-1H-pyrazol-4-yl | |
| 3.663 | 3-Me—Ph | H | O | H | $CHCH_3$ | 3-methyl-1-propyl-1H-pyrazol-4-yl | |
| 3.664 | 3-Cl-5-Me—Ph | H | O | H | $CHCH_3$ | 3-methyl-1-propyl-1H-pyrazol-4-yl | |
| 3.665 | 3-Cl-4-F—Ph | H | O | H | $CHCH_3$ | 3-methyl-1-propyl-1H-pyrazol-4-yl | |
| 3.666 | 3-$CF_3$O—Ph | H | O | H | $CHCH_3$ | 3-methyl-1-propyl-1H-pyrazol-4-yl | |
| 3.667 | 4-Cl-3,5-$F_2$—Ph | H | O | H | $CHCH_3$ | 3-methyl-1-propyl-1H-pyrazol-4-yl | |
| 3.668 | 3,5-$Cl_2$—Ph | H | O | H | $CHCH_3$ | 3-methyl-1-propyl-1H-pyrazol-4-yl | |
| 3.669 | Ph | H | O | H | $CHCH_3$ | 3-methyl-1-propyl-1H-pyrazol-4-yl | |
| 3.670 | 3,5-$Cl_2$—Ph | H | O | H | $CHCH_3$ | 4-(methoxy-carbonyl)phenyl | |
| 3.671 | 3,5-$F_2$—Ph | H | O | H | $CHCH_3$ | 4-(trifluoromethyl)-1,3-thiazol-2-yl | |
| 3.672 | 3-F—Ph | H | O | H | $CHCH_3$ | 4-(trifluoromethyl)-1,3-thiazol-2-yl | |
| 3.673 | 3,5-$Cl_2$—Ph | H | O | H | $CHCH_3$ | 4-(trifluoromethyl)-1,3-thiazol-2-yl | |
| 3.674 | 3,5-$F_2$—Ph | H | O | H | $CHCH_3$ | 4-chloro-1-methyl-1H-pyrazol-3-yl | |
| 3.675 | 3,5-$Cl_2$—Ph | H | O | H | $CHCH_3$ | 4-chloro-1-methyl-1H-pyrazol-3-yl | |
| 3.676 | 3-F—Ph | H | O | H | $CHCH_3$ | 4-chloro-1-methyl-1H-pyrazol-3-yl | |
| 3.677 | 3,5-$F_2$—Ph | H | O | H | $CHCH_3$ | 4-chloro-1-methyl-1H-pyrazol-5-yl | |
| 3.678 | 3,5-$F_2$—Ph | H | O | H | $CHCH_3$ | 5-chloro-1-methyl-1H-pyrazol-4-yl | |
| 3.679 | 3-F—Ph | H | O | H | $CHCH_3$ | 5-chloro-1-methyl-1H-pyrazol-4-yl | |

TABLE 3-continued

Compounds of the general formula (I) according to the invention in which $R^2$ is hydrogen and $R^3$ is trifluoroomethyl and aryl is the radical

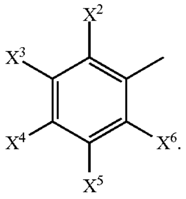

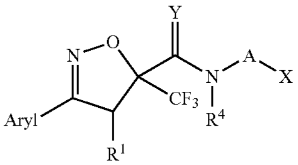

| No. | Aryl | $R^1$ | Y | $R^4$ | A | X | Physical data |
|---|---|---|---|---|---|---|---|
| 3.680 | 3,5-$F_2$—Ph | H | S | H | $CHCH_3$ | 5-chloro-1-methyl-1H-pyrazol-4-yl | |
| 3.681 | 3,5-$Cl_2$—Ph | H | O | H | $CHCH_3$ | 5-chloro-1-methyl-1H-pyrazol-4-yl | |
| 3.682 | Ph | H | O | H | $CHCH_3$ | 5-chloro-1-methyl-1H-pyrazol-4-yl | |
| 3.683 | 3,5-$F_2$—Ph | H | O | H | $CHCH_3$ | 5-methoxy-1,3-dimethyl-1H-pyrazol-4-yl | |
| 3.684 | 3,5-$Cl_2$—Ph | H | O | H | $CHCH_3$ | 5-methoxy-1,3-dimethyl-1H-pyrazol-4-yl | |
| 3.685 | 3-F—Ph | H | O | H | $CHCH_3$ | 5-methoxy-1,3-dimethyl-1H-pyrazol-4-yl | |
| 3.686 | 3,5-$Cl_2$—Ph | H | O | H | $CHCH_3$ | 5-methyl-1,2,4-oxadiazol-3-yl | |
| 3.687 | 3,5-$F_2$—Ph | H | O | H | $CHCH_3$ | 5-methyl-1,2,4-oxadiazol-3-yl | |
| 3.688 | 3,5-$Cl_2$—Ph | H | O | H | $CHCH_3$ | 5-methyl-1,2-oxazol-3-yl | |
| 3.689 | 3-F—Ph | H | O | H | $CHCH_3$ | 5-methyl-1-propyl-1H-pyrazol-4-yl | |
| 3.690 | 3,5-$F_2$—Ph | H | O | H | $CHCH_3$ | 5-methyl-1-propyl-1H-pyrazol-4-yl | |
| 3.691 | 3,5-$Cl_2$—Ph | H | O | H | $CHCH_3$ | 5-methyl-1-propyl-1H-pyrazol-4-yl | |
| 3.692 | Ph | H | O | H | $CHCH_3$ | 5-methyl-1-propyl-1H-pyrazol-4-yl | |
| 3.693 | 3,5-$F_2$—Ph | H | O | H | $CHCH_3$ | 6-chloropyridin-3-yl | |
| 3.694 | 3,5-$F_2$—Ph | H | O | H | $CHCH_3$ | furan-2-yl | |
| 3.695 | 3,5-$Cl_2$—Ph | H | O | H | $CHCH_3$ | pyridin-2-yl | |
| 3.696 | 3,5-$F_2$—Ph | H | O | H | $CHCH_3$ | pyridin-2-yl | |
| 3.697 | 3,5-$F_2$—Ph | H | O | H | $CHCH_3$ | pyridin-3-yl | |
| 3.698 | 3-F—Ph | H | O | H | $CHCH_3$ | pyridin-3-yl | |
| 3.699 | 3,5-$F_2$—Ph | H | O | H | $CHCH_3$ | pyridin-4-yl | |
| 3.700 | 3-F—Ph | H | O | H | $CHCH_3$ | pyridin-4-yl | |
| 3.701 | 3,5-$Cl_2$—Ph | H | O | H | $CHCH_3$ | pyrimidin-2-yl | |

TABLE 4

Compounds of the general formula (I) according to the invention in which $R^2$ is hydrogen and $R^3$ is cyano and aryl is the radical

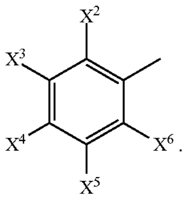

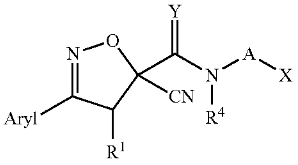

| No. | Aryl | $R^1$ | Y | $R^4$ | A | X | Physical data |
|---|---|---|---|---|---|---|---|
| 4.001 | 3,5-$(CF_3)_2$—Ph | H | O | H | bond | 1,3-dimethyl-1H-pyrazol-5-yl | |
| 4.002 | 3,5-$Cl_2$—Ph | H | O | H | bond | 1,3-dimethyl-1H-pyrazol-5-yl | |
| 4.003 | 3,5-$Cl_2$—Ph | H | O | H | bond | 1,5-dimethyl-1H-pyrazol-4-yl | |
| 4.004 | 3,5-$F_2$—Ph | H | O | H | bond | 1,5-dimethyl-1H-pyrazol-4-yl | |
| 4.005 | Ph | H | O | H | bond | 1,5-dimethyl-1H-pyrazol-4-yl | |
| 4.006 | 3-F—Ph | H | O | H | bond | 1,5-dimethyl-1H-pyrazol-4-yl | |
| 4.007 | 3-Me—Ph | H | O | H | bond | 1,5-dimethyl-1H-pyrazol-4-yl | |
| 4.008 | 3,5-$F_2$—Ph | H | O | H | bond | 1-ethyl-3-(methoxy-carbonyl)-1H-pyrazol-4-yl | |
| 4.009 | 3,5-$Cl_2$—Ph | H | O | H | bond | 1-ethyl-3-(methoxy-carbonyl)-1H-pyrazol-4-yl | |
| 4.010 | 3-F—Ph | H | O | H | bond | 1-ethyl-3-(methoxy-carbonyl)-1H-pyrazol-4-yl | |
| 4.011 | 3,5-$F_2$—Ph | H | O | H | bond | 1-ethyl-3-methyl-1H-pyrazol-4-yl | |
| 4.012 | 3-F—Ph | H | O | H | bond | 1-ethyl-3-methyl-1H-pyrazol-4-yl | |
| 4.013 | 3,5-$Cl_2$—Ph | H | O | H | bond | 1-methyl-1H-1,2,4-triazol-3-yl | |
| 4.014 | 3,5-$Cl_2$—Ph | H | O | H | bond | 1-methyl-1H-imidazol-2-yl | |
| 4.015 | 3,5-$F_2$—Ph | H | O | H | bond | 1-methyl-1H-pyrazol-4-yl | |
| 4.016 | 3,5-$Cl_2$—Ph | H | O | H | bond | 1-methyl-1H-pyrazol-4-yl | |
| 4.017 | 3-F—Ph | H | O | H | bond | 1-methyl-1H-pyrazol-4-yl | |
| 4.018 | Ph | H | O | H | bond | 1-methyl-1H-pyrazol-4-yl | |
| 4.019 | 3,5-$Cl_2$—Ph | H | O | H | bond | 1-propyl-1H-1,2,4-triazol-3-yl | |
| 4.020 | 3,5-$F_2$—Ph | H | O | H | bond | 1-propyl-1H-1,2,4-triazol-3-yl | |
| 4.021 | 3,5-$Cl_2$—Ph | H | O | H | bond | 2,4-difluorophenyl | |
| 4.022 | 3,5-$Cl_2$—Ph | H | O | H | bond | 2-chloropyridin-3-yl | |
| 4.023 | 3,5-$Cl_2$—Ph | H | O | H | bond | 3-(2-methoxy-2-oxoethyl)phenyl | |
| 4.024 | 3,5-$Cl_2$—Ph | H | O | H | bond | 3-(carboxymethyl)-phenyl | |

TABLE 4-continued

Compounds of the general formula (I) according to the invention in which $R^2$ is hydrogen and $R^3$ is cyano and aryl is the radical

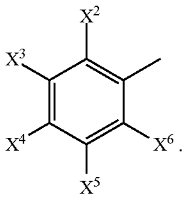

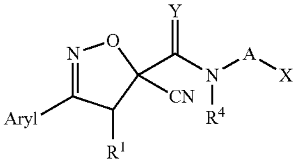

| No. | Aryl | $R^1$ | Y | $R^4$ | A | X | Physical data |
|---|---|---|---|---|---|---|---|
| 4.025 | 3,5-$Cl_2$—Ph | H | O | H | bond | 3-(methoxy-carbonyl)phenyl | |
| 4.026 | 3-F—Ph | H | O | H | bond | 3-(methoxy-carbonyl)phenyl | |
| 4.027 | 3,5-$Cl_2$-Ph | H | O | H | bond | 3,5-dimethoxyphenyl | |
| 4.028 | Ph | H | O | H | bond | 3,5-dimethyl-1H-pyrazol-4-yl | |
| 4.029 | 3,5-$Cl_2$—Ph | H | O | H | bond | 3,5-dimethyl-1H-pyrazol-4-yl | |
| 4.030 | 3,5-$Cl_2$—Ph | H | O | H | bond | 3-[2-(methylamino)-2-oxoethyl]phenyl | |
| 4.031 | 3,5-$Cl_2$—Ph | H | O | H | bond | 3-carboxyphenyl | |
| 4.032 | 3,5-$Cl_2$—Ph | H | O | H | bond | 3-chloropyridin-2-yl | |
| 4.033 | 3,5-$Cl_2$—Ph | H | O | H | bond | 3-methyl-1,2-oxazol-5-yl | |
| 4.034 | 3,5-$Cl_2$—Ph | H | O | H | bond | 3-methyl-1-propyl-1H-pyrazol-4-yl | |
| 4.035 | 3,5-$Cl_2$—Ph | H | O | H | bond | 4-(2-ethoxy-2-oxoethyl)phenyl | |
| 4.036 | 3,5-$Cl_2$—Ph | H | O | H | bond | 4-(carboxymethyl)-phenyl | |
| 4.037 | 3,5-$F_2$—Ph | H | O | H | bond | 4-(methoxy-carbonyl)-3-thienyl | |
| 4.038 | 3,5-$Cl_2$—Ph | H | O | H | bond | 4-(methoxy-carbonyl)phenyl | |
| 4.039 | 3,5-$Cl_2$—Ph | H | O | H | bond | 4,5-dimethyl-4H-1,2,4-triazol-3-yl | |
| 4.040 | 3,5-$Cl_2$—Ph | H | O | H | bond | 4-carboxyphenyl | |
| 4.041 | 3,5-$Cl_2$—Ph | H | O | H | bond | 4-chloro-2-(methoxy-carbonyl)-6-methylphenyl | |
| 4.042 | 3,5-$F_2$—Ph | H | O | H | bond | 4-cyano-1-ethyl-1H-pyrazol-3-yl | |
| 4.043 | 3,5-$F_2$—Ph | H | O | H | bond | 4-formyl-3-(1-methyl c-Pr)-1,2-oxazol-5-yl | |
| 4.044 | 3,5-$Cl_2$—Ph | H | O | H | bond | 4-methyl-1,2,5-oxadiazol-3-yl | |
| 4.045 | 3,5-$F_2$—Ph | H | O | H | bond | 4-methyl-1,3-thiazol-2-yl | |
| 4.046 | 3,5-$Cl_2$—Ph | H | O | H | bond | 5-(methoxy-carbonyl)-1,3-thiazol-4-yl | |
| 4.047 | 3,5-$F_2$—Ph | H | O | H | bond | 5-(methoxy-carbonyl)-1,3-thiazol-4-yl | |
| 4.048 | 3,5-$Cl_2$—Ph | H | O | H | bond | 5-methoxy-1-methyl-1H-1,2,4-triazol-3-yl | |

TABLE 4-continued

Compounds of the general formula (I) according to the invention in which $R^2$ is hydrogen and $R^3$ is cyano and aryl is the radical

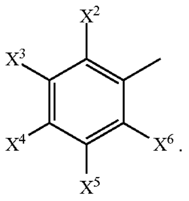

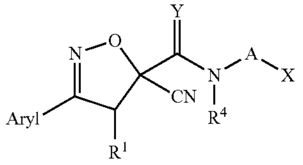

| No. | Aryl | $R^1$ | Y | $R^4$ | A | X | Physical data |
|---|---|---|---|---|---|---|---|
| 4.049 | 3,5-$F_2$—Ph | H | O | H | bond | 5-methoxy-1-methyl-1H-1,2,4-triazol-3-yl | |
| 4.050 | 3,5-$Cl_2$—Ph | H | O | H | bond | 6-chloropyridin-3-yl | |
| 4.051 | 3,5-$Cl_2$—Ph | H | O | H | bond | pyridin-4-yl | |
| 4.052 | 3,5-$F_2$—Ph | H | O | H | $CH_2$ | 1-(2,2,2-trifluoroethyl)-1H-pyrazol-4-yl | |
| 4.053 | 3,5-$F_2$—Ph | H | O | H | $CH_2$ | 1-(2-chloroethyl)-1H-pyrazol-4-yl | |
| 4.054 | 3,5-$F_2$—Ph | H | O | H | $CH_2$ | 1,3-dimethyl-1H-pyrazol-4-yl | |
| 4.055 | 3-F—Ph | H | O | H | $CH_2$ | 1,3-dimethyl-1H-pyrazol-4-yl | |
| 4.056 | 3,5-$F_2$—Ph | H | O | H | $CH_2$ | 1,3-dimethyl-1H-pyrazol-5-yl | |
| 4.057 | 3,5-$F_2$—Ph | H | O | H | $CH_2$ | 1,5-dimethyl-1H-pyrazol-4-yl | |
| 4.058 | 3,5-$F_2$—Ph | H | O | H | $CH_2$ | 1-butyl-3-methyl-1H-pyrazol-4-yl | |
| 4.059 | 3,5-$F_2$—Ph | H | O | H | $CH_2$ | 1-butyl-5-methyl-1H-pyrazol-4-yl | |
| 4.060 | 3,5-$Cl_2$—Ph | H | O | H | $CH_2$ | 1-c-Pr-1H-pyrazol-4-yl | |
| 4.061 | 3,5-$F_2$—Ph | H | O | H | $CH_2$ | 1-c-Pr-1H-pyrazol-4-yl | |
| 4.062 | 3-F—Ph | H | O | H | $CH_2$ | 1-c-Pr-1H-pyrazol-4-yl | |
| 4.063 | Ph | H | O | H | $CH_2$ | 1-c-Pr-1H-pyrazol-4-yl | |
| 4.064 | 3,5-$Cl_2$—Ph | H | O | H | $CH_2$ | 1-ethyl-1H-pyrazol-4-yl | |
| 4.065 | 3,5-$F_2$—Ph | H | O | H | $CH_2$ | 1-ethyl-1H-pyrazol-4-yl | [$CDCl_3$] 1.48 (t, 3H); 4.05 (AB, 2H); 4.16 (q, 2H); 4.32 (dd, 1H); 4.43 (dd,1H); 6.88 (s, br, 1H); 6.96 (m, 1H); 7.16 (m, 2H); 7.41 (s,1H); 7.45 (s, 1H). |
| 4.066 | 3-Br-5-$CF_3$—Ph | H | O | H | $CH_2$ | 1-ethyl-1H-pyrazol-4-yl | |
| 4.067 | 3-F-5-MeO—Ph | H | O | H | $CH_2$ | 1-ethyl-1H-pyrazol-4-yl | |
| 4.068 | 3-F—Ph | H | O | H | $CH_2$ | 1-ethyl-1H-pyrazol-4-yl | |
| 4.069 | 3-Me—Ph | H | O | H | $CH_2$ | 1-ethyl-1H-pyrazol-4-yl | |
| 4.070 | 3,5-$F_2$—Ph | H | O | H | $CH_2$ | 1-ethyl-1H-pyrazol-5-yl | |
| 4.071 | 3,4,5-$F_3$—Ph | H | O | H | $CH_2$ | 1-ethyl-3-methyl-1H-pyrazol-4-yl | |
| 4.072 | 3,4-$F_2$—Ph | H | O | H | $CH_2$ | 1-ethyl-3-methyl-1H-pyrazol-4-yl | |
| 4.073 | 3,5-$Cl_2$—Ph | H | O | H | $CH_2$ | 1-ethyl-3-methyl-1H-pyrazol-4-yl | [$CDCl_3$] 7.52 5.51; 7.51 8.63; 7.50 2.81; 7.49 |

TABLE 4-continued

Compounds of the general formula (I) according to the invention in which $R^2$ is hydrogen and $R^3$ is cyano and aryl is the radical

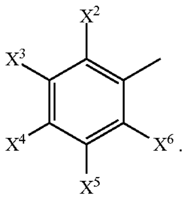

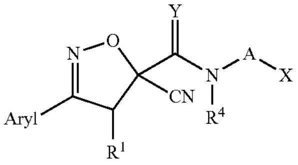

| No. | Aryl | $R^1$ | Y | $R^4$ | A | X | Physical data |
|---|---|---|---|---|---|---|---|
| | | | | | | | 2.71; 7.49 1.24; 7.31 3.77; 7.26 20.34; 6.74 0.60; 5.30 2.35; 4.42 0.82; 4.40 0.82; 4.38 1.45; 4.36 1.46; 4.29 1.48; 4.28 1.53; 4.25 0.86; 4.24 0.84; 4.13 2.06; 4.10 1.28; 4.09 4.27; 4.08 4.18; 4.06 4.01; 4.05 1.35; 4.01 3.82; 3.96 1.99; 2.22 16.00; 2.04 0.35; 1.57 10.25; 1.47 4.98; 1.46 10.40; 1.44 4.91; 1.26 0.46; 0.01 0.39; 0.00 13.40; −0.01 0.47; −0.01 0.60 |
| 4.074 | 3,5-$F_2$—Ph | H | O | H | $CH_2$ | 1-ethyl-3-methyl-1H-pyrazol-4-yl | [$CDCl_3$] 7.31 3.63; 7.26 12.71; 7.19 0.34; 7.18 1.53; 7.17 2.09; 7.17 1.29; 7.16 1.17; 7.16 1.93; 7.15 1.72; 6.99 0.40; 6.99 0.70; 6.98 0.38; 6.97 0.82; 6.96 1.44; 6.96 0.72; 6.95 0.43; 6.94 0.74; 6.94 0.37; 6.76 0.52; 4.42 0.87; 4.40 0.85; 4.38 1.57; 4.37 1.54; 4.29 1.52; 4.28 1.54; 4.26 0.87; 4.24 0.84; 4.13 1.95; 4.10 1.32; 4.09 0.47; 4.08 6.27; 4.08 0.83; 4.06 4.05; 4.05 1.34; 4.01 3.93; 3.96 1.91; 2.28 0.46; 2.25 1.37; 2.21 16.00; 1.61 0.39; 1.60 0.43; 1.47 4.84; 1.47 0.50; 1.45 9.90; 1.44 4.80; 1.43 2.00; 1.41 0.84; 1.39 0.42; 1.26 0.91; 0.00 6.04 |
| 4.075 | 3,5-$F_2$—Ph | H | S | H | $CH_2$ | 1-ethyl-3-methyl-1H-pyrazol-4-yl | |
| 4.076 | 3-Br-5-F—Ph | H | O | H | $CH_2$ | 1-ethyl-3-methyl-1H-pyrazol-4-yl | |
| 4.077 | 3-Cl-5-CN—Ph | H | O | H | $CH_2$ | 1-ethyl-3-methyl-1H-pyrazol-4-yl | |
| 4.078 | 3-Cl-5-Me—Ph | H | O | H | $CH_2$ | 1-ethyl-3-methyl-1H-pyrazol-4-yl | |
| 4.079 | 3-Cl-5—$CF_3O$—Ph | H | O | H | $CH_2$ | 1-ethyl-3-methyl-1H-pyrazol-4-yl | |
| 4.080 | 3-cPr-5-F—Ph | H | O | H | $CH_2$ | 1-ethyl-3-methyl-1H-pyrazol-4-yl | |

TABLE 4-continued

Compounds of the general formula (I) according to the invention in which $R^2$ is hydrogen and $R^3$ is cyano and aryl is the radical

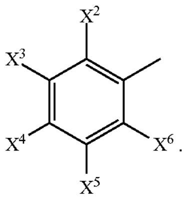

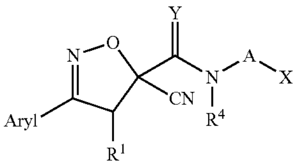

| No. | Aryl | $R^1$ | Y | $R^4$ | A | X | Physical data |
|---|---|---|---|---|---|---|---|
| 4.081 | 3-F-5-Me—Ph | H | O | H | $CH_2$ | 1-ethyl-3-methyl-1H-pyrazol-4-yl | |
| 4.082 | 3-F—Ph | H | O | H | $CH_2$ | 1-ethyl-3-methyl-1H-pyrazol-4-yl | |
| 4.083 | 3-Me—Ph | H | O | H | $CH_2$ | 1-ethyl-3-methyl-1H-pyrazol-4-yl | |
| 4.084 | 3,5-$F_2$—Ph | H | O | H | $CH_2$ | 1-ethyl-3-methyl-1H-pyrazol-5-yl | |
| 4.085 | 3,5-$F_2$—Ph | H | O | H | $CH_2$ | 1-isobutyl-1H-pyrazol-4-yl | |
| 4.086 | 3,5-$F_2$—Ph | H | O | H | $CH_2$ | 1-isopropyl-1H-pyrazol-4-yl | |
| 4.087 | 3-F—Ph | H | O | H | $CH_2$ | 1-isopropyl-1H-pyrazol-4-yl | |
| 4.088 | 3-Me—Ph | H | O | H | $CH_2$ | 1-methyl-1H-pyrazol-4-yl | |
| 4.089 | 3,5-$F_2$—Ph | H | O | H | $CH_2$ | 1-methyl-1H-pyrazol-5-yl | |
| 4.090 | 3-F—Ph | H | O | H | $CH_2$ | 1-methyl-1H-pyrazol-5-yl | |
| 4.091 | 3,5-$F_2$—Ph | H | O | H | $CH_2$ | 1-propyl-1H-pyrazol-4-yl | |
| 4.092 | 3,5-$F_2$—Ph | H | O | H | $CH_2$ | 1-tert-butyl-1H-pyrazol-4-yl | |
| 4.093 | 3,5-$F_2$—Ph | H | O | H | $CH_2$ | 2-chloropyridin-4-yl | [$CDCl_3$] 4.09 (AB, 2H); 4.51 (dd, 1H); 4.47 (dd, 1H); 7.00 (m, 1H); 7.13 (m, 2H); 7.19 (m, 4H); 8.39 (d, 1H). |
| 4.094 | 3-F—Ph | H | O | H | $CH_2$ | 2-chloropyridin-4-yl | |
| 4.095 | 3,5-$F_2$—Ph | H | O | H | $CH_2$ | 3-chloro-1-ethyl-1H-pyrazol-4-yl | |
| 4.096 | 3-F—Ph | H | O | H | $CH_2$ | 3-chloro-1-ethyl-1H-pyrazol-4-yl | |
| 4.097 | 3,5-F2—Ph | H | O | H | $CH_2$ | 3-chloro-1-isopropyl-1H-pyrazol-4-yl | |
| 4.098 | 3,5-$F_2$—Ph | H | O | H | $CH_2$ | 3-methyl-1-propyl-1H-pyrazol-4-yl | |
| 4.099 | 3-Cl-5-$CF_3$O—Ph | H | O | H | $CH_2$ | 3-methyl-1-propyl-1H-pyrazol-4-yl | |
| 4.100 | 3-Cl-5-F—Ph | H | O | H | $CH_2$ | 3-methyl-1-propyl-1H-pyrazol-4-yl | |
| 4.101 | 3-F-5-Me—Ph | H | O | H | $CH_2$ | 3-methyl-1-propyl-1H-pyrazol-4-yl | |
| 4.102 | 3-F—Ph | H | O | H | $CH_2$ | 3-methyl-1-propyl-1H-pyrazol-4-yl | |
| 4.103 | 3-Me—Ph | H | O | H | $CH_2$ | 3-methyl-1-propyl-1H-pyrazol-4-yl | |

TABLE 4-continued

Compounds of the general formula (I) according to the invention in which $R^2$ is hydrogen and $R^3$ is cyano and aryl is the radical

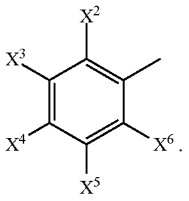

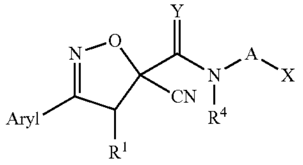

| No. | Aryl | $R^1$ | Y | $R^4$ | A | X | Physical data |
|---|---|---|---|---|---|---|---|
| 4.104 | 3-F—Ph | H | O | H | $CH_2$ | 5-methyl-1-propyl-1H-pyrazol-4-yl | |
| 4.105 | 3,5-$F_2$—Ph | H | O | H | $CH_2CH_2$ | 1-(2,2,2-trifluoroethyl)-1H-pyrazol-4-yl | |
| 4.106 | 3,5-$F_2$—Ph | H | O | H | $CH_2CH_2$ | 1-(2-chloroethyl)-1H-pyrazol-4-yl | |
| 4.107 | 3,5-$F_2$—Ph | H | O | H | $CH_2CH_2$ | 1,3-dimethyl-1H-pyrazol-4-yl | |
| 4.108 | 3-F—Ph | H | O | H | $CH_2CH_2$ | 1,3-dimethyl-1H-pyrazol-4-yl | |
| 4.109 | 3,5-$F_2$—Ph | H | O | H | $CH_2CH_2$ | 1,3-dimethyl-1H-pyrazol-5-yl | |
| 4.110 | 3,5-$F_2$—Ph | H | O | H | $CH_2CH_2$ | 1,5-dimethyl-1H-pyrazol-4-yl | |
| 4.111 | 3,5-$F_2$—Ph | H | O | H | $CH_2CH_2$ | 1-butyl-3-methyl-1H-pyrazol-4-yl | |
| 4.112 | 3,5-$F_2$—Ph | H | O | H | $CH_2CH_2$ | 1-butyl-5-methyl-1H-pyrazol-4-yl | |
| 4.113 | 3,5-$F_2$-Ph | H | 0 | H | $CH_2CH_2$ | 1- c-Pr-1H-pyrazol-4-yl | |
| 4.114 | Ph | H | O | H | $CH_2CH_2$ | 1-c-Pr-1H-pyrazol-4-yl | |
| 4.115 | 3-F—Ph | H | O | H | $CH_2CH_2$ | 1-c-Pr-1H-pyrazol-4-yl | |
| 4.116 | 3,5-$Cl_2$—Ph | O | H | H | $CH_2CH_2$ | 1-c-Pr-1H-pyrazol-4-yl | |
| 4.117 | 3,5-$Cl_2$—Ph | H | O | H | $CH_2CH_2$ | 1-ethyl-1H-pyrazol-4-yl | |
| 4.118 | 3-F—Ph | H | O | H | $CH_2CH_2$ | 1-ethyl-1H-pyrazol-4-yl | |
| 4.119 | 3,5-$F_2$—Ph | H | O | H | $CH_{2C}H_2$ | 1-ethyl-1H-pyrazol-4-yl | |
| 4.120 | 3-Br-5-$CF_3$—Ph | H | O | H | CH2CH2 | 1-ethyl-1H-pyrazol-4-yl | |
| 4.121 | 3-Me—Ph | H | O | H | $CH_2CH_2$ | 1-ethyl-1H-pyrazol-4-yl | |
| 4.122 | 3-F-5-MeO—Ph | H | O | H | $CH_2CH_2$ | 1-ethyl-1H-pyrazol-4-yl | |
| 4.123 | 3,5-$F_2$—Ph | H | O | H | $CH_2CH_2$ | 1-ethyl-1H-pyrazol-5-yl | |
| 4.124 | 3,5-$F_2$—Ph | H | O | H | $CH_2CH_2$ | 1-ethyl-3-methyl-1H-pyrazol-4-yl | |
| 4.125 | 3-Me—Ph | H | O | H | $CH_2CH_2$ | 1-ethyl-3-methyl-1H-pyrazol-4-yl | |
| 4.126 | 3-Br-5-F—Ph | H | O | H | $CH_2CH_2$ | 1-ethyl-3-methyl-1H-pyrazol-4-yl | |
| 4.127 | 3,4,5-$F_3$—Ph | H | O | H | $CH_2CH_2$ | 1-ethyl-3-methyl-1H-pyrazol-4-yl | |
| 4.128 | 3,4-$F_2$—Ph | H | O | H | $CH_2CH_2$ | 1-ethyl-3-methyl-1H-pyrazol-4-yl | |
| 4.129 | 3,5-$F_2$—Ph | H | S | H | $CH_2CH_2$ | 1-ethyl-3-methyl-1H-pyrazol-4-yl | |
| 4.130 | 3-F-5-Me—Ph | O | H | H | $CH_2CH_2$ | 1-ethyl-3-methyl-1H-pyrazol-4-yl | |

TABLE 4-continued

Compounds of the general formula (I) according to the invention in which $R^2$ is hydrogen and $R^3$ is cyano and aryl is the radical

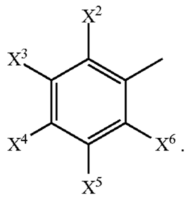

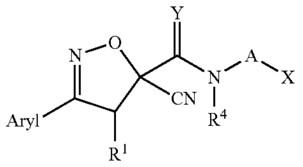

| No. | Aryl | $R^1$ | Y | $R^4$ | A | X | Physical data |
|---|---|---|---|---|---|---|---|
| 4.131 | 3-Cl-5-CN—Ph | H | O | H | $CH_2CH_2$ | 1-ethyl-3-methyl-1H-pyrazol-4-yl | |
| 4.132 | 3-F—Ph | H | O | H | $CH_2CH_2$ | 1-ethyl-3-methyl-1H-pyrazol-4-yl | |
| 4.133 | 3-cPr-5-F—Ph | H | O | H | $CH_2CH_2$ | 1-ethyl-3-methyl-1H-pyrazol-4-yl | |
| 4.134 | 3-Cl-5-Me—Ph | H | O | H | $CH_2CH_2$ | 1-ethyl-3-methyl-1H-pyrazol-4-yl | |
| 4.135 | 3-Cl-5-$CF_3O$—Ph | H | O | H | $CH_2CH_2$ | 1-ethyl-3-methyl-1H-pyrazol-4-yl | |
| 4.136 | 3,5-$F_2$—Ph | H | O | H | $CH_2CH_2$ | 1-ethyl-3-methyl-1H-pyrazol-5-yl | |
| 4.137 | 3,5-$F_2$—Ph | H | O | H | CH2CH2 | 1-isobutyl-1H-pyrazol-4-yl | |
| 4.138 | 3,5-$F_2$—Ph | H | O | H | $CH_2CH_2$ | 1-isopropyl-1H-pyrazol-4-yl | |
| 4.139 | 3-F—Ph | H | O | H | $CH_2CH_2$ | 1-isopropyl-1H-pyrazol-4-yl | |
| 4.140 | 3-Me—Ph | H | O | H | $CH_2CH_2$ | 1-methyl-1H-pyrazol-4-yl | |
| 4.141 | 3,5-$F_2$—Ph | H | O | H | $CH_2CH_2$ | 1-methyl-1H-pyrazol-5-yl | |
| 4.142 | 3-F—Ph | H | O | H | $CH_2CH_2$ | 1-methyl-1H-pyrazol-5-yl | |
| 4.143 | 3,5-$F_2$—Ph | H | O | H | $CH_2CH_2$ | 1-propyl-1H-pyrazol-4-yl | |
| 4.144 | 3,5-$F_2$—Ph | H | O | H | $CH_2CH_2$ | 1-tert-butyl-1H-pyrazol-4-yl | |
| 4.145 | 3,5-$F_2$—Ph | H | O | H | $CH_2CH_2$ | 2-chloropyridin-4-yl | |
| 4.146 | 3-F—Ph | H | O | H | $CH_2CH_2$ | 2-chloropyridin-4-yl | |
| 4.147 | 3,5-$F_2$—Ph | H | O | H | $CH_2CH_2$ | 3-chloro-1-ethyl-1H-pyrazol-4-yl | |
| 4.148 | 3-F—Ph | H | O | H | $CH_2CH_2$ | 3-chloro-1-ethyl-1H-pyrazol-4-yl | |
| 4.149 | 3,5-$F_2$—Ph | H | O | H | $CH_2CH_2$ | 3-chloro-1-isopropyl-1H-pyrazol-4-yl | |
| 4.150 | 3-F—Ph | H | O | H | $CH_2CH_2$ | 3-methyl-1-propyl-1H-pyrazol-4-yl | |
| 4.151 | 3,5-$F_2$—Ph | H | O | H | $CH_2CH_2$ | 3-methyl-1-propyl-1H-pyrazol-4-yl | |
| 4.152 | 3-Cl-5-F—Ph | H | O | H | $CH_2CH_2$ | 3-methyl-1-propyl-1H-pyrazol-4-yl | |
| 4.153 | 3-Cl-5-CF3O—Ph | H | O | H | $CH_2CH_2$ | 3-methyl-1-propyl-1H-pyrazol-4-yl | |
| 4.154 | 3-F-5-Me—Ph | H | O | H | $CH_2CH_2$ | 3-methyl-1-propyl-1H-pyrazol-4-yl | |

TABLE 4-continued

Compounds of the general formula (I) according to the invention in which $R^2$ is hydrogen and $R^3$ is cyano and aryl is the radical

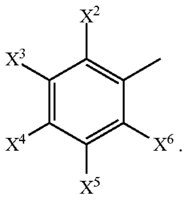

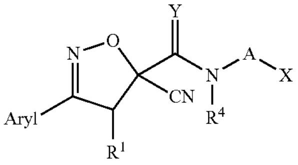

| No. | Aryl | $R^1$ | Y | $R^4$ | A | X | Physical data |
|---|---|---|---|---|---|---|---|
| 4.155 | 3-Me—Ph | H | O | H | $CH_2CH_2$ | 3-methyl-1-propyl-1H-pyrazol-4-yl | |
| 4.156 | 3-F—Ph | H | O | H | $CH_2CH_2$ | 5-methyl-1-propyl-1H-pyrazol-4-yl | |
| 4.157 | 3,5-$F_2$—Ph | H | O | H | $CHCH_3$ | 1-(2,2,2-trifluoroethyl)-1H-pyrazol-4-yl | |
| 4.158 | 3,5-$F_2$—Ph | H | O | H | $CHCH_3$ | 1-(2-chloroethyl)-1H-pyrazol-4-yl | |
| 4.159 | 3,5-$F_2$—Ph | H | O | H | $CHCH_3$ | 1,3-dimethyl-1H-pyrazol-4-yl | |
| 4.160 | 3-F—Ph | H | O | H | $CHCH_3$ | 1,3-dimethyl-1H-pyrazol-4-yl | |
| 4.161 | 3,5-$F_2$-Ph | H | O | H | $CHCH_3$ | 1,3-dimethyl-1H-pyrazol-5-yl | |
| 4.162 | 3,5-$F_2$—Ph | H | O | H | $CHCH_3$ | 1,5-dimethyl-1H-pyrazol-4-yl | |
| 4.163 | 3,5-$F_2$—Ph | H | O | H | $CHCH_3$ | 1-butyl-3-methyl-1H-pyrazol-4-yl | |
| 4.164 | 3,5-$F_2$—Ph | H | O | H | $CHCH_3$ | 1-butyl-5-methyl-1H-pyrazol-4-yl | |
| 4.165 | 3,5-$F_2$—Ph | H | O | H | $CHCH_3$ | 1-c-Pr-1H-pyrazol-4-yl | |
| 4.166 | Ph | H | O | H | $CHCH_3$ | 1-c-Pr-1H-pyrazol-4-yl | |
| 4.167 | 3-F—Ph | H | O | H | $CHCH_3$ | 1-c-Pr-1H-pyrazol-4-yl | |
| 4.168 | 3,5-$Cl_2$—Ph | H | O | H | $CHCH_3$ | 1-c-Pr-1H-pyrazol-4-yl | |
| 4.169 | 3,5-$Cl_2$-Ph | H | O | H | $CHCH_3$ | 1-ethyl-1H-pyrazol-4-yl | |
| 4.170 | 3-F—Ph | H | O | H | $CHCH_3$ | 1-ethyl-1H-pyrazol-4-yl | |
| 4.171 | 3,5-$F_2$—Ph | H | O | H | $CHCH_3$ | 1-ethyl-1H-pyrazol-4-yl | |
| 4.172 | 3-Br-5-$CF_3$—Ph | H | O | H | $CHCH_3$ | 1-ethyl-1H-pyrazol-4-yl | |
| 4.173 | 3-Me—Ph | H | O | H | $CHCH_3$ | 1-ethyl-1H-pyrazol-4-yl | |
| 4.174 | 3-F-5-MeO—Ph | H | O | H | $CHCH_3$ | 1-ethyl-1H-pyrazol-4-yl | |
| 4.175 | 3,5-$F_2$—Ph | H | O | H | $CHCH_3$ | 1-ethyl-1H-pyrazol-5-yl | |
| 4.176 | 3,5-$F_2$—Ph | H | O | H | $CHCH_3$ | 1-ethyl-3-methyl-1H-pyrazol-4-yl | |
| 4.177 | 3-Me—Ph | H | O | H | $CHCH_3$ | 1-ethyl-3-methyl-1H-pyrazol-4-yl | |
| 4.178 | 3-Br-5-F—Ph | O | H | H | $CHCH_3$ | 1-ethyl-3-methyl-1H-pyrazol-4-yl | |
| 4.179 | 3,4,5-$F_3$—Ph | H | O | H | $CHCH_3$ | 1-ethyl-3-methyl-1H-pyrazol-4-yl | |
| 4.180 | 3,4-$F_2$—Ph | H | O | H | $CHCH_3$ | 1-ethyl-3-methyl-1H-pyrazol-4-yl | |

TABLE 4-continued

Compounds of the general formula (I) according to the invention in which $R^2$ is hydrogen and $R^3$ is cyano and aryl is the radical

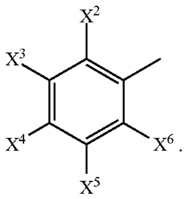

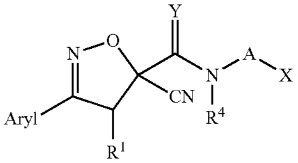

| No. | Aryl | $R^1$ | Y | $R^4$ | A | X | Physical data |
|---|---|---|---|---|---|---|---|
| 4.181 | 3,5-$F_2$-Ph | H | S | H | $CHCH_3$ | 1-ethyl-3-methyl-1H-pyrazol-4-yl | |
| 4.182 | 3-F-5-Me—Ph | H | O | H | $CHCH_3$ | 1-ethyl-3-methyl-1H-pyrazol-4-yl | |
| 4.183 | 3-Cl-5-CN—Ph | H | O | H | $CHCH_3$ | 1-ethyl-3-methyl-1H-pyrazol-4-yl | |
| 4.184 | 3-F—Ph | H | O | H | $CHCH_3$ | 1-ethyl-3-methyl-1H-pyrazol-4-yl | |
| 4.185 | 3-cPr-S—F—Ph | O | H | H | $CHCH_3$ | 1-ethyl-3-methyl-1H-pyrazol-4-yl | |
| 4.186 | 3-Cl-5-Me—Ph | O | H | H | $CHCH_3$ | 1-ethyl-3-methyl-1H-pyrazol-4-yl | |
| 4.187 | 3-Cl-5-$CF_3$O—Ph | O | H | H | $CHCH_3$ | 1-ethyl-3-methyl-1H-pyrazol-4-yl | |
| 4.188 | 3,5-F2—Ph | H | O | H | $CHCH_3$ | 1-ethyl-3-methyl-1H-pyrazol-S-yl | |
| 4.189 | 3,5-F2—Ph | H | O | H | $CHCH_3$ | 1-isobutyl-1H-pyrazol-4-yl | |
| 4.190 | 3,5-F2—Ph | H | O | H | $CHCH_3$ | 1-isopropyl-1H-pyrazol-4-yl | |
| 4.191 | 3-F—Ph | H | O | H | $CHCH_3$ | 1-isopropyl-1H-pyrazol-4-yl | |
| 4.192 | 3-Me—Ph | H | O | H | $CHCH_3$ | 1-methyl-1H-pyrazol-4-yl | |
| 4.193 | 3,5-$F_2$—Ph | H | O | H | $CHCH_3$ | 1-methyl-1H-pyrazol-S-yl | |
| 4.194 | 3-F—Ph | H | O | H | $CHCH_3$ | 1-methyl-1H-pyrazol-5-yl | |
| 4.195 | 3,5-$F_2$—Ph | H | O | H | $CHCH_3$ | 1-propyl-1H-pyrazol-4-yl | |
| 4.196 | 3,5-$F_2$—Ph | H | O | H | $CHCH_3$ | 1-tert-butyl-1H-pyrazol-4-yl | |
| 4.197 | 3,5-$F_2$—Ph | H | O | H | $CHCH_3$ | 2-chloropyridin-4-yl | |
| 4.198 | 3-F—Ph | H | O | H | $CHCH_3$ | 2-chloropyridin-4-yl | |
| 4.199 | 3,5-$F_2$—Ph | H | O | H | $CHCH_3$ | 3-chloro-1-ethyl-1H-pyrazol-4-yl | |
| 4.200 | 3-F—Ph | H | O | H | $CHCH_3$ | 3-chloro-1-ethyl-1H-pyrazol-4-yl | |
| 4.201 | 3,5-$F_2$-Ph | H | O | H | $CHCH_3$ | 3-chloro-1-isopropyl-1H-pyrazol-4-yl | |
| 4.202 | 3-F—Ph | H | O | H | $CHCH_3$ | 3-methyl-1-propyl-1H-pyrazol-4-yl | |
| 4.203 | 3,5-$F_2$—Ph | H | O | H | $CHCH_3$ | 3-methyl-1-propyl-1H-pyrazol-4-yl | |
| 4.204 | 3-Cl-5-F—Ph | H | O | H | $CHCH_3$ | 3-methyl-1-propyl-1H-pyrazol-4-yl | |
| 4.205 | 3-Cl-5-$CF_3$O—Ph | H | O | H | $CHCH_3$ | 3-methyl-1-propyl-1H-pyrazol-4-yl | |

TABLE 4-continued

Compounds of the general formula (I) according to the invention in which $R^2$ is hydrogen and $R^3$ is cyano and aryl is the radical

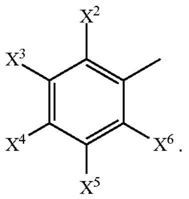

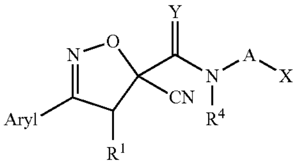

| No. | Aryl | $R^1$ | Y | $R^4$ | A | X | Physical data |
|---|---|---|---|---|---|---|---|
| 4.206 | 3-F-5-Me—Ph | H | O | H | $CHCH_3$ | 3-methyl-1-propyl-1H-pyrazol-4-yl | |
| 4.207 | 3-Me—Ph | H | O | H | $CHCH_3$ | 3-methyl-1-propyl-1H-pyrazol-4-yl | |
| 4.208 | 3-F—Ph | H | O | H | $CHCH_3$ | 5-methyl-1-propyl-1H-pyrazol-4-yl | |
| 4.209 | 3,5-$F_2$—Ph | H | O | H | $CH_2$ | 2,6-dimethylpyridin-4-yl | |
| 4.210 | 3,5-$F_2$—Ph | H | O | H | $CH_2$ | 2-chloropyridin-3-yl | |
| 4.211 | 3,5-$F_2$—Ph | H | O | H | $CH_2$ | 2-fluoropyrid in-4-yl | [$CDCl_3$] 4.05 (d, 1H); 4.16 (d, 1H); 4.53 (dd, 1H); 4.62 (dd, 1H); 6.61 (s, 1H); 6.98 (m, 1H); 7.07 (d, 1H); 7.17 (m, 2H); 7.28 (s, br, 1H); 8.23 (d, 1H). |
| 4.212 | 3,5-$F_2$—Ph | H | O | H | $CH_2$ | 2-methoxypyridin-4-yl | [$CDCl_3$] 3.92 (s, 3H); 4.08 (AB, 2H); 4.48 (ABd, 2H); 6.59 (s, 1H); 6.74 (d, 1H); 6.98 (m, 1H); 7.09 (t br, 1H); 7.18 (m ,2H); 8.14 (d, 1H). |
| 4.213 | 3,5-$F_2$—Ph | H | O | H | $CH_2$ | 2-tert-butylpyridin-4-yl | |
| 4.214 | 3,5-$F_2$—Ph | H | O | H | $CH_2$ | 3,5-dimethyl-1,2-oxazol-4-yl | |
| 4.215 | 3,5-$F_2$—Ph | H | O | H | $CH_2$ | 6-chloropyridin-3-yl | |

TABLE 5

Compounds of the general formula (I) according to the invention in which $R^2$ is hydrogen and aryl is the radical

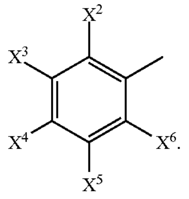

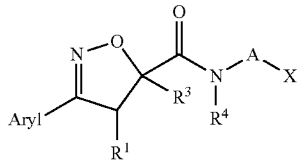

| No. | Aryl | $R^1$ | $R^3$ | Y | $R^4$ | A | X | Physical data |
|---|---|---|---|---|---|---|---|---|
| 5.001 | Ph | H | $C(OH)CH(CH_3)_2$ | O | H | $CH_2$ | 1-ethyl-3-methyl-1H-pyrazol-4-yl | |
| 5.002 | 2,4-$Cl_2$—Ph | H | $C(OH)CH(CH_3)_2$ | O | H | $CH_2$ | 1-ethyl-3-methyl-1H-pyrazol-4-yl | |
| 5.003 | 4-Cl—Ph | H | $C(OH)CH(CH_3)_2$ | O | H | $CH_2$ | 1-ethyl-3-methyl-1H-pyrazol-4-yl | |
| 5.004 | 3-Cl—Ph | H | $CH(CH_3)OH$ | O | H | $CH_2$ | 1-ethyl-3-methyl-1H-pyrazol-4-yl | |
| 5.005 | 2,4-$Cl_2$—Ph | H | $CH(CH_3)OH$ | O | H | $CH_2$ | 1-ethyl-3-methyl-1H-pyrazol-4-yl | |
| 5.006 | Ph | H | $CH(CH_3)OH$ | O | H | $CH_2$ | 1-ethyl-3-methyl-1H-pyrazol-4-yl | |
| 5.007 | 2-$CF_3$—Ph | H | $CH(CH_3)OH$ | O | H | $CH_2$ | 1-ethyl-3-methyl-1H-pyrazol-4-yl | |
| 5.008 | 3,5-$Cl_2$—Ph | H | $CH(CH_3)OH$ | O | H | $CH_2$ | 1-ethyl-3-methyl-1H-pyrazol-4-yl | |
| 5.009 | 4-Cl—Ph | H | $CH(CH_3)OH$ | O | H | $CH_2$ | 1-ethyl-3-methyl-1H-pyrazol-4-yl | |
| 5.010 | 3-Cl—Ph | H | $C(OCH_3)CH(CH_3)_2$ | O | H | $CH_2$ | 1-ethyl-3-methyl-1H-pyrazol-4-yl | |
| 5.011 | Ph | H | $CH(CH_3)OCH_3$ | O | H | $CH_2$ | 1-ethyl-3-methyl-1H-pyrazol-4-yl | |
| 5.012 | 3-Cl—Ph | H | $CH(CH_3)OCH_3$ | O | H | $CH_2$ | 1-ethyl-3-methyl-1H-pyrazol-4-yl | |
| 5.013 | 4-Cl—Ph | H | $CH(CH_3)OCH_3$ | O | H | $CH_2$ | 1-ethyl-3-methyl-1H-pyrazol-4-yl | |
| 5.014 | 3,5-$Cl_2$—Ph | H | $CH(CH_3)OCH_3$ | O | H | $CH_2$ | 1-ethyl-3-methyl-1H-pyrazol-4-yl | |
| 5.015 | 2-$CF_3$—Ph | H | $CH(CH_3)OCH_3$ | O | H | $CH_2$ | 1-ethyl-3-methyl-1H-pyrazol-4-yl | |
| 5.016 | 2,4-$Cl_2$—Ph | H | $CH(CH_3)OCH_3$ | O | H | $CH_2$ | 1-ethyl-3-methyl-1H-pyrazol-4-yl | |
| 5.017 | 3,5-$Cl_2$—Ph | H | $(CH_2)_2OCH_3$ | O | H | $CH_2$ | 1-ethyl-3-methyl-1H-pyrazol-4-yl | [$CDCl_3$] 1.42 (t, 3H); 2.20 (s, 3H); 2.25 (m, 1H); 2.35 (m, 1H); 3.26 (s, 3H); 3.47 (d, 1H); 3.52 (m, 2H); 3.70 (d, 1H); 4.06 (q, 2H); 4.18 (dd, 1H); 4.31 (dd, 1H); 6.85 (t br, 1H); 7.43 (s, 1H); 7.52 (s, 2H). |
| 5.018 | 3,5-$Cl_2$—Ph | H | cPr | O | H | $CH_2$ | 1-ethyl-3-methyl-1H-pyrazol-4-yl | [$CDCl_3$] 0.55 (m, 4H); 1.44 (t, 3H); 1.57 (m, 1H), 2.21 (s, 3H); 3.35 (d, 1H); 3.82 (d, 1H); 4.08 (q, 2H); 4.18 (dd, 1H); 4.35 (dd, 1H); 6.74 (t br, 1H); 7.42 (s, 1H); 7.50 (s, 2H) |

TABLE 5-continued

Compounds of the general formula (I) according to the invention in which $R^2$ is hydrogen and aryl is the radical

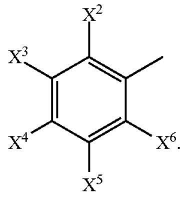

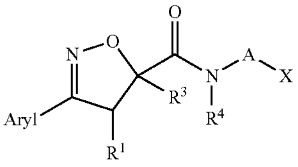

| No. | Aryl | $R^1$ | $R^3$ | Y | $R^4$ | A | X | Physical data |
|---|---|---|---|---|---|---|---|---|
| 5.019 | 3,5-$Cl_2$—Ph | H | $CH_2OH$ | O | H | $CH_2$ | 1-ethyl-3-methyl-1H-pyrazol-4-yl | |
| 5.020 | 3-Cl—Ph | H | $CH_2OH$ | O | H | $CH_2$ | 1-ethyl-3-methyl-1H-pyrazol-4-yl | |
| 5.021 | 4-Cl—Ph | H | $CH_2OH$ | O | H | $CH_2$ | 1-ethyl-3-methyl-1H-pyrazol-4-yl | |
| 5.022 | Ph | H | $CH_2OH$ | O | H | $CH_2$ | 1-ethyl-3-methyl-1H-pyrazol-4-yl | |
| 5.023 | 2-$CF_3$—Ph | H | $CH_2OH$ | O | H | $CH_2$ | 1-ethyl-3-methyl-1H-pyrazol-4-yl | |
| 5.024 | 2,4-$Cl_2$—Ph | H | $CH_2OH$ | O | H | $CH_2$ | 1-ethyl-3-methyl-1H-pyrazol-4-yl | |
| 5.025 | 4-Cl—Ph | H | $CH_2OCH_3$ | O | H | $CH_2$ | 1-ethyl-3-methyl-1H-pyrazol-4-yl | |
| 5.026 | 2,4-$Cl_2$—Ph | H | $CH_2OCH_3$ | O | H | $CH_2$ | 1-ethyl-3-methyl-1H-pyrazol-4-yl | |
| 5.027 | Ph | H | $CH_2OCH_3$ | O | H | $CH_2$ | 1-ethyl-3-methyl-1H-pyrazol-4-yl | |
| 5.028 | 3-Cl—Ph | H | $CH_2OCH_3$ | O | H | $CH_2$ | 1-ethyl-3-methyl-1H-pyrazol-4-yl | |
| 5.029 | 3,5-$Cl_2$—Ph | H | $CH_2OCH_3$ | O | H | $CH_2$ | 1-ethyl-3-methyl-1H-pyrazol-4-yl | |
| 5.030 | 3,5-$Cl_2$—Ph | H | iPr | O | H | $CH_2$ | 1-ethyl-3-methyl-1H-pyrazol-4-yl | [$CDCl_3$] 1.00 (t, 3H); 1.44 (t, 3H); 2.20 (s, 3H); 2.32 (m, 1H); 3.30 (d, 1H), 3.66 (d, 1H); 4.06 (q, 2H); 4.17 (dd, 1H); 4.32 (dd, 1H); 6.84 (t br, 1H); 7.21 (m, 1H); 7.52 (m, 2H) |
| 5.031 | 3,5-$F_2$—Ph | H | $CH_2F$ | O | H | $CH_2$ | 1-(2,2,2-trifluoroethyl)-1H-pyrazol-4-yl | [$CDCl_3$] 1.55 (s, 3H); 3.43 (d, 1H); 3.67 (d, 1H); 4.37 (AB d, 2H); 4.63 (d, 0.5H); 4.65 (q, 2H); 4.75 (m, 1H); 4.87 (d, 0.5H); 6.98 (m, 1H); 7.13 (m, 3H); 7.46 (s, 1H); 7.51 (s, 2H). |
| 5.032 | 3,5-$F_2$—Ph | H | F | O | H | $CH_2$ | 1-ethyl-1H-pyrazol-4-yl | [$CDCl_3$] 1.49 (t, 3H); 3.57 (dd, 1H); 4.16 (q, 2H); 4.21 (dd, 1H); 4.42 (m, 2H); 6.74 (s br, 1H); 6.94 (m, 1H); 7.22 (m, 2H); 7.42 (s, 1H); 7.48 (s, 1H). |

TABLE 5-continued

Compounds of the general formula (I) according to the invention in which $R^2$ is hydrogen and aryl is the radical

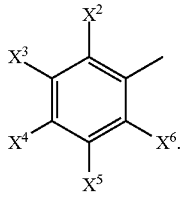

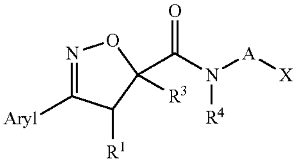

| No. | Aryl | $R^1$ | $R^3$ | Y | $R^4$ | A | X | Physical data |
|---|---|---|---|---|---|---|---|---|
| 5.033 | 3,5-$Cl_2$—Ph | H | F | O | H | $CH_2$ | 1-ethyl-1H-pyrazol-4-yl | [$CDCl_3$] 1.49 (t, 3H); 3.57 (dd, 1H); 4.18 (q, 2H); 4.20 (dd, 1H); 4.42 (m, 2H); 6.74 (s br, 1H); 7.42 (s, 1H); 7.47 (s, 1H); 7.48 (s, 1H); 7.57 (s, 2H). |
| 5.034 | 3,5-$F_2$—Ph | H | $CH_2F$ | O | H | $CH_2$ | 1-ethyl-1H-pyrazol-4-yl | [$CDCl_3$] 1.47 (t, 3H); 3.45 (d, 1H); 3.68 (d, 1H); 4.13 (q, 2H); 2.26 (dd, 1H); 4.40 (dd, 1H); 4.64 (d, 0.5H); 4.75 (m, 1H); 4.86 (0.5H); 6.90 (m, 1H); 7.05 (s br, 1H); 7.18 (m, 2H); 7.33 (s, 1H); 7.42 (s, 1H). |
| 5.035 | 3-F—Ph | H | $CH_2F$ | O | H | $CH_2$ | 1-ethyl-1H-pyrazol-4-yl | |
| 5.036 | 3,5-$F_2$—Ph | H | $CH_2Cl$ | O | H | $CH_2$ | 1-ethyl-1H-pyrazol-4-yl | [$CDCl_3$] 1.46 (t, 3H); 3.55 (d, 1H); 3.70 (d, 1H); 3.94 (d, 1H); 4.03 (d, 1H); 4.13 (q, 2H); 4.24 (dd, 1H); 4.42 (dd, 1H); 6.90 (m, 1H); 7.05 (s br, 1H); 7.16 (m, 2H); 7.35 (s, 1H); 7.42 (s, 1H). |
| 5.037 | 3,5-$Cl_2$—Ph | H | $CH_2Cl$ | O | H | $CH_2$ | 1-ethyl-1H-pyrazol-4-yl | [$CDCl_3$] 1.47 (t, 3H); 3.64 (AB, 2H); 3.99 (AB, 2H); 4.13 (q, 2H); 4.34 (AB d, 2H); 7.04 (t br, 1H); 7.36 (s, 1H); 7.42 (s, 1H); 7.43 (s, 1H); 7.52 (s, 2H). |
| 5.038 | 3,5-$F_2$—Ph | H | vinyl | O | H | $CH_2$ | 1-ethyl-1H-pyrazol-4-yl | [$CDCl_3$] 1.46 (t, 3H); 3.32 (d, 1H); 3.94 |

TABLE 5-continued

Compounds of the general formula (I) according to the invention in which $R^2$ is hydrogen and aryl is the radical

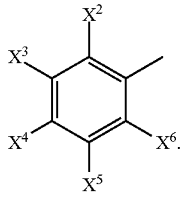

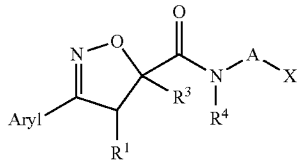

| No. | Aryl | $R^1$ | $R^3$ | Y | $R^4$ | A | X | Physical data |
|---|---|---|---|---|---|---|---|---|
| | | | | | | | | (d, 1H); 4.13 (q, 2H); 4.26 (dd, 1H); 4.38 (dd, 1H); 5.35 (d, 1H); 5.53 (d, 1H); 6.18 (dd, 1H); 6.90 (m, 1H); 6.94 (s br, 1H); 7.18 (m, 2H); 7.33 (s, 1H); 7.41 (s, 1H). |
| 5.039 | 3-F—Ph | H | $CH_2Cl$ | O | H | $CH_2$ | 1-ethyl-1H-pyrazol-4-yl | [$CDCl_3$] 1.46 (t, 3H); 3.65 (AB, 2H); 4.01 (AB, 2H); 4.14 (q, 2H); 4.34 (AB, 2H); 7.08 (s br, 1H); 7.15 (m, 1H); 7.39 (m, 5H). |
| 5.040 | 3,5-$F_2$—Ph | H | F | O | H | $CH_2$ | 1-ethyl-3-methyl-1H-pyrazol-4-yl | [$CDCl_3$] 1.47 (t, 3H); 2.27 (s, 3H); 3.56 (dd, 1H); 4.08 (q, 2H); 4.20 (dd, 1H); 4.37 (m, 2H); 6.61 (s br, 1H); 6.95 (m, 1H); 7.21 (m, 2H); 7.34 (s, 1H). |
| 5.041 | 3,5-$Cl_2$—Ph | H | F | O | H | $CH_2$ | 1-ethyl-3-methyl-1H-pyrazol-4-yl | [$CDCl_3$] 1.47 (t, 3H); 2.27 (s, 3H); 3.57 (dd, 1H); 4.08 (q, 2H); 4.19 (dd, 1H); 4.37 (m, 2H); 6.59 (s br, 1H); 7.34 (s, 1H); 7.48 (s, 1H); 7.57 (s, 2H). |
| 5.042 | 3-F—Ph | H | $CH_2F$ | O | H | $CH_2$ | 1-ethyl-3-methyl-1H-pyrazol-4-yl | [$CDCl_3$] 1.43 (t, 3H); 2.18 (s, 3H); 3.45 (d, 1H); 3.71 (d, 1H); 4.04 (q, 2H); 4.22 (dd, 1H); 4.34 (dd, 1H); 4.63 (d, 0.5H); 4.73 (d, 0.5H); 4.76 (d, 0.5H); 4.88 (d, 0.5H); 6.97 (s br, 1H); 7.16 |

TABLE 5-continued

Compounds of the general formula (I) according to the invention in which $R^2$ is hydrogen and aryl is the radical

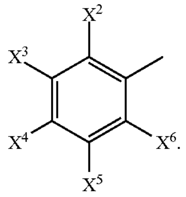

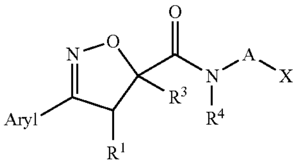

| No. | Aryl | $R^1$ | $R^3$ | Y | $R^4$ | A | X | Physical data |
|---|---|---|---|---|---|---|---|---|
| | | | | | | | | (m, 1H); 7.25 (s, 1H); 7.37 (m, 3H). |
| 5.043 | 3,5-$F_2$—Ph | H | $CH_2F$ | O | H | $CH_2$ | 1-ethyl-3-methyl-1H-pyrazol-4-yl | [$CDCl_3$] 1.44 (t, 3H); 2.19 (s, 3H); 3.43 (d, 1H); 3.68 (d, 1H); 4.06 (q, 2H); 4.21 (dd, 1H); 4.36 (dd, 1H); 4.64 (d, 0.5H); 4.75 (d, 1H); 4.88 (d, 0.5H); 6.43 (m, 2H); 7.17 (m, 2H). |
| 5.044 | 3,5-$Cl_2$—Ph | H | acetyl | O | H | $CH_2$ | 1-ethyl-3-methyl-1H-pyrazol-4-yl | |
| 5.045 | 3,5-$F_2$—Ph | H | acetyl | O | H | $CH_2$ | 1-ethyl-3-methyl-1H-pyrazol-4-yl | |
| 5.046 | 3,5-$Cl_2$—Ph | H | prop-1-en-2-yl | O | H | $CH_2$ | 1-ethyl-3-methyl-1H-pyrazol-4-yl | [$CDCl_3$] 1.44 (t, 3H); 1.84 (s, 3H); 2.19 (s, 3H); 3.34 (d, 1H); 4.02 (d, 1H); 4.07 (q, 2H); 4.19 (dd, 1H); 4.32 (dd, 1H); 5.08 (s, 1H); 5.27 (s, 1H); 6.76 (s br, 1H); 7.23 (s, 1H); 7.41 (s, 1H); 7.53 (s, 2H). |
| 5.047 | 3,5-$F_2$—Ph | H | prop-1-en-2-yl | O | H | $CH_2$ | 1-ethyl-3-methyl-1H-pyrazol-4-yl | [$CDCl_3$] 1.43 (t, 3H); 1.89 (s, 3H); 2.19 (s, 3H); 3.35 (d, 1H); 4.02 (d, 1H); 4.06 (q, 2H); 4.20 (dd, 1H); 4.33 (dd, 1H); 5.08 (s, 1H); 5.27 (s, 1H); 6.77 (t br, 1H); 6.87 (m, 1H); 7.17 (m, 1H); 7.24 (s, 1H); |
| 5.048 | 3,5-$F_2$—Ph | H | vinyl | O | H | $CH_2$ | 1-ethyl-3-methyl-1H-pyrazol-4-yl | [$CDCl_3$] 1.43 (t, 3H); 2.19 (s, 3H); 3.33 (d, 1H); 3.94 (d, 1H); 4.07 (q, 2H); 4.20 |

TABLE 5-continued

Compounds of the general formula (I) according to the invention in which $R^2$ is hydrogen and aryl is the radical

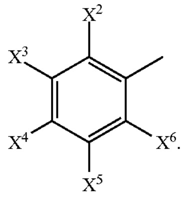

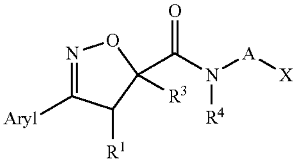

| No. | Aryl | $R^1$ | $R^3$ | Y | $R^4$ | A | X | Physical data |
|---|---|---|---|---|---|---|---|---|
| | | | | | | | | (dd, 1H); 4.33 (dd, 1H); 5.34 (d, 1H); 5.55 (d, 1H); 6.20 (dd, 1H); 6.81 (s br, 1H); 6.89 (m, 1H); 7.17 (m, 2H); 7.24 (s, 1H). |
| 5.049 | 3,5-$Cl_2$—Ph | H | $CH_2Cl$ | O | H | $CH_2$ | 1-ethyl-3-methyl-1H-pyrazol-4-yl | [$CDCl_3$] 1.42 (t, 3H); 2.20 (s, 3H); 3.55 (d, 1H); 3.71 (d, 1H); 3.94 (d, 1H); 4.03 (d, 1H); 4.07 (q, 2H); 4.20 (dd, 1H); 4.34 (dd, 1H); 6.91 (s br, 1H); 7.44 (s, 1H); 7.52 (s, 2H). |
| 5.050 | 3,5-$F_2$—Ph | H | $CH_2Cl$ | O | H | $CH_2$ | 1-ethyl-3-methyl-1H-pyrazol-4-yl | [$CDCl_3$] 1.44 (t, 3H); 2.20 (s, 3H); 3.55 (d, 1H); 3.72 (d, 1H); 3.95 (d, 1H); 4.05 (d, 1H); 4.07 (q, 2H); 4.21 (dd, 1H); 4.36 (dd, 1H); 6.92 (m, 2H); 7.15 (m, 2H); 7.27 (s, 1H). |
| 5.051 | 3-F—Ph | H | $CH_2Cl$ | O | H | $CH_2$ | 1-ethyl-3-methyl-1H-pyrazol-4-yl | [$CDCl_3$] 1.44 (t, 3H); 2.19 (s, 3H); 3.57 (d, 1H); 3.73 (d, 1H); 3.84 (d, 1H); 4.04 (d, 1H); 4.05 (q, 2H); 4.20 (dd, 1H); 4.36 (dd, 1H); 6.96 (s br, 1H); 7.15 (m, 1H); 7.38 (m, 3H). |
| 5.052 | 3,5-$Cl_2$—Ph | H | vinyl | O | H | $CH_2$ | 1-ethyl-3-methyl-1H-pyrazol-4-yl | [$CDCl_3$] 1.44 (t, 3H); 2.18 (s, 3H); 3.32 (d, 1H); 3.94 (d, 1H); 4.03 (q, 2H); 4.20 (dd, 1H); 4.33 (dd, 1H); 5.33 |

TABLE 5-continued

Compounds of the general formula (I) according to the invention in which $R^2$ is hydrogen and aryl is the radical

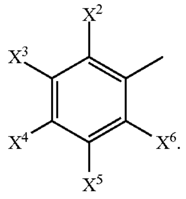

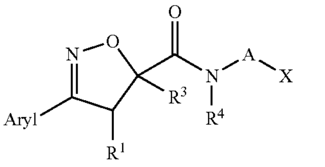

| No. | Aryl | $R^1$ | $R^3$ | Y | $R^4$ | A | X | Physical data |
|---|---|---|---|---|---|---|---|---|
| | | | | | | | | (d, 1H); 5.52 (d, 1H); 6.16 (dd, 1H); 6.80 (t br, 1H); 7.24 (s, 1H); 7.42 (s, 1H); 7.52 (s, 2H). |
| 5.053 | 3,5-$F_2$—Ph | H | $CH_2Cl$ | O | H | $CH_2$ | 2-bromopyridin-4-yl | [$CDCl_3$] 3.54 (d, 1H); 3.73 (d, 1H); 3.95 (d, 1H); 4.11 (d, 1H); 4.35 (dd, 1H); 4.60 (dd, 1H); 6.93 (m, 1H); 7.18 (m, 2H); 7.39 (m, 2H); 8.33 (d, 1H). |
| 5.054 | 3,5-$F_2$—Ph | H | $CH_2F$ | O | H | $CH_2$ | 2-bromopyridin-4-yl | [$CDCl_3$] 1.56 (s, 3H); 3.42 (d, 1H); 3.71 (d, 1H); 4.47 (AB d, 2H); 4.85 (AB, 1H); 4.74 (AB, 1H); 6.91 (m, 1H); 7.12 (d, 1H); 7.18 (m, 2H); 7.35 (s, 1H); 7.39 (t br, 1H); 8.31 (d, 1H). |
| 5.055 | 3,5-$Cl_2$—Ph | H | $CH_2Cl$ | O | H | $CH_2$ | 2-bromopyridin-4-yl | [$CDCl_3$] 3.54 (d, 1H); 3.73 (d, 1H); 3.93 (d, 1H); 4.10 (d, 1H); 4.33 (dd, 1H); 4.58 (dd, 1H); 7.14 (d, 1H); 7.38 (s, 2H); 7.45 (s, 1H); 7.54 (s, 2H); 8.32 (d, 1H). |
| 5.056 | 3-F—Ph | H | $CH_2Cl$ | O | H | $CH_2$ | 2-bromopyridin-4-yl | [$CDCl_3$] 3.56 (d, 1H); 3.76 (d, 1H); 3.94 (d, 1H); 4.12 (d, 1H); 4.34 (dd, 1H); 4.61 (dd, 1H); 7.18 (m, 2H); 7.40 (m, 5H); 8.31 (d, 1H). |
| 5.057 | 3,5-$F_2$—Ph | H | F | O | H | $CH_2$ | 2-chloropyridin-4-yl | [$CDCl_3$] 3.62 (dd, 1H); 4.25 (dd, 1H); 4.57 (m, 2H); 6.95 |

TABLE 5-continued

Compounds of the general formula (I) according to the invention in which $R^2$ is hydrogen and aryl is the radical

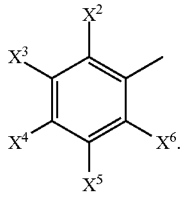

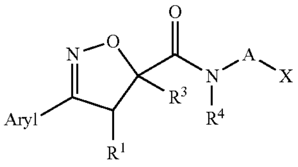

| No. | Aryl | $R^1$ | $R^3$ | Y | $R^4$ | A | X | Physical data |
|---|---|---|---|---|---|---|---|---|
| | | | | | | | | (m, 1H); 7.03 (s br, 1H); 7.15 (d, 1H); 7.25 (m, 3H); 8.40 (d, 1H). |
| 5.058 | 3,5-$F_2$—Ph | H | $CH_2F$ | O | H | $CH_2$ | 2-chloropyridin-4-yl | [$CDCl_3$] 3.42 (d, 1H); 3.72 (d, 1H); 4.38 (dd, 1H); 4.61 (dd, 1H); 4.65 (d, 0.5H); 4.76 (d, 0.5H); 4.82 (d, 0.5H); 4.94 (d, 0.5H); 6.94 (m, 1H); 7.08 (d, 1H); 7.18 (m, 2H); 7.27 (m, 1H); 7.38 (s br, 1H); 8.34 (d, 1H). |
| 5.059 | 3,5-$Cl_2$—Ph | H | acetyl | O | H | $CH_2$ | 2-chloropyridin-4-yl | |
| 5.060 | 3,5-$F_2$—Ph | H | acetyl | O | H | $CH_2$ | 2-chloropyridin-4-yl | |
| 5.061 | 3-F—Ph | H | $CH_2F$ | O | H | $CH_2$ | 2-chloropyridin-4-yl | |
| 5.062 | 3,5-$F_2$—Ph | H | $CH_2Cl$ | O | H | $CH_2$ | 2-chloropyridin-4-yl | [$CDCl_3$] 3.55 (d, 1H); 3.74 (d, 1H); 3.94 (d, 1H); 4.10 (d, 1H); 4.37 (dd, 1H); 4.63 (dd, 1H); 6.92 (m, 1H); 7.12 (d, 1H); 7.18 (m, 2H); 7.23 (s, 1H); 7.38 (t br, 1H); 8.35 (d, 1H). |
| 5.063 | 3,5-$Cl_2$—Ph | H | $CH_2Cl$ | O | H | $CH_2$ | 2-chloropyridin-4-yl | |
| 5.064 | 3,5-$F_2$—Ph | H | vinyl | O | H | $CH_2$ | 2-chloropyridin-4-yl | [$CDCl_3$] 3.38 (d, 1H); 3.97 (d, 1H); 4.40 (dd, 1H); 4.54 (dd, 1H); 5.42 (d, 1H); 5.59 (d, 1H); 6.20 (dd, 1H); 6.91 (m, 1H); 7.07 (d, 1H); 7.18 (m, 2H); 7.29 (s br, 1H); 8.33 (d, 1H). |
| 5.065 | 3-F—Ph | H | $CH_2Cl$ | O | H | $CH_2$ | 2-chloropyridin-4-yl | |

TABLE 5-continued

Compounds of the general formula (I) according to the invention in which $R^2$ is hydrogen and aryl is the radical

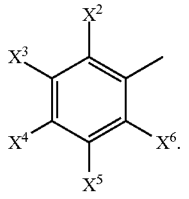

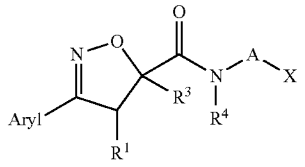

| No. | Aryl | $R^1$ | $R^3$ | Y | $R^4$ | A | X | Physical data |
|---|---|---|---|---|---|---|---|---|
| 5.066 | 3,5-$F_2$—Ph | H | $CH_2F$ | O | H | $CH_2$ | 2-cyclopropyl-pyridin-4-yl | [$CDCl_3$] 0.99 (m, 4H); 1.97 (m, 1H); 3.44 (d, 1H); 3.72 (d, 1H); 4.34 (dd, 1H); 4.56 (dd, 1H); 4.67 (d, 0.5H); 4.78 (d, 0.5H); 4.82 (d, 0.5H); 4.93 (d, 0.5H); 6.93 (m, 3H); 7.18 (m, 2H); 7.32 (t br, 1h); 8.36 (d, 1H). |
| 5.067 | 3,5-$F_2$—Ph | H | $CH_2F$ | O | H | $CH_2$ | 2-ethylpyridin-4-yl | [$CDCl_3$] 1.27 (t, 3H); 2.78 (q, 2H); 3.43 (d, 1H); 3.73 (d, 1H); 4.37 (dd, 1H); 4.60 (dd, 1H); 4.66 (d, 0.5H); 4.78 (d, 0.5H); 4.83 (d, 0.5H); 4.94 (d, 0.5H); 6.93 (m, 1H); 6.98 (d, 1H); 7.01 (s, 1H); 7.19 (m, 2H); 7.33 (s br, 1H); 8.46 (d, 1H). |
| 5.068 | 3,5-$F_2$—Ph | H | $CH_2F$ | O | H | $CH_2$ | 2-fluoropyridin-4-yl | [$CDCl_3$] 3.42 (d, 1H); 3.71 (d, 1H); 4.40 (dd, 1H); 4.64 (dd, 1H); 4.65 (d, 0.5H); 4.78 (d, 0.5H); 4.82 (d, 0.5H); 4.94 (d, 0.5H); 6.80 (s, 1H); 6.92 (m, 1H); 7.04 (d, 1H); 7.18 (m, 2H); 7.39 (s, br, 1H); 8.18 (d, 1H). |
| 5.069 | 3-F—Ph | H | $CH_2F$ | O | H | $CH_2$ | 2-fluoropyridin-4-yl | |
| 5.070 | 3,5-$F_2$—Ph | H | $CH_2F$ | O | H | $CH_2$ | 2-methoxypyridin-4-yl | [$CDCl_3$] 3.45 (d, 1H); 3.71 (d, 1H); 3.91 (s, 3H); 4.34 (dd, 1H); 4.55 (dd, 1H); 4.66 (d, 0.5H); 4.78 |

TABLE 5-continued

Compounds of the general formula (I) according to the invention in which $R^2$ is hydrogen and aryl is the radical

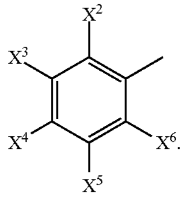

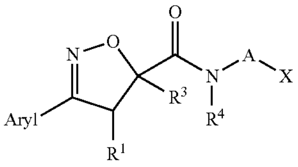

| No. | Aryl | $R^1$ | $R^3$ | Y | $R^4$ | A | X | Physical data |
|---|---|---|---|---|---|---|---|---|
| | | | | | | | | (d, 0.5H); 4.80 (d, 0.5H); 4.92 (d, 0.5H); 6.57 (s, 1H); 6.73 (d, 1H); 6.92 (m, 1H); 7.19 (m, 2H); 7.29 (m, 1H); 8.10 (d, 1H). |
| 5.071 | 3,5-$F_2$—Ph | H | $CH_2F$ | O | H | $CH_2$ | 2-methylpyridin-4-yl | |
| 5.072 | 3,5-$F_2$—Ph | H | $CH_2F$ | O | H | $CH_2$ | 3,5-dimethyl-1,2-oxazol-4-yl | [$CDCl_3$] 2.20 (s, 3H); 2.38 (s, 3H); 3.41 (d, 1H); 3.66 (d, 1H); 4.13 (dd, 1H); 4.30 (dd, 1H); 4.61 (d, 0.5H); 4.72 (d, 0.5H); 4.75 (d, 0.5H); 4.86 (d, 0.5H); 6.91 (m, 1H); 6.98 (s br, 1H); 7.15 (m, 2H). |
| 5.073 | 3,5-$F_2$—Ph | H | $CH_2F$ | O | H | $CH_2$ | 3-ethyl-5-methyl-1,2-oxazol-4-yl | |
| 5.074 | 3,5-$F_2$—Ph | H | $CH_2Cl$ | O | H | $CH_2$ | 3-ethyl-5-methyl-1,2-oxazol-4-yl | [$CDCl_3$] 1.24 (t, 3H); 2.38 (s, 3H); 2.61 (q, 2H); 3.53 (d, 1H); 3.68 (d, 1H); 3.90 (d, 1H); 4.02 (d, 1H); 4.16 (dd, 1H); 4.28 (dd, 1H); 6.92 (m, 2H); 7.15 (m, 2H). |
| 5.075 | 3,5-$F_2$—Ph | H | $CH_2F$ | O | H | $CH_2$ | 6-(trifluoromethyl)-pyridin-3-yl | |

TABLE 6

Compounds of the general formula (I) according to the invention in which $R^2$ is hydrogen and $R^3$ is methyl and aryl is the radical

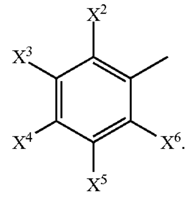

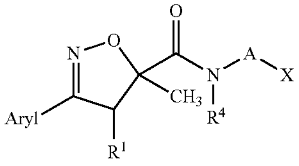

| No. | Aryl | $R^1$ | Y | $R^4$ | A | X | Physical data |
|---|---|---|---|---|---|---|---|
| 6.001 | 3,5-$Cl_2$—Ph | H | O | H | $(CH_2)_4$ | COOH | [$CDCl_3$] 1.72 (s, 3H); 2.88 (t, 2H); 3.18 (d, 1H); 3.30 (m, 2H); 3.56 (m, 2H); 3.78 (d, 1H); 6.88 (t br, 1H); 7.40 (m, 1H); 7.50 (m, 2H) |
| 6.002 | 3,5-$Cl_2$—Ph | H | O | H | $(CH_2)_4$ | ethoxycarbonyl | [$CDCl_3$] 1.23 (t, 3H); 1.57-1.68 (m, 4H); 1.71 (s, 3H); 2.31 (t, 2H); 3.17 (d, 1H); 3.18-3.37 (m, 2H); 3.78 (d, 1H); 4.11 (q, 2H); 6.83 (br, 1H); 7.41 (m, 1H); 7.51 (m, 2H). |
| 6.003 | 3-Br-5-Cl—Ph | H | O | H | $(CH_2)_4$ | ethoxycarbonyl | [$CDCl_3$] 1.22 (t, 3H); 1.58 (m, 4H); 1.68 (s, 3H); 2.32 (t, 2H); 3.25 (m, 2H); 3.38 (d, 1H); 3.74 (d, 1H); 4.09 (q, 2H); 7.69 (m, 2H); 7.80 (m, 1H) |
| 6.004 | Ph | H | O | H | $(CH_2)_4$ | ethoxycarbonyl | |
| 6.005 | 3,5-$Cl_2$—Ph | H | O | H | $(CH_2)_4$ | hydroxy | [$CDCl_3$] 1.60 (m, 4H); 1.72 (s, 3H); 3.17 (d, 1H); 3.26 (m, 1H); 3.35 (m, 1H); 3.68 (t, 2H); 3.78 (d, 1H); 6.97 (t br, 1H); 7.41 (t, 1H); 7.52 (m, 2H) |
| 6.006 | 3,5-$Cl_2$—Ph | H | O | H | $(CH_2)_4$ | methoxy | [$CDCl_3$] 1.61 (m, 4H); 1.73 (s, 3H); 3.16 (d, 1H); 3.26 (m, 2H); 3.36 (m, 3H); 3.39 (m, 2H); 3.78 (d, 1H); 7.00 (t br, 3H); 7.41 (m, 1H); 7.53 (m, 2H). |
| 6.007 | 3,5-$Cl_2$—Ph | H | O | H | $(CH_2)_6$ | COOH | [$CDCl_3$] 1.33 (m, 4H); 1.52 (m, 2H); 1.61 (m, 2H); 1.72 (s, 3H); 2.32 (t, 2H); 3.18 (d, 1H); 3.20 (m, 1H); 3.28 (m, 1H); 3.77 (d, 1H); 6.80 (t br, 1H); 7.41 (t, 1H), 7.51 (d, 2H) |
| 6.008 | 3,5-$Cl_2$—Ph | H | O | H | $(CH_2)_6$ | ethoxycarbonyl | [$CDCl_3$] 1.25 (t, 3H); 1.32 (m, 4H); 1.55 (m, 4H); 2.26 (t, 2H); 3.17 (d, 1H); 3.19 (m, 1H); 3.28 (m, 1H); 3.78 (d, 1H); 4.13 (q, 2H); 6.78 (t br, 1H); 7.41 (m, 1H); 7.51 (d, 2H) |
| 6.009 | 3,5-$Cl_2$—Ph | H | O | H | c-Pr-1,1-diyl | ethoxycarbonyl | |
| 6.010 | 3,5-$F_2$—Ph | H | O | H | bond | 1-cyanocyclopropyl | [$CDCl_3$] 7.52 0.35; 7.28 0.32; 7.28 0.36; 7.28 0.40; 7.28 0.45; 7.28 0.51; 7.28 0.55; 7.28 0.62; 7.28 0.69; 7.27 0.95; 7.26 45.19; 7.26 61.18; 7.26 3.27; 7.26 2.84; 7.25 2.54; 7.25 2.34; 7.25 2.15; 7.25 1.96; 7.25 1.78; 7.25 1.61; 7.25 1.47; 7.25 1.33; 7.25 1.21; 7.25 1.11; 7.25 1.02; 7.25 0.92; 7.24 0.82; 7.24 0.75; 7.24 0.69; 7.24 0.63; 7.24 0.57; 7.24 0.53; 7.24 0.48; 7.24 0.44; 7.24 0.43; 7.24 0.39; 7.24 0.33; 7.21 0.34; 7.21 0.44; 7.18 0.39; 7.17 0.49; 7.17 2.02; 7.16 2.14; 7.16 2.16; 7.16 1.43; 7.15 1.56; 7.15 2.41; 7.14 1.64; 7.13 0.33; 7.13 0.33; 7.00 0.35; 6.93 0.48; 6.92 0.76; 6.92 0.41; 6.91 0.96; 6.90 1.49; 6.89 0.73; 6.88 0.50; 6.88 0.74; 6.87 |

TABLE 6-continued

Compounds of the general formula (I) according to the invention in which $R^2$ is hydrogen and $R^3$ is methyl and aryl is the radical

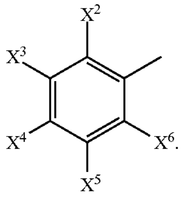

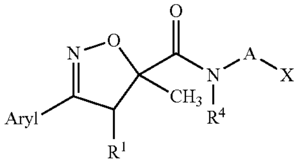

| No. | Aryl | $R^1$ | Y | $R^4$ | A | X | Physical data |
|---|---|---|---|---|---|---|---|
| | | | | | | | 0.37; 5.30 1.41; 3.80 2.64; 3.76 3.09; 3.24 2.90; 3.19 2.51; 1.75 0.46; 1.71 16.00; 1.60 1.28; 1.59 1.80; 1.59 1.80; 1.59 2.61; 1.58 1.83; 1.58 1.56; 1.57 1.53; 1.54 20.23; 1.28 0.34; 1.27 1.28; 1.27 1.40; 1.26 2.77; 1.26 4.26; 1.25 3.18; 1.24 0.87; 1.24 0.74; 0.01 0.36; 0.01 1.97; 0.00 19.66; 0.00 26.96 |
| 6.011 | 3,5-$Cl_2$—Ph | H | O | H | bond | 1-cyanocyclopropyl | [$CDCl_3$] 7.52 1.88; 7.51 6.69; 7.51 7.56; 7.44 1.97; 7.43 3.25; 7.43 1.63; 7.36 0.32; 7.31 1.01; 7.28 1.01; 7.28 1.07; 7.27 1.11; 7.27 1.07; 7.26 335.49; 7.21 0.88; 7.21 0.44; 7.00 1.84; 3.81 2.75; 3.76 3.17; 3.24 3.01; 3.20 2.60; 2.01 0.73; 1.71 16.00; 1.60 1.38; 1.59 1.92; 1.59 2.53; 1.58 1.70; 1.57 1.88; 1.55 196.84; 1.50 0.62; 1.27 1.18; 1.26 1.80; 1.26 3.20; 1.25 2.91; 1.24 0.89; 0.15 0.56; 0.05 0.37; 0.01 4.15; 0.00 139.19; −0.01 4.68; −0.05 0.36; −0.15 0.49 |
| 6.012 | 3,5-$Cl_2$—Ph | H | O | H | bond | 1-methylcyclopropyl | [$CDCl_3$] 1.36 (s, 3H); 1.68 (s, 3H); 3.13 (d, 1H); 3.77 (d, 1H); 7.00 (s br, 1H); 7.42 (s, 1H); 7.51 (s, 2H). |
| 6.013 | 3,5-$Cl_2$—Ph | H | O | H | bond | 2-(ethoxy-carbonyl)cyclohex-1-en-1-yl | |
| 6.014 | 3,5-$Cl_2$—Ph | H | O | H | bond | 2-(ethoxy-carbonyl)cyclohexyl | |
| 6.015 | 3,5-$Cl_2$—Ph | H | O | H | bond | 2-(methylcarbamoyl)-cyclohexyl | |
| 6.016 | 3,5-$Cl_2$—Ph | H | O | H | bond | 2-carboxycyclohexyl | |
| 6.017 | 3,5-$Cl_2$—Ph | H | O | H | bond | 3-(2-ethoxy-2-oxoethyl)oxetan-3-yl | |
| 6.018 | 3,5-$F_2$—Ph | H | O | H | bond | 3-(2-ethoxy-2-oxoethyl)oxetan-3-yl | [$CDCl_3$] 7.41 1.66; 7.26 18.58; 7.20 0.32; 7.18 0.54; 7.17 1.73; 7.17 2.57; 7.15 2.49; 7.15 2.28; 7.14 0.41; 6.92 0.39; 6.91 0.75; 6.90 0.48; 6.89 0.85; 6.89 1.56; 6.88 0.98; 6.87 0.53; 6.87 0.88; 4.76 2.00; 4.74 2.70; 4.74 2.52; 4.72 2.67; 4.62 2.80; 4.61 3.09; 4.60 2.34; 4.60 2.45; 4.41 0.34; 4.36 0.35; 4.11 0.45; 4.10 0.64; 4.09 0.55; 4.08 2.21; 4.07 3.01; 4.05 2.13; 4.04 0.62; 4.03 0.67; 4.02 0.48; 3.74 3.27; 3.70 3.12; 3.19 2.95; 3.14 6.76; 3.10 0.40; 3.10 0.36; 3.06 0.34; 1.71 2.42; 1.70 16.00; 1.57 9.84; 1.26 0.47; 1.19 4.60; 1.17 9.35; 1.16 4.63 |

TABLE 6-continued

Compounds of the general formula (I) according to the invention in which $R^2$ is hydrogen and $R^3$ is methyl and aryl is the radical

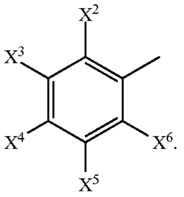

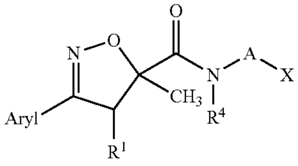

| No. | Aryl | $R^1$ | Y | $R^4$ | A | X | Physical data |
|---|---|---|---|---|---|---|---|
| 6.019 | 2,4-$Cl_2$—Ph | H | O | $CH_3$ | bond | CH3 | |
| 6.020 | 2-Cl—Ph | H | O | $CH_3$ | bond | CH3 | |
| 6.021 | 3,4-$F_2$—Ph | H | O | H | bond | CH3 | |
| 6.022 | 3,5-$Br_2$—Ph | H | O | H | bond | CH3 | |
| 6.023 | 3,5-$Cl_2$—Ph | $CH_3$ | O | H | bond | CH3 | |
| 6.024 | 3,5-$Cl_2$—Ph | $CH_3$ | O | H | bond | CH3 | |
| 6.025 | 3,5-$Cl_2$—Ph | H | O | $CH_3$ | bond | CH3 | |
| 6.026 | 3,5-$Cl_2$—Ph | H | O | H | bond | CH3 | [$CDCl_3$] 1.72 (s, 3H); 2.83 (d, 3H); 3.18 (d, 1H); 3.78 (d, 1H); 6.80 (m, 1H); 7.40 (t, 1H); 7.50 (m, 2H) |
| 6.027 | 3,5-$F_2$—Ph | H | O | H | bond | CH3 | [$CDCl_3$] 1.72 (s, 3H); 2.84 (d, 3H); 3.18 (d, 1H); 3.78 (d, 1H); 6.82 (br, 1H); 6.88 (m, 1H); 7.16 (M, 2H). |
| 6.028 | 3-Cl-4-F—Ph | H | O | H | bond | CH3 | |
| 6.029 | 3,5-$Cl_2$—Ph | H | O | H | bond | cyclobutyl | [$CDCl_3$] 1.72 (s, 3H); 1.73 (m, 2H); 1.92 (m, 2H); 2.35 (m, 2H); 3.16 (d, 1H); 3.76 (d, 1H); 4.32 (m, 1H); 6.90 (d br, 1H); 7.41 (s, 1H); 7.52 (s, 2H). |
| 6.030 | 3,5-$F_2$—Ph | H | O | H | bond | cyclobutyl | [$CDCl_3$] 7.52 0.82; 7.31 4.11; 7.26 132.61; 7.18 0.95; 7.17 2.86; 7.16 2.72; 7.15 2.64; 7.13 0.34; 7.00 0.77; 6.90 1.45; 6.90 1.64; 6.89 1.31; 6.88 1.52; 6.88 1.75; 6.87 0.92; 6.86 0.64; 6.85 0.84; 4.37 0.73; 4.35 1.27; 4.33 1.20; 4.31 0.59; 3.78 2.56; 3.74 2.93; 3.18 2.78; 3.14 2.37; 2.39 0.69; 2.38 0.84; 2.37 0.97; 2.36 0.90; 2.35 1.02; 2.34 0.98; 2.34 0.97; 2.33 0.90; 2.32 0.94; 2.31 0.85; 2.30 0.87; 2.29 0.67; 1.97 0.43; 1.95 1.06; 1.92 1.62; 1.90 1.30; 1.88 1.46; 1.86 0.98; 1.83 0.43; 1.78 0.58; 1.76 1.63; 1.75 1.76; 1.74 2.35; 1.73 2.72; 1.71 3.72; 1.70 16.00; 1.69 0.80; 1.67 0.36; 1.58 1.86; 1.53 57.66; 0.05 1.88; 0.00 60.02 |
| 6.031 | 3,5-$Cl_2$—Ph | H | O | H | bond | cyclopentyl | |
| 6.032 | 3,5-$F_2$—Ph | H | O | H | bond | cyclopentyl | [$CDCl_3$] 7.52 0.56; 7.26 105.40; 7.24 0.54; 7.21 0.44; 7.18 0.35; 7.17 1.79; 7.17 2.04; 7.16 1.21; 7.15 1.30; 7.15 2.08; 7.15 1.64; 7.14 0.35; 7.00 0.59; 6.90 0.43; 6.90 0.72; 6.89 0.38; 6.88 0.89; 6.88 1.45; 6.87 0.71; 6.86 0.46; 6.85 0.71; 6.85 0.35; 6.72 0.45; 6.70 0.46; 4.18 0.45; 4.16 0.87; 4.15 0.87; 4.13 0.49; 3.79 2.66; 3.75 3.05; 3.18 2.71; 3.14 2.35; 2.03 0.34; 2.02 0.48; 2.00 0.67; 1.99 0.57; 1.98 0.60; 1.97 0.57; 1.95 0.52; 1.93 0.37; 1.71 16.00; 1.70 1.15; 1.68 0.95; 1.68 0.86; 1.66 0.73; 1.65 0.59; 1.63 |

TABLE 6-continued
Compounds of the general formula (I) according to the invention in which $R^2$ is hydrogen and $R^3$ is methyl and aryl is the radical
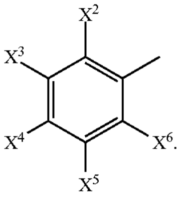
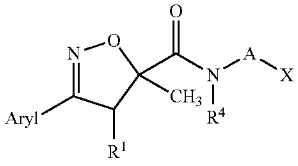
| No. | Aryl | $R^1$ | Y | $R^4$ | A | X | Physical data |
|---|---|---|---|---|---|---|---|
| | | | | | | | 0.77; 1.62 0.64; 1.62 0.58; 1.61 1.00; 1.60 0.76; 1.59 0.90; 1.59 0.78; 1.58 0.50; 1.58 0.50; 1.57 0.47; 1.54 21.22; 1.45 0.44; 1.43 0.51; 1.42 0.54; 1.40 0.40; 1.40 0.37; 1.38 0.50; 1.36 0.52; 1.34 0.48; 1.33 0.34; 0.01 2.35 |
| 6.033 | 2-$CF_3$—Ph | H | O | H | bond | c-Pr | |
| 6.034 | 2,3,4-$F_3$—Ph | H | O | H | bond | c-Pr | [$CDCl_3$] 7.53 0.33; 7.52 0.96; 7.51 0.46; 7.51 0.46; 7.51 0.47; 7.50 0.38; 7.50 0.33; 7.50 0.42; 7.49 0.48; 7.49 0.45; 7.49 0.45; 7.48 0.37; 7.31 0.34; 7.27 0.38; 7.27 0.45; 7.27 0.51; 7.27 0.57; 7.27 0.68; 7.26 0.88; 7.26 1.18; 7.26 1.93; 7.26 3.78; 7.26 131.17; 7.26 2.84; 7.26 1.88; 7.25 1.38; 7.25 1.03; 7.25 0.76; 7.25 0.59; 7.25 0.50; 7.25 0.46; 7.25 0.39; 7.25 0.35; 7.25 0.33; 7.21 0.35; 7.06 0.34; 7.05 0.39; 7.04 0.35; 7.03 1.01; 7.03 0.73; 7.02 0.65; 7.01 0.98; 7.00 0.36; 7.00 0.74; 6.99 0.33; 6.80 0.43; 3.91 1.12; 3.90 1.16; 3.86 1.33; 3.86 1.32; 3.31 1.19; 3.30 1.22; 3.26 1.06; 3.26 1.05; 2.77 0.53; 2.76 0.75; 2.75 1.08; 2.74 1.20; 2.73 0.70; 2.72 0.55; 1.70 16.00; 1.55 0.37; 1.55 0.40; 1.55 0.49; 1.55 0.63; 1.55 0.75; 1.55 1.06; 1.54 1.74; 1.54 78.78; 1.54 2.72; 1.54 1.74; 1.54 1.25; 1.54 0.96; 1.54 0.78; 1.53 0.60; 1.53 0.48; 1.53 0.39; 1.53 0.38; 0.83 0.51; 0.81 0.76; 0.81 1.87; 0.80 1.66; 0.80 0.91; 0.79 0.72; 0.79 1.63; 0.78 1.77; 0.78 0.92; 0.77 0.58; 0.55 0.49; 0.54 0.43; 0.54 0.71; 0.53 1.30; 0.53 1.93; 0.52 1.78; 0.52 1.38; 0.51 0.67; 0.51 0.36; 0.50 0.39; 0.01 0.34; 0.01 1.40; 0.01 0.73; 0.01 0.43; 0.01 0.44; 0.00 0.54; 0.00 0.82; 0.00 1.53; 0.00 2.33; 0.00 50.35; 0.00 2.26; 0.00 1.44; −0.01 0.94; −0.01 0.68; −0.01 0.56; −0.01 1.64; −0.01 0.85; −0.01 0.66; −0.01 0.33 |
| 6.035 | 2,3,5-$F_3$—Ph | H | O | H | bond | c-Pr | |
| 6.036 | 2,3-$F_2$—Ph | H | O | H | bond | c-Pr | [$CDCl_3$] 7.53 0.40; 7.52 0.74; 7.52 0.55; 7.51 0.48; 7.51 0.94; 7.50 1.05; 7.50 0.56; 7.49 0.49; 7.49 0.80; 7.49 0.48; 7.27 0.50; 7.26 37.84; 7.25 1.15; 7.25 1.22; 7.25 1.06; 7.25 1.16; 7.23 0.60; 7.23 0.93; 7.22 0.65; 7.21 0.49; 7.20 |

TABLE 6-continued
Compounds of the general formula (I) according to the invention in which $R^2$ is hydrogen and $R^3$ is methyl and aryl is the radical
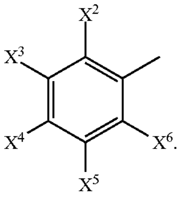
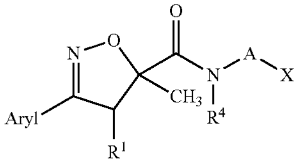
| No. | Aryl | $R^1$ | Y | $R^4$ | A | X | Physical data |
|---|---|---|---|---|---|---|---|
| | | | | | | | 0.45; 7.15 0.52; 7.14 0.54; 7.13 0.55; 7.13 0.60; 7.13 0.80; 7.12 0.81; 7.11 0.77; 7.11 0.82; 7.11 0.41; 7.10 0.38; 7.09 0.34; 7.09 0.34; 6.82 0.62; 3.92 1.29; 3.92 1.32; 3.88 1.53; 3.87 1.54; 3.34 1.44; 3.34 1.49; 3.30 1.27; 3.29 1.26; 2.77 0.53; 2.76 0.78; 2.75 1.16; 2.74 1.23; 2.73 0.76; 2.72 0.57; 2.00 0.45; 1.70 16.00; 1.55 22.93; 0.82 0.52; 0.81 0.93; 0.81 2.02; 0.80 1.84; 0.80 1.35; 0.79 0.90; 0.79 1.85; 0.78 1.99; 0.76 0.64; 0.56 0.33; 0.55 0.52; 0.54 0.58; 0.53 1.62; 0.53 2.16; 0.53 2.30; 0.52 1.64; 0.52 0.91; 0.50 0.43; 0.00 9.41; −0.01 0.44 |
| 6.037 | 2,4-$Cl_2$—Ph | H | O | H | bond | c-Pr | |
| 6.038 | 2,5-$F_2$—Ph | H | O | H | bond | c-Pr | |
| 6.039 | 2,5-$Me_2$—Ph | H | O | H | bond | c-Pr | [$CDCl_3$] 7.26 10.26; 7.16 0.82; 7.14 2.64; 7.12 5.17; 7.10 0.79; 6.94 0.69; 3.88 2.67; 3.84 3.08; 3.29 3.01; 3.24 2.63; 2.77 0.52; 2.76 0.80; 2.75 1.19; 2.74 1.16; 2.73 0.84; 2.72 0.55; 2.46 11.41; 2.32 10.91; 1.70 16.00; 1.61 1.28; 1.26 0.50; 0.82 0.35; 0.81 1.36; 0.80 1.64; 0.80 1.78; 0.79 1.15; 0.78 1.65; 0.78 1.82; 0.76 0.40; 0.56 0.42; 0.54 0.45; 0.53 1.44; 0.53 1.43; 0.52 2.20; 0.52 1.03; 0.51 1.38; 0.51 1.05; 0.50 0.42; 0.48 0.33; 0.00 2.75 |
| 6.040 | 2-Cl-3-F-5-MeO—Ph | H | O | H | bond | c-Pr | [$CDCl_3$] 7.26 9.99; 7.26 8.46; 6.92 1.29; 6.91 2.33; 6.91 2.53; 6.91 2.71; 6.90 1.46; 6.85 1.05; 6.81 1.41; 6.81 1.32; 6.80 1.40; 6.80 1.16; 6.78 1.36; 6.78 1.26; 6.78 1.37; 6.77 1.13; 3.95 2.44; 3.95 2.15; 3.91 2.81; 3.91 2.50; 3.82 0.49; 3.81 16.00; 3.81 14.12; 3.39 2.71; 3.38 2.42; 3.34 2.33; 3.34 2.09; 2.78 0.45; 2.78 0.42; 2.77 0.75; 2.77 0.68; 2.76 1.09; 2.76 1.00; 2.75 1.15; 2.75 1.00; 2.74 0.82; 2.74 0.74; 2.73 0.56; 2.73 0.48; 1.71 14.52; 1.71 13.08; 0.83 0.34; 0.81 3.22; 0.79 3.40; 0.78 0.57; 0.77 0.42; 0.57 0.39; 0.56 0.49; 0.55 0.47; 0.55 1.73; 0.54 2.01; 0.53 3.20; 0.52 2.20; 0.52 0.63; 0.00 2.93; 0.00 2.48 |
| 6.041 | 2-Cl-5-F—Ph | H | O | H | bond | c-Pr | |
| 6.042 | 2-EtO-3,4,5,6-$F_4$—Ph | H | O | H | bond | c-Pr | |

TABLE 6-continued

Compounds of the general formula (I) according to the invention in which $R^2$ is hydrogen and $R^3$ is methyl and aryl is the radical

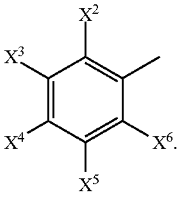

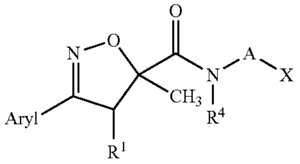

| No. | Aryl | $R^1$ | Y | $R^4$ | A | X | Physical data |
|---|---|---|---|---|---|---|---|
| 6.043 | 2-F-3-Me—Ph | H | O | H | bond | c-Pr | [$CDCl_3$] 7.58 0.72; 7.56 1.37; 7.56 1.37; 7.54 0.78; 7.28 0.70; 7.27 0.78; 7.26 12.94; 7.26 1.52; 7.26 1.54; 7.24 0.77; 7.24 0.81; 7.08 1.32; 7.06 2.23; 7.04 1.01; 6.87 0.82; 3.92 1.41; 3.91 1.31; 3.87 1.69; 3.87 1.52; 3.35 1.64; 3.34 1.46; 3.30 1.44; 3.30 1.26; 2.76 0.54; 2.75 0.76; 2.74 1.22; 2.74 1.18; 2.73 0.82; 2.72 0.55; 2.30 7.45; 2.29 6.73; 1.69 16.00; 1.60 4.93; 0.82 0.51; 0.80 1.59; 0.80 2.04; 0.79 2.10; 0.79 1.03; 0.78 1.44; 0.78 1.97; 0.77 2.34; 0.77 0.97; 0.76 0.63; 0.56 0.39; 0.55 0.43; 0.55 0.53; 0.53 1.58; 0.53 1.68; 0.52 3.01; 0.52 2.17; 0.51 1.68; 0.51 0.92; 0.50 0.49; 0.00 2.27 |
| 6.044 | 3-(2-MeOEtO)—Ph | H | O | H | bond | c-Pr | |
| 6.045 | 3-iPrO—Ph | H | O | H | bond | c-Pr | |
| 6.046 | 3-$CF_3$O—Ph | H | O | H | bond | c-Pr | [$CDCl_3$] 0.52 (m, 2H); 0.79 (m, 2H); 1.72 (s, 3H); 2.73 (m, 1H); 3.20 (d, 1H); 3.82 (d, 1H); 6.83 (brs, 1H); 7.28 (m, 1H); 7.44 (m, 1H); 7.52 (m, 2H). |
| 6.047 | 3-$CF_3$—Ph | H | O | H | bond | c-Pr | [$CDCl_3$] 7.90 2.85; 7.81 1.54; 7.79 1.76; 7.70 1.37; 7.68 1.76; 7.57 1.32; 7.55 2.06; 7.53 0.85; 7.26 10.56; 6.85 1.01; 5.30 0.44; 3.89 2.64; 3.85 2.99; 3.26 2.91; 3.22 2.52; 2.76 0.60; 2.75 0.90; 2.75 1.28; 2.74 1.26; 2.73 0.86; 2.72 0.53; 1.72 16.00; 1.59 6.08; 0.83 0.33; 0.83 0.51; 0.81 1.59; 0.81 1.87; 0.80 2.07; 0.79 1.67; 0.79 1.65; 0.78 2.00; 0.77 0.37; 0.77 0.36; 0.76 0.59; 0.57 0.51; 0.55 0.61; 0.54 1.86; 0.54 2.04; 0.53 3.18; 0.52 1.68; 0.51 0.43; 0.50 0.45 |
| 6.048 | 3,4,5-$F_3$—Ph | H | O | H | bond | c-Pr | [$CDCl_3$] 0.52 (m, 2H); 0.80 (m, 2H); 1.70 (s, 3H); 2.73 (m, 1H); 3.15 (d, 1H); 3.78 (d, 1H); 6.81 (s br, 1H); 7.27 (m, 2H) |
| 6.049 | 3,5-$Br_2$—Ph | H | O | H | bond | c-Pr | [$CDCl_3$] 0.50 (m, 2H); 0.79 (m, 2H); 1.70 (s, 3H); 2.72 (m, 1H); 3.14 (d, 1H); 3.78 (d, 1H); 6.79 (bs, 1H); 7.70 (m, 3H). |
| 6.050 | 3,5-$Cl_2$-4-MeO—Ph | H | O | H | bond | c-Pr | [$CDCl_3$] 7.57 10.28; 7.57 7.83; 7.26 13.80; 7.26 10.49; 6.82 0.93; 3.98 0.39; 3.98 0.41; 3.96 0.42; 3.96 0.50; 3.95 0.43; 3.93 16.00; 3.93 12.64; 3.79 2.22; 3.75 2.53; 3.17 2.40; 3.13 2.10; 2.75 0.45; 2.74 0.76; 2.73 1.05; 2.72 1.12; 2.71 0.80; 2.71 0.54; 1.70 12.94; 1.58 |

TABLE 6-continued

Compounds of the general formula (I) according to the invention in which $R^2$ is hydrogen and $R^3$ is methyl and aryl is the radical

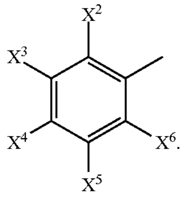

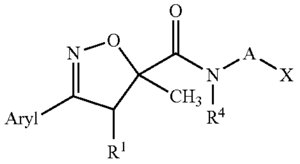

| No. | Aryl | $R^1$ | Y | $R^4$ | A | X | Physical data |
|---|---|---|---|---|---|---|---|
| | | | | | | | 1.64; 0.82 0.45; 0.81 0.72; 0.80 1.70; 0.79 1.57; 0.79 1.72; 0.79 1.11; 0.78 1.60; 0.78 1.75; 0.77 1.83; 0.76 0.56; 0.55 0.35; 0.54 0.51; 0.53 1.56; 0.52 2.08; 0.52 2.75; 0.51 1.70; 0.49 0.47; 0.48 0.34 |
| 6.051 | 3,5-$Cl_2$-4-OH—Ph | H | O | H | bond | c-Pr | |
| 6.052 | 3,5-$Cl_2$—Ph | $CH_3$ | O | H | bond | c-Pr | |
| 6.053 | 3,5-$Cl_2$—Ph | H | O | H | bond | c-Pr | [$CDCl_3$] 7.51 6.38; 7.51 7.04; 7.41 1.81; 7.41 3.09; 7.41 1.63; 7.26 8.25; 6.80 0.74; 3.81 2.74; 3.77 3.13; 3.18 2.96; 3.14 2.61; 2.76 0.52; 2.75 0.82; 2.74 1.17; 2.73 1.22; 2.72 0.84; 2.71 0.56; 1.70 16.00; 1.26 0.72; 0.82 0.48; 0.81 0.83; 0.80 1.93; 0.80 1.72; 0.80 1.33; 0.79 0.93; 0.79 1.73; 0.78 1.88; 0.76 0.60; 0.56 0.36; 0.55 0.54; 0.54 0.49; 0.53 1.65; 0.52 2.33; 0.52 2.46; 0.52 1.74; 0.51 0.99; 0.51 0.55; 0.50 0.46; 0.00 1.79 |
| 6.054 | 3,5-$Cl_2$—Ph | H | O | H | bond | c-Pr | [$CDCl_3$] 0.52 (m, 2H); 0.79 (m, 2H); 1.70 (s, 3H); 2.73 (m, 1H); 3.17 (d, 1H); 3.79 (d, 1H); 6.80 (s br, 1H); 7.41 (m, 1H); 7.51 (m, 1H) |
| 6.055 | 3,5-$Cl_2$—Ph | H | O | H | bond | c-Pr | |
| 6.056 | 3,5-$F_2$—Ph | H | O | H | bond | c-Pr | [$CDCl_3$] 7.26 9.41; 7.26 8.88; 7.16 1.75; 7.16 2.41; 7.15 2.09; 7.14 2.22; 7.14 2.00; 7.13 0.36; 7.13 0.34; 6.91 0.38; 6.90 0.70; 6.89 0.40; 6.88 0.76; 6.88 1.38; 6.87 0.78; 6.86 0.45; 6.86 0.75; 6.85 0.45; 6.81 0.76; 3.81 2.63; 3.76 3.01; 3.19 2.96; 3.15 2.57; 2.76 0.49; 2.75 0.83; 2.74 1.17; 2.73 1.21; 2.72 0.87; 2.71 0.54; 1.71 16.00; 1.58 4.61; 0.83 0.48; 0.81 0.79; 0.81 1.86; 0.80 1.69; 0.80 1.71; 0.79 1.10; 0.79 1.68; 0.78 1.89; 0.78 1.83; 0.77 0.34; 0.76 0.63; 0.56 0.41; 0.55 0.56; 0.53 1.73; 0.52 2.71; 0.52 1.69; 0.50 0.46; 0.49 0.33 |
| 6.057 | 3,5-$F_2$—Ph | H | O | H | bond | c-Pr | [$CDCl_3$] 7.26 8.51; 7.26 12.86; 7.18 0.35; 7.16 2.26; 7.16 2.20; 7.16 2.28; 7.16 1.35; 7.15 2.01; 7.15 2.48; 7.14 1.53; 6.91 0.51; 6.90 0.74; 6.89 0.40; 6.88 1.02; 6.88 1.47; 6.87 0.71; 6.86 0.56; 6.86 0.78; 6.85 0.41; 6.82 0.81; 3.81 2.63; 3.76 3.01; 3.19 2.86; 3.15 2.49; 2.76 0.55; 2.75 0.80; 2.74 1.21; 2.73 1.17; 2.72 0.82; 2.71 0.53; 1.71 16.00; 1.57 2.99; 1.57 4.37; 0.83 0.44; 0.81 1.45; 0.81 |

TABLE 6-continued
Compounds of the general formula (I) according to the invention in which $R^2$ is hydrogen and $R^3$ is methyl and aryl is the radical
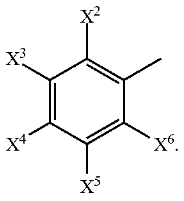
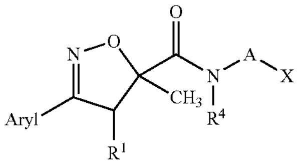
| No. | Aryl | $R^1$ | Y | $R^4$ | A | X | Physical data |
|---|---|---|---|---|---|---|---|
| | | | | | | | 1.90; 0.80 1.98; 0.80 1.26; 0.79 1.35; 0.79 1.68; 0.78 2.07; 0.78 0.88; 0.76 0.60; 0.56 0.42; 0.55 0.47; 0.55 0.53; 0.54 1.67; 0.53 1.78; 0.53 3.06; 0.52 2.21; 0.52 1.69; 0.51 0.85; 0.51 0.43; 0.50 0.46; 0.00 3.41 |
| 6.058 | 3,5-$F_2$—Ph | H | O | H | bond | c-Pr | [$CDCl_3$] 7.26 18.77; 7.17 1.56; 7.16 1.90; 7.16 1.06; 7.15 1.07; 7.15 1.90; 7.14 1.57; 6.91 0.39; 6.90 0.71; 6.90 0.37; 6.89 0.80; 6.88 1.42; 6.88 0.71; 6.87 0.44; 6.86 0.74; 6.85 0.41; 6.83 0.52; 3.81 2.73; 3.76 3.10; 3.19 2.83; 3.15 2.48; 2.76 0.52; 2.75 0.72; 2.74 1.16; 2.73 1.17; 2.72 0.75; 2.71 0.55; 1.71 16.00; 1.58 5.14; 1.58 13.06; 0.83 0.43; 0.81 0.78; 0.81 1.71; 0.80 1.56; 0.80 0.91; 0.80 0.80; 0.79 1.42; 0.78 1.70; 0.78 0.85; 0.77 0.53; 0.56 0.35; 0.55 0.50; 0.54 0.46; 0.54 0.89; 0.54 1.38; 0.53 2.15; 0.53 1.93; 0.52 1.44; 0.52 0.74; 0.51 0.39; 0.50 0.38; 0.00 7.98 |
| 6.059 | 3,5-$F_2$—Ph | H | S | H | bond | c-Pr | [$CDCl_3$] 8.54 0.59; 7.52 0.55; 7.52 0.49; 7.26 99.80; 7.26 87.79; 7.17 1.47; 7.17 1.99; 7.16 2.63; 7.16 2.43; 7.15 2.34; 7.15 2.53; 7.14 2.40; 7.13 0.32; 7.00 0.54; 6.99 0.49; 6.91 0.37; 6.90 0.69; 6.90 0.45; 6.88 0.78; 6.88 1.43; 6.88 1.37; 6.87 0.87; 6.86 0.42; 6.86 0.74; 6.85 0.45; 4.27 2.71; 4.27 2.59; 4.23 2.92; 4.22 2.85; 3.38 2.82; 3.37 2.80; 3.33 2.53; 3.33 2.54; 3.29 0.49; 3.28 0.68; 3.27 0.80; 3.27 1.04; 3.26 1.11; 3.25 0.68; 3.24 0.55; 1.87 16.00; 1.87 15.76; 1.53 46.50; 1.53 41.45; 0.99 0.49; 0.98 1.74; 0.98 1.74; 0.97 2.03; 0.96 1.85; 0.96 1.61; 0.95 1.73; 0.95 1.97; 0.93 0.67; 0.73 0.35; 0.72 0.52; 0.70 2.43; 0.69 2.54; 0.69 2.86; 0.69 2.50; 0.67 0.44; 0.01 1.31; 0.01 1.26 |
| 6.060 | 3,5-$(MeO)_2$—Ph | H | O | H | bond | c-Pr | [$CDCl_3$] 7.26 10.18; 7.26 11.63; 6.87 0.40; 6.78 2.40; 6.77 2.70; 6.77 2.62; 6.77 2.68; 6.53 0.61; 6.52 0.73; 6.52 1.16; 6.52 1.27; 6.52 0.62; 6.51 0.62; 3.82 1.12; 3.82 1.25; 3.81 14.21; 3.80 16.00; 3.78 1.28; 3.78 1.39; 3.22 1.13; 3.22 1.25; 3.18 0.98; 3.18 1.09; 2.75 0.36; 2.74 0.53; 2.73 0.49; 2.73 0.49; 2.72 0.37; 1.94 |

TABLE 6-continued

Compounds of the general formula (I) according to the invention in which $R^2$ is hydrogen and $R^3$ is methyl and aryl is the radical

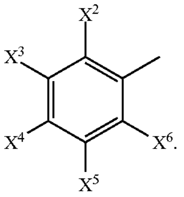

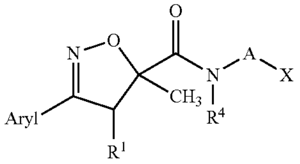

| No. | Aryl | $R^1$ | Y | $R^4$ | A | X | Physical data |
|---|---|---|---|---|---|---|---|
| | | | | | | | 0.33; 1.94 0.32; 1.94 0.33; 1.94 0.33; 1.70 6.13; 1.69 6.75; 1.57 3.52; 1.56 4.40; 0.80 0.41; 0.80 0.83; 0.80 0.87; 0.79 0.69; 0.79 0.91; 0.79 0.45; 0.78 0.38; 0.78 0.69; 0.78 0.75; 0.77 0.77; 0.77 0.94; 0.77 0.39; 0.53 0.83; 0.53 0.77; 0.52 1.32; 0.52 1.00; 0.51 0.69; 0.51 0.75; 0.51 0.40; 0.00 4.20; 0.00 4.80 |
| 6.061 | 3,5-$Me_2$—Ph | H | O | H | bond | c-Pr | [$CDCl_3$] 0.50 (m, 2H); 0.78 (m, 2H); 1.70 (s, 3H); 2.34 (s, 6H); 2.72 (m, 1H); 3.20 (d, 1H); 3.82 (d, 1H); 6.90 (s br, 1H); 7.07 (s, 1H); 7.24 (s, 2H). |
| 6.062 | 3-Ac—Ph | H | O | H | bond | c-Pr | [$CDCl_3$] 8.19 0.98; 8.19 1.87; 8.19 1.06; 8.18 1.05; 8.03 0.65; 8.02 0.85; 8.02 0.88; 8.02 0.72; 8.01 0.75; 8.00 0.94; 8.00 0.99; 8.00 0.77; 7.85 0.64; 7.85 0.83; 7.85 0.88; 7.84 0.71; 7.83 0.77; 7.83 1.02; 7.82 0.78; 7.54 1.05; 7.52 1.70; 7.52 1.90; 7.50 0.78; 7.50 0.87; 7.26 15.22; 6.86 0.46; 5.30 0.78; 3.91 2.13; 3.87 2.43; 3.28 2.24; 3.24 1.97; 2.76 0.42; 2.75 0.60; 2.75 0.94; 2.74 0.98; 2.73 0.62; 2.72 0.48; 2.65 1.15; 2.63 16.00; 2.36 1.13; 1.72 12.20; 1.70 1.40; 1.58 1.17; 0.82 0.33; 0.81 0.61; 0.80 0.94; 0.80 0.82; 0.80 0.81; 0.79 0.89; 0.79 1.05; 0.79 0.87; 0.78 0.86; 0.78 0.98; 0.77 0.92; 0.77 0.36; 0.76 0.40; 0.76 0.39; 0.57 0.32; 0.55 0.44; 0.54 0.40; 0.54 0.63; 0.54 0.83; 0.54 0.78; 0.53 1.24; 0.53 1.62; 0.52 0.87; 0.52 0.96; 0.51 0.68; 0.51 0.45; 0.50 0.35; 0.00 4.12 |
| 6.063 | 3-Br-5-$CF_3$—Ph | H | O | H | bond | c-Pr | [$CDCl_3$] 0.51 (m, 2H); 0.79 (m, 2H); 1.71 (s, 3H); 2.71 (m, 1H); 3.20 (d, 1H); 3.84 (d, 1H); 6.80 (br, 1H); 7.80 (s, 2H); 7.95 (s, 1H). |
| 6.064 | 3-Br-5-Cl—Ph | H | O | H | bond | c-Pr | [$CDCl_3$] 0.51 (m, 2H); 0.79 (m, 2H); 1.71 (s, 3H); 2.72 (m, 1H); 3.16 (d, 1H); 3.79 (d, 1H); 6.80 (br, 1H); 7.55 (m, 2H); 7.66 (m, 1H). |
| 6.065 | 3-Br-5-F—Ph | H | O | H | bond | c-Pr | [$CDCl_3$] 0.52 (m, 2H); 0.79 (m, 2H); 1.70 (s, 3H); 2.72 (m, 1H); 3.18 (d, 1H); 3.79 (d, 1H); 6.80 (br, 1H); 7.30 (m, 2H); 7.55 (m, 1H). |
| 6.066 | 3-Cl-4-F—Ph | H | O | H | bond | c-Pr | [$CDCl_3$] 0.51 (m, 2H); 0.78 (m, 2H); 1.70 (s, 3H); 2.73 (m, 1H); 3.18 (d, 1H); 3.80 (d, 1H); 6.84 (s br, 1H); 7.16 (t, 1H); 7.49 (m, 1H), 7.72 (dd, 1H) |

TABLE 6-continued

Compounds of the general formula (I) according to the invention in which $R^2$ is hydrogen and $R^3$ is methyl and aryl is the radical

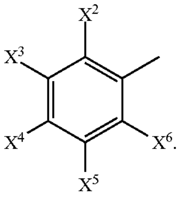

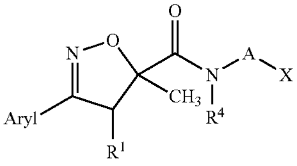

| No. | Aryl | $R^1$ | Y | $R^4$ | A | X | Physical data |
|---|---|---|---|---|---|---|---|
| 6.067 | 3-Cl-4-Me—Ph | H | O | H | bond | c-Pr | |
| 6.068 | 3-Cl-5-$CF_3$—Ph | H | O | H | bond | c-Pr | [$CDCl_3$] 0.52 (m, 2H); 0.80 (m, 2H); 1.72 (s, 3H); 2.74 (m, 1H); 3.21 (d, 1H); 3.85 (d, 1H); 6.81 (s br, 1H); 7.66 (s, 1H); 7.75 (s, 1H); 7.80 (s, 1H) |
| 6.069 | 3-Cl-5-CN—Ph | H | O | H | bond | c-Pr | [$CDCl_3$] 7.84 2.47; 7.84 3.25; 7.83 1.85; 7.80 3.19; 7.80 3.73; 7.80 1.59; 7.68 2.56; 7.68 2.87; 7.67 1.47; 7.27 6.24; 7.26 11.73; 6.78 1.00; 5.30 0.84; 3.85 2.70; 3.80 3.08; 3.20 2.96; 3.16 2.62; 2.76 0.55; 2.75 0.86; 2.74 1.25; 2.73 1.23; 2.72 0.88; 2.71 0.57; 1.76 0.33; 1.72 16.00; 1.58 1.89; 0.83 0.51; 0.82 1.50; 0.81 1.72; 0.81 1.89; 0.80 1.40; 0.80 1.39; 0.80 1.47; 0.79 2.05; 0.77 0.63; 0.57 0.51; 0.55 0.58; 0.54 1.59; 0.54 1.58; 0.53 2.97; 0.52 1.61; 0.52 0.92; 0.50 0.52; 0.49 0.35; 0.49 0.34; 0.00 4.54 |
| 6.070 | 3-Cl-5-Et—Ph | H | O | H | bond | c-Pr | [$CDCl_3$] 7.52 0.33; 7.44 3.02; 7.33 3.34; 7.26 58.22; 7.26 59.30; 7.25 3.17; 7.00 0.34; 6.86 1.05; 3.83 2.63; 3.79 3.00; 3.21 2.90; 3.17 2.55; 2.75 0.55; 2.75 0.86; 2.74 1.26; 2.73 1.22; 2.72 0.94; 2.71 0.56; 2.68 1.16; 2.66 3.67; 2.64 3.76; 2.62 1.29; 1.70 16.00; 1.56 19.09; 1.26 4.37; 1.26 4.64; 1.24 8.50; 1.24 9.25; 1.22 4.09; 1.22 4.37; 0.82 0.49; 0.80 1.88; 0.79 1.96; 0.79 1.34; 0.78 1.67; 0.77 2.03; 0.76 0.65; 0.56 0.46; 0.55 0.57; 0.53 1.87; 0.52 3.13; 0.51 1.72; 0.50 0.48; 0.49 0.33; 0.01 0.90; 0.00 24.52 |
| 6.071 | 3-Cl-5-F—Ph | H | O | H | bond | c-Pr | [$CDCl_3$] 0.52 (m, 2H); 0.80 (m, 2H); 1.71 (s, 3H); 2.73 (m, 1H); 3.17 (d, 1H); 3.78 (d, 1H); 6.81 (s br, 1H); 7.15 (m, 1H); 7.27 (m, 1H); 7.39 (s, 1H) |
| 6.072 | 3-Cl-5-Me—Ph | H | O | H | bond | c-Pr | [$CDCl_3$] 0.51 (m, 1H); 0.78 (m, 1H) 1.70 (s, 3H); 2.33 (s, 3H); 2.72 (m, 1H); 3.19 (d, 1H); 3.80 (d, 1H); 6.86 (brt, 1H); 7.22 (m, 1H); 7.31 (m, 1H); 7.43 (m, 1H). |
| 6.073 | 3-Cl-5-$CF_3O$—Ph | H | O | H | bond | c-Pr | [$CDCl_3$] 0.53 (m, 2H); 0.80 (m, 2H); 1.72 (s, 3H); 2.73 (m, 1H); 3.18 (d, 1H); 3.79 (d, 1H); 6.80 (brs, 1H); 7.28 (s, 1H); 7.39 (s, 1H); 7.53 (s, 1H). |
| 6.074 | 3-Cl—Ph | H | O | H | bond | c-Pr | [$CDCl_3$] 0.54 (m, 2H); 0.78 (m, 2H); 1.70 (s, 3H); 2.74 (m, 1H); 3.21 (d, |

TABLE 6-continued
Compounds of the general formula (I) according to the invention in which $R^2$ is hydrogen and $R^3$ is methyl and aryl is the radical
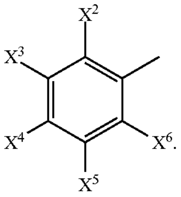
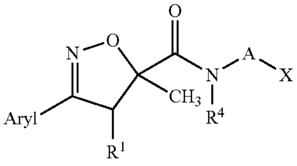
| No. | Aryl | $R^1$ | Y | $R^4$ | A | X | Physical data |
|---|---|---|---|---|---|---|---|
| | | | | | | | 1H); 3.81 (d, 1H); 6.85 (s br, 1H); 7.35 (t, 1H); 7.41 (m, 1H); 7.49 (s, 1H); 7.65 (s, 1H) |
| 6.075 | 3-CN-5-F—Ph | H | O | H | bond | c-Pr | |
| 6.076 | 3-c-Pr-5-F—Ph | H | O | H | bond | c-Pr | [$CDCl_3$] 7.26 8.77; 7.26 8.29; 7.13 1.36; 7.12 1.06; 7.11 4.50; 7.10 4.15; 6.85 0.89; 6.82 1.33; 6.80 0.92; 6.79 1.39; 6.79 0.84; 3.82 2.69; 3.82 2.61; 3.77 3.07; 3.77 3.00; 3.20 2.96; 3.16 2.59; 3.16 2.55; 2.76 0.52; 2.75 0.52; 2.75 0.88; 2.74 1.18; 2.74 1.22; 2.73 1.27; 2.72 0.90; 2.71 0.56; 2.71 0.54; 1.92 0.61; 1.91 0.68; 1.90 1.26; 1.89 0.72; 1.88 0.68; 1.87 0.34; 1.70 16.00; 1.69 15.74; 1.60 1.31; 1.25 0.36; 1.04 0.73; 1.04 0.72; 1.03 2.27; 1.03 2.09; 1.02 2.40; 1.02 1.59; 1.02 1.05; 1.01 1.17; 1.01 2.29; 1.00 2.20; 0.99 0.89; 0.99 0.83; 0.82 0.51; 0.80 0.87; 0.80 1.91; 0.79 1.84; 0.79 1.06; 0.78 1.72; 0.77 2.02; 0.76 0.34; 0.75 0.72; 0.74 0.33; 0.73 0.33; 0.73 0.91; 0.73 0.88; 0.72 2.82; 0.71 2.39; 0.71 2.38; 0.70 2.12; 0.70 2.89; 0.69 0.76; 0.69 0.73; 0.56 0.44; 0.54 0.58; 0.53 1.72; 0.52 2.80; 0.51 1.70; 0.49 0.48; 0.48 0.32 |
| 6.077 | 3-EtO—Ph | H | O | H | bond | c-Pr | |
| 6.078 | 3-Et-5-F—Ph | H | O | H | bond | c-Pr | [$CDCl_3$] 7.26 16.87; 7.22 2.64; 7.19 0.82; 7.18 1.06; 7.18 0.78; 7.16 0.81; 7.16 1.05; 7.15 0.79; 6.98 0.99; 6.96 1.00; 6.86 0.73; 3.83 2.67; 3.79 3.07; 3.22 2.93; 3.17 2.57; 2.76 0.54; 2.75 0.83; 2.74 1.23; 2.73 1.23; 2.72 0.87; 2.71 0.58; 2.69 0.99; 2.67 3.03; 2.65 3.13; 2.64 1.08; 1.70 16.00; 1.57 4.76; 1.57 6.26; 1.26 4.63; 1.24 9.27; 1.22 4.43; 0.82 0.45; 0.80 0.87; 0.80 1.80; 0.79 1.74; 0.79 1.15; 0.78 0.99; 0.78 1.58; 0.77 1.88; 0.77 1.07; 0.75 0.58; 0.56 0.40; 0.55 0.54; 0.54 0.55; 0.53 1.61; 0.52 2.43; 0.52 2.25; 0.51 1.61; 0.51 0.91; 0.51 0.51; 0.50 0.45; 0.00 5.31 |
| 6.079 | 3-Et—Ph | H | O | H | bond | c-Pr | [$CDCl_3$] 7.49 3.03; 7.44 1.35; 7.42 1.90; 7.34 1.22; 7.32 2.77; 7.30 1.72; 7.28 2.24; 7.27 13.51; 7.26 14.49; 6.91 0.94; 3.86 2.56; 3.86 2.62; 3.82 2.92; 3.82 3.01; 3.25 2.95; 3.21 2.59; 2.75 0.55; 2.75 0.89; 2.74 1.27; 2.73 1.26; 2.72 |

TABLE 6-continued
Compounds of the general formula (I) according to the invention in which $R^2$ is hydrogen and $R^3$ is methyl and aryl is the radical
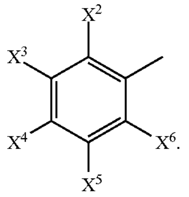
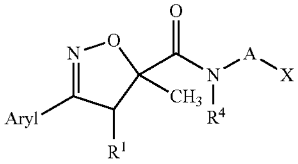
| No. | Aryl | $R^1$ | Y | $R^4$ | A | X | Physical data |
|---|---|---|---|---|---|---|---|
| | | | | | | | 0.92; 2.71 0.60; 2.70 1.35; 2.68 3.68; 2.66 3.78; 2.64 1.30; 1.70 16.00; 1.60 5.16; 1.27 4.35; 1.27 4.54; 1.25 8.56; 1.25 8.94; 1.23 4.13; 1.23 4.27; 0.81 0.48; 0.79 1.85; 0.79 1.89; 0.78 1.39; 0.78 1.65; 0.77 2.05; 0.76 0.34; 0.75 0.63; 0.56 0.48; 0.55 0.58; 0.53 1.76; 0.52 3.07; 0.51 1.69; 0.49 0.49; 0.48 0.34; 0.00 5.01; 0.00 5.33 |
| 6.080 | 3-F-5-MeS—Ph | H | O | H | bond | c-Pr | [$CDCl_3$] 7.26 19.37; 7.24 1.62; 7.24 2.50; 7.23 1.42; 7.11 0.77; 7.10 0.82; 7.10 0.88; 7.10 0.71; 7.08 0.77; 7.08 0.83; 7.08 0.85; 7.07 0.69; 7.00 0.78; 7.00 1.01; 6.99 0.60; 6.98 0.78; 6.97 0.91; 6.97 0.58; 6.83 0.55; 3.81 2.23; 3.77 2.55; 3.20 2.37; 3.16 2.08; 2.76 0.47; 2.75 0.62; 2.74 0.98; 2.73 0.98; 2.72 0.64; 2.71 0.46; 2.52 0.46; 2.50 16.00; 2.30 0.44; 1.70 12.94; 1.56 3.70; 0.82 0.38; 0.81 0.82; 0.80 1.63; 0.80 1.44; 0.79 0.85; 0.79 0.82; 0.78 1.44; 0.78 1.53; 0.77 0.76; 0.76 0.48; 0.55 0.44; 0.54 0.52; 0.53 0.91; 0.53 1.31; 0.52 1.99; 0.52 1.79; 0.52 1.38; 0.51 0.68; 0.51 0.37; 0.50 0.35; 0.01 0.33; 0.00 7.71 |
| 6.081 | 3-F-5-$MeSO_2$—Ph | H | O | H | bond | c-Pr | [$CDCl_3$] 7.95 1.27; 7.95 2.69; 7.94 1.88; 7.72 0.59; 7.72 0.74; 7.72 0.95; 7.71 0.88; 7.70 0.68; 7.70 0.78; 7.70 0.96; 7.69 0.86; 7.67 0.74; 7.67 0.91; 7.66 0.89; 7.66 0.77; 7.65 0.77; 7.64 0.94; 7.64 0.88; 7.64 0.76; 7.27 0.46; 7.26 18.95; 6.80 0.67; 5.30 1.65; 3.90 2.31; 3.85 2.62; 3.25 2.44; 3.20 2.15; 3.09 16.00; 2.76 0.46; 2.75 0.70; 2.74 1.01; 2.73 1.08; 2.73 0.71; 2.72 0.51; 2.04 1.00; 1.73 13.43; 1.57 4.11; 1.26 0.66; 0.84 0.40; 0.82 0.69; 0.82 0.70; 0.82 1.08; 0.81 1.06; 0.81 0.90; 0.81 1.02; 0.80 1.16; 0.80 1.21; 0.80 0.99; 0.80 1.03; 0.79 1.19; 0.79 1.12; 0.77 0.48; 0.57 0.34; 0.56 0.49; 0.55 0.41; 0.55 0.71; 0.54 1.00; 0.54 1.01; 0.53 1.83; 0.53 0.99; 0.52 1.03; 0.52 0.84; 0.52 0.53; 0.51 0.41; 0.00 7.05 |
| 6.082 | 3-F-5-MeO—Ph | H | O | H | bond | c-Pr | [$CDCl_3$] 7.26 12.30; 6.96 0.76; 6.95 1.38; 6.95 1.19; 6.94 0.95; 6.94 0.65; 6.94 0.97; 6.94 0.57; 6.92 0.77; 6.92 0.73; 6.92 0.83; 6.91 0.67; 6.87 0.39; 6.70 0.65; 6.69 |

TABLE 6-continued

Compounds of the general formula (I) according to the invention in which $R^2$ is hydrogen and $R^3$ is methyl and aryl is the radical

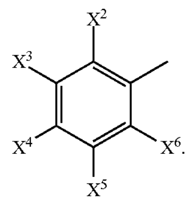

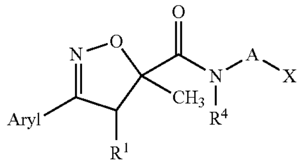

| No. | Aryl | $R^1$ | Y | $R^4$ | A | X | Physical data |
|---|---|---|---|---|---|---|---|
| | | | | | | | 1.21; 6.69 0.61; 6.67 0.66; 6.67 1.21; 6.66 0.59; 3.82 16.00; 3.81 2.41; 3.77 2.62; 3.21 2.36; 3.16 2.08; 2.76 0.45; 2.75 0.59; 2.74 1.00; 2.73 1.00; 2.72 0.62; 2.72 0.48; 1.70 13.00; 0.82 0.36; 0.81 0.60; 0.80 1.53; 0.80 1.31; 0.79 0.73; 0.79 0.61; 0.79 1.31; 0.78 1.45; 0.78 0.73; 0.76 0.47; 0.55 0.42; 0.54 0.37; 0.54 0.64; 0.54 1.10; 0.53 1.68; 0.53 1.53; 0.52 1.24; 0.52 0.61; 0.51 0.34; 0.50 0.32; 0.00 2.65 |
| 6.083 | 3-F-5-Me—Ph | H | O | H | bond | c-Pr | [$CDCl_3$] 7.26 0.36; 7.26 16.01; 7.26 0.43; 7.19 1.69; 7.19 1.78; 7.19 1.41; 7.18 0.54; 7.17 0.69; 7.15 0.50; 7.15 0.68; 7.15 0.50; 6.96 0.52; 6.96 0.58; 6.96 0.66; 6.96 0.56; 6.95 0.49; 6.94 0.52; 6.94 0.58; 6.93 0.65; 6.93 0.56; 6.93 0.49; 6.85 0.43; 3.82 2.76; 3.77 3.14; 3.21 2.84; 3.16 2.50; 2.75 0.52; 2.74 0.70; 2.74 1.14; 2.73 1.15; 2.72 0.70; 2.71 0.55; 2.37 8.78; 1.70 16.00; 1.57 6.97; 0.82 0.43; 0.80 0.70; 0.80 1.30; 0.79 1.27; 0.79 0.81; 0.78 0.72; 0.78 1.05; 0.77 1.48; 0.77 0.80; 0.75 0.52; 0.56 0.35; 0.54 0.50; 0.53 0.43; 0.53 0.72; 0.53 1.17; 0.52 1.75; 0.52 1.41; 0.51 1.17; 0.51 0.67; 0.50 0.37; 0.49 0.39; 0.00 8.45 |
| 6.084 | 3-F-5-Me—Ph | H | S | H | bond | c-Pr | [$CDCl_3$] 0.69 (m, 2H); 0.94 (m, 2H); 1.84 (s, 3H), 2.36 (s, 3H); 3.25 (m, 1H); 3.37 (d, 1H); 4.23 (d, 1H); 6.93 (m, 1H); 7.18 (m, 2H); 8.60 (brs, 1H). |
| 6.085 | 3-F—Ph | H | O | H | bond | c-Pr | [$CDCl_3$] 0.51 (m, 1H); 0.79 (m, 1H) 1.70 (s, 3H); 2.72 (m, 1H); 3.20 (d, 1H); 3.80 (d, 1H); 6.85 (brs, 1H); 7.13 (m, 1H); 7.38 (m, 3H). |
| 6.086 | 3-OH—Ph | H | O | H | bond | c-Pr | |
| 6.087 | 3-iPr—Ph | H | O | H | bond | c-Pr | |
| 6.088 | 3-MeO—Ph | H | O | H | bond | c-Pr | |
| 6.089 | 3-Me-5-$CF_3O$—Ph | H | O | H | bond | c-Pr | [$CDCl_3$] 7.34 2.42; 7.31 1.77; 7.26 18.27; 7.09 1.72; 6.85 0.74; 3.84 2.74; 3.79 3.13; 3.22 2.98; 3.18 2.61; 2.76 0.53; 2.75 0.82; 2.74 1.18; 2.73 1.24; 2.72 0.84; 2.71 0.57; 2.40 11.98; 1.70 16.00; 1.59 5.69; 0.82 0.45; 0.81 0.75; 0.80 1.85; 0.79 1.63; 0.79 1.17; 0.79 0.97; 0.78 1.63; 0.78 1.74; 0.77 1.15; 0.76 0.53; 0.56 0.37; 0.55 0.53; 0.54 0.45; 0.53 1.65; 0.53 2.26; 0.52 2.43; 0.52 1.62; 0.51 |

TABLE 6-continued
Compounds of the general formula (I) according to the invention in which $R^2$ is hydrogen and $R^3$ is methyl and aryl is the radical
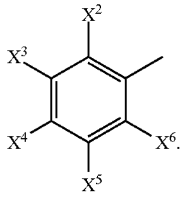
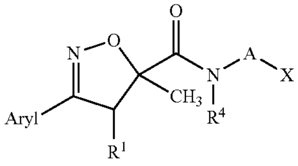
| No. | Aryl | $R^1$ | Y | $R^4$ | A | X | Physical data |
|---|---|---|---|---|---|---|---|
| | | | | | | | 0.94; 0.51 0.49; 0.50 0.43 |
| 6.090 | 3-Me—Ph | H | O | H | bond | c-Pr | [$CDCl_3$] 7.47 2.35; 7.46 2.36; 7.42 1.15; 7.40 1.49; 7.31 1.02; 7.29 2.32; 7.27 1.63; 7.26 12.66; 7.25 1.72; 7.23 0.83; 6.89 0.72; 3.85 2.68; 3.80 3.06; 3.24 2.91; 3.19 2.55; 2.75 0.54; 2.74 0.79; 2.73 1.21; 2.72 1.16; 2.72 0.81; 2.71 0.54; 2.37 12.17; 1.70 16.00; 1.59 2.73; 0.81 0.48; 0.79 1.27; 0.79 1.48; 0.78 1.60; 0.78 1.18; 0.78 1.15; 0.77 1.27; 0.76 1.76; 0.75 0.59; 0.55 0.45; 0.54 0.55; 0.53 1.35; 0.52 1.39; 0.52 2.50; 0.51 1.37; 0.50 0.80; 0.49 0.48; 0.00 4.84 |
| 6.091 | 3-$NO_2$—Ph | H | O | H | bond | c-Pr | [$CDCl_3$] 8.48 1.21; 8.47 1.98; 8.47 1.33; 8.30 0.83; 8.29 0.90; 8.29 0.82; 8.29 0.82; 8.28 0.90; 8.27 0.93; 8.27 0.89; 8.27 0.85; 7.98 0.84; 7.98 1.06; 7.98 0.99; 7.97 0.86; 7.96 0.97; 7.96 1.15; 7.96 1.13; 7.95 0.93; 7.63 1.38; 7.61 2.29; 7.59 1.18; 7.26 14.84; 6.83 0.46; 5.30 0.78; 3.92 2.79; 3.88 3.15; 3.28 2.88; 3.24 2.55; 2.77 0.53; 2.76 0.71; 2.75 1.17; 2.74 1.17; 2.73 0.74; 2.72 0.56; 1.74 16.00; 1.57 7.80; 0.83 0.36; 0.82 0.73; 0.81 1.09; 0.81 0.84; 0.81 0.85; 0.80 0.95; 0.80 1.26; 0.80 0.82; 0.79 0.82; 0.79 1.02; 0.78 0.81; 0.77 0.44; 0.77 0.36; 0.57 0.39; 0.56 0.51; 0.55 0.42; 0.55 0.75; 0.54 0.92; 0.54 0.79; 0.54 1.40; 0.53 1.63; 0.53 1.17; 0.53 0.82; 0.52 0.80; 0.52 0.70; 0.52 0.37; 0.51 0.37; 0.00 7.97 |
| 6.092 | 4-Cl-3,5-$F_2$—Ph | H | O | H | bond | c-Pr | [$CDCl_3$] 7.28 0.61; 7.27 1.23; 7.26 57.08; 7.25 3.82; 7.24 0.68; 7.23 0.36; 7.21 0.33; 6.80 0.66; 5.30 0.63; 3.80 2.66; 3.76 3.02; 3.17 2.86; 3.13 2.50; 2.80 1.28; 2.76 0.52; 2.75 0.79; 2.74 1.17; 2.73 1.18; 2.72 0.81; 2.71 0.52; 2.17 0.92; 1.71 16.00; 1.57 5.19; 1.43 1.74; 1.26 1.09; 1.24 0.72; 1.22 1.41; 1.13 0.49; 0.85 0.38; 0.84 0.34; 0.83 0.57; 0.82 0.88; 0.81 1.63; 0.80 1.58; 0.80 1.07; 0.80 0.94; 0.79 1.35; 0.79 1.77; 0.77 0.57; 0.56 0.40; 0.55 0.51; 0.54 0.52; 0.53 1.43; 0.53 2.28; 0.52 1.41; 0.51 0.77; 0.51 0.43; 0.50 0.42; 0.01 0.82; 0.00 26.80; −0.01 0.88 |

TABLE 6-continued

Compounds of the general formula (I) according to the invention in which $R^2$ is hydrogen and $R^3$ is methyl and aryl is the radical

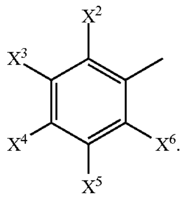

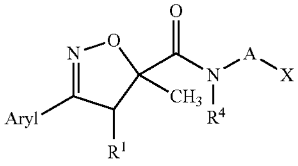

| No. | Aryl | $R^1$ | Y | $R^4$ | A | X | Physical data |
|---|---|---|---|---|---|---|---|
| 6.093 | 4-EtO—Ph | H | O | H | bond | c-Pr | [$CDCl_3$] 7.56 4.41; 7.54 4.23; 7.54 4.33; 7.26 13.43; 7.26 15.57; 6.91 5.82; 6.89 4.33; 6.89 4.28; 4.09 1.33; 4.07 3.70; 4.07 4.16; 4.06 3.77; 4.05 4.21; 4.04 1.25; 4.04 1.36; 3.83 2.35; 3.82 2.67; 3.78 2.69; 3.78 3.05; 3.22 2.62; 3.21 2.95; 3.17 2.29; 3.17 2.58; 2.75 0.46; 2.75 0.55; 2.74 0.84; 2.73 1.24; 2.73 1.13; 2.72 1.21; 2.72 0.86; 2.71 0.51; 2.71 0.55; 1.69 14.28; 1.69 16.00; 1.57 2.98; 1.45 3.79; 1.44 4.33; 1.43 7.63; 1.43 8.71; 1.41 3.75; 1.41 4.17; 0.81 0.47; 0.79 1.75; 0.79 1.80; 0.78 2.08; 0.77 1.63; 0.77 1.64; 0.76 2.12; 0.74 0.60; 0.55 0.50; 0.54 0.57; 0.54 0.56; 0.52 1.87; 0.52 1.75; 0.51 3.32; 0.51 1.72; 0.50 1.00; 0.49 0.50; 0.48 0.37; 0.00 6.42; 0.00 7.41 |
| 6.094 | $F_5$—Ph | H | O | H | bond | c-Pr | |
| 6.095 | Ph | H | O | H | bond | c-Pr | [$CDCl_3$] 0.53 (m, 2H); 0.78 (m, 2H); 1.70 (s, 3H); 2.73 (m, 1H); 3.23 (d, 1H); 3.84 (d, 1H); 6.89 (s br, 1H); 7.42 (m, 3H); 7.64 (m, 2H). |
| 6.096 | 3,5-$Cl_2$—Ph | H | O | H | bond | decahydro-naphthalen-2-yl | |
| 6.097 | 3,5-$Cl_2$—Ph | H | O | H | bond | H | [$CDCl_3$] 1.76 (s, 3H); 3.19 (d, 1H); 3.80 (d, 1H); 5.39 (s br, 1H); 6.72 (s br, 1H); 7.43 (m, 1H); 7.52 (m, 2H) |
| 6.098 | 3,5-$F_2$—Ph | H | O | H | bond | H | [$CDCl_3$] 7.52 0.36; 7.26 63.20; 7.19 0.38; 7.17 2.53; 7.16 2.64; 7.00 0.33; 6.91 0.55; 6.91 0.74; 6.90 0.40; 6.89 1.09; 6.88 1.53; 6.88 0.72; 6.86 0.76; 6.86 0.36; 6.72 0.65; 5.39 0.68; 3.82 2.53; 3.78 2.91; 3.21 2.83; 3.17 2.43; 1.76 16.00; 1.54 28.33 |
| 6.099 | 3,5-$F_2$—Ph | H | S | H | bond | H | [$CDCl_3$] 7.52 1.22; 7.31 0.62; 7.27 0.42; 7.26 212.46; 7.21 0.93; 7.18 1.50; 7.17 1.79; 7.17 0.99; 7.16 0.98; 7.16 1.73; 7.15 1.54; 7.00 1.18; 6.91 0.36; 6.91 0.66; 6.90 0.34; 6.89 0.73; 6.88 1.36; 6.88 0.68; 6.87 0.39; 6.86 0.67; 4.24 2.60; 4.20 2.87; 3.40 2.59; 3.36 2.34; 1.91 16.00; 1.53 53.71; 1.51 0.33; 0.15 0.36; 0.01 2.78 |
| 6.100 | 3-F—Ph | H | O | H | bond | H | |
| 6.101 | 3-Me—Ph | H | O | H | bond | H | [$CDCl_3$] 7.48 1.99; 7.43 0.96; 7.41 1.27; 7.32 0.91; 7.30 2.11; 7.28 1.38; 7.26 14.75; 7.25 1.70; 7.23 0.71; 6.81 0.45; 5.49 0.45; 3.86 2.60; 3.82 2.99; 3.26 2.84; 3.22 |

TABLE 6-continued
Compounds of the general formula (I) according to the invention in which $R^2$ is hydrogen and $R^3$ is methyl and aryl is the radical
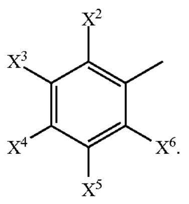
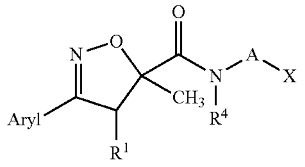
| No. | Aryl | $R^1$ | Y | $R^4$ | A | X | Physical data |
|---|---|---|---|---|---|---|---|
| | | | | | | | 2.47; 2.37 10.51; 2.05 0.71; 1.74 16.00; 1.59 4.98; 1.26 0.40; 0.00 5.71 |
| 6.102 | 3-Me—Ph | H | S | H | bond | H | [$CDCl_3$] 8.33 0.57; 7.52 0.64; 7.46 3.38; 7.44 1.65; 7.42 2.07; 7.31 1.13; 7.30 2.58; 7.28 1.77; 7.26 18.73; 7.26 18.69; 7.23 1.20; 4.26 2.60; 4.26 2.56; 4.22 2.89; 4.22 2.87; 3.45 2.81; 3.45 2.78; 3.41 2.54; 3.41 2.53; 2.37 15.02; 1.91 16.00; 1.90 15.73; 1.58 9.98; 0.00 3.92 |
| 6.103 | 3,5-$Cl_2$—Ph | H | O | $CH_3$ | bond | hydroxy | |
| 6.104 | 2,3,4-$F_3$—Ph | H | O | H | bond | oxetan-3-yl | [$CDCl_3$] 7.56 0.34; 7.55 0.34; 7.54 0.38; 7.54 0.47; 7.54 0.48; 7.54 0.48; 7.53 0.41; 7.53 0.37; 7.52 0.50; 7.52 0.47; 7.52 0.55; 7.52 0.37; 7.51 0.33; 7.50 0.34; 7.34 0.38; 7.32 0.39; 7.26 17.81; 7.07 0.35; 7.06 0.38; 7.05 0.36; 7.05 1.02; 7.04 0.71; 7.03 0.66; 7.02 0.99; 7.02 0.36; 7.00 0.32; 5.30 0.50; 5.05 0.41; 5.04 0.83; 5.03 0.54; 5.02 0.47; 5.02 1.04; 5.02 0.36; 5.00 0.55; 5.00 0.57; 4.96 1.34; 4.94 1.75; 4.94 1.84; 4.92 0.95; 4.91 1.25; 4.90 1.75; 4.89 1.90; 4.88 0.96; 4.56 1.26; 4.55 1.89; 4.53 0.95; 4.52 1.26; 4.50 1.87; 4.48 1.02; 3.88 1.12; 3.87 1.16; 3.83 1.36; 3.83 1.35; 3.33 1.21; 3.33 1.26; 3.29 1.07; 3.28 1.08; 1.72 16.00; 1.57 11.99; 1.25 0.40; 0.00 8.12 |
| 6.105 | 2,3-$F_2$—Ph | H | O | H | bond | oxetan-3-yl | [$CDCl_3$] 7.56 0.44; 7.55 0.74; 7.55 0.44; 7.54 1.11; 7.53 1.11; 7.53 0.50; 7.52 0.55; 7.52 0.86; 7.51 0.43; 7.35 0.55; 7.33 0.56; 7.28 0.37; 7.28 0.36; 7.26 16.48; 7.24 0.63; 7.24 1.01; 7.22 0.48; 7.21 0.43; 7.16 0.55; 7.16 0.48; 7.15 0.58; 7.14 0.60; 7.14 0.86; 7.14 0.78; 7.13 0.83; 7.12 0.77; 7.12 0.40; 7.12 0.34; 7.11 0.34; 5.30 0.41; 5.06 0.40; 5.06 0.45; 5.04 1.00; 5.02 1.12; 5.01 0.67; 5.01 0.56; 4.95 1.43; 4.94 2.18; 4.92 1.10; 4.91 1.35; 4.89 2.21; 4.88 1.08; 4.57 1.37; 4.55 2.23; 4.54 1.11; 4.52 1.38; 4.51 2.22; 4.49 1.14; 4.13 0.52; 4.11 0.53; 3.90 1.30; 3.89 1.29; 3.85 1.58; 3.85 1.53; 3.37 1.54; 3.36 1.48; 3.32 1.33; 3.32 1.27; 2.04 2.32; 1.73 |

TABLE 6-continued

Compounds of the general formula (I) according to the invention in which $R^2$ is hydrogen and $R^3$ is methyl and aryl is the radical

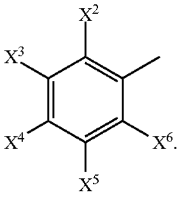

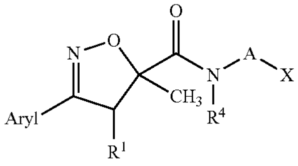

| No. | Aryl | $R^1$ | Y | $R^4$ | A | X | Physical data |
|---|---|---|---|---|---|---|---|
| | | | | | | | 16.00; 1.56 9.23; 1.28 0.67; 1.26 1.38; 1.24 0.62; 0.00 10.24; −0.01 0.39 |
| 6.106 | 2,5-$F_2$—Ph | H | O | H | bond | oxetan-3-yl | |
| 6.107 | 3,5-$Cl_2$—Ph | H | O | H | bond | oxetan-3-yl | [$CDCl_3$] 1.72 (s, 3H); 3.18 (d, 1H); 3.75 (d, 1H); 4.52 (m, 2H); 4.91 (m, 2H); 5.03 (m, 1H); 7.31 (s br, 1H); 7.42 (s, 1H); 7.52 (s, 2H). |
| 6.108 | 3,5-$F_2$—Ph | H | O | H | bond | oxetan-3-Yl | [$CDCl_3$] 1.73 (s, 3H); 3.20 (d, 1H); 3.73 (d, 1H); 4.51 (m, 2H); 4.90 (m, 1H); 5.02 (m, 1H); 6.88 (m, 1H); 7.15 (m, 2H); 7.33 (brd, 1H). |
| 6.109 | 3-Cl-5-$CF_3O$—Ph | H | O | H | bond | oxetan-3-Yl | [$CDCl_3$] 1.73 (s, 3H); 3.20 (d, 1H); 3.76 (d, 1H); 4.52 (m, 2H); 4.90 (m 2H); 5.02 (m, 1H); 7.30 (s, 1H); 7.32 (brt, 1H); 7.41 (s, 1H); 7.55 (s, 1H). |
| 6.110 | 3-F-5-Me—Ph | H | O | H | bond | oxetan-3-yl | [$CDCl_3$] 7.39 0.37; 7.37 0.37; 7.26 14.63; 7.20 0.74; 7.20 1.19; 7.20 1.79; 7.20 1.87; 7.20 1.49; 7.20 1.03; 7.18 0.47; 7.18 0.53; 7.18 0.70; 7.17 0.63; 7.17 0.49; 7.17 0.42; 7.16 0.44; 7.16 0.51; 7.15 0.53; 7.15 0.68; 7.15 0.61; 7.15 0.50; 7.15 0.44; 6.97 0.40; 6.97 0.52; 6.97 0.59; 6.97 0.67; 6.97 0.58; 6.97 0.51; 6.96 0.41; 6.95 0.41; 6.95 0.52; 6.95 0.59; 6.95 0.66; 6.94 0.57; 6.94 0.50; 6.94 0.39; 5.30 0.56; 5.04 0.40; 5.03 0.84; 5.03 0.53; 5.01 0.49; 5.01 1.01; 5.01 0.34; 5.00 0.55; 4.99 0.56; 4.95 1.30; 4.93 1.71; 4.93 1.61; 4.91 0.92; 4.90 1.18; 4.88 1.72; 4.88 1.75; 4.86 0.95; 4.57 1.22; 4.55 1.89; 4.53 0.91; 4.52 1.22; 4.50 1.85; 4.48 0.99; 3.78 2.80; 3.74 3.19; 3.23 2.88; 3.19 2.49; 2.37 8.67; 2.37 9.04; 1.72 16.00; 1.58 8.71; 0.00 6.71 |
| 6.111 | 3-F—Ph | H | O | H | bond | oxetan-3-yl | [$CDCl_3$] 1.72 (s, 3H); 3.22 (d, 1H); 3.78 (d, 1H); 4.52 (m, 2H); 4.90 (m, 1H); 5.03 (m, 1H); 7.13 (m, 1H); 7.39 (m, 4H). |
| 6.112 | 3-$NO_2$—Ph | H | O | H | bond | oxetan-3-yl | [$CDCl_3$] 8.47 1.26; 8.46 2.10; 8.46 1.34; 8.31 0.88; 8.31 0.96; 8.30 0.86; 8.30 0.87; 8.29 0.96; 8.28 0.99; 8.28 0.94; 8.28 0.90; 8.00 0.89; 8.00 1.05; 8.00 1.06; 8.00 0.90; 7.98 1.00; 7.98 1.21; 7.98 0.98; 7.64 1.45; 7.62 2.45; 7.60 1.22; 7.37 0.40; 7.35 0.40; 7.27 0.38; 7.26 15.13; 7.26 0.40; 5.30 1.87; 5.05 0.44; 5.04 0.88; 5.04 0.55; 5.02 0.50; 5.02 1.05; 5.02 0.34; 5.00 0.57; 5.00 0.56; 4.96 |

TABLE 6-continued

Compounds of the general formula (I) according to the invention in which $R^2$ is hydrogen and $R^3$ is methyl and aryl is the radical

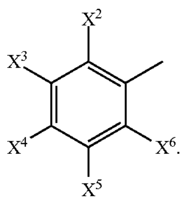

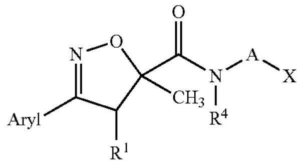

| No. | Aryl | $R^1$ | Y | $R^4$ | A | X | Physical data |
|---|---|---|---|---|---|---|---|
| | | | | | | | 1.33; 4.94 1.80; 4.92 0.93; 4.91 1.18; 4.89 1.80; 4.87 0.96; 4.58 1.26; 4.56 1.88; 4.54 0.93; 4.52 1.28; 4.51 1.82; 4.49 1.03; 3.89 2.80; 3.85 3.19; 3.31 2.91; 3.27 2.54; 2.04 0.32; 1.76 16.00; 1.58 7.71; 1.26 0.37; 0.00 7.59 |
| 6.113 | Ph | H | O | H | bond | oxetan-3-yl | [$CDCl_3$] 7.65 2.02; 7.65 2.24; 7.64 0.98; 7.64 0.81; 7.64 0.81; 7.63 1.96; 7.63 2.52; 7.45 0.85; 7.45 1.10; 7.44 1.86; 7.43 5.25; 7.43 2.56; 7.42 1.18; 7.42 1.48; 7.41 2.35; 7.41 0.57; 7.41 0.48; 7.40 0.49; 7.40 0.71; 7.39 0.37; 7.39 0.51; 7.26 12.18; 5.06 0.33; 5.06 0.42; 5.04 0.89; 5.04 0.54; 5.02 0.55; 5.02 0.99; 5.02 0.36; 5.01 0.55; 5.00 0.54; 4.95 1.30; 4.93 1.83; 4.91 0.96; 4.90 1.19; 4.88 1.87; 4.86 0.99; 4.57 1.25; 4.56 2.01; 4.54 0.99; 4.52 1.27; 4.51 1.99; 4.49 1.04; 3.83 2.83; 3.79 3.28; 3.28 3.02; 3.24 2.61; 1.73 16.00; 1.61 3.77; 0.00 5.40 |
| 6.114 | 3,5-$Cl_2$—Ph | H | O | H | bond | tetrahydro-2H-pyran-4-yl | [$CDCl_3$] 1.40-1.55 (m, 2H); 1.71 (s, 3H); 1.80-1.95 (m, 2H); 3.19 (d, 1H); 3.46 (m, 1H); 3.78 (d, 1H); 3.87-4.00 (m, 2H); 6.70 (br, 1H); 7.41 (m, 1H); 7.51 (m, 2H). |
| 6.115 | 3,5-$Cl_2$—Ph | H | O | H | $C(CH_3)_2$ | 3-methoxyprop-1-yn-1-yl | [$CDCl_3$] 1.64 (s, 6H); 1.70 (s, 3H); 3.15 (d, 1H); 3.33 (s, 3H); 3.78 (d, 1H); 4.10 (s, 2H); 6.84 (s, 1H); 7.40 (t, 1H); 7.52 (m, 2H) |
| 6.116 | 3,5-$Cl_2$—Ph | H | O | H | $C(CH_3)_2$ | carbamoyl | [$CDCl_3$] 1.58 (s, 3H); 1.59 (s, 3H); 1.72 (s, 3H); 3.18 (d, 1H); 3.76 (d, 1H); 5.24 (s, br, 1H); 6.35 (s br, 1H); 7.43 (s, 1H); 7.53 (s, 2H). |
| 6.117 | 3,5-$Cl_2$—Ph | H | O | H | $C(CH_3)_2$ | CH3 | [$CDCl_3$] 1.36 (s, 9H); 1.70 (s, 3H); 3.13 (d, 1H); 3.78 (d, 1H); 6.61 (s br, 1H), 7.41 (s, 1H); 7.53 (s, 2H). |
| 6.118 | 3-Cl-4-F—Ph | H | O | H | $C(CH_3)_2$ | CH3 | [$CDCl_3$] 7.74 0.39; 7.74 0.40; 7.72 0.39; 7.72 0.40; 7.26 0.39; 7.26 0.60; 7.26 39.69; 7.25 0.60; 7.25 0.43; 7.20 0.46; 7.18 0.84; 7.16 0.38; 3.80 0.75; 3.76 0.86; 3.16 0.77; 3.12 0.68; 1.68 4.85; 1.54 14.50; 1.35 16.00; 0.01 0.52; 0.00 0.32; 0.00 0.59; 0.00 0.93; 0.00 18.89; 0.00 0.53; −0.01 0.32; −0.01 0.58 |
| 6.119 | 3,5-$Cl_2$—Ph | H | O | H | $C(CH_3)_2$ | COOH | [$CDCl_3$] 1.57 (s, 3H); 1.59 (s, 3H); 1.72 (s, 3H); 3.18 (d, 1H); 3.78 (d, 1H); 7.15 (s, br, 1H); 7.44 (s, 1H); 7.53 (s, 2H). |
| 6.120 | 3,5-$(CF_3)_2$—Ph | H | O | H | $C(CH_3)_2$ | ethynyl | |

TABLE 6-continued

Compounds of the general formula (I) according to the invention in which $R^2$ is hydrogen and $R^3$ is methyl and aryl is the radical

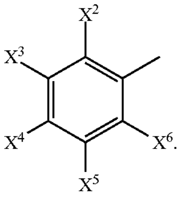

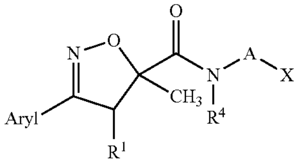

| No. | Aryl | $R^1$ | Y | $R^4$ | A | X | Physical data |
|---|---|---|---|---|---|---|---|
| 6.121 | 3,5-$Cl_2$—Ph | H | O | H | $C(CH_3)_2$ | ethynyl | |
| 6.122 | 3,5-$Cl_2$—Ph | H | O | H | $C(CH_3)_2$ | methoxycarbonyl | [$CDCl_3$] 1.52 (s, 3H); 1.53 (s, 3H); 1.71 (s, 3H); 3.16 (d, 1H); 3.72 (s, 3H); 3.75 (d, 1H); 7.18 (s br, 1H); 7.42 (s, 1H); 7.53 (s, 2H). |
| 6.123 | 3,5-$Cl_2$—Ph | H | O | H | $C(CH_3)_2$ | methylcarbamoyl | |
| 6.124 | 3-Cl—Ph | H | O | H | $C(CH_3)_2CH_2$ | (propan-2-yloxy)carbonyl | [$CDCl_3$] 7.67 1.29; 7.67 2.22; 7.66 1.42; 7.52 0.75; 7.52 1.21; 7.51 0.69; 7.51 0.67; 7.50 0.92; 7.50 1.51; 7.49 0.86; 7.49 0.84; 7.41 0.48; 7.40 0.73; 7.40 0.51; 7.40 0.49; 7.40 0.50; 7.39 1.14; 7.38 1.52; 7.38 1.22; 7.38 0.92; 7.38 0.90; 7.36 2.02; 7.34 2.09; 7.32 0.82; 7.26 10.98; 7.26 12.75; 7.10 0.96; 4.99 0.41; 4.97 1.06; 4.95 1.42; 4.94 1.07; 4.92 0.42; 3.82 2.28; 3.78 2.60; 3.19 2.50; 3.14 2.20; 2.70 7.87; 1.70 0.67; 1.69 13.41; 1.58 2.50; 1.45 0.49; 1.44 0.61; 1.43 12.30; 1.43 12.29; 1.21 0.39; 1.20 16.00; 1.18 15.60; 0.00 4.71 |
| 6.125 | 3-F—Ph | H | O | H | $C(CH_3)_2CH_2$ | (propan-2-yloxy)carbonyl | [$CDCl_3$] 7.41 1.28; 7.39 4.36; 7.38 3.90; 7.36 0.91; 7.27 7.86; 7.26 19.86; 7.15 0.76; 7.13 1.20; 7.12 1.53; 7.12 1.90; 7.11 1.96; 4.99 0.57; 4.97 1.13; 4.96 1.36; 4.94 0.92; 4.92 0.36; 3.83 0.74; 3.82 1.67; 3.78 1.95; 3.19 1.90; 3.15 1.66; 2.71 5.80; 1.69 10.35; 1.56 8.77; 1.43 16.00; 1.26 0.35; 1.20 13.35; 1.18 10.41; 0.01 1.75; 0.00 4.29 |
| 6.126 | 3,5-$Cl_2$—Ph | H | O | H | $C(CH_3)_2CH_2$ | COOH | [$CDCl_3$] 7.93 0.35; 7.91 0.43; 7.52 10.34; 7.41 3.52; 7.41 3.59; 7.31 0.83; 7.28 0.64; 7.26 166.63; 7.26 176.93; 7.26 172.00; 6.99 1.03; 6.92 2.11; 5.30 1.33; 5.30 1.37; 3.79 2.49; 3.75 2.87; 3.16 2.79; 3.12 2.41; 2.93 1.58; 2.89 3.54; 2.84 3.58; 2.80 1.56; 1.85 0.35; 1.69 15.59; 1.65 1.09; 1.54 17.30; 1.46 16.00; 1.42 15.33; 1.36 0.71; 1.34 0.52; 1.31 0.43; 1.31 0.40; 1.30 0.44; 1.28 0.47; 1.25 0.83; 1.24 1.45; 1.23 0.54; 1.22 1.41; 0.84 0.43; 0.82 0.43; 0.81 0.46; 0.15 0.43; 0.05 0.45; 0.00 76.33; 0.00 83.19; 0.00 81.49; −0.15 0.52 |
| 6.127 | 3-Cl—Ph | H | O | H | $C(CH_3)_2CH_2$ | COOH | [$CDCl_3$] 7.66 1.64; 7.65 2.75; 7.65 1.65; 7.50 0.97; 7.50 1.50; 7.50 0.88; 7.48 1.26; 7.48 1.94; 7.48 1.11; 7.41 0.65; 7.41 0.86; 7.40 0.65; 7.39 1.53; 7.38 1.73; 7.38 1.18; 7.36 2.24; 7.34 2.46; 7.32 |

TABLE 6-continued
Compounds of the general formula (I) according to the invention in which $R^2$ is hydrogen and $R^3$ is methyl and aryl is the radical
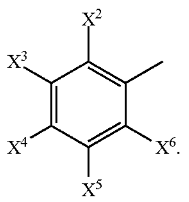
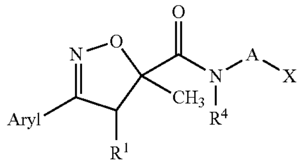
| No. | Aryl | $R^1$ | Y | $R^4$ | A | X | Physical data |
|---|---|---|---|---|---|---|---|
| | | | | | | | 0.95; 7.26 25.93; 6.94 1.71; 3.81 2.76; 3.77 3.14; 3.18 2.98; 3.14 2.63; 2.89 1.12; 2.85 3.82; 2.83 3.88; 2.79 1.15; 2.06 3.22; 2.04 0.87; 1.69 0.79; 1.68 16.00; 1.45 12.64; 1.41 12.50; 1.28 0.32; 1.26 0.86; 0.01 0.38 |
| 6.128 | 3-F—Ph | H | O | H | $C(CH_3)_2CH_2$ | COOH | [$CDCl_3$] 7.40 1.25; 7.40 1.46; 7.39 1.36; 7.39 1.38; 7.39 1.27; 7.37 5.11; 7.37 4.79; 7.36 2.74; 7.36 2.85; 7.35 0.61; 7.35 0.46; 7.26 7.20; 7.26 12.84; 7.14 0.57; 7.14 0.59; 7.14 0.89; 7.13 0.55; 7.13 0.84; 7.12 0.99; 7.12 0.96; 7.12 0.96; 7.12 0.94; 7.11 0.66; 7.11 0.54; 7.10 0.59; 7.10 0.36; 7.09 0.40; 6.95 2.22; 3.81 1.85; 3.81 2.74; 3.77 2.11; 3.77 3.11; 3.19 2.08; 3.19 2.98; 3.15 1.83; 3.14 2.62; 2.87 0.90; 2.84 4.04; 2.82 4.04; 2.78 0.92; 2.05 1.16; 2.05 1.95; 1.68 11.42; 1.68 16.00; 1.45 13.08; 1.41 13.04; 0.00 1.66; 0.00 3.02 |
| 6.129 | 3,5-$Cl_2$—Ph | H | O | H | $C(CH_3)_2CH_2$ | ethoxycarbonyl | [$CDCl_3$] 7.53 6.43; 7.53 5.75; 7.53 7.28; 7.53 6.08; 7.41 1.68; 7.41 1.55; 7.41 3.15; 7.40 2.74; 7.40 1.64; 7.26 9.82; 7.26 8.26; 7.03 1.32; 4.09 1.44; 4.08 4.50; 4.06 4.62; 4.04 1.53; 3.80 2.72; 3.75 3.08; 3.15 2.94; 3.11 2.60; 2.75 5.29; 2.74 5.64; 1.69 16.00; 1.66 1.05; 1.43 13.64; 1.42 13.63; 1.23 4.91; 1.23 4.33; 1.21 9.95; 1.21 8.79; 1.19 4.77; 0.00 6.56; 0.00 5.69 |
| 6.130 | 3-Cl—Ph | H | O | H | $C(CH_3)_2CH_2$ | ethoxycarbonyl | [$CDCl_3$] 7.67 1.26; 7.67 2.35; 7.66 1.58; 7.52 0.87; 7.52 1.41; 7.51 0.92; 7.50 1.03; 7.50 1.77; 7.50 1.14; 7.41 0.55; 7.41 0.74; 7.41 0.63; 7.40 0.66; 7.39 1.31; 7.39 1.34; 7.39 1.54; 7.38 1.23; 7.36 1.97; 7.34 2.20; 7.32 0.86; 7.27 0.40; 7.26 0.60; 7.26 16.06; 7.05 0.92; 4.08 1.49; 4.07 4.71; 4.05 4.80; 4.03 1.60; 3.82 2.82; 3.78 3.19; 3.18 2.96; 3.14 2.63; 2.75 9.20; 1.70 0.77; 1.69 16.00; 1.57 2.83; 1.45 1.16; 1.44 11.67; 1.42 11.77; 1.23 0.38; 1.21 5.31; 1.20 10.68; 1.18 5.03; 0.00 0.34; 0.00 0.53 |
| 6.131 | 3-F—Ph | H | O | H | $C(CH_3)_2CH_2$ | ethoxycarbonyl | [$CDCl_3$] 7.41 0.95; 7.41 1.00; 7.41 0.99; 7.39 2.01; 7.39 2.09; 7.38 3.41; 7.38 3.32; 7.38 3.01; 7.37 1.39; 7.26 17.10; 7.26 25.00; 7.15 0.45; 7.14 0.48; 7.14 0.58; 7.13 |

TABLE 6-continued

Compounds of the general formula (I) according to the invention in which $R^2$ is hydrogen and $R^3$ is methyl and aryl is the radical

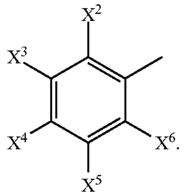

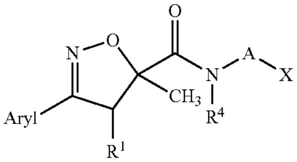

| No. | Aryl | $R^1$ | Y | $R^4$ | A | X | Physical data |
|---|---|---|---|---|---|---|---|
| | | | | | | | 0.47; 7.13 0.89; 7.12 1.03; 7.11 0.77; 7.11 1.03; 7.10 1.36; 4.08 1.42; 4.07 4.46; 4.05 4.53; 4.03 1.49; 3.82 2.70; 3.78 3.08; 3.20 2.99; 3.15 2.66; 2.75 9.56; 1.69 16.00; 1.44 13.13; 1.43 13.17; 1.21 4.81; 1.19 9.92; 1.18 4.76; 0.01 0.48; 0.00 11.62; 0.00 17.19; −0.01 0.52; −0.01 0.59 |
| 6.132 | 3,5-$Cl_2$—Ph | H | O | H | $C(CH_3)_2CH_2$ | hydroxy | [$CDCl_3$] 1.27 (s, 3H); 1.32 (s, 3H); 1.71 (s, 3H); 3.18 (d, 1H); 3.59 (s, 2H); 3.77 (d, 1H); 4.31 (s br, 1H); 6.82 (s br, 1H); 7.42 (t, 1H); 7.52 (m, 2H) |
| 6.133 | 3-Cl—Ph | H | O | H | $C(CH_3)_2CH_2$ | methoxycarbonyl | [$CDCl_3$] 7.67 1.50; 7.67 2.73; 7.66 1.72; 7.52 1.36; 7.51 1.63; 7.50 1.65; 7.41 0.74; 7.41 0.94; 7.41 0.73; 7.40 0.57; 7.39 1.55; 7.39 1.98; 7.39 1.60; 7.36 2.06; 7.34 2.35; 7.32 0.84; 7.26 17.80; 7.26 18.90; 7.00 0.63; 6.99 1.17; 3.83 2.33; 3.83 2.30; 3.78 2.63; 3.78 2.63; 3.62 0.59; 3.62 0.60; 3.57 16.00; 3.57 15.83; 3.18 2.57; 3.14 2.27; 2.83 0.48; 2.79 4.25; 2.78 4.38; 2.75 0.48; 1.70 0.80; 1.69 14.02; 1.69 13.97; 1.44 13.37; 1.41 12.92; 1.26 0.42; 1.26 0.42; 1.23 0.46; 0.00 6.84 |
| 6.134 | 3-F—Ph | H | O | H | $C(CH_3)_2CH_2$ | methoxycarbonyl | [$CDCl_3$] 7.41 0.71; 7.41 0.68; 7.41 0.58; 7.39 1.69; 7.39 2.47; 7.38 2.87; 7.37 1.04; 7.26 7.98; 7.15 0.36; 7.14 0.36; 7.14 0.41; 7.13 0.49; 7.13 0.48; 7.13 0.41; 7.12 0.61; 7.12 0.35; 7.11 0.33; 7.11 0.54; 6.99 0.68; 3.83 2.32; 3.78 2.63; 3.56 16.00; 3.19 2.47; 3.15 2.17; 2.83 0.55; 2.80 3.29; 2.78 3.33; 2.75 0.56; 1.69 13.35; 1.58 2.82; 1.44 9.86; 1.41 9.80; 0.00 4.38 |
| 6.135 | 3,5-$Cl_2$—Ph | H | O | H | $C(CH_3)_2CH_2$ | methylsulfanyl | |
| 6.136 | 3,5-$Cl_2$—Ph | H | O | H | $C(CH_3)_2CH_2$ | methylsulfonyl | |
| 6.137 | 2,4-$Cl_2$—Ph | H | O | H | $C(iPr)CH_2$ | cyanogen | |
| 6.138 | 3,5-$Cl_2$—Ph | H | O | H | C(iPr)Me | cyanogen | [$CDCl_3$] 1.02, 1.06 (2 × d, ratio 2:1, 3H); 1.11, 1.13 (2 × d, ratio 2:1, 3H); 1.60, 1.66 (2 × s, ratio 1:2, 3H); 1.75 (2 overlapping s, 3H); 2.29, 2.39 (2 × m, ratio 2:1, 1H); 3.19 (d, 1H); 3.81 (2 overlapping d, 1H); 6.82, 6.86 (2 × m, ratio 1:2, 1H); 7.41 (m, 1H); 7.51 (m, 2H). |
| 6.139 | 3,5-$Cl_2$—Ph | H | O | H | $CH(CF3)CH_2$ | ethoxycarbonyl | [$CDCl_3$] 1.17, 1.31 (2 × t, ratio 3:4, 3H); 1.72, 1.76 (2 × s, ratio 4:3, 3H); 2.51 (m, 2H); 3.19, 3.22 (2 × d, ratio 3:4, 1H); 3.75, 3.79 (2 × d, ratio 4:3, 1H); 4.02, 4.19 (2 × m, |

TABLE 6-continued

Compounds of the general formula (I) according to the invention in which $R^2$ is hydrogen and $R^3$ is methyl and aryl is the radical

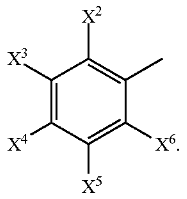

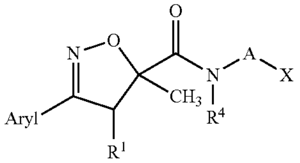

| No. | Aryl | $R^1$ | Y | $R^4$ | A | X | Physical data |
|---|---|---|---|---|---|---|---|
| | | | | | | | ratio 3:4, 2H); 4.99 (m, 1H); 7.35 (m, 1H); 7.42 (m, 1H); 7.52 (m, 2H). |
| 6.140 | 3,5-$Cl_2$—Ph | H | O | H | $CH(CH_2CH_2SCH_3)$ | methoxycarbonyl | [$CDCl_3$] 1.74 (ds, 3H); 1.96-2.26 (m, 2H); 2.02, 2.11 (ds, 3H); 2.43, 2.53 (dt, 2H); 3.19 (d, 1H); 3.71, 3.77 (ds, 3H); 3.73, 3.79 (dd, 1H); 4.66 (m, 1H); 7.34 (br, 1H); 7.41 (m, 1H); 7.52 (m, 2H). |
| 6.141 | 3,5-$Cl_2$—Ph | H | O | H | $CH(CH_2CH_3)CH_2$ | cyanogen | [$CDCl_3$] 0.91, 1.00 (dt, 3H); 1.61-1.79 (m, 2H); 1,72, 1.74 (ds, 3H); 2.50-2.82 (m, 1H); 3.20 (dd, 1H); 3.78 (dd, 1H); 3.91-4.05 (m, 1H); 6.82 (t, 1H); 7.41 (m, 1H); 7.51 (m, 2H). |
| 6.142 | 3,5-$Cl_2$—Ph | H | O | H | $CH(Et)CH_2$ | methoxycarbonyl | [$CDCl_3$] 7.53 3.47; 7.53 4.15; 7.52 8.54; 7.52 9.35; 7.52 8.22; 7.52 6.20; 7.42 1.40; 7.41 2.45; 7.41 3.55; 7.41 4.40; 7.26 79.46; 7.26 80.34; 7.09 0.53; 7.05 0.92; 7.03 0.82; 7.00 0.50; 7.00 0.49; 4.15 0.61; 4.13 0.98; 4.13 1.06; 4.12 0.91; 4.11 1.12; 4.11 0.71; 4.10 0.62; 3.81 2.14; 3.80 2.34; 3.79 1.41; 3.78 1.57; 3.76 2.43; 3.76 2.70; 3.74 1.87; 3.69 14.49; 3.69 16.00; 3.59 9.75; 3.59 10.73; 3.18 4.31; 3.14 3.78; 2.61 0.53; 2.60 0.54; 2.57 1.87; 2.56 1.83; 2.54 2.20; 2.53 2.02; 2.50 1.81; 2.49 1.77; 2.48 1.35; 2.46 1.28; 2.44 0.34; 2.43 0.33; 1.73 8.69; 1.72 9.65; 1.71 12.83; 1.71 14.24; 1.66 0.44; 1.65 1.05; 1.62 6.02; 1.59 3.03; 1.57 2.23; 1.56 1.34; 1.56 1.44; 1.54 1.61; 1.53 1.13; 1.51 0.60; 1.49 0.35; 0.96 2.40; 0.94 4.86; 0.92 2.19; 0.86 3.62; 0.84 7.26; 0.82 3.29; 0.01 0.75; 0.01 0.93; 0.00 31.44 |
| 6.143 | 3,5-$Cl_2$—Ph | H | O | H | $CH(CH_2iPr)CH_2$ | methoxycarbonyl | [$CDCl_3$] 0.85-0.96 (m, 6H); 1.53-1.70 (m, 2H); 1.72 (ds, 3H); 3.19 (dd, 1H); 3.68, 3.73 (ds, 3H); 3.76 (dd, 1H); 4. 56 (m, 1H); 7.05 (br, 1H); 7.41 (m, 1H); 7.52 (m, 2H). |
| 6.144 | 3,5-$Cl_2$—Ph | H | O | H | $CH(CH_2OCH_3)$ | methoxymethyl | |
| 6.145 | 3,5-$Cl_2$—Ph | H | O | H | $CH(CH_3)$ | $CF_3$ | diastereomer D1: [$CDCl_3$] 1.32 (d, 3H); 1.71 (s, 3H); 3.19 (d, 1H); 3.71 (d, 1H); 4.63 (m, 1H); 6.88 (t br, 1H); 7.42 (m, 1H); 7.51 (m, 2H). diastereomer D2: [$CDCl_3$] 1.38 (d, 3H); 1.72 (s, 3H); 3.23 (d, 1H); 3.83 (d, 1H); 4.63 (m, 1H); 6.88 (t br, 1H); 7.42 (m, 1H); 7.51 (m, 2H). |
| 6.146 | 2,3,4-$F_3$—Ph | H | O | H | $CH(CH_3)$ | $CH_3$ | |
| 6.147 | 2,3,5-$F_3$—Ph | H | O | H | $CH(CH_3)$ | $CH_3$ | |

TABLE 6-continued

Compounds of the general formula (I) according to the invention in which $R^2$ is hydrogen and $R^3$ is methyl and aryl is the radical

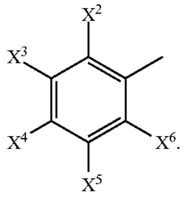

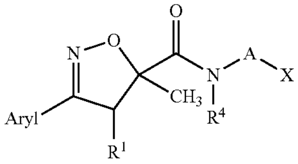

| No. | Aryl | $R^1$ | Y | $R^4$ | A | X | Physical data |
|---|---|---|---|---|---|---|---|
| 6.148 | 2,3,6-$Cl_3$—Ph | H | O | H | $CH(CH_3)$ | $CH_3$ | |
| 6.149 | 2,3-$Cl_2$-5-MeO—Ph | H | O | H | $CH(CH_3)$ | $CH_3$ | |
| 6.150 | 2,3-$Cl_2$—Ph | H | O | H | $CH(CH_3)$ | $CH_3$ | |
| 6.151 | 2,3-$F_2$—Ph | H | O | H | $CH(CH_3)$ | $CH_3$ | |
| 6.152 | 2,5-$Cl_2$—Ph | H | O | H | $CH(CH_3)$ | $CH_3$ | |
| 6.153 | 2,5-$F_2$—Ph | H | O | H | $CH(CH_3)$ | $CH_3$ | [$CDCl_3$] 7.53 0.37; 7.52 0.43; 7.52 0.54; 7.52 0.39; 7.51 0.45; 7.51 0.42; 7.50 0.81; 7.50 0.72; 7.50 0.40; 7.49 0.43; 7.49 0.39; 7.48 0.44; 7.48 0.37; 7.26 29.13; 7.26 0.51; 7.26 0.38; 7.11 0.83; 7.11 0.91; 7.11 1.49; 7.10 0.83; 7.10 1.62; 7.09 1.99; 7.09 0.88; 7.09 0.82; 7.08 0.73; 7.08 1.33; 7.07 0.78; 4.06 0.57; 4.04 0.80; 4.04 0.60; 4.03 0.63; 4.02 0.79; 4.01 0.58; 3.89 1.24; 3.89 1.26; 3.85 1.48; 3.84 1.45; 3.33 1.37; 3.32 1.39; 3.28 1.20; 3.27 1.19; 1.70 16.00; 1.55 20.14; 1.20 7.30; 1.18 7.24; 1.15 7.25; 1.14 7.19; 0.01 0.41; 0.00 2.04; 0.00 14.15; −0.01 0.42; −0.01 0.44 |
| 6.154 | 2-F—Ph | H | O | H | $CH(CH_3)$ | $CH_3$ | |
| 6.155 | 3-($CF_3CH_2O$)—Ph | H | O | H | $CH(CH_3)$ | $CH_3$ | |
| 6.156 | 3-($ClCH_2CH_2O$)—Ph | H | O | H | $CH(CH_3)$ | $CH_3$ | |
| 6.157 | 3-(2-MeOEtO)—Ph | H | O | H | $CH(CH_3)$ | $CH_3$ | |
| 6.158 | 3-$Me_2N$—Ph | H | O | H | $CH(CH_3)$ | $CH_3$ | |
| 6.159 | 3-iPrCOO—Ph | H | O | H | $CH(CH_3)$ | $CH_3$ | |
| 6.160 | 3-iPrO—Ph | H | O | H | $CH(CH_3)$ | $CH_3$ | |
| 6.161 | 3-$CF_3O$—Ph | H | O | H | $CH(CH_3)$ | $CH_3$ | |
| 6.162 | 3,4-$Cl_2$—Ph | H | O | H | $CH(CH_3)$ | $CH_3$ | |
| 6.163 | 3,5-$(CF_3)_2$—Ph | H | O | H | $CH(CH_3)$ | $CH_3$ | [$CDCl_3$] 1.13 (d, 3H); 1.20 (d, 3H); 1.73 (s, 3H); 3.24 (d, 1H); 3.89 (d, 1H); 4.04 (m, 1H); 6.59 (bd, 1H); 7.91 (m, 1H), 8.08 (m, 2H). |
| 6.164 | 3,5-$Cl_2$—Ph | $CH_3$ | O | H | $CH(CH_3)$ | $CH_3$ | |
| 6.165 | 3,5-$Cl_2$—Ph | H | O | H | $CH(CH_3)$ | $CH_3$ | [$CDCl_3$] 1.12 (d, 3H); 1.18 (d, 3H); 1.70 (s, 3H); 2.83 (d, 3H); 3.16 (d, 1H); 3.77 (d, 1H); 4.02 (m, 1H), 6.59 (d br, 1H); 7.40 (t, 1H); 7.50 (m, 2H) |
| 6.166 | 3,5-$Cl_2$—Ph | H | O | OH | $CH(CH_3)$ | $CH_3$ | [DMSO-$D_6$] 1.08 (d, 6H); 1.85 (s, 3H); 3.33 (d, 1H); 3.80 (d, 1H); 4.49 (sept, 1H); 7.66 (m, 2H); 7.72 (m, 1H); 9.41 (s, 1H). |
| 6.167 | 3,5-$Cl_2$—Ph | H | S | H | $CH(CH_3)$ | $CH_3$ | [$CDCl_3$] 8.46 0.39; 8.45 0.38; 7.52 6.09; 7.52 7.42; 7.42 1.71; 7.41 3.05; 7.41 1.50; 7.31 0.90; 7.26 149.56; 7.26 156.14; 7.24 0.39; 7.21 0.65; 7.00 0.87; 4.58 0.62; 4.56 |

TABLE 6-continued

Compounds of the general formula (I) according to the invention in which $R^2$ is hydrogen and $R^3$ is methyl and aryl is the radical

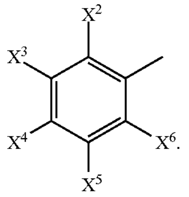

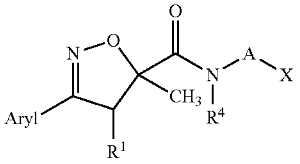

| No. | Aryl | $R^1$ | Y | $R^4$ | A | X | Physical data |
|---|---|---|---|---|---|---|---|
| | | | | | | | 0.88; 4.56 0.70; 4.54 0.72; 4.54 0.87; 4.52 0.65; 4.27 2.76; 4.23 3.04; 3.37 2.95; 3.32 2.66; 1.86 16.00; 1.58 0.35; 1.53 60.51; 1.31 8.20; 1.29 8.14; 1.25 8.17; 1.23 8.11; 0.05 0.35; 0.01 1.90; 0.00 60.44; 0.00 61.70 |
| 6.168 | 3,5-$F_2$—Ph | H | O | H | $CH(CH_3)$ | $CH_3$ | [$CDCl_3$] 1.12 (d, 3H); 1.18 (d, 3H); 1.71 (s, 3H); 3.15 (d, 1H); 3.76 (d, 1H); 4.01 (m, 1H); 6.61 (d, 1H); 6.87 (m, 1H); 7.15 (m, 2H). |
| 6.169 | 3,5-$Me_2$—Ph | H | O | H | $CH(CH_3)$ | $CH_3$ | [$CDCl_3$] 1.12 (d, 3H); 1.18 (d, 3H); 1.70 (s, 3H); 2.32 (s, 6H); 3.20 (d, 1H); 3.79 (d, 1H); 4.02 (m, 1H); 6.70 (d br, 1H); 7.06 (s, 1H); 7.27 (s, 2H). |
| 6.170 | R002 | H | O | H | $CH(CH_3)$ | $CH_3$ | |
| 6.171 | R003 | H | O | H | $CH(CH_3)$ | $CH_3$ | |
| 6.172 | 3-$CNCH_2N(Me)$—Ph | H | O | H | $CH(CH_3)$ | $CH_3$ | |
| 6.173 | 3-$Me_2NCONH$—Ph | H | O | H | $CH(CH_3)$ | $CH_3$ | |
| 6.174 | 3-$Me_2NSO_2O$—Ph | H | O | H | $CH(CH_3)$ | $CH_3$ | |
| 6.175 | 3-EtNHCOO—Ph | H | O | H | $CH(CH_3)$ | $CH_3$ | |
| 6.176 | 3-$EtSO_2O$—Ph | H | O | H | $CH(CH_3)$ | $CH_3$ | |
| 6.177 | 3-$MeSO_2NH$—Ph | H | O | H | $CH(CH_3)$ | $CH_3$ | |
| 6.178 | 3-$MeSO_2O$—Ph | H | O | H | $CH(CH_3)$ | $CH_3$ | |
| 6.179 | 3-tert•BuOCONH—Ph | H | O | H | $CH(CH_3)$ | $CH_3$ | |
| 6.180 | 3-$CF_3CONH$—Ph | H | O | H | $CH(CH_3)$ | $CH_3$ | |
| 6.181 | 3-AcO-5-Cl—Ph | H | O | H | $CH(CH_3)$ | $CH_3$ | |
| 6.182 | 3-AcO—Ph | H | O | H | $CH(CH_3)$ | $CH_3$ | |
| 6.183 | 3-$NH_2$—Ph | H | O | H | $CH(CH_3)$ | $CH_3$ | |
| 6.184 | 3-Br-5-$CF_3$—Ph | H | O | H | $CH(CH_3)$ | $CH_3$ | [$CDCl_3$] 1.13, 1.19 (dd, 6H); 1.71 (s, 3H); 3.20 (d, 1H); 3.82 (d, 1H); 4.01 (m, 1H); 6.59 (br, 1H); 7.81 (m, 2H); 7.96 (m, 1H). |
| 6.185 | 3-Br-5-Cl—Ph | H | O | H | $CH(CH_3)$ | $CH_3$ | [$CDCl_3$] 1.14 (d, 3H); 1.18 (d, 3H); 1.71 (s, 3H); 3.15 (d, 1H); 3.78 (d, 1H); 3.96-4.06 (m, 1H); 6.60 (br, 1H); 7.56 (m, 2H); 7.67 (m, 1H). |
| 6.186 | 3-Cl-4-F—Ph | H | O | H | $CH(CH_3)$ | $CH_3$ | [$CDCl_3$] 1.12 (d, 3H); 1.18 (d, 3H); 1.71 (s, 3H); 3.16 (d, 1H); 3.78 (d, 1H); 4.02 (m, 1H); 6.63 (d br, 1H); 7.18 (t, 1H); 7.50 (m, 1H), 7.73 (dd, 1H) |
| 6.187 | 3-Cl-4-Me—Ph | H | O | H | $CH(CH_3)$ | $CH_3$ | |

TABLE 6-continued

Compounds of the general formula (I) according to the invention in which $R^2$ is hydrogen and $R^3$ is methyl and aryl is the radical

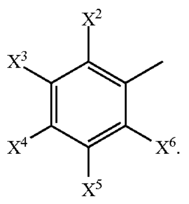

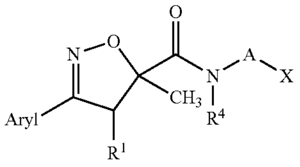

| No. | Aryl | $R^1$ | Y | $R^4$ | A | X | Physical data |
|---|---|---|---|---|---|---|---|
| 6.188 | 3-Cl-5-$CF_3$—Ph | H | O | H | $CH(CH_3)$ | $CH_3$ | [$CDCl_3$] 1.12 (d, 3H); 1.18 (d, 3H); 1.18 (d, 3H); 1.72 (s, 3H); 3.20 (d, 1H); 3.83 (d, 1H); 4.02 (m, 1H); 6.60 (d br, 1H); 7.67 (s, 1H), 7.78 (s, 1H); 7.81 (s, 1H) |
| 6.189 | R001 | H | O | H | $CH(CH_3)$ | $CH_3$ | |
| 6.190 | 3-Cl-5-F—Ph | H | O | H | $CH(CH_3)$ | $CH_3$ | [$CDCl_3$] 1.13 (d, 3H); 1.20 (d, 3H); 1.71 (s, 3H); 3.18 (d, 1H); 3.77 (d, 1H); 4.02 (m, 1H); 6.62 (d br, 1H); 7.14 (d, 1H); 7.28 (d, 1H); 7.40 (s, 1H). |
| 6.191 | 3-Cl-5-MeO—Ph | H | O | H | $CH(CH_3)$ | $CH_3$ | [$CDCl_3$] 1.15 (d, 3H); 1.19 (d, 3H); 1.70 (s, 3H); 3.16 (d, 1H); 3.77 (d, 1H); 3.82 (s, 1H); 4.02 (m, 1H); 6.63 (d br, 1H); 6.95 (t, 1H); 7.08 (s, 1H); 7.19 (s, 1H) |
| 6.192 | 3-Cl-5-Me—Ph | H | O | H | $CH(CH_3)$ | $CH_3$ | [$CDCl_3$] 1.12 (d, 3H); 1.19 (d, 3H); 1.70 (s, 3H); 2.34 (s, 3H); 3.18 (d, 1H); 3.78 (d, 1H); 4.01 (m, 1H); 6.64 (brd, 1H); 7.22 (m, 1H); 7.31 (m, 1H); 7.43 (m, 1H). |
| 6.193 | 3-Cl-5-$(CF_3CH_2O)$—Ph | H | O | H | $CH(CH_3)$ | $CH_3$ | |
| 6.194 | 3-Cl-5-$(ClCH_2CH_2O)$—Ph | H | O | H | $CH(CH_3)$ | $CH_3$ | |
| 6.195 | 3-Cl-5-$(EtOCOCH_2O)$—Ph | H | O | H | $CH(CH_3)$ | $CH_3$ | [$CDCl_3$] 1.13 (d, 3H); 1.18 (d, 3H); 1.30 (t, 3H); 1.70 (s, 3H); 3.16 (d, 1H); 3.74 (d, 1H); 4.01 (m, 1H); 4.25 (q, 2H); 4.62 (s, 2H); 6.61 (brd, 1H); 6.96 (m, 1H); 7.10 (m, 1H); 7.23 (m, 1H). |
| 6.196 | 3-Cl-5-$CF_3O$—Ph | H | O | H | $CH(CH_3)$ | $CH_3$ | [$CDCl_3$] 1.13 (d, 3H); 1.19 (d, 3H); 1.71 (s, 3H); 3.18 (d, 1H); 3.79 (d, 1H); 4.02 (m, 1H); 6.60 (brd, 1H); 7.28 (s, 1H); 7.41 (s, 1H); 7.54 (s, 1H). |
| 6.197 | 3-Cl-5-$Me_2NSO_2O$—Ph | H | O | H | $CH(CH_3)$ | $CH_3$ | |
| 6.198 | 3-Cl-5-$(MeSO_2O)$—Ph | H | O | H | $CH(CH_3)$ | $CH_3$ | |
| 6.199 | 3-Cl-5-iPrO—Ph | H | O | H | $CH(CH_3)$ | $CH_3$ | |
| 6.200 | 3-Cl—Ph | H | O | H | $CH(CH_3)$ | $CH_3$ | [$CDCl_3$] 1.16 (dd, 6H); 1.70 (s, 3H); 3.18 (d, 1H); 3.80 (d, 1H); 4.02 (m, 1H); 6.65 (d br, 1H); 7.38 (m, 2H); 7.50 (d, 1H); 7.66 (s, 1H) |
| 6.201 | 3-EtO—Ph | H | O | H | $CH(CH_3)$ | $CH_3$ | |
| 6.202 | 3-F-5-Me—Ph | H | O | H | $CH(CH_3)$ | $CH_3$ | [$CDCl_3$] 7.26 0.33; 7.26 14.80; 7.26 0.56; 7.26 0.33; 7.21 0.69; 7.20 1.08; 7.20 1.69; 7.20 1.75; 7.20 1.39; 7.20 0.97; 7.19 0.47; 7.19 0.52; 7.18 0.64; 7.18 0.58; 7.18 0.44; 7.16 0.42; 7.16 0.47; 7.16 0.49; 7.16 0.63; 7.16 0.45; 7.15 0.39; 6.96 0.37; 6.96 0.48; 6.96 0.53; 6.96 0.62; 6.96 0.53; 6.95 |

TABLE 6-continued

Compounds of the general formula (I) according to the invention in which $R^2$ is hydrogen and $R^3$ is methyl and aryl is the radical

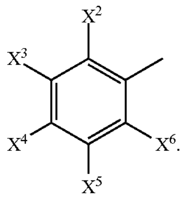

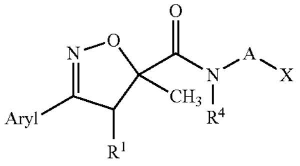

| No. | Aryl | $R^1$ | Y | $R^4$ | A | X | Physical data |
|---|---|---|---|---|---|---|---|
| | | | | | | | 0.47; 6.95 0.37; 6.94 0.37; 6.94 0.49; 6.94 0.54; 6.93 0.61; 6.93 0.52; 6.93 0.46; 6.93 0.36; 4.05 0.55; 4.03 0.78; 4.03 0.58; 4.01 0.60; 4.01 0.77; 3.99 0.57; 3.80 2.81; 3.76 3.20; 3.20 2.81; 3.16 2.46; 2.37 8.09; 2.37 8.33; 1.70 16.00; 1.58 7.48; 1.19 7.06; 1.18 6.99; 1.14 7.01; 1.12 6.94; 0.00 0.41; 0.00 7.41; 0.00 0.37 |
| 6.203 | 3-F—Ph | H | O | H | $CH(CH_3)$ | $CH_3$ | [$CDCl_3$] 1.12 (d, 3H); 1.17 (d, 3H); 1.71 (s, 3H); 3.20 (d, 1H); 3.79 (d, 1H); 4.01 (m, 1H); 6.64 (d, 1H); 7.12 (m, 1H); 7.39 (m, 3H). |
| 6.204 | 3-OH—Ph | H | O | H | $CH(CH_3)$ | $CH_3$ | |
| 6.205 | 3-MeO—Ph | H | O | H | $CH(CH_3)$ | $CH_3$ | [MeOD] 1.18 (dd, 6H); 1.66 (s, 3H); 3.36 (d, 1H); 3.75 (d, 1H); 3.84 (s, 3H); 4.02 (sept, 1H); 7.03 (m, 1H); 7.23 (m, 2H); 7.36 (m, 1H). |
| 6.206 | 3-Me—Ph | H | O | H | $CH(CH_3)$ | $CH_3$ | [$CDCl_3$] 7.48 2.57; 7.43 1.18; 7.43 1.19; 7.41 1.55; 7.41 1.56; 7.31 0.94; 7.29 2.17; 7.27 1.41; 7.26 9.31; 7.26 10.41; 7.25 1.91; 7.23 0.93; 6.70 0.54; 6.68 0.55; 5.30 0.34; 5.30 0.40; 4.05 0.50; 4.05 0.71; 4.03 0.71; 4.03 1.15; 4.03 0.63; 4.02 0.57; 4.01 1.13; 4.01 0.81; 4.00 0.67; 3.99 0.58; 3.83 2.26; 3.83 2.70; 3.79 2.60; 3.79 3.09; 3.24 2.41; 3.23 2.88; 3.19 2.11; 3.19 2.52; 2.37 12.20; 1.70 13.47; 1.70 16.00; 1.60 1.98; 1.19 6.27; 1.19 7.54; 1.18 6.25; 1.17 7.43; 1.14 6.25; 1.13 7.52; 1.12 6.23; 1.12 7.39; 0.00 3.45; 0.00 4.08 |
| 6.207 | $3-NO_2$—Ph | H | O | H | $CH(CH_3)$ | $CH_3$ | [$CDCl_3$] 8.49 1.22; 8.48 2.00; 8.48 1.28; 8.30 0.82; 8.29 0.91; 8.29 0.83; 8.29 0.85; 8.27 0.88; 8.27 0.96; 8.27 0.90; 8.27 0.90; 7.99 0.83; 7.99 1.00; 7.99 1.08; 7.98 0.90; 7.97 0.94; 7.97 1.07; 7.97 1.24; 7.96 0.97; 7.63 1.44; 7.61 2.37; 7.59 1.01; 7.59 1.21; 7.26 16.88; 4.06 0.55; 4.04 0.78; 4.04 0.60; 4.03 0.61; 4.02 0.78; 4.01 0.58; 3.91 2.79; 3.87 3.16; 3.28 2.82; 3.23 2.49; 1.74 16.00; 1.57 7.60; 1.21 7.25; 1.19 7.18; 1.15 7.20; 1.13 7.15; 0.00 9.53 |
| 6.208 | $F_5$—Ph | H | O | H | $CH(CH_3)$ | $CH_3$ | |
| 6.209 | Ph | H | O | H | $CH(CH_3)$ | $CH_3$ | |
| 6.210 | $3,5-Cl_2$—Ph | H | O | H | $CH(CH_3)$ | COOH | [$CDCl_3$] 1.48, 1.51 (dd, 3H); 1.74 (ds, 3H); 3.20, 3.21 (dd, 1H); 3.72, 3.79 (dd, 1H); 4.55 (m, 1H); 7.19 (br, 1H); 7.41 (m, 1H); 7.52 (m, 2H). |

TABLE 6-continued
Compounds of the general formula (I) according to the invention in which $R^2$ is hydrogen and $R^3$ is methyl and aryl is the radical
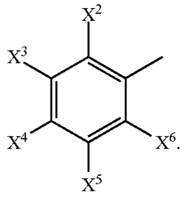
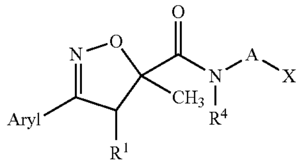
| No. | Aryl | $R^1$ | Y | $R^4$ | A | X | Physical data |
|---|---|---|---|---|---|---|---|
| 6.211 | 3-Cl-4-F—Ph | H | O | H | $CH(CH_3)$ | COOH | |
| 6.212 | 3,5-$Cl_2$—Ph | H | O | H | $CH(CH_3)$ | c-Pr | [$CDCl_3$] 7.53 7.22; 7.52 10.86; 7.52 6.24; 7.42 2.04; 7.42 4.36; 7.41 3.80; 7.41 1.40; 7.26 19.00; 6.76 0.83; 6.74 0.83; 5.30 2.69; 3.79 2.99; 3.79 2.38; 3.75 3.41; 3.75 2.74; 3.39 0.39; 3.38 0.58; 3.37 0.75; 3.37 0.79; 3.36 1.17; 3.35 1.02; 3.35 0.54; 3.34 1.02; 3.34 0.81; 3.33 0.49; 3.32 0.37; 3.32 0.50; 3.19 3.01; 3.18 2.40; 3.15 2.64; 3.14 2.10; 1.73 12.47; 1.70 16.00; 1.58 8.26; 1.24 8.17; 1.22 8.04; 1.18 6.26; 1.16 6.18; 0.87 0.36; 0.86 0.70; 0.85 0.46; 0.85 0.47; 0.84 0.84; 0.83 0.58; 0.83 0.45; 0.83 0.54; 0.82 1.00; 0.81 0.59; 0.81 0.61; 0.80 0.99; 0.79 0.54; 0.78 0.39; 0.54 0.53; 0.53 0.63; 0.52 0.56; 0.51 0.86; 0.51 0.55; 0.50 0.72; 0.49 1.26; 0.48 1.31; 0.48 0.83; 0.47 0.67; 0.47 1.18; 0.47 0.88; 0.46 1.14; 0.46 0.76; 0.45 0.62; 0.45 0.81; 0.42 0.45; 0.40 0.60; 0.40 0.59; 0.40 0.51; 0.39 0.66; 0.38 0.67; 0.38 0.88; 0.37 0.71; 0.37 0.70; 0.36 0.42; 0.36 0.47; 0.36 0.55; 0.35 0.46; 0.35 0.79; 0.33 0.84; 0.32 0.67; 0.26 0.63; 0.26 0.49; 0.25 1.01; 0.25 0.89; 0.24 1.30; 0.23 1.01; 0.23 1.15; 0.22 0.87; 0.21 0.62; 0.20 0.67; 0.19 0.94; 0.18 1.04; 0.16 0.85; 0.15 0.47; 0.01 0.33; 0.00 11.04; −0.01 0.40 |
| 6.213 | 3,5-$F_2$—Ph | H | O | H | $CH(CH_3)$ | c-Pr | [$CDCl_3$] 7.52 0.43; 7.26 78.76; 7.19 0.41; 7.19 0.54; 7.18 1.67; 7.18 3.36; 7.17 2.55; 7.17 1.96; 7.16 2.51; 7.16 3.41; 7.15 1.85; 7.14 0.52; 7.14 0.41; 7.00 0.45; 6.91 0.41; 6.90 0.80; 6.90 0.89; 6.89 0.44; 6.89 0.83; 6.88 1.56; 6.88 1.78; 6.87 0.81; 6.87 0.48; 6.86 0.80; 6.86 0.89; 6.85 0.40; 6.77 0.76; 6.75 0.77; 3.79 2.66; 3.78 2.93; 3.74 3.03; 3.74 3.35; 3.39 0.46; 3.39 0.33; 3.38 0.47; 3.38 0.71; 3.37 0.93; 3.37 0.59; 3.36 0.96; 3.36 1.05; 3.35 0.65; 3.35 0.85; 3.34 0.68; 3.34 0.52; 3.33 0.32; 3.33 0.39; 3.19 2.54; 3.19 2.94; 3.15 2.21; 3.14 2.56; 1.73 16.00; 1.71 13.77; 1.55 66.31; 1.24 6.84; 1.22 6.76; 1.18 7.89; 1.16 7.79; 0.88 0.34; 0.87 0.46; 0.86 0.87; 0.85 0.58; 0.85 0.56; 0.84 |

TABLE 6-continued
Compounds of the general formula (I) according to the invention in which $R^2$ is hydrogen and $R^3$ is methyl and aryl is the radical
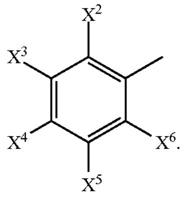
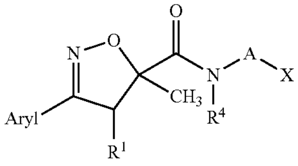
| No. | Aryl | $R^1$ | Y | $R^4$ | A | X | Physical data |
|---|---|---|---|---|---|---|---|
| | | | | | | | 1.03; 0.83 0.54; 0.83 0.63; 0.82 0.91; 0.81 0.53; 0.81 0.56; 0.80 0.82; 0.79 0.47; 0.78 0.32; 0.55 0.33; 0.54 0.67; 0.53 0.78; 0.52 0.69; 0.51 0.84; 0.51 0.57; 0.50 0.70; 0.50 0.46; 0.49 0.98; 0.49 0.75; 0.48 0.81; 0.48 0.99; 0.48 0.88; 0.48 0.97; 0.47 0.95; 0.47 1.03; 0.46 1.00; 0.46 0.79; 0.46 0.57; 0.45 0.69; 0.45 0.53; 0.45 0.53; 0.44 0.37; 0.41 0.38; 0.40 0.49; 0.40 0.51; 0.39 0.42; 0.39 0.52; 0.38 0.73; 0.37 0.63; 0.37 0.62; 0.36 0.83; 0.35 1.06; 0.33 1.03; 0.32 0.83; 0.31 0.37; 0.26 0.83; 0.25 1.32; 0.24 1.74; 0.22 1.43; 0.21 0.89; 0.20 0.66; 0.19 0.77; 0.17 0.86; 0.16 0.68; 0.15 0.39; 0.01 1.32; 0.00 41.85; −0.01 1.55 |
| 6.214 | Ph | H | O | H | $CH(CH_3)$ | c-Pr | [$CDCl_3$] 7.66 1.74; 7.66 3.59; 7.65 3.15; 7.65 1.92; 7.64 2.48; 7.64 3.63; 7.63 2.80; 7.52 0.88; 7.44 1.19; 7.42 6.56; 7.42 5.08; 7.42 2.33; 7.41 3.15; 7.40 0.98; 7.39 0.77; 7.39 0.50; 7.38 0.36; 7.26 148.91; 7.00 0.82; 6.85 0.78; 6.83 0.78; 3.84 4.54; 3.79 5.12; 3.40 0.50; 3.39 0.54; 3.38 1.15; 3.37 0.88; 3.36 1.06; 3.35 1.08; 3.34 0.66; 3.33 0.43; 3.26 2.37; 3.25 3.03; 3.22 2.04; 3.21 2.63; 1.72 16.00; 1.70 12.51; 1.54 47.85; 1.23 6.26; 1.22 6.20; 1.17 7.96; 1.16 7.86; 0.88 0.38; 0.87 0.49; 0.86 0.93; 0.85 0.66; 0.84 0.61; 0.84 1.12; 0.82 0.74; 0.82 0.99; 0.81 0.57; 0.80 0.58; 0.79 0.80; 0.78 0.43; 0.53 0.69; 0.52 0.78; 0.51 0.77; 0.51 0.78; 0.50 0.56; 0.49 0.75; 0.49 0.69; 0.49 0.82; 0.48 0.81; 0.48 0.78; 0.47 0.87; 0.47 0.85; 0.46 1.22; 0.45 0.89; 0.44 0.68; 0.43 0.41; 0.42 0.33; 0.40 0.34; 0.38 0.46; 0.37 0.44; 0.37 0.78; 0.36 0.92; 0.36 0.91; 0.35 1.29; 0.33 1.08; 0.32 0.85; 0.31 0.35; 0.26 0.46; 0.25 1.09; 0.24 1.62; 0.23 1.66; 0.22 1.11; 0.21 0.58; 0.19 0.48; 0.18 0.72; 0.17 0.81; 0.16 0.62; 0.15 0.80; 0.01 3.90; 0.00 101.51; −0.01 3.64; −0.15 0.38 |

TABLE 6-continued

Compounds of the general formula (I) according to the invention in which $R^2$ is hydrogen and $R^3$ is methyl and aryl is the radical

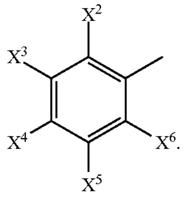

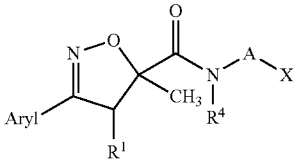

| No. | Aryl | $R^1$ | Y | $R^4$ | A | X | Physical data |
|---|---|---|---|---|---|---|---|
| 6.215 | 3-Cl-4-F—Ph | H | O | H | $CH(CH_3)$ | dimethylcarbamoyl | |
| 6.216 | 3,5-$Cl_2$—Ph | H | O | H | $CH(CH_3)$ | ethynyl | diastereomer D1: [$CDCl_3$] 1.40 (d, 3H); 1.73 (s, 3H); 3.31 (d, 1H); 3.19 (d, 1H); 3.76 (d, 1H); 4.75 (m, 1H); 6.96 (d br, 1H), 7.42 (s, 1H); 7.53 (m, 2H). diastereomer D2: [$CDCl_3$] 1.46 (d, 3H); 1.69 (s, 3H); 3.31 (d, 1H); 3.19 (d, 1H); 3.77 (d, 1H); 4.75 (m, 1H); 6.96 (d br, 1H), 7.42 (s, 1H); 7.53 (m, 2H). |
| 6.217 | 3,5-$Cl_2$—Ph | H | O | H | $CH(CH_3)$ | ethyl | diastereomers D1 plus D2: [$CDCl_3$] 0.83 (t, 3H); 0.93 (t, 3H); 1.10 (d, 3H) 1.16 (d, 3H); 1.45 (m, 4H); 1.72 (s, 6H); 3.17 (dd, 2H); 3.78 (dd, 2H); 3.87 (m, 2H); 6.55 (t br, 2H); 7.40 (s, 1H); 7.53 (m, 2H). |
| 6.218 | 3,5-$Cl_2$—Ph | $CH_3$ | O | H | $CH(CH_3)$ | methoxycarbonyl | |
| 6.219 | 3,5-$Cl_2$—Ph | H | O | H | $CH(CH_3)$ | methoxycarbonyl | [$CDCl_3$] 1.41, 1.46 (dd, 3H); 1.73, 1.74 (ds, 3H); 3.19 (dd, 1H); 3.70, 3.76 (ds, 3H); 3.77 (dd, 1H); 4.52 (m, 1H); 7.20 (br, 1H); 7.41 (m, 1H); 7.52 (m, 2H). |
| 6.220 | 3-Cl-4-F—Ph | H | O | H | $CH(CH_3)$ | methoxycarbonyl | |
| 6.221 | 3-Cl-4-F—Ph | H | O | H | $CH(CH_3)$ | methylcarbamoyl | |
| 6.222 | 3,5-$Cl_2$—Ph | H | O | H | $CH(CH_3)$ | pentyl | diastereomer D1: [$CDCl_3$] 0.80 (t, 3H); 1.18 (d, 3H); 1.20 (m, 4H); 1.41 (m, 4H); 1.71 (s, 3H); 3.16 (d, 1H); 3.78 (d, 1H); 3.92 (m, 1H); 6.56 (t br, 1H); 7.41 (m, 1H); 7.52 (m, 2H). diastereomer D2: [$CDCl_3$] 0.88 (t, 3H); 1.10 (d, 3H); 1.31 (m, 4H); 1.46 (m, 4H); 1.71 (s, 3H); 3.17 (d, 1H); 3.79 (d, 1H); 3.92 (m, 1H); 6.56 (t br, 1H); 7.41 (m, 1H); 7.52 (m, 2H). |
| 6.223 | 3,5-$Cl_2$—Ph | H | O | H | $CH(CH_3)CH_2$ | (2,2,2-trifluoroethoxy)-carbonyl | [$CDCl_3$] 7.52 7.09; 7.52 7.00; 7.52 14.65; 7.51 11.52; 7.51 9.55; 7.51 6.57; 7.42 3.51; 7.42 3.44; 7.41 6.34; 7.41 5.22; 7.41 3.80; 7.26 50.07; 7.26 37.25; 7.00 1.06; 6.98 1.04; 6.96 1.08; 6.94 0.95; 4.54 0.38; 4.52 0.60; 4.51 0.50; 4.51 0.52; 4.51 0.79; 4.51 0.80; 4.50 1.87; 4.49 1.97; 4.49 1.83; 4.48 2.13; 4.47 1.91; 4.47 1.72; 4.46 1.05; 4.46 1.21; 4.46 1.07; 4.45 1.16; 4.44 0.95; 4.43 1.70; 4.42 0.82; 4.41 1.74; 4.40 1.53; 4.40 1.74; 4.38 0.86; 4.38 1.77; 4.37 0.99; 4.35 1.49; 4.34 1.16; 4.34 1.58; 4.32 1.54; 4.32 1.52; 4.30 1.06; 4.28 0.44; 4.13 0.33; 4.11 0.32; 3.79 2.61; 3.75 5.23; 3.71 3.08; 3.71 2.73; 3.49 0.36; 3.19 3.10; 3.18 3.18; 3.14 2.71; 3.14 2.76; 2.67 5.16; 2.65 5.17; 2.61 |

TABLE 6-continued
Compounds of the general formula (I) according to the invention in which $R^2$ is hydrogen and $R^3$ is methyl and aryl is the radical
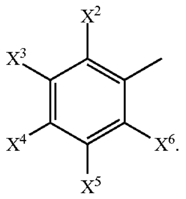
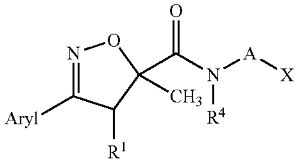
| No. | Aryl | $R^1$ | Y | $R^4$ | A | X | Physical data |
|---|---|---|---|---|---|---|---|
| | | | | | | | 5.24; 2.59 5.29; 2.04 1.47; 2.04 1.22; 2.00 0.97; 2.00 0.72; 1.71 16.00; 1.69 15.86; 1.54 10.37; 1.30 8.18; 1.29 8.37; 1.28 1.56; 1.27 1.45; 1.26 9.12; 1.24 8.08; 0.90 0.59; 0.88 1.45; 0.86 0.66; 0.01 0.43; 0.00 10.43; 0.00 7.36; −0.01 0.65 |
| 6.224 | 3,5-$F_2$—Ph | H | O | H | $CH(CH_3)CH_2$ | (2,2,2-trifluoroethoxy)-carbonyl | [$CDCl_3$] 7.26 39.00; 7.26 20.75; 7.25 29.25; 7.19 0.55; 7.18 0.77; 7.17 1.93; 7.17 4.86; 7.16 5.97; 7.15 4.24; 7.15 5.80; 7.14 4.84; 7.13 0.75; 7.00 1.25; 6.99 1.03; 6.97 1.55; 6.95 1.05; 6.91 0.84; 6.90 1.91; 6.90 1.72; 6.89 0.73; 6.89 1.63; 6.88 3.75; 6.87 3.34; 6.87 1.17; 6.86 0.91; 6.86 1.89; 6.85 1.69; 4.54 0.37; 4.53 0.34; 4.52 0.58; 4.52 0.49; 4.51 0.47; 4.51 0.91; 4.50 2.08; 4.50 1.38; 4.49 1.82; 4.48 2.93; 4.48 1.52; 4.47 1.84; 4.46 1.89; 4.46 0.86; 4.45 0.77; 4.45 0.94; 4.44 0.86; 4.44 0.81; 4.43 0.79; 4.42 0.55; 4.42 1.68; 4.41 1.88; 4.40 1.75; 4.39 2.91; 4.38 1.43; 4.38 1.04; 4.37 2.47; 4.36 1.60; 4.36 1.45; 4.35 1.61; 4.35 1.30; 4.34 2.44; 4.32 2.06; 4.31 1.27; 4.29 0.45; 3.79 2.42; 3.78 1.94; 3.75 2.90; 3.75 4.51; 3.74 3.99; 3.71 3.02; 3.70 2.41; 3.19 3.00; 3.18 4.91; 3.18 2.30; 3.15 2.58; 3.14 4.24; 3.14 1.96; 2.67 4.77; 2.67 4.08; 2.66 4.77; 2.65 3.84; 2.61 5.19; 2.60 4.37; 2.59 5.15; 2.59 4.16; 2.00 0.42; 1.71 16.00; 1.70 13.09; 1.6 9 14.80; 1.69 11.89; 1.55 19.21; 1.5 5 10.63; 1.54 13.77; 1.30 7.80; 1.30 6.58; 1.29 7.83; 1.28 6.39; 1.26 7.30; 1.26 6.22; 1.25 7.17; 1.24 5.87; 0.01 0.34; 0.00 8.52; 0.00 4.59; −0.01 6.50 |
| 6.225 | 3,5-$Cl_2$—Ph | H | O | H | $CH(CH_3)CH_2$ | (2-hydroxyethoxy)-carbonyl | [$CDCl_3$] 7.53 4.13; 7.53 3.59; 7.53 4.14; 7.51 3.65; 7.51 3.20; 7.51 3.66; 7.42 3.16; 7.41 2.70; 7.26 8.35; 7.26 11.98; 7.11 0.50; 7.09 0.57; 7.07 0.56; 7.05 0.49; 5.30 5.14; 4.47 0.62; 4.45 0.74; 4.43 0.60; 4.43 0.60; 4.41 0.32; 4.38 0.33; 4.37 0.38; 4.36 0.37; 4.36 0.39; 4.35 0.44; 4.34 0.47; 4.33 0.47; 4.33 0.47; 4.24 0.36; 4.23 0.40; 4.22 0.40; 4.22 0.44; 4.21 0.53; 4.20 0.58; 4.19 0.58; 4.19 0.57; 4.14 0.44; 4.13 0.56; 4.13 |

TABLE 6-continued
Compounds of the general formula (I) according to the invention in which $R^2$ is hydrogen and $R^3$ is methyl and aryl is the radical
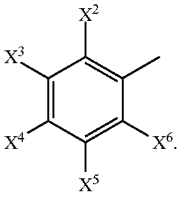
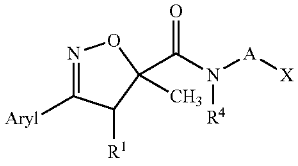
| No. | Aryl | $R^1$ | Y | $R^4$ | A | X | Physical data |
|---|---|---|---|---|---|---|---|
| | | | | | | | 0.49; 4.13 0.55; 4.12 0.50; 4.11 0.53; 4.10 0.36; 4.10 0.46; 4.09 0.38; 4.07 0.52; 4.06 0.57; 4.05 0.59; 4.05 0.62; 4.04 0.38; 4.03 0.38; 4.03 0.45; 4.02 0.41; 3.84 0.49; 3.83 0.87; 3.80 3.50; 3.78 0.64; 3.75 3.73; 3.18 2.71; 3.14 2.37; 2.89 0.37; 2.64 0.54; 2.63 0.56; 2.61 0.91; 2.60 0.89; 2.59 0.67; 2.57 0.66; 2.55 1.01; 2.54 0.98; 2.50 0.92; 2.48 0.91; 2.46 0.58; 2.44 0.58; 2.42 1.04; 2.40 1.01; 2.39 0.68; 2.37 0.67; 2.04 1.14; 1.71 16.00; 1.59 0.39; 1.29 4.77; 1.27 4.76; 1.26 0.79; 1.24 4.35; 1.22 4.16; 0.00 7.68 |
| 6.226 | 3,5-$F_2$—Ph | H | O | H | $CH(CH_3)CH_2$ | (2-hydroxyethoxy)-carbonyl | [$CDCl_3$] 7.26 20.48; 7.19 1.60; 7.18 2.02; 7.17 2.96; 7.16 2.78; 7.15 1.40; 7.15 1.99; 7.14 1.46; 7.14 0.36; 7.13 0.45; 7.12 0.52; 7.09 0.63; 7.08 0.66; 7.06 0.54; 6.91 0.58; 6.91 0.81; 6.90 0.81; 6.90 0.49; 6.89 1.16; 6.88 1.61; 6.88 1.59; 6.88 0.91; 6.87 0.60; 6.86 0.81; 6.86 0.80; 5.30 1.30; 4.49 0.43; 4.48 0.53; 4.47 0.72; 4.47 0.73; 4.46 0.60; 4.46 0.75; 4.45 0.84; 4.45 0.87; 4.45 0.69; 4.45 0.69; 4.44 0.66; 4.44 0.70; 4.43 0.70; 4.43 0.51; 4.42 0.42; 4.38 0.48; 4.37 0.54; 4.36 0.53; 4.36 0.56; 4.35 0.63; 4.34 0.68; 4.33 0.67; 4.33 0.64; 4.23 0.47; 4.22 0.50; 4.21 0.52; 4.21 0.57; 4.20 0.68; 4.20 0.71; 4.19 0.73; 4.18 0.70; 4.14 0.61; 4.13 0.66; 4.13 0.73; 4.12 0.69; 4.11 0.53; 4.10 0.51; 4.10 0.60; 4.09 0.52; 4.07 0.67; 4.06 0.70; 4.05 0.77; 4.05 0.73; 4.04 0.48; 4.03 0.49; 4.02 0.57; 4.02 0.50; 3.82 0.83; 3.81 0.77; 3.80 2.85; 3.79 2.70; 3.76 0.55; 3.75 2.86; 3.75 2.87; 3.18 2.95; 3.18 2.77; 3.14 2.56; 3.14 2.42; 2.95 0.36; 2.94 0.58; 2.92 0.36; 2.89 0.36; 2.88 0.56; 2.64 0.76; 2.63 0.77; 2.61 1.24; 2.60 1.20; 2.59 0.81; 2.57 0.80; 2.55 1.23; 2.54 1.16; 2.50 1.31; 2.48 1.30; 2.46 0.83; 2.44 0.83; 2.42 1.32; 2.40 1.29; 2.39 0.87; 2.37 0.85; 1.71 16.00; 1.71 14.17; 1.59 2.29; 1.29 5.87; 1.27 5.82; 1.26 0.40; 1.24 5.78; 1.22 5.66; 0.00 4.36 |

TABLE 6-continued
Compounds of the general formula (I) according to the invention in which $R^2$ is hydrogen and $R^3$ is methyl and aryl is the radical
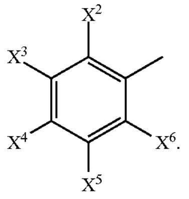
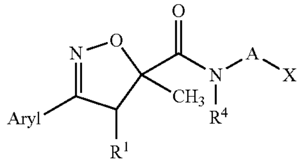
| No. | Aryl | $R^1$ | Y | $R^4$ | A | X | Physical data |
|---|---|---|---|---|---|---|---|
| 6.227 | 3,5-$Cl_2$—Ph | H | O | H | $CH(CH_3)CH_2$ | (allyloxy)carbonyl | [$CDCl_3$] 7.52 6.41; 7.52 13.26; 7.51 8.13; 7.41 4.36; 7.26 45.03; 7.12 0.66; 7.10 0.74; 7.08 0.76; 7.06 0.69; 5.96 0.66; 5.95 0.39; 5.94 0.39; 5.93 0.79; 5.92 0.88; 5.90 0.46; 5.90 0.48; 5.90 0.40; 5.89 0.86; 5.88 0.73; 5.88 0.47; 5.87 0.45; 5.87 0.43; 5.86 0.80; 5.84 0.87; 5.83 0.46; 5.83 0.47; 5.81 0.84; 5.80 0.43; 5.35 1.30; 5.35 1.43; 5.35 0.64; 5.31 1.15; 5.31 1.24; 5.30 0.56; 5.28 1.38; 5.28 1.50; 5.28 0.68; 5.27 1.41; 5.27 1.44; 5.24 2.42; 5.24 1.93; 5.20 1.41; 5.20 1.47; 5.17 1.30; 5.17 1.37; 4.61 1.85; 4.61 3.21; 4.61 2.11; 4.60 1.91; 4.59 3.16; 4.59 2.06; 4.52 2.96; 4.51 2.89; 4.34 0.43; 4.33 0.74; 4.33 1.00; 4.31 1.39; 4.30 0.58; 4.30 1.04; 4.29 0.80; 4.28 0.44; 4.11 0.33; 3.80 2.62; 3.77 2.73; 3.75 3.00; 3.72 3.12; 3.18 3.12; 3.17 3.22; 3.13 2.74; 3.13 2.83; 2.58 5.02; 2.57 4.99; 2.52 5.04; 2.50 4.97; 2.04 1.34; 2.00 1.05; 1.71 16.00; 1.69 15.46; 1.55 13.64; 1.28 8.17; 1.27 8.89; 1.26 2.02; 1.24 7.72; 1.22 7.60; 0.90 0.50; 0.88 1.47; 0.86 0.64; 0.00 8.51 |
| 6.228 | 3,5-$F_2$—Ph | H | O | H | $CH(CH_3)CH_2$ | (allyloxy)carbonyl | [$CDCl_3$] 7.26 15.90; 7.26 15.72; 7.19 0.43; 7.18 0.53; 7.17 2.00; 7.17 3.43; 7.17 3.37; 7.16 1.82; 7.15 3.41; 7.15 3.49; 7.15 1.99; 7.14 0.64; 7.13 0.66; 7.13 0.64; 7.10 0.72; 7.09 0.76; 7.07 0.62; 6.90 0.67; 6.90 1.19; 6.89 0.64; 6.88 1.36; 6.87 2.35; 6.87 1.20; 6.86 0.71; 6.85 1.17; 6.85 0.59; 5.97 0.32; 5.96 0.66; 5.95 0.41; 5.95 0.38; 5.93 0.85; 5.92 0.85; 5.91 0.48; 5.90 0.45; 5.90 0.39; 5.89 0.86; 5.88 0.70; 5.88 0.46; 5.87 0.42; 5.87 0.39; 5.86 0.83; 5.84 0.84; 5.83 0.47; 5.82 0.44; 5.81 0.82; 5.80 0.41; 5.36 0.54; 5.35 1.32; 5.35 1.36; 5.35 0.54; 5.32 0.47; 5.31 1.17; 5.31 1.18; 5.31 0.48; 5.28 0.56; 5.28 1.36; 5.28 1.41; 5.27 0.95; 5.27 1.47; 5.27 1.37; 5.24 1.69; 5.24 2.00; 5.23 1.29; 5.23 0.50; 5.19 1.42; 5.19 1.35; 5.17 1.29; 5.16 1.24; 4.61 2.03; 4.61 3.26; 4.61 1.93; 4.60 2.03; 4.60 3.19; 4.59 1.84; 4.52 3.06; 4.50 2.96; 4.35 |

TABLE 6-continued
Compounds of the general formula (I) according to the invention in which $R^2$ is hydrogen and $R^3$ is methyl and aryl is the radical
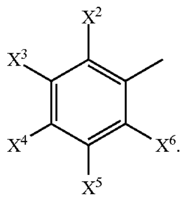
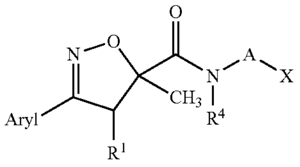
| No. | Aryl | $R^1$ | Y | $R^4$ | A | X | Physical data |
|---|---|---|---|---|---|---|---|
| | | | | | | | 0.39; 4.35 0.42; 4.34 0.78; 4.33 0.99; 4.32 0.96; 4.32 1.38; 4.30 1.00; 4.29 0.45; 4.28 0.40; 3.79 2.66; 3.76 2.69; 3.75 3.06; 3.72 3.08; 3.18 3.21; 3.18 3.16; 3.14 2.79; 3.14 2.76; 2.58 5.22; 2.57 5.15; 2.52 5.21; 2.51 5.13; 1.71 16.00; 1.70 15.93; 1.59 5.42; 1.28 7.89; 1.27 7.84; 1.24 7.84; 1.22 7.74; 0.00 3.42 |
| 6.229 | 3,5-$Cl_2$—Ph | H | O | H | $CH(CH_3)CH_2$ | (cyclopropylsulfonyl)-(methyl)carbamoyl | [$CDCl_3$] 7.53 5.15; 7.52 6.27; 7.52 4.26; 7.52 3.97; 7.41 1.87; 7.41 2.33; 7.41 3.33; 7.40 1.94; 7.26 30.63; 7.09 0.69; 7.07 0.90; 7.05 0.52; 4.40 0.58; 4.38 0.89; 4.36 0.88; 4.35 0.52; 3.79 0.35; 3.78 3.01; 3.73 3.45; 3.24 8.71; 3.17 16.00; 3.13 1.30; 3.12 2.22; 2.97 1.08; 2.96 1.14; 2.96 1.18; 2.95 1.12; 2.92 0.43; 2.91 0.42; 2.91 0.46; 2.90 3.59; 2.88 3.44; 2.87 0.50; 2.86 1.25; 2.86 0.71; 2.85 1.64; 2.85 0.65; 2.84 1.17; 2.83 0.41; 2.83 0.68; 2.82 0.63; 2.04 0.33; 2.00 0.49; 1.70 12.69; 1.69 10.08; 1.56 10.56; 1.35 0.34; 1.34 1.03; 1.34 1.05; 1.33 1.05; 1.32 6.83; 1.31 1.05; 1.31 6.19; 1.30 1.72; 1.29 1.98; 1.29 5.22; 1.28 2.37; 1.27 1.42; 1.27 3.97; 1.26 0.55; 1.25 0.33; 1.17 0.34; 1.15 0.44; 1.15 0.48; 1.14 0.82; 1.13 0.89; 1.13 0.67; 1.12 0.85; 1.12 0.97; 1.11 0.58; 1.10 0.92; 1.10 1.19; 1.10 0.85; 1.09 1.02; 1.08 1.78; 1.07 0.59; 1.06 0.95; 1.01 0.33; 0.00 3.50 |
| 6.230 | 3,5-$F_2$—Ph | H | O | H | $CH(CH_3)CH_2$ | (cyclopropylsulfonyl)-(methyl)carbamoyl | [$CDCl_3$] 7.26 26.42; 7.18 1.37; 7.18 1.77; 7.17 1.99; 7.17 2.01; 7.16 2.22; 7.16 2.14; 7.15 1.54; 7.15 1.25; 7.09 0.57; 7.07 0.71; 7.06 0.54; 6.90 0.44; 6.90 0.78; 6.89 0.43; 6.88 0.89; 6.87 1.56; 6.87 0.82; 6.86 0.48; 6.85 0.79; 6.85 0.40; 4.41 0.58; 4.39 0.83; 4.39 0.80; 4.37 0.91; 4.35 0.58; 3.77 3.34; 3.73 3.86; 3.24 12.33; 3.18 1.95; 3.17 2.77; 3.17 16.00; 3.13 1.68; 3.13 2.18; 2.97 1.42; 2.97 1.43; 2.96 1.47; 2.95 1.42; 2.92 0.50; 2.91 0.56; 2.91 0.66; 2.90 3.47; 2.89 3.94; 2.88 0.71; 2.88 0.37; 2.86 1.05; 2.86 0.63; 2.85 0.75; 2.84 1.20; 2.84 0.39; 2.83 0.65; 2.82 0.63; 2.04 0.40; 2.00 0.38; 1.70 13.51; 1.70 11.80; 1.58 |

TABLE 6-continued
Compounds of the general formula (I) according to the invention in which $R^2$ is hydrogen and $R^3$ is methyl and aryl is the radical
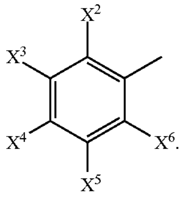
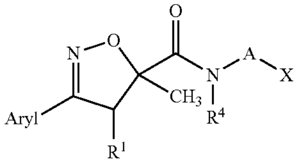
| No. | Aryl | $R^1$ | Y | $R^4$ | A | X | Physical data |
|---|---|---|---|---|---|---|---|
| | | | | | | | 6.81; 1.35 0.45; 1.34 1.24; 1.34 1.16; 1.33 1.22; 1.32 7.42; 1.31 1.13; 1.31 6.36; 1.30 1.19; 1.30 1.54; 1.29 5.86; 1.28 1.99; 1.27 4.99; 1.26 0.47; 1.15 0.42; 1.15 0.46; 1.15 0.57; 1.14 0.62; 1.14 0.98; 1.13 0.93; 1.13 0.76; 1.12 0.87; 1.12 1.07; 1.11 0.64; 1.11 0.62; 1.10 0.96; 1.10 0.83; 1.10 0.96; 1.10 0.70; 1.09 0.81; 1.08 0.82; 1.08 1.28; 1.08 1.59; 1.07 0.57; 1.06 0.79; 1.06 0.97; 0.00 3.30 |
| 6.231 | 3,5-$Cl_2$—Ph | H | O | H | $CH(CH_3)CH_2$ | (cyclopropylsulfonyl)-carbamoyl | [$CDCl_3$] 8.02 1.69; 7.53 6.40; 7.52 7.18; 7.52 6.00; 7.51 5.65; 7.43 1.44; 7.42 2.79; 7.41 3.88; 7.41 1.87; 7.31 0.59; 7.26 232.92; 7.05 0.90; 7.04 0.91; 7.00 1.37; 4.28 0.49; 4.26 0.62; 4.25 0.52; 4.23 0.34; 4.22 0.37; 4.21 0.42; 4.19 0.37; 3.82 1.08; 3.81 1.91; 3.78 1.20; 3.77 2.14; 3.49 0.35; 3.21 4.42; 3.16 3.94; 3.12 8.84; 3.06 6.99; 3.06 7.70; 2.98 0.39; 2.96 0.35; 2.95 0.38; 2.94 0.68; 2.93 0.39; 2.92 0.33; 2.89 0.47; 2.88 0.37; 2.87 0.45; 2.85 0.57; 2.84 0.60; 2.68 0.34; 2.67 0.35; 2.64 0.70; 2.63 0.74; 2.61 0.43; 2.60 1.11; 2.59 1.08; 2.57 1.33; 2.56 0.77; 2.56 1.00; 2.54 1.48; 2.53 1.45; 2.51 0.42; 2.49 0.42; 2.46 0.51; 2.45 0.48; 2.44 0.83; 2.43 0.32; 2.43 0.54; 2.42 0.41; 2.17 0.42; 2.00 3.21; 1.72 16.00; 1.70 0.56; 1.69 0.54; 1.56 23.04; 1.39 0.98; 1.38 1.05; 1.38 1.14; 1.36 6.81; 1.34 8.02; 1.33 5.71; 1.31 4.59; 1.29 0.55; 1.26 1.19; 1.24 0.35; 1.22 0.51; 1.22 0.43; 1.21 0.53; 1.20 0.50; 1.17 1.10; 1.17 1.00; 1.16 1.02; 1.16 1.15; 1.15 0.44; 1.14 0.44; 1.11 0.97; 1.11 1.02; 1.09 1.07; 1.09 0.98; 1.08 0.45; 1.07 0.56; 1.06 1.17; 1.04 1.31; 1.04 1.28; 1.02 0.87; 0.97 0.42; 0.96 1.02; 0.95 1.15; 0.94 1.11; 0.93 1.03; 0.92 0.37; 0.90 0.34; 0.88 0.74; 0.86 0.33; 0.01 1.27; 0.00 47.27; −0.01 1.68 |
| 6.232 | 3,5-$F_2$—Ph | H | O | H | $CH(CH_3)CH_2$ | (cyclopropylsulfonyl)-carbamoyl | [$CDCl_3$] 8.02 0.61; 7.52 0.37; 7.27 0.34; 7.27 0.41; 7.27 0.50; 7.27 0.67; 7.26 65.12; 7.26 61.20; 7.25 1.00; 7.25 0.79; 7.25 0.60; 7.25 0.52; 7.25 0.46; 7.25 0.39; 7.18 1.35; 7.17 1.98; 7.17 2.18; 7.16 2.18; 7.16 2.03; 7.15 1.61; 7.07 |

TABLE 6-continued
Compounds of the general formula (I) according to the invention in which $R^2$ is hydrogen and $R^3$ is methyl and aryl is the radical
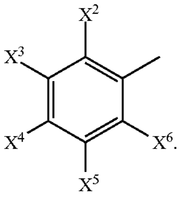
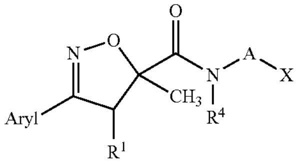
| No. | Aryl | $R^1$ | Y | $R^4$ | A | X | Physical data |
|---|---|---|---|---|---|---|---|
| | | | | | | | 0.81; 7.05 0.88; 7.00 0.38; 6.91 0.67; 6.90 0.69; 6.89 0.58; 6.89 1.36; 6.88 1.37; 6.87 0.65; 6.87 0.70; 6.86 0.69; 4.30 0.46; 4.28 0.57; 4.26 0.51; 4.24 0.48; 4.22 0.57; 4.21 0.42; 3.82 1.45; 3.81 1.62; 3.78 1.66; 3.77 1.88; 3.21 3.74; 3.17 3.29; 3.13 2.85; 3.06 2.57; 2.96 0.42; 2.95 0.45; 2.94 0.82; 2.93 0.44; 2.92 0.40; 2.88 0.37; 2.87 0.43; 2.86 0.71; 2.85 0.47; 2.84 0.39; 2.69 0.38; 2.67 0.36; 2.65 1.05; 2.64 1.02; 2.62 0.39; 2.61 1.14; 2.60 0.45; 2.60 1.17; 2.58 1.19; 2.57 0.62; 2.56 1.21; 2.55 1.46; 2.54 1.37; 2.52 0.40; 2.50 0.35; 2.00 0.89; 1.72 16.00; 1.59 7.13; 1.40 0.36; 1.39 1.08; 1.38 1.14; 1.38 1.27; 1.37 0.63; 1.37 0.55; 1.35 5.27; 1.34 6.26; 1.33 5.84; 1.32 2.08; 1.31 4.73; 1.28 0.60; 1.26 1.49; 1.17 0.43; 1.17 0.41; 1.16 0.38; 1.16 0.44; 1.11 1.09; 1.11 1.28; 1.09 1.21; 1.09 1.14; 1.08 0.41; 1.07 0.33; 1.06 0.58; 1.06 0.95; 1.04 0.97; 1.04 1.24; 1.02 0.84; 1.01 0.39; 0.95 0.38; 0.94 0.36; 0.93 0.37; 0.90 0.69; 0.88 1.85; 0.86 0.82; 0.01 0.35; 0.00 13.21; 0.00 12.75; −0.01 0.46; −0.01 0.49 |
| 6.233 | 3,5-$Cl_2$—Ph | H | O | H | $CH(CH_3)CH_2$ | (ethylsulfonyl)-(methyl)carbamoyl | [$CDCl_3$] 7.53 4.36; 7.53 5.78; 7.53 5.21; 7.52 6.58; 7.52 5.23; 7.52 6.22; 7.52 5.29; 7.51 6.33; 7.42 2.80; 7.41 3.44; 7.41 4.85; 7.41 3.70; 7.41 2.54; 7.27 28.99; 7.26 36.97; 7.08 0.80; 7.07 1.23; 7.05 0.89; 4.37 0.60; 4.36 0.75; 4.35 0.74; 4.35 0.78; 4.34 0.75; 4.34 0.75; 4.33 0.80; 4.31 0.63; 3.78 4.04; 3.73 4.58; 3.45 0.68; 3.44 0.63; 3.43 1.77; 3.42 1.72; 3.41 1.77; 3.40 1.80; 3.39 0.62; 3.38 0.95; 3.38 0.81; 3.37 0.61; 3.36 1.88; 3.36 1.77; 3.34 1.89; 3.34 1.61; 3.34 1.84; 3.32 0.65; 3.32 0.68; 3.26 12.45; 3.26 16.00; 3.20 12.23; 3.19 15.69; 3.18 2.62; 3.17 2.56; 3.13 2.26; 3.12 2.21; 2.97 0.58; 2.96 0.60; 2.93 1.63; 2.92 1.58; 2.90 0.54; 2.89 1.59; 2.88 0.61; 2.88 1.60; 2.86 1.75; 2.85 0.77; 2.84 1.79; 2.84 2.19; 2.82 2.04; 2.81 0.34; 2.81 0.41; 2.80 0.45; 2.78 0.41; 2.04 0.42; 2.01 0.41; 2.00 0.52; 1.70 13.42; 1.69 |

TABLE 6-continued
Compounds of the general formula (I) according to the invention in which $R^2$ is hydrogen and $R^3$ is methyl and aryl is the radical
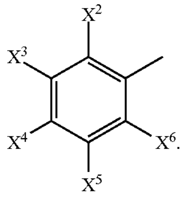
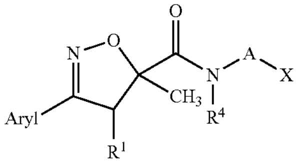
| No. | Aryl | $R^1$ | Y | $R^4$ | A | X | Physical data |
|---|---|---|---|---|---|---|---|
| | | | | | | | 13.59; 1.61 5.37; 1.60 7.96; 1.41 3.82; 1.39 6.36; 1.39 8.01; 1.37 3.19; 1.37 3.76; 1.35 3.83; 1.34 6.14; 1.34 7.88; 1.32 6.66; 1.32 3.73; 1.32 4.20; 1.31 6.43; 1.29 6.59; 1.27 6.49; 1.26 0.50; 0.00 4.19; 0.00 5.48 |
| 6.234 | 3,5-$F_2$—Ph | H | O | H | $CH(CH_3)CH_2$ | (ethylsulfonyl)-(methyl)carbamoyl | [$CDCl_3$] 7.26 29.49; 7.26 17.30; 7.18 1.52; 7.18 1.82; 7.18 2.26; 7.17 2.63; 7.17 2.13; 7.17 2.68; 7.16 3.03; 7.16 2.69; 7.15 2.35; 7.15 1.86; 7.15 1.74; 7.13 0.33; 7.08 0.79; 7.06 1.07; 7.05 0.79; 6.90 0.53; 6.90 0.98; 6.88 1.10; 6.88 1.96; 6.86 0.60; 6.85 0.98; 4.37 0.58; 4.36 0.71; 4.35 0.89; 4.34 0.59; 4.34 0.89; 4.33 0.76; 4.32 0.51; 4.32 0.58; 3.77 3.96; 3.73 4.52; 3.45 0.49; 3.44 0.52; 3.43 1.42; 3.42 1.45; 3.41 1.46; 3.40 1.56; 3.39 0.52; 3.38 1.10; 3.37 0.59; 3.36 1.86; 3.36 1.75; 3.35 1.79; 3.34 1.84; 3.33 0.60; 3.32 0.71; 3.26 13.41; 3.26 8.10; 3.19 16.00; 3.19 9.53; 3.18 2.39; 3.17 2.69; 3.14 1.87; 3.13 2.26; 2.98 0.48; 2.96 0.50; 2.93 1.34; 2.92 1.33; 2.90 0.47; 2.89 1.33; 2.89 0.63; 2.88 1.34; 2.86 1.77; 2.85 0.68; 2.85 1.88; 2.84 1.95; 2.83 1.76; 2.80 0.43; 2.79 0.40; 2.04 0.34; 2.00 0.50; 1.70 13.64; 1.69 12.38; 1.57 7.44; 1.57 4.87; 1.41 3.14; 1.39 6.64; 1.39 4.08; 1.37 3.17; 1.35 3.83; 1.34 7.92; 1.33 5.04; 1.32 6.71; 1.32 4.25; 1.31 6.64; 1.29 5.50; 1.27 5.47; 1.26 0.40; 1.26 0.37; 0.00 3.33; 0.00 2.12 |
| 6.235 | 3,5-$Cl_2$—Ph | H | O | H | $CH(CH_3)CH_2$ | (ethylsulfonyl)-carbamoyl | [$CDCl_3$] 8.05 0.94; 7.53 4.50; 7.52 5.14; 7.52 4.79; 7.51 5.12; 7.42 1.28; 7.42 2.54; 7.42 2.56; 7.41 2.86; 7.41 1.25; 7.26 70.76; 7.07 0.97; 7.05 1.01; 7.00 0.41; 4.31 0.35; 4.29 0.46; 4.27 0.38; 4.25 0.33; 4.24 0.40; 4.22 0.47; 4.20 0.37; 3.83 0.94; 3.82 1.59; 3.79 1.14; 3.77 1.84; 3.49 0.39; 3.48 0.47; 3.46 1.29; 3.44 1.34; 3.42 0.51; 3.38 0.79; 3.36 0.80; 3.34 0.35; 3.21 3.16; 3.17 2.80; 3.13 5.19; 3.07 0.47; 3.05 5.12; 3.05 5.10; 3.03 1.67; 3.01 0.49; 2.65 0.77; 2.63 0.80; 2.61 1.02; 2.59 1.03; 2.57 0.89; 2.56 1.48; 2.55 1.05; 2.54 1.14; 2.00 0.97; 1.72 |

TABLE 6-continued
Compounds of the general formula (I) according to the invention in which $R^2$ is hydrogen and $R^3$ is methyl and aryl is the radical
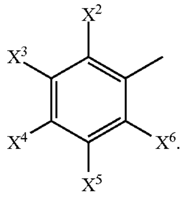
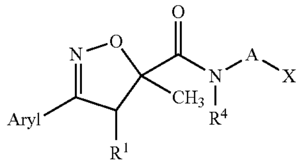
| No. | Aryl | $R^1$ | Y | $R^4$ | A | X | Physical data |
|---|---|---|---|---|---|---|---|
| | | | | | | | 16.00; 1.70 0.88; 1.69 0.70; 1.68 0.38; 1.67 0.40; 1.66 0.39; 1.60 0.84; 1.55 0.48; 1.44 0.43; 1.41 2.81; 1.39 6.01; 1.37 2.77; 1.35 4.64; 1.33 7.35; 1.32 4.84; 1.32 5.92; 1.31 4.62; 1.30 2.81; 1.29 0.60; 1.26 0.95; 1.26 0.89; 1.25 0.39; 0.90 0.37; 0.88 1.14; 0.86 0.48; 0.01 0.41; 0.00 13.61; −0.01 0.59 |
| 6.236 | 3,5-$F_2$—Ph | H | O | H | $CH(CH_3)CH_2$ | (ethylsulfonyl)-carbamoyl | [$CDCl_3$] 8.05 0.57; 7.26 56.72; 7.26 52.27; 7.18 1.91; 7.17 1.99; 7.16 2.66; 7.16 2.09; 7.15 1.70; 7.07 1.10; 7.05 1.14; 7.00 0.35; 6.99 0.36; 6.91 0.62; 6.90 0.69; 6.89 1.24; 6.88 1.33; 6.87 0.71; 6.86 0.74; 4.30 0.50; 4.28 0.63; 4.27 0.53; 4.25 0.39; 4.23 0.42; 4.22 0.52; 4.20 0.40; 3.82 1.14; 3.81 1.25; 3.78 1.31; 3.77 1.42; 3.49 0.37; 3.48 0.51; 3.46 1.38; 3.44 1.44; 3.42 0.60; 3.40 0.47; 3.38 1.16; 3.36 1.16; 3.34 0.49; 3.21 2.98; 3.17 2.65; 3.13 2.41; 3.05 3.02; 3.03 0.81; 2.65 0.76; 2.63 0.77; 2.61 0.93; 2.59 1.00; 2.57 1.15; 2.56 1.99; 2.54 1.33; 2.00 0.78; 2.00 0.71; 1.72 16.00; 1.66 0.42; 1.59 1.73; 1.41 2.09; 1.41 2.02; 1.39 4.27; 1.39 4.20; 1.37 2.10; 1.37 2.04; 1.35 5.24; 1.33 8.58; 1.33 4.46; 1.32 6.16; 1.31 6.21; 1.31 4.38; 1.30 2.69; 1.25 0.93; 0.00 11.53; 0.00 10.20 |
| 6.237 | 3,5-$Cl_2$—Ph | H | O | H | $CH(CH_3)CH_2$ | (heptan-2-yloxy)carbonyl | [$CDCl_3$] 7.52 6.44; 7.52 11.15; 7.51 6.29; 7.41 1.78; 7.41 4.56; 7.40 4.37; 7.40 1.59; 7.27 0.35; 7.26 103.36; 7.25 0.76; 7.25 0.51; 7.24 0.41; 7.24 0.40; 7.24 0.32; 7.23 0.49; 7.21 0.52; 7.20 0.65; 7.18 0.52; 7.16 0.75; 7.14 0.69; 7.00 0.58; 4.96 0.53; 4.95 0.99; 4.93 1.02; 4.92 0.61; 4.89 0.38; 4.88 0.85; 4.86 1.07; 4.84 0.86; 4.83 0.40; 4.33 0.37; 4.31 0.87; 4.29 1.10; 4.29 0.97; 4.28 0.89; 4.26 0.45; 3.82 0.38; 3.80 0.76; 3.79 2.55; 3.77 2.50; 3.75 2.48; 3.73 2.36; 3.49 0.75; 3.18 3.95; 3.13 3.44; 2.52 3.24; 2.51 3.34; 2.47 1.34; 2.46 3.17; 2.46 1.51; 2.45 2.88; 2.00 2.59; 1.71 16.00; 1.70 12.34; 1.62 0.41; 1.60 0.52; 1.59 0.60; 1.58 0.58; 1.57 0.61; 1.54 12.80; 1.50 0.75; 1.48 0.82; 1.47 0.88; 1.46 1.34; 1.44 1.37; 1.43 |

TABLE 6-continued
Compounds of the general formula (I) according to the invention in which $R^2$ is hydrogen and $R^3$ is methyl and aryl is the radical
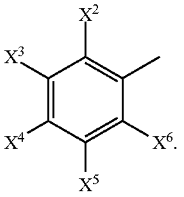
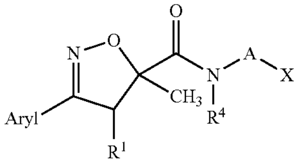
| No. | Aryl | $R^1$ | Y | $R^4$ | A | X | Physical data |
|---|---|---|---|---|---|---|---|
| | | | | | | | 1.89; 1.42 1.79; 1.41 1.12; 1.41 1.10; 1.40 1.30; 1.36 0.61; 1.35 1.15; 1.33 2.09; 1.33 2.08; 1.32 3.85; 1.30 5.42; 1.29 6.52; 1.27 11.09; 1.25 10.39; 1.24 11.06; 1.22 12.96; 1.20 4.27; 1.20 5.79; 1.19 13.26; 1.18 12.48; 1.17 5.66; 1.16 5.04; 1.15 5.58; 1.15 4.97; 0.91 2.61; 0.89 7.66; 0.88 7.55; 0.87 7.91; 0.85 2.90; 0.01 0.60; 0.00 20.43; −0.01 0.58; −0.01 0.64 |
| 6.238 | 3,5-$F_2$—Ph | H | O | H | $CH(CH_3)CH_2$ | (heptan-2-yloxy)carbonyl | [$CDCl_3$] 7.26 43.19; 7.26 20.77; 7.23 0.53; 7.20 1.02; 7.18 1.32; 7.17 4.76; 7.16 5.24; 7.15 4.21; 7.15 5.21; 7.14 4.21; 7.13 0.78; 6.90 1.18; 6.89 1.46; 6.88 0.92; 6.88 1.06; 6.87 2.36; 6.87 2.84; 6.86 1.66; 6.86 0.84; 6.85 1.21; 6.85 1.43; 6.84 0.82; 4.96 0.62; 4.95 1.15; 4.93 1.18; 4.92 0.64; 4.89 0.39; 4.88 0.78; 4.86 0.94; 4.85 0.76; 4.83 0.38; 4.33 0.50; 4.31 1.13; 4.30 1.49; 4.28 1.28; 4.26 0.63; 3.79 2.19; 3.77 2.17; 3.75 2.42; 3.72 2.43; 3.18 4.49; 3.14 3.87; 2.52 3.99; 2.51 1.70; 2.51 4.05; 2.47 1.27; 2.47 1.08; 2.46 2.76; 2.46 3.69; 2.45 2.54; 2.45 2.51; 2.00 0.50; 1.71 16.00; 1.70 10.60; 1.70 11.88; 1.70 12.51; 1.62 0.59; 1.60 0.74; 1.58 0.84; 1.55 16.52; 1.55 9.14; 1.53 0.84; 1.53 0.79; 1.51 0.88; 1.50 0.81; 1.48 0.68; 1.46 0.87; 1.44 0.90; 1.42 0.81; 1.40 0.54; 1.38 0.43; 1.28 7.23; 1.27 13.61; 1.25 12.12; 1.24 13.18; 1.22 13.82; 1.21 4.44; 1.20 6.77; 1.18 1.27; 1.17 0.82; 1.16 5.12; 1.16 6.90; 1.15 5.15; 1.15 6.79; 0.89 3.73; 0.88 9.05; 0.86 8.89; 0.85 2.89; 0.00 8.21; −0.01 4.17 |
| 6.239 | 3,5-$Cl_2$—Ph | H | O | H | $CH(CH_3)CH_2$ | (isopropylsulfonyl)-(methyl)carbamoyl | [$CDCl_3$] 7.53 3.51; 7.53 6.86; 7.52 7.84; 7.52 5.61; 7.52 4.64; 7.42 0.73; 7.41 2.41; 7.41 4.12; 7.41 3.50; 7.40 1.45; 7.26 17.36; 7.26 30.67; 7.12 0.77; 7.10 1.21; 7.08 0.63; 4.37 0.61; 4.37 0.44; 4.36 0.81; 4.35 0.81; 4.34 0.62; 4.34 0.81; 4.32 0.45; 4.32 0.43; 4.31 0.43; 3.78 3.19; 3.78 0.50; 3.74 3.72; 3.74 0.85; 3.72 0.81; 3.70 0.61; 3.67 0.36; 3.65 0.85; 3.63 1.15; 3.62 0.87; 3.60 0.34; 3.26 6.73; 3.26 11.18; 3.19 9.68; 3.19 16.00; 3.18 1.39; 3.17 1.97; 3.17 |

TABLE 6-continued
Compounds of the general formula (I) according to the invention in which $R^2$ is hydrogen and $R^3$ is methyl and aryl is the radical
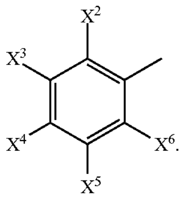
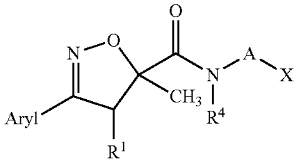
| No. | Aryl | $R^1$ | Y | $R^4$ | A | X | Physical data |
|---|---|---|---|---|---|---|---|
| | | | | | | | 1.80; 3.17 2.56; 3.13 1.00; 3.13 1.62; 3.13 1.48; 3.12 2.18; 3.03 0.55; 3.01 0.55; 2.99 0.60; 2.98 0.91; 2.97 0.89; 2.95 0.52; 2.95 0.77; 2.94 0.50; 2.94 0.77; 2.91 1.32; 2.90 0.88; 2.90 1.29; 2.87 0.87; 2.85 0.88; 2.84 0.54; 2.84 0.87; 2.83 0.83; 2.83 1.29; 2.81 1.06; 2.81 1.31; 2.79 1.27; 2.77 0.49; 2.77 0.76; 2.75 0.73; 2.05 0.36; 2.04 0.61; 2.00 0.35; 1.71 8.21; 1.70 12.98; 1.69 6.23; 1.69 9.22; 1.68 0.41; 1.68 0.45; 1.57 4.45; 1.57 7.45; 1.41 3.26; 1.41 6.93; 1.41 5.18; 1.39 7.56; 1.39 5.30; 1.38 1.15; 1.38 1.74; 1.35 4.42; 1.35 7.24; 1.35 5.12; 1.35 7.14; 1.34 4.71; 1.33 7.30; 1.33 5.13; 1.33 7.03; 1.32 4.34; 1.32 6.43; 1.30 4.18; 1.30 6.24; 1.28 2.99; 1.28 4.48; 1.27 2.97; 1.26 4.46; 1.26 0.77; 0.00 2.82; 0.00 5.01 |
| 6.240 | 3,5-$F_2$—Ph | H | O | H | $CH(CH_3)CH_2$ | (isopropylsulfonyl)-(methyl)carbamoyl | [$CDCl_3$] 7.26 28.24; 7.18 1.47; 7.18 2.03; 7.17 2.07; 7.17 1.87; 7.16 2.23; 7.16 2.23; 7.15 1.22; 7.14 0.36; 7.12 0.65; 7.10 0.95; 7.08 0.50; 6.90 0.54; 6.89 0.74; 6.89 0.41; 6.88 1.08; 6.87 1.48; 6.87 0.77; 6.85 0.56; 6.85 0.75; 6.85 0.38; 4.38 0.57; 4.37 0.46; 4.36 0.67; 4.36 0.80; 4.34 0.81; 4.32 0.43; 4.32 0.37; 3.78 2.56; 3.74 3.24; 3.72 0.77; 3.70 0.56; 3.67 0.34; 3.66 0.86; 3.64 1.21; 3.62 0.90; 3.60 0.36; 3.26 10.08; 3.18 16.00; 3.18 2.20; 3.17 2.75; 3.13 1.44; 3.13 2.27; 3.03 0.51; 3.01 0.51; 2.99 0.84; 2.97 0.84; 2.95 0.81; 2.94 0.80; 2.91 1.38; 2.90 1.35; 2.87 0.81; 2.86 0.82; 2.83 0.59; 2.81 1.55; 2.80 1.35; 2.77 0.79; 2.76 0.76; 2.04 0.41; 2.00 0.46; 1.70 13.46; 1.69 8.78; 1.68 0.39; 1.57 7.36; 1.43 0.99; 1.42 1.17; 1.41 4.84; 1.41 5.17; 1.39 5.05; 1.39 5.37; 1.38 0.61; 1.35 7.26; 1.35 7.58; 1.33 7.37; 1.33 7.58; 1.32 6.74; 1.30 6.53; 1.28 4.19; 1.27 4.13; 1.26 0.54; 0.00 3.16 |
| 6.241 | 3,5-$Cl_2$—Ph | H | O | H | $CH(CH_3)CH_2$ | (isopropylsulfonyl)-carbamoyl | [$CDCl_3$] 8.03 0.93; 7.53 5.11; 7.52 5.78; 7.52 5.51; 7.51 5.21; 7.43 1.25; 7.42 3.58; 7.42 3.64; 7.41 1.34; 7.31 0.73; 7.27 0.32; 7.27 0.35; 7.27 0.33; 7.27 0.51; 7.27 0.64; 7.27 0.80; 7.27 1.01; 7.26 169.20; 7.25 1.61; 7.25 1.29; 7.25 |

TABLE 6-continued
Compounds of the general formula (I) according to the invention in which $R^2$ is hydrogen and $R^3$ is methyl and aryl is the radical
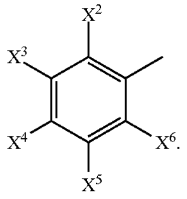
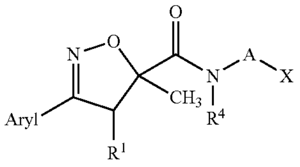
| No. | Aryl | $R^1$ | Y | $R^4$ | A | X | Physical data |
|---|---|---|---|---|---|---|---|
| | | | | | | | 1.26; 7.25 0.67; 7.25 0.60; 7.24 0.55; 7.24 0.55; 7.24 0.33; 7.06 0.76; 7.04 0.79; 7.00 0.98; 4.29 0.38; 4.27 0.46; 4.25 0.35; 4.22 0.35; 4.20 0.37; 3.82 0.99; 3.82 1.79; 3.80 0.32; 3.78 1.40; 3.77 2.03; 3.76 0.39; 3.70 0.34; 3.21 3.45; 3.16 3.07; 3.15 0.49; 3.13 5.43; 3.11 0.49; 3.05 4.38; 3.05 4.30; 2.98 0.38; 2.65 0.59; 2.64 0.57; 2.61 0.86; 2.59 0.86; 2.58 0.65; 2.56 0.76; 2.55 1.24; 2.54 0.95; 2.17 0.35; 2.00 2.34; 1.72 16.00; 1.70 0.60; 1.70 0.55; 1.57 14.64; 1.44 3.66; 1.43 5.32; 1.43 5.08; 1.42 3.58; 1.42 5.26; 1.41 4.96; 1.39 3.92; 1.37 3.96; 1.36 7.16; 1.35 6.13; 1.35 5.16; 1.34 7.41; 1.33 6.10; 1.33 5.10; 1.32 4.55; 1.31 3.97; 1.29 0.39; 1.26 1.09; 0.88 0.39; 0.01 0.96; 0.00 34.32; −0.01 1.13 |
| 6.242 | 3,5-$F_2$—Ph | H | O | H | $CH(CH_3)CH_2$ | (isopropylsulfonyl)-carbamoyl | [$CDCl_3$] 8.03 0.56; 7.52 0.52; 7.27 0.45; 7.27 0.71; 7.27 0.82; 7.27 0.93; 7.26 58.34; 7.26 92.12; 7.25 2.28; 7.25 1.39; 7.25 0.86; 7.24 0.55; 7.24 0.36; 7.18 1.56; 7.18 1.99; 7.17 2.12; 7.17 2.38; 7.16 2.37; 7.16 1.96; 7.16 2.14; 7.15 1.67; 7.07 0.94; 7.06 1.01; 7.00 0.34; 7.00 0.49; 6.91 0.73; 6.90 0.71; 6.89 1.46; 6.88 1.44; 6.87 0.78; 6.86 0.74; 4.30 0.45; 4.28 0.57; 4.26 0.50; 4.25 0.38; 4.23 0.44; 4.22 0.54; 4.20 0.43; 3.82 1.42; 3.81 1.57; 3.80 0.50; 3.78 0.73; 3.77 1.62; 3.77 1.64; 3.77 2.11; 3.72 0.40; 3.70 0.55; 3.69 0.44; 3.21 3.45; 3.17 2.99; 3.13 2.71; 3.05 2.48; 3.05 2.28; 2.70 0.33; 2.68 0.35; 2.66 0.83; 2.64 0.78; 2.63 0.35; 2.61 1.12; 2.60 1.02; 2.59 1.04; 2.57 1.24; 2.56 1.47; 2.54 1.17; 2.52 0.38; 2.51 0.32; 2.01 0.74; 2.00 1.21; 1.72 16.00; 1.70 0.46; 1.58 9.36; 1.44 2.50; 1.43 4.91; 1.43 5.98; 1.43 5.21; 1.42 2.68; 1.42 4.70; 1.41 5.90; 1.41 5.12; 1.38 4.93; 1.37 4.95; 1.36 2.50; 1.36 3.72; 1.35 5.57; 1.34 5.95; 1.34 4.61; 1.33 5.75; 1.32 8.16; 1.31 4.05; 1.26 0.68; 0.88 0.39; 0.01 0.59; 0.00 9.79; 0.00 16.18; −0.01 0.61 |

TABLE 6-continued

Compounds of the general formula (I) according to the invention in which $R^2$ is hydrogen and $R^3$ is methyl and aryl is the radical

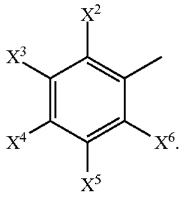

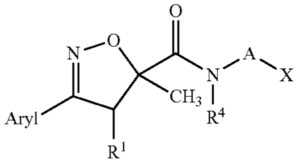

| No. | Aryl | $R^1$ | Y | $R^4$ | A | X | Physical data |
|---|---|---|---|---|---|---|---|
| 6.243 | 3,5-$Cl_2$—Ph | H | O | H | $CH(CH_3)CH_2$ | (methylsulfonyl)-carbamoyl | [$CDCl_3$] 8.61 0.37; 7.52 3.99; 7.52 7.60; 7.51 7.59; 7.51 4.41; 7.50 3.67; 7.50 4.15; 7.42 0.97; 7.42 1.76; 7.41 2.46; 7.41 2.95; 7.41 1.54; 7.40 1.63; 7.40 1.12; 7.40 1.67; 7.39 0.90; 7.26 0.36; 7.26 42.78; 7.25 0.40; 7.25 0.37; 7.25 0.34; 7.17 0.48; 7.16 0.92; 7.14 0.83; 7.12 0.53; 7.10 0.45; 4.35 0.71; 4.34 0.49; 4.33 0.86; 4.32 0.68; 4.31 0.68; 4.31 0.36; 4.30 0.36; 4.29 0.37; 4.27 0.40; 4.26 0.33; 3.84 1.34; 3.81 1.37; 3.81 1.46; 3.80 2.60; 3.77 1.53; 3.77 1.67; 3.75 1.40; 3.29 9.39; 3.27 6.03; 3.21 1.48; 3.20 11.56; 3.19 1.63; 3.17 1.27; 3.16 2.27; 3.15 1.32; 3.12 2.30; 2.97 0.59; 2.89 0.54; 2.64 0.93; 2.63 0.92; 2.62 0.94; 2.60 3.09; 2.59 2.27; 2.58 0.43; 2.56 2.44; 2.55 2.28; 2.54 1.18; 2.53 1.21; 2.52 1.11; 2.52 1.15; 2.10 1.96; 2.04 1.53; 1.71 16.00; 1.70 7.49; 1.35 3.47; 1.33 3.48; 1.32 6.39; 1.30 6.39; 1.28 0.75; 1.27 3.55; 1.26 1.46; 1.25 3.95; 1.24 0.55; 0.01 0.45; 0.00 19.09; −0.01 0.73 |
| 6.244 | 3,5-$F_2$—Ph | H | O | H | $CH(CH_3)CH_2$ | (methylsulfonyl)-carbamoyl | diastereomer D1: [$CDCl_3$] 1.32 (d, 3H); 1.72 (s, 3H); 2.53 (m, 2H); 3.19 (d, 1H); 3.28 (s, 3H); 3.80 (d, 1H); 4.22 (m, 1H); 6.89 (m, 1H); 7.05 (d br, 1H); 7.16 (m, 2H); 9.45 (s br, 1H). diastereomer D2: [$CDCl_3$] 1.34 (d, 3H); 1.72 (s, 3H); 2.61 (m, 2H); 3.12 (s, 3H); 3.20 (d, 1H); 3.81 (d, 1H); 4.28 (m, 1H); 6.89 (m, 1H); 7.05 (d br, 1H); 7.16 (m, 2H); 9.45 (s br, 1H). |
| 6.245 | 3,5-$Cl_2$—Ph | H | O | H | $CH(CH_3)CH_2$ | (prop-2-Yn-1-yloxy)carbonyl | [$CDCl_3$] 7.52 5.25; 7.52 6.02; 7.52 10.77; 7.52 7.64; 7.52 6.35; 7.41 2.58; 7.41 4.80; 7.40 2.69; 7.26 53.36; 7.26 52.35; 7.06 0.65; 7.04 0.72; 7.02 0.74; 7.00 0.68; 7.00 0.77; 4.70 4.84; 4.70 5.11; 4.62 2.51; 4.62 2.57; 4.61 4.95; 4.61 2.93; 4.35 0.33; 4.34 0.40; 4.34 0.70; 4.33 0.92; 4.31 1.29; 4.30 0.98; 4.29 0.83; 4.28 0.75; 4.27 0.60; 4.27 0.45; 4.13 0.76; 4.11 0.76; 3.80 2.11; 3.77 2.26; 3.76 2.45; 3.73 2.58; 3.18 2.56; 3.17 2.46; 3.14 2.22; 3.13 2.17; 2.61 4.31; 2.59 4.27; 2.54 4.60; 2.53 4.56; 2.49 1.19; 2.48 1.19; 2.48 2.60; 2.48 2.62; 2.47 1.62; 2.47 |

TABLE 6-continued
Compounds of the general formula (I) according to the invention in which $R^2$ is hydrogen and $R^3$ is methyl and aryl is the radical
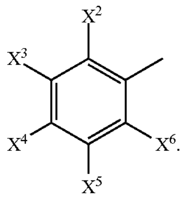
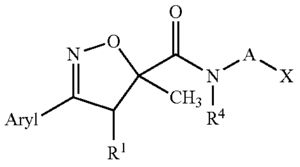
| No. | Aryl | $R^1$ | Y | $R^4$ | A | X | Physical data |
|---|---|---|---|---|---|---|---|
| | | | | | | | 0.34; 2.42 1.23; 2.42 1.27; 2.42 2.57; 2.42 2.51; 2.41 1.40; 2.41 1.29; 2.04 3.33; 2.04 3.25; 2.00 1.21; 2.00 1.20; 1.70 15.17; 1.70 16.00; 1.56 0.34; 1.54 16.61; 1.54 15.42; 1.29 6.93; 1.28 7.87; 1.26 2.46; 1.26 2.47; 1.25 6.70; 1.24 1.42; 1.24 1.42; 1.23 6.53; 0.90 0.43; 0.88 1.03; 0.86 0.49; 0.00 9.93; 0.00 9.91 |
| 6.246 | 3,5-$F_2$—Ph | H | O | H | $CH(CH_3)CH_2$ | (prop-2-Yn-1-yloxy)carbonyl | [$CDCl_3$] 7.26 11.85; 7.26 7.40; 7.25 9.27; 7.17 4.50; 7.16 4.51; 7.16 4.72; 7.15 4.60; 7.15 4.31; 7.06 0.95; 7.03 1.29; 7.01 0.93; 6.90 0.53; 6.90 1.16; 6.89 1.29; 6.89 1.08; 6.88 1.38; 6.88 2.27; 6.87 2.45; 6.87 1.93; 6.86 1.27; 6.85 1.20; 6.85 1.22; 6.84 0.93; 4.70 3.29; 4.70 5.38; 4.69 4.67; 4.69 2.87; 4.61 2.01; 4.61 4.14; 4.60 5.22; 4.60 3.78; 4.32 1.40; 4.32 1.59; 4.31 1.61; 4.30 1.43; 3.80 1.54; 3.79 1.29; 3.77 1.62; 3.76 1.46; 3.75 1.94; 3.74 1.47; 3.72 1.84; 3.71 1.52; 3.19 1.86; 3.18 3.07; 3.17 1.49; 3.14 1.62; 3.14 2.64; 3.13 1.29; 2.61 3.14; 2.59 3.65; 2.59 2.40; 2.58 2.62; 2.54 3.29; 2.53 3.81; 2.52 2.50; 2.52 2.72; 2.49 0.93; 2.48 2.28; 2.47 2.36; 2.47 2.01; 2.46 0.91; 2.42 0.96; 2.41 2.34; 2.41 2.36; 2.40 1.94; 2.40 0.80; 1.71 11.29; 1.70 16.00; 1.70 14.99; 1.57 4.91; 1.57 3.50; 1.56 4.02; 1.29 4.89; 1.28 4.44; 1.28 5.28; 1.27 3.83; 1.27 4.21; 1.25 4.87; 1.24 4.32; 1.24 5.03; 1.23 3.61; 1.23 3.93; 0.00 2.47; −0.01 2.03 |
| 6.247 | 3,5-$Cl_2$—Ph | H | O | H | $CH(CH_3)CH_2$ | (propan-2-yloxy)carbonyl | [$CDCl_3$] 7.52 4.40; 7.52 5.89; 7.52 5.48; 7.51 5.22; 7.41 1.21; 7.41 3.16; 7.40 3.09; 7.40 1.18; 7.26 27.60; 7.19 0.46; 7.17 0.48; 7.14 0.47; 7.12 0.46; 5.07 0.32; 5.06 0.83; 5.04 1.13; 5.02 0.85; 5.01 0.34; 4.99 0.35; 4.97 0.90; 4.96 1.22; 4.94 0.92; 4.93 0.37; 4.33 0.33; 4.31 0.71; 4.30 0.75; 4.29 0.87; 4.27 0.74; 4.26 0.35; 3.79 1.76; 3.77 1.93; 3.75 2.01; 3.73 2.20; 3.18 2.68; 3.13 2.32; 2.51 3.23; 2.49 3.22; 2.45 3.69; 2.44 3.66; 2.04 0.49; 2.00 0.77; 1.71 11.37; 1.70 10.56; 1.55 7.71; 1.27 |

TABLE 6-continued
Compounds of the general formula (I) according to the invention in which $R^2$ is hydrogen and $R^3$ is methyl and aryl is the radical
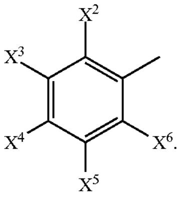
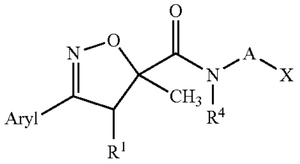
| No. | Aryl | $R^1$ | Y | $R^4$ | A | X | Physical data |
|---|---|---|---|---|---|---|---|
| | | | | | | | 16.00; 1.25 13.40; 1.22 5.21; 1.20 14.23; 1.18 11.37; 0.90 0.62; 0.88 1.80; 0.86 0.78; 0.00 5.23 |
| 6.248 | 3,5-$F_2$—Ph | H | O | H | $CH(CH_3)CH_2$ | (propan-2-yloxy)carbonyl | [$CDCl_3$] 7.27 0.35; 7.27 0.40; 7.27 0.47; 7.27 0.54; 7.26 19.69; 7.26 16.41; 7.19 0.74; 7.18 0.74; 7.17 1.75; 7.17 2.91; 7.16 2.59; 7.16 2.22; 7.16 2.19; 7.15 2.18; 7.15 2.47; 7.15 2.95; 7.14 1.93; 7.14 0.73; 7.13 0.68; 6.90 0.71; 6.89 0.72; 6.88 0.35; 6.88 0.60; 6.87 1.41; 6.87 1.40; 6.86 0.59; 6.86 0.38; 6.85 0.73; 6.85 0.70; 5.06 0.80; 5.04 1.07; 5.02 0.81; 5.01 0.32; 4.99 0.33; 4.97 0.82; 4.96 1.11; 4.94 0.83; 4.92 0.33; 4.33 0.33; 4.32 0.59; 4.31 0.70; 4.31 0.73; 4.30 0.98; 4.28 0.77; 4.28 0.60; 4.26 0.32; 3.79 1.71; 3.77 1.76; 3.75 1.94; 3.73 2.00; 3.18 3.42; 3.14 2.96; 2.51 3.34; 2.50 3.30; 2.45 3.48; 2.44 3.55; 2.04 0.73; 1.71 10.70; 1.70 10.53; 1.56 4.49; 1.27 16.00; 1.25 15.53; 1.24 0.60; 1.22 5.11; 1.20 5.36; 1.20 12.52; 1.19 11.03; 1.18 11.98; 1.18 10.59; 0.90 0.32; 0.88 0.80; 0.86 0.37; 0.00 3.91; 0.00 3.28 |
| 6.249 | 3-Cl—Ph | H | O | H | $CH(CH_3)CH_2$ | (propan-2-yloxy)carbonyl | [$CDCl_3$] 7.65 2.56; 7.65 2.51; 7.65 2.58; 7.51 0.53; 7.51 1.03; 7.50 0.94; 7.50 0.82; 7.50 0.89; 7.49 0.85; 7.49 1.02; 7.49 1.39; 7.49 1.27; 7.48 1.07; 7.48 1.10; 7.48 0.94; 7.41 0.42; 7.41 0.70; 7.41 0.85; 7.40 0.93; 7.40 0.80; 7.40 0.53; 7.40 0.35; 7.39 0.89; 7.39 1.32; 7.39 1.80; 7.38 1.89; 7.38 1.55; 7.38 1.02; 7.36 1.53; 7.35 1.25; 7.34 1.69; 7.34 1.69; 7.33 1.38; 7.32 0.65; 7.31 0.58; 7.26 18.09; 7.26 13.12; 7.20 0.42; 7.18 0.45; 7.16 0.55; 7.13 0.54; 5.07 0.32; 5.05 0.83; 5.04 1.15; 5.02 0.87; 5.01 0.37; 4.96 0.65; 4.95 0.89; 4.93 0.67; 4.33 0.35; 4.31 0.71; 4.31 0.74; 4.30 0.95; 4.30 0.90; 4.28 0.73; 4.26 0.33; 3.82 1.78; 3.80 1.41; 3.77 2.04; 3.75 1.61; 3.21 3.14; 3.17 2.74; 2.51 3.52; 2.49 3.51; 2.45 1.47; 2.45 1.85; 2.44 1.46; 2.43 1.64; 1.72 0.45; 1.71 8.53; 1.70 10.86; 1.58 4.78; 1.27 16.00; 1.25 14.20; 1.25 14.13; 1.24 0.44; 1.22 5.36; 1.20 5.36; 1.19 9.55; 1.17 9.59; 0.00 7.46 |

TABLE 6-continued
Compounds of the general formula (I) according to the invention in which $R^2$ is hydrogen and $R^3$ is methyl and aryl is the radical
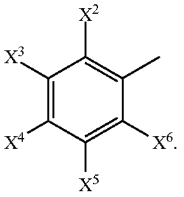
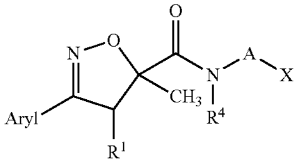
| No. | Aryl | $R^1$ | Y | $R^4$ | A | X | Physical data |
|---|---|---|---|---|---|---|---|
| 6.250 | 3-F—Ph | H | O | H | $CH(CH_3)CH_2$ | (propan-2-yloxy)carbonyl | [$CDCl_3$] 7.40 1.42; 7.39 1.47; 7.39 1.67; 7.38 1.62; 7.38 3.18; 7.37 5.34; 7.37 4.14; 7.36 2.11; 7.36 2.04; 7.35 0.39; 7.26 23.44; 7.20 0.55; 7.18 0.60; 7.16 0.47; 7.16 0.48; 7.15 0.56; 7.14 1.10; 7.14 1.28; 7.13 0.82; 7.13 0.83; 7.13 1.02; 7.12 1.22; 7.12 0.87; 7.11 0.90; 7.11 0.93; 7.11 0.67; 7.10 0.53; 7.09 0.37; 5.05 0.69; 5.04 0.95; 5.02 0.71; 4.98 0.44; 4.96 1.12; 4.95 1.54; 4.93 1.15; 4.92 0.46; 4.32 0.67; 4.32 0.73; 4.30 0.78; 4.30 1.03; 4.29 0.50; 4.28 0.80; 4.27 0.37; 3.82 1.51; 3.80 2.49; 3.78 1.75; 3.75 2.86; 3.22 3.48; 3.17 3.02; 2.51 2.86; 2.50 2.87; 2.45 2.55; 2.45 2.46; 2.44 2.50; 2.44 2.40; 1.71 14.75; 1.70 9.37; 1.58 10.94; 1.27 15.86; 1.25 16.00; 1.22 4.35; 1.20 4.36; 1.18 13.79; 1.17 13.78; 0.00 7.47 |
| 6.251 | 3,5-$Cl_2$—Ph | H | O | H | $CH(CH_3)CH_2$ | [2-(methylsulfanyl)-ethoxy]carbonyl | [$CDCl_3$] 7.52 8.99; 7.52 13.37; 7.51 8.65; 7.41 2.22; 7.41 4.90; 7.41 4.45; 7.26 28.09; 7.26 23.40; 7.15 0.77; 7.12 0.95; 7.11 0.97; 7.09 0.79; 4.34 0.37; 4.34 0.38; 4.33 0.83; 4.32 0.99; 4.31 0.93; 4.31 1.30; 4.31 1.38; 4.30 1.19; 4.30 1.84; 4.29 2.13; 4.28 2.47; 4.28 3.20; 4.27 2.27; 4.26 1.33; 4.26 1.56; 4.26 1.03; 4.21 0.97; 4.21 0.88; 4.20 1.16; 4.20 0.96; 4.20 1.87; 4.19 1.75; 4.19 2.05; 4.18 1.25; 4.18 1.07; 4.17 1.17; 4.17 0.90; 4.16 0.32; 3.80 1.86; 3.79 1.59; 3.78 2.04; 3.78 1.71; 3.75 2.25; 3.75 2.01; 3.74 2.42; 3.74 2.19; 3.18 3.80; 3.13 3.32; 2.76 2.10; 2.76 1.83; 2.74 3.90; 2.74 3.33; 2.73 2.22; 2.72 1.81; 2.71 0.40; 2.71 0.35; 2.69 1.97; 2.67 3.75; 2.66 1.92; 2.57 3.31; 2.56 3.39; 2.51 1.95; 2.51 2.89; 2.50 2.13; 2.49 2.89; 2.16 14.26; 2.15 11.69; 2.11 16.00; 2.10 12.91; 2.00 0.40; 2.00 0.33; 1.71 11.99; 1.71 10.55; 1.70 11.97; 1.70 9.98; 1.55 7.98; 1.55 6.76; 1.29 5.78; 1.29 5.14; 1.27 5.88; 1.27 5.12; 1.25 5.48; 1.24 4.82; 1.23 5.48; 1.23 4.78; 0.00 5.23; 0.00 4.45 |
| 6.252 | 3,5-$F_2$—Ph | H | O | H | $CH(CH_3)CH_2$ | [2-(methylsulfanyl)-ethoxy]carbonyl | [$CDCl_3$] 7.26 16.77; 7.19 0.49; 7.17 2.46; 7.17 3.35; 7.15 3.62; 7.15 3.25; 7.14 0.90; 7.13 0.79; 7.13 0.76; 7.12 0.73; 7.10 0.56; 6.90 |

TABLE 6-continued

Compounds of the general formula (I) according to the invention in which $R^2$ is hydrogen and $R^3$ is methyl and aryl is the radical

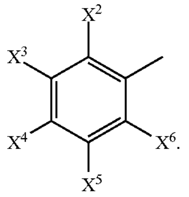

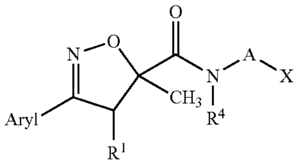

| No. | Aryl | $R^1$ | Y | $R^4$ | A | X | Physical data |
|---|---|---|---|---|---|---|---|
| | | | | | | | 0.56; 6.90 1.06; 6.89 0.58; 6.88 1.19; 6.88 2.07; 6.87 1.14; 6.86 0.65; 6.85 1.05; 6.85 0.55; 4.33 0.83; 4.31 1.07; 4.30 1.55; 4.29 1.73; 4.28 2.23; 4.28 2.31; 4.26 1.21; 4.26 1.18; 4.21 0.93; 4.20 1.04; 4.20 1.84; 4.19 1.88; 4.18 1.12; 4.17 1.04; 3.79 1.80; 3.78 1.97; 3.77 0.83; 3.75 2.37; 3.75 2.52; 3.73 3.45; 3.72 0.93; 3.18 3.88; 3.14 3.38; 2.76 2.07; 2.74 3.83; 2.73 2.80; 2.71 3.00; 2.70 1.66; 2.69 1.95; 2.67 3.55; 2.65 1.80; 2.57 3.21; 2.56 3.24; 2.51 2.11; 2.51 2.33; 2.50 2.16; 2.50 2.37; 2.16 13.82; 2.12 0.79; 2.11 12.48; 2.10 16.00; 2.09 1.18; 1.71 11.79; 1.70 11.23; 1.55 11.81; 1.29 5.63; 1.27 5.66; 1.25 5.23; 1.23 5.25; 0.01 0.78; 0.00 22.19 |
| 6.253 | 3,5-$F_2$—Ph | H | O | H | $CH(CH_3)CH_2$ | [2-(methylsulfonyl)-ethoxy]carbonyl | diastereomer D1: [$CDCl_3$] 1.25 (d, 3H); 1.70 (s, 3H); 2.50 (m, 2H); 3.00 (s, 3H); 3.16 (d, 1H); 3.32 (m, 2H); 3.75 (d, 1H); 4.30 (m, 1H); 4.53 (m, 2H); 6.88 (m, 1H); 7.05 (d, br 1H); 7.17 (m, 2H). diastereomer D2: [$CDCl_3$] 1.30 (d, 3H); 1.70 (s, 3H); 2.57 (m, 2H); 3.03 (s, 3H); 3.17 (d, 1H); 3.38 (m, 2H); 3.76 (d, 1H); 4.30 (m, 1H); 4.41 (m, 1H); 4.60 (m, 1H); 6.88 (m, 1H); 7.10 (d, br 1H); 7.17 (m, 2H). |
| 6.254 | 3,5-$Cl_2$—Ph | H | O | H | $CH(CH_3)CH_2$ | butoxycarbonyl | [$CDCl_3$] 7.52 5.77; 7.52 5.73; 7.52 11.42; 7.52 12.91; 7.52 11.08; 7.51 12.92; 7.51 6.16; 7.41 1.52; 7.41 4.38; 7.41 4.02; 7.40 5.50; 7.40 3.82; 7.26 25.95; 7.26 23.13; 7.26 19.06; 7.16 0.92; 7.14 0.99; 7.12 0.93; 7.09 0.87; 5.30 8.90; 5.30 7.74; 5.30 6.24; 4.33 0.62; 4.31 1.33; 4.29 1.66; 4.28 1.43; 4.26 0.69; 4.12 2.30; 4.10 4.79; 4.09 2.47; 4.03 2.55; 4.01 5.30; 4.00 2.73; 3.80 2.27; 3.77 2.68; 3.75 2.62; 3.73 3.03; 3.18 3.17; 3.17 4.36; 3.13 2.77; 3.13 3.81; 2.54 4.54; 2.53 4.57; 2.48 5.30; 2.47 5.32; 1.71 16.00; 1.70 14.20; 1.66 0.64; 1.65 1.86; 1.63 2.26; 1.61 1.97; 1.59 1.28; 1.57 2.33; 1.57 10.39; 1.57 9.69; 1.57 8.42; 1.56 2.95; 1.54 2.33; 1.52 0.95; 1.43 0.33; 1.42 1.22; 1.40 2.11; 1.38 2.12; 1.37 0.65; 1.37 0.63; 1.36 1.26; 1.35 1.51; 1.34 0.54; 1.33 2.50; 1.31 2.45; 1.29 1.41; 1.27 |

TABLE 6-continued

Compounds of the general formula (I) according to the invention in which $R^2$ is hydrogen and $R^3$ is methyl and aryl is the radical

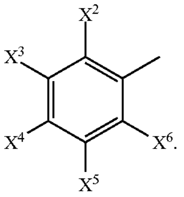

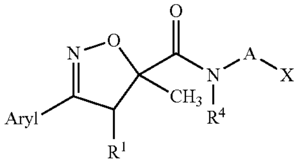

| No. | Aryl | $R^1$ | Y | $R^4$ | A | X | Physical data |
|---|---|---|---|---|---|---|---|
| | | | | | | | 8.22; 1.26 8.26; 1.22 6.94; 1.21 6.96; 0.96 4.00; 0.94 7.58; 0.92 3.60; 0.91 4.93; 0.90 8.87; 0.88 4.07; 0.00 12.74; 0.00 11.15; 0.00 9.01; −0.01 0.87; −0.01 0.52 |
| 6.255 | 3,5-$F_2$—Ph | H | O | H | $CH(CH_3)CH_2$ | butoxycarbonyl | [$CDCl_3$] 7.26 32.25; 7.26 34.66; 7.19 0.70; 7.17 5.41; 7.17 5.65; 7.15 5.96; 7.15 5.64; 7.14 1.66; 7.12 1.05; 7.10 0.93; 6.90 1.38; 6.89 1.15; 6.87 2.76; 6.87 2.25; 6.85 1.38; 4.34 0.71; 4.32 1.53; 4.30 1.84; 4.28 1.59; 4.27 0.76; 4.12 2.58; 4.11 5.27; 4.09 2.69; 4.03 2.61; 4.02 5.32; 4.00 2.69; 3.79 2.51; 3.79 2.40; 3.77 2.58; 3.77 2.52; 3.75 2.89; 3.75 2.80; 3.73 2.97; 3.72 2.88; 3.18 5.12; 3.14 4.43; 2.55 5.08; 2.53 5.05; 2.49 5.24; 2.47 5.22; 2.05 0.46; 2.01 0.36; 2.00 0.36; 1.71 16.00; 1.71 15.69; 1.70 15.73; 1.70 15.07; 1.67 0.65; 1.65 2.04; 1.63 2.70; 1.61 2.26; 1.59 1.38; 1.58 2.27; 1.56 14.92; 1.56 15.04; 1.54 2.43; 1.52 0.84; 1.44 0.43; 1.42 1.50; 1.40 2.60; 1.38 2.53; 1.36 1.44; 1.35 1.59; 1.33 2.66; 1.31 2.79; 1.29 1.91; 1.28 9.17; 1.26 9.25; 1.23 7.77; 1.21 7.68; 0.96 4.76; 0.94 9.06; 0.94 8.91; 0.92 4.20; 0.91 4.68; 0.90 9.08; 0.89 8.76; 0.88 2.32; 0.88 2.34; 0.88 4.18; 0.87 1.05; 0.00 5.44; 0.00 5.99 |
| 6.256 | 3-$CF_3$—Ph | H | O | H | $CH(CH_3)CH_2$ | COOH | |
| 6.257 | 3,5-$Cl_2$—Ph | H | O | H | $CH(CH_3)CH_2$ | COOH | diastereomer D1: [$CDCl_3$] 1.27 (d, 3H); 1.71 (s, 3H); 2.53 (m, 1H); 2.60 (m, 1H); 3.18 (d, 1H); 3.76 (d, 1H); 4.33 (m, 1H); 7.09 (d br, 1H); 7.39 (m, 1H); 7.51 (s, 1H). diastereomer D2: [$CDCl_3$] 1.32 (d, 3H); 1.70 (s, 3H); 2.53 (m, 1H); 2.60 (m, 1H); 3.19 (d, 1H); 3.78 (d, 1H); 4.33 (m, 1H); 7.12 (d br, 1H); 7.40 (m, 1H); 7.51 (s, 1H); 9 (s br, 1H). |
| 6.258 | 3,5-$F_2$—Ph | H | O | H | $CH(CH_3)CH_2$ | COOH | [$CDCl_3$] 7.52 0.44; 7.27 0.34; 7.27 0.39; 7.27 0.41; 7.27 0.56; 7.27 0.63; 7.27 0.75; 7.26 35.02; 7.26 76.68; 7.25 1.16; 7.25 0.97; 7.25 0.84; 7.25 0.64; 7.25 0.48; 7.25 0.36; 7.25 0.34; 7.19 0.49; 7.17 2.71; 7.17 2.97; 7.17 3.40; 7.16 2.68; 7.15 3.32; 7.15 3.09; 7.15 2.44; 7.14 0.48; 7.11 0.80; 7.08 0.87; 7.07 0.59; 7.05 0.44; 7.00 0.43; 6.90 0.63; 6.90 0.61; 6.89 |

TABLE 6-continued

Compounds of the general formula (I) according to the invention in which $R^2$ is hydrogen and $R^3$ is methyl and aryl is the radical

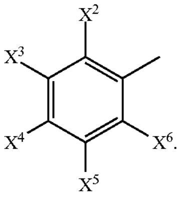

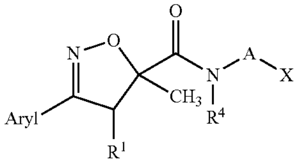

| No. | Aryl | $R^1$ | Y | $R^4$ | A | X | Physical data |
|---|---|---|---|---|---|---|---|
| | | | | | | | 0.67; 6.89 0.82; 6.89 0.67; 6.88 1.26; 6.88 1.23; 6.87 1.30; 6.87 1.64; 6.86 0.91; 6.86 0.68; 6.85 0.63; 6.85 0.66; 6.85 0.79; 6.84 0.36; 4.36 0.33; 4.34 0.84; 4.33 1.09; 4.32 0.92; 4.31 0.98; 4.29 0.63; 4.13 0.42; 4.11 0.43; 3.80 1.28; 3.78 2.59; 3.76 1.48; 3.73 2.97; 3.20 2.84; 3.19 1.44; 3.16 2.50; 3.14 1.27; 2.61 2.35; 2.59 2.24; 2.53 2.91; 2.53 2.69; 2.52 2.81; 2.51 2.60; 2.05 1.02; 2.04 2.05; 1.72 16.00; 1.70 8.05; 1.31 7.58; 1.30 7.50; 1.27 3.87; 1.26 3.43; 1.26 3.99; 1.24 0.44; 1.24 0.67; 0.01 0.62; 0.01 1.47; 0.00 20.09; 0.00 44.06; −0.01 1.61 |
| 6.259 | 3,5-(tert•Bu)$_2$—Ph | H | O | H | $CH(CH_3)CH_2$ | COOH | diastereomer D1: [DMSO-$D_6$] 1.12 (d, 3H); 1.31 (s, 18H); 1.52 (s, 3H); 2.38 (m, 2H); 3.39 (d, 1H); 3.73 (d, 1H); 4.14 (m, 1H); 7.44 (m, 2H); 7.49 (m, 1H); 7.94 (brd, 1H); 12.10 (brs, 1H). diastereomer D2: 1.07 (d, 3H); 1.30 (s, 18H); 1.52 (s, 3H); 2.38 (m, 2H); 3.33 (d, 1H); 3.68 (d, 1H); 4.14 (m, 1H); 7.44 (m, 2H); 7.49 (m, 1H); 7.94 (brd, 1H); 12.10 (brs, 1H). |
| 6.260 | 3-Br-5-$CF_3$—Ph | H | O | H | $CH(CH_3)CH_2$ | COOH | [$CDCl_3$] 7.97 4.23; 7.96 2.56; 7.81 5.27; 7.81 4.88; 7.80 2.08; 7.80 1.89; 7.80 1.81; 7.52 0.33; 7.26 57.09; 7.14 0.64; 7.12 0.67; 7.10 0.86; 7.07 0.84; 5.30 2.89; 4.35 0.70; 4.34 0.95; 4.34 0.93; 4.33 0.84; 4.32 0.94; 4.32 1.03; 4.30 0.83; 4.28 0.34; 3.87 2.85; 3.84 2.20; 3.82 3.22; 3.80 2.48; 3.24 2.31; 3.23 2.98; 3.20 2.06; 3.18 2.68; 2.61 4.76; 2.59 4.73; 2.53 1.75; 2.52 1.93; 2.52 1.87; 2.51 1.87; 2.09 3.15; 2.05 0.36; 2.03 0.55; 1.73 12.39; 1.71 16.00; 1.60 0.35; 1.32 5.81; 1.30 5.92; 1.27 7.68; 1.26 8.72; 1.24 0.51; 1.23 0.49; 0.01 0.50 |
| 6.261 | 3-Cl-5-$CF_3$—Ph | H | O | H | $CH(CH_3)CH_2$ | COOH | diasteromer D1: [$CDCl_3$] 1.31 (d, 3H); 1.73 (s, 3H); 2.53 (m, 2H); 3.23 (d, 1H); 3.83 (d, 1H); 4.32 (m, 1H); 7.13 (d, 1H); 7.65 (s, 1H); 7.77 (s, 1H); 7.82 (s, 1H). diasteromer D2: [$CDCl_3$] 1.26 (d, 3H); 1.72 (s, 3H); 2.61 (d, 2H); 3.22 (d, 1H); 3.85 (d, 1H); 4.32 (m, 1H); 7.09 (d, 1H); 7.66 (s, 1H); 7.77 (s, 1H); 7.82 (s, 1H). |

TABLE 6-continued
Compounds of the general formula (I) according to the invention in which $R^2$ is hydrogen and $R^3$ is methyl and aryl is the radical
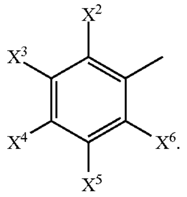
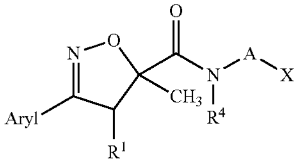
| No. | Aryl | $R^1$ | Y | $R^4$ | A | X | Physical data |
|---|---|---|---|---|---|---|---|
| 6.262 | 3-Cl—Ph | H | O | H | $CH(CH_3)CH_2$ | COOH | [$CDCl_3$] 7.65 1.36; 7.65 1.43; 7.65 2.77; 7.64 2.73; 7.64 2.42; 7.64 1.45; 7.52 0.35; 7.51 1.01; 7.50 2.04; 7.50 2.13; 7.50 0.91; 7.49 1.33; 7.49 2.63; 7.48 2.63; 7.48 1.09; 7.42 0.69; 7.41 0.96; 7.41 0.76; 7.41 0.85; 7.40 0.68; 7.40 0.84; 7.40 0.70; 7.40 1.86; 7.39 1.72; 7.39 1.73; 7.39 1.49; 7.38 1.52; 7.38 1.54; 7.38 1.49; 7.38 1.12; 7.36 2.17; 7.36 2.00; 7.35 1.91; 7.35 1.76; 7.34 2.55; 7.33 1.92; 7.33 2.19; 7.32 0.99; 7.32 0.89; 7.31 0.92; 7.31 0.88; 7.31 0.57; 7.27 0.39; 7.26 57.07; 7.25 0.77; 7.25 0.65; 7.25 0.54; 7.25 0.51; 7.25 0.45; 7.25 0.40; 7.25 0.37; 7.25 0.32; 7.21 0.43; 7.16 0.62; 7.14 0.65; 7.11 0.74; 7.09 0.72; 7.00 0.33; 4.35 0.35; 4.34 0.61; 4.33 0.77; 4.33 0.74; 4.32 0.76; 4.32 0.84; 4.31 0.85; 4.31 0.85; 4.30 0.76; 4.29 0.67; 4.29 0.35; 4.28 0.32; 3.83 2.81; 3.80 2.40; 3.79 3.21; 3.76 2.75; 3.23 2.56; 3.22 2.97; 3.18 2.25; 3.17 2.65; 2.60 3.21; 2.60 2.91; 2.59 2.99; 2.59 2.80; 2.53 3.86; 2.52 3.68; 2.04 0.53; 1.73 0.44; 1.71 13.99; 1.70 16.00; 1.31 6.31; 1.29 6.28; 1.28 0.38; 1.27 7.42; 1.26 0.88; 1.25 7.36; 1.24 0.45; 0.01 0.60; 0.00 22.67 |
| 6.263 | 3-Et-5-F—Ph | H | O | H | $CH(CH_3)CH_2$ | COOH | [DMSO-$D_6$] 12.14 1.03; 7.95 1.16; 7.93 1.19; 7.37 1.98; 7.36 1.78; 7.31 0.51; 7.30 0.71; 7.30 0.70; 7.29 0.68; 7.28 0.82; 7.28 0.74; 7.27 0.71; 7.27 0.63; 7.26 0.52; 7.20 1.21; 7.17 1.25; 4.16 0.52; 4.15 0.60; 4.14 0.63; 4.14 0.84; 4.13 0.56; 4.13 0.43; 4.12 0.69; 4.12 0.48; 3.74 1.52; 3.70 3.00; 3.66 1.67; 3.38 1.73; 3.36 2.17; 3.33 1.61; 3.31 55.93; 3.26 0.51; 2.68 1.21; 2.67 0.34; 2.67 3.94; 2.65 3.88; 2.63 1.32; 2.52 0.90; 2.52 0.83; 2.51 14.74; 2.51 32.90; 2.50 45.41; 2.50 32.87; 2.49 15.59; 2.48 1.88; 2.47 0.82; 2.47 1.31; 2.46 0.80; 2.43 0.91; 2.42 1.00; 2.41 1.17; 2.39 1.17; 2.38 1.05; 2.37 0.73; 2.36 1.10; 2.35 0.73; 2.34 0.59; 2.32 0.58; 2.18 0.38; 1.53 16.00; 1.36 2.96; 1.24 |

TABLE 6-continued
Compounds of the general formula (I) according to the invention in which $R^2$ is hydrogen and $R^3$ is methyl and aryl is the radical
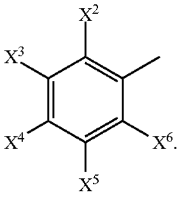
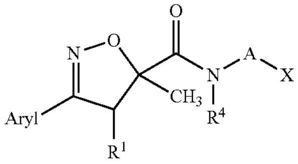
| No. | Aryl | $R^1$ | Y | $R^4$ | A | X | Physical data |
|---|---|---|---|---|---|---|---|
| | | | | | | | 0.58; 1.21 5.63; 1.19 12.01; 1.17 5.68; 1.12 4.10; 1.10 4.10; 1.07 4.78; 1.06 4.78 |
| 6.264 | 3-Et—Ph | H | O | H | $CH(CH_3)CH_2$ | COOH | [DMSO-$D_6$] 12.17 0.82; 7.97 1.43; 7.95 1.48; 7.52 1.64; 7.51 1.51; 7.51 1.50; 7.50 0.59; 7.49 0.88; 7.49 0.67; 7.48 0.83; 7.48 0.99; 7.47 1.17; 7.47 0.91; 7.46 1.04; 7.46 0.59; 7.38 1.18; 7.36 2.84; 7.34 1.91; 7.32 2.07; 7.31 0.93; 5.76 2.22; 4.16 0.50; 4.16 0.60; 4.15 0.58; 4.14 0.84; 4.14 0.52; 4.13 0.38; 4.12 0.66; 4.12 0.46; 3.73 1.50; 3.70 1.49; 3.69 1.96; 3.65 1.66; 3.37 1.67; 3.36 1.97; 3.33 32.92; 3.32 2.12; 2.67 1.16; 2.65 3.57; 2.63 3.68; 2.61 1.25; 2.52 0.72; 2.51 7.01; 2.51 16.03; 2.50 22.19; 2.50 15.88; 2.49 7.33; 2.48 1.35; 2.47 0.72; 2.47 1.16; 2.46 0.50; 2.43 0.98; 2.42 0.99; 2.41 1.12; 2.39 1.11; 2.38 1.03; 2.37 0.71; 2.36 1.06; 2.35 0.64; 2.34 0.54; 2.32 0.52; 1.91 0.38; 1.53 16.00; 1.36 0.52; 1.21 5.53; 1.19 11.96; 1.18 0.83; 1.17 5.60; 1.12 3.85; 1.10 3.84; 1.07 4.38; 1.05 4.37; 0.00 1.43 |
| 6.265 | 3-F-5-MeO—Ph | H | O | H | $CH(CH_3)CH_2$ | COOH | [$CDCl_3$] 7.26 26.67; 7.16 0.50; 7.14 0.51; 7.12 0.65; 7.10 0.62; 6.97 1.06; 6.96 2.04; 6.96 2.37; 6.95 1.21; 6.95 0.96; 6.94 1.53; 6.94 1.15; 6.93 0.56; 6.93 0.77; 6.92 1.36; 6.92 1.20; 6.91 0.55; 6.70 0.67; 6.69 1.23; 6.69 1.11; 6.68 1.00; 6.67 0.56; 6.67 0.76; 6.67 1.25; 6.66 1.11; 6.65 0.98; 6.65 0.47; 5.30 2.12; 4.34 0.42; 4.33 0.64; 4.32 0.53; 4.32 0.76; 4.31 0.63; 4.30 0.63; 4.30 0.54; 3.82 16.00; 3.81 12.97; 3.81 2.54; 3.78 1.61; 3.76 2.44; 3.73 1.85; 3.21 1.76; 3.20 2.29; 3.17 1.55; 3.16 2.02; 2.60 2.24; 2.60 2.37; 2.59 2.13; 2.59 2.25; 2.54 2.79; 2.52 2.71; 2.09 4.18; 2.04 0.41; 1.71 9.33; 1.69 12.09; 1.31 4.48; 1.29 4.53; 1.28 0.39; 1.27 5.91; 1.25 5.99; 1.24 0.48 |
| 6.266 | 3-F—Ph | H | O | H | $CH(CH_3)CH_2$ | COOH | [$CDCl_3$] 7.39 2.18; 7.39 2.01; 7.38 2.20; 7.38 4.15; 7.37 3.61; 7.37 7.21; 7.36 3.64; 7.26 22.09; 7.18 0.63; 7.16 0.97; 7.15 0.93; 7.15 0.90; 7.14 1.34; 7.13 1.60; 7.13 1.51; 7.12 1.53; 7.12 1.62; 7.11 1.10; 7.10 0.46; 4.34 0.57; 4.34 |

TABLE 6-continued
Compounds of the general formula (I) according to the invention in which $R^2$ is hydrogen and $R^3$ is methyl and aryl is the radical
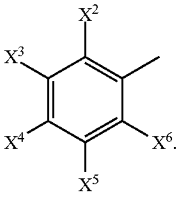
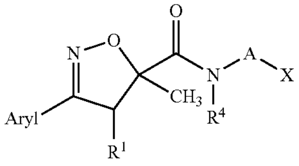
| No. | Aryl | $R^1$ | Y | $R^4$ | A | X | Physical data |
|---|---|---|---|---|---|---|---|
| | | | | | | | 0.79; 4.33 0.73; 4.32 1.01; 4.31 0.75; 4.30 0.84; 4.30 0.62; 4.29 0.36; 3.84 2.02; 3.80 2.05; 3.79 2.36; 3.76 2.36; 3.24 2.32; 3.23 2.33; 3.19 2.04; 3.18 2.05; 2.60 2.93; 2.59 2.74; 2.53 4.03; 2.52 4.02; 2.09 16.00; 1.72 12.49; 1.70 12.36; 1.31 5.98; 1.29 6.01; 1.27 5.94; 1.25 5.97; 0.00 10.19; −0.01 0.50 |
| 6.267 | 3-Me—Ph | H | O | H | $CH(CH_3)CH_2$ | COOH | [DMSO-$D_6$] 8.05 0.67; 8.03 0.85; 8.02 0.56; 7.49 1.47; 7.49 1.99; 7.47 0.84; 7.46 1.05; 7.45 1.02; 7.45 1.31; 7.35 1.06; 7.33 2.46; 7.31 1.57; 7.29 2.13; 7.27 1.09; 5.75 4.30; 4.14 0.45; 4.13 0.64; 4.12 0.58; 4.12 0.82; 4.11 0.67; 4.10 0.62; 4.09 0.56; 3.72 1.28; 3.69 1.71; 3.67 1.60; 3.65 2.12; 3.40 0.37; 3.39 0.39; 3.35 2.43; 3.34 1.87; 3.31 2.03; 3.30 1.57; 3.17 0.39; 2.52 0.40; 2.51 7.76; 2.51 16.97; 2.50 23.98; 2.50 17.70; 2.49 8.68; 2.47 0.42; 2.45 0.36; 2.43 0.52; 2.41 0.66; 2.40 0.38; 2.38 0.90; 2.37 0.87; 2.36 0.94; 2.35 0.78; 2.34 15.97; 2.32 1.20; 2.30 0.44; 1.52 16.00; 1.12 4.77; 1.10 4.76; 1.07 3.56; 1.05 3.54; 0.00 2.99 |
| 6.268 | 3-Me—Ph | H | O | H | $CH(CH_3)CH_2$ | COOH | [DMSO-$D_6$] 7.95 1.42; 7.93 1.43; 7.49 2.67; 7.47 1.35; 7.45 1.74; 7.35 1.25; 7.33 2.90; 7.32 1.82; 7.29 2.09; 7.27 1.06; 5.75 0.58; 4.17 0.35; 4.15 0.78; 4.14 0.88; 4.13 0.84; 4.12 0.78; 4.10 0.36; 3.69 2.41; 3.64 3.03; 3.36 3.28; 3.34 0.81; 3.31 9.10; 2.51 7.60; 2.51 16.35; 2.50 22.79; 2.50 16.48; 2.49 7.86; 2.47 0.91; 2.45 0.88; 2.43 1.75; 2.41 1.74; 2.38 1.83; 2.36 1.87; 2.34 15.07; 2.32 0.97; 1.52 16.00; 1.24 0.34; 1.12 7.29; 1.10 7.24; 1.07 0.53; 1.05 0.49; 0.00 2.23 |
| 6.269 | 4-MeO—Ph | H | O | H | $CH(CH_3)CH_2$ | COOH | [DMSO-$D_6$] 12.16 1.08; 7.95 1.11; 7.93 1.13; 7.62 1.93; 7.62 0.74; 7.61 1.76; 7.61 1.02; 7.60 2.19; 7.59 0.71; 7.59 1.87; 7.02 0.36; 7.01 3.57; 7.01 1.14; 6.99 1.03; 6.99 3.38; 6.98 0.36; 4.16 0.34; 4.15 0.42; 4.14 0.40; 4.13 0.58; 4.12 0.46; 3.80 16.00; 3.70 0.99; 3.66 0.96; 3.65 1.30; 3.62 1.06; 3.34 1.31; 3.33 15.85; 3.29 0.91; 3.28 0.98; 2.51 5.51; 2.51 |

TABLE 6-continued

Compounds of the general formula (I) according to the invention in which $R^2$ is hydrogen and $R^3$ is methyl and aryl is the radical

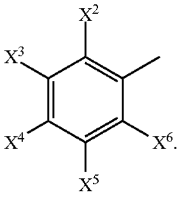

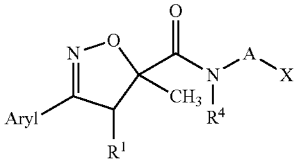

| No. | Aryl | $R^1$ | Y | $R^4$ | A | X | Physical data |
|---|---|---|---|---|---|---|---|
| | | | | | | | 12.22; 2.50 17.30; 2.50 12.51; 2.49 5.86; 2.48 0.82; 2.47 0.42; 2.46 0.72; 2.45 0.32; 2.43 0.63; 2.41 0.65; 2.40 0.76; 2.39 0.74; 2.38 0.66; 2.37 0.46; 2.36 0.67; 2.35 0.41; 2.34 0.34; 1.51 10.62; 1.36 0.48; 1.11 2.48; 1.09 2.48; 1.07 2.95; 1.05 2.94 |
| 6.270 | 3-$CF_3$—Ph | H | O | H | $CH(CH_3)CH_2$ | ethoxycarbonyl | [$CDCl_3$] 7.91 3.41; 7.821.14; 7.81 1.01; 7.81 1.34; 7.79 1.07; 7.69 1.53; 7.67 2.03; 7.56 1.40; 7.56 1.40; 7.54 2.22; 7.54 2.21; 7.52 0.93; 7.52 0.97; 7.26 23.51; 7.19 0.48; 7.16 0.56; 7.15 0.66; 7.13 0.60; 5.30 1.48; 4.34 0.48; 4.33 1.01; 4.31 1.12; 4.31 1.12; 4.29 1.01; 4.28 0.50; 4.19 1.47; 4.17 4.62; 4.15 4.64; 4.14 1.53; 4.08 1.14; 4.06 3.59; 4.04 3.69; 4.02 1.24; 3.88 2.73; 3.85 2.28; 3.84 3.08; 3.81 2.58; 3.25 3.01; 3.25 3.23; 3.21 2.59; 3.21 2.80; 2.54 5.14; 2.53 5.03; 2.48 4.21; 2.47 4.17; 1.73 13.34; 1.72 16.00; 1.59 10.11; 1.30 5.19; 1.28 15.86; 1.26 11.34; 1.23 7.79; 1.21 7.70; 1.20 4.22; 1.18 8.44; 1.16 4.08; 0.00 9.01 |
| 6.271 | 3,5-$Cl_2$-4-MeO—Ph | H | O | H | $CH(CH_3)CH_2$ | ethoxycarbonyl | [$CDCl_3$] 7.58 5.70; 7.58 6.28; 7.26 16.92; 7.17 0.34; 7.15 0.37; 7.13 0.36; 7.11 0.35; 4.32 0.53; 4.30 0.63; 4.30 0.65; 4.28 0.60; 4.19 0.62; 4.17 1.94; 4.15 1.98; 4.13 0.68; 4.11 0.71; 4.09 1.96; 4.07 2.01; 4.05 0.67; 3.93 16.00; 3.78 1.10; 3.76 1.16; 3.74 1.32; 3.72 1.33; 3.16 1.38; 3.16 1.51; 3.12 1.20; 3.12 1.32; 2.54 2.09; 2.52 2.08; 2.47 2.18; 2.46 2.17; 1.70 6.69; 1.69 6.52; 1.58 3.57; 1.30 2.10; 1.28 4.32; 1.27 3.75; 1.26 2.43; 1.26 3.82; 1.23 2.27; 1.22 3.37; 1.21 4.64; 1.21 3.54; 1.19 2.23 |
| 6.272 | 3,5-$Cl_2$—Ph | H | O | H | $CH(CH_3)CH_2$ | ethoxycarbonyl | [$CDCl_3$] 7.52 6.95; 7.51 7.68; 7.41 1.87; 7.40 3.31; 7.40 1.66; 7.26 16.11; 7.16 0.54; 7.14 0.55; 4.32 0.59; 4.31 0.34; 4.30 0.66; 4.30 0.66; 4.29 0.35; 4.28 0.63; 4.10 1.47; 4.08 4.70; 4.07 4.82; 4.05 1.60; 3.77 2.80; 3.73 3.22; 3.18 3.00; 3.14 2.63; 2.48 5.09; 2.46 5.04; 1.71 16.00; 1.59 0.50; 1.27 7.93; 1.26 8.02; 1.23 5.37; 1.21 10.90; 1.19 5.23; 0.00 2.49 |
| 6.273 | 3,5-$Cl_2$—Ph | H | O | H | $CH(CH_3)CH_2$ | ethoxycarbonyl | [$CDCl_3$] 7.53 3.74; 7.52 11.10; 7.52 15.52; 7.51 7.31; 7.42 1.04; 7.41 3.43; 7.41 5.31; 7.40 3.86; 7.40 |

TABLE 6-continued

Compounds of the general formula (I) according to the invention in which $R^2$ is hydrogen and $R^3$ is methyl and aryl is the radical

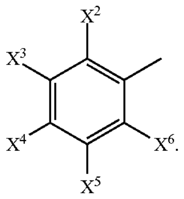

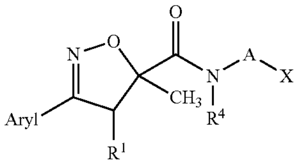

| No. | Aryl | $R^1$ | Y | $R^4$ | A | X | Physical data |
|---|---|---|---|---|---|---|---|
| | | | | | | | 1.62; 7.27 9.41; 7.26 19.96; 7.16 0.57; 7.14 0.63; 7.12 0.74; 7.10 0.70; 4.34 0.47; 4.33 0.53; 4.32 1.26; 4.32 0.91; 4.31 0.63; 4.30 1.02; 4.30 1.53; 4.30 1.29; 4.29 0.88; 4.28 1.07; 4.28 1.12; 4.27 0.43; 4.27 0.61; 4.19 0.79; 4.19 1.50; 4.17 2.46; 4.17 4.76; 4.16 2.53; 4.15 4.84; 4.14 0.89; 4.14 1.59; 4.11 0.68; 4.10 1.28; 4.09 2.10; 4.08 4.02; 4.07 2.17; 4.07 4.14; 4.05 0.75; 4.05 1.37; 3.80 1.46; 3.80 2.77; 3.78 1.28; 3.77 2.42; 3.76 1.69; 3.75 3.17; 3.73 1.48; 3.73 2.77; 3.18 1.50; 3.18 4.00; 3.18 3.08; 3.14 1.32; 3.14 3.49; 3.13 2.72; 2.54 2.69; 2.54 4.75; 2.53 2.77; 2.52 4.69; 2.48 2.38; 2.48 4.25; 2.47 2.44; 2.46 4.18; 2.00 0.39; 1.71 7.62; 1.71 13.95; 1.70 9.15; 1.70 16.00; 1.59 3.39; 1.59 5.22; 1.30 2.66; 1.30 5.44; 1.28 5.65; 1.28 11.92; 1.28 4.83; 1.27 7.04; 1.27 3.20; 1.26 7.09; 1.26 6.90; 1.23 6.01; 1.23 10.03; 1.21 9.77; 1.21 11.93; 1.19 2.45; 1.19 4.71; 0.00 1.65; 0.00 3.76 |
| 6.274 | 3,5-$Cl_2$—Ph | H | O | H | $CH(CH_3)CH_2$ | ethoxycarbonyl | diastereomer D1: [$CDCl_3$] 1.20 (t, 3H); 1.27 (d, 3H); 1.71 (s, 3H); 2.52 (d, 2H); 3.16 (d, 1H); 3.75 (d, 1H); 4.08 (q, 2H); 4.31 (m, 1H); 7.15 (d br, 1H); 7.40 (s, 1H); 7.52 (s, 1H). diastereomer D2: [$CDCl_3$] 1.23 (d, 3H); 1.30 (t, 3H); 1.72 (s, 3H); 2.53 (d, 2H); 3.16 (d, 1H); 3.79 (d, 1H); 4.17 (q, 2H); 4.31 (m, 1H); 7.17 (d br, 1H); 7.40 (s, 1H); 7.52 (s, 1H). |
| 6.275 | 3,5-$Cl_2$—Ph | H | O | H | $CH(CH_3)CH_2$ | ethoxycarbonyl | [$CDCl_3$] 7.52 6.04; 7.52 11.75; 7.52 12.59; 7.51 8.55; 7.51 7.81; 7.41 1.70; 7.41 4.19; 7.41 4.19; 7.41 4.66; 7.40 4.68; 7.26 23.09; 7.26 26.02; 7.16 0.78; 7.14 0.84; 7.12 0.89; 7.09 0.84; 4.33 0.69; 4.32 1.35; 4.30 1.52; 4.30 1.59; 4.28 1.49; 4.27 0.73; 4.19 1.38; 4.17 4.26; 4.15 4.37; 4.14 1.51; 4.10 1.38; 4.08 4.23; 4.07 4.33; 4.05 1.48; 3.80 2.58; 3.77 2.61; 3.75 2.98; 3.73 3.00; 3.18 3.11; 3.18 3.77; 3.14 2.71; 3.13 3.26; 2.54 5.10; 2.52 5.14; 2.48 5.17; 2.46 5.18; 1.71 15.70; 1.70 16.00; 1.57 2.34; 1.30 5.03; 1.28 10.31; 1.27 9.86; 1.26 8.19; 1.26 10.14; 1.23 |

TABLE 6-continued
Compounds of the general formula (I) according to the invention in which $R^2$ is hydrogen and $R^3$ is methyl and aryl is the radical
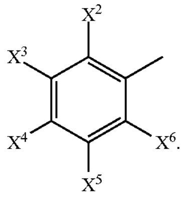
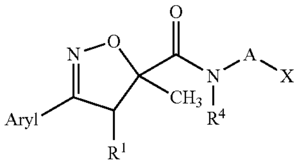
| No. | Aryl | $R^1$ | Y | $R^4$ | A | X | Physical data |
|---|---|---|---|---|---|---|---|
| | | | | | | | 12.05; 1.21 15.49; 1.19 4.68; 0.90 1.36; 0.88 3.60; 0.86 1.67; 0.01 0.45; 0.00 14.41; 0.00 16.45 |
| 6.276 | 3,5-$Cl_2$—Ph | H | O | H | $CH(CH_3)CH_2$ | ethoxycarbonyl | [$CDCl_3$] 7.52 7.95; 7.52 6.62; 7.41 2.69; 7.41 3.23; 7.40 1.51; 7.26 23.63; 7.12 0.92; 7.10 0.92; 4.33 0.39; 4.32 0.83; 4.30 0.98; 4.28 0.76; 4.27 0.39; 4.19 1.42; 4.17 4.36; 4.15 4.41; 4.14 1.49; 3.80 2.65; 3.75 3.02; 3.17 2.96; 3.13 2.59; 2.54 5.34; 2.52 5.25; 1.70 16.00; 1.60 0.34; 1.56 1.00; 1.30 4.95; 1.28 9.70; 1.26 6.44; 1.26 3.73; 1.23 8.42; 1.21 8.28; 0.88 0.57; 0.86 0.39; 0.85 0.43; 0.00 11.06 |
| 6.277 | 3,5-$Cl_2$—Ph | H | O | H | $CH(CH_3)CH_2$ | ethoxycarbonyl | [$CDCl_3$] 7.52 5.01; 7.52 7.56; 7.52 5.78; 7.52 7.77; 7.41 1.37; 7.41 2.05; 7.41 2.50; 7.41 3.41; 7.41 1.31; 7.40 1.64; 7.26 21.92; 7.26 35.10; 7.26 0.58; 7.25 0.45; 7.25 0.38; 7.12 0.67; 7.10 0.69; 4.33 0.33; 4.32 0.70; 4.30 0.75; 4.30 0.72; 4.29 0.43; 4.28 0.63; 4.28 0.61; 4.27 0.34; 4.19 1.48; 4.17 4.69; 4.15 4.77; 4.14 1.56; 3.80 2.73; 3.75 3.13; 3.18 2.90; 3.13 2.58; 2.54 5.00; 2.52 4.92; 2.00 0.42; 1.70 16.00; 1.56 1.79; 1.30 3.89; 1.30 5.44; 1.28 7.78; 1.28 11.19; 1.26 3.90; 1.26 5.26; 1.23 7.92; 1.21 7.82; 0.00 2.43; 0.00 4.13 |
| 6.278 | 3,5-$Cl_2$—Ph | H | O | H | $CH(CH_3)CH_2$ | ethoxycarbonyl | [$CDCl_3$] 7.52 6.23; 7.51 7.85; 7.41 1.66; 7.40 3.27; 7.40 2.03; 7.26 20.86; 7.16 0.71; 7.14 0.72; 4.32 0.63; 4.30 0.74; 4.30 0.81; 4.28 0.73; 4.27 0.35; 4.10 1.43; 4.08 4.45; 4.07 4.58; 4.05 1.54; 3.77 2.73; 3.73 3.13; 3.18 2.99; 3.14 2.61; 2.48 5.23; 2.46 5.23; 1.71 16.00; 1.27 8.20; 1.26 9.10; 1.23 4.91; 1.21 9.75; 1.19 4.80; 0.00 9.73 |
| 6.279 | 3,5-$Et_2$—Ph | H | O | H | $CH(CH_3)CH_2$ | ethoxycarbonyl | [$CDCl_3$] 7.30 5.51; 7.29 5.38; 7.29 4.64; 7.26 28.59; 7.26 25.83; 7.19 0.62; 7.17 0.65; 7.16 0.43; 7.14 0.72; 7.12 0.71; 7.10 2.90; 4.34 0.54; 4.32 1.11; 4.32 0.72; 4.30 1.22; 4.30 1.17; 4.29 0.78; 4.28 1.08; 4.27 0.54; 4.18 1.10; 4.17 3.37; 4.15 3.41; 4.13 1.15; 4.08 1.00; 4.06 3.05; 4.04 3.09; 4.03 1.05; 3.85 1.96; 3.82 1.94; 3.81 2.26; 3.78 2.19; 3.24 2.56; 3.24 2.57; 3.20 2.23; 3.19 2.25; 2.67 2.12; 2.66 2.11; 2.65 6.40; 2.64 6.16; 2.63 6.62; 2.61 2.38; 2.53 |

TABLE 6-continued
Compounds of the general formula (I) according to the invention in which $R^2$ is hydrogen and $R^3$ is methyl and aryl is the radical
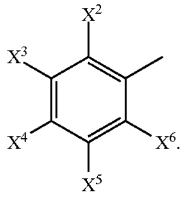
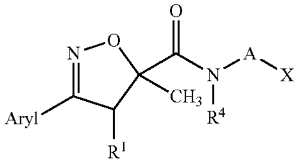
| No. | Aryl | $R^1$ | Y | $R^4$ | A | X | Physical data |
|---|---|---|---|---|---|---|---|
| | | | | | | | 2.99; 2.52 2.60; 2.49 1.74; 2.47 1.80; 2.47 1.76; 2.45 1.64; 2.43 0.40; 2.41 0.39; 1.70 11.89; 1.69 11.99; 1.57 9.49; 1.30 3.70; 1.29 3.51; 1.28 7.93; 1.28 7.85; 1.27 6.64; 1.25 14.22; 1.24 15.64; 1.24 15.89; 1.23 16.00; 1.23 14.18; 1.22 13.58; 1.22 9.06; 1.20 6.47; 1.20 4.12; 1.18 6.96; 1.18 6.60; 1.16 3.38; 1.16 3.13; 0.01 0.75 |
| 6.280 | 3,5-$F_2$—Ph | H | O | H | $CH(CH_3)CH_2$ | ethoxycarbonyl | [$CDCl_3$] 7.26 14.00; 7.26 23.21; 7.18 0.41; 7.17 2.52; 7.17 2.67; 7.17 2.95; 7.15 2.72; 7.15 3.08; 7.15 2.18; 7.14 1.04; 6.90 0.48; 6.89 0.75; 6.89 0.38; 6.88 0.97; 6.87 1.09; 6.87 1.49; 6.87 0.72; 6.86 0.51; 6.85 0.75; 6.84 0.36; 4.34 0.34; 4.32 0.78; 4.31 0.90; 4.30 0.80; 4.29 0.72; 4.27 0.38; 4.10 1.40; 4.08 4.32; 4.06 4.40; 4.05 1.47; 3.77 2.66; 3.73 3.07; 3.18 2.95; 3.14 2.57; 2.48 5.18; 2.46 5.07; 1.71 16.00; 1.70 0.76; 1.57 1.68; 1.28 7.93; 1.26 8.03; 1.22 3.11; 1.22 4.84; 1.21 6.23; 1.20 9.77; 1.19 3.08; 1.19 4.69; 0.00 1.63; 0.00 2.76 |
| 6.281 | 3,5-$F_2$—Ph | H | O | H | $CH(CH_3)CH_2$ | ethoxycarbonyl | [$CDCl_3$] 7.27 8.73; 7.26 8.54; 7.19 0.42; 7.18 0.49; 7.18 2.04; 7.17 3.56; 7.17 3.29; 7.16 2.20; 7.16 3.55; 7.15 3.59; 7.15 1.96; 7.14 1.03; 7.13 0.85; 7.13 0.77; 7.10 0.67; 6.90 0.47; 6.90 0.86; 6.89 0.75; 6.88 0.97; 6.88 1.72; 6.87 1.49; 6.86 0.53; 6.85 0.88; 6.85 0.75; 4.34 0.51; 4.32 1.09; 4.31 1.22; 4.30 1.21; 4.29 1.10; 4.27 0.56; 4.19 1.41; 4.17 4.35; 4.15 4.44; 4.14 1.50; 4.10 1.07; 4.08 3.29; 4.06 3.36; 4.05 1.13; 3.79 2.64; 3.77 2.03; 3.75 3.04; 3.73 2.34; 3.18 3.32; 3.14 2.53; 3.14 2.90; 2.54 5.26; 2.53 5.19; 2.48 4.04; 2.47 3.99; 1.71 12.27; 1.70 16.00; 1.63 2.66; 1.30 4.56; 1.30 4.64; 1.28 10.07; 1.28 10.50; 1.28 6.84; 1.26 7.02; 1.26 6.82; 1.23 8.01; 1.22 3.87; 1.22 3.91; 1.21 8.04; 1.20 7.30; 1.20 7.29; 1.19 3.52; 1.19 3.46; 0.00 2.05; 0.00 2.07 |
| 6.282 | 3,5-$F_2$—Ph | H | O | H | $CH(CH_3)CH_2$ | ethoxycarbonyl | [$CDCl_3$] 7.26 16.54; 7.19 0.44; 7.18 0.55; 7.17 1.80; 7.17 3.73; 7.17 3.81; 7.16 2.43; 7.15 3.78; 7.15 4.18; 7.15 2.62; 7.14 1.25; 7.13 1.11; 7.12 0.75; 7.10 0.65; 6.90 0.87; 6.89 0.94; 6.89 0.53; 6.87 |

TABLE 6-continued
Compounds of the general formula (I) according to the invention in which $R^2$ is hydrogen and $R^3$ is methyl and aryl is the radical
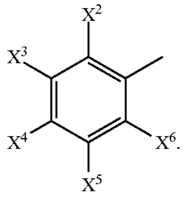
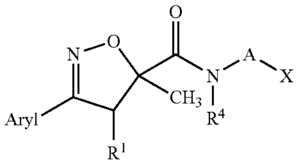
| No. | Aryl | $R^1$ | Y | $R^4$ | A | X | Physical data |
|---|---|---|---|---|---|---|---|
| | | | | | | | 1.74; 6.87 1.88; 6.87 1.00; 6.85 0.90; 6.85 0.96; 4.34 0.58; 4.32 1.18; 4.31 1.32; 4.30 1.36; 4.29 1.26; 4.27 0.62; 4.19 1.35; 4.17 4.20; 4.15 4.27; 4.13 1.44; 4.10 1.39; 4.08 4.32; 4.06 4.41; 4.05 1.48; 3.79 2.55; 3.77 2.67; 3.75 2.94; 3.73 3.06; 3.18 3.24; 3.18 3.59; 3.14 2.82; 3.14 3.11; 2.54 4.94; 2.53 4.92; 2.48 5.19; 2.46 5.17; 1.71 16.00; 1.70 15.64; 1.58 4.02; 1.30 4.52; 1.28 9.69; 1.28 8.83; 1.26 8.80; 1.23 7.62; 1.22 5.18; 1.21 7.70; 1.20 9.78; 1.19 4.68; 0.00 5.93 |
| 6.283 | 3,5-$F_2$—Ph | H | O | H | $CH(CH_3)CH_2$ | ethoxycarbonyl | [$CDCl_3$] 7.52 0.44; 7.31 0.39; 7.26 75.34; 7.19 0.37; 7.17 1.86; 7.17 2.43; 7.15 2.48; 7.15 1.99; 7.14 0.51; 7.12 0.71; 7.10 0.72; 7.00 0.43; 6.90 0.44; 6.90 0.75; 6.89 0.40; 6.88 0.85; 6.87 1.49; 6.87 0.78; 6.86 0.46; 6.85 0.74; 6.85 0.38; 4.34 0.34; 4.32 0.74; 4.31 0.81; 4.30 0.80; 4.28 0.71; 4.27 0.36; 4.19 1.43; 4.17 4.39; 4.15 4.43; 4.13 1.51; 3.79 2.64; 3.75 3.01; 3.49 0.71; 3.18 2.94; 3.14 2.59; 2.54 5.22; 2.52 5.13; 2.48 0.33; 2.00 1.18; 1.71 1.20; 1.70 16.00; 1.54 10.97; 1.30 4.74; 1.28 9.47; 1.26 5.04; 1.23 8.03; 1.21 7.94; 1.20 0.88; 1.19 0.33; 0.00 9.39 |
| 6.284 | 3,5-$F_2$—Ph | H | O | H | $CH(CH_3)CH_2$ | ethoxycarbonyl | [$CDCl_3$] 7.26 12.60; 7.18 1.57; 7.17 2.25; 7.17 1.64; 7.16 1.32; 7.16 2.19; 7.15 2.10; 7.14 0.50; 7.13 0.40; 7.12 0.60; 7.10 0.61; 6.90 0.38; 6.90 0.74; 6.89 0.45; 6.88 0.80; 6.87 1.49; 6.87 0.88; 6.86 0.45; 6.85 0.76; 6.85 0.44; 4.32 0.60; 4.32 0.45; 4.31 0.71; 4.30 0.77; 4.29 0.39; 4.29 0.69; 4.19 1.44; 4.17 4.50; 4.15 4.56; 4.14 1.52; 3.79 2.71; 3.75 3.09; 3.18 2.92; 3.14 2.57; 2.54 4.93; 2.53 4.93; 1.71 0.72; 1.70 16.00; 1.30 5.00; 1.28 10.18; 1.26 5.05; 1.23 7.76; 1.21 7.74; 0.00 2.32 |
| 6.285 | 3,5-$F_2$—Ph | H | O | H | $CH(CH_3)CH_2$ | ethoxycarbonyl | |
| 6.286 | 3,5-$F_2$—Ph | H | O | H | $CH(CH_3)CH_2$ | ethoxycarbonyl | [$CDCl_3$] 7.26 9.01; 7.18 0.38; 7.18 0.38; 7.17 1.86; 7.17 2.47; 7.16 1.88; 7.15 2.61; 7.15 2.14; 7.14 0.93; 7.13 0.84; 6.90 0.40; 6.89 0.72; 6.89 0.39; 6.88 0.81; 6.87 1.42; 6.87 0.74; 6.86 0.43; 6.85 0.72; 6.84 0.37; 4.32 0.65; 4.31 0.73; 4.30 0.72; 4.29 0.42; 4.29 |

TABLE 6-continued

Compounds of the general formula (I) according to the invention in which $R^2$ is hydrogen and $R^3$ is methyl and aryl is the radical

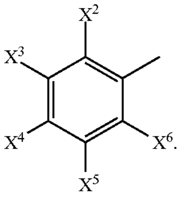

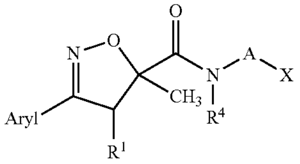

| No. | Aryl | $R^1$ | Y | $R^4$ | A | X | Physical data |
|---|---|---|---|---|---|---|---|
| | | | | | | | 0.66; 4.27 0.33; 4.10 1.40; 4.08 4.37; 4.06 4.46; 4.05 1.50; 3.77 2.67; 3.73 3.07; 3.18 2.95; 3.14 2.56; 2.48 5.22; 2.46 5.18; 1.71 16.00; 1.28 8.04; 1.26 8.30; 1.22 4.78; 1.20 9.47; 1.19 4.66; 0.00 2.79 |
| 6.287 | 3,5-$(MeO)_2$—Ph | H | O | H | $CH(CH_3)CH_2$ | ethoxycarbonyl | [$CDCl_3$] 7.26 17.06; 6.79 2.31; 6.78 4.22; 6.78 2.64; 6.52 0.64; 6.52 1.52; 6.51 1.58; 6.51 0.62; 4.33 0.44; 4.31 0.49; 4.30 0.45; 4.29 0.41; 4.18 0.44; 4.17 1.38; 4.15 1.39; 4.13 0.46; 4.09 0.53; 4.07 1.67; 4.06 1.72; 4.04 0.57; 3.83 0.34; 3.81 15.35; 3.80 16.00; 3.78 1.07; 3.77 0.95; 3.74 1.16; 3.21 1.26; 3.21 0.96; 3.17 1.10; 3.17 0.84; 2.54 1.45; 2.52 1.39; 2.49 0.89; 2.48 1.08; 2.47 1.02; 2.46 0.85; 1.96 0.33; 1.70 5.79; 1.69 4.49; 1.57 5.17; 1.30 1.49; 1.28 3.55; 1.27 3.53; 1.26 2.20; 1.26 3.28; 1.23 2.26; 1.21 3.48; 1.19 3.89; 1.17 1.88 |
| 6.288 | 3,5-$Me_2$—Ph | H | O | H | $CH(CH_3)CH_2$ | ethoxycarbonyl | [$CDCl_3$] 7.26 57.42; 7.22 0.38; 7.20 0.41; 7.18 0.42; 7.06 1.69; 7.06 1.68; 4.34 0.34; 4.32 0.69; 4.31 0.42; 4.30 0.76; 4.30 0.76; 4.29 0.42; 4.28 0.72; 4.27 0.36; 4.18 0.99; 4.17 3.11; 4.15 3.14; 4.13 1.03; 4.08 0.53; 4.06 1.63; 4.04 1.70; 4.03 0.57; 3.82 1.79; 3.80 1.55; 3.78 2.05; 3.75 1.75; 3.23 1.71; 3.22 2.05; 3.18 1.49; 3.18 1.81; 2.53 3.17; 2.52 3.13; 2.51 0.41; 2.48 1.44; 2.47 2.27; 2.45 1.28; 2.33 16.00; 2.33 15.01; 1.70 8.97; 1.69 10.65; 1.30 3.51; 1.28 7.38; 1.27 4.58; 1.26 3.75; 1.26 4.52; 1.22 5.10; 1.20 5.85; 1.18 6.05; 1.16 2.89; 0.01 0.70; 0.00 25.68; −0.01 0.97 |
| 6.289 | 3,5-(tert•Bu)$_2$—Ph | H | O | H | $CH(CH_3)CH_2$ | ethoxycarbonyl | [$CDCl_3$] 7.50 0.46; 7.49 0.90; 7.48 0.91; 7.48 0.53; 7.26 6.10; 4.17 0.47; 4.15 0.47; 4.06 0.44; 4.04 0.45; 3.27 0.51; 3.23 0.44; 2.54 0.49; 2.52 0.44; 1.71 1.62; 1.70 1.57; 1.56 1.05; 1.35 2.05; 1.33 16.00; 1.30 0.51; 1.28 1.53; 1.26 1.28; 1.23 0.81; 1.21 0.79; 1.19 0.51; 1.17 1.07; 1.15 0.48 |
| 6.290 | 3-Br-5-$CF_3$—Ph | H | O | H | $CH(CH_3)CH_2$ | ethoxycarbonyl | [$CDCl_3$] 7.97 2.73; 7.97 2.65; 7.81 4.32; 7.80 3.78; 7.26 32.32; 7.18 0.52; 7.16 0.56; 7.13 0.72; 7.11 0.71; 4.34 0.55; 4.32 1.09; 4.31 1.22; 4.30 1.21; 4.29 0.68; 4.28 1.11; 4.27 0.54; 4.19 1.47; 4.17 |

TABLE 6-continued
Compounds of the general formula (I) according to the invention in which $R^2$ is hydrogen and $R^3$ is methyl and aryl is the radical
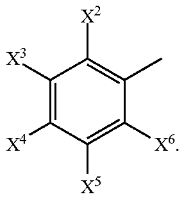
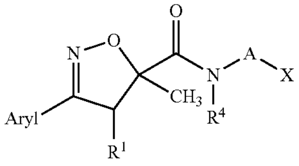
| No. | Aryl | $R^1$ | Y | $R^4$ | A | X | Physical data |
|---|---|---|---|---|---|---|---|
| | | | | | | | 4.58; 4.16 4.67; 4.14 1.57; 4.10 1.13; 4.08 3.50; 4.06 3.57; 4.04 1.19; 3.85 2.68; 3.83 2.08; 3.81 3.06; 3.78 2.38; 3.22 2.57; 3.22 3.18; 3.18 2.23; 3.17 2.80; 2.54 4.66; 2.53 4.60; 2.48 2.73; 2.46 2.64; 1.73 12.30; 1.71 16.00; 1.57 16.05; 1.30 4.96; 1.28 10.72; 1.28 6.98; 1.26 6.95; 1.26 6.99; 1.23 8.05; 1.22 4.44; 1.21 8.17; 1.20 7.76; 1.18 3.77; 0.01 0.42 |
| 6.291 | 3-Cl-5-Et—Ph | H | O | H | $CH(CH_3)CH_2$ | ethoxycarbonyl | [$CDCl_3$] 8.10 0.39; 8.08 0.42; 7.88 0.36; 7.86 0.43; 7.45 1.46; 7.45 3.34; 7.44 3.07; 7.35 1.40; 7.35 2.57; 7.35 2.25; 7.34 2.37; 7.34 2.01; 7.34 2.04; 7.34 1.10; 7.26 30.18; 7.24 1.46; 7.24 3.03; 7.24 2.76; 7.23 1.08; 7.17 0.43; 7.15 0.46; 7.13 0.62; 7.11 0.59; 6.37 1.41; 4.34 0.47; 4.32 1.02; 4.32 0.57; 4.30 1.10; 4.30 1.11; 4.29 0.59; 4.28 1.02; 4.27 0.51; 4.19 1.54; 4.17 4.89; 4.15 4.96; 4.13 1.61; 4.09 0.97; 4.07 3.11; 4.05 3.26; 4.04 1.11; 3.82 2.78; 3.79 2.13; 3.77 3.17; 3.75 2.44; 3.21 2.43; 3.20 3.11; 3.16 2.12; 3.16 2.74; 2.68 1.16; 2.66 3.59; 2.64 3.70; 2.62 1.28; 2.54 5.06; 2.52 4.95; 2.48 2.10; 2.48 2.06; 2.47 2.03; 2.46 1.99; 1.70 12.18; 1.69 16.00; 1.60 1.60; 1.30 5.59; 1.28 11.77; 1.27 6.40; 1.26 6.72; 1.26 10.68; 1.24 11.83; 1.24 9.72; 1.22 8.27; 1.22 6.36; 1.22 4.99; 1.21 8.65; 1.19 8.69; 1.17 4.13; 0.01 0.33 |
| 6.292 | 3-Cl-5-$CF_3$—Ph | H | O | H | $CH(CH_3)CH_2$ | ethoxycarbonyl | [$CDCl_3$] 7.82 2.45; 7.81 2.52; 7.81 2.11; 7.80 1.34; 7.77 4.10; 7.77 3.89; 7.66 3.20; 7.26 43.17; 7.25 0.41; 7.18 0.49; 7.15 0.53; 7.13 0.67; 7.11 0.66; 4.34 0.52; 4.32 1.08; 4.31 1.20; 4.30 1.20; 4.29 0.64; 4.29 1.09; 4.27 0.53; 4.19 1.50; 4.17 4.71; 4.16 4.80; 4.14 1.59; 4.10 1.17; 4.08 3.63; 4.06 3.70; 4.04 1.23; 3.86 2.72; 3.83 2.15; 3.81 3.10; 3.79 2.47; 3.22 2.64; 3.22 3.24; 3.18 2.31; 3.18 2.85; 2.54 4.39; 2.53 4.36; 2.48 2.59; 2.48 2.58; 2.46 2.49; 2.46 2.55; 1.73 12.62; 1.72 16.00; 1.56 9.58; 1.30 5.35; 1.28 12.04; 1.28 7.41; 1.26 7.83; 1.26 7.30; 1.23 7.97; 1.22 4.98; 1.21 8.19; 1.20 8.50; 1.18 4.06; 0.01 0.44; 0.01 0.54; 0.00 20.36 |

TABLE 6-continued
Compounds of the general formula (I) according to the invention in which $R^2$ is hydrogen and $R^3$ is methyl and aryl is the radical
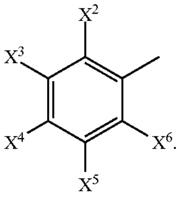
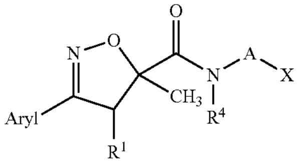
| No. | Aryl | $R^1$ | Y | $R^4$ | A | X | Physical data |
|---|---|---|---|---|---|---|---|
| 6.293 | 3-Cl—Ph | H | O | H | $CH(CH_3)CH_2$ | ethoxycarbonyl | [$CDCl_3$] 7.65 2.44; 7.51 0.55; 7.51 0.94; 7.50 0.99; 7.50 0.86; 7.50 0.56; 7.49 0.77; 7.49 1.24; 7.48 1.31; 7.48 1.09; 7.48 0.65; 7.41 0.43; 7.41 0.80; 7.41 0.81; 7.40 0.44; 7.39 0.94; 7.39 1.72; 7.39 1.58; 7.38 0.75; 7.36 1.46; 7.36 1.33; 7.34 1.66; 7.34 1.49; 7.32 0.65; 7.32 0.59; 7.27 38.32; 7.17 0.35; 7.15 0.40; 7.14 0.46; 7.11 0.41; 5.30 0.47; 4.34 0.33; 4.32 0.70; 4.31 0.76; 4.30 0.78; 4.28 0.71; 4.27 0.36; 4.19 0.94; 4.17 2.94; 4.15 2.99; 4.13 1.01; 4.09 0.73; 4.07 2.29; 4.05 2.36; 4.03 0.81; 3.82 1.77; 3.79 1.54; 3.78 2.04; 3.75 1.77; 3.21 1.85; 3.21 2.12; 3.17 1.62; 3.16 1.86; 2.54 3.39; 2.52 3.36; 2.48 2.72; 2.46 2.61; 1.72 0.41; 1.71 9.20; 1.70 10.64; 1.67 16.00; 1.30 3.22; 1.28 6.82; 1.27 4.82; 1.26 3.79; 1.26 4.77; 1.25 0.37; 1.23 5.18; 1.21 7.68; 1.19 5.60; 1.17 2.72; 0.01 0.45; 0.00 14.48; −0.01 0.66 |
| 6.294 | 3-c-Pr-5-F—Ph | H | O | H | $CH(CH_3)CH_2$ | ethoxycarbonyl | [$CDCl_3$] 7.26 35.66; 7.17 0.47; 7.14 1.27; 7.14 1.92; 7.13 2.12; 7.13 1.63; 7.12 4.84; 7.11 4.89; 6.82 0.81; 6.81 1.57; 6.81 1.45; 6.80 0.63; 6.79 0.84; 6.79 1.65; 6.78 1.50; 6.78 0.60; 4.34 0.49; 4.32 1.09; 4.30 1.19; 4.30 1.17; 4.29 0.66; 4.28 1.06; 4.27 0.54; 4.19 1.49; 4.17 4.70; 4.15 4.77; 4.13 1.57; 4.09 0.98; 4.07 3.11; 4.05 3.23; 4.04 1.10; 3.80 2.72; 3.78 2.10; 3.76 3.13; 3.74 2.40; 3.20 2.62; 3.19 3.11; 3.16 2.27; 3.15 2.72; 2.54 5.15; 2.52 5.07; 2.48 2.21; 2.48 2.06; 2.46 2.12; 2.46 2.00; 1.93 0.33; 1.92 0.69; 1.91 0.81; 1.90 1.44; 1.89 0.90; 1.88 0.78; 1.87 0.39; 1.70 12.33; 1.69 16.00; 1.57 5.20; 1.30 5.23; 1.28 11.03; 1.27 6.39; 1.26 5.90; 1.26 6.46; 1.22 7.96; 1.21 8.58; 1.19 8.06; 1.17 3.88; 1.04 1.11; 1.03 3.15; 1.03 3.09; 1.01 1.57; 1.01 3.25; 1.00 2.92; 0.99 1.29; 0.73 1.03; 0.73 0.84; 0.72 3.34; 0.72 3.84; 0.71 2.69; 0.70 3.96; 0.70 2.52; 0.69 0.90; 0.69 0.68; 0.01 0.47 |
| 6.295 | 3-Et-5-F—Ph | H | O | H | $CH(CH_3)CH_2$ | ethoxycarbonyl | [$CDCl_3$] 7.26 50.70; 7.23 3.28; 7.19 1.78; 7.19 1.67; 7.17 1.53; 7.17 2.20; 7.16 1.94; 7.15 0.67; 7.13 0.74; 7.11 0.67; 6.98 1.62; 6.98 |

TABLE 6-continued
Compounds of the general formula (I) according to the invention in which $R^2$ is hydrogen and $R^3$ is methyl and aryl is the radical
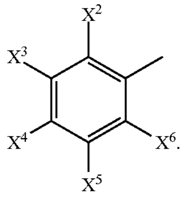
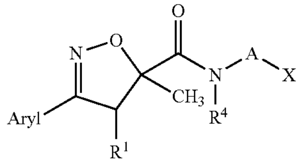
| No. | Aryl | $R^1$ | Y | $R^4$ | A | X | Physical data |
|---|---|---|---|---|---|---|---|
| | | | | | | | 1.53; 6.96 1.64; 6.95 1.53; 4.34 0.53; 4.32 1.17; 4.31 1.32; 4.30 1.24; 4.29 1.12; 4.27 0.58; 4.19 1.50; 4.17 4.73; 4.15 4.78; 4.13 1.57; 4.09 1.14; 4.07 3.66; 4.05 3.79; 4.03 1.28; 3.82 2.70; 3.79 2.40; 3.77 3.10; 3.75 2.75; 3.21 3.17; 3.21 3.19; 3.17 2.75; 3.16 2.77; 2.69 1.38; 2.67 4.22; 2.65 4.35; 2.63 1.49; 2.54 5.13; 2.52 5.03; 2.48 2.62; 2.48 2.43; 2.47 2.52; 2.46 2.33; 1.70 14.23; 1.69 16.00; 1.56 17.95; 1.56 19.48; 1.30 5.15; 1.28 11.53; 1.27 7.48; 1.26 12.07; 1.24 11.83; 1.24 10.32; 1.22 11.06; 1.21 9.18; 1.19 9.12; 1.17 4.43; 0.01 0.59; 0.00 15.78; −0.01 0.54 |
| 6.296 | 3-Et—Ph | H | O | H | $CH(CH_3)CH_2$ | ethoxycarbonyl | [$CDCl_3$] 7.50 2.64; 7.50 2.64; 7.45 0.64; 7.44 1.08; 7.44 1.17; 7.44 1.05; 7.43 0.67; 7.43 0.96; 7.42 1.52; 7.42 1.60; 7.42 1.39; 7.41 0.82; 7.34 1.00; 7.33 0.92; 7.32 2.28; 7.31 2.02; 7.30 1.49; 7.30 1.32; 7.27 1.91; 7.27 1.95; 7.27 2.06; 7.27 2.06; 7.26 43.40; 7.26 1.68; 7.19 0.47; 7.17 0.54; 7.16 0.41; 7.15 0.60; 7.13 0.57; 4.34 0.50; 4.33 1.05; 4.32 0.62; 4.31 1.13; 4.30 1.14; 4.29 0.63; 4.29 1.05; 4.27 0.53; 4.18 1.51; 4.17 4.76; 4.15 4.83; 4.13 1.58; 4.07 0.90; 4.06 2.87; 4.04 3.01; 4.02 1.05; 3.85 2.78; 3.82 2.50; 3.81 3.19; 3.78 2.86; 3.25 2.87; 3.24 3.21; 3.20 2.52; 3.20 2.81; 2.70 0.98; 2.69 0.94; 2.68 3.00; 2.68 2.85; 2.66 3.11; 2.66 2.93; 2.64 1.10; 2.64 1.03; 2.54 3.41; 2.52 3.20; 2.52 3.13; 2.51 0.46; 2.49 2.04; 2.47 3.64; 2.46 1.94; 2.43 0.34; 2.42 0.33; 1.71 14.23; 1.69 16.00; 1.59 24.54; 1.30 5.39; 1.28 11.42; 1.27 7.31; 1.27 5.79; 1.26 9.34; 1.26 7.47; 1.25 11.16; 1.24 10.21; 1.23 5.36; 1.22 5.61; 1.22 8.26; 1.20 7.71; 1.19 4.87; 1.18 9.79; 1.16 4.67; 0.01 0.56 |
| 6.297 | 3-F-5-MeS—Ph | H | O | H | $CH(CH_3)CH_2$ | ethoxycarbonyl | [$CDCl_3$] 7.26 16.72; 7.26 15.43; 7.25 2.35; 7.25 2.68; 7.24 2.13; 7.16 0.39; 7.14 0.44; 7.12 0.78; 7.11 1.35; 7.11 1.38; 7.10 0.83; 7.09 0.70; 7.09 1.21; 7.08 1.13; 7.08 0.41; 6.99 1.01; 6.99 1.15; 6.99 1.05; 6.97 1.15; 6.97 1.03; 4.34 0.34; 4.32 0.62; 4.32 |

TABLE 6-continued
Compounds of the general formula (I) according to the invention in which $R^2$ is hydrogen and $R^3$ is methyl and aryl is the radical
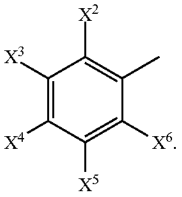
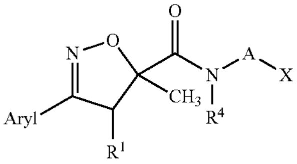
| No. | Aryl | $R^1$ | Y | $R^4$ | A | X | Physical data |
|---|---|---|---|---|---|---|---|
| | | | | | | | 0.72; 4.31 0.79; 4.30 0.78; 4.30 0.75; 4.30 0.71; 4.29 0.52; 4.28 0.72; 4.27 0.35; 4.19 0.73; 4.18 0.67; 4.17 2.24; 4.17 2.07; 4.15 2.27; 4.15 2.09; 4.13 0.77; 4.13 0.71; 4.10 0.62; 4.09 0.61; 4.08 1.91; 4.08 1.85; 4.06 1.99; 4.06 1.89; 4.04 0.67; 4.04 0.63; 3.80 1.18; 3.80 1.14; 3.78 1.19; 3.78 1.15; 3.76 1.35; 3.76 1.32; 3.73 1.34; 3.73 1.30; 3.19 1.53; 3.19 1.98; 3.15 1.32; 3.15 1.70; 3.15 1.20; 2.54 2.37; 2.54 2.35; 2.52 2.35; 2.52 2.30; 2.49 16.00; 2.48 2.35; 2.46 2.27; 1.96 0.42; 1.96 0.73; 1.96 0.70; 1.96 0.68; 1.70 7.01; 1.70 7.05; 1.69 7.15; 1.69 6.96; 1.58 0.36; 1.30 2.28; 1.30 2.21; 1.29 0.50; 1.29 0.52; 1.28 5.10; 1.28 5.44; 1.27 4.07; 1.27 4.66; 1.26 3.07; 1.26 3.88; 1.26 4.21; 1.26 4.39; 1.23 3.55; 1.23 3.54; 1.22 2.49; 1.22 2.70; 1.21 3.63; 1.21 3.55; 1.20 4.58; 1.20 4.40; 1.18 2.19; 1.18 2.08; 0.01 0.61; 0.00 1.18 |
| 6.298 | 3-F-5-$MeSO_2$—Ph | H | O | H | $CH(CH_3)CH_2$ | ethoxycarbonyl | [$CDCl_3$] 7.95 2.95; 7.72 0.90; 7.71 1.04; 7.71 1.02; 7.70 0.99; 7.69 1.08; 7.69 1.04; 7.69 0.73; 7.69 0.70; 7.68 0.75; 7.68 0.92; 7.68 0.87; 7.67 0.48; 7.66 0.65; 7.66 0.74; 7.66 0.90; 7.65 0.85; 7.65 0.78; 7.26 22.07; 7.26 34.64; 7.19 0.39; 7.16 0.41; 7.14 0.43; 7.12 0.43; 4.34 0.36; 4.33 0.66; 4.31 0.73; 4.30 0.73; 4.29 0.65; 4.27 0.33; 4.19 0.74; 4.18 2.35; 4.16 2.48; 4.14 1.00; 4.11 0.74; 4.10 2.16; 4.08 2.22; 4.06 0.76; 3.88 1.29; 3.86 1.28; 3.84 1.46; 3.81 1.44; 3.24 1.85; 3.19 1.62; 3.12 0.54; 3.11 0.32; 3.09 16.00; 2.55 1.66; 2.53 1.76; 2.48 2.06; 2.46 2.03; 1.73 7.36; 1.72 7.68; 1.58 1.06; 1.55 0.53; 1.53 0.37; 1.30 2.58; 1.29 6.45; 1.28 4.51; 1.27 5.35; 1.24 3.41; 1.23 4.16; 1.22 6.45; 1.22 4.48; 1.20 2.52; 0.01 0.40; 0.00 8.36 |
| 6.299 | 3-F-5-MeO—Ph | H | O | H | $CH(CH_3)CH_2$ | ethoxycarbonyl | [$CDCl_3$] 7.27 10.87; 7.26 15.03; 7.17 0.43; 7.14 0.50; 7.13 0.62; 7.11 0.56; 6.97 2.59; 6.96 0.74; 6.95 1.27; 6.95 1.49; 6.95 1.51; 6.94 1.19; 6.93 1.14; 6.93 1.46; 6.92 1.46; 6.92 1.19; 6.69 1.40; 6.69 1.10; 6.68 0.49; 6.66 |

TABLE 6-continued
Compounds of the general formula (I) according to the invention in which $R^2$ is hydrogen and $R^3$ is methyl and aryl is the radical
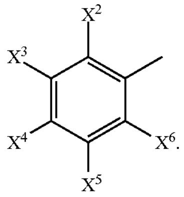
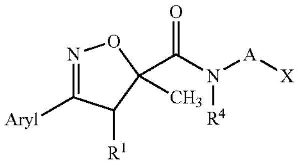
| No. | Aryl | $R^1$ | Y | $R^4$ | A | X | Physical data |
|---|---|---|---|---|---|---|---|
| | | | | | | | 1.41; 6.66 1.09; 6.65 0.46; 4.34 0.34; 4.33 0.78; 4.31 0.98; 4.29 0.79; 4.27 0.38; 4.19 0.63; 4.19 0.81; 4.17 1.96; 4.17 2.53; 4.15 2.02; 4.15 2.54; 4.14 0.70; 4.13 0.86; 4.10 0.48; 4.09 0.60; 4.08 1.47; 4.08 1.85; 4.06 1.52; 4.06 1.91; 4.04 0.52; 4.04 0.64; 3.82 16.00; 3.82 10.59; 3.80 1.24; 3.80 1.54; 3.77 0.97; 3.77 1.24; 3.76 1.38; 3.75 1.73; 3.73 1.06; 3.73 1.35; 3.20 2.52; 3.19 1.84; 3.15 2.20; 3.15 1.62; 2.54 2.89; 2.53 2.48; 2.52 2.91; 2.48 2.02; 2.47 2.02; 1.71 5.56; 1.70 7.03; 1.70 7.84; 1.69 9.19; 1.59 5.10; 1.30 2.06; 1.30 2.79; 1.28 4.43; 1.28 7.32; 1.27 4.13; 1.26 2.71; 1.26 5.51; 1.26 3.97; 1.23 3.66; 1.23 4.45; 1.21 5.52; 1.21 4.72; 1.20 3.46; 1.20 4.47; 1.18 1.64; 1.18 2.17; 0.00 4.23 |
| 6.300 | 3-F—Ph | H | O | H | $CH(CH_3)CH_2$ | ethoxycarbonyl | [$CDCl_3$] 7.40 1.29; 7.40 1.47; 7.39 1.39; 7.39 1.48; 7.39 1.20; 7.38 4.19; 7.37 5.41; 7.37 4.26; 7.36 2.09; 7.26 49.10; 7.17 0.49; 7.15 0.79; 7.15 1.06; 7.14 1.10; 7.14 1.33; 7.13 1.19; 7.13 1.27; 7.13 1.24; 7.12 1.29; 7.12 1.17; 7.11 1.10; 7.11 1.07; 7.10 0.62; 7.10 0.54; 7.10 0.52; 4.34 0.44; 4.32 0.88; 4.31 0.96; 4.30 0.96; 4.29 0.92; 4.27 0.44; 4.19 1.12; 4.17 3.51; 4.15 3.57; 4.13 1.17; 4.08 1.24; 4.07 3.96; 4.05 4.11; 4.03 1.40; 3.82 2.12; 3.80 2.73; 3.78 2.43; 3.75 3.15; 3.22 3.17; 3.21 2.51; 3.17 2.75; 3.17 2.20; 2.54 3.88; 2.52 3.82; 2.48 4.49; 2.46 4.20; 1.71 16.00; 1.70 12.48; 1.55 22.62; 1.30 3.94; 1.28 8.63; 1.28 8.04; 1.26 5.35; 1.26 7.99; 1.23 5.96; 1.21 6.14; 1.21 5.51; 1.19 10.15; 1.17 4.85; 0.01 0.54; 0.00 19.81; −0.01 0.60 |
| 6.301 | 3-Me-5-$CF_3O$—Ph | H | O | H | $CH(CH_3)CH_2$ | ethoxycarbonyl | [$CDCl_3$] 7.36 2.53; 7.36 2.46; 7.35 2.03; 7.35 1.91; 7.35 1.96; 7.32 2.97; 7.31 0.52; 7.31 0.89; 7.27 4.65; 7.26 33.17; 7.26 51.99; 7.25 0.46; 7.17 0.52; 7.16 0.36; 7.16 0.35; 7.15 0.60; 7.13 0.72; 7.11 0.70; 7.09 2.87; 4.34 0.46; 4.32 0.96; 4.31 1.12; 4.30 1.05; 4.29 0.94; 4.27 0.47; 4.19 1.20; 4.17 3.76; 4.15 3.82; 4.13 1.24; 4.08 0.85; 4.07 2.65; 4.05 2.72; 4.03 |

TABLE 6-continued
Compounds of the general formula (I) according to the invention in which $R^2$ is hydrogen and $R^3$ is methyl and aryl is the radical
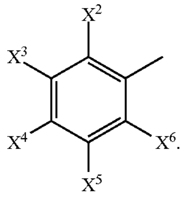
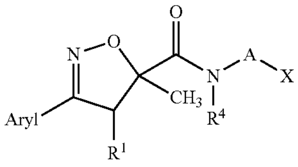
| No. | Aryl | $R^1$ | Y | $R^4$ | A | X | Physical data |
|---|---|---|---|---|---|---|---|
| | | | | | | | 0.92; 3.82 2.13; 3.80 1.71; 3.78 2.45; 3.75 1.96; 3.21 2.84; 3.21 2.55; 3.17 2.46; 3.16 2.22; 2.54 4.18; 2.52 4.07; 2.48 3.25; 2.47 3.15; 2.43 0.32; 2.40 16.00; 2.40 15.78; 1.71 10.42; 1.70 12.73; 1.56 23.07; 1.30 4.25; 1.28 10.44; 1.28 5.71; 1.26 7.63; 1.23 6.34; 1.21 6.48; 1.20 3.48; 1.18 6.86; 1.17 3.16; 0.01 1.68; 0.00 12.26; 0.00 18.70 |
| 6.302 | 3-Me—Ph | H | O | H | $CH(CH_3)CH_2$ | ethoxycarbonyl | [$CDCl_3$] 7.47 2.96; 7.47 2.94; 7.43 1.47; 7.41 1.96; 7.41 1.97; 7.31 1.03; 7.30 1.00; 7.29 2.42; 7.28 2.32; 7.27 1.69; 7.26 31.39; 7.24 2.55; 7.24 2.55; 7.22 1.27; 7.18 0.58; 7.16 0.68; 7.14 0.75; 7.12 0.65; 4.34 0.58; 4.32 1.16; 4.31 1.31; 4.30 1.32; 4.28 1.26; 4.27 0.61; 4.18 1.34; 4.17 4.15; 4.15 4.28; 4.13 1.57; 4.08 1.05; 4.06 3.29; 4.04 3.38; 4.02 1.16; 3.83 2.48; 3.81 2.31; 3.79 2.84; 3.76 2.65; 3.23 2.69; 3.23 3.12; 3.19 2.32; 3.18 2.72; 2.53 4.13; 2.52 4.14; 2.51 0.45; 2.48 2.07; 2.47 3.88; 2.45 1.99; 2.43 0.36; 2.41 0.33; 2.37 16.00; 2.04 0.69; 1.70 13.92; 1.69 15.14; 1.58 2.88; 1.30 4.53; 1.28 9.53; 1.27 7.61; 1.26 5.44; 1.25 7.44; 1.24 0.42; 1.22 7.36; 1.20 7.49; 1.20 5.57; 1.18 8.42; 1.16 4.12; 0.88 0.65; 0.00 8.34; 0.00 6.71; −0.01 0.40 |
| 6.303 | 4-EtO—Ph | H | O | H | $CH(CH_3)CH_2$ | ethoxycarbonyl | [$CDCl_3$] 7.57 4.51; 7.57 5.30; 7.55 5.41; 7.54 4.78; 7.26 37.85; 7.17 0.99; 7.15 1.22; 7.14 1.13; 7.12 0.89; 6.91 4.97; 6.90 5.72; 6.89 5.36; 6.88 4.44; 5.30 1.06; 4.34 0.66; 4.32 1.42; 4.30 1.70; 4.28 1.38; 4.27 0.67; 4.18 1.21; 4.16 3.67; 4.14 3.71; 4.13 1.24; 4.09 2.27; 4.07 7.45; 4.05 9.48; 4.04 5.75; 4.02 1.36; 3.81 2.19; 3.78 2.61; 3.77 2.52; 3.74 3.00; 3.21 3.73; 3.21 2.72; 3.17 3.21; 3.16 2.36; 2.53 3.23; 2.52 3.23; 2.50 0.49; 2.48 2.43; 2.47 4.31; 2.45 2.30; 2.43 0.38; 2.41 0.38; 2.00 6.00; 1.69 16.00; 1.68 13.46; 1.57 10.05; 1.44 7.85; 1.43 15.77; 1.41 7.60; 1.29 3.97; 1.27 8.64; 1.27 8.33; 1.26 5.42; 1.25 8.03; 1.22 6.78; 1.20 7.14; 1.20 4.07; 1.19 5.00; 1.18 9.19; 1.16 4.48 |

TABLE 6-continued

Compounds of the general formula (I) according to the invention in which $R^2$ is hydrogen and $R^3$ is methyl and aryl is the radical

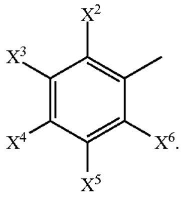

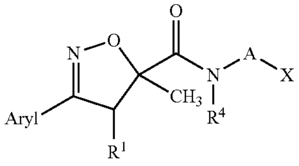

| No. | Aryl | $R^1$ | Y | $R^4$ | A | X | Physical data |
|---|---|---|---|---|---|---|---|
| 6.304 | 4-MeO—Ph | H | O | H | $CH(CH_3)CH_2$ | ethoxycarbonyl | [$CDCl_3$] 7.59 2.18; 7.58 2.73; 7.58 0.85; 7.57 0.76; 7.56 2.82; 7.56 2.61; 7.55 0.33; 7.26 19.98; 7.18 0.36; 7.15 0.45; 7.14 0.46; 7.12 0.38; 6.93 2.29; 6.92 2.95; 6.92 0.87; 6.91 0.71; 6.90 2.67; 6.90 2.38; 4.32 0.62; 4.30 0.67; 4.30 0.69; 4.28 0.63; 4.18 0.71; 4.16 2.21; 4.15 2.25; 4.13 0.75; 4.07 0.62; 4.06 1.95; 4.04 2.02; 4.02 0.70; 3.84 16.00; 3.81 1.37; 3.79 1.49; 3.77 1.51; 3.74 1.61; 3.21 1.64; 3.21 1.62; 3.17 1.43; 3.17 1.43; 2.53 1.44; 2.53 1.51; 2.52 1.58; 2.51 1.46; 2.48 1.25; 2.47 1.78; 2.45 1.20; 1.69 8.24; 1.68 7.85; 1.57 5.13; 1.29 2.37; 1.28 4.91; 1.27 4.33; 1.26 2.65; 1.25 4.28; 1.22 3.89; 1.20 3.90; 1.20 2.77; 1.18 5.07; 1.16 2.46 |
| 6.305 | 3,5-$Cl_2$—Ph | H | O | H | $CH(CH_3)CH_2$ | hydroxy | [$CDCl_3$] 1.20 (dd, 3H); 1.72 (ds, 3H); 3.19 (dd, 1H); 3.49-3.71 (m, 2H); 3.79 (d, 1H); 4.00-4.07 (m, 1H); 6.88 (br, 1H); 7.41 (m, 1H); 7.51 (m, 2H). |
| 6.306 | 3,5-$Cl_2$—Ph | H | O | H | $CH(CH_3)CH_2$ | isobutoxycarbonyl | [$CDCl_3$] 7.52 6.63; 7.52 11.61; 7.51 7.35; 7.41 1.81; 7.41 3.70; 7.40 3.63; 7.40 1.73; 7.26 25.30; 7.15 0.52; 7.13 0.58; 7.11 0.64; 7.09 0.59; 5.30 14.15; 4.34 0.35; 4.34 0.36; 4.32 0.64; 4.32 0.85; 4.31 0.83; 4.30 1.14; 4.30 0.89; 4.29 0.91; 4.28 0.72; 4.27 0.36; 4.27 0.40; 3.90 3.19; 3.90 3.48; 3.88 3.41; 3.88 3.59; 3.81 4.81; 3.80 2.70; 3.79 5.19; 3.77 2.47; 3.75 2.93; 3.73 2.79; 3.18 2.77; 3.17 3.05; 3.13 2.43; 3.13 2.69; 2.56 3.44; 2.55 3.11; 2.50 4.35; 2.49 4.31; 2.00 0.40; 1.98 0.48; 1.96 1.00; 1.95 1.29; 1.93 1.05; 1.91 0.57; 1.90 0.50; 1.88 0.96; 1.87 1.25; 1.85 1.01; 1.83 0.51; 1.71 14.01; 1.70 14.84; 1.57 4.37; 1.28 6.84; 1.26 7.05; 1.23 7.18; 1.22 7.12; 0.95 16.00; 0.93 15.62; 0.88 9.59; 0.88 10.49; 0.87 9.38; 0.87 10.10; 0.00 8.16 |
| 6.307 | 3,5-$F_2$—Ph | H | O | H | $CH(CH_3)CH_2$ | isobutoxycarbonyl | [$CDCl_3$] 7.26 55.50; 7.19 0.39; 7.18 0.42; 7.17 1.72; 7.17 2.75; 7.17 2.93; 7.16 3.06; 7.15 3.28; 7.15 3.31; 7.15 3.25; 7.14 2.26; 7.14 0.79; 7.13 0.86; 7.12 0.59; 7.09 0.52; 6.90 0.46; 6.90 0.53; 6.90 0.77; 6.89 0.86; 6.89 0.52; 6.89 0.46; 6.88 0.86; 6.88 1.03; 6.87 |

TABLE 6-continued

Compounds of the general formula (I) according to the invention in which $R^2$ is hydrogen and $R^3$ is methyl and aryl is the radical

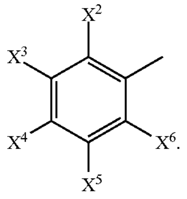

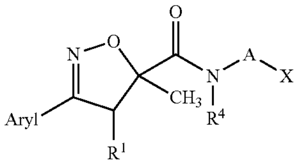

| No. | Aryl | $R^1$ | Y | $R^4$ | A | X | Physical data |
|---|---|---|---|---|---|---|---|
| | | | | | | | 1.65; 6.87 1.74; 6.87 0.92; 6.87 0.88; 6.86 0.49; 6.86 0.56; 6.85 0.78; 6.85 0.88; 6.84 0.46; 4.34 0.34; 4.34 0.35; 4.33 0.86; 4.31 0.86; 4.31 1.08; 4.29 0.89; 4.27 0.40; 3.90 2.95; 3.90 3.21; 3.88 3.24; 3.88 3.32; 3.81 4.62; 3.79 6.88; 3.77 2.72; 3.75 2.92; 3.72 3.02; 3.18 3.02; 3.18 3.01; 3.14 2.60; 3.13 2.61; 2.56 3.21; 2.55 2.83; 2.50 4.55; 2.49 4.55; 2.20 0.48; 1.98 0.45; 1.96 1.01; 1.95 1.28; 1.93 1.00; 1.91 0.55; 1.90 0.53; 1.88 1.05; 1.87 1.31; 1.85 1.04; 1.83 0.53; 1.71 15.66; 1.70 15.01; 1.53 37.19; 1.28 7.28; 1.26 7.34; 1.23 6.89; 1.22 6.91; 0.95 16.00; 0.93 15.59; 0.88 9.87; 0.88 10.53; 0.87 9.68; 0.86 10.24; 0.01 2.05; 0.00 75.54; −0.01 2.62 |
| 6.308 | 3,5-$Cl_2$—Ph | H | O | H | $CH(CH_3)CH_2$ | methoxy | diastereomer D1: [$CDCl_3$] 1.17 (d, 3H); 1.71 (s, 3H); 3.17 (d, 1H); 3.36 (m, 2H); 3.38 (s, 3H); 3.79 (d, 1H); 4.10 (m, 1H); 6.90 (t br, 1H), 7.42 (s, 1H); 7.53 (m, 2H). diastereomer D2: [$CDCl_3$] 1.21 (d, 3H); 1.71 (s, 3H); 3.17 (d, 1H); 3.29 (s, 3H); 3.33 (m, 2H); 3.78 (d, 1H); 4.10 (m, 1H); 6.90 (t br, 1H), 7.42 (s, 1H); 7.53 (m, 2H). |
| 6.309 | 2,5-$Me_2$—Ph | H | O | H | $CH(CH_3)CH_2$ | methoxycarbonyl | [$CDCl_3$] 7.26 13.91; 7.26 13.63; 7.16 1.75; 7.14 3.58; 7.12 7.44; 7.10 1.00; 4.36 0.44; 4.34 0.93; 4.32 1.05; 4.32 1.01; 4.30 0.93; 4.29 0.47; 3.86 1.70; 3.84 1.57; 3.82 1.97; 3.79 1.83; 3.69 11.59; 3.58 10.57; 3.29 1.83; 3.28 2.00; 3.25 1.58; 3.24 1.75; 2.56 2.72; 2.54 2.72; 2.50 1.56; 2.50 1.64; 2.49 1.63; 2.48 1.72; 2.47 16.00; 2.32 15.70; 1.71 9.51; 1.69 10.47; 1.60 5.43; 1.28 4.78; 1.26 4.83; 1.23 5.18; 1.22 5.15; 0.00 6.44; 0.00 6.21 |
| 6.310 | 2-Cl-3-F-5-MeO—Ph | H | O | H | $CH(CH_3)CH_2$ | methoxycarbonyl | |
| 6.311 | 2-F-3-Me—Ph | H | O | H | $CH(CH_3)CH_2$ | methoxycarbonyl | [$CDCl_3$] 7.60 1.20; 7.58 2.32; 7.56 1.31; 7.27 1.00; 7.27 1.35; 7.27 1.33; 7.27 1.47; 7.27 1.54; 7.27 23.35; 7.26 24.36; 7.26 2.11; 7.26 2.08; 7.26 2.53; 7.25 2.82; 7.25 2.72; 7.24 0.45; 7.24 1.24; 7.24 1.45; 7.23 1.42; 7.12 0.69; 7.09 1.28; 7.08 2.92; 7.06 4.05; 7.04 1.81; 4.35 0.58; 4.33 1.24; 4.32 1.39; 4.31 1.38; 4.30 1.25; 4.28 |

TABLE 6-continued
Compounds of the general formula (I) according to the invention in which $R^2$ is hydrogen and $R^3$ is methyl and aryl is the radical
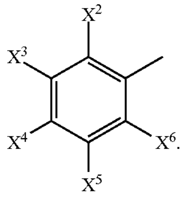
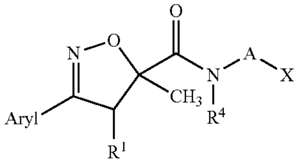
| No. | Aryl | $R^1$ | Y | $R^4$ | A | X | Physical data |
|---|---|---|---|---|---|---|---|
| | | | | | | | 0.62; 3.91 1.17; 3.90 1.23; 3.90 1.18; 3.87 1.05; 3.87 1.11; 3.87 1.09; 3.86 1.45; 3.86 1.48; 3.86 1.44; 3.83 1.17; 3.83 1.23; 3.82 1.25; 3.82 1.19; 3.70 15.76; 3.70 16.00; 3.60 13.74; 3.60 13.81; 3.35 1.26; 3.34 2.46; 3.34 1.54; 3.30 1.08; 3.30 2.14; 3.29 1.32; 2.55 4.12; 2.54 3.97; 2.50 2.42; 2.50 2.39; 2.49 2.24; 2.48 2.21; 2.30 12.80; 2.29 13.28; 2.01 0.33; 2.01 0.35; 1.70 12.21; 1.70 12.37; 1.69 14.20; 1.69 14.22; 1.60 9.92; 1.60 9.00; 1.28 6.08; 1.28 6.15; 1.26 6.18; 1.26 6.24; 1.23 7.00; 1.23 7.02; 1.22 6.95; 1.21 6.99; 0.00 4.22; 0.00 4.65 |
| 6.312 | 3-$CF_3$—Ph | H | O | H | $CH(CH_3)CH_2$ | methoxycarbonyl | [$CDCl_3$] 7.91 3.14; 7.91 3.27; 7.82 1.65; 7.80 1.93; 7.69 1.76; 7.67 2.35; 7.57 1.87; 7.55 2.97; 7.53 1.24; 7.26 17.99; 7.26 22.80; 7.15 0.50; 7.13 0.57; 7.11 0.66; 7.09 0.61; 5.30 0.85; 5.30 1.08; 4.34 0.52; 4.33 1.13; 4.31 1.12; 4.31 1.20; 4.31 1.13; 4.31 1.19; 4.30 0.73; 4.29 1.10; 4.27 0.57; 3.88 1.95; 3.88 2.34; 3.85 1.64; 3.85 1.99; 3.84 2.17; 3.84 2.61; 3.81 1.88; 3.81 2.29; 3.70 13.05; 3.70 16.00; 3.58 11.28; 3.58 13.68; 3.26 2.26; 3.25 2.57; 3.21 1.97; 3.21 2.26; 2.56 4.36; 2.55 4.31; 2.49 3.73; 2.48 3.66; 1.73 11.88; 1.72 13.65; 1.59 9.09; 1.59 10.18; 1.28 5.89; 1.26 5.87; 1.23 6.71; 1.22 6.67; 0.00 5.81 |
| 6.313 | 3,5-$Cl_2$—Ph | H | O | H | $CH(CH_3)CH_2$ | methoxycarbonyl | [$CDCl_3$] 7.52 9.59; 7.52 11.43; 7.41 2.20; 7.41 4.13; 7.40 2.42; 7.27 0.38; 7.27 0.44; 7.27 0.52; 7.26 58.48; 7.12 0.58; 7.10 0.63; 7.07 0.59; 7.05 0.57; 7.00 0.34; 4.33 0.51; 4.32 1.01; 4.30 1.16; 4.30 1.20; 4.28 1.08; 4.26 0.53; 3.80 2.08; 3.77 2.33; 3.76 2.41; 3.73 2.66; 3.70 14.35; 3.61 16.00; 3.18 2.64; 3.17 2.50; 3.14 2.31; 3.13 2.20; 2.55 4.00; 2.54 4.01; 2.49 4.10; 2.48 4.09; 2.00 1.54; 1.71 13.78; 1.70 12.66; 1.54 16.61; 1.27 6.96; 1.26 7.17; 1.23 6.24; 1.21 6.23; 0.01 0.35; 0.00 11.27 |
| 6.314 | 3,5-$F_2$—Ph | H | O | H | $CH(CH_3)CH_2$ | methoxycarbonyl | [$CDCl_3$] 7.26 26.60; 7.19 0.57; 7.18 3.31; 7.17 3.84; 7.16 4.02; 7.15 2.88; 7.14 0.58; 7.14 0.63; 7.13 0.38; 7.12 0.58; 7.09 0.68; 7.08 0.68; 7.06 0.59; 6.90 0.69; 6.90 |

TABLE 6-continued
Compounds of the general formula (I) according to the invention in which $R^2$ is hydrogen and $R^3$ is methyl and aryl is the radical
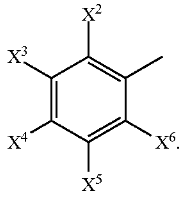
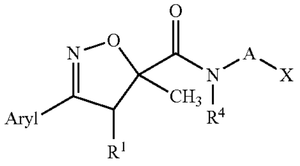
| No. | Aryl | $R^1$ | Y | $R^4$ | A | X | Physical data |
|---|---|---|---|---|---|---|---|
| | | | | | | | 1.11; 6.89 0.57; 6.88 1.39; 6.87 2.18; 6.87 1.10; 6.86 0.73; 6.85 1.11; 6.85 0.53; 4.34 0.55; 4.32 1.19; 4.31 1.37; 4.30 1.23; 4.28 1.10; 4.27 0.57; 3.79 2.23; 3.77 2.33; 3.75 2.58; 3.73 2.69; 3.70 15.36; 3.60 16.00; 3.18 2.94; 3.18 2.59; 3.14 2.55; 3.14 2.28; 2.56 4.36; 2.54 4.29; 2.49 3.61; 2.48 3.50; 1.71 14.16; 1.70 13.52; 1.56 9.85; 1.28 7.05; 1.26 7.18; 1.23 6.71; 1.22 6.61; 0.00 4.60 |
| 6.315 | 3-Cl—Ph | H | O | H | $CH(CH_3)CH_2$ | methoxycarbonyl | [$CDCl_3$] 7.66 1.69; 7.66 1.76; 7.66 3.48; 7.65 2.09; 7.65 1.88; 7.51 0.74; 7.51 0.98; 7.51 1.20; 7.51 1.17; 7.51 1.20; 7.51 0.95; 7.50 0.75; 7.49 0.95; 7.49 1.54; 7.49 1.54; 7.49 1.21; 7.48 0.96; 7.41 0.54; 7.41 0.83; 7.41 0.97; 7.41 0.76; 7.40 0.56; 7.39 1.17; 7.39 1.67; 7.39 2.00; 7.39 1.64; 7.38 0.98; 7.36 1.68; 7.36 2.32; 7.36 1.54; 7.34 2.42; 7.34 2.19; 7.32 0.71; 7.32 0.94; 7.32 0.65; 7.27 0.35; 7.27 0.47; 7.27 0.70; 7.26 26.97; 7.26 0.64; 7.26 0.49; 7.26 0.40; 7.26 0.34; 7.11 0.36; 7.10 0.38; 7.08 0.33; 4.34 0.39; 4.32 0.84; 4.32 0.54; 4.32 0.42; 4.32 0.44; 4.31 0.91; 4.30 0.88; 4.29 0.46; 4.29 0.42; 4.28 0.83; 4.27 0.40; 3.82 2.14; 3.80 2.02; 3.78 2.44; 3.75 2.32; 3.70 0.82; 3.70 16.00; 3.63 0.45; 3.59 14.93; 3.21 2.11; 3.21 2.23; 3.17 1.84; 3.16 1.98; 2.55 3.48; 2.54 3.39; 2.49 3.27; 2.48 3.23; 1.72 0.46; 1.71 11.65; 1.70 12.20; 1.59 0.80; 1.28 5.41; 1.27 0.50; 1.26 5.44; 1.25 0.35; 1.23 5.74; 1.21 5.68; 0.00 11.17 |
| 6.316 | 3-F-5-MeO—Ph | H | O | H | $CH(CH_3)CH_2$ | methoxycarbonyl | [$CDCl_3$] 7.26 11.01; 7.13 0.68; 7.10 0.71; 6.97 2.39; 6.95 0.96; 6.95 1.35; 6.92 1.29; 6.92 1.08; 6.69 0.71; 6.69 1.35; 6.68 0.82; 6.67 0.74; 6.66 1.36; 6.66 0.81; 4.32 0.64; 4.31 0.74; 4.30 0.80; 4.28 0.72; 4.27 0.33; 3.82 16.00; 3.77 2.25; 3.73 2.56; 3.69 0.62; 3.59 15.65; 3.20 2.49; 3.15 2.16; 2.49 4.46; 2.48 4.47; 1.70 13.78; 1.69 1.24; 1.27 6.79; 1.26 6.83; 0.00 2.34 |
| 6.317 | 3-F-5-MeO—Ph | H | O | H | $CH(CH_3)CH_2$ | methoxycarbonyl | [$CDCl_3$] 7.27 5.35; 7.27 4.07; 7.11 0.47; 7.09 0.47; 6.97 1.09; 6.97 1.68; 6.96 1.40; 6.95 0.83; 6.95 0.75; 6.95 0.97; 6.94 0.67; 6.93 |

TABLE 6-continued
Compounds of the general formula (I) according to the invention in which $R^2$ is hydrogen and $R^3$ is methyl and aryl is the radical
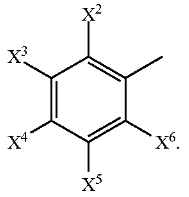
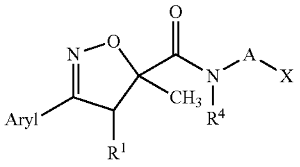
| No. | Aryl | $R^1$ | Y | $R^4$ | A | X | Physical data |
|---|---|---|---|---|---|---|---|
| | | | | | | | 0.77; 6.93 0.81; 6.92 0.90; 6.92 0.72; 6.70 0.66; 6.69 1.20; 6.68 0.61; 6.67 0.67; 6.66 1.22; 6.66 0.61; 5.30 0.39; 4.33 0.52; 4.31 0.58; 4.30 0.56; 4.29 0.54; 3.82 16.00; 3.80 2.25; 3.75 2.53; 3.70 15.89; 3.59 0.86; 3.19 2.39; 3.15 2.10; 2.56 4.11; 2.54 4.03; 1.71 0.80; 1.69 12.74; 1.28 0.37; 1.26 0.40; 1.23 6.39; 1.21 6.30; 0.00 1.36; 0.00 1.07 |
| 6.318 | 3-F—Ph | H | O | H | $CH(CH_3)CH_2$ | methoxycarbonyl | [$CDCl_3$] 7.40 1.10; 7.40 1.39; 7.40 1.48; 7.39 1.18; 7.39 1.56; 7.38 7.01; 7.38 4.10; 7.37 4.11; 7.37 2.46; 7.26 33.01; 7.15 0.49; 7.14 0.82; 7.14 0.86; 7.13 1.49; 7.12 1.32; 7.11 1.04; 7.11 0.90; 7.10 0.89; 7.07 0.44; 4.34 0.45; 4.32 0.97; 4.31 1.06; 4.30 1.04; 4.29 0.98; 4.27 0.48; 3.82 2.33; 3.80 2.10; 3.78 2.67; 3.75 2.41; 3.69 16.00; 3.58 14.29; 3.22 2.34; 3.21 2.61; 3.18 2.03; 3.17 2.29; 2.55 4.21; 2.54 4.09; 2.49 3.82; 2.48 3.77; 1.71 12.31; 1.70 13.70; 1.56 11.27; 1.28 6.03; 1.26 6.10; 1.23 6.64; 1.21 6.60; 0.01 0.37; 0.00 13.72; −0.01 0.44 |
| 6.319 | 3,5-$Cl_2$—Ph | H | O | H | $CH(CH_3)CH_2$ | methyl(methyl-sulfonyl)carbamoyl | [$CDCl_3$] 7.53 4.73; 7.53 5.49; 7.52 4.54; 7.51 4.97; 7.42 2.51; 7.41 4.34; 7.41 2.44; 7.26 28.56; 7.01 0.84; 7.00 0.86; 7.00 0.95; 4.37 0.50; 4.36 0.62; 4.35 0.62; 4.35 0.61; 4.34 0.60; 4.34 0.60; 4.33 0.63; 4.33 0.61; 4.31 0.47; 3.78 0.45; 3.77 1.68; 3.76 1.91; 3.72 1.91; 3.72 2.19; 3.26 12.15; 3.26 12.87; 3.21 13.40; 3.20 13.33; 3.17 1.94; 3.17 2.21; 3.13 1.64; 3.12 1.87; 3.12 0.67; 2.95 0.47; 2.93 0.35; 2.91 1.23; 2.89 1.44; 2.88 1.79; 2.87 1.27; 2.86 1.41; 2.84 1.51; 2.83 0.38; 2.80 1.22; 2.79 1.21; 2.76 0.55; 2.75 0.55; 2.00 0.33; 1.69 16.00; 1.55 10.62; 1.33 5.13; 1.31 5.16; 1.29 4.61; 1.28 4.55; 1.26 0.42; 0.00 5.33 |
| 6.320 | 3,5-$F_2$—Ph | H | O | H | $CH(CH_3)CH_2$ | methyl(methyl-sulfonyl)carbamoyl | [$CDCl_3$] 7.26 12.85; 7.26 16.81; 7.18 1.96; 7.18 2.02; 7.18 2.10; 7.17 1.29; 7.17 2.35; 7.16 2.58; 7.16 1.99; 7.16 1.58; 7.15 0.75; 7.15 0.82; 7.15 0.71; 7.15 0.63; 7.03 0.83; 7.01 0.86; 6.91 0.49; 6.90 0.61; 6.90 0.79; 6.90 0.41; 6.89 0.99; 6.88 1.22; 6.88 1.57; 6.88 0.70; 6.87 0.76; 6.86 |

TABLE 6-continued
Compounds of the general formula (I) according to the invention in which $R^2$ is hydrogen and $R^3$ is methyl and aryl is the radical
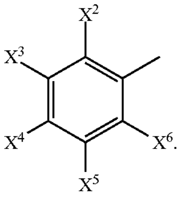
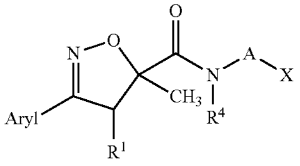
| No. | Aryl | $R^1$ | Y | $R^4$ | A | X | Physical data |
|---|---|---|---|---|---|---|---|
| | | | | | | | 0.52; 6.86 0.61; 6.86 0.79; 6.85 0.37; 4.38 0.60; 4.38 0.61; 4.36 0.76; 4.36 0.79; 4.36 0.65; 4.34 0.73; 4.33 0.38; 3.76 1.79; 3.76 2.23; 3.72 2.05; 3.71 2.58; 3.27 3.30; 3.26 4.87; 3.26 3.75; 3.26 4.40; 3.21 12.00; 3.21 16.00; 3.20 11.82; 3.19 15.74; 3.18 0.99; 3.17 2.52; 3.14 0.77; 3.13 2.14; 2.91 0.59; 2.90 0.73; 2.89 0.71; 2.89 0.84; 2.89 0.52; 2.87 1.40; 2.86 1.58; 2.85 1.50; 2.81 1.52; 2.79 1.49; 2.77 0.71; 2.75 0.69; 2.04 0.42; 1.70 15.87; 1.57 3.35; 1.57 3.87; 1.33 6.45; 1.31 6.39; 1.30 1.78; 1.28 1.75; 1.26 0.35; 0.00 1.43; 0.00 2.00 |
| 6.321 | 3,5-$Cl_2$—Ph | H | O | H | $CH(CH_3)CH_2$ | methylcarbamoyl | [$CDCl_3$] 1.28 (d, 3H); 1.71 (s, 3H); 2.35 (t, 2H); 2.74 (d, 3H); 3.17 (d, 1H); 3.75 (d, 1H); 4.24 (m, 1H); 5.65 (s br, 1H); 7.40 (t, 1H); 7.52 (d, 2H) |
| 6.322 | 3,5-$Cl_2$—Ph | H | O | H | $CH(CH_3)CH_2$ | propoxycarbonyl | [$CDCl_3$] 7.52 6.03; 7.52 5.86; 7.52 12.22; 7.51 7.98; 7.41 1.67; 7.41 4.33; 7.41 3.68; 7.41 4.10; 7.40 4.13; 7.40 2.03; 7.31 0.34; 7.27 0.39; 7.26 76.88; 7.26 63.77; 7.25 0.49; 7.24 0.40; 7.16 0.71; 7.13 0.77; 7.11 0.77; 7.09 0.72; 7.00 0.45; 4.33 0.49; 4.32 1.07; 4.30 1.34; 4.28 1.14; 4.27 0.54; 4.08 2.59; 4.06 5.38; 4.05 2.70; 3.99 2.75; 3.97 5.75; 3.95 2.90; 3.80 2.50; 3.77 2.63; 3.75 2.82; 3.73 2.99; 3.50 0.55; 3.48 0.56; 3.18 3.10; 3.17 3.19; 3.13 2.68; 3.13 2.78; 2.55 4.82; 2.54 4.78; 2.49 5.03; 2.47 5.01; 2.00 2.17; 2.00 1.83; 1.71 15.65; 1.70 16.00; 1.68 2.88; 1.66 3.01; 1.64 1.56; 1.64 0.48; 1.63 0.42; 1.62 1.57; 1.60 2.91; 1.58 3.18; 1.57 1.63; 1.55 0.46; 1.54 23.13; 1.54 19.48; 1.28 8.19; 1.26 8.55; 1.24 0.35; 1.23 7.40; 1.21 7.32; 0.97 4.30; 0.95 8.53; 0.93 4.02; 0.90 4.76; 0.88 9.86; 0.86 4.81; 0.01 0.39; 0.01 0.37; 0.00 14.42; 0.00 12.00; −0.01 0.65 |
| 6.323 | 3,5-$F_2$—Ph | H | O | H | $CH(CH_3)CH_2$ | propoxycarbonyl | [$CDCl_3$] 7.26 14.19; 7.26 16.69; 7.19 0.47; 7.19 0.56; 7.18 0.62; 7.17 3.27; 7.17 4.43; 7.17 4.41; 7.17 3.69; 7.16 3.82; 7.15 4.76; 7.15 4.60; 7.15 3.62; 7.15 2.22; 7.14 1.30; 7.14 1.32; 7.13 1.20; 7.10 0.75; 6.90 0.71; 6.90 |

TABLE 6-continued
Compounds of the general formula (I) according to the invention in which $R^2$ is hydrogen and $R^3$ is methyl and aryl is the radical
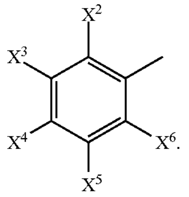
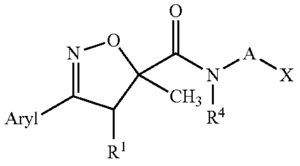
| No. | Aryl | $R^1$ | Y | $R^4$ | A | X | Physical data |
|---|---|---|---|---|---|---|---|
| | | | | | | | 0.94; 6.90 1.20; 6.89 0.97; 6.89 0.65; 6.89 0.45; 6.88 1.45; 6.88 1.91; 6.87 2.39; 6.87 1.90; 6.87 1.24; 6.87 0.78; 6.86 0.77; 6.86 0.98; 6.85 1.20; 6.85 0.95; 6.85 0.60; 6.84 0.37; 4.34 0.48; 4.34 0.55; 4.33 1.17; 4.32 1.16; 4.31 1.42; 4.31 1.41; 4.29 1.16; 4.29 1.19; 4.27 0.58; 4.08 2.18; 4.08 2.47; 4.07 4.54; 4.06 5.13; 4.05 2.29; 4.05 2.59; 3.99 2.14; 3.99 2.45; 3.97 4.44; 3.97 5.06; 3.96 2.25; 3.95 2.51; 3.79 2.12; 3.79 2.42; 3.77 2.07; 3.77 2.36; 3.75 2.44; 3.75 2.79; 3.73 2.36; 3.73 2.71; 3.18 4.22; 3.18 2.88; 3.14 3.65; 3.14 2.52; 2.55 4.65; 2.54 4.55; 2.49 4.50; 2.48 4.42; 1.71 12.69; 1.71 14.23; 1.70 14.06; 1.70 16.00; 1.68 2.94; 1.66 2.87; 1.65 1.56; 1.64 0.37; 1.64 0.38; 1.63 0.38; 1.63 0.43; 1.62 1.40; 1.60 2.80; 1.58 6.14; 1.57 1.53; 1.55 0.39; 1.55 0.42; 1.28 6.26; 1.28 6.99; 1.26 6.52; 1.26 7.13; 1.23 6.38; 1.23 7.12; 1.22 6.39; 1.21 7.04; 0.97 3.60; 0.97 4.15; 0.95 7.12; 0.95 8.37; 0.94 3.34; 0.93 3.78; 0.90 3.67; 0.90 4.17; 0.88 7.07; 0.88 8.08; 0.86 3.26; 0.86 3.65; 0.00 2.89; 0.00 3.48 |
| 6.324 | 3,5-$Cl_2$—Ph | H | O | H | $CH(CH_3)CH_2$ | sec-butoxycarbonyl | [$CDCl_3$] 7.52 7.75; 7.52 9.89; 7.51 5.54; 7.51 5.45; 7.51 5.41; 7.41 2.05; 7.41 5.32; 7.40 5.14; 7.40 1.86; 7.27 0.41; 7.27 0.48; 7.26 0.58; 7.26 129.76; 7.25 1.01; 7.25 0.83; 7.20 0.50; 7.18 0.50; 7.16 0.51; 7.15 0.45; 7.14 0.48; 7.00 0.73; 4.91 0.42; 4.89 0.90; 4.88 0.91; 4.86 0.48; 4.83 0.33; 4.82 0.38; 4.81 0.62; 4.81 0.66; 4.80 0.63; 4.79 0.67; 4.78 0.37; 4.77 0.39; 4.33 0.34; 4.32 0.82; 4.31 0.66; 4.30 0.72; 4.30 1.05; 4.29 0.97; 4.29 0.59; 4.28 0.66; 4.28 0.74; 4.28 0.86; 4.27 0.39; 4.27 0.32; 4.26 0.40; 3.79 2.36; 3.77 2.96; 3.75 2.69; 3.73 3.39; 3.50 0.35; 3.48 0.36; 3.18 3.67; 3.13 3.20; 2.53 4.12; 2.51 4.23; 2.47 3.33; 2.46 1.90; 2.45 3.41; 2.04 0.45; 2.00 3.55; 1.71 16.00; 1.70 10.59; 1.70 8.64; 1.67 0.41; 1.65 0.57; 1.63 1.01; 1.61 1.15; 1.60 0.52; 1.60 0.98; 1.58 0.92; 1.58 0.99; 1.58 0.44; 1.57 0.67; 1.57 |

TABLE 6-continued
Compounds of the general formula (I) according to the invention in which $R^2$ is hydrogen and $R^3$ is methyl and aryl is the radical
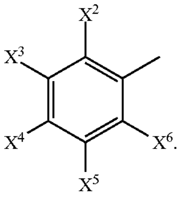
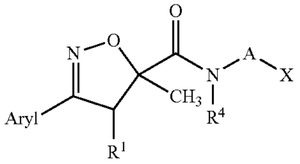
| No. | Aryl | $R^1$ | Y | $R^4$ | A | X | Physical data |
|---|---|---|---|---|---|---|---|
| | | | | | | | 1.57; 1.55 1.73; 1.54 33.77; 1.52 0.43; 1.52 0.92; 1.51 0.80; 1.50 0.58; 1.50 1.05; 1.49 0.60; 1.48 0.66; 1.48 0.76; 1.46 0.48; 1.46 0.34; 1.27 5.17; 1.27 5.37; 1.26 5.49; 1.25 5.35; 1.24 10.10; 1.22 4.44; 1.22 14.54; 1.21 3.98; 1.20 5.05; 1.16 8.06; 1.15 8.06; 0.93 2.84; 0.92 2.39; 0.91 6.03; 0.90 4.97; 0.89 2.72; 0.89 2.26; 0.88 0.88; 0.86 2.50; 0.85 2.62; 0.84 5.19; 0.84 5.45; 0.82 2.28; 0.82 2.35; 0.01 0.75; 0.00 30.04; −0.01 0.94 |
| 6.325 | 3,5-$F_2$—Ph | H | O | H | $CH(CH_3)CH_2$ | sec-butoxycarbonyl | [$CDCl_3$] 7.51 0.35; 7.50 0.37; 7.44 0.35; 7.37 0.52; 7.33 0.64; 7.33 0.73; 7.26 34.81; 7.24 16.12; 7.22 1.04; 7.15 8.75; 6.89 1.60; 6.89 1.44; 6.87 2.90; 6.87 3.19; 6.86 2.35; 6.85 2.59; 6.85 2.24; 4.91 0.72; 4.89 1.48; 4.87 1.78; 4.86 1.29; 4.84 0.69; 4.82 0.70; 4.81 1.30; 4.79 1.50; 4.78 1.11; 4.30 2.39; 4.28 2.28; 3.79 2.10; 3.77 2.91; 3.75 3.07; 3.72 3.31; 3.71 1.33; 3.18 4.14; 3.16 2.51; 3.14 3.63; 3.12 2.05; 2.53 4.08; 2.52 6.02; 2.50 2.57; 2.47 3.78; 2.46 5.58; 2.44 2.31; 2.04 0.83; 2.03 0.42; 2.00 0.42; 1.78 0.45; 1.76 0.55; 1.71 12.89; 1.70 16.00; 1.65 1.46; 1.63 1.83; 1.61 2.25; 1.60 2.40; 1.58 2.45; 1.56 3.15; 1.55 15.65; 1.53 8.81; 1.51 2.20; 1.50 1.97; 1.48 1.81; 1.46 1.32; 1.44 0.93; 1.43 0.68; 1.41 0.57; 1.40 0.47; 1.38 0.51; 1.38 0.63; 1.27 7.14; 1.26 11.02; 1.24 10.90; 1.22 15.20; 1.21 12.20; 1.16 6.91; 1.14 9.84; 1.13 3.99; 1.11 0.64; 1.10 0.56; 1.07 0.45; 1.06 0.47; 1.05 0.43; 1.04 0.46; 1.03 0.41; 1.00 0.48; 0.99 0.47; 0.98 0.47; 0.97 0.52; 0.95 0.63; 0.93 0.78; 0.92 3.32; 0.90 7.29; 0.89 6.36; 0.85 3.67; 0.83 7.15; 0.82 5.65; 0.80 1.95; 0.78 0.42; 0.01 0.35; 0.00 6.95; −0.02 3.41 |
| 6.326 | 3,5-$Cl_2$—Ph | H | O | H | $CH(COOCH_3)CH_2$ | methoxycarbonyl | [$CDCl_3$] 1.71, 1.75 (ds, 3H); 2.75-3.21 (m, 3H); 3.64, 3.70 (ds, 3H); 3.72, 3.78 (ds, 3H); 3.77 (d, 1H); 4.82 (m, 1H); 7.40 (m, 1H); 7.52 (m, 2H); 7.63 (br, 1H). |
| 6.327 | 3,5-$Cl_2$—Ph | H | O | H | CH(cycloPr) | c-Pr | |

TABLE 6-continued
Compounds of the general formula (I) according to the invention in which $R^2$ is hydrogen and $R^3$ is methyl and aryl is the radical
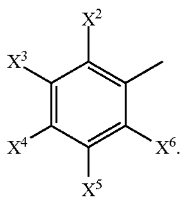
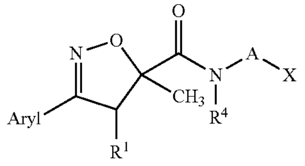
| No. | Aryl | $R^1$ | Y | $R^4$ | A | X | Physical data |
|---|---|---|---|---|---|---|---|
| 6.328 | 3,5-$F_2$—Ph | H | O | H | CH(cycloPr) | c-Pr | [$CDCl_3$] 7.52 0.50; 7.27 0.34; 7.27 0.42; 7.26 92.76; 7.18 1.68; 7.18 2.00; 7.17 1.11; 7.17 1.17; 7.16 2.04; 7.16 1.72; 7.14 0.33; 7.00 0.48; 6.91 0.43; 6.90 0.73; 6.90 0.38; 6.89 0.84; 6.88 1.50; 6.88 0.76; 6.87 0.43; 6.86 0.76; 6.86 0.37; 6.80 0.42; 6.78 0.42; 3.78 2.75; 3.73 3.15; 3.19 2.87; 3.15 2.50; 3.07 0.49; 3.05 1.08; 3.03 1.06; 3.01 0.50; 1.73 16.00; 1.55 0.38; 1.55 0.43; 1.54 73.05; 1.53 0.57; 1.53 0.40; 1.53 0.38; 0.95 0.47; 0.94 0.85; 0.93 0.54; 0.92 0.57; 0.92 0.94; 0.91 0.54; 0.90 0.72; 0.90 0.56; 0.89 0.85; 0.88 0.58; 0.88 0.51; 0.87 0.87; 0.86 0.51; 0.85 0.42; 0.56 0.33; 0.56 0.33; 0.55 0.97; 0.54 0.68; 0.54 0.62; 0.54 0.63; 0.53 0.81; 0.53 0.65; 0.52 0.47; 0.52 0.50; 0.51 0.47; 0.50 0.35; 0.50 0.45; 0.49 0.43; 0.49 0.36; 0.48 0.46; 0.48 0.37; 0.48 0.71; 0.47 0.68; 0.47 0.75; 0.47 0.60; 0.46 0.92; 0.45 0.81; 0.45 0.80; 0.45 0.65; 0.45 0.57; 0.44 1.13; 0.44 0.64; 0.43 0.75; 0.43 0.48; 0.42 0.85; 0.41 0.34; 0.41 0.34; 0.40 0.38; 0.38 0.50; 0.37 0.80; 0.36 0.68; 0.35 1.10; 0.35 1.20; 0.35 0.68; 0.35 0.83; 0.34 1.22; 0.34 1.13; 0.33 1.39; 0.33 0.97; 0.33 1.20; 0.32 1.19; 0.31 1.22; 0.30 0.67; 0.29 0.57; 0.27 0.42; 0.26 0.66; 0.25 1.30; 0.25 1.58; 0.24 1.35; 0.23 1.57; 0.23 1.23; 0.23 0.62; 0.22 0.48; 0.01 1.28; 0.00 48.23; −0.01 1.61; −0.01 0.38 |
| 6.329 | 3,5-$Cl_2$—Ph | H | O | H | CH(iPr) | methoxycarbonyl | [$CDCl_3$] 0.86-0.98 (m, 6H); 1.74 (s, 3H); 2.13-2.27 (m, 1H); 3.18 (d, 1H); 3.75 (s, 3H); 3.77 (d, 1H); 4.47 (m, 1H); 7.69 (br, 1H); 7.40 (m, 1H); 7.52 (m, 2H). |
| 6.330 | 3,5-$Cl_2$—Ph | H | O | H | CH(iPr)$CH_2$ | methoxycarbonyl | [$CDCl_3$] 16.08 0.40; 7.53 3.70; 7.52 4.31; 7.52 10.46; 7.51 6.34; 7.41 1.61; 7.41 3.31; 7.41 2.32; 7.40 0.97; 7.36 0.41; 7.33 0.34; 7.31 0.38; 7.31 1.21; 7.31 0.59; 7.30 0.60; 7.30 0.55; 7.30 0.48; 7.30 0.52; 7.30 0.39; 7.30 0.44; 7.30 0.44; 7.30 0.37; 7.30 0.39; 7.30 0.42; 7.30 0.54; 7.29 0.45; 7.29 0.55; 7.29 0.60; 7.29 0.50; 7.28 0.57; 7.28 0.66; 7.28 0.63; 7.28 0.66; 7.28 0.71; 7.28 0.63; 7.28 |

TABLE 6-continued
Compounds of the general formula (I) according to the invention in which $R^2$ is hydrogen and $R^3$ is methyl and aryl is the radical
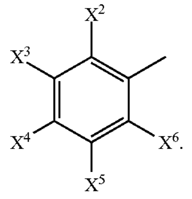
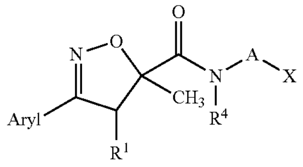
| No. | Aryl | $R^1$ | Y | $R^4$ | A | X | Physical data |
|---|---|---|---|---|---|---|---|
| | | | | | | | 0.62; 7.28 0.71; 7.28 0.58; 7.28 0.72; 7.28 0.73; 7.27 0.77; 7.27 0.81; 7.27 0.85; 7.27 0.88; 7.27 1.25; 7.27 1.36; 7.27 1.47; 7.27 1.85; 7.27 2.15; 7.27 2.39; 7.27 2.47; 7.27 3.43; 7.26 4.39; 7.26 5.62; 7.26 7.75; 7.26 864.63; 7.25 1.02; 7.23 0.35; 7.23 0.36; 7.21 1.04; 7.20 0.32; 7.20 0.37; 7.20 0.39; 7.19 0.38; 7.16 0.42; 7.16 0.40; 7.05 0.56; 7.04 0.51; 7.03 0.52; 7.00 4.68; 4.08 0.39; 4.05 0.56; 4.04 0.70; 4.03 0.61; 4.02 0.53; 3.80 2.10; 3.79 1.44; 3.76 2.20; 3.74 1.51; 3.68 16.00; 3.55 10.07; 3.49 0.78; 3.18 3.06; 3.13 2.57; 2.60 0.43; 2.59 0.62; 2.56 1.43; 2.55 1.16; 2.53 1.54; 2.51 1.44; 2.49 1.10; 2.47 0.83; 2.46 0.93; 2.45 0.94; 2.43 0.38; 2.01 0.59; 1.89 0.41; 1.87 0.49; 1.85 0.56; 1.84 0.46; 1.82 0.82; 1.81 0.70; 1.79 0.54; 1.73 7.48; 1.71 11.87; 1.59 0.66; 1.57 0.47; 1.54 397.48; 1.51 0.66; 1.49 0.67; 1.48 0.36; 1.44 0.44; 1.33 0.33; 1.28 0.46; 1.25 0.88; 0.96 3.43; 0.95 3.53; 0.94 3.41; 0.93 3.45; 0.88 5.26; 0.86 5.19; 0.84 5.53; 0.83 0.71; 0.82 5.42; 0.15 1.45; 0.10 0.41; 0.05 0.64; 0.05 0.52; 0.05 0.39; 0.04 0.35; 0.04 0.32; 0.04 0.33; 0.04 0.32; 0.04 0.37; 0.04 0.40; 0.03 0.35; 0.03 0.37; 0.03 0.42; 0.03 0.42; 0.02 0.40; 0.02 0.46; 0.02 0.39; 0.02 0.41; 0.02 0.61; 0.02 0.62; 0.02 0.52; 0.02 0.57; 0.01 0.73; 0.01 0.73; 0.01 0.95; 0.01 1.24; 0.01 1.59; 0.01 11.71; 0.01 3.39; 0.01 3.45; 0.00 4.16; 0.00 6.15; 0.00 461.74; −0.01 4.09; −0.01 12.15; −0.02 0.48; −0.05 0.61; −0.15 1.42; −2.35 0.33 |
| 6.331 | 3,5-$F_2$—Ph | H | O | H | $CH_2$ | (2-hydroxyethyl)-carbamoyl | [DMSO-$D_6$] 1.55 (s, 3H); 3.12 (m, 2H); 3.37 (m, 2H); 3.38 (d, 1H); 3.69 (m, 2H); 3.71 (d, 1H); 4.63 (t, 1H); 7.40 (m, 3H); 7.81 (t, 1H); 8.08 (m, 1H). |
| 6.332 | 3,5-$Cl_2$—Ph | H | O | H | $CH_2$ | (cyclopropylsulfonyl)-carbamoyl | [$CDCl_3$] 1.06 (m, 2H); 1.32 (m, 2H); 1.74 (s, 3H); 2.83 (m, 2H); 3.22 (d, 1H); 3.79 (d, 1H); 3.9-4.2 (m, 2H); 7.4 (s br, 1H); 7.40 (s, 1H); 7.51 (s, 2H). |

TABLE 6-continued

Compounds of the general formula (I) according to the invention in which $R^2$ is hydrogen and $R^3$ is methyl and aryl is the radical

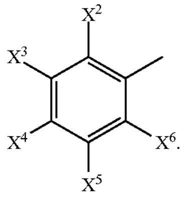

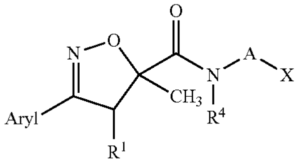

| No. | Aryl | $R^1$ | Y | $R^4$ | A | X | Physical data |
|---|---|---|---|---|---|---|---|
| 6.333 | 3,5-$F_2$—Ph | H | O | H | $CH_2$ | (cyclopropylsulfonyl)-carbamoyl | [DMSO-$D_6$] 1.00 (m, 4H); 1.58 (s, 3H); 2.89 (m, 1H); 3.42 (d, 1H); 3.72 (d, 1H); 3.78 (d, 2H); 7.42 (m, 3H); 8.24 (t br, 1H). |
| 6.334 | 3,5-$Cl_2$—Ph | H | O | H | $CH_2$ | (ethylsulfonyl)-carbamoyl | [DMSO-$D_6$] 1.18 (t, 3H); 1.57 (s, 3H); 3.26 (q, 2H); 3.43 (d, 1H); 3.72 (d, 1H); 3.78 (d, 2H); 7.72 (m, 2H); 7.78 (m, 1H); 8.18 (t br, 1H). |
| 6.335 | 3,5-$F_2$—Ph | H | O | H | $CH_2$ | (ethylsulfonyl)-carbamoyl | [DMSO-$D_6$] 1.18 (t, 3H); 1.56 (s, 3H); 3.24 (q, 2H); 3.40 (d, 1H); 3.71 (d, 1H); 3.77 (d, 2H); 7.41 (m, 3H); 8.23 (t br, 1H);. |
| 6.336 | 3,5-$F_2$—Ph | H | O | H | $CH_2$ | (hydroxyimino)-methyl | diastereomer D1: [$CDCl_3$] 1.75 (s, 3H); 3.22 (d, 1H); 3.80 (d, 1H); 4.18 (m, 2H); 6.89 (m, 1H); 7.17 (m, 2H); 7.31 (brt, 1H); 7.43 (t, 1H); 8.05 (brs, 1H). diastereomer D2: 1.74 (s, 3H); 3.21 (d, 1H); 3.79 (d, 1H); 4.04 (m, 2H); 6.74 (t, 1H); 6.89 (m, 1H); 7.17 (m, 2H); 7.28 (brt, 1H); 7.71 (brs, 1H). |
| 6.337 | 3,5-$Cl_2$—Ph | H | O | H | $CH_2$ | (isopropylsulfonyl)-carbamoyl | [DMSO-$D_6$] 1.23 (d, 6H); 1.57 (s, 3H); 3.45 (d, 1H); 3.53 (pent, 1H); 3.72 (d, 1H); 3.78 (d, 2H); 7.72 (m, 2H); 7.76 (m, 1H); 8.24 (t br, 1H). |
| 6.338 | 3,5-$F_2$—Ph | H | O | H | $CH_2$ | (isopropylsulfonyl)-carbamoyl | [DMSO-$D_6$] 1.24 (d, 6H); 1.56 (s, 3H); 3.40 (d, 1H); 3.52 (sept, 1H); 3.72 (d, 1H); 3.78 (d, 2H); 7.40 (m, 3H); 8.23 (t br, 1H). |
| 6.339 | 3,5-$Cl_2$—Ph | H | O | H | $CH_2$ | (methylsulfonyl)-carbamoyl | [DMSO-$D_6$] 1.57 (s, 3H); 3.16 (s, 3H); 3.46 (d, 1H); 3.73 (d, 1H); 3.78 (d, 2H); 7.72 (m, 2H); 7.74 (m, 1H); 8.23 (t br, 1H). |
| 6.340 | 3,5-$F_2$—Ph | H | O | H | $CH_2$ | (methylsulfonyl)-carbamoyl | [DMSO-$D_6$] 1.59 (s, 3H); 3.16 (s, 3H); 3.43 (d, 1H); 3.71 (d, 1H); 3.78 (d, 2H); 7.42 (m, 3H); 8.23 (t br, 1H). |
| 6.341 | 3-Cl—Ph | H | O | H | $CH_2$ | (propan-2-yloxy)carbonyl | [$CDCl_3$] 7.66 1.33; 7.65 2.40; 7.65 1.51; 7.51 0.77; 7.51 1.28; 7.51 0.78; 7.49 0.98; 7.49 1.64; 7.49 0.98; 7.41 0.56; 7.41 0.74; 7.40 0.60; 7.39 1.22; 7.39 1.41; 7.38 1.05; 7.36 2.00; 7.34 2.26; 7.32 0.92; 7.29 0.44; 7.28 0.63; 7.26 17.54; 5.09 0.49; 5.08 1.23; 5.06 1.64; 5.05 1.22; 5.03 0.48; 4.07 0.93; 4.06 0.91; 4.03 2.03; 4.01 1.95; 3.95 1.96; 3.94 1.98; 3.91 0.99; 3.89 0.91; 3.83 2.52; 3.79 2.89; 3.24 2.74; 3.20 2.39; 1.75 14.85; 1.56 4.00; 1.26 0.42; 1.25 16.00; 1.23 15.68; 0.00 6.63 |
| 6.342 | 3-F—Ph | H | O | H | $CH_2$ | (propan-2-yloxy)carbonyl | [$CDCl_3$] 7.40 0.98; 7.39 1.05; 7.39 1.24; 7.38 1.14; 7.38 4.91; 7.37 3.20; 7.37 3.33; 7.36 1.78; 7.29 0.67; 7.27 0.36; 7.27 0.36; 7.26 |

TABLE 6-continued
Compounds of the general formula (I) according to the invention in which $R^2$ is hydrogen and $R^3$ is methyl and aryl is the radical
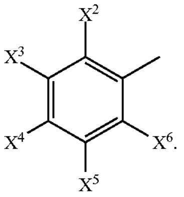
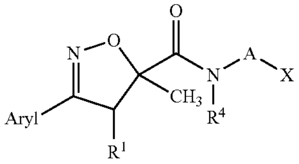
| No. | Aryl | $R^1$ | Y | $R^4$ | A | X | Physical data |
|---|---|---|---|---|---|---|---|
| | | | | | | | 11.52; 7.15 0.43; 7.14 0.45; 7.14 0.53; 7.13 0.67; 7.13 0.85; 7.12 0.92; 7.11 0.52; 7.11 0.55; 7.10 0.36; 5.09 0.47; 5.08 1.21; 5.06 1.63; 5.04 1.24; 5.03 0.50; 4.07 0.95; 4.06 0.96; 4.03 2.07; 4.01 2.06; 3.96 2.05; 3.94 2.11; 3.91 0.96; 3.90 0.96; 3.83 2.69; 3.79 3.09; 3.25 2.95; 3.21 2.57; 1.75 15.82; 1.58 1.93; 1.25 0.39; 1.24 15.96; 1.23 16.00; 0.00 2.62 |
| 6.343 | 3,5-$Cl_2$—Ph | H | O | H | $CH_2$ | 1,1-dioxidotetrahydro-thiophen-3-yl | [$CDCl_3$] 7.52 1.63; 7.52 11.95; 7.51 13.66; 7.44 2.33; 7.43 2.45; 7.43 3.99; 7.43 4.09; 7.43 2.07; 7.43 1.93; 7.31 0.62; 7.27 0.50; 7.27 0.55; 7.27 0.71; 7.27 0.93; 7.27 1.33; 7.26 251.03; 7.25 0.82; 7.21 0.43; 7.04 0.87; 7.00 1.45; 4.13 0.46; 4.11 0.54; 3.79 2.83; 3.78 2.83; 3.75 3.25; 3.74 3.26; 3.54 0.42; 3.52 0.85; 3.51 0.80; 3.49 0.85; 3.49 1.06; 3.48 0.46; 3.47 0.64; 3.47 0.67; 3.45 1.05; 3.43 1.47; 3.42 0.84; 3.40 0.75; 3.38 1.53; 3.37 0.88; 3.35 0.72; 3.33 0.89; 3.32 1.06; 3.30 0.79; 3.28 0.75; 3.27 0.48; 3.25 0.44; 3.24 0.60; 3.23 0.86; 3.23 5.40; 3.22 1.14; 3.21 1.71; 3.20 1.67; 3.19 1.06; 3.18 5.79; 3.16 1.11; 3.08 0.64; 3.06 0.74; 3.06 0.87; 3.05 0.73; 3.05 0.66; 3.03 0.70; 3.03 0.56; 3.02 0.62; 3.02 0.50; 3.00 0.48; 2.82 0.72; 2.79 1.49; 2.79 0.56; 2.77 1.15; 2.76 1.19; 2.75 0.33; 2.74 1.19; 2.72 0.48; 2.71 0.50; 2.71 0.52; 2.70 0.60; 2.68 0.47; 2.67 0.44; 2.67 0.38; 2.33 0.38; 2.33 0.40; 2.32 0.58; 2.32 0.51; 2.31 0.56; 2.31 0.73; 2.30 0.54; 2.30 0.76; 2.29 0.58; 2.29 0.63; 2.28 0.63; 2.28 0.51; 2.27 0.45; 2.27 0.32; 2.26 0.34; 2.05 2.56; 1.94 0.68; 1.92 0.70; 1.91 0.80; 1.90 0.58; 1.89 0.72; 1.89 0.52; 1.88 0.72; 1.87 0.33; 1.86 0.58; 1.86 0.33; 1.73 15.81; 1.73 16.00; 1.63 0.39; 1.59 2.40; 1.57 13.88; 1.32 0.38; 1.30 0.68; 1.29 0.37; 1.28 0.73; 1.26 1.46; 1.24 0.73; 0.01 2.80; 0.01 0.50; 0.00 0.54; 0.00 109.72; −0.01 1.14; −0.01 0.91; −0.01 0.83; −0.01 3.20; −0.01 0.45; −0.15 0.33 |

TABLE 6-continued
Compounds of the general formula (I) according to the invention in which $R^2$ is hydrogen and $R^3$ is methyl and aryl is the radical
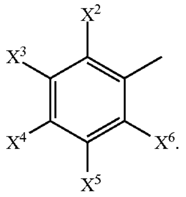
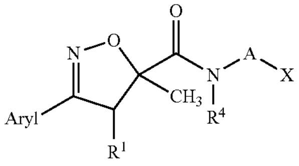
| No. | Aryl | $R^1$ | Y | $R^4$ | A | X | Physical data |
|---|---|---|---|---|---|---|---|
| 6.344 | 3,5-$F_2$—Ph | H | O | H | $CH_2$ | 1,1-dioxidotetrahydro-thiophen-3-yl | [$CDCl_3$] 7.52 1.17; 7.31 0.60; 7.27 0.34; 7.27 0.36; 7.27 0.45; 7.27 0.53; 7.27 0.57; 7.27 0.63; 7.27 0.79; 7.27 0.94; 7.27 1.40; 7.27 2.45; 7.26 208.93; 7.26 7.88; 7.26 5.58; 7.26 4.26; 7.26 3.38; 7.26 2.65; 7.26 2.11; 7.25 1.77; 7.25 1.45; 7.25 1.26; 7.25 1.09; 7.25 0.92; 7.25 0.85; 7.25 0.76; 7.25 0.70; 7.25 0.65; 7.25 0.63; 7.25 0.59; 7.25 0.49; 7.24 0.45; 7.24 0.36; 7.24 0.34; 7.24 0.36; 7.24 0.36; 7.21 0.62; 7.18 0.55; 7.18 0.43; 7.17 2.83; 7.17 3.50; 7.16 2.04; 7.15 1.95; 7.15 3.47; 7.15 2.93; 7.14 0.50; 7.13 0.57; 7.05 0.92; 7.00 1.21; 6.93 0.47; 6.93 0.47; 6.92 0.80; 6.92 0.85; 6.92 0.44; 6.91 0.92; 6.90 0.99; 6.90 1.65; 6.90 1.66; 6.90 0.90; 6.89 0.86; 6.89 0.50; 6.88 0.51; 6.88 0.84; 6.88 0.86; 6.87 0.43; 3.78 2.72; 3.78 2.71; 3.74 3.17; 3.73 3.16; 3.54 0.46; 3.53 0.90; 3.51 0.80; 3.49 1.75; 3.49 0.42; 3.48 0.63; 3.47 0.64; 3.45 1.08; 3.43 1.50; 3.42 0.87; 3.40 0.77; 3.39 1.61; 3.37 0.90; 3.35 0.70; 3.34 0.95; 3.32 1.08; 3.31 0.79; 3.29 0.76; 3.27 0.47; 3.25 0.42; 3.24 0.58; 3.23 5.84; 3.22 1.11; 3.21 1.92; 3.20 1.63; 3.19 5.41; 3.18 1.72; 3.16 1.19; 3.08 0.55; 3.08 0.59; 3.06 0.62; 3.06 1.06; 3.05 0.83; 3.05 0.44; 3.04 0.62; 3.03 0.83; 3.02 0.71; 3.02 0.46; 3.00 0.44; 3.00 0.41; 2.82 0.77; 2.79 1.40; 2.79 0.56; 2.77 1.20; 2.76 1.22; 2.75 0.36; 2.74 1.21; 2.72 0.57; 2.71 0.61; 2.70 0.73; 2.68 0.46; 2.33 0.41; 2.32 0.56; 2.32 0.55; 2.31 0.55; 2.31 0.68; 2.30 0.58; 2.30 0.76; 2.29 0.59; 2.29 0.62; 2.28 0.63; 2.28 0.57; 2.27 0.44; 2.27 0.36; 2.26 0.33; 2.05 1.29; 1.94 0.36; 1.94 0.78; 1.92 0.79; 1.91 0.92; 1.91 0.63; 1.89 0.87; 1.89 0.67; 1.88 0.79; 1.87 0.38; 1.86 0.61; 1.86 0.33; 1.74 15.73; 1.73 16.00; 1.58 13.90; 1.28 0.36; 1.26 0.73; 1.24 0.34; 0.15 0.36; 0.05 0.35; 0.01 0.32; 0.01 0.36; 0.01 2.50; 0.01 0.69; 0.01 0.70; 0.00 0.89; 0.00 93.62; −0.01 2.62; −0.15 0.34 |

TABLE 6-continued
Compounds of the general formula (I) according to the invention in which $R^2$ is hydrogen and $R^3$ is methyl and aryl is the radical
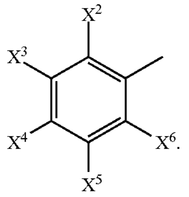
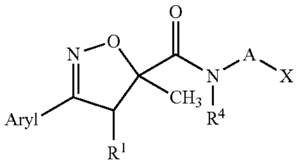
| No. | Aryl | $R^1$ | Y | $R^4$ | A | X | Physical data |
|---|---|---|---|---|---|---|---|
| 6.345 | 3-F—Ph | H | O | H | $CH_2$ | 1,1-dioxidotetrahydro-thiophen-3-yl | [$CDCl_3$] 7.43 0.57; 7.41 0.43; 7.41 1.71; 7.39 2.32; 7.39 2.29; 7.39 2.91; 7.38 2.08; 7.38 1.86; 7.38 2.86; 7.38 5.97; 7.37 2.88; 7.37 1.40; 7.37 1.26; 7.36 1.75; 7.36 2.11; 7.36 1.52; 7.35 0.56; 7.26 33.79; 7.17 0.60; 7.17 0.66; 7.17 0.69; 7.17 0.98; 7.16 0.61; 7.16 0.57; 7.15 1.18; 7.15 1.14; 7.15 1.51; 7.14 0.95; 7.14 0.73; 7.13 0.94; 7.13 1.38; 7.12 1.04; 7.12 1.05; 7.11 0.90; 3.81 2.80; 3.81 2.77; 3.77 3.23; 3.77 3.20; 3.53 0.41; 3.52 0.88; 3.50 0.80; 3.48 1.36; 3.47 1.19; 3.45 1.06; 3.43 1.39; 3.42 0.84; 3.40 0.73; 3.38 1.51; 3.37 0.88; 3.35 0.70; 3.34 0.62; 3.33 0.42; 3.33 1.06; 3.31 0.81; 3.29 0.73; 3.28 0.48; 3.26 5.67; 3.25 0.42; 3.24 0.65; 3.23 0.85; 3.22 5.39; 3.21 1.91; 3.20 1.16; 3.19 2.16; 3.18 1.88; 3.17 0.63; 3.16 1.15; 3.07 0.62; 3.06 0.59; 3.06 0.68; 3.05 0.71; 3.05 0.92; 3.05 0.72; 3.05 0.71; 3.05 0.68; 3.04 0.47; 3.03 0.60; 3.03 0.67; 3.03 0.69; 3.03 0.69; 3.02 0.52; 3.02 0.52; 3.02 0.65; 3.02 0.50; 3.01 0.49; 3.00 0.42; 3.00 0.46; 2.99 0.45; 2.82 0.72; 2.80 1.46; 2.79 0.56; 2.77 1.14; 2.76 1.21; 2.75 0.37; 2.74 1.13; 2.74 0.56; 2.72 0.50; 2.71 0.52; 2.71 0.49; 2.70 0.67; 2.68 0.44; 2.68 0.44; 2.33 0.39; 2.32 0.41; 2.32 0.54; 2.31 0.52; 2.31 0.56; 2.30 0.63; 2.30 0.62; 2.29 0.70; 2.29 0.61; 2.29 0.61; 2.28 0.59; 2.28 0.52; 2.27 0.42; 2.27 0.33; 1.94 0.66; 1.92 0.69; 1.91 0.79; 1.90 0.57; 1.89 0.73; 1.89 0.48; 1.88 0.58; 1.88 0.68; 1.86 0.56; 1.85 0.35; 1.74 15.70; 1.73 16.00; 1.63 0.56; 0.01 0.40; 0.00 16.29; −0.01 0.50 |
| 6.346 | Ph | H | O | H | $CH_2$ | 1,1-dioxidotetrahydro-thiophen-3-yl | [$CDCl_3$] 7.65 0.34; 7.65 3.59; 7.64 4.05; 7.64 1.64; 7.63 1.37; 7.63 4.03; 7.62 4.80; 7.52 1.04; 7.47 0.39; 7.47 0.34; 7.45 1.20; 7.45 1.40; 7.45 0.89; 7.44 2.47; 7.44 7.20; 7.43 3.59; 7.43 1.27; 7.42 1.78; 7.42 4.08; 7.41 0.57; 7.40 1.09; 7.40 0.54; 7.40 0.70; 7.40 0.80; 7.31 0.39; 7.31 0.34; 7.27 0.60; 7.26 180.50; 7.26 1.93; 7.26 1.39; 7.26 1.13; 7.25 0.90; 7.25 |

TABLE 6-continued
Compounds of the general formula (I) according to the invention in which $R^2$ is hydrogen and $R^3$ is methyl and aryl is the radical
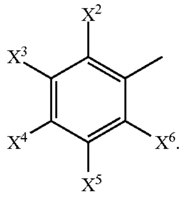
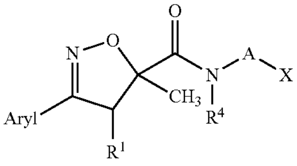
| No. | Aryl | $R^1$ | Y | $R^4$ | A | X | Physical data |
|---|---|---|---|---|---|---|---|
| | | | | | | | 0.78; 7.25 0.64; 7.25 0.53; 7.25 0.48; 7.25 0.34; 7.14 0.50; 7.12 0.79; 7.00 1.06; 3.84 2.78; 3.83 2.83; 3.79 3.19; 3.79 3.23; 3.52 0.38; 3.51 0.86; 3.49 0.89; 3.48 0.42; 3.47 1.10; 3.46 0.68; 3.45 0.65; 3.44 1.05; 3.42 1.41; 3.41 0.85; 3.39 0.74; 3.38 1.50; 3.36 0.88; 3.34 1.19; 3.33 1.39; 3.31 0.79; 3.29 5.75; 3.28 0.47; 3.24 4.92; 3.23 0.73; 3.22 0.64; 3.21 1.73; 3.20 1.19; 3.19 1.63; 3.18 2.20; 3.17 0.63; 3.16 1.11; 3.07 0.76; 3.05 0.80; 3.04 0.80; 3.04 0.82; 3.03 0.55; 3.02 0.80; 3.01 0.61; 3.01 0.57; 3.01 0.56; 2.99 0.53; 2.81 0.78; 2.79 1.68; 2.78 0.59; 2.76 1.22; 2.75 1.33; 2.74 0.36; 2.73 1.17; 2.72 0.48; 2.71 0.53; 2.70 0.59; 2.69 0.64; 2.68 0.57; 2.67 0.53; 2.67 0.49; 2.32 0.36; 2.32 0.43; 2.31 0.52; 2.31 0.51; 2.30 0.56; 2.30 0.59; 2.29 0.62; 2.29 0.63; 2.29 0.60; 2.28 0.58; 2.28 0.58; 2.27 0.52; 2.27 0.44; 2.26 0.33; 2.05 1.14; 1.93 0.60; 1.91 0.81; 1.90 0.58; 1.89 0.64; 1.88 0.49; 1.87 0.66; 1.85 0.51; 1.85 0.38; 1.74 15.58; 1.73 16.00; 1.56 110.51; 1.28 0.38; 1.26 0.77; 1.24 0.37; 0.01 0.33; 0.01 2.13; 0.01 1.05; 0.01 0.48; 0.00 0.66; 0.00 1.11; 0.00 92.02; −0.01 0.72; −0.01 2.42 |
| 6.347 | Ph | H | O | H | $CH_2$ | 1,4-dimethyl-5-oxo-4,5-dihydro-1H-1,2,4-triazol-3-yl | |
| 6.348 | 3,5-$Cl_2$—Ph | H | O | H | $CH_2$ | 3-(2-ethoxy-2-oxoethyl)oxetan-3-yl | |
| 6.349 | 3,5-$F_2$—Ph | H | O | H | $CH_2$ | 3-(2-ethoxy-2-oxoethyl)oxetan-3-yl | [$CDCl_3$] 7.26 38.96; 7.22 0.47; 7.21 0.46; 7.21 0.84; 7.19 0.56; 7.18 0.55; 7.18 0.44; 7.17 1.79; 7.16 2.36; 7.15 2.32; 7.14 1.93; 7.13 0.36; 6.91 0.41; 6.91 0.75; 6.90 0.43; 6.89 0.84; 6.88 1.48; 6.88 0.80; 6.87 0.46; 6.86 0.74; 6.86 0.39; 4.53 0.51; 4.51 8.44; 4.49 5.03; 4.49 4.60; 4.47 1.06; 4.18 1.43; 4.16 4.46; 4.14 4.51; 4.12 1.53; 3.79 2.67; 3.76 1.12; 3.75 3.17; 3.74 1.33; 3.73 1.58; 3.71 1.55; 3.59 1.56; 3.57 1.61; 3.55 1.10; 3.54 1.05; 3.21 2.96; 3.17 2.57; 2.70 7.80; 1.74 16.00; 1.55 17.28; 1.28 4.93; 1.26 10.34; 1.24 4.81; 0.01 0.39 |

TABLE 6-continued

Compounds of the general formula (I) according to the invention in which $R^2$ is hydrogen and $R^3$ is methyl and aryl is the radical

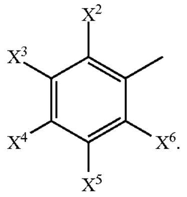

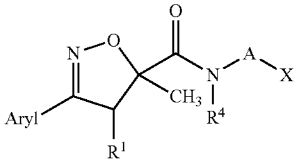

| No. | Aryl | $R^1$ | Y | $R^4$ | A | X | Physical data |
|---|---|---|---|---|---|---|---|
| 6.350 | 3,5-$Cl_2$—Ph | H | O | H | $CH_2$ | 3-(cyclopropyl-carbamoyl)-4,5-dihydro-1,2-oxazol-5-yl | diastereomers D1 plus D2: [$CDCl_3$] 0.53 (m, 2H); 0.58 (m, 2H); 0.80 (m, 2H); 0.83 (m, 2H); 1.71 (s, 3H); 1.73 (s, 3H); 2.67 (m, 1H); 2.78 (m, 1H); 2.98 (dd, 2H); 3.18 (d, 2H); 3.22-3.32 (m, 2H); 3.33-3.41 (m, 1H); 3.42-3.63 (m, 3H); 3.76 (d, 2H); 4.88 (m, 2H); 6.59 (s br, 1H); 6.68 (s br, 1H); 7.08 (t br, 1H); 7.12 (t br, 1H); 7.42 (m, 2H); 7.52 (m, 4H). |
| 6.351 | 3,5-$Cl_2$—Ph | H | O | H | $CH_2$ | 3-(ethoxycarbonyl)-4,5-dihydro-1,2-oxazol-5-yl | [$CDCl_3$] 7.52 7.26; 7.51 7.90; 7.51 8.01; 7.50 8.22; 7.42 4.16; 7.41 7.04; 7.41 3.61; 7.26 51.41; 7.16 0.58; 7.15 0.89; 7.13 0.63; 7.12 0.60; 7.11 0.85; 7.09 0.50; 4.96 0.35; 4.95 0.38; 4.95 0.42; 4.94 0.87; 4.93 1.23; 4.92 1.04; 4.91 1.30; 4.90 0.94; 4.89 0.70; 4.88 0.47; 4.37 1.49; 4.35 4.58; 4.34 4.64; 4.32 1.54; 4.29 0.36; 4.28 0.69; 4.27 1.10; 4.26 2.20; 4.25 2.38; 4.24 2.40; 4.24 2.25; 4.23 1.12; 4.22 0.76; 4.21 0.36; 4.15 0.87; 4.13 2.57; 4.11 2.58; 4.09 0.88; 3.79 2.56; 3.78 2.79; 3.75 2.95; 3.73 3.22; 3.66 0.59; 3.65 0.67; 3.65 0.61; 3.64 0.64; 3.63 0.84; 3.62 1.12; 3.61 0.83; 3.60 1.20; 3.59 0.42; 3.58 0.93; 3.57 1.22; 3.55 0.94; 3.54 0.95; 3.53 1.07; 3.53 0.98; 3.52 0.99; 3.51 0.38; 3.50 0.41; 3.49 0.37; 3.48 0.33; 3.44 0.81; 3.42 1.26; 3.41 0.92; 3.40 0.75; 3.39 0.96; 3.37 0.59; 3.30 1.06; 3.29 1.25; 3.28 1.12; 3.26 2.47; 3.24 1.65; 3.23 1.40; 3.22 1.54; 3.20 5.28; 3.20 0.63; 3.16 4.59; 3.00 1.46; 2.98 1.45; 2.96 1.09; 2.94 1.10; 2.92 1.59; 2.91 1.53; 2.88 1.23; 2.86 1.23; 2.35 0.57; 2.04 11.45; 1.75 0.38; 1.73 16.00; 1.72 0.78; 1.71 1.07; 1.69 14.65; 1.55 24.53; 1.39 0.52; 1.38 4.85; 1.36 9.92; 1.34 5.09; 1.34 5.53; 1.32 11.17; 1.30 6.19; 1.28 5.19; 1.26 5.97; 1.26 9.05; 1.24 3.54; 0.90 2.75; 0.88 8.23; 0.86 3.44; 0.01 1.08; 0.00 35.46; −0.01 1.61; −0.01 0.41 |
| 6.352 | 3,5-$Cl_2$—Ph | H | O | H | $CH_2$ | 3-(methylcarbamoyl)-4,5-dihydro-1,2-oxazol-5-yl | |

TABLE 6-continued

Compounds of the general formula (I) according to the invention in which $R^2$ is hydrogen and $R^3$ is methyl and aryl is the radical

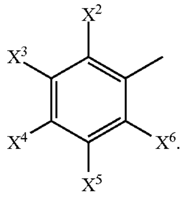

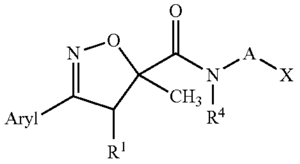

| No. | Aryl | $R^1$ | Y | $R^4$ | A | X | Physical data |
|---|---|---|---|---|---|---|---|
| 6.353 | 3,5-$Cl_2$—Ph | H | O | H | $CH_2$ | 3-carboxy-4,5-dihydro-1,2-oxazol-5-yl | [$CDCl_3$] 7.51 5.74; 7.51 7.53; 7.50 7.27; 7.50 7.12; 7.49 0.67; 7.49 0.68; 7.48 0.34; 7.42 1.67; 7.42 2.88; 7.41 1.68; 7.41 1.97; 7.40 3.01; 7.40 1.51; 7.31 0.42; 7.31 0.42; 7.30 0.85; 7.27 0.83; 7.26 33.35; 5.30 16.00; 5.01 0.54; 4.99 0.70; 4.99 0.82; 4.98 0.86; 4.97 0.66; 4.97 0.59; 4.96 0.53; 3.82 2.31; 3.81 2.52; 3.79 0.67; 3.77 2.75; 3.76 2.93; 3.75 1.01; 3.75 0.72; 3.74 0.92; 3.72 0.65; 3.66 0.63; 3.65 0.86; 3.65 0.64; 3.64 0.91; 3.63 0.79; 3.62 0.66; 3.62 1.27; 3.61 0.82; 3.60 1.37; 3.58 0.66; 3.56 0.64; 3.55 0.68; 3.55 0.70; 3.54 0.66; 3.53 0.40; 3.51 0.80; 3.50 1.05; 3.48 0.62; 3.48 0.50; 3.46 0.69; 3.44 0.39; 3.32 0.70; 3.30 0.84; 3.29 0.82; 3.28 1.11; 3.27 1.01; 3.26 1.19; 3.25 0.99; 3.23 2.62; 3.23 3.42; 3.19 2.06; 3.18 2.23; 3.04 0.94; 3.02 0.95; 2.99 0.73; 2.97 0.71; 2.95 1.04; 2.94 1.03; 2.91 0.82; 2.89 0.82; 2.45 0.33; 2.15 1.58; 1.75 11.29; 1.73 0.54; 1.71 10.17; 1.27 0.41; 1.25 1.05; 1.24 0.39; 1.08 0.58; 1.06 1.18; 1.04 0.57; 0.01 0.41; 0.00 15.11; −0.01 0.59 |
| 6.354 | 3,5-$Cl_2$—Ph | H | O | H | $CH_2$ | 3-isopropyl-4,5-dihydro-1,2-oxazol-5-yl | [$CDCl_3$] 1.08-1.17 (m, 6H); 1.74 (s, 3H); 2.52-3.96 (m, 6H); 4.13-5.87 (m, 2H); 6.88-7.16 (br, 1H); 7.41 (m, 1H); 7.51 (m, 2H). |
| 6.355 | 3,5-$Cl_2$—Ph | H | O | H | $CH_2$ | 3-methyl-4,5-dihydro-1,2-oxazol-5-yl | [$CDCl_3$] 1.70, 1.72 (ds, 3H); 1.89, 1.98 (ds, 3H); 2.53-2.70 (m, 1H); 2.96-3.05 (m, 1H); 3.18 (d, 1H); 3.25-3.47 (m, 1H); 3.45-3.60 (m, 1H); 3.78 (d, 1H); 4.63-4.71 (m, 1H); 7.13 (br, 1H); 7.41 (s, 1H); 7.51 (s, 2H). |
| 6.356 | 3,5-$F_2$—Ph | H | O | H | $CH_2$ | 5-(ethoxycarbonyl)-4,5-dihydro-1,2-oxazol-3-yl | [$CDCl_3$] 7.26 19.10; 7.26 16.83; 7.25 0.59; 7.25 0.56; 7.25 0.53; 7.25 0.52; 7.25 0.52; 7.25 0.51; 7.25 0.52; 7.25 0.52; 7.25 0.52; 7.25 0.52; 7.24 0.54; 7.24 0.73; 7.18 0.34; 7.17 1.71; 7.17 2.24; 7.15 2.26; 7.15 1.79; 7.14 0.32; 7.13 0.33; 6.91 0.33; 6.90 0.61; 6.90 0.35; 6.89 0.69; 6.88 1.23; 6.88 0.67; 6.87 0.37; 6.86 0.62; 6.86 0.32; 5.03 0.83; 5.01 2.12; 5.00 0.81; 4.99 0.84; 4.99 0.86; 4.30 0.34; 4.30 0.33; 4.29 0.36; 4.28 0.34; 4.27 0.76; 4.26 0.75; 4.25 2.62; 4.24 0.82; 4.23 |

TABLE 6-continued
Compounds of the general formula (I) according to the invention in which $R^2$ is hydrogen and $R^3$ is methyl and aryl is the radical
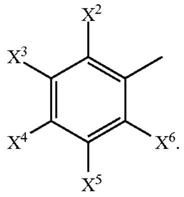
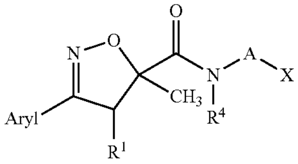
| No. | Aryl | $R^1$ | Y | $R^4$ | A | X | Physical data |
|---|---|---|---|---|---|---|---|
| | | | | | | | 2.48; 4.21 2.46; 4.20 2.75; 4.18 1.64; 4.17 0.71; 4.15 0.32; 4.14 0.55; 4.13 0.34; 3.79 2.71; 3.75 3.13; 3.23 3.03; 3.23 2.58; 3.22 2.70; 3.21 2.44; 3.20 0.90; 3.18 1.44; 3.18 1.55; 1.76 0.49; 1.74 16.00; 1.57 5.74; 1.33 2.48; 1.31 5.02; 1.31 4.47; 1.30 2.59; 1.29 2.52; 1.28 5.02; 1.28 4.47; 1.26 2.46; 0.00 10.27; 0.00 8.86; −0.01 0.36 |
| 6.357 | 3,5-$Cl_2$—Ph | H | O | H | $CH_2$ | 5,5-dimethyl-4,5-dihydro-1,2-oxazol-3-yl | [$CDCl_3$] 7.51 7.81; 7.51 8.48; 7.42 2.13; 7.41 3.72; 7.41 1.80; 7.26 51.75; 7.21 0.64; 7.21 0.45; 7.20 0.38; 5.30 2.98; 4.24 0.33; 4.24 0.59; 4.22 0.33; 4.22 0.60; 4.20 0.65; 4.19 1.20; 4.19 0.67; 4.18 0.67; 4.18 1.19; 4.18 0.65; 4.12 0.67; 4.12 1.19; 4.11 0.67; 4.10 0.71; 4.10 1.21; 4.07 0.61; 4.06 0.61; 3.79 2.80; 3.75 3.24; 3.22 2.91; 3.17 2.56; 2.75 0.34; 2.67 1.86; 2.67 3.52; 2.67 2.38; 2.67 2.42; 2.66 3.60; 2.66 1.89; 1.74 16.00; 1.55 9.52; 1.43 0.45; 1.40 2.17; 1.38 12.65; 1.36 12.64; 0.01 0.73; 0.00 26.18; −0.01 0.58; −0.01 1.03 |
| 6.358 | 3,5-$Cl_2$—Ph | H | O | H | $CH_2$ | 5-ethyl-4,5-dihydro-1,2-oxazol-3-yl | |
| 6.359 | 3,5-$Cl_2$—Ph | H | O | H | $CH_2$ | 5-isopropyl-4,5-dihydro-1,2-oxazol-3-yl | [$CDCl_3$] 7.52 1.13; 7.52 13.51; 7.51 14.98; 7.42 3.46; 7.42 6.11; 7.41 2.96; 7.31 0.43; 7.26 142.43; 7.22 0.68; 7.21 0.91; 7.21 1.04; 7.20 0.67; 7.00 0.81; 5.30 9.52; 4.39 0.62; 4.38 0.65; 4.37 0.66; 4.36 1.04; 4.36 1.33; 4.36 0.77; 4.35 0.75; 4.34 1.35; 4.34 1.05; 4.33 0.74; 4.32 0.69; 4.32 0.70; 4.25 0.52; 4.23 0.59; 4.21 0.44; 4.21 1.08; 4.19 1.24; 4.19 1.39; 4.17 1.15; 4.15 1.17; 4.13 2.01; 4.12 1.05; 4.11 0.44; 4.09 0.86; 4.08 0.50; 3.80 2.79; 3.80 2.88; 3.76 3.16; 3.75 3.30; 3.22 5.05; 3.18 4.32; 2.90 0.71; 2.89 0.66; 2.88 0.69; 2.87 0.70; 2.86 0.73; 2.86 0.96; 2.85 0.94; 2.83 0.87; 2.82 0.91; 2.65 0.85; 2.63 0.83; 2.61 1.40; 2.59 1.38; 2.57 0.62; 2.55 0.60; 1.84 0.65; 1.83 1.16; 1.81 1.36; 1.80 1.36; 1.78 1.21; 1.76 0.76; 1.75 15.85; 1.74 16.00; 1.56 45.35; 1.25 0.60; 0.95 8.11; 0.94 |

TABLE 6-continued

Compounds of the general formula (I) according to the invention in which $R^2$ is hydrogen and $R^3$ is methyl and aryl is the radical

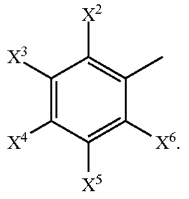

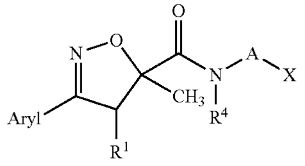

| No. | Aryl | $R^1$ | Y | $R^4$ | A | X | Physical data |
|---|---|---|---|---|---|---|---|
| | | | | | | | 7.82; 0.92 8.04; 0.91 7.77; 0.89 8.11; 0.87 7.81; 0.85 7.99; 0.83 7.70; 0.01 1.71; 0.00 0.34; 0.00 70.41; −0.01 2.20 |
| 6.360 | 3,5-$Cl_2$—Ph | H | O | H | $CH_2$ | 5-methyl-4,5-dihydro-1,2-oxazol-3-yl | [$CDCl_3$] 7.52 5.98; 7.51 6.61; 7.42 1.92; 7.41 3.31; 7.41 1.65; 7.26 22.23; 7.23 0.41; 7.22 0.66; 5.30 5.88; 4.77 0.34; 4.75 0.34; 4.75 0.50; 4.75 0.49; 4.74 0.43; 4.73 0.43; 4.73 0.50; 4.72 0.53; 4.72 0.37; 4.71 0.37; 4.71 0.32; 4.26 0.33; 4.25 0.34; 4.25 0.36; 4.23 0.60; 4.22 0.71; 4.21 0.70; 4.21 0.68; 4.20 0.64; 4.15 0.62; 4.14 0.90; 4.13 0.89; 4.12 0.63; 4.09 0.45; 4.09 0.43; 4.08 0.33; 3.80 2.74; 3.75 3.15; 3.22 2.90; 3.17 2.52; 3.05 0.45; 3.03 0.46; 3.02 0.46; 3.01 0.86; 2.99 0.55; 2.98 0.53; 2.96 0.50; 2.55 0.52; 2.53 0.54; 2.53 0.49; 2.52 0.56; 2.51 0.55; 2.50 0.59; 2.49 0.47; 2.48 0.42; 2.48 0.48; 2.46 0.43; 1.74 16.00; 1.57 4.89; 1.34 5.01; 1.33 4.88; 1.32 4.99; 1.31 4.79; 0.00 12.15; −0.01 0.52 |
| 6.361 | 3,5-$Cl_2$—Ph | H | O | H | $CH_2$ | carbamoyl | [$CDCl_3$] 1.73 (s, 3H); 3.20 (d, 1H); 3.78 (d, 1H); 3.90 (dd, 1H); 4.0 (dd, 1H); 5.3 (s br, 1H); 5.7 (s br, 1H); 7.42 (s, 1H); 7.52 (s, 2H). |
| 6.362 | 3-Cl—Ph | H | O | H | $CH_2$ | carbamoyl | |
| 6.363 | 2-$CF_3$—Ph | H | O | H | $CH_2$ | $CF_3$ | |
| 6.364 | 2,3,4-$F_3$—Ph | H | O | H | $CH_2$ | $CF_3$ | [$CDCl_3$] 7.55 0.33; 7.54 0.34; 7.53 0.37; 7.53 0.43; 7.53 0.45; 7.53 0.43; 7.52 0.40; 7.52 0.42; 7.52 0.43; 7.51 0.45; 7.51 0.44; 7.51 0.43; 7.50 0.36; 7.50 0.33; 7.49 0.33; 7.26 0.37; 7.26 31.40; 7.26 0.45; 7.25 0.34; 7.11 0.34; 7.07 0.38; 7.06 0.39; 7.05 0.38; 7.05 1.02; 7.04 0.71; 7.03 0.67; 7.02 0.99; 7.02 0.35; 7.00 0.32; 4.05 0.40; 4.03 0.42; 4.03 0.43; 4.01 0.63; 4.01 0.49; 3.99 0.58; 3.99 0.63; 3.97 0.58; 3.89 1.12; 3.89 1.23; 3.87 0.59; 3.85 2.04; 3.84 1.79; 3.83 0.97; 3.81 0.40; 3.81 0.60; 3.79 0.39; 3.37 1.18; 3.36 1.22; 3.32 1.03; 3.32 1.03; 1.75 16.00; 1.55 24.76; 0.01 0.42; 0.00 15.34; −0.01 0.45 |
| 6.365 | 2,3,5-$F_3$—Ph | H | O | H | $CH_2$ | $CF_3$ | |
| 6.366 | 2,3,6-$Cl_3$—Ph | H | O | H | $CH_2$ | $CF_3$ | |
| 6.367 | 2,3-$F_2$—Ph | H | O | H | $CH_2$ | $CF_3$ | [$CDCl_3$] 7.55 0.36; 7.54 0.69; 7.54 0.40; 7.53 0.42; 7.53 0.98; 7.52 1.03; 7.52 0.54; 7.51 0.44; 7.51 |

TABLE 6-continued
Compounds of the general formula (I) according to the invention in which $R^2$ is hydrogen and $R^3$ is methyl and aryl is the radical
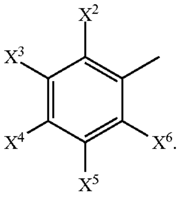
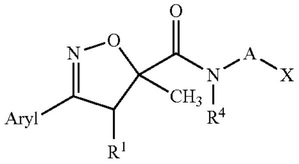
| No. | Aryl | $R^1$ | Y | $R^4$ | A | X | Physical data |
|---|---|---|---|---|---|---|---|
| | | | | | | | 0.78; 7.50 0.41; 7.28 0.34; 7.26 29.97; 7.25 0.70; 7.24 0.99; 7.24 0.56; 7.22 0.47; 7.22 0.41; 7.16 0.62; 7.15 0.68; 7.15 0.80; 7.14 0.83; 7.14 1.12; 7.13 1.16; 7.13 1.05; 7.12 1.02; 7.12 0.64; 7.11 0.57; 7.11 0.43; 7.10 0.39; 4.06 0.40; 4.04 0.46; 4.04 0.45; 4.02 0.66; 4.02 0.51; 4.00 0.61; 4.00 0.65; 3.98 0.58; 3.91 1.27; 3.91 1.28; 3.87 1.55; 3.86 1.65; 3.86 0.67; 3.84 0.71; 3.84 0.62; 3.82 0.98; 3.81 0.41; 3.80 0.61; 3.78 0.42; 3.40 1.43; 3.40 1.43; 3.36 1.24; 3.35 1.21; 1.75 16.00; 1.55 35.04; 0.01 0.38; 0.00 13.17; −0.01 0.51 |
| 6.368 | 2,5-$F_2$—Ph | H | O | H | $CH_2$ | $CF_3$ | [$CDCl_3$] 7.53 0.35; 7.53 0.37; 7.52 0.41; 7.52 0.50; 7.51 0.46; 7.51 0.77; 7.50 0.42; 7.50 0.44; 7.50 0.39; 7.49 0.41; 7.49 0.41; 7.48 0.41; 7.48 0.41; 7.26 23.22; 7.14 0.37; 7.13 0.38; 7.13 0.91; 7.12 1.63; 7.12 1.16; 7.12 1.00; 7.11 1.03; 7.11 1.43; 7.10 1.62; 7.10 0.88; 7.10 1.00; 7.10 0.97; 7.09 0.72; 7.09 0.78; 7.08 0.80; 4.06 0.40; 4.04 0.42; 4.04 0.44; 4.02 0.60; 4.02 0.48; 4.01 0.56; 4.00 0.61; 3.98 0.56; 3.90 1.26; 3.90 1.29; 3.86 1.60; 3.85 0.75; 3.85 1.60; 3.84 0.69; 3.83 0.60; 3.82 0.97; 3.80 0.70; 3.80 0.42; 3.79 0.61; 3.78 0.40; 3.39 1.36; 3.38 1.39; 3.34 1.21; 3.33 1.18; 1.74 16.00; 1.65 0.56; 1.64 0.36; 1.55 3.13; 1.54 0.63; 1.53 0.39; 1.26 0.33; 0.00 0.39; 0.00 11.14; 0.00 0.63; 0.00 0.41; −0.01 0.35 |
| 6.369 | 2-Cl-3-F-5-MeO—Ph | H | O | H | $CH_2$ | $CF_3$ | [$CDCl_3$] 7.26 6.08; 7.18 0.41; 6.91 1.26; 6.91 1.29; 6.90 1.46; 6.90 1.43; 6.82 1.39; 6.81 1.19; 6.79 1.37; 6.79 1.22; 3.99 0.32; 3.97 0.36; 3.97 0.79; 3.95 0.90; 3.95 0.94; 3.95 0.87; 3.93 2.68; 3.93 1.02; 3.93 0.98; 3.92 0.40; 3.91 0.87; 3.91 0.40; 3.89 3.04; 3.82 0.57; 3.81 16.00; 3.46 2.76; 3.42 2.32; 1.76 13.90; 1.74 0.54; 0.00 1.11 |
| 6.370 | 3-(2-MeOEtO)—Ph | H | O | H | $CH_2$ | $CF_3$ | |
| 6.371 | 3-iPrO—Ph | H | O | H | $CH_2$ | $CF_3$ | |
| 6.372 | 3-$CF_3$O—Ph | H | O | H | $CH_2$ | $CF_3$ | |
| 6.373 | 3-$CF_3$—Ph | H | O | H | $CH_2$ | $CF_3$ | [$CDCl_3$] 7.89 2.73; 7.82 1.46; 7.81 1.70; 7.71 1.28; 7.69 1.71; 7.57 |

TABLE 6-continued

Compounds of the general formula (I) according to the invention in which $R^2$ is hydrogen and $R^3$ is methyl and aryl is the radical

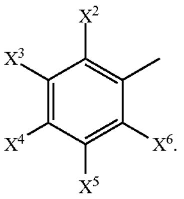

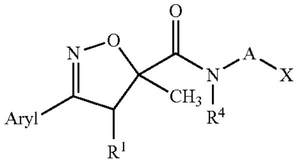

| No. | Aryl | $R^1$ | Y | $R^4$ | A | X | Physical data |
|---|---|---|---|---|---|---|---|
| | | | | | | | 1.23; 7.56 1.95; 7.54 0.81; 7.26 13.83; 7.26 9.32; 7.16 0.77; 5.30 0.34; 4.08 0.51; 4.07 0.34; 4.06 0.62; 4.06 0.73; 4.05 0.38; 4.04 0.78; 4.04 0.89; 4.03 0.51; 4.02 0.65; 4.02 0.97; 4.01 0.61; 4.00 0.60; 4.00 0.58; 3.88 2.65; 3.88 1.93; 3.84 3.30; 3.83 2.82; 3.82 0.74; 3.81 0.65; 3.81 0.67; 3.81 0.49; 3.80 1.03; 3.79 0.79; 3.78 0.47; 3.78 0.44; 3.77 0.66; 3.77 0.48; 3.76 0.43; 3.75 0.34; 3.32 2.88; 3.32 2.14; 3.28 2.48; 3.28 1.83; 1.77 16.00; 1.76 11.84; 1.56 8.84; 1.56 6.11; 0.00 5.16 |
| 6.374 | 3,4-$Cl_2$—Ph | H | O | H | $CH_2$ | $CF_3$ | |
| 6.375 | 3,5-$Br_2$—Ph | H | O | H | $CH_2$ | $CF_3$ | [$CDCl_3$] 1.73 (s, 3H); 3.21 (d, 1H); 3.79 (m, 2H); 4.03 (m, 1H); 7.09 (m, 1H); 7.70 (m, 2H); 7.73 (m, 1H). |
| 6.376 | 3,5-$Cl_2$-4-MeO—Ph | H | O | H | $CH_2$ | $CF_3$ | [$CDCl_3$] 7.58 10.21; 7.26 20.81; 7.12 0.41; 4.06 0.32; 4.04 0.35; 4.03 0.36; 4.02 0.49; 4.02 0.41; 4.00 0.45; 4.00 0.50; 3.98 0.46; 3.93 16.00; 3.90 0.79; 3.83 0.46; 3.82 0.54; 3.81 0.47; 3.80 0.77; 3.78 2.23; 3.78 0.53; 3.76 0.33; 3.74 2.46; 3.23 2.28; 3.19 1.98; 1.74 12.19; 1.55 10.29 |
| 6.377 | 3,5-$Cl_2$—Ph | H | O | H | $CH_2$ | $CF_3$ | [$CDCl_3$] 1.75 (s, 3H); 3.23 (d, 1H); 3.78 (d, 1H); 3.81 (m, 1H), 4.02 (m, 1H); 7.11 (t br, 1H); 7.42 (m, 1H); 7.52 (m, 2H) |
| 6.378 | 3,5-$F_2$—Ph | H | O | H | $CH_2$ | $CF_3$ | [$CDCl_3$] 1.74 (s, 3H); 3.22 (d, 1H); 3.73 (d, 1H); 3.79 (m, 1H); 4.02 (m, 1H); 6.89 (m, 1H); 7.05-7.16 (m, 3H). |
| 6.379 | 3,5-$(MeO)_2$—Ph | H | O | H | $CH_2$ | $CF_3$ | [$CDCl_3$] 7.27 0.93; 7.26 9.53; 7.25 0.51; 6.77 2.70; 6.77 2.77; 6.53 0.75; 6.53 1.29; 6.52 0.69; 3.81 16.00; 3.79 0.38; 3.77 0.50; 3.76 1.35; 3.76 0.36; 3.75 0.33; 3.27 1.19; 3.23 1.03; 1.74 6.34; 1.55 1.81; 0.01 0.36; 0.00 4.01 |
| 6.380 | 3,5-$Me_2$—Ph | H | O | H | $CH_2$ | $CF_3$ | [$CDCl_3$] 1.72 (s, 3H); 2.33 (s, 6H); 3.27 (d, 1H); 3.77 (m, 1H); 3.80 (d, 1H); 4.03 (m, 1H); 7.08 (s, 1H); 7.20 (t br, 1H); 7.25 (s, 2H). |
| 6.381 | 3-Br-5-Cl—Ph | H | O | H | $CH_2$ | $CF_3$ | [$CDCl_3$] 1.75 (s, 3H); 3.22 (d, 1H); 3.78 (d, 1H); 3.73-3.85 (m, 1H); 3.96-4.09 (m, 1H); 7.11 (br, 1H); 7.57 (m, 2H); 7.66 (m, 1H). |
| 6.382 | 3-Br-5-F—Ph | H | O | H | $CH_2$ | $CF_3$ | [$CDCl_3$] 7.55 2.38; 7.54 1.43; 7.52 0.35; 7.34 0.46; 7.34 1.39; 7.33 2.10; 7.33 1.45; 7.32 0.97; 7.32 1.37; 7.31 1.33; 7.31 1.44; 7.30 |

TABLE 6-continued

Compounds of the general formula (I) according to the invention in which $R^2$ is hydrogen and $R^3$ is methyl and aryl is the radical

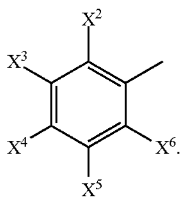

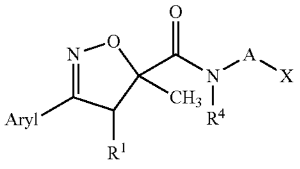

| No. | Aryl | $R^1$ | Y | $R^4$ | A | X | Physical data |
|---|---|---|---|---|---|---|---|
| | | | | | | | 1.33; 7.30 0.56; 7.26 60.87; 7.11 0.50; 7.00 0.34; 4.07 0.41; 4.05 0.47; 4.05 0.47; 4.03 0.66; 4.03 0.54; 4.01 0.60; 4.01 0.65; 3.99 0.58; 3.93 0.70; 3.83 0.56; 3.82 0.72; 3.81 0.64; 3.80 3.63; 3.79 0.35; 3.78 0.48; 3.77 0.66; 3.76 0.58; 3.75 3.20; 3.25 2.88; 3.20 2.49; 1.75 16.00; 1.54 7.47; 0.01 1.25; 0.00 39.97; −0.01 1.55 |
| 6.383 | 3-Cl-5-$CF_3$—Ph | H | O | H | $CH_2$ | $CF_3$ | [$CDCl_3$] 1.77 (s, 3H); 3.28 (d, 1H); 3.80 (m, 1H); 3.83 (d, 1H); 4.04 (m, 1H); 7.21 (s br, 1H); 7.68 (s, 1H); 7.76 (s, 1H); 7.80 (s, 1H) |
| 6.384 | 3-Cl-5-Et—Ph | H | O | H | $CH_2$ | $CF_3$ | [$CDCl_3$] 7.44 1.22; 7.43 2.29; 7.43 1.40; 7.34 2.18; 7.26 19.14; 7.17 0.48; 4.07 0.43; 4.06 0.46; 4.05 0.48; 4.04 0.62; 4.03 0.51; 4.02 0.59; 4.01 0.63; 4.00 0.57; 3.82 3.28; 3.80 0.72; 3.80 0.61; 3.78 1.09; 3.77 3.31; 3.77 0.48; 3.76 0.65; 3.74 0.43; 3.27 2.98; 3.23 2.57; 2.68 0.87; 2.66 2.68; 2.64 2.76; 2.62 0.94; 1.74 16.00; 1.56 6.13; 1.26 4.75; 1.24 9.55; 1.22 4.50; 0.00 6.79 |
| 6.385 | 3-Cl-5-F—Ph | H | O | H | $CH_2$ | $CF_3$ | [$CDCl_3$] 1.73 (s, 3H); 3.22 (d, 1H); 3.78 (d, 1H); 3.80 (m, 1H), 4.03 (m, 1H); 7.12 (t br, 1H); 7.18 (d, 1H); 7.27 (d, 1H); 7.39 (s, 1H). |
| 6.386 | 3-Cl-5-Me—Ph | H | O | H | $CH_2$ | $CF_3$ | [$CDCl_3$] 1.73 (s, 3H); 2.34 (s, 3H); 3.22 (d, 1H); 3.78 (d, 1H); 3.78 (m, 1H); 4.08 (m, 1H); 7.16 (brt, 1H); 7.23 (m, 1H); 7.31 (m, 1H); 7.43 (m, 1H). |
| 6.387 | 3-Cl-5-$CF_3O$—Ph | H | O | H | $CH_2$ | $CF_3$ | [$CDCl_3$] 1.75 (s, 3H); 3.24 (d, 1H); 3.80 (d, 1H); 3.80 (m, 1H); 4.03 (m, 1H); 7.12 (brt, 1H); 7.31 (brs, 1H); 7.41 (brs, 1H); 7.53 (brs, 1H). |
| 6.388 | 3-Cl—Ph | H | O | H | $CH_2$ | $CF_3$ | [$CDCl_3$] 1.74 (s, 3H); 3.25 (d, 1H); 3.79 (d, 1H); 3.80 (m, 1H); 4.03 (m, 1H); 7.16 (t br, 1H); 7.36 (m, 1H); 7.42 (m, 1H); 7.50 (m, 1H); 7.64 (m, 1H). |
| 6.389 | 3-EtO—Ph | H | O | H | $CH_2$ | $CF_3$ | |
| 6.390 | 3-Et-5-F—Ph | H | O | H | $CH_2$ | $CF_3$ | [$CDCl_3$] 7.26 13.50; 7.26 21.12; 7.25 1.75; 7.22 2.90; 7.18 1.52; 7.16 1.48; 7.16 1.62; 7.00 1.17; 6.97 1.08; 4.08 0.45; 4.06 0.52; 4.05 0.53; 4.04 0.74; 4.03 0.59; 4.02 0.65; 4.02 0.71; 4.00 0.59; 3.82 3.18; 3.80 0.74; 3.80 0.66; 3.78 1.20; 3.78 3.35; 3.77 0.67; 3.76 0.69; 3.74 0.43; 3.28 2.89; 3.23 2.49; 2.70 1.00; 2.68 3.10; 2.66 3.19; 2.64 1.09; 1.74 |

TABLE 6-continued
Compounds of the general formula (I) according to the invention in which $R^2$ is hydrogen and $R^3$ is methyl and aryl is the radical
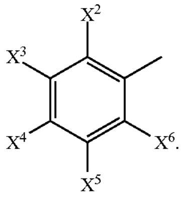
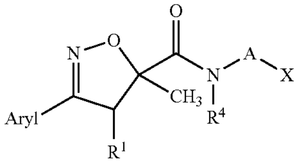
| No. | Aryl | $R^1$ | Y | $R^4$ | A | X | Physical data |
|---|---|---|---|---|---|---|---|
| | | | | | | | 16.00; 1.55 5.91; 1.55 8.64; 1.26 4.55; 1.25 9.24; 1.23 4.36; 0.00 4.17; 0.00 6.85; −0.01 0.62 |
| 6.391 | 3-Et—Ph | H | O | H | $CH_2$ | $CF_3$ | [$CDCl_3$] 7.49 2.92; 7.44 1.33; 7.42 1.89; 7.35 1.15; 7.33 2.65; 7.31 1.65; 7.29 2.22; 7.27 1.11; 7.26 14.76; 7.26 14.88; 7.22 0.76; 7.21 0.57; 7.21 0.63; 4.08 0.47; 4.06 0.61; 4.04 0.78; 4.02 0.78; 4.00 0.59; 3.85 2.57; 3.81 3.48; 3.79 0.74; 3.78 0.63; 3.77 1.01; 3.75 0.48; 3.75 0.65; 3.73 0.44; 3.31 2.96; 3.26 2.53; 2.70 1.16; 2.68 3.59; 2.66 3.68; 2.64 1.26; 1.74 16.00; 1.57 6.12; 1.27 4.38; 1.25 8.61; 1.23 4.14; 0.00 6.50 |
| 6.392 | 3-F-5-MeS—Ph | H | O | H | $CH_2$ | $CF_3$ | [$CDCl_3$] 7.26 14.07; 7.24 1.56; 7.24 2.58; 7.24 1.46; 7.16 0.37; 7.15 0.56; 7.11 0.77; 7.10 0.94; 7.10 0.75; 7.08 0.74; 7.08 0.93; 7.08 0.72; 7.01 0.73; 7.01 1.02; 7.00 0.61; 6.99 0.74; 6.98 1.03; 6.98 0.60; 4.07 0.38; 4.06 0.44; 4.05 0.43; 4.04 0.61; 4.03 0.49; 4.02 0.57; 4.01 0.61; 4.00 0.56; 3.83 0.51; 3.81 0.70; 3.80 2.77; 3.79 0.89; 3.77 0.41; 3.77 0.70; 3.76 2.71; 3.75 0.42; 3.26 2.54; 3.22 2.18; 2.53 0.88; 2.52 0.55; 2.50 16.00; 1.74 13.72; 1.26 0.64 |
| 6.393 | 3-F-5-$MeSO_2$—Ph | H | O | H | $CH_2$ | $CF_3$ | [$CDCl_3$] 7.94 3.34; 7.94 3.20; 7.74 0.65; 7.73 1.32; 7.73 1.34; 7.72 0.76; 7.71 1.31; 7.71 1.28; 7.68 1.28; 7.68 1.28; 7.68 1.13; 7.66 0.85; 7.66 1.31; 7.66 1.29; 7.65 1.13; 7.26 14.44; 7.26 11.06; 7.13 0.52; 7.11 0.90; 7.10 0.55; 5.53 0.51; 5.30 1.66; 5.30 1.27; 4.06 0.41; 4.04 0.54; 4.04 0.57; 4.02 0.85; 4.00 0.61; 4.00 0.81; 3.98 0.60; 3.98 0.54; 3.88 2.43; 3.87 0.61; 3.85 0.72; 3.85 0.68; 3.84 3.17; 3.83 1.05; 3.81 0.44; 3.81 0.66; 3.79 0.39; 3.31 2.56; 3.27 2.24; 3.11 0.71; 3.11 1.12; 3.10 0.89; 3.09 16.00; 3.09 12.71; 2.04 0.37; 1.77 13.88; 1.57 6.63 |
| 6.394 | 3-F-5-$CF_3$—Ph | H | O | H | $CH_2$ | $CF_3$ | [$CDCl_3$] 1.78 (s, 3H); 3.28 (d, 1H); 3.80 (m, 1H); 3.84 (d, 1H); 4.03 (m, 1H); 7.10 (t br, 1H); 7.40 (d, 1H); 7.54 (d, 1H); 7.64 (s, 1H) |
| 6.395 | 3-F-5-MeO—Ph | H | O | H | $CH_2$ | $CF_3$ | [$CDCl_3$] 7.26 7.19; 7.26 10.69; 7.17 0.78; 6.96 2.55; 6.94 1.29; 6.94 1.26; 6.94 1.29; 6.92 1.26; 6.92 1.28; 6.91 1.27; 6.71 1.01; 6.71 1.37; 6.70 0.65; 6.68 1.02; 6.68 |

TABLE 6-continued
Compounds of the general formula (I) according to the invention in which $R^2$ is hydrogen and $R^3$ is methyl and aryl is the radical
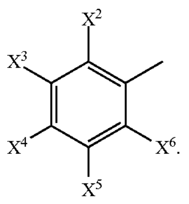
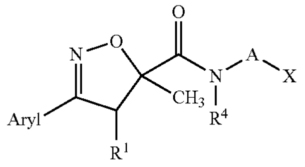
| No. | Aryl | $R^1$ | Y | $R^4$ | A | X | Physical data |
|---|---|---|---|---|---|---|---|
| | | | | | | | 1.35; 6.67 0.63; 4.08 0.37; 4.08 0.41; 4.06 0.49; 4.06 0.63; 4.05 0.45; 4.04 0.83; 4.02 0.82; 4.02 0.68; 4.00 0.63; 3.91 0.96; 3.83 11.63; 3.82 16.00; 3.82 0.84; 3.81 0.94; 3.80 2.59; 3.79 1.03; 3.78 0.32; 3.77 0.52; 3.77 0.62; 3.76 3.06; 3.26 2.65; 3.22 2.27; 1.75 1.33; 1.74 14.32; 0.00 1.72; 0.00 2.51 |
| 6.396 | 3-F-5-Me—Ph | H | O | H | $CH_2$ | $CF_3$ | [$CDCl_3$] 7.26 16.01; 7.20 1.16; 7.20 1.74; 7.19 1.86; 7.19 1.56; 7.19 1.14; 7.18 0.77; 7.17 0.92; 7.17 0.89; 7.17 0.72; 7.16 0.74; 7.15 0.90; 6.98 0.50; 6.97 0.56; 6.97 0.64; 6.97 0.57; 6.97 0.50; 6.95 0.38; 6.95 0.50; 6.95 0.56; 6.95 0.64; 6.95 0.56; 6.94 0.49; 6.23 1.92; 4.07 0.42; 4.05 0.44; 4.05 0.45; 4.03 0.58; 4.03 0.48; 4.01 0.55; 4.01 0.59; 3.99 0.55; 3.82 0.55; 3.81 3.29; 3.80 0.63; 3.79 0.98; 3.77 0.46; 3.76 3.58; 3.75 0.41; 3.26 2.84; 3.22 2.45; 2.37 9.01; 1.74 16.00; 1.56 8.27; 1.25 0.40; 0.00 8.98 |
| 6.397 | 3-F—Ph | H | O | H | $CH_2$ | $CF_3$ | [$CDCl_3$] 1.73 (s, 3H); 3.24 (d, 1H); 3.78 (m, 1H); 3.80 (d, 1H); 4.02 (m, 1H); 7.10-7.20 (m, 2H); 7.38 (m, 3H). |
| 6.398 | 3-OH—Ph | H | O | H | $CH_2$ | $CF_3$ | |
| 6.399 | 3-iPr—Ph | H | O | H | $CH_2$ | $CF_3$ | |
| 6.400 | 3-Me—Ph | H | O | H | $CH_2$ | $CF_3$ | [$CDCl_3$] 7.47 2.13; 7.43 1.03; 7.41 1.37; 7.32 0.95; 7.30 2.26; 7.28 1.51; 7.26 17.09; 7.24 0.79; 7.20 0.54; 4.07 0.44; 4.05 0.50; 4.05 0.48; 4.03 0.67; 4.03 0.54; 4.02 0.63; 4.01 0.64; 3.99 0.58; 3.84 2.70; 3.81 0.58; 3.79 3.29; 3.79 0.80; 3.77 0.99; 3.76 0.44; 3.75 0.62; 3.74 0.42; 3.29 2.97; 3.25 2.54; 2.38 11.52; 1.74 16.00; 1.56 5.71; 1.55 6.00; 0.00 5.52 |
| 6.401 | 3-$NO_2$—Ph | H | O | H | $CH_2$ | $CF_3$ | [$CDCl_3$] 8.47 1.17; 8.46 1.97; 8.46 1.65; 8.46 1.18; 8.46 1.28; 8.31 0.81; 8.31 0.91; 8.31 0.81; 8.30 0.83; 8.29 0.88; 8.29 0.94; 8.29 0.89; 8.28 0.88; 8.00 0.84; 8.00 0.99; 8.00 1.08; 8.00 0.91; 7.98 0.97; 7.98 1.05; 7.98 1.25; 7.98 0.98; 7.65 1.17; 7.65 1.43; 7.63 2.36; 7.61 1.03; 7.61 1.21; 7.26 17.38; 7.14 0.37; 5.30 0.51; 4.07 0.41; 4.05 0.44; 4.05 0.45; 4.03 0.60; 4.03 0.50; 4.02 0.55; 4.01 0.61; 3.99 0.56; 3.91 2.80; 3.87 |

TABLE 6-continued
Compounds of the general formula (I) according to the invention in which $R^2$ is hydrogen and $R^3$ is methyl and aryl is the radical
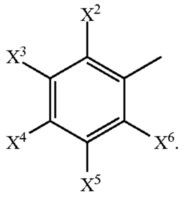
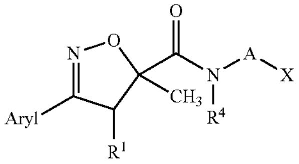
| No. | Aryl | $R^1$ | Y | $R^4$ | A | X | Physical data |
|---|---|---|---|---|---|---|---|
| | | | | | | | 3.19; 3.85 0.57; 3.84 0.69; 3.83 0.60; 3.82 0.98; 3.80 0.40; 3.79 0.62; 3.78 0.40; 3.35 2.84; 3.30 2.47; 1.78 16.00; 1.56 11.36; 0.00 0.37; 0.00 9.84 |
| 6.402 | 4-EtO—Ph | H | O | H | $CH_2$ | $CF_3$ | [$CDCl_3$] 7.57 0.46; 7.57 4.20; 7.56 1.30; 7.55 1.39; 7.54 4.44; 7.54 0.51; 7.26 18.62; 7.24 0.38; 7.22 0.56; 7.21 0.35; 7.21 0.34; 6.92 0.49; 6.92 4.34; 6.91 1.29; 6.90 1.28; 6.89 3.99; 6.89 0.45; 4.09 1.30; 4.07 4.29; 4.06 4.54; 4.04 1.91; 4.02 0.63; 4.02 0.66; 4.00 0.61; 3.81 2.81; 3.80 0.59; 3.78 0.72; 3.77 0.76; 3.77 3.36; 3.76 1.07; 3.75 0.46; 3.74 0.65; 3.72 0.44; 3.27 3.02; 3.23 2.61; 1.73 16.00; 1.56 7.49; 1.45 4.46; 1.43 9.23; 1.41 4.35 |
| 6.403 | 4-MeO—Ph | H | O | H | $CH_2$ | $CF_3$ | [$CDCl_3$] 7.59 0.36; 7.58 3.64; 7.58 1.12; 7.56 1.12; 7.56 3.89; 7.55 0.43; 7.26 13.86; 7.24 0.34; 7.22 0.51; 7.21 0.35; 6.94 0.39; 6.93 3.86; 6.93 1.17; 6.92 1.06; 6.91 3.59; 6.90 0.38; 4.08 0.40; 4.06 0.43; 4.05 0.44; 4.04 0.57; 4.04 0.48; 4.02 0.61; 4.02 0.59; 4.00 0.52; 3.84 16.00; 3.82 2.39; 3.80 0.53; 3.79 0.66; 3.78 0.65; 3.77 2.86; 3.76 0.95; 3.75 0.41; 3.74 0.57; 3.73 0.39; 3.27 2.67; 3.23 2.29; 1.73 14.13; 1.56 4.88; 0.00 5.74 |
| 6.404 | $F_5$—Ph | H | O | H | $CH_2$ | $CF_3$ | [$CDCl_3$] 7.31 0.35; 7.26 0.43; 7.26 0.61; 7.26 0.92; 7.26 46.03; 7.26 1.06; 7.26 0.75; 7.25 0.54; 7.25 0.42; 7.10 0.35; 4.03 0.34; 4.01 0.41; 4.01 0.38; 3.99 0.67; 3.99 0.57; 3.97 0.62; 3.97 0.69; 3.95 0.63; 3.93 0.37; 3.91 0.61; 3.89 0.70; 3.89 0.67; 3.87 0.91; 3.85 0.35; 3.85 0.53; 3.84 0.66; 3.84 1.21; 3.84 0.72; 3.83 0.40; 3.80 0.76; 3.80 1.45; 3.79 0.86; 3.37 0.65; 3.37 1.29; 3.37 0.72; 3.33 0.56; 3.32 1.07; 3.32 0.61; 1.77 16.00; 1.54 21.79; 0.01 0.67; 0.01 0.33; 0.00 0.36; 0.00 0.71; 0.00 1.12; 0.00 25.63; 0.00 0.83; −0.01 0.58; −0.01 0.41; −0.01 0.33; −0.01 0.87; −0.01 0.48; −0.01 0.37 |
| 6.405 | Ph | H | O | H | $CH_2$ | $CF_3$ | [$CDCl_3$] 1.73 (s, 3H); 3.29 (d, 1H); 3.78 (m, 1H); 3.83 (d, 1H); 4.05 (m, 1H); 7.20 (s br, 1H); 7.42 (m, 3H); 7.64 (m, 2H). |

TABLE 6-continued

Compounds of the general formula (I) according to the invention in which $R^2$ is hydrogen and $R^3$ is methyl and aryl is the radical

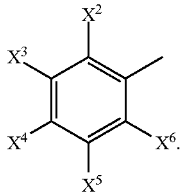

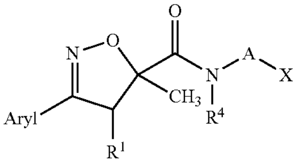

| No. | Aryl | $R^1$ | Y | $R^4$ | A | X | Physical data |
|---|---|---|---|---|---|---|---|
| 6.406 | 2,3,5-$F_3$—Ph | H | O | H | $CH_2$ | $CH_3$ | |
| 6.407 | 2,3-$F_2$—Ph | H | O | H | $CH_2$ | $CH_3$ | [$CDCl_3$] 7.54 0.37; 7.53 0.71; 7.53 0.50; 7.52 1.09; 7.51 1.12; 7.51 0.60; 7.50 0.47; 7.50 0.80; 7.50 0.52; 7.26 23.00; 7.25 0.92; 7.24 1.05; 7.23 0.53; 7.22 0.96; 7.22 0.70; 7.20 0.45; 7.20 0.45; 7.15 0.48; 7.14 0.55; 7.13 0.52; 7.13 0.59; 7.13 0.79; 7.12 0.86; 7.11 0.76; 7.11 0.85; 7.11 0.41; 7.10 0.39; 7.09 0.35; 6.78 0.47; 3.92 1.27; 3.91 1.37; 3.87 1.52; 3.87 1.57; 3.38 0.37; 3.37 0.59; 3.36 0.53; 3.35 2.58; 3.34 1.74; 3.33 0.90; 3.33 1.09; 3.31 0.83; 3.31 0.74; 3.30 1.35; 3.30 1.73; 3.29 1.16; 3.28 0.85; 3.27 0.91; 3.26 0.96; 3.24 0.58; 3.23 0.36; 1.72 16.00; 1.56 24.95; 1.18 4.34; 1.16 8.75; 1.14 4.24; 0.00 9.88; −0.01 0.52 |
| 6.408 | 3,4-$F_2$—Ph | H | O | H | $CH_2$ | $CH_3$ | [$CDCl_3$] 1.15 (t, 3H); 1.71 (s, 3H); 3.18 (d, 1H); 3.19-3.39 (m, 2H); 3.79 (d, 1H); 6.80 (br, 1H); 7.17-7.22 (m, 1H); 7.30-7.34 (m, 1H); 7.50-7.55 (m, 1H). |
| 6.409 | 3,5-$Cl_2$—Ph | H | O | H | $CH_2$ | $CH_3$ | [$CDCl_3$] 1.16 (t, 3H); 1.72 (s, 3H); 3.16 (d, 1H); 3.30 (m, 2H); 3.78 (d, 1H); 6.76 (s br, 1H); 7.41 (s, 1H); 7.52 (s, 2H). |
| 6.410 | 3,5-$F_2$—Ph | H | O | H | $CH_2$ | $CH_3$ | [$CDCl_3$] 1.17 (t, 3H); 1.71 (s, 3H); 3.18 (d, 1H); 3.21-3.40 (m, 2H); 3.78 (d, 1H); 6.78 (br, 1H); 6.88 (m, 1H); 7.16 (m, 2H). |
| 6.411 | 3-Cl-5-$CF_3$—Ph | H | O | H | $CH_2$ | $CH_3$ | [$CDCl_3$] 1.17 (t, 3H); 1.74 (s, 3H); 3.21 (d, 1H); 3.21-3.40 (m, 2H); 3.84 (d, 1H); 6.75 (br, 1H); 7.66 (s, 1H); 7.78 (s, 1H); 7.81 (s, 1H). |
| 6.412 | 3-Cl-5-Me—Ph | H | O | H | $CH_2$ | $CH_3$ | [$CDCl_3$] 7.44 0.83; 7.44 1.12; 7.44 1.95; 7.43 1.86; 7.43 1.44; 7.43 1.29; 7.32 0.85; 7.32 1.42; 7.32 2.07; 7.32 2.28; 7.31 1.90; 7.31 1.36; 7.26 13.97; 7.26 0.50; 7.23 0.86; 7.23 1.27; 7.23 1.60; 7.22 1.83; 7.22 1.78; 7.22 1.48; 7.22 1.11; 6.80 0.43; 3.81 2.78; 3.77 3.17; 3.37 0.41; 3.35 0.62; 3.35 0.48; 3.34 1.17; 3.32 0.81; 3.32 1.02; 3.30 0.81; 3.30 0.36; 3.28 0.79; 3.26 0.82; 3.26 0.88; 3.24 0.91; 3.24 0.89; 3.23 0.41; 3.23 0.40; 3.22 0.59; 3.21 0.53; 3.21 2.98; 3.16 2.53; 2.35 9.43; 2.35 11.54; 1.71 16.00; 1.58 8.76; 1.17 4.62; 1.15 9.51; 1.13 4.46; 0.00 6.54 |

TABLE 6-continued

Compounds of the general formula (I) according to the invention in which $R^2$ is hydrogen and $R^3$ is methyl and aryl is the radical

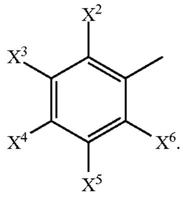

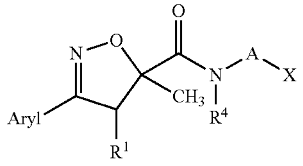

| No. | Aryl | $R^1$ | Y | $R^4$ | A | X | Physical data |
|---|---|---|---|---|---|---|---|
| 6.413 | 3-Cl-5-$CF_3O$—Ph | H | O | H | $CH_2$ | $CH_3$ | [$CDCl_3$] 1.16 (t, 3H); 1.72 (s, 3H); 3.18 (d, 1H); 3.26 (m, 1H); 3.35 (m, 1H); 3.80 (d, 1H); 6.76 (brs, 1H); 7.29 (brs, 1H); 7.41 (brs, 1H); 7.55 (brs, 1H). |
| 6.414 | 3-EtO—Ph | H | O | H | $CH_2$ | $CH_3$ | |
| 6.415 | 3-Et—Ph | H | O | H | $CH_2$ | $CH_3$ | [$CDCl_3$] 7.50 2.49; 7.44 1.19; 7.42 1.64; 7.34 1.14; 7.32 2.58; 7.30 1.58; 7.28 1.79; 7.26 14.64; 7.26 15.50; 6.86 0.53; 3.86 2.68; 3.81 3.09; 3.37 0.37; 3.36 0.63; 3.35 0.49; 3.34 1.12; 3.32 0.86; 3.32 0.98; 3.30 0.74; 3.28 0.74; 3.26 1.01; 3.26 3.68; 3.24 1.09; 3.23 0.47; 3.22 0.64; 3.21 2.69; 2.70 1.01; 2.68 3.17; 2.66 3.28; 2.64 1.13; 1.72 16.00; 1.59 5.80; 1.26 4.49; 1.25 8.74; 1.25 8.92; 1.23 4.27; 1.17 4.41; 1.15 8.86; 1.13 4.28; 0.00 6.39 |
| 6.416 | 3-F—Ph | H | O | H | $CH_2$ | $CH_3$ | |
| 6.417 | 3-Me—Ph | H | O | H | $CH_2$ | $CH_3$ | [$CDCl_3$] 7.47 2.31; 7.47 2.33; 7.43 1.15; 7.41 1.48; 7.31 1.00; 7.29 2.33; 7.27 1.79; 7.26 8.31; 7.25 1.75; 7.23 0.84; 6.85 0.57; 3.84 2.68; 3.80 3.07; 3.37 0.38; 3.35 0.70; 3.35 0.44; 3.33 1.15; 3.32 1.00; 3.32 0.94; 3.30 0.85; 3.28 0.41; 3.28 0.44; 3.27 0.78; 3.26 1.02; 3.26 0.88; 3.24 3.98; 3.23 0.56; 3.22 0.58; 3.21 0.55; 3.20 2.60; 2.37 12.06; 1.71 16.00; 1.61 4.09; 1.17 4.44; 1.15 8.81; 1.13 4.25; 0.00 3.58 |
| 6.418 | $F_5$—Ph | H | O | H | $CH_2$ | $CH_3$ | |
| 6.419 | Ph | H | O | H | $CH_2$ | $CH_3$ | |
| 6.420 | 3,5-$Cl_2$—Ph | H | O | H | $CH_2$ | COOH | [$CDCl_3$] 1.74 (s, 3H); 3.20 (d, 1H); 3.79 (d, 1H); 4.04 (dd, 1H); 4.16 (dd, 1H); 7.41 (m, 1H); 7.52 (m, 2H). |
| 6.421 | 3,5-$F_2$—Ph | H | O | H | $CH_2$ | COOH | [$CDCl_3$] 7.28 1.18; 7.26 38.31; 7.19 0.42; 7.17 1.95; 7.17 2.60; 7.15 2.56; 7.15 2.06; 7.14 0.38; 6.91 0.47; 6.91 0.77; 6.90 0.49; 6.89 0.93; 6.89 1.56; 6.88 0.89; 6.87 0.51; 6.86 0.78; 6.86 0.44; 4.18 0.83; 4.17 0.81; 4.13 2.07; 4.12 2.06; 4.08 2.04; 4.06 2.08; 4.03 0.82; 4.02 0.83; 3.80 2.59; 3.76 3.03; 3.24 2.92; 3.19 2.53; 1.76 16.00; 1.25 0.38; 0.00 54.37 |
| 6.422 | 3-Cl—Ph | H | O | H | $CH_2$ | COOH | [$CDCl_3$] 7.64 1.80; 7.64 3.34; 7.63 2.32; 7.50 1.67; 7.50 1.20; 7.48 2.12; 7.48 1.51; 7.41 1.17; 7.41 1.02; 7.39 2.71; 7.38 1.33; 7.36 0.78; 7.36 2.58; 7.34 2.80; 7.32 |

TABLE 6-continued

Compounds of the general formula (I) according to the invention in which $R^2$ is hydrogen and $R^3$ is methyl and aryl is the radical

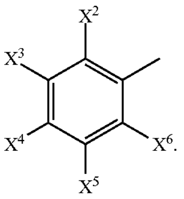

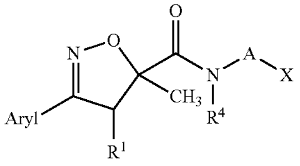

| No. | Aryl | $R^1$ | Y | $R^4$ | A | X | Physical data |
|---|---|---|---|---|---|---|---|
| | | | | | | | 1.04; 7.26 22.28; 5.30 0.42; 4.16 0.82; 4.14 0.84; 4.11 1.89; 4.10 1.85; 4.05 1.83; 4.03 1.89; 4.00 0.85; 3.99 0.81; 3.83 2.61; 3.79 3.00; 3.26 2.92; 3.21 2.56; 1.74 16.00; 1.28 0.37; 1.28 0.33; 1.26 1.83; 0.88 0.33 |
| 6.423 | 3-F—Ph | H | O | H | $CH_2$ | COOH | [$CDCl_3$] 7.39 2.34; 7.38 2.69; 7.38 3.66; 7.37 3.93; 7.35 0.54; 7.34 0.78; 7.32 0.46; 7.31 0.41; 7.26 51.59; 7.26 49.97; 7.16 0.45; 7.15 0.81; 7.15 0.48; 7.14 0.48; 7.13 0.78; 7.13 0.76; 7.12 0.44; 7.11 0.37; 4.17 0.80; 4.16 0.82; 4.13 1.85; 4.11 1.87; 4.06 1.83; 4.05 1.89; 4.01 0.84; 4.00 0.84; 3.83 2.66; 3.79 3.09; 3.49 0.87; 3.49 0.87; 3.27 3.05; 3.22 2.66; 2.00 2.01; 2.00 2.05; 1.79 0.87; 1.75 16.00; 1.43 0.64; 1.26 1.80; 0.00 9.94; 0.00 10.58; −0.01 0.59; −0.01 0.55 |
| 6.424 | 3,5-$Cl_2$—Ph | H | O | H | $CH_2$ | cyanogen | [$CDCl_3$] 1.76 (s, 3H); 3.25 (d, 1H); 3.77 (d, 1H); 4.16 (dd, 1H); 4.23 (dd, 1H); 7.19 (t br, 1H); 7.42 (m, 1H); 7.51 (m, 2H) |
| 6.425 | 3,5-$F_2$—Ph | H | O | H | $CH_2$ | cyanogen | [DMSO-$D_6$] 1.55 (s, 3H); 3.43 (d, 1H); 3.76 (d, 1H); 4.10 (d, 2H); 7.40 (m, 3H); 8.91 (t, 1H). |
| 6.426 | 3-Cl-5-$CF_3O$—Ph | H | O | H | $CH_2$ | cyanogen | [$CDCl_3$] 1.75 (s, 3H); 3.24 (d, 1H); 3.80 (d, 1H); 4.15 (dd, 1H); 4.25 (dd, 1H); 7.22 (brt, 1H); 7.31 (m, 1H); 7.41 (m, 1H); 7.53 (m, 1H). |
| 6.427 | 3-F-5-Me—Ph | H | O | H | $CH_2$ | cyanogen | [$CDCl_3$] 7.30 0.39; 7.30 0.39; 7.26 11.89; 7.26 0.47; 7.19 0.69; 7.19 1.13; 7.19 1.66; 7.19 1.76; 7.19 1.36; 7.18 0.96; 7.17 0.51; 7.17 0.65; 7.16 0.45; 7.15 0.43; 7.15 0.48; 7.14 0.64; 7.14 0.56; 7.14 0.46; 7.14 0.39; 6.98 0.38; 6.98 0.52; 6.98 0.58; 6.98 0.64; 6.97 0.54; 6.97 0.47; 6.97 0.36; 6.96 0.38; 6.96 0.50; 6.95 0.56; 6.95 0.62; 6.95 0.53; 6.95 0.46; 6.95 0.36; 5.30 0.62; 4.27 1.05; 4.25 1.08; 4.23 2.55; 4.21 2.51; 4.17 2.42; 4.16 2.58; 4.13 1.04; 4.11 1.04; 3.81 2.72; 3.77 3.11; 3.28 2.79; 3.24 2.41; 2.37 8.22; 2.37 8.29; 1.74 16.00; 1.43 0.75; 0.00 6.56 |
| 6.428 | 3-F—Ph | H | O | H | $CH_2$ | cyanogen | [$CDCl_3$] 1.73 (s, 3H); 3.27 (d, 1H); 3.80 (d, 1H); 4.12 (dd, 1H); 4.23 (dd, 1H); 7.13 (m, 1H); 7.28 (brt, 1H); 7.37 (m, 3H). |

TABLE 6-continued

Compounds of the general formula (I) according to the invention in which $R^2$ is hydrogen and $R^3$ is methyl and aryl is the radical

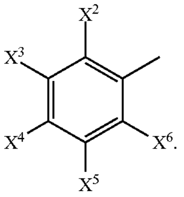

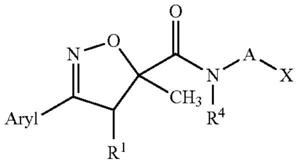

| No. | Aryl | $R^1$ | Y | $R^4$ | A | X | Physical data |
|---|---|---|---|---|---|---|---|
| 6.429 | 3-$NO_2$—Ph | H | O | H | $CH_2$ | cyanogen | [$CDCl_3$] 8.46 1.21; 8.46 2.01; 8.45 1.29; 8.32 0.82; 8.31 0.93; 8.31 0.80; 8.31 0.84; 8.29 0.91; 8.29 0.94; 8.29 0.90; 8.29 0.87; 8.00 0.85; 7.99 1.01; 7.99 1.06; 7.99 0.88; 7.98 0.96; 7.98 1.09; 7.97 1.21; 7.97 0.96; 7.65 1.43; 7.63 2.36; 7.61 1.21; 7.27 0.33; 7.27 0.34; 7.27 0.37; 7.26 16.08; 7.26 0.62; 7.26 0.58; 7.26 0.55; 7.25 0.54; 7.25 0.52; 7.25 0.51; 7.25 0.48; 7.25 0.46; 7.25 0.43; 7.25 0.36; 7.25 0.35; 7.25 0.33; 5.30 1.23; 4.27 0.61; 4.26 0.62; 4.23 2.82; 4.21 2.76; 4.21 2.74; 4.19 2.81; 4.16 0.63; 4.15 0.61; 3.91 2.71; 3.87 3.16; 3.36 2.88; 3.32 2.50; 1.78 16.00; 1.56 5.15; 0.00 8.95 |
| 6.430 | 3,5-$Cl_2$—Ph | H | O | H | $CH_2$ | cyclohexyl | |
| 6.431 | 3,5-$Cl_2$—Ph | H | O | H | $CH_2$ | c-Pr | [$CDCl_3$] 0.20 (m, 2H); 0.52 (m, 2H); 0.94 (m, 1H); 1.73 (s, 3H); 3.05 (m, 1H); 3.16 (m, 1H); 3.19 (d, 1H); 3.79 (d, 1H); 6.88 (t br, 1H); 7.40 (m, 1H); 7.52 (m, 2H) |
| 6.432 | 3,5-$F_2$—Ph | H | O | H | $CH_2$ | c-Pr | [$CDCl_3$] 7.52 0.37; 7.26 63.59; 7.18 1.58; 7.17 2.11; 7.16 2.06; 7.15 1.68; 7.00 0.35; 6.91 0.69; 6.90 1.09; 6.89 0.84; 6.88 1.30; 6.88 1.83; 6.87 1.07; 6.86 0.58; 6.86 0.81; 6.85 0.42; 3.80 2.66; 3.76 3.05; 3.22 0.48; 3.20 3.48; 3.18 1.08; 3.16 1.13; 3.16 2.64; 3.15 0.92; 3.09 0.82; 3.08 0.90; 3.07 0.92; 3.06 0.89; 3.04 0.51; 3.04 0.54; 3.02 0.48; 1.73 16.00; 1.54 3.20; 0.96 0.50; 0.96 0.45; 0.95 0.37; 0.94 0.82; 0.93 0.49; 0.93 0.58; 0.91 0.36; 0.54 0.41; 0.54 0.39; 0.53 1.99; 0.53 2.21; 0.52 0.86; 0.51 2.13; 0.51 1.97; 0.50 0.50; 0.50 0.46; 0.22 0.75; 0.21 2.53; 0.20 2.42; 0.19 0.64; 0.01 1.30; 0.00 42.85; −0.01 2.11 |
| 6.433 | 3,5-$Cl_2$—Ph | H | O | H | $CH_2$ | diethoxyphosphoryl | |
| 6.434 | 3,5-$F_2$—Ph | H | O | H | $CH_2$ | diethoxyphosphoryl | |
| 6.435 | 3-F—Ph | H | O | H | $CH_2$ | diethoxyphosphoryl | |
| 6.436 | Ph | H | O | H | $CH_2$ | diethoxyphosphoryl | |
| 6.437 | 3,5-$Cl_2$—Ph | H | O | H | $CH_2$ | difluoromethyl | [$CDCl_3$] 1.73 (s, 3H); 3.22 (d, 1H); 3.58 (m, 1H); 3.73 (m, 1H); 3.78 (d, 1H); 3.83 (t t, 1H); 7.06 (t br, 1H); 7.42 (s, 1H); 7.52 (s, 2H). |

TABLE 6-continued

Compounds of the general formula (I) according to the invention in which $R^2$ is hydrogen and $R^3$ is methyl and aryl is the radical

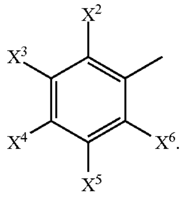

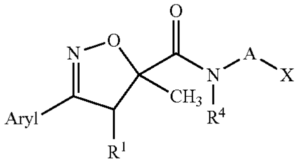

| No. | Aryl | $R^1$ | Y | $R^4$ | A | X | Physical data |
|---|---|---|---|---|---|---|---|
| 6.438 | 3,5-$Cl_2$—Ph | H | O | H | $CH_2$ | dimethoxymethyl | [$CDCl_3$] 1.72 (s, 3H); 3.18 (d, 1H); 3.33 (m, 1H); 3.36 (s, 3H); 3.37 (s, 3H); 3.46 (m, 1H); 3.79 (d, 1H); 4.38 (t, 1H) 6.95 (s br, 1H); 7.42 (s, 1H); 7.52 (s, 2H). |
| 6.439 | 3-Cl—Ph | H | O | H | $CH_2$ | dimethoxymethyl | [$CDCl_3$] 1.72 (s, 3H); 3.22 (d, 1H); 3.34 (m, 1H); 3.38 (s, 3H); 3.39 (s, 3H); 3.48 m, 1H); 3.80 (d, 1H); 4.37 (t, 1H); 7.00 (s, 1H); 7.35 (m, 1H); 7.40 (m, 1H); 7.50 (m, 1H); 7.68 (s, 1H). |
| 6.440 | 3,5-$Cl_2$—Ph | H | O | H | $CH_2$ | dimethylcarbamoyl | [$CDCl_3$] 1.74 (s, 3H); 2.99 (s, 3H); 3.01 (s, 3H); 3.18 (d, 1H); 3.78 (d, 1H); 4.04 (qd, 2H); 7.42 (s, 1H); 7.53 (s, 2H); 7.74 (s br, 1H). |
| 6.441 | 3,5-$Cl_2$—Ph | H | O | H | $CH_2$ | ethenyl | [$CDCl_3$] 1.73 (s, 3H); 3.20 (d, 1H); 3.80 (d, 1H); 3.88 (m, 2H); 5.15 (m, 2H); 5.83 (m, 1H); 6.88 (t br, 1H); 7.42 (s, 1H); 7.52 (s, 2H). |
| 6.442 | 3,5-$Cl_2$—Ph | H | O | prop-2-en-1-yl | $CH_2$ | ethenyl | [$CDCl_3$] 1.74 (s, 3H); 3.09 (d, 1H); 3.80 (m, 1H); 4.01-4.13 (m, 2H); 4.38 (d, 1H); 4.40 (m, 1H); 5.09-5.28 (m, 4H); 5.70-5.80 (m, 1H); 5.83-5.93 (m, 1H); 7.39 (m, 1H); 7.55 (m, 2H). |
| 6.443 | 3,5-$F_2$—Ph | H | O | H | $CH_2$ | ethenyl | [$CDCl_3$] 7.52 1.15; 7.52 1.02; 7.32 0.99; 7.31 1.33; 7.26 181.64; 7.26 144.69; 7.26 141.95; 7.26 190.50; 7.21 0.84; 7.21 0.96; 7.17 3.74; 7.16 2.32; 7.16 3.26; 7.15 3.78; 7.14 0.83; 7.00 1.14; 7.00 1.09; 6.91 1.72; 6.90 1.88; 6.89 2.85; 6.88 2.65; 6.86 1.29; 6.86 1.18; 5.87 0.45; 5.86 0.79; 5.85 0.63; 5.83 0.91; 5.82 1.01; 5.80 0.79; 5.79 0.88; 5.78 0.48; 5.19 2.18; 5.16 2.32; 5.16 2.44; 5.16 2.35; 5.15 2.24; 5.14 2.16; 5.14 2.16; 3.97 0.49; 3.96 0.70; 3.95 0.67; 3.94 0.54; 3.93 0.98; 3.91 1.59; 3.88 0.88; 3.87 1.61; 3.85 0.89; 3.83 0.77; 3.81 2.86; 3.77 2.70; 3.77 3.04; 3.50 0.35; 3.22 2.67; 3.21 2.79; 3.17 2.59; 1.75 14.52; 1.75 16.00; 1.59 0.37; 1.58 0.43; 1.53 51.87; 1.53 41.84; 1.53 39.97; 1.53 54.24; 0.15 0.41; 0.06 0.38; 0.05 0.55; 0.01 2.07; 0.01 68.59; 0.00 54.81; 0.00 54.33; 0.00 72.20; −0.05 0.47; −0.15 0.50; −2.15 0.35 |
| 6.444 | 3-F—Ph | H | O | H | $CH_2$ | ethenyl | |
| 6.445 | Ph | H | O | H | $CH_2$ | ethenyl | |

TABLE 6-continued

Compounds of the general formula (I) according to the invention in which $R^2$ is hydrogen and $R^3$ is methyl and aryl is the radical

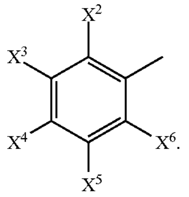

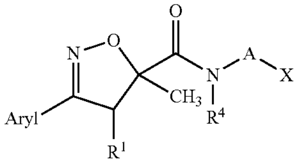

| No. | Aryl | $R^1$ | Y | $R^4$ | A | X | Physical data |
|---|---|---|---|---|---|---|---|
| 6.446 | 3,5-$(CF_3)_2$—Ph | H | O | H | $CH_2$ | ethynyl | [$CDCl_3$] 1.76 (s, 3H); 2.50 (t, 3H); 3.28 (d, 1H); 3.88 (d, 1H); 3.98 (m, 1H); 4.04 (m, 1H); 4.10 (m, 1H), 6.82 (t br, 1H); 7.92 (s, 1H); 8.07 (s, 2H) |
| 6.447 | 3,5-$Cl_2$—Ph | H | O | H | $CH_2$ | ethynyl | [$CDCl_3$] 1.70 (s, 3H); 2.25 (m, 1H); 3.19 (d, 1H); 3.78 (d, 1H); 4.05 (m, 2H); 6.99 (t br, 1H); 7.41 (m, 1H); 7.51 (m, 2H) |
| 6.448 | 3,5-$Cl_2$—Ph | H | O | prop-2-yn-1-yl | $CH_2$ | ethynyl | |
| 6.449 | 3,5-$F_2$—Ph | H | O | H | $CH_2$ | ethynyl | [$CDCl_3$] 7.52 0.40; 7.27 0.37; 7.26 0.52; 7.26 71.56; 7.17 1.41; 7.17 1.97; 7.15 1.09; 7.15 1.90; 7.15 1.62; 7.13 0.32; 7.00 0.74; 6.98 0.50; 6.91 0.37; 6.91 0.68; 6.90 0.34; 6.89 0.76; 6.88 1.35; 6.88 0.70; 6.87 0.39; 6.86 0.68; 6.86 0.35; 4.14 0.44; 4.13 0.50; 4.12 0.45; 4.12 0.46; 4.09 1.06; 4.09 1.07; 4.08 1.06; 4.07 1.08; 4.03 1.05; 4.03 1.08; 4.02 1.09; 4.01 1.08; 3.99 0.46; 3.98 0.47; 3.97 0.44; 3.97 0.45; 3.79 2.64; 3.75 3.03; 3.22 2.90; 3.17 2.50; 2.25 1.36; 2.25 2.76; 2.24 1.41; 1.74 16.00; 1.53 29.18; 0.01 1.20; 0.01 1.22; 0.01 0.54; 0.01 0.51; 0.00 46.94; 0.00 46.98; −0.01 1.32; −0.01 1.69; −0.01 1.56; −0.01 0.36 |
| 6.450 | 3,5-$Cl_2$—Ph | H | O | cPr | $CH_2$ | ethoxycarbonyl | |
| 6.451 | 3-Cl—Ph | H | O | H | $CH_2$ | ethoxycarbonyl | [$CDCl_3$] 7.66 1.51; 7.65 2.60; 7.65 1.66; 7.51 0.90; 7.51 1.42; 7.51 0.82; 7.51 0.79; 7.49 1.14; 7.49 1.78; 7.49 1.04; 7.49 1.00; 7.41 0.63; 7.41 0.86; 7.41 0.65; 7.40 0.61; 7.40 0.60; 7.39 1.37; 7.39 1.71; 7.39 1.45; 7.38 1.09; 7.36 2.32; 7.34 2.53; 7.32 1.12; 7.30 0.51; 7.29 0.68; 7.28 0.50; 7.27 0.44; 7.26 11.54; 7.26 12.86; 4.23 1.42; 4.21 4.32; 4.19 4.36; 4.18 1.46; 4.11 0.93; 4.09 0.93; 4.06 2.03; 4.05 2.00; 3.99 2.00; 3.98 2.02; 3.94 0.93; 3.93 0.91; 3.83 2.69; 3.79 3.12; 3.25 2.98; 3.20 2.60; 1.75 16.00; 1.57 3.22; 1.28 4.97; 1.26 9.09; 1.26 9.87; 1.24 4.45; 1.24 4.77; 0.00 4.98; 0.00 5.69 |
| 6.452 | 3-F—Ph | H | O | H | $CH_2$ | ethoxycarbonyl | [$CDCl_3$] 7.40 0.95; 7.39 0.99; 7.39 0.86; 7.39 1.20; 7.38 1.13; 7.38 4.82; 7.37 2.79; 7.37 2.46; 7.37 2.85; 7.36 1.60; 7.29 0.58; 7.26 8.05; 7.15 0.42; 7.14 0.48; 7.14 0.48; 7.14 0.60; 7.13 0.83; 7.12 |

TABLE 6-continued

Compounds of the general formula (I) according to the invention in which $R^2$ is hydrogen and $R^3$ is methyl and aryl is the radical

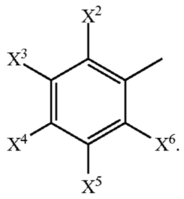

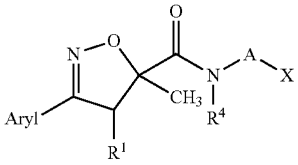

| No. | Aryl | $R^1$ | Y | $R^4$ | A | X | Physical data |
|---|---|---|---|---|---|---|---|
| | | | | | | | 0.88; 7.12 0.39; 7.11 0.48; 7.11 0.53; 7.10 0.33; 4.23 1.39; 4.21 4.21; 4.19 4.26; 4.17 1.42; 4.11 0.91; 4.09 0.90; 4.06 1.97; 4.05 1.94; 3.99 1.95; 3.98 1.96; 3.94 0.91; 3.93 0.89; 3.83 2.71; 3.79 3.11; 3.25 2.99; 3.21 2.59; 1.75 16.00; 1.58 2.08; 1.28 4.86; 1.26 9.72; 1.24 4.70; 0.00 3.62 |
| 6.453 | 3,5-$F_2$—Ph | H | O | H | $CH_2$ | formyl | |
| 6.454 | 3,5-$Cl_2$—Ph | H | O | H | $CH_2$ | methoxycarbonyl | [$CDCl_3$] 1.75 (s, 3H); 3.20 (d, 1H); 3.75 (s, 3H); 3.77 (d, 1H); 3.98 (dd, 1H); 4.09 (dd, 1H); 7.24 (s br, 1H); 7.41 (m, 1H), 7.52 (m, 2H) |
| 6.455 | 3,5-$F_2$—Ph | H | O | H | $CH_2$ | methoxycarbonyl | [$CDCl_3$] 7.26 17.21; 7.26 16.28; 7.18 1.41; 7.17 1.85; 7.16 1.15; 7.16 1.86; 7.15 1.47; 6.91 0.32; 6.90 0.59; 6.90 0.33; 6.89 0.65; 6.88 1.18; 6.87 0.64; 6.86 0.34; 6.86 0.59; 4.13 0.72; 4.11 0.77; 4.08 1.63; 4.07 1.61; 4.02 1.61; 4.00 1.63; 3.97 0.72; 3.96 0.69; 3.80 2.21; 3.75 16.00; 3.23 2.44; 3.18 2.11; 1.75 13.27; 1.56 6.30; 0.00 4.22; 0.00 4.14 |
| 6.456 | 3-Cl—Ph | H | O | H | $CH_2$ | methoxycarbonyl | [$CDCl_3$] 7.65 1.04; 7.65 2.02; 7.65 1.21; 7.51 0.72; 7.51 1.09; 7.51 0.76; 7.49 0.90; 7.49 1.39; 7.49 0.94; 7.41 0.52; 7.41 0.66; 7.41 0.55; 7.40 0.57; 7.39 1.15; 7.39 1.14; 7.39 1.28; 7.38 0.98; 7.36 1.61; 7.36 1.58; 7.34 1.99; 7.32 0.80; 7.32 0.79; 7.30 0.36; 7.29 0.42; 7.26 13.38; 4.13 0.73; 4.11 0.73; 4.08 1.57; 4.07 1.55; 4.01 1.54; 3.99 1.56; 3.96 0.74; 3.95 0.75; 3.83 2.54; 3.78 2.90; 3.76 0.54; 3.75 16.00; 3.25 2.62; 3.21 2.30; 1.76 0.86; 1.75 14.41; 1.57 3.33; 0.00 5.55 |
| 6.457 | 3-F—Ph | H | O | H | $CH_2$ | methoxycarbonyl | [$CDCl_3$] 7.40 0.68; 7.40 0.81; 7.39 0.86; 7.39 1.23; 7.38 0.95; 7.38 3.91; 7.37 1.96; 7.37 2.61; 7.37 1.42; 7.31 0.33; 7.30 0.47; 7.26 6.58; 7.15 0.37; 7.14 0.45; 7.14 0.45; 7.13 0.72; 7.12 0.77; 7.11 0.43; 7.11 0.47; 4.13 0.79; 4.12 0.79; 4.09 1.70; 4.07 1.68; 4.01 1.68; 4.00 1.70; 3.96 0.80; 3.95 0.79; 3.83 2.45; 3.79 2.83; 3.75 16.00; 3.25 2.72; 3.21 2.36; 1.75 14.54; 1.58 2.05; 0.00 2.93 |

TABLE 6-continued

Compounds of the general formula (I) according to the invention in which $R^2$ is hydrogen and $R^3$ is methyl and aryl is the radical

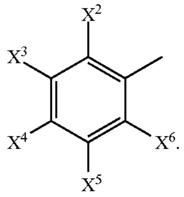

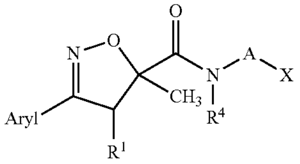

| No. | Aryl | $R^1$ | Y | $R^4$ | A | X | Physical data |
|---|---|---|---|---|---|---|---|
| 6.458 | 3-Cl-5-F—Ph | H | O | H | $CH_2$ | nonyl | [$CDCl_3$] 0.88 (t, 3H); 1.28 (m, 3H); 1.50 (m, 5H); 1.72 (s, 3H); 3.17 (d, 1H); 3.20 (m, 1H); 3.27 (m, 1H); 3.78 (d, 1H); 6.77 (t br, 1H); 7.15 (m, 1H); 7.26 (m, 1H); 7.40 (s, 1H) |
| 6.459 | 3,5-$Cl_2$—Ph | H | O | H | $CH_2$ | pentafluoroethyl | [$CDCl_3$] 1.72 (s, 3H); 3.22 (d, 1H); 3.28 (m, 1H); 3.78 (d, 1H); 3.87 (m, 1H); 4.08 (m, 1H); 7.10 (t br, 1H); 7.43 (m, 1H); 7.51 (s, 1H). |
| 6.460 | 3,5-$Cl_2$—Ph | H | O | H | $CH_2$ | pentyl | [$CDCl_3$] 7.52 0.43; 7.52 7.92; 7.51 8.96; 7.41 2.07; 7.41 3.70; 7.40 1.75; 7.26 0.40; 7.26 0.63; 7.26 41.98; 7.26 0.90; 7.26 0.66; 7.25 0.52; 7.25 0.45; 7.25 0.37; 7.25 0.33; 6.77 0.41; 3.80 2.86; 3.76 3.24; 3.31 0.47; 3.30 0.87; 3.28 0.50; 3.28 1.10; 3.26 0.85; 3.26 0.55; 3.25 0.45; 3.24 0.43; 3.22 0.47; 3.22 0.91; 3.20 1.01; 3.20 0.55; 3.19 3.30; 3.17 0.47; 3.14 2.56; 1.72 16.00; 1.55 6.43; 1.52 0.61; 1.50 0.99; 1.48 0.89; 1.47 0.33; 1.31 0.57; 1.30 0.81; 1.29 1.04; 1.29 1.77; 1.28 2.58; 1.28 2.78; 1.28 3.15; 1.27 4.34; 1.26 0.90; 1.25 0.53; 0.88 0.50; 0.88 1.17; 0.87 0.93; 0.86 5.05; 0.85 0.68; 0.84 1.27; 0.01 0.52; 0.00 19.95 |
| 6.461 | 3,5-$F_2$—Ph | H | O | H | $CH_2$ | pentyl | [$CDCl_3$] 7.31 0.35; 7.26 37.79; 7.26 43.64; 7.25 3.44; 7.25 3.41; 7.21 0.37; 7.21 0.45; 7.17 2.14; 7.17 2.63; 7.16 2.58; 7.15 2.40; 7.15 2.75; 7.15 2.40; 7.13 0.49; 6.90 0.41; 6.90 0.73; 6.89 0.45; 6.88 0.86; 6.88 1.47; 6.87 0.90; 6.86 0.52; 6.85 0.79; 6.85 0.48; 6.78 0.79; 3.80 2.62; 3.75 3.03; 3.32 0.60; 3.30 1.05; 3.29 1.40; 3.27 1.24; 3.25 0.49; 3.24 0.45; 3.22 1.05; 3.21 1.36; 3.19 3.55; 3.17 0.61; 3.15 2.58; 1.72 16.00; 1.55 17.54; 1.54 21.13; 1.52 1.25; 1.51 2.01; 1.49 1.27; 1.49 1.72; 1.47 0.63; 1.33 0.33; 1.31 0.95; 1.27 7.44; 0.88 2.00; 0.86 5.77; 0.84 2.34; 0.01 0.43; 0.01 0.55; 0.00 16.83 |
| 6.462 | 3,5-$Cl_2$—Ph | H | O | H | $CH_2$ | piperidin-2-yl | [$CDCl_3$] 7.71 0.83; 7.70 0.63; 7.67 0.69; 7.52 0.53; 7.51 0.35; 7.51 0.38; 7.46 7.07; 7.46 7.90; 7.44 8.21; 7.43 9.33; 7.37 2.23; 7.36 5.18; 7.36 5.34; 7.35 2.27; 7.26 84.84; 7.00 0.48; 3.96 1.95; 3.92 2.14; 3.87 2.60; 3.83 2.88; 3.67 0.38; 3.66 0.43; 3.65 0.52; 3.64 |

TABLE 6-continued
Compounds of the general formula (I) according to the invention in which $R^2$ is hydrogen and $R^3$ is methyl and aryl is the radical
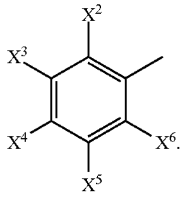
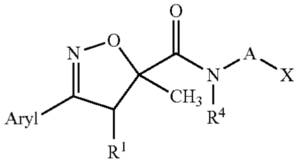
| No. | Aryl | $R^1$ | Y | $R^4$ | A | X | Physical data |
|---|---|---|---|---|---|---|---|
| | | | | | | | 0.59; 3.63 1.04; 3.61 1.84; 3.60 1.39; 3.55 0.52; 3.53 0.60; 3.52 0.68; 3.50 0.41; 3.49 0.54; 3.48 0.78; 3.45 1.23; 3.41 0.65; 3.15 2.94; 3.15 2.69; 3.13 0.53; 3.11 3.37; 3.10 3.22; 3.09 0.95; 2.82 0.41; 2.81 0.60; 2.79 0.95; 2.78 0.91; 2.77 0.81; 2.77 0.72; 2.75 0.60; 2.74 0.41; 2.31 0.67; 2.28 0.33; 1.90 0.95; 1.86 1.40; 1.83 1.17; 1.78 16.00; 1.74 13.54; 1.71 1.13; 1.55 0.67; 1.52 0.84; 1.51 0.85; 1.48 1.09; 1.48 1.09; 1.46 0.76; 1.25 1.27; 0.01 0.84; 0.00 47.52; −0.01 2.07 |
| 6.463 | 3,5-$F_2$—Ph | H | O | H | $CH_2$ | piperidin-2-yl | [$CDCl_3$] 7.26 40.25; 7.18 0.36; 7.17 1.65; 7.17 2.12; 7.15 2.20; 7.15 1.82; 7.14 0.65; 7.13 0.60; 6.90 0.37; 6.90 0.68; 6.89 0.36; 6.88 0.78; 6.88 1.38; 6.87 0.70; 6.86 0.41; 6.85 0.69; 6.85 0.35; 3.81 1.33; 3.80 1.22; 3.76 1.51; 3.76 1.42; 3.30 0.39; 3.23 0.35; 3.21 0.65; 3.19 2.70; 3.18 0.41; 3.15 1.85; 3.09 0.33; 3.08 0.72; 3.04 0.72; 2.68 0.40; 2.66 0.45; 2.65 0.44; 2.63 0.43; 2.62 0.36; 2.60 0.62; 2.23 0.44; 2.21 0.33; 1.78 0.55; 1.78 0.51; 1.73 16.00; 1.72 0.65; 1.62 0.89; 1.59 2.34; 1.57 3.13; 1.38 0.60; 1.37 0.63; 1.35 1.19; 1.32 0.68; 1.32 0.49; 1.25 0.35; 0.01 0.61; 0.00 24.90; −0.01 0.94 |
| 6.464 | Ph | H | O | H | $CH_2$ | piperidin-2-yl | [$CDCl_3$] 7.65 1.85; 7.64 2.11; 7.63 2.15; 7.62 2.39; 7.52 0.35; 7.43 0.89; 7.42 5.03; 7.40 2.56; 7.39 0.68; 7.38 0.43; 7.27 0.34; 7.26 61.43; 7.25 0.77; 7.25 0.66; 7.25 0.65; 7.24 0.62; 7.00 0.35; 3.86 1.24; 3.85 1.34; 3.82 1.41; 3.81 1.54; 3.30 0.43; 3.26 1.80; 3.25 1.76; 3.23 0.95; 3.21 1.95; 3.21 1.68; 3.13 0.36; 3.12 0.41; 3.08 0.72; 3.06 0.66; 2.69 0.49; 2.68 0.50; 2.68 0.48; 2.62 0.38; 2.60 0.53; 2.60 0.49; 2.59 0.51; 2.55 0.44; 2.17 7.61; 1.79 0.51; 1.78 0.77; 1.76 0.75; 1.75 0.77; 1.73 16.00; 1.69 2.64; 1.64 1.19; 1.61 1.13; 1.57 0.96; 1.40 0.34; 1.39 0.35; 1.37 0.83; 1.36 0.71; 1.35 1.14; 1.34 0.92; 1.33 0.46; 1.32 0.66; 1.31 0.45; 1.29 0.33; 1.25 |

TABLE 6-continued

Compounds of the general formula (I) according to the invention in which $R^2$ is hydrogen and $R^3$ is methyl and aryl is the radical

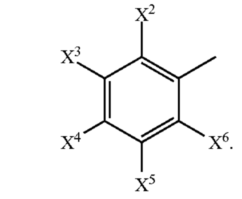

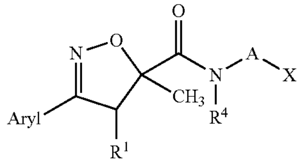

| No. | Aryl | $R^1$ | Y | $R^4$ | A | X | Physical data |
|---|---|---|---|---|---|---|---|
| | | | | | | | 1.46; 1.16 0.32; 1.15 0.37; 1.12 0.46; 1.09 0.35; 0.01 0.90; 0.00 36.52; −0.01 1.01; −0.01 1.40 |
| 6.465 | 3,5-$Cl_2$—Ph | H | O | $CH_3$ | $CH_2$ | propan-2-yl | |
| 6.466 | 3,5-$Cl_2$—Ph | H | O | H | $CH_2$ | propan-2-yl | [$CDCl_3$] 0.89 (dd, 6H); 1.72 (s, 3H); 1.78 (m, 1H); 3.02 (m, 1H); 3.12 (m, 1H); 3.17 (d, 1H); 3.79 (d, 1H); 6.82 (br, 1H); 7.41 (m, 1H); 7.51 (m, 2H). |
| 6.467 | 3,5-$Cl_2$—Ph | H | O | H | $CH_2$ | pyrrolidin-1-ylcarbonyl | |
| 6.468 | 3,5-$Cl_2$—Ph | H | O | H | $CH_2$ | tert-butyl | [$CDCl_3$] 7.53 1.40; 7.52 2.39; 7.52 2.85; 7.52 2.11; 7.43 0.40; 7.42 0.90; 7.42 1.09; 7.41 1.10; 7.41 0.44; 7.27 7.35; 7.26 10.23; 3.82 0.59; 3.81 0.82; 3.78 0.67; 3.77 0.95; 3.20 0.65; 3.20 0.89; 3.16 0.64; 3.15 1.01; 3.15 0.38; 3.14 0.38; 3.13 0.52; 3.12 0.38; 3.11 0.50; 3.01 0.36; 3.00 0.51; 3.00 0.38; 2.99 0.51; 2.97 0.35; 2.95 0.33; 1.75 3.58; 1.74 4.88; 1.56 2.54; 1.55 2.24; 1.55 3.80; 1.27 0.65; 0.90 11.58; 0.90 16.00; 0.89 1.27; 0.88 0.72; 0.01 3.35 |
| 6.469 | 3,5-$F_2$—Ph | H | O | H | $CH_2$ | tert-butyl | [$CDCl_3$] 7.26 11.15; 7.17 0.65; 7.17 0.69; 7.16 0.44; 7.16 0.52; 7.15 0.73; 7.15 0.52; 6.90 0.36; 6.88 0.49; 6.88 0.62; 6.87 0.36; 3.81 0.82; 3.76 0.95; 3.20 0.85; 3.16 0.60; 3.16 0.80; 3.14 0.34; 3.13 0.51; 3.11 0.49; 3.01 0.50; 2.99 0.51; 2.98 0.34; 2.96 0.33; 1.75 4.93; 1.55 4.04; 0.90 16.00 |
| 6.470 | 3,5-$Cl_2$—Ph | H | O | H | $CH_2$ | tetrahydrofuran-2-yl | diastereomers D1 plus D2: [$CDCl_3$] 1.71 (s, 3H); 1.72 (s, 3H); 1.80-2.02 (m, 6H); 3.16 (d, 1H); 3,17 (d, 1H); 3,30 (m, 1H); 3.44 (m, 1H); 3.54 (m, 1H); 3.71 (m, 2H); 3.78 (d, 1H); 3.79 (d, 1H); 3.88 (m, 2H); 3.96 (m, 2H); 7.10 (s, br, 2H); 7.42 (s, 1H); 7.51 (s, 2H). |
| 6.471 | 3,5-$F_2$—Ph | H | O | H | $CH_2$ | tetrahydrofuran-2-yl | [$CDCl_3$] 1.40-1.55 (m, 1H); 1.72 (2 × s, 3H); 1.28-2.00 (m, 3H); 3.13-3.32 (m, 1H); 3.15 (2 × d, 1H); 3.40-3.55 (m, 1H); 3.70-4.00 (m, 4H); 6.86 (m, 1H); 7.03-7.20 (m, 3H). |
| 6.472 | 3-F—Ph | H | O | H | $CH_2$ | tetrahydrofuran-2-yl | |
| 6.473 | Ph | H | O | H | $CH_2$ | tetrahydrofuran-2-yl | |
| 6.474 | 3,5-$Cl_2$—Ph | H | O | H | $CH_2$ | tetrahydrofuran-3-yl | [$CDCl_3$] 7.52 8.94; 7.52 9.26; 7.51 9.84; 7.42 2.51; 7.42 4.49; 7.41 2.06; 7.26 26.46; 7.26 27.93; 6.94 0.61; 6.92 0.62; 6.91 0.41; 6.90 0.33; 5.30 2.73; 5.30 2.84; 3.89 0.44; 3.89 0.46; 3.88 0.49; 3.88 0.51; 3.87 1.07; 3.86 1.12; 3.85 |

TABLE 6-continued
Compounds of the general formula (I) according to the invention in which $R^2$ is hydrogen and $R^3$ is methyl and aryl is the radical
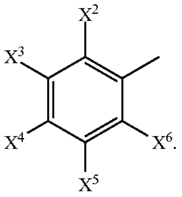
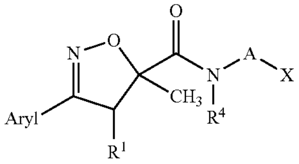
| No. | Aryl | $R^1$ | Y | $R^4$ | A | X | Physical data |
|---|---|---|---|---|---|---|---|
| | | | | | | | 0.70; 3.85 0.68; 3.84 0.64; 3.84 0.65; 3.82 1.01; 3.81 1.01; 3.80 4.85; 3.80 2.26; 3.79 1.33; 3.78 1.20; 3.78 1.19; 3.76 1.07; 3.76 4.45; 3.74 1.76; 3.72 1.47; 3.70 0.65; 3.52 1.03; 3.52 1.01; 3.51 1.07; 3.50 1.09; 3.50 1.01; 3.49 0.92; 3.48 0.94; 3.48 0.91; 3.39 0.37; 3.38 0.38; 3.37 0.50; 3.36 0.52; 3.35 0.94; 3.34 1.03; 3.34 0.81; 3.33 0.94; 3.32 0.62; 3.31 0.69; 3.26 0.62; 3.25 1.27; 3.25 0.76; 3.23 1.42; 3.22 1.17; 3.21 0.52; 3.20 4.48; 3.18 0.41; 3.16 3.56; 2.50 0.32; 2.48 0.69; 2.46 0.86; 2.45 0.68; 2.43 0.33; 2.06 0.34; 2.05 0.38; 2.04 0.63; 2.03 0.85; 2.02 0.46; 2.01 0.89; 2.00 0.74; 1.99 0.39; 1.98 0.35; 1.73 16.00; 1.61 0.37; 1.60 0.57; 1.59 0.59; 1.59 0.69; 1.58 8.08; 1.56 0.40; 0.01 0.34; 0.00 11.78; 0.00 12.69; −0.01 0.41; −0.01 0.41 |
| 6.475 | 3,5-$F_2$—Ph | H | O | H | $CH_2$ | tetrahydrofuran-3-yl | [$CDCl_3$] 7.52 1.37; 7.31 0.59; 7.28 0.33; 7.28 0.35; 7.27 0.32; 7.27 0.34; 7.27 0.43; 7.27 0.44; 7.27 0.50; 7.27 0.53; 7.27 0.50; 7.27 0.60; 7.27 0.79; 7.27 0.94; 7.27 1.15; 7.27 1.45; 7.26 1.75; 7.26 2.27; 7.26 3.56; 7.26 238.88; 7.26 3.34; 7.25 2.37; 7.25 1.79; 7.25 1.41; 7.25 1.09; 7.25 0.97; 7.25 0.94; 7.25 0.68; 7.25 0.49; 7.25 0.44; 7.25 0.40; 7.25 0.38; 7.25 0.35; 7.21 0.62; 7.18 0.57; 7.18 0.42; 7.17 2.51; 7.16 2.96; 7.16 1.60; 7.16 0.43; 7.15 1.55; 7.15 2.99; 7.14 2.65; 7.14 0.40; 7.13 0.50; 7.00 1.41; 6.94 0.55; 6.93 0.53; 6.91 0.91; 6.91 1.36; 6.90 0.70; 6.89 1.32; 6.88 2.35; 6.88 1.16; 6.87 0.67; 6.86 1.20; 6.86 0.57; 3.89 0.41; 3.89 0.39; 3.88 0.43; 3.87 0.86; 3.87 0.87; 3.86 0.87; 3.85 0.92; 3.85 0.63; 3.84 0.59; 3.83 0.59; 3.82 1.03; 3.81 1.03; 3.80 1.17; 3.80 2.34; 3.79 5.47; 3.78 1.24; 3.77 1.19; 3.76 0.80; 3.75 5.39; 3.74 1.73; 3.72 1.42; 3.70 0.59; 3.70 0.59; 3.52 1.03; 3.51 1.04; 3.51 1.05; 3.50 1.12; 3.50 1.00; 3.49 0.94; 3.48 0.94; 3.48 0.91; 3.39 0.38; 3.38 0.41; 3.37 0.47; 3.36 0.49; 3.35 1.04; 3.35 1.12; 3.34 0.79; 3.33 0.86; 3.33 0.93; 3.32 0.67; 3.31 |

TABLE 6-continued
Compounds of the general formula (I) according to the invention in which $R^2$ is hydrogen and $R^3$ is methyl and aryl is the radical
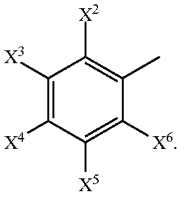
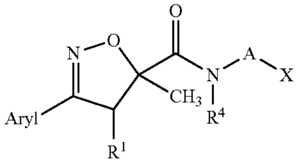
| No. | Aryl | $R^1$ | Y | $R^4$ | A | X | Physical data |
|---|---|---|---|---|---|---|---|
| | | | | | | | 0.73; 3.27 0.66; 3.25 1.33; 3.25 0.79; 3.24 0.79; 3.24 1.50; 3.22 1.12; 3.22 0.50; 3.20 4.98; 3.19 0.43; 3.16 3.86; 2.48 0.62; 2.46 0.81; 2.45 0.64; 2.04 0.78; 2.04 0.60; 2.03 0.84; 2.01 0.43; 2.01 0.85; 2.00 0.69; 1.99 0.36; 1.98 0.34; 1.79 0.36; 1.73 15.38; 1.73 16.00; 1.62 0.32; 1.61 0.37; 1.60 0.59; 1.59 0.45; 1.59 0.62; 1.59 0.68; 1.58 0.61; 1.57 0.66; 1.56 0.55; 1.54 31.75; 1.26 0.53; 1.25 0.39; 0.15 0.39; 0.01 2.87; 0.01 0.59; 0.00 0.65; 0.00 105.75; −0.01 3.15; −0.01 0.47; −0.01 0.37; −0.01 0.33; −0.15 0.40 |
| 6.476 | 3-F—Ph | H | O | H | $CH_2$ | tetrahydrofuran-3-yl | [$CDCl_3$] 7.41 0.44; 7.40 0.33; 7.39 2.60; 7.39 1.33; 7.39 1.34; 7.38 2.08; 7.38 3.06; 7.37 4.29; 7.37 5.76; 7.36 0.62; 7.36 0.56; 7.36 0.51; 7.35 0.48; 7.27 0.34; 7.27 0.54; 7.26 25.85; 7.26 0.82; 7.26 0.56; 7.26 0.43; 7.26 0.35; 7.16 0.67; 7.15 0.98; 7.15 0.60; 7.14 0.65; 7.14 0.89; 7.13 0.90; 7.13 1.28; 7.12 0.89; 7.12 0.92; 7.11 0.55; 7.00 0.47; 6.98 0.57; 6.97 0.58; 5.30 8.04; 3.89 0.39; 3.88 0.42; 3.87 0.45; 3.87 0.97; 3.86 0.90; 3.85 0.90; 3.85 1.16; 3.84 0.63; 3.83 0.61; 3.83 0.70; 3.82 4.44; 3.81 1.07; 3.80 1.09; 3.80 2.13; 3.79 1.19; 3.78 5.67; 3.76 0.97; 3.74 1.76; 3.72 1.53; 3.70 0.72; 3.52 1.02; 3.51 1.03; 3.50 1.09; 3.50 1.31; 3.49 0.92; 3.48 0.94; 3.48 0.91; 3.38 0.36; 3.38 0.38; 3.36 0.49; 3.36 0.51; 3.35 0.98; 3.34 1.06; 3.33 0.85; 3.32 0.95; 3.31 0.65; 3.31 0.71; 3.27 0.63; 3.26 0.74; 3.25 0.80; 3.25 0.79; 3.24 5.06; 3.22 0.98; 3.22 0.47; 3.22 0.45; 3.21 0.45; 3.20 0.57; 3.20 0.52; 3.20 3.75; 3.19 0.54; 2.48 0.69; 2.46 0.91; 2.44 0.71; 2.04 0.34; 2.04 0.58; 2.02 0.87; 2.02 0.36; 2.01 0.45; 2.01 0.43; 2.00 0.88; 1.99 0.68; 1.99 0.37; 1.97 0.32; 1.73 14.99; 1.73 16.00; 1.63 0.39; 1.62 0.40; 1.61 0.49; 1.60 0.78; 1.59 0.63; 1.59 0.74; 1.58 0.62; 1.57 0.72; 1.56 0.39; 0.00 11.99; −0.01 0.38 |
| 6.477 | Ph | H | O | H | $CH_2$ | tetrahydrofuran-3-yl | [$CDCl_3$] 7.65 0.37; 7.65 3.27; 7.64 3.56; 7.64 1.53; 7.64 1.24; 7.63 1.22; 7.63 2.89; 7.62 4.17; 7.52 |

TABLE 6-continued

Compounds of the general formula (I) according to the invention in which $R^2$ is hydrogen and $R^3$ is methyl and aryl is the radical

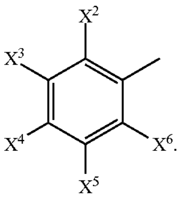

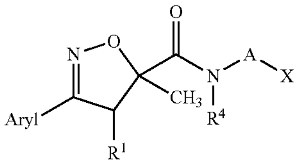

| No. | Aryl | $R^1$ | Y | $R^4$ | A | X | Physical data |
|---|---|---|---|---|---|---|---|
| | | | | | | | 1.79; 7.46 0.37; 7.45 0.36; 7.44 1.02; 7.44 1.34; 7.43 1.34; 7.43 2.33; 7.42 7.54; 7.42 2.67; 7.42 1.28; 7.41 1.69; 7.41 3.12; 7.40 0.49; 7.40 0.56; 7.39 0.97; 7.39 0.44; 7.38 0.68; 7.31 1.08; 7.26 330.76; 7.21 0.70; 7.02 0.52; 7.00 2.16; 3.88 0.41; 3.88 0.39; 3.87 0.45; 3.86 0.97; 3.86 0.91; 3.85 4.99; 3.84 0.68; 3.83 0.63; 3.82 0.64; 3.82 1.03; 3.82 1.03; 3.80 6.11; 3.80 2.33; 3.79 1.26; 3.78 1.21; 3.78 1.16; 3.75 1.16; 3.73 1.66; 3.72 1.43; 3.70 0.86; 3.51 1.02; 3.51 1.03; 3.50 1.14; 3.49 1.70; 3.48 1.09; 3.48 0.93; 3.47 0.95; 3.38 0.39; 3.37 0.41; 3.36 0.43; 3.35 0.45; 3.34 1.04; 3.34 1.10; 3.32 0.79; 3.32 0.91; 3.31 0.67; 3.30 0.73; 3.27 4.94; 3.26 0.75; 3.25 0.75; 3.25 0.77; 3.24 0.79; 3.24 0.81; 3.23 0.89; 3.22 4.81; 3.22 0.53; 3.21 0.50; 3.21 0.48; 3.20 0.47; 3.20 0.38; 3.19 0.42; 2.49 0.32; 2.48 0.67; 2.46 0.84; 2.44 0.67; 2.04 0.33; 2.04 0.37; 2.03 0.54; 2.02 0.80; 2.00 0.72; 2.00 0.84; 1.99 0.61; 1.98 0.36; 1.73 15.20; 1.73 16.00; 1.62 0.32; 1.61 0.39; 1.60 0.50; 1.60 0.75; 1.59 0.95; 1.58 0.72; 1.58 0.64; 1.57 0.77; 1.56 0.52; 1.55 0.58; 1.55 0.65; 1.55 0.83; 1.55 0.82; 1.55 0.97; 1.54 154.21; 1.49 0.38; 1.25 0.46; 0.15 0.46; 0.05 0.39; 0.01 3.48; 0.00 135.34; −0.01 3.84; −0.15 0.49 |
| 6.478 | 3,5-$Cl_2$—Ph | H | O | H | $CH_2C(CH_3)_2$ | COOH | [$CDCl_3$] 1.20 (s, 3H); 1.23 (s, 3H); 1.74 (s, 3H); 3.17 (d, 1H); 3.35 (dd, 1H); 3.45 (dd, 1H); 3.78 (d, 1H); 2.27 (m, 1H); 7.48 (m, 1H); 7.50 (m, 2H). |
| 6.479 | 3,5-$Cl_2$—Ph | H | O | H | $CH_2C(CH_3)_2$ | ethoxycarbonyl | [$CDCl_3$] 1.16 (s, 3H); 1.19 (s, 3H); 1.29 (t, 3H); 1.72 (s, 3H); 3.17 (d, 1H); 3.31 (dd, 1H); 3.41 (dd, 1H); 3.77 (d, 1H); 4.18 (q, 2H); 7.28 (m, 1H); 7.40 (m, 1H); 7.50 (m, 2H). |
| 6.480 | 3,5-$Cl_2$—Ph | H | O | H | $CH_2CH(CH_3)$ | ethoxycarbonyl | [$CDCl_3$] 1.16 (dd, 3H); 1.22, 1.28 (dt, 3H); 1.71 (s, 3H); 2.60-2.71 (m, 1H); 3.16 (d, 1H); 3.25-3.55 (m, 2H); 3.75 (d, 1H); 4.10-4.20 (m, 2H); 7.18 (br, 1H); 7.41 (m, 1H); 7.51 (m, 2H). |
| 6.481 | 3,5-$Cl_2$—Ph | H | O | H | $CH_2CH_2$ | (2,2,2-trifluoroethoxy)-carbonyl | [$CDCl_3$] 7.51 6.99; 7.51 8.47; 7.42 1.92; 7.41 3.47; 7.41 1.98; 7.26 24.95; 7.19 0.39; 7.17 0.64; 7.16 |

TABLE 6-continued

Compounds of the general formula (I) according to the invention in which $R^2$ is hydrogen and $R^3$ is methyl and aryl is the radical

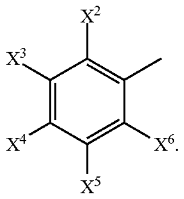

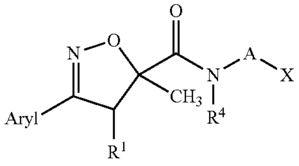

| No. | Aryl | $R^1$ | Y | $R^4$ | A | X | Physical data |
|---|---|---|---|---|---|---|---|
| | | | | | | | 0.41; 4.51 0.64; 4.51 0.70; 4.50 0.44; 4.49 1.97; 4.49 2.12; 4.47 2.05; 4.46 2.15; 4.45 0.75; 4.44 0.72; 3.78 2.78; 3.73 3.19; 3.64 0.52; 3.63 0.49; 3.62 0.54; 3.62 0.62; 3.61 1.14; 3.59 0.96; 3.59 0.96; 3.58 0.47; 3.57 0.48; 3.55 0.91; 3.55 0.82; 3.54 0.75; 3.54 1.03; 3.52 0.56; 3.52 0.61; 3.50 0.48; 3.19 2.93; 3.15 2.56; 2.69 1.19; 2.68 1.26; 2.67 1.47; 2.67 1.78; 2.67 1.88; 2.66 1.94; 2.66 1.29; 2.65 1.23; 2.04 0.49; 2.00 0.46; 1.70 16.00; 1.55 11.05; 1.26 0.47; 0.88 0.45; 0.00 4.61 |
| 6.482 | 3,5-$Cl_2$—Ph | H | O | H | $CH_2CH_2$ | (2-hydroxyethoxy)-carbonyl | [$CDCl_3$] 7.51 6.58; 7.51 7.64; 7.42 1.82; 7.41 3.26; 7.41 1.72; 7.30 0.42; 7.29 0.67; 7.27 0.43; 7.26 12.33; 5.30 0.60; 4.26 0.36; 4.24 1.24; 4.23 3.71; 4.22 3.84; 4.21 1.39; 4.19 0.38; 3.84 1.05; 3.83 2.01; 3.81 2.06; 3.80 1.09; 3.79 2.88; 3.75 3.14; 3.65 0.43; 3.64 0.48; 3.63 0.60; 3.62 1.21; 3.60 1.43; 3.58 1.45; 3.57 1.20; 3.55 0.56; 3.55 0.52; 3.53 0.43; 3.19 2.97; 3.14 2.61; 2.59 2.02; 2.57 3.47; 2.55 1.78; 2.53 0.72; 2.52 1.38; 2.50 0.67; 1.71 16.00; 1.60 3.12; 0.00 1.99 |
| 6.483 | 3,5-$Cl_2$—Ph | H | O | H | $CH_2CH_2$ | (2-methoxy-2-oxoethyl)carbamoyl | [$CDCl_3$] 1.71 (s, 3H); 2.49 (t, 2H); 3.15 (d, 1H); 3.58 (q, 2H); 3.74 (s, 3H); 3.80 (d, 1H); 4.02 (m, 2H); 6.01 (brt, 1H); 7.37 (brt, 1H); 7.40 (m, 1H); 7.52 (m, 2H) |
| 6.484 | 3,5-$Cl_2$—Ph | H | O | H | $CH_2CH_2$ | (allyloxy)carbonyl | [$CDCl_3$] 7.51 7.07; 7.51 7.11; 7.41 2.05; 7.41 3.26; 7.40 1.56; 7.26 8.02; 7.22 0.72; 7.21 0.43; 5.94 0.34; 5.93 0.70; 5.92 0.46; 5.91 0.40; 5.90 0.90; 5.90 0.52; 5.89 0.88; 5.87 0.53; 5.87 0.46; 5.86 0.88; 5.85 0.44; 5.33 0.72; 5.33 1.57; 5.32 1.51; 5.32 0.58; 5.30 7.05; 5.29 0.64; 5.28 1.38; 5.28 1.31; 5.28 0.50; 5.25 1.63; 5.24 1.45; 5.22 1.52; 5.22 1.37; 4.60 2.41; 4.60 3.36; 4.60 1.96; 4.59 2.37; 4.58 3.25; 3.78 2.75; 3.74 3.16; 3.61 0.51; 3.60 0.66; 3.59 0.58; 3.58 1.20; 3.56 1.24; 3.55 0.62; 3.55 0.58; 3.54 1.25; 3.52 1.23; 3.50 0.67; 3.50 0.62; 3.49 0.52; 3.19 2.99; 3.14 2.61; 2.59 1.69; 2.59 1.52; 2.57 3.11; 2.56 1.58; 2.55 1.44; 1.71 16.00; 1.60 2.78; 0.00 2.09 |

TABLE 6-continued

Compounds of the general formula (I) according to the invention in which $R^2$ is hydrogen and $R^3$ is methyl and aryl is the radical

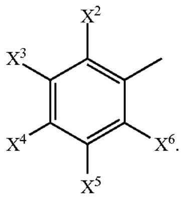

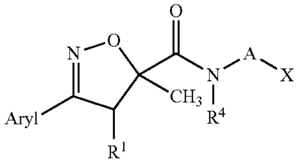

| No. | Aryl | $R^1$ | Y | $R^4$ | A | X | Physical data |
|---|---|---|---|---|---|---|---|
| 6.485 | 3,5-$Cl_2$—Ph | H | O | H | $CH_2CH_2$ | (cyclopropylsulfonyl)-(methyl)carbamoyl | [$CDCl_3$] 7.51 5.51; 7.51 6.29; 7.41 1.56; 7.41 2.71; 7.40 1.41; 7.27 0.46; 7.27 0.46; 7.27 0.44; 7.27 0.44; 7.27 0.44; 7.27 0.46; 7.26 12.34; 7.26 10.55; 7.24 0.44; 3.78 2.26; 3.74 2.58; 3.66 0.34; 3.64 0.42; 3.64 0.48; 3.62 1.13; 3.61 1.25; 3.60 1.27; 3.58 1.14; 3.57 0.51; 3.55 0.35; 3.24 16.00; 3.18 2.53; 3.14 2.19; 2.95 1.04; 2.94 1.07; 2.93 1.79; 2.93 1.89; 2.92 1.03; 2.91 1.00; 2.85 0.60; 2.84 0.63; 2.83 0.43; 2.83 1.20; 2.81 0.67; 2.81 0.64; 2.04 0.51; 1.70 13.38; 1.57 3.23; 1.34 0.39; 1.32 1.19; 1.32 1.27; 1.32 1.44; 1.31 2.00; 1.31 1.31; 1.30 1.44; 1.30 1.93; 1.29 0.51; 1.26 0.33; 1.13 0.36; 1.11 1.81; 1.09 1.58; 1.09 1.68; 1.09 1.61; 0.00 3.73 |
| 6.486 | 3,5-$F_2$—Ph | H | O | H | $CH_2CH_2$ | (cyclopropylsulfonyl)-(methyl)carbamoyl | [$CDCl_3$] 7.29 0.50; 7.28 0.90; 7.26 14.18; 7.26 13.51; 7.17 1.33; 7.17 2.04; 7.16 2.31; 7.16 2.23; 7.15 2.17; 7.15 2.34; 7.14 2.03; 7.14 1.45; 6.90 0.39; 6.90 0.60; 6.90 0.65; 6.90 0.35; 6.89 0.34; 6.89 0.66; 6.88 0.80; 6.88 1.21; 6.88 1.29; 6.87 0.69; 6.87 0.64; 6.86 0.36; 6.86 0.41; 6.86 0.61; 6.86 0.64; 6.85 0.34; 3.78 2.13; 3.78 2.30; 3.74 2.43; 3.74 2.64; 3.67 0.42; 3.65 0.62; 3.63 1.17; 3.62 1.20; 3.61 0.48; 3.61 0.49; 3.60 0.52; 3.60 1.15; 3.58 1.21; 3.56 0.69; 3.55 0.44; 3.24 15.23; 3.24 16.00; 3.19 2.33; 3.19 2.53; 3.15 2.02; 3.15 2.20; 2.95 1.21; 2.94 1.15; 2.93 2.17; 2.93 2.31; 2.93 2.23; 2.92 1.15; 2.91 1.11; 2.87 0.35; 2.86 0.56; 2.86 0.61; 2.85 0.62; 2.85 0.73; 2.85 0.41; 2.84 1.12; 2.84 1.21; 2.83 0.41; 2.83 0.73; 2.83 0.66; 2.82 0.61; 2.82 0.62; 1.71 12.73; 1.71 13.77; 1.59 2.97; 1.34 0.40; 1.34 0.41; 1.32 1.59; 1.32 1.55; 1.32 2.20; 1.31 2.26; 1.31 1.63; 1.30 2.27; 1.30 1.87; 1.29 0.51; 1.29 0.56; 1.25 0.35; 1.13 0.37; 1.13 0.38; 1.12 1.44; 1.11 2.39; 1.11 2.12; 1.11 1.51; 1.09 2.29; 1.09 2.05; 1.09 1.59; 0.00 5.12; 0.00 5.00 |
| 6.487 | 3,5-$Cl_2$—Ph | H | O | H | $CH_2CH_2$ | (cyclopropylsulfonyl)-carbamoyl | [$CDCl_3$] 7.52 5.50; 7.51 7.46; 7.51 7.39; 7.51 8.39; 7.42 1.51; 7.41 2.09; 7.41 2.94; 7.41 3.60; 7.40 1.88; 7.38 0.63; 7.36 1.21; 7.35 |

TABLE 6-continued
Compounds of the general formula (I) according to the invention in which $R^2$ is hydrogen and $R^3$ is methyl and aryl is the radical
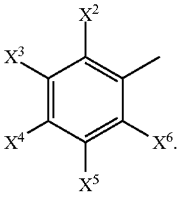
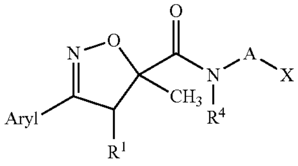
| No. | Aryl | $R^1$ | Y | $R^4$ | A | X | Physical data |
|---|---|---|---|---|---|---|---|
| | | | | | | | 0.67; 7.26 12.63; 7.26 16.17; 3.81 2.63; 3.76 3.02; 3.65 0.33; 3.63 0.55; 3.61 1.27; 3.60 1.38; 3.59 1.35; 3.57 1.28; 3.56 0.68; 3.54 0.36; 3.21 2.95; 3.16 2.62; 2.93 0.67; 2.92 0.79; 2.91 1.34; 2.90 0.77; 2.89 0.77; 2.89 0.71; 2.87 0.35; 2.67 1.05; 2.66 1.99; 2.65 2.18; 2.63 1.07; 2.58 0.35; 2.35 0.34; 2.05 0.49; 2.04 0.71; 1.71 16.00; 1.38 0.52; 1.37 1.72; 1.36 2.00; 1.36 2.44; 1.36 2.43; 1.35 2.16; 1.35 2.55; 1.33 0.83; 1.32 0.51; 1.31 0.48; 1.29 0.36; 1.28 0.50; 1.26 4.03; 1.22 0.39; 1.22 0.57; 1.21 0.45; 1.21 0.54; 1.21 0.45; 1.21 0.55; 1.20 0.51; 1.20 0.66; 1.13 0.49; 1.12 0.43; 1.11 1.99; 1.11 1.88; 1.11 1.90; 1.10 1.69; 1.09 1.87; 1.09 1.84; 1.09 1.78; 1.08 1.69; 1.07 0.46; 1.07 0.44; 1.07 0.53; 1.06 0.57; 1.06 0.57; 1.06 0.67; 1.06 0.62; 1.04 0.51; 1.04 0.50; 1.04 0.49; 1.04 0.43; 0.88 0.47; 0.88 0.59; 0.00 2.91; 0.00 3.66 |
| 6.488 | 3,5-$F_2$—Ph | H | O | H | $CH_2CH_2$ | (cyclopropylsulfonyl)-carbamoyl | [$CDCl_3$] 8.58 0.42; 7.52 0.39; 7.34 0.55; 7.33 0.88; 7.31 0.52; 7.31 0.44; 7.27 0.46; 7.26 65.06; 7.26 63.25; 7.25 0.66; 7.18 0.62; 7.17 2.20; 7.16 2.88; 7.15 2.79; 7.15 2.28; 7.13 0.49; 7.00 0.34; 6.99 0.38; 6.91 0.47; 6.90 0.80; 6.90 0.51; 6.89 0.96; 6.88 1.64; 6.87 0.97; 6.86 0.59; 6.86 0.87; 6.85 0.55; 4.60 0.33; 4.59 0.43; 3.80 2.15; 3.76 2.58; 3.65 0.38; 3.63 0.52; 3.61 1.16; 3.60 1.28; 3.59 1.15; 3.57 1.06; 3.56 0.58; 3.54 0.37; 3.21 2.87; 3.17 2.60; 2.89 0.74; 2.68 0.34; 2.65 1.00; 2.63 1.83; 2.62 1.89; 2.61 0.97; 2.59 0.49; 2.58 0.55; 2.57 0.79; 2.56 0.49; 2.55 0.43; 2.17 0.54; 2.04 0.50; 1.78 0.42; 1.71 16.00; 1.69 1.37; 1.68 0.72; 1.64 0.73; 1.60 0.89; 1.56 0.77; 1.55 0.72; 1.38 0.48; 1.36 2.06; 1.35 2.32; 1.33 1.23; 1.28 0.74; 1.26 5.65; 1.23 0.59; 1.22 1.31; 1.21 1.21; 1.21 1.22; 1.20 1.53; 1.19 0.85; 1.18 0.57; 1.17 0.55; 1.13 0.33; 1.12 0.53; 1.10 1.55; 1.08 1.56; 1.07 1.66; 1.06 1.27; 1.06 1.48; 1.04 1.22; 1.04 1.17; 1.02 0.32; 0.90 0.42; 0.88 0.87; 0.86 0.46; 0.01 |

TABLE 6-continued

Compounds of the general formula (I) according to the invention in which $R^2$ is hydrogen and $R^3$ is methyl and aryl is the radical

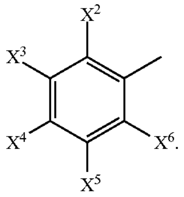

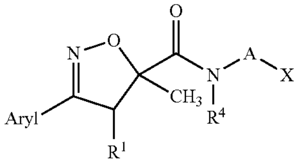

| No. | Aryl | $R^1$ | Y | $R^4$ | A | X | Physical data |
|---|---|---|---|---|---|---|---|
| | | | | | | | 0.69; 0.01 0.79; 0.00 29.09; 0.00 28.85; −0.01 1.60 |
| 6.489 | 3,5-$Cl_2$—Ph | H | O | H | $CH_2CH_2$ | (ethylsulfonyl)-(methyl)carbamoyl | [$CDCl_3$] 7.51 5.68; 7.51 6.25; 7.41 1.55; 7.41 2.72; 7.41 1.34; 7.26 11.22; 7.25 0.63; 3.78 2.17; 3.74 2.47; 3.63 0.40; 3.61 0.94; 3.60 0.45; 3.60 0.96; 3.59 0.96; 3.58 0.48; 3.57 0.99; 3.56 0.44; 3.40 1.03; 3.39 3.40; 3.37 3.48; 3.35 1.11; 3.24 16.00; 3.18 2.31; 3.14 2.04; 2.90 0.85; 2.89 0.87; 2.88 1.26; 2.88 1.33; 2.87 0.85; 2.86 0.82; 1.70 12.35; 1.57 3.23; 1.36 3.69; 1.34 7.87; 1.33 3.59; 0.00 2.77 |
| 6.490 | 3,5-$F_2$—Ph | H | O | H | $CH_2CH_2$ | (ethylsulfonyl)-(methyl)carbamoyl | [$CDCl_3$] 7.29 0.49; 7.26 11.22; 7.17 1.79; 7.16 2.21; 7.15 2.18; 7.14 1.76; 6.91 0.38; 6.90 0.66; 6.90 0.36; 6.89 0.77; 6.88 1.32; 6.88 0.69; 6.87 0.41; 6.86 0.66; 6.85 0.34; 3.78 2.29; 3.74 2.64; 3.66 0.39; 3.64 0.54; 3.62 1.18; 3.61 1.46; 3.59 1.45; 3.57 1.22; 3.56 0.58; 3.54 0.41; 3.41 1.14; 3.39 3.58; 3.38 3.66; 3.36 1.22; 3.25 16.00; 3.19 2.57; 3.15 2.24; 2.90 1.20; 2.89 1.21; 2.88 2.19; 2.88 2.26; 2.87 1.17; 2.86 1.12; 1.71 13.87; 1.60 4.29; 1.36 3.84; 1.35 7.86; 1.33 3.74; 0.00 4.20 |
| 6.491 | 3,5-$Cl_2$—Ph | H | O | H | $CH_2CH_2$ | (ethylsulfonyl)-carbamoyl | [DMSO-$D_6$] 11.56 2.47; 8.13 0.71; 8.12 1.49; 8.10 0.74; 7.74 2.14; 7.74 4.65; 7.73 3.02; 7.70 0.40; 7.69 10.81; 7.68 9.31; 3.74 2.54; 3.70 3.21; 3.41 3.17; 3.38 0.49; 3.37 2.71; 3.36 0.94; 3.35 1.01; 3.33 3.69; 3.31 69.66; 3.29 6.89; 3.28 1.93; 3.17 1.05; 2.67 0.41; 2.52 0.72; 2.51 22.75; 2.51 47.13; 2.50 66.09; 2.50 48.20; 2.49 25.06; 2.48 1.84; 2.33 0.39; 2.07 0.61; 1.56 0.46; 1.54 16.00; 1.24 0.81; 1.22 0.66; 1.19 5.11; 1.17 11.60; 1.15 4.86; 0.00 3.84 |
| 6.492 | 3,5-$F_2$—Ph | H | O | H | $CH_2CH_2$ | (ethylsulfonyl)-carbamoyl | [$CDCl_3$] 1.36 (t, 3H)); 1.71 (s, 3H); 2.63 (m, 2H); 3.20 (d, 1H); 3.41 (m, 2H); 3.59 (m, 2H); 3.78 (d, 1H); 6.88 (m, 1H); 7.16 (m, 2H); 7.33 (tr br, 1H); 8.57 (s br, 1H). |
| 6.493 | 3,5-$Cl_2$—Ph | H | O | H | $CH_2CH_2$ | (heptan-2-yloxy)carbonyl | [$CDCl_3$] 7.52 0.60; 7.51 7.71; 7.51 8.06; 7.41 2.14; 7.40 3.57; 7.40 1.74; 7.26 4.52; 7.26 48.42; 7.24 0.61; 7.23 0.58; 4.95 0.50; 4.93 0.95; 4.92 0.95; 4.90 0.50; 3.78 2.85; 3.74 3.21; 3.59 0.37; 3.57 0.56; 3.57 0.61; 3.55 0.76; 3.54 0.54; 3.52 0.32; 3.51 0.53; 3.50 |

TABLE 6-continued

Compounds of the general formula (I) according to the invention in which $R^2$ is hydrogen and $R^3$ is methyl and aryl is the radical

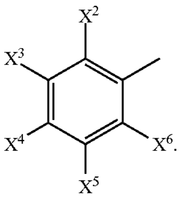

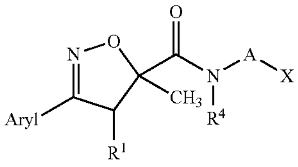

| No. | Aryl | $R^1$ | Y | $R^4$ | A | X | Physical data |
|---|---|---|---|---|---|---|---|
| | | | | | | | 0.60; 3.50 0.71; 3.49 0.63; 3.47 0.35; 3.47 0.37; 3.18 3.00; 3.14 2.64; 2.53 0.88; 2.53 0.97; 2.52 0.97; 2.52 0.87; 2.51 1.83; 2.51 1.99; 2.50 0.95; 2.49 0.97; 2.49 0.95; 2.49 0.71; 2.00 0.95; 1.70 16.00; 1.59 0.36; 1.58 0.38; 1.58 0.37; 1.57 0.39; 1.57 0.47; 1.54 22.69; 1.49 0.33; 1.49 0.41; 1.47 0.51; 1.46 0.42; 1.46 0.45; 1.44 0.33; 1.44 0.34; 1.43 0.33; 1.29 1.82; 1.28 2.26; 1.28 2.87; 1.27 3.66; 1.24 0.56; 1.22 5.11; 1.20 5.48; 1.20 5.05; 1.18 4.67; 0.89 1.63; 0.89 1.80; 0.88 3.55; 0.87 3.59; 0.86 1.54; 0.86 1.41; 0.01 0.35; 0.00 8.48 |
| 6.494 | 3,5-$F_2$—Ph | H | O | H | $CH_2CH_2$ | (hydroxyimino)-methyl | diasteromer D1: [DMSO-$D_6$] 1.53 (s, 3H); 2.40 (m, 2H); 3.27 (m, 2H); 3.72 (m, 1H); 6.63 (t, 1H); 7.40 (m, 3H); 8.29 (m, 1H); 10.85 (s, 1H). diasteromer D2: [DMSO-$D_6$] 1.53 (s, 3H); 2.24 (m, 2H); 3.15 (m, 2H); 3.72 (m, 1H); 7.23 (t, 1H); 7.40 (m, 3H); 8.19 (m, 1H); 10.48 (s, 1H). |
| 6.495 | 3,5-$Cl_2$—Ph | H | O | H | $CH_2CH_2$ | (isopropylsulfonyl)-(methyl)carbamoyl | [$CDCl_3$] 7.51 6.45; 7.51 3.91; 7.51 6.73; 7.41 1.97; 7.41 3.08; 7.41 1.01; 7.40 1.45; 7.27 1.70; 7.26 7.00; 7.26 14.68; 7.24 0.41; 3.78 2.14; 3.74 2.48; 3.71 0.78; 3.69 1.07; 3.67 0.80; 3.66 0.38; 3.62 0.43; 3.61 0.98; 3.60 0.58; 3.59 1.19; 3.59 1.10; 3.58 0.68; 3.57 1.05; 3.55 0.50; 3.23 16.00; 3.18 2.27; 3.14 1.99; 2.91 0.86; 2.90 1.46; 2.89 1.38; 2.89 1.43; 2.87 0.79; 1.70 12.37; 1.57 3.57; 1.43 0.94; 1.42 0.93; 1.39 6.52; 1.37 6.98; 1.36 6.73; 1.34 6.44; 0.00 1.12; 0.00 2.57 |
| 6.496 | 3,5-$F_2$—Ph | H | O | H | $CH_2CH_2$ | (isopropylsulfonyl)-(methyl)carbamoyl | [$CDCl_3$] 7.29 0.59; 7.27 11.35; 7.26 20.71; 7.18 0.36; 7.17 2.48; 7.16 2.14; 7.16 2.22; 7.16 1.31; 7.15 2.10; 7.15 2.58; 7.14 1.42; 7.14 0.34; 6.91 0.61; 6.90 0.74; 6.90 0.34; 6.89 1.24; 6.88 1.46; 6.87 0.62; 6.86 0.63; 6.86 0.73; 3.78 1.49; 3.78 2.25; 3.74 1.97; 3.74 2.91; 3.72 0.85; 3.70 1.12; 3.68 0.84; 3.67 0.43; 3.65 0.37; 3.64 0.61; 3.63 0.46; 3.62 1.00; 3.60 1.39; 3.59 1.42; 3.57 1.18; 3.55 0.66; 3.54 0.36; 3.24 9.95; 3.24 16.00; 3.19 1.69; 3.19 2.43; 3.15 1.45; 3.15 2.11; 2.91 1.09; 2.90 1.62; 2.90 1.85; 2.90 1.92; 2.89 |

TABLE 6-continued
Compounds of the general formula (I) according to the invention in which $R^2$ is hydrogen and $R^3$ is methyl and aryl is the radical
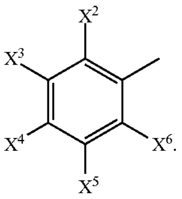
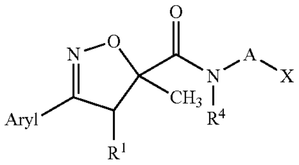
| No. | Aryl | $R^1$ | Y | $R^4$ | A | X | Physical data |
|---|---|---|---|---|---|---|---|
| | | | | | | | 1.94; 2.88 1.10; 2.88 0.90; 1.71 9.30; 1.70 13.28; 1.57 7.60; 1.39 4.78; 1.39 6.89; 1.37 8.72; 1.36 7.15; 1.35 4.81; 1.35 6.77; 0.00 3.33; 0.00 6.58 |
| 6.497 | 3,5-$Cl_2$—Ph | H | O | H | $CH_2CH_2$ | (isopropylsulfonyl)-carbamoyl | [$CDCl_3$] 7.52 7.93; 7.51 8.87; 7.41 2.12; 7.41 3.90; 7.40 2.01; 7.38 0.52; 7.36 1.02; 7.35 0.55; 7.26 16.17; 3.81 2.77; 3.79 0.42; 3.78 1.02; 3.76 3.45; 3.74 1.07; 3.72 0.41; 3.62 0.38; 3.62 0.50; 3.60 1.12; 3.59 1.35; 3.57 1.03; 3.55 0.56; 3.21 3.07; 3.17 2.65; 2.69 0.90; 2.68 2.00; 2.66 2.26; 2.65 0.93; 2.04 0.39; 1.70 16.00; 1.47 1.55; 1.45 1.55; 1.43 3.05; 1.41 10.90; 1.40 8.73; 1.39 9.04; 1.37 8.60; 1.26 2.87; 0.88 0.46; 0.00 3.11 |
| 6.498 | 3,5-$F_2$—Ph | H | O | H | $CH_2CH_2$ | (isopropylsulfonyl)-carbamoyl | [$CDCl_3$] 7.52 1.03; 7.31 0.64; 7.29 0.95; 7.26 137.40; 7.26 184.93; 7.21 0.61; 7.18 0.48; 7.17 1.88; 7.16 2.39; 7.15 2.47; 7.14 1.90; 7.00 1.02; 6.91 0.46; 6.91 0.76; 6.90 0.46; 6.89 0.88; 6.88 1.54; 6.88 0.76; 6.87 0.48; 6.86 0.80; 4.13 0.80; 4.11 0.91; 4.09 0.33; 3.79 2.76; 3.77 0.82; 3.76 1.07; 3.75 3.02; 3.74 1.02; 3.72 0.37; 3.64 0.34; 3.62 0.58; 3.60 1.22; 3.59 0.73; 3.59 1.35; 3.58 1.19; 3.56 1.19; 3.55 0.55; 3.53 0.35; 3.21 2.92; 3.17 2.50; 3.13 0.54; 3.05 0.44; 2.66 1.02; 2.65 2.06; 2.63 2.17; 2.62 1.10; 2.04 3.70; 1.72 16.00; 1.69 0.53; 1.54 61.29; 1.47 1.53; 1.45 1.65; 1.44 2.13; 1.42 8.05; 1.41 8.15; 1.40 8.42; 1.38 7.89; 1.36 0.61; 1.34 0.60; 1.28 0.34; 1.28 1.22; 1.26 3.24; 1.24 1.10; 0.15 0.39; 0.01 3.19; 0.00 74.01; 0.00 101.27; −0.01 4.01; −0.01 4.06; −0.05 0.33; −0.15 0.52 |
| 6.499 | 3,5-$Cl_2$—Ph | H | O | H | $CH_2CH_2$ | (methylsulfonyl)-carbamoyl | [$CDCl_3$] 9.35 0.94; 7.52 5.89; 7.51 6.28; 7.42 1.67; 7.41 2.78; 7.41 1.43; 7.36 0.44; 7.35 0.82; 7.33 0.44; 7.26 32.96; 3.80 2.23; 3.76 2.56; 3.63 0.43; 3.61 1.46; 3.60 2.19; 3.58 1.54; 3.56 0.49; 3.28 16.00; 3.22 2.43; 3.17 2.14; 2.66 1.36; 2.64 2.78; 2.63 1.32; 2.10 0.73; 2.04 0.52; 1.78 0.50; 1.71 13.21; 1.69 0.33; 1.64 0.54; 1.62 0.65; 1.28 0.45; 1.26 3.31; 0.88 0.47; 0.01 0.38; 0.00 14.26; −0.01 0.51 |

TABLE 6-continued
Compounds of the general formula (I) according to the invention in which $R^2$ is hydrogen and $R^3$ is methyl and aryl is the radical
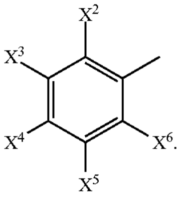
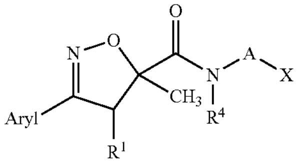
| No. | Aryl | $R^1$ | Y | $R^4$ | A | X | Physical data |
|---|---|---|---|---|---|---|---|
| 6.500 | 3,5-$F_2$—Ph | H | O | H | $CH_2CH_2$ | (methylsulfonyl)-carbamoyl | [$CDCl_3$] 7.52 0.39; 7.34 0.42; 7.33 0.78; 7.32 0.47; 7.26 72.73; 7.18 0.40; 7.18 0.41; 7.17 1.85; 7.17 2.44; 7.15 2.42; 7.15 2.05; 7.13 0.46; 7.00 0.42; 6.91 0.43; 6.91 0.77; 6.90 0.44; 6.89 0.90; 6.88 1.53; 6.88 0.87; 6.87 0.56; 6.86 0.82; 6.86 0.46; 3.80 2.41; 3.76 2.78; 3.63 0.53; 3.61 1.47; 3.59 1.93; 3.58 1.44; 3.56 0.57; 3.26 10.36; 3.22 2.93; 3.17 2.58; 3.11 9.57; 2.65 1.20; 2.64 1.27; 2.63 2.57; 2.62 1.19; 2.61 1.27; 2.18 0.96; 2.04 1.57; 1.78 0.39; 1.72 16.00; 1.69 0.83; 1.69 0.91; 1.64 0.39; 1.57 1.64; 1.30 0.37; 1.28 0.53; 1.28 0.70; 1.26 5.77; 1.24 0.49; 0.94 0.41; 0.88 0.66; 0.86 0.35; 0.01 1.07; 0.00 42.56; −0.01 1.95 |
| 6.501 | 3,5-$Cl_2$—Ph | H | O | H | $CH_2CH_2$ | (prop-2-yn-1-yloxy)carbonyl | [$CDCl_3$] 7.51 7.09; 7.51 7.71; 7.41 1.91; 7.41 3.32; 7.40 1.63; 7.26 17.69; 7.21 0.32; 7.21 0.33; 7.20 0.54; 7.19 0.33; 5.30 1.05; 4.70 5.60; 4.69 5.64; 3.78 2.81; 3.74 3.21; 3.63 0.49; 3.61 0.51; 3.61 0.48; 3.61 0.54; 3.59 1.06; 3.58 0.97; 3.56 0.48; 3.55 0.47; 3.54 0.96; 3.52 0.96; 3.51 0.55; 3.51 0.55; 3.49 0.47; 3.19 2.95; 3.14 2.59; 2.62 1.23; 2.61 1.23; 2.60 1.42; 2.60 1.67; 2.60 1.89; 2.59 1.19; 2.58 1.21; 2.48 1.77; 2.47 3.64; 2.46 1.79; 1.71 16.00; 1.56 6.82; 0.00 3.15 |
| 6.502 | 3,5-$Cl_2$—Ph | H | O | H | $CH_2CH_2$ | (propan-2-yloxy)carbonyl | [$CDCl_3$] 7.51 6.69; 7.51 5.10; 7.51 7.55; 7.51 5.59; 7.41 1.82; 7.41 1.45; 7.41 3.21; 7.40 2.52; 7.40 1.69; 7.27 0.34; 7.27 0.42; 7.27 0.52; 7.26 0.66; 7.26 25.04; 7.26 17.85; 7.25 0.76; 7.25 0.70; 7.25 0.69; 7.25 0.67; 7.25 0.65; 7.25 0.63; 7.25 0.61; 7.25 0.59; 7.25 0.57; 7.24 0.56; 7.24 0.54; 7.24 0.54; 7.24 0.54; 7.24 0.54; 7.24 0.54; 7.24 0.58; 7.23 0.70; 7.23 0.71; 7.23 0.71; 7.22 0.45; 7.22 0.44; 7.22 0.44; 7.21 0.38; 5.06 0.47; 5.04 1.25; 5.03 1.67; 5.01 1.29; 5.00 0.51; 3.78 2.62; 3.74 3.03; 3.59 0.50; 3.57 0.59; 3.57 0.63; 3.55 1.19; 3.54 1.15; 3.52 0.68; 3.51 1.07; 3.49 1.24; 3.48 0.58; 3.48 0.63; 3.46 0.51; 3.18 2.84; 3.14 2.49; 2.51 1.32; 2.51 1.40; 2.50 2.19; 2.50 2.47; 2.49 |

TABLE 6-continued
Compounds of the general formula (I) according to the invention in which $R^2$ is hydrogen and $R^3$ is methyl and aryl is the radical
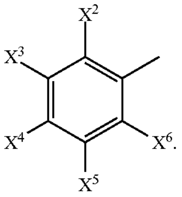
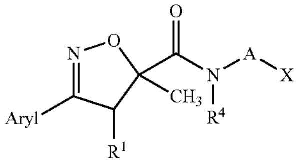
| No. | Aryl | $R^1$ | Y | $R^4$ | A | X | Physical data |
|---|---|---|---|---|---|---|---|
| | | | | | | | 2.38; 2.48 1.31; 2.48 1.40; 2.00 0.51; 2.00 0.38; 1.71 15.56; 1.55 9.63; 1.25 8.15; 1.23 16.00; 1.21 8.20; 0.00 4.66; 0.00 3.09 |
| 6.503 | 3,5-$Cl_2$—Ph | H | O | H | $CH_2CH_2$ | [2-(methylsulfanyl)-ethoxy]carbonyl | [$CDCl_3$] 7.51 5.14; 7.51 5.98; 7.41 1.43; 7.41 2.56; 7.40 1.47; 7.26 11.92; 5.30 4.44; 4.29 2.33; 4.27 4.84; 4.26 2.46; 3.78 2.19; 3.74 2.54; 3.61 0.44; 3.59 0.61; 3.58 1.15; 3.56 1.09; 3.55 0.46; 3.55 0.51; 3.54 1.05; 3.52 1.13; 3.50 0.63; 3.49 0.45; 3.18 2.40; 3.14 2.09; 2.73 2.42; 2.72 4.69; 2.70 2.34; 2.58 1.64; 2.56 2.95; 2.55 1.58; 2.14 16.00; 2.11 0.91; 1.71 13.02; 1.57 4.55; 0.00 5.61 |
| 6.504 | 3,5-$Cl_2$—Ph | H | O | H | $CH_2CH_2$ | 1,3-dioxolan-2-yl | [$CDCl_3$] 7.52 6.91; 7.51 7.11; 7.41 2.05; 7.40 3.32; 7.40 1.64; 7.31 0.79; 7.26 12.42; 4.95 1.40; 4.94 2.97; 4.93 1.42; 4.01 0.39; 4.00 0.78; 3.99 3.17; 3.98 2.57; 3.97 1.05; 3.95 0.80; 3.89 0.76; 3.88 1.18; 3.86 2.75; 3.86 4.47; 3.84 0.80; 3.83 0.35; 3.80 2.72; 3.75 3.09; 3.48 0.52; 3.47 0.60; 3.46 0.55; 3.45 1.39; 3.43 1.41; 3.43 0.57; 3.42 0.60; 3.41 1.21; 3.40 1.29; 3.38 0.60; 3.38 0.50; 3.36 0.47; 3.18 2.93; 3.13 2.58; 1.92 1.32; 1.91 1.70; 1.91 2.73; 1.90 2.79; 1.89 1.51; 1.88 1.29; 1.71 16.00; 1.59 6.31; 0.00 6.74 |
| 6.505 | 3,5-$F_2$—Ph | H | O | H | $CH_2CH_2$ | 1,3-dioxolan-2-yl | [$CDCl_3$] 7.32 0.46; 7.31 0.44; 7.26 9.45; 7.17 1.64; 7.17 1.24; 7.17 1.93; 7.16 1.09; 7.15 1.03; 7.15 1.98; 7.15 1.65; 6.90 0.41; 6.89 0.73; 6.89 0.37; 6.88 0.82; 6.87 1.45; 6.87 0.72; 6.86 0.42; 6.85 0.73; 6.84 0.35; 4.95 1.33; 4.94 2.87; 4.93 1.36; 4.01 0.38; 4.00 0.74; 3.98 2.35; 3.98 1.62; 3.97 2.21; 3.96 1.07; 3.95 0.75; 3.89 0.98; 3.87 1.23; 3.86 2.61; 3.86 2.56; 3.85 3.69; 3.84 0.84; 3.82 0.36; 3.79 2.78; 3.75 3.18; 3.49 0.49; 3.47 0.52; 3.47 0.52; 3.45 1.23; 3.44 1.25; 3.43 0.52; 3.42 0.54; 3.41 1.06; 3.40 1.09; 3.38 0.52; 3.38 0.43; 3.37 0.41; 3.18 2.86; 3.14 2.52; 1.93 1.24; 1.92 1.36; 1.91 2.47; 1.90 2.45; 1.89 1.33; 1.88 1.19; 1.72 16.00; 1.61 1.61; 0.00 5.55 |
| 6.506 | 3-F—Ph | H | O | H | $CH_2CH_2$ | 1,3-dioxolan-2-yl | [$CDCl_3$] 7.40 0.95; 7.40 0.99; 7.40 0.92; 7.40 0.99; 7.39 0.86; 7.39 1.09; 7.38 1.59; 7.37 2.88; 7.37 |

TABLE 6-continued

Compounds of the general formula (I) according to the invention in which $R^2$ is hydrogen and $R^3$ is methyl and aryl is the radical

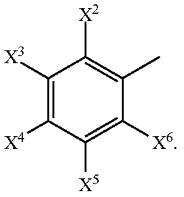

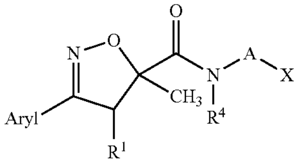

| No. | Aryl | $R^1$ | Y | $R^4$ | A | X | Physical data |
|---|---|---|---|---|---|---|---|
| | | | | | | | 3.22; 7.37 3.15; 7.36 2.11; 7.36 2.28; 7.36 2.22; 7.35 0.75; 7.34 0.61; 7.26 11.65; 7.15 0.45; 7.14 0.75; 7.13 0.47; 7.13 0.51; 7.13 0.66; 7.12 0.73; 7.12 0.63; 7.12 0.67; 7.11 0.66; 7.11 0.43; 7.11 0.41; 7.10 0.44; 7.10 0.36; 4.95 1.32; 4.94 2.84; 4.93 1.36; 4.01 0.39; 4.00 0.45; 3.99 0.68; 3.98 2.61; 3.98 2.46; 3.97 1.68; 3.97 1.46; 3.97 2.03; 3.96 0.88; 3.95 0.58; 3.94 0.71; 3.88 0.90; 3.87 1.15; 3.85 2.74; 3.85 3.63; 3.83 0.93; 3.82 2.84; 3.82 0.53; 3.78 3.12; 3.48 0.49; 3.47 0.55; 3.46 0.54; 3.45 1.26; 3.43 1.30; 3.43 0.54; 3.42 0.57; 3.41 1.13; 3.40 1.12; 3.38 0.55; 3.38 0.46; 3.36 0.41; 3.22 2.90; 3.17 2.55; 1.92 1.24; 1.91 1.49; 1.91 2.54; 1.90 2.55; 1.89 1.41; 1.88 1.21; 1.72 16.00; 1.60 0.42; 0.00 7.83 |
| 6.507 | Ph | H | O | H | $CH_2CH_2$ | 1,3-dioxolan-2-yl | [$CDCl_3$] 7.65 2.06; 7.65 2.35; 7.64 1.12; 7.64 1.11; 7.64 1.13; 7.63 1.95; 7.63 2.62; 7.43 0.61; 7.42 0.88; 7.42 0.85; 7.41 4.28; 7.41 4.20; 7.41 1.63; 7.40 1.57; 7.40 2.36; 7.40 2.13; 7.39 0.61; 7.38 0.73; 7.38 0.43; 7.37 0.57; 7.35 0.57; 7.26 10.61; 4.95 1.31; 4.94 2.79; 4.93 1.34; 4.00 0.40; 3.99 0.48; 3.99 0.48; 3.99 0.51; 3.98 2.33; 3.97 2.27; 3.96 1.63; 3.96 1.31; 3.96 1.93; 3.95 0.74; 3.95 0.48; 3.94 0.44; 3.94 0.55; 3.93 0.70; 3.87 0.89; 3.86 1.10; 3.85 3.64; 3.84 3.75; 3.84 4.04; 3.82 0.79; 3.80 3.24; 3.48 0.50; 3.47 0.56; 3.46 0.53; 3.45 1.26; 3.43 1.30; 3.42 0.53; 3.42 0.55; 3.41 1.13; 3.39 1.11; 3.38 0.56; 3.37 0.47; 3.36 0.43; 3.24 2.93; 3.20 2.57; 1.92 1.24; 1.91 1.47; 1.91 2.53; 1.89 2.53; 1.89 1.40; 1.88 1.21; 1.74 0.42; 1.71 16.00; 1.61 5.11; 0.00 6.27; 0.00 2.46 |
| 6.508 | 3,5-$Cl_2$—Ph | H | O | H | $CH_2CH_2$ | 1-methylpyrrolidin-2-yl | |
| 6.509 | 3,5-$Cl_2$—Ph | H | O | H | $CH_2CH_2$ | 2-oxopyrrolidin-1-yl | [$CDCl_3$] 1.70 (s, 3H); 1.94-2.02 (m, 2H); 2.31 (t, 2H); 3.14 (d, 1H); 3.32-3.52 (m, 6H); 3.77 (d, 1H); 7.13 (br, 1H); 7.41 (m, 1H); 7.52 (m, 2H). |
| 6.510 | 3,5-$Cl_2$—Ph | H | O | H | $CH_2CH_2$ | butoxycarbonyl | [$CDCl_3$] 7.51 7.05; 7.51 7.74; 7.41 1.92; 7.41 3.35; 7.40 1.61; 7.26 17.19; 7.24 0.42; 7.23 0.67; 7.21 |

TABLE 6-continued

Compounds of the general formula (I) according to the invention in which $R^2$ is hydrogen and $R^3$ is methyl and aryl is the radical

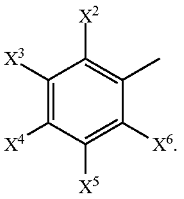

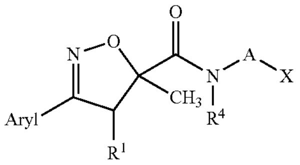

| No. | Aryl | $R^1$ | Y | $R^4$ | A | X | Physical data |
|---|---|---|---|---|---|---|---|
| | | | | | | | 0.41; 5.30 14.70; 4.11 1.96; 4.09 4.13; 4.08 2.12; 3.78 2.76; 3.74 3.17; 3.60 0.47; 3.58 0.60; 3.58 0.62; 3.58 0.54; 3.56 1.12; 3.55 1.15; 3.53 0.86; 3.52 1.20; 3.50 1.13; 3.50 1.11; 3.49 0.64; 3.48 0.63; 3.47 0.49; 3.18 2.93; 3.14 2.57; 2.55 1.51; 2.55 1.39; 2.53 2.85; 2.52 1.44; 2.51 1.35; 1.71 16.00; 1.63 0.54; 1.62 1.67; 1.61 0.49; 1.60 1.88; 1.60 1.98; 1.58 1.81; 1.56 5.29; 1.41 0.37; 1.39 1.26; 1.37 1.94; 1.35 1.95; 1.33 1.22; 1.31 0.36; 0.94 4.50; 0.92 9.23; 0.91 3.85; 0.01 0.35; 0.00 11.69; −0.01 0.41 |
| 6.511 | 3,4,5-$F_3$—Ph | H | O | H | $CH_2CH_2$ | butylcarbamoyl | |
| 6.512 | 3,5-$Cl_2$—Ph | H | O | H | $CH_2CH_2$ | carbamoyl | [$CDCl_3$] 1.70 (s, 3H); 2.48 (m, 2H); 3.18 (d, 1H); 3.55 (m, 2H); 3.75 (d, 1H); 5.30 (s br, 1H); 5.58 (s br, 1H); 7.40 (m, 1H); 7.52 (d, 1H) |
| 6.513 | 3-Cl-4-Me—Ph | H | O | H | $CH_2CH_2$ | carbamoyl | |
| 6.514 | 3,5-$Cl_2$—Ph | H | O | H | $CH_2CH_2$ | $CF_3$ | [$CDCl_3$] 1.72 (s, 3H); 2.37 (m, 2H); 3.20 d, 1H); 3.50 (m, 1H); 3.77 (d, 1H); 7.02 (t br, 1H); 7.43 (m, 1H); 7.50 (s, 2H). |
| 6.515 | 3,5-$F_2$—Ph | H | O | H | $CH_2CH_2$ | $CF_3$ | [$CDCl_3$] 7.26 36.28; 7.17 1.75; 7.16 2.09; 7.16 1.27; 7.15 2.18; 7.14 1.65; 7.13 0.32; 7.04 0.56; 6.91 0.42; 6.91 0.71; 6.90 0.37; 6.89 0.83; 6.89 1.40; 6.88 0.71; 6.87 0.43; 6.86 0.71; 6.86 0.35; 3.78 2.65; 3.73 3.08; 3.61 0.64; 3.59 0.79; 3.59 0.57; 3.57 1.38; 3.55 1.37; 3.54 0.49; 3.53 0.47; 3.51 1.23; 3.49 1.30; 3.48 0.67; 3.47 0.65; 3.46 0.58; 3.21 2.88; 3.17 2.49; 2.40 0.48; 2.39 0.76; 2.37 1.38; 2.36 0.84; 2.36 0.81; 2.35 1.38; 2.33 0.73; 2.32 0.49; 1.72 16.00; 1.55 32.93; 0.00 19.24; −0.01 0.79 |
| 6.516 | 3,5-$Cl_2$—Ph | H | O | H | $CH_2CH_2$ | $CH_3$ | |
| 6.517 | 3,5-$F_2$—Ph | H | O | H | $CH_2CH_2$ | $CH_3$ | [$CDCl_3$] 0.91 (m, 3H); 1.55 (m, 2H); 1.75 (d, 3H); 3.18 (dd, 1H); 3.19 (m, 1H); 3.27 (m, 1H); 3.37 (dd, 1H); 6.80 (sbr, 1H); 6.89 (m, 1H); 7.16 (m, 2H). |
| 6.518 | 3,5-$Cl_2$—Ph | H | O | H | $CH_2CH_2$ | chlorine | [$CDCl_3$] 1.73 (s, 3H); 3.20 (d, 1H); 3.55 (m, H); 3.62 (m, 1H), 3.68 (m, 1H); 3.78 (d, 1H); 7.17 (s br, 1H); 7.42 (m, 1H); 7.52 (s, 2H). |
| 6.519 | 2,3,4,5-$F_4$-6-OH—Ph | H | O | H | $CH_2CH_2$ | COOH | |

TABLE 6-continued
Compounds of the general formula (I) according to the invention in which $R^2$ is hydrogen and $R^3$ is methyl and aryl is the radical
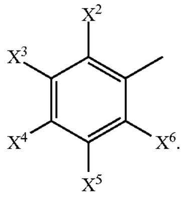
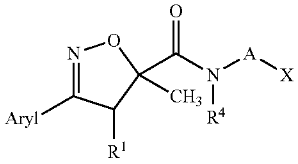
| No. | Aryl | $R^1$ | Y | $R^4$ | A | X | Physical data |
|---|---|---|---|---|---|---|---|
| 6.520 | 2,3,5-$F_3$—Ph | H | O | H | $CH_2CH_2$ | COOH | [$CDCl_3$] 7.52 0.40; 7.32 0.32; 7.32 0.42; 7.32 0.44; 7.31 0.51; 7.31 0.49; 7.31 0.46; 7.30 0.48; 7.30 0.49; 7.30 0.49; 7.30 0.46; 7.29 0.56; 7.29 0.44; 7.28 0.46; 7.28 0.41; 7.26 72.59; 7.26 1.07; 7.25 0.58; 7.25 0.54; 7.25 0.50; 7.25 0.50; 7.25 0.51; 7.25 0.40; 7.25 0.40; 7.25 0.39; 7.24 0.39; 7.24 0.40; 7.24 0.40; 7.24 0.40; 7.24 0.41; 7.24 0.51; 7.24 0.50; 7.04 0.35; 7.03 0.34; 7.02 0.39; 7.02 0.40; 7.01 0.55; 7.01 0.41; 7.01 0.40; 7.00 0.44; 7.00 0.84; 6.99 0.36; 6.99 0.36; 6.98 0.34; 5.30 0.78; 3.90 1.21; 3.89 1.26; 3.85 1.48; 3.84 1.44; 3.63 0.41; 3.61 0.44; 3.61 0.46; 3.59 1.06; 3.58 0.98; 3.57 0.46; 3.56 0.46; 3.55 1.02; 3.54 1.04; 3.52 0.49; 3.52 0.49; 3.50 0.43; 3.34 1.30; 3.33 1.36; 3.29 1.17; 3.28 1.17; 2.63 1.51; 2.62 3.07; 2.60 1.41; 1.72 16.00; 0.01 1.03; 0.00 40.27; −0.01 1.12 |
| 6.521 | 2,3-$F_2$—Ph | H | O | H | $CH_2CH_2$ | COOH | [$CDCl_3$] 7.53 0.40; 7.53 0.77; 7.52 0.47; 7.52 0.53; 7.51 1.01; 7.51 1.04; 7.50 0.52; 7.50 0.47; 7.49 0.84; 7.49 0.47; 7.31 0.51; 7.30 0.61; 7.28 0.41; 7.26 49.33; 7.25 0.83; 7.25 0.90; 7.24 0.96; 7.24 0.42; 7.23 0.59; 7.22 0.90; 7.22 0.56; 7.22 0.54; 7.20 0.48; 7.20 0.45; 7.14 0.55; 7.14 0.54; 7.13 0.56; 7.13 0.57; 7.12 0.81; 7.12 0.81; 7.11 0.79; 7.11 0.79; 7.10 0.41; 7.10 0.36; 7.09 0.33; 7.09 0.33; 5.30 0.64; 3.91 1.26; 3.90 1.31; 3.86 1.54; 3.85 1.51; 3.63 0.44; 3.62 0.49; 3.61 0.47; 3.60 0.96; 3.58 0.90; 3.56 0.53; 3.55 0.90; 3.53 0.89; 3.52 0.53; 3.51 0.51; 3.50 0.43; 3.49 0.35; 3.35 1.40; 3.35 1.43; 3.31 1.27; 3.30 1.25; 2.63 1.29; 2.62 1.23; 2.61 1.67; 2.61 2.21; 2.60 1.27; 2.59 1.22; 1.72 16.00; 1.26 1.65; 0.01 0.68; 0.00 25.32; −0.01 0.92 |
| 6.522 | 2,5-$Cl_2$—Ph | H | O | H | $CH_2CH_2$ | COOH | |
| 6.523 | 2,5-$F_2$—Ph | H | O | H | $CH_2CH_2$ | COOH | [$CDCl_3$] 7.52 0.68; 7.52 0.39; 7.51 0.44; 7.51 0.41; 7.50 0.45; 7.50 0.45; 7.50 0.79; 7.49 0.69; 7.49 0.42; 7.48 0.44; 7.48 0.42; 7.48 0.45; 7.47 0.41; 7.28 0.48; 7.27 0.37; 7.27 0.38; 7.27 0.37; 7.27 0.44; 7.27 0.49; 7.26 0.55; 7.26 |

TABLE 6-continued
Compounds of the general formula (I) according to the invention in which $R^2$ is hydrogen and $R^3$ is methyl and aryl is the radical
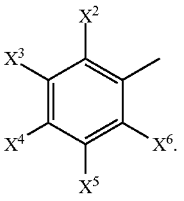
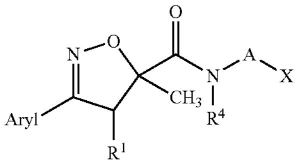
| No. | Aryl | $R^1$ | Y | $R^4$ | A | X | Physical data |
|---|---|---|---|---|---|---|---|
| | | | | | | | 0.72; 7.26 56.53; 7.26 1.29; 7.26 0.91; 7.25 0.69; 7.25 0.54; 7.25 0.46; 7.25 0.35; 7.11 0.74; 7.11 0.91; 7.10 1.49; 7.10 0.70; 7.09 1.49; 7.09 1.87; 7.08 0.90; 7.08 0.98; 7.08 0.99; 7.07 0.78; 7.07 0.92; 7.07 0.84; 3.89 1.25; 3.88 1.30; 3.85 1.56; 3.84 1.50; 3.63 0.43; 3.61 0.43; 3.61 0.45; 3.59 1.01; 3.58 0.87; 3.56 0.43; 3.56 0.45; 3.55 0.93; 3.53 0.93; 3.52 0.47; 3.51 0.48; 3.50 0.43; 3.34 1.37; 3.34 1.40; 3.30 1.24; 3.29 1.20; 2.63 1.36; 2.63 1.37; 2.62 2.78; 2.60 1.23; 2.60 1.30; 2.17 1.94; 1.71 16.00; 0.01 0.94; 0.00 0.35; 0.00 0.44; 0.00 0.69; 0.00 1.15; 0.00 30.87; 0.00 1.18; 0.00 0.71; 0.00 0.38; −0.01 0.80; −0.01 0.36 |
| 6.524 | 2-Cl-5-F—Ph | H | O | H | $CH_2CH_2$ | COOH | |
| 6.525 | 2-F-3-Me—Ph | H | O | H | $CH_2CH_2$ | COOH | [$CDCl_3$] 7.57 0.93; 7.55 1.78; 7.53 1.04; 7.42 0.71; 7.41 1.23; 7.39 0.74; 7.27 8.28; 7.26 12.54; 7.25 2.20; 7.23 1.03; 7.23 1.03; 7.07 1.53; 7.05 2.59; 7.03 1.18; 3.90 1.62; 3.90 1.39; 3.86 1.95; 3.85 1.62; 3.63 0.54; 3.62 0.85; 3.60 1.18; 3.58 1.17; 3.57 0.46; 3.55 0.43; 3.54 1.15; 3.52 1.27; 3.51 0.86; 3.49 0.58; 3.36 1.99; 3.36 1.62; 3.32 1.72; 3.31 1.38; 2.62 1.55; 2.61 1.53; 2.60 2.95; 2.60 2.69; 2.59 1.73; 2.58 1.36; 2.29 9.75; 2.28 8.32; 1.71 16.00; 1.26 1.00; 0.00 1.75; 0.00 2.95 |
| 6.526 | 3-$CF_3$—Ph | H | O | H | $CH_2CH_2$ | COOH | [$CDCl_3$] 7.89 1.94; 7.81 1.05; 7.79 1.21; 7.69 0.82; 7.69 0.92; 7.67 1.08; 7.67 1.20; 7.56 1.02; 7.54 1.61; 7.52 0.68; 7.52 0.59; 7.35 0.38; 7.33 0.67; 7.32 0.39; 7.27 0.34; 7.27 0.43; 7.26 20.59; 7.26 0.49; 7.25 0.39; 7.25 0.32; 5.30 2.06; 3.88 2.79; 3.84 3.16; 3.63 0.48; 3.62 0.50; 3.62 0.49; 3.62 0.50; 3.60 0.97; 3.58 0.85; 3.58 0.76; 3.57 0.40; 3.55 0.37; 3.54 0.84; 3.52 0.75; 3.52 0.86; 3.51 0.51; 3.51 0.56; 3.49 0.38; 3.49 0.44; 3.28 2.92; 3.23 2.57; 2.63 1.16; 2.62 1.19; 2.61 1.44; 2.61 1.77; 2.61 1.95; 2.60 1.16; 2.59 1.18; 2.27 0.62; 2.27 0.46; 2.26 0.64; 1.73 16.00 |

TABLE 6-continued

Compounds of the general formula (I) according to the invention in which $R^2$ is hydrogen and $R^3$ is methyl and aryl is the radical

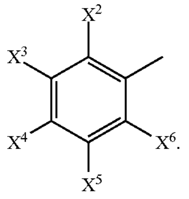

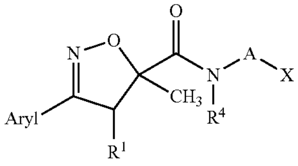

| No. | Aryl | $R^1$ | Y | $R^4$ | A | X | Physical data |
|---|---|---|---|---|---|---|---|
| 6.527 | 3,4,5-$F_3$—Ph | H | O | H | $CH_2CH_2$ | COOH | [$CDCl_3$] 1.71 (s, 3H); 2.61 (q, 2H); 3.15 (d, 1H); 3.55 (m, 2H); 3.75 (d, 1H); 7.26 (m, 2H) |
| 6.528 | 3,4-$F_2$—Ph | H | O | H | $CH_2CH_2$ | COOH | [$CDCl_3$] 1.71 (s, 3H); 2.62 (m, 2H); 3.19 (d, 1H); 3.53 (m, 1H); 3.60 (m, 1H); 3.78 (d, 1H); 7.25 (m, 3H); 7.53 (t, 1H). |
| 6.529 | 3,5-$Br_2$—Ph | H | O | H | $CH_2CH_2$ | COOH | [$CDCl_3$] 1.70 (s, 3H); 2.62 (m, 2H); 3.16 (d, 1H); 3.55 (m, 2H); 3.75 (d, 1H); 7.71 (s, 3H) |
| 6.530 | 3,5-$Cl_2$—Ph | H | O | $CH_3$ | $CH_2CH_2$ | COOH | |
| 6.531 | 3,5-$Cl_2$—Ph | H | O | H | $CH_2CH_2$ | COOH | |
| 6.532 | 3,5-$F_2$—Ph | H | O | H | $CH_2CH_2$ | COOH | [$CDCl_3$] 1.70 (s, 3H); 2.60 (m, 2H); 3.18 (d, 1H); 3.55 (m, 2H); 3.76 (d, 1H); 6.86 (m, 1H); 7.14 (m, 2H); 7.20 (t, 1H). |
| 6.533 | 3,5-$Me_2$—Ph | H | O | H | $CH_2CH_2$ | COOH | [$CDCl_3$] 1.70 (s, 3H); 2.32 (s, 6H); 2.59 (m, 2H); 3.21 (d, 1H); 3.43-3.53 (m, 1H); 3.55-3.64 (m, 1H); 3.80 (d, 1H); 7.06 (s, 1H); 7.24 (s, 2H); 7.38 (br, 1H). |
| 6.534 | 3,5-(tert•Bu)$_2$—Ph | H | O | H | $CH_2CH_2$ | COOH | [$CDCl_3$] 1.25 (s, 18H); 1.66 (s, 3H); 2.52 (m, 2H); 3.19 (d, 1H); 3.42 (m, 1H); 3.54 (m, 1H); 3.80 (d, 1H); 7.37 (tbr, 1H); 7.40 (m, 2H); 7.42 (m, 1H). |
| 6.535 | 3-Br-5-Cl—Ph | H | O | H | $CH_2CH_2$ | COOH | [$CDCl_3$] 1.71 (s, 3H); 2.61 (m, 2H); 3.18 (d, 1H); 3.51 (m, 1H); 3.57 (m, 1H); 3.77 (d, 1H); 7.56 (m, 2H); 7.67 (m, 1H) |
| 6.536 | 3-Br-5-F—Ph | H | O | H | $CH_2CH_2$ | COOH | [$CDCl_3$] 1.71 (s, 3H); 2.61 (t, 2H); 3.18 (d, 1H); 3.52 (m, 1H); 3.58 (m, 1H); 3.76 (d, 1H); 7.30 (m, 2H); 7.55 (s, 1H) |
| 6.537 | 3-Br-5-$CF_3$—Ph | H | O | H | $CH_2CH_2$ | COOH | [$CDCl_3$] 7.96 2.64; 7.96 1.91; 7.80 5.05; 7.80 5.30; 7.80 4.91; 7.30 0.43; 7.28 0.85; 7.26 30.04; 7.21 0.35; 5.30 0.42; 3.85 2.84; 3.81 3.21; 3.63 0.50; 3.61 0.54; 3.61 0.60; 3.59 1.15; 3.57 0.99; 3.56 0.65; 3.54 0.95; 3.53 1.06; 3.51 0.57; 3.51 0.68; 3.49 0.54; 3.24 3.00; 3.20 2.68; 2.62 1.13; 2.62 1.35; 2.60 2.51; 2.59 1.29; 2.59 1.49; 2.10 0.83; 1.73 16.00; 1.43 0.54; 1.26 1.37; 0.00 7.56 |
| 6.538 | 3-Cl-4-F—Ph | H | O | H | $CH_2CH_2$ | COOH | [$CDCl_3$] 1.71 (s, 3H); 2.60 (t, 2H); 3.18 (d, 1H); 3.52 (m, 1H); 3.58 (m, 1H); 3.79 (s, 3H); 7.17 (t, 1H); 7.24 (s br, 1H); 7.50 (m, 1H); 7.72 (m, 1H). |
| 6.539 | 3-Cl-4-Me—Ph | H | O | H | $CH_2CH_2$ | COOH | |

TABLE 6-continued

Compounds of the general formula (I) according to the invention in which $R^2$ is hydrogen and $R^3$ is methyl and aryl is the radical

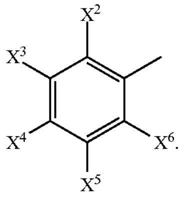

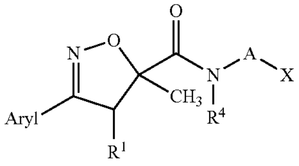

| No. | Aryl | $R^1$ | Y | $R^4$ | A | X | Physical data |
|---|---|---|---|---|---|---|---|
| 6.540 | 3-Cl-5-F—Ph | H | O | H | $CH_2CH_2$ | COOH | [$CDCl_3$] 1.70 (s, 3H); 2.60 (m, 2H); 3.18 (d, 1H); 3.52 (m, 1H); 3.59 (m, 1H); 3.76 (d, 1H); 7.15 (m, 1H); 7.28 (m, 1H); 7.40 (m, 1H) |
| 6.541 | 3-Cl-5-$CF_3O$—Ph | H | O | H | $CH_2CH_2$ | COOH | [$CDCl_3$] 1.72 (s, 3H); 2.60 (t, 2H); 3.20 (d, 1H); 3.55 (m, 2H); 3.78 (d, 1H); 7.23 (brs, 1H); 7.29 (brs, 1H); 7.39 (brs, 1H); 7.53 (brs, 1H). |
| 6.542 | 3-Cl-5-$CF_3$—Ph | H | O | H | $CH_2CH_2$ | COOH | [$CDCl_3$] 7.81 3.00; 7.76 3.16; 7.66 2.80; 7.31 0.50; 7.31 0.58; 7.29 1.08; 7.28 0.65; 7.26 29.31; 7.26 28.65; 5.30 1.01; 5.30 0.99; 3.86 2.72; 3.81 3.09; 3.63 0.59; 3.61 0.71; 3.61 0.71; 3.59 1.31; 3.58 1.25; 3.56 0.72; 3.55 1.21; 3.53 1.29; 3.51 0.74; 3.49 0.60; 3.25 3.02; 3.21 2.65; 2.63 1.49; 2.63 1.57; 2.61 3.10; 2.60 1.49; 2.60 1.56; 1.73 16.00; 0.01 0.36; 0.01 0.38; 0.00 12.87 |
| 6.543 | 3-Cl-5-Me—Ph | H | O | H | $CH_2CH_2$ | COOH | [DMSO-$D_6$] 1.52 (s, 3H); 2.33 (s, 3H); 2.38 (t, 2H); 3.29 (m, 2H); 3.35 (d, 1H); 3.70 (d, 1H); 7.38 (s, 1H); 7.47 (s, 1H); 7.50 (s, 1H); 8.06 (t, 1H) |
| 6.544 | 3-Et-5-F—Ph | H | O | H | $CH_2CH_2$ | COOH | [DMSO-$D_6$] 8.07 0.75; 8.06 1.47; 8.05 0.75; 7.37 3.33; 7.30 0.91; 7.29 1.22; 7.27 1.21; 7.20 1.17; 7.17 1.20; 5.75 0.33; 3.73 2.52; 3.68 3.14; 3.38 3.20; 3.37 0.48; 3.35 0.96; 3.33 4.64; 3.32 5.60; 3.30 2.58; 3.30 2.68; 3.29 1.82; 3.27 1.65; 3.25 1.02; 3.24 0.49; 2.68 1.12; 2.66 3.54; 2.64 3.62; 2.63 1.23; 2.51 5.63; 2.51 12.21; 2.50 17.45; 2.50 12.86; 2.49 6.21; 2.42 2.56; 2.41 5.42; 2.39 2.41; 2.18 0.40; 1.54 16.00; 1.36 2.84; 1.23 0.35; 1.21 5.04; 1.19 10.74; 1.17 5.00; 0.00 2.07; 0.00 1.66 |
| 6.545 | 3-Et—Ph | H | O | H | $CH_2CH_2$ | COOH | [DMSO-$D_6$] 12.21 0.66; 8.09 0.70; 8.07 1.40; 8.06 0.72; 7.51 2.89; 7.48 1.45; 7.47 1.96; 7.38 1.21; 7.36 2.91; 7.34 1.95; 7.32 2.25; 7.30 0.97; 3.72 2.53; 3.68 3.17; 3.38 0.76; 3.38 3.16; 3.37 0.44; 3.33 68.84; 3.31 2.16; 3.30 1.76; 3.28 1.87; 3.27 1.32; 3.25 0.86; 3.23 0.43; 2.66 1.15; 2.65 3.44; 2.63 3.56; 2.61 1.22; 2.53 0.34; 2.52 0.53; 2.51 10.01; 2.51 21.84; 2.50 30.44; 2.50 21.94; 2.49 10.22; 2.42 2.37; 2.40 5.07; 2.39 2.22; 1.54 16.00; 1.36 0.87; 1.21 5.25; 1.19 11.30; 1.17 5.12 |

TABLE 6-continued
Compounds of the general formula (I) according to the invention in which $R^2$ is hydrogen and $R^3$ is methyl and aryl is the radical
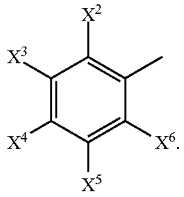
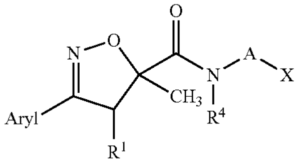
| No. | Aryl | $R^1$ | Y | $R^4$ | A | X | Physical data |
|---|---|---|---|---|---|---|---|
| 6.546 | 3-F-5-MeO—Ph | H | O | H | $CH_2CH_2$ | COOH | [$CDCl_3$] 8.02 1.15; 8.01 1.01; 7.35 0.64; 7.34 1.14; 7.32 0.67; 7.26 12.52; 7.26 11.31; 6.95 2.86; 6.95 2.96; 6.94 1.00; 6.93 1.56; 6.93 1.45; 6.91 0.90; 6.91 1.52; 6.91 1.47; 6.69 0.74; 6.69 1.49; 6.68 1.42; 6.68 0.65; 6.67 0.79; 6.66 1.52; 6.66 1.43; 6.65 0.64; 4.13 0.63; 4.13 0.58; 4.11 0.64; 4.11 0.60; 3.82 16.00; 3.81 14.67; 3.80 2.30; 3.79 2.12; 3.75 2.55; 3.75 2.40; 3.63 0.52; 3.61 0.81; 3.59 1.22; 3.58 1.09; 3.56 0.41; 3.56 0.42; 3.55 0.41; 3.53 1.04; 3.52 1.17; 3.50 0.81; 3.49 0.50; 3.22 2.43; 3.21 2.29; 3.17 2.13; 3.17 2.00; 2.62 2.00; 2.61 3.61; 2.59 1.92; 2.05 2.81; 2.04 2.54; 1.71 13.44; 1.71 12.46; 1.28 0.77; 1.27 0.69; 1.26 1.56; 1.26 1.38; 1.24 0.75; 1.24 0.66; 0.00 4.99 |
| 6.547 | 3-F-5-Me—Ph | H | O | H | $CH_2CH_2$ | COOH | [$CDCl_3$] 7.37 0.38; 7.36 0.67; 7.34 0.37; 7.26 17.29; 7.19 2.10; 7.18 2.18; 7.17 0.69; 7.17 0.86; 7.15 0.63; 7.14 0.84; 6.95 0.83; 6.93 0.82; 5.30 1.77; 3.81 2.79; 3.76 3.20; 3.63 0.45; 3.61 0.46; 3.61 0.44; 3.59 0.90; 3.58 0.78; 3.56 0.36; 3.55 0.33; 3.53 0.81; 3.51 0.81; 3.50 0.47; 3.50 0.52; 3.48 0.42; 3.22 2.97; 3.18 2.62; 2.62 1.01; 2.61 1.04; 2.60 1.62; 2.60 1.85; 2.59 1.04; 2.58 1.08; 2.36 10.86; 1.71 16.00; 0.00 6.64 |
| 6.548 | 3-F—Ph | H | O | H | $CH_2CH_2$ | COOH | |
| 6.549 | 3-Me—Ph | H | O | H | $CH_2CH_2$ | COOH | [DMSO-$D_6$] 8.07 0.60; 8.05 1.18; 8.04 0.61; 7.49 2.50; 7.47 1.25; 7.45 1.61; 7.35 1.17; 7.33 2.73; 7.31 1.74; 7.29 1.85; 7.27 0.94; 5.75 0.99; 3.71 2.54; 3.66 3.17; 3.36 3.36; 3.35 0.77; 3.33 1.23; 3.31 3.74; 3.30 1.64; 3.28 1.56; 3.27 1.54; 3.25 1.00; 3.24 0.56; 2.51 4.51; 2.51 9.89; 2.50 13.91; 2.50 9.97; 2.49 4.69; 2.42 2.17; 2.40 4.60; 2.38 2.04; 2.34 13.16; 1.53 16.00; 0.00 3.42 |
| 6.550 | 4-Cl—Ph | H | O | H | $CH_2CH_2$ | COOH | |
| 6.551 | 4-EtO—Ph | H | O | H | $CH_2CH_2$ | COOH | [DMSO-$D_6$] 12.21 0.67; 8.07 0.74; 8.06 1.52; 8.04 0.77; 7.60 0.50; 7.60 5.02; 7.59 1.58; 7.58 1.61; 7.58 5.57; 7.57 0.59; 7.00 0.55; 6.99 5.31; 6.99 1.62; 6.97 1.58; 6.97 4.96; 6.96 0.53; 5.76 0.34; 4.09 1.37; 4.08 4.69; 4.06 4.74; 4.04 1.43; 3.68 2.59; 3.63 |

TABLE 6-continued

Compounds of the general formula (I) according to the invention in which $R^2$ is hydrogen and $R^3$ is methyl and aryl is the radical

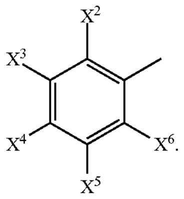

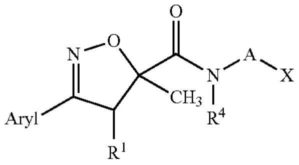

| No. | Aryl | $R^1$ | Y | $R^4$ | A | X | Physical data |
|---|---|---|---|---|---|---|---|
| | | | | | | | 3.23; 3.34 0.74; 3.33 3.92; 3.32 16.21; 3.31 1.82; 3.29 3.47; 3.28 1.10; 3.27 1.22; 3.26 1.31; 3.24 0.89; 3.22 0.46; 2.52 0.40; 2.52 0.54; 2.51 10.32; 2.51 22.67; 2.50 31.61; 2.50 22.71; 2.49 10.55; 2.42 2.38; 2.40 5.09; 2.38 2.24; 1.54 0.33; 1.52 16.00; 1.36 1.00; 1.35 4.86; 1.33 10.24; 1.31 4.70; 0.01 0.42 |
| 6.552 | Ph | H | O | H | $CH_2CH_2$ | COOH | |
| 6.553 | 3,5-$Cl_2$—Ph | H | O | H | $CH_2CH_2$ | cyanogen | [$CDCl_3$] 1.73 (s, 3H); 2.63 (m, 2H); 3.21 (d, 1H); 3.50 (m, 1H); 3.60 (m, 1H); 3.78 (d, 1H); 7.19 (s br, 1H); 7.42 (s, 1H); 7.52 (s, 2H). |
| 6.554 | 3-Cl—Ph | H | O | H | $CH_2CH_2$ | cyanogen | [$CDCl_3$] 1.73 (s, 3H); 2.65 (m, 2H); 3.22 (d, 1H); 3.50 (m, 1H); 3.61 (m, 1H); 3.81 (d, 1H); 7.22 (s br, 1H); 7.35 (m, 1H); 7.42 (m, 1H); 7.51 (m, 1H); 7.65 (s, 1H). |
| 6.555 | 3,5-$Cl_2$—Ph | H | O | H | $CH_2CH_2$ | cyclopropyl-carbamoyl | [$CDCl_3$] 0.45 (m, 2H); 0.78 (m, 2H); 1.70 (s, 3H); 2.38 (m, 2H); 2.69 (m, 1H); 3.16 (d, 1H); 3.54 (m, 2H); 3.75 (d, 1H); 5.72 (bs, 1H); 7.35 (bs, 1H); 7.41 (m, 1H); 7.52 (m, 2H). |
| 6.556 | 3,5-$Cl_2$—Ph | H | O | H | $CH_2CH_2$ | diethoxymethyl | [$CDCl_3$] 1.22 (t, 6H); 1.70 (s, 3H); 1.82 (q, 2H); 3.15 (d, 1H); 3.27-3.36 (m, 1H); 3.38-3.46 (m, 1H); 3.46-3.54 (m, 1H); 3.63-3.71 (m, 1H); 3.76 (d, 1H); 4.55 (t, 1H); 7.39 (br, 1H); 7.40 (m, 1H); 7.51 (m, 2H). |
| 6.557 | 3,5-$Cl_2$—Ph | H | O | H | $CH_2CH_2$ | diethoxyphosphoryl | [$CDCl_3$] 1.35 (t, 6H); 1.71 (s, 3H); 1.98 (m, 2H); 3.16 (d, 1H); 3.55 (m, 2H); 3.76 (d, 1H); 4.12 (m, 4H); 7.32 (t br, 1H); 7.40 (t, 1H), 7.50 (d, 2H) |
| 6.558 | Ph | H | O | H | $CH_2CH_2$ | diethoxyphosphoryl | |
| 6.559 | 3,5-$Cl_2$—Ph | H | O | H | $CH_2CH_2$ | dimethoxymethyl | [$CDCl_3$] 1.71 (s, 3H); 1.82 (q, 2H); 3.16 (d, 1H); 3.25-3.42 (m, 2H); 3.34 (s, 6H); 3.27 (d, 1H); 4.41 (t, 1H); 7.24 (br, 1H); 7.41 (m, 1H); 7.51 (m, 2H). |
| 6.560 | 3,5-$Cl_2$—Ph | H | O | H | $CH_2CH_2$ | dimethylcarbamoyl | [$CDCl_3$] 1.71 (s, 3H); 2.50 (q, 2H); 2.96 (s, 6H); 3.14 (d, 1H); 3.56 (m, 2H); 3.75 (d, 1H); 7.25 (m, 1H); 7.50 (m, 1H); 7.53 (m, 2H). |
| 6.561 | 3,5-$Cl_2$—Ph | H | O | H | $CH_2CH_2$ | ethoxy | [$CDCl_3$] 1.20 (t, 3H); 1.72 (s, 3H); 3.18 (d, 1H); 3.38 (m, 2H); 3.49 (m, 4H); 3.78 (d, 1H); 7.08 (t br, 1H); 7.40 (t, 1H); 7.50 (d, 2H) |

TABLE 6-continued

Compounds of the general formula (I) according to the invention in which $R^2$ is hydrogen and $R^3$ is methyl and aryl is the radical

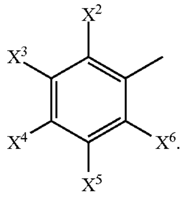

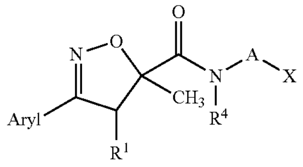

| No. | Aryl | $R^1$ | Y | $R^4$ | A | X | Physical data |
|---|---|---|---|---|---|---|---|
| 6.562 | 3-Cl—Ph | H | O | H | $CH_2CH_2$ | ethoxy | [$CDCl_3$] 1.19 (t, 3H); 1.73 (s, 3H); 3.21 (d, H); 3.50 (m, 6H); 3.80 (d, 1H); 7.16 (t br, 1H), 7.35 (t, 1H); 7.40 (m, 1H); 7.49 (m, 1H); 7.65 (m, 1H) |
| 6.563 | 2-Cl-5-F—Ph | H | O | H | $CH_2CH_2$ | ethoxycarbonyl | |
| 6.564 | 3-$CF_3$—Ph | H | O | H | $CH_2CH_2$ | ethoxycarbonyl | [$CDCl_3$] 7.90 2.20; 7.82 1.20; 7.80 1.40; 7.69 1.03; 7.67 1.37; 7.56 1.12; 7.54 1.78; 7.52 0.81; 7.26 10.94; 4.17 1.37; 4.15 4.27; 4.13 4.38; 4.12 1.48; 3.86 2.71; 3.82 3.10; 3.61 0.55; 3.59 0.63; 3.59 0.65; 3.57 1.25; 3.56 1.17; 3.54 0.53; 3.54 0.55; 3.52 1.14; 3.51 1.23; 3.49 0.59; 3.49 0.69; 3.47 0.55; 3.26 2.95; 3.22 2.58; 2.55 1.69; 2.53 3.19; 2.52 1.66; 1.73 16.00; 1.60 5.74; 1.26 5.04; 1.24 9.92; 1.22 4.87 |
| 6.565 | 3,5-$Cl_2$—Ph | H | O | cPr | $CH_2CH_2$ | ethoxycarbonyl | |
| 6.566 | 3,5-$Cl_2$—Ph | H | O | H | $CH_2CH_2$ | ethoxycarbonyl | [$CDCl_3$] 1.24 (t, 3H); 1.71 (s, 3H); 2.52 (t, 2H); 3.18 (d, 1H); 3.44-3.61 (m, 2H); 3.76 (d, 1H); 4.15 (q, 2H); 7.24 (br, 1H); 7.41 (m, 1H); 7.51 (m, 2H). |
| 6.567 | 3,5-$F_2$—Ph | H | O | H | $CH_2CH_2$ | ethoxycarbonyl | |
| 6.568 | 3-Br-5-$CF_3$—Ph | H | O | H | $CH_2CH_2$ | ethoxycarbonyl | [$CDCl_3$] 7.96 2.48; 7.81 4.60; 7.26 16.01; 7.25 0.77; 5.30 0.65; 4.18 1.48; 4.16 4.59; 4.14 4.67; 4.12 1.55; 3.84 2.74; 3.79 3.14; 3.60 0.52; 3.59 0.64; 3.59 0.57; 3.57 1.14; 3.56 1.13; 3.54 0.87; 3.52 1.17; 3.51 1.13; 3.49 0.65; 3.49 0.61; 3.47 0.50; 3.23 2.93; 3.18 2.58; 2.55 1.61; 2.54 1.46; 2.53 2.87; 2.52 1.51; 2.51 1.39; 1.73 16.00; 1.59 10.06; 1.27 5.36; 1.25 10.65; 1.23 5.14 |
| 6.569 | 3-Cl-5-Et—Ph | H | O | H | $CH_2CH_2$ | ethoxycarbonyl | [$CDCl_3$] 8.10 0.37; 8.08 0.40; 7.88 0.35; 7.86 0.41; 7.59 0.32; 7.44 1.47; 7.44 2.58; 7.43 1.60; 7.34 2.66; 7.27 0.45; 7.26 17.24; 7.24 1.88; 7.24 2.56; 6.37 1.24; 4.17 1.42; 4.15 4.45; 4.14 4.56; 4.12 1.54; 3.80 2.75; 3.76 3.17; 3.60 0.54; 3.59 0.66; 3.58 0.59; 3.57 1.15; 3.55 1.17; 3.54 0.50; 3.53 0.48; 3.52 1.18; 3.50 1.10; 3.50 1.10; 3.48 0.65; 3.48 0.66; 3.47 0.53; 3.21 2.99; 3.17 2.62; 2.67 0.99; 2.65 3.07; 2.64 3.16; 2.62 1.09; 2.54 1.45; 2.54 1.43; 2.53 2.65; 2.51 1.40; 2.51 1.40; 1.70 16.00; 1.59 1.84; 1.26 5.44; 1.26 5.38; 1.24 10.84; 1.24 10.36; 1.23 5.33; 1.22 4.80; 0.00 6.75 |

TABLE 6-continued
Compounds of the general formula (I) according to the invention in which $R^2$ is hydrogen and $R^3$ is methyl and aryl is the radical
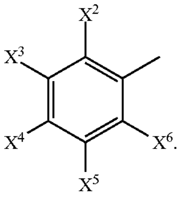
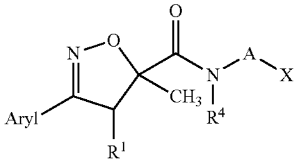
| No. | Aryl | $R^1$ | Y | $R^4$ | A | X | Physical data |
|---|---|---|---|---|---|---|---|
| 6.570 | 3-Cl-5-$CF_3$—Ph | H | O | H | $CH_2CH_2$ | ethoxycarbonyl | [$CDCl_3$] 7.81 2.10; 7.80 1.50; 7.76 2.01; 7.76 2.13; 7.66 1.84; 7.26 34.12; 7.24 0.41; 7.24 0.40; 6.37 0.41; 4.18 1.47; 4.16 4.68; 4.14 4.80; 4.12 1.59; 3.84 2.81; 3.80 3.20; 3.61 0.51; 3.59 0.51; 3.59 0.57; 3.57 1.11; 3.56 0.95; 3.56 0.93; 3.54 0.52; 3.54 0.54; 3.52 1.01; 3.51 1.06; 3.49 0.57; 3.49 0.61; 3.47 0.50; 3.23 2.92; 3.19 2.58; 2.55 1.29; 2.55 1.37; 2.53 2.40; 2.52 1.24; 2.51 1.39; 1.73 16.00; 1.57 15.81; 1.27 5.64; 1.25 11.76; 1.23 5.63 |
| 6.571 | 3-Et-5-F—Ph | H | O | H | $CH_2CH_2$ | ethoxycarbonyl | [$CDCl_3$] 7.26 13.65; 7.26 24.51; 7.25 0.69; 7.25 0.66; 7.23 2.69; 7.22 3.03; 7.22 3.15; 7.19 1.10; 7.18 1.22; 7.16 1.09; 7.16 1.20; 6.98 1.05; 6.98 1.09; 6.98 1.16; 6.96 1.06; 6.96 1.10; 6.95 1.17; 4.17 1.40; 4.15 4.30; 4.13 4.43; 4.12 1.50; 3.80 1.89; 3.80 2.75; 3.76 2.17; 3.76 3.16; 3.61 0.55; 3.59 0.85; 3.59 0.59; 3.57 1.24; 3.56 1.24; 3.54 0.53; 3.53 0.50; 3.52 1.33; 3.50 1.32; 3.50 1.18; 3.48 0.88; 3.48 0.71; 3.47 0.57; 3.47 0.51; 3.22 2.89; 3.17 2.53; 2.69 1.08; 2.67 3.25; 2.65 3.32; 2.63 1.15; 2.55 1.93; 2.54 1.50; 2.53 3.23; 2.51 1.82; 2.51 1.36; 1.70 16.00; 1.57 5.84; 1.56 7.98; 1.26 8.65; 1.26 5.53; 1.25 7.73; 1.24 15.72; 1.24 10.91; 1.23 1.02; 1.23 3.79; 1.23 6.49; 1.22 3.61; 1.22 4.89; 0.01 0.68; 0.00 4.92; 0.00 9.38 |
| 6.572 | 3-Et—Ph | H | O | H | $CH_2CH_2$ | ethoxycarbonyl | [$CDCl_3$] 7.50 2.32; 7.44 0.66; 7.43 1.17; 7.43 0.81; 7.42 0.90; 7.41 1.62; 7.41 1.11; 7.33 1.09; 7.32 2.53; 7.31 0.42; 7.30 1.92; 7.27 2.08; 7.27 1.67; 7.26 22.06; 7.25 1.07; 4.16 1.30; 4.15 4.11; 4.13 4.23; 4.11 1.42; 3.83 2.75; 3.79 3.14; 3.61 0.55; 3.59 0.61; 3.59 0.65; 3.57 1.17; 3.56 1.05; 3.54 0.45; 3.53 0.42; 3.51 1.01; 3.50 1.10; 3.48 0.55; 3.48 0.66; 3.46 0.53; 3.25 2.99; 3.21 2.60; 2.69 0.94; 2.67 2.94; 2.66 3.01; 2.64 1.03; 2.55 1.29; 2.54 1.41; 2.53 2.03; 2.53 2.41; 2.51 1.27; 2.51 1.37; 1.71 16.00; 1.59 11.49; 1.59 9.99; 1.26 4.86; 1.26 5.59; 1.24 10.17; 1.24 12.07; 1.22 4.95; 1.22 6.22 |

TABLE 6-continued

Compounds of the general formula (I) according to the invention in which $R^2$ is hydrogen and $R^3$ is methyl and aryl is the radical

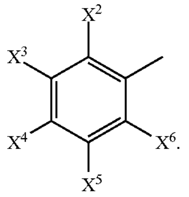

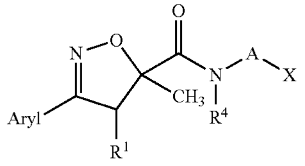

| No. | Aryl | $R^1$ | Y | $R^4$ | A | X | Physical data |
|---|---|---|---|---|---|---|---|
| 6.573 | 3-F-5-MeO—Ph | H | O | H | $CH_2CH_2$ | ethoxycarbonyl | [$CDCl_3$] 7.26 13.03; 6.96 1.02; 6.96 1.59; 6.96 1.30; 6.94 0.79; 6.94 0.72; 6.94 0.92; 6.93 0.66; 6.92 0.75; 6.92 0.77; 6.91 0.86; 6.91 0.69; 6.69 0.67; 6.69 1.23; 6.68 0.63; 6.67 0.68; 6.66 1.23; 6.66 0.62; 4.17 1.15; 4.15 3.59; 4.14 3.69; 4.12 1.25; 3.82 16.00; 3.78 2.30; 3.74 2.62; 3.61 0.46; 3.59 0.49; 3.59 0.47; 3.57 0.93; 3.56 0.85; 3.54 0.40; 3.53 0.37; 3.52 0.87; 3.50 0.89; 3.49 0.47; 3.48 0.51; 3.47 0.44; 3.20 2.44; 3.16 2.13; 2.55 1.12; 2.54 1.13; 2.53 2.05; 2.52 1.09; 2.51 1.12; 1.70 13.11; 1.59 3.42; 1.27 4.37; 1.26 0.39; 1.25 8.80; 1.23 4.27 |
| 6.574 | 3-Me-5-$CF_3O$—Ph | H | O | H | $CH_2CH_2$ | ethoxycarbonyl | [$CDCl_3$] 7.35 2.18; 7.31 1.62; 7.26 34.09; 7.09 1.56; 4.17 1.43; 4.15 4.52; 4.13 4.63; 4.12 1.54; 3.81 2.73; 3.76 3.13; 3.60 0.54; 3.59 0.62; 3.59 0.56; 3.57 1.15; 3.55 1.10; 3.54 0.50; 3.53 0.48; 3.52 1.11; 3.50 1.11; 3.49 0.57; 3.48 0.61; 3.47 0.53; 3.21 2.96; 3.17 2.60; 2.55 1.45; 2.54 1.46; 2.53 2.82; 2.51 1.36; 2.51 1.42; 2.39 11.14; 1.71 16.00; 1.56 20.92; 1.26 5.26; 1.24 10.55; 1.22 5.11; 0.01 0.35 |
| 6.575 | 3,5-$Cl_2$—Ph | H | O | H | $CH_2CH_2$ | ethylcarbamoyl | [$CDCl_3$] 1.12 (t, 3H); 1.70 (s, 3H); 2.38 (q, 2H); 3.17 (d, 1H); 3.28 (m, 2H); 3.55 (m, 2H); 3.75 (d, 1H); 5.58 (s br, 1H); 7.40 (m, 2H); 7.50 (d, 2H) |
| 6.576 | 3,5-$F_2$—Ph | H | O | H | $CH_2CH_2$ | formyl | [$CDCl_3$] 9.79 1.72; 9.79 3.71; 9.79 2.19; 7.26 17.48; 7.17 1.57; 7.16 1.99; 7.16 1.18; 7.15 1.21; 7.15 2.08; 7.14 1.95; 7.13 0.62; 7.13 0.59; 7.12 0.39; 6.91 0.38; 6.90 0.70; 6.90 0.35; 6.89 0.78; 6.88 1.41; 6.87 0.70; 6.86 0.41; 6.86 0.71; 6.85 0.35; 3.76 2.74; 3.72 3.16; 3.64 0.46; 3.62 0.45; 3.62 0.37; 3.62 0.51; 3.60 1.10; 3.59 0.98; 3.59 0.81; 3.57 0.90; 3.56 0.91; 3.54 0.95; 3.54 0.36; 3.53 0.54; 3.52 0.45; 3.51 0.43; 3.19 2.84; 3.15 2.47; 2.75 0.76; 2.75 0.86; 2.74 0.83; 2.74 0.88; 2.74 0.87; 2.73 1.58; 2.73 1.34; 2.73 1.72; 2.72 0.78; 2.72 0.84; 2.71 0.81; 2.71 0.84; 1.70 16.00; 1.60 10.83; 0.00 6.69 |

TABLE 6-continued

Compounds of the general formula (I) according to the invention in which $R^2$ is hydrogen and $R^3$ is methyl and aryl is the radical

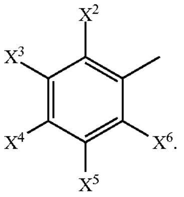

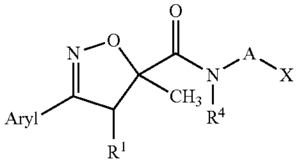

| No. | Aryl | $R^1$ | Y | $R^4$ | A | X | Physical data |
|---|---|---|---|---|---|---|---|
| 6.577 | 3,5-$Cl_2$—Ph | H | O | H | $CH_2CH_2$ | hydroxy | [$CDCl_3$] 1.73 (s, 3H); 2.20 (s br, 1H); 3.18 (d, 1H); 3.45 (m, 2H); 3.73 (m, 2H); 3.78 (d, 1H); 7.19 (s, 1H); 7.42 (s, 1H); 7.52 (s, 2H). |
| 6.578 | 3,5-$F_2$—Ph | H | O | H | $CH_2CH_2$ | hydroxy | [$CDCl_3$] 7.26 4.58; 7.26 8.56; 7.21 0.50; 7.18 0.40; 7.17 1.65; 7.17 1.88; 7.17 2.08; 7.16 1.30; 7.15 2.09; 7.15 1.43; 7.15 1.67; 6.91 0.37; 6.90 0.69; 6.90 0.36; 6.89 0.76; 6.88 1.38; 6.88 0.71; 6.87 0.41; 6.86 0.70; 6.85 0.36; 3.80 2.65; 3.76 3.20; 3.75 1.26; 3.74 2.41; 3.73 1.43; 3.52 0.48; 3.50 0.44; 3.49 0.56; 3.48 1.15; 3.47 0.98; 3.47 1.00; 3.45 0.46; 3.45 0.55; 3.43 1.13; 3.42 1.18; 3.41 0.50; 3.40 0.61; 3.38 0.56; 3.22 2.89; 3.18 2.51; 2.34 0.43; 1.84 0.57; 1.74 16.00; 0.00 2.18; 0.00 4.14 |
| 6.579 | 3-Cl—Ph | H | O | H | $CH_2CH_2$ | hydroxy | |
| 6.580 | 3,5-$Cl_2$—Ph | H | O | H | $CH_2CH_2$ | isobutoxycarbonyl | [$CDCl_3$] 7.51 4.58; 7.51 5.36; 7.51 5.64; 7.51 5.99; 7.41 1.24; 7.41 1.49; 7.41 2.37; 7.41 2.64; 7.40 1.37; 7.40 1.35; 7.26 17.36; 7.26 18.75; 7.24 0.45; 7.22 0.67; 7.21 0.43; 7.21 0.43; 5.30 0.37; 5.30 0.41; 3.89 5.03; 3.87 5.15; 3.78 2.32; 3.74 2.66; 3.60 0.45; 3.59 0.59; 3.57 1.18; 3.55 1.17; 3.54 0.48; 3.54 0.49; 3.53 1.17; 3.51 1.18; 3.50 0.67; 3.48 0.47; 3.18 2.56; 3.14 2.23; 2.57 1.64; 2.55 3.09; 2.53 1.59; 2.01 0.33; 2.00 0.35; 1.94 0.46; 1.93 0.94; 1.91 1.21; 1.89 0.99; 1.88 0.51; 1.71 13.85; 1.55 8.08; 1.55 8.72; 0.92 16.00; 0.90 15.56; 0.00 3.01; 0.00 3.25 |
| 6.581 | 3,5-$Cl_2$—Ph | H | O | H | $CH_2CH_2$ | methoxy | [$CDCl_3$] 1.72 (s, 3H); 3.16 (d, 1H); 3.38 (s, 3H); 3.46 (m, 2H); 3.78 (d, 1H); 7.08 (t br, 1H); 7.40 (t, 1H), 7.50 (d, 1H) |
| 6.582 | 3-Cl-5-$CF_3$—Ph | H | O | H | $CH_2CH_2$ | methoxy | [$CDCl_3$] 1.74 (s, 3H); 3.21 (d, 1H); 3.36 (s, 3H); 3.37-3.53 (m, 4H); 3.82 (d, 1H); 7.09 (br, 1H); 7.66 (s, 1H); 7.78 (s, 1H); 7.82 (s, 1H). |
| 6.583 | 3-Cl—Ph | H | O | H | $CH_2CH_2$ | methoxy | [$CDCl_3$] 1.73 (s, 3H); 3.21 (d, 1H); 3.35 (s, 3H); 3.40 (m, 1H); 3.44 (m, 2H); 3.50 (m, 1H); 3.80 (d, 1H); 7.14 (s br, 1H); 7.34 (m, 1H); 7.40 (m, 1H); 7.50 (m, 1H); 7.67 (s, 1H). |
| 6.584 | 2,3,4-$F_3$—Ph | H | O | H | $CH_2CH_2$ | methoxycarbonyl | [$CDCl_3$] 7.54 0.41; 7.53 0.43; 7.53 0.36; 7.52 0.33; 7.52 0.42; 7.51 0.42; 7.26 9.42; 7.26 9.22; 7.21 0.41; 7.03 0.86; 7.03 0.60; 7.01 |

TABLE 6-continued
Compounds of the general formula (I) according to the invention in which $R^2$ is hydrogen and $R^3$ is methyl and aryl is the radical
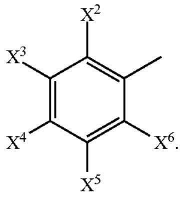
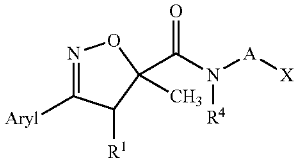
| No. | Aryl | $R^1$ | Y | $R^4$ | A | X | Physical data |
|---|---|---|---|---|---|---|---|
| | | | | | | | 0.55; 7.01 0.83; 3.88 1.03; 3.87 1.06; 3.83 1.23; 3.83 1.21; 3.69 16.00; 3.62 0.48; 3.60 0.52; 3.60 0.41; 3.58 0.92; 3.57 0.87; 3.55 0.39; 3.54 0.38; 3.53 0.90; 3.51 0.86; 3.49 0.39; 3.49 0.53; 3.48 0.46; 3.31 1.10; 3.31 1.13; 3.27 0.99; 3.26 0.98; 2.57 1.18; 2.56 1.13; 2.55 2.38; 2.54 1.12; 2.53 1.13; 1.70 13.59; 1.59 7.69; 0.00 4.92; 0.00 4.81 |
| 6.585 | 2,3,5-$F_3$—Ph | H | O | H | $CH_2CH_2$ | methoxycarbonyl | |
| 6.586 | 2,3-$F_2$—Ph | H | O | H | $CH_2CH_2$ | methoxycarbonyl | [$CDCl_3$] 7.55 0.34; 7.55 0.65; 7.54 0.42; 7.54 0.39; 7.53 0.92; 7.53 0.97; 7.52 0.50; 7.52 0.41; 7.51 0.71; 7.51 0.42; 7.26 9.89; 7.26 4.11; 7.25 0.77; 7.24 0.98; 7.24 0.64; 7.23 0.85; 7.22 1.25; 7.22 1.26; 7.22 1.12; 7.20 0.72; 7.20 0.62; 7.14 0.46; 7.14 0.48; 7.13 0.48; 7.13 0.52; 7.12 0.72; 7.12 0.73; 7.11 0.67; 7.11 0.72; 7.10 0.37; 7.10 0.33; 5.30 0.97; 3.90 1.11; 3.89 1.16; 3.85 1.34; 3.85 1.35; 3.69 16.00; 3.62 0.50; 3.60 0.55; 3.60 0.56; 3.58 1.08; 3.57 0.98; 3.55 0.43; 3.55 0.41; 3.53 1.00; 3.51 1.07; 3.50 0.54; 3.50 0.62; 3.48 0.47; 3.34 1.25; 3.34 1.31; 3.30 1.10; 3.29 1.12; 2.57 1.55; 2.55 2.93; 2.54 1.47; 1.71 13.99; 1.58 4.16; 1.58 1.61; 0.00 6.60; 0.00 2.78 |
| 6.587 | 2,5-$Cl_2$—Ph | H | O | H | $CH_2CH_2$ | methoxycarbonyl | |
| 6.588 | 2,5-$F_2$—Ph | H | O | H | $CH_2CH_2$ | methoxycarbonyl | [$CDCl_3$] 7.53 0.37; 7.52 0.34; 7.52 0.61; 7.51 0.65; 7.51 0.56; 7.50 0.34; 7.50 0.35; 7.50 0.35; 7.49 0.36; 7.49 0.36; 7.26 0.39; 7.26 0.63; 7.26 51.47; 7.21 0.50; 7.11 0.62; 7.11 0.74; 7.10 1.23; 7.10 0.58; 7.09 1.20; 7.09 1.55; 7.08 0.72; 7.08 0.85; 7.08 0.91; 7.07 0.63; 7.07 0.74; 7.07 0.71; 3.88 1.09; 3.88 1.20; 3.84 1.32; 3.83 1.28; 3.69 16.00; 3.61 0.45; 3.60 0.44; 3.59 0.45; 3.58 0.95; 3.56 0.81; 3.56 0.81; 3.55 0.46; 3.55 0.47; 3.53 0.89; 3.51 0.92; 3.50 0.48; 3.50 0.49; 3.48 0.44; 3.33 1.15; 3.32 1.20; 3.29 1.05; 3.28 1.03; 2.56 1.15; 2.55 2.20; 2.53 1.01; 2.53 1.10; 1.70 13.84; 1.55 41.80; 1.54 0.54; 1.54 0.40; 0.01 0.58; 0.00 0.56; 0.00 0.91; 0.00 25.27; −0.01 0.67 |

TABLE 6-continued
Compounds of the general formula (I) according to the invention in which $R^2$ is hydrogen and $R^3$ is methyl and aryl is the radical
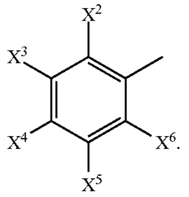
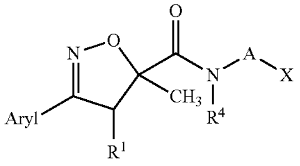
| No. | Aryl | $R^1$ | Y | $R^4$ | A | X | Physical data |
|---|---|---|---|---|---|---|---|
| 6.589 | 2,5-$Me_2$—Ph | H | O | H | $CH_2CH_2$ | methoxycarbonyl | [$CDCl_3$] 7.31 0.52; 7.26 10.55; 7.16 0.71; 7.14 2.15; 7.12 3.97; 7.10 0.68; 3.85 2.35; 3.81 2.72; 3.67 16.00; 3.58 0.54; 3.57 1.23; 3.56 0.56; 3.55 1.27; 3.55 1.29; 3.54 0.56; 3.53 1.27; 3.52 0.52; 3.51 0.44; 3.29 2.61; 3.25 2.27; 2.57 1.15; 2.56 1.27; 2.55 2.32; 2.53 1.10; 2.53 1.18; 2.47 9.34; 2.32 8.83; 1.70 13.66; 1.60 2.54; 0.00 4.86 |
| 6.590 | 2-Cl-3-F-5-MeO—Ph | H | O | H | $CH_2CH_2$ | methoxycarbonyl | [$CDCl_3$] 7.27 6.27; 7.26 12.30; 7.25 0.61; 6.94 1.66; 6.94 1.93; 6.94 1.88; 6.93 1.45; 6.81 0.73; 6.81 1.39; 6.80 0.78; 6.80 1.25; 6.78 0.74; 6.78 1.38; 6.78 0.79; 6.77 1.27; 3.93 1.42; 3.92 2.39; 3.88 1.69; 3.88 2.84; 3.82 8.86; 3.81 16.00; 3.81 1.47; 3.70 8.60; 3.70 15.63; 3.68 0.45; 3.68 0.68; 3.59 0.47; 3.59 0.61; 3.59 0.67; 3.58 1.51; 3.57 1.49; 3.57 1.42; 3.57 1.39; 3.56 1.54; 3.56 1.51; 3.56 1.39; 3.54 0.63; 3.54 0.64; 3.40 2.68; 3.36 1.33; 3.36 2.28; 2.58 1.95; 2.56 3.03; 2.55 1.82; 1.72 13.77; 1.71 0.51; 1.70 0.65; 0.00 0.79; 0.00 1.65 |
| 6.591 | 2-F-3-Me—Ph | H | O | H | $CH_2CH_2$ | methoxycarbonyl | [$CDCl_3$] 7.60 0.68; 7.58 1.24; 7.56 0.74; 7.27 7.78; 7.26 12.98; 7.25 1.85; 7.24 1.16; 7.23 1.16; 7.08 0.83; 7.08 1.09; 7.06 1.42; 7.06 1.81; 7.04 0.64; 7.04 0.83; 3.89 0.76; 3.89 1.32; 3.88 1.11; 3.85 0.91; 3.85 1.60; 3.84 1.29; 3.69 10.45; 3.69 16.00; 3.62 0.35; 3.61 0.45; 3.60 0.71; 3.59 0.48; 3.58 0.94; 3.58 0.97; 3.57 0.78; 3.56 0.99; 3.55 0.64; 3.54 0.44; 3.53 0.73; 3.53 1.06; 3.51 0.81; 3.51 1.04; 3.50 0.74; 3.49 0.54; 3.48 0.36; 3.48 0.43; 3.36 0.87; 3.35 1.64; 3.35 1.24; 3.31 0.75; 3.31 1.43; 3.30 1.06; 2.57 1.71; 2.56 1.23; 2.55 2.96; 2.53 1.59; 2.53 1.12; 2.29 7.39; 2.05 0.85; 2.05 1.37; 1.70 9.51; 1.70 13.74; 1.60 2.90; 1.60 4.42; 1.28 0.39; 1.26 0.50; 1.26 0.79; 1.24 0.36; 0.00 1.25; 0.00 2.34 |
| 6.592 | 3-$CF_3$—Ph | H | O | H | $CH_2CH_2$ | methoxycarbonyl | [$CDCl_3$] 7.90 2.25; 7.82 1.23; 7.80 1.42; 7.69 1.06; 7.67 1.39; 7.56 1.12; 7.54 1.78; 7.52 0.75; 7.26 12.70; 7.26 12.10; 5.30 0.65; 5.30 0.59; 3.86 2.46; 3.86 2.21; 3.82 2.72; 3.82 2.42; 3.68 16.00; 3.68 |

TABLE 6-continued

Compounds of the general formula (I) according to the invention in which $R^2$ is hydrogen and $R^3$ is methyl and aryl is the radical

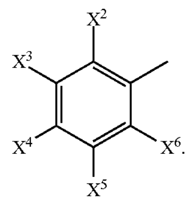

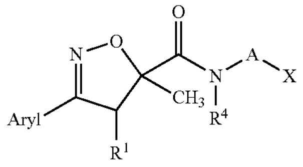

| No. | Aryl | $R^1$ | Y | $R^4$ | A | X | Physical data |
|---|---|---|---|---|---|---|---|
| | | | | | | | 14.19; 3.61 0.56; 3.60 0.69; 3.60 0.69; 3.58 1.25; 3.56 1.18; 3.55 0.44; 3.54 0.45; 3.52 1.17; 3.51 1.27; 3.49 0.81; 3.47 0.56; 3.26 2.61; 3.22 2.27; 2.56 1.76; 2.55 3.14; 2.53 1.68; 1.73 14.35; 1.58 6.04; 1.58 5.93; 0.00 3.98 |
| 6.593 | 3,4,5-$F_3$—Ph | H | O | H | $CH_2CH_2$ | methoxycarbonyl | [$CDCl_3$] 1.70 (s, 3H); 2.54 (t, 2H); 3.13 (d, 1H); 3.49 (m, 1H); 3.57 (m, 1H); 3.69 (s, 3H); 3.73 (d, 1H); 7.24 (m, 2H) |
| 6.594 | 3,4-$F_2$—Ph | H | O | H | $CH_2CH_2$ | methoxycarbonyl | [$CDCl_3$] 1.70 (s, 3H); 2.55 (t, 2H); 3.18 (d, 1H); 3.49 (m, 1H); 3.58 (m, 1H); 3.68 (s, 3H); 3.76 (d, 1H); 7.20 (m, 1H); 7.25 (m, 1H); 7.31 (m, 1H); 7.53 (m, 1H). |
| 6.595 | 3,5-$Br_2$—Ph | H | O | H | $CH_2CH_2$ | methoxycarbonyl | [$CDCl_3$] 1.70 (s, 3H); 2.54 (t, 2H); 3.16 (d, 1H); 3.52 (m, 2H); 3.70 (s, 3H); 3.75 (d, 1H); 7.22 (t br, 1H); 7.70 (s, 3H) |
| 6.596 | 3,5-$Cl_2$-4-MeO—Ph | H | O | H | $CH_2CH_2$ | methoxycarbonyl | [$CDCl_3$] 7.57 10.19; 7.26 20.36; 7.24 0.35; 7.22 0.54; 7.21 0.33; 3.93 16.00; 3.77 2.12; 3.72 2.45; 3.70 0.47; 3.69 14.69; 3.60 0.44; 3.59 0.50; 3.58 0.51; 3.57 0.94; 3.55 0.87; 3.54 0.41; 3.53 0.39; 3.52 0.83; 3.50 0.91; 3.48 0.46; 3.48 0.51; 3.46 0.42; 3.17 2.28; 3.13 1.99; 2.56 1.04; 2.55 1.11; 2.54 1.93; 2.53 1.00; 2.52 1.04; 1.70 12.22; 1.66 0.34; 1.57 9.77 |
| 6.597 | 3,5-$Cl_2$—Ph | $CH_3$ | O | H | $CH_2CH_2$ | methoxycarbonyl | |
| 6.598 | 3,5-$Cl_2$—Ph | H | O | $CH_3$ | $CH_2CH_2$ | methoxycarbonyl | |
| 6.599 | 3,5-$Cl_2$—Ph | H | O | H | $CH_2CH_2$ | methoxycarbonyl | [$CDCl_3$] 1.71 (s, 3H); 2.54 (q, 2H); 3.17 (d, 1H); 3.47-3.61 (m, 2H); 3.69 (s, 3H); 3.76 (d, 1H); 4.07 (q, 2H); 6.87 (m, 1H); 7.22 (t br, 1H); 7.41 (s, 1H); 7.52 (s, 2H). |
| 6.600 | 3,5-$Et_2$—Ph | H | O | H | $CH_2CH_2$ | methoxycarbonyl | [$CDCl_3$] 7.29 4.28; 7.29 4.23; 7.27 2.75; 7.26 16.81; 7.10 1.91; 3.83 2.17; 3.79 2.48; 3.67 15.37; 3.61 0.44; 3.59 0.53; 3.59 0.50; 3.57 0.89; 3.56 0.84; 3.54 0.38; 3.53 0.36; 3.51 0.90; 3.50 0.76; 3.49 0.90; 3.48 0.55; 3.48 0.55; 3.46 0.43; 3.25 2.31; 3.20 2.03; 2.92 0.77; 2.67 1.43; 2.65 4.45; 2.63 4.58; 2.61 1.58; 2.56 1.16; 2.55 1.15; 2.54 1.84; 2.54 1.92; 2.53 1.14; 2.52 1.07; 1.70 12.54; 1.57 0.47; 1.25 7.55; 1.24 16.00; 1.22 7.29; 0.01 0.91 |

TABLE 6-continued

Compounds of the general formula (I) according to the invention in which $R^2$ is hydrogen and $R^3$ is methyl and aryl is the radical

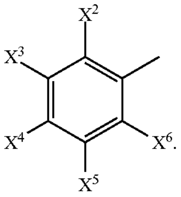

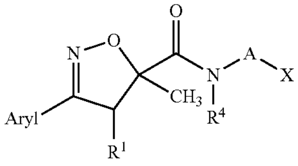

| No. | Aryl | $R^1$ | Y | $R^4$ | A | X | Physical data |
|---|---|---|---|---|---|---|---|
| 6.601 | 3,5-$F_2$—Ph | H | O | H | $CH_2CH_2$ | methoxycarbonyl | [$CDCl_3$] 1.71 (s, 3H); 2.52 (m, 2H); 3.17 (d, 1H); 3.43-3.62 (m, 2H); 3.68 (s, 3H); 3.75 (d, 1H); 6.88 (m, 1H); 7.15 (m, 2H); 7.23 (t, 1H). |
| 6.602 | 3,5-$(MeO)_2$—Ph | H | O | H | $CH_2CH_2$ | methoxycarbonyl | [$CDCl_3$] 7.26 10.03; 7.26 0.33; 6.78 2.75; 6.77 2.87; 6.52 0.66; 6.51 1.24; 6.51 0.62; 3.80 16.00; 3.79 1.21; 3.75 1.26; 3.68 7.92; 3.58 0.44; 3.56 0.42; 3.52 0.44; 3.50 0.36; 3.50 0.41; 3.22 1.16; 3.18 1.02; 2.56 0.54; 2.56 0.52; 2.54 0.98; 2.53 0.50; 2.53 0.50; 1.70 6.21; 1.58 4.06; 0.00 3.92 |
| 6.603 | 3,5-$Me_2$—Ph | H | O | H | $CH_2CH_2$ | methoxycarbonyl | [$CDCl_3$] 1.70 (s, 3H); 2.32 (s, 6H); 2.53 (t, 2H); 3.20 (d, 1H); 3.52 (m, 2H); 3.68 (s, 3H); 3.79 (d, 1H); 7.05 (s br, 1H); 7.24 (m, 2H). |
| 6.604 | 3,5-(tert•Bu)$_2$—Ph | H | O | H | $CH_2CH_2$ | methoxycarbonyl | [$CDCl_3$] 1.32 (s, 18H); 1.71 (s, 3H); 2.55 (m, 2H); 3.25 (d, 1H); 3.49 (m, 1H); 3.58 (m, 1H); 3.69 (s, 3H); 3.84 (d, 1H); 7.29 (tbr, 1H); 7.48 (m, 2H); 7.51 (m, 1H). |
| 6.605 | 3-$CF_3S$—Ph | H | O | H | $CH_2CH_2$ | methoxycarbonyl | [$CDCl_3$] 7.92 1.85; 7.77 0.79; 7.76 1.07; 7.76 0.76; 7.75 0.91; 7.74 1.21; 7.74 0.88; 7.72 0.83; 7.70 0.97; 7.50 1.28; 7.48 2.16; 7.46 0.94; 7.26 10.25; 7.25 0.50; 3.84 2.31; 3.80 2.65; 3.68 16.00; 3.62 0.48; 3.60 0.55; 3.60 0.46; 3.58 0.97; 3.57 0.93; 3.55 0.40; 3.54 0.39; 3.53 1.00; 3.51 0.96; 3.49 0.52; 3.49 0.61; 3.48 0.46; 3.25 2.48; 3.20 2.17; 2.57 1.49; 2.55 2.83; 2.53 1.40; 1.72 13.30; 1.59 0.75; 1.26 0.67 |
| 6.606 | 3-Ac—Ph | H | O | H | $CH_2CH_2$ | methoxycarbonyl | [$CDCl_3$] 8.19 1.03; 8.19 1.78; 8.19 1.02; 8.02 0.73; 8.02 0.89; 8.02 0.81; 8.02 0.68; 8.01 0.81; 8.00 0.94; 8.00 0.91; 8.00 0.72; 7.86 0.74; 7.86 0.86; 7.86 0.81; 7.85 0.66; 7.84 0.86; 7.84 0.94; 7.84 0.95; 7.83 0.73; 7.54 0.97; 7.54 0.91; 7.52 1.83; 7.50 0.80; 7.50 0.74; 7.26 15.99; 3.89 2.06; 3.84 2.35; 3.68 14.76; 3.62 0.41; 3.61 0.45; 3.60 0.39; 3.59 0.59; 3.59 0.77; 3.57 0.74; 3.56 0.34; 3.54 0.32; 3.52 0.79; 3.52 0.46; 3.51 0.62; 3.51 0.75; 3.49 0.47; 3.49 0.47; 3.47 0.38; 3.29 2.13; 3.24 1.88; 2.63 16.00; 2.57 0.98; 2.56 0.91; 2.55 1.24; 2.55 1.61; 2.54 0.94; 2.53 0.89; 1.73 11.64; 1.58 0.73; 0.00 4.15 |

TABLE 6-continued

Compounds of the general formula (I) according to the invention in which $R^2$ is hydrogen and $R^3$ is methyl and aryl is the radical

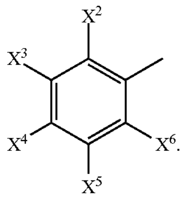

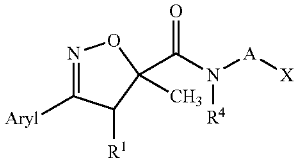

| No. | Aryl | $R^1$ | Y | $R^4$ | A | X | Physical data |
|---|---|---|---|---|---|---|---|
| 6.607 | 3-Br-5-Cl—Ph | H | O | H | $CH_2CH_2$ | methoxycarbonyl | [$CDCl_3$] 1.71 (s, 3H); 2.54 (t, 2H); 3.17 (d, 1H); 3.44-3.62 (m, 2H); 3.68 (s, 3H); 3.75 (d, 1H); 7.21 (br, 1H); 7.56 (s, 2H); 7.66 (s, 1H). |
| 6.608 | 3-Br-5-F—Ph | H | O | H | $CH_2CH_2$ | methoxycarbonyl | [$CDCl_3$] 1.71 (s, 3H); 2.54 (t, 2H); 3.17 (d, 1H); 3.44-3.62 (m, 2H); 3.69 (s, 3H); 3.76 (d, 1H); 7.22 (br, 1H); 7.31 (m, 2H); 7.55 (m, 1H). |
| 6.609 | 3-Br-5-$CF_3$—Ph | H | O | H | $CH_2CH_2$ | methoxycarbonyl | [$CDCl_3$] 7.97 0.80; 7.97 1.43; 7.96 0.84; 7.81 2.56; 7.81 2.45; 7.81 2.27; 7.26 21.88; 7.24 0.36; 3.84 2.14; 3.79 2.44; 3.69 16.00; 3.61 0.38; 3.60 0.38; 3.60 0.34; 3.59 0.38; 3.58 0.51; 3.58 0.76; 3.56 0.68; 3.56 0.55; 3.55 0.35; 3.54 0.33; 3.52 0.73; 3.52 0.44; 3.51 0.57; 3.51 0.71; 3.49 0.43; 3.49 0.42; 3.47 0.34; 3.23 2.16; 3.19 1.90; 2.57 0.89; 2.56 0.85; 2.55 1.01; 2.55 1.31; 2.55 1.36; 2.54 0.81; 2.53 0.82; 1.73 11.91; 1.59 7.28; 0.00 1.80 |
| 6.610 | 3-$NH_2CO$—Ph | H | O | H | $CH_2CH_2$ | methoxycarbonyl | [$CDCl_3$] 8.09 1.36; 8.09 2.36; 8.08 1.42; 7.91 1.08; 7.91 1.10; 7.90 0.84; 7.89 0.90; 7.89 1.25; 7.88 0.93; 7.79 0.76; 7.79 1.10; 7.79 1.12; 7.78 0.86; 7.77 0.91; 7.77 1.32; 7.76 0.98; 7.53 1.22; 7.51 2.14; 7.49 0.97; 7.29 0.38; 7.28 0.65; 7.26 16.24; 5.30 1.48; 3.88 2.18; 3.83 2.50; 3.68 16.00; 3.61 0.46; 3.60 0.54; 3.59 0.50; 3.58 1.06; 3.56 0.97; 3.55 0.46; 3.54 0.47; 3.53 0.97; 3.51 1.04; 3.50 0.51; 3.49 0.58; 3.48 0.46; 3.27 2.35; 3.23 2.06; 2.57 1.66; 2.55 3.13; 2.53 1.58; 1.72 12.82; 1.61 10.80; 0.00 8.00; −0.01 0.35 |
| 6.611 | 3-Cl-4-F—Ph | H | O | H | $CH_2CH_2$ | methoxycarbonyl | [$CDCl_3$] 1.71 (s, 3H); 2.55 (t, 2H); 3.18 (d, 1H); 3.50 (m, 1H); 3.58 (m, 1H); 3.69 (s, 3H); 3.78 (d, 1H); 7.18 (t, 1H); 7.24 (s br, 1H); 7.50 (m, 1H); 7.72 (s, 1H). |
| 6.612 | 3-Cl-4-Me—Ph | H | O | H | $CH_2CH_2$ | methoxycarbonyl | |
| 6.613 | 3-Cl-5-CN—Ph | H | O | H | $CH_2CH_2$ | methoxycarbonyl | [$CDCl_3$] 7.85 1.32; 7.85 2.52; 7.85 1.67; 7.80 1.61; 7.80 3.04; 7.80 1.78; 7.68 1.47; 7.67 2.44; 7.67 1.57; 7.26 12.66; 7.26 0.34; 7.25 0.33; 7.25 0.33; 7.25 0.34; 7.25 0.35; 7.25 0.35; 7.25 0.36; 7.25 0.36; 7.25 0.36; 7.25 0.35; 7.25 0.34; 7.25 0.33; 7.23 0.58; 7.22 0.33; 3.82 2.22; 3.77 2.53; 3.70 16.00; 3.62 0.49; 3.60 0.54; 3.60 0.54; 3.58 0.97; 3.57 0.91; 3.55 |

TABLE 6-continued

Compounds of the general formula (I) according to the invention in which $R^2$ is hydrogen and $R^3$ is methyl and aryl is the radical

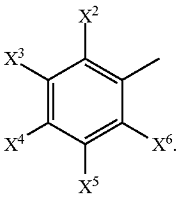

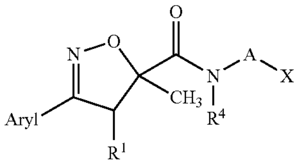

| No. | Aryl | $R^1$ | Y | $R^4$ | A | X | Physical data |
|---|---|---|---|---|---|---|---|
| | | | | | | | 0.39; 3.54 0.38; 3.52 0.87; 3.51 0.95; 3.49 0.53; 3.47 0.46; 3.21 2.42; 3.16 2.12; 3.03 1.17; 2.57 1.13; 2.56 1.16; 2.55 2.14; 2.54 1.09; 2.53 1.14; 2.05 1.01; 1.73 13.24; 1.28 0.55; 1.26 0.98; 1.26 1.20; 1.24 0.36; 0.90 0.44; 0.88 1.27; 0.86 0.57; 0.00 7.82 |
| 6.614 | 3-Cl-5-Et—Ph | H | O | H | $CH_2CH_2$ | methoxycarbonyl | [$CDCl_3$] 7.44 1.34; 7.44 2.28; 7.43 1.37; 7.34 2.30; 7.26 11.95; 7.24 1.94; 7.24 2.46; 3.80 2.32; 3.76 2.66; 3.68 16.00; 3.61 0.51; 3.59 0.61; 3.57 1.06; 3.56 1.06; 3.54 0.42; 3.53 0.39; 3.52 1.03; 3.50 1.03; 3.48 0.57; 3.48 0.58; 3.47 0.50; 3.21 2.57; 3.17 2.23; 2.68 0.89; 2.66 2.75; 2.64 2.81; 2.62 0.96; 2.56 1.33; 2.56 1.26; 2.54 2.49; 2.53 1.26; 2.53 1.21; 1.70 13.71; 1.59 3.20; 1.26 4.26; 1.24 8.08; 1.22 3.78 |
| 6.615 | 3-Cl-5-F—Ph | H | O | H | $CH_2CH_2$ | methoxycarbonyl | [$CDCl_3$] 1.72 (s, 3H); 2.55 (t, 2H); 3.18 (d, 1H); 3.50 (m, 1H); 3.57 (m, 1H); 3.69 (s, 3H); 3.76 (d, 1H); 7.15 (m, 1H); 7.27 (m, 1H); 7.39 (m, 1H) |
| 6.616 | 3-Cl-5-MeO—Ph | H | O | H | $CH_2CH_2$ | methoxycarbonyl | [$CDCl_3$] 7.52 0.55; 7.31 0.68; 7.26 104.31; 7.24 0.72; 7.21 0.70; 7.18 1.87; 7.18 2.86; 7.08 1.65; 7.08 2.22; 7.00 0.63; 6.96 1.62; 6.95 2.60; 6.95 1.36; 3.82 16.00; 3.78 2.29; 3.74 2.67; 3.68 15.86; 3.61 0.57; 3.59 0.71; 3.58 1.17; 3.56 1.16; 3.54 0.49; 3.53 0.50; 3.52 1.12; 3.50 1.13; 3.48 0.67; 3.47 0.54; 3.20 2.69; 3.16 2.16; 2.56 1.63; 2.54 2.99; 2.53 1.45; 1.70 13.71; 1.60 0.38; 1.55 45.79; 1.50 0.33; 1.43 1.47; 1.26 0.35; 1.22 0.33; 0.01 1.57; 0.00 50.39; −0.01 2.47 |
| 6.617 | 3-Cl-5-$CF_3O$—Ph | H | O | H | $CH_2CH_2$ | methoxycarbonyl | [$CDCl_3$] 1.72 (s, 3H); 2.53 (m, 2H); 3.18 (d, 1H); 3.50 (m, 1H); 3.58 (m. 1H); 3.69 (s, 3H); 3.78 (d, 1H); 7.22 (brt, 1H); 7.29 (brs, 1H); 7.41 (brs, 1H); 7.55 (brs, 1H). |
| 6.618 | 3-Cl-5-$CF_3$—Ph | H | O | H | $CH_2CH_2$ | methoxycarbonyl | [$CDCl_3$] 7.81 2.91; 7.76 3.06; 7.66 2.76; 7.31 0.45; 7.27 2.32; 7.26 17.93; 7.26 16.00; 7.24 1.02; 6.37 0.38; 6.37 0.35; 3.84 2.35; 3.84 2.22; 3.80 2.65; 3.80 2.52; 3.74 0.39; 3.69 16.00; 3.69 14.84; 3.61 0.57; 3.60 0.81; 3.58 1.33; 3.56 1.23; 3.55 0.48; 3.54 0.47; 3.52 1.19; 3.51 1.30; 3.49 0.84; 3.47 0.56; 3.23 2.59; 3.23 2.48; 3.19 2.25; 3.19 2.15; 2.56 1.85; 2.55 |

TABLE 6-continued

Compounds of the general formula (I) according to the invention in which $R^2$ is hydrogen and $R^3$ is methyl and aryl is the radical

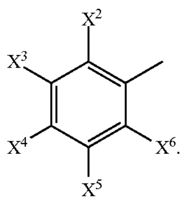

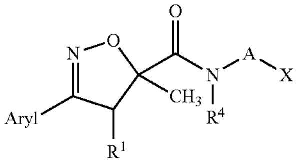

| No. | Aryl | $R^1$ | Y | $R^4$ | A | X | Physical data |
|---|---|---|---|---|---|---|---|
| | | | | | | | 3.32; 2.53 1.79; 1.77 0.34; 1.73 14.14; 1.73 13.48; 1.58 9.70; 1.58 9.50; 0.01 0.44; 0.00 3.04 |
| 6.619 | 3-Cl-5-Me—Ph | H | O | H | $CH_2CH_2$ | methoxycarbonyl | [$CDCl_3$] 1.70 (s, 3H); 2.53 (brt, 2H); 3.18 (d, 1H); 3.53 (m, 2H); 3.68 (s, 3H); 3.78 (d, 1H); 7.22 (brs, 1H); 7.23 (brs, 1H); 7.31 (brs, 1H); 7.43 (brs, 1H). |
| 6.620 | 3-CN-5-F—Ph | H | O | H | $CH_2CH_2$ | methoxycarbonyl | [$CDCl_3$] 7.70 2.52; 7.69 1.54; 7.62 0.69; 7.62 0.81; 7.62 0.86; 7.61 0.72; 7.60 0.70; 7.60 0.82; 7.60 0.84; 7.59 0.72; 7.43 0.71; 7.42 0.80; 7.42 0.77; 7.42 0.70; 7.41 0.74; 7.41 0.82; 7.40 0.76; 7.40 0.68; 7.26 9.44; 7.23 0.50; 5.30 0.64; 3.82 2.26; 3.77 2.58; 3.70 16.00; 3.62 0.46; 3.60 0.49; 3.60 0.49; 3.60 0.48; 3.58 0.93; 3.57 0.88; 3.55 0.39; 3.54 0.37; 3.52 0.87; 3.51 0.91; 3.49 0.49; 3.49 0.54; 3.47 0.43; 3.21 2.41; 3.16 2.12; 2.57 1.10; 2.56 1.11; 2.55 2.07; 2.54 1.06; 2.53 1.09; 1.90 0.39; 1.73 13.29; 0.00 4.57 |
| 6.621 | 3-CN—Ph | H | O | H | $CH_2CH_2$ | methoxycarbonyl | [DMSO-$D_6$] 8.18 0.53; 8.17 1.01; 8.15 0.54; 8.08 2.52; 8.03 1.27; 8.01 1.42; 7.95 1.32; 7.93 1.50; 7.69 1.27; 7.67 2.20; 7.65 1.00; 3.77 1.85; 3.73 2.34; 3.61 0.41; 3.54 16.00; 3.42 2.27; 3.38 2.03; 3.36 0.71; 3.34 1.12; 3.34 0.54; 3.33 1.07; 3.31 24.04; 3.29 0.90; 3.27 0.32; 2.52 0.34; 2.51 18.95; 2.50 27.06; 2.50 18.72; 2.49 4.49; 2.47 1.83; 1.55 11.78; 0.00 6.03 |
| 6.622 | 3-c-Pr-5-F—Ph | H | O | H | $CH_2CH_2$ | methoxycarbonyl | [$CDCl_3$] 7.26 13.21; 7.24 0.62; 7.13 0.64; 7.13 1.02; 7.12 1.06; 7.11 2.69; 7.11 2.28; 7.10 1.14; 7.10 0.62; 6.82 0.69; 6.81 0.92; 6.81 0.66; 6.79 0.71; 6.79 0.94; 6.78 0.64; 3.79 2.27; 3.75 2.61; 3.68 16.00; 3.61 0.49; 3.59 0.58; 3.59 0.52; 3.57 1.02; 3.56 0.97; 3.54 0.42; 3.53 0.40; 3.52 0.98; 3.50 0.99; 3.49 0.56; 3.48 0.57; 3.47 0.46; 3.21 2.46; 3.16 2.14; 2.56 1.30; 2.56 1.26; 2.54 2.42; 2.53 1.26; 2.53 1.22; 1.92 0.46; 1.91 0.51; 1.90 0.94; 1.89 0.54; 1.88 0.51; 1.70 13.25; 1.58 1.29; 1.04 0.67; 1.03 1.70; 1.03 1.84; 1.02 0.98; 1.01 1.00; 1.01 1.82; 1.00 1.67; 0.99 0.78; 0.73 0.79; 0.72 2.26; 0.71 1.83; 0.71 1.81; 0.70 2.28; 0.69 0.66; 0.00 5.65 |

TABLE 6-continued
Compounds of the general formula (I) according to the invention in which $R^2$ is hydrogen and $R^3$ is methyl and aryl is the radical
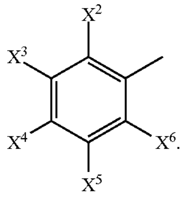
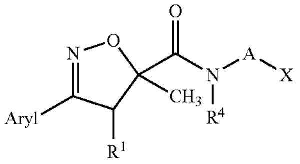
| No. | Aryl | $R^1$ | Y | $R^4$ | A | X | Physical data |
|---|---|---|---|---|---|---|---|
| 6.623 | 3-Et-5-F—Ph | H | O | H | $CH_2CH_2$ | methoxycarbonyl | [$CDCl_3$] 7.26 21.13; 7.25 0.55; 7.22 2.21; 7.19 0.61; 7.18 0.78; 7.18 0.58; 7.16 0.59; 7.16 0.76; 7.15 0.58; 6.98 0.71; 6.95 0.72; 3.80 2.18; 3.76 2.51; 3.68 16.00; 3.61 0.47; 3.59 0.53; 3.59 0.47; 3.58 0.94; 3.56 0.92; 3.54 0.39; 3.53 0.37; 3.52 0.90; 3.50 0.89; 3.49 0.49; 3.48 0.52; 3.47 0.44; 3.22 2.37; 3.17 2.06; 2.69 0.76; 2.67 2.33; 2.65 2.40; 2.63 0.82; 2.56 1.17; 2.56 1.16; 2.54 2.24; 2.53 1.12; 2.53 1.13; 1.70 12.90; 1.56 7.95; 1.26 3.83; 1.24 7.82; 1.22 3.67; 0.00 6.46 |
| 6.624 | 3-F-5-MeS—Ph | H | O | H | $CH_2CH_2$ | methoxycarbonyl | [$CDCl_3$] 7.26 14.40; 7.26 1.37; 7.25 1.74; 7.24 2.88; 7.24 2.03; 7.11 0.67; 7.10 0.79; 7.10 0.91; 7.10 0.81; 7.08 0.69; 7.08 0.81; 7.08 0.89; 7.08 0.80; 7.00 0.77; 6.99 0.97; 6.99 0.70; 6.98 0.71; 6.97 0.96; 6.97 0.68; 3.79 2.22; 3.74 2.55; 3.72 0.35; 3.71 0.48; 3.68 15.50; 3.61 0.51; 3.59 0.60; 3.59 0.53; 3.58 1.00; 3.56 0.89; 3.54 0.40; 3.53 0.39; 3.52 0.89; 3.50 0.94; 3.49 0.50; 3.48 0.54; 3.47 0.46; 3.20 2.40; 3.16 2.09; 2.56 1.23; 2.56 1.27; 2.54 2.43; 2.53 1.19; 2.53 1.25; 2.50 16.00; 1.70 12.95; 1.58 2.35; 0.00 6.10 |
| 6.625 | 3-F-5-$MeSO_2$—Ph | H | O | H | $CH_2CH_2$ | methoxycarbonyl | [$CDCl_3$] 7.95 1.34; 7.94 2.67; 7.94 1.78; 7.72 0.59; 7.71 0.96; 7.71 0.86; 7.70 0.67; 7.70 0.82; 7.70 0.96; 7.69 0.84; 7.68 0.80; 7.67 0.94; 7.67 0.86; 7.67 0.71; 7.66 0.82; 7.65 0.95; 7.65 0.84; 7.65 0.69; 7.26 24.82; 7.24 0.45; 7.23 0.62; 7.21 0.40; 3.87 2.17; 3.82 2.45; 3.71 0.60; 3.70 16.00; 3.62 0.48; 3.60 0.49; 3.60 0.52; 3.58 0.95; 3.57 0.83; 3.55 0.41; 3.54 0.39; 3.52 0.83; 3.51 0.90; 3.49 0.49; 3.49 0.58; 3.47 0.44; 3.25 2.30; 3.20 2.02; 3.09 15.25; 2.57 1.10; 2.56 1.20; 2.55 2.04; 2.54 1.09; 2.53 1.14; 1.73 12.57; 1.56 4.51; 1.55 0.40; 0.01 0.34; 0.00 10.23 |
| 6.626 | 3-F-5-MeO—Ph | H | O | H | $CH_2CH_2$ | methoxycarbonyl | [$CDCl_3$] 7.27 4.77; 7.25 0.36; 7.25 0.36; 6.96 1.89; 6.96 1.49; 6.94 0.84; 6.94 1.04; 6.93 0.71; 6.92 0.78; 6.92 0.86; 6.92 0.99; 6.91 0.73; 6.69 0.69; 6.69 1.26; 6.68 0.65; 6.67 0.70; 6.66 1.26; 6.66 0.64; 5.30 0.39; 3.82 16.00; 3.78 |

TABLE 6-continued

Compounds of the general formula (I) according to the invention in which $R^2$ is hydrogen and $R^3$ is methyl and aryl is the radical

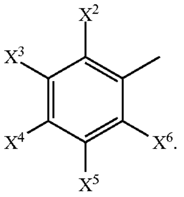

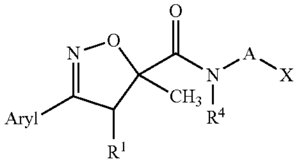

| No. | Aryl | $R^1$ | Y | $R^4$ | A | X | Physical data |
|---|---|---|---|---|---|---|---|
| | | | | | | | 2.35; 3.74 2.67; 3.68 15.82; 3.61 0.54; 3.60 0.61; 3.59 0.56; 3.58 1.10; 3.56 1.03; 3.55 0.42; 3.54 0.41; 3.52 0.99; 3.51 1.08; 3.49 0.61; 3.47 0.51; 3.20 2.60; 3.16 2.26; 2.56 1.53; 2.55 2.91; 2.53 1.46; 1.70 13.72; 0.00 0.97 |
| 6.627 | 3-F-5-Me—Ph | H | O | H | $CH_2CH_2$ | methoxycarbonyl | [$CDCl_3$] 7.27 0.33; 7.26 10.72; 7.26 4.46; 7.26 0.42; 7.26 0.36; 7.26 0.33; 7.25 0.32; 7.25 0.33; 7.25 0.35; 7.25 0.36; 7.25 0.37; 7.25 0.38; 7.25 0.38; 7.25 0.38; 7.24 0.37; 7.20 0.65; 7.20 1.06; 7.20 1.66; 7.20 1.82; 7.19 1.56; 7.19 1.11; 7.18 0.51; 7.18 0.49; 7.17 0.64; 7.17 0.63; 7.17 0.41; 7.16 0.49; 7.15 0.50; 7.15 0.62; 7.15 0.60; 7.15 0.50; 7.15 0.45; 6.96 0.34; 6.96 0.48; 6.96 0.54; 6.95 0.61; 6.95 0.57; 6.95 0.50; 6.95 0.42; 6.94 0.35; 6.94 0.49; 6.93 0.56; 6.93 0.61; 6.93 0.56; 6.93 0.50; 6.93 0.41; 3.79 2.22; 3.75 2.58; 3.68 16.00; 3.61 0.47; 3.59 0.47; 3.59 0.47; 3.57 0.96; 3.56 0.77; 3.56 0.83; 3.54 0.38; 3.53 0.36; 3.52 0.83; 3.52 0.72; 3.50 0.59; 3.50 0.92; 3.49 0.44; 3.48 0.50; 3.48 0.40; 3.47 0.45; 3.21 2.30; 3.16 2.01; 2.56 0.98; 2.56 1.03; 2.54 1.90; 2.53 0.94; 2.53 1.05; 2.37 7.37; 2.37 8.54; 1.70 13.11; 1.59 5.31; 1.59 3.40; 0.00 5.03 |
| 6.628 | 3-F—Ph | H | O | H | $CH_2CH_2$ | methoxycarbonyl | [$CDCl_3$] 1.71 (s, 3H); 2.53 (m, 2H); 3.20 (d, 1H); 3.43-3.62 (m, 2H); 3.68 (s, 3H); 3.79 (d, 1H); 7.12 (m, 1H); 7.22 (brt, 1H); 7.34-7.40 (m, 3H). |
| 6.629 | 3-Me—Ph | H | O | H | $CH_2CH_2$ | methoxycarbonyl | [$CDCl_3$] 7.47 1.97; 7.47 2.03; 7.42 0.97; 7.40 1.25; 7.31 0.91; 7.29 2.19; 7.27 1.95; 7.26 14.44; 7.24 1.76; 7.23 0.77; 3.82 2.34; 3.78 2.68; 3.67 16.00; 3.61 0.50; 3.59 0.66; 3.57 1.02; 3.56 1.04; 3.54 0.43; 3.53 0.41; 3.52 1.06; 3.50 1.01; 3.48 0.69; 3.48 0.57; 3.47 0.48; 3.24 2.55; 3.19 2.22; 2.56 1.36; 2.55 1.19; 2.54 2.31; 2.53 1.37; 2.52 1.17; 2.37 10.30; 1.70 13.76; 1.58 0.93; 0.00 4.63 |
| 6.630 | 3-$NO_2$—Ph | H | O | H | $CH_2CH_2$ | methoxycarbonyl | [$CDCl_3$] 8.47 1.03; 8.46 1.70; 8.46 1.12; 8.29 0.69; 8.29 0.75; 8.29 0.69; 8.29 0.68; 8.27 0.76; 8.27 0.78; 8.27 0.75; 8.27 0.71; 8.00 0.71; 7.99 0.90; 7.99 0.71; 7.98 |

TABLE 6-continued

Compounds of the general formula (I) according to the invention in which $R^2$ is hydrogen and $R^3$ is methyl and aryl is the radical

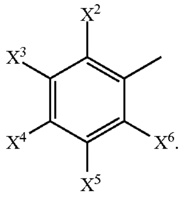

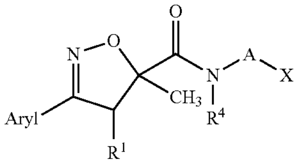

| No. | Aryl | $R^1$ | Y | $R^4$ | A | X | Physical data |
|---|---|---|---|---|---|---|---|
| | | | | | | | 0.80; 7.97 0.97; 7.97 0.97; 7.97 0.77; 7.63 1.16; 7.61 1.94; 7.59 0.99; 7.26 13.20; 7.25 0.34; 7.25 0.35; 7.25 0.35; 7.25 0.38; 3.90 2.26; 3.85 2.57; 3.69 16.00; 3.62 0.42; 3.61 0.43; 3.60 0.41; 3.59 0.82; 3.57 0.76; 3.56 0.37; 3.54 0.35; 3.53 0.79; 3.53 0.48; 3.51 0.58; 3.51 0.76; 3.50 0.43; 3.49 0.45; 3.48 0.38; 3.28 2.35; 3.24 2.06; 2.57 0.97; 2.57 0.95; 2.55 1.10; 2.55 1.58; 2.54 0.91; 2.53 0.92; 1.74 12.92; 1.57 5.94; 1.43 0.44; 0.00 7.15 |
| 6.631 | 4-Cl—Ph | H | O | H | $CH_2CH_2$ | methoxycarbonyl | |
| 6.632 | 4-EtO—Ph | H | O | H | $CH_2CH_2$ | methoxycarbonyl | [$CDCl_3$] 1.42 (t, 3H); 1.69 (s, 3H); 2.53 (t, 2H); 3.19 (d, 1H); 3.50 (m, 1H); 3.58 (m, 1H); 3.68 (s, 3H); 3.77 (d, 1H); 4.05 (q, 2H); 6.89 (d, 2H); 7.28 (tbr, 1H); 7.55 (d, 2H). |
| 6.633 | 4-MeO—Ph | H | O | H | $CH_2CH_2$ | methoxycarbonyl | |
| 6.634 | $F_5$—Ph | H | O | H | $CH_2CH_2$ | methoxycarbonyl | |
| 6.635 | Ph | H | O | H | $CH_2CH_2$ | methoxycarbonyl | |
| 6.636 | 3,5-$Cl_2$—Ph | H | O | H | $CH_2CH_2$ | methyl(methyl-sulfonyl)carbamoyl | [$CDCl_3$] 7.51 5.64; 7.51 5.80; 7.42 1.53; 7.41 2.61; 7.41 1.32; 7.26 13.38; 7.25 0.70; 7.24 0.38; 3.78 2.22; 3.76 0.55; 3.73 2.54; 3.66 0.32; 3.64 0.42; 3.64 0.45; 3.62 1.07; 3.61 1.19; 3.59 1.21; 3.58 1.14; 3.56 0.49; 3.56 0.41; 3.54 0.34; 3.25 15.79; 3.21 16.00; 3.19 2.49; 3.18 1.23; 3.14 2.15; 3.11 1.12; 3.05 0.54; 2.88 1.10; 2.88 1.07; 2.87 1.87; 2.87 1.96; 2.85 1.01; 2.85 1.02; 1.70 13.04; 1.56 2.48; 1.26 0.51; 0.00 3.88 |
| 6.637 | 3,5-$F_2$—Ph | H | O | H | $CH_2CH_2$ | methyl(methyl-sulfonyl)carbamoyl | [$CDCl_3$] 7.28 0.39; 7.28 0.38; 7.26 12.86; 7.26 12.81; 7.17 1.47; 7.16 1.89; 7.15 1.17; 7.15 1.89; 7.14 1.47; 6.91 0.35; 6.90 0.62; 6.90 0.32; 6.89 0.70; 6.88 1.23; 6.88 0.62; 6.87 0.37; 6.86 0.62; 3.78 2.28; 3.73 2.64; 3.67 0.41; 3.65 0.48; 3.65 0.45; 3.63 1.09; 3.62 1.08; 3.61 0.45; 3.60 0.48; 3.59 1.11; 3.58 1.16; 3.56 0.49; 3.56 0.50; 3.54 0.44; 3.25 15.92; 3.22 16.00; 3.19 2.58; 3.15 2.22; 2.88 1.39; 2.87 2.71; 2.85 1.28; 2.05 0.41; 1.71 13.58; 1.59 4.37; 0.00 4.20; 0.00 4.21 |
| 6.638 | 2,5-$Cl_2$—Ph | H | O | H | $CH_2CH_2$ | methylcarbamoyl | |

TABLE 6-continued

Compounds of the general formula (I) according to the invention in which $R^2$ is hydrogen and $R^3$ is methyl and aryl is the radical

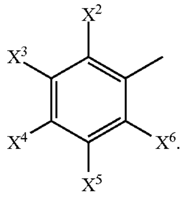

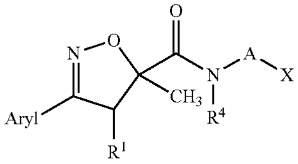

| No. | Aryl | $R^1$ | Y | $R^4$ | A | X | Physical data |
|---|---|---|---|---|---|---|---|
| 6.639 | 3,5-$Cl_2$—Ph | H | O | H | $CH_2CH_2$ | methylcarbamoyl | [$CDCl_3$] 1.71 (s, 3H); 2.40 (m, 2H); 2.79 (d, 3H); 3.17 (d, 1H); 3.47-3.63 (m, 2H); 3.74 (d, 1H); 5.60 (br, 1H); 7.40 (br, 1H); 7.41 (m, 1H); 7.51 (m, 2H). |
| 6.640 | 3-Cl-4-F—Ph | H | O | H | $CH_2CH_2$ | methylcarbamoyl | |
| 6.641 | 3-Cl-4-Me—Ph | H | O | H | $CH_2CH_2$ | methylcarbamoyl | |
| 6.642 | 3,5-$Cl_2$—Ph | H | O | H | $CH_2CH_2$ | methylsulfanyl | [$CDCl_3$] 1.74 (s, 3H); 2.13 (s, 3H); 2.64 (t, 2H); 3.19 (d, 1H); 3.48 (m, 2H); 3.78 (d, 1H); 3.83 (t t, 1H); 7.10 (s br, 1H); 7.42 (s, 1H); 7.52 (s, 2H). |
| 6.643 | 3,5-$Cl_2$—Ph | H | O | H | $CH_2CH_2$ | methylsulfonyl | [$CDCl_3$] 1.71 (s, 3H); 2.94 (s, 3H); 3.18 (d, 1H); 3.24 (t, 2H); 3.77 (d, 1H); 3.73-3.84 (m, 2H); 7.35 (br, 1H); 7.41 (s, 1H); 7.51 (s, 2H). |
| 6.644 | 3,5-$Cl_2$—Ph | H | O | H | $CH_2CH_2$ | morpholin-4-yl | [$CDCl_3$] 7.52 9.93; 7.51 7.65; 7.51 0.46; 7.42 3.25; 7.41 3.83; 7.41 1.52; 7.27 10.70; 7.26 22.64; 7.26 0.41; 7.22 0.55; 7.22 0.58; 7.21 1.01; 3.80 2.84; 3.76 3.17; 3.71 4.72; 3.70 6.43; 3.69 4.25; 3.43 0.58; 3.42 0.77; 3.41 0.52; 3.40 1.16; 3.38 1.10; 3.37 0.43; 3.35 0.43; 3.34 1.04; 3.32 1.21; 3.30 0.70; 3.30 0.60; 3.29 0.58; 3.20 2.99; 3.15 2.59; 2.51 2.15; 2.49 3.88; 2.48 2.30; 2.46 4.01; 2.45 4.95; 1.73 16.00; 1.70 0.60; 1.30 0.41; 1.26 1.91; 0.88 0.43; 0.00 4.55 |
| 6.645 | 3,5-$Cl_2$—Ph | H | O | H | $CH_2CH_2$ | morpholin-4-ylcarbonyl | [$CDCl_3$] 1.71 (s, 3H); 2.51 (q, 2H); 3.16 (d, 1H); 3.56 (m, 2H); 3.40 (m, 2H); 3.63 (n, 8H); 3.75 (d, 1H); 7.40 (m, 1H); 7.43 (m, 1H); 7.52 (m, 2H). |
| 6.646 | 3,5-$Cl_2$—Ph | H | O | H | $CH_2CH_2$ | phosphono | |
| 6.647 | Ph | H | O | H | $CH_2CH_2$ | phosphono | |
| 6.648 | 3,5-$Cl_2$—Ph | H | O | H | $CH_2CH_2$ | piperidin-1-yl | |
| 6.649 | 3,5-$Cl_2$—Ph | H | O | H | $CH_2CH_2$ | piperidin-1-ylcarbonyl | [$CDCl_3$] 1.55 (m, 6H); 1.71 (s, 3H); 2.50 (t, 2H); 3.14 (d, 1H); 3.33 (t, 2H); 3.54 (m, 4H); 3.77 (d, 1H); 7.40 (m, 1H); 7.48 (m, 1H); 7.52 (m, 2H). |
| 6.650 | 3,5-$Cl_2$—Ph | H | O | H | $CH_2CH_2$ | propan-2-yloxy | [$CDCl_3$] 1.13 (t, 3H); 1.72 (s, 3H); 3.18 (d, 1H); 3.34-3.60 (m, 5H); 3.78 (d, 1H); 7.12 (br, 1H); 7.40 (m, 1H); 7.51 (m, 2H). |
| 6.651 | 3,5-$Cl_2$—Ph | H | O | H | $CH_2CH_2$ | propoxy | [$CDCl_3$] 0.90 (t, 3H); 1.58 (m, 4H); 1.73 (s, 3H); 3.18 (d, 1H); 3.39 (t, 2H); 3.50 (m, 2H); 3.78 (d, 1H); 7.13 (s br, 1H); 7.42 (s, 1H); 7.53 (s, 2H). |
| 6.652 | 3,5-$Cl_2$—Ph | H | O | H | $CH_2CH_2$ | propoxycarbonyl | [$CDCl_3$] 7.51 7.25; 7.51 7.08; 7.41 2.15; 7.41 3.26; 7.40 1.50; 7.26 25.82; 7.23 0.78; 7.21 0.49; 4.07 |

TABLE 6-continued

Compounds of the general formula (I) according to the invention in which $R^2$ is hydrogen and $R^3$ is methyl and aryl is the radical

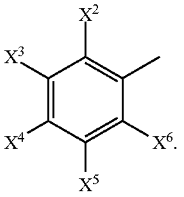

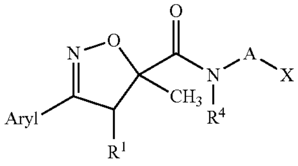

| No. | Aryl | $R^1$ | Y | $R^4$ | A | X | Physical data |
|---|---|---|---|---|---|---|---|
| | | | | | | | 2.82; 4.05 5.78; 4.03 2.90; 3.78 2.71; 3.74 3.12; 3.60 0.50; 3.58 0.69; 3.57 1.26; 3.55 1.27; 3.54 0.58; 3.53 0.55; 3.52 1.31; 3.51 1.31; 3.49 0.75; 3.49 0.65; 3.47 0.52; 3.18 2.93; 3.14 2.56; 2.55 1.93; 2.54 3.50; 2.52 1.82; 2.00 0.43; 1.71 16.00; 1.68 0.39; 1.67 1.42; 1.65 3.02; 1.63 2.90; 1.61 1.67; 1.59 0.40; 1.55 10.81; 0.94 4.69; 0.92 9.31; 0.91 4.23; 0.00 4.36 |
| 6.653 | 3,5-$Cl_2$—Ph | H | O | H | $CH_2CH_2$ | pyrrolidin-1-yl | |
| 6.654 | 3,5-$Cl_2$—Ph | H | O | H | $CH_2CH_2$ | sec-butoxycarbonyl | [$CDCl_3$] 7.51 7.17; 7.51 7.13; 7.51 8.05; 7.41 2.83; 7.40 5.06; 7.40 2.46; 7.26 22.84; 7.25 0.67; 7.23 0.92; 7.22 0.57; 5.30 6.32; 4.89 1.00; 4.88 1.81; 4.86 1.83; 4.85 1.05; 3.78 3.76; 3.74 4.30; 3.59 0.65; 3.58 0.78; 3.57 0.77; 3.56 1.66; 3.54 1.59; 3.54 0.56; 3.53 0.50; 3.53 0.72; 3.52 1.15; 3.52 1.10; 3.50 1.20; 3.50 0.98; 3.49 0.53; 3.49 0.86; 3.47 0.45; 3.47 0.34; 3.18 4.25; 3.14 3.72; 2.54 1.08; 2.53 1.70; 2.52 1.29; 2.51 3.45; 2.50 1.19; 2.50 1.69; 1.71 16.00; 1.71 15.49; 1.62 0.36; 1.62 0.40; 1.60 0.48; 1.60 0.84; 1.59 0.92; 1.58 1.21; 1.57 9.96; 1.56 1.56; 1.55 1.06; 1.55 1.32; 1.54 1.15; 1.53 1.05; 1.53 1.41; 1.51 1.08; 1.49 0.63; 1.21 8.16; 1.20 12.71; 1.18 7.55; 0.90 3.37; 0.88 7.16; 0.88 4.13; 0.87 3.36; 0.86 7.80; 0.84 3.32; 0.00 6.35 |
| 6.655 | 3,5-$F_2$—Ph | H | O | H | $CH_2CH_2$ | sulfamoyl | [$CDCl_3$] 7.52 0.93; 7.33 0.90; 7.31 1.10; 7.26 169.57; 7.18 0.48; 7.16 2.26; 7.16 2.71; 7.14 2.74; 7.14 2.06; 7.13 0.43; 7.00 0.98; 6.90 0.53; 6.90 0.85; 6.89 0.49; 6.88 1.04; 6.88 1.70; 6.87 0.92; 6.86 0.56; 6.86 0.85; 5.00 2.16; 3.91 0.57; 3.89 0.73; 3.87 1.06; 3.86 1.09; 3.84 0.48; 3.81 2.62; 3.80 1.17; 3.78 1.33; 3.77 3.23; 3.76 0.75; 3.74 0.66; 3.28 2.62; 3.26 4.34; 3.25 2.25; 3.21 2.82; 3.16 2.42; 1.73 16.00; 1.69 0.41; 1.55 15.32; 1.46 0.37; 1.29 0.68; 1.26 2.68; 0.88 0.49 |
| 6.656 | 3,5-$Cl_2$—Ph | H | O | H | $CH_2CH_2$ | tert-butoxycarbonyl | [$CDCl_3$] 1.44 (s, 9H); 1.71 (s, 3H); 2.44 (t, 2H); 3.17 (d, 1H); 3.40-3.56 (m, 2H); 3.76 (d, 1H); 7.23 (br, 1H); 7.41 (m, 1H); 7.51 (m, 2H). |

TABLE 6-continued

Compounds of the general formula (I) according to the invention in which $R^2$ is hydrogen and $R^3$ is methyl and aryl is the radical

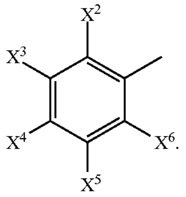

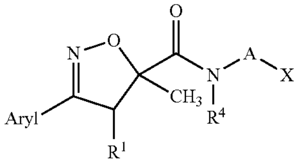

| No. | Aryl | $R^1$ | Y | $R^4$ | A | X | Physical data |
|---|---|---|---|---|---|---|---|
| 6.657 | 3,5-$F_2$—Ph | H | O | H | $CH_2CH_2$ | tert-butoxycarbonyl | [$CDCl_3$] 1.55 (s, 9H); 1.72 (s, 3H); 2.44 (t, 2H); 3.17 (d, 1H); 3.49 (m, 2H); 3.76 (d, 1H); 6.87 (m, 1H); 7.16 (m, 2H) |
| 6.658 | 3,5-$Cl_2$—Ph | H | O | H | $CH_2CH_2$ | tetrahydrofuran-2-yl | [$CDCl_3$] 1.50 (m, 2H); 1.70 (s, 3H); 1.87 (m, 2H); 2.00 (m, 2H); 3.15 (d, 1H); 3.31 (m, 1H); 3.50 (m, 2H); 3.75 (d, 1H); 3.86 (m, 2H); 7.40 (t, 1H); 7.50 (d, 2H) |
| 6.659 | 3,5-$Cl_2$—Ph | H | O | H | $CH_2CH_2$ | trifluoromethoxy | [$CDCl_3$] 7.52 5.27; 7.52 7.33; 7.51 6.25; 7.51 7.25; 7.43 1.45; 7.42 2.19; 7.42 2.65; 7.42 3.34; 7.41 1.53; 7.31 0.32; 7.31 0.55; 7.27 0.33; 7.27 0.39; 7.27 0.45; 7.26 42.66; 7.26 57.78; 7.25 0.51; 7.25 0.37; 7.12 0.73; 7.11 0.49; 4.06 1.30; 4.05 2.05; 4.05 1.40; 4.04 2.10; 4.04 2.27; 4.04 2.10; 4.03 1.44; 4.03 1.25; 4.03 1.41; 3.79 2.16; 3.79 2.74; 3.75 2.49; 3.74 3.15; 3.66 0.46; 3.65 0.45; 3.64 0.46; 3.62 0.75; 3.61 0.70; 3.60 0.32; 3.54 0.36; 3.52 0.70; 3.51 0.71; 3.50 0.57; 3.49 0.66; 3.47 0.44; 3.22 2.36; 3.22 2.92; 3.18 2.06; 3.18 2.53; 2.01 0.68; 2.01 0.91; 1.74 12.92; 1.73 16.00; 1.55 21.03; 1.55 29.85; 0.01 0.40; 0.00 8.32; 0.00 11.57; −0.01 0.37; −0.01 0.38 |
| 6.660 | 3,5-$F_2$—Ph | H | O | H | $CH_2CH_2$ | trifluoromethoxy | [$CDCl_3$] 7.52 0.41; 7.26 74.90; 7.18 0.36; 7.17 1.90; 7.16 2.42; 7.15 2.58; 7.14 2.18; 7.14 0.89; 7.13 0.94; 7.00 0.43; 6.91 0.42; 6.91 0.73; 6.90 0.40; 6.89 0.88; 6.89 1.51; 6.88 0.82; 6.87 0.47; 6.86 0.75; 6.86 0.37; 4.06 1.33; 4.05 1.46; 4.05 1.55; 4.04 2.37; 4.03 1.62; 4.03 1.61; 3.78 2.63; 3.74 3.06; 3.66 0.41; 3.65 0.40; 3.64 0.43; 3.62 0.70; 3.61 0.66; 3.59 0.32; 3.54 0.34; 3.53 0.68; 3.52 0.68; 3.51 0.38; 3.50 0.42; 3.49 1.04; 3.48 0.47; 3.23 2.88; 3.18 2.51; 2.01 1.48; 1.74 16.00; 1.55 30.76; 0.00 13.51; −0.01 1.15; −0.01 0.78 |
| 6.661 | 3-F—Ph | H | O | H | $CH_2CH_2$ | trifluoromethoxy | [$CDCl_3$] 7.40 1.53; 7.39 1.30; 7.38 2.95; 7.38 3.40; 7.37 3.54; 7.36 1.65; 7.26 22.32; 7.17 0.71; 7.16 0.93; 7.16 1.13; 7.15 0.71; 7.14 0.75; 7.14 0.90; 7.13 0.91; 7.13 0.62; 7.12 0.61; 7.11 0.39; 4.06 1.33; 4.05 1.83; 4.04 2.21; 4.03 1.53; 4.03 1.51; 3.81 2.63; 3.77 3.06; 3.66 0.46; 3.65 0.45; 3.64 |

TABLE 6-continued
Compounds of the general formula (I) according to the invention in which $R^2$ is hydrogen and $R^3$ is methyl and aryl is the radical
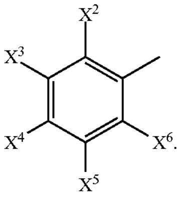
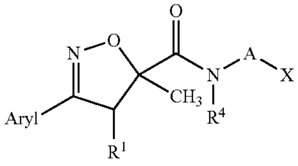
| No. | Aryl | $R^1$ | Y | $R^4$ | A | X | Physical data |
|---|---|---|---|---|---|---|---|
| | | | | | | | 0.48; 3.62 0.75; 3.61 0.71; 3.60 0.33; 3.54 0.36; 3.52 0.71; 3.51 0.72; 3.49 0.53; 3.49 0.52; 3.47 0.45; 3.26 2.98; 3.21 2.57; 2.01 0.42; 1.74 16.00; 1.56 9.62; 0.00 3.98 |
| 6.662 | Ph | H | O | H | $CH_2CH_2$ | trifluoromethoxy | [$CDCl_3$] 7.65 1.84; 7.64 3.20; 7.64 2.49; 7.64 1.31; 7.62 3.43; 7.62 2.50; 7.52 0.50; 7.52 0.36; 7.44 0.63; 7.44 1.12; 7.43 1.81; 7.43 5.46; 7.42 5.08; 7.41 1.37; 7.41 3.05; 7.40 0.70; 7.39 0.83; 7.39 0.69; 7.39 0.63; 7.27 0.33; 7.27 0.40; 7.27 0.44; 7.27 0.44; 7.27 0.50; 7.27 0.58; 7.27 0.63; 7.27 0.85; 7.27 1.18; 7.26 90.28; 7.26 62.78; 7.26 56.29; 7.21 0.88; 7.21 0.87; 7.00 0.48; 6.99 0.33; 4.06 1.17; 4.05 1.10; 4.05 2.13; 4.04 1.95; 4.04 1.76; 4.04 2.24; 4.03 2.39; 4.03 2.39; 4.02 1.54; 4.01 0.40; 3.84 2.67; 3.84 2.09; 3.79 3.08; 3.79 2.44; 3.66 0.50; 3.65 0.50; 3.64 0.51; 3.63 0.83; 3.61 0.77; 3.60 0.36; 3.53 0.36; 3.51 0.78; 3.50 1.00; 3.48 0.60; 3.46 0.51; 3.28 2.88; 3.28 2.39; 3.24 2.53; 3.24 2.04; 2.01 1.82; 2.01 1.26; 1.73 16.00; 1.73 12.93; 1.55 43.26; 1.55 34.50; 0.01 0.45; 0.00 16.77; 0.00 11.28; 0.00 9.71; −0.01 0.64; −0.01 0.54 |
| 6.663 | 3-Cl—Ph | H | O | H | $CH_2CH_2CH_2$ | (propan-2-yloxy)carbonyl | [$CDCl_3$] 7.65 3.38; 7.65 3.52; 7.51 1.87; 7.50 1.87; 7.50 0.80; 7.49 2.38; 7.48 2.39; 7.41 1.24; 7.41 1.26; 7.41 0.62; 7.39 2.59; 7.39 2.46; 7.36 2.23; 7.36 2.28; 7.34 2.70; 7.32 0.95; 7.27 12.91; 7.26 13.55; 7.26 15.50; 6.95 1.02; 5.03 0.55; 5.01 1.29; 5.01 1.33; 5.00 1.73; 5.00 1.77; 4.98 1.31; 4.98 1.31; 4.97 0.52; 3.82 2.56; 3.82 2.60; 3.78 2.95; 3.78 3.00; 3.38 0.69; 3.36 1.14; 3.35 1.55; 3.33 1.34; 3.31 0.48; 3.29 0.44; 3.27 1.26; 3.26 1.53; 3.24 1.13; 3.22 3.59; 3.18 2.51; 3.18 2.53; 2.31 2.62; 2.29 5.39; 2.27 2.90; 1.88 0.81; 1.86 2.78; 1.84 3.89; 1.83 2.46; 1.81 0.62; 1.72 16.00; 1.72 16.00; 1.59 3.54; 1.59 3.48; 1.58 4.69; 1.23 11.69; 1.21 11.65; 0.00 5.27; 0.00 5.58 |
| 6.664 | 3-F—Ph | H | O | H | $CH_2CH_2CH_2$ | (propan-2-yloxy)carbonyl | [$CDCl_3$] 7.39 2.23; 7.38 4.88; 7.37 4.50; 7.26 26.22; 7.15 0.47; 7.15 0.78; 7.14 0.55; 7.13 0.93; 7.13 |

TABLE 6-continued
Compounds of the general formula (I) according to the invention in which $R^2$ is hydrogen and $R^3$ is methyl and aryl is the radical
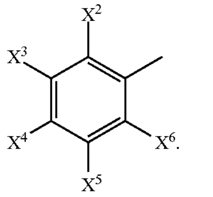
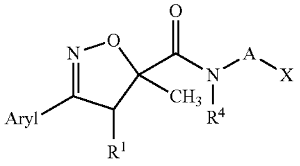
| No. | Aryl | $R^1$ | Y | $R^4$ | A | X | Physical data |
|---|---|---|---|---|---|---|---|
| | | | | | | | 1.04; 7.12 0.72; 7.11 0.59; 7.10 0.40; 6.96 0.74; 5.03 0.51; 5.01 1.28; 5.00 1.75; 4.98 1.33; 4.96 0.53; 3.82 2.68; 3.78 3.09; 3.38 0.62; 3.36 0.97; 3.34 1.38; 3.33 1.07; 3.31 0.44; 3.29 0.42; 3.27 1.06; 3.25 1.14; 3.24 1.09; 3.23 3.22; 3.22 0.64; 3.19 2.61; 2.31 2.27; 2.29 5.10; 2.27 2.83; 1.88 0.68; 1.86 2.50; 1.84 3.58; 1.82 2.28; 1.81 0.55; 1.74 0.62; 1.72 16.00; 1.57 11.70; 1.25 0.50; 1.23 8.69; 1.22 9.57; 1.21 8.92; 1.21 9.55; 0.00 10.78 |
| 6.665 | 3,5-$Cl_2$—Ph | H | O | H | $CH_2CH_2CH_2$ | 2-carboxyethyl | [$CDCl_3$] 1.34-1.69 (m, 6H); 1.71 (s, 3H); 2.34 (t, 2H); 3.17 (d, 1H); 3.18-3.34 (m, 2H); 3.78 (d, 1H); 6.80 (br, 1H); 7.41 (m, 2H); 7.51 (m, 1H). |
| 6.666 | 3,5-$Cl_2$—Ph | H | O | H | $CH_2CH_2CH_2$ | 2-methyl-1,3-dioxolan-2-yl | [$CDCl_3$] 7.52 7.34; 7.51 7.78; 7.41 2.03; 7.41 3.47; 7.41 1.66; 7.26 15.83; 7.00 0.36; 6.98 0.51; 3.96 1.58; 3.95 1.45; 3.95 2.31; 3.95 2.68; 3.94 4.86; 3.93 4.14; 3.93 1.85; 3.92 0.95; 3.92 1.46; 3.91 0.83; 3.90 0.40; 3.80 2.72; 3.76 3.11; 3.34 0.39; 3.33 0.57; 3.31 0.82; 3.29 0.66; 3.27 0.35; 3.25 0.74; 3.24 0.81; 3.22 0.43; 3.22 0.45; 3.20 0.36; 3.19 2.92; 3.15 2.53; 1.78 0.49; 1.72 15.33; 1.68 0.57; 1.67 0.83; 1.66 0.80; 1.66 1.85; 1.65 3.19; 1.64 1.58; 1.64 1.64; 1.63 1.00; 1.63 1.18; 1.62 0.85; 1.62 0.51; 1.61 0.65; 1.61 0.38; 1.60 0.45; 1.29 16.00; 0.00 8.03 |
| 6.667 | 3,5-$F_2$—Ph | H | O | H | $CH_2CH_2CH_2$ | 2-methyl-1,3-dioxolan-2-yl | [$CDCl_3$] 7.27 15.28; 7.17 1.69; 7.16 1.93; 7.16 1.01; 7.15 1.00; 7.15 1.91; 7.14 1.67; 7.00 0.45; 7.00 0.50; 6.91 0.42; 6.90 0.75; 6.89 0.38; 6.88 0.84; 6.88 1.51; 6.87 0.74; 6.86 0.44; 6.86 0.76; 6.85 0.36; 3.96 1.57; 3.95 1.48; 3.95 2.31; 3.94 2.72; 3.94 2.51; 3.94 5.09; 3.93 4.00; 3.93 1.89; 3.92 1.00; 3.92 0.97; 3.92 1.40; 3.91 0.87; 3.90 0.40; 3.79 2.82; 3.75 3.22; 3.35 0.40; 3.33 0.56; 3.31 0.82; 3.30 0.66; 3.27 0.33; 3.25 0.73; 3.24 0.79; 3.22 0.42; 3.22 0.45; 3.21 0.36; 3.19 2.95; 3.15 2.54; 1.78 0.59; 1.72 16.00; 1.68 0.49; 1.67 0.75; 1.66 1.70; 1.66 2.92; 1.65 2.72; 1.64 1.40; 1.64 1.50; 1.64 0.84; 1.63 0.98; 1.63 |

TABLE 6-continued
Compounds of the general formula (I) according to the invention in which $R^2$ is hydrogen and $R^3$ is methyl and aryl is the radical
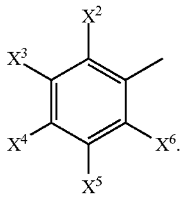
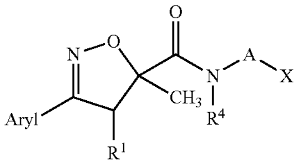
| No. | Aryl | $R^1$ | Y | $R^4$ | A | X | Physical data |
|---|---|---|---|---|---|---|---|
| | | | | | | | 0.69; 1.62 0.36; 1.61 0.51; 1.29 15.77; 0.00 7.38 |
| 6.668 | Ph | H | O | H | $CH_2CH_2CH_2$ | 2-methyl-1,3-dioxolan-2-yl | [$CDCl_3$] 7.65 2.03; 7.64 2.23; 7.64 0.97; 7.64 0.75; 7.63 0.77; 7.63 1.59; 7.62 2.57; 7.52 0.60; 7.43 0.57; 7.43 0.68; 7.43 0.47; 7.42 1.63; 7.42 3.48; 7.42 3.25; 7.41 1.56; 7.41 1.62; 7.41 1.07; 7.40 1.79; 7.40 1.71; 7.39 0.39; 7.39 0.59; 7.38 0.38; 7.27 0.36; 7.27 0.49; 7.27 0.63; 7.27 0.85; 7.27 1.27; 7.26 106.89; 7.26 2.98; 7.26 2.00; 7.26 1.45; 7.26 1.12; 7.26 0.92; 7.25 0.79; 7.25 0.70; 7.25 0.59; 7.25 0.49; 7.25 0.40; 7.25 0.32; 7.04 0.42; 7.00 0.62; 3.94 1.40; 3.94 1.48; 3.93 3.70; 3.92 1.97; 3.92 3.54; 3.92 2.32; 3.91 1.60; 3.91 1.65; 3.90 0.81; 3.90 1.17; 3.90 1.42; 3.88 0.63; 3.85 2.83; 3.80 3.23; 3.49 0.37; 3.34 0.39; 3.32 0.56; 3.31 0.76; 3.29 0.61; 3.27 0.34; 3.25 3.41; 3.24 0.78; 3.22 0.47; 3.21 2.68; 3.20 0.36; 2.05 1.04; 1.72 16.00; 1.69 0.51; 1.68 0.88; 1.66 1.31; 1.64 4.83; 1.63 4.94; 1.63 3.92; 1.62 3.31; 1.60 1.32; 1.60 0.84; 1.59 0.76; 1.59 0.50; 1.58 0.39; 1.29 15.08; 1.28 0.49; 1.26 0.62; 0.01 0.33; 0.01 1.29; 0.01 0.33; 0.01 0.37; 0.00 0.49; 0.00 0.75; 0.00 1.44; 0.00 48.22; 0.00 2.91; 0.00 2.07; 0.00 1.29; 0.00 0.80; −0.01 0.63; −0.01 0.53; −0.01 1.39 |
| 6.669 | 3,5-$Cl_2$—Ph | H | O | H | $CH_2CH_2CH_2$ | 2-oxopyrrolidin-1-yl | |
| 6.670 | 3,5-$Cl_2$—Ph | H | O | H | $CH_2CH_2CH_2$ | $CF_3$ | [$CDCl_3$] 1.71 (s, 3H); 1.80 (m, 2H); 2.11 (m, 2H); 3.19 (d, 1H); 3.28 (m, 1H); 3.39 (m, 1H); 3.77 (d, 1H); 6.88 (t br, 1H); 7.42 (m, 1H); 7.52 (s, 1H). |
| 6.671 | 3,5-$Cl_2$—Ph | H | O | H | $CH_2CH_2CH_2$ | $CH_3$ | [$CDCl_3$] 7.52 10.02; 7.51 9.40; 7.41 4.39; 7.32 0.42; 7.27 25.81; 7.27 26.89; 7.27 26.72; 7.26 31.60; 7.26 28.58; 7.22 0.55; 6.77 1.66; 3.80 2.53; 3.76 3.00; 3.33 0.75; 3.31 1.22; 3.30 1.62; 3.28 1.44; 3.27 0.58; 3.22 1.32; 3.20 1.73; 3.19 4.02; 3.14 2.61; 1.72 16.00; 1.55 12.60; 1.55 12.96; 1.55 14.35; 1.52 2.61; 1.50 4.09; 1.48 2.99; 1.36 1.78; 1.35 3.24; 1.33 3.20; 1.31 1.72; 0.93 4.53; 0.92 8.38; 0.90 3.92; 0.90 4.02; 0.01 11.90; 0.01 12.32; 0.01 12.32 |

TABLE 6-continued

Compounds of the general formula (I) according to the invention in which $R^2$ is hydrogen and $R^3$ is methyl and aryl is the radical

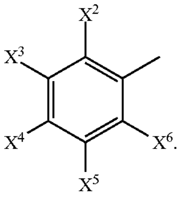

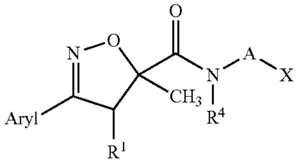

| No. | Aryl | $R^1$ | Y | $R^4$ | A | X | Physical data |
|---|---|---|---|---|---|---|---|
| 6.672 | 3,5-$F_2$—Ph | H | O | H | $CH_2CH_2CH_2$ | $CH_3$ | [$CDCl_3$] 7.52 0.93; 7.31 0.76; 7.31 0.47; 7.30 0.56; 7.30 0.66; 7.30 0.78; 7.29 1.36; 7.28 4.16; 7.28 6.35; 7.28 6.16; 7.27 7.73; 7.27 9.55; 7.26 174.54; 7.19 0.42; 7.18 0.68; 7.17 2.20; 7.16 2.31; 7.16 1.46; 7.15 1.39; 7.15 1.41; 7.15 2.24; 7.14 1.72; 7.14 0.37; 7.13 0.35; 7.00 0.95; 6.90 0.52; 6.90 0.91; 6.89 0.59; 6.88 1.02; 6.88 1.58; 6.87 0.78; 6.86 0.58; 6.85 0.78; 6.85 0.40; 6.78 0.56; 6.77 0.43; 6.76 0.37; 3.80 2.71; 3.75 3.06; 3.33 0.54; 3.32 1.02; 3.30 1.16; 3.28 0.90; 3.27 0.48; 3.24 0.55; 3.23 0.71; 3.22 1.03; 3.21 1.26; 3.21 0.85; 3.19 3.33; 3.18 0.62; 3.17 0.43; 3.16 0.56; 3.15 2.36; 1.72 16.00; 1.58 0.41; 1.54 70.48; 1.53 3.14; 1.53 2.61; 1.53 2.17; 1.53 1.81; 1.53 1.71; 1.53 1.55; 1.53 1.45; 1.53 1.34; 1.52 1.34; 1.52 1.28; 1.52 1.82; 1.52 1.59; 1.51 1.05; 1.50 1.95; 1.50 1.82; 1.49 1.15; 1.49 0.59; 1.48 1.63; 1.48 0.58; 1.46 0.62; 1.38 0.49; 1.36 1.27; 1.34 1.64; 1.33 0.97; 1.33 1.53; 1.31 0.46; 1.31 0.95; 0.93 4.38; 0.91 8.68; 0.90 3.33; 0.04 0.35; 0.02 2.81; 0.01 6.25 |
| 6.673 | 3,5-$Cl_2$—Ph | H | O | H | $CH_2CH_2CH_2$ | COOH | |
| 6.674 | 3,5-$F_2$—Ph | H | O | H | $CH_2CH_2CH_2$ | COOH | [$CDCl_3$] 1.73 (s, 3H); 1.89 (pent, 2H); 2.40 (t, 2H); 3.19 (d, 1H); 3.35 (m, 2H); 3.78 (d, 1H); 6.38 (m, 1H); 7.02 (t br, 1H); 7.16 (m, 2H). |
| 6.675 | 3-Br-5-Cl—Ph | H | O | H | $CH_2CH_2CH_2$ | COOH | [$CDCl_3$] 1.72 (s, 3H); 1.87 (m, 2H); 2.38 (t, 2H); 3.18 (d, 1H); 3.31 (m, 1H); 3.38 (m, 1H); 3.77 (d, 1H); 7.00 (t br, 1H); 7.56 (m, 2H); 7.66 (d, 1H) |
| 6.676 | 3-Cl—Ph | H | O | H | $CH_2CH_2CH_2$ | COOH | [$CDCl_3$] 7.64 3.79; 7.64 3.47; 7.50 1.86; 7.50 1.80; 7.48 2.28; 7.48 2.13; 7.41 1.42; 7.41 1.24; 7.39 2.77; 7.39 2.40; 7.36 2.20; 7.34 2.42; 7.34 2.12; 7.32 0.62; 7.30 0.67; 7.27 4.56; 7.26 35.18; 7.26 27.71; 7.20 0.78; 7.16 0.33; 7.06 1.16; 5.30 0.40; 5.29 0.33; 3.82 2.68; 3.82 2.16; 3.78 2.95; 3.78 2.39; 3.41 0.57; 3.39 1.02; 3.38 1.56; 3.36 1.27; 3.34 0.72; 3.32 1.28; 3.30 1.44; 3.29 0.94; 3.27 0.58; 3.23 2.93; 3.23 2.41; 3.19 2.46; 2.40 2.39; 2.38 4.92; 2.36 2.55; 1.90 0.79; 1.89 2.64; 1.87 3.55; 1.85 2.20; 1.84 0.54; 1.77 |

TABLE 6-continued

Compounds of the general formula (I) according to the invention in which $R^2$ is hydrogen and $R^3$ is methyl and aryl is the radical

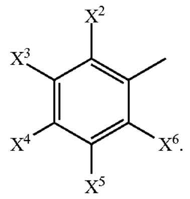

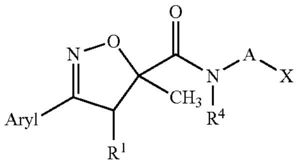

| No. | Aryl | $R^1$ | Y | $R^4$ | A | X | Physical data |
|---|---|---|---|---|---|---|---|
| | | | | | | | 0.34; 1.72 16.00; 1.72 13.16; 1.67 0.37; 0.01 1.80 |
| 6.677 | 3-F—Ph | H | O | H | $CH_2CH_2CH_2$ | COOH | [$CDCl_3$] 7.39 1.86; 7.39 1.29; 7.38 1.26; 7.38 1.57; 7.38 1.62; 7.37 2.80; 7.37 2.58; 7.37 3.39; 7.36 3.83; 7.35 0.60; 7.26 8.22; 7.26 13.70; 7.16 0.52; 7.15 0.76; 7.15 0.51; 7.14 0.78; 7.14 0.81; 7.13 0.81; 7.13 0.95; 7.13 1.07; 7.12 0.82; 7.11 1.12; 7.11 0.86; 7.10 0.83; 7.08 0.49; 6.98 0.43; 3.83 2.71; 3.79 3.11; 3.41 0.53; 3.40 0.95; 3.38 1.25; 3.36 1.15; 3.35 0.42; 3.33 0.41; 3.32 0.96; 3.32 0.96; 3.30 1.26; 3.28 0.91; 3.27 0.57; 3.24 3.02; 3.20 2.60; 2.40 1.91; 2.38 4.44; 2.36 2.45; 2.27 0.70; 2.10 0.46; 2.10 0.75; 1.91 0.63; 1.89 2.32; 1.87 3.17; 1.85 1.97; 1.84 0.50; 1.73 16.00; 1.43 3.71; 1.43 5.78; 1.26 0.80; 0.00 5.45; 0.00 9.08; −0.01 0.32; −0.01 0.34; −0.01 0.35 |
| 6.678 | Ph | H | O | H | $CH_2CH_2CH_2$ | COOH | [$CDCl_3$] 1.72 (s, 3H); 1.86 (quin, 2H); 2.38 (t, 2H); 3.25 (d, 1H); 3.27-3.43 (m, 2H); 4.33 (d, 1H); 7.13 (br, 1H); 7.39-7.46 (m, 3H); 7.63 (m, 2H). |
| 6.679 | 3,5-$Cl_2$—Ph | H | O | H | $CH_2CH_2CH_2$ | dimethylamino | |
| 6.680 | Ph | H | O | ethyl-carbamoyl | $CH_2CH_2CH_2$ | dimethylamino | |
| 6.681 | 3,5-$Cl_2$—Ph | H | O | H | $CH_2CH_2CH_2$ | ethoxy | [$CDCl_3$] 1.25 (t, 3H); 1.72 (s, 3H); 1.78 (m, 2H); 3.16 (d, 1H); 3.34 (m, 1H); 3.38-3.55 (m, 5H); 3.77 (d, 1H); 7.38 (s br, 1H); 7.40 (s, 1H); 7.52 (s, 2H). |
| 6.682 | 3,5-$Cl_2$—Ph | H | O | H | $CH_2CH_2CH_2$ | ethoxycarbonyl | [$CDCl_3$] 1.24 (t, 3H); 1.71 (s, 3H); 1.85 (q, 2H); 2.31 (t, 2H); 3.18 (d, 1H); 3.20-3.40 (m, 2H); 3.78 (d, 1H); 4.12 (q, 2H); 6.93 (br, 1H); 7.41 (m, 1H); 7.51 (m, 2H). |
| 6.683 | 3-Cl—Ph | H | O | H | $CH_2CH_2CH_2$ | ethoxycarbonyl | [$CDCl_3$] 7.65 3.29; 7.65 3.22; 7.50 1.82; 7.50 1.77; 7.48 2.34; 7.48 2.24; 7.41 1.15; 7.41 1.14; 7.39 2.41; 7.39 2.23; 7.36 2.21; 7.36 2.05; 7.34 2.55; 7.32 0.90; 7.32 0.84; 7.26 10.87; 7.26 10.34; 6.95 0.96; 4.15 1.39; 4.15 1.28; 4.13 4.24; 4.13 3.85; 4.12 4.30; 4.11 3.83; 4.10 1.45; 4.09 1.29; 3.82 2.60; 3.81 2.36; 3.77 2.98; 3.77 2.71; 3.38 0.68; 3.36 1.15; 3.35 1.53; 3.33 1.28; 3.31 0.47; 3.29 0.44; 3.28 1.27; 3.26 1.47; 3.24 1.10; 3.22 3.06; 3.21 0.39; 3.18 2.53; 3.17 2.31; 2.34 2.56; 2.32 |

TABLE 6-continued

Compounds of the general formula (I) according to the invention in which $R^2$ is hydrogen and $R^3$ is methyl and aryl is the radical

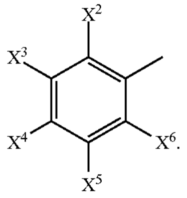

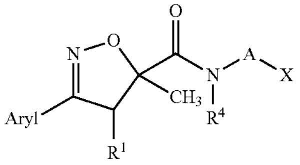

| No. | Aryl | $R^1$ | Y | $R^4$ | A | X | Physical data |
|---|---|---|---|---|---|---|---|
| | | | | | | | 5.35; 2.30 2.85; 1.89 0.75; 1.87 2.72; 1.85 3.84; 1.84 2.45; 1.82 0.61; 1.72 16.00; 1.72 14.45; 1.59 2.30; 1.26 4.62; 1.26 4.34; 1.24 9.01; 1.24 8.29; 1.23 0.42; 1.22 4.44; 1.22 4.04; 0.00 4.90; 0.00 4.72 |
| 6.684 | 3-F—Ph | H | O | H | $CH_2CH_2CH_2$ | ethoxycarbonyl | [$CDCl_3$] 7.40 0.70; 7.39 1.00; 7.39 1.83; 7.38 2.19; 7.37 4.46; 7.36 3.94; 7.36 0.36; 7.26 8.96; 7.15 0.44; 7.15 0.70; 7.14 0.44; 7.14 0.40; 7.13 0.57; 7.13 0.64; 7.12 0.81; 7.12 0.49; 7.11 0.48; 7.10 0.36; 6.96 0.47; 4.15 1.44; 4.13 4.48; 4.12 4.55; 4.10 1.51; 3.82 2.78; 3.78 3.18; 3.38 0.52; 3.37 0.92; 3.35 1.20; 3.33 1.00; 3.32 0.42; 3.30 0.40; 3.28 0.54; 3.28 0.92; 3.26 1.02; 3.25 0.71; 3.23 3.25; 3.18 2.60; 2.34 2.04; 2.32 4.72; 2.30 2.62; 1.89 0.62; 1.87 2.38; 1.85 3.40; 1.84 2.10; 1.82 0.51; 1.72 16.00; 1.59 2.07; 1.26 5.26; 1.24 10.53; 1.22 5.11; 0.00 3.86 |
| 6.685 | 3,5-$Cl_2$—Ph | H | O | H | $CH_2CH_2CH_2$ | hydroxy | [$CDCl_3$] 1.71 (m, 2H); 1.73 (s, 3H); 3.19 (d, 1H); 3.40 (m, 1H); 3.49 (m, 1H); 3.60 (t, 2H); 3.77 (d, 1H); 7.12 (m, 1H); 7.42 (m, 1H); 7.52 (m, 2H). |
| 6.686 | 3,5-$F_2$—Ph | H | O | H | $CH_2CH_2CH_2$ | hydroxy | [DMSO-$D_6$] 8.09 0.55; 8.08 1.02; 8.07 0.56; 7.40 2.99; 7.40 1.40; 7.39 1.73; 7.39 2.93; 7.38 2.22; 7.37 1.03; 7.37 0.68; 5.75 0.55; 4.43 0.51; 3.75 2.34; 3.71 2.90; 3.40 1.03; 3.38 3.95; 3.37 1.38; 3.33 3.35; 3.32 58.08; 3.20 0.35; 3.18 0.75; 3.17 1.26; 3.16 0.62; 3.15 1.19; 3.14 1.13; 3.13 0.62; 3.13 1.26; 3.11 0.72; 3.09 0.34; 2.52 0.54; 2.52 0.85; 2.51 14.13; 2.51 30.50; 2.50 41.64; 2.50 29.48; 2.49 13.49; 1.60 0.60; 1.58 1.95; 1.56 3.20; 1.55 16.00; 1.53 0.63; 0.00 5.94 |
| 6.687 | 3,5-$Cl_2$—Ph | H | O | H | $CH_2CH_2CH_2$ | methoxy | [$CDCl_3$] 1.71 (t, 3H); 1.75-1.81 (m, 2H); 3.16 (d, 1H); 3.25-3.47 (m, 4H); 3.77 (d, 1H); 7.41 (m, 1H); 7.51 (m, 2H). |
| 6.688 | 3,5-$F_2$—Ph | H | O | H | $CH_2CH_2CH_2$ | methoxycarbonyl | [$CDCl_3$] 1.73 (s, 3H); 1.86 (m, 2H); 2.34 (t, 2H); 3.18 (d, 1H); 3.30 (m, 2H); 3.68 (s, 3H); 3.77 (d, 1H); 6.8 (m, 1H); 6.92 (m, 1H); 7.15 (m, 2H) |

TABLE 6-continued

Compounds of the general formula (I) according to the invention in which $R^2$ is hydrogen and $R^3$ is methyl and aryl is the radical

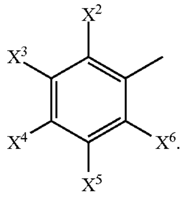

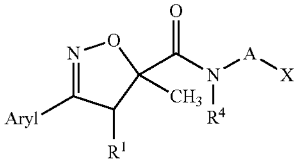

| No. | Aryl | $R^1$ | Y | $R^4$ | A | X | Physical data |
|---|---|---|---|---|---|---|---|
| 6.689 | 3-Br-5-Cl—Ph | H | O | H | $CH_2CH_2CH_2$ | methoxycarbonyl | [$CDCl_3$] 1.71 (s, 3H); 1.85 (quin, 2H); 2.33 (t, 2H); 3.17 (d, 1H); 3.20-3.39 (m, 2H); 3.67 (s, 3H); 3.76 (d, 1H); 6.91 (br, 1H); 7.56 (s, 2H); 7.67 (s, 1H). |
| 6.690 | 3-Cl-5-MeO—Ph | H | O | H | $CH_2CH_2CH_2$ | methoxycarbonyl | |
| 6.691 | 3-Cl—Ph | H | O | H | $CH_2CH_2CH_2$ | methoxycarbonyl | [$CDCl_3$] 7.65 2.35; 7.64 1.40; 7.50 1.05; 7.50 1.29; 7.50 0.69; 7.49 1.36; 7.48 1.66; 7.48 0.88; 7.41 0.70; 7.41 0.83; 7.41 0.68; 7.41 0.52; 7.39 1.46; 7.39 1.61; 7.39 1.47; 7.39 0.91; 7.36 1.92; 7.34 2.19; 7.32 0.81; 7.26 11.92; 6.95 0.59; 5.30 0.57; 3.81 2.36; 3.77 2.73; 3.68 0.64; 3.67 16.00; 3.38 0.51; 3.37 0.96; 3.35 1.18; 3.33 1.09; 3.31 0.40; 3.30 0.38; 3.28 0.86; 3.28 0.86; 3.26 1.15; 3.25 0.84; 3.23 0.61; 3.22 2.61; 3.18 2.25; 2.36 2.13; 2.34 4.51; 2.32 2.41; 1.89 0.64; 1.88 2.36; 1.86 3.31; 1.84 2.07; 1.82 0.50; 1.73 0.84; 1.72 14.07; 1.58 2.68; 0.00 3.20; 0.00 5.06 |
| 6.692 | 3-F—Ph | H | O | H | $CH_2CH_2CH_2$ | methoxycarbonyl | [$CDCl_3$] 7.40 0.61; 7.39 0.97; 7.39 1.46; 7.38 1.80; 7.37 3.71; 7.36 3.82; 7.26 9.34; 7.15 0.37; 7.15 0.58; 7.14 0.37; 7.14 0.35; 7.13 0.48; 7.13 0.55; 7.12 0.75; 7.12 0.45; 7.11 0.43; 6.95 0.41; 3.82 2.36; 3.77 2.70; 3.67 16.00; 3.38 0.46; 3.37 0.81; 3.35 1.07; 3.33 0.89; 3.32 0.38; 3.30 0.36; 3.28 0.81; 3.26 0.90; 3.25 0.64; 3.23 2.80; 3.18 2.23; 2.36 1.79; 2.34 4.10; 2.32 2.24; 1.89 0.56; 1.88 2.14; 1.86 3.03; 1.84 1.88; 1.82 0.46; 1.72 13.77; 1.58 2.85; 0.00 3.47 |
| 6.693 | Ph | H | O | H | $CH_2CH_2CH_2$ | methoxycarbonyl | |
| 6.694 | 3,5-$F_2$—Ph | H | O | H | $CH_2CH_2CH_2$ | methylcarbamoyl | [$CDCl_3$] 1.74 (s, 3H); 1.86 (pent, 2H); 2.17 (t, 2H); 2.81 (d, 3H); 3.18 (d, 1H); 3.27 (m, 1H); 3.36 (m, 1H); 3.75 (d, 1H); 6.00 (s br, 1H); 6.89 (m, 1H); 7.07 (s br, 1H); 7.16 (m, 2H). |
| 6.695 | 3,5-$Cl_2$—Ph | H | O | H | $CH_2CH_2CH_2$ | morpholin-4-yl | |
| 6.696 | 3,5-$Cl_2$—Ph | H | O | H | $(CH_2)_6$ | methoxycarbonyl | [$CDCl_3$] 1.32 (m, 2H); 1.62 (m, 4H); 1.71 (s, 3H); 2.29 (t, 2H); 3.18 (d, 1H); 3.18-3.34 (m, 2H); 3.65 (s, 3H); 3.79 (d, 1H); 6.69 (br, 1H); 7.41 (m, 1H); 7.51 (m, 2H). |

TABLE 6-continued

Compounds of the general formula (I) according to the invention in which $R^2$ is hydrogen and $R^3$ is methyl and aryl is the radical

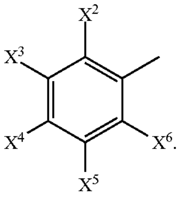

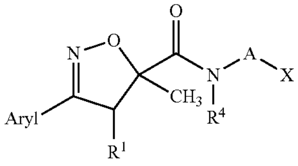

| No. | Aryl | $R^1$ | Y | $R^4$ | A | X | Physical data |
|---|---|---|---|---|---|---|---|
| 6.697 | 3,5-$Cl_2$—Ph | H | O | H | bond | 1-(methoxy-carbonyl)-3-(2-methoxyethoxy)-cyclohexyl | |
| 6.698 | 3,5-$F_2$—Ph | H | O | H | bond | 1-(methoxy-carbonyl)-3-(2-methoxyethoxy)-cyclohexyl | |
| 6.699 | 3,5-$F_2$—Ph | H | O | H | bond | 1-(methoxy-carbonyl)cyclohexyl | |
| 6.700 | 3,5-$Cl_2$—Ph | H | O | H | bond | 1-(methoxy-carbonyl)cyclohexyl | |
| 6.701 | 3,5-$F_2$—Ph | H | O | H | bond | 1-(trifluoromethyl)-cyclohexyl | |
| 6.702 | 3,5-$F_2$—Ph | H | O | H | bond | 1-(trifluoromethyl)-cyclopentyl | |
| 6.703 | 3,5-$F_2$—Ph | H | O | H | bond | 1,5-dimethoxy-1,5-dioxopentan-3-yl | |
| 6.704 | 3-F—Ph | H | O | H | bond | 1-cyano-1-cyclopropylethyl | |
| 6.705 | 3,5-$Cl_2$—Ph | H | O | H | bond | 1-cyano-1-cyclopropylethyl | |
| 6.706 | 3-F—Ph | H | O | H | bond | 1-cyanocyclopropyl | |
| 6.707 | 3,5-$F_2$—Ph | H | O | H | bond | 1-cyclopropylethoxy | |
| 6.708 | 3,5-$F_2$—Ph | H | O | H | bond | 1-ethoxy-3-methyl-1-oxopentan-2-yl | |
| 6.709 | 3,5-$F_2$—Ph | H | O | H | bond | 1-ethoxy-3-methyl-1-oxopentan-2-yl | |
| 6.710 | 3,5-$F_2$—Ph | H | O | H | bond | 1-methylcyclopropyl | [$CDCl_3$] 0.65 (m, 2H); 0.73 (m, 2H); 1.36 (s, 3H); 1.68 (s, 3H); 3.15 (d, 1H); 3.75 (d, 1H); 6.88 (m, 1H); 7.02 (s br, 1H); 7.16 (m, 2H). |
| 6.711 | 3-F—Ph | H | O | H | bond | 1-methylcyclopropyl | |
| 6.712 | 3,5-$F_2$—Ph | H | O | H | bond | 1-methylpiperidin-4-yl | [$CDCl_3$] 1.71 (s, 3H); 1.94-2.23 (m,, 4H); 2.79 (m, 2H); 2.30 (s, 3H); 3.18 (d, 1H); 3.66 (m, 1H); 3.73 (d, 1H); 3.92 (m, 2H); 6.89 (m, 1H); 6.91 (s br, 1H); 7.15 (m, 2H). |
| 6.713 | 3,5-$F_2$—Ph | H | O | H | bond | 2-(ethoxy-carbonyl)cyclohexyl | |
| 6.714 | 3,5-$Cl_2$—Ph | H | O | H | bond | 2-(ethoxy-carbonyl)cyclohexyl | |
| 6.715 | 3,5-$F_2$—Ph | H | O | H | bond | 2-(ethoxy-carbonyl)cyclo-pentyl | |
| 6.716 | 3,5-$Cl_2$—Ph | H | O | H | bond | 2-(ethoxy-carbonyl)cyclo-pentyl | |
| 6.717 | 3,5-$F_2$—Ph | H | O | H | bond | 2-(trifluoromethyl)-cyclopropyl | [$CDCl_3$] 1.09 (m, 1H); 1.29 (m, 1H); 1.72 (s, 3H); 1.75 (m, 1H); 3.06 (m, 1H); 3.19 (d, 1H); 3.78 (dd, 1H); 6.90 (m, 2H); 7.15 (m, 2H) |

TABLE 6-continued

Compounds of the general formula (I) according to the invention in which $R^2$ is hydrogen and $R^3$ is methyl and aryl is the radical

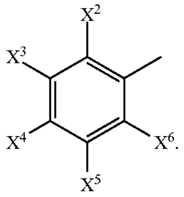

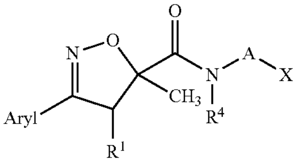

| No. | Aryl | $R^1$ | Y | $R^4$ | A | X | Physical data |
|---|---|---|---|---|---|---|---|
| 6.718 | 3,5-$Cl_2$—Ph | H | O | H | bond | 2-(trifluoromethyl)-cyclopropyl | [$CDCl_3$] 1.08 (m, 1H); 1.29 (m, 1H); 1.69 (s, 3H); 1.72 (m, 1H); 3.06 (m, 1H); 3.18 (d, 1H); 3.78 (dd, 1H); 6.89 (br,s, 1H); 7.42 (m, 1H); 7.50 (m, 2H) |
| 6.719 | 3-F—Ph | H | O | H | bond | 2-(trifluoromethyl)-cyclopropyl | |
| 6.720 | 3,5-$F_2$—Ph | H | O | H | bond | 2,2,2-trifluoro-1-(tetrahydrofuran-2-yl)ethyl | |
| 6.721 | 3,5-$Cl_2$—Ph | H | O | H | bond | 2,2,2-trifluoro-1-(tetrahydrofuran-2-yl)ethyl | |
| 6.722 | 3-F—Ph | H | O | H | bond | 2,2,2-trifluoro-1-(tetrahydrofuran-2-yl)ethyl | |
| 6.723 | 3,5-$F_2$—Ph | H | O | H | bond | 2-allylcyclopentyl | |
| 6.724 | 3,5-$F_2$—Ph | H | O | H | bond | 2-allylcyclopentyl | |
| 6.725 | 3,5-$F_2$—Ph | H | O | H | bond | 2-chlorocyclopentyl | |
| 6.726 | 3,5-$F_2$—Ph | H | O | H | bond | 2-chlorocyclopentyl | |
| 6.727 | 3,5-$Cl_2$—Ph | H | O | H | bond | 2-cyanobutan-2-yl | |
| 6.728 | 3,5-$F_2$—Ph | H | O | H | bond | 2-cyanobutan-2-yl | |
| 6.729 | 3-F—Ph | H | O | H | bond | 2-cyanobutan-2-yl | |
| 6.730 | 3,5-$Cl_2$—Ph | H | O | H | bond | 2-cyanopentan-2-yl | |
| 6.731 | 3-F—Ph | H | O | H | bond | 2-cyanopentan-2-yl | |
| 6.732 | 3,5-$F_2$—Ph | H | O | H | bond | 2-fluorocyclopropyl | |
| 6.733 | 3-F—Ph | H | O | H | bond | 2-fluorocyclopropyl | |
| 6.734 | 3,5-$Cl_2$—Ph | H | O | H | bond | 2-fluorocyclopropyl | |
| 6.735 | 3,5-$F_2$—Ph | H | O | H | bond | 2-oxotetrahydrofuran-3-yl | |
| 6.736 | 3,5-$F_2$—Ph | H | O | H | bond | 3-(ethoxy-carbonyl)cyclo-pentyl | |
| 6.737 | 3,5-$Cl_2$—Ph | H | O | H | bond | 3-(ethoxy-carbonyl)cyclo-pentyl | [DMSO-$D_6$] D1 1.16 (t, 3H), 1.53 (s, 3H), 1.53-1.85 (m, 5H), 2.05 (m, 1H), 2.79 (m, 1H), 3.36 (d, 1H), 3.75 (d, 1H), 4.05 (m, 3H), 7.70 (c, 2H), 7.74 (s, 1H), 8.00 (d, 1H). D2 1.19 (t, 3H), 1.53 (s, 3H), 1.53-1.85 (m, 5H), 2.09 (m, 1H), 2.79 (m, 1H), 3.36 (d, 1H), 3.75 (d, 1H), 4.05 (m, 3H), 7.70 (c, 2H), 7.74 (s, 1H), 8.00 (d, 1H). |
| 6.738 | 3,5-$F_2$—Ph | H | O | H | bond | 3-(methoxy-carbonyl)cyclohexyl | |
| 6.739 | 3,5-$Cl_2$—Ph | H | O | H | bond | 3-(methoxy-carbonyl)cyclohexyl | |
| 6.740 | 3,5-$Cl_2$—Ph | H | O | H | bond | 3-(methoxy-carbonyl)cyclohexyl | [DMSO-$D_6$) D1 1.25 (m, 4H), 1.52 (s, 3H), 1.77 (m, 4H), 2.89 (m, 1H), 3.36 (d, 1H), 3.55 (s, 3H), 3.61 (m, 1H), 3.75 (d, 1H), 7.69 (m, 2H), 7.73 (m, 1H), 7.90 (d, 1H). D2 1.25 (m, 4H), 1.53 (s, 3H), 1.77 (m, 4H), 2.89 (m, 1H), 3.35 (d, 1H), 3.59 (s, 3H), 3.61 (m, 1H), 3.76 (d, |

TABLE 6-continued

Compounds of the general formula (I) according to the invention in which $R^2$ is hydrogen and $R^3$ is methyl and aryl is the radical

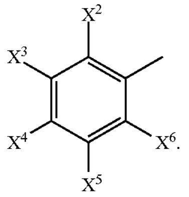

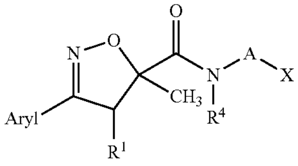

| No. | Aryl | $R^1$ | Y | $R^4$ | A | X | Physical data |
|---|---|---|---|---|---|---|---|
| | | | | | | | 1H), 7.69 (m, 2H), 7.73 (m, 1H), 7.92 (d, 1H). |
| 6.741 | 3,5-$F_2$—Ph | H | O | H | bond | 3-(methoxy-carbonyl)cyclohexyl | |
| 6.742 | 3,5-$F_2$—Ph | H | O | H | bond | 3-(methoxy-carbonyl)tetrahydro-2H-pyran-3-yl | |
| 6.743 | 3,5-$F_2$—Ph | H | O | H | bond | 3,5-dimethyl-1,2-oxazol-4-yl | [$CDCl_3$] 1.84 (s, 3H); 2.15 (s, 3H); 2.30 (s, 3H); 3.28 (d, 1H); 3.84 (d, 1H); 6.92 (m, 1H); 7.18 (m, 2H); 7.85 (s br, 1H). |
| 6.744 | 3,5-$F_2$—Ph | H | O | H | bond | 3-cyanotetrahydro-2H-pyran-3-yl | |
| 6.745 | 3,5-$F_2$—Ph | H | O | H | bond | 4-(ethoxy-carbonyl)cyclohexyl | |
| 6.746 | 3,5-$Cl_2$—Ph | H | O | H | bond | 4-(ethoxy-carbonyl)cyclohexyl | |
| 6.747 | 3,5-$Cl_2$—Ph | H | O | H | bond | 4-(methoxy-carbonyl)cyclohexyl | |
| 6.748 | 3,5-$F_2$—Ph | H | O | H | bond | 4-(methoxy-carbonyl)cyclohexyl | |
| 6.749 | 3,5-$F_2$—Ph | H | O | H | bond | 4-cyanotetrahydro-2H-pyran-4-yl | |
| 6.750 | 3,5-$Cl_2$—Ph | H | O | H | bond | 4-ethoxy-1-(methoxy-carbonyl)cyclohexyl | |
| 6.751 | 3,5-$F_2$—Ph | H | O | H | bond | 4-ethoxy-1-(methoxy-carbonyl)cyclohexyl | |
| 6.752 | 3,5-$F_2$—Ph | H | O | H | bond | Bicyclo[4.1.0]hept-7-yl | |
| 6.753 | 3,5-$F_2$—Ph | H | O | H | bond | Bicyclo[4.1.0]hept-7-yl | |
| 6.754 | 3-F—Ph | H | O | H | bond | Bicyclo[4.1.0]hept-7-yl | |
| 6.755 | 3,5-$F_2$—Ph | H | O | $CH_3$ | bond | CH3 | |
| 6.756 | 4-F—Ph | H | O | H | bond | CH3 | |
| 6.757 | 3,5-$F_2$—Ph | H | O | H | bond | cyanogen | [DMSO-$D_6$] 1.51 (s, 3H); 3.24 (d, 1H); 3.85 (d, 1H); 6.20 (s br, 1H); 7.37 (m, 3H). |
| 6.758 | 3,5-$F_2$—Ph | H | O | H | bond | cyclohexyl | |
| 6.759 | 3-(MeOCO)Ph | H | O | H | bond | c-Pr | |
| 6.760 | 2-F-5-MeO—Ph | H | O | H | bond | c-Pr | |
| 6.761 | 4-F-3,5-$Me_2$—Ph | H | O | H | bond | c-Pr | |
| 6.762 | 3-Cl-2-F-5-$CF_3$—Ph | H | O | H | bond | c-Pr | |
| 6.763 | 3-($F_2$—MeO)Ph | H | O | H | bond | c-Pr | |
| 6.764 | 3-Br-5-Me—Ph | H | O | H | bond | c-Pr | [$CDCl_3$] 0.52 (m, 2H); 0.78 (m, 2H); 1.69 (s, 3H); 2.35 (s, 3H); 2.73 (m, 1H); 3.18 (d, 1H); 3.79 (d, 1H); 6.84 (s br, 1H); 7.35 (s, 1H); 7.38 (s, 1H); 7.59 (s, 1H). |

TABLE 6-continued

Compounds of the general formula (I) according to the invention in which $R^2$ is hydrogen and $R^3$ is methyl and aryl is the radical

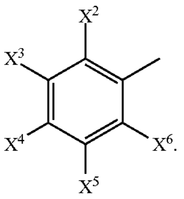

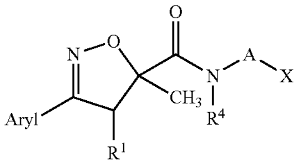

| No. | Aryl | $R^1$ | Y | $R^4$ | A | X | Physical data |
|---|---|---|---|---|---|---|---|
| 6.765 | 5-Br-2-F—Ph | H | O | H | bond | c-Pr | |
| 6.766 | 3-$SF_5$—Ph | H | O | H | bond | c-Pr | |
| 6.767 | 3,5-$I_2$—Ph | H | O | H | bond | c-Pr | |
| 6.768 | 3-COOH—Ph | H | O | H | bond | c-Pr | |
| 6.769 | 3-I—Ph | H | O | H | bond | c-Pr | |
| 6.770 | 3,5-$CN_2$Ph | H | O | H | bond | c-Pr | |
| 6.771 | 3-CN-5-$CF_3$—Ph | H | O | H | bond | c-Pr | |
| 6.772 | 3-F-5-vinylPh | H | O | H | bond | c-Pr | |
| 6.773 | 3-vinylPh | H | O | H | bond | c-Pr | [$CDCl_3$] 0.59 (m, 2H); 0.77 (m, 2H); 1.71 (s, 3H); 2.73 (m, 1H); 3.24 (d, 1H); 3.86 (d, 1H); 5.31 (d, 1H); 5.79 (d, 1H); 6.71 (dd, 1H); 6.91 (s br, 1H); 7.37 (m, 1H); 7.50 (m, 2H); 7.61 (s, 1H). |
| 6.774 | 3-Br-5-CN—Ph | H | O | H | bond | c-Pr | [$CDCl_3$] 0.52 (m, 2H); 0.80 (m, 2H); 1.72 (s, 3H); 2.73 (m, 1H); 3.17 (d, 1H); 3.82 (d, 1H); 6.78 (br, s, 1H); 7.84 (m, 2H); 7.99 (m, 1H). |
| 6.775 | 3-ethynyl-Ph | H | O | H | bond | c-Pr | |
| 6.776 | 3-CN-5-Me—Ph | H | O | H | bond | c-Pr | |
| 6.777 | 3,4-$F_2$—Ph | H | O | H | bond | c-Pr | |
| 6.778 | 3,5-$F_2$—Ph | $CH_2CH_3$ | O | H | bond | c-Pr | |
| 6.779 | 3,5-$F_2$—Ph | H | O | H | bond | ethoxy | [$CDCl_3$] 1.28 (t, 3H); 1.76 (s, 3H); 3.21 (d, 1H); 3.81 (d, 1H); 3.98 (q, 2H); 6.89 (m, 1H); 7.16 (m, 2H); 9.15 (s, 1H). |
| 6.780 | 3,5-$F_2$—Ph | H | O | H | bond | methoxy | |
| 6.781 | 3,5-$F_2$—Ph | H | O | H | bond | tetrahydro-2H-pyran-3-yl | |
| 6.782 | 3,5-$F_2$—Ph | H | O | H | bond | tetrahydro-2H-pyran-3-yl | |
| 6.783 | 3,5-$F_2$—Ph | H | O | H | bond | tetrahydro-2H-pyran-4-yl | |
| 6.784 | 3,5-$F_2$—Ph | H | O | H | bond | tetrahydrofuran-3-yl | [$CDCl_3$] D1 and D2 1.72 (s, 3H); 1.70-1.89 (m, 2H); 2.20-2.36 (m, 2H); 3.18 (d, 1H); 3.60 (dd, 0.5H); 3.68 (dd, 0.5H); 3.78 (m, 1H); 3.75-3.90 (m, 2H); 3.93 (m, 1H); 4.46 (m, 1H); 6.88 (m, 1H); 6.93 (s br, 1H); 7.15 (m, 2H). |
| 6.785 | 3,5-$F_2$—Ph | H | O | H | $CH_2$ | (E)-(isobutoxyimino)-methyl | [$CDCl_3$] D1 plus D2 0.90 (m, 3H) 1.12 (m, 3H); 1.50 (m, 0.4H); 1.65 (m, 0.6H); 1.74 (s, 3H); 3.20 (d, 1H); 3.78 (d, 1H); 4.02 (m, 1H); 4.13 (m, 2H); 6.65 (t, 0.4H); 6.88 (m, 1H); 7.15 (m, 2H); 7.21 (s br, 1H); 7.35 (t, 0.6H). |
| 6.786 | 3,5-$F_2$—Ph | H | O | H | $CH_2$ | (E)-(isopropoxyimino)-methyl | |

TABLE 6-continued

Compounds of the general formula (I) according to the invention in which $R^2$ is hydrogen and $R^3$ is methyl and aryl is the radical

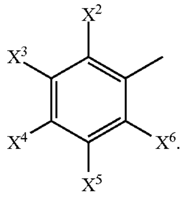

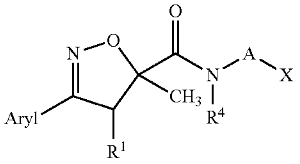

| No. | Aryl | $R^1$ | Y | $R^4$ | A | X | Physical data |
|---|---|---|---|---|---|---|---|
| 6.787 | 3,5-$F_2$—Ph | H | O | H | $CH_2$ | (E)-(methoxyimino)-methyl | [$CDCl_3$] E Z Gemisch 1.74 (s, 3H); 3.20 (d, 1H); 3.78 (d, 1H); 3.83 (s, 2.1H); 3.90 (s, 0.9H); 3.92-4.18 (m, 2H); 6.64 (t, 0.3H); 6.89 (m, 1H); 7.15 (m, 2H); 7.20 (s br, 1H); 7.36 (t, 0.7H). |
| 6.788 | 3,5-$F_2$—Ph | H | O | H | $CH_2$ | (E)-(sec-butoxyimino)methyl | [$CDCl_3$] D1 plus D2 1.23 (m, 6H); 1.74 (s, 3H); 3.20 (d, 1H); 3.77 (d, 1H); 3.94-4.18 (m, 2H) 4.23-4.40 (m, 2H); 6.65 (t, 0.3H); 6.88 (m, 1H); 7.18 (m, 2H); 7.35 (t, 0.7H). |
| 6.789 | 3,5-$F_2$—Ph | H | O | H | $CH_2$ | (E)-[(cyclopentyloxy)-imino]methyl | |
| 6.790 | 3,5-$F_2$—Ph | H | O | H | $CH_2$ | (E)-[(prop-2-yn-1-yloxy)imino]methyl | [$CDCl_3$] isomer 1 1.74 (s, 3H); 2,48 (m, 1H); 3.20 (d, 1H); 3.77 (d, 1H); 4.05 (m, 2H); 4.62 (s, 2H); 6.91 (m, 1H); 7.16 (m, 3H); 7.43 (t, 1H). isomer 2 1.74 (s, 3H); 2.48 (m, 1H); 3.20 (d, 1H); 3.77 (d, 1H); 4.14 (m, 2H); 4.69 (s, 2H); 6.76 (t, 1H); 6.91 (m, 1H); 7.16 (m, 3H). |
| 6.791 | 3,5-$F_2$—Ph | H | O | H | $CH_2$ | (ethylsulfamoyl)-methyl | |
| 6.792 | 3-F—Ph | H | O | H | $CH_2$ | (ethylsulfanyl)-methyl | |
| 6.793 | 3,5-$Cl_2$—Ph | H | O | H | $CH_2$ | (ethylsulfanyl)-methyl | |
| 6.794 | 3,5-$F_2$—Ph | H | O | H | $CH_2$ | (ethylsulfanyl)-methyl | |
| 6.795 | 3,5-$F_2$—Ph | H | O | H | $CH_2$ | (hydroxyimino)-methyl | [$CDCl_3$] isomer 1 1.75 (s, 3H); 3.20 (d, 1H); 3.78 (d, 1H); 3.95-4.20 (m, 2H); 6.89 (m, 1H); 7.16 (m, 2H); 7.19 (s br, 1H); 7.45 (t, 1H). isomer 2 1.75 (s, 3H); 3.20 (d, 1H); 3.77 (d, 1H); 4.18 (m, 2H); 6.74 (t, 1H); 6.89 (m, 1H); 7.16 (m, 2H); 7.23 (s br, 1H). |
| 6.796 | 3,5-$F_2$—Ph | H | O | H | $CH_2$ | (isobutyrylamino)-methyl | |
| 6.797 | 3,5-$F_2$—Ph | H | O | H | $CH_2$ | [(chloroacetyl)-amino]methyl | |
| 6.798 | 3,5-$F_2$—Ph | H | O | H | $CH_2$ | [(cyclopropyl-carbamoyl)amino]-methyl | [$CDCl_3$] 0.53 (m, 2H); 0.71 (m, 2H); 1.72 (s, 3H); 2.37 (m, 1H); 3.17 (d, 1H); 3.42 (m, 4H); 3.77 (d, 1H); 4.96 (s br, 1H); 5.40 (s br 1H); 6.88 (m, 1H); 7.15 (m, 2H); 7.41 (s br, 1H). |
| 6.799 | 3,5-$F_2$—Ph | H | O | H | $CH_2$ | [(cyclopropyl-carbonyl)amino]-methyl | [$CDCl_3$] 0.70 (m, 2H); 0.93 (m, 2H); 1.33 (m, 1H); 1.72 (s, 1H); 3.18 (d, 1H); 3.41 (m, 4H); 3.76 (d, 1H); 6.05 (s br, 1H); 6.89 (m, 1H); 7.17 (m, 2H); 7.24 (s br, 1H). |

TABLE 6-continued

Compounds of the general formula (I) according to the invention in which $R^2$ is hydrogen and $R^3$ is methyl and aryl is the radical

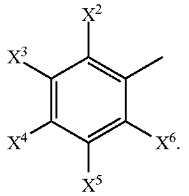

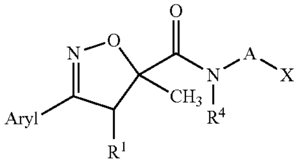

| No. | Aryl | $R^1$ | Y | $R^4$ | A | X | Physical data |
|---|---|---|---|---|---|---|---|
| 6.800 | 3,5-$F_2$—Ph | H | O | H | $CH_2$ | [(ethoxy-carbonyl)amino]-methyl | [$CDCl_3$] 1.20 (t, 3H); 1.72 (s, 3H); 3.18 (d, 1H); 3.25-3.48 (m, 4H); 3.78 (d, 1H); 4.05 (q, 2H); 4.95 (s br, 1H); 6.88 (m, 1H); 7.15 (m, 2H); 7.4 (s br, 1H). |
| 6.801 | 3,5-$F_2$—Ph | H | O | H | $CH_2$ | [(ethylcarbamoyl)-amino]methyl | |
| 6.802 | 3,5-$F_2$—Ph | H | O | H | $CH_2$ | [(methylsulfonyl)-amino]methyl | [$CDCl_3$] 1.73 (s, 3H); 3.22 (d, 1H); 3.48 (m, 2H); 3.55 (m, 2H); 3.75 (d, 1H); 6.88 (t, 1H); 7.16 (m, 2H); 7.29 (s br, 1H); 7.53 (s br, 1H). |
| 6.803 | 3,5-$F_2$—Ph | H | O | H | $CH_2$ | [(pyrrolidin-1-ylcarbonyl)amino]-methyl | |
| 6.804 | 3,5-$F_2$—Ph | H | O | H | $CH_2$ | [(tert-butoxy-carbonyl)amino]-methyl | [$CDCl_3$] 1.42 (s, 9H); 1.72 (s, 3H); 3.18 (d, 1H); 2.29 (m, 2H); 3.33 (m, 1H); 3.42 (m, 1H); 3.78 (d, 1H); 4.78 (s br, 1H); 6.88 (m, 1H); 7.15 (m, 2H); 7.22 (s br, 1H). |
| 6.805 | 3,5-$F_2$—Ph | H | O | H | $CH_2$ | [(trifluoroacetyl)-amino]methyl | [$CDCl_3$] 1.73 (s, 3H); 3.21 (d, 1H); 3.52 (m, 4H); 3.74 (d, 1H); 6.88 (m, 1H); 7.14 (m, 2H); 7.32 (s br, 1H); 7.59 (s br, 1H). |
| 6.806 | 3,5-$F_2$—Ph | H | O | H | $CH_2$ | [methyl(methyl-sulfonyl)amino]-methyl | [$CDCl_3$] 1.73 (s, 3H); 2.89 (s, 3H); 3.14 (d, 1H); 3.27 (m, 2H); 3.46 (m, 2H); 3.80 (d, 1H); 6.87 (m, 1H); 7.15 (m, 3H). |
| 6.807 | 3,5-$F_2$—Ph | H | O | H | $CH_2$ | {[(2,2,2-trifluoroethyl)-carbamoyl]amino}-methyl | [$CDCl_3$] 1.72 (s, 3H); 3.18 (d, 1H); 3.32-3.48 (m, 2H); 3.74 (d, 1H); 3.78-3.92 (m, 4H); 5.08 (s br, 2H); 6.88 (m, 1H); 7.16 (m, 2H). |
| 6.808 | 3,5-$F_2$—Ph | H | O | H | $CH_2$ | {[trifluoromethyl)-sulfonyl]amino}-methyl | [$CDCl_3$] 1.73 (s, 3H); 3.22 (d, 1H); 3.48 (m, 2H); 3.55 (m, 2H); 3.75 (d, 1H); 6.88 (t, 1H); 7.16 (m, 2H); 7.29 (s br, 1H); 7.53 (s br, 1H). |
| 6.809 | 3,5-$F_2$—Ph | H | O | H | $CH_2$ | 1,3-dioxolan-2-yl | [$CDCl_3$] 1.74 (s, 3H); 3.18 (d, 1H); 3.51 (mc, 2H); 3.78 (d, 1H); 3.85-4.01(m, 4H); 4.97 (m, 1H); 6.87 (m, 1H); 7.02 (t br, 1H); 7.15 (m, 2H). |
| 6.810 | 3,5-$F_2$—Ph | H | O | H | $CH_2$ | 2-(pyrrolidin-1-yl)propan-2-yl | |
| 6.811 | 3,5-$Cl_2$—Ph | H | O | H | $CH_2$ | 2-(pyrrolidin-1-yl)propan-2-yl | |
| 6.812 | 3-($F_2$—MeO)Ph | H | O | H | $CH_2$ | 2-chloropyridin-4-yl | |
| 6.813 | 3-F-5-vinylPh | H | O | H | $CH_2$ | 2-chloropyridin-4-yl | |
| 6.814 | 3,5-$F_2$—Ph | H | O | H | $CH_2$ | 3-chloroprop-1-yn-1-yl | [$CDCl_3$] 1.74 (s, 3H); 3.20 (d, 1H); 3.77 (d, 1H); 4.04-4.20 (m, 4H); 6.89 (m, 1H); 6.98 (s, 1H); 7.16 (m, 2H). |
| 6.815 | 3,5-$F_2$—Ph | H | O | H | $CH_2$ | 3-methoxyprop-1-yn-1-yl | [$CDCl_3$] 1.73 (s, 3H); 3.19 (d, 1H); 3.36 (s, 3H); 3.77 (d, 1H); 4.03-4.18 (m, 4H); 6.89 (m, 1H); 6.91 (s br, 1H); 7.16 (m, 2H). |
| 6.816 | 3,5-$F_2$—Ph | H | O | H | $CH_2$ | acetamidomethyl | |
| 6.817 | 5-Br-2-F—Ph | H | O | H | $CH_2$ | CF3 | |

TABLE 6-continued

Compounds of the general formula (I) according to the invention in which $R^2$ is hydrogen and $R^3$ is methyl and aryl is the radical

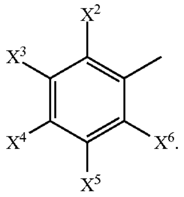

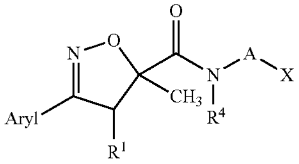

| No. | Aryl | $R^1$ | Y | $R^4$ | A | X | Physical data |
|---|---|---|---|---|---|---|---|
| 6.818 | 2-F-5-MeO—Ph | H | O | H | $CH_2$ | CF3 | |
| 6.819 | 4-F-3,5-Me2—Ph | H | O | H | $CH_2$ | CF3 | [$CDCl_3$] 1.73 (s, 3H); 2.27 (d, 6H); 3.24 (d, 1H); 3.78 (m, 1H); 3.79 (d, 1H); 4.02 (m, 1H); 7.21 (br, t, 1H); 7.29 (m, 2H). |
| 6.820 | 3-($F_2$—MeO)Ph | H | O | H | $CH_2$ | CF3 | |
| 6.821 | 3-$SF_5$—Ph | H | O | H | $CH_2$ | CF3 | |
| 6.822 | 3-(MeOCO)Ph | H | O | H | $CH_2$ | CF3 | [$CDCl_3$] 1.76 (s, 3H); 3.32 (d, 1H); 3.78 (m, 1H); 3.87 (d, 1H); 3.94 (s, 3H); 4.05 (m, 1H); 7.18 (t br, 1H); 7.51 (t, 1H); 7.89 (d, 1H); 8.10 (d, 1H); 8.23 (s, 1H). |
| 6.823 | 3-I—Ph | H | O | H | $CH_2$ | CF3 | |
| 6.824 | 3,5-$CN_2$Ph | H | O | H | $CH_2$ | CF3 | |
| 6.825 | 3-CN-5-$CF_3$—Ph | H | O | H | $CH_2$ | CF3 | |
| 6.826 | 3,5-$F_2$—Ph | H | O | H | $CH_2$ | difluoromethyl | [DMSO-$D_6$] 1.57 (s, 3H); 3.42 (d, 1H); 3.49 (m, 2H); 3.75 (d, 1H); 6.01 (tt, 1H); 7.40 (m, 2H); 8.47 (t br, 1H). |
| 6.827 | 3-F—Ph | H | O | H | $CH_2$ | difluoromethyl | [DMSO-$D_6$] 1.57 (s, 3H); 3.44 (d, 1H); 3.50 (m, 2H); 3.74 (d, 1H); 6.01 (tt, 1H); 7.33 (m, 1H); 7.52 (m, 3H); 8.46 (t br, 1H). |
| 6.828 | 3,5-$F_2$—Ph | H | O | H | $CH_2$ | dimethoxymethyl | |
| 6.829 | 3,5-$F_2$—Ph | H | O | H | $CH_2$ | Formamidomethyl | |
| 6.830 | 4-F—Ph | H | O | $CH_3$ | $CH_2$ | methoxycarbonyl | |
| 6.831 | 3,5-$F_2$—Ph | H | O | H | $CH_2$ | pentafluoroethyl | [DMSO-$D_6$] 1.58 (s, 3H); 3.44 (d, 1H); 3.75 (d, 1H); 3.93 (m, 2H); 7.41 (m, 3H); 8.76 (t, 1H). |
| 6.832 | 3-F—Ph | H | O | H | $CH_2$ | pentafluoroethyl | [DMSO-$D_6$] 1.58 (s, 1H); 3.45 (d, 1H); 3.73 (d, 1H); 3.93 (td, 2H); 7.32 (m, 1H); 7.52 (m, 3H); 8.75 (t br, 1H). |
| 6.833 | 3,5-$F_2$—Ph | H | O | H | $CH_2$ | prop-1-yn-1-yl | |
| 6.834 | 3,5-$F_2$—Ph | H | O | H | $CH_2$ | propan-2-yl | [$CDCl_3$] 0.90 (d, 3H); ; 0.91 (d, 3H); 1.74 (s, 3H); 1.78 (m, 1H); 3.03 (m, 1H); 3.14 (m, 1H); 3.18 (d, 1H); 3.79 (d, 1H); 6.88 (m, 1H); 7.16 (m, 2H). |
| 6.835 | 3,5-$F_2$—Ph | H | O | H | $CH(CH_3)$ | (E)-(hydroxyimino)-methyl | [$CDCl_3$] D1 1.32 (d, 3H); 1.73 (s, 3H); 3.18 (d, 1H); 3.77 (d, 1H); 4.63 (m, 1H); 6.89 (m, 1H); 7.16 (m, 2H); 7.28 (s br, 1H). D2 1.37 (d, 3H); 1.73 (s, 3H); 3.18 (d, 1H); 3.77 (d, 1H); 4.63 (m, 1H); 6.89 (m, 1H); 7.16 (m, 2H); 7.28 (s br, 1H). |
| 6.836 | 3,5-$F_2$—Ph | H | O | H | $CH(CH_3)$ | (E)-(isobutoxyimino)-methyl | |
| 6.837 | 3,5-$F_2$—Ph | H | O | H | $CH(CH_3)$ | (E)-(isopropoxyimino)-methyl | |

TABLE 6-continued

Compounds of the general formula (I) according to the invention in which $R^2$ is hydrogen and $R^3$ is methyl and aryl is the radical

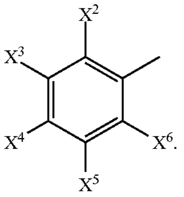

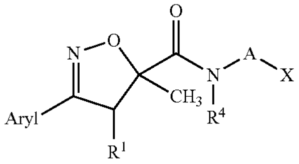

| No. | Aryl | $R^1$ | Y | $R^4$ | A | X | Physical data |
|---|---|---|---|---|---|---|---|
| 6.838 | 3,5-$F_2$—Ph | H | O | H | $CH(CH_3)$ | (E)-(methoxyimino)-methyl | [$CDCl_3$] D1 1.31 (d, 3H); 1.73 (s, 3H); 3.19 (d, 1H); 3.76 (d, 1H); 3.81 (s, 3H); 4.60 (m, 1H); 6.88 (m, 1H); 7.17 (m, 3H); 7.32 d, 1H). D2 1.36 (d, 3H); 1.73 (s, 3H); 3.19 (d, 1H); 3.78 (d, 1H); 3.85 (s, 3H); 4.60 (m, 1H); 6.88 (m, 1H); 7.17 (m, 3H); 7.37 (d, 1H). |
| 6.839 | 3,5-$F_2$—Ph | H | O | H | $CH(CH_3)$ | (E)-(sec-butoxyimino)methyl | |
| 6.840 | 3,5-$F_2$—Ph | H | O | H | $CH(CH_3)$ | (E)-[(cyclopentyloxy)-imino]methyl | |
| 6.841 | 3,5-$F_2$—Ph | H | O | H | $CH(CH_3)$ | (E)-[(prop-2-yn-1-yloxy)imino]methyl | [$CDCl_3$] D1 1.25 (d, 3H); 1.72 (s, 3H); 2.41 (m, 1H); 3.19 (d, 1H); 3.76 (d, 1H); 4.56 (s, 2H); 4.67 (m, 1H); 6.88 (m, 1H); 7.16 (s br, 1H); 7.17 (m, 2H); 7.39 (d, 1H). D2 1.37 (d, 3H); 1.72 (s, 3H); 2.48 (m, 1H); 3.20 (d, 1H); 3.78 (d, 1H); 4.67 (s, 2H); 4.69 (m, 1H); 6.88 (m, 1H); 7.16 (s br, 1H); 7.17 (m, 2H); 7.49 (d, 1H). |
| 6.842 | 3,5-$Cl_2$—Ph | H | O | H | $CH(CH_3)$ | (methylsulfanyl)-methyl | [DMSO-$D_6$] 1.13 (d, 3H); 1.55 (s, 3H); 2.53 (m, 2H); 3.41 (d, 1H); 3.74 (d, 1H); 3.94 (m, 1H); 7.70 (s, 2H); 7.74 (m, 1H); 9.91 (d br, 1H). |
| 6.843 | 3,5-$F_2$—Ph | H | O | H | $CH(CH_3)$ | (methylsulfanyl)-methyl | |
| 6.844 | 3,5-$Cl_2$—Ph | H | O | H | $CH(CH_3)$ | (methylsulfanyl)-methyl | |
| 6.845 | 3-F—Ph | H | O | H | $CH(CH_3)$ | (methylsulfanyl)-methyl | |
| 6.846 | 3,5-$F_2$—Ph | H | O | H | $CH(CH_3)$ | 1,3-dioxolan-2-yl | [$CDCl_3$] 1.13 (d, 3H); 1.72 (s, 3H); 3.18 (d, 1H); 3.78 (d, 1H); 3.90-4.06 (m, 4H); 4.24 (m, 1H); 4.86 (d, 1H); 6.89 (m, 2H); 7.16 (m, 2H). |
| 6.847 | 3,5-$F_2$—Ph | H | O | H | $CH(CH_3)$ | 1,3-dioxolan-2-yl | |
| 6.848 | 3,5-$F_2$—Ph | H | O | H | $CH(CH_3)$ | CF3 | [DMSO-$D_6$] 1.31 (d, 3H); 1.59 (s, 3H); 3.41 (d, 1H); 3.76 (d, 1H); 4.61 (m, 1H); 7.40 (m, 3H); 8.67 (d, 1H). |
| 6.849 | 3,5-$F_2$—Ph | H | O | H | $CH(CH_3)$ | CF3 | |
| 6.850 | 3,5-$F_2$—Ph | H | O | $CH_3$ | $CH(CH_3)$ | CH3 | |
| 6.851 | 3,5-$F_2$—Ph | H | O | H | $CH(CH_3)$ | cyanogen | [$CDCl_3$] D1 1.62 (d, 3H); 1.72 (s, 3H); 3.25 (d, 1H); 3.77 (d, 1H); 4.86 (m, 1H); 6.90 (m, 1H); 7.10 (d br, 1H); 7.17 (m, 2H). D2 1.58 (d, 3H); 1.76 (s, 3H); 3,22 (d, 1H); 3.77 (d, 1H); 4.84 (m, 1H); 6.90 (m, 1H); 7.10 (d br, 1H); 7.17 (m, 2H). |
| 6.852 | 3-F—Ph | H | O | H | $CH(CH_3)$ | cyanogen | [DMSO-$D_6$] D1 1.46 (d, 3H); 1.56 (s, 3H); 3.43 (d, 1H); 3.77 (d, 1H); 4.82 (m, 1H); 7.33 (m, 1H); 7.54 (m, 3H); 8.98 (t br, 1H). D2 1.44 |

TABLE 6-continued

Compounds of the general formula (I) according to the invention in which $R^2$ is hydrogen and $R^3$ is methyl and aryl is the radical

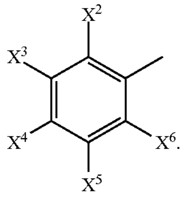

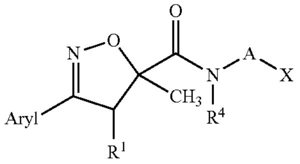

| No. | Aryl | $R^1$ | Y | $R^4$ | A | X | Physical data |
|---|---|---|---|---|---|---|---|
| | | | | | | | (d, 3H); 1.58 (s, 3H); 3.42 (d, 1H); 3.76 (d, 1H); 4.82 (m, 1H); 7.33 (m, 1H); 7.54 (m, 3H); 8.98 (t br, 1H). |
| 6.853 | 3,5-$Cl_2$—Ph | H | O | H | $CH(CH_3)$ | cyanogen | [$CDCl_3$] D1 1.57 (d, 3H); 1.76 (s, 3H); 3.22 (d, 1H); 3.78 (d, 1H); 4.83 (q, 1H); 7.06 (d br, 1H); 7.43 (s, 1H); 7.51 (s, 2H). |
| 6.854 | 3,5-$F_2$—Ph | H | O | H | $CH(CH_3)$ | cyanogen | |
| 6.855 | 3,5-$F_2$—Ph | H | O | H | $CH(CH_3)$ | cyanogen | |
| 6.856 | 3,5-$Cl_2$—Ph | H | O | H | $CH(CH_3)$ | cyanogen | |
| 6.857 | 3,5-$Cl_2$—Ph | H | O | H | $CH(CH_3)$ | cyanogen | |
| 6.858 | 3-F—Ph | H | O | H | $CH(CH_3)$ | cyanogen | |
| 6.859 | 3-F—Ph | H | O | H | $CH(CH_3)$ | cyanogen | |
| 6.860 | 3,5-$Cl_2$—Ph | H | O | H | $CH(CH_3)$ | dimethoxymethyl | [$CDCl_3$] 1.10 (d, 3H); 1.72 (s, 3H); 3.16 (d, 1H); 3.44 (s, 6H); 3.78 (d, 1H); 4.12 (m, 1H); 4.19 (d, 1H); 6.87 (d br, 1H); 7.41 (m, 1H); 7.52 (s, 2H). |
| 6.861 | 3,5-$F_2$—Ph | H | O | H | $CH(CH_3)$ | dimethoxymethyl | |
| 6.862 | 3,5-$F_2$—Ph | H | O | H | $CH(CH_3)$ | dimethoxymethyl | |
| 6.863 | 3-F—Ph | H | O | H | $CH(CH_3)$ | dimethoxymethyl | |
| 6.864 | 3-F—Ph | H | O | H | $CH(CH_3)$ | dimethoxymethyl | |
| 6.865 | 3,5-$Cl_2$—Ph | H | O | H | $CH(CH_3)$ | dimethoxymethyl | |
| 6.866 | 3,5-$F_2$—Ph | H | O | H | $CH(CH_3)$ | ethynyl | [DMSO-$D_6$] D1 1.31 (d, 3H); 1.55 (s, 3H); 3.14 (d, 1H); 3.37 (d, 1H); 3.74 (d, 1H); 4.61 (m, 1H); 7.40 (m, 3H); 8.46 (d br, 1H). D2 1.33 (d, 3H); 1.55 (s, 3H); 3.12 (d, 1H); 3.30 (d, 1H); 3.78 (d, 1H); 4.61 (m, 1H); 7.40 (m, 3H); 8.50 (d br, 1H). |
| 6.867 | 3-F—Ph | H | O | H | $CH(CH_3)$ | ethynyl | |
| 6.868 | 3,5-$F_2$—Ph | H | O | H | $CH(CH_3)$ | ethyl | [$CDCl_3$] 0.86 (td, 3H); 1.13 (dd, 3H); 1.46 (m, 1H); 1.73 (s, 3H); 3.78 (dd, 1H); 3.86 (m, 1H); 6.59 (br, t, 1H); 6.88 (t, 1H); 7.16 (s, 1H). |
| 6.869 | 3,5-$F_2$—Ph | H | O | H | c-Pr-1,1-diyl | cyclohexyl | |
| 6.870 | 3,5-$Cl_2$—Ph | H | O | H | c-Pr-1,1-diyl | cyclohexyl | |
| 6.871 | 3-F—Ph | H | O | H | c-Pr-1,1-diyl | cyclohexyl | |
| 6.872 | 3,5-$F_2$—Ph | H | O | H | c-Pr-1,1-diyl | ethoxycarbonyl | |
| 6.873 | 3-F—Ph | H | O | H | c-Pr-1,1-diyl | methoxycarbonyl | |
| 6.874 | 3,5-$F_2$—Ph | H | O | H | c-Pr-1,1-diyl | methoxycarbonyl | |
| 6.875 | 3,5-$Cl_2$—Ph | H | O | H | c-Pr-1,1-diyl | methoxycarbonyl | |
| 6.876 | 3,5-$F_2$—Ph | H | O | H | c-Pr-1,1-diyl | sec-butoxycarbonyl | |
| 6.877 | 3,5-$Cl_2$—Ph | H | O | H | c-Pr-1,1-diyl | sec-butoxycarbonyl | |

TABLE 6-continued

Compounds of the general formula (I) according to the invention in which $R^2$ is hydrogen and $R^3$ is methyl and aryl is the radical

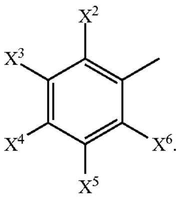

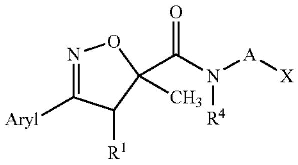

| No. | Aryl | $R^1$ | Y | $R^4$ | A | X | Physical data |
|---|---|---|---|---|---|---|---|
| 6.878 | 3-F—Ph | H | O | H | c-Pr-1,1-diyl | sec-butoxycarbonyl | |
| 6.879 | 3,5-$F_2$—Ph | H | O | H | $C(CH_3)_2$ | $CH_3$ | |
| 6.880 | 3,5-$Cl_2$—Ph | H | O | H | $C(CH_3)_2$ | cyanogen | |
| 6.881 | 3,5-$F_2$—Ph | H | O | H | $C(CH_3)_2$ | cyanogen | |
| 6.882 | 3-F—Ph | H | O | H | $C(CH_3)_2$ | cyanogen | |
| 6.883 | 3,5-$F_2$—Ph | H | O | H | $C(CH_3)_2$ | ethynyl | [DMSO-$D_6$] 1.53 (s, 3H); 1.55 (s, 3H); 2.51 (m, 1H); 3.31 (s, 3H); 3.35 (d, 1H); 3.77 (d, 1H); 7.39 (m, 2H); 7.64 (s, 1H). |
| 6.884 | 3,5-$F_2$—Ph | H | O | H | CH(iPr) | 2-ethoxy-2-oxoethyl | |
| 6.885 | 3,5-$F_2$—Ph | H | O | H | CH(iPr) | 2-ethoxy-2-oxoethyl | |
| 6.886 | 3,5-$Cl_2$—Ph | H | O | H | CH(iPr) | $CF_3$ | |
| 6.887 | 3-F—Ph | H | O | H | CH(iPr) | $CF_3$ | |
| 6.888 | 3,5-$F_2$—Ph | H | O | H | CH(iPr) | $CF_3$ | |
| 6.889 | 3,5-$F_2$—Ph | H | O | H | CH(iPr) | $CH_3$ | |
| 6.890 | 3,5-$Cl_2$—Ph | H | O | H | CH(iPr) | $CH_3$ | |
| 6.891 | 3-F—Ph | H | O | H | CH(iPr) | $CH_3$ | |
| 6.892 | 3,5-$F_2$—Ph | H | O | H | $CH(CH_2OCH_3)$ | methoxymethyl | |
| 6.893 | 3,5-$F_2$—Ph | H | O | H | $CH_2CH_2$ | chlorine | [$CDCl_3$] 1.74 (s, 3H); 3.19 (d, 2H); 3.50-3.72 (m, 4H); 3.77 (d, 1H); 6.88 (m, 1H); 7.15 (m, 3H). |
| 6.894 | 3-iPr—Ph | H | O | H | $CH_2CH_2$ | COOH | |
| 6.895 | 3,5-$I_2$—Ph | H | O | H | $CH_2CH_2$ | COOH | |
| 6.896 | 3-I—Ph | H | O | H | $CH_2CH_2$ | COOH | |
| 6.897 | 3-$SF_5$—Ph | H | O | H | $CH_2CH_2$ | COOH | |
| 6.898 | 3,5-$F_2$—Ph | H | O | H | $CH_2CH_2$ | cyanogen | [DMSO-$D_6$] 1.57 (s, 3H); 2.69 (t, 2H); 3.31 (s, 3H); §.32 (m, 2H); 3.41 (d, 1H); 3.73 (d, 1H); 7.39 (m, 3H); 8.46 (t, 1H). |
| 6.899 | 3-F—Ph | H | O | H | $CH_2CH_2$ | cyanogen | |
| 6.900 | 3-iPr—Ph | H | O | H | $CH_2CH_2$ | ethoxycarbonyl | |
| 6.901 | 5-Br-2-F—Ph | H | O | H | $CH_2CH_2$ | ethoxycarbonyl | |
| 6.902 | 2-F-5-MeO—Ph | H | O | H | $CH_2CH_2$ | ethoxycarbonyl | |
| 6.903 | 4-F-3,5-$Me_2$—Ph | H | O | H | $CH_2CH_2$ | ethoxycarbonyl | [$CDCl_3$] 1.24 (t, 3H); 1.70 (s, 3H); 2.27 (s, 6H); 2.52 (m, 2H); 3.19 (d, 1H); 3.48 (m, 1H); 3.57 (m, 1H); 3.78 (d, 1H); 4.14 (q, 2H); 7.29 (m, 2H). |
| 6.904 | 3-$SF_5$—Ph | H | O | H | $CH_2CH_2$ | ethoxycarbonyl | |
| 6.905 | 3-($F_2$—MeO)Ph | H | O | H | $CH_2CH_2$ | ethoxycarbonyl | |
| 6.906 | 3-Br-5-Me—Ph | H | O | H | $CH_2CH_2$ | ethoxycarbonyl | [$CDCl_3$] 1.25 (t, 3H); 1.70 (s, 3H); 2.35 (s, 3H); 2.53 (m, 2H); 3.18 (d, 1H); 3.50 (m, 1H); 3.58 (m, 1H); 3.76 (d, 1H); 4.14 (q, 2H); 7.28 (t, 1H); 7.36 (s, 1H); 7.38 (s, 1H); 7.58 (s, 1H). |
| 6.907 | 3,5-$I_2$—Ph | H | O | H | $CH_2CH_2$ | ethoxycarbonyl | |
| 6.908 | 3-(MeOCO)Ph | H | O | H | $CH_2CH_2$ | ethoxycarbonyl | |
| 6.909 | 3-I—Ph | H | O | H | $CH_2CH_2$ | ethoxycarbonyl | [$CDCl_3$] 1.70 (s, 3H); 1.25 (t, 3H); 2.53 (m, 2H); 3.18 (d, 1H); 3.52 (m, 2H); 3.78 (d, 2H); 4.14 (q, 2H); |

TABLE 6-continued

Compounds of the general formula (I) according to the invention in which $R^2$ is hydrogen and $R^3$ is methyl and aryl is the radical

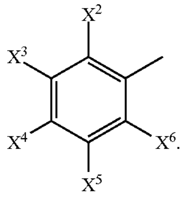

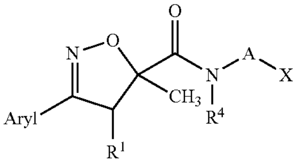

| No. | Aryl | $R^1$ | Y | $R^4$ | A | X | Physical data |
|---|---|---|---|---|---|---|---|
| | | | | | | | 7.14 (t, 1H); 7.26 (br, t, 1H); 7.58 (m, 1H); 7.75 (m, 1H); 8.00 (m, 1H). |
| 6.910 | 3,5-$CN_2$Ph | H | O | H | $CH_2CH_2$ | ethoxycarbonyl | |
| 6.911 | 3-CN-5-$CF_3$—Ph | H | O | H | $CH_2CH_2$ | ethoxycarbonyl | |
| 6.912 | 3-F-5-vinylPh | H | O | H | $CH_2CH_2$ | ethoxycarbonyl | |
| 6.913 | 3,5-$F_2$—Ph | H | O | H | $CH_2CH_2$ | methoxy | |
| 6.914 | 4-F-3,5-$Me_2$—Ph | H | O | H | $CH_2CH_2$ | methoxycarbonyl | [$CDCl_3$] 1.69 (s, 3H); 2.26 (d, 3H); 2.54 (m, 2H); 3.18 (d, 1H); 3.49 (m, 1H); 3.58 (m, 1H); 3.69 (s, 3H); 3.77 (d, 1H); 7.27 (br, t, 1H); 7.29 (m, 2H). |
| 6.915 | 3-ethynyl-Ph | H | O | H | $CH_2CH_2$ | methoxycarbonyl | |
| 6.916 | 3,5-$F_2$—Ph | $CH_2CH_3$ | O | H | $CH_2CH_2$ | methoxycarbonyl | |
| 6.917 | 3,5-$F_2$—Ph | H | O | H | $CH_2CH_2$ | methylsulfanyl | |
| 6.918 | 3,5-$F_2$—Ph | H | O | H | $CH_2CH_2$ | morpholin-4-yl | |
| 6.919 | 3,5-$F_2$—Ph | H | O | H | $CH_2CH_2$ | pyrrolidin-1-yl | |
| 6.920 | 3,5-$Cl_2$—Ph | H | O | H | $CH_2CH_2$ | sulfamoyl | [$CDCl_3$] 1.73 (s, 3H); 3.18 (d, 1H); 3.27 (t, 2H); 3.80 (d, 1H); 3.81 (m, 2H); 5.05 (s, 2H); 7.34 (t br, 1H); 7.41 (s, 1H); 7.51 (s, 2H). |
| 6.921 | 3-F—Ph | H | O | H | $CH_2CH_2$ | sulfamoyl | |
| 6.922 | 3,5-$F_2$—Ph | H | O | H | $CH(CH_3)CH_2$ | $CF_3$ | |
| 6.923 | 3,5-$F_2$—Ph | H | O | H | $CH(CH_3)CH_2$ | $CF_3$ | |
| 6.924 | 3-COOH—Ph | H | O | H | $CH(CH_3)CH_2$ | COOH | |
| 6.925 | 3,5-$I_2$—Ph | H | O | H | $CH(CH_3)CH_2$ | COOH | |
| 6.926 | 3-I—Ph | H | O | H | $CH(CH_3)CH_2$ | COOH | |
| 6.927 | 3-iPr—Ph | H | O | H | $CH(CH_3)CH_2$ | COOH | |
| 6.928 | 3-$SF_5$—Ph | H | O | H | $CH(CH_3)CH_2$ | COOH | |
| 6.929 | 3-Me—Ph | H | O | H | $CH(CH_3)CH_2$ | COOH | |
| 6.930 | 3,5-$F_2$—Ph | H | O | H | $CH(CH_3)CH_2$ | cyanogen | [$CDCl_3$] D1 1.37 (d, 3H); 1.72 (s, 3H); 2.63 (AB d, 2H); 3.18 (d, 1H); 3.73 (d, 1H); 4.19 (m, 1H); 6.89 (m, 2H); 7.17 (m, 2H). D2 1.42 (d, 3H); 1.74 (s, 3H); 2.67 (AB d, 2H); 3.23 (d, 1H); 3.79 (d, 1H); 4.19 (m, 1H); 6.89 (m, 2H); 7.17 (m, 2H). |
| 6.931 | 3,5-$Cl_2$—Ph | H | O | H | $CH(CH_3)CH_2$ | cyanogen | [$CDCl_3$] D1 1.37 (d, 3H); 1.72 (s, 3H); 2.68 (AB d, 2H); 3.18 (d, 1H); 3.75 (d, 1H); 4.19 (m, 1H); 6.87 (d br, 1H); 6.89 (s, 1H); 7.42 (s, 2H). D2 1.42 (d, 3H); 1.74 (s, 3H); 2.62 (AB d, 2H); 3.23 (d, 1H); 3.80 (d, 1H); 4.19 (m, 1H); 6.89 (m, 2H); 7.17 (m, 2H). |
| 6.932 | 3-F—Ph | H | O | H | $CH(CH_3)CH_2$ | cyanogen | |
| 6.933 | 3-iPr—Ph | H | O | H | $CH(CH_3)CH_2$ | ethoxycarbonyl | |
| 6.934 | 4-F-3,5-Me2—Ph | H | O | H | $CH(CH_3)CH_2$ | ethoxycarbonyl | [$CDCl_3$] 1.20 (m, 3H); 1.27 (m, 3H); 1.68 (s, 3H); 2.26 (d, 6H); 2.48 (m, 1H); 2.52 (m, 1H); 3.16 (dd, 1H); |

TABLE 6-continued

Compounds of the general formula (I) according to the invention in which $R^2$ is hydrogen and $R^3$ is methyl and aryl is the radical

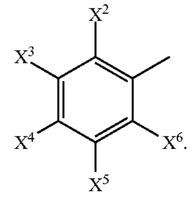

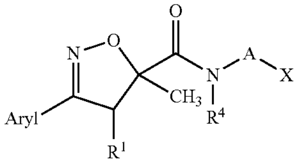

| No. | Aryl | $R^1$ | Y | $R^4$ | A | X | Physical data |
|---|---|---|---|---|---|---|---|
| | | | | | | | 3.75 (dd, 1H); 4.05 (q, 1H); 4.15 (q, 1H); 7.30 (m, 2H); 4.28 (m, 1H); 7.15 (br, m, 1H). |
| 6.935 | 2-F-5-MeO—Ph | H | O | H | $CH(CH_3)CH_2$ | ethoxycarbonyl | |
| 6.936 | 3-$SF_5$—Ph | H | O | H | $CH(CH_3)CH_2$ | ethoxycarbonyl | |
| 6.937 | 3-Cl-2-F-5-$CF_3$—Ph | H | O | H | $CH(CH_3)CH_2$ | ethoxycarbonyl | |
| 6.938 | 5-Br-2-F—Ph | H | O | H | $CH(CH_3)CH_2$ | ethoxycarbonyl | |
| 6.939 | 3-($F_2$—MeO)Ph | H | O | H | $CH(CH_3)CH_2$ | ethoxycarbonyl | |
| 6.940 | 3-Br-5-Me—Ph | H | O | H | $CH(CH_3)CH_2$ | ethoxycarbonyl | |
| 6.941 | 3,5-$I_2$—Ph | H | O | H | $CH(CH_3)CH_2$ | ethoxycarbonyl | |
| 6.942 | 3-(MeOCO)Ph | H | O | H | $CH(CH_3)CH_2$ | ethoxycarbonyl | |
| 6.943 | 3-I—Ph | H | O | H | $CH(CH_3)CH_2$ | ethoxycarbonyl | |
| 6.944 | 3,5-$CN_2$Ph | H | O | H | $CH(CH_3)CH_2$ | ethoxycarbonyl | |
| 6.945 | 3-CN-5-$CF_3$—Ph | H | O | H | $CH(CH_3)CH_2$ | ethoxycarbonyl | |
| 6.946 | 3-Br-5-CN—Ph | H | O | H | $CH(CH_3)CH_2$ | ethoxycarbonyl | |
| 6.947 | 3,5-$F_2$—Ph | $CH_2CH_3$ | O | H | $CH(CH_3)CH_2$ | ethoxycarbonyl | |
| 6.948 | 3-F—Ph | H | O | H | $CH(CH_3)CH_2$ | ethyl | |
| 6.949 | 3-F—Ph | H | O | H | $CH(CH_3)CH_2$ | ethyl | |
| 6.950 | 3,5-$Cl_2$—Ph | H | O | H | $CH(CH_3)CH_2$ | ethyl | |
| 6.951 | 3,5-$F_2$—Ph | H | O | H | $CH(CH_3)CH_2$ | ethyl | |
| 6.952 | 3,5-$Cl_2$—Ph | H | O | H | $CH(CF_3)CH_2$ | CH3 | |
| 6.953 | 3-F—Ph | H | O | H | $CH(CF_3)CH_2$ | CH3 | |
| 6.954 | 3,5-$F_2$—Ph | H | O | H | $CH(CF_3)CH_2$ | CH3 | |
| 6.955 | 3,5-$F_2$—Ph | H | O | H | $CH(CH_2H_3)CH_2$ | cyanogen | |
| 6.956 | 3,5-$F_2$—Ph | H | O | H | $CH(CH_2iPr)CH_2$ | methoxycarbonyl | |
| 6.957 | 3,5-$F_2$—Ph | H | O | H | $CH(CH_2iPr)CH_2$ | methoxycarbonyl | |
| 6.958 | 3,5-$F_2$—Ph | H | O | H | $CH_2CH_2CH_2$ | 2-oxopyrrolidin-1-yl | |
| 6.959 | 3,5-$F_2$—Ph | H | O | H | $CH_2CH_2CH_2$ | methoxy | |
| 6.960 | 3,5-$F_2$—Ph | H | O | H | $CH_2CH_2O$ | (2,2,2-trifluoroethyl)-carbamoyl | [DMSO-$D_6$] 3.30 (m, 2H); 3.37 (d, 1H); 3.70 (m, 2H); 3.73 (d, 1H); 4.07 (m, 2H); 7.39 (m, 3H); 7.88 (t br, 1H); 8.15 (t br, 1H). |
| 6.961 | 3,5-$F_2$—Ph | H | O | H | $CH_2CH_2O$ | (cyclopropylmethyl)-carbamothioyl | [$CDCl_3$] 0.26 (m, 2H); 0.56 (m, 2H); 1.05 (m, 1H); 1.73 (s, 3H); 3.18 (d, 1H); 3.35 (m, 2H); 3.50-3.70 (m, 2H); 4.56 (m, 2H); 6.42 (s br, 1H); 6.88 (m, 1H); 7.08 (s br, 1H); 7.15 (m, 2H); |
| 6.962 | 3,5-$F_2$—Ph | H | O | H | $CH_2CH_2O$ | cyclopropyl-carbamothioyl | [$CDCl_3$] isomer 1 0.58 (2H); 0.78 (m, 2H); 1.70 (s, 3H); 2.70 (m, 1H); 3.20 (d, 1H); 3.54 (m, 1H); 3.70 (m, 1H); 3.78 (d, 1H); 4.53 (m, 2H); 6.38 (s br, 1H); 6.88 (m, 1H); 7.05 (s br, 1H); 7.16 (m, 2H). isomer 2 0.63 (2H); 0.87 (m, 2H); 1.72 (s, 3H); 2.94 (m, 1H); 3.20 (d, 1H); 3.64 (m, 2H); 3.78 (d, 1H); 4.63 (m, 2H); 6.67 (s br, 1H); 6.88 (m, 1H); 7.16 (m, 3H). |

TABLE 6-continued

Compounds of the general formula (I) according to the invention in which $R^2$ is hydrogen and $R^3$ is methyl and aryl is the radical

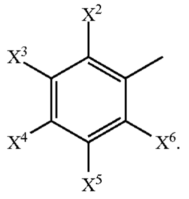

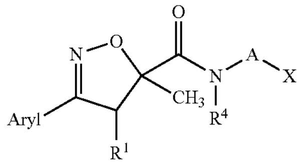

| No. | Aryl | $R^1$ | Y | $R^4$ | A | X | Physical data |
|---|---|---|---|---|---|---|---|
| 6.963 | 3,5-$F_2$—Ph | H | O | H | $CH_2CH_2O$ | cyclopropyl-carbamoyl | [DMSO-$D_6$] 0.34 (m, 2H); 0.50 (m, 2H); 1.55 (s, 3H); 2.38 (m, 1H); 3.29 (m, 2H); 3.38 (d, 1H); 3.73 (d, 1H); 3.98 (m, 2H); 7.26 (s br, 1H); 7.38 (m, 3H); 8.10 (s br, 1H). |
| 6.964 | 3,5-$F_2$—Ph | H | O | H | $CH_2CH_2O$ | ethylcarbamothioyl | [$CDCl_3$] 1.23 (t, 3H); 1.73 (s, 3H); 3.18 (d, 1H); 3.29 (m, 1H); 3.55 (m, 2H); 3.64 (m, 1H); 3.78 (d, 1H); 4.58 (m, 2H); 6.24 (s br, 1H); 6.88 (m, 1H); 7.07 (s br, 1H); 7.16 (m, 2H); |
| 6.965 | 3,5-$F_2$—Ph | H | O | H | $CH_2CH_2O$ | ethylcarbamoyl | [$CDCl_3$] 1.12 (t, 3H); 1.73 (s, 3H); 3.17 (m, 2H); 3.18 (d, 1H); 3.47 (m, 1H); 3.54 (d, 1H); 4.16 (m, 2H); 4.67 (s br, 1H); 6.88 (m, 1H); 7.12 (sbr, 1H); 7.15 (m, 2H); |
| 6.966 | 3,5-$F_2$—Ph | H | O | H | $CH_2CH_2O$ | isopropyl-carbamothioyl | [$CDCl_3$] 1.22 (dd, 6H); 1.73 (s, 3H); 3.18 (d, 1H); 3.54 (m, 1H); 3.63 (m, 1H); 3.78 (d, 1H); 4.33 m, 1H); 4.46-4.69 (m, 2H); 6.13 (s br, 1H); 6.89 (m, 1H); 7.08 (s br, 1H); 7.14 (m, 2H): |
| 6.967 | 3,5-$Cl_2$—Ph | H | O | H | $(CH_2)_4$ | $CH_3$ | |
| 6.968 | 3,5-$F_2$—Ph | H | O | H | $(CH_2)_4$ | $CH_3$ | |
| 6.969 | 3,5-$F_2$—Ph | H | O | H | $(CH_2)_6$ | $CH_3$ | |
| 6.970 | 3,5-$F_2$—Ph | H | O | H | $(CH_2)_6$ | ethyl | |

TABLE 7

Compounds of the general formula (I) according to the invention in which $R^2$ is hydrogen and $R^3$ is ethyl and aryl is the radical

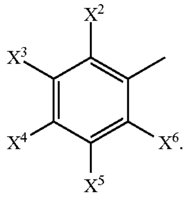

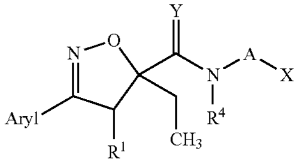

| No. | Aryl | $R^1$ | Y | $R^4$ | A | X | Physical data |
|---|---|---|---|---|---|---|---|
| 7.001 | 3,5-$Cl_2$—Ph | H | O | H | $(CH_2)_4$ | COOH | |
| 7.002 | 3,5-$Cl_2$—Ph | H | O | H | $(CH_2)_4$ | ethoxycarbonyl | |

TABLE 7-continued

Compounds of the general formula (I) according to the invention in which $R^2$ is hydrogen and $R^3$ is ethyl and aryl is the radical

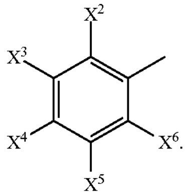

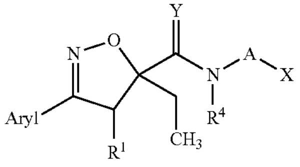

| No. | Aryl | $R^1$ | Y | $R^4$ | A | X | Physical data |
|---|---|---|---|---|---|---|---|
| 7.003 | 3-Br-5-Cl—Ph | H | O | H | $(CH_2)_4$ | ethoxycarbonyl | |
| 7.004 | Ph | H | O | H | $(CH_2)_4$ | ethoxycarbonyl | |
| 7.005 | 3,5-$Cl_2$—Ph | H | O | H | $(CH_2)_4$ | hydroxy | |
| 7.006 | 3,5-$Cl_2$—Ph | H | O | H | $(CH_2)_4$ | methoxy | |
| 7.007 | 3,5-$Cl_2$—Ph | H | O | H | $(CH_2)_6$ | COOH | |
| 7.008 | 3,5-$Cl_2$—Ph | H | O | H | $(CH_2)_6$ | ethoxycarbonyl | |
| 7.009 | 3,5-$Cl_2$—Ph | H | O | H | c-Pr-1,1-diyl | ethoxycarbonyl | |
| 7.010 | 3,5-$F_2$—Ph | H | O | H | bond | 1-cyanocyclopropyl | |
| 7.011 | 3,5-$Cl_2$—Ph | H | O | H | bond | 1-cyanocyclopropyl | |
| 7.012 | 3,5-$Cl_2$—Ph | H | O | H | bond | 1-methylcyclopropyl | |
| 7.013 | 3,5-$Cl_2$—Ph | H | O | H | bond | 2-(ethoxy-carbonyl)cyclohex-1-en-1-yl | |
| 7.014 | 3,5-$Cl_2$—Ph | H | O | H | bond | 2-(ethoxy-carbonyl)cyclohexyl | |
| 7.015 | 3,5-$Cl_2$—Ph | H | O | H | bond | 2-(methylcarbamoyl)-cyclohexyl | |
| 7.016 | 3,5-$Cl_2$—Ph | H | O | H | bond | 2-carboxycyclohexyl | |
| 7.017 | 3,5-$Cl_2$—Ph | H | O | H | bond | 3-(2-ethoxy-2-oxoethyl)oxetan-3-yl | |
| 7.018 | 3,5-$F_2$—Ph | H | O | H | bond | 3-(2-ethoxy-2-oxoethyl)oxetan-3-yl | |
| 7.019 | 2,4-$Cl_2$—Ph | H | O | $CH_3$ | bond | CH3 | |
| 7.020 | 2-Cl—Ph | H | O | $CH_3$ | bond | CH3 | |
| 7.021 | 3,4-$F_2$—Ph | H | O | H | bond | CH3 | |
| 7.022 | 3,5-$Br_2$—Ph | H | O | H | bond | CH3 | |
| 7.023 | 3,5-$Cl_2$—Ph | $CH_3$ | O | H | bond | CH3 | |
| 7.024 | 3,5-$Cl_2$—Ph | H | O | $CH_3$ | bond | CH3 | |
| 7.025 | 3,5-$Cl_2$—Ph | H | O | H | bond | CH3 | |
| 7.026 | 3,5-$F_2$—Ph | H | O | H | bond | CH3 | |
| 7.027 | 3-Cl-4-F—Ph | H | O | H | bond | CH3 | |
| 7.028 | 3,5-$Cl_2$—Ph | H | O | H | bond | cyclobutyl | |
| 7.029 | 3,5-$F_2$—Ph | H | O | H | bond | cyclobutyl | |
| 7.030 | 3,5-$Cl_2$—Ph | H | O | H | bond | cyclopentyl | |
| 7.031 | 3,5-$F_2$—Ph | H | O | H | bond | cyclopentyl | |
| 7.032 | 2-$CF_3$—Ph | H | O | H | bond | c-Pr | |
| 7.033 | 2,3,4-$F_3$—Ph | H | O | H | bond | c-Pr | |
| 7.034 | 2,3,5-$F_3$—Ph | H | O | H | bond | c-Pr | |
| 7.035 | 2,3-$F_2$—Ph | H | O | H | bond | c-Pr | |
| 7.036 | 2,4-$Cl_2$—Ph | H | O | H | bond | c-Pr | |
| 7.037 | 2,5-$F_2$—Ph | H | O | H | bond | c-Pr | |
| 7.038 | 2,5-$Me_2$—Ph | H | O | H | bond | c-Pr | |
| 7.039 | 2-Cl-3-F-5-MeO—Ph | H | O | H | bond | c-Pr | |
| 7.040 | 2-Cl-5-F—Ph | H | O | H | bond | c-Pr | |
| 7.041 | 2-EtO-3,4,5,6-$F_4$—Ph | H | O | H | bond | c-Pr | |
| 7.042 | 2-F-3-Me—Ph | H | O | H | bond | c-Pr | |
| 7.043 | 3-(2-MeOEtO)—Ph | H | O | H | bond | c-Pr | |
| 7.044 | 3-iPrO—Ph | H | O | H | bond | c-Pr | |
| 7.045 | 3-$CF_3$O—Ph | H | O | H | bond | c-Pr | |
| 7.046 | 3-$CF_3$—Ph | H | O | H | bond | c-Pr | |
| 7.047 | 3,4,5-$F_3$—Ph | H | O | H | bond | c-Pr | |
| 7.048 | 3,5-$Br_2$—Ph | H | O | H | bond | c-Pr | |

TABLE 7-continued

Compounds of the general formula (I) according to the invention in which $R^2$ is hydrogen and $R^3$ is ethyl and aryl is the radical

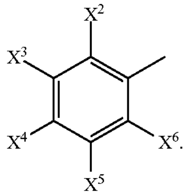

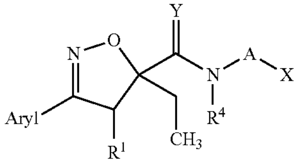

| No. | Aryl | $R^1$ | Y | $R^4$ | A | X | Physical data |
|---|---|---|---|---|---|---|---|
| 7.049 | 3,5-$Cl_2$-4-MeO—Ph | H | O | H | bond | c-Pr | |
| 7.050 | 3,5-$Cl_2$-4-OH—Ph | H | O | H | bond | c-Pr | |
| 7.051 | 3,5-$Cl_2$—Ph | $CH_3$ | O | H | bond | c-Pr | |
| 7.052 | 3,5-$Cl_2$—Ph | H | O | H | bond | c-Pr | [$CDCl_3$] 0.52 (m, 2H); 0.80 (m, 2H); 0.98 (t, 3H); 1.94 (m, 1H); 2.14 (m, 1H); 2.23 (m, 1H); 3.18 (d, 1H); 3.70 (d, 1H); 6.82 (s, 1H); 7.40 (t, 1H), 7.50 (d, 1H) |
| 7.053 | 3,5-$F_2$—Ph | H | O | H | bond | c-Pr | |
| 7.054 | 3,5-$F_2$—Ph | H | O | H | bond | c-Pr | |
| 7.055 | 3,5-$F_2$—Ph | H | S | H | bond | c-Pr | |
| 7.056 | 3,5-$(MeO)_2$—Ph | H | O | H | bond | c-Pr | |
| 7.057 | 3,5-$Me_2$—Ph | H | O | H | bond | c-Pr | |
| 7.058 | 3-Ac—Ph | H | O | H | bond | c-Pr | |
| 7.059 | 3-Br-5-$CF_3$—Ph | H | O | H | bond | c-Pr | |
| 7.060 | 3-Br-5-Cl—Ph | H | O | H | bond | c-Pr | |
| 7.061 | 3-Br-5-F—Ph | H | O | H | bond | c-Pr | |
| 7.062 | 3-Cl-4-F—Ph | H | O | H | bond | c-Pr | |
| 7.063 | 3-Cl-4-Me—Ph | H | O | H | bond | c-Pr | |
| 7.064 | 3-Cl-5-$CF_3$—Ph | H | O | H | bond | c-Pr | |
| 7.065 | 3-Cl-5-CN—Ph | H | O | H | bond | c-Pr | |
| 7.066 | 3-Cl-5-Et—Ph | H | O | H | bond | c-Pr | |
| 7.067 | 3-Cl-5-F—Ph | H | O | H | bond | c-Pr | |
| 7.068 | 3-Cl-5-Me—Ph | H | O | H | bond | c-Pr | |
| 7.069 | 3-Cl-5-$CF_3O$—Ph | H | O | H | bond | c-Pr | |
| 7.070 | 3-Cl—Ph | H | O | H | bond | c-Pr | |
| 7.071 | 3-CN-5-F—Ph | H | O | H | bond | c-Pr | |
| 7.072 | 3-c-Pr-5-F—Ph | H | O | H | bond | c-Pr | |
| 7.073 | 3-EtO—Ph | H | O | H | bond | c-Pr | |
| 7.074 | 3-Et-5-F—Ph | H | O | H | bond | c-Pr | |
| 7.075 | 3-Et—Ph | H | O | H | bond | c-Pr | |
| 7.076 | 3-F-5-MeS—Ph | H | O | H | bond | c-Pr | |
| 7.077 | 3-F-5-$MeSO_2$—Ph | H | O | H | bond | c-Pr | |
| 7.078 | 3-F-5-MeO—Ph | H | O | H | bond | c-Pr | |
| 7.079 | 3-F-5-Me—Ph | H | O | H | bond | c-Pr | |
| 7.080 | 3-F-5-Me—Ph | H | S | H | bond | c-Pr | |
| 7.081 | 3-F—Ph | H | O | H | bond | c-Pr | [CDCl3] 0.54 (m, 2H); 0.80 (m, 2H); 1.01 (t, 3H); 1.94 (m, 1H); 2.13 (m, 1H); 2.75 (m, 1H); 3.23 (d, 1H); 3.73 (d, 1H); 6.87 (s br, 1H); 7.14 (m, 1H); 7.39 (m, 3H). |
| 7.082 | 3-OH—Ph | H | O | H | bond | c-Pr | |
| 7.083 | 3-iPr—Ph | H | O | H | bond | c-Pr | |
| 7.084 | 3-MeO—Ph | H | O | H | bond | c-Pr | |
| 7.085 | 3-Me-5-$CF_3O$—Ph | H | O | H | bond | c-Pr | |

TABLE 7-continued

Compounds of the general formula (I) according to the invention in which $R^2$ is hydrogen and $R^3$ is ethyl and aryl is the radical

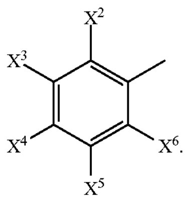

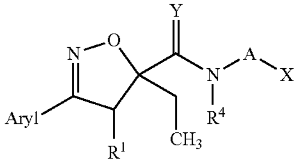

| No. | Aryl | $R^1$ | Y | $R^4$ | A | X | Physical data |
|---|---|---|---|---|---|---|---|
| 7.086 | 3-Me—Ph | H | O | H | bond | c-Pr | |
| 7.087 | 3-$NO_2$—Ph | H | O | H | bond | c-Pr | |
| 7.088 | 4-Cl-3,5-$F_2$—Ph | H | O | H | bond | c-Pr | |
| 7.089 | 4-EtO—Ph | H | O | H | bond | c-Pr | |
| 7.090 | $F_5$—Ph | H | O | H | bond | c-Pr | |
| 7.091 | Ph | H | O | H | bond | c-Pr | |
| 7.092 | 3,5-$Cl_2$—Ph | H | O | H | bond | decahydronaphthalen-2-yl | |
| 7.093 | 3,5-$Cl_2$—Ph | H | O | H | bond | H | |
| 7.094 | 3,5-$F_2$—Ph | H | O | H | bond | H | |
| 7.095 | 3,5-$F_2$—Ph | H | S | H | bond | H | |
| 7.096 | 3-F—Ph | H | O | H | bond | H | |
| 7.097 | 3-Me—Ph | H | O | H | bond | H | |
| 7.098 | 3-Me—Ph | H | S | H | bond | H | |
| 7.099 | 3,5-$Cl_2$—Ph | H | O | $CH_3$ | bond | hydroxy | |
| 7.100 | 2,3,4-$F_3$—Ph | H | O | H | bond | oxetan-3-yl | |
| 7.101 | 2,3-$F_2$—Ph | H | O | H | bond | oxetan-3-yl | |
| 7.102 | 2,5-$F_2$—Ph | H | O | H | bond | oxetan-3-yl | |
| 7.103 | 3,5-$Cl_2$—Ph | H | O | H | bond | oxetan-3-yl | |
| 7.104 | 3,5-$F_2$—Ph | H | O | H | bond | oxetan-3-yl | |
| 7.105 | 3-Cl-5-$CF_3O$—Ph | H | O | H | bond | oxetan-3-yl | |
| 7.106 | 3-F-5-Me—Ph | H | O | H | bond | oxetan-3-yl | |
| 7.107 | 3-F—Ph | H | O | H | bond | oxetan-3-yl | |
| 7.108 | 3-$NO_2$—Ph | H | O | H | bond | oxetan-3-yl | |
| 7.109 | Ph | H | O | H | bond | oxetan-3-yl | |
| 7.110 | 3,5-$Cl_2$—Ph | H | O | H | bond | tetrahydro-2H-pyran-4-yl | |
| 7.111 | 3,5-$Cl_2$—Ph | H | O | H | $C(CH_3)_2$ | 3-methoxyprop-1-yn-1-yl | |
| 7.112 | 3,5-$Cl_2$—Ph | H | O | H | $C(CH_3)_2$ | carbamoyl | |
| 7.113 | 3,5-$Cl_2$—Ph | H | O | H | $C(CH_3)_2$ | CH3 | |
| 7.114 | 3-Cl-4-F—Ph | H | O | H | $C(CH_3)_2$ | CH3 | |
| 7.115 | 3,5-$Cl_2$—Ph | H | O | H | $C(CH_3)_2$ | COOH | |
| 7.116 | 3,5-$(CF_3)_2$—Ph | H | O | H | $C(CH_3)_2$ | ethynyl | |
| 7.117 | 3,5-$Cl_2$—Ph | H | O | H | $C(CH_3)_2$ | ethynyl | |
| 7.118 | 3,5-$Cl_2$—Ph | H | O | H | $C(CH_3)_2$ | methoxycarbonyl | |
| 7.119 | 3,5-$Cl_2$—Ph | H | O | H | $C(CH_3)_2$ | methylcarbamoyl | |
| 7.120 | 3-Cl—Ph | H | O | H | $C(CH_3)_2CH_2$ | (propan-2-yloxy)carbonyl | |
| 7.121 | 3-F—Ph | H | O | H | $C(CH_3)_2CH_2$ | (propan-2-yloxy)carbonyl | |
| 7.122 | 3,5-$Cl_2$—Ph | H | O | H | $C(CH_3)_2CH_2$ | COOH | |
| 7.123 | 3-Cl—Ph | H | O | H | $C(CH_3)_2CH_2$ | COOH | |
| 7.124 | 3-F—Ph | H | O | H | $C(CH_3)_2CH_2$ | COOH | |
| 7.125 | 3,5-$Cl_2$—Ph | H | O | H | $C(CH_3)_2CH_2$ | ethoxycarbonyl | |
| 7.126 | 3-Cl—Ph | H | O | H | $C(CH_3)_2CH_2$ | ethoxycarbonyl | |
| 7.127 | 3-F—Ph | H | O | H | $C(CH_3)_2CH_2$ | ethoxycarbonyl | |
| 7.128 | 3,5-$Cl_2$—Ph | H | O | H | $C(CH_3)_2CH_2$ | hydroxy | |
| 7.129 | 3-Cl—Ph | H | O | H | $C(CH_3)_2CH_2$ | methoxycarbonyl | |
| 7.130 | 3-F—Ph | H | O | H | $C(CH_3)_2CH_2$ | methoxycarbonyl | |
| 7.131 | 3,5-$Cl_2$—Ph | H | O | H | $C(CH_3)_2CH_2$ | methylsulfanyl | |
| 7.132 | 3,5-$Cl_2$—Ph | H | O | H | $C(CH_3)2CH_2$ | methylsulfonyl | |
| 7.133 | 2,4-$Cl_2$—Ph | H | O | H | $C(iPr)CH_3$ | cyanogen | |
| 7.134 | 3,5-$Cl_2$—Ph | H | O | H | $C(iPr)CH_3$ | cyanogen | |
| 7.135 | 3,5-$Cl_2$—Ph | H | O | H | $CH(CF_3)CH_2$ | ethoxycarbonyl | |

TABLE 7-continued

Compounds of the general formula (I) according to the invention in which $R^2$ is hydrogen and $R^3$ is ethyl and aryl is the radical

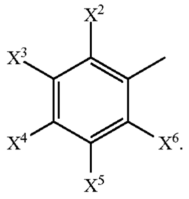

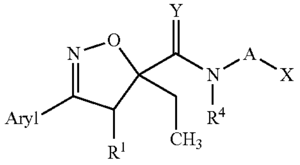

| No. | Aryl | $R^1$ | Y | $R^4$ | A | X | Physical data |
|---|---|---|---|---|---|---|---|
| 7.136 | 3,5-$Cl_2$—Ph | H | O | H | $CH(CH_2CH_2SCH_3)$ | methoxycarbonyl | |
| 7.137 | 3,5-$Cl_2$—Ph | H | O | H | $CH(CH_2CH_3)CH_2$ | cyanogen | |
| 7.138 | 3,5-$Cl_2$—Ph | H | O | H | $CH(CH_2CH_3)CH_2$ | methoxycarbonyl | |
| 7.139 | 3,5-$Cl_2$—Ph | H | O | H | $CH(CH_2iPr)CH_2$ | methoxycarbonyl | |
| 7.140 | 3,5-$Cl_2$—Ph | H | O | H | $CH(CH_2OCH_3)$ | methoxymethyl | |
| 7.141 | 3,5-$Cl_2$—Ph | H | O | H | $CH(CH_3)$ | CF3 | |
| 7.142 | 2,3,4-$F_3$—Ph | H | O | H | $CH(CH_3)$ | CH3 | |
| 7.143 | 2,3,5-$F_3$—Ph | H | O | H | $CH(CH_3)$ | CH3 | |
| 7.144 | 2,3,6-$Cl_3$—Ph | H | O | H | $CH(CH_3)$ | CH3 | |
| 7.145 | 2,3-$Cl_2$-5-MeO—Ph | H | O | H | $CH(CH_3)$ | CH3 | |
| 7.146 | 2,3-$Cl_2$—Ph | H | O | H | $CH(CH_3)$ | CH3 | |
| 7.147 | 2,3-$F_2$—Ph | H | O | H | $CH(CH_3)$ | CH3 | |
| 7.148 | 2,5-$Cl_2$—Ph | H | O | H | $CH(CH_3)$ | CH3 | |
| 7.149 | 2,5-$F_2$—Ph | H | O | H | $CH(CH_3)$ | CH3 | |
| 7.150 | 2-F—Ph | H | O | H | $CH(CH_3)$ | CH3 | |
| 7.151 | 3-($CF_3CH_2O$)—Ph | H | O | H | $CH(CH_3)$ | CH3 | |
| 7.152 | 3-($ClCH_2CH_2O$)—Ph | H | O | H | $CH(CH_3)$ | CH3 | |
| 7.153 | 3-(2-MeOEtO)—Ph | H | O | H | $CH(CH_3)$ | CH3 | |
| 7.154 | 3-$Me_2N$—Ph | H | O | H | $CH(CH_3)$ | CH3 | |
| 7.155 | 3-iPrCOO—Ph | H | O | H | $CH(CH_3)$ | CH3 | |
| 7.156 | 3-iPrO—Ph | H | O | H | $CH(CH_3)$ | CH3 | |
| 7.157 | 3-$CF_3O$—Ph | H | O | H | $CH(CH_3)$ | CH3 | |
| 7.158 | 3,4-$Cl_2$—Ph | H | O | H | $CH(CH_3)$ | CH3 | |
| 7.159 | 3,5-$(CF_3)_2$—Ph | H | O | H | $CH(CH_3)$ | CH3 | |
| 7.160 | 3,5-$Cl_2$—Ph | $CH_3$ | O | H | $CH(CH_3)$ | CH3 | |
| 7.161 | 3,5-$Cl_2$—Ph | H | O | H | $CH(CH_3)$ | CH3 | [$CDCl_3$] 1.00 (t, 3H); 1.13 (d, 3H); 1.18 (d, 3H); 1.93 (m, 1H); 2.14 (m, 1H); 3.18 (d, 1H); 3.69 (d, 1H); 4.05 (m, 1H); 6.62 (d, 1H); 7.40 (t, 1H); 7.50 (d, 1H) |
| 7.162 | 3,5-$Cl_2$—Ph | H | O | OH | $CH(CH_3)$ | CH3 | |
| 7.163 | 3,5-$Cl_2$—Ph | H | S | H | $CH(CH_3)$ | CH3 | |
| 7.164 | 3,5-$F_2$—Ph | H | O | H | $CH(CH_3)$ | CH3 | |
| 7.165 | 3,5-$Me_2$—Ph | H | O | H | $CH(CH_3)$ | CH3 | |
| 7.166 | R002 | H | O | H | $CH(CH_3)$ | CH3 | |
| 7.167 | R003 | H | O | H | $CH(CH_3)$ | CH3 | |
| 7.168 | 3-$CNCH_2N(Me)$—Ph | H | O | H | $CH(CH_3)$ | CH3 | |
| 7.169 | 3-$Me_2NCONH$—Ph | H | O | H | $CH(CH_3)$ | CH3 | |
| 7.170 | 3-$Me_2NSO_2O$—Ph | H | O | H | $CH(CH_3)$ | CH3 | |
| 7.171 | 3-EtNHCOO—Ph | H | O | H | $CH(CH_3)$ | CH3 | |
| 7.172 | 3-$EtSO_2O$—Ph | H | O | H | $CH(CH_3)$ | CH3 | |
| 7.173 | 3-$MeSO_2NH$—Ph | H | O | H | $CH(CH_3)$ | CH3 | |
| 7.174 | 3-$MeSO_2O$—Ph | H | O | H | $CH(CH_3)$ | CH3 | |

TABLE 7-continued

Compounds of the general formula (I) according to the invention in which $R^2$ is hydrogen and $R^3$ is ethyl and aryl is the radical

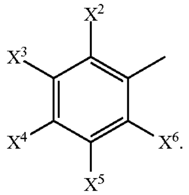

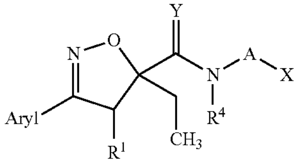

| No. | Aryl | $R^1$ | Y | $R^4$ | A | X | Physical data |
|---|---|---|---|---|---|---|---|
| 7.175 | 3-tert•BuOCONH—Ph | H | O | H | $CH(CH_3)$ | CH3 | |
| 7.176 | 3-$CF_3$CONH—Ph | H | O | H | $CH(CH_3)$ | CH3 | |
| 7.177 | 3-AcO-5-Cl—Ph | H | O | H | $CH(CH_3)$ | CH3 | |
| 7.178 | 3-AcO—Ph | H | O | H | $CH(CH_3)$ | CH3 | |
| 7.179 | 3-$NH_2$—Ph | H | O | H | $CH(CH_3)$ | CH3 | |
| 7.180 | 3-Br-5-$CF_3$—Ph | H | O | H | $CH(CH_3)$ | CH3 | |
| 7.181 | 3-Br-5-Cl—Ph | H | O | H | $CH(CH_3)$ | CH3 | |
| 7.182 | 3-Cl-4-F—Ph | H | O | H | $CH(CH_3)$ | CH3 | |
| 7.183 | 3-Cl-4-Me—Ph | H | O | H | $CH(CH_3)$ | CH3 | |
| 7.184 | 3-Cl-5-$CF_3$—Ph | H | O | H | $CH(CH_3)$ | CH3 | |
| 7.185 | R001 | H | O | H | $CH(CH_3)$ | CH3 | |
| 7.186 | 3-Cl-5-F—Ph | H | O | H | $CH(CH_3)$ | CH3 | |
| 7.187 | 3-Cl-5-MeO—Ph | H | O | H | $CH(CH_3)$ | CH3 | |
| 7.188 | 3-Cl-5-Me—Ph | H | O | H | $CH(CH_3)$ | CH3 | |
| 7.189 | 3-Cl-5-($CF_3CH_2O$)—Ph | H | O | H | $CH(CH_3)$ | CH3 | |
| 7.190 | 3-Cl-5-($ClCH_2CH_2O$)—Ph | H | O | H | $CH(CH_3)$ | CH3 | |
| 7.191 | 3-Cl-5-($EtOCOCH_2O$)—Ph | H | O | H | $CH(CH_3)$ | CH3 | |
| 7.192 | 3-Cl-5-$CF_3O$—Ph | H | O | H | $CH(CH_3)$ | CH3 | |
| 7.193 | 3-Cl-5-$Me_2NSO_2O$—Ph | H | O | H | $CH(CH_3)$ | CH3 | |
| 7.194 | 3-Cl-5-($MeSO_2O$)—Ph | H | O | H | $CH(CH_3)$ | CH3 | |
| 7.195 | 3-Cl-5-iPrO—Ph | H | O | H | $CH(CH_3)$ | CH3 | |
| 7.196 | 3-Cl—Ph | H | O | H | $CH(CH_3)$ | CH3 | |
| 7.197 | 3-EtO—Ph | H | O | H | $CH(CH_3)$ | CH3 | |
| 7.198 | 3-F-5-Me—Ph | H | O | H | $CH(CH_3)$ | CH3 | |
| 7.199 | 3-F—Ph | H | O | H | $CH(CH_3)$ | CH3 | |
| 7.200 | 3-OH—Ph | H | O | H | $CH(CH_3)$ | CH3 | |
| 7.201 | 3-MeO—Ph | H | O | H | $CH(CH_3)$ | CH3 | |
| 7.202 | 3-Me—Ph | H | O | H | $CH(CH_3)$ | CH3 | |
| 7.203 | 3-$NO_2$—Ph | H | O | H | $CH(CH_3)$ | CH3 | |
| 7.204 | $F_5$—Ph | H | O | H | $CH(CH_3)$ | CH3 | |
| 7.205 | Ph | H | O | H | $CH(CH_3)$ | CH3 | |
| 7.206 | 3,5-$Cl_2$—Ph | H | O | H | $CH(CH_3)$ | COOH | |
| 7.207 | 3-Cl-4-F—Ph | H | O | H | $CH(CH_3)$ | COOH | |
| 7.208 | 3,5-$Cl_2$—Ph | H | O | H | $CH(CH_3)$ | c-Pr | |
| 7.209 | 3,5-$F_2$—Ph | H | O | H | $CH(CH_3)$ | c-Pr | |
| 7.210 | Ph | H | O | H | $CH(CH_3)$ | c-Pr | |
| 7.211 | 3-Cl-4-F—Ph | H | O | H | $CH(CH_3)$ | dimethylcarbamoyl | |
| 7.212 | 3,5-$Cl_2$—Ph | H | O | H | $CH(CH_3)$ | ethynyl | |
| 7.213 | 3,5-$Cl_2$—Ph | H | O | H | $CH(CH_3)$ | ethyl | |
| 7.214 | 3,5-$Cl_2$—Ph | $CH_3$ | O | H | $CH(CH_3)$ | methoxycarbonyl | |
| 7.215 | 3,5-$Cl_2$—Ph | H | O | H | $CH(CH_3)$ | methoxycarbonyl | |
| 7.216 | 3-Cl-4-F—Ph | H | O | H | $CH(CH_3)$ | methoxycarbonyl | |
| 7.217 | 3-Cl-4-F—Ph | H | O | H | $CH(CH_3)$ | methylcarbamoyl | |
| 7.218 | 3,5-$Cl_2$—Ph | H | O | H | $CH(CH_3)$ | pentyl | |
| 7.219 | 3,5-$Cl_2$—Ph | H | O | H | $CH(CH_3)CH_2$ | (2,2,2-trifluoroethoxy)-carbonyl | |

TABLE 7-continued

Compounds of the general formula (I) according to the invention in which $R^2$ is hydrogen and $R^3$ is ethyl and aryl is the radical

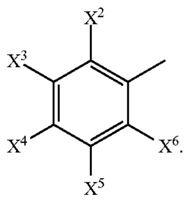

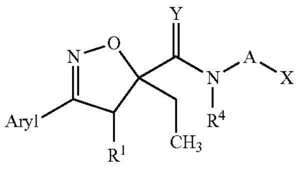

| No. | Aryl | $R^1$ | Y | $R^4$ | A | X | Physical data |
|---|---|---|---|---|---|---|---|
| 7.220 | 3,5-$F_2$—Ph | H | O | H | $CH(CH_3)CH_2$ | (2,2,2-trifluoroethoxy)-carbonyl | |
| 7.221 | 3,5-$Cl_2$—Ph | H | O | H | $CH(CH_3)CH_2$ | (2-hydroxyethoxy)-carbonyl | |
| 7.222 | 3,5-$F_2$—Ph | H | O | H | $CH(CH_3)CH_2$ | (2-hydroxyethoxy)-carbonyl | |
| 7.223 | 3,5-$Cl_2$—Ph | H | O | H | $CH(CH_3)CH_2$ | (allyloxy)carbonyl | |
| 7.224 | 3,5-$F_2$—Ph | H | O | H | $CH(CH_3)CH_2$ | (allyloxy)carbonyl | |
| 7.225 | 3,5-$Cl_2$—Ph | H | O | H | $CH(CH_3)CH_2$ | (cyclopropylsulfonyl)-(methyl)carbamoyl | |
| 7.226 | 3,5-$F_2$—Ph | H | O | H | $CH(CH_3)CH_2$ | (cyclopropylsulfonyl)-(methyl)carbamoyl | |
| 7.227 | 3,5-$Cl_2$—Ph | H | O | H | $CH(CH_3)CH_2$ | (cyclopropylsulfonyl)-carbamoyl | |
| 7.228 | 3,5-$F_2$—Ph | H | O | H | $CH(CH_3)CH_2$ | (cyclopropylsulfonyl)-carbamoyl | |
| 7.229 | 3,5-$Cl_2$—Ph | H | O | H | $CH(CH_3)CH_2$ | (ethylsulfonyl)(methyl)-carbamoyl | |
| 7.230 | 3,5-$F_2$—Ph | H | O | H | $CH(CH_3)CH_2$ | (ethylsulfonyl)(methyl)-carbamoyl | |
| 7.231 | 3,5-$Cl_2$—Ph | H | O | H | $CH(CH_3)CH_2$ | (ethylsulfonyl)-carbamoyl | |
| 7.232 | 3,5-$F_2$—Ph | H | O | H | $CH(CH_3)CH_2$ | (ethylsulfonyl)-carbamoyl | |
| 7.233 | 3,5-$Cl_2$—Ph | H | O | H | $CH(CH_3)CH_2$ | (heptan-2-yloxy)carbonyl | |
| 7.234 | 3,5-$F_2$—Ph | H | O | H | $CH(CH_3)CH_2$ | (heptan-2-yloxy)carbonyl | |
| 7.235 | 3,5-$Cl_2$—Ph | H | O | H | $CH(CH_3)CH_2$ | (isopropylsulfonyl)-(methyl)carbamoyl | |
| 7.236 | 3,5-$F_2$—Ph | H | O | H | $CH(CH_3)CH_2$ | (isopropylsulfonyl)-(methyl)carbamoyl | |
| 7.237 | 3,5-$Cl_2$—Ph | H | O | H | $CH(CH_3)CH_2$ | (isopropylsulfonyl)-carbamoyl | |
| 7.238 | 3,5-$F_2$—Ph | H | O | H | $CH(CH_3)CH_2$ | (isopropylsulfonyl)-carbamoyl | |
| 7.239 | 3,5-$Cl_2$—Ph | H | O | H | $CH(CH_3)CH_2$ | (methylsulfonyl)-carbamoyl | |
| 7.240 | 3,5-$F_2$—Ph | H | O | H | $CH(CH_3)CH_2$ | (methylsulfonyl)-carbamoyl | |
| 7.241 | 3,5-$Cl_2$—Ph | H | O | H | $CH(CH_3)CH_2$ | (prop-2-Yn-1-yloxy)carbonyl | |
| 7.242 | 3,5-$F_2$—Ph | H | O | H | $CH(CH_3)CH_2$ | (prop-2-Yn-1-yloxy)carbonyl | |
| 7.243 | 3,5-$Cl_2$—Ph | H | O | H | $CH(CH_3)CH_2$ | (propan-2-yloxy)carbonyl | |
| 7.244 | 3,5-$F_2$—Ph | H | O | H | $CH(CH_3)CH_2$ | (propan-2-yloxy)carbonyl | |
| 7.245 | 3-Cl—Ph | H | O | H | $CH(CH_3)CH_2$ | (propan-2-yloxy)carbonyl | |
| 7.246 | 3-F—Ph | H | O | H | $CH(CH_3)CH_2$ | (propan-2-yloxy)carbonyl | |
| 7.247 | 3,5-$Cl_2$—Ph | H | O | H | $CH(CH_3)CH_2$ | [2-(methylsulfanyl)-ethoxy]carbonyl | |
| 7.248 | 3,5-$F_2$—Ph | H | O | H | $CH(CH_3)CH_2$ | [2-(methylsulfanyl)-ethoxy]carbonyl | |

TABLE 7-continued

Compounds of the general formula (I) according to the invention in which $R^2$ is hydrogen and $R^3$ is ethyl and aryl is the radical

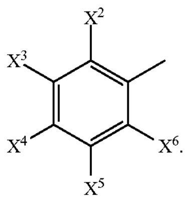

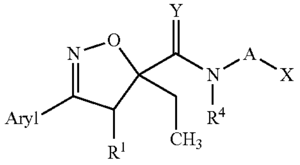

| No. | Aryl | $R^1$ | Y | $R^4$ | A | X | Physical data |
|---|---|---|---|---|---|---|---|
| 7.249 | 3,5-$F_2$—Ph | H | O | H | $CH(CH_3)CH_2$ | [2-(methylsulfonyl)-ethoxy]carbonyl | |
| 7.250 | 3,5-$Cl_2$—Ph | H | O | H | $CH(CH_3)CH_2$ | butoxycarbonyl | |
| 7.251 | 3,5-$F_2$—Ph | H | O | H | $CH(CH_3)CH_2$ | butoxycarbonyl | |
| 7.252 | 3-$CF_3$—Ph | H | O | H | $CH(CH_3)CH_2$ | COOH | |
| 7.253 | 3,5-$Cl_2$—Ph | H | O | H | $CH(CH_3)CH_2$ | COOH | |
| 7.254 | 3,5-$F_2$—Ph | H | O | H | $CH(CH_3)CH_2$ | COOH | |
| 7.255 | 3,5-(tert•Bu)$_2$—Ph | H | O | H | $CH(CH_3)CH_2$ | COOH | |
| 7.256 | 3-Br-5-$CF_3$—Ph | H | O | H | $CH(CH_3)CH_2$ | COOH | |
| 7.257 | 3-Cl-5-$CF_3$—Ph | H | O | H | $CH(CH_3)CH_2$ | COOH | |
| 7.258 | 3-Cl—Ph | H | O | H | $CH(CH_3)CH_2$ | COOH | |
| 7.259 | 3-Et-5-F—Ph | H | O | H | $CH(CH_3)CH_2$ | COOH | |
| 7.260 | 3-Et—Ph | H | O | H | $CH(CH_3)CH_2$ | COOH | |
| 7.261 | 3-F-5-MeO—Ph | H | O | H | $CH(CH_3)CH_2$ | COOH | |
| 7.262 | 3-F—Ph | H | O | H | $CH(CH_3)CH_2$ | COOH | |
| 7.263 | 3-Me—Ph | H | O | H | $CH(CH_3)CH_2$ | COOH | |
| 7.264 | 4-MeO—Ph | H | O | H | $CH(CH_3)CH_2$ | COOH | |
| 7.265 | 3-$CF_3$—Ph | H | O | H | $CH(CH_3)CH_2$ | ethoxycarbonyl | |
| 7.266 | 3,5-$Cl_2$-4-MeO—Ph | H | O | H | $CH(CH_3)CH_2$ | ethoxycarbonyl | |
| 7.267 | 3,5-$Cl_2$—Ph | H | O | H | $CH(CH_3)CH_2$ | ethoxycarbonyl | |
| 7.268 | 3,5-$Et_2$—Ph | H | O | H | $CH(CH_3)CH_2$ | ethoxycarbonyl | |
| 7.269 | 3,5-$F_2$—Ph | H | O | H | $CH(CH_3)CH_2$ | ethoxycarbonyl | |
| 7.270 | 3,5-(MeO)$_2$—Ph | H | O | H | $CH(CH_3)CH_2$ | ethoxycarbonyl | |
| 7.271 | 3,5-$Me_2$—Ph | H | O | H | $CH(CH_3)CH_2$ | ethoxycarbonyl | |
| 7.272 | 3,5-(tert•Bu)$_2$—Ph | H | O | H | $CH(CH_3)CH_2$ | ethoxycarbonyl | |
| 7.273 | 3-Br-5-$CF_3$—Ph | H | O | H | $CH(CH_3)CH_2$ | ethoxycarbonyl | |
| 7.274 | 3-Cl-5-Et—Ph | H | O | H | $CH(CH_3)CH_2$ | ethoxycarbonyl | |
| 7.275 | 3-Cl-5-$CF_3$—Ph | H | O | H | $CH(CH_3)CH_2$ | ethoxycarbonyl | |
| 7.276 | 3-Cl—Ph | H | O | H | $CH(CH_3)CH_2$ | ethoxycarbonyl | |
| 7.277 | 3-c-Pr-5-F—Ph | H | O | H | $CH(CH_3)CH_2$ | ethoxycarbonyl | |
| 7.278 | 3-Et-5-F—Ph | H | O | H | $CH(CH_3)CH_2$ | ethoxycarbonyl | |
| 7.279 | 3-Et—Ph | H | O | H | $CH(CH_3)CH_2$ | ethoxycarbonyl | |
| 7.280 | 3-F-5-MeS—Ph | H | O | H | $CH(CH_3)CH_2$ | ethoxycarbonyl | |
| 7.281 | 3-F-5-$MeSO_2$—Ph | H | O | H | $CH(CH_3)CH_2$ | ethoxycarbonyl | |
| 7.282 | 3-F-5-MeO—Ph | H | O | H | $CH(CH_3)CH_2$ | ethoxycarbonyl | |
| 7.283 | 3-F—Ph | H | O | H | $CH(CH_3)CH_2$ | ethoxycarbonyl | D1 [CDCl3] 0.99 (t, 3H); 1.22 (t, 3H); 1.27 (d, 3H); 1.94 (m, 1H); 2.14 (m, 1H); 2.48 (d, 2H); 3.20 (d, 1H); 3.71 (d, 1H); 4.05 (q, 2H); 4.33 (m, 1H); 7.12 (m, 2H); 7.38 (m, 3H). D2 [CDCl3] 1.00 (t, 3H); 1.23 (t, 3H); 1.28 (d, 3H); 1.94 (m, 1H); 2.14 (m, 1H); 2.53 (m, 2H); 3.20 (d, 1H); 3.72 (d, 1H); 4.15 |

TABLE 7-continued

Compounds of the general formula (I) according to the invention in which $R^2$ is hydrogen and $R^3$ is ethyl and aryl is the radical

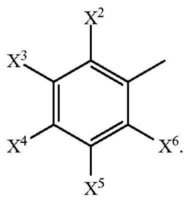

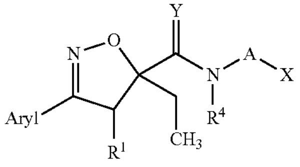

| No. | Aryl | $R^1$ | Y | $R^4$ | A | X | Physical data |
|---|---|---|---|---|---|---|---|
| | | | | | | | (q, 2H); 4.33 (m, 1H); 7.12 (m, 1H); 7.21 (d br, 1H); 7.38 (m, 3H). |
| 7.284 | 3-Me-5-$CF_3O$—Ph | H | O | H | $CH(CH_3)CH_2$ | ethoxycarbonyl | |
| 7.285 | 3-Me—Ph | H | O | H | $CH(CH_3)CH_2$ | ethoxycarbonyl | |
| 7.286 | 4-EtO—Ph | H | O | H | $CH(CH_3)CH_2$ | ethoxycarbonyl | |
| 7.287 | 4-MeO—Ph | H | O | H | $CH(CH_3)CH_2$ | ethoxycarbonyl | |
| 7.288 | 3,5-$Cl_2$—Ph | H | O | H | $CH(CH_3)CH_2$ | hydroxy | |
| 7.289 | 3,5-$Cl_2$—Ph | H | O | H | $CH(CH_3)CH_2$ | isobutoxycarbonyl | |
| 7.290 | 3,5-$F_2$—Ph | H | O | H | $CH(CH_3)CH_2$ | isobutoxycarbonyl | |
| 7.291 | 3,5-$Cl_2$—Ph | H | O | H | $CH(CH_3)CH_2$ | methoxy | |
| 7.292 | 2,5-$Me_2$—Ph | H | O | H | $CH(CH_3)CH_2$ | methoxycarbonyl | |
| 7.293 | 2-Cl-3-F-5-MeO—Ph | H | O | H | $CH(CH_3)CH_2$ | methoxycarbonyl | |
| 7.294 | 2-F-3-Me—Ph | H | O | H | $CH(CH_3)CH_2$ | methoxycarbonyl | |
| 7.295 | 3-$CF_3$—Ph | H | O | H | $CH(CH_3)CH_2$ | methoxycarbonyl | |
| 7.296 | 3,5-$Cl_2$—Ph | H | O | H | $CH(CH_3)CH_2$ | methoxycarbonyl | |
| 7.297 | 3,5-$F_2$—Ph | H | O | H | $CH(CH_3)CH_2$ | methoxycarbonyl | |
| 7.298 | 3-Cl—Ph | H | O | H | $CH(CH_3)CH_2$ | methoxycarbonyl | |
| 7.299 | 3-F-5-MeO—Ph | H | O | H | $CH(CH_3)CH_2$ | methoxycarbonyl | |
| 7.300 | 3-F—Ph | H | O | H | $CH(CH_3)CH_2$ | methoxycarbonyl | |
| 7.301 | 3,5-$Cl_2$—Ph | H | O | H | $CH(CH_3)CH_2$ | methyl(methylsulfonyl)-carbamoyl | |
| 7.302 | 3,5-$F_2$—Ph | H | O | H | $CH(CH_3)CH_2$ | methyl(methylsulfonyl)-carbamoyl | |
| 7.303 | 3,5-$Cl_2$—Ph | H | O | H | $CH(CH_3)CH_2$ | methylcarbamoyl | |
| 7.304 | 3,5-$Cl_2$—Ph | H | O | H | $CH(CH_3)CH_2$ | propoxycarbonyl | |
| 7.305 | 3,5-$F_2$—Ph | H | O | H | $CH(CH_3)CH_2$ | propoxycarbonyl | |
| 7.306 | 3,5-$Cl_2$—Ph | H | O | H | $CH(CH_3)CH_2$ | sec-butoxycarbonyl | |
| 7.307 | 3,5-$F_2$—Ph | H | O | H | $CH(CH_3)CH_2$ | sec-butoxycarbonyl | |
| 7.308 | 3,5-$Cl_2$—Ph | H | O | H | $CH(COOCH_3)CH_2$ | methoxycarbonyl | |
| 7.309 | 3,5-$Cl_2$—Ph | H | O | H | CH(cycloPr) | c-Pr | |
| 7.310 | 3,5-$F_2$—Ph | H | O | H | CH(cycloPr) | c-Pr | |
| 7.311 | 3,5-$Cl_2$—Ph | H | O | H | CH(iPr) | methoxycarbonyl | |
| 7.312 | 3,5-$Cl_2$—Ph | H | O | H | $CH(iPr)CH_2$ | methoxycarbonyl | |
| 7.313 | 3,5-$F_2$—Ph | H | O | H | $CH_2$ | (2-hydroxyethyl)-carbamoyl | |
| 7.314 | 3,5-$Cl_2$—Ph | H | O | H | $CH_2$ | (cyclopropylsulfonyl)-carbamoyl | |
| 7.315 | 3,5-$F_2$—Ph | H | O | H | $CH_2$ | (cyclopropylsulfonyl)-carbamoyl | |
| 7.316 | 3,5-$Cl_2$—Ph | H | O | H | $CH_2$ | (ethylsulfonyl)-carbamoyl | |
| 7.317 | 3,5-$F_2$—Ph | H | O | H | $CH_2$ | (ethylsulfonyl)-carbamoyl | |
| 7.318 | 3,5-$F_2$—Ph | H | O | H | $CH_2$ | (hydroxyimino)methyl | |
| 7.319 | 3,5-$Cl_2$—Ph | H | O | H | $CH_2$ | (isopropylsulfonyl)-carbamoyl | |
| 7.320 | 3,5-$F_2$—Ph | H | O | H | $CH_2$ | (isopropylsulfonyl)-carbamoyl | |
| 7.321 | 3,5-$Cl_2$—Ph | H | O | H | $CH_2$ | (methylsulfonyl)-carbamoyl | |
| 7.322 | 3,5-$F_2$—Ph | H | O | H | $CH_2$ | (methylsulfonyl)-carbamoyl | |

TABLE 7-continued

Compounds of the general formula (I) according to the invention in which $R^2$ is hydrogen and $R^3$ is ethyl and aryl is the radical

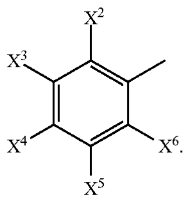

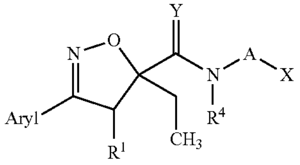

| No. | Aryl | $R^1$ | Y | $R^4$ | A | X | Physical data |
|---|---|---|---|---|---|---|---|
| 7.323 | 3-Cl—Ph | H | O | H | $CH_2$ | (propan-2-yloxy)carbonyl | |
| 7.324 | 3-F—Ph | H | O | H | $CH_2$ | (propan-2-yloxy)carbonyl | |
| 7.325 | 3,5-$Cl_2$—Ph | H | O | H | $CH_2$ | 1,1-dioxidotetrahydro-thiophen-3-yl | |
| 7.326 | 3,5-$F_2$—Ph | H | O | H | $CH_2$ | 1,1-dioxidotetrahydro-thiophen-3-yl | |
| 7.327 | 3-F—Ph | H | O | H | $CH_2$ | 1,1-dioxidotetrahydro-thiophen-3-yl | |
| 7.328 | Ph | H | O | H | $CH_2$ | 1,1-dioxidotetrahydro-thiophen-3-yl | |
| 7.329 | Ph | H | O | H | $CH_2$ | 1,4-dimethyl-5-oxo-4,5-dihydro-1H-1,2,4-triazol-3-yl | |
| 7.330 | 3,5-$Cl_2$—Ph | H | O | H | $CH_2$ | 3-(2-ethoxy-2-oxoethyl)oxetan-3-yl | |
| 7.331 | 3,5-$F_2$—Ph | H | O | H | $CH_2$ | 3-(2-ethoxy-2-oxoethyl)oxetan-3-yl | |
| 7.332 | 3,5-$Cl_2$—Ph | H | O | H | $CH_2$ | 3-(cyclopropyl-carbamoyl)-4,5-dihydro-1,2-oxazol-5-yl | |
| 7.333 | 3,5-$Cl_2$—Ph | H | O | H | $CH_2$ | 3-(ethoxycarbonyl)-4,5-dihydro-1,2-oxazol-5-yl | |
| 7.334 | 3,5-$Cl_2$—Ph | H | O | H | $CH_2$ | 3-(methylcarbamoyl)-4,5-dihydro-1,2-oxazol-5-yl | |
| 7.335 | 3,5-$Cl_2$—Ph | H | O | H | $CH_2$ | 3-carboxy-4,5-dihydro-1,2-oxazol-5-yl | |
| 7.336 | 3,5-$Cl_2$—Ph | H | O | H | $CH_2$ | 3-isopropyl-4,5-dihydro-1,2-oxazol-5-yl | |
| 7.337 | 3,5-$Cl_2$—Ph | H | O | H | $CH_2$ | 3-methyl-4,5-dihydro-1,2-oxazol-5-yl | |
| 7.338 | 3,5-$F_2$—Ph | H | O | H | $CH_2$ | 5-(ethoxycarbonyl)-4,5-dihydro-1,2-oxazol-3-yl | |
| 7.339 | 3,5-$Cl_2$—Ph | H | O | H | $CH_2$ | 5,5-dimethyl-4,5-dihydro-1,2-oxazol-3-yl | |
| 7.340 | 3,5-$Cl_2$—Ph | H | O | H | $CH_2$ | 5-ethyl-4,5-dihydro-1,2-oxazol-3-yl | |
| 7.341 | 3,5-$Cl_2$—Ph | H | O | H | $CH_2$ | 5-isopropyl-4,5-dihydro-1,2-oxazol-3-yl | |
| 7.342 | 3,5-$Cl_2$—Ph | H | O | H | $CH_2$ | 5-methyl-4,5-dihydro-1,2-oxazol-3-yl | |
| 7.343 | 3,5-$Cl_2$—Ph | H | O | H | $CH_2$ | carbamoyl | |
| 7.344 | 3-Cl—Ph | H | O | H | $CH_2$ | carbamoyl | |
| 7.345 | 2-$CF_3$—Ph | H | O | H | $CH_2$ | $CF_3$ | |
| 7.346 | 2,3,4-$F_3$—Ph | H | O | H | $CH_2$ | $CF_3$ | |
| 7.347 | 2,3,5-$F_3$—Ph | H | O | H | $CH_2$ | $CF_3$ | |
| 7.348 | 2,3,6-$Cl_3$—Ph | H | O | H | $CH_2$ | $CF_3$ | |

TABLE 7-continued

Compounds of the general formula (I) according to the invention in which $R^2$ is hydrogen and $R^3$ is ethyl and aryl is the radical

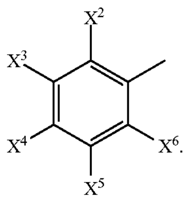

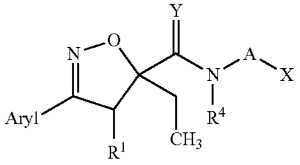

| No. | Aryl | $R^1$ | Y | $R^4$ | A | X | Physical data |
|---|---|---|---|---|---|---|---|
| 7.349 | 2,3-$F_2$—Ph | H | O | H | $CH_2$ | $CF_3$ | |
| 7.350 | 2,5-$F_2$—Ph | H | O | H | $CH_2$ | $CF_3$ | |
| 7.351 | 2-Cl-3-F-5-MeO—Ph | H | O | H | $CH_2$ | $CF_3$ | |
| 7.352 | 3-(2-MeOEtO)—Ph | H | O | H | $CH_2$ | $CF_3$ | |
| 7.353 | 3-iPrO—Ph | H | O | H | $CH_2$ | $CF_3$ | |
| 7.354 | 3-$CF_3$O—Ph | H | O | H | $CH_2$ | $CF_3$ | |
| 7.355 | 3-$CF_3$—Ph | H | O | H | $CH_2$ | $CF_3$ | |
| 7.356 | 3,4-$Cl_2$—Ph | H | O | H | $CH_2$ | $CF_3$ | |
| 7.357 | 3,5-$Br_2$—Ph | H | O | H | $CH_2$ | $CF_3$ | |
| 7.358 | 3,5-$Cl_2$-4-MeO—Ph | H | O | H | $CH_2$ | $CF_3$ | |
| 7.359 | 3,5-$Cl_2$—Ph | H | O | H | $CH_2$ | $CF_3$ | |
| 7.360 | 3,5-$F_2$—Ph | H | O | H | $CH_2$ | $CF_3$ | |
| 7.361 | 3,5-$(MeO)_2$—Ph | H | O | H | $CH_2$ | $CF_3$ | |
| 7.362 | 3,5-$Me_2$—Ph | H | O | H | $CH_2$ | $CF_3$ | |
| 7.363 | 3-Br-5-Cl—Ph | H | O | H | $CH_2$ | $CF_3$ | |
| 7.364 | 3-Br-5-F—Ph | H | O | H | $CH_2$ | $CF_3$ | |
| 7.365 | 3-Cl-5-$CF_3$—Ph | H | O | H | $CH_2$ | $CF_3$ | |
| 7.366 | 3-Cl-5-Et—Ph | H | O | H | $CH_2$ | $CF_3$ | |
| 7.367 | 3-Cl-5-F—Ph | H | O | H | $CH_2$ | $CF_3$ | |
| 7.368 | 3-Cl-5-Me—Ph | H | O | H | $CH_2$ | $CF_3$ | |
| 7.369 | 3-Cl-5-$CF_3$O—Ph | H | O | H | $CH_2$ | $CF_3$ | |
| 7.370 | 3-Cl—Ph | H | O | H | $CH_2$ | $CF_3$ | |
| 7.371 | 3-EtO—Ph | H | O | H | $CH_2$ | $CF_3$ | |
| 7.372 | 3-Et-5-F—Ph | H | O | H | $CH_2$ | $CF_3$ | |
| 7.373 | 3-Et—Ph | H | O | H | $CH_2$ | $CF_3$ | |
| 7.374 | 3-F-5-MeS—Ph | H | O | H | $CH_2$ | $CF_3$ | |
| 7.375 | 3-F-5-$MeSO_2$—Ph | H | O | H | $CH_2$ | $CF_3$ | |
| 7.376 | 3-F-5-$CF_3$—Ph | H | O | H | $CH_2$ | $CF_3$ | |
| 7.377 | 3-F-5-MeO—Ph | H | O | H | $CH_2$ | $CF_3$ | |
| 7.378 | 3-F-5-Me—Ph | H | O | H | $CH_2$ | $CF_3$ | |
| 7.379 | 3-F—Ph | H | O | H | $CH_2$ | $CF_3$ | [CDCl3] 1.02 (t, 3H); 1.96 (m, 1H); 2.19 (m, 1H); 3.28 (d, 1H); 3.70 (m, 1H); 3.72 (d, 1H); 4.13 (m, 1H); 7.13 (m, 1H); 7.18 (s br, 1H); 7.38 (m, 3H). |
| 7.380 | 3-OH—Ph | H | O | H | $CH_2$ | $CF_3$ | |
| 7.381 | 3-iPr—Ph | H | O | H | $CH_2$ | $CF_3$ | |
| 7.382 | 3-Me—Ph | H | O | H | $CH_2$ | $CF_3$ | |
| 7.383 | 3-$NO_2$—Ph | H | O | H | $CH_2$ | $CF_3$ | |
| 7.384 | 4-EtO—Ph | H | O | H | $CH_2$ | $CF_3$ | |
| 7.385 | 4-MeO—Ph | H | O | H | $CH_2$ | $CF_3$ | |
| 7.386 | $F_5$—Ph | H | O | H | $CH_2$ | $CF_3$ | |
| 7.387 | Ph | H | O | H | $CH_2$ | $CF_3$ | |
| 7.388 | 2,3,5-$F_3$—Ph | H | O | H | $CH_2$ | $CH_3$ | |
| 7.389 | 2,3-$F_2$—Ph | H | O | H | $CH_2$ | $CH_3$ | |
| 7.390 | 3,4-$F_2$—Ph | H | O | H | $CH_2$ | $CH_3$ | |
| 7.391 | 3,5-$Cl_2$—Ph | H | O | H | $CH_2$ | $CH_3$ | |
| 7.392 | 3,5-$F_2$—Ph | H | O | H | $CH_2$ | $CH_3$ | |
| 7.393 | 3-Cl-5-$CF_3$—Ph | H | O | H | $CH_2$ | $CH_3$ | |

TABLE 7-continued

Compounds of the general formula (I) according to the invention in which $R^2$ is hydrogen and $R^3$ is ethyl and aryl is the radical

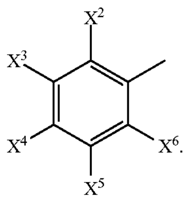

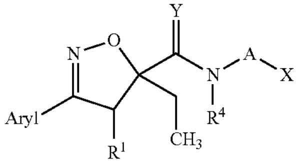

| No. | Aryl | $R^1$ | Y | $R^4$ | A | X | Physical data |
|---|---|---|---|---|---|---|---|
| 7.394 | 3-Cl-5-Me—Ph | H | O | H | $CH_2$ | $CH_3$ | |
| 7.395 | 3-Cl-5-$CF_3O$—Ph | H | O | H | $CH_2$ | $CH_3$ | |
| 7.396 | 3-EtO—Ph | H | O | H | $CH_2$ | $CH_3$ | |
| 7.397 | 3-Et—Ph | H | O | H | $CH_2$ | $CH_3$ | |
| 7.398 | 3-F—Ph | H | O | H | $CH_2$ | $CH_3$ | |
| 7.399 | 3-Me—Ph | H | O | H | $CH_2$ | $CH_3$ | |
| 7.400 | $F_5$—Ph | H | O | H | $CH_2$ | $CH_3$ | |
| 7.401 | Ph | H | O | H | $CH_2$ | $CH_3$ | |
| 7.402 | 3,5-$Cl_2$—Ph | H | O | H | $CH_2$ | COOH | |
| 7.403 | 3,5-$F_2$—Ph | H | O | H | $CH_2$ | COOH | |
| 7.404 | 3-Cl—Ph | H | O | H | $CH_2$ | COOH | |
| 7.405 | 3-F—Ph | H | O | H | $CH_2$ | COOH | |
| 7.406 | 3,5-$Cl_2$—Ph | H | O | H | $CH_2$ | cyanogen | |
| 7.407 | 3,5-$F_2$—Ph | H | O | H | $CH_2$ | cyanogen | |
| 7.408 | 3-Cl-5-$CF_3O$—Ph | H | O | H | $CH_2$ | cyanogen | |
| 7.409 | 3-F-5-Me—Ph | H | O | H | $CH_2$ | cyanogen | |
| 7.410 | 3-F—Ph | H | O | H | $CH_2$ | cyano | |
| 7.411 | 3-$NO_2$—Ph | H | O | H | $CH_2$ | cyano | |
| 7.412 | 3,5-$Cl_2$—Ph | H | O | H | $CH_2$ | cyclohexyl | |
| 7.413 | 3,5-$Cl_2$—Ph | H | O | H | $CH_2$ | c-Pr | |
| 7.414 | 3,5-$F_2$—Ph | H | O | H | $CH_2$ | c-Pr | |
| 7.415 | 3,5-$Cl_2$—Ph | H | O | H | $CH_2$ | diethoxyphosphoryl | |
| 7.416 | 3,5-$F_2$—Ph | H | O | H | $CH_2$ | diethoxyphosphoryl | |
| 7.417 | 3-F—Ph | H | O | H | $CH_2$ | diethoxyphosphoryl | |
| 7.418 | Ph | H | O | H | $CH_2$ | diethoxyphosphoryl | |
| 7.419 | 3,5-$Cl_2$—Ph | H | O | H | $CH_2$ | difluoromethyl | |
| 7.420 | 3,5-$Cl_2$—Ph | H | O | H | $CH_2$ | dimethoxymethyl | |
| 7.421 | 3-Cl—Ph | H | O | H | $CH_2$ | dimethoxymethyl | |
| 7.422 | 3,5-$Cl_2$—Ph | H | O | H | $CH_2$ | dimethylcarbamoyl | |
| 7.423 | 3,5-$Cl_2$—Ph | H | O | H | $CH_2$ | ethenyl | |
| 7.424 | 3,5-$Cl_2$—Ph | H | O | prop-2-en-1-yl | $CH_2$ | ethenyl | |
| 7.425 | 3,5-$F_2$—Ph | H | O | H | $CH_2$ | ethenyl | |
| 7.426 | 3-F—Ph | H | O | H | $CH_2$ | ethenyl | |
| 7.427 | Ph | H | O | H | $CH_2$ | ethenyl | |
| 7.428 | 3,5-$(CF_3)_2$—Ph | H | O | H | $CH_2$ | ethynyl | |
| 7.429 | 3,5-$Cl_2$—Ph | H | O | H | $CH_2$ | ethynyl | |
| 7.430 | 3,5-$Cl_2$—Ph | H | O | prop-2-yn-1-yl | $CH_2$ | ethynyl | |
| 7.431 | 3,5-$F_2$—Ph | H | O | H | $CH_2$ | ethynyl | |
| 7.432 | 3,5-$Cl_2$—Ph | H | O | cPr | $CH_2$ | ethoxycarbonyl | |
| 7.433 | 3-Cl—Ph | H | O | H | $CH_2$ | ethoxycarbonyl | |
| 7.434 | 3-F—Ph | H | O | H | $CH_2$ | ethoxycarbonyl | |
| 7.435 | 3,5-$F_2$—Ph | H | O | H | $CH_2$ | formyl | |
| 7.436 | 3,5-$Cl_2$—Ph | H | O | H | $CH_2$ | methoxycarbonyl | |
| 7.437 | 3,5-$F_2$—Ph | H | O | H | $CH_2$ | methoxycarbonyl | |
| 7.438 | 3-Cl—Ph | H | O | H | $CH_2$ | methoxycarbonyl | |
| 7.439 | 3-F—Ph | H | O | H | $CH_2$ | methoxycarbonyl | |
| 7.440 | 3-Cl-5-F—Ph | H | O | H | $CH_2$ | methoxycarbonyl | |
| 7.441 | 3,5-$Cl_2$—Ph | H | O | H | $CH_2$ | pentafluoroethyl | |
| 7.442 | 3,5-$Cl_2$—Ph | H | O | H | $CH_2$ | pentyl | |
| 7.443 | 3,5-$F_2$—Ph | H | O | H | $CH_2$ | pentyl | |
| 7.444 | 3,5-$Cl_2$—Ph | H | O | H | $CH_2$ | piperidin-2-yl | |
| 7.445 | 3,5-$F_2$—Ph | H | O | H | $CH_2$ | piperidin-2-yl | |

TABLE 7-continued

Compounds of the general formula (I) according to the invention in which $R^2$ is hydrogen and $R^3$ is ethyl and aryl is the radical

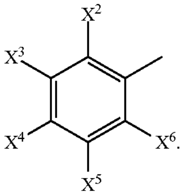

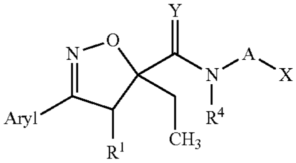

| No. | Aryl | $R^1$ | Y | $R^4$ | A | X | Physical data |
|---|---|---|---|---|---|---|---|
| 7.446 | Ph | H | O | H | $CH_2$ | piperidin-2-yl | |
| 7.447 | 3,5-$Cl_2$—Ph | H | O | $CH_3$ | $CH_2$ | propan-2-yl | |
| 7.448 | 3,5-$Cl_2$—Ph | H | O | H | $CH_2$ | propan-2-yl | |
| 7.449 | 3,5-$Cl_2$—Ph | H | O | H | $CH_2$ | pyrrolidin-1-ylcarbonyl | |
| 7.450 | 3,5-$Cl_2$—Ph | H | O | H | $CH_2$ | tert-butyl | |
| 7.451 | 3,5-$F_2$—Ph | H | O | H | $CH_2$ | tert-butyl | |
| 7.452 | 3,5-$Cl_2$—Ph | H | O | H | $CH_2$ | tetrahydrofuran-2-yl | |
| 7.453 | 3,5-$F_2$—Ph | H | O | H | $CH_2$ | tetrahydrofuran-2-yl | |
| 7.454 | 3-F—Ph | H | O | H | $CH_2$ | tetrahydrofuran-2-yl | |
| 7.455 | Ph | H | O | H | $CH_2$ | tetrahydrofuran-2-yl | |
| 7.456 | 3,5-$Cl_2$—Ph | H | O | H | $CH_2$ | tetrahydrofuran-3-yl | |
| 7.457 | 3,5-$F_2$—Ph | H | O | H | $CH_2$ | tetrahydrofuran-3-yl | |
| 7.458 | 3-F—Ph | H | O | H | $CH_2$ | tetrahydrofuran-3-yl | |
| 7.459 | Ph | H | O | H | $CH_2$ | tetrahydrofuran-3-yl | |
| 7.460 | 3,5-$Cl_2$—Ph | H | O | H | $CH_2C(CH_3)_2$ | COOH | |
| 7.461 | 3,5-$Cl_2$—Ph | H | O | H | $CH_2C(CH_3)_2$ | ethoxycarbonyl | |
| 7.462 | 3,5-$Cl_2$—Ph | H | O | H | $CH_2CH(CH_3)$ | ethoxycarbonyl | |
| 7.463 | 3,5-$Cl_2$—Ph | H | O | H | $CH_2CH_2$ | (2,2,2-trifluoroethoxy)-carbonyl | |
| 7.464 | 3,5-$Cl_2$—Ph | H | O | H | $CH_2CH_2$ | (2-hydroxyethoxy)-carbonyl | |
| 7.465 | 3,5-$Cl_2$—Ph | H | O | H | $CH_2CH_2$ | (2-methoxy-2-oxoethyl)carbamoyl | |
| 7.466 | 3,5-$Cl_2$—Ph | H | O | H | $CH_2CH_2$ | (allyloxy)carbonyl | |
| 7.467 | 3,5-$Cl_2$—Ph | H | O | H | $CH_2CH_2$ | (cyclopropylsulfonyl)-(methyl)carbamoyl | |
| 7.468 | 3,5-$F_2$—Ph | H | O | H | $CH_2CH_2$ | (cyclopropylsulfonyl)-(methyl)carbamoyl | |
| 7.469 | 3,5-$Cl_2$—Ph | H | O | H | $CH_2CH_2$ | (cyclopropylsulfonyl)-carbamoyl | |
| 7.470 | 3,5-$F_2$—Ph | H | O | H | $CH_2CH_2$ | (cyclopropylsulfonyl)-carbamoyl | |
| 7.471 | 3,5-$Cl_2$—Ph | H | O | H | $CH_2CH_2$ | (ethylsulfonyl)(methyl)-carbamoyl | |
| 7.472 | 3,5-$F_2$—Ph | H | O | H | $CH_2CH_2$ | (ethylsulfonyl)(methyl)-carbamoyl | |
| 7.473 | 3,5-$Cl_2$—Ph | H | O | H | $CH_2CH_2$ | (ethylsulfonyl)-carbamoyl | |
| 7.474 | 3,5-$F_2$—Ph | H | O | H | $CH_2CH_2$ | (ethylsulfonyl)-carbamoyl | |
| 7.475 | 3,5-$Cl_2$—Ph | H | O | H | $CH_2CH_2$ | (heptan-2-yloxy)carbonyl | |
| 7.476 | 3,5-$F_2$—Ph | H | O | H | $CH_2CH_2$ | (hydroxyimino)methyl | |
| 7.477 | 3,5-$Cl_2$—Ph | H | O | H | $CH_2CH_2$ | (isopropylsulfonyl)-(methyl)carbamoyl | |
| 7.478 | 3,5-$F_2$—Ph | H | O | H | $CH_2CH_2$ | (isopropylsulfonyl)-(methyl)carbamoyl | |
| 7.479 | 3,5-$Cl_2$—Ph | H | O | H | $CH_2CH_2$ | (isopropylsulfonyl)-carbamoyl | |
| 7.480 | 3,5-$F_2$—Ph | H | O | H | $CH_2CH_2$ | (isopropylsulfonyl)-carbamoyl | |
| 7.481 | 3,5-$Cl_2$—Ph | H | O | H | $CH_2CH_2$ | (methylsulfonyl)-carbamoyl | |
| 7.482 | 3,5-$F_2$—Ph | H | O | H | $CH_2CH_2$ | (methylsulfonyl)-carbamoyl | |

TABLE 7-continued

Compounds of the general formula (I) according to the invention in which $R^2$ is hydrogen and $R^3$ is ethyl and aryl is the radical

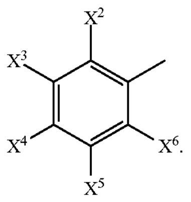

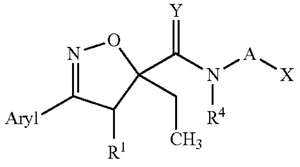

| No. | Aryl | $R^1$ | Y | $R^4$ | A | X | Physical data |
|---|---|---|---|---|---|---|---|
| 7.483 | 3,5-$Cl_2$—Ph | H | O | H | $CH_2CH_2$ | (prop-2-yn-1-yloxy)carbonyl | |
| 7.484 | 3,5-$Cl_2$—Ph | H | O | H | $CH_2CH_2$ | (propan-2-yloxy)carbonyl | |
| 7.485 | 3,5-$Cl_2$—Ph | H | O | H | $CH_2CH_2$ | [2-(methylsulfanyl)-ethoxy]carbonyl | |
| 7.486 | 3,5-$Cl_2$—Ph | H | O | H | $CH_2CH_2$ | 1,3-dioxolan-2-yl | |
| 7.487 | 3,5-$F_2$—Ph | H | O | H | $CH_2CH_2$ | 1,3-dioxolan-2-yl | |
| 7.488 | 3-F—Ph | H | O | H | $CH_2CH_2$ | 1,3-dioxolan-2-yl | |
| 7.489 | Ph | H | O | H | $CH_2CH_2$ | 1,3-dioxolan-2-yl | |
| 7.490 | 3,5-$Cl_2$—Ph | H | O | H | $CH_2CH_2$ | 1-methylpyrrolidin-2-yl | |
| 7.491 | 3,5-$Cl_2$—Ph | H | O | H | $CH_2CH_2$ | 2-oxopyrrolidin-1-yl | |
| 7.492 | 3,5-$Cl_2$—Ph | H | O | H | $CH_2CH_2$ | butoxycarbonyl | |
| 7.493 | 3,4,5-$F_3$—Ph | H | O | H | $CH_2CH_2$ | butylcarbamoyl | |
| 7.494 | 3,5-$Cl_2$—Ph | H | O | H | $CH_2CH_2$ | carbamoyl | |
| 7.495 | 3-Cl-4-Me—Ph | H | O | H | $CH_2CH_2$ | carbamoyl | |
| 7.496 | 3,5-$Cl_2$—Ph | H | O | H | $CH_2CH_2$ | CF3 | |
| 7.497 | 3,5-$F_2$—Ph | H | O | H | $CH_2CH_2$ | CF3 | |
| 7.498 | 3,5-$Cl_2$—Ph | H | O | H | $CH_2CH_2$ | CH3 | |
| 7.499 | 3,5-$F_2$—Ph | H | O | H | $CH_2CH_2$ | CH3 | |
| 7.500 | 3,5-$Cl_2$—Ph | H | O | H | $CH_2CH_2$ | chlorine | |
| 7.501 | 2,3,4,5-$F_4$-6-OH—Ph | H | O | H | $CH_2CH_2$ | COOH | |
| 7.502 | 2,3,5-$F_3$—Ph | H | O | H | $CH_2CH_2$ | COOH | |
| 7.503 | 2,3-$F_2$—Ph | H | O | H | $CH_2CH_2$ | COOH | |
| 7.504 | 2,5-$Cl_2$—Ph | H | O | H | $CH_2CH_2$ | COOH | |
| 7.505 | 2,5-$F_2$—Ph | H | O | H | $CH_2CH_2$ | COOH | |
| 7.506 | 2-Cl-5-F—Ph | H | O | H | $CH_2CH_2$ | COOH | |
| 7.507 | 2-F-3-Me—Ph | H | O | H | $CH_2CH_2$ | COOH | |
| 7.508 | 3-$CF_3$—Ph | H | O | H | $CH_2CH_2$ | COOH | |
| 7.509 | 3,4,5-$F_3$—Ph | H | O | H | $CH_2CH_2$ | COOH | |
| 7.510 | 3,4-$F_2$—Ph | H | O | H | $CH_2CH_2$ | COOH | |
| 7.511 | 3,5-$Br_2$—Ph | H | O | H | $CH_2CH_2$ | COOH | |
| 7.512 | 3,5-$Cl_2$—Ph | H | O | $CH_3$ | $CH_2CH_2$ | COOH | |
| 7.513 | 3,5-$Cl_2$—Ph | H | O | H | $CH_2CH_2$ | COOH | [$CDCl_3$] 1.00 (t, 3H); 1.95 (m, 1H); 2.15 (m, 1H); 2.62 (m, 2H); 3.20 (d, 1H); 3.51 (m, 1H); 3.62 (m, 1H); 3.69 (d, 1H); 7.41 (s, 1H); 7,52 (s, 2H). |
| 7.514 | 3,5-$F_2$—Ph | H | O | H | $CH_2CH_2$ | COOH | [$CDCl_3$] 1.00 (t, 3H); 1.95 (m, 1H); 2.14 (m, 1H); 2.61 (m, 2H); 3.20 (d, 1H); 3.50 (m, 1H); 3.61 (m, 1H); 3.69 (d, 1H); 6.88 (m, 1H); 7.14 (m, 2H) |
| 7.515 | 3,5-$Me_2$—Ph | H | O | H | $CH_2CH_2$ | COOH | |
| 7.516 | 3,5-(tert•Bu)$_2$—Ph | H | O | H | $CH_2CH_2$ | COOH | |
| 7.517 | 3-Br-5-Cl—Ph | H | O | H | $CH_2CH_2$ | COOH | |
| 7.518 | 3-Br-5-F—Ph | H | O | H | $CH_2CH_2$ | COOH | |
| 7.519 | 3-Br-5-$CF_3$—Ph | H | O | H | $CH_2CH_2$ | COOH | |
| 7.520 | 3-Cl-4-F—Ph | H | O | H | $CH_2CH_2$ | COOH | |
| 7.521 | 3-Cl-4-Me—Ph | H | O | H | $CH_2CH_2$ | COOH | |

TABLE 7-continued

Compounds of the general formula (I) according to the invention in which $R^2$ is hydrogen and $R^3$ is ethyl and aryl is the radical

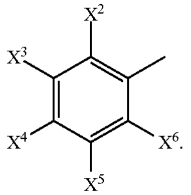

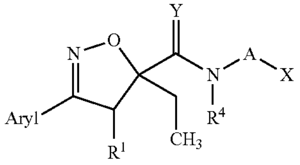

| No. | Aryl | $R^1$ | Y | $R^4$ | A | X | Physical data |
|---|---|---|---|---|---|---|---|
| 7.522 | 3-Cl-5-F—Ph | H | O | H | $CH_2CH_2$ | COOH | |
| 7.523 | 3-Cl-5-$CF_3O$—Ph | H | O | H | $CH_2CH_2$ | COOH | |
| 7.524 | 3-Cl-5-$CF_3$—Ph | H | O | H | $CH_2CH_2$ | COOH | |
| 7.525 | 3-Cl-5-Me—Ph | H | O | H | $CH_2CH_2$ | COOH | |
| 7.526 | 3-Et-5-F—Ph | H | O | H | $CH_2CH_2$ | COOH | |
| 7.527 | 3-Et—Ph | H | O | H | $CH_2CH_2$ | COOH | |
| 7.528 | 3-F-5-MeO—Ph | H | O | H | $CH_2CH_2$ | COOH | |
| 7.529 | 3-F-5-Me—Ph | H | O | H | $CH_2CH_2$ | COOH | |
| 7.530 | 3-F—Ph | H | O | H | $CH_2CH_2$ | COOH | |
| 7.531 | 3-Me—Ph | H | O | H | $CH_2CH_2$ | COOH | |
| 7.532 | 4-Cl—Ph | H | O | H | $CH_2CH_2$ | COOH | |
| 7.533 | 4-EtO—Ph | H | O | H | $CH_2CH_2$ | COOH | |
| 7.534 | Ph | H | O | H | $CH_2CH_2$ | COOH | |
| 7.535 | 3,5-$Cl_2$—Ph | H | O | H | $CH_2CH_2$ | cyanogen | |
| 7.536 | 3-Cl—Ph | H | O | H | $CH_2CH_2$ | cyanogen | |
| 7.537 | 3,5-$Cl_2$—Ph | H | O | H | $CH_2CH_2$ | cyclopropylcarbamoyl | |
| 7.538 | 3,5-$Cl_2$—Ph | H | O | H | $CH_2CH_2$ | diethoxymethyl | |
| 7.539 | 3,5-$Cl_2$—Ph | H | O | H | $CH_2CH_2$ | diethoxyphosphoryl | |
| 7.540 | Ph | H | O | H | $CH_2CH_2$ | diethoxyphosphoryl | |
| 7.541 | 3,5-$Cl_2$—Ph | H | O | H | $CH_2CH_2$ | dimethoxymethyl | |
| 7.542 | 3,5-$Cl_2$—Ph | H | O | H | $CH_2CH_2$ | dimethylcarbamoyl | |
| 7.543 | 3,5-$Cl_2$—Ph | H | O | H | $CH_2CH_2$ | ethoxy | |
| 7.544 | 3-Cl—Ph | H | O | H | $CH_2CH_2$ | ethoxy | |
| 7.545 | 2-Cl-5-F—Ph | H | O | H | $CH_2CH_2$ | ethoxycarbonyl | |
| 7.546 | 3-$CF_3$—Ph | H | O | H | $CH_2CH_2$ | ethoxycarbonyl | |
| 7.547 | 3,5-$Cl_2$—Ph | H | O | cPr | $CH_2CH_2$ | ethoxycarbonyl | |
| 7.548 | 3,5-$Cl_2$—Ph | H | O | H | $CH_2CH_2$ | ethoxycarbonyl | |
| 7.549 | 3,5-$F_2$—Ph | H | O | H | $CH_2CH_2$ | ethoxycarbonyl | |
| 7.550 | 3-Br-5-$CF_3$—Ph | H | O | H | $CH_2CH_2$ | ethoxycarbonyl | |
| 7.551 | 3-Cl-5-Et—Ph | H | O | H | $CH_2CH_2$ | ethoxycarbonyl | |
| 7.552 | 3-Cl-5-$CF_3$—Ph | H | O | H | $CH_2CH_2$ | ethoxycarbonyl | |
| 7.553 | 3-Et-5-F—Ph | H | O | H | $CH_2CH_2$ | ethoxycarbonyl | |
| 7.554 | 3-Et—Ph | H | O | H | $CH_2CH_2$ | ethoxycarbonyl | |
| 7.555 | 3-F-5-MeO—Ph | H | O | H | $CH_2CH_2$ | ethoxycarbonyl | |
| 7.556 | 3-Me-5-$CF_3O$—Ph | H | O | H | $CH_2CH_2$ | ethoxycarbonyl | |
| 7.557 | 3,5-$Cl_2$—Ph | H | O | H | $CH_2CH_2$ | ethylcarbamoyl | |
| 7.558 | 3,5-$F_2$—Ph | H | O | H | $CH_2CH_2$ | formyl | |
| 7.559 | 3,5-$Cl_2$—Ph | H | O | H | $CH_2CH_2$ | hydroxy | |
| 7.560 | 3,5-$F_2$—Ph | H | O | H | $CH_2CH_2$ | hydroxy | |
| 7.561 | 3-Cl—Ph | H | O | H | $CH_2CH_2$ | hydroxy | |
| 7.562 | 3,5-$Cl_2$—Ph | H | O | H | $CH_2CH_2$ | isobutoxycarbonyl | |
| 7.563 | 3,5-$Cl_2$—Ph | H | O | H | $CH_2CH_2$ | methoxy | |
| 7.564 | 3-Cl-5-$CF_3$—Ph | H | O | H | $CH_2CH_2$ | methoxy | |
| 7.565 | 3-Cl—Ph | H | O | H | $CH_2CH_2$ | methoxy | |
| 7.566 | 2,3,4-$F_3$—Ph | H | O | H | $CH_2CH_2$ | methoxycarbonyl | |
| 7.567 | 2,3,5-$F_3$—Ph | H | O | H | $CH_2CH_2$ | methoxycarbonyl | |
| 7.568 | 2,3-$F_2$—Ph | H | O | H | $CH_2CH_2$ | methoxycarbonyl | |
| 7.569 | 2,5-$Cl_2$—Ph | H | O | H | $CH_2CH_2$ | methoxycarbonyl | |
| 7.570 | 2,5-$F_2$—Ph | H | O | H | $CH_2CH_2$ | methoxycarbonyl | |
| 7.571 | 2,5-$Me_2$—Ph | H | O | H | $CH_2CH_2$ | methoxycarbonyl | |
| 7.572 | 2-Cl-3-F-5-MeO—Ph | H | O | H | $CH_2CH_2$ | methoxycarbonyl | |
| 7.573 | 2-F-3-Me—Ph | H | O | H | $CH_2CH_2$ | methoxycarbonyl | |
| 7.574 | 3-$CF_3$—Ph | H | O | H | $CH_2CH_2$ | methoxycarbonyl | |

TABLE 7-continued

Compounds of the general formula (I) according to the invention in which $R^2$ is hydrogen and $R^3$ is ethyl and aryl is the radical

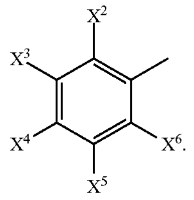

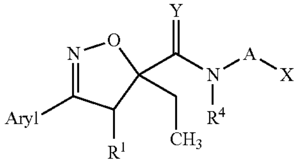

| No. | Aryl | $R^1$ | Y | $R^4$ | A | X | Physical data |
|---|---|---|---|---|---|---|---|
| 7.575 | 3,4,5-$F_3$—Ph | H | O | H | $CH_2CH_2$ | methoxycarbonyl | |
| 7.576 | 3,4-$F_2$—Ph | H | O | H | $CH_2CH_2$ | methoxycarbonyl | |
| 7.577 | 3,5-$Br_2$—Ph | H | O | H | $CH_2CH_2$ | methoxycarbonyl | |
| 7.578 | 3,5-$Cl_2$-4-MeO—Ph | H | O | H | $CH_2CH_2$ | methoxycarbonyl | |
| 7.579 | 3,5-$Cl_2$—Ph | $CH_3$ | O | H | $CH_2CH_2$ | methoxycarbonyl | |
| 7.580 | 3,5-$Cl_2$—Ph | H | O | $CH_3$ | $CH_2CH_2$ | methoxycarbonyl | |
| 7.581 | 3,5-$Cl_2$—Ph | H | O | H | $CH_2CH_2$ | methoxycarbonyl | [$CDCl_3$] 0.97 (t, 3H); 1.87-1.97 (m, 1H), 2.09-2.19 (m, 1H); 2.53-2.58 (m, 2H); 3.19 (d, 1H); 3.43-3.52 (m, 1H); 3.58-3.66 (m, 1H); 3.68 (d, 1H); 3.69 (s, 3H); 7.23 (br, 1H); 7.41 (m, 1H); 7.51 (m, 2H). |
| 7.582 | 3,5-$Et_2$—Ph | H | O | H | $CH_2CH_2$ | methoxycarbonyl | |
| 7.583 | 3,5-$F_2$—Ph | H | O | H | $CH_2CH_2$ | methoxycarbonyl | [$CDCl_3$] 7.26 29.42; 7.24 0.35; 7.23 0.51; 7.21 0.36; 7.17 1.39; 7.17 1.80; 7.16 1.07; 7.15 1.74; 7.15 1.43; 6.90 0.34; 6.89 0.61; 6.88 0.68; 6.87 1.21; 6.87 0.62; 6.86 0.36; 6.85 0.62; 3.69 2.41; 3.69 16.00; 3.65 2.73; 3.63 0.56; 3.63 0.53; 3.61 0.87; 3.60 0.80; 3.58 0.38; 3.52 0.35; 3.51 0.78; 3.49 0.82; 3.48 0.64; 3.46 0.48; 3.22 2.37; 3.17 2.01; 2.57 1.05; 2.57 1.07; 2.56 1.22; 2.56 1.34; 2.55 1.78; 2.54 1.05; 2.54 1.05; 2.17 0.66; 2.15 0.85; 2.13 1.06; 2.11 0.96; 1.96 0.90; 1.94 1.10; 1.92 0.91; 1.91 0.68; 1.55 8.93; 1.43 1.50; 1.22 0.43; 1.00 3.33; 0.99 6.94; 0.97 3.11; 0.01 0.56; 0.00 19.10; −0.01 0.72 |
| 7.584 | 3,5-$(MeO)_2$—Ph | H | O | H | $CH_2CH_2$ | methoxycarbonyl | |
| 7.585 | 3,5-$Me_2$—Ph | H | O | H | $CH_2CH_2$ | methoxycarbonyl | |
| 7.586 | 3,5-(tert•Bu)$_2$—Ph | H | O | H | $CH_2CH_2$ | methoxycarbonyl | |
| 7.587 | 3-$CF_3$S—Ph | H | O | H | $CH_2CH_2$ | methoxycarbonyl | |
| 7.588 | 3-Ac—Ph | H | O | H | $CH_2CH_2$ | methoxycarbonyl | |
| 7.589 | 3-Br-5-Cl—Ph | H | O | H | $CH_2CH_2$ | methoxycarbonyl | |
| 7.590 | 3-Br-5-F—Ph | H | O | H | $CH_2CH_2$ | methoxycarbonyl | |
| 7.591 | 3-Br-5-$CF_3$—Ph | H | O | H | $CH_2CH_2$ | methoxycarbonyl | |

TABLE 7-continued

Compounds of the general formula (I) according to the invention in which $R^2$ is hydrogen and $R^3$ is ethyl and aryl is the radical

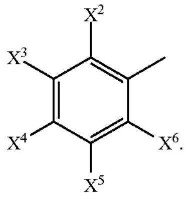

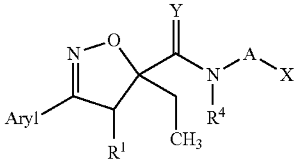

| No. | Aryl | $R^1$ | Y | $R^4$ | A | X | Physical data |
|---|---|---|---|---|---|---|---|
| 7.592 | 3-$NH_2$CO—Ph | H | O | H | $CH_2CH_2$ | methoxycarbonyl | |
| 7.593 | 3-Cl-4-F—Ph | H | O | H | $CH_2CH_2$ | methoxycarbonyl | |
| 7.594 | 3-Cl-4-Me—Ph | H | O | H | $CH_2CH_2$ | methoxycarbonyl | |
| 7.595 | 3-Cl-5-CN—Ph | H | O | H | $CH_2CH_2$ | methoxycarbonyl | |
| 7.596 | 3-Cl-5-Et—Ph | H | O | H | $CH_2CH_2$ | methoxycarbonyl | |
| 7.597 | 3-Cl-5-F—Ph | H | O | H | $CH_2CH_2$ | methoxycarbonyl | |
| 7.598 | 3-Cl-5-MeO—Ph | H | O | H | $CH_2CH_2$ | methoxycarbonyl | |
| 7.599 | 3-Cl-5-$CF_3$O—Ph | H | O | H | $CH_2CH_2$ | methoxycarbonyl | |
| 7.600 | 3-Cl-5-$CF_3$—Ph | H | O | H | $CH_2CH_2$ | methoxycarbonyl | |
| 7.601 | 3-Cl-5-Me—Ph | H | O | H | $CH_2CH_2$ | methoxycarbonyl | |
| 7.602 | 3-CN-5-F—Ph | H | O | H | $CH_2CH_2$ | methoxycarbonyl | |
| 7.603 | 3-CN—Ph | H | O | H | $CH_2CH_2$ | methoxycarbonyl | |
| 7.604 | 3-c-Pr-5-F—Ph | H | O | H | $CH_2CH_2$ | methoxycarbonyl | |
| 7.605 | 3-Et-5-F—Ph | H | O | H | $CH_2CH_2$ | methoxycarbonyl | |
| 7.606 | 3-F-5-MeS—Ph | H | O | H | $CH_2CH_2$ | methoxycarbonyl | |
| 7.607 | 3-F-5-$MeSO_2$—Ph | H | O | H | $CH_2CH_2$ | methoxycarbonyl | |
| 7.608 | 3-F-5-MeO—Ph | H | O | H | $CH_2CH_2$ | methoxycarbonyl | |
| 7.609 | 3-F-5-Me—Ph | H | O | H | $CH_2CH_2$ | methoxycarbonyl | |
| 7.610 | 3-F—Ph | H | O | H | $CH_2CH_2$ | methoxycarbonyl | |
| 7.611 | 3-Me—Ph | H | O | H | $CH_2CH_2$ | methoxycarbonyl | |
| 7.612 | 3-$NO_2$—Ph | H | O | H | $CH_2CH_2$ | methoxycarbonyl | |
| 7.613 | 4-Cl—Ph | H | O | H | $CH_2CH_2$ | methoxycarbonyl | |
| 7.614 | 4-EtO—Ph | H | O | H | $CH_2CH_2$ | methoxycarbonyl | |
| 7.615 | 4-MeO—Ph | H | O | H | $CH_2CH_2$ | methoxycarbonyl | |
| 7.616 | $F_5$—Ph | H | O | H | $CH_2CH_2$ | methoxycarbonyl | |
| 7.617 | Ph | H | O | H | $CH_2CH_2$ | methoxycarbonyl | |
| 7.618 | 3,5-$Cl_2$—Ph | H | O | H | $CH_2CH_2$ | methyl(methylsulfonyl)-carbamoyl | |
| 7.619 | 3,5-$F_2$—Ph | H | O | H | $CH_2CH_2$ | methyl(methylsulfonyl)-carbamoyl | |
| 7.620 | 2,5-$Cl_2$—Ph | H | O | H | $CH_2CH_2$ | methylcarbamoyl | |
| 7.621 | 3,5-$Cl_2$—Ph | H | O | H | $CH_2CH_2$ | methylcarbamoyl | |
| 7.622 | 3-Cl-4-F—Ph | H | O | H | $CH_2CH_2$ | methylcarbamoyl | |
| 7.623 | 3-Cl-4-Me—Ph | H | O | H | $CH_2CH_2$ | methylcarbamoyl | |
| 7.624 | 3,5-$Cl_2$—Ph | H | O | H | $CH_2CH_2$ | methylsulfanyl | |
| 7.625 | 3,5-$Cl_2$—Ph | H | O | H | $CH_2CH_2$ | methylsulfonyl | |
| 7.626 | 3,5-$Cl_2$—Ph | H | O | H | $CH_2CH_2$ | morpholin-4-yl | |
| 7.627 | 3,5-$Cl_2$—Ph | H | O | H | $CH_2CH_2$ | morpholin-4-ylcarbonyl | |
| 7.628 | 3,5-$Cl_2$—Ph | H | O | H | $CH_2CH_2$ | phosphono | |
| 7.629 | Ph | H | O | H | $CH_2CH_2$ | phosphono | |
| 7.630 | 3,5-$Cl_2$—Ph | H | O | H | $CH_2CH_2$ | piperidin-1-yl | |
| 7.631 | 3,5-$Cl_2$—Ph | H | O | H | $CH_2CH_2$ | piperidin-1-ylcarbonyl | |
| 7.632 | 3,5-$Cl_2$—Ph | H | O | H | $CH_2CH_2$ | propan-2-yloxy | |
| 7.633 | 3,5-$Cl_2$—Ph | H | O | H | $CH_2CH_2$ | propoxy | |
| 7.634 | 3,5-$Cl_2$—Ph | H | O | H | $CH_2CH_2$ | propoxycarbonyl | |
| 7.635 | 3,5-$Cl_2$—Ph | H | O | H | $CH_2CH_2$ | pyrrolidin-1-yl | |
| 7.636 | 3,5-$Cl_2$—Ph | H | O | H | $CH_2CH_2$ | sec-butoxycarbonyl | |
| 7.637 | 3,5-$F_2$—Ph | H | O | H | $CH_2CH_2$ | sulfamoyl | |
| 7.638 | 3,5-$Cl_2$—Ph | H | O | H | $CH_2CH_2$ | tert-butoxycarbonyl | |
| 7.639 | 3,5-$F_2$—Ph | H | O | H | $CH_2CH_2$ | tert-butoxycarbonyl | |
| 7.640 | 3,5-$Cl_2$—Ph | H | O | H | $CH_2CH_2$ | tetrahydrofuran-2-yl | |
| 7.641 | 3,5-$Cl_2$—Ph | H | O | H | $CH_2CH_2$ | trifluoromethoxy | |

TABLE 7-continued

Compounds of the general formula (I) according to the invention in which $R^2$ is hydrogen and $R^3$ is ethyl and aryl is the radical

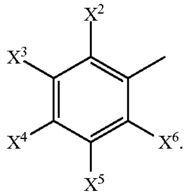

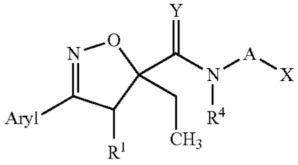

| No. | Aryl | $R^1$ | Y | $R^4$ | A | X | Physical data |
|---|---|---|---|---|---|---|---|
| 7.642 | 3,5-$F_2$—Ph | H | O | H | $CH_2CH_2$ | trifluoromethoxy | |
| 7.643 | 3-F—Ph | H | O | H | $CH_2CH_2$ | trifluoromethoxy | |
| 7.644 | Ph | H | O | H | $CH_2CH_2$ | trifluoromethoxy | |
| 7.645 | 3-Cl—Ph | H | O | H | $CH_2CH_2CH_2$ | (propan-2-yloxy)carbonyl | |
| 7.646 | 3-F—Ph | H | O | H | $CH_2CH_2CH_2$ | (propan-2-yloxy)carbonyl | |
| 7.647 | 3,5-$Cl_2$—Ph | H | O | H | $CH_2CH_2CH_2$ | 2-carboxyethyl | |
| 7.648 | 3,5-$Cl_2$—Ph | H | O | H | $CH_2CH_2CH_2$ | 2-methyl-1,3-dioxolan-2-yl | |
| 7.649 | 3,5-$F_2$—Ph | H | O | H | $CH_2CH_2CH_2$ | 2-methyl-1,3-dioxolan-2-yl | |
| 7.650 | Ph | H | O | H | $CH_2CH_2CH_2$ | 2-methyl-1,3-dioxolan-2-yl | |
| 7.651 | 3,5-$Cl_2$—Ph | H | O | H | $CH_2CH_2CH_2$ | 2-oxopyrrolidin-1-yl | |
| 7.652 | 3,5-$Cl_2$—Ph | H | O | H | $CH_2CH_2CH_2$ | CF3 | |
| 7.653 | 3,5-$Cl_2$—Ph | H | O | H | $CH_2CH_2CH_2$ | CH3 | |
| 7.654 | 3,5-$F_2$—Ph | H | O | H | $CH_2CH_2CH_2$ | CH3 | |
| 7.655 | 3,5-$Cl_2$—Ph | H | O | H | $CH_2CH_2CH_2$ | COOH | |
| 7.656 | 3,5-$F_2$—Ph | H | O | H | $CH_2CH_2CH_2$ | COOH | |
| 7.657 | 3-Br-5-Cl—Ph | H | O | H | $CH_2CH_2CH_2$ | COOH | |
| 7.658 | 3-Cl—Ph | H | O | H | $CH_2CH_2CH_2$ | COOH | |
| 7.659 | 3-F—Ph | H | O | H | $CH_2CH_2CH_2$ | COOH | |
| 7.660 | Ph | H | O | H | $CH_2CH_2CH_2$ | COOH | |
| 7.661 | 3,5-$Cl_2$—Ph | H | O | H | $CH_2CH_2CH_2$ | dimethylamino | |
| 7.662 | Ph | H | O | ethyl-carbamoyl | $CH_2CH_2CH_2$ | dimethylamino | |
| 7.663 | 3,5-$Cl_2$—Ph | H | O | H | $CH_2CH_2CH_2$ | ethoxy | |
| 7.664 | 3,5-$Cl_2$—Ph | H | O | H | $CH_2CH_2CH_2$ | ethoxycarbonyl | |
| 7.665 | 3-Cl—Ph | H | O | H | $CH_2CH_2CH_2$ | ethoxycarbonyl | |
| 7.666 | 3-F—Ph | H | O | H | $CH_2CH_2CH_2$ | ethoxycarbonyl | |
| 7.667 | 3,5-$Cl_2$—Ph | H | O | H | $CH_2CH_2CH_2$ | hydroxy | |
| 7.668 | 3,5-$F_2$—Ph | H | O | H | $CH_2CH_2CH_2$ | hydroxy | |
| 7.669 | 3,5-$Cl_2$—Ph | H | O | H | $CH_2CH_2CH_2$ | methoxy | |
| 7.670 | 3,5-$F_2$—Ph | H | O | H | $CH_2CH_2CH_2$ | methoxycarbonyl | |
| 7.671 | 3-Br-5-Cl—Ph | H | O | H | $CH_2CH_2CH_2$ | methoxycarbonyl | |
| 7.672 | 3-Cl-5-MeO—Ph | H | O | H | $CH_2CH_2CH_2$ | methoxycarbonyl | |
| 7.673 | 3-Cl—Ph | H | O | H | $CH_2CH_2CH_2$ | methoxycarbonyl | |
| 7.674 | 3-F—Ph | H | O | H | $CH_2CH_2CH_2$ | methoxycarbonyl | |
| 7.675 | Ph | H | O | H | $CH_2CH_2CH_2$ | methoxycarbonyl | |
| 7.676 | 3,5-$F_2$—Ph | H | O | H | $CH_2CH_2CH_2$ | methylcarbamoyl | |
| 7.677 | 3,5-$Cl_2$—Ph | H | O | H | $CH_2CH_2CH_2$ | morpholin-4-yl | |
| 7.678 | 3,5-$Cl_2$—Ph | H | O | H | $(CH_2)_6$ | methoxycarbonyl | |
| 7.679 | 3,5-$F_2$—Ph | H | O | H | $CH(CH_3)$ | cyano | [$CDCl_3$] D1 1.00 (t, 3H); 1.58 (d, 3H); 2.01 (m, 1H); 2.17 (m, 1H); 3.25 (d, 1H); 3.69 (d, 1H); 4.87 (m, 1H); 6.88 (m, 1H); 7.12 (d br, 1H); 7.15 (m, 2H). D2 1.05 (t, 3H); 1.62 (d, 3H); 2.01 (m, 1H); 2.17 (m, 1H); 3.28 (d, 1H); 3.69 (d ,1H); 4.87 |

TABLE 7-continued

Compounds of the general formula (I) according to the invention in which $R^2$ is hydrogen and $R^3$ is ethyl and aryl is the radical

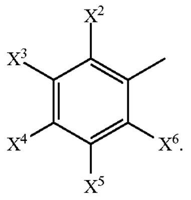

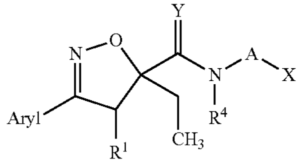

| No. | Aryl | $R^1$ | Y | $R^4$ | A | X | Physical data |
|---|---|---|---|---|---|---|---|
| | | | | | | | (m, 1H); 6.88 (m, 1H); 7.12 (d br, 1H); 7.15 (m, 2H) |
| 7.680 | 3,5-$F_2$—Ph | H | O | H | $CH(CH_3)CH_2$ | ethoxycarbonyl | [$CDCl_3$] D1 0.97 (t, 3H); 1.20 (t, 3H); 1.28 (d, 3H); 1.93 (m, 2H); 2.50 (d, 2H); 3.19 (d, 1H); 3.67 (d, 1H); 4.08 (q, 2H); 4.33 (m, 1H); 6.88 (m, 1H); 7.18 (m, 3H). D2 1.00 (t, 3H); 1.22 (t, 3H); 1.29 (d, 3H); 2.14 (m, 2H); 2.55 (m, 2H); 3.19 (d, 1H); 3.70 (d, 1H); 4.16 (q, 2H); 4.33 (m, 1H); 6.88 (m, 1H); 7.18 (m, 3H). |

TABLE 8

Compounds of the general formula (I) according to the invention in which $R^2$ is hydrogen and $R^3$ is trifluoroomethyl and aryl is the radical

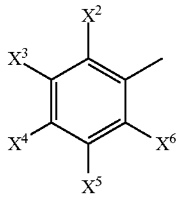

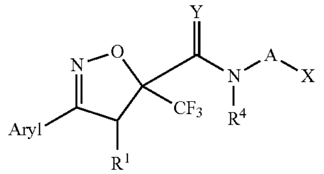

| No. | Aryl | $R^1$ | Y | $R^4$ | A | X | Physical data |
|---|---|---|---|---|---|---|---|
| 8.001 | 3,5-$Cl_2$—Ph | H | O | H | $(CH_2)_4$ | COOH | |
| 8.002 | 3,5-$Cl_2$—Ph | H | O | H | $(CH_2)_4$ | ethoxycarbonyl | |
| 8.003 | 3-Br-5-Cl—Ph | H | O | H | $(CH_2)_4$ | ethoxycarbonyl | |
| 8.004 | Ph | H | O | H | $(CH_2)_4$ | ethoxycarbonyl | |
| 8.005 | 3,5-$Cl_2$—Ph | H | O | H | $(CH_2)_4$ | hydroxy | |
| 8.006 | 3,5-$Cl_2$—Ph | H | O | H | $(CH_2)_4$ | methoxy | |
| 8.007 | 3,5-$Cl_2$—Ph | H | O | H | $(CH_2)_6$ | COOH | |
| 8.008 | 3,5-$Cl_2$—Ph | H | O | H | $(CH_2)_6$ | ethoxycarbonyl | |

TABLE 8-continued

Compounds of the general formula (I) according to the invention in which $R^2$ is hydrogen and $R^3$ is trifluoroomethyl and aryl is the radical

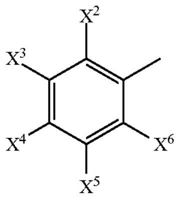

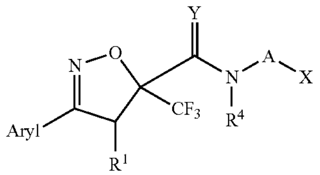

| No. | Aryl | $R^1$ | Y | $R^4$ | A | X | Physical data |
|---|---|---|---|---|---|---|---|
| 8.009 | 3,5-$Cl_2$—Ph | H | O | H | c-Pr-1,1-diyl | ethoxycarbonyl | |
| 8.010 | 3,5-$F_2$—Ph | H | O | H | bond | 1-cyanocyclopropyl | |
| 8.011 | 3,5-$Cl_2$—Ph | H | O | H | bond | 1-cyanocyclopropyl | |
| 8.012 | 3,5-$Cl_2$—Ph | H | O | H | bond | 1-methylcyclopropyl | |
| 8.013 | 3,5-$Cl_2$—Ph | H | O | H | bond | 2-(ethoxy-carbonyl)cyclohex-1-en-1-yl | |
| 8.014 | 3,5-$Cl_2$—Ph | H | O | H | bond | 2-(ethoxy-carbonyl)cyclohexyl | |
| 8.015 | 3,5-$Cl_2$—Ph | H | O | H | bond | 2-(methylcarbamoyl)-cyclohexyl | |
| 8.016 | 3,5-$Cl_2$—Ph | H | O | H | bond | 2-carboxycyclohexyl | |
| 8.017 | 3,5-$Cl_2$—Ph | H | O | H | bond | 3-(2-ethoxy-2-oxoethyl)oxetan-3-yl | |
| 8.018 | 3,5-$F_2$—Ph | H | O | H | bond | 3-(2-ethoxy-2-oxoethyl)oxetan-3-yl | |
| 8.019 | 2,4-$Cl_2$—Ph | H | O | $CH_3$ | bond | $CH_3$ | |
| 8.020 | 2-Cl—Ph | H | O | $CH_3$ | bond | $CH_3$ | |
| 8.021 | 3,4-$F_2$—Ph | H | O | H | bond | $CH_3$ | |
| 8.022 | 3,5-$Br_2$—Ph | H | O | H | bond | $CH_3$ | |
| 8.023 | 3,5-$Cl_2$—Ph | $CH_3$ | O | H | bond | $CH_3$ | |
| 8.024 | 3,5-$Cl_2$—Ph | H | O | $CH_3$ | bond | $CH_3$ | |
| 8.025 | 3,5-$Cl_2$—Ph | H | O | H | bond | $CH_3$ | [$CDCl_3$] 2.91 (d, 3H); 3.72 (d, 1H); 3.96 (d, 1 H); 6.82 (bs, 1H); 7.47 (m, 1H); 7.54 (m, 2H). |
| 8.026 | 3,5-$F_2$—Ph | H | O | H | bond | $CH_3$ | |
| 8.027 | 3-Cl-4-F—Ph | H | O | H | bond | $CH_3$ | |
| 8.028 | 3,5-$Cl_2$—Ph | H | O | H | bond | cyclobutyl | |
| 8.029 | 3,5-$F_2$—Ph | H | O | H | bond | cyclobutyl | |
| 8.030 | 3,5-$Cl_2$—Ph | H | O | H | bond | cyclopentyl | |
| 8.031 | 3,5-$F_2$—Ph | H | O | H | bond | cyclopentyl | |
| 8.032 | 2-$CF_3$—Ph | H | O | H | bond | c-Pr | |
| 8.033 | 2,3,4-$F_3$—Ph | H | O | H | bond | c-Pr | |
| 8.034 | 2,3,5-$F_3$—Ph | H | O | H | bond | c-Pr | |
| 8.035 | 2,3-$F_2$—Ph | H | O | H | bond | c-Pr | |
| 8.036 | 2,4-$Cl_2$—Ph | H | O | H | bond | c-Pr | |
| 8.037 | 2,5-$F_2$—Ph | H | O | H | bond | c-Pr | |
| 8.038 | 2,5-$Me_2$—Ph | H | O | H | bond | c-Pr | |
| 8.039 | 2-Cl-3-F-5-MeO—Ph | H | O | H | bond | c-Pr | |
| 8.040 | 2-Cl-5-F—Ph | H | O | H | bond | c-Pr | |
| 8.041 | 2-EtO-3,4,5,6-$F_4$—Ph | H | O | H | bond | c-Pr | |
| 8.042 | 2-F-3-Me—Ph | H | O | H | bond | c-Pr | |
| 8.043 | 3-(2-MeOEtO)—Ph | H | O | H | bond | c-Pr | |
| 8.044 | 3-iPrO—Ph | H | O | H | bond | c-Pr | |
| 8.045 | 3-$CF_3O$—Ph | H | O | H | bond | c-Pr | |
| 8.046 | 3-$CF_3$—Ph | H | O | H | bond | c-Pr | |
| 8.047 | 3,4,5-$F_3$—Ph | H | O | H | bond | c-Pr | |
| 8.048 | 3,5-$Br_2$—Ph | H | O | H | bond | c-Pr | |
| 8.049 | 3,5-$Cl_2$-4-MeO—Ph | H | O | H | bond | c-Pr | |
| 8.050 | 3,5-$Cl_2$-4-OH—Ph | H | O | H | bond | c-Pr | |
| 8.051 | 3,5-$Cl_2$—Ph | $CH_3$ | O | H | bond | c-Pr | |
| 8.052 | 3,5-$Cl_2$—Ph | H | O | H | bond | c-Pr | [$CDCl_3$] 0.60 (m, 2H); 0.85 (m, 2H); 2.78 (m, 1H); 3.72 |

TABLE 8-continued

Compounds of the general formula (I) according to the invention in which $R^2$ is hydrogen and $R^3$ is trifluoroomethyl and aryl is the radical

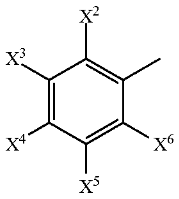

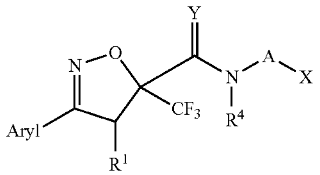

| No. | Aryl | $R^1$ | Y | $R^4$ | A | X | Physical data |
|---|---|---|---|---|---|---|---|
| | | | | | | | (d,1H); 3.97 (d, 1H); 6.82 (s br, 1H); 7.48 (t, 1H); 7.53 (m, 2H) |
| 8.053 | 3,5-$F_2$—Ph | H | O | H | bond | c-Pr | |
| 8.054 | 3,5-$F_2$—Ph | H | O | H | bond | c-Pr | |
| 8.055 | 3,5-$F_2$—Ph | H | S | H | bond | c-Pr | |
| 8.056 | 3,5-$(MeO)_2$—Ph | H | O | H | bond | c-Pr | |
| 8.057 | 3,5-$Me_2$—Ph | H | O | H | bond | c-Pr | |
| 8.058 | 3-Ac—Ph | H | O | H | bond | c-Pr | |
| 8.059 | 3-Br-5-$CF_3$—Ph | H | O | H | bond | c-Pr | |
| 8.060 | 3-Br-5-Cl—Ph | H | O | H | bond | c-Pr | |
| 8.061 | 3-Br-5-F—Ph | H | O | H | bond | c-Pr | |
| 8.062 | 3-Cl-4-F—Ph | H | O | H | bond | c-Pr | [$CDCl_3$] 0.59 (m, 2H); 0.84 (m, 2H); 2.78 (m, 1H); 3.74 (d, 1 H); 3.99 (d,1H); 6.85 (s br, 1H); 7.21 (m, 1H); 7.53 (m, 1H); 7.73 (m, 1H) |
| 8.063 | 3-Cl-4-Me—Ph | H | O | H | bond | c-Pr | |
| 8.064 | 3-Cl-5-$CF_3$—Ph | H | O | H | bond | c-Pr | |
| 8.065 | 3-Cl-5-CN—Ph | H | O | H | bond | c-Pr | |
| 8.066 | 3-Cl-5-Et—Ph | H | O | H | bond | c-Pr | |
| 8.067 | 3-Cl-5-F—Ph | H | O | H | bond | c-Pr | |
| 8.068 | 3-Cl-5-Me—Ph | H | O | H | bond | c-Pr | |
| 8.069 | 3-Cl-5-$CF_3O$—Ph | H | O | H | bond | c-Pr | |
| 8.070 | 3-Cl—Ph | H | O | H | bond | c-Pr | |
| 8.071 | 3-CN-5-F—Ph | H | O | H | bond | c-Pr | |
| 8.072 | 3-c-Pr-5-F—Ph | H | O | H | bond | c-Pr | |
| 8.073 | 3-EtO—Ph | H | O | H | bond | c-Pr | |
| 8.074 | 3-Et-5-F—Ph | H | O | H | bond | c-Pr | |
| 8.075 | 3-Et—Ph | H | O | H | bond | c-Pr | |
| 8.076 | 3-F-5-MeS—Ph | H | O | H | bond | c-Pr | |
| 8.077 | 3-F-5-$MeSO_2$—Ph | H | O | H | bond | c-Pr | |
| 8.078 | 3-F-5-MeO—Ph | H | O | H | bond | c-Pr | |
| 8.079 | 3-F-5-Me—Ph | H | O | H | bond | c-Pr | |
| 8.080 | 3-F-5-Me—Ph | H | S | H | bond | c-Pr | |
| 8.081 | 3-F—Ph | H | O | H | bond | c-Pr | |
| 8.082 | 3-OH—Ph | H | O | H | bond | c-Pr | |
| 8.083 | 3-iPr—Ph | H | O | H | bond | c-Pr | |
| 8.084 | 3-MeO—Ph | H | O | H | bond | c-Pr | |
| 8.085 | 3-Me-5-$CF_3O$—Ph | H | O | H | bond | c-Pr | |
| 8.086 | 3-Me—Ph | H | O | H | bond | c-Pr | |
| 8.087 | 3-$NO_2$—Ph | H | O | H | bond | c-Pr | |
| 8.088 | 4-Cl-3,5-$F_2$—Ph | H | O | H | bond | c-Pr | |
| 8.089 | 4-EtO—Ph | H | O | H | bond | c-Pr | |
| 8.090 | $F_5$—Ph | H | O | H | bond | c-Pr | |
| 8.091 | Ph | H | O | H | bond | c-Pr | |
| 8.092 | 3,5-$Cl_2$—Ph | H | O | H | bond | decahydro-naphthalen-2-yl | |
| 8.093 | 3,5-$Cl_2$—Ph | H | O | H | bond | H | |
| 8.094 | 3,5-$F_2$—Ph | H | O | H | bond | H | |
| 8.095 | 3,5-$F_2$—Ph | H | S | H | bond | H | |
| 8.096 | 3-F—Ph | H | O | H | bond | H | |

TABLE 8-continued

Compounds of the general formula (I) according to the invention in which $R^2$ is hydrogen and $R^3$ is trifluoroomethyl and aryl is the radical

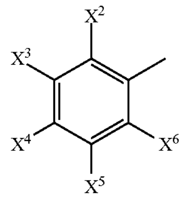

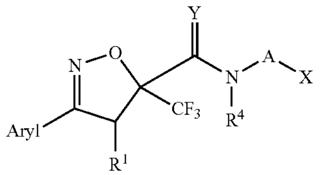

| No. | Aryl | $R^1$ | Y | $R^4$ | A | X | Physical data |
|---|---|---|---|---|---|---|---|
| 8.097 | 3-Me—Ph | H | O | H | bond | H | |
| 8.098 | 3-Me—Ph | H | S | H | bond | H | |
| 8.099 | 3,5-$Cl_2$—Ph | H | O | $CH_3$ | bond | hydroxy | |
| 8.100 | 2,3,4-$F_3$—Ph | H | O | H | bond | oxetan-3-yl | |
| 8.101 | 2,3-$F_2$—Ph | H | O | H | bond | oxetan-3-yl | |
| 8.102 | 2,5-$F_2$—Ph | H | O | H | bond | oxetan-3-yl | |
| 8.103 | 3,5-$Cl_2$—Ph | H | O | H | bond | oxetan-3-yl | |
| 8.104 | 3,5-$F_2$—Ph | H | O | H | bond | oxetan-3-yl | |
| 8.105 | 3-Cl-5-$CF_3O$—Ph | H | O | H | bond | oxetan-3-yl | |
| 8.106 | 3-F-5-Me—Ph | H | O | H | bond | oxetan-3-yl | |
| 8.107 | 3-F—Ph | H | O | H | bond | oxetan-3-yl | |
| 8.108 | 3-$NO_2$—Ph | H | O | H | bond | oxetan-3-yl | |
| 8.109 | Ph | H | O | H | bond | oxetan-3-yl | |
| 8.110 | 3,5-$Cl_2$—Ph | H | O | H | bond | tetrahydro-2H-pyran-4-yl | |
| 8.111 | 3,5-$Cl_2$—Ph | H | O | H | $C(CH_3)_2$ | 3-methoxyprop-1-yn-1-yl | |
| 8.112 | 3,5-$Cl_2$—Ph | H | O | H | $C(CH_3)_2$ | carbamoyl | |
| 8.113 | 3,5-$Cl_2$—Ph | H | O | H | $C(CH_3)_2$ | $CH_3$ | |
| 8.114 | 3-Cl-4-F—Ph | H | O | H | $C(CH_3)_2$ | $CH_3$ | |
| 8.115 | 3,5-$Cl_2$—Ph | H | O | H | $C(CH_3)_2$ | COOH | |
| 8.116 | 3,5-$(CF_3)_2$—Ph | H | O | H | $C(CH_3)_2$ | ethynyl | |
| 8.117 | 3,5-$Cl_2$—Ph | H | O | H | $C(CH_3)_2$ | ethynyl | |
| 8.118 | 3,5-$Cl_2$—Ph | H | O | H | $C(CH_3)_2$ | methoxycarbonyl | |
| 8.119 | 3,5-$Cl_2$—Ph | H | O | H | $C(CH_3)_2$ | methylcarbamoyl | |
| 8.120 | 3-Cl—Ph | H | O | H | $C(CH_3)_2CH_2$ | (propan-2-yloxy)carbonyl | |
| 8.121 | 3-F—Ph | H | O | H | $C(CH_3)_2CH_2$ | (propan-2-yloxy)carbonyl | |
| 8.122 | 3,5-$Cl_2$—Ph | H | O | H | $C(CH_3)_2CH_2$ | COOH | |
| 8.123 | 3-Cl—Ph | H | O | H | $C(CH_3)_2CH_2$ | COOH | |
| 8.124 | 3-F—Ph | H | O | H | $C(CH_3)_2CH_2$ | COOH | |
| 8.125 | 3,5-$Cl_2$—Ph | H | O | H | $C(CH_3)_2CH_2$ | ethoxycarbonyl | |
| 8.126 | 3-Cl—Ph | H | O | H | $C(CH_3)_2CH_2$ | ethoxycarbonyl | |
| 8.127 | 3-F—Ph | H | O | H | $C(CH_3)_2CH_2$ | ethoxycarbonyl | |
| 8.128 | 3,5-$Cl_2$—Ph | H | O | H | $C(CH_3)_2CH_2$ | hydroxy | |
| 8.129 | 3-Cl—Ph | H | O | H | $C(CH_3)_2CH_2$ | methoxycarbonyl | |
| 8.130 | 3-F—Ph | H | O | H | $C(CH_3)_2CH_2$ | methoxycarbonyl | |
| 8.131 | 3,5-$Cl_2$—Ph | H | O | H | $C(CH_3)_2CH_2$ | methylsulfanyl | |
| 8.132 | 3,5-$Cl_2$—Ph | H | O | H | $C(CH_3)_2CH_2$ | methylsulfonyl | |
| 8.133 | 2,4-$Cl_2$—Ph | H | O | H | $C(iPr)CH_3$ | cyano | |
| 8.134 | 3,5-$Cl_2$—Ph | H | O | H | $C(iPr)CH_3$ | cyano | |
| 8.135 | 3,5-$Cl_2$—Ph | H | O | H | $CH(CF_3)CH_2$ | ethoxycarbonyl | |
| 8.136 | 3,5-$Cl_2$—Ph | H | O | H | $CH(CH_2CH_2SCH_3)$ | methoxycarbonyl | |
| 8.137 | 3,5-$Cl_2$—Ph | H | O | H | $CH(CH_2CH_3)CH_2$ | cyano | |
| 8.138 | 3,5-$Cl_2$—Ph | H | O | H | $CH(CH_2CH_3)CH_2$ | methoxycarbonyl | |
| 8.139 | 3,5-$Cl_2$—Ph | H | O | H | $CH(CH_2iPr)CH_2$ | methoxycarbonyl | |
| 8.140 | 3,5-$Cl_2$—Ph | H | O | H | $CH(CH_2OCH_3)$ | methoxymethyl | |
| 8.141 | 3,5-$Cl_2$—Ph | H | O | H | $CH(CH_3)$ | $CF_3$ | |
| 8.142 | 2,3,4-$F_3$—Ph | H | O | H | $CH(CH_3)$ | $CH_3$ | |
| 8.143 | 2,3,5-$F_3$—Ph | H | O | H | $CH(CH_3)$ | $CH_3$ | |
| 8.144 | 2,3,6-$Cl_3$—Ph | H | O | H | $CH(CH_3)$ | $CH_3$ | |
| 8.145 | 2,3-$Cl_2$-5-MeO—Ph | H | O | H | $CH(CH_3)$ | $CH_3$ | |
| 8.146 | 2,3-$Cl_2$—Ph | H | O | H | $CH(CH_3)$ | $CH_3$ | |
| 8.147 | 2,3-$F_2$—Ph | H | O | H | $CH(CH_3)$ | $CH_3$ | |
| 8.148 | 2,5-$Cl_2$—Ph | H | O | H | $CH(CH_3)$ | $CH_3$ | |

TABLE 8-continued

Compounds of the general formula (I) according to the invention in which $R^2$ is hydrogen and $R^3$ is trifluoroomethyl and aryl is the radical

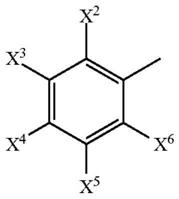

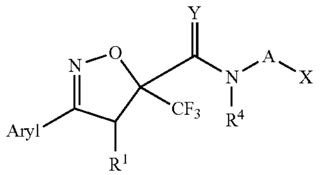

| No. | Aryl | $R^1$ | Y | $R^4$ | A | X | Physical data |
|---|---|---|---|---|---|---|---|
| 8.149 | 2,5-$F_2$—Ph | H | O | H | $CH(CH_3)$ | $CH_3$ | |
| 8.150 | 2-F—Ph | H | O | H | $CH(CH_3)$ | $CH_3$ | |
| 8.151 | 3-($CF_3CH_2O$)—Ph | H | O | H | $CH(CH_3)$ | $CH_3$ | |
| 8.152 | 3-($ClCH_2CH_2O$)—Ph | H | O | H | $CH(CH_3)$ | $CH_3$ | |
| 8.153 | 3-(2-MeOEtO)—Ph | H | O | H | $CH(CH_3)$ | $CH_3$ | |
| 8.154 | 3-$Me_2N$—Ph | H | O | H | $CH(CH_3)$ | $CH_3$ | |
| 8.155 | 3-iPrCOO—Ph | H | O | H | $CH(CH_3)$ | $CH_3$ | |
| 8.156 | 3-iPrO—Ph | H | O | H | $CH(CH_3)$ | $CH_3$ | |
| 8.157 | 3-$CF_3O$—Ph | H | O | H | $CH(CH_3)$ | $CH_3$ | |
| 8.158 | 3,4-$Cl_2$—Ph | H | O | H | $CH(CH_3)$ | $CH_3$ | |
| 8.159 | 3,5-$(CF_3)_2$—Ph | H | O | H | $CH(CH_3)$ | $CH_3$ | |
| 8.160 | 3,5-$Cl_2$—Ph | $CH_3$ | O | H | $CH(CH_3)$ | $CH_3$ | |
| 8.161 | 3,5-$Cl_2$—Ph | H | O | H | $CH(CH_3)$ | $CH_3$ | |
| 8.162 | 3,5-$Cl_2$—Ph | H | O | OH | $CH(CH_3)$ | $CH_3$ | |
| 8.163 | 3,5-$Cl_2$—Ph | H | S | H | $CH(CH_3)$ | $CH_3$ | |
| 8.164 | 3,5-$F_2$—Ph | H | O | H | $CH(CH_3)$ | $CH_3$ | |
| 8.165 | 3,5-$Me_2$—Ph | H | O | H | $CH(CH_3)$ | $CH_3$ | |
| 8.166 | R002 | H | O | H | $CH(CH_3)$ | $CH_3$ | |
| 8.167 | R003 | H | O | H | $CH(CH_3)$ | $CH_3$ | |
| 8.168 | 3-$CNCH_2N(Me)$—Ph | H | O | H | $CH(CH_3)$ | $CH_3$ | |
| 8.169 | $Me_2NCONH$—Ph | H | O | H | $CH(CH_3)$ | $CH_3$ | |
| 8.170 | 3-$Me_2NSO_2O$—Ph | H | O | H | $CH(CH_3)$ | $CH_3$ | |
| 8.171 | 3-EtNHCOO—Ph | H | O | H | $CH(CH_3)$ | $CH_3$ | |
| 8.172 | 3-$EtSO_2O$—Ph | H | O | H | $CH(CH_3)$ | $CH_3$ | |
| 8.173 | 3-$MeSO_2NH$—Ph | H | O | H | $CH(CH_3)$ | $CH_3$ | |
| 8.174 | 3-$MeSO_2O$—Ph | H | O | H | $CH(CH_3)$ | $CH_3$ | |
| 8.175 | 3-tert.BuOCONH—Ph | H | O | H | $CH(CH_3)$ | $CH_3$ | |
| 8.176 | 3-$CF_3CONH$—Ph | H | O | H | $CH(CH_3)$ | $CH_3$ | |
| 8.177 | 3-AcO-5-Cl—Ph | H | O | H | $CH(CH_3)$ | $CH_3$ | |
| 8.178 | 3-AcO—Ph | H | O | H | $CH(CH_3)$ | $CH_3$ | |
| 8.179 | 3-$NH_2$—Ph | H | O | H | $CH(CH_3)$ | $CH_3$ | |
| 8.180 | 3-Br-5-$CF_3$—Ph | H | O | H | $CH(CH_3)$ | $CH_3$ | |
| 8.181 | 3-Br-5-Cl-Ph | H | O | H | $CH(CH_3)$ | $CH_3$ | |
| 8.182 | 3-Cl-4-F—Ph | H | O | H | $CH(CH_3)$ | $CH_3$ | |
| 8.183 | 3-Cl-4-Me—Ph | H | O | H | $CH(CH_3)$ | $CH_3$ | |
| 8.184 | 3-Cl-5-$CF_3$—Ph | H | O | H | $CH(CH_3)$ | $CH_3$ | |
| 8.185 | R001 | H | O | H | $CH(CH_3)$ | $CH_3$ | |
| 8.186 | 3-Cl-5-F—Ph | H | O | H | $CH(CH_3)$ | $CH_3$ | |
| 8.187 | 3-Cl-5-MeO—Ph | H | O | H | $CH(CH_3)$ | $CH_3$ | |
| 8.188 | 3-Cl-5-Me—Ph | H | O | H | $CH(CH_3)$ | $CH_3$ | |
| 8.189 | 3-Cl-5-($CF_3CH_2O$)—Ph | H | O | H | $CH(CH_3)$ | $CH_3$ | |
| 8.190 | 3-Cl-5-($ClCH_2CH_2O$)—Ph | H | O | H | $CH(CH_3)$ | $CH_3$ | |
| 8.191 | 3-Cl-5-($EtOCOCH_2O$)—Ph | H | O | H | $CH(CH_3)$ | $CH_3$ | |
| 8.192 | 3-Cl-5-$CF_3O$—Ph | H | O | H | $CH(CH_3)$ | $CH_3$ | |
| 8.193 | 3-Cl-5-$Me_2NSO_2O$—Ph | H | O | H | $CH(CH_3)$ | $CH_3$ | |
| 8.194 | 3-Cl-5-($MeSO_2O$)—Ph | H | O | H | $CH(CH_3)$ | $CH_3$ | |
| 8.195 | 3-Cl-5-iPrO—Ph | H | O | H | $CH(CH_3)$ | $CH_3$ | |
| 8.196 | 3-Cl—Ph | H | O | H | $CH(CH_3)$ | $CH_3$ | |
| 8.197 | 3-EtO—Ph | H | O | H | $CH(CH_3)$ | $CH_3$ | |
| 8.198 | 3-F-5-Me—Ph | H | O | H | $CH(CH_3)$ | $CH_3$ | |
| 8.199 | 3-F—Ph | H | O | H | $CH(CH_3)$ | $CH_3$ | |
| 8.200 | 3-OH—Ph | H | O | H | $CH(CH_3)$ | $CH_3$ | |
| 8.201 | 3-MeO—Ph | H | O | H | $CH(CH_3)$ | $CH_3$ | |
| 8.202 | 3-Me—Ph | H | O | H | $CH(CH_3)$ | $CH_3$ | |
| 8.203 | 3-$NO_2$—Ph | H | O | H | $CH(CH_3)$ | $CH_3$ | |
| 8.204 | $F_5$—Ph | H | O | H | $CH(CH_3)$ | $CH_3$ | |

TABLE 8-continued

Compounds of the general formula (I) according to the invention in which $R^2$ is hydrogen and $R^3$ is trifluoroomethyl and aryl is the radical

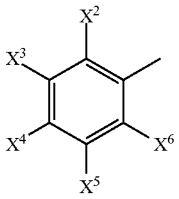

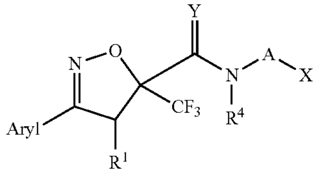

| No. | Aryl | $R^1$ | Y | $R^4$ | A | X | Physical data |
|---|---|---|---|---|---|---|---|
| 8.205 | Ph | H | O | H | $CH(CH_3)$ | $CH_3$ | |
| 8.206 | 3,5-$Cl_2$—Ph | H | O | H | $CH(CH_3)$ | COOH | |
| 8.207 | 3-Cl-4-F-Ph | H | O | H | $CH(CH_3)$ | COOH | |
| 8.208 | 3,5-$Cl_2$—Ph | H | O | H | $CH(CH_3)$ | c-Pr | |
| 8.209 | 3,5-$F_2$—Ph | H | O | H | $CH(CH_3)$ | c-Pr | |
| 8.210 | Ph | H | O | H | $CH(CH_3)$ | c-Pr | |
| 8.211 | 3-Cl-4-F—Ph | H | O | H | $CH(CH_3)$ | dimethylcarbamoyl | |
| 8.212 | 3,5-$Cl_2$—Ph | H | O | H | $CH(CH_3)$ | ethynyl | |
| 8.213 | 3,5-$Cl_2$—Ph | H | O | H | $CH(CH_3)$ | ethyl | |
| 8.214 | 3,5-$Cl_2$—Ph | $CH_3$ | O | H | $CH(CH_3)$ | methoxycarbonyl | |
| 8.215 | 3,5-$Cl_2$—Ph | H | O | H | $CH(CH_3)$ | methoxycarbonyl | |
| 8.216 | 3-Cl-4-F—Ph | H | O | H | $CH(CH_3)$ | methoxycarbonyl | |
| 8.217 | 3-Cl-4-F—Ph | H | O | H | $CH(CH_3)$ | methylcarbamoyl | |
| 8.218 | 3,5-$Cl_2$—Ph | H | O | H | $CH(CH_3)$ | pentyl | |
| 8.219 | 3,5-$Cl_2$—Ph | H | O | H | $CH(CH_3)CH_2$ | (2,2,2-trifluoroethoxy)-carbonyl | |
| 8.220 | 3,5-$F_2$—Ph | H | O | H | $CH(CH_3)CH_2$ | (2,2,2-trifluoroethoxy)-carbonyl | |
| 8.221 | 3,5-$Cl_2$—Ph | H | O | H | $CH(CH_3)CH_2$ | (2-hydroxyethoxy)-carbonyl | |
| 8.222 | 3,5-$F_2$—Ph | H | O | H | $CH(CH_3)CH_2$ | (2-hydroxyethoxy)-carbonyl | |
| 8.223 | 3,5-$Cl_2$—Ph | H | O | H | $CH(CH_3)CH_2$ | (allyloxy)carbonyl | |
| 8.224 | 3,5-$F_2$—Ph | H | O | H | $CH(CH_3)CH_2$ | (allyloxy)carbonyl | |
| 8.225 | 3,5-$Cl_2$—Ph | H | O | H | $CH(CH_3)CH_2$ | (cyclopropylsulfonyl)-(methyl)carbamoyl | |
| 8.226 | 3,5-$F_2$—Ph | H | O | H | $CH(CH_3)CH_2$ | (cyclopropylsulfonyl)-(methyl)carbamoyl | |
| 8.227 | 3,5-$Cl_2$—Ph | H | O | H | $CH(CH_3)CH_2$ | (cyclopropylsulfonyl)-carbamoyl | |
| 8.228 | 3,5-$F_2$—Ph | H | O | H | CH(CH3)CH2 | (cyclopropylsulfonyl)-carbamoyl | |
| 8.229 | 3,5-$Cl_2$—Ph | H | O | H | $CH(CH_3)CH_2$ | (ethylsulfonyl)(methyl)-carbamoyl | |
| 8.230 | 3,5-$F_2$—Ph | H | O | H | $CH(CH_3)CH_2$ | (ethylsulfonyl)(methyl)-carbamoyl | |
| 8.231 | 3,5-$Cl_2$—Ph | H | O | H | $CH(CH_3)CH_2$ | (ethylsulfonyl)-carbamoyl | |
| 8.232 | 3,5-$F_2$—Ph | H | O | H | $CH(CH_3)CH_2$ | (ethylsulfonyl)-carbamoyl | |
| 8.233 | 3,5-$Cl_2$—Ph | H | O | H | $CH(CH_3)CH_2$ | (heptan-2-yloxy)carbonyl | |
| 8.234 | 3,5-$F_2$—Ph | H | O | H | $CH(CH_3)CH_2$ | (heptan-2-yloxy)carbonyl | |
| 8.235 | 3,5-$Cl_2$—Ph | H | O | H | $CH(CH_3)CH_2$ | (isopropylsulfonyl)-(methyl)carbamoyl | |
| 8.236 | 3,5-$F_2$—Ph | H | O | H | $CH(CH_3)CH_2$ | (isopropylsulfonyl)-(methyl)carbamoyl | |
| 8.237 | 3,5-$Cl_2$—Ph | H | O | H | $CH(CH_3)CH_2$ | (isopropylsulfonyl)-carbamoyl | |
| 8.238 | 3,5-$F_2$—Ph | H | O | H | $CH(CH_3)CH_2$ | (isopropylsulfonyl)-carbamoyl | |
| 8.239 | 3,5-$Cl_2$—Ph | H | O | H | $CH(CH_3)CH_2$ | (methylsulfonyl)-carbamoyl | |
| 8.240 | 3,5-$F_2$—Ph | H | O | H | $CH(CH_3)CH_2$ | (methylsulfonyl)-carbamoyl | |

TABLE 8-continued

Compounds of the general formula (I) according to the invention in which $R^2$ is hydrogen and $R^3$ is trifluoroomethyl and aryl is the radical

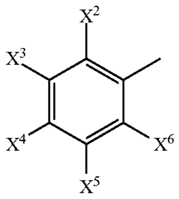

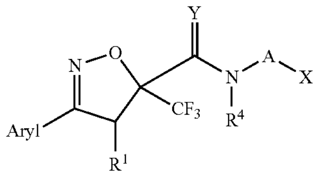

| No. | Aryl | $R^1$ | Y | $R^4$ | A | X | Physical data |
|---|---|---|---|---|---|---|---|
| 8.241 | 3,5-$Cl_2$—Ph | H | O | H | $CH(CH_3)CH_2$ | (prop-2-yn-1-yloxy)carbonyl | |
| 8.242 | 3,5-$F_2$—Ph | H | O | H | $CH(CH_3)CH_2$ | (prop-2-yn-1-yloxy)carbonyl | |
| 8.243 | 3,5-$Cl_2$—Ph | H | O | H | $CH(CH_3)CH_2$ | (propan-2-yloxy)carbonyl | |
| 8.244 | 3,5-$F_2$—Ph | H | O | H | $CH(CH_3)CH_2$ | (propan-2-yloxy)carbonyl | |
| 8.245 | 3-Cl—Ph | H | O | H | $CH(CH_3)CH_2$ | (propan-2-yloxy)carbonyl | |
| 8.246 | 3-F—Ph | H | O | H | $CH(CH_3)CH_2$ | (propan-2-yloxy)carbonyl | |
| 8.247 | 3,5-$Cl_2$—Ph | H | O | H | $CH(CH_3)CH_2$ | [2-(methylsulfanyl)-ethoxy]carbonyl | |
| 8.248 | 3,5-$F_2$—Ph | H | O | H | $CH(CH_3)CH_2$ | [2-(methylsulfanyl)-ethoxy]carbonyl | |
| 8.249 | 3,5-$F_2$—Ph | H | O | H | $CH(CH_3)CH_2$ | [2-(methylsulfonyl)-ethoxy]carbonyl | |
| 8.250 | 3,5-$Cl_2$—Ph | H | O | H | $CH(CH_3)CH_2$ | butoxycarbonyl | |
| 8.251 | 3,5-$F_2$—Ph | H | O | H | $CH(CH_3)CH_2$ | butoxycarbonyl | |
| 8.252 | 3-$CF_3$—Ph | H | O | H | $CH(CH_3)CH_2$ | COOH | |
| 8.253 | 3,5-$Cl_2$—Ph | H | O | H | $CH(CH_3)CH_2$ | COOH | |
| 8.254 | 3,5-$F_2$—Ph | H | O | H | $CH(CH_3)CH_2$ | COOH | |
| 8.255 | 3,5-(tert.Bu)$_2$—Ph | H | O | H | $CH(CH_3)CH_2$ | COOH | |
| 8.256 | 3-Br-5-$CF_3$—Ph | H | O | H | $CH(CH_3)CH_2$ | COOH | |
| 8.257 | 3-Cl-5-$CF_3$—Ph | H | O | H | $CH(CH_3)CH_2$ | COOH | |
| 8.258 | 3-Cl—Ph | H | O | H | $CH(CH_3CH_2)$ | COOH | |
| 8.259 | 3-Et-5-F—Ph | H | O | H | $CH(CH_3)CH_2$ | COOH | |
| 8.260 | 3-Et—Ph | H | O | H | $CH(CH_3)CH_2$ | COOH | |
| 8.261 | 3-F-5-MeO—Ph | H | O | H | $CH(CH_3)CH_2$ | COOH | |
| 8.262 | 3-F—Ph | H | O | H | $CH(CH_3)CH_2$ | COOH | |
| 8.263 | 3-Me—Ph | H | O | H | $CH(CH_3)CH_2$ | COOH | |
| 8.264 | 4-MeO—Ph | H | O | H | $CH(CH_3)CH_2$ | COOH | |
| 8.265 | 3-$CF_3$—Ph | H | O | H | $CH(CH_3)CH_2$ | ethoxycarbonyl | |
| 8.266 | 3,5-$Cl_2$-4-MeO—Ph | H | O | H | $CH(CH_3)CH_2$ | ethoxycarbonyl | |
| 8.267 | 3,5-$Cl_2$—Ph | H | O | H | $CH(CH_3)CH_2$ | ethoxycarbonyl | |
| 8.268 | 3,5-$Et_2$—Ph | H | O | H | $CH(CH_3)CH_2$ | ethoxycarbonyl | |
| 8.269 | 3,5-$F_2$—Ph | H | O | H | $CH(CH_3)CH_2$ | ethoxycarbonyl | |
| 8.270 | 3,5-(MeO)$_2$—Ph | H | O | H | $CH(CH_3)CH_2$ | ethoxycarbonyl | |
| 8.271 | 3,5-$Me_2$—Ph | H | O | H | $CH(CH_3)CH_2$ | ethoxycarbonyl | |
| 8.272 | 3,5-(tert.Bu)$_2$—Ph | H | O | H | $CH(CH_3)CH_2$ | ethoxycarbonyl | |
| 8.273 | 3-Br-5-$CF_3$—Ph | H | O | H | $CH(CH_3)CH_2$ | ethoxycarbonyl | |
| 8.274 | 3-Cl-5-Et—Ph | H | O | H | $CH(CH_3)CH_2$ | ethoxycarbonyl | |
| 8.275 | 3-Cl-5-$CF_3$—Ph | H | O | H | $CH(CH_3)CH_2$ | ethoxycarbonyl | |
| 8.276 | 3-Cl—Ph | H | O | H | $CH(CH_3)CH_2$ | ethoxycarbonyl | |
| 8.277 | 3-c-Pr-S—F—Ph | H | O | H | $CH(CH_3)CH_2$ | ethoxycarbonyl | |
| 8.278 | 3-Et-5-F—Ph | H | O | H | $CH(CH_3)CH_2$ | ethoxycarbonyl | |
| 8.279 | 3-Et—Ph | H | O | H | $CH(CH_3)CH_2$ | ethoxycarbonyl | |
| 8.280 | 3-F-5-MeS—Ph | H | O | H | $CH(CH_3)CH_2$ | ethoxycarbonyl | |
| 8.281 | 3-F-5-$MeSO_2$—Ph | H | O | H | $CH(CH_3)CH_2$ | ethoxycarbonyl | |
| 8.282 | 3-F-5-MeO—Ph | H | O | H | $CH(CH_3)CH_2$ | ethoxycarbonyl | |
| 8.283 | 3-F—Ph | H | O | H | $CH(CH_3)CH_2$ | ethoxycarbonyl | |
| 8.284 | 3-Me-5-$CF_3O$—Ph | H | O | H | $CH(CH_3)CH_2$ | ethoxycarbonyl | |
| 8.285 | 3-Me—Ph | H | O | H | $CH(CH_3)CH_2$ | ethoxycarbonyl | |
| 8.286 | 4-EtO—Ph | H | O | H | $CH(CH_3)CH_2$ | ethoxycarbonyl | |
| 8.287 | 4-MeO—Ph | H | O | H | $CH(CH_3)CH_2$ | ethoxycarbonyl | |

TABLE 8-continued

Compounds of the general formula (I) according to the invention in which $R^2$ is hydrogen and $R^3$ is trifluoroomethyl and aryl is the radical

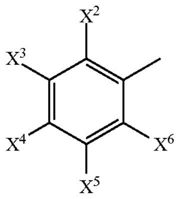

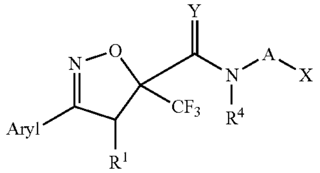

| No. | Aryl | $R^1$ | Y | $R^4$ | A | X | Physical data |
|---|---|---|---|---|---|---|---|
| 8.288 | 3,5-$Cl_2$—Ph | H | O | H | $CH(CH_3)CH_2$ | hydroxy | |
| 8.289 | 3,5-$Cl_2$—Ph | H | O | H | $CH(CH_3)CH_2$ | isobutoxycarbonyl | |
| 8.290 | 3,5-$F_2$—Ph | H | O | H | $CH(CH_3)CH_2$ | isobutoxycarbonyl | |
| 8.291 | 3,5-$Cl_2$—Ph | H | O | H | $CH(CH_3)CH_2$ | methoxy | |
| 8.292 | 2,5-$Me_2$—Ph | H | O | H | $CH(CH_3)CH_2$ | methoxycarbonyl | |
| 8.293 | 2-Cl-3-F-5-MeO—Ph | H | O | H | $CH(CH_3)CH_2$ | methoxycarbonyl | |
| 8.294 | 2-F-3-Me—Ph | H | O | H | $CH(CH_3)CH_2$ | methoxycarbonyl | |
| 8.295 | 3-$CF_3$—Ph | H | O | H | $CH(CH_3)CH_2$ | methoxycarbonyl | |
| 8.296 | 3,5-$Cl_2$—Ph | H | O | H | $CH(CH_3)CH_2$ | methoxycarbonyl | |
| 8.297 | 3,5-$F_2$—Ph | H | O | H | $CH(CH_3)CH_2$ | methoxycarbonyl | |
| 8.298 | 3-Cl—Ph | H | O | H | $CH(CH_3)CH_2$ | methoxycarbonyl | |
| 8.299 | 3-F-5-MeO—Ph | H | O | H | $CH(CH_3)CH_2$ | methoxycarbonyl | |
| 8.300 | 3-F—Ph | H | O | H | $CH(CH_3)CH_2$ | methoxycarbonyl | |
| 8.301 | 3,5-$Cl_2$—Ph | H | O | H | $CH(CH_3)CH_2$ | methyl(methylsulfonyl)-carbamoyl | |
| 8.302 | 3,5-$F_2$—Ph | H | O | H | $CH(CH_3)CH_2$ | methyl(methylsulfonyl)-carbamoyl | |
| 8.303 | 3,5-$Cl_2$—Ph | H | O | H | $CH(CH_3)CH_2$ | methylcarbamoyl | |
| 8.304 | 3,5-$Cl_2$—Ph | H | O | H | $CH(CH_3)CH_2$ | propoxycarbonyl | |
| 8.305 | 3,5-$F_2$—Ph | H | O | H | $CH(CH_3)CH_2$ | propoxycarbonyl | |
| 8.306 | 3,5-$Cl_2$—Ph | H | O | H | $CH(CH_3)CH_2$ | sec-butoxycarbonyl | |
| 8.307 | 3,5-$F_2$—Ph | H | O | H | $CH(CH_3)CH_2$ | sec-butoxycarbonyl | |
| 8.308 | 3,5-$Cl_2$—Ph | H | O | H | $CH(COOCH_3)CH_2$ | methoxycarbonyl | |
| 8.309 | 3,5-$Cl_2$—Ph | H | O | H | CH(cycloPr) | c-Pr | |
| 8.310 | 3,5-$F_2$—Ph | H | O | H | CH(cycloPr) | c-Pr | |
| 8.311 | 3,5-$Cl_2$—Ph | H | O | H | CH(iPr) | methoxycarbonyl | |
| 8.312 | 3,5-$Cl_2$—Ph | H | O | H | CH(iPr)$CH_2$ | methoxycarbonyl | |
| 8.313 | 3,5-$F_2$—Ph | H | O | H | $CH_2$ | (2-hydroxyethyl)-carbamoyl | |
| 8.314 | 3,5-$Cl_2$—Ph | H | O | H | $CH_2$ | (cyclopropylsulfonyl)-carbamoyl | |
| 8.315 | 3,5-$F_2$—Ph | H | O | H | $CH_2$ | (cyclopropylsulfonyl)-carbamoyl | |
| 8.316 | 3,5-$Cl_2$—Ph | H | O | H | $CH_2$ | (ethylsulfonyl)-carbamoyl | |
| 8.317 | 3,5-$F_2$—Ph | H | O | H | $CH_2$ | (ethylsulfonyl)-carbamoyl | |
| 8.318 | 3,5-$F_2$—Ph | H | O | H | $CH_2$ | (hydroxyimino)methyl | |
| 8.319 | 3,5-$Cl_2$—Ph | H | O | H | $CH_2$ | (isopropylsulfonyl)-carbamoyl | |
| 8.320 | 3,5-$F_2$—Ph | H | O | H | $CH_2$ | (isopropylsulfonyl)-carbamoyl | |
| 8.321 | 3,5-$Cl_2$—Ph | H | O | H | $CH_2$ | (methylsulfonyl)-carbamoyl | |
| 8.322 | 3,5-$F_2$—Ph | H | O | H | $CH_2$ | (methylsulfonyl)-carbamoyl | |
| 8.323 | 3-Cl—Ph | H | O | H | $CH_2$ | (propan-2-yloxy)carbonyl | |
| 8.324 | 3-F—Ph | H | O | H | $CH_2$ | (propan-2-yloxy)carbonyl | |
| 8.325 | 3,5-$Cl_2$—Ph | H | O | H | $CH_2$ | 1,1-dioxidotetrahydro-thiophen-3-yl | |
| 8.326 | 3,5-$F_2$—Ph | H | O | H | $CH_2$ | 1,1-dioxidotetrahydro-thiophen-3-yl | |
| 8.327 | 3-F—Ph | H | O | H | $CH_2$ | 1,1-dioxidotetrahydro-thiophen-3-yl | |

TABLE 8-continued

Compounds of the general formula (I) according to the invention in which $R^2$ is hydrogen and $R^3$ is trifluoroomethyl and aryl is the radical

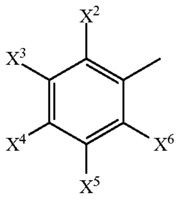

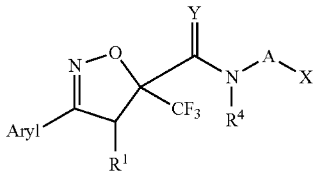

| No. | Aryl | $R^1$ | Y | $R^4$ | A | X | Physical data |
|---|---|---|---|---|---|---|---|
| 8.328 | Ph | H | O | H | $CH_2$ | 1,1-dioxidotetrahydro-thiophen-3-yl | |
| 8.329 | Ph | H | O | H | $CH_2$ | 1,4-dimethyl-5-oxo-4,5-dihydro-1H-1,2,4-triazol-3-yl | |
| 8.330 | 3,5-$Cl_2$—Ph | H | O | H | $CH_2$ | 3-(2-ethoxy-2-oxoethyl)oxetan-3-yl | |
| 8.331 | 3,5-$F_2$—Ph | H | O | H | $CH_2$ | 3-(2-ethoxy-2-oxoethyl)oxetan-3-yl | |
| 8.332 | 3,5-$Cl_2$—Ph | H | O | H | $CH_2$ | 3-(cyclopropyl-carbamoyl)-4,5-dihydro-1,2-oxazol-5-yl | |
| 8.333 | 3,5-$Cl_2$—Ph | H | O | H | $CH_2$ | 3-(ethoxycarbonyl)-4,5-dihydro-1,2-oxazol-5-yl | |
| 8.334 | 3,5-$Cl_2$—Ph | H | O | H | $CH_2$ | 3-(methylcarbamoyl)-4,5-dihydro-1,2-oxazol-5-yl | |
| 8.335 | 3,5-$Cl_2$—Ph | H | O | H | $CH_2$ | 3-carboxy-4,5-dihydro-1,2-oxazol-5-yl | |
| 8.336 | 3,5-$Cl_2$—Ph | H | O | H | $CH_2$ | 3-isopropyl-4,5-dihydro-1,2-oxazol-5-yl | |
| 8.337 | 3,5-$Cl_2$—Ph | H | O | H | $CH_2$ | 3-methyl-4,5-dihydro-1,2-oxazol-5-yl | |
| 8.338 | 3,5-$F_2$—Ph | H | O | H | $CH_2$ | 5-(ethoxycarbonyl)-4,5-dihydro-1,2-oxazol-3-yl | |
| 8.339 | 3,5-$Cl_2$—Ph | H | O | H | $CH_2$ | 5,5-dimethyl-4,5-dihydro-1,2-oxazol-3-yl | |
| 8.340 | 3,5-$Cl_2$—Ph | H | O | H | $CH_2$ | 5-ethyl-4,5-dihydro-1,2-oxazol-3-yl | |
| 8.341 | 3,5-$Cl_2$—Ph | H | O | H | $CH_2$ | 5-isopropyl-4,5-dihydro-1,2-oxazol-3-yl | |
| 8.342 | 3,5-$Cl_2$—Ph | H | O | H | $CH_2$ | 5-methyl-4,5-dihydro-1,2-oxazol-3-yl | |
| 8.343 | 3,5-$Cl_2$—Ph | H | O | H | $CH_2$ | carbamoyl | |
| 8.344 | 3-Cl—Ph | H | O | H | $CH_2$ | carbamoyl | |
| 8.345 | 2-$CF_3$—Ph | H | O | H | $CH_2$ | $CF_3$ | |
| 8.346 | 2,3,4-$F_3$—Ph | H | O | H | $CH_2$ | $CF_3$ | |
| 8.347 | 2,3,5-$F_3$—Ph | H | O | H | $CH_2$ | $CF_3$ | |
| 8.348 | 2,3,6-$Cl_3$—Ph | H | O | H | $CH_2$ | $CF_3$ | |
| 8.349 | 2,3-$F_2$—Ph | H | O | H | $CH_2$ | $CF_3$ | |
| 8.350 | 2,5-$F_2$—Ph | H | O | H | $CH_2$ | $CF_3$ | |
| 8.351 | 2-Cl-3-F-5-MeO—Ph | H | O | H | $CH_2$ | $CF_3$ | |
| 8.352 | 3-(2-MeOEtO)—Ph | H | O | H | $CH_2$ | $CF_3$ | |
| 8.353 | 3-iPrO—Ph | H | O | H | $CH_2$ | $CF_3$ | |
| 8.354 | 3-$CF_3$O—Ph | H | O | H | $CH_2$ | $CF_3$ | |
| 8.355 | 3-$CF_3$—Ph | H | O | H | $CH_2$ | $CF_3$ | |
| 8.356 | 3,4-$Cl_2$—Ph | H | O | H | $CH_2$ | $CF_3$ | |
| 8.357 | 3,5-$Br_2$—Ph | H | O | H | $CH_2$ | $CF_3$ | |
| 8.358 | 3,5-$Cl_2$-4-MeO—Ph | H | O | H | $CH_2$ | $CF_3$ | |

TABLE 8-continued

Compounds of the general formula (I) according to the invention in which $R^2$ is hydrogen and $R^3$ is trifluoroomethyl and aryl is the radical

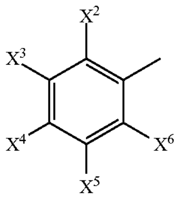

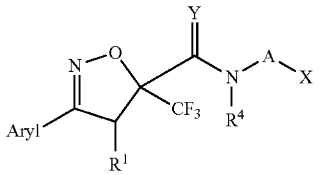

| No. | Aryl | $R^1$ | Y | $R^4$ | A | X | Physical data |
|---|---|---|---|---|---|---|---|
| 8.359 | 3,5-$Cl_2$—Ph | H | O | H | $CH_2$ | $CF_3$ | [$CDCl_3$] 3.78 (d, 1H); 4.00 (m, 3H); 7.10 (m, 1H); 7.5O (m, 1H); 7.56 (m, 2H). |
| 8.360 | 3,5-$F_2$—Ph | H | O | H | $CH_2$ | $CF_3$ | |
| 8.361 | 3,5-$(MeO)_2$—Ph | H | O | H | $CH_2$ | $CF_3$ | |
| 8.362 | 3,5-$Me_2$—Ph | H | O | H | $CH_2$ | $CF_3$ | |
| 8.363 | 3-Br-5-Cl—Ph | H | O | H | $CH_2$ | $CF_3$ | |
| 8.364 | 3-Br-5-F—Ph | H | O | H | $CH_2$ | $CF_3$ | |
| 8.365 | 3-Cl-5-$CF_3$—Ph | H | O | H | $CH_2$ | $CF_3$ | |
| 8.366 | 3-Cl-5-Et—Ph | H | O | H | $CH_2$ | $CF_3$ | |
| 8.367 | 3-Cl-5-F—Ph | H | O | H | $CH_2$ | $CF_3$ | |
| 8.368 | 3-Cl-5-Me—Ph | H | O | H | $CH_2$ | $CF_3$ | |
| 8.369 | 3-Cl-5-$CF_3O$—Ph | H | O | H | $CH_2$ | $CF_3$ | |
| 8.370 | 3-Cl—Ph | H | O | H | $CH_2$ | $CF_3$ | |
| 8.371 | 3-EtO—Ph | H | O | H | $CH_2$ | $CF_3$ | |
| 8.372 | 3-Et-5-F—Ph | H | O | H | $CH_2$ | $CF_3$ | |
| 8.373 | 3-Et—Ph | H | O | H | $CH_2$ | $CF_3$ | |
| 8.374 | 3-F-5-MeS—Ph | H | O | H | $CH_2$ | $CF_3$ | |
| 8.375 | 3-F-5-$MeSO_2$—Ph | H | O | H | $CH_2$ | $CF_3$ | |
| 8.376 | 3-F-5-$CF_3$—Ph | H | O | H | $CH_2$ | $CF_3$ | |
| 8.377 | 3-F-5-MeO—Ph | H | O | H | $CH_2$ | $CF_3$ | |
| 8.378 | 3-F-5-Me—Ph | H | O | H | $CH_2$ | $CF_3$ | |
| 8.379 | 3-F—Ph | H | O | H | $CH_2$ | $CF_3$ | |
| 8.380 | 3-OH—Ph | H | O | H | $CH_2$ | $CF_3$ | |
| 8.381 | 3-iPr—Ph | H | O | H | $CH_2$ | $CF_3$ | |
| 8.382 | 3-Me—Ph | H | O | H | $CH_2$ | $CF_3$ | |
| 8.383 | 3-$NO_2$—Ph | H | O | H | $CH_2$ | $CF_3$ | |
| 8.384 | 4-EtO—Ph | H | O | H | $CH_2$ | $CF_3$ | |
| 8.385 | 4-MeO—Ph | H | O | H | $CH_2$ | $CF_3$ | |
| 8.386 | $F_5$—Ph | H | O | H | $CH_2$ | $CF_3$ | |
| 8.387 | Ph | H | O | H | $CH_2$ | $CF_3$ | |
| 8.388 | 2,3,5-$F_3$—Ph | H | O | H | $CH_2$ | $CH_3$ | |
| 8.389 | 2,3-$F_2$—Ph | H | O | H | $CH_2$ | $CH_3$ | |
| 8.390 | 3,4-$F_2$—Ph | H | O | H | $CH_2$ | $CH_3$ | |
| 8.391 | 3,5-$Cl_2$—Ph | H | O | H | $CH_2$ | $CH_3$ | |
| 8.392 | 3,5-$F_2$—Ph | H | O | H | $CH_2$ | $CH_3$ | |
| 8.393 | 3-Cl-5-$CF_3$—Ph | H | O | H | $CH_2$ | $CH_3$ | |
| 8.394 | 3-Cl-5-Me—Ph | H | O | H | $CH_2$ | $CH_3$ | |
| 8.395 | 3-Cl-5-$CF_3O$—Ph | H | O | H | $CH_2$ | $CH_3$ | |
| 8.396 | 3-EtO—Ph | H | O | H | $CH_2$ | $CH_3$ | |
| 8.397 | 3-Et—Ph | H | O | H | $CH_2$ | $CH_3$ | |
| 8.398 | 3-F—Ph | H | O | H | $CH_2$ | $CH_3$ | |
| 8.399 | 3-Me—Ph | H | O | H | $CH_2$ | $CH_3$ | |
| 8.400 | $F_5$—Ph | H | O | H | $CH_2$ | $CH_3$ | |
| 8.401 | Ph | H | O | H | $CH_2$ | $CH_3$ | |
| 8.402 | 3,5-$Cl_2$—Ph | H | O | H | $CH_2$ | COOH | |
| 8.403 | 3,5-$F_2$—Ph | H | O | H | $CH_2$ | COOH | |
| 8.404 | 3-Cl—Ph | H | O | H | $CH_2$ | COOH | |
| 8.405 | 3-F—Ph | H | O | H | $CH_2$ | COOH | |
| 8.406 | 3,5-$Cl_2$—Ph | H | O | H | $CH_2$ | cyano | |
| 8.407 | 3,5-$F_2$—Ph | H | O | H | $CH_2$ | cyano | |
| 8.408 | 3-Cl-5-$CF_3O$—Ph | H | O | H | $CH_2$ | cyano | |
| 8.409 | 3-F-5-Me—Ph | H | O | H | $CH_2$ | cyano | |
| 8.410 | 3-F—Ph | H | O | H | $CH_2$ | cyano | |

TABLE 8-continued

Compounds of the general formula (I) according to the invention in which $R^2$ is hydrogen and $R^3$ is trifluoroomethyl and aryl is the radical

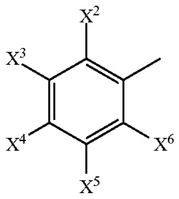

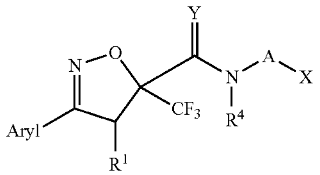

| No. | Aryl | $R^1$ | Y | $R^4$ | A | X | Physical data |
|---|---|---|---|---|---|---|---|
| 8.411 | 3-$NO_2$—Ph | H | O | H | $CH_2$ | cyano | |
| 8.412 | 3,5-$Cl_2$—Ph | H | O | H | $CH_2$ | cyclohexyl | |
| 8.413 | 3,5-$Cl_2$—Ph | H | O | H | $CH_2$ | c-Pr | |
| 8.414 | 3,5-$F_2$—Ph | H | O | H | $CH_2$ | c-Pr | |
| 8.415 | 3,5-$Cl_2$—Ph | H | O | H | $CH_2$ | diethoxyphosphoryl | |
| 8.416 | 3,5-$F_2$—Ph | H | O | H | $CH_2$ | diethoxyphosphoryl | |
| 8.417 | 3-F—Ph | H | O | H | $CH_2$ | diethoxyphosphoryl | |
| 8.418 | Ph | H | O | H | $CH_2$ | diethoxyphosphoryl | |
| 8.419 | 3,5-$Cl_2$—Ph | H | O | H | $CH_2$ | difluoromethyl | |
| 8.420 | 3,5-$Cl_2$—Ph | H | O | H | $CH_2$ | dimethoxymethyl | |
| 8.421 | 3-Cl—Ph | H | O | H | $CH_2$ | dimethoxymethyl | |
| 8.422 | 3,5-$Cl_2$—Ph | H | O | H | $CH_2$ | dimethylcarbamoyl | |
| 8.423 | 3,5-$Cl_2$—Ph | H | O | H | $CH_2$ | ethenyl | |
| 8.424 | 3,5-$Cl_2$—Ph | H | O | prop-2-en-1-yl | $CH_2$ | ethenyl | |
| 8.425 | 3,5-$F_2$—Ph | H | O | H | $CH_2$ | ethenyl | |
| 8.426 | 3-F—Ph | H | O | H | $CH_2$ | ethenyl | |
| 8.427 | Ph | H | O | H | $CH_2$ | ethenyl | |
| 8.428 | 3,5-$(CF_3)_2$—Ph | H | O | H | $CH_2$ | ethynyl | |
| 8.429 | 3,5-$Cl_2$—Ph | H | O | H | $CH_2$ | ethynyl | |
| 8.430 | 3,5-$Cl_2$—Ph | H | O | prop-2-yn-1-yl | $CH_2$ | ethynyl | |
| 8.431 | 3,5-$F_2$—Ph | H | O | H | $CH_2$ | ethynyl | |
| 8.432 | 3,5-$Cl_2$—Ph | H | O | cPr | $CH_2$ | ethoxycarbonyl | |
| 8.433 | 3-Cl—Ph | H | O | H | $CH_2$ | ethoxycarbonyl | |
| 8.434 | 3-F—Ph | H | O | H | $CH_2$ | ethoxycarbonyl | |
| 8.435 | 3,5-F2—Ph | H | O | H | $CH_2$ | formyl | |
| 8.436 | 3,5-Cl2—Ph | H | O | H | $CH_2$ | methoxycarbonyl | |
| 8.437 | 3,5-F2—Ph | H | O | H | $CH_2$ | methoxycarbonyl | |
| 8.438 | 3-Cl—Ph | H | O | H | $CH_2$ | methoxycarbonyl | |
| 8.439 | 3-F—Ph | H | O | H | $CH_2$ | methoxycarbonyl | |
| 8.440 | 3-Cl-5-F—Ph | H | O | H | $CH_2$ | ony | |
| 8.441 | 3,5-$Cl_2$—Ph | H | O | H | $CH_2$ | pentafluoroethyl | |
| 8.442 | 3,5-$Cl_2$—Ph | H | O | H | $CH_2$ | pentyl | |
| 8.443 | 3,5-$F_2$—Ph | H | O | H | $CH_2$ | pentyl | |
| 8.444 | 3,5-$Cl_2$—Ph | H | O | H | $CH_2$ | piperidin-2-yl | |
| 8.445 | 3,5-$F_2$—Ph | H | O | H | $CH_2$ | piperidin-2-yl | |
| 8.446 | Ph | H | O | H | $CH_2$ | piperidin-2-yl | |
| 8.447 | 3,5-$Cl_2$—Ph | H | O | $CH_3$ | $CH_2$ | propan-2-yl | |
| 8.448 | 3,5-$Cl_2$—Ph | H | O | H | $CH_2$ | propan-2-yl | |
| 8.449 | 3,5-$Cl_2$—Ph | H | O | H | $CH_2$ | pyrrolidin-1-ylcarbonyl | |
| 8.450 | 3,5-$Cl_2$—Ph | H | O | H | $CH_2$ | tert-butyl | |
| 8.451 | 3,5-$F_2$—Ph | H | O | H | $CH_2$ | tert-butyl | |
| 8.452 | 3,5-$Cl_2$—Ph | H | O | H | $CH_2$ | tetrahydrofuran-2-yl | |
| 8.453 | 3,5-$F_2$—Ph | H | O | H | $CH_2$ | tetrahydrofuran-2-yl | |
| 8.454 | 3-F—Ph | H | O | H | $CH_2$ | tetrahydrofuran-2-yl | |
| 8.455 | Ph | H | O | H | $CH_2$ | tetrahydrofuran-2-yl | |
| 8.456 | 3,5-$Cl_2$—Ph | H | O | H | $CH_2$ | tetrahydrofuran-3-yl | |
| 8.457 | 3,5-$F_2$—Ph | H | O | H | $CH_2$ | tetrahydrofuran-3-yl | |
| 8.458 | 3-F—Ph | H | O | H | $CH_2$ | tetrahydrofuran-3-yl | |
| 8.459 | Ph | H | O | H | $CH_2$ | tetrahydrofuran-3-yl | |
| 8.460 | 3,5-$Cl_2$—Ph | H | O | H | $CH_2C(CH_3)_2$ | COOH | |
| 8.461 | 3,5-$Cl_2$—Ph | H | O | H | $CH_2C(CH_3)_2$ | ethoxycarbonyl | |
| 8.462 | 3,5-$Cl_2$—Ph | H | O | H | $CH_2CH(CH_3)$ | ethoxycarbonyl | |
| 8.463 | 3,5-$Cl_2$—Ph | H | O | H | $CH_2CH_2$ | (2,2,2-trifluoroethoxy)-carbonyl | |

TABLE 8-continued

Compounds of the general formula (I) according to the invention in which $R^2$ is hydrogen and $R^3$ is trifluoroomethyl and aryl is the radical

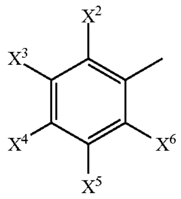

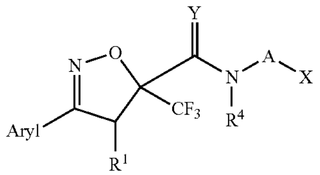

| No. | Aryl | $R^1$ | Y | $R^4$ | A | X | Physical data |
|---|---|---|---|---|---|---|---|
| 8.464 | 3,5-$Cl_2$—Ph | H | O | H | $CH_2CH_2$ | (2-hydroxyethoxy)-carbonyl | |
| 8.465 | 3,5-$Cl_2$—Ph | H | O | H | $CH_2CH_2$ | (2-methoxy-2-oxoethyl)carbamoyl | |
| 8.466 | 3,5-$Cl_2$—Ph | H | O | H | $CH_2CH_2$ | (allyloxy)carbonyl | |
| 8.467 | 3,5-$Cl_2$—Ph | H | O | H | $CH_2CH_2$ | (cyclopropylsulfonyl)-(methyl)carbamoyl | |
| 8.468 | 3,5-$F_2$—Ph | H | O | H | $CH_2CH_2$ | (cyclopropylsulfonyl)-(methyl)carbamoyl | |
| 8.469 | 3,5-$Cl_2$—Ph | H | O | H | $CH_2CH_2$ | (cyclopropylsulfonyl)-carbamoyl | |
| 8.470 | 3,5-$F_2$—Ph | H | O | H | $CH_2CH_2$ | (cyclopropylsulfonyl)-carbamoyl | |
| 8.471 | 3,5-$Cl_2$—Ph | H | O | H | $CH_2CH_2$ | (ethylsulfonyl)(methyl)-carbamoyl | |
| 8.472 | 3,5-$F_2$—Ph | H | O | H | $CH_2CH_2$ | (ethylsulfonyl)(methyl)-carbamoyl | |
| 8.473 | 3,5-$Cl_2$—Ph | H | O | H | $CH_2CH_2$ | (ethylsulfonyl)-carbamoyl | |
| 8.474 | 3,5-$F_2$—Ph | H | O | H | $CH_2CH_2$ | (ethylsulfonyl)-carbamoyl | |
| 8.475 | 3,5-$Cl_2$—Ph | H | O | H | $CH_2CH_2$ | (heptan-2-yloxy)carbonyl | |
| 8.476 | 3,5-$F_2$—Ph | H | O | H | $CH_2CH_2$ | (hydroxyimino)methyl | |
| 8.477 | 3,5-$Cl_2$—Ph | H | O | H | $CH_2CH_2$ | (isopropylsulfonyl)-(methyl)carbamoyl | |
| 8.478 | 3,5-$F_2$—Ph | H | O | H | $CH_2CH_2$ | (isopropylsulfonyl)-(methyl)carbamoyl | |
| 8.479 | 3,5-$Cl_2$—Ph | H | O | H | $CH_2CH_2$ | (isopropylsulfonyl)-carbamoyl | |
| 8.480 | 3,5-$F_2$—Ph | H | O | H | $CH_2CH_2$ | (isopropylsulfonyl)-carbamoyl | |
| 8.481 | 3,5-$Cl_2$—Ph | H | O | H | $CH_2CH_2$ | (methylsulfonyl)-carbamoyl | |
| 8.482 | 3,5-$F_2$—Ph | H | O | H | $CH_2CH_2$ | (methylsulfonyl)-carbamoyl | |
| 8.483 | 3,5-$Cl_2$—Ph | H | O | H | $CH_2CH_2$ | (prop-2-yn-1-yloxy)carbonyl | |
| 8.484 | 3,5-$Cl_2$—Ph | H | O | H | $CH_2CH_2$ | (propan-2-yloxy)carbonyl | |
| 8.485 | 3,5-$Cl_2$—Ph | H | O | H | $CH_2CH_2$ | [2-(methylsulfanyl)-ethoxy]carbonyl | |
| 8.486 | 3,5-$Cl_2$—Ph | H | O | H | $CH_2CH_2$ | 1,3-dioxolan-2-yl | |
| 8.487 | 3,5-$F_2$—Ph | H | O | H | $CH_2CH_2$ | 1,3-dioxolan-2-yl | |
| 8.488 | 3-F—Ph | H | O | H | $CH_2CH_2$ | 1,3-dioxolan-2-yl | |
| 8.489 | Ph | H | O | H | $CH_2CH_2$ | 1,3-dioxolan-2-yl | |
| 8.490 | 3,5-$Cl_2$—Ph | H | O | H | $CH_2CH_2$ | 1-methylpyrrolidin-2-yl | |
| 8.491 | 3,5-$Cl_2$—Ph | H | O | H | $CH_2CH_2$ | 2-oxopyrrolidin-1-yl | |
| 8.492 | 3,5-$Cl_2$—Ph | H | O | H | $CH_2CH_2$ | butoxycarbonyl | |
| 8.493 | 3,4,5-$F_3$-Ph | H | O | H | $CH_2CH_2$ | butylcarbamoyl | |
| 8.494 | 3,5-$Cl_2$—Ph | H | O | H | $CH_2CH_2$ | carbamoyl | |
| 8.495 | 3-Cl-4-Me—Ph | H | O | H | $CH_2CH_2$ | carbamoyl | |
| 8.496 | 3,5-$Cl_2$—Ph | H | O | H | $CH_2CH_2$ | $CF_3$ | |
| 8.497 | 3,5-$F_2$—Ph | H | O | H | $CH_2CH_2$ | $CF_3$ | |
| 8.498 | 3,5-$Cl_2$—Ph | H | O | H | $CH_2CH_2$ | $CH_3$ | |
| 8.499 | 3,5-$F_2$—Ph | H | O | H | $CH_2CH_2$ | $CH_3$ | |

TABLE 8-continued

Compounds of the general formula (I) according to the invention in which $R^2$ is hydrogen and $R^3$ is trifluoroomethyl and aryl is the radical

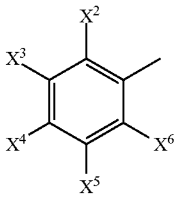

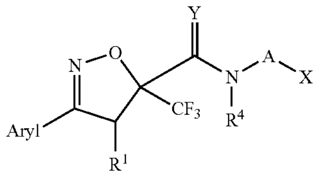

| No. | Aryl | $R^1$ | Y | $R^4$ | A | X | Physical data |
|---|---|---|---|---|---|---|---|
| 8.500 | 3,5-$Cl_2$—Ph | H | O | H | $CH_2CH_2$ | chlorine | |
| 8.501 | 2,3,4,5-$F_4$-6-OH—Ph | H | O | H | $CH_2CH_2$ | COOH | |
| 8.502 | 2,3,5-$F_3$—Ph | H | O | H | $CH_2CH_2$ | COOH | |
| 8.503 | 2,3-$F_2$—Ph | H | O | H | $CH_2CH_2$ | COOH | |
| 8.504 | 2,5-$Cl_2$—Ph | H | O | H | $CH_2CH_2$ | COOH | |
| 8.505 | 2,5-$F_2$—Ph | H | O | H | $CH_2CH_2$ | COOH | |
| 8.506 | 2-Cl-5-F—Ph | H | O | H | $CH_2CH_2$ | COOH | |
| 8.507 | 2-F-3-Me—Ph | H | O | H | $CH_2CH_2$ | COOH | |
| 8.508 | 3-$CF_3$—Ph | H | O | H | $CH_2CH_2$ | COOH | |
| 8.509 | 3,4,5-$F_3$—Ph | H | O | H | $CH_2CH_2$ | COOH | |
| 8.510 | 3,4-$F_2$—Ph | H | O | H | $CH_2CH_2$ | COOH | |
| 8.511 | 3,5-$Br_2$—Ph | H | O | H | $CH_2CH_2$ | COOH | |
| 8.512 | 3,5-$Cl_2$—Ph | H | O | $CH_3$ | $CH_2CH_2$ | COOH | |
| 8.513 | 3,5-$Cl_2$—Ph | H | O | H | $CH_2CH_2$ | COOH | |
| 8.514 | 3,5-$F_2$—Ph | H | O | H | $CH_2CH_2$ | COOH | |
| 8.515 | 3,5-$Me_2$—Ph | H | O | H | $CH_2CH_2$ | COOH | |
| 8.516 | 3,5-(tert.Bu)$_2$—Ph | H | O | H | $CH_2CH_2$ | COOH | |
| 8.517 | 3-Br-5-Cl—Ph | H | O | H | $CH_2CH_2$ | COOH | |
| 8.518 | 3-Br-5-F—Ph | H | O | H | $CH_2CH_2$ | COOH | |
| 8.519 | 3-Br-5-$CF_3$—Ph | H | O | H | $CH_2CH_2$ | COOH | |
| 8.520 | 3-Cl-4-F—Ph | H | O | H | $CH_2CH_2$ | COOH | |
| 8.521 | 3-Cl-4-Me—Ph | H | O | H | $CH_2CH_2$ | COOH | |
| 8.522 | 3-Cl-5-F—Ph | H | O | H | $CH_2CH_2$ | COOH | |
| 8.523 | 3-Cl-5-$CF_3$O—Ph | H | O | H | $CH_2CH_2$ | COOH | |
| 8.524 | 3-Cl-5-$CF_3$—Ph | H | O | H | $CH_2CH_2$ | COOH | |
| 8.525 | 3-Cl-5-Me—Ph | H | O | H | $CH_2CH_2$ | COOH | |
| 8.526 | 3-Et-5-F—Ph | H | O | H | $CH_2CH_2$ | COOH | |
| 8.527 | 3-Et—Ph | H | O | H | $CH_2CH_2$ | COOH | |
| 8.528 | 3-F-5-MeO—Ph | H | O | H | $CH_2CH_2$ | COOH | |
| 8.529 | 3-F-5-Me—Ph | H | O | H | $CH_2CH_2$ | COOH | |
| 8.530 | 3-F—Ph | H | O | H | $CH_2CH_2$ | COOH | |
| 8.531 | 3-Me—Ph | H | O | H | $CH_2CH_2$ | COOH | |
| 8.532 | 4-Cl—Ph | H | O | H | $CH_2CH_2$ | COOH | |
| 8.533 | 4-EtO—Ph | H | O | H | $CH_2CH_2$ | COOH | |
| 8.534 | Ph | H | O | H | $CH_2CH_2$ | COOH | |
| 8.535 | 3,5-$Cl_2$—Ph | H | O | H | $CH_2CH_2$ | cyano | |
| 8.536 | 3-Cl—Ph | H | O | H | $CH_2CH_2$ | cyano | |
| 8.537 | 3,5-$Cl_2$—Ph | H | O | H | $CH_2CH_2$ | cyclopropylcarbamoyl | |
| 8.538 | 3,5-$Cl_2$—Ph | H | O | H | $CH_2CH_2$ | diethoxymethyl | |
| 8.539 | 3,5-$Cl_2$—Ph | H | O | H | $CH_2CH_2$ | diethoxyphosphoryl | |
| 8.540 | Ph | H | O | H | $CH_2CH_2$ | diethoxyphosphoryl | |
| 8.541 | 3,5-$Cl_2$—Ph | H | O | H | $CH_2CH_2$ | dimethoxymethyl | |
| 8.542 | 3,5-$Cl_2$—Ph | H | O | H | $CH_2CH_2$ | dimethylcarbamoyl | |
| 8.543 | 3,5-$Cl_2$—Ph | H | O | H | $CH_2CH_2$ | ethoxy | |
| 8.544 | 3-Cl—Ph | H | O | H | $CH_2CH_2$ | ethoxy | |
| 8.545 | 2-Cl-5-F—Ph | H | O | H | $CH_2CH_2$ | ethoxycarbonyl | |
| 8.546 | 3-$CF_3$—Ph | H | O | H | $CH_2CH_2$ | ethoxycarbonyl | |
| 8.547 | 3,5-$Cl_2$—Ph | H | O | cPr | $CH_2CH_2$ | ethoxycarbonyl | |
| 8.548 | 3,5-$Cl_2$—Ph | H | O | H | $CH_2CH_2$ | ethoxycarbonyl | |
| 8.549 | 3,5-$F_2$—Ph | H | O | H | $CH_2CH_2$ | ethoxycarbonyl | |
| 8.550 | 3-Br-5-$CF_3$—Ph | H | O | H | $CH_2CH_2$ | ethoxycarbonyl | |
| 8.551 | 3-Cl-5-Et—Ph | H | O | H | $CH_2CH_2$ | ethoxycarbonyl | |
| 8.552 | 3-Cl-5-$CF_3$-Ph | H | O | H | $CH_2CH_2$ | ethoxycarbonyl | |
| 8.553 | 3-Et-5-F—Ph | H | O | H | $CH_2CH_2$ | ethoxycarbonyl | |
| 8.554 | 3-Et—Ph | H | O | H | $CH_2CH_2$ | ethoxycarbonyl | |
| 8.555 | 3-F-5-MeO—Ph | H | O | H | $CH_2CH_2$ | ethoxycarbonyl | |

TABLE 8-continued

Compounds of the general formula (I) according to the invention in which $R^2$ is hydrogen and $R^3$ is trifluoroomethyl and aryl is the radical

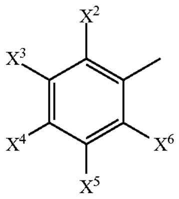

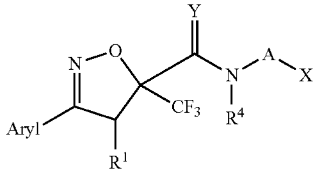

| No. | Aryl | $R^1$ | Y | $R^4$ | A | X | Physical data |
|---|---|---|---|---|---|---|---|
| 8.556 | 3-Me-5-$CF_3$O—Ph | H | O | H | $CH_2CH_2$ | ethoxycarbonyl | |
| 8.557 | 3,5-$Cl_2$—Ph | H | O | H | $CH_2CH_2$ | ethylcarbamoyl | |
| 8.558 | 3,5-$F_2$—Ph | H | O | H | $CH_2CH_2$ | formyl | |
| 8.559 | 3,5-$Cl_2$—Ph | H | O | H | $CH_2CH_2$ | hydroxy | |
| 8.560 | 3,5-$F_2$—Ph | H | O | H | $CH_2CH_2$ | hydroxy | |
| 8.561 | 3-Cl—Ph | H | O | H | $CH_2CH_2$ | hydroxy | |
| 8.562 | 3,5-$Cl_2$—Ph | H | O | H | $CH_2CH_2$ | isobutoxycarbonyl | |
| 8.563 | 3,5-$Cl_2$—Ph | H | O | H | $CH_2CH_2$ | methoxy | |
| 8.564 | 3-Cl-5-$CF_3$—Ph | H | O | H | $CH_2CH_2$ | methoxy | |
| 8.565 | 3-Cl—Ph | H | O | H | $CH_2CH_2$ | methoxy | |
| 8.566 | 2,3,4-$F_3$—Ph | H | O | H | $CH_2CH_2$ | methoxycarbonyl | |
| 8.567 | 2,3,5-$F_3$—Ph | H | O | H | $CH_2CH_2$ | methoxycarbonyl | |
| 8.568 | 2,3-$F_2$—Ph | H | O | H | $CH_2CH_2$ | methoxycarbonyl | |
| 8.569 | 2,5-$Cl_2$—Ph | H | O | H | $CH_2CH_2$ | methoxycarbonyl | |
| 8.570 | 2,5-F2—Ph | H | O | H | $CH_2CH_2$ | methoxycarbonyl | |
| 8.571 | 2,5-$Me_2$—Ph | H | O | H | $CH_2CH_2$ | methoxycarbonyl | |
| 8.572 | 2-Cl-3-F-5-MeO—Ph | H | O | H | $CH_2CH_2$ | methoxycarbonyl | |
| 8.573 | 2-F-3-Me—Ph | H | O | H | $CH_2CH_2$ | methoxycarbonyl | |
| 8.574 | 3-$CF_3$—Ph | H | O | H | $CH_2CH_2$ | methoxycarbonyl | |
| 8.575 | 3,4,5-$F_3$—Ph | H | O | H | $CH_2CH_2$ | methoxycarbonyl | |
| 8.576 | 3,4-$F_2$—Ph | H | O | H | $CH_2CH_2$ | methoxycarbonyl | |
| 8.577 | 3,5-$Br_2$—Ph | H | O | H | $CH_2CH_2$ | methoxycarbonyl | |
| 8.578 | 3,5-$Cl_2$-4-MeO—Ph | H | O | H | $CH_2CH_2$ | methoxycarbonyl | |
| 8.579 | 3,5-$Cl_2$—Ph | $CH_3$ | O | H | $CH_2CH_2$ | methoxycarbonyl | |
| 8.580 | 3,5-$Cl_2$—Ph | H | O | $CH_3$ | $CH_2CH_2$ | methoxycarbonyl | |
| 8.581 | 3,5-$Cl_2$—Ph | H | O | H | $CH_2CH_2$ | methoxycarbonyl | |
| 8.582 | 3,5-$Et_2$—Ph | H | O | H | $CH_2CH_2$ | methoxycarbonyl | |
| 8.583 | 3,5-$F_2$—Ph | H | O | H | $CH_2CH_2$ | methoxycarbonyl | |
| 8.584 | 3,5-$(MeO)_2$—Ph | H | O | H | $CH_2CH_2$ | methoxycarbonyl | |
| 8.585 | 3,5-$Me_2$—Ph | H | O | H | $CH_2CH_2$ | methoxycarbonyl | |
| 8.586 | 3,5-$(tert.Bu)_2$—Ph | H | O | H | $CH_2CH_2$ | methoxycarbonyl | |
| 8.587 | 3-$CF_3$S—Ph | H | O | H | $CH_2CH_2$ | methoxycarbonyl | |
| 8.588 | 3-Ac—Ph | H | O | H | $CH_2CH_2$ | methoxycarbonyl | |
| 8.589 | 3-Br-5-Cl—Ph | H | O | H | $CH_2CH_2$ | methoxycarbonyl | |
| 8.590 | 3-Br-5-F—Ph | H | O | H | $CH_2CH_2$ | methoxycarbonyl | |
| 8.591 | 3-Br-5-$CF_3$—Ph | H | O | H | $CH_2CH_2$ | methoxycarbonyl | |
| 8.592 | 3-$NH_2$CO—Ph | H | O | H | $CH_2CH_2$ | methoxycarbonyl | |
| 8.593 | 3-Cl-4-F—Ph | H | O | H | $CH_2CH_2$ | methoxycarbonyl | |
| 8.594 | 3-Cl-4-Me—Ph | H | O | H | $CH_2CH_2$ | methoxycarbonyl | |
| 8.595 | 3-Cl-5-CN—Ph | H | O | H | $CH_2CH_2$ | methoxycarbonyl | |
| 8.596 | 3-Cl-5-Et—Ph | H | O | H | $CH_2CH_2$ | methoxycarbonyl | |
| 8.597 | 3-Cl-5-F—Ph | H | O | H | $CH_2CH_2$ | methoxycarbonyl | |
| 8.598 | 3-Cl-5-MeO—Ph | H | O | H | $CH_2CH_2$ | methoxycarbonyl | |
| 8.599 | 3-Cl-5-$CF_3$O—Ph | H | O | H | $CH_2CH_2$ | methoxycarbonyl | |
| 8.600 | 3-Cl-5-$CF_3$—Ph | H | O | H | $CH_2CH_2$ | methoxycarbonyl | |
| 8.601 | 3-Cl-5-Me—Ph | H | O | H | $CH_2CH_2$ | methoxycarbonyl | |
| 8.602 | 3-CN-5-F—Ph | H | O | H | $CH_2CH_2$ | methoxycarbonyl | |
| 8.603 | 3-CN—Ph | H | O | H | $CH_2CH_2$ | methoxycarbonyl | |
| 8.604 | 3-c-Pr-5-F—Ph | H | O | H | $CH_2CH_2$ | methoxycarbonyl | |
| 8.605 | 3-Et-5-F—Ph | H | O | H | $CH_2CH_2$ | methoxycarbonyl | |
| 8.606 | 3-F-5-MeS—Ph | H | O | H | $CH_2CH_2$ | methoxycarbonyl | |
| 8.607 | 3-F-5-$MeSO_2$—Ph | H | O | H | $CH_2CH_2$ | methoxycarbonyl | |
| 8.608 | 3-F-5-MeO—Ph | H | O | H | $CH_2CH_2$ | methoxycarbonyl | |
| 8.609 | 3-F-5-Me—Ph | H | O | H | $CH_2CH_2$ | methoxycarbonyl | |
| 8.610 | 3-F—Ph | H | O | H | $CH_2CH_2$ | methoxycarbonyl | |
| 8.611 | 3-Me—Ph | H | O | H | $CH_2CH_2$ | methoxycarbonyl | |

TABLE 8-continued

Compounds of the general formula (I) according to the invention in which $R^2$ is hydrogen and $R^3$ is trifluoroomethyl and aryl is the radical

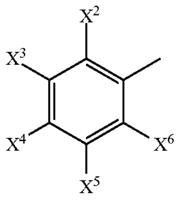

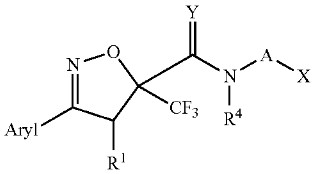

| No. | Aryl | $R^1$ | Y | $R^4$ | A | X | Physical data |
|---|---|---|---|---|---|---|---|
| 8.612 | 3-$NO_2$—Ph | H | O | H | $CH_2CH_2$ | methoxycarbonyl | |
| 8.613 | 4-Cl—Ph | H | O | H | $CH_2CH_2$ | methoxycarbonyl | |
| 8.614 | 4-EtO—Ph | H | O | H | $CH_2CH_2$ | methoxycarbonyl | |
| 8.615 | 4-MeO—Ph | H | O | H | $CH_2CH_2$ | methoxycarbonyl | |
| 8.616 | $F_5$—Ph | H | O | H | $CH_2CH_2$ | methoxycarbonyl | |
| 8.617 | Ph | H | O | H | $CH_2CH_2$ | methoxycarbonyl | |
| 8.618 | 3,5-$Cl_2$—Ph | H | O | H | $CH_2CH_2$ | methyl(methylsulfonyl)-carbamoyl | |
| 8.619 | 3,5-$F_2$—Ph | H | O | H | $CH_2CH_2$ | methyl(methylsulfonyl)-carbamoyl | |
| 8.620 | 2,5-$Cl_2$—Ph | H | O | H | $CH_2CH_2$ | methylcarbamoyl | |
| 8.621 | 3,5-$Cl_2$—Ph | H | O | H | $CH_2CH_2$ | methylcarbamoyl | |
| 8.622 | 3-Cl-4-F—Ph | H | O | H | $CH_2CH_2$ | methylcarbamoyl | |
| 8.623 | 3-Cl-4-Me—Ph | H | O | H | $CH_2CH_2$ | methylcarbamoyl | |
| 8.624 | 3,5-$Cl_2$—Ph | H | O | H | $CH_2CH_2$ | methylsulfanyl | |
| 8.625 | 3,5-$Cl_2$—Ph | H | O | H | $CH_2CH_2$ | methylsulfonyl | |
| 8.626 | 3,5-$Cl_2$—Ph | H | O | H | $CH_2CH_2$ | morpholin-4-yl | |
| 8.627 | 3,5-$Cl_2$—Ph | H | O | H | $CH_2CH_2$ | morpholin-4-ylcarbonyl | |
| 8.628 | 3,5-$Cl_2$—Ph | H | O | H | $CH_2CH_2$ | phosphono | |
| 8.629 | Ph | H | O | H | $CH_2CH_2$ | phosphono | |
| 8.630 | 3,5-$Cl_2$—Ph | H | O | H | $CH_2CH_2$ | piperidin-1-yl | |
| 8.631 | 3,5-$Cl_2$—Ph | H | O | H | $CH_2CH_2$ | piperidin-1-ylcarbonyl | |
| 8.632 | 3,5-$Cl_2$—Ph | H | O | H | $CH_2CH_2$ | propan-2-yloxy | |
| 8.633 | 3,5-$Cl_2$—Ph | H | O | H | $CH_2CH_2$ | propoxy | |
| 8.634 | 3,5-$Cl_2$—Ph | H | O | H | $CH_2CH_2$ | propoxycarbonyl | |
| 8.635 | 3,5-$Cl_2$—Ph | H | O | H | $CH_2CH_2$ | pyrrolidin-1-yl | |
| 8.636 | 3,5-$Cl_2$—Ph | H | O | H | $CH_2CH_2$ | sec-butoxycarbonyl | |
| 8.637 | 3,5-$F_2$—Ph | H | O | H | $CH_2CH_2$ | sulfamoyl | |
| 8.638 | 3,5-$Cl_2$—Ph | H | O | H | $CH_2CH_2$ | tert-butoxycarbonyl | |
| 8.639 | 3,5-$F_2$—Ph | H | O | H | $CH_2CH_2$ | tert-butoxycarbonyl | |
| 8.640 | 3,5-$Cl_2$—Ph | H | O | H | $CH_2CH_2$ | tetrahydrofuran-2-yl | |
| 8.641 | 3,5-$Cl_2$—Ph | H | O | H | $CH_2CH_2$ | trifluoromethoxy | |
| 8.642 | 3,5-$F_2$—Ph | H | O | H | $CH_2CH_2$ | trifluoromethoxy | |
| 8.643 | 3-F—Ph | H | O | H | $CH_2CH_2$ | trifluoromethoxy | |
| 8.644 | Ph | H | O | H | $CH_2CH_2$ | trifluoromethoxy | |
| 8.645 | 3-Cl—Ph | H | O | H | $(CH_2)_3$ | (propan-2-yloxy)carbonyl | |
| 8.646 | 3-F—Ph | H | O | H | $(CH_2)_3$ | (propan-2-yloxy)carbonyl | |
| 8.647 | 3,5-$Cl_2$—Ph | H | O | H | $(CH_2)_3$ | 2-carboxyethyl | |
| 8.648 | 3,5-$Cl_2$—Ph | H | O | H | $(CH_2)_3$ | 2-methyl-1,3-dioxolan-2-yl | |
| 8.649 | 3,5-$F_2$—Ph | H | O | H | $(CH_2)_3$ | 2-methyl-1,3-dioxolan-2-yl | |
| 8.650 | Ph | H | O | H | $(CH_2)_3$ | 2-methyl-1,3-dioxolan-2-yl | |
| 8.651 | 3,5-$Cl_2$—Ph | H | O | H | $(CH_2)_3$ | 2-oxopyrrolidin-1-yl | |
| 8.652 | 3,5-$Cl_2$—Ph | H | O | H | $(CH_2)_3$ | $CF_3$ | |
| 8.653 | 3,5-$Cl_2$—Ph | H | O | H | $(CH_2)_3$ | $CH_3$ | |
| 8.654 | 3,5-$F_2$—Ph | H | O | H | $(CH_2)_3$ | $CH_3$ | |
| 8.655 | 3,5-$Cl_2$—Ph | H | O | H | $(CH_2)_3$ | COOH | |
| 8.656 | 3,5-$F_2$—Ph | H | O | H | $(CH_2)_3$ | COOH | |
| 8.657 | 3-Br-5-Cl—Ph | H | O | H | $(CH_2)_3$ | COOH | |
| 8.658 | 3-Cl—Ph | H | O | H | $(CH_2)_3$ | COOH | |
| 8.659 | 3-F—Ph | H | O | H | $(CH_2)_3$ | COOH | |

TABLE 8-continued

Compounds of the general formula (I) according to the invention in which $R^2$ is hydrogen and $R^3$ is trifluoroomethyl and aryl is the radical

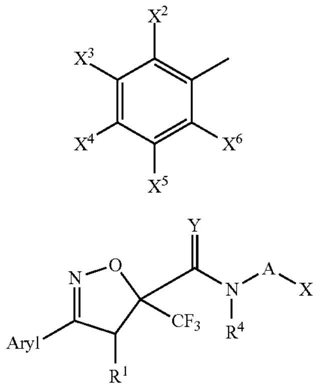

| No. | Aryl | $R^1$ | Y | $R^4$ | A | X | Physical data |
|---|---|---|---|---|---|---|---|
| 8.660 | Ph | H | O | H | $(CH_2)_3$ | COOH | |
| 8.661 | 3,5-$Cl_2$—Ph | H | O | H | $(CH_2)_3$ | dimethylamino | |
| 8.662 | Ph | H | O | Et-carbamoyl | $(CH_2)_3$ | dimethylamino | |
| 8.663 | 3,5-$Cl_2$—Ph | H | O | H | $(CH_2)_3$ | ethoxy | |
| 8.664 | 3,5-$Cl_2$—Ph | H | O | H | $(CH_2)_3$ | ethoxycarbonyl | |
| 8.665 | 3-Cl—Ph | H | O | H | $(CH_2)_3$ | ethoxycarbonyl | |
| 8.666 | 3-F—Ph | H | O | H | $(CH_2)_3$ | ethoxycarbonyl | |
| 8.667 | 3,5-$Cl_2$—Ph | H | O | H | $(CH_2)_3$ | hydroxy | |
| 8.668 | 3,5-$F_2$—Ph | H | O | H | $(CH_2)_3$ | hydroxy | |
| 8.669 | 3,5-$Cl_2$—Ph | H | O | H | $(CH_2)_3$ | methoxy | |
| 8.670 | 3,5-$F_2$—Ph | H | O | H | $(CH_2)_3$ | methoxycarbonyl | |
| 8.671 | 3-Br-5-Cl—Ph | H | O | H | $(CH_2)_3$ | methoxycarbonyl | |
| 8.672 | 3-Cl-5-MeO—Ph | H | O | H | $(CH_2)_3$ | methoxycarbonyl | |
| 8.673 | 3-Cl—Ph | H | O | H | $(CH_2)_3$ | methoxycarbonyl | |
| 8.674 | 3-F—Ph | H | O | H | $(CH_2)_3$ | methoxycarbonyl | |
| 8.675 | Ph | H | O | H | $(CH_2)_3$ | methoxycarbonyl | |
| 8.676 | 3,5-$F_2$—Ph | H | O | H | $(CH_2)_3$ | methylcarbamoyl | |
| 8.677 | 3,5-$Cl_2$—Ph | H | O | H | $(CH_2)_3$ | morpholin-4-yl | |
| 8.678 | 3,5-$Cl_2$—Ph | H | O | H | $(CH_2)_6$ | methoxycarbonyl | |

TABLE 9

Compounds of the general formula (I) according to the invention in which $R^2$ is hydrogen and $R^3$ is cyano and aryl is the radical

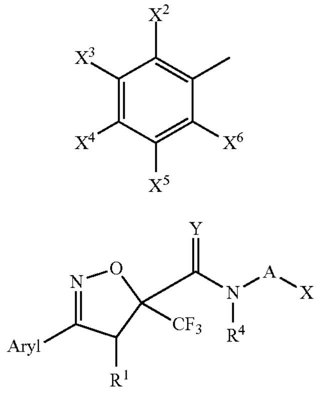

| No. | Aryl | $R^1$ | Y | $R^4$ | A | X | Physical data |
|---|---|---|---|---|---|---|---|
| 9.001 | 3,5-$Cl_2$—Ph | H | O | H | $(CH_2)_4$ | COOH | |
| 9.002 | 3,5-$Cl_2$—Ph | H | O | H | $(CH_2)_4$ | ethoxycarbonyl | |
| 9.003 | 3-Br-5-Cl—Ph | H | O | H | $(CH_2)_4$ | ethoxycarbonyl | |
| 9.004 | Ph | H | O | H | $(CH_2)_4$ | ethoxycarbonyl | |
| 9.005 | 3,5-$Cl_2$—Ph | H | O | H | $(CH_2)_4$ | hydroxy | |
| 9.006 | 3,5-$Cl_2$—Ph | H | O | H | $(CH_2)_4$ | methoxy | |

TABLE 9-continued

Compounds of the general formula (I) according to the invention in which $R^2$ is hydrogen and $R^3$ is cyano and aryl is the radical

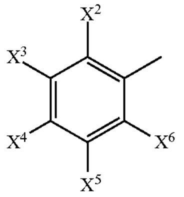

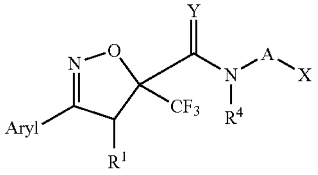

| No. | Aryl | $R^1$ | Y | $R^4$ | A | X | Physical data |
|---|---|---|---|---|---|---|---|
| 9.007 | 3,5-$Cl_2$—Ph | H | O | H | $(CH_2)_6$ | COOH | |
| 9.008 | 3,5-$Cl_2$—Ph | H | O | H | $(CH_2)_6$ | ethoxycarbonyl | |
| 9.009 | 3,5-$Cl_2$—Ph | H | O | H | c- Pr-1,1-diyl | ethoxycarbonyl | |
| 9.010 | 3,5-$F_2$—Ph | H | O | H | bond | 1-cyanocyclopropyl | |
| 9.011 | 3,5-$Cl_2$—Ph | H | O | H | bond | 1-cyanocyclopropyl | |
| 9.012 | 3,5-$Cl_2$—Ph | H | O | H | bond | 1-methylcyclopropyl | |
| 9.013 | 3,5-$Cl_2$—Ph | H | O | H | bond | 2-(ethoxy-carbonyl)cyclohex-1-en-1-yl | |
| 9.014 | 3,5-$Cl_2$—Ph | H | O | H | bond | 2-(ethoxy-carbonyl)cyclohexyl | |
| 9.015 | 3,5-$Cl_2$—Ph | H | O | H | bond | 2-(methylcarbamoyl)-cyclohexyl | |
| 9.016 | 3,5-$Cl_2$—Ph | H | O | H | bond | 2-carboxycyclohexyl | |
| 9.017 | 3,5-$Cl_2$—Ph | H | O | H | bond | 3-(2-ethoxy-2-oxoethyl)oxetan-3-yl | |
| 9.018 | 3,5-$F_2$—Ph | H | O | H | bond | 3-(2-ethoxy-2-oxoethyl)oxetan-3-yl | |
| 9.019 | 2,4-$Cl_2$—Ph | H | O | $CH_3$ | bond | $CH_3$ | |
| 9.020 | 2-Cl-Ph | H | O | $CH_3$ | bond | $CH_3$ | |
| 9.021 | 3,4-$F_2$—Ph | H | O | H | bond | $CH_3$ | |
| 9.022 | 3,5-$Br_2$—Ph | H | O | H | bond | $CH_3$ | |
| 9.023 | 3,5-$Cl_2$—Ph | $CH_3$ | O | H | bond | $CH_3$ | |
| 9.024 | 3,5-$Cl_2$—Ph | H | O | $CH_3$ | bond | $CH_3$ | |
| 9.025 | 3,5-$Cl_2$—Ph | H | O | H | bond | $CH_3$ | |
| 9.026 | 3,5-$F_2$—Ph | H | O | H | bond | $CH_3$ | |
| 9.027 | 3-Cl-4-F—Ph | H | O | H | bond | $CH_3$ | |
| 9.028 | 3,5-$Cl_2$—Ph | H | O | H | bond | cyclobutyl | |
| 9.029 | 3,5-$F_2$—Ph | H | O | H | bond | cyclobutyl | |
| 9.030 | 3,5-$Cl_2$—Ph | H | O | H | bond | cyclopentyl | |
| 9.031 | 3,5-$F_2$—Ph | H | O | H | bond | cyclopentyl | |
| 9.032 | 2-$CF_3$—Ph | H | O | H | bond | c-Pr | |
| 9.033 | 2,3,4-$F_3$—Ph | H | O | H | bond | c-Pr | |
| 9.034 | 2,3,5-$F_3$—Ph | H | O | H | bond | c-Pr | |
| 9.035 | 2,3-$F_2$—Ph | H | O | H | bond | c-Pr | |
| 9.036 | 2,4-$Cl_2$—Ph | H | O | H | bond | c-Pr | |
| 9.037 | 2,5-$F_2$—Ph | H | O | H | bond | c-Pr | |
| 9.038 | 2,5-$Me_2$—Ph | H | O | H | bond | c-Pr | |
| 9.039 | 2-Cl-3-F-5-MeO—Ph | H | O | H | bond | c-Pr | |
| 9.040 | 2-Cl-5-F—Ph | H | O | H | bond | c-Pr | |
| 9.041 | 2-EtO-3,4,5,6-$F_4$—Ph | H | O | H | bond | c-Pr | |
| 9.042 | 2-F-3-Me—Ph | H | O | H | bond | c-Pr | |
| 9.043 | 3-(2-MeOEtO)—Ph | H | O | H | bond | c-Pr | |
| 9.044 | 3-iPrO—Ph | H | O | H | bond | c-Pr | |
| 9.045 | 3-$CF_3$O—Ph | H | O | H | bond | c-Pr | |
| 9.046 | 3-$CF_3$—Ph | H | O | H | bond | c-Pr | |
| 9.047 | 3,4,5-$F_3$—Ph | H | O | H | bond | c-Pr | |
| 9.048 | 3,5-$Br_2$-Ph | H | O | H | bond | c-Pr | |
| 9.049 | 3,5-$Cl_2$-4-MeO—Ph | H | O | H | bond | c-Pr | |

TABLE 9-continued

Compounds of the general formula (I) according to the invention in which $R^2$ is hydrogen and $R^3$ is cyano and aryl is the radical

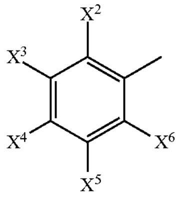

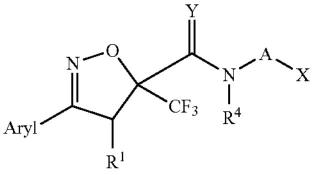

| No. | Aryl | $R^1$ | Y | $R^4$ | A | X | Physical data |
|---|---|---|---|---|---|---|---|
| 9.050 | 3,5-$Cl_2$-4-OH—Ph | H | O | H | bond | c-Pr | |
| 9.051 | 3,5-$Cl_2$—Ph | $CH_3$ | O | H | bond | c-Pr | |
| 9.052 | 3,5-$Cl_2$—Ph | H | O | H | bond | c-Pr | [$CDCl_3$] 0.63 (m, 2H); 0.87 (m, 2H); 2.79 (m, 1H); 3.97 (d, 1H); 4.11 (d, 1H); 6.77 (brs, 1H); 7.47 (m, 1H); 7.52 (m, 2H). |
| 9.053 | 3,5-$F_2$—Ph | H | O | H | bond | c-Pr | |
| 9.054 | 3,5-$F_2$—Ph | H | O | H | bond | c-Pr | |
| 9.055 | 3,5-$F_2$—Ph | H | S | H | bond | c-Pr | |
| 9.056 | 3,5-$(MeO)_2$—Ph | H | O | H | bond | c-Pr | |
| 9.057 | 3,5-$Me_2$—Ph | H | O | H | bond | c-Pr | |
| 9.058 | 3-Ac—Ph | H | O | H | bond | c-Pr | |
| 9.059 | 3-Br-5-$CF_3$—Ph | H | O | H | bond | c-Pr | |
| 9.060 | 3-Br-5-Cl—Ph | H | O | H | bond | c-Pr | |
| 9.061 | 3-Br-5-F—Ph | H | O | H | bond | c-Pr | |
| 9.062 | 3-Cl-4-F—Ph | H | O | H | bond | c-Pr | |
| 9.063 | 3-Cl-4-Me—Ph | H | O | H | bond | c-Pr | |
| 9.064 | 3-Cl-5-$CF_3$—Ph | H | O | H | bond | c-Pr | |
| 9.065 | 3-Cl-5-CN—Ph | H | O | H | bond | c-Pr | |
| 9.066 | 3-Cl-5-Et—Ph | H | O | H | bond | c-Pr | |
| 9.067 | 3-Cl-5-F—Ph | H | O | H | bond | c-Pr | |
| 9.068 | 3-Cl-5-Me—Ph | H | O | H | bond | c-Pr | |
| 9.069 | 3-Cl-5-$CF_3O$—Ph | H | O | H | bond | c-Pr | |
| 9.070 | 3-Cl—Ph | H | O | H | bond | c-Pr | |
| 9.071 | 3-CN-5-F—Ph | H | O | H | bond | c-Pr | |
| 9.072 | 3-c-Pr-5-F—Ph | H | O | H | bond | c-Pr | |
| 9.073 | 3-EtO—Ph | H | O | H | bond | c-Pr | |
| 9.074 | 3-Et-5-F—Ph | H | O | H | bond | c-Pr | |
| 9.075 | 3-Et—Ph | H | O | H | bond | c-Pr | |
| 9.076 | 3-F-5-MeS—Ph | H | O | H | bond | c-Pr | |
| 9.077 | 3-F-5-$MeSO_2$—Ph | H | O | H | bond | c-Pr | |
| 9.078 | 3-F-5-MeO—Ph | H | O | H | bond | c-Pr | |
| 9.079 | 3-F-5-Me—Ph | H | O | H | bond | c-Pr | |
| 9.080 | 3-F-5-Me—Ph | H | S | H | bond | c-Pr | |
| 9.081 | 3-F—Ph | H | O | H | bond | c-Pr | |
| 9.082 | 3-OH—Ph | H | O | H | bond | c-Pr | |
| 9.083 | 3-iPr—Ph | H | O | H | bond | c-Pr | |
| 9.084 | 3-MeO—Ph | H | O | H | bond | c-Pr | |
| 9.085 | 3-Me-5-$CF_3O$—Ph | H | O | H | bond | c-Pr | |
| 9.086 | 3-Me—Ph | H | O | H | bond | c-Pr | |
| 9.087 | 3-NO2—Ph | H | O | H | bond | c-Pr | |
| 9.088 | 4-Cl-3,5-$F_2$—Ph | H | O | H | bond | c-Pr | |
| 9.089 | 4-EtO—Ph | H | O | H | bond | c-Pr | |
| 9.090 | $F_5$—Ph | H | O | H | bond | c-Pr | |
| 9.091 | Ph | H | O | H | bond | c-Pr | |
| 9.092 | 3,5-$Cl_2$—Ph | H | O | H | bond | c-Pr | |
| 9.093 | 3,5-$Cl_2$—Ph | H | O | H | bond | decahydronaphthalen-2-yl | |
| 9.094 | 3,5-$F_2$—Ph | H | O | H | bond | H | |

TABLE 9-continued

Compounds of the general formula (I) according to the invention in which $R^2$ is hydrogen and $R^3$ is cyano and aryl is the radical

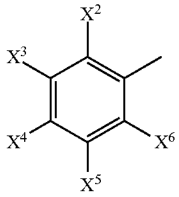

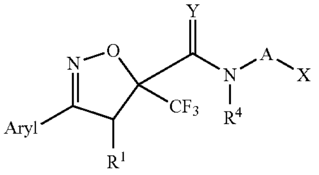

| No. | Aryl | $R^1$ | Y | $R^4$ | A | X | Physical data |
|---|---|---|---|---|---|---|---|
| 9.095 | 3,5-$F_2$—Ph | H | S | H | bond | H | |
| 9.096 | 3-F—Ph | H | O | H | bond | H | |
| 9.097 | 3-Me—Ph | H | O | H | bond | H | |
| 9.098 | 3-Me—Ph | H | S | H | bond | H | |
| 9.099 | 3,5-$Cl_2$—Ph | H | O | CH3 | bond | H | |
| 9.100 | 2,3,4-$F_3$—Ph | H | O | H | bond | hydroxy | |
| 9.101 | 2,3-$F_2$—Ph | H | O | H | bond | oxetan-3-yl | |
| 9.102 | 2,5-$F_2$—Ph | H | O | H | bond | oxetan-3-yl | |
| 9.103 | 3,5-$Cl_2$—Ph | H | O | H | bond | oxetan-3-yl | |
| 9.104 | 3,5-$F_2$—Ph | H | O | H | bond | oxetan-3-yl | |
| 9.105 | 3-Cl-5-$CF_3O$—Ph | H | O | H | bond | oxetan-3-yl | |
| 9.106 | 3-F-5-Me—Ph | H | O | H | bond | oxetan-3-yl | |
| 9.107 | 3-F—Ph | H | O | H | bond | oxetan-3-yl | |
| 9.108 | 3-$NO_2$—Ph | H | O | H | bond | oxetan-3-yl | |
| 9.109 | Ph | H | O | H | bond | oxetan-3-yl | |
| 9.110 | 3,5-$Cl_2$—Ph | H | O | H | bond | oxetan-3-yl | |
| 9.111 | 3,5-$Cl_2$—Ph | H | O | H | $C(CH_3)_2$ | tetrahydro-2H-pyran-4-yl | |
| 9.112 | 3,5-$Cl_2$—Ph | H | O | H | $C(CH_3)_2$ | 3-methoxyprop-1-yn-1-yl | |
| 9.113 | 3,5-$Cl_2$—Ph | H | O | H | $C(CH_3)_2$ | carbamoyl | |
| 9.114 | 3-Cl-4-F—Ph | H | O | H | $C(CH_3)_2$ | $CH_3$ | |
| 9.115 | 3,5-$Cl_2$—Ph | H | O | H | $C(CH_3)_2$ | $CH_3$ | |
| 9.116 | 3,5-$(CF_3)_2$-Ph | H | O | H | $C(CH_3)_2$ | COOH | |
| 9.117 | 3,5-$Cl_2$—Ph | H | O | H | $C(CH_3)_2$ | ethynyl | |
| 9.118 | 3,5-$Cl_2$—Ph | H | O | H | $C(CH_3)_2$ | ethynyl | |
| 9.119 | 3,5-$Cl_2$—Ph | H | O | H | $C(CH_3)_2$ | methoxycarbonyl | |
| 9.120 | 3-Cl—Ph | H | O | H | $C(CH_3)_2CH_2$ | methylcarbamoyl | |
| 9.121 | 3-F—Ph | H | O | H | $C(CH_3)_2CH_2$ | (propan-2-yloxy)carbonyl | |
| 9.122 | 3,5-$Cl_2$—Ph | H | O | H | $C(CH_3)_2CH_2$ | (propan-2-yloxy)carbonyl | |
| 9.123 | 3-Cl—Ph | H | O | H | $C(CH_3)_2CH_2$ | COOH | |
| 9.124 | 3-F—Ph | H | O | H | $C(CH_3)_2CH_2$ | COOH | |
| 9.125 | 3,5-$Cl_2$—Ph | H | O | H | $C(CH_3)_2CH_2$ | COOH | |
| 9.126 | 3-Cl—Ph | H | O | H | $C(CH_3)_2CH_2$ | ethoxycarbonyl | |
| 9.127 | 3-F—Ph | H | O | H | $C(CH_3)_2CH_2$ | ethoxycarbonyl | |
| 9.128 | 3,5-$Cl_2$—Ph | H | O | H | $C(CH_3)_2CH_2$ | ethoxycarbonyl | |
| 9.129 | 3-Cl—Ph | H | O | H | $C(CH_3)_2CH_2$ | hydroxy | |
| 9.130 | 3-F—Ph | H | O | H | $C(CH_3)_2CH_2$ | methoxycarbonyl | |
| 9.131 | 3,5-$Cl_2$—Ph | H | O | H | $C(CH_3)_2CH_2$ | methoxycarbonyl | |
| 9.132 | 3,5-$Cl_2$—Ph | H | O | H | $C(CH_3)_2CH_2$ | methylsulfanyl | |
| 9.133 | 2,4-$Cl_2$—Ph | H | O | H | $C(iPr)CH_3$ | methylsulfonyl | |
| 9.134 | 3,5-$Cl_2$—Ph | H | O | H | $C(iPr)CH_3$ | cyano | |
| 9.135 | 3,5-$Cl_2$—Ph | H | O | H | $CH(CF_3)CH_2$ | cyano | |
| 9.136 | 3,5-$Cl_2$—Ph | H | O | H | $CH(CH_2CH_2SCH_3)$ | ethoxycarbonyl | |
| 9.137 | 3,5-$Cl_2$—Ph | H | O | H | $CH(CH_2CH_3)CH_2$ | methoxycarbonyl | |
| 9.138 | 3,5-$Cl_2$—Ph | H | O | H | $CH(CH_2CH_3)CH_2$ | cyano | |
| 9.139 | 3,5-$Cl_2$—Ph | H | O | H | $CH(CH_2iPr)CH_2$ | methoxycarbonyl | |
| 9.140 | 3,5-$Cl_2$—Ph | H | O | H | $CH(CH_2OCH_3)$ | methoxycarbonyl | |
| 9.141 | 3,5-$Cl_2$—Ph | H | O | H | $CH(CH_3)$ | methoxymethyl | |
| 9.142 | 2,3,4-$F_3$—Ph | H | O | H | $CH(CH_3)$ | $CF_3$ | |
| 9.143 | 2,3,5-$F_3$—Ph | H | O | H | $CH(CH_3)$ | $CH_3$ | |
| 9.144 | 2,3,6-$Cl_3$—Ph | H | O | H | $CH(CH_3)$ | $CH_3$ | |
| 9.145 | 2,3-$Cl_2$-5-MeO—Ph | H | O | H | $CH(CH_3)$ | $CH_3$ | |
| 9.146 | 2,3-$Cl_2$—Ph | H | O | H | $CH(CH_3)$ | $CH_3$ | |

TABLE 9-continued

Compounds of the general formula (I) according to the invention in which $R^2$ is hydrogen and $R^3$ is cyano and aryl is the radical

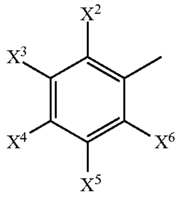

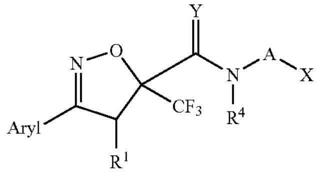

| No. | Aryl | $R^1$ | Y | $R^4$ | A | X | Physical data |
|---|---|---|---|---|---|---|---|
| 9.147 | 2,3-$F_2$—Ph | H | O | H | $CH(CH_3)$ | $CH_3$ | |
| 9.148 | 2,5-$Cl_2$—Ph | H | O | H | $CH(CH_3)$ | $CH_3$ | |
| 9.149 | 2,5-$F_2$—Ph | H | O | H | $CH(CH_3)$ | $CH_3$ | |
| 9.150 | 2-F—Ph | H | O | H | $CH(CH_3)$ | $CH_3$ | |
| 9.151 | 3-($CF_3CH_2O$)—Ph | H | O | H | $CH(CH_3)$ | $CH_3$ | |
| 9.152 | 3-($ClCH_2CH_2O$)—Ph | H | O | H | $CH(CH_3)$ | $CH_3$ | |
| 9.153 | 3-(2-MeOEtO)—Ph | H | O | H | $CH(CH_3)$ | $CH_3$ | |
| 9.154 | 3-$Me_2N$—Ph | H | O | H | CH(CH3) | $CH_3$ | |
| 9.155 | 3-iPrCOO—Ph | H | O | H | CH(CH3) | $CH_3$ | |
| 9.156 | 3-iPrO—Ph | H | O | H | CH(CH3) | $CH_3$ | |
| 9.157 | 3-$CF_3O$—Ph | H | O | H | CH(CH3) | $CH_3$ | |
| 9.158 | 3,4-$Cl_2$—Ph | H | O | H | CH(CH3) | CH3 | |
| 9.159 | 3,5-$(CF_3)_2$—Ph | H | O | H | $CH(CH_3)$ | $CH_3$ | |
| 9.160 | 3,5-$Cl_2$—Ph | CH3 | O | H | $CH(CH_3)$ | $CH_3$ | |
| 9.161 | 3,5-$Cl_2$—Ph | H | O | H | $CH(CH_3)$ | $CH_3$ | |
| 9.162 | 3,5-$Cl_2$—Ph | H | O | OH | $CH(CH_3)$ | $CH_3$ | |
| 9.163 | 3,5-$Cl_2$—Ph | H | S | H | $CH(CH_3)$ | $CH_3$ | |
| 9.164 | 3,5-$F_2$—Ph | H | O | H | $CH(CH_3)$ | $CH_3$ | |
| 9.165 | 3,5-$Me_2$—Ph | H | O | H | $CH(CH_3)$ | $CH_3$ | |
| 9.166 | R002 | H | O | H | $CH(CH_3)$ | $CH_3$ | |
| 9.167 | R003 | H | O | H | $CH(CH_3)$ | $CH_3$ | |
| 9.168 | 3-$CNCH_2N(Me)$—Ph | H | O | H | $CH(CH_3)$ | $CH_3$ | |
| 9.169 | 3-$Me_2NCONH$—Ph | H | O | H | $CH(CH_3)$ | $CH_3$ | |
| 9.170 | 3-$Me_2NSO_2O$—Ph | H | O | H | $CH(CH_3)$ | $CH_3$ | |
| 9.171 | 3-EtNHCOO—Ph | H | O | H | $CH(CH_3)$ | $CH_3$ | |
| 9.172 | 3-$EtSO_2O$—Ph | H | O | H | $CH(CH_3)$ | $CH_3$ | |
| 9.173 | 3-$MeSO_2NH$—Ph | H | O | H | $CH(CH_3)$ | $CH_3$ | |
| 9.174 | 3-$MeSO_2O$—Ph | H | O | H | $CH(CH_3)$ | $CH_3$ | |
| 9.175 | 3-tert.BuOCONH—Ph | H | O | H | $CH(CH_3)$ | $CH_3$ | |
| 9.176 | 3-$CF_3CONH$—Ph | H | O | H | $CH(CH_3)$ | $CH_3$ | |
| 9.177 | 3-AcO-5-Cl—Ph | H | O | H | $CH(CH_3)$ | $CH_3$ | |
| 9.178 | 3-AcO—Ph | H | O | H | $CH(CH_3)$ | $CH_3$ | |
| 9.179 | 3-$NH_2$—Ph | H | O | H | $CH(CH_3)$ | $CH_3$ | |
| 9.180 | 3-Br-5-$CF_3$—Ph | H | O | H | $CH(CH_3)$ | $CH_3$ | |
| 9.181 | 3-Br-5-Cl—Ph | H | O | H | $CH(CH_3)$ | $CH_3$ | |
| 9.182 | 3-Cl-4-F—Ph | H | O | H | $CH(CH_3)$ | $CH_3$ | |
| 9.183 | 3-Cl-4-Me—Ph | H | O | H | $CH(CH_3)$ | $CH_3$ | |
| 9.184 | 3-Cl-5-$CF_3$—Ph | H | O | H | $CH(CH_3)$ | $CH_3$ | |
| 9.185 | R001 | H | O | H | $CH(CH_3)$ | $CH_3$ | |
| 9.186 | 3-Cl-5-F—Ph | H | O | H | $CH(CH_3)$ | $CH_3$ | |
| 9.187 | 3-Cl-5-MeO—Ph | H | O | H | $CH(CH_3)$ | $CH_3$ | |
| 9.188 | 3-Cl-5-Me—Ph | H | O | H | $CH(CH_3)$ | $CH_3$ | |
| 9.189 | 3-Cl-5-($CF_3CH_2O$)—Ph | H | O | H | $CH(CH_3)$ | $CH_3$ | |

TABLE 9-continued

Compounds of the general formula (I) according to the invention in which $R^2$ is hydrogen and $R^3$ is cyano and aryl is the radical

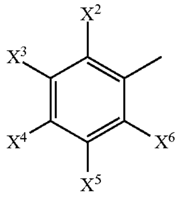

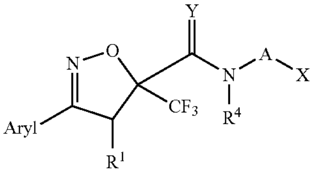

| No. | Aryl | $R^1$ | Y | $R^4$ | A | X | Physical data |
|---|---|---|---|---|---|---|---|
| 9.190 | 3-Cl-5-($ClCH_2CH_2O$)-Ph | H | O | H | $CH(CH_3)$ | $CH_3$ | |
| 9.191 | 3-Cl-5-($EtOCOCH_2O$)—Ph | H | O | H | $CH(CH_3)$ | $CH_3$ | |
| 9.192 | 3-Cl-5-$CF_3O$—Ph | H | O | H | $CH(CH_3)$ | $CH_3$ | |
| 9.193 | 3-Cl-5-$Me_2NSO_2O$—Ph | H | O | H | $CH(CH_3)$ | $CH_3$ | |
| 9.194 | 3-Cl-5-($MeSO_2O$)—Ph | H | O | H | $CH(CH_3)$ | $CH_3$ | |
| 9.195 | 3-Cl-5-iPrO—Ph | H | O | H | $CH(CH_3)$ | $CH_3$ | |
| 9.196 | 3-Cl—Ph | H | O | H | $CH(CH_3)$ | $CH_3$ | |
| 9.197 | 3-EtO—Ph | H | O | H | $CH(CH_3)$ | $CH_3$ | |
| 9.198 | 3-F-5-Me—Ph | H | O | H | $CH(CH_3)$ | $CH_3$ | |
| 9.199 | 3-F—Ph | H | O | H | $CH(CH_3)$ | $CH_3$ | |
| 9.200 | 3-OH—Ph | H | O | H | $CH(CH_3)$ | $CH_3$ | |
| 9.201 | 3-MeO—Ph | H | O | H | $CH(CH_3)$ | $CH_3$ | |
| 9.202 | 3-Me—Ph | H | O | H | $CH(CH_3)$ | $CH_3$ | |
| 9.203 | 3-$NO_2$—Ph | H | O | H | $CH(CH_3)$ | $CH_3$ | |
| 9.204 | F5—Ph | H | O | H | $CH(CH_3)$ | $CH_3$ | |
| 9.205 | Ph | H | O | H | $CH(CH_3)$ | $CH_3$ | |
| 9.206 | 3,5-Cl2—Ph | H | O | H | $CH(CH_3)$ | $CH_3$ | |
| 9.207 | 3-Cl-4-F—Ph | H | O | H | $CH(CH_3)$ | COOH | |
| 9.208 | 3,5-Cl2—Ph | H | O | H | $CH(CH_3)$ | COOH | |
| 9.209 | 3,5-F2—Ph | H | O | H | CH(CH3) | c-Pr | |
| 9.210 | Ph | H | O | H | $CH(CH_3)$ | c-Pr | |
| 9.211 | 3-Cl-4-F—Ph | H | O | H | $CH(CH_3)$ | c-Pr | |
| 9.212 | 3,5-$Cl_2$—Ph | H | O | H | $CH(CH_3)$ | dimethylcarbamoyl | |
| 9.213 | 3,5-$Cl_2$—Ph | H | O | H | $CH(CH_3)$ | ethynyl | |
| 9.214 | 3,5-$Cl_2$—Ph | $CH_3$ | O | H | $CH(CH_3)$ | ethyl | |
| 9.215 | 3,5-$Cl_2$—Ph | H | O | H | $CH(CH_3)$ | methoxycarbonyl | |
| 9.216 | 3-Cl-4-F—Ph | H | O | H | $CH(CH_3)$ | methoxycarbonyl | |
| 9.217 | 3-Cl-4-F—Ph | H | O | H | $CH(CH_3)$ | methoxycarbonyl | |
| 9.218 | 3,5-$Cl_2$—Ph | H | O | H | $CH(CH_3)$ | methylcarbamoyl | |
| 9.219 | 3,5-$Cl_2$—Ph | H | O | H | $CH(CH_3)CH_2$ | pentyl | |
| 9.220 | 3,5-$F_2$—Ph | H | O | H | $CH(CH_3)CH_2$ | (2,2,2-trifluoroethoxy)-carbonyl | |
| 9.221 | 3,5-$Cl_2$—Ph | H | O | H | $CH(CH_3)CH_2$ | (2,2,2-trifluoroethoxy)-carbonyl | |
| 9.222 | 3,5-$F_2$—Ph | H | O | H | $CH(CH_3)CH_2$ | (2-hydroxyethoxy)carbonyl | |
| 9.223 | 3,5-$Cl_2$—Ph | H | O | H | $CH(CH_3)CH_2$ | (2-hydroxyethoxy)carbonyl | |
| 9.224 | 3,5-$F_2$—Ph | H | O | H | $CH(CH_3)CH_2$ | (allyloxy)carbonyl | |
| 9.225 | 3,5-$Cl_2$—Ph | H | O | H | $CH(CH_3)CH_2$ | (allyloxy)carbonyl | |
| 9.226 | 3,5-$F_2$—Ph | H | O | H | $CH(CH_3)CH_2$ | (cyclopropylsulfonyl)-(methyl)carbamoyl | |
| 9.227 | 3,5-$Cl_2$—Ph | H | O | H | $CH(CH_3)CH_2$ | (cyclopropylsulfonyl)-(methyl)carbamoyl | |
| 9.228 | 3,5-$F_2$—Ph | H | O | H | $CH(CH_3)CH_2$ | (cyclopropylsulfonyl)-carbamoyl | |
| 9.229 | 3,5-$Cl_2$—Ph | H | O | H | $CH(CH_3)CH_2$ | (cyclopropylsulfonyl)-carbamoyl | |
| 9.230 | 3,5-$F_2$—Ph | H | O | H | $CH(CH_3)CH_2$ | (ethylsulfonyl)(methyl)-carbamoyl | |

TABLE 9-continued

Compounds of the general formula (I) according to the invention in which $R^2$ is hydrogen and $R^3$ is cyano and aryl is the radical

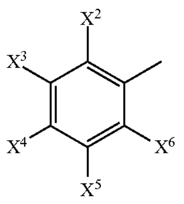

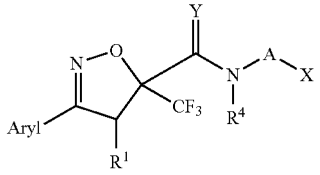

| No. | Aryl | $R^1$ | Y | $R^4$ | A | X | Physical data |
|---|---|---|---|---|---|---|---|
| 9.231 | 3,5-$Cl_2$—Ph | H | O | H | $CH(CH_3)CH_2$ | (ethylsulfonyl)(methyl)-carbamoyl | |
| 9.232 | 3,5-$F_2$—Ph | H | O | H | $CH(CH_3)CH_2$ | (ethylsulfonyl)carbamoyl | |
| 9.233 | 3,5-$Cl_2$—Ph | H | O | H | $CH(CH_3)CH_2$ | (ethylsulfonyl)carbamoyl | |
| 9.234 | 3,5-$F_2$—Ph | H | O | H | $CH(CH_3)CH_2$ | (heptan-2-yloxy)carbonyl | |
| 9.235 | 3,5-$Cl_2$—Ph | H | O | H | $CH(CH_3)CH_2$ | (heptan-2-yloxy)carbonyl | |
| 9.236 | 3,5-$F_2$—Ph | H | O | H | $CH(CH_3)CH_2$ | (isopropylsulfonyl)-(methyl)carbamoyl | |
| 9.237 | 3,5-$Cl_2$—Ph | H | O | H | $CH(CH_3)CH_2$ | (isopropylsulfonyl)-(methyl)carbamoyl | |
| 9.238 | 3,5-$F_2$—Ph | H | O | H | $CH(CH_3)CH_2$ | (isopropylsulfonyl)-carbamoyl | |
| 9.239 | 3,5-$Cl_2$—Ph | H | O | H | $CH(CH_3)CH_2$ | (isopropylsulfonyl)-carbamoyl | |
| 9.240 | 3,5-$F_2$—Ph | H | O | H | $CH(CH_3)CH_2$ | (methylsulfonyl)-carbamoyl | |
| 9.241 | 3,5-$Cl_2$—Ph | H | O | H | $CH(CH_3)CH_2$ | (methylsulfonyl)-carbamoyl | |
| 9.242 | 3,5-$F_2$—Ph | H | O | H | $CH(CH_3)CH_2$ | (prop-2-yn-1-yloxy)carbonyl | |
| 9.243 | 3,5-$Cl_2$—Ph | H | O | H | $CH(CH_3)CH_2$ | (prop-2-yn-1-yloxy)carbonyl | |
| 9.244 | 3,5-$F_2$—Ph | H | O | H | $CH(CH_3)CH_2$ | (propan-2-yloxy)carbonyl | |
| 9.245 | 3-Cl—Ph | H | O | H | $CH(CH_3)CH_2$ | (propan-2- | |
| 9.246 | 3-F—Ph | H | O | H | $CH(CH_3)CH_2$ | (propan-2-yloxy)carbonyl | |
| 9.247 | 3,5-$Cl_2$—Ph | H | O | H | $CH(CH_3)CH_2$ | (propan-2-yloxy)carbonyl | |
| 9.248 | 3,5-$F_2$—Ph | H | O | H | $CH(CH_3)CH_2$ | [2-(methylsulfanyl)ethoxy]-carbonyl | |
| 9.249 | 3,5-$F_2$—Ph | H | O | H | $CH(CH_3)CH_2$ | [2-(methylsulfanyl)ethoxy]-carbonyl | |
| 9.250 | 3,5-$Cl_2$—Ph | H | O | H | $CH(CH_3)CH_2$ | [2-(methylsulfonyl)ethoxy]-carbonyl | |
| 9.251 | 3,5-$F_2$—Ph | H | O | H | $CH(CH_3)CH_2$ | butoxycarbonyl | |
| 9.252 | 3-$CF_3$—Ph | H | O | H | $CH(CH_3)CH_2$ | butoxycarbonyl | |
| 9.253 | 3,5-$Cl_2$—Ph | H | O | H | $CH(CH_3)CH_2$ | COOH | |
| 9.254 | 3,5-$F_2$—Ph | H | O | H | $CH(CH_3)CH_2$ | COOH | |
| 9.255 | 3,5-(tert.Bu)$_2$—Ph | H | O | H | $CH(CH_3)CH_2$ | COOH | |
| 9.256 | 3-Br-5-$CF_3$—Ph | H | O | H | $CH(CH_3)CH_2$ | COOH | |
| 9.257 | 3-Cl-5-$CF_3$—Ph | H | O | H | $CH(CH_3)CH_2$ | COOH | |
| 9.258 | 3-Cl—Ph | H | O | H | $CH(CH_3)CH_2$ | COOH | |
| 9.259 | 3-Et-5-F—Ph | H | O | H | $CH(CH_3)CH_2$ | COOH | |
| 9.260 | 3-Et—Ph | H | O | H | $CH(CH_3)CH_2$ | COOH | |
| 9.261 | 3-F-5-MeO—Ph | H | O | H | $CH(CH_3)CH_2$ | COOH | |
| 9.262 | 3-F—Ph | H | O | H | $CH(CH_3)CH_2$ | COOH | |
| 9.263 | 3-Me—Ph | H | O | H | $CH(CH_3)CH_2$ | COOH | |
| 9.264 | 4-MeO—Ph | H | O | H | $CH(CH_3)CH_2$ | COOH | |
| 9.265 | 3-$CF_3$—Ph | H | O | H | $CH(CH_3)CH_2$ | COOH | |

TABLE 9-continued

Compounds of the general formula (I) according to the invention in which $R^2$ is hydrogen and $R^3$ is cyano and aryl is the radical

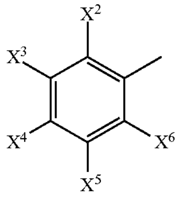

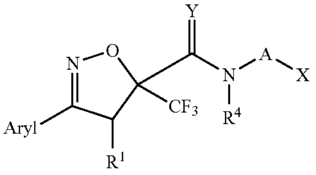

| No. | Aryl | $R^1$ | Y | $R^4$ | A | X | Physical data |
|---|---|---|---|---|---|---|---|
| 9.266 | 3,5-$Cl_2$-4-MeO—Ph | H | O | H | $CH(CH_3)CH_2$ | ethoxycarbonyl | |
| 9.267 | 3,5-$Cl_2$—Ph | H | O | H | $CH(CH_3)CH_2$ | ethoxycarbonyl | |
| 9.268 | 3,5-$Et_2$—Ph | H | O | H | $CH(CH_3)CH_2$ | ethoxycarbonyl | |
| 9.269 | 3,5-$F_2$—Ph | H | O | H | $CH(CH_3)CH_2$ | ethoxycarbonyl | |
| 9.270 | 3,5-$(MeO)_2$—Ph | H | O | H | $CH(CH_3)CH_2$ | ethoxycarbonyl | |
| 9.271 | 3,5-$Me_2$—Ph | H | O | H | $CH(CH_3)CH_2$ | ethoxycarbonyl | |
| 9.272 | 3,5-$(tert.Bu)_2$—Ph | H | O | H | $CH(CH_3)CH_2$ | ethoxycarbonyl | |
| 9.273 | 3-Br-5-$CF_3$—Ph | H | O | H | $CH(CH_3)CH_2$ | ethoxycarbonyl | |
| 9.274 | 3-Cl-5-Et—Ph | H | O | H | $CH(CH_3)CH_2$ | ethoxycarbonyl | |
| 9.275 | 3-Cl-5-$CF_3$—Ph | H | O | H | $CH(CH_3)CH_2$ | ethoxycarbonyl | |
| 9.276 | 3-Cl—Ph | H | O | H | $CH(CH_3)CH_2$ | ethoxycarbonyl | |
| 9.277 | 3-c-Pr-5-F—Ph | H | O | H | $CH(CH_3)CH_2$ | ethoxycarbonyl | |
| 9.278 | 3-Et-5-F—Ph | H | O | H | $CH(CH_3)CH_2$ | ethoxycarbonyl | |
| 9.279 | 3-Et—Ph | H | O | H | $CH(CH_3)CH_2$ | ethoxycarbonyl | |
| 9.280 | 3-F-5-MeS—Ph | H | O | H | $CH(CH_3)CH_2$ | ethoxycarbonyl | |
| 9.281 | 3-F-5-$MeSO_2$—Ph | H | O | H | $CH(CH_3)CH_2$ | ethoxycarbonyl | |
| 9.282 | 3-F-5-MeO—Ph | H | O | H | $CH(CH_3)CH_2$ | ethoxycarbonyl | |
| 9.283 | 3-F—Ph | H | O | H | $CH(CH_3)CH_2$ | ethoxycarbonyl | |
| 9.284 | 3-Me-5-$CF_3O$—Ph | H | O | H | $CH(CH_3)CH_2$ | ethoxycarbonyl | |
| 9.285 | 3-Me—Ph | H | O | H | $CH(CH_3)CH_2$ | ethoxycarbonyl | |
| 9.286 | 4-EtO—Ph | H | O | H | $CH(CH_3)CH_2$ | ethoxycarbonyl | |
| 9.287 | 4-MeO—Ph | H | O | H | $CH(CH_3)CH_2$ | ethoxycarbonyl | |
| 9.288 | 3,5-$Cl_2$—Ph | H | O | H | $CH(CH_3)CH_2$ | ethoxycarbonyl | |
| 9.289 | 3,5-$Cl_2$—Ph | H | O | H | $CH(CH_3)CH_2$ | hydroxy | |
| 9.290 | 3,5-$F_2$—Ph | H | O | H | $CH(CH_3)CH_2$ | isobutoxycarbonyl | |
| 9.291 | 3,5-$Cl_2$—Ph | H | O | H | $CH(CH_3)CH_2$ | isobutoxycarbonyl | |
| 9.292 | 2,5-$Me_2$—Ph | H | O | H | $CH(CH_3)CH_2$ | methoxy | |
| 9.293 | 2-Cl-3-F-5-MeO—Ph | H | O | H | $CH(CH_3)CH_2$ | methoxycarbonyl | |
| 9.294 | 2-F-3-Me—Ph | H | O | H | $CH(CH_3)CH_2$ | methoxycarbonyl | |
| 9.295 | 3-$CF_3$—Ph | H | O | H | $CH(CH_3)CH_2$ | methoxycarbonyl | |
| 9.296 | 3,5-$Cl_2$—Ph | H | O | H | $CH(CH_3)CH_2$ | methoxycarbonyl | |
| 9.297 | 3,5-$F_2$—Ph | H | O | H | $CH(CH_3)CH_2$ | methoxycarbonyl | |
| 9.298 | 3-Cl—Ph | H | O | H | $CH(CH_3)CH_2$ | methoxycarbonyl | |
| 9.299 | 3-F-5-MeO—Ph | H | O | H | $CH(CH_3)CH_2$ | methoxycarbonyl | |
| 9.300 | 3-F—Ph | H | O | H | $CH(CH_3)CH_2$ | methoxycarbonyl | |
| 9.301 | 3,5-$Cl_2$—Ph | H | O | H | $CH(CH_3)CH_2$ | methoxycarbonyl | |
| 9.302 | 3,5-$F_2$—Ph | H | O | H | $CH(CH_3)CH_2$ | methyl(methylsulfonyl)-carbamoyl | |
| 9.303 | 3,5-$Cl_2$—Ph | H | O | H | $CH(CH_3)CH_2$ | methyl(methylsulfonyl)-carbamoyl | |
| 9.304 | 3,5-$Cl_2$—Ph | H | O | H | $CH(CH_3)CH_2$ | methylcarbamoyl | |
| 9.305 | 3,5-$F_2$—Ph | H | O | H | $CH(CH_3)CH_2$ | propoxycarbonyl | |
| 9.306 | 3,5-$Cl_2$—Ph | H | O | H | $CH(CH_3)CH_2$ | propoxycarbonyl | |
| 9.307 | 3,5-$F_2$—Ph | H | O | H | $CH(CH_3)CH_2$ | sec-butoxycarbonyl | |
| 9.308 | 3,5-$Cl_2$—Ph | H | O | H | $CH(COOCH_3)CH_2$ | sec-butoxycarbonyl | |
| 9.309 | 3,5-$Cl_2$—Ph | H | O | H | CH(cycloPr) | methoxycarbonyl | |
| 9.310 | 3,5-$F_2$—Ph | H | O | H | CH(cycloPr) | c-Pr | |
| 9.311 | 3,5-$Cl_2$—Ph | H | O | H | CH(iPr) | c-Pr | |
| 9.312 | 3,5-$Cl_2$—Ph | H | O | H | CH(iPr) | methoxycarbonyl | |
| 9.313 | 3,5-$F_2$—Ph | H | O | H | $CH_2$ | methoxycarbonyl | |
| 9.314 | 3,5-$Cl_2$—Ph | H | O | H | $CH_2$ | (2-hydroxyethyl)carbamoyl | |

TABLE 9-continued

Compounds of the general formula (I) according to the invention in which $R^2$ is hydrogen and $R^3$ is cyano and aryl is the radical

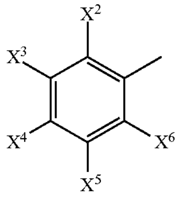

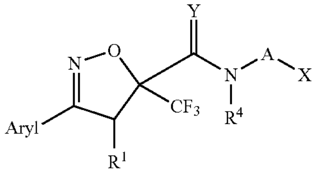

| No. | Aryl | $R^1$ | Y | $R^4$ | A | X | Physical data |
|---|---|---|---|---|---|---|---|
| 9.315 | 3,5-$F_2$—Ph | H | O | H | $CH_2$ | (cyclopropylsulfonyl)-carbamoyl | |
| 9.316 | 3,5-$Cl_2$—Ph | H | O | H | $CH_2$ | (cyclopropylsulfonyl)-carbamoyl | |
| 9.317 | 3,5-$F_2$—Ph | H | O | H | $CH_2$ | (ethylsulfonyl)carbamoyl | |
| 9.318 | 3,5-$F_2$—Ph | H | O | H | $CH_2$ | (ethylsulfonyl)carbamoyl | |
| 9.319 | 3,5-$Cl_2$—Ph | H | O | H | $CH_2$ | (hydroxyimino)methyl | |
| 9.320 | 3,5-$F_2$—Ph | H | O | H | $CH_2$ | (isopropylsulfonyl)-carbamoyl | |
| 9.321 | 3,5-$Cl_2$—Ph | H | O | H | $CH_2$ | (isopropylsulfonyl)-carbamoyl | |
| 9.322 | 3,5-$F_2$—Ph | H | O | H | $CH_2$ | (methylsulfonyl)-carbamoyl | |
| 9.323 | 3-Cl—Ph | H | O | H | $CH_2$ | (methylsulfonyl)-carbamoyl | |
| 9.324 | 3-F—Ph | H | O | H | $CH_2$ | (propan-2-yloxy)carbonyl | |
| 9.325 | 3,5-$Cl_2$—Ph | H | O | H | $CH_2$ | (propan-2-yloxy)carbonyl | |
| 9.326 | 3,5-$F_2$—Ph | H | O | H | $CH_2$ | 1,1-dioxidotetrahydro-thiophen-3-yl | |
| 9.327 | 3-F—Ph | H | O | H | $CH_2$ | 1,1-dioxidotetrahydro-thiophen-3-yl | |
| 9.328 | Ph | H | O | H | $CH_2$ | 1,1-dioxidotetrahydro-thiophen-3-yl | |
| 9.329 | Ph | H | O | H | $CH_2$ | 1,1-dioxidotetrahydro-thiophen-3-yl | |
| 9.330 | 3,5-$Cl_2$—Ph | H | O | H | $CH_2$ | 1,4-dimethyl-5-oxo-4,5-dihydro-1H-1,2,4-triazol-3-yl | |
| 9.331 | 3,5-$F_2$—Ph | H | O | H | $CH_2$ | 3-(2-ethoxy-2-oxoethyl)oxetan-3-yl | |
| 9.332 | 3,5-$Cl_2$—Ph | H | O | H | $CH_2$ | 3-(2-ethoxy-2-oxoethyl)oxetan-3-yl | |
| 9.333 | 3,5-$Cl_2$—Ph | H | O | H | $CH_2$ | 3-(cyclopropylcarbamoyl)-4,5-dihydro-1,2-oxazol-5-yl | |
| 9.334 | 3,5-$Cl_2$—Ph | H | O | H | $CH_2$ | 3-(ethoxycarbonyl)-4,5-dihydro-1,2-oxazol-5-yl | |
| 9.335 | 3,5-$Cl_2$—Ph | H | O | H | $CH_2$ | 3-(methylcarbamoyl)-4,5-dihydro-1,2-oxazol-5-yl | |
| 9.336 | 3,5-$Cl_2$—Ph | H | O | H | $CH_2$ | 3-carboxy-4,5-dihydro-1,2-oxazol-5-yl | |
| 9.337 | 3,5-$Cl_2$—Ph | H | O | H | $CH_2$ | 3-isopropyl-4,5-dihydro-1,2-oxazol-5-yl | |
| 9.338 | 3,5-$F_2$—Ph | H | O | H | $CH_2$ | 3-methyl-4,5-dihydro-1,2-oxazol-5-yl | |
| 9.339 | 3,5-$Cl_2$—Ph | H | O | H | $CH_2$ | 5-(ethoxycarbonyl)-4,5-dihydro-1,2-oxazol-3-yl | |
| 9.340 | 3,5-$Cl_2$—Ph | H | O | H | $CH_2$ | 5,5-dimethyl-4,5-dihydro-1,2-oxazol-3-yl | |
| 9.341 | 3,5-$Cl_2$—Ph | H | O | H | $CH_2$ | 5-ethyl-4,5-dihydro-1,2-oxazol-3-yl | |

TABLE 9-continued

Compounds of the general formula (I) according to the invention in which $R^2$ is hydrogen and $R^3$ is cyano and aryl is the radical

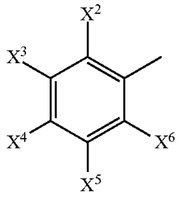

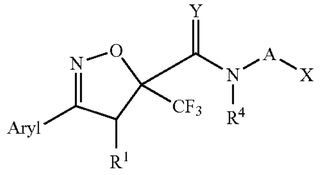

| No. | Aryl | $R^1$ | Y | $R^4$ | A | X | Physical data |
|---|---|---|---|---|---|---|---|
| 9.342 | 3,5-$Cl_2$—Ph | H | O | H | $CH_2$ | 5-isopropyl-4,5-dihydro-1,2-oxazol-3-yl | |
| 9.343 | 3,5-$Cl_2$—Ph | H | O | H | $CH_2$ | 5-methyl-4,5-dihydro-1,2-oxazol-3-yl | |
| 9.344 | 3-Cl—Ph | H | O | H | $CH_2$ | carbamoyl | |
| 9.345 | 2-$CF_3$—Ph | H | O | H | $CH_2$ | carbamoyl | |
| 9.346 | 2,3,4-$F_3$—Ph | H | O | H | $CH_2$ | $CF_3$ | |
| 9.347 | 2,3,5-$F_3$—Ph | H | O | H | $CH_2$ | $CF_3$ | |
| 9.348 | 2,3,6-$Cl_3$—Ph | H | O | H | $CH_2$ | $CF_3$ | |
| 9.349 | 2,3-$F_2$—Ph | H | O | H | $CH_2$ | $CF_3$ | |
| 9.350 | 2,5-$F_2$—Ph | H | O | H | $CH_2$ | $CF_3$ | |
| 9.351 | 2-Cl-3-F-5-MeO—Ph | H | O | H | $CH_2$ | $CF_3$ | |
| 9.352 | 3-(2-MeOEtO)—Ph | H | O | H | $CH_2$ | $CF_3$ | |
| 9.353 | 3-i PrO—Ph | H | O | H | $CH_2$ | $CF_3$ | |
| 9.354 | 3-$CF_3$O—Ph | H | O | H | $CH_2$ | $CF_3$ | |
| 9.355 | 3-$CF_3$—Ph | H | O | H | $CH_2$ | $CF_3$ | |
| 9.356 | 3,4-$Cl_2$—Ph | H | O | H | $CH_2$ | $CF_3$ | |
| 9.357 | 3,5-$Br_2$—Ph | H | O | H | $CH_2$ | $CF_3$ | |
| 9.358 | 3,5-$Cl_2$-4-MeO—Ph | H | O | H | $CH_2$ | $CF_3$ | |
| 9.359 | 3,5-$Cl_2$—Ph | H | O | H | $CH_2$ | $CF_3$ | |
| 9.360 | 3,5-$F_2$—Ph | H | O | H | $CH_2$ | $CF_3$ | |
| 9.361 | 3,5-$(MeO)_2$—Ph | H | O | H | $CH_2$ | $CF_3$ | |
| 9.362 | 3,5-$Me_2$—Ph | H | O | H | $CH_2$ | $CF_3$ | |
| 9.363 | 3-Br-5-Cl—Ph | H | O | H | $CH_2$ | $CF_3$ | |
| 9.364 | 3-Br-5-F—Ph | H | O | H | $CH_2$ | $CF_3$ | |
| 9.365 | 3-Cl-5-$CF_3$—Ph | H | O | H | $CH_2$ | $CF_3$ | |
| 9.366 | 3-Cl-5-Et—Ph | H | O | H | $CH_2$ | $CF_3$ | |
| 9.367 | 3-Cl-5-F—Ph | H | O | H | $CH_2$ | $CF_3$ | |
| 9.368 | 3-Cl-5-Me—Ph | H | O | H | $CH_2$ | $CF_3$ | |
| 9.369 | 3-Cl-5-$CF_3$O—Ph | H | O | H | $CH_2$ | $CF_3$ | |
| 9.370 | 3-Cl—Ph | H | O | H | $CH_2$ | $CF_3$ | |
| 9.371 | 3-EtO—Ph | H | O | H | $CH_2$ | $CF_3$ | |
| 9.372 | 3-Et-5-F—Ph | H | O | H | $CH_2$ | $CF_3$ | |
| 9.373 | 3-Et—Ph | H | O | H | $CH_2$ | $CF_3$ | |
| 9.374 | 3-F-5-MeS—Ph | H | O | H | $CH_2$ | $CF_3$ | |
| 9.375 | 3-F-5-$MeSO_2$—Ph | H | O | H | $CH_2$ | $CF_3$ | |
| 9.376 | 3-F-5-$CF_3$—Ph H | O | H | $CH_2$ | $CF_3$ | | |
| 9.377 | 3-F-5-MeO—Ph | H | O | H | $CH_2$ | $CF_3$ | |
| 9.378 | 3-F-5-Me—Ph | H | O | H | $CH_2$ | $CF_3$ | |
| 9.379 | 3-F—Ph | H | O | H | $CH_2$ | $CF_3$ | |
| 9.380 | 3-OH—Ph | H | O | H | $CH_2$ | $CF_3$ | |
| 9.381 | 3-iPr—Ph | H | O | H | $CH_2$ | $CF_3$ | |
| 9.382 | 3-Me—Ph | H | O | H | CH2 | CF3 | |
| 9.383 | 3-$NO_2$—Ph | H | O | H | $CH_2$ | $CF_3$ | |
| 9.384 | 4-EtO—Ph | H | O | H | $CH_2$ | $CF_3$ | |
| 9.385 | 4-MeO—Ph | H | O | H | $CH_2$ | $CF_3$ | |
| 9.386 | $F_5$—Ph | H | O | H | $CH_2$ | $CF_3$ | |
| 9.387 | Ph | H | O | H | $CH_2$ | $CF_3$ | |
| 9.388 | 2,3,5-$F_3$—Ph | H | O | H | $CH_2$ | $CF_3$ | |
| 9.389 | 2,3-$F_2$—Ph | H | O | H | $CH_2$ | $CH_3$ | |

TABLE 9-continued

Compounds of the general formula (I) according to the invention in which $R^2$ is hydrogen and $R^3$ is cyano and aryl is the radical

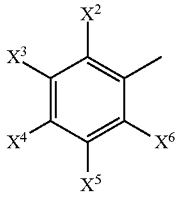

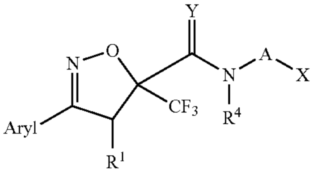

| No. | Aryl | $R^1$ | Y | $R^4$ | A | X | Physical data |
|---|---|---|---|---|---|---|---|
| 9.390 | 3,4-$F_2$—Ph | H | O | H | $CH_2$ | $CH_3$ | |
| 9.391 | 3,5-$Cl_2$—Ph | H | O | H | $CH_2$ | $CH_3$ | |
| 9.392 | 3,5-$F_2$—Ph | H | O | H | $CH_2$ | $CH_3$ | |
| 9.393 | 3-Cl-5-CF3—Ph | H | O | H | $CH_2$ | $CH_3$ | |
| 9.394 | 3-Cl-5-Me—Ph | H | O | H | $CH_2$ | $CH_3$ | |
| 9.395 | 3-Cl-5-$CF_3O$—Ph | H | O | H | $CH_2$ | $CH_3$ | |
| 9.396 | 3-EtO—Ph | H | O | H | $CH_2$ | $CH_3$ | |
| 9.397 | 3-Et—Ph | H | O | H | $CH_2$ | $CH_3$ | |
| 9.398 | 3-F—Ph | H | O | H | $CH_2$ | $CH_3$ | |
| 9.399 | 3-Me—Ph | H | O | H | $CH_2$ | $CH_3$ | |
| 9.400 | $F_5$—Ph | H | O | H | $CH_2$ | $CH_3$ | |
| 9.401 | Ph | H | O | H | $CH_2$ | $CH_3$ | |
| 9.402 | 3,5-$Cl_2$—Ph | H | O | H | $CH_2$ | $CH_3$ | |
| 9.403 | 3,5-$F_2$—Ph | H | O | H | $CH_2$ | COOH | |
| 9.404 | 3-Cl—Ph | H | O | H | $CH_2$ | COOH | |
| 9.405 | 3-F—Ph | H | O | H | $CH_2$ | COOH | |
| 9.406 | 3,5-$Cl_2$—Ph | H | O | H | $CH_2$ | COOH | |
| 9.407 | 3,5-$F_2$—Ph | H | O | H | $CH_2$ | cyano | |
| 9.408 | 3-Cl-5-$CF_3O$—Ph | H | O | H | $CH_2$ | cyano | |
| 9.409 | 3-F-5-Me—Ph | H | O | H | $CH_2$ | cyano | |
| 9.410 | 3-F—Ph | H | O | H | $CH_2$ | cyano | |
| 9.411 | 3-$NO_2$—Ph | H | O | H | $CH_2$ | cyano | |
| 9.412 | 3,5-$Cl_2$—Ph | H | O | H | $CH_2$ | cyano | |
| 9.413 | 3,5-$Cl_2$—Ph | H | O | H | $CH_2$ | cyclohexyl | |
| 9.414 | 3,5-$F_2$—Ph | H | O | H | $CH_2$ | c-Pr | |
| 9.415 | 3,5-$Cl_2$—Ph | H | O | H | $CH_2$ | c-Pr | |
| 9.416 | 3,5-$F_2$—Ph | H | O | H | $CH_2$ | diethoxyphosphoryl | |
| 9.417 | 3-F—Ph | H | O | H | $CH_2$ | diethoxyphosphoryl | |
| 9.418 | Ph | H | O | H | $CH_2$ | diethoxyphosphoryl | |
| 9.419 | 3,5-$Cl_2$—Ph | H | O | H | $CH_2$ | diethoxyphosphoryl | |
| 9.420 | 3,5-$Cl_2$—Ph | H | O | H | $CH_2$ | difluoromethyl | |
| 9.421 | 3-Cl—Ph | H | O | H | $CH_2$ | dimethoxymethyl | |
| 9.422 | 3,5-$Cl_2$—Ph | H | O | H | $CH_2$ | dimethoxymethyl | |
| 9.423 | 3,5-$Cl_2$—Ph | H | O | H | $CH_2$ | dimethylcarbamoyl | |
| 9.424 | 3,5-$Cl_2$—Ph | H | O | prop-2-en-1-yl | $CH_2$ | ethenyl | |
| 9.425 | 3,5-$F_2$—Ph | H | O | H | $CH_2$ | ethenyl | |
| 9.426 | 3-F—Ph | H | O | H | $CH_2$ | ethenyl | |
| 9.427 | Ph | H | O | H | $CH_2$ | ethenyl | |
| 9.428 | 3,5-$(CF_3)_2$-Ph H | O | H | $CH_2$ | ethenyl | | |
| 9.429 | 3,5-$Cl_2$—Ph | H | O | H | $CH_2$ | ethynyl | |
| 9.430 | 3,5-$Cl_2$—Ph | H | O | prop-2-yn-1-yl | $CH_2$ | ethynyl | |
| 9.431 | 3,5-$F_2$—Ph | H | O | H | $CH_2$ | ethynyl | |
| 9.432 | 3,5-$Cl_2$—Ph | H | O | cPr | $CH_2$ | ethynyl | |
| 9.433 | 3-Cl—Ph | H | O | H | $CH_2$ | ethoxycarbonyl | |
| 9.434 | 3-F—Ph | H | O | H | $CH_2$ | ethoxycarbonyl | |
| 9.435 | 3,5-$F_2$—Ph | H | O | H | $CH_2$ | ethoxycarbonyl | |
| 9.436 | 3,5-$Cl_2$—Ph | H | O | H | $CH_2$ | formyl | |
| 9.437 | 3,5-$F_2$—Ph | H | O | H | $CH_2$ | methoxycarbonyl | |
| 9.438 | 3-Cl—Ph | H | O | H | $CH_2$ | methoxycarbonyl | |

TABLE 9-continued

Compounds of the general formula (I) according to the invention in which $R^2$ is hydrogen and $R^3$ is cyano and aryl is the radical

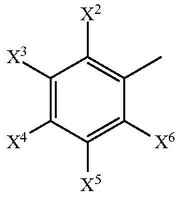

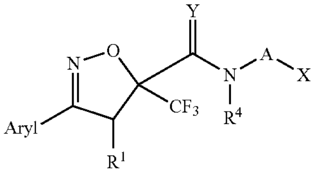

| No. | Aryl | $R^1$ | Y | $R^4$ | A | X | Physical data |
|---|---|---|---|---|---|---|---|
| 9.439 | 3-F—Ph | H | O | H | $CH_2$ | methoxycarbonyl | |
| 9.440 | 3-Cl-5-F—Ph | H | O | H | $CH_2$ | methoxycarbonyl | |
| 9.441 | 3,5-$Cl_2$—Ph | H | O | H | $CH_2$ | nonyl | |
| 9.442 | 3,5-$Cl_2$—Ph | H | O | H | $CH_2$ | pentafluoroethyl | |
| 9.443 | 3,5-$F_2$—Ph | H | O | H | $CH_2$ | pentyl | |
| 9.444 | 3,5-$Cl_2$—Ph | H | O | H | $CH_2$ | pentyl | |
| 9.445 | 3,5-$F_2$—Ph | H | O | H | $CH_2$ | piperidin-2-yl | |
| 9.446 | Ph | H | O | H | $CH_2$ | piperidin-2-yl | |
| 9.447 | 3,5-$Cl_2$—Ph | H | O | $CH_3$ | $CH_2$ | piperidin-2-yl | |
| 9.448 | 3,5-$Cl_2$—Ph | H | O | H | $CH_2$ | propan-2-yl | |
| 9.449 | 3,5-$Cl_2$—Ph | H | O | H | $CH_2$ | propan-2-yl | |
| 9.450 | 3,5-$Cl_2$—Ph | H | O | H | $CH_2$ | pyrrolidin-1-ylcarbonyl | |
| 9.451 | 3,5-$F_2$—Ph | H | O | H | $CH_2$ | tert-butyl | |
| 9.452 | 3,5-$Cl_2$—Ph | H | O | H | $CH_2$ | tert-butyl | |
| 9.453 | 3,5-$F_2$—Ph | H | O | H | $CH_2$ | tetrahydrofuran-2-yl | |
| 9.454 | 3-F—Ph | H | O | H | $CH_2$ | tetrahydrofuran-2-yl | |
| 9.455 | Ph | H | O | H | $CH_2$ | tetrahydrofuran-2-yl | |
| 9.456 | 3,5-$Cl_2$—Ph | H | O | H | $CH_2$ | tetrahydrofuran-2-yl | |
| 9.457 | 3,5-$F_2$—Ph | H | O | H | $CH_2$ | tetrahydrofuran-3-yl | |
| 9.458 | 3-F—Ph | H | O | H | $CH_2$ | tetrahydrofuran-3-yl | |
| 9.459 | Ph | H | O | H | $CH_2$ | tetrahydrofuran-3-yl | |
| 9.460 | 3,5-$Cl_2$—Ph | H | O | H | $CH_2C(CH_3)_2$ | tetrahydrofuran-3-yl | |
| 9.461 | 3,5-$Cl_2$—Ph | H | O | H | $CH_2C(CH_3)_2$ | COOH | |
| 9.462 | 3,5-$Cl_2$—Ph | H | O | H | $CH_2CH(CH_3)$ | ethoxycarbonyl | |
| 9.463 | 3,5-$Cl_2$—Ph | H | O | H | $CH_2CH_2$ | ethoxycarbonyl | |
| 9.464 | 3,5-$Cl_2$—Ph | H | O | H | $CH_2CH_2$ | (2,2,2-trifluoroethoxy)-carbonyl | |
| 9.465 | 3,5-$Cl_2$—Ph | H | O | H | $CH_2CH_2$ | (2-hydroxyethoxy)carbonyl | |
| 9.466 | 3,5-$Cl_2$—Ph | H | O | H | $CH_2CH_2$ | (2-methoxy-2-oxoethyl)carbamoyl | |
| 9.467 | 3,5-$Cl_2$—Ph | H | O | H | $CH_2CH_2$ | (allyloxy)carbonyl | |
| 9.468 | 3,5-$F_2$—Ph | H | O | H | $CH_2CH_2$ | (cyclopropylsulfonyl)-(methyl)carbamoyl | |
| 9.469 | 3,5-$Cl_2$—Ph | H | O | H | $CH_2CH_2$ | (cyclopropylsulfonyl)-(methyl)carbamoyl | |
| 9.470 | 3,5-$F_2$—Ph | H | O | H | $CH_2CH_2$ | (cyclopropylsulfonyl)-carbamoyl | |
| 9.471 | 3,5-$Cl_2$—Ph | H | O | H | $CH_2CH_2$ | (cyclopropylsulfonyl)-carbamoyl | |
| 9.472 | 3,5-$F_2$—Ph | H | O | H | $CH_2CH_2$ | (ethylsulfonyl)(methyl)-carbamoyl | |
| 9.473 | 3,5-$Cl_2$—Ph | H | O | H | $CH_2CH_2$ | (ethylsulfonyl)(methyl)-carbamoyl | |
| 9.474 | 3,5-$F_2$—Ph | H | O | H | $CH_2CH_2$ | (ethylsulfonyl)carbamoyl | |
| 9.475 | 3,5-$Cl_2$—Ph | H | O | H | $CH_2CH_2$ | (ethylsulfonyl)carbamoyl | |
| 9.476 | 3,5-$F_2$—Ph | H | O | H | $CH_2CH_2$ | (heptan-2-yloxy)carbonyl | |
| 9.477 | 3,5-$Cl_2$—Ph | H | O | H | $CH_2CH_2$ | (hydroxyimino)methyl | |
| 9.478 | 3,5-$F_2$—Ph | H | O | H | $CH_2CH_2$ | (isopropylsulfonyl)-(methyl)carbamoyl | |
| 9.479 | 3,5-$Cl_2$—Ph | H | O | H | $CH_2CH_2$ | (isopropylsulfonyl)-(methyl)carbamoyl | |
| 9.480 | 3,5-$F_2$—Ph | H | O | H | $CH_2CH_2$ | (isopropylsulfonyl)-carbamoyl | |

TABLE 9-continued

Compounds of the general formula (I) according to the invention in which $R^2$ is hydrogen and $R^3$ is cyano and aryl is the radical

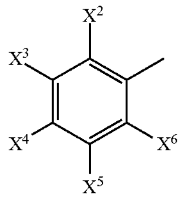

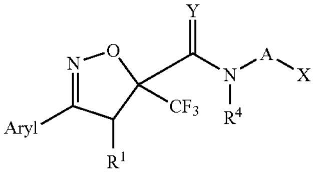

| No. | Aryl | $R^1$ | Y | $R^4$ | A | X | Physical data |
|---|---|---|---|---|---|---|---|
| 9.481 | 3,5-$Cl_2$—Ph | H | O | H | $CH_2CH_2$ | (isopropylsulfonyl)-carbamoyl | |
| 9.482 | 3,5-$F_2$—Ph | H | O | H | $CH_2CH_2$ | (methylsulfonyl)-carbamoyl | |
| 9.483 | 3,5-$Cl_2$—Ph | H | O | H | $CH_2CH_2$ | (methylsulfonyl)-carbamoyl | |
| 9.484 | 3,5-$Cl_2$—Ph | H | O | H | $CH_2CH_2$ | (prop-2-yn-1-yloxy)carbonyl | |
| 9.485 | 3,5-$Cl_2$—Ph | H | O | H | $CH_2CH_2$ | (propan-2-yloxy)carbonyl | |
| 9.486 | 3,5-$Cl_2$—Ph | H | O | H | $CH_2CH_2$ | [2-(methylsulfanyl)ethoxy]-carbonyl | |
| 9.487 | 3,5-$F_2$—Ph | H | O | H | $CH_2CH_2$ | 1,3-dioxolan-2-yl | |
| 9.488 | 3-F—Ph | H | O | H | $CH_2CH_2$ | 1,3-dioxolan-2-yl | |
| 9.489 | Ph | H | O | H | $CH_2CH_2$ | 1,3-dioxolan-2-yl | |
| 9.490 | 3,5-$Cl_2$—Ph | H | O | H | $CH_2CH_2$ | 1,3-dioxolan-2-yl | |
| 9.491 | 3,5-$Cl_2$—Ph | H | O | H | $CH_2CH_2$ | 1-methylpyrrolidin-2-yl | |
| 9.492 | 3,5-$Cl_2$—Ph | H | O | H | $CH_2CH_2$ | 2-oxopyrrolidin-1-yl | |
| 9.493 | 3,4,5-$F_3$—Ph | H | O | H | $CH_2CH_2$ | butoxycarbonyl | |
| 9.494 | 3,5-$Cl_2$—Ph | H | O | H | $CH_2CH_2$ | butylcarbamoyl | |
| 9.495 | 3-Cl-4-Me—Ph | H | O | H | $CH_2CH_2$ | carbamoyl | |
| 9.496 | 3,5-$Cl_2$—Ph | H | O | H | $CH_2CH_2$ | carbamoyl | |
| 9.497 | 3,5-$F_2$—Ph | H | O | H | $CH_2CH_2$ | $CF_3$ | |
| 9.498 | 3,5-$Cl_2$—Ph | H | O | H | $CH_2CH_2$ | $CF_3$ | |
| 9.499 | 3,5-$F_2$—Ph | H | O | H | $CH_2CH_2$ | $CH_3$ | |
| 9.500 | 3,5-$Cl_2$—Ph | H | O | H | $CH_2CH_2$ | $CH_3$ | |
| 9.501 | 2,3,4,5-$F_4$-6-OH—Ph | H | O | H | $CH_2CH_2$ | chlorine | |
| 9.502 | 2,3,5-$F_3$—Ph | H | O | H | $CH_2CH_2$ | COOH | |
| 9.503 | 2,3-$F_2$—Ph | H | O | H | $CH_2CH_2$ | COOH | |
| 9.504 | 2,5-$Cl_2$—Ph | H | O | H | $CH_2CH_2$ | COOH | |
| 9.505 | 2,5-$F_2$—Ph | H | O | H | $CH_2CH_2$ | COOH | |
| 9.506 | 2-Cl-5-F—Ph | H | O | H | $CH_2CH_2$ | COOH | |
| 9.507 | 2-F-3-Me—Ph | H | O | H | $CH_2CH_2$ | COOH | |
| 9.508 | 3-$CF_3$—Ph | H | O | H | $CH_2CH_2$ | COOH | |
| 9.509 | 3,4,5-$F_3$—Ph | H | O | H | $CH_2CH_2$ | COOH | |
| 9.510 | 3,4-$F_2$—Ph | H | O | H | $CH_2CH_2$ | COOH | |
| 9.511 | 3,5-$Br_2$—Ph | H | O | H | $CH_2CH_2$ | COOH | |
| 9.512 | 3,5-$Cl_2$—Ph | H | O | $CH_3$ | $CH_2CH_2$ | COOH | |
| 9.513 | 3,5-$Cl_2$—Ph | H | O | H | $CH_2CH_2$ | COOH | |
| 9.514 | 3,5-$F_2$—Ph | H | O | H | $CH_2CH_2$ | COOH | |
| 9.515 | 3,5-$Me_2$—Ph | H | O | H | $CH_2CH_2$ | COOH | |
| 9.516 | 3,5-(tert.Bu)$_2$—Ph | H | O | H | $CH_2CH_2$ | COOH | |
| 9.517 | 3-Br-5-Cl—Ph | H | O | H | $CH_2CH_2$ | COOH | |
| 9.518 | 3-Br-5-F—Ph | H | O | H | $CH_2CH_2$ | COOH | |
| 9.519 | 3-Br-5-CF3—Ph | H | O | H | $CH_2CH_2$ | COOH | |
| 9.520 | 3-Cl-4-F—Ph | H | O | H | $CH_2CH_2$ | COOH | |
| 9.521 | 3-Cl-4-Me—Ph | H | O | H | $CH_2CH_2$ | COOH | |
| 9.522 | 3-Cl-5-F—Ph | H | O | H | $CH_2CH_2$ | COOH | |
| 9.523 | 3-Cl-5-$CF_3$O—Ph | H | O | H | $CH_2CH_2$ | COOH | |
| 9.524 | 3-Cl-5-$CF_3$—Ph | H | O | H | $CH_2CH_2$ | COOH | |
| 9.525 | 3-Cl-5-Me—Ph | H | O | H | $CH_2CH_2$ | COOH | |
| 9.526 | 3-Et-5-F—Ph | H | O | H | $CH_2CH_2$ | COOH | |

TABLE 9-continued

Compounds of the general formula (I) according to the invention in which $R^2$ is hydrogen and $R^3$ is cyano and aryl is the radical

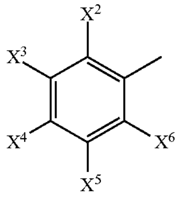

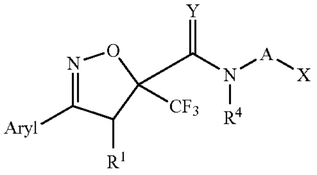

| No. | Aryl | $R^1$ | Y | $R^4$ | A | X | Physical data |
|---|---|---|---|---|---|---|---|
| 9.527 | 3-Et—Ph | H | O | H | $CH_2CH_2$ | COOH | |
| 9.528 | 3-F-5-MeO—Ph | H | O | H | $CH_2CH_2$ | COOH | |
| 9.529 | 3-F-5-Me—Ph | H | O | H | $CH_2CH_2$ | COOH | |
| 9.530 | 3-F—Ph | H | O | H | $CH_2CH_2$ | COOH | |
| 9.531 | 3-Me—Ph | H | O | H | $CH_2CH_2$ | COOH | |
| 9.532 | 4-Cl—Ph | H | O | H | $CH_2CH_2$ | COOH | |
| 9.533 | 4-EtO—Ph | H | O | H | $CH_2CH_2$ | COOH | |
| 9.534 | Ph | H | O | H | $CH_2CH_2$ | COOH | |
| 9.535 | 3,5-$Cl_2$—Ph | H | O | H | $CH_2CH_2$ | COOH | |
| 9.536 | 3-Cl—Ph | H | O | H | $CH_2CH_2$ | cyano | |
| 9.537 | 3,5-$Cl_2$—Ph | H | O | H | $CH_2CH_2$ | cyano | |
| 9.538 | 3,5-$Cl_2$—Ph | H | O | H | $CH_2CH_2$ | cyclopropylcarbamoyl | |
| 9.539 | 3,5-$Cl_2$—Ph | H | O | H | $CH_2CH_2$ | diethoxymethyl | |
| 9.540 | Ph | H | O | H | $CH_2CH_2$ | diethoxyphosphoryl | |
| 9.541 | 3,5-$Cl_2$—Ph | H | O | H | $CH_2CH_2$ | diethoxyphosphoryl | |
| 9.542 | 3,5-$Cl_2$—Ph | H | O | H | $CH_2CH_2$ | dimethoxymethyl | |
| 9.543 | 3,5-$Cl_2$—Ph | H | O | H | $CH_2CH_2$ | dimethylcarbamoyl | |
| 9.544 | 3-Cl—Ph | H | O | H | $CH_2CH_2$ | ethoxy | |
| 9.545 | 2-Cl-5-F—Ph | H | O | H | $CH_2CH_2$ | ethoxy | |
| 9.546 | 3-$CF_3$—Ph | H | O | H | $CH_2CH_2$ | ethoxycarbonyl | |
| 9.547 | 3,5-$Cl_2$—Ph | H | O | cPr | $CH_2CH_2$ | ethoxycarbonyl | |
| 9.548 | 3,5-$Cl_2$—Ph | H | O | H | $CH_2CH_2$ | ethoxycarbonyl | |
| 9.549 | 3,5-$F_2$—Ph | H | O | H | $CH_2CH_2$ | ethoxycarbonyl | |
| 9.550 | 3-Br-5-$CF_3$—Ph | H | O | H | $CH_2CH_2$ | ethoxycarbonyl | |
| 9.551 | 3-Cl-5-Et—Ph | H | O | H | $CH_2CH_2$ | ethoxycarbonyl | |
| 9.552 | 3-Cl-5-$CF_3$—Ph | H | O | H | $CH_2CH_2$ | ethoxycarbonyl | |
| 9.553 | 3-Et-5-F—Ph | H | O | H | $CH_2CH_2$ | ethoxycarbonyl | |
| 9.554 | 3-Et—Ph | H | O | H | $CH_2CH_2$ | ethoxycarbonyl | |
| 9.555 | 3-F-5-MeO—Ph | H | O | H | $CH_2CH_2$ | ethoxycarbonyl | |
| 9.556 | 3-Me-5-$CF_3$O—Ph | H | O | H | $CH_2CH_2$ | ethoxycarbonyl | |
| 9.557 | 3,5-$Cl_2$—Ph | H | O | H | $CH_2CH_2$ | ethoxycarbonyl | |
| 9.558 | 3,5-$F_2$—Ph | H | O | H | $CH_2CH_2$ | ethylcarbamoyl | |
| 9.559 | 3,5-$Cl_2$—Ph | H | O | H | $CH_2CH_2$ | formyl | |
| 9.560 | 3,5-$F_2$—Ph | H | O | H | $CH_2CH_2$ | hydroxy | |
| 9.561 | 3-Cl—Ph | H | O | H | $CH_2CH_2$ | hydroxy | |
| 9.562 | 3,5-$Cl_2$—Ph | H | O | H | $CH_2CH_2$ | hydroxy | |
| 9.563 | 3,5-$Cl_2$—Ph | H | O | H | $CH_2CH_2$ | isobutoxycarbonyl | |
| 9.564 | 3-Cl-5-$CF_3$—Ph | H | O | H | $CH_2CH_2$ | methoxy | |
| 9.565 | 3-Cl—Ph | H | O | H | $CH_2CH_2$ | methoxy | |
| 9.566 | 2,3,4-$F_3$—Ph | H | O | H | $CH_2CH_2$ | methoxy | |
| 9.567 | 2,3,5-$F_3$—Ph | H | O | H | $CH_2CH_2$ | methoxycarbonyl | |
| 9.568 | 2,3-$F_2$—Ph | H | O | H | $CH_2CH_2$ | methoxycarbonyl | |
| 9.569 | 2,5-$Cl_2$—Ph | H | O | H | $CH_2CH_2$ | methoxycarbonyl | |
| 9.570 | 2,5-$F_2$—Ph | H | O | H | $CH_2CH_2$ | methoxycarbonyl | |
| 9.571 | 2,5-$Me_2$—Ph | H | O | H | $CH_2CH_2$ | methoxycarbonyl | |
| 9.572 | 2-Cl-3-F-5-MeO—Ph | H | O | H | $CH_2CH_2$ | methoxycarbonyl | |
| 9.573 | 2-F-3-Me—Ph | H | O | H | $CH_2CH_2$ | methoxycarbonyl | |
| 9.574 | 3-$CF_3$—Ph | H | O | H | $CH_2CH_2$ | methoxycarbonyl | |
| 9.575 | 3,4,5-$F_3$—Ph | H | O | H | $CH_2CH_2$ | methoxycarbonyl | |
| 9.576 | 3,4-$F_2$—Ph | H | O | H | $CH_2CH_2$ | methoxycarbonyl | |
| 9.577 | 3,5-$Br_2$—Ph | H | O | H | $CH_2CH_2$ | methoxycarbonyl | |
| 9.578 | 3,5-$Cl_2$-4-MeO—Ph | H | O | H | $CH_2CH_2$ | methoxycarbonyl | |

TABLE 9-continued

Compounds of the general formula (I) according to the invention in which $R^2$ is hydrogen and $R^3$ is cyano and aryl is the radical

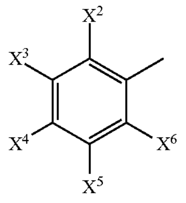

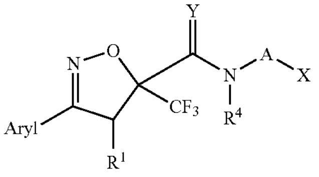

| No. | Aryl | $R^1$ | Y | $R^4$ | A | X | Physical data |
|---|---|---|---|---|---|---|---|
| 9.579 | 3,5-$Cl_2$—Ph | $CH_3$ | O | H | $CH_2CH_2$ | methoxycarbonyl | |
| 9.580 | 3,5-$Cl_2$—Ph | H | O | CH3 | $CH_2CH_2$ | methoxycarbonyl | |
| 9.581 | 3,5-$Cl_2$—Ph | H | O | H | $CH_2CH_2$ | methoxycarbonyl | [$CDCl_3$] 7.71<br>0.67; 7.71 0.71; 7.53<br>4.91; 7.52 6.49; 7.49<br>1.78; 7.49 2.59; 7.48<br>1.17; 7.48 0.34; 7.34<br>0.42; 7.26 18.46; 7.19<br>0.71; 5.30 0.41; 4.10<br>1.44; 4.06 3.46; 4.00<br>3.43; 3.96 1.43; 3.75<br>2.10; 3.74 0.69; 3.72<br>16.00; 3.69 0.42; 3.67<br>0.38; 3.67 0.40; 3.66<br>0.49; 3.65 0.84; 3.64<br>0.77; 3.64 0.53; 3.62<br>0.39; 3.61 0.36; 3.60<br>0.72; 3.59 0.47; 3.58<br>0.52; 3.58 0.72; 3.56<br>0.44; 3.56 0.42; 3.54<br>0.36; 2.68 0.32; 2.63<br>0.98; 2.62 0.98; 2.61<br>1.05; 2.61 1.53; 2.59<br>0.96; 2.59 0.97; 1.58<br>8.31;0.00 7.16 |
| 9.582 | 3,5-$Et_2$—Ph | H | O | H | $CH_2CH_2$ | methoxycarbonyl | |
| 9.583 | 3,5-$F_2$—Ph | H | O | H | $CH_2CH_2$ | methoxycarbonyl | [$CDCl_3$] 7.34<br>0.32; 7.34 0.32; 7.32<br>0.49; 7.31 0.38; 7.31<br>0.39; 7.26 14.30; 7.26<br>11.16; 7.19 1.35; 7.18<br>1.33; 7.18 1.98; 7.17<br>1.24; 7.17 1.77; 7.17<br>1.86; 7.16 1.58; 6.99<br>0.35; 6.98 0.61; 6.98<br>0.34; 6.97 0.71; 6.96<br>1.24; 6.95 0.66; 6.94<br>0.38; 6.94 0.64; 6.93<br>0.34; 4.10 1.51; 4.05<br>3.62; 4.00 3.65; 3.95<br>1.48; 3.75 0.55; 3.72<br>16.00; 3.71 0.33; 3.69<br>0.50; 3.67 0.50; 3.67<br>0.53; 3.66 0.99; 3.64<br>0.86; 3.63 0.42; 3.61<br>0.40; 3.60 0.84; 3.58<br>0.57; 3.58 0.87; 3.57<br>0.48; 3.57 0.48; 3.56<br>0.52; 3.55 0.44; 2.62<br>1.14; 2.62 1.18; 2.61<br>1.27; 2.61 2.20; 2.59<br>1.16; 2.59 1.19; 2.04<br>0.47; 1.56 3.55; 1.26<br>0.43; 1.26 0.42; 0.00<br>6.65; 0.00 5.26 |

TABLE 9-continued

Compounds of the general formula (I) according to the invention in which $R^2$ is hydrogen and $R^3$ is cyano and aryl is the radical

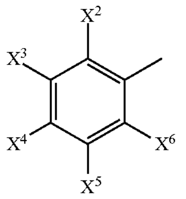

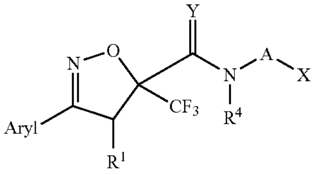

| No. | Aryl | $R^1$ | Y | $R^4$ | A | X | Physical data |
|---|---|---|---|---|---|---|---|
| 9.584 | 3,5-(MeO)$_2$—Ph | H | O | H | $CH_2CH_2$ | methoxycarbonyl | |
| 9.585 | 3,5-Me$_2$—Ph | H | O | H | $CH_2CH_2$ | methoxycarbonyl | |
| 9.586 | 3,5-(tert.Bu)$_2$—Ph | H | O | H | $CH_2CH_2$ | methoxycarbonyl | |
| 9.587 | 3-$CF_3$S—Ph | H | O | H | $CH_2CH_2$ | methoxycarbonyl | |
| 9.588 | 3-Ac—Ph | H | O | H | $CH_2CH_2$ | methoxycarbonyl | |
| 9.589 | 3-Br-5-Cl—Ph | H | O | H | $CH_2CH_2$ | methoxycarbonyl | |
| 9.590 | 3-Br-5-F—Ph | H | O | H | $CH_2CH_2$ | methoxycarbonyl | |
| 9.591 | 3-Br-5-$CF_3$—Ph | H | O | H | $CH_2CH_2$ | methoxycarbonyl | |
| 9.592 | 3-$NH_2$CO—Ph | H | O | H | $CH_2CH_2$ | methoxycarbonyl | |
| 9.593 | 3-Cl-4-F—Ph | H | O | H | $CH_2CH_2$ | methoxycarbonyl | |
| 9.594 | 3-Cl-4-Me—Ph | H | O | H | $CH_2CH_2$ | methoxycarbonyl | |
| 9.595 | 3-Cl-5-CN—Ph | H | O | H | $CH_2CH_2$ | methoxycarbonyl | |
| 9.596 | 3-Cl-5-Et—Ph | H | O | H | $CH_2CH_2$ | methoxycarbonyl | |
| 9.597 | 3-Cl-5-F—Ph | H | O | H | $CH_2CH_2$ | methoxycarbonyl | |
| 9.598 | 3-Cl-5-MeO—Ph | H | O | H | $CH_2CH_2$ | methoxycarbonyl | |
| 9.599 | 3-Cl-5-$CF_3$O—Ph | H | O | H | $CH_2CH_2$ | methoxycarbonyl | |
| 9.600 | 3-Cl-5-$CF_3$—Ph | H | O | H | $CH_2CH_2$ | methoxycarbonyl | |
| 9.601 | 3-Cl-5-Me—Ph | H | O | H | $CH_2CH_2$ | methoxycarbonyl | |
| 9.602 | 3-CN-5-F—Ph | H | O | H | $CH_2CH_2$ | methoxycarbonyl | |
| 9.603 | 3-CN—Ph | H | O | H | $CH_2CH_2$ | methoxycarbonyl | |
| 9.604 | 3-c-Pr-S-F—Ph | H | O | H | $CH_2CH_2$ | methoxycarbonyl | |
| 9.605 | 3-Et-5-F—Ph | H | O | H | $CH_2CH_2$ | methoxycarbonyl | |
| 9.606 | 3-F-5-MeS—Ph | H | O | H | $CH_2CH_2$ | methoxycarbonyl | |
| 9.607 | 3-F-5-$MeSO_2$—Ph | H | O | H | $CH_2CH_2$ | methoxycarbonyl | |
| 9.608 | 3-F-5-MeO—Ph | H | O | H | $CH_2CH_2$ | methoxycarbonyl | |
| 9.609 | 3-F-5-Me—Ph | H | O | H | $CH_2CH_2$ | methoxycarbonyl | |
| 9.610 | 3-F—Ph | H | O | H | $CH_2CH_2$ | methoxycarbonyl | |
| 9.611 | 3-Me—Ph | H | O | H | $CH_2CH_2$ | methoxycarbonyl | |
| 9.612 | 3-$NO_2$—Ph | H | O | H | $CH_2CH_2$ | methoxycarbonyl | |
| 9.613 | 4-Cl—Ph | H | O | H | $CH_2CH_2$ | methoxycarbonyl | |
| 9.614 | 4-EtO—Ph | H | O | H | $CH_2CH_2$ | methoxycarbonyl | |
| 9.615 | 4-MeO—Ph | H | O | H | $CH_2CH_2$ | methoxycarbonyl | |
| 9.616 | $F_5$—Ph | H | O | H | $CH_2CH_2$ | methoxycarbonyl | |
| 9.617 | Ph | H | O | H | $CH_2CH_2$ | methoxycarbonyl | |
| 9.618 | 3,5-$Cl_2$—Ph | H | O | H | $CH_2CH_2$ | methoxycarbonyl | |
| 9.619 | 3,5-$F_2$—Ph | H | O | H | $CH_2CH_2$ | methoxycarbonyl | |
| 9.620 | 2,5-$Cl_2$—Ph | H | O | H | $CH_2CH_2$ | methoxycarbonyl | |
| 9.621 | 3,5-$Cl_2$—Ph | H | O | H | $CH_2CH_2$ | methyl(methylsulfonyl)-carbamoyl | |
| 9.622 | 3-Cl-4-F—Ph | H | O | H | $CH_2CH_2$ | methyl(methylsulfonyl)-carbamoyl | |
| 9.623 | 3-Cl-4-Me—Ph | H | O | H | $CH_2CH_2$ | methylcarbamoyl | |
| 9.624 | 3,5-$Cl_2$—Ph | H | O | H | $CH_2CH_2$ | methylcarbamoyl | |
| 9.625 | 3,5-$Cl_2$—Ph | H | O | H | $CH_2CH_2$ | methylcarbamoyl | |
| 9.626 | 3,5-$Cl_2$—Ph | H | O | H | $CH_2CH_2$ | methylcarbamoyl | |
| 9.627 | 3,5-$Cl_2$—Ph | H | O | H | $CH_2CH_2$ | methylsulfanyl | |
| 9.628 | 3,5-$Cl_2$—Ph | H | O | H | $CH_2CH_2$ | methylsulfonyl | |
| 9.629 | Ph | H | O | H | $CH_2CH_2$ | morpholin-4-yl | |
| 9.630 | 3,5-$Cl_2$—Ph | H | O | H | $CH_2CH_2$ | morpholin-4-ylcarbonyl | |
| 9.631 | 3,5-$Cl_2$—Ph | H | O | H | $CH_2CH_2$ | phosphono | |
| 9.632 | 3,5-$Cl_2$—Ph | H | O | H | $CH_2CH_2$ | phosphono | |
| 9.633 | 3,5-$Cl_2$—Ph | H | O | H | $CH_2CH_2$ | piperidin-1-yl | |

TABLE 9-continued

Compounds of the general formula (I) according to the invention in which $R^2$ is hydrogen and $R^3$ is cyano and aryl is the radical

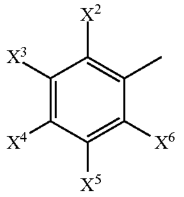

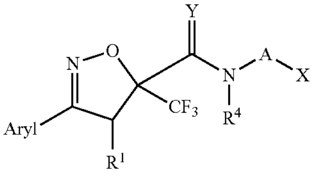

| No. | Aryl | $R^1$ | Y | $R^4$ | A | X | Physical data |
|---|---|---|---|---|---|---|---|
| 9.634 | 3,5-$Cl_2$—Ph | H | O | H | $CH_2CH_2$ | piperidin-1-ylcarbonyl | |
| 9.635 | 3,5-$Cl_2$—Ph | H | O | H | $CH_2CH_2$ | propan-2-yloxy | |
| 9.636 | 3,5-$Cl_2$—Ph | H | O | H | $CH_2CH_2$ | propoxy | |
| 9.637 | 3,5-$F_2$—Ph | H | O | H | $CH_2CH_2$ | propoxycarbonyl | |
| 9.638 | 3,5-$Cl_2$—Ph | H | O | H | $CH_2CH_2$ | pyrrolidin-1-yl | |
| 9.639 | 3,5-$F_2$—Ph | H | O | H | $CH_2CH_2$ | sec-butoxycarbonyl | |
| 9.640 | 3,5-$Cl_2$—Ph | H | O | H | $CH_2CH_2$ | sulfamoyl | |
| 9.641 | 3,5-$Cl_2$- Ph | H | O | H | $CH_2CH_2$ | tert-butoxycarbonyl | |
| 9.642 | 3,5-$F_2$—Ph | H | O | H | $CH_2CH_2$ | 2 tert-butoxycarbonyl | |
| 9.643 | 3-F—Ph | H | O | H | $CH_2CH_2$ | tetrahydrofuran-2-yl | |
| 9.644 | Ph | H | O | H | $CH_2CH_2$ | trifluoromethoxy | |
| 9.645 | 3-Cl-Ph | H | O | H | $(CH_2)_3$ | trifluoromethoxy | |
| 9.646 | 3-F-Ph | H | O | H | $(CH_2)_3$ | trifluoromethoxy | |
| 9.647 | 3,5-$Cl_2$- Ph | H | O | H | $(CH_2)_3$ | trifluoromethoxy | |
| 9.648 | 3,5-$Cl_2$- Ph | H | O | H | $(CH_2)_3$ | (propan-2-yloxy)carbonyl | |
| 9.649 | 3,5-$F_2$—Ph | H | O | H | $(CH_2)_3$ | (propan-2-yloxy)carbonyl | |
| 9.650 | Ph | H | O | H | $(CH_2)_3$ | 2-carboxyethyl | |
| 9.651 | 3,5-$Cl_2$—Ph | H | O | H | $(CH_2)_3$ | 2-methyl-1,3-dioxolan-2-yl | |
| 9.652 | 3,5-$Cl_2$—Ph | H | O | H | $(CH_2)_3$ | 2-methyl-1,3-dioxolan-2-yl | |
| 9.653 | 3,5-$Cl_2$—Ph | H | O | H | $(CH_2)_3$ | 2-methyl-1,3-dioxolan-2-yl | |
| 9.654 | 3,5-$F_2$—Ph | H | O | H | $(CH_2)_3$ | 2-oxopyrrolidin-1-yl | |
| 9.655 | 3,5-$Cl_2$—Ph | H | O | H | $(CH_2)_3$ | $CF_3$ | |
| 9.656 | 3,5-$F_2$—Ph | H | O | H | $(CH_2)_3$ | $CH_3$ | |
| 9.657 | 3-Br-5-Cl—Ph | H | O | H | $(CH_2)_3$ | $CH_3$ | |
| 9.658 | 3-Cl—Ph | H | O | H | $(CH_2)_3$ | COOH | |
| 9.659 | 3-F—Ph | H | O | H | $(CH_2)_3$ | COOH | |
| 9.660 | Ph | H | O | H | $(CH_2)_3$ | COOH | |
| 9.661 | 3,5-$Cl_2$—Ph | H | O | H | $(CH_2)_3$ | COOH | |
| 9.662 | Ph | H | O | Et-carbamoyl | $(CH_2)_3$ | COOH | |
| 9.663 | 3,5-$Cl_2$—Ph | H | O | H | $(CH_2)_3$ | COOH | |
| 9.664 | 3,5-$Cl_2$—Ph | H | O | H | $(CH_2)_3$ | dimethylamino | |
| 9.665 | 3-Cl—Ph | H | O | H | $(CH_2)_3$ | dimethylamino | |
| 9.666 | 3-F—Ph | H | O | H | $(CH_2)_3$ | ethoxy | |
| 9.667 | 3,5-$Cl_2$—Ph | H | O | H | $(CH_2)_3$ | ethoxycarbonyl | |
| 9.668 | 3,5-$F_2$—Ph | H | O | H | $(CH_2)_3$ | ethoxycarbonyl | |
| 9.669 | 3,5-$Cl_2$—Ph | H | O | H | $(CH_2)_3$ | ethoxycarbonyl | |
| 9.670 | 3,5-$F_2$—Ph | H | O | H | $(CH_2)_3$ | hydroxy | |
| 9.671 | 3-Br-5-Cl—Ph | H | O | H | $(CH_2)_3$ | hydroxy | |
| 9.672 | 3-Cl-5-MeO—Ph | H | O | H | $(CH_2)_3$ | methoxy | |
| 9.673 | 3-Cl—Ph | H | O | H | $(CH_2)_3$ | methoxycarbonyl | |
| 9.674 | 3-F—Ph | H | O | H | $(CH_2)_3$ | methoxycarbonyl | |
| 9.675 | Ph | H | O | H | $(CH_2)_3$ | methoxycarbonyl | |
| 9.676 | 3,5-$F_2$—Ph | H | O | H | $(CH_2)_3$ | methoxycarbonyl | |
| 9.677 | 3,5-$Cl_2$—Ph | H | O | H | $(CH_2)_3$ | methoxycarbonyl | |

TABLE 9-continued

Compounds of the general formula (I) according to the invention in which $R^2$ is hydrogen and $R^3$ is cyano and aryl is the radical

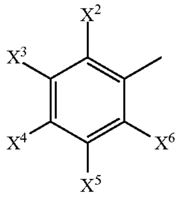

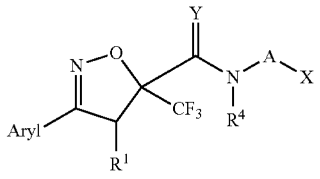

| No. | Aryl | $R^1$ | Y | $R^4$ | A | X | Physical data |
|---|---|---|---|---|---|---|---|
| 9.678 | 3,5-$Cl_2$—Ph | H | O | H | $(CH_2)_6$ | methoxycarbonyl<br>methylcarbamoyl<br>morpholin-4-yl<br>methoxycarbonyl | |

TABLE 10

Compounds of the general formula (I) according to the invention in which $R^2$ is hydrogen and aryl is the radical

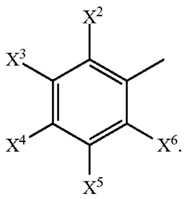

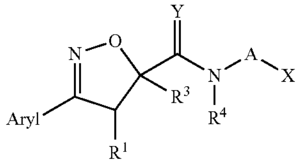

| No. | Aryl | $R^1$ | $R^3$ | Y | $R^4$ | A | X | Data |
|---|---|---|---|---|---|---|---|---|
| 10.001 | 3,5-$Cl_2$—Ph | H | (methylsulfan-yl)methyl | O | H | bond | $CH_3$ | |
| 10.002 | 3,5-$Cl_2$—Ph | H | (methylsulfan-yl)methyl | O | H | bond | c-Pr | |
| 10.003 | 3,5-$Cl_2$—Ph | H | (methylsulfan-yl)methyl | O | H | $CH_2CH_2$ | methoxy-carbonyl | |
| 10.004 | 3,5-$Cl_2$—Ph | H | (methylsulfon-yl)methyl | O | H | bond | $CH_3$ | |
| 10.005 | 2-$CF_3$—Ph | H | $C(OH)CH(CH_3)_2$ | O | H | bond | $CH_3$ | |
| 10.006 | 2,4-$Cl_2$—Ph | H | $C(OH)CH(CH_3)_2$ | O | H | bond | $CH_3$ | |
| 10.007 | 3-Cl—Ph | H | $C(OH)CH(CH_3)_2$ | O | H | bond | $CH_3$ | |
| 10.008 | 4-Cl—Ph | H | $C(OH)CH(CH_3)_2$ | O | H | bond | $CH_3$ | |
| 10.009 | Ph | H | $C(OH)CH(CH_3)_2$ | O | H | bond | $CH_3$ | |
| 10.010 | 2,4-$Cl_2$—Ph | H | $C(OH)CH(CH_3)_2$ | O | H | bond | c-Pr | |
| 10.011 | 3-$CF_3$—Ph | H | $C(OH)CH(CH_3)_2$ | O | H | bond | c-Pr | |
| 10.012 | 3,5-$Cl_2$—Ph | H | $C(OH)CH(CH_3)_2$ | O | H | bond | c-Pr | |
| 10.013 | 3-Cl—Ph | H | $C(OH)CH(CH_3)_2$ | O | H | bond | c-Pr | |
| 10.014 | 4-Cl—Ph | H | $C(OH)CH(CH_3)_2$ | O | H | bond | c-Pr | |
| 10.015 | Ph | H | $C(OH)CH(CH_3)_2$ | O | H | bond | c-Pr | |
| 10.016 | 2-$CF_3$—Ph | H | 1-hydroxyethyl | O | H | bond | $CH_3$ | |
| 10.017 | 2,4-$Cl_2$—Ph | H | $CH(CH_3)OH$ | O | H | bond | $CH_3$ | |
| 10.018 | 3,5-$Cl_2$—Ph | H | $CH(CH_3)OH$ | O | H | bond | $CH_3$ | |

TABLE 10-continued

Compounds of the general formula (I) according to the invention in which $R^2$ is hydrogen and aryl is the radical

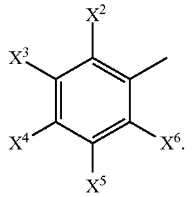

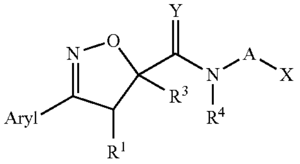

| No. | Aryl | $R^1$ | $R^3$ | Y | $R^4$ | A | X | Data |
|---|---|---|---|---|---|---|---|---|
| 10.019 | 3-Cl—Ph | H | $CH(CH_3)OH$ | O | H | bond | $CH_3$ | |
| 10.020 | 4-Cl—Ph | H | $CH(CH_3)OH$ | O | H | bond | $CH_3$ | |
| 10.021 | Ph | H | $CH(CH_3)OH$ | O | H | bond | $CH_3$ | |
| 10.022 | 2-Cl—Ph | H | $CH(CH_3)OH$ | O | H | bond | c-Pr | |
| 10.023 | 3,5-$Cl_2$—Ph | H | $CH(CH_3)OH$ | O | H | bond | c-Pr | |
| 10.024 | 3-Cl—Ph | H | $CH(CH_3)OH$ | O | H | bond | c-Pr | |
| 10.025 | 4-Cl—Ph | H | $CH(CH_3)OH$ | O | H | bond | c-Pr | |
| 10.026 | Ph | H | $CH(CH_3)OH$ | O | H | bond | c-Pr | |
| 10.027 | 2,4-$Cl_2$—Ph | H | $CH(CH_3)OH$ | O | H | bond | c-Pr | |
| 10.028 | 3-Cl—Ph | H | $CH(CH_3)OH$ | O | H | bond | $CH_3$ | |
| 10.029 | Ph | H | $CH(CH_3)OH$ | O | H | bond | $CH_3$ | |
| 10.030 | 3,5-$Cl_2$—Ph | H | $CH(CH_3)OH$ | O | H | bond | c-Pr | |
| 10.031 | 3,5-$Cl_2$—Ph | H | bromomethyl | O | H | $CH_2$ | $CF_3$ | |
| 10.032 | 3,5-$Cl_2$—Ph | H | cPr | O | H | $CH(CH_3)$ | $CH_3$ | |
| 10.033 | 3,5-$Cl_2$—Ph | H | cPr | O | H | $CH_2$ | $CF_3$ | |
| 10.034 | 2-$CF_3$—Ph | H | $CH_2OH$ | O | H | bond | $CH_3$ | |
| 10.035 | 2,4-$Cl_2$—Ph | H | $CH_2OH$ | O | H | bond | $CH_3$ | |
| 10.036 | 3,5-$Cl_2$—Ph | H | $CH_2OH$ | O | H | bond | $CH_3$ | |
| 10.037 | 3-Cl—Ph | H | $CH_2OH$ | O | H | bond | $CH_3$ | |
| 10.038 | 4-Cl—Ph | H | $CH_2OH$ | O | H | bond | $CH_3$ | |
| 10.039 | Ph | H | $CH_2OH$ | O | H | bond | $CH_3$ | |
| 10.040 | 2-$CF_3$—Ph | H | $CH_2OH$ | O | H | bond | c-Pr | |
| 10.041 | 2,4-$Cl_2$—Ph | H | $CH_2OH$ | O | H | bond | c-Pr | |
| 10.042 | 3,5-$Cl_2$—Ph | H | $CH_2OH$ | O | H | bond | c-Pr | |
| 10.043 | 3-Cl—Ph | H | $CH_2OH$ | O | H | bond | c-Pr | |
| 10.044 | 4-Cl—Ph | H | $CH_2OH$ | O | H | bond | c-Pr | |
| 10.045 | Ph | H | $CH_2OH$ | O | H | bond | c-Pr | |
| 10.046 | 2-$CF_3$—Ph | H | $CH_2OH$ | O | H | bond | CH3 | |
| 10.047 | 3,5-$Cl_2$—Ph | H | $CH_2OH$ | O | H | bond | CH3 | |
| 10.048 | 3-Cl—Ph | H | $CH_2OH$ | O | H | bond | $CH_3$ | |
| 10.049 | 4-Cl—Ph | H | $CH_2OH$ | O | H | bond | $CH_3$ | |
| 10.050 | Ph | H | $CH_2OH$ | O | H | bond | $CH_3$ | |
| 10.051 | 3,5-$Cl_2$—Ph | H | $CH_2OH$ | O | H | bond | c-Pr | |
| 10.052 | 3,5-$Cl_2$—Ph | H | iPr | O | H | bond | H | |
| 10.053 | 3,5-$Cl_2$—Ph | H | iPr | O | H | $C(CH_3)_2$ | cyano | |
| 10.054 | 3,5-$Cl_2$—Ph | H | iPr | O | H | $C(CH_3)_2$ | ethynyl | |
| 10.055 | 3,5-$Cl_2$—Ph | H | iPr | O | H | $CH(CH_3)$ | $CH_3$ | |
| 10.056 | 3,5-$Cl_2$—Ph | H | iPr | O | H | $CH_2$ | $CF_3$ | |
| 10.057 | 3,5-$Cl_2$—Ph | H | acetyl | O | $CH_3$ | bond | $CH_3$ | |
| 10.058 | 3,5-$F_2$—Ph | H | acetyl | O | $CH_3$ | bond | $CH_3$ | |
| 10.059 | 3,5-$F_2$—Ph | H | F | O | H | bond | c-Pr | [$CDCl_3$] 0.66 (m, 2H); 0.90 (m, 2H); 2.33 (m, 1H); 3.55 (dd, 1H); 4.20 (dd, 1H); 6.61 (s br, 1H); 6.95 (m, 1H); 7.20 (m, 2H). |
| 10.060 | 3,5-$Cl_2$—Ph | H | F | O | H | bond | c-Pr | [$CDCl_3$] 0.65 (m, 2H); 0.90 (m, 2H); 2.85 (m, 1H); 3.55 (dd, 1H); 4.20 (dd, 1H); 6.61 (s br, 1H); 7.48 |

TABLE 10-continued

Compounds of the general formula (I) according to the invention in which $R^2$ is hydrogen and aryl is the radical

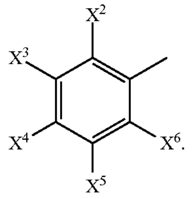

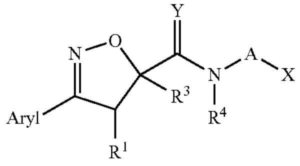

| No. | Aryl | $R^1$ | $R^3$ | Y | $R^4$ | A | X | Data |
|---|---|---|---|---|---|---|---|---|
| | | | | | | | | (s, 1H); 7.58 (s, 2H). |
| 10.061 | 3,5-$F_2$—Ph | H | $CH_2F$ | O | H | bond | c-Pr | [$CDCl_3$] 0.55 (m, 2H); 0.83 (m, 2H); 2.76 (m, 1H); 3.43 (d, 1H); 3.68 (d, 1H); 4.62 (d, 1H); 4.63 (d, 0.5H); 4.72 (d, 0.5H); 4.74 (d, 0.5H); 4.84 (d, 0.5H); 6.88 (m, 2H); 7.16 (m, 2H). |
| 10.062 | 3,5-$Cl_2$—Ph | H | acetyl | O | H | bond | c-Pr | [$CDCl_3$] 0.59 (m, 2H); 0.86 (m, 2H); 2.23 (s, 3H); 2.81 (m, 1H); 3.53 (d, 1H); 4.15 (d, 1H); 6.94 (s br, 1H); 7.44 (s, 1H); 7.54 (s, 2H). |
| 10.063 | 3-F—Ph | H | $CH_2F$ | O | H | bond | c-Pr | |
| 10.064 | 3,5-$F_2$—Ph | H | acetyl | O | H | bond | c-Pr | |
| 10.065 | 3,5-$F_2$—Ph | H | $CH_2OH$ | O | H | bond | c-Pr | |
| 10.066 | 3,5-$F_2$—Ph | H | prop-1-en-2-yl | O | H | bond | c-Pr | [$CDCl_3$] 0.54 (m, 2H); 0.80 (m, 2H); 1.78 (s, 3H); 2.74 (m, 1H); 3.32 (d, 1H); 4.01 (d, 1H); 5.07 (s, 1H); 5.26 (s, 1H); 6.75 (s br, 1H); 6.88 (m, 1H); 7.19 (m, 2H). |
| 10.067 | 3,5-$F_2$—Ph | H | $CH_2Cl$ | O | H | bond | c-Pr | |
| 10.068 | 3,5-$Cl_2$—Ph | H | prop-1-en-2-yl | O | H | bond | c-Pr | [$CDCl_3$] 0.51 (m, 2H); 0.81 (m, 2H); 1.88 (s, 3H); 2.74 (m, 1H); 3.31 (d, 1H); 4.02 (d, 1H); 5.06 (s, 1H); 5.25 (s, 1H); 6.72 (s br, 1H); 7.41 (s, 1H); 7.53 (s, 2H). |
| 10.069 | 3,5-$Cl_2$—Ph | H | $CH_2Cl$ | O | H | bond | c-Pr | [$CDCl_3$] 0.55 (m, 2H); 0.83 (m, 2H); 2.75 (m, 1H); 3.54 |

TABLE 10-continued

Compounds of the general formula (I) according to the invention in which $R^2$ is hydrogen and aryl is the radical

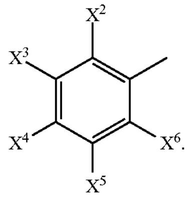

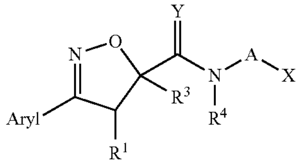

| No. | Aryl | $R^1$ | $R^3$ | Y | $R^4$ | A | X | Data |
|---|---|---|---|---|---|---|---|---|
| | | | | | | | | (d, 1H); 3.71 (d, 1H); 3.97 (AB, 2H); 6.99 (s br, 1H); 7.43 (s, 1H); 7.53 (s, 2H); |
| 10.070 | 3,5-$F_2$—Ph | H | vinyl | O | H | bond | c-Pr | [$CDCl_3$] 0.55 (m, 2H); 0.82 (m, 2H); 2.74 (m, 1H); 3.30 (d, 1H); 3.93 (d, 1H); 5.34 (d, 1H); 5.51 (d, 1H); 6.15 (dd, 1H); 6.78 (s br, 1H); 6.88 (m, 1H); 7.15 (m, 2H); |
| 10.071 | 3-F—Ph | H | $CH_2Cl$ | O | H | bond | c-Pr | |
| 10.072 | 3,5-$Cl_2$—Ph | H | vinyl | O | H | bond | c-Pr | [$CDCl_3$] 0.54 (m, 2H); 0.80 (m, 2H); 2.73 (m, 1H); 3.29 (d, 1H); 3.94 (d, 1H); 5.32 (d, 1H); 5.51 (d, 1H); 6.15 (dd, 1H); 7.00 (s br, 1H); 7.42 (s, 1H); 7.52 (s, 2H). |
| 10.073 | 3-F—Ph | H | $CH_2F$ | O | H | $CH_2$ | 1-c-Pr-1H-pyrazol-4-yl | [$CDCl_3$] 0.98 (m, 2H); 1.07 (m, 2H); 3.47 (d, 1H); 3.55 (m, 1H); 3.71 (d, 1H); 4.24 (dd, 1H); 4.38 (dd, 1H); 4.64 (d, 0.5H); 4.74 (d, 0.5H); 4.75 (d, 0.5H); 4.87 (d, 0.5H); 7.07 (s br, 1H); 7.16 (m, 1H); 7.40 (m, 3H). |
| 10.074 | 3,5-$F_2$—Ph | H | $CH_2F$ | O | H | $CH_2$ | $CF_3$ | [$CDCl_3$] 3.48 (d, 1H); 3.68 (d, 1H); 3.83-4.06 (m, 2H); 4.63 (d, 0.5H); 4.75 (d, 1H); 4.86 (d, 0.5H); 6.91 (m, 1H); 7.18 (m, 3H). |

TABLE 10-continued

Compounds of the general formula (I) according to the invention in which $R^2$ is hydrogen and aryl is the radical

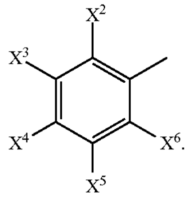

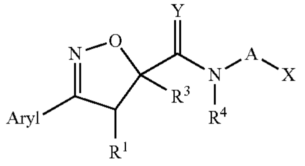

| No. | Aryl | $R^1$ | $R^3$ | Y | $R^4$ | A | X | Data |
|---|---|---|---|---|---|---|---|---|
| 10.075 | 3,5-$Cl_2$—Ph | H | acetyl | O | H | $CH_2$ | $CF_3$ | |
| 10.076 | 3,5-$F_2$—Ph | H | acetyl | O | H | $CH_2$ | $CF_3$ | |
| 10.077 | 3-F—Ph | H | $CH_2F$ | O | H | $CH_2$ | $CF_3$ | |
| 10.078 | 3,5-$F_2$—Ph | H | $CH_2Cl$ | O | H | $CH_2$ | $CF_3$ | |
| 10.079 | 3,5-$Cl_2$—Ph | H | $CH_2Cl$ | O | H | $CH_2$ | $CF_3$ | |
| 10.080 | 3-F—Ph | H | $CH_2Cl$ | O | H | $CH_2$ | $CF_3$ | |
| 10.081 | 3,5-$F_2$—Ph | H | $CH_2F$ | O | H | $CH(CH_3)$ | $CH_3$ | [$CDCl_3$] 1.16 (d, 3H); 1.20 (d, 3H); 3.44 (d, 1H); 3.67 (d, 1H); 4.05 (m, 1H); 4.62 (d, 0.5H); 4.73 (m, 2H); 4.83 (d, 0.5H); 6.69 (d br, 1H); 6.92 (m, 1H); 7.17 (m, 2H). |
| 10.082 | 3-F—Ph | H | $CH_2F$ | O | H | $CH(CH_3)$ | $CH_3$ | |
| 10.083 | 3,5-$F_2$—Ph | H | $CH_2Cl$ | O | H | $CH(CH_3)$ | $CH_3$ | [$CDCl_3$] 1.17 (d, 3H); 1.22 (d, 3H); 3.53 (d, 1H); 3.69 (d, 1H); 3.93 (d, 1H); 4.02 (d, 1H); 4.07 (m, 1H); 6.70 (d br, 1H); 6.91 (m, 1H); 7.18 (m, 2H). |
| 10.084 | 3,5-$Cl_2$—Ph | H | $CH_2Cl$ | O | H | $CH(CH_3)$ | $CH_3$ | [$CDCl_3$] 1.70 (dd, 6H); 3.52 (d, 1H); 3.71 (d, 1H); 3.98 (AB, 2H); 4.06 (m, 1H); 6.70 (d br, 1H); 6.90 (m, 1H); 7.16 (m, 2H). |
| 10.085 | 3-F—Ph | H | $CH_2Cl$ | O | H | $CH(CH_3)$ | $CH_3$ | |
| 10.086 | 3,5-$F_2$—Ph | H | $CH_2F$ | O | H | $CH(CH_3)$ | cyano | |
| 10.087 | 3-F—Ph | H | $CH_2F$ | O | H | $CH_2CH_2$ | COOH | |
| 10.088 | 3,5-$Cl_2$—Ph | H | $CH(CH_3)OH$ | O | H | $CH_2CH_2$ | COOH | |
| 10.089 | 3,5-$F_2$—Ph | H | $CH(CH_3)OH$ | O | H | $CH_2CH_2$ | COOH | |
| 10.090 | 3,5-$Cl_2$—Ph | H | $CH(CH_3)OH$ | O | H | $CH_2CH_2$ | ethoxy-carbon-yl | |
| 10.091 | 3,5-$F_2$—Ph | H | $CH(CH_3)OH$ | O | H | $CH_2CH_2$ | ethoxy-carbon-yl | |
| 10.092 | 3,5-$F_2$—Ph | H | F | O | H | $CH_2CH_2$ | meth-oxy-carbon-yl | [$CDCl_3$] 2.64 (m, 2H); 3.56 (dd, 1H); 3.67 (m, 2H); 3.74 (s, 3H); 4.18 (dd, 1H); 6.94 |

TABLE 10-continued

Compounds of the general formula (I) according to the invention in which $R^2$ is hydrogen and aryl is the radical

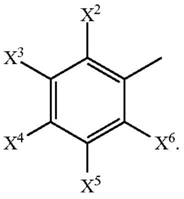

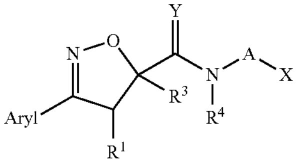

| No. | Aryl | $R^1$ | $R^3$ | Y | $R^4$ | A | X | Data |
|---|---|---|---|---|---|---|---|---|
| | | | | | | | | (m, 1H); 7.21 (m, 3H). |
| 10.093 | 3,5-$Cl_2$—Ph | H | F | O | H | $CH_2CH_2$ | meth-oxy-carbon-yl | [$CDCl_3$] 2.63 (m, 2H); 3.56 (dd, 1H); 3.67 (m, 2H); 3.74 (s, 3H); 4.18 (dd, 1H); 7.17 (s br, 1H); 7.47 (s, 1H); 7.56 (s, 2H). |
| 10.094 | 3,5-$F_2$—Ph | H | $CH_2F$ | O | H | $CH_2CH_2$ | meth-oxy-carbon-yl | [$CDCl_3$] 2.56 (t, 2H); 3.44 (d, 1H); 3.52 (m, 1H); 6.62 (m, 1H); 3.65 (d, 1H); 4.62 (d, 0.5H), 4.73 (m, 1H); 4.84 (d, 0.5H); 6.90 (m, 1H); 7.18 (m, 2H); 7.35 (s br, 1H). |
| 10.095 | 3,5-$Cl_2$—Ph | H | acetyl | O | H | $CH_2CH_2$ | meth-oxy-carbon-yl | [$CDCl_3$] 2.33 (s, 3H); 2.59 (m, 2H); 3.51 (d, 1H); 3.56 (m, 1H); 3.64 (m, 1H); 3.71 (s, 3H); 4.14 (d, 1H); 7.41 (t br, 1H); 7.44 (s, 1H); 7.54 (s, 2H). |
| 10.096 | 3,5-$F_2$—Ph | H | acetyl | O | H | $CH_2CH_2$ | meth-oxy-carbon-yl | |
| 10.097 | 3-F—Ph | H | $CH_2F$ | O | H | $CH_2CH_2$ | meth-oxy-carbon-yl | |
| 10.098 | 3,5-$F_2$—Ph | H | $CH_2Cl$ | O | H | $CH_2CH_2$ | meth-oxy-carbon-yl | [$CDCl_3$] 2.57 (m, 2H); 3.52 (m, 1H); 3,53 (d, 1H); 3.63 (m, 1H); 3.68 (d, 1H); 3.69 (s, 3H); 3.97 (AB, 2H); 6.89 (m, 1H); 7.18 (m, 2H); 7.33 (t br, 1H). |
| 10.099 | 3,5-$Cl_2$—Ph | H | $CH_2Cl$ | O | H | $CH_2CH_2$ | meth-oxy-carbon- | [$CDCl_3$] 2.57 (m, 2H); 3.50 (m, 1H); 3.53 |

TABLE 10-continued

Compounds of the general formula (I) according to the invention in which $R^2$ is hydrogen and aryl is the radical

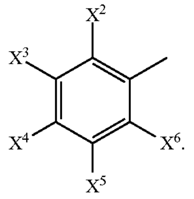

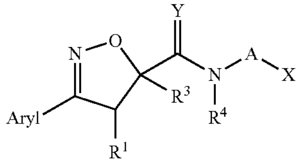

| No. | Aryl | $R^1$ | $R^3$ | Y | $R^4$ | A | X | Data |
|---|---|---|---|---|---|---|---|---|
| | | | | | | | yl | (d, 1H); 3.62 (m, 1H); 3.68 (d, 1H); 3.71 (s, 3H); 3.92 (d, 1H); 4.01 (d, 1H); 7.33 (s br, 1H); 7.43 (s, 1H); 7.53 (s, 2H). |
| 10.100 | 3,5-$Cl_2$—Ph | H | prop-1-en-2-yl | O | H | $CH_2CH_2$ | meth-oxy-carbon-yl | [$CDCl_3$] 1.86 (s, 3H); 2.55 (m, 2H); 3.32 (d, 1H); 3.52 (m, 1H); 3.58 (m, 1H); 3.69 (s, 3H); 3.97 (d, 1H); 5.07 (s, 1H); 5.26 (s, 1H); 7.15 (t br, 1H); 7.40 (s, 1H); 7.55 (s, 2H). |
| 10.101 | 3,5-$F_2$—Ph | H | prop-1-en-2-yl | O | H | $CH_2CH_2$ | meth-oxy-carbon-yl | [$CDCl_3$] 1.86 (s, 3H); 2.55 (m, 2H); 3.32 (d, 1H); 3.52 (m, 1H); 3.58 (m, 1H); 3.79 (s, 3H); 3.98 (d, 1H); 5.09 (s, 1H); 5.26 (s, 1H); 6.87 (m, 1H); 7.18 (m, 3H). |
| 10.102 | 3,5-$F_2$—Ph | H | vinyl | O | H | $CH_2CH_2$ | meth-oxy-carbon-yl | [$CDCl_3$] 2.55 (t, 3H); 3.31 (d, 1H); 3.56 (m, 2H); 3.71 (s, 3H); 3.92 (d, 1H); 5.34 (d, 1H); 5.54 (d, 1H); 6.15 (dd, 1H); 6.88 (m, 1H); 7.17 (m, 2H); 7.2 (d br, 1H). |
| 10.103 | 3-F—Ph | H | $CH_2Cl$ | O | H | $CH_2CH_2$ | meth-oxy-carbon-yl | |
| 10.104 | 3,5-$Cl_2$—Ph | H | vinyl | O | H | $CH_2CH_2$ | meth-oxy-carbon-yl | [$CDCl_3$] 2.55 (t, 3H); 3.20 (d, 1H); 3.55 (m, 2H); 3.69 (s, 3H); 3.90 (d, 1H); 5.30 |

TABLE 10-continued

Compounds of the general formula (I) according to the invention in which $R^2$ is hydrogen and aryl is the radical

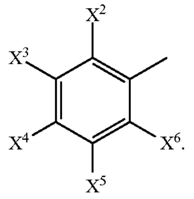

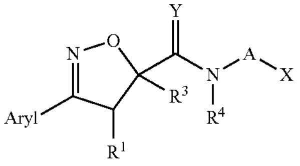

| No. | Aryl | $R^1$ | $R^3$ | Y | $R^4$ | A | X | Data |
|---|---|---|---|---|---|---|---|---|
| | | | | | | | | (d, 1H); 5.52 (d, 1H); 6.15 (dd, 1H); 7.20 (s br, 1H); 7.41 (s, 1H); 7.52 (s, 1H). |
| 10.105 | 3-F—Ph | H | $CH_2F$ | O | H | $CH(CH_3)CH_2$ | COOH | |
| 10.106 | 3,5-$F_2$—Ph | H | $CH_2F$ | O | H | $CH(CH_3)CH_2$ | ethoxy-carbon-yl | |
| 10.107 | 3-F—Ph | H | $CH_2F$ | O | H | $CH(CH_3)CH_2$ | ethoxy-carbon-yl | |
| 10.108 | 3,5-$F_2$—Ph | H | $CH_2Cl$ | O | H | $CH(CH_3)CH_2$ | ethoxy-carbon-yl | [$CDCl_3$] D1 plus D2 1.17-1.32 (m, 5H); 2.48 (AB, 0.8H); 2.56 (d, 1.2H); 3.60 (m, 2H); 3.97 (AB, 2H); 4.08 (q, 0.8H); 4.15 (q, 1.2H); 4.33 (m, 1H); 6.88 (m, 1H); 7.18 (m, 2H); 7.26 (s br, 1H). |
| 10.109 | 3,5-$Cl_2$—Ph | H | $CH_2Cl$ | O | H | $CH(CH_3)CH_2$ | ethoxy-carbon-yl | [$CDCl_3$] D1 [$CDCl_3$] 1.23 (t, 3H); 1.28 (t, 3H); 1.29 (d, 3H); 2.49 (m, 2H); 3.51 (d, 2H); 3.69 (d, 1H); 3.93 (dd, 1H); 4.04 (dd, 1H); 4.10 (q, 2H); 4.33 (m, 1H); 7.26 (s br, 1H); 7.43 (s, 1H); 7.53 (s, 2H). D2 [$CDCl_3$] 1.23 (t, 3H); 1.28 (t, 3H); 1.29 (d, 3H); 2.56 (d, 2H); 3.52 (d, 2H); 3.70 (d, 1H); 3.93 (dd, 1H); 4.04 (dd, 1H); 4.18 (q, 2H); 4.33 (m, 1H); 7.26 (s br, 1H); 7.43 (s, 1H); 7.53 (s, 2H). |

TABLE 10-continued

Compounds of the general formula (I) according to the invention in which $R^2$ is hydrogen and aryl is the radical

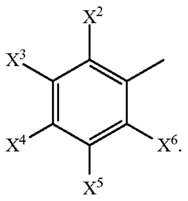

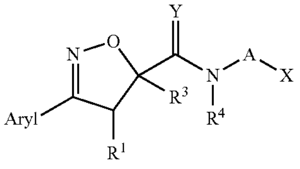

| No. | Aryl | $R^1$ | $R^3$ | Y | $R^4$ | A | X | Data |
|---|---|---|---|---|---|---|---|---|
| 10.110 | 3-F—Ph | H | $CH_2Cl$ | O | H | $CH(CH_3)CH_2$ | ethoxy-carbon-yl | |
| 10.111 | 3,5-$F_2$—Ph | H | F | O | H | $CH(CH_3)CH_2$ | meth-oxy-carbon-yl | [$CDCl_3$] 1.32 (d, 3H); 2.61 (m 2H); 3.56 (dd, 1H); 3.73 (s, 3H); 4.18 (dd, 1H); 4.43 (m, 1H); 6.93 (m, 1H); 7.24 (m, 3H). |
| 10.112 | 3-F—Ph | H | $CH_2F$ | O | H | $CH_2CH_2CH_2$ | COOH | |
| 10.113 | 3,5-$F_2$—Ph | H | F | O | H | $CH_2CH_2CH_2$ | ethoxy-carbon-yl | [$CDCl_3$] 1.27 (t, 3H); 1.95 (pent, 2H); 2.42 (t, 2H); 3.44 (q, 2H); 3.55 (dd, 1H); 4.17 (q, 2H); 4.20 (dd, 1H); 6.86 (s br, 1H); 6.93 (m, 1H); 7.20 (m, 2H). |
| 10.114 | 3,5-$Cl_2$—Ph | H | F | O | H | $CH_2CH_2CH_2$ | ethoxy-carbon-yl | [$CDCl_3$] 1.27 (t, 3H); 1.94 (pent, 2H); 3.41 (t, 2H); 3.45 (q, 2H); 3.56 (dd, 1H); 4.16 (q, 2H); 4.20 (dd, 1H); 6.88 (s br, 1H); 7.47 (s, 1H); 7.57 s, 2H). |
| 10.115 | 3,5-$F_2$—Ph | H | $CH_2F$ | O | H | $CH_2CH_2CH_2$ | meth-oxy-carbon-yl | [$CDCl_3$] 1.88 (pent, 2H); 2.35 (t, 2H); 3.28 (m, 1H); 3.36 (m, 1H); 3.43 (d, 1H); 3.65 (d, 1H); 3.67 (s, 3H); 4.62 (d, 0.5H); 4.74 (m, 1H); 4.85 (d, 0.5H); 6.90 (m, 1H); 7.04 (s br, 1H); 7.18 (m, 2H). |
| 10.116 | 3-F—Ph | H | $CH_2F$ | O | H | $CH_2CH_2CH_2$ | meth-oxy-carbon-yl | |

TABLE 11

Compounds of the general formula (I) according to the invention in which $R^2$ is hydrogen, $R^4$—N—A—X form a ring and aryl is the radical

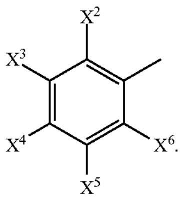

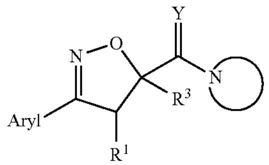

| No. | Aryl | $R^1$ | $R^3$ | Y | $R^4$—N—A—X | Data |
|---|---|---|---|---|---|---|
| 11.001 | 3,5-$Cl_2$—Ph | H | $CF_3$ | O | 1,2-oxazolidin-2-yl | |
| 11.002 | 3,5-$Cl_2$—Ph | H | $CF_3$ | O | 1,3-thiazolidin-3-yl | |
| 11.003 | 3,5-$Cl_2$—Ph | H | $CF_3$ | O | 2-(ethoxycarbonyl)-piperidin-1-yl | |
| 11.004 | 3,5-$Cl_2$—Ph | H | $CF_3$ | O | 2-(methoxycarbonyl)-pyrrolidin-1-yl | |
| 11.005 | 3,5-$Cl_2$—Ph | H | $CF_3$ | O | 3-(ethoxycarbonyl)-piperidin-1-yl | |
| 11.006 | 3,5-$Cl_2$—Ph | H | $CF_3$ | O | 4-(ethoxycarbonyl)-piperidin-1-yl | |
| 11.007 | 3,5-$Cl_2$—Ph | H | $CF_3$ | O | 4-(THF-2-ylcarbonyl)-piperazin-1-yl | |
| 11.008 | 3,5-$Cl_2$—Ph | H | $CF_3$ | O | 4-acetyl-piperazin-1-yl | |
| 11.009 | 3,5-$Cl_2$—Ph | H | $CF_3$ | O | decahydro-naphthalen-1-ylamino | |
| 11.010 | 3,5-$Cl_2$—Ph | H | $CF_3$ | O | morpholin-4-yl | |
| 11.011 | 3,5-$Cl_2$—Ph | H | $CF_3$ | O | pyrrolidin-1-yl | |
| 11.012 | 3-F—Ph | H | $CF_3$ | O | pyrrolidin-1-yl | |
| 11.013 | 3-OH—Ph | H | $CF_3$ | O | pyrrolidin-1-yl | |
| 11.014 | 3-iPrO—Ph | H | $CF_3$ | O | pyrrolidin-1-yl | |
| 11.015 | 3-(2-MeOEtO)—Ph | H | $CF_3$ | O | pyrrolidin-1-yl | |
| 11.016 | 3-EtO—Ph | H | $CF_3$ | O | pyrrolidin-1-yl | |
| 11.017 | 3-$CF_3O$—Ph | H | $CF_3$ | O | pyrrolidin-1-yl | |
| 11.018 | 3,5-$F_2$—Ph | H | $CF_3$ | O | pyrrolidin-1-yl | |
| 11.019 | 3-Cl-5-Me—Ph | H | $CF_3$ | O | pyrrolidin-1-yl | |
| 11.020 | 3,5-$Cl_2$—Ph | H | $C_2H_5$ | O | 1,2-oxazolidin-2-yl | |
| 11.021 | 3,5-$Cl_2$—Ph | H | $C_2H_5$ | O | 1,3-thiazolidin-3-yl | |
| 11.022 | 3,5-$Cl_2$—Ph | H | $C_2H_5$ | O | 2-(ethoxycarbonyl)-piperidin-1-yl | |
| 11.023 | 3,5-$Cl_2$—Ph | H | $C_2H_5$ | O | 2-(methoxycarbonyl)-pyrrolidin-1-yl | |
| 11.024 | 3,5-$Cl_2$—Ph | H | $C_2H_5$ | O | 3-(ethoxycarbonyl)-piperidin-1-yl | |
| 11.025 | 3,5-$Cl_2$—Ph | H | $C_2H_5$ | O | 4-(ethoxycarbonyl)-piperidin-1-yl | |
| 11.026 | 3,5-$Cl_2$—Ph | H | $C_2H_5$ | O | 4-(THF-2-ylcarbonyl)-piperazin-1-yl | |

TABLE 11-continued

Compounds of the general formula (I) according to the invention in which $R^2$ is hydrogen, $R^4$—N—A—X form a ring and aryl is the radical

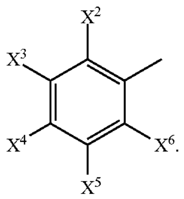

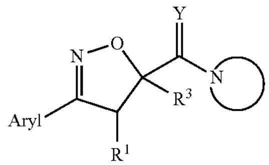

| No. | Aryl | $R^1$ | $R^3$ | Y | $R^4$—N—A—X | Data |
|---|---|---|---|---|---|---|
| 11.027 | 3,5-$Cl_2$—Ph | H | $C_2H_5$ | O | 4-acetyl-piperazin-1-yl | |
| 11.028 | 3,5-$Cl_2$—Ph | H | $C_2H_5$ | O | decahydro-naphthalen-1-ylamino | |
| 11.029 | 3,5-$Cl_2$—Ph | H | $C_2H_5$ | O | morpholin-4-yl | |
| 11.030 | 3,5-$Cl_2$—Ph | H | $C_2H_5$ | O | pyrrolidin-1-yl | |
| 11.031 | 3-F—Ph | H | $C_2H_5$ | O | pyrrolidin-1-yl | |
| 11.032 | 3-OH—Ph | H | $C_2H_5$ | O | pyrrolidin-1-yl | |
| 11.033 | 3-iPrO—Ph | H | $C_2H_5$ | O | pyrrolidin-1-yl | |
| 11.034 | 3-(2-MeOEtO)—Ph | H | $C_2H_5$ | O | pyrrolidin-1-yl | |
| 11.035 | 3-EtO—Ph | H | $C_2H_5$ | O | pyrrolidin-1-yl | |
| 11.036 | 3-$CF_3O$—Ph | H | $C_2H_5$ | O | pyrrolidin-1-yl | |
| 11.037 | 3,5-$F_2$—Ph | H | $C_2H_5$ | O | pyrrolidin-1-yl | |
| 11.038 | 3-Cl-5-Me—Ph | H | $C_2H_5$ | O | pyrrolidin-1-yl | |
| 11.039 | 3,5-$Cl_2$—Ph | H | $CH_3$ | O | 1,2-oxazolidin-2-yl | |
| 11.040 | 3,5-$Cl_2$—Ph | H | $CH_3$ | O | 1,3-thiazolidin-3-yl | |
| 11.041 | 3,5-$Cl_2$—Ph | H | $CH_3$ | O | 2-(ethoxycarbonyl)-piperidin-1-yl | |
| 11.042 | 3,5-$Cl_2$—Ph | H | $CH_3$ | O | 2-(methoxycarbonyl)-pyrrolidin-1-yl | |
| 11.043 | 3,5-$Cl_2$—Ph | H | $CH_3$ | O | 3-(ethoxycarbonyl)-piperidin-1-yl | |
| 11.044 | 3,5-$Cl_2$—Ph | H | $CH_3$ | O | 4-(ethoxycarbonyl)-piperidin-1-yl | |
| 11.045 | 3,5-$Cl_2$—Ph | H | $CH_3$ | O | 4-(THF-2-ylcarbonyl)-piperazin-1-yl | |
| 11.046 | 3,5-$Cl_2$—Ph | H | $CH_3$ | O | 4-acetyl-piperazin-1-yl | |
| 11.047 | 3,5-$Cl_2$—Ph | H | $CH_3$ | O | decahydro-naphthalen-1-ylamino | |
| 11.048 | 3,5-$Cl_2$—Ph | H | $CH_3$ | O | morpholin-4-yl | |
| 11.049 | 3,5-$Cl_2$—Ph | H | $CH_3$ | O | pyrrolidin-1-yl | |
| 11.050 | 3-F—Ph | H | $CH_3$ | O | pyrrolidin-1-yl | |
| 11.051 | 3-OH—Ph | H | $CH_3$ | O | pyrrolidin-1-yl | |
| 11.052 | 3-iPrO—Ph | H | $CH_3$ | O | pyrrolidin-1-yl | |
| 11.053 | 3-(2-MeOEtO)—Ph | H | $CH_3$ | O | pyrrolidin-1-yl | |
| 11.054 | 3-EtO—Ph | H | $CH_3$ | O | pyrrolidin-1-yl | |
| 11.055 | 3-$CF_3O$—Ph | H | $CH_3$ | O | pyrrolidin-1-yl | |
| 11.056 | 3,5-$F_2$—Ph | H | $CH_3$ | O | pyrrolidin-1-yl | [$CDCl_3$] 7.27 11.63; 7.26 11.98; 7.20 1.52; 7.20 |

TABLE 11-continued

Compounds of the general formula (I) according to the invention in which $R^2$ is hydrogen, $R^4$—N—A—X form a ring and aryl is the radical

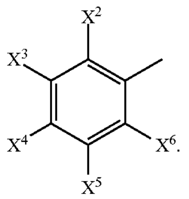

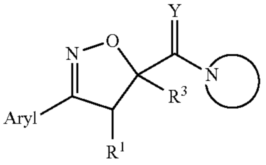

| No. | Aryl | $R^1$ | $R^3$ | Y | $R^4$—N—A—X | Data |
|---|---|---|---|---|---|---|
| | | | | | | 2.03; 7.20 |
| | | | | | | 2.41; 7.19 |
| | | | | | | 2.18; 7.18 |
| | | | | | | 2.11; 7.18 |
| | | | | | | 2.44; 7.18 |
| | | | | | | 1.96; 7.17 |
| | | | | | | 1.52; 7.17 |
| | | | | | | 0.34; 6.89 |
| | | | | | | 0.42; 6.88 |
| | | | | | | 0.66; 6.88 |
| | | | | | | 0.68; 6.88 |
| | | | | | | 0.38; 6.87 |
| | | | | | | 0.35; 6.87 |
| | | | | | | 0.75; 6.86 |
| | | | | | | 0.84; 6.86 |
| | | | | | | 1.33; 6.86 |
| | | | | | | 1.35; 6.85 |
| | | | | | | 0.72; 6.85 |
| | | | | | | 0.67; 6.84 |
| | | | | | | 0.39; 6.84 |
| | | | | | | 0.43; 6.84 |
| | | | | | | 0.68; 6.84 |
| | | | | | | 0.68; 6.83 |
| | | | | | | 0.36; 6.83 |
| | | | | | | 0.33; 5.30 |
| | | | | | | 0.92; 5.30 |
| | | | | | | 0.97; 4.25 |
| | | | | | | 2.58; 4.25 |
| | | | | | | 2.60; 4.21 |
| | | | | | | 2.74; 4.21 |
| | | | | | | 2.79; 3.90 |
| | | | | | | 0.34; 3.88 |
| | | | | | | 0.78; 3.87 |
| | | | | | | 0.63; 3.86 |
| | | | | | | 0.55; 3.85 |
| | | | | | | 1.32; 3.83 |
| | | | | | | 0.71; 3.78 |
| | | | | | | 0.52; 3.77 |
| | | | | | | 0.86; 3.76 |
| | | | | | | 0.80; 3.75 |
| | | | | | | 1.02; 3.74 |
| | | | | | | 0.57; 3.72 |
| | | | | | | 0.44; 3.53 |
| | | | | | | 1.14; 3.53 |
| | | | | | | 1.20; 3.51 |
| | | | | | | 2.65; 3.51 |
| | | | | | | 1.40; 3.49 |
| | | | | | | 1.54; 3.12 |
| | | | | | | 2.70; 3.12 |
| | | | | | | 2.71; 3.07 |
| | | | | | | 2.51; 3.07 |
| | | | | | | 2.55; 2.02 |
| | | | | | | 0.58; 2.01 |
| | | | | | | 0.81; 1.99 |
| | | | | | | 1.03; 1.97 |

TABLE 11-continued

Compounds of the general formula (I) according to the invention in which $R^2$ is hydrogen, $R^4$—N—A—X form a ring and aryl is the radical

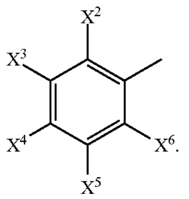

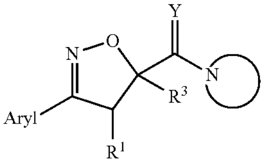

| No. | Aryl | $R^1$ | $R^3$ | Y | $R^4$—N—A—X | Data |
|---|---|---|---|---|---|---|
| | | | | | | 0.69; 1.96 |
| | | | | | | 0.70; 1.94 |
| | | | | | | 0.81; 1.92 |
| | | | | | | 0.83; 1.91 |
| | | | | | | 0.46; 1.90 |
| | | | | | | 0.76; 1.89 |
| | | | | | | 0.78; 1.87 |
| | | | | | | 1.11; 1.86 |
| | | | | | | 1.24; 1.84 |
| | | | | | | 0.99; 1.82 |
| | | | | | | 0.41; 1.82 |
| | | | | | | 0.96; 1.81 |
| | | | | | | 0.39; 1.80 |
| | | | | | | 0.67; 1.79 |
| | | | | | | 0.43; 1.71 |
| | | | | | | 15.61; 1.71 |
| | | | | | | 16.00; 1.60 |
| | | | | | | 4.26; 1.59 |
| | | | | | | 4.34; 0.00 |
| | | | | | | 5.42 |
| 11.057 | 3-Cl-5-Me—Ph | H | $CH_3$ | O | pyrrolidin-1-yl | |
| 11.058 | 3,5-$Cl_2$—Ph | H | CN | O | 1,2-oxazolidin-2-yl | |
| 11.059 | 3,5-$Cl_2$—Ph | H | CN | O | 1,3-thiazolidin-3-yl | |
| 11.060 | 3,5-$Cl_2$—Ph | H | CN | O | 2-(ethoxy-carbonyl)-piperidin-1-yl | |
| 11.061 | 3,5-$Cl_2$—Ph | H | CN | O | 2-(methoxy-carbonyl)-pyrrolidin-1-yl | |
| 11.062 | 3,5-$Cl_2$—Ph | H | CN | O | 3-(ethoxy-carbonyl)-piperidin-1-yl | |
| 11.063 | 3,5-$Cl_2$—Ph | H | CN | O | 4-(ethoxy-carbonyl)-piperidin-1-yl | |
| 11.064 | 3,5-$Cl_2$—Ph | H | CN | O | 4-(THF-2-ylcarbonyl)-piperazin-1-yl | |
| 11.065 | 3,5-$Cl_2$—Ph | H | CN | O | 4-acetyl-piperazin-1-yl | |
| 11.066 | 3,5-$Cl_2$—Ph | H | CN | O | decahydro-naphthalen-1-ylamino | |
| 11.067 | 3,5-$Cl_2$—Ph | H | CN | O | morpholin-4-yl | |
| 11.068 | 3,5-$Cl_2$—Ph | H | CN | O | pyrrolidin-1-yl | |
| 11.069 | 3-F—Ph | H | CN | O | pyrrolidin-1-yl | |
| 11.070 | 3-OH—Ph | H | CN | O | pyrrolidin-1-yl | |
| 11.071 | 3-iPrO—Ph | H | CN | O | pyrrolidin-1-yl | |
| 11.072 | 3-(2-MeOEtO)—Ph | H | CN | O | pyrrolidin-1-yl | |
| 11.073 | 3-EtO—Ph | H | CN | O | pyrrolidin-1-yl | |
| 11.074 | 3-$CF_3$O—Ph | H | CN | O | pyrrolidin-1-yl | |

TABLE 11-continued

Compounds of the general formula (I) according to the invention in which $R^2$ is hydrogen, $R^4$—N—A—X form a ring and aryl is the radical

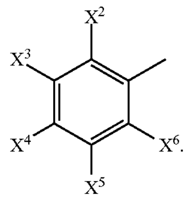

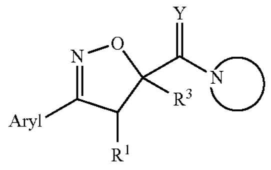

| No. | Aryl | $R^1$ | $R^3$ | Y | $R^4$—N—A—X | Data |
|---|---|---|---|---|---|---|
| 11.075 | 3,5-$F_2$—Ph | H | CN | O | pyrrolidin-1-yl | |
| 11.076 | 3-Cl-5-Me—Ph | H | CN | O | pyrrolidin-1-yl | |
| 11.077 | 3,5-$F_2$—Ph | H | $CH_3$ | O | 2-oxopyrrolidin-1-yl | |
| 11.078 | 3,5-$F_2$—Ph | H | $CH_3$ | O | 3-(ethoxycarbonyl)-piperidin-1-yl | |
| 11.079 | 3,5-$F_2$—Ph | H | $CH_3$ | O | 4-(ethoxycarbonyl)-piperidin-1-yl | |
| 11.080 | 3,5-$F_2$—Ph | H | $CH_3$ | O | 4,4-difluoro-piperidin-1-yl | |
| 11.081 | 3,5-$F_2$—Ph | H | $CH_3$ | O | 4-methyl-piperazin-1-yl | |
| 11.082 | 3,5-$F_2$—Ph | H | $CH_3$ | O | morpholin-4-yl | |

The abbreviations used mean:

Ac acetoxy Bu butyl Et ethyl Me menthyl Pr propyl Pen pentyl Hex hexyl Ph phenyl c cyclo s secondary i iso t tertiary THF tetrahydrofuran R001 is the radical 3-chloro-5-{[1-methyl-3-(trifluoromethyl)-1H-pyrazol-5-yl]oxy}phenyl.

R002 is the radical 3-[(2-bromo-1-fluorovinyl)oxy]-5-chlorophenyl.

R003 is the radical 3-[(2-bromo-1-fluorovinyl)oxy]phenyl.

E1, E2, E3, E4 denote enantiomerically pure compounds. D1, D2 denote diastereomers of a diastereomer pair which are present as a racemate of two enantiomers.

B. FORMULATION EXAMPLES

1. Dusts

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

3. Dispersion Concentrate

A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-Dispersible Granules

Water-dispersible granules are obtained by mixing 75 parts by weight of a compound of the formula (I), 10 parts by weight of calcium lignosulfonate, 5 parts by weight of sodium laurylsulfate, 3 parts by weight of polyvinyl alcohol and 7 parts by weight of kaolin, grinding the mixture in a pinned-disk mill and granulating the powder in a fluidized bed by spraying on water as a granulating liquid.

Water-dispersible granules are also obtained by homogenizing and precomminuting, in a colloid mill, 25 parts by weight of a compound of the formula (I), 5 parts by weight of sodium 2,2'-dinaphthylmethane-6,6'-disulfonate, 2 parts by weight of sodium oleoylmethyltaurinate, 1 part by weight of polyvinyl alcohol and 17 parts by weight of calcium carbonate and 50 parts by weight of water, then grinding the mixture in a bead mill and atomizing and drying the resulting suspension in a spray tower by means of a one-substance nozzle.

C. BIOLOGICAL EXAMPLES

1. Pre-Emergence Herbicidal Action Against Harmful Plants

Seeds or rhizome pieces of mono- and dicotyledonous harmful plants are placed in sandy loam soil in pots having a diameter of 9 to 13 cm and covered with soil. The herbicides, formulated as emulsifiable concentrates or dusts, are then applied in various dosages as aqueous dispersions or suspensions or emulsions at an application rate of 300 to 800 l of water/ha (converted) to the surface of the covering soil. For further cultivation of the plants, the pots are then kept under optimum conditions in a greenhouse. After the test plants were left to stand in the greenhouse for 3 to 4 weeks under optimum growth conditions, the activity of the compounds according to the invention is scored visually. Thus, for example, the compounds nos. 1.130, 1.175, 1.183, 1.189, 1.204, 1.250, 1.373, 1.421, 1.676, 2.189, 4.074, 6.058, 6.115, 6.163, 6.321, 6.431, 6.470, 6.504, 6.248, 6.288, 6.666, 6.669 and 6.687 each show, at an application rate of 320 grams per hectare, an activity of at least 90% against *Echinochloa crus galli, Lolium multiflorum* and *Setaria viridis*. The compounds nos. 1.140, 1.270, 6.202, 6.122, 6.357, 6.372, 6.433, 6.485, 6.617 and 8.359 each show, at an application rate of 320 grams per hectare, an activity of at least 90% against *Alopecurus myosuroides, Lolium multiflorum* and *Veronica persica*. The compounds nos. 1.139, 1.201, 1.262, 1.394, 6.082, 6.195, 6.351 and 9.581 each show, at an application rate of 320 grams per hectare, an activity of at least 90% against *Fallopia convolvulus* and *Stellaria media*.

2. Post-Emergence Herbicidal Action Against Harmful Plants

Seeds of monocotyledonous and dicotyledonous harmful plants are laid out in sandy loam in cardboard pots, covered with soil and cultivated in a greenhouse under good growth conditions. Two to three weeks after sowing, the test plants are treated at the three-leaf stage. The compounds according to the invention, formulated as wettable powders or as emulsion concentrates, are sprayed onto the surface of the green parts of the plants using a water application rate of from 600 to 800 l/ha (converted).

After the test plants were left to stand in the greenhouse for 3 to 4 weeks under optimum growth conditions, the activity of the compounds according to the invention is scored visually. Thus, for example, the compounds nos. 1.111, 1.252, 1.903, 2.189, 6.485, 6.504, 6.510, 6.559 and 6.599 each show, at an application rate of 320 grams per hectare, an activity of at least 90% against *Lolium multiflorum, Stellaria media* and *Veronica persica*. The compounds nos. 6.248, 6.279, 6.420, 6.504, 6.491, 6.616 and 6.617 each show, at an application rate of 320 grams per hectare, an activity of at least 90% against *Alopecurus myosuroides* and *Avena fatua*. The compounds nos. 1.373, 1.183, 1.250, 1.344, 1.338, 1.676, 6.305, 6.541, 6.556 and 6.608 each show, at an application rate of 320 grams per hectare, an activity of at least 90% against *Echinochloa crus galli* and *Veronica persica*.

3. Fungicidal Action

Example A

In vivo test *Peronospora parasitica* (downy mildew on cabbage) To prepare an appropriate active compound formulation, the active compound is mixed with acetone/Tween/DMSO and the mixture is diluted with water to the desired concentration. Cabbage plants are cultivated in 50/50 peat/pozzolan soil in small pots at 18-20° C. and sprayed at the cotyledon stage at the respective stated application rates to test for protective activity. Control plants were treated in the same manner, but using an aqueous solution without any active compounds. 24 hours after the spraying, the plants were sprayed with a spore suspension of *Peronospora parasitica* (50 000 spores/ml).

The plants were placed in a cabin at 20° C. in a humid atmosphere for 5 days. Evaluation is carried out 5 days after the infection. 0% means an efficacy which corresponds to that of the control, whereas an efficacy of 100% means that no infection is observed.

At an application rate of 1200 g/ha, the following efficacies are found for the following compounds.

| Example No. | Activity [%] |
|---|---|
| 1.197 | 100 |
| 6.190 | 100 |
| 6.681 | 97 |
| 6.006 | 100 |
| 6.217 | 100 |

-continued

| Example No. | Activity [%] |
|---|---|
| 7.161 | 97 |
| 2.136 | 100 |
| 1.374 | 100 |
| 1.458 | 81 |
| 8.052 | 100 |
| 2.003 | 90 |
| 1.291 | 88 |
| 1.195 | 100 |
| 1.194 | 100 |
| 10.032 | 96 |

At an application rate of 500 g/ha, the following efficacies are found for the following compounds.

| Example No. | Activity [%] |
|---|---|
| 1.222 | 100 |
| 6.431 | 71 |
| 6.165 | 95 |
| 1.224 | 99 |
| 2.163 | 100 |
| 6.470 | 71 |
| 8.025 | 100 |
| 3.161 | 100 |
| 1.285 | 100 |
| 1.108 | 100 |
| 1.116 | 100 |
| 1.122 | 100 |
| 2.257 | 99 |
| 1.138 | 98 |
| 6.117 | 92 |
| 6.216 | 75 |
| 5.018 | 100 |
| 1.064 | 95 |
| 6.192 | 96 |
| 1.181 | 100 |
| 6.656 | 92 |
| 6.115 | 100 |
| 1.676 | 85 |
| 5.029 | 87 |
| 1.339 | 100 |
| 6.433 | 100 |
| 1.343 | 99 |
| 1.341 | 95 |
| 1.340 | 97 |
| 1.352 | 83 |
| 1.379 | 96 |
| 3.170 | 94 |
| 1.363 | 71 |
| 1.903 | 85 |
| 1.120 | 99 |

Example B

In Vivo Test *Phytophthora infestans* (Tomato)

Tomato plants (cultivar Rentita) are cultivated in 50/50 peat pozzolan substrate at 20-25° C. and sprayed at the Z16 stage with the active compound preparation given in Example A. After 24 hours, the plants are sprayed with a spore suspension of *Phytophthora infestans* (20 000 spores/ml). The inoculated plants are placed at 20° C. and in a humid atmosphere for 5 days. Evaluation is carried out 5 days after the infection. 0% means an efficacy which corresponds to that of the control, whereas an efficacy of 100% means that no infection is observed. At an application rate of 1200 g/ha, the following efficacies are found for the following compounds.

| Example No. | Activity [%] |
|---|---|
| 1.222 | 100 |
| 1.197 | 100 |
| 6.006 | 70 |
| 2.136 | 90 |
| 1.374 | 100 |
| 1.195 | 100 |
| 1.194 | 100 |
| 5.018 | 75 |

Example C

In Vivo Test *Botrytis cinerea* (Gray Mold on Cucumbers)

Cucumber plants (Vert petit de Paris) are cultivated in 50/50 peat pozzolan substrate at 20-25° C. and sprayed at the Z16 stage with the active compound preparation given in Example 1. After 24 hours, the upper sides of the leaves of the plants are sprayed with a spore suspension of *Botrytis cinerea* (150 000 spores/ml). The spores of a 15-day old culture are collected and suspended in a nutrient solution consisting of 20 g/l of gelatin;

50 g/l of D-fructose;

2 g/l of NH4NO3;

1 g/L of KH2PO4.

The inoculated cucumber plants are placed at 15-11° C. (day/night) and at 80% relative atmospheric humidity for 5-7 days. Evaluation is carried out 5-7 days after the infection. 0% means an efficacy which corresponds to that of the control, whereas an efficacy of 100% means that no infection is observed. At an application rate of 1200 g/ha, the following efficacies are found for the following compounds.

| Example No. | Activity [%] |
|---|---|
| 6.217 | 100 |
| 7.161 | 100 |
| 1.374 | 98 |
| 1.194 | 95 |
| 6.191 | 100 |

At an application rate of 500 g/ha, the following efficacies are found for the following compounds.

| Example No. | Activity [%] |
|---|---|
| 6.165 | 93 |
| 6.188 | 86 |
| 1.060 | 100 |
| 1.064 | 100 |
| 1.181 | 70 |
| 1.035 | 89 |

Example

In Vivo Test *Alternaria brassicae* (Salad Radish)

Salad radish (cultivar Pernot) are cultivated in 50/50 peat pozzolan substrate at 18-20° C. and sprayed at the cotyledon stage with the active compound preparation given above. After 24 hours, the plants are sprayed with a spore suspension of *Alternaria brassicae* (40 000 spores/cm3). The inoculated plants are placed at 18° C. and in a humid atmosphere for 6-7 days. Evaluation is carried out 6-7 days after the inoculation. 0% means an efficacy which corresponds to that of the control, whereas an efficacy of 100% means that no infection is observed. At an application rate of g/ha, the following efficacies are found for the following compounds.

| Example No. | Activity [%] |
|---|---|
| 6.377 | 77 |
| 6.054 | 94 |
| 6.431 | 77 |
| 6.165 | 95 |
| 7.359 | 86 |
| 6.217 | 81 |
| 6.188 | 73 |
| 6.117 | 73 |
| 6.216 | 82 |
| 6.064 | 91 |

Example E

In Vivo Test *Sphaerotheca fuliginea* (Cucumber)

Cucumber plants (cultivar: Vert petit de Paris) are cultivated in 50/50 peat pozzolan substrate at 20/23° C. and sprayed at the cotyledon stage with the active compound preparation given in Example A. After 24 hours, the plants are sprayed with a spore suspension of *Sphaerotheca fuliginea* (100 000 spores/ml). The inoculated plants are placed at 20/25° C. and at 60/70% relative atmospheric humidity. Evaluation is carried out 12 days after the inoculation. 0% means an efficacy which corresponds to that of the control, whereas an efficacy of 100% means that no infection is observed. At an application rate of 1200 g/ha, the following efficacies are found for the following compounds.

| Example No. | Activity [%] |
|---|---|
| 1.197 | 100 |
| 1.374 | 99 |

At an application rate of 500 g/ha, the following efficacies are found for the following compounds.

| Example No. | Activity [%] |
|---|---|
| 1.285 | 89 |
| 1.122 | 72 |
| 6.193 | 85 |
| 6.183 | 98 |
| 1.007 | 75 |

Example G

In Vivo Test *Leptosphaeria nodorum* (Wheat)

Wheat plants (cultivar: (Scipion) are cultivated in 50/50 peat pozzolan substrate at 12° C. and sprayed at the 1-leaf stage with the active compound preparation as given in Example A. After 24 hours, the plants are sprayed with a spore suspension of *Leptosphaeria nodorum* (250 000 spores/ml). The inoculated plants are placed at 18° C. and at 100% relative humidity for 72 h and then at 90% relative atmospheric humidity for a further 15-17 days. Evaluation is carried out 15-17 days after the inoculation. 0% means an efficacy which corresponds to that of the control, whereas an efficacy of 100% means that no infection is observed. At an application rate of 1200 g/ha, the following efficacies are found for the following compounds.

| Example No. | Activity [%] |
|---|---|
| 6.006 | 100 |

Example H

In Vivo Test *Mycosphaerella graminicola* (Wheat)

Wheat plants (cultivar: (Scipion) are cultivated in 50/50 peat pozzolan substrate at 12° C. and sprayed at the 1-leaf stage with the active compound preparation as given in Example A. After 24 hours, the plants are sprayed with a spore suspension of *Mycosphaerella graminicola* (500 000 spores/ml). The inoculated plants are placed at 18° C. and at 100% relative humidity for 72 h and then at 90% relative atmospheric humidity for a further 21-28 days. Evaluation is carried out 21-28 days after the inoculation. 0% means an efficacy which corresponds to that of the control, whereas an efficacy of 100% means that no infection is observed.

At an application rate of 1200 g/ha, the following efficacies are found for the following compounds.

| Example No. | Activity [%] |
|---|---|
| 1.222 | 96 |
| 7.161 | 85 |
| 2.136 | 88 |
| 1.194 | 88 |
| 5.018 | 88 |

At an application rate of 500 g/ha, the following efficacies are found for the following compounds.

| Example No. | Activity [%] |
|---|---|
| 6.377 | 100 |
| 6.054 | 100 |
| 6.431 | 100 |
| 6.430 | 81 |
| 6.165 | 100 |
| 1.224 | 95 |
| 7.359 | 100 |
| 2.163 | 96 |
| 6.470 | 100 |
| 1.459 | 100 |
| 6.188 | 100 |
| 6.022 | 98 |
| 1.285 | 75 |
| 1.122 | 75 |
| 2.257 | 79 |
| 1.195 | 79 |
| 1.138 | 75 |
| 6.117 | 91 |
| 6.064 | 100 |
| 1.421 | 87 |
| 6.184 | 100 |
| 1.064 | 75 |
| 6.386 | 100 |
| 6.412 | 100 |
| 6.192 | 97 |
| 1.181 | 85 |
| 6.072 | 98 |
| 6.566 | 98 |
| 6.656 | 98 |

-continued

| Example No. | Activity [%] |
|---|---|
| 6.480 | 88 |
| 6.193 | 95 |
| 1.339 | 85 |
| 1.315 | 100 |
| 1.343 | 92 |
| 1.340 | 88 |
| 1.057 | 91 |
| 1.035 | 91 |
| 1.036 | 73 |
| 1.903 | 97 |
| 1.017 | 88 |
| 1.007 | 73 |

The invention claimed is:

1. A 3-phenylisoxazoline-5-carboxamide or 3-phenylisoxazoline-5-thioamide of formula (I) and/or a salt thereof (I)

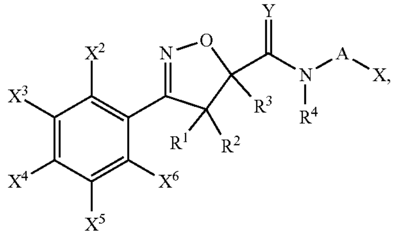

in which $R^1$ and $R^2$ independently of one another are each hydrogen, fluorine, chlorine, bromine, iodine, cyano, or $(C_1-C_4)$-alkyl or $(C_1-C_4)$-alkoxy substituted by in each case m radicals selected from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, $(C_1-C_3)$-alkylcarbonyloxy or $S(O)_nR^5$, or $(C_1-C_6)$-alkyl, $(C_3-C_6)$-cycloalkyl, $(C_2-C_6)$-alkenyl or $(C_2-C_6)$-alkynyl substituted by in each case m radicals selected from the group consisting of fluorine, chlorine, bromine, iodine, cyano, $(C_1-C_4)$-alkoxy and hydroxy, or $(C_1-C_6)$-alkylcarbonyl, $(C_2-C_6)$-alkenylcarbonyl or $(C_3-C_6)$-cycloalkylcarbonyl substituted by in each case m radicals selected from the group consisting of fluorine, chlorine, bromine, iodine, cyano and $(C_1-C_6)$-alkoxy;

$R^4$ is hydrogen, cyano, or $(C_1-C_8)$-alkyl or $(C_3-C_8)$-cycloalkyl substituted by in each case m radicals selected from the group consisting of fluorine, chlorine, bromine, iodine, cyano, hydroxy and $(C_1-C_6)$-alkoxy;

A is a bond or a divalent unit from the group consisting of

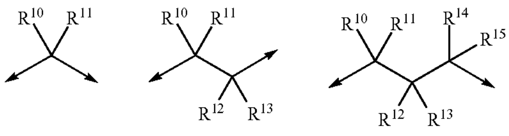

-continued

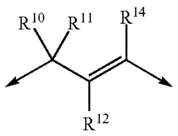

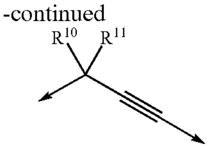

and

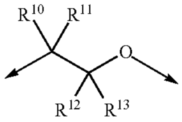

$R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano;

or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, Y is oxygen or sulfur;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl substituted by in each case m radicals selected from the group consisting of fluorine, chlorine, bromine, iodine, cyano, hydroxy, $OR^7$, $X^1$, $OX^1$, $NHX^1$, $S(O)_nR^5$, $SO_2NR^6R^7$, $SO_2NR^6R^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6){=}NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements selected from the group consisting of $NR^7$ and $NCOR^7$ as ring atoms, where a carbon atom carries p oxo groups;

$X^1$ is a 5- or 6-membered saturated, partially unsaturated, fully unsaturated or aromatic ring which is constructed of r carbon atoms, s nitrogen atoms, n sulphur atoms and n oxygen atoms and which is substituted by n radicals selected from the group consisting of $R^6$, $R^{6a}$, $R^8$ and $R^9$;

$X^2$, $X^4$ and $X^6$ independently of one another are each hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl, each of which is substituted by m radicals selected from the group consisting of fluorine, chlorine, bromine, iodine, cyano and ($C_1$-$C_4$)-alkoxy;

$X^3$ is fluorine, chlorine, bromine, iodine, hydroxy, cyano, nitro, $SF_5$, $CONR^8SO_2R^5$, $CONR^6R^8$, $COR^6$, $CO_2R^8$, $CONR^6R^8$, $C(R^6){=}NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, $X^5$ is hydrogen or $X^3$;

$R^5$ is ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or ($C_1$-$C_6$)-alkoxy, ($C_2$-$C_6$)-alkenyloxy or ($C_3$-$C_6$)-alkynyloxy, each of which is substituted by m radicals selected from the group consisting of fluorine, chlorine, bromine, cyano and ($C_1$-$C_2$)-alkoxy;

$R^7$ is hydrogen or ($C_1$-$C_6$)-alkyl, ($C_3$-$C_6$)-cycloalkyl, ($C_2$-$C_4$)-alkenyl or ($C_2$-$C_4$)-alkynyl, each of which is substituted by m radicals selected from the group consisting of fluorine, chlorine, bromine, cyano and ($C_1$-$C_2$)-alkoxy;

$R^8$ is $R^7$;

$R^9$ is ($C_1$-$C_3$)-alkyl or ($C_1$-$C_3$)-alkoxy;

k is 3, 4, 5 or 6;

m is 0, 1, 2, 3, 4 or 5;

p is 0 or 1;

q is 3, 4 or 5;

r is 1, 2, 3, 4 or 5;

s is 0, 1, 2, 3, or 4;

with the proviso that $X^3$ and $X^4$ are not both substituted or unsubstituted alkoxy.

2. A 3-phenylisoxazoline-5-carboxamide or 3-phenylisoxazoline-5-thioamide and/or salt thereof of formula (I)

(I)

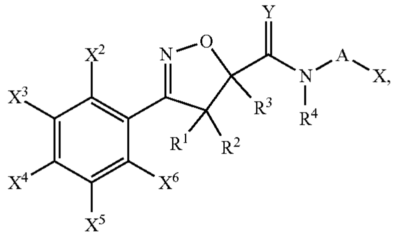

in which $R^1$ and $R^2$ independently of one another are each hydrogen, fluorine, chlorine, bromine, iodine, cyano, or ($C_1$-$C_4$)-alkyl or ($C_1$-$C_4$)-alkoxy substituted by in each case m radicals selected from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, ($C_1$-$C_3$)-alkylcarbonyloxy or $S(O)_nR^5$, or ($C_1$-$C_6$)-alkyl, ($C_3$-$C_6$)-cycloalkyl, ($C_2$-$C_6$)-alkenyl or ($C_2$-$C_6$)-alkynyl substituted by in each case m radicals selected from the group consisting of fluorine, chlorine, bromine, iodine, cyano, ($C_1$-$C_4$)-alkoxy and hydroxy, or ($C_1$-$C_6$)-alkylcarbonyl, ($C_2$-$C_6$)-alkenylcarbonyl or ($C_3$-$C_6$)-cycloalkylcarbonyl substituted by in each case m radicals selected from the group consisting of fluorine, chlorine, bromine, iodine, cyano and ($C_1$-$C_6$)-alkoxy;

$R^4$ is hydrogen, cyano, or ($C_1$-$C_8$)-alkyl or ($C_3$-$C_8$)-cycloalkyl substituted by in each case m radicals selected from the group consisting of fluorine, chlorine, bromine, iodine, cyano, hydroxy and ($C_1$-$C_6$)-alkoxy;

A is a bond or a divalent unit selected from the group consisting of

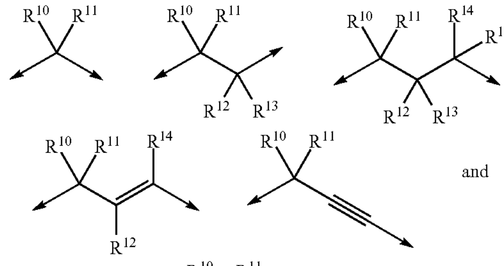

and

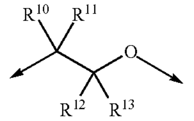

$R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano;

or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, Y is oxygen or sulfur;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl substituted by in each case m radicals selected from the group consisting of fluorine, chlorine, bromine, iodine, cyano, hydroxy, $OR^7$, $X^1$, $OX^1$, $NHX^1$, $S(O)_nR^5$, $SO_2NR^6R^7$, $SO_2NR^6R^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6){=}NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements selected from the group consisting of $NR^7$ and $NCOR^7$ as ring atoms, where a carbon atom carries p oxo groups;

$X^1$ is a ring, substituted by n radicals selected from the group consisting of $R^6$, $R^{6a}$, $R^8$ and $R^9$, said ring being selected from the group consisting of

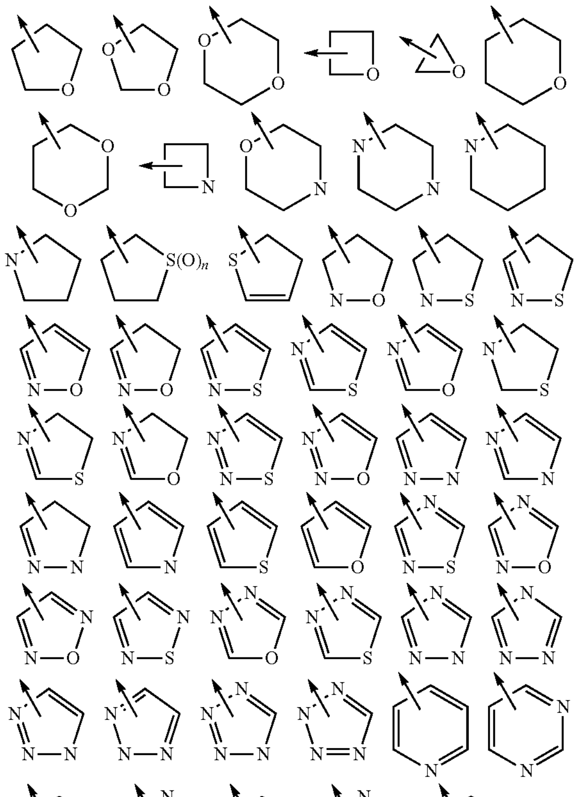

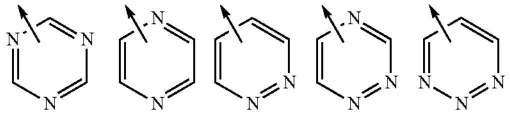

and

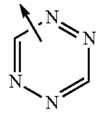

$X^2$, $X^4$ and $X^6$ independently of one another are each hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl, each of which is substituted by m radicals selected from the group consisting of fluorine, chlorine, bromine, iodine, cyano and ($C_1$-$C_4$)-alkoxy;

$X^3$ is fluorine, chlorine, bromine, iodine, hydroxy, cyano, nitro, $SF_5$, $CONR^8SO_2R^5$, $CONR^6R^8$, $COR^8$, $CO_2R^8$, $CONR^6R^8$, $C(R^6){=}NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, $X^5$ is hydrogen or $X^3$;

$R^5$ is ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or $(C_1\text{-}C_6)$-alkoxy, $(C_2\text{-}C_6)$-alkenyloxy or $(C_2\text{-}C_6)$-alkynyloxy, each of which is substituted by m radicals selected from the group consisting of fluorine, chlorine, bromine, cyano and $(C_1\text{-}C_2)$-alkoxy;

$R^7$ is hydrogen or $(C_1\text{-}C_6)$-alkyl, $(C_3\text{-}C_6)$-cycloalkyl, $(C_2\text{-}C_4)$-alkenyl or $(C_2\text{-}C_4)$-alkynyl, each of which is substituted by m radicals selected from the group consisting of fluorine, chlorine, bromine, cyano and $(C_1\text{-}C_2)$-alkoxy;

$R^8$ is $R^7$;

$R^9$ is $(C_1\text{-}C_3)$-alkyl or $(C_1\text{-}C_3)$-alkoxy;

k is 3, 4, 5 or 6;

m is 0, 1, 2, 3, 4 or 5;

n is 0, 1 or 2;

p is 0 or 1;

q is 3, 4 or 5;

with the proviso that $X^3$ and $X^4$ are not both substituted or unsubstituted alkoxy.

3. The 3-phenylisoxazoline-5-carboxamide or 3-phenylisoxazoline-5-thioamide of formula (I)

(I)

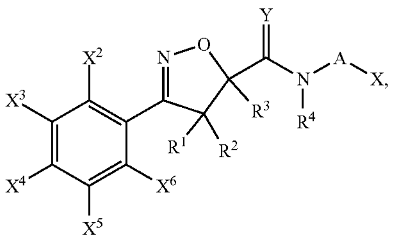

and/or salt thereof in which $R^1$ and $R^2$ independently of one another are each hydrogen, fluorine, chlorine, bromine, iodine, cyano, or $(C_1\text{-}C_4)$-alkyl substituted by in each case m radicals selected from the group consisting of fluorine, chlorine, bromine, iodine and cyano, $R^3$ is fluorine, chlorine, cyano, or $(C_1\text{-}C_6)$-alkyl, $(C_3\text{-}C_6)$-cycloalkyl, $(C_2\text{-}C_6)$-alkenyl, $(C_2\text{-}C_6)$-alkynyl, each of which is substituted by m radicals selected from the group consisting of fluorine and chlorine, or $(C_1\text{-}C_6)$-alkylcarbonyl which is substituted by at least one m radical selected from the group consisting of fluorine and chlorine;

A is a bond or a divalent unit selected from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH{=}CH$, $C(CH_3)_2C{\equiv}C$, $CH(CF_3)CH_2$, $CH(CH_3)CH_2O$, $CH_2CH_2O$, $CH(cPr)CH_2O$, $CH(CH_2OCH_3)$, $CH(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

$R^4$ is hydrogen or $(C_1\text{-}C_8)$-alkyl;

Y is oxygen or sulfur;

X is hydrogen, cyano, hydroxy, $X^1$, or $(C_1\text{-}C_{12})$-alkyl, $(C_3\text{-}C_8)$-cycloalkyl, $(C_2\text{-}C_{12})$-alkenyl or $(C_2\text{-}C_{12})$-alkynyl, each of which is substituted by m radicals selected from the group consisting of fluorine, chlorine, cyano, hydroxy, $OR^7$, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring, substituted by n radicals selected from the group consisting of $R^6$, $R^{6a}$, $R^8$ and $R^9$, said ring being selected from the group consisting of

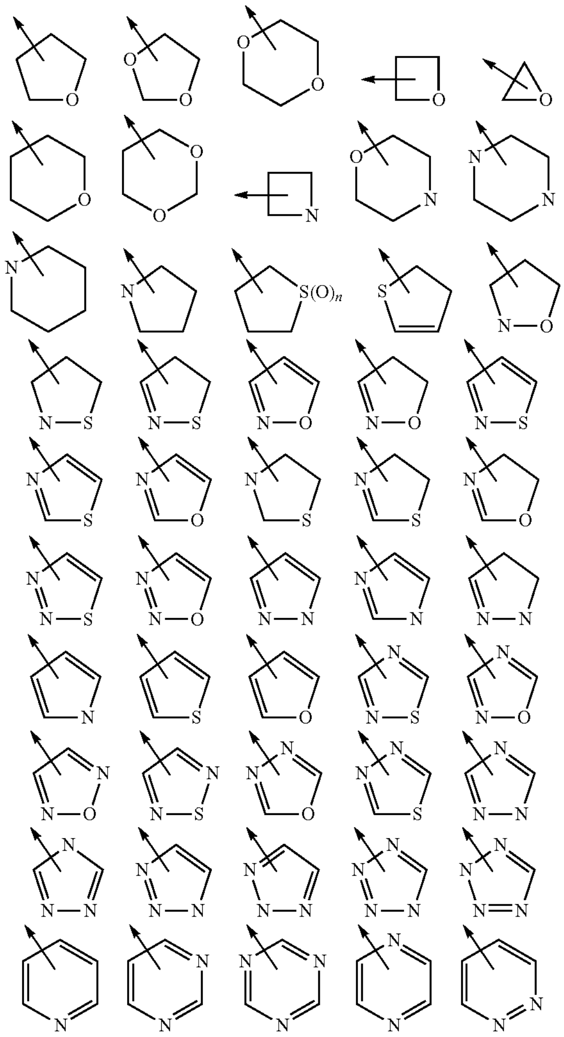

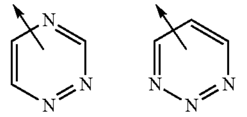

and

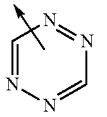

$X^2$, $X^4$ and $X^6$ independently of one another are each hydrogen, fluorine or chlorine, or $(C_1\text{-}C_4)$-alkyl or $(C_1\text{-}C_4)$-alkoxy, each of which is substituted by m radicals selected from the group consisting of fluorine, chlorine, cyano and $(C_1\text{-}C_4)$-alkoxy;

$X^3$ is fluorine, chlorine, bromine, cyano, or $(C_1\text{-}C_6)$-alkyl which is in each case substituted by m radicals selected from the group consisting of fluorine and chlorine;

or $(C_1\text{-}C_6)$-alkoxy which is substituted by m radicals selected from the group consisting of fluorine and chlorine;

$X^5$ is hydrogen or $X^3$;

$R^5$ is methyl or ethyl;

$R^6$ is hydrogen or $R^5$;

$R^{6a}$ is fluorine, chlorine, bromine, iodine, cyano, hydroxy, $S(O)_nR^5$ or $(C_1\text{-}C_6)$-alkoxy, $(C_2\text{-}C_6)$-alkenyloxy or $(C_2\text{-}$ $C_6$)-alkynyloxy, each of which is substituted by m radicals selected from the group consisting of fluorine, chlorine, bromine, cyano and ($C_1$-$C_2$)-alkoxy;

$R^7$ is hydrogen or ($C_1$-$C_6$)-alkyl which is substituted by in each case m radicals selected from the group consisting of fluorine and chlorine;

$R^8$ is $R^7$;

$R^9$ is ($C_1$-$C_3$)-alkoxy;

m is 0, 1, 2 or 3;

n is 0, 1 or 2;

with the proviso that $X^3$ and $X^4$ are not both substituted or unsubstituted alkoxy.

4. A herbicidal composition which comprises a herbicidally effective amount of at least one compound of formula (I) and/or salt thereof as claimed in claim 1.

5. The herbicidal composition as claimed in claim 4, in a mixture with at least one formulation auxiliary.

6. The herbicidal composition as claimed in claim 4, comprising at least one further pesticidally active compound selected from the group consisting of an insecticide, an acaricide, a herbicide, a fungicide, a safener and a growth regulator.

7. The herbicidal composition as claimed in claim 6, comprising a safener.

8. The herbicidal composition as claimed in claim 7, where the safener is selected from the group consisting of mefenpyr-diethyl, cyprosulfamide, isoxadifenethyl, cloquintocet-mexyl, benoxacor and dichlormid.

9. The herbicidal composition as claimed in claim 6, comprising a further herbicide.

10. A 3-phenylisoxazoline-5-carboxamide or 3-phenyl-isoxazoline-5-thioamide of formula (Ia)

(Ia)

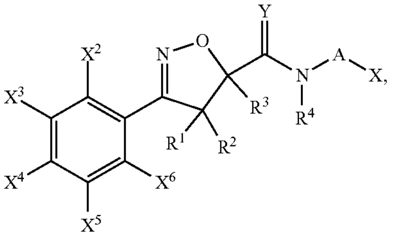

in which $R^1$ and $R^2$ independently of one another are each hydrogen, fluorine, chlorine, bromine, iodine, cyano, or ($C_1$-$C_4$)-alkyl or ($C_1$-$C_4$)-alkoxy substituted by in each case m radicals selected from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, ($C_1$-$C_3$)-alkylcarbonyloxy or $(O)_nR^5$, or ($C_1$-$C_6$)-alkyl, ($C_3$-$C_6$)-cycloalkyl, ($C_2$-$C_6$)-alkenyl or ($C_2$-$C_6$)-alkynyl substituted by in each case m radicals selected from the group consisting of fluorine, chlorine, bromine, iodine, cyano, ($C_1$-$C_4$)-alkoxy and hydroxy, or ($C_1$-$C_6$)-alkylcarbonyl, ($C_2$-$C_6$)-alkenylcarbonyl or ($C_3$-$C_6$)-cycloalkylcarbonyl substituted by in each case m radicals selected from the group consisting of fluorine, chlorine, bromine, iodine, cyano and ($C_1$-$C_6$)-alkoxy;

$R^4$ is hydrogen, cyano, hydroxy, or ($C_1$-$C_8$)-alkyl or ($C_3$-$C_8$)-cycloalkyl substituted by in each case m radicals selected from the group consisting of fluorine, chlorine, bromine, iodine, cyano, hydroxy and ($C_1$-$C_6$)-alkoxy;

A is a bond or a divalent unit selected from the group consisting of

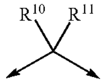

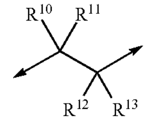

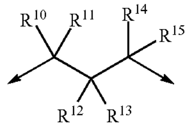

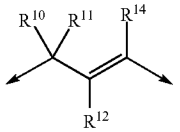

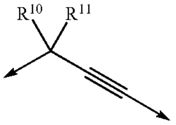

and

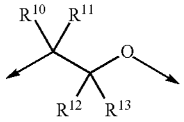

$R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano;

or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, Y is oxygen or sulfur;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl substituted by in each case m radicals selected from the group consisting of fluorine, chlorine, bromine, iodine, cyano, hydroxy, $OR^7$, $X^1$, $OX^1$, $NHX^1$, $S(O)_nR^5$, $SO_2NR^6R^7$, $SO_2NR^6R^8$, $CO_2R^8$, $CONR^6R^8$, $COR^8$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)$=$NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements selected from the group consisting of $NR^7$ and $NCOR^7$ as ring atoms, where a carbon atom carries p oxo groups;

$X^1$ is a 5- or 6-membered saturated, partially unsaturated, fully unsaturated or aromatic ring which is constructed of r carbon atoms, s nitrogen atoms, n sulphur atoms and n oxygen atoms and which is substituted by at least one n radical selected from the group consisting of $R^6$, $R^{6a}$, $R^8$ and $R^9$;

or phenyl which is substituted by n radicals selected from the group consisting of $R^6$, $R^8$ and $R^9$;

$X^2$, $X^4$ and $X^6$ independently of one another are each hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl, each of which is substituted by m radicals selected from the group consisting of fluorine, chlorine, bromine, iodine, cyano and ($C_1$-$C_4$)-alkoxy;

$X^3$ is hydrogen, fluorine, chlorine, bromine, iodine, hydroxy, cyano, nitro, $SF_5$, $CONR^8SO_2R^5$, $CONR^6R^8$, $COR^6$, $CO_2R^8$, $CONR^6R^8$, $C(R^6)$=$NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, $X^5$ is hydrogen or $X^3$;

$R^5$ is ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or ($C_1$-$C_6$)-alkoxy, ($C_2$-$C_6$)-alkenyloxy or ($C_2$-$C_6$)-alkynyloxy, each of which is substituted by m radicals selected from the group consisting of fluorine, chlorine, bromine, cyano and ($C_1$-$C_2$)-alkoxy;

$R^7$ is hydrogen or ($C_1$-$C_6$)-alkyl, ($C_3$-$C_6$)-cycloalkyl, ($C_2$-$C_4$)-alkenyl or ($C_2$-$C_4$)-alkynyl, each of which is substituted by m radicals selected from the group consisting of fluorine, chlorine, bromine, cyano and ($C_1$-$C_2$)-alkoxy;

$R^8$ is $R^7$;

$R^9$ is ($C_1$-$C_3$)-alkyl or ($C_1$-$C_3$)-alkoxy;

k is 3, 4, 5 or 6;

m is 0, 1, 2, 3, 4 or 5;

n is 0, 1 or 2;

p is 0 or 1;

q is 3, 4 or 5;

r is 1, 2, 3, 4 or 5;

s is 0, 1, 2, 3 or 4;

capable of being used for controlling an unwanted plant.

11. A 3-phenylisoxazoline-5-carboxamide or 3-phenylisoxazoline-5-thioamide of formula (Ia) capable of being used for controlling an unwanted plant (Ia)

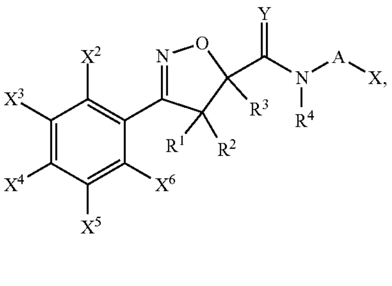

in which $R^1$ and $R^2$ independently of one another are each hydrogen, fluorine, chlorine, bromine, iodine, cyano, or ($C_1$-$C_4$)-alkyl or ($C_1$-$C_4$)-alkoxy substituted by in each case m radicals selected from the group consisting of fluorine, chlorine, bromine, iodine and cyano, or $R^1$ and $R^2$ together with the carbon atom to which they are attached form a saturated, partially or fully unsaturated three-, four- or 5-membered ring which is constructed of q carbon atoms and p oxygen atoms;

$R^3$ is fluorine, chlorine, cyano, ($C_1$-$C_3$)-alkylcarbonyloxy or $(O)_nR^5$, or ($C_1$-$C_6$)-alkyl, ($C_3$-$C_6$)-cycloalkyl, ($C_2$-$C_6$)-alkenyl or ($C_2$-$C_6$)-alkynyl substituted by in each case m radicals selected from the group consisting of fluorine, chlorine, bromine, iodine, cyano, ($C_1$-$C_4$)-alkoxy and hydroxy, or ($C_1$-$C_6$)-alkylcarbonyl, ($C_2$-$C_6$)-alkenylcarbonyl or ($C_3$-$C_6$)-cycloalkylcarbonyl substituted by in each case m radicals selected from the group consisting of fluorine, chlorine, bromine, iodine, cyano and ($C_1$-$C_6$)-alkoxy;

$R^4$ is hydrogen, cyano, hydroxy, or ($C_1$-$C_8$)-alkyl or ($C_3$-$C_8$)-cycloalkyl substituted by in each case m radicals selected from the group consisting of fluorine, chlorine, bromine, iodine, cyano, hydroxy and ($C_1$-$C_6$)-alkoxy;

A is a bond or a divalent unit selected from the group consisting of

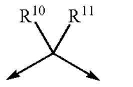

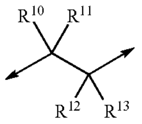

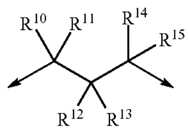

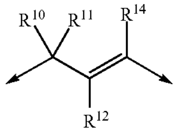

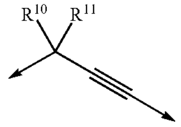

and

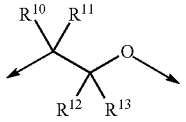

$R^{10}$, $R^{11}$, $R^{12}$, $R^{13}$, $R^{14}$ and $R^{15}$ are each independently of one another hydrogen, fluorine, chlorine, bromine, iodine, hydroxy, cyano, $CO_2R^8$, $CONR^6R^8$, $R^5$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano;

or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, Y is oxygen or sulfur;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl substituted by in each case at least one m radical selected from the group consisting of fluorine, chlorine, bromine, iodine, cyano, hydroxy, $X^1$, $OX^1$, $NHX^1$, $S(O)_nR^5$, $SO_2NR^6R^7$, $SO_2NR^6R^8$, $CO_2R^8$, $CONR^6R^8$, $COR^8$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6){=}NOR^8$, or X, A and $R^4$ together with the nitrogen atom to which they are attached form a saturated, partially or fully unsaturated five-, six- or seven-membered ring which, in addition to this nitrogen atom, contains k carbon atoms, n oxygen atoms, p sulphur atoms and p elements selected from the group consisting of $NR^7$ and $NCOR^7$ as ring atoms, where a carbon atom carries p oxo groups;

$X^1$ is a ring, substituted by n radicals selected from the group consisting of $R^6$, $R^{6a}$, $R^8$ and $R^9$, wherein the ring is selected from the group consisting of

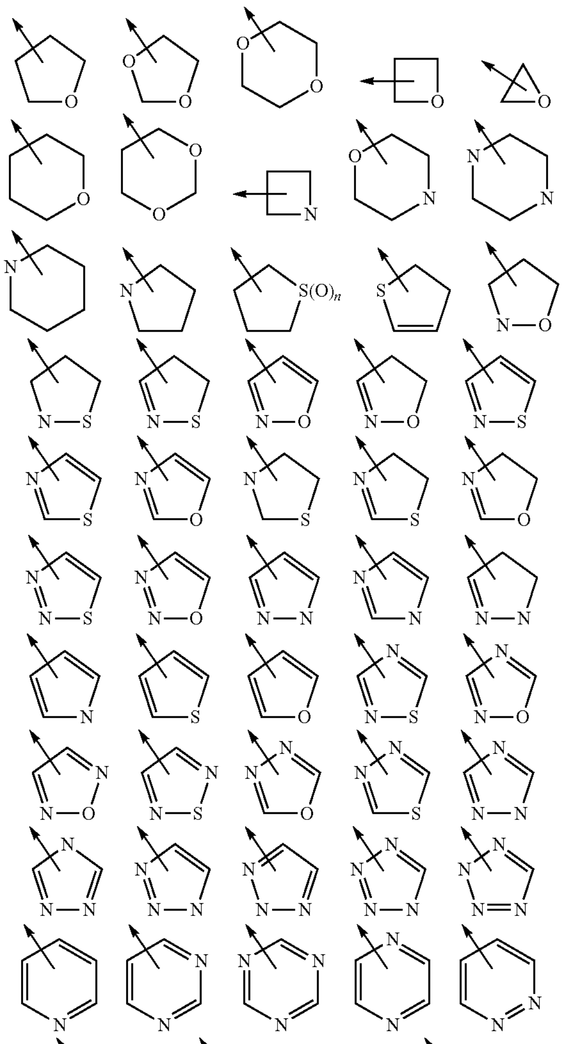

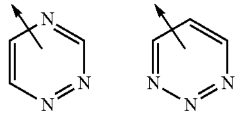

and

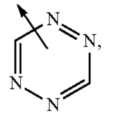

or phenyl which is substituted by n radicals selected from the group consisting of $R^6$, $R^8$, and $R^9$;

$X^2$, $X^4$ and $X^6$ independently of one another are each hydrogen, fluorine, chlorine, bromine, iodine, cyano, nitro, or ($C_1$-$C_4$)-alkyl, ($C_3$-$C_5$)-cycloalkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy or ($C_1$-$C_4$)-alkylcarbonyl, each of which is substituted by m radicals selected from the group consisting of fluorine, chlorine, bromine, iodine, cyano and ($C_1$-$C_4$)-alkoxy;

$X^3$ is hydrogen, fluorine, chlorine, bromine, iodine, hydroxy, cyano, nitro, $SF_5$, $CONR^8SO_2R^5$, $CONR^6R^8$, $COR^6$, $CO_2R^8$, $CONR^6R^8$, $C(R^6){=}NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $R^5$, $S(O)_nR^5$, $SO_2NR^6R^8$, $OSO_2NR^6R^8$, or ($C_1$-$C_6$)-alkyl, ($C_3$-$C_5$)-cycloalkyl, ($C_2$-$C_6$)-alkenyl, ($C_2$-$C_6$)-alkynyl, each of which is substituted by m radicals selected from the group consisting of fluorine, chlorine, bromine, iodine, hydroxy and cyano, or ($C_1$-$C_6$)-alkoxy, ($C_3$-$C_6$)-cycloalkoxy, ($C_2$-$C_6$)-alkenyloxy or ($C_2$-$C_6$)-alkynyloxy, each of which is substituted by m radicals selected from the group consisting of fluorine, chlorine, bromine, iodine, cyano and ($C_1$-$C_2$)-alkoxy, $X^5$ is hydrogen or $X^3$;

$R^5$ is ($C_1$-$C_6$)-alkyl or ($C_3$-$C_6$)-cycloalkyl, each of which is substituted by m radicals selected from the group consisting of fluorine, chlorine, bromine, iodine, cyano and hydroxy;

$R^6$ is hydrogen or $R^5$;

$R^{6a}$ is fluorine, chlorine, bromine, iodine, cyano, hydroxy, $S(O)_nR^5$ or ($C_1$-$C_6$)-alkoxy, ($C_2$-$C_6$)-alkenyloxy or ($C_2$-$C_6$)-alkynyloxy, each of which is substituted by m radicals selected from the group consisting of fluorine, chlorine, bromine, cyano and ($C_1$-$C_2$)-alkoxy;

$R^7$ is hydrogen or ($C_1$-$C_6$)-alkyl, ($C_3$-$C_6$)-cycloalkyl, ($C_2$-$C_4$)-alkenyl or ($C_2$-$C_4$)-alkynyl, each of which is substituted by m radicals selected from the group consisting of fluorine, chlorine, bromine, cyano and ($C_1$-$C_2$)-alkoxy;

$R^8$ is $R^7$;

$R^9$ is ($C_1$-$C_3$)-alkyl or ($C_1$-$C_3$)-alkoxy;

k is 3, 4, 5 or 6;

m is 0, 1, 2, 3, 4 or 5;

n is 0, 1 or 2;

p is 0 or 1;

q is 3, 4 or 5.

12. A 3-phenylisoxazoline-5-carboxamide or 3-phenylisoxazoline-5-thioamide of formula (Ia)

(Ia)

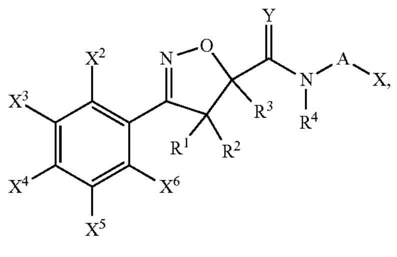

capable of being used for controlling an unwanted plant in which $R^1$ and $R^2$ independently of one another are each hydrogen, fluorine, chlorine, bromine, iodine, cyano, or ($C_1$-$C_4$)-alkyl substituted by in each case m radicals selected from the group consisting of fluorine, chlorine, bromine, iodine and cyano, $R^3$ is fluorine, chlorine or cyano, or ($C_1$-$C_6$)-alkyl, ($C_3$-$C_6$)-cycloalkyl, ($C_2$-$C_6$)-alkenyl, ($C_2$-$C_6$)-alkynyl, each of which is substituted by m radicals from the group consisting of fluorine and chlorine, or ($C_1$-$C_6$)-alkylcarbonyl which is substituted by m radicals selected from the group consisting of fluorine and chlorine;

$R^4$ is hydrogen, hydroxy or ($C_1$-$C_8$)-alkyl;

A is a bond or a divalent unit selected from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH{=}CH$, $C(CH_3)_2C{\equiv}C$, $CH(CF_3)CH_2$, $CH(CH_3)CH_2O$, $CH_2CH_2O$, $CH(cPr)CH_2O$, $CH(CH_2OCH_3)$, $CH(CH_2CH_2SCH_3)$, CH(COOH), $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

Y is O or S;

X is hydrogen, cyano, hydroxy, $X^1$, or ($C_1$-$C_{12}$)-alkyl, ($C_3$-$C_8$)-cycloalkyl, ($C_2$-$C_{12}$)-alkenyl or ($C_2$-$C_{12}$)-alkynyl, each of which is substituted by m radicals selected from the group consisting of fluorine, chlorine, cyano, hydroxy, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring, substituted by n radicals from the group consisting of $R^6$, $R^{6a}$, $R^8$ and $R^9$, wherein the the ring is selected from the group consisting of

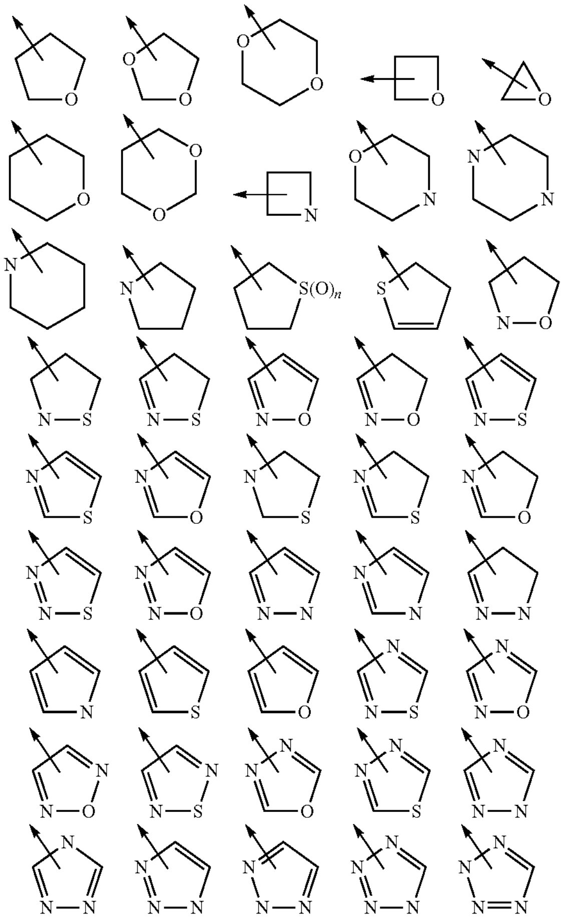

-continued

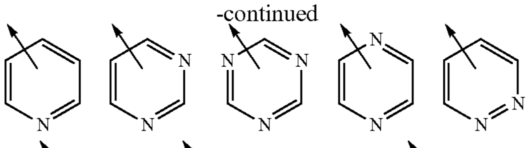

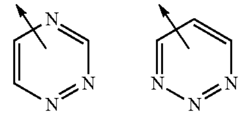

and

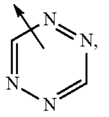

or phenyl which is substituted by n radicals selected from the group consisting of $R^6$, $R^8$ and $R^9$;

$X^2$, $X^4$ and $X^6$ independently of one another are each hydrogen, fluorine or chlorine, or ($C_1$-$C_4$)-alkyl or ($C_1$-$C_4$)-alkoxy, each of which is substituted by m radicals selected from the group consisting of fluorine, chlorine, cyano and ($C_1$-$C_4$)-alkoxy;

$X^3$ is hydrogen, fluorine, chlorine, bromine, cyano, or ($C_1$-$C_6$)-alkyl which is in each case substituted by m radicals selected from the group consisting of fluorine and chlorine;

or ($C_1$-$C_6$)-alkoxy which is substituted by m radicals selected from the group consisting of fluorine and chlorine;

$X^5$ is hydrogen or $X^3$;

$R^5$ is methyl or ethyl;

$R^6$ is hydrogen or $R^5$;

$R^{6a}$ is fluorine, chlorine, bromine, iodine, cyano, hydroxy, $S(O)_nR^5$ or ($C_1$-$C_6$)-alkoxy, ($C_2$-$C_6$)-alkenyloxy or ($C_2$-$C_6$)-alkynyloxy, each of which is substituted by m radicals selected from the group consisting of fluorine, chlorine, bromine, cyano and ($C_1$-$C_2$)-alkoxy;

$R^7$ is hydrogen or ($C_1$-$C_6$)-alkyl which is substituted by in each case m radicals selected from the group consisting of fluorine and chlorine;

$R^8$ is $R^7$;

$R^9$ is ($C_1$-$C_3$)-alkoxy;

m is 0, 1, 2 or 3;

n is 0, 1 or 2.

13. A method for controlling an unwanted plant, comprising applying an effective amount of at least one compound of formula (I) and/or salt thereof as claimed in claim 1, to a plant and/or a site of an unwanted vegetation.

14. A compound of formula (I) and/or salt thereof as claimed in claim 1, capable of being used for controlling an unwanted plant.

15. A compound of formula (I) and/or salt, capable of being used as claimed in claim 14, wherein said compound of formula (I) is used for controlling an unwanted plant in a crop of a useful plant.

16. A compound of formula (I) and/or salt thereof capable of being used as claimed in claim 15, wherein said useful plant is a transgenic useful plant.

17. A fungicidal composition which comprises a fungicidally effective amount of at least one compound of the formula (I) and/or salt thereof as claimed in claim 1.

18. The fungicidal composition as claimed in claim 17, in a mixture with at least one formulation auxiliary.

19. The fungicidal composition as claimed in claim 17, comprising at least one further pesticidally active compound selected from the group consisting of an insecticide, an acaricide, a herbicide, a fungicide, a safener and a growth regulator.

* * * * *